US010300075B2

(12) United States Patent
Brown et al.

(10) Patent No.: US 10,300,075 B2
(45) Date of Patent: May 28, 2019

(54) COMPOUNDS THAT INHIBIT MCL-1 PROTEIN

(71) Applicant: AMGEN INC., Thousand Oaks, CA (US)

(72) Inventors: Sean P. Brown, Agoura Hills, CA (US); Kexue Li, Newbury Park, CA (US); Yunxiao Li, Thousand Oaks, CA (US); Markian M. Stec, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/938,001

(22) Filed: Mar. 28, 2018

(65) Prior Publication Data

US 2018/0289720 A1 Oct. 11, 2018

Related U.S. Application Data

(60) Provisional application No. 62/247,230, filed on Mar. 30, 2017, provisional application No. 62/479,171, filed on Mar. 30, 2017.

(51) Int. Cl.
| | | |
|---|---|---|
| A61K 31/553 | (2006.01) | |
| C07D 498/08 | (2006.01) | |
| A61P 35/00 | (2006.01) | |
| A61P 35/02 | (2006.01) | |

(52) U.S. Cl.
CPC ............ *A61K 31/553* (2013.01); *A61P 35/00* (2018.01); *A61P 35/02* (2018.01); *C07D 498/08* (2013.01)

(58) Field of Classification Search
CPC .................................................. A61K 31/553
USPC ................................................... 514/211.09
See application file for complete search history.

(56) References Cited

U.S. PATENT DOCUMENTS

| | | | |
|---|---|---|---|
| 4,522,811 | A | 6/1985 | Eppstein et al. |
| 6,468,798 | B1 | 10/2002 | Deb et al. |
| 6,471,996 | B1 | 10/2002 | Sokoll et al. |
| 6,472,375 | B1 | 10/2002 | Hoon et al. |
| 9,562,061 | B2 | 2/2017 | Brown et al. |
| 2009/0054402 | A1 | 2/2009 | Wang et al. |
| 2014/0051683 | A1 | 2/2014 | Wang et al. |
| 2015/0045357 | A1 | 2/2015 | Nikolovska-Coleska et al. |
| 2015/0284328 | A1 | 10/2015 | Wang et al. |
| 2017/0088560 | A1 | 3/2017 | Brown et al. |

FOREIGN PATENT DOCUMENTS

| | | |
|---|---|---|
| WO | 2008/131000 A2 | 10/2008 |
| WO | 2011/094708 A2 | 8/2011 |
| WO | 2013/052943 A2 | 4/2013 |
| WO | 2013/149124 A1 | 10/2013 |
| WO | 2013/033486 A1 | 3/2016 |
| WO | 2017/147410 A1 | 8/2017 |

OTHER PUBLICATIONS

Beroukhim,R., et al., "The landscape of somatic copy-number alteration across human cancers," Nature 463, 899-905 (2010).
Lessene, G., et al., "BCL-2 family antagonists for cancer therapy," Nat. Rev. Drug. Discov., vol. 7, 989-1000 (2008).
Akgul, C., "Mcl-1 is a potential therapeutic target in multiple types of cancer," Cell. Mol. Life Sci. vol. 66 1326-1336 (2009).
Mandelin II, A. M. et al., "Myeloid cell leukemia-1 as a therapeutic target," Expert Opin. Ther. Targets, 11(3):363-373 (2007).
Rowe, R. C., et al., Handbook of Pharmaceutical Excipients, 5th Edition (2005).
Berge, S. M. et al. "Pharmaceutical Salts", J. Pharm. Sci. 66: 1-19 (1977).
Hamajima, K. et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., 88(2), 205-210 (1998).
Higuchi, T. et al., "Pro-drugs as Novel Delivery Systems," vol. 14 of the A.C.S. Symposium Series (1975).
Roche, E.B., "Bioreversible Carriers in Drug Design", ed. Edward B. Roche, American Pharmaceutical Association and Pergamon Press, (1987).
Brubaker, J. D., et al., "A Practical, Enantioselective Synthetic Route to a Key Precursor to the Tetracycline Antibiotics," Org. Lett., 9, 3523-3525 (2007).

(Continued)

*Primary Examiner* — Kahsay Habte
(74) *Attorney, Agent, or Firm* — Bernard P. Friedrichsen

(57) ABSTRACT

Provided herein are myeloid cell leukemia 1 protein (Mcl-1) inhibitors, methods of their preparation, related pharmaceutical compositions, and methods of using the same. For example, provided herein are compounds of Formula I, (I)

or a stereoisomer thereof; and pharmaceutically acceptable salts thereof and pharmaceutical compositions containing the compounds. The compounds and compositions provided herein may be used, for example, in the treatment of diseases or conditions, such as cancer.

39 Claims, 13 Drawing Sheets

(56) References Cited

OTHER PUBLICATIONS

Krasovskiy, A et al., "Convenient Titration Method for Organometallic Zinc, Magnesium, and Lanthanide Reagents," Synthesis, 890-891 (2006).
Sigman, M. S. et al., "Palladium-Catalyzed Allylic Cross-Coupling Reactions of Primary and Secondary Homoallylic Electrophiles," J. Am. Chem. Soc., 134(28), 11408-11411 (2012).
International Search Report and Written Opinion of analogous PCT application PCT/US2018/02473 dated Jun. 4, 2018.
Farrell, R. P. "Breaking Symmetry Towards Development and Scale Up of a Complex Drug Candidate," American Chemical Society Meeting Presentation, Philadelphia, PA, Aug. 22, 2016.
Brown, B. "Interdiction at a Protein-Protein Interface: Structure-Based Design of Mcl-1 Inhibitors," American Chemical Society Meeting Presentation, Philadelphia, PA, Aug. 22, 2016.
Brown, S. "Interdiction at a Protein-Protein Interface: Structure-Based Design of Mcl-1 Inhibitors," Presentation at Caltech, Pasadena, CA, Jun. 1, 2016.
Brown, S. "Interdiction at a Protein-Protein Interface: Structure-Based Design of Mcl-1 Inhibitors," American Chemical Society Meeting Presentation, San Francisco, CA, Apr. 5, 2017.
Caenepeel, S. R. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Washington DC, Apr. 1-5, 2017.
Hata, A. N. et al., "Combined targeting of MEK and MCL-1 induces apoptosis and tumor regression of KRAS mutant NSCLC," Poster Presentation at American Association for Cancer Research Meeting, Washington DC, Apr. 1-5, 2017.
Hata, A. N. et al., untitled structure slide, Poster Presentation at American Association for Cancer Research Meeting, Washington DC, Apr. 1-5, 2017.
Caenepeel, S. et al. "Preclinical Evaluation of AMG 176, a Novel, Potent and Selective Mcl-1 Inhibitor with Robust Anti-tumor Activity in Mcl-1 Dependent Cancer Models," Poster Presentation at American Association for Cancer Research Meeting, Chicago, IL, Apr. 14-18, 2018.
Caenepeel, S. et al. "Combined Inhibition of MCL1 and BCL-2 With AMG 176 and Venetoclax Induces Anti-tumor Effects in Acute Myeloid Leukemia," Poster Presentation at American Association for Cancer Research Meeting, Chicago, IL, Apr. 14-18, 2018.
Belmontes, B., "The Utilization of a Human MCL1 Knock-In Mouse Suggests that Reductions in B Cells and Monocytes may Serve as Clinically Relevant Pharmacodynamic namic markers of MCL1 Inhibition," Poster Presentation at American Association for Cancer Research Meeting, Chicago, IL, Apr. 14-18, 2018.
Brown, S. "Interdiction at a Protein-Protein Interface: Structure-Based Design of the Mcl-1 Inhibitor AMG 176," American Chemical Society Meeting Presentation, New Orleans, LA, Mar. 19, 2018.
Hughes, P. "The Discovery and Preclinical Characterization of AMG 176: A First-In-Class MCL-1 Inhibitor in Clinical Development for Multiple Myeloma," Poster Presentation at American Association for Cancer Research Meeting, Chicago, IL, Apr. 14-18, 2018.

COMPOUNDS THAT INHIBIT MCL-1 PROTEIN

CROSS REFERENCES TO RELATED APPLICATIONS

This application claims the benefit of U.S. Provisional Application No. 62/479,171, filed on Mar. 30, 2017, and U.S. Provisional Application No. 62/479,230, filed on Mar. 30, 2017, both of which are hereby incorporated by reference in their entireties and for all purposes as if fully set forth herein.

FIELD OF THE INVENTION

The present invention relates to compounds that inhibit myeloid cell leukemia 1 protein (Mcl-1, also abbreviated as MCl-1, MCL-1 or MCL1); methods of treating diseases or conditions, such as cancer, using the compounds; and pharmaceutical compositions containing the compounds.

BACKGROUND OF THE INVENTION

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions.

Research has shown that Mcl-1 inhibitors can be useful for the treatment of cancers. MCl-1 is overexpressed in numerous cancers. See Beroukhim et al. (2010) Nature 463, 899-90. Cancer cells containing amplifications surrounding the Mcl-1 and Bcl-2-1-1 anti-apoptotic genes depend on the expression of these genes for survival. Beroukhim et al. Mcl-1 is a relevant target for the re-iniation of apoptosis in numerous cancer cells. See G. Lessene, P. Czabotar and P. Colman, Nat. Rev. Drug. Discov., 2008, 7, 989-1000; C. Akgul Cell. Mol. Life Sci. Vol. 66, 2009; and Arthur M. Mandelin II, Richard M. Pope, Expert Opin. Ther. Targets (2007) 11(3):363-373.

New compositions and methods for preparing and formulating Mcl-1 inhibitors would be useful.

SUMMARY OF THE INVENTION

In one aspect, the present invention comprises a compound of Formula I:

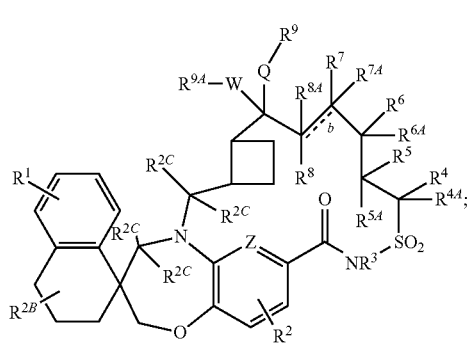

(I)

a stereoisomer thereof, a pharmaceutically acceptable salt thereof, or a pharmaceutically acceptable salt of the stereoisomer thereof, wherein:

Z is C or N;

Q is O, S, $CR^{WA}R^{WB}$, or $NR^aR^b$;

W is $CR^{WA}R^{WB}$, —C=O, or is absent;

$R^{WA}$ and $R^{WB}$ are independently selected from H, —$C_{1-3}$ alkyl, —$C_{2-3}$alkenyl, —$C_{2-3}$alkynyl, halo, —OH, or —O—$C_{1-3}$alkyl;

b, represented by the symbol ==== is a single or double chemical bond which may be cis or trans;

$R^1$ is independently selected from H, halo, $C_{1-6}$alkylhalo, $C_{1-6}$alkyl, $C_{2-6}$alkenyl, —$(CH_2CH_2O)_nR^a$, —$SO_2R^a$, —C(=O)$R^a$, —C(=O)O$R^a$, or —C(=O)N$R^aR^b$; $R^2$ is selected from H, halo, $C_{1-6}$haloalkyl, $C_{1-6}$alkyl, O—$C_{1-6}$ alkyl, $C_{2-6}$alkenyl, $C_{1-6}$alkenylene, —$C_{1-6}$alkyl-O—$C_{1-6}$ alkyl, —$(CH_2CH_2O)_nR^a$, —$SO_2R^a$, —C(=O)$R^a$, —C(=O)O$R^a$, —OC(=O)$R^a$, —C(=O)N$R^aR^b$, a 6- to 12-membered aryl or heteroaryl, a 5- to 12-membered spirocycloalkyl or spiroheterocycloalkyl, or a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl or heterocycloalkyl group have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$;

$R^3$ is selected from H, —$C_{1-6}$alkylhalo, —$C_{1-6}$alkyl, —$C_{2-6}$alkenyl, —$(CH_2CH_2O)_nR^a$, —C(=O)$R^a$, —C(=O) O$R^a$, or —C(=O)N$R^aR^b$;

each of $R^{2B}$, $R^{2C}$, $R^4$, $R^5$, $R^6$, $R^7$, and $R^8$ is independently selected from H, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, —C(=O)N$R^aR^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

alternatively $R^3$ and $R^4$ together with the atoms to which they are bonded may form a 5- to 12-membered ring, optionally containing a heteroatom selected from a N, O or S atom, in addition to the S and N atoms present in the ring, wherein the ring may optionally contain at least one double bond; and the ring may be substituted with 0, 1, 2, or 3 $R^{3A}$ substituents;

wherein $R^{3A}$ is selected from H, halo, —OH, $C_{1-6}$haloalkyl, $C_{1-6}$alkyl, O—$C_{1-6}$alkyl, $C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, or —C(=O)N$R^aR^b$;

each of $R^{4A}$, $R^{5A}$, $R^{6A}$, $R^{7A}$, and $R^{8A}$ is independently selected from H, OH, halo, or —$C_{1-6}$alkyl;

$R^{7A}$ and $R^{8A}$ are absent when b is a double chemical bond;

alternatively $R^7$ and $R^8$ together with the atoms to which they are bonded may form a 3- to 12-membered ring, wherein the ring may optionally contain at least one double bond;

$R^9$ is independently selected from H, OH, —(=O), —$C_{1-6}$haloalkyl, —$C_{1-6}$alkyl, —$C_{1-6}$alkenylene, —(CH$_2$CH$_2$O)$_n$R$^a$, —C(=O)R$^a$, —C(=O)OR$^a$, —C(=O)NR$^a$R$^b$, —$C_{1-6}$ alkyl-O—$C_{1-6}$alkyl, cyano, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl or heterocycloalkyl groups have 1, 2, 3 or 4 heteroatoms independently selected from O, N or S, and the cycloalkyl, spirocycloalkyl, spiroheterocycloalkyl, and heterocycloalkyl group may include a C=O group, and further wherein the spiroheterocycloalkyl, and heterocycloalkyl groups may include a S=O or SO$_2$;

$R^{9A}$ is independently selected from H, —OH, halo, cyano, —$C_{1-6}$haloalkyl, —$C_{1-6}$alkyl, —$C_2$-$C_6$ alkenyl, —$C_2$-$C_6$ alkynyl, —$C_{1-6}$alkenylene, —(CH$_2$CH$_2$O)$_n$R$^a$, —P(=O)OR$^a$OR$^b$, —CSR$^a$, —CS(=O)R$^a$, —SR$^a$, —SOR$^a$, —OSO$_2$R$^a$, —SO$_2$R$^a$, —(CH$_2$CH$_2$O)$_n$CH$_3$, —(=O), —C(=O), —C(=O)R$^a$, —C(=O)OR$^a$, —C(=O)NR$^a$R$^b$, —CH$_2$—NR$^a$R$^b$, —NR$^a$R$^b$, —$C_{1-6}$alkyl-O—$C_{1-6}$alkyl, —OC$_{1-6}$alkyl, —O—$C_{1-6}$alkyl-O—$C_{1-6}$alkyl, phenyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may contain a double bond and may contain a C=O group, and further wherein the spiroheterocycloalkyl, and heterocycloalkyl groups may include a S=O or SO$_2$;

wherein $R^{9A}$ is not H when W is absent;

wherein the aryl, heteroaryl, cycloalkyl, heterocycloalkyl, spirocycloalkyl and spiroheterocycloalkyl groups of the $R^{9A}$ substituent can be unsubstituted or substituted with 1, 2, 3 or 4 $R^{10}$ substituents independently selected from OH, halo, —NR$^c$R$^d$, —$C_{1-6}$alkyl, —$C_2$-$C_6$ alkenyl, —$C_2$-$C_6$alkynyl, —OC$_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

alternatively $R^7$ and $R^{9A}$ together with the atoms to which they are bonded may form a 3- to 12-membered ring, wherein the ring may optionally contain at least one double bond;

alternatively $R^9$ and $R^{9A}$ together with Q, W, and the C to which W and Q are bonded, may form a 3- to 12-membered monocyclic or bicyclic ring, optionally containing a heteroatom in addition to Q that is selected from N, O or S, wherein the ring may contain a double bond, wherein the ring may optionally include a C=O group, and further wherein the ring optionally may be substituted by 1, 2, or 3 $R^{11}$ substituents;

$R^{11}$ is independently selected from H, —OH, halo, —$C_{1-6}$alkyl, —OC$_{1-6}$alkyl, —$C_{1-6}$alkyl-OH, —$C_{1-6}$alkyl-O—$C_{1-6}$alkyl, —$C_{1-6}$haloalkyl, —O-halo$C_{1-6}$alkyl, —SO$_2$R$^c$, —CN, —NR$^c$R$^d$, —C(=O)NR$^c$R$^d$, —C(=O)R$^c$, —OC(=O)R$^c$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3 or 4 heteroatoms independently selected from O, N or S, wherein the cycloalkyl, spirocycloalkyl, spiroheterocycloalkyl, and heterocycloalkyl group may include a double bond, and wherein the cycloalkyl, spirocycloalkyl, spiroheterocycloalkyl, and heterocycloalkyl group may include a C=O group, and further wherein the spiroheterocycloalkyl, and heterocycloalkyl groups may include a S=O or SO$_2$;

wherein the $C_{1-6}$alkyl, $C_{2-6}$ alkenyl, $C_{2-6}$ alkynyl or —OC$_{1-6}$alkyl of any of the $R^1$, $R^2$, $R^3$, $R^4$, $R^5$, $R^6$, $R^7$, $R^8$, $R^9$, $R^{10}$, $R^{11}$, $R^{4A}$, $R^{5A}$, $R^{6A}$, $R^{7A}$, $R^{8A}$, $R^{9A}$, $R^{WA}$ and $R^{WB}$ substituents is unsubstituted or substituted by 1, 2 or 3 $R^{12}$ substituents independently selected from OH, —OC$_{1-6}$alkyl, —$C_{1-6}$alkyl-O—$C_{1-6}$alkyl, halo, —O-halo$C_{1-6}$alkyl, —CN, —NR$^a$R$^b$, —(NR$^a$R$^b$R$^c$)$_n$, —OSO$_2$R$^a$, —SO$_2$R$^a$, —(CH$_2$CH$_2$O)$_n$CH$_3$, —(=O), —C(=O), —C(=O)R$^a$, —OC(=O)R$^a$, —C(=O)OR$^a$, —C(=O)NR$^a$R$^b$, —O—SiR$^a$R$^b$R$^c$, —SiR$^a$R$^b$R$^c$, —O-(3- to 10-membered heterocycloakyl), a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the aryl, heteroaryl, cycloalkyl, heterocycloalkyl, spirocycloalkyl and spiroheterocycloalkyl group of any of the $R^2$, $R^4$, $R^5$, $R^6$, $R^7$, $R^8$, $R^9$, $R^{9A}$, $R^{10}$, $R^{11}$, $R^{12}$, $R^{WA}$ and $R^{WB}$ substituents can be unsubstituted or substituted with 1, 2, 3 or 4 $R^{13}$ substituents independently selected from OH, halo, —NR$^c$R$^d$, —$C_{1-6}$alkyl, —OC$_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups of $R^{13}$ have 1, 2, 3 or 4 heteroatoms independently selected from O, N or S, wherein the cycloalkyl, spirocycloalkyl, and spiroheterocycloalkyl groups of $R^{13}$ or the heterocycloalkyl group of $R^{13}$ may include a C=O group, and further wherein the spiroheterocycloalkyl and heterocycloalkyl groups may include a S=O or SO$_2$;

wherein each $R^a$, $R^b$, $R^c$, and $R^d$ is independently hydrogen, OH, —$C_{1-6}$alkyl, —$C_{2-6}$alkenyl, —$C_{2-6}$alkynyl, —$C_{1-6}$alkyl-NR$^{14}$R$^{14}$, —NR$^{14}$R$^{14}$, —SO$_2$R$^{14}$, —(CH$_2$CH$_2$O)$_n$ CH$_3$, —(=O), —C(=O)R$^{14}$, —OC(=O)R$^{14}$, —C(=O)OR$^{14}$, —C(=O)NR$^{14}$R$^{14}$, —C$_{1-6}$haloalkyl, —O-haloC$_{1-6}$alkyl, —C$_{1-6}$alkyl-O—C$_{1-6}$alkyl, benzyl, phenyl, —C$_{1-6}$alkyl-C(=O)OH, —C$_{1-6}$alkyl-C(=O)—O—C$_{1-6}$alkyl, —C$_{1-6}$alkyl-cycloalkyl, —C$_{1-6}$alkyl-heterocycloalkyl, —C$_{1-6}$alkyl-6- to 10-membered aryl, —C$_{1-6}$alkyl-6- to 10-membered heteroaryl, a 6- to 12-membered aryl or heteroaryl, a 5- to 12-membered spirocycloalkyl or spiroheterocycloalkyl, or a 3- to 12-membered cycloalkenyl, a 3- to 12-membered monocyclic or bicyclic cycloalkyl, or a 3- to 12-membered monocyclic or bicyclic heterocycloalkyl group, where the heteroaryl, spiroheterocycloalkyl, heterocycloalkyl group or the —C$_{1-6}$alkyl-heterocycloalkyl groups have 1, 2, 3 or 4 heteroatoms independently selected from O, N or S, and the cycloalkyl, spirocycloalkyl, spiroheterocycloalkyl, heterocycloalkyl, group of R$^a$, R$^b$, R$^c$, and R$^d$ or the heterocycloalkyl group or the —C$_{1-6}$alkyl-heterocycloalkyl group may include a double bond and may contain a C=O group, and the spiroheterocycloalkyl, or heterocycloalkyl may include a S=O or SO$_2$;

the alkyl, aryl, heteroaryl, spirocycloalkyl, spiroheterocycloalkyl, cycloalkyl, or heterocycloalkyl group of R$^a$, R$^b$, R$^c$, and R$^d$ and the heterocycloalkyl group of the —C$_{1-6}$alkyl-heterocycloalkyl group of R$^a$, R$^b$, R$^c$, and R$^d$ can be unsubstituted or substituted with 1, 2, 3, or 4 R$^{14}$ substituents, wherein each R$^{14}$ is independently selected from H, —OH, —N=N=N, halo, —C$_{1-6}$alkyl, —C$_{1-6}$haloalkyl, —OC$_{1-6}$alkyl, —C$_{1-6}$alkyl-O—C$_{1-6}$alkyl, —C$_{1-6}$haloalkyl, —O-haloC$_{1-6}$alkyl, phenyl, tolyl, —C(=O)C$_{1-6}$alkyl, —C(=O)O—C$_{1-6}$alkyl, N(CH$_3$)$_2$ or —SO$_2$—N(CH$_3$)$_2$; and wherein n is independently in each instance an integer of 1, 2, 3 or 4.

In another aspect, the present invention comprises a compound of Formula I':

(I')

a stereoisomer thereof, a pharmaceutically acceptable salt thereof, or a pharmaceutically acceptable salt of the stereoisomer thereof,
wherein:
Z is C or N;
Q is O or S;
W is CR$^{WA}$R$^{WB}$ or C=O;
R$^{WA}$ and R$^{WB}$ are independently selected from H, C$_{1-3}$alkyl, halo, —OH, or —O—C$_{1-3}$alkyl;
b, represented by the symbol ===== is a single or double chemical bond which may be cis or trans;
R$^1$ is independently selected from H, halo, C$_{1-6}$alkylhalo, C$_{1-6}$alkyl, —(CH$_2$CH$_2$O)$_n$R$^a$, —SO$_2$R$^a$, —C(=O)R$^a$, —C(=O)OR$^a$, or —C(=O)NR$^a$R$^b$;
R$^2$ is selected from H, halo, —C$_{1-6}$haloalkyl, —C$_{1-6}$alkyl, —O—C$_{1-6}$alkyl, —C$_{2-6}$alkenyl, —C$_{1-6}$alkyl-O—C$_{1-6}$alkyl, —(CH$_2$CH$_2$O)$_n$R$^a$, —SO$_2$R$^a$, —C(=O)R$^a$, —C(=O)OR$^a$, —OC(=O)R$^a$, or —C(=O)NR$^a$R$^b$, R$^3$ is independently selected from H, —C$_{1-6}$alkylhalo, —C$_{1-6}$alkyl, —C$_{2-6}$ alkenyl, —(CH$_2$CH$_2$O)$_n$R$^a$, —C(=O)R$^a$, —C(=O)OR$^a$, or —C(=O)NR$^a$R$^b$;

each of R$^4$, R$^5$, R$^6$, R$^7$, and R$^8$ is independently selected from H, halo, —C$_{1-6}$haloalkyl, —C$_{1-6}$alkyl, —O—C$_{1-6}$alkyl, —C$_{2-6}$alkenyl, —C$_{1-6}$alkyl-O—C$_{1-6}$alkyl, —(CH$_2$CH$_2$O)$_n$R$^a$, —SO$_2$R$^a$, —C(=O)R$^a$, —C(=O)OR$^a$, —OC(=O)R$^a$, —C(=O)NR$^a$R$^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

alternatively R$^3$ and R$^4$ together with the atoms to which they are bonded may form a 5- to 12-membered ring, optionally containing a heteroatom selected from a N, O or S atom, in addition to the S and N atoms present in the ring, wherein the ring may optionally contain at least one double bond; and the ring may be substituted with 0, 1, 2, or 3 R$^{3A}$ substituents;

R$^{3A}$ is independently selected from H, halo, —OH, C$_{1-6}$haloalkyl, C$_{1-6}$alkyl, O—C$_{1-6}$alkyl, C$_{2-6}$alkenyl, —C$_{1-6}$alkyl-O—C$_{1-6}$alkyl, —(CH$_2$CH$_2$O)$_n$R$^a$, —SO$_2$R$^a$, —C(=O)R$^a$, —C(=O)OR$^a$, —OC(=O)R$^a$, —C(=O)NR$^a$R$^b$;

each of R$^{4A}$, R$^{5A}$, R$^{6A}$, R$^{7A}$, and R$^{8A}$ is independently selected from H, OH, halo, —C$_{1-6}$alkyl;

R$^{7A}$ and R$^{8A}$ are absent when b is a double chemical bond;

R$^9$ is independently selected from H, —C$_{1-6}$haloalkyl, —C$_{1-6}$alkyl, —C$_{2-6}$alkenyl, —C$_{2-6}$alkynyl, —(CH$_2$CH$_2$O)$_n$R$^a$, —C(=O)R$^a$, —C(=O)OR$^a$, —C(=O)NR$^a$R$^b$, —C$_{1-6}$alkyl-O—C$_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

R$^{9A}$ is independently selected from H, C$_{1-6}$haloalkyl, C$_{1-6}$alkyl, —C$_{2-6}$alkenyl, —C$_{2-6}$alkynyl, —(CH$_2$CH$_2$O)$_n$R$^a$, —SO$_2$R$^a$, —C(=O)R$^a$, —C(=O)OR$^a$, —C(=O)NR$^a$R$^b$, —NR$^a$R$^b$, —N=N=N, —C$_{1-6}$alkyl-O—C$_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein the aryl, heteroaryl, cycloalkyl, heterocycloalkyl, spirocycloalkyl and spiroheterocycloalkyl groups of the $R^{9A}$ substituent can be unsubstituted or substituted with 1, 2, 3 or 4 $R^{10}$ substituents independently selected from OH, halo, —$NR^cR^d$, —$C_{1-6}$alkyl, —$C_2$-$C_6$ alkenyl, —$C_2$-$C_6$alkynyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —C(=O)$NR^cR^d$, —C(=O)$R^c$, —OC(=O)$R^a$, —C(=O)$OR^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

alternatively $R^9$ and $R^{9A}$ together with Q, W, and the C to which W and Q are bonded, may form a 3- to 12-membered monocyclic or bicyclic ring, optionally containing a heteroatom in addition to Q that is selected from N, O or S, wherein the ring may contain a double bond, wherein the ring may optionally include a C=O group, and further wherein the ring optionally may be substituted by 1, 2, or 3 $R^{11}$ substituents;

$R^{11}$ is independently selected from OH, halo, —$NR^cR^d$, —$C_{1-6}$alkyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —C(=O)$NR^cR^d$, —C(=O)$R^c$, —OC(=O)$R^a$, —C(=O)$OR^c$, a 6- to 12-membered aryl or heteroaryl, a 6- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl group have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the —$C_{1-6}$alkyl of any of the $R^1$, $R^2$, $R^3$, $R^4$, $R^5$, $R^6$, $R^7$, $R^8$, $R^9$, $R^{10}$, $R^{11}$, $R^{4A}$, $R^{5A}$, $R^{6A}$, $R^{7A}$, $R^{8A}$, and $R^{9A}$ substituents is unsubstituted or substituted by 1, 2 or 3 $R^{12}$ substituents independently selected from OH, —$OC_{1-6}$alkyl, —$C_{1-6}$alkyl-O—$C_{1-6}$alkyl, halo, —O-halo$C_{1-6}$alkyl, —CN, —$NR^aR^b$, —$(NR^aR^bR^c)_n$, —$SO_2R^a$, —$(CH_2CH_2O)_nCH_3$, (=O), —C(=O), —C(=O)$R^a$, —OC(=O)$R^a$, —C(=O)$OR^a$, —C(=O)$NR^aR^b$, —O—$SiR^aR^bR^c$, —O-(3- to 12-membered heterocycloakyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the aryl, heteroaryl, cycloalkyl, heterocycloalkyl, spirocycloalkyl and spiroheterocycloalkyl groups of any of the $R^2$, $R^4$, $R^5$, $R^6$, $R^7$, $R^8$, $R^9$, $R^{10}$, $R^{11}$ and $R^{12}$ substituents can be unsubstituted or substituted with 1, 2, 3 or 4 $R^{13}$ substituents independently selected from OH, halo, —$C_{1-6}$alkyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —$NR^cR^d$, —CN, —C(=O)$NR^cR^d$, —C(=O)$R^c$, —OC(=O)$R^a$, —C(=O)$OR^c$, —$B(OH)_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein each $R^a$, $R^b$, $R^c$, and $R^d$ is independently H, OH, —$C_{1-6}$alkyl, —$C_{1-6}$alkenyl, —$C_{2-6}$alkynyl, —$C_{1-6}$alkyl-$NR^{14}R^{14}$, $NR^{14}R^{14}$, —$SO_2R^{14}$, —$(CH_2CH_2O)_nCH_3$, (=O), —C(=O)$R^{14}$, —OC(=O)$R^{14}$, —C(=O)$OR^{14}$, —C(=O)$NR^{14}R^{14}$, $C_{1-6}$haloalkyl, —O-halo$C_{1-6}$alkyl, —$C_{1-6}$alkyl-O—$C_{1-6}$alkyl, —$C_{1-6}$alkyl-OH, benzyl, phenyl, a —$C_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and r the heterocycloalkyl group of the —$C_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —$C_{1-6}$alkyl-heterocycloalkyl group may include a C=O group, and further wherein the spiroheterocycloalkyl and heterocycloalkyl groups may include a S=O or $SO_2$;

the alkyl, aryl, heteroaryl, spirocycloalkyl, spiroheterocycloalkyl, cycloalkyl, heterocycloalkyl and the heterocycloalkyl groups of the —$C_{1-6}$alkyl-heterocycloalkyl groups of $R^a$, $R^b$, $R^c$, and $R^d$ can be unsubstituted or substituted with 1, 2, 3, or 4 $R^{14}$ substituents independently selected from H, OH, —N=N=N, halo, —$C_{1-6}$alkyl, —$OC_{1-6}$alkyl, $C_{1-6}$haloalkyl, —O-halo$C_{1-6}$alkyl, phenyl, tolyl, —C(O)$C_{1-6}$alkyl, —C(O)$OCH_3$, $SO_2$-phenyl, or —$SO_2$—$N(CH_3)_2$; and n is independently, in each instance, an integer of 1, 2, 3 or 4.

In another aspect, the compound of Formula I' has Formula II'a:

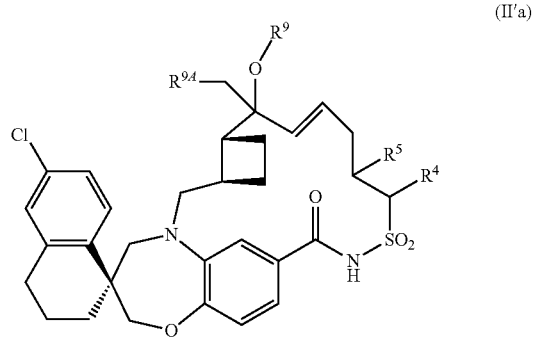

(II'a)

or the stereoisomer thereof, the pharmaceutically acceptable salt thereof, or the pharmaceutically acceptable salt of the stereoisomer thereof.

Another aspect of the present invention provides a pharmaceutical composition that includes the compound of any of the embodiments or the pharmaceutically acceptable salt thereof, and a pharmaceutically acceptable carrier or diluent.

Another aspect of the present invention provides a method of treating cancer. Such methods include: administering to a patient in need thereof a therapeutically effective amount of the compound of any of the embodiments or a pharmaceutically acceptable salt thereof. In some such methods, the cancer is a hematologic malignancy. In some such methods, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In some other such methods, the cancer is multiple myeloma. In some other such methods, the cancer is acute myelogenous leukemia. In some other such methods, the cancer is non-Hodgkin's lymphoma. In another aspect, the method further includes administering to a patient in need thereof a therapeutically effective amount of an additional pharmaceutically active compound. For example, in some such methods the additional pharmaceutically active compound is carfilzomib. In others, the additional pharmaceutically active compound is venetoclax. In still other such methods, the additional pharmaceutically active compound is cytarabine.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the Claims.

DETAILED DESCRIPTION

Figure 1:
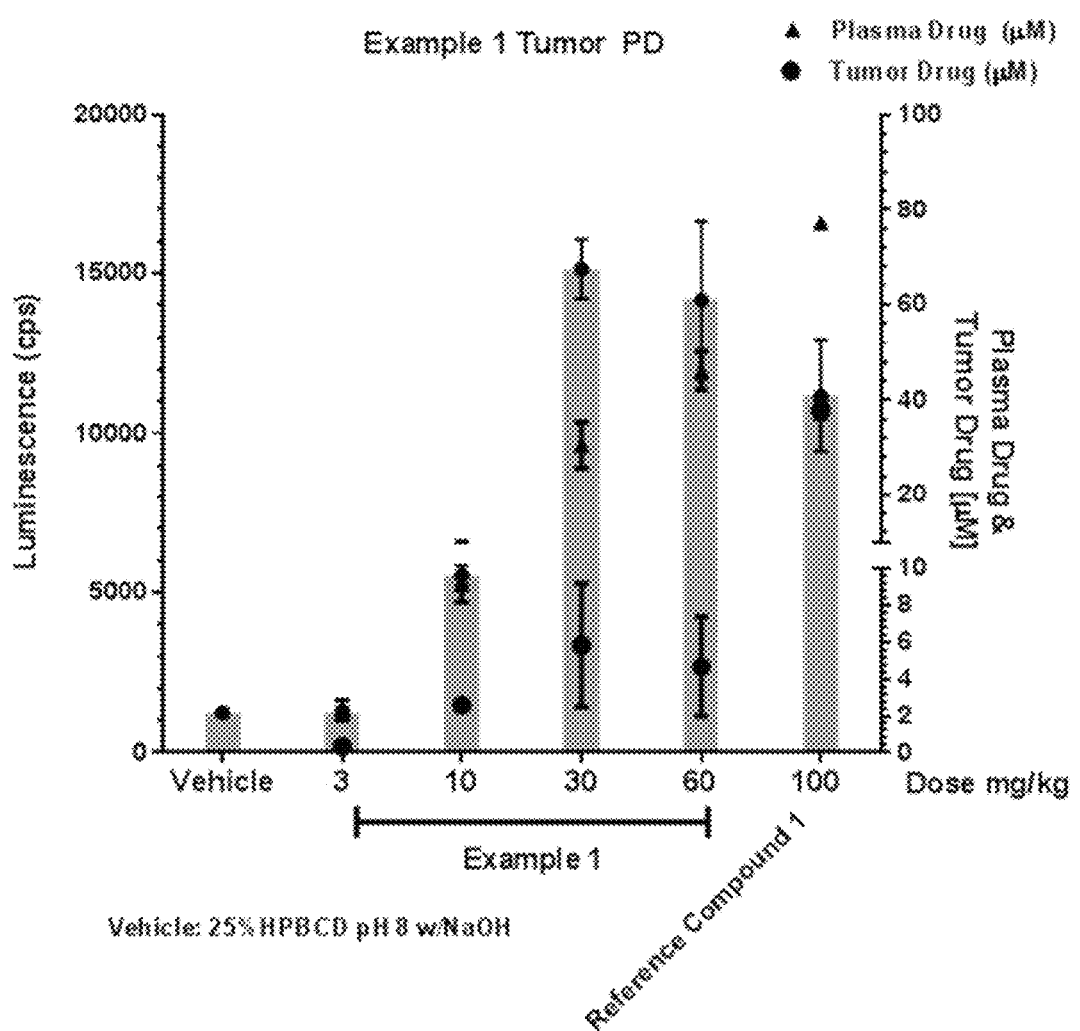
FIG. 1 demonstrates the superior in vivo efficacy of Example 1 relative to Reference Compound 1 in a tumor PD model. Both compounds were dosed orally to female athymic nude mice inoculated with OPM-2 Luc cells.

The symbol "—" represents a covalent bond and can also be used in a radical group to indicate the point of attachment to another group. In chemical structures, the symbol — is commonly used to represent a methyl group in a molecule.

As used herein, chemical structures which contain one or more stereocenters depicted with dashed and bold bonds (i.e., ⋯⋯ and ▬) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$ alkyl.

The term "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "cycloalkyl" means a cyclic, nonaromatic hydrocarbon. Representative examples of cycloalkyl groups include cyclopropyl, cyclobutyl, cyclopentyl, cyclohexyl and cycloheptyl. A cycloalkyl group can contain one or more double bonds. Representative examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "excipient", as used herein, means any pharmaceutically acceptable additive, carrier, diluent, adjuvant or other ingredient, other than the active pharmaceutical ingredient (API), which is typically included for formulation and/or administration to a patient. Handbook of Pharmaceutical Excipients, 5$^{th}$ Edition, R. C. Rowe, P. J. Sheskey, and S. C. Owen, editors, Pharmaceutical Press, 2005, Hardback, 928, 0853696187.

For the terms "for example" and "such as" and grammatical equivalences thereof, the phrase "and without limitation" is understood to follow unless explicitly stated otherwise.

The term "halogen" or "halo" means F, Cl, Br or I.

The term "patient" means subjects including animals, such as dogs, cats, cows, horses, sheep and humans. Particular patients are mammals. The term patient includes males and females.

The term "patient in need" means a patient having, or at risk of having, one or more diseases or conditions where the Mcl-1 protein is involved, such as cancers. Identifying a patient in need can be in the judgment of a subject or a health care professional and can be subjective (e.g., opinion) or objective (e.g., measurable by a test or diagnostic method).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The term "pharmaceutically acceptable" is employed herein to refer to those ligands, materials, compositions, and/or dosage forms which are, within the scope of sound medical judgment, suitable for administration to a patient, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain Claims, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19). The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

The term "therapeutically effective amount" means an amount of a compound that ameliorates, attenuates or eliminates one or more symptom of a particular disease or condition, or prevents or delays the onset of one of more symptom of a particular disease or condition. The terms "treating", "treat" or "treatment" and the like include preventative (e.g., prophylactic) and palliative treatment.

Embodiments A

The embodiments listed below are presented in numbered form for convenience and for ease and clarity of reference in referring back to multiple embodiments.

In a first embodiment, the present invention comprises a compound of Formula I':

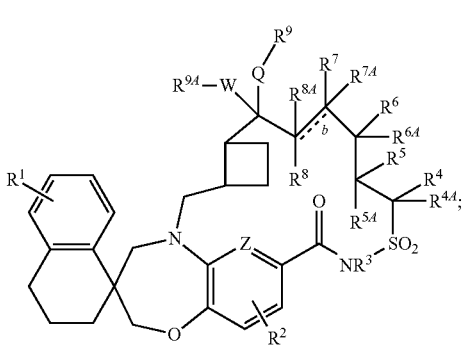

(I')

a stereoisomer thereof, a pharmaceutically acceptable salt thereof, or a pharmaceutically acceptable salt of the stereoisomer thereof,
wherein:
Z is C or N;
Q is O or S;
W is $CR^{WA}R^{WB}$ or C=O;
$R^{WA}$ and $R^{WB}$ are independently selected from H, $C_{1-3}$alkyl, halo, —OH, or —O—$C_{1-3}$alkyl;
b, represented by the symbol ===== is a single or double chemical bond which may be cis or trans;
$R^1$ is independently selected from H, halo, $C_{1-6}$alkylhalo, $C_{1-6}$alkyl, —$(CH_2CH_2O)_nR^a$, —$SO_2R^a$, —C(=O)$R^a$, —C(=O)O$R^a$, or —C(=O)N$R^aR^b$;
$R^2$ is selected from H, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, or —C(=O)N$R^aR^b$;
$R^3$ is independently selected from H, —$C_{1-6}$alkylhalo, —$C_{1-6}$alkyl, —$C_{2-6}$alkenyl, —$(CH_2CH_2O)_nR^a$, —C(=O)$R^a$, —C(=O)O$R^a$, or —C(=O)N$R^aR^b$;
each of $R^4$, $R^5$, $R^6$, $R^7$, and $R^8$ is independently selected from H, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, —C(=O)N$R^aR^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
alternatively $R^3$ and $R^4$ together with the atoms to which they are bonded may form a 5- to 12-membered ring, optionally containing a heteroatom selected from a N, O or S atom, in addition to the S and N atoms present in the ring, wherein the ring may optionally contain at least one double bond; and the ring may be substituted with 0, 1, 2, or 3 $R^{3A}$ substituents;
$R^{3A}$ is independently selected from H, halo, —OH, $C_{1-6}$haloalkyl, $C_{1-6}$alkyl, O—$C_{1-6}$alkyl, $C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, —C(=O)N$R^aR^b$;

each of $R^{4A}$, $R^{5A}$, $R^{6A}$, $R^{7A}$, and $R^{8A}$ is independently selected from H, OH, halo, —$C_{1-6}$alkyl;
$R^{7A}$ and $R^{8A}$ are absent when b is a double chemical bond;
$R^9$ is independently selected from H, —$C_{1-6}$haloalkyl, —$C_{1-6}$alkyl, —$C_{2-6}$alkenyl, —$C_{2-6}$alkynyl, —$(CH_2CH_2O)_nR^a$, —C(=O)$R^a$, —C(=O)O$R^a$, —C(=O)N$R^aR^b$, —$C_{1-6}$alkyl-O—$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
$R^{9A}$ is independently selected from H, $C_{1-6}$haloalkyl, $C_{1-6}$alkyl, —$C_{2-6}$alkenyl, —$C_{2-6}$alkynyl, —$(CH_2CH_2O)_nR^a$, —$SO_2R^a$, —C(=O)$R^a$, —C(=O)O$R^a$, —C(=O)N$R^aR^b$, —N$R^aR^b$, —N=N=N, —$C_{1-6}$alkyl-O—$C_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
wherein the aryl, heteroaryl, cycloalkyl, heterocycloalkyl, spirocycloalkyl and spiroheterocycloalkyl groups of the $R^{9A}$ substituent can be unsubstituted or substituted with 1, 2, 3 or 4 $R^{10}$ substituents independently selected from OH, halo, —N$R^cR^d$, —$C_{1-6}$alkyl, —$C_2$-$C_6$ alkenyl, —$C_2$-$C_6$alkynyl, —O$C_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —C(=O)N$R^cR^d$, —C(=O)$R^c$, —OC(=O)$R^a$, —C(=O)O$R^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
alternatively $R^9$ and $R^{9A}$ together with Q, W, and the C to which W and Q are bonded, may form a 3- to 12-membered monocyclic or bicyclic ring, optionally containing a heteroatom in addition to Q that is selected from N, O or S, wherein the ring may contain a double bond, wherein the ring may optionally include a C=O group, and further wherein the ring optionally may be substituted by 1, 2, or 3 $R^{11}$ substituents;
$R^{11}$ is independently selected from OH, halo, —N$R^cR^d$, —$C_{1-6}$alkyl, —O$C_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —C(=O)N$R^cR^d$, —C(=O)$R^c$, —OC(=O)$R^a$, —C(=O)O$R^c$, a 6- to 12-membered aryl or heteroaryl, a 6- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl group have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein the —C$_{1-6}$alkyl of any of the R$^1$, R$^2$, R$^3$, R$^4$, R$^5$, R$^6$, R$^7$, R$^8$, R$^9$, R$^{10}$, R$^{11}$, R$^{4A}$, R$^{5A}$, R$^{6A}$, R$^{7A}$, R$^{8A}$, and R$^{9A}$ substituents is unsubstituted or substituted by 1, 2 or 3 R$^{12}$ substituents independently selected from OH, —OC$_{1-6}$alkyl, —C$_{1-6}$alkyl-O—C$_{1-6}$alkyl, halo, —O-haloC$_{1-6}$alkyl, —CN, —NR$^a$R$^b$, —(NR$^a$R$^b$R$^c$)$_n$, —SO$_2$R$^a$, —(CH$_2$CH$_2$O)$_n$CH$_3$, (=O), —C(=O), —C(=O)R$^a$, —OC(=O)R$^a$, —C(=O)OR$^a$, —C(=O)NR$^a$R$^b$, —O—SiR$^a$R$^b$R$^c$, —O-(3- to 12-membered heterocycloakyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein the aryl, heteroaryl, cycloalkyl, heterocycloalkyl, spirocycloalkyl and spiroheterocycloalkyl groups of any of the R$^2$, R$^4$, R$^5$, R$^6$, R$^7$, R$^8$, R$^9$, R$^{10}$, R$^{11}$ and R$^{12}$ substituents can be unsubstituted or substituted with 1, 2, 3 or 4 R$^{13}$ substituents independently selected from OH, halo, —C$_{1-6}$alkyl, —OC$_{1-6}$alkyl, —C$_{1-6}$alkyl-OH, —C$_{1-6}$alkyl-O—C$_{1-6}$alkyl, C$_{1-6}$haloalkyl, —O-haloC$_{1-6}$alkyl, —SO$_2$R$^c$, —NR$^c$R$^d$, —CN, —C(=O)NR$^c$R$^d$, —C(=O)R$^c$, —OC(=O)R$^a$, —C(=O)OR$^c$, —B(OH)$_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein each R$^a$, R$^b$, R$^c$, and R$^d$ is independently H, OH, —C$_{1-6}$alkyl, —C$_{1-6}$alkenyl, —C$_{2-6}$alkynyl, —C$_{1-6}$alkyl-NR$^{14}$R$^{14}$, NR$^{14}$R$^{14}$, —SO$_2$R$^{14}$, —(CH$_2$CH$_2$O)$_n$CH$_3$, (=O), —C(=O)R$^{14}$, —OC(=O)R$^{14}$, —C(=O)OR$^{14}$, —C(=O) NR$^{14}$R$^{14}$, C$_{1-6}$haloalkyl, —O-haloC$_{1-6}$alkyl, —C$_{1-6}$alkyl-O—C$_{1-6}$alkyl, —C$_{1-6}$alkyl-OH, benzyl, phenyl, a —C$_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and r the heterocycloalkyl group of the —C$_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —C$_{1-6}$alkyl-heterocycloalkyl group may include a C=O group, and further wherein the spiroheterocycloalkyl and heterocycloalkyl groups may include a S=O or SO$_2$;

the alkyl, aryl, heteroaryl, spirocycloalkyl, spiroheterocycloalkyl, cycloalkyl, heterocycloalkyl and the heterocycloalkyl groups of the —C$_{1-6}$alkyl-heterocycloalkyl groups of R$^a$, R$^b$, R$^c$, and R$^d$ can be unsubstituted or substituted with 1, 2, 3, or 4 R$^{14}$ substituents independently selected from H, OH, —N=N=N, halo, —C$_{1-6}$alkyl, —OC$_{1-6}$alkyl, C$_{1-6}$haloalkyl, —O-haloC$_{1-6}$alkyl, phenyl, tolyl, —C(O)C$_{1-6}$alkyl, —C(O)OCH$_3$, SO$_2$-phenyl, or —SO$_2$—N(CH$_3$)$_2$; and n is independently, in each instance, an integer of 1, 2, 3 or 4.

2. Another embodiment of the present invention comprises the compound of Embodiment 1, wherein the compound of Formula I' has the Formula I'a:

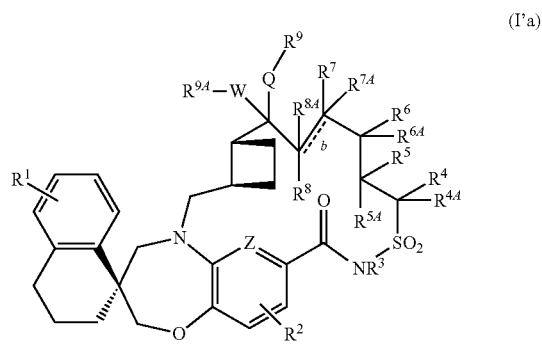

(I'a)

or the stereoisomer thereof, the pharmaceutically acceptable salt thereof, or the pharmaceutically acceptable salt of the stereoisomer thereof.

3. The compound of any one of Embodiments 1 or 2, or the stereoisomer thereof, the pharmaceutically acceptable salt thereof, or the pharmaceutically acceptable salt of the stereoisomer thereof, wherein b is a double bond.

4. The compound of any one of Embodiments 1 or 2, or the stereoisomer thereof, the pharmaceutically acceptable salt thereof, or the pharmaceutically acceptable salt of the stereoisomer thereof, wherein b is a single bond.

5. The compound of any one of Embodiments 1-4, or the stereoisomer thereof, the pharmaceutically acceptable salt thereof, or the pharmaceutically acceptable salt of the stereoisomer thereof, wherein Z is C.

6. The compound of any one of Embodiments 1-4, or the stereoisomer thereof, the pharmaceutically acceptable salt thereof, or the pharmaceutically acceptable salt of the stereoisomer thereof, wherein Z is N.

7. The compound of any one of Embodiments 1-6, or the stereoisomer thereof, the pharmaceutically acceptable salt thereof, or the pharmaceutically acceptable salt of the stereoisomer thereof, wherein Q is O.

8. The compound of any one of Embodiments 1-6, or the stereoisomer thereof, the pharmaceutically acceptable salt thereof, or the pharmaceutically acceptable salt of the stereoisomer thereof, wherein Q is S.

9. The compound of any one of Embodiments 1-8, or the stereoisomer thereof, the pharmaceutically acceptable salt thereof, or the pharmaceutically acceptable salt of the stereoisomer thereof, wherein W is C=O.

10. The compound of any one of Embodiments 1-8, or the stereoisomer thereof, the pharmaceutically acceptable salt thereof, or the pharmaceutically acceptable salt of the stereoisomer thereof, wherein W is $CR^{WA}R^{WB}$.

11. The compound of any one of Embodiments 1-8 and 10, or the stereoisomer thereof, the pharmaceutically acceptable salt thereof, or the pharmaceutically acceptable salt of the stereoisomer thereof, wherein $R^{WA}$ and $R^{WB}$ are both H.

12. The compound of any one of Embodiments 1-11, or the stereoisomer thereof, the pharmaceutically acceptable salt thereof, or the pharmaceutically acceptable salt of the stereoisomer thereof, wherein $R^1$ is halo.

13. The compound of any one of Embodiments 1-12, or the stereoisomer thereof, the pharmaceutically acceptable salt thereof, or the pharmaceutically acceptable salt of the stereoisomer thereof, wherein $R^1$ is Cl.

14. The compound of any one of Embodiments 1-13, or the stereoisomer thereof, the pharmaceutically acceptable salt thereof, or the pharmaceutically acceptable salt of the stereoisomer thereof, wherein $R^2$ is H.

15. The compound of any one of Embodiments 1-14, or the stereoisomer thereof, the pharmaceutically acceptable salt thereof, or the pharmaceutically acceptable salt of the stereoisomer thereof, wherein $R^3$ is H or —$C_{1-6}$ alkyl.

16. The compound of any one of Embodiments 1-15, or the stereoisomer thereof, the pharmaceutically acceptable salt thereof, or the pharmaceutically acceptable salt of the stereoisomer thereof, wherein $R^3$ is —$CH_3$.

17. The compound of any one of Embodiments 1-15, or the stereoisomer thereof, the pharmaceutically acceptable salt thereof, or the pharmaceutically acceptable salt of the stereoisomer thereof, wherein $R^3$ is H.

18. The compound of any one of Embodiments 1-17, or the stereoisomer thereof, the pharmaceutically acceptable salt thereof, or the pharmaceutically acceptable salt of the stereoisomer thereof, wherein $R^4$ is independently selected from H, —$C_{1-6}$alkyl, —$C_{1-6}$alkylhalo, —$C_{1-6}$alkyl-O—$C_{1-6}$alkyl, or —$(CH_2CH_2O)_nR^a$, wherein the —$C_{1-6}$alkyl is unsubstituted or substituted with —OH, (=O), phenyl, —O—$SiR^aR^bR^c$, —$NR^aR^b$, a 3- to 12-membered cycloalkyl, or a 3- to 12-membered monocyclic or bicyclic heterocycloalkyl having 1, 2, 3, or 4 heteroatoms independently selected from O, N or S.

19. The compound of any one of Embodiments 1-18, or the stereoisomer thereof, the pharmaceutically acceptable salt thereof, or the pharmaceutically acceptable salt of the stereoisomer thereof, wherein $R^4$ is H.

20. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl.

21. The compound of any one of Embodiments 1-18 or 20, or the stereoisomer thereof, the pharmaceutically acceptable salt thereof, or the pharmaceutically acceptable salt of the stereoisomer thereof, wherein $R^4$ is —$CH_3$.

22. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-O—$C_{1-6}$alkyl.

23. The compound of any one of Embodiments 1-18 or 22, or the stereoisomer thereof, the pharmaceutically acceptable salt thereof, or the pharmaceutically acceptable salt of the stereoisomer thereof, wherein $R^4$ is —$CH_2CH_2OCH_3$.

24. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-OH.

25. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl=O.

26. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-phenyl.

27. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-O—$SiR^aR^bR^c$.

28. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-$NR^aR^b$.

29. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-$C_3$-$C_6$cycloalkyl.

30. The compound of any one of Embodiments 1-18, or the stereoisomer thereof, the pharmaceutically acceptable salt thereof, or the pharmaceutically acceptable salt of the stereoisomer thereof, wherein $R^4$ is —$C_{1-6}$alkyl-$C_3$-$C_{10}$heterocycloalkyl having 1, 2, 3, or 4 heteroatoms independently selected from O, N or S.

31. The compound of any one of Embodiments 1-18, or the stereoisomer thereof, the pharmaceutically acceptable salt thereof, or the pharmaceutically acceptable salt of the stereoisomer thereof, wherein $R^4$ is

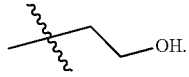

32. The compound of any one of Embodiments 1-18, or the stereoisomer thereof, the pharmaceutically acceptable salt thereof, or the pharmaceutically acceptable salt of the stereoisomer thereof, wherein $R^4$ is

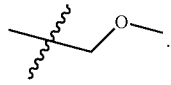

33. The compound of any one of Embodiments 1-18, or the stereoisomer thereof, the pharmaceutically acceptable salt thereof, or the pharmaceutically acceptable salt of the stereoisomer thereof, wherein $R^4$ is independently selected from —$CH_3$, —$CH_2CH_2OCH_3$,

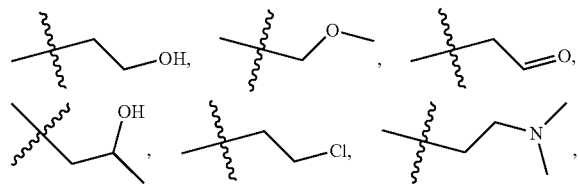

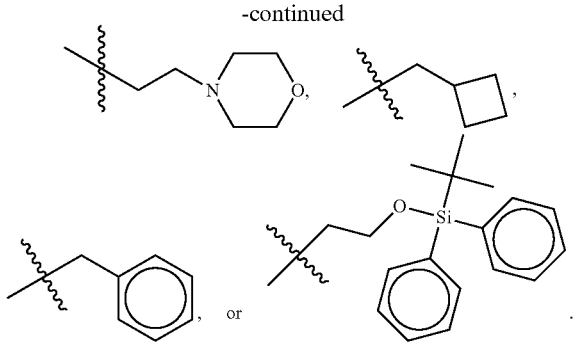

34. The compound of any one of Embodiments 1-14, or the stereoisomer thereof, the pharmaceutically acceptable salt thereof, or the pharmaceutically acceptable salt of the stereoisomer thereof, wherein $R^3$ and $R^4$, together with the atoms to which they are bonded, form a 5- to 12-membered ring, optionally containing a heteroatom selected from N, O or S in addition to the S and N atoms present in the ring, wherein the ring may optionally contain at least one double bond; and further wherein the ring is substituted with 0, 1, 2, or 3 $R^{3A}$ substituents.

35. The compound of any one of Embodiments 1-14 or 34, or the stereoisomer thereof, the pharmaceutically acceptable salt thereof, or the pharmaceutically acceptable salt of the stereoisomer thereof, wherein $R^3$ and $R^4$ together with the atoms to which they are attached form

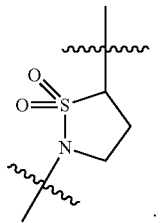 [SMILES: *C1CCN(*)S1(=O)=O]

36. The compound of any one of Embodiments 1-35, or the stereoisomer thereof, the pharmaceutically acceptable salt thereof, or the pharmaceutically acceptable salt of the stereoisomer thereof, wherein $R^5$ is H or —$C_{1-6}$ alkyl.

37. The compound of any one of Embodiments 1-36, or the stereoisomer thereof, the pharmaceutically acceptable salt thereof, or the pharmaceutically acceptable salt of the stereoisomer thereof, wherein $R^5$ is —$CH_3$.

38. The compound of any one of Embodiments 1-36, or the stereoisomer thereof, the pharmaceutically acceptable salt thereof, or the pharmaceutically acceptable salt of the stereoisomer thereof, wherein $R^5$ is H.

39. The compound of any one of Embodiments 1-38, or the stereoisomer thereof, the pharmaceutically acceptable salt thereof, or the pharmaceutically acceptable salt of the stereoisomer thereof, wherein $R^6$ is H or —$C_{1-6}$ alkyl.

40. The compound of any one of Embodiments 1-38, or the stereoisomer thereof, the pharmaceutically acceptable salt thereof, or the pharmaceutically acceptable salt of the stereoisomer thereof, wherein $R^6$ is —$CH_3$.

41. The compound of any one of Embodiments 1-38, or the stereoisomer thereof, the pharmaceutically acceptable salt thereof, or the pharmaceutically acceptable salt of the stereoisomer thereof, wherein $R^6$ is H.

42. The compound of any one of Embodiments 1-41, or the stereoisomer thereof, the pharmaceutically acceptable salt thereof, or the pharmaceutically acceptable salt of the stereoisomer thereof, wherein each of $R^{4A}$, $R^{5A}$, $R^{6A}$, $R^{7A}$ and $R^{8A}$ is independently selected from H, OH, halo, or —$C_{1-6}$alkyl.

43. The compound of Embodiment 42, or the stereoisomer thereof, the pharmaceutically acceptable salt thereof, or the pharmaceutically acceptable salt of the stereoisomer thereof, wherein each of $R^{4A}$, $R^{5A}$, $R^{6A}$, $R^{7A}$ and $R^{8A}$ is H.

44. The compound of any one of Embodiments 1, 2, or 4-43, or the stereoisomer thereof, the pharmaceutically acceptable salt thereof, or the pharmaceutically acceptable salt of the stereoisomer thereof, wherein $R^{7A}$ and $R^{8A}$ are both H.

45. The compound of any one of Embodiments 1-44, or the stereoisomer thereof, the pharmaceutically acceptable salt thereof, or the pharmaceutically acceptable salt of the stereoisomer thereof, wherein $R^7$ and $R^8$ are both H.

46. The compound of any one of Embodiments 1-45, or the stereoisomer thereof, the pharmaceutically acceptable salt thereof, or the pharmaceutically acceptable salt of the stereoisomer thereof, wherein $R^9$ is independently selected from H, —$C_{1-6}$alkyl, —$C_{2-6}$alkenyl, or —$C_{1-6}$alkyl-O—$C_{1-6}$ alkyl or —$C_{1-6}$haloalkyl.

47. The compound of any one of Embodiments 1-46, or the stereoisomer thereof, the pharmaceutically acceptable salt thereof, or the pharmaceutically acceptable salt of the stereoisomer thereof, wherein $R^9$ is H.

48. The compound of any one of Embodiments 1-46, or the stereoisomer thereof, the pharmaceutically acceptable salt thereof, or the pharmaceutically acceptable salt of the stereoisomer thereof, wherein $R^9$ is —$CH_3$.

49. The compound of any one of Embodiments 1-46, or the stereoisomer thereof, the pharmaceutically acceptable salt thereof, or the pharmaceutically acceptable salt of the stereoisomer thereof, wherein $R^9$ is —$CH_2CH_3$.

50. The compound of any one of Embodiments 1-46, or the stereoisomer thereof, the pharmaceutically acceptable salt thereof, or the pharmaceutically acceptable salt of the stereoisomer thereof, wherein $R^9$ is —$CH_2CH(CH_3)_2$.

51. The compound of any one of Embodiments 1-46, or the stereoisomer thereof, the pharmaceutically acceptable salt thereof, or the pharmaceutically acceptable salt of the stereoisomer thereof, wherein $R^9$ is —$CH_2CH_2OCH_3$.

52. The compound of any one of Embodiments 1-46, or the stereoisomer thereof, the pharmaceutically acceptable salt thereof, or the pharmaceutically acceptable salt of the stereoisomer thereof, wherein $R^9$ is —$CF_3$.

53. The compound of any one of Embodiments 1-52, or the stereoisomer thereof, the pharmaceutically acceptable salt thereof, or the pharmaceutically acceptable salt of the stereoisomer thereof, wherein $R^{9A}$ is selected from H, $C_{1-6}$haloalkyl, $C_{1-6}$alkyl, —$C_{2-6}$alkenyl-$(CH_2CH_2O)_nR^a$, —$SO_2R^a$, —$C(=O)R^a$, —$C(=O)OR^a$, —$C(=O)NR^aR^b$, —$NR^aR^b$, —N=N=N, —$C_{1-6}$alkyl-O—$C_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$.

54. The compound of any one of Embodiments 1-53, or the stereoisomer thereof, the pharmaceutically acceptable salt thereof, or the pharmaceutically acceptable salt of the stereoisomer thereof, wherein R$^{9A}$ is —C$_{1-6}$alkyl.

55. The compound of any one of Embodiments 1-53, or the stereoisomer thereof, the pharmaceutically acceptable salt thereof, or the pharmaceutically acceptable salt of the stereoisomer thereof, wherein R$^{9A}$ is —C(=O)R$^a$.

56. The compound of any one of Embodiments 1-53, or the stereoisomer thereof, the pharmaceutically acceptable salt thereof, or the pharmaceutically acceptable salt of the stereoisomer thereof, wherein R$^{9A}$ is a 3- to 12-membered monocyclic or bicyclic heterocycloalkyl group, wherein the heterocycloalkyl group has 1, 2, 3 or 4 heteroatoms independently selected from O, N or S.

57. The compound of any one of Embodiments 1-53, or the stereoisomer thereof, the pharmaceutically acceptable salt thereof, or the pharmaceutically acceptable salt of the stereoisomer thereof, wherein R$^{9A}$ is a 3- to 12-membered monocyclic heterocycloalkyl group, wherein the heterocycloalkyl group has 1, 2, 3 or 4 heteroatoms independently selected from O or N.

58. The compound of any one of Embodiments 1-53, 56 or 57, or the stereoisomer thereof, the pharmaceutically acceptable salt thereof, or the pharmaceutically acceptable salt of the stereoisomer thereof, wherein the 3- to 12-membered monocyclic heterocycloalkyl R$^{9A}$ group can be unsubstituted or substituted with 1, 2, 3 or 4 R$^{10}$ substituents independently selected from OH, halo, —NR$^c$R$^d$, —C$_{1-6}$alkyl, —C$_2$-C$_6$ alkenyl, —C$_2$-C$_6$alkynyl, —OC$_{1-6}$alkyl, —C$_{1-6}$alkyl-OH, —C$_{1-6}$alkyl-O—C$_{1-6}$alkyl, C$_{1-6}$haloalkyl, —O-haloC$_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, or heterocycloalkyl group have from 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$.

59. The compound of any one of Embodiments 1-58, or the stereoisomer thereof, the pharmaceutically acceptable salt thereof, or the pharmaceutically acceptable salt of the stereoisomer thereof, wherein the 1, 2, 3 or 4 R$^{10}$ substituents are independently selected from —C$_{1-6}$alkyl or a 3- to 12-membered monocyclic heterocycloalkyl group, wherein the heterocycloalkyl group has 1, 2, 3 or 4 heteroatoms independently selected from O, N or S.

60. The compound of any one of Embodiments 1-59, or the stereoisomer thereof, the pharmaceutically acceptable salt thereof, or the pharmaceutically acceptable salt of the stereoisomer thereof, wherein R$^{10}$ is —C$_{1-6}$alkyl.

61. The compound of any one of Embodiments 1-59, or the stereoisomer thereof, the pharmaceutically acceptable salt thereof, or the pharmaceutically acceptable salt of the stereoisomer thereof, wherein R$^{10}$ is a 3- to 12-membered monocyclic heterocycloalkyl group, wherein the heterocycloalkyl group has 1, 2, 3 or 4 heteroatoms independently selected from O, N or S.

62. The compound of any one of Embodiments 1-53, or the stereoisomer thereof, the pharmaceutically acceptable salt thereof, or the pharmaceutically acceptable salt of the stereoisomer thereof, wherein R$^{9A}$ is a 5- to 12-membered bicyclic heterocycloalkyl group, wherein the heterocycloalkyl group has 1, 2, 3 or 4 heteroatoms independently selected from O or N.

63. The compound of any one of Embodiments 1-52, or the stereoisomer thereof, the pharmaceutically acceptable salt thereof, or the pharmaceutically acceptable salt of the stereoisomer thereof, wherein R$^{9A}$ is independently selected from —N=N=N,

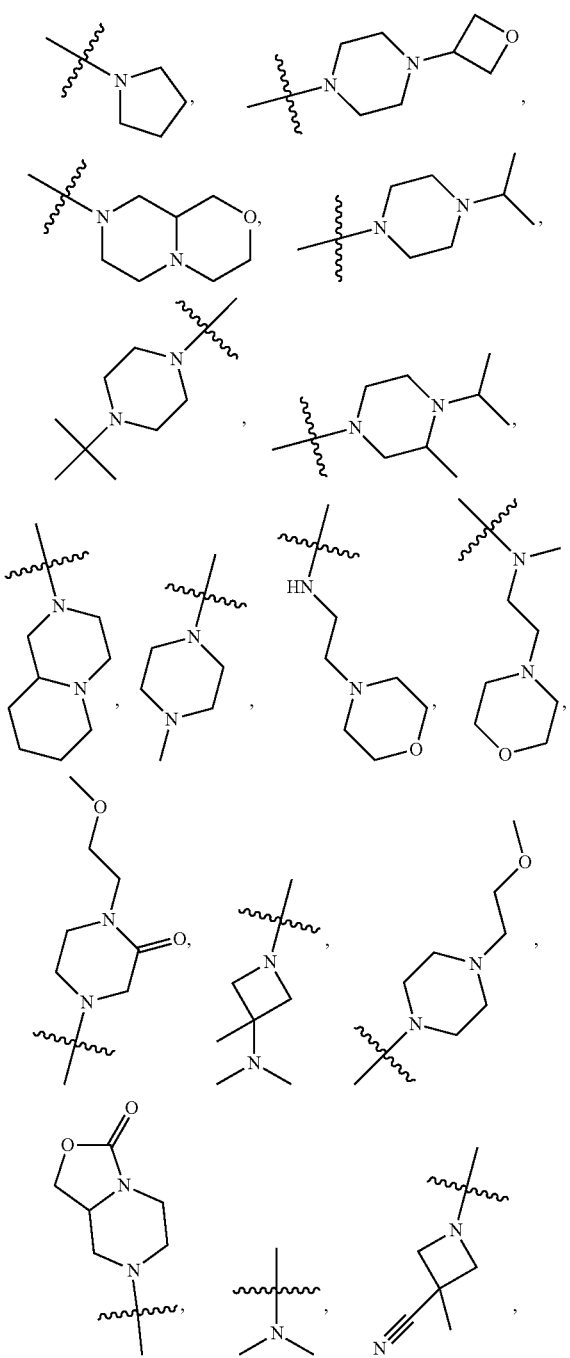

-continued
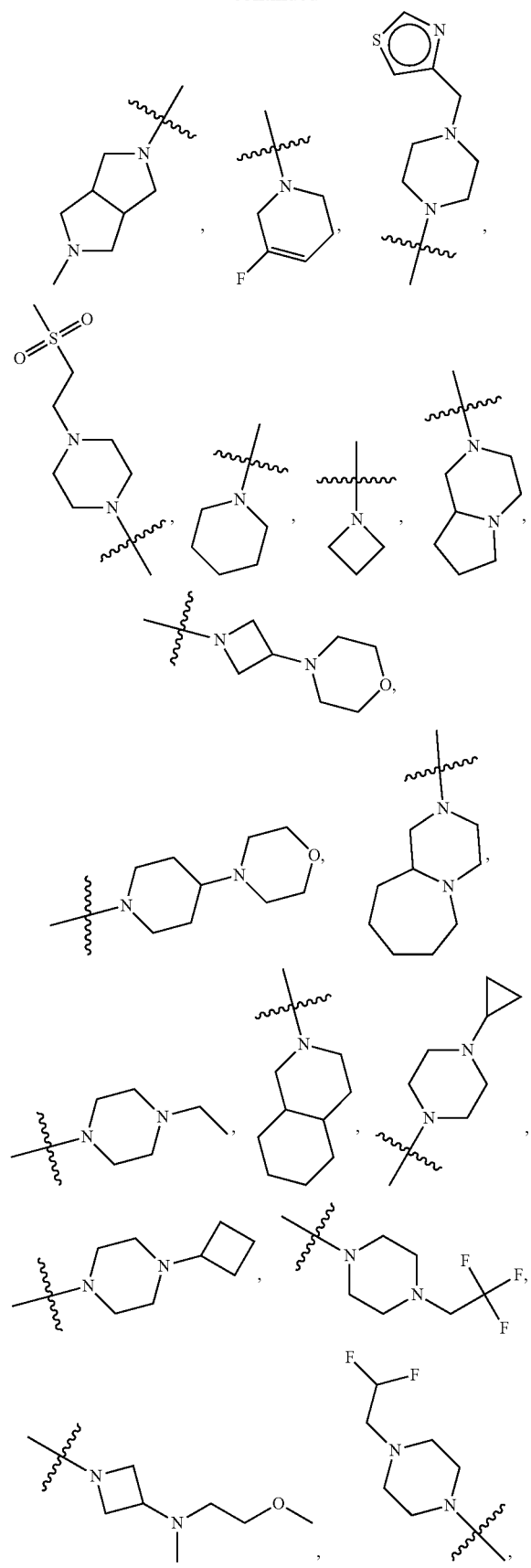
-continued
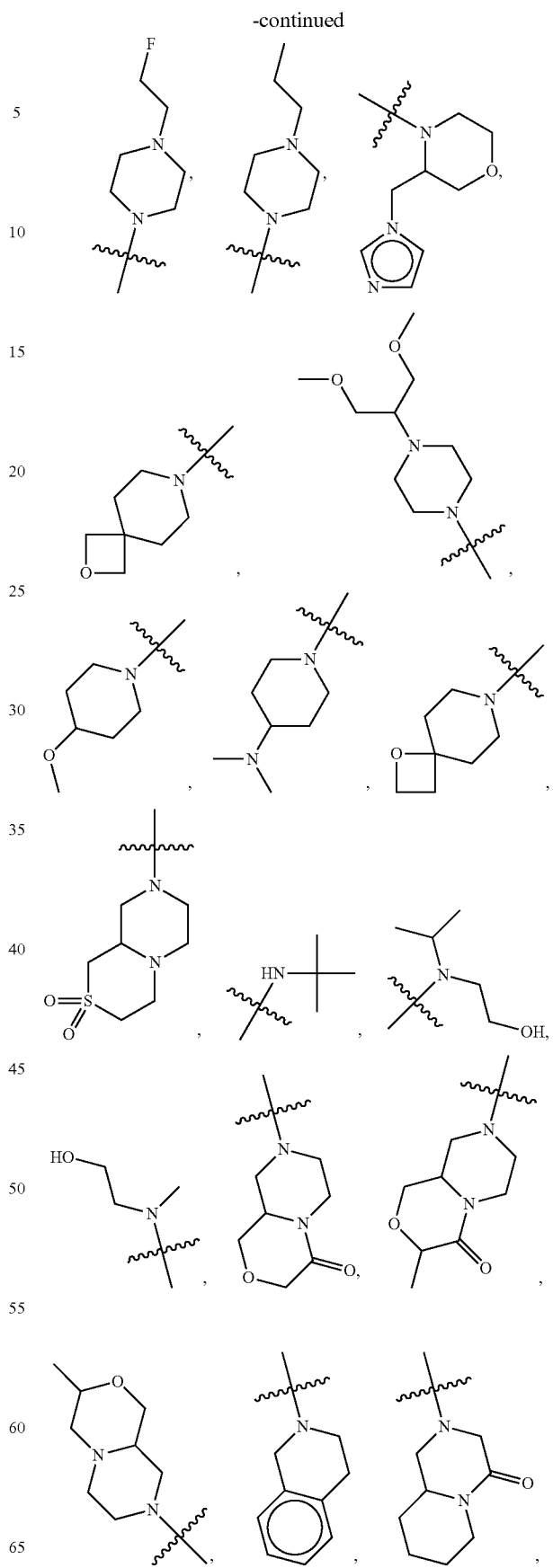

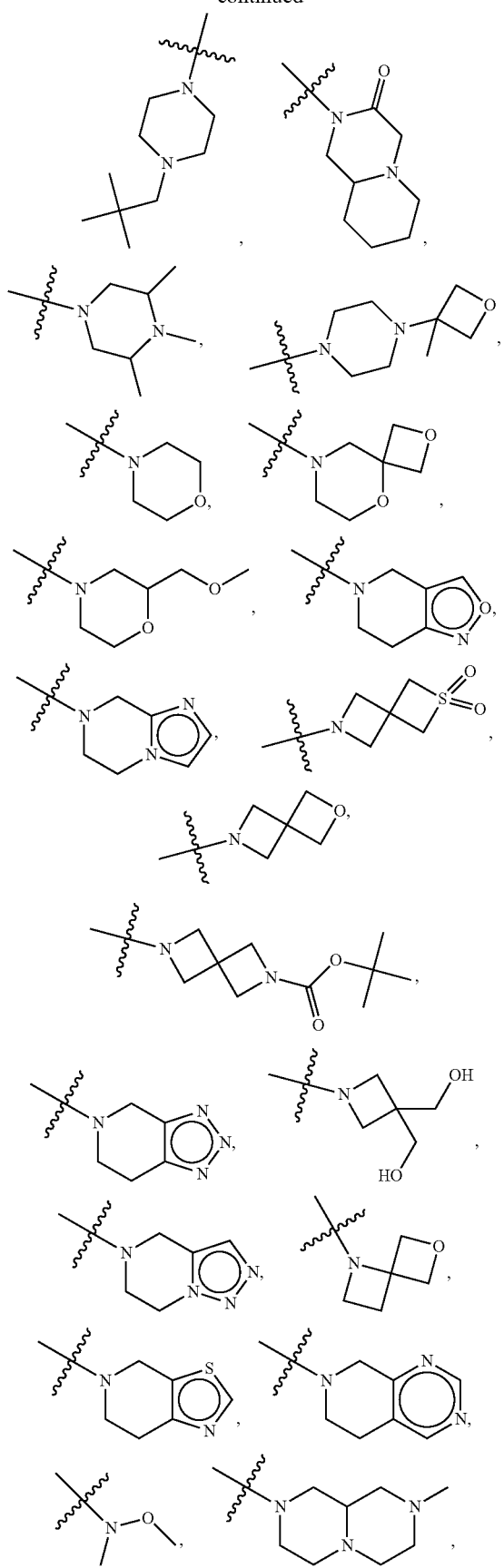
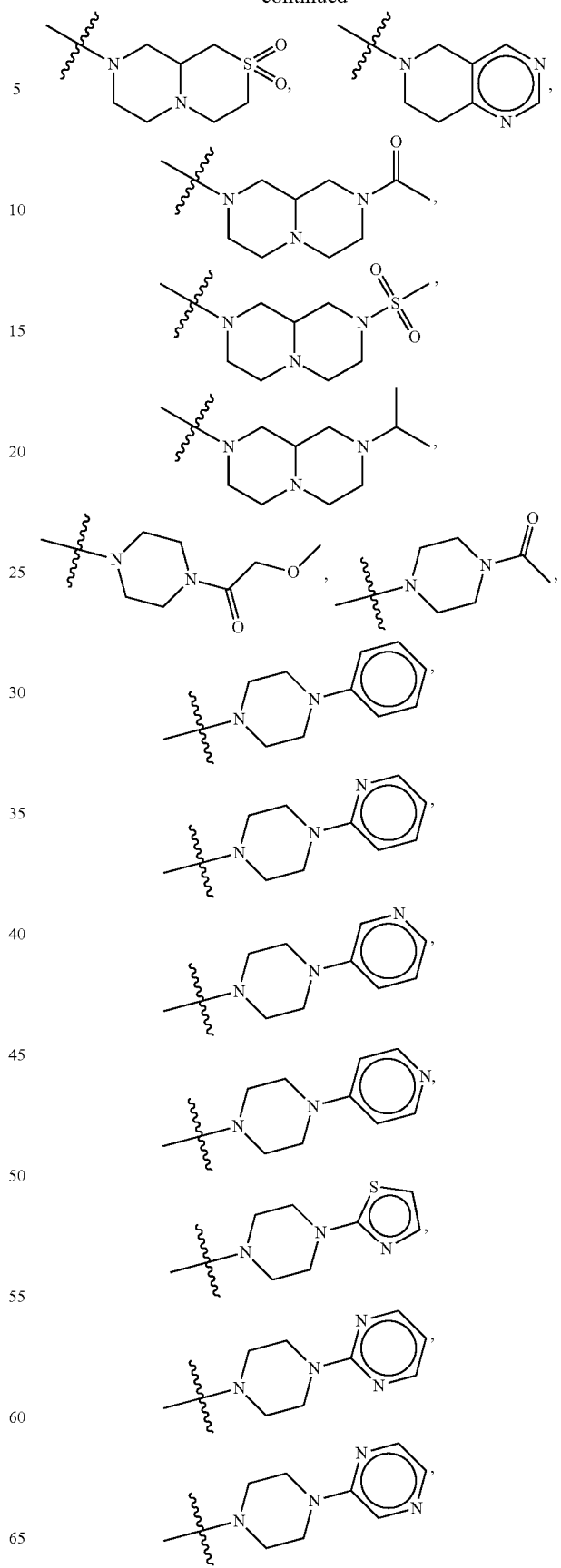

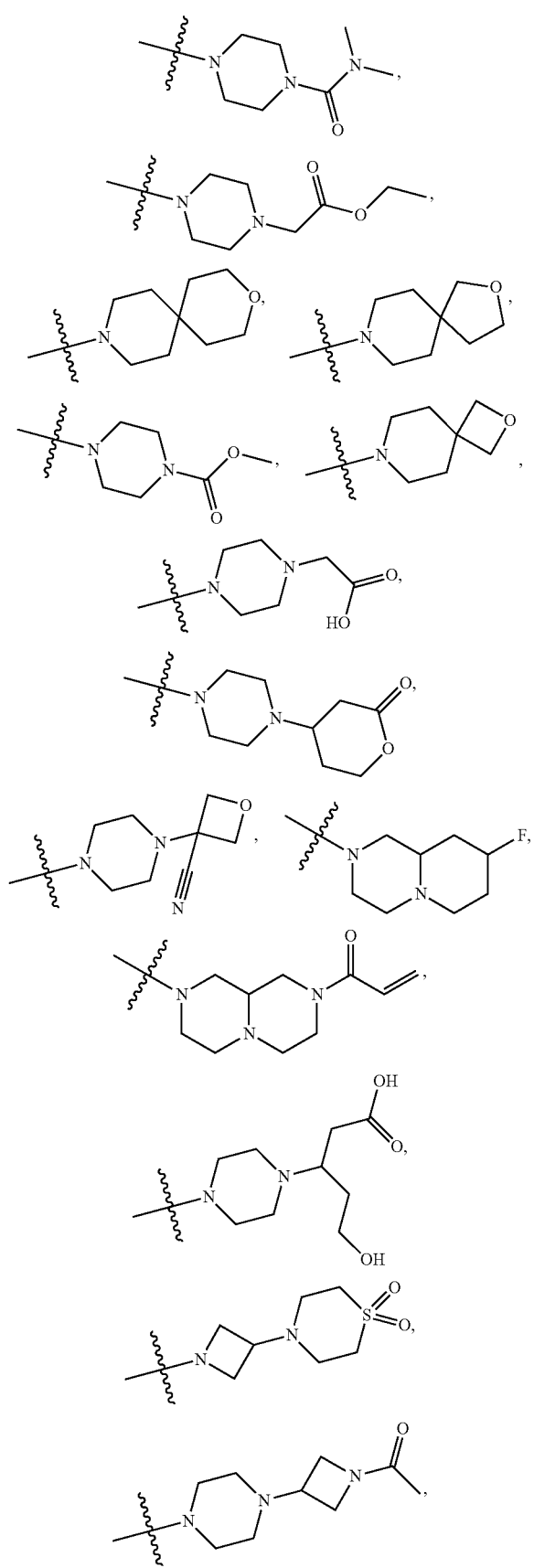
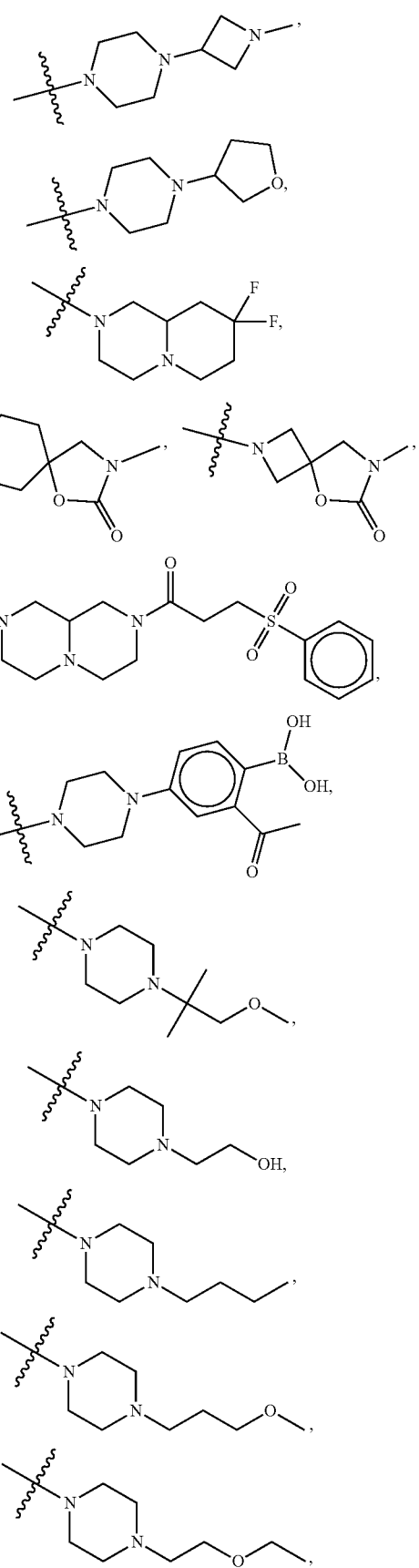

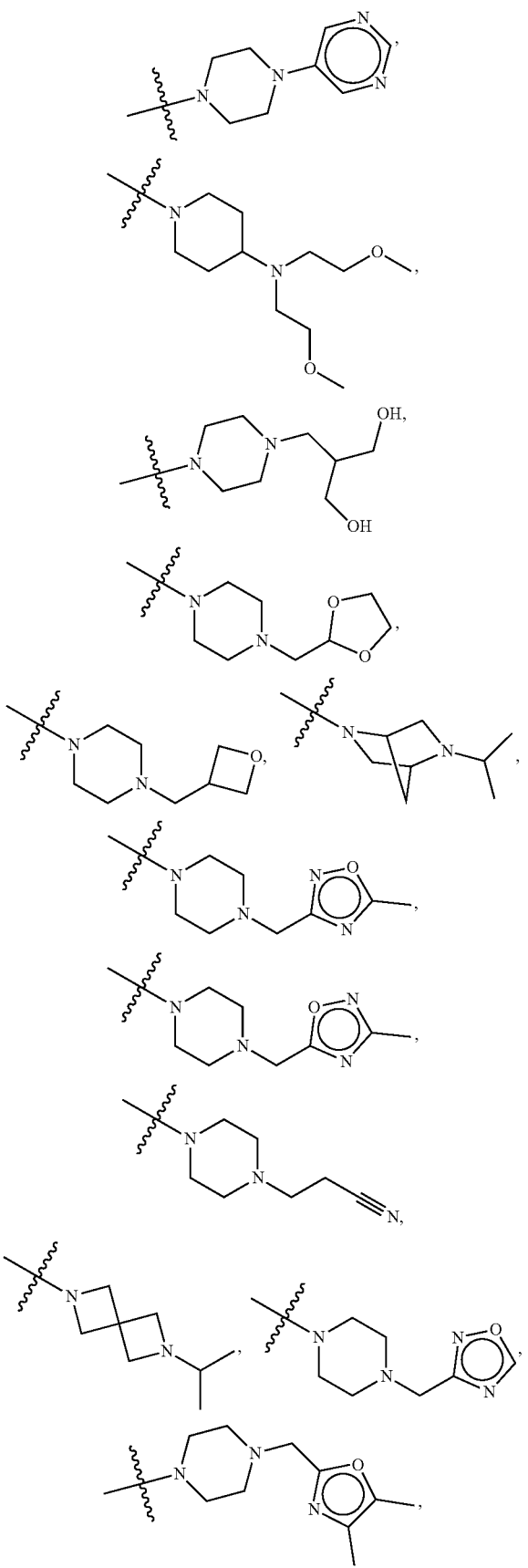
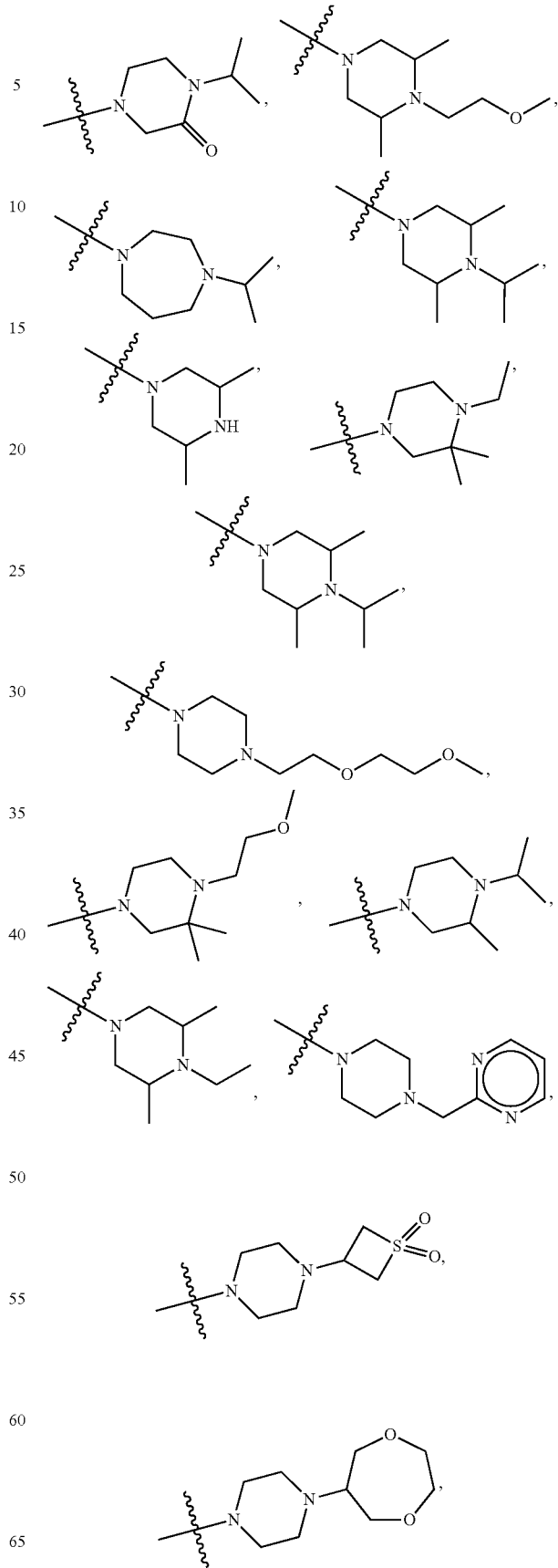

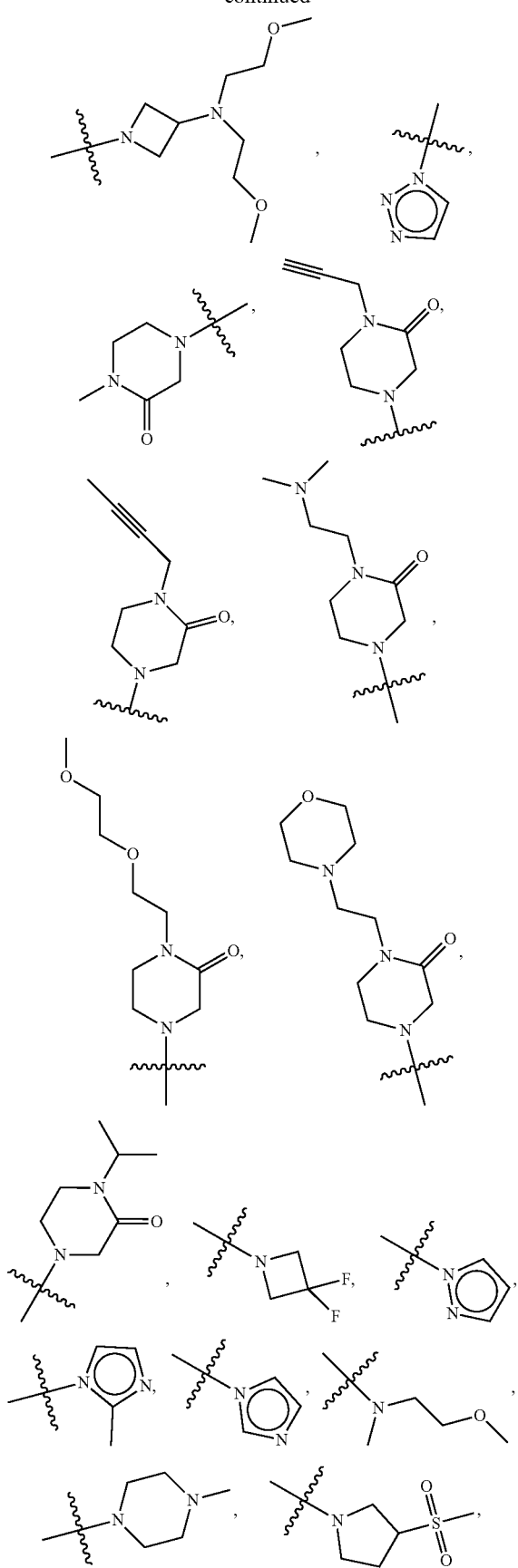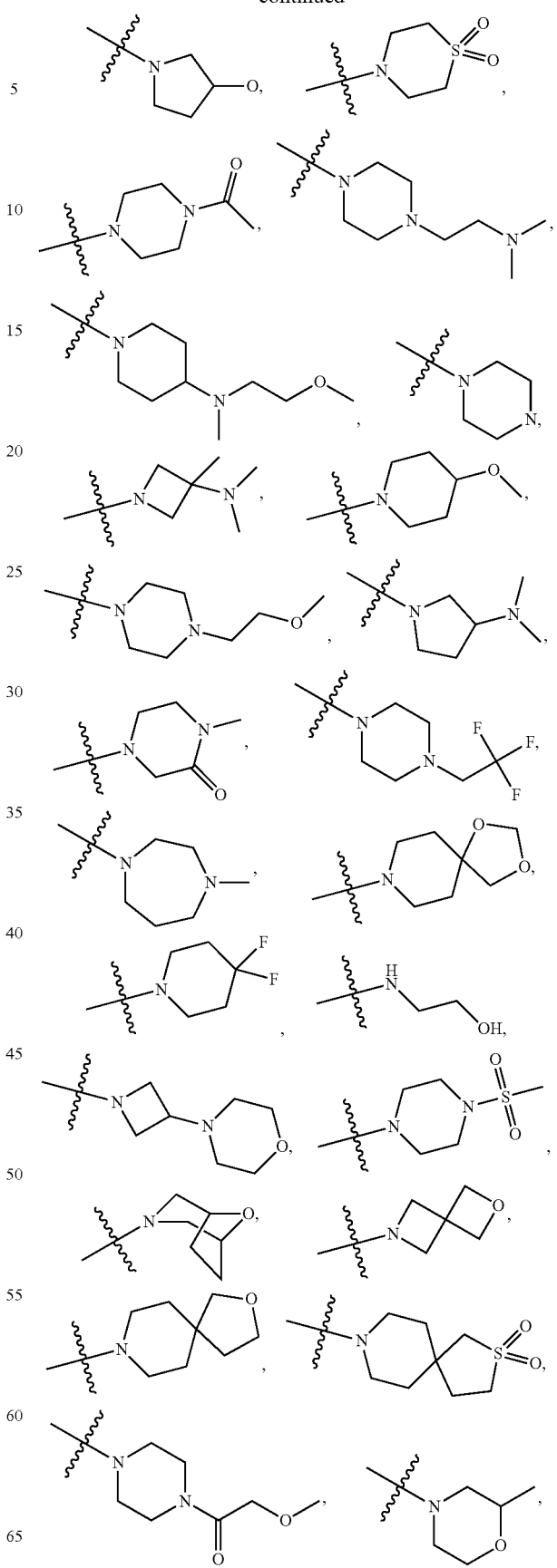

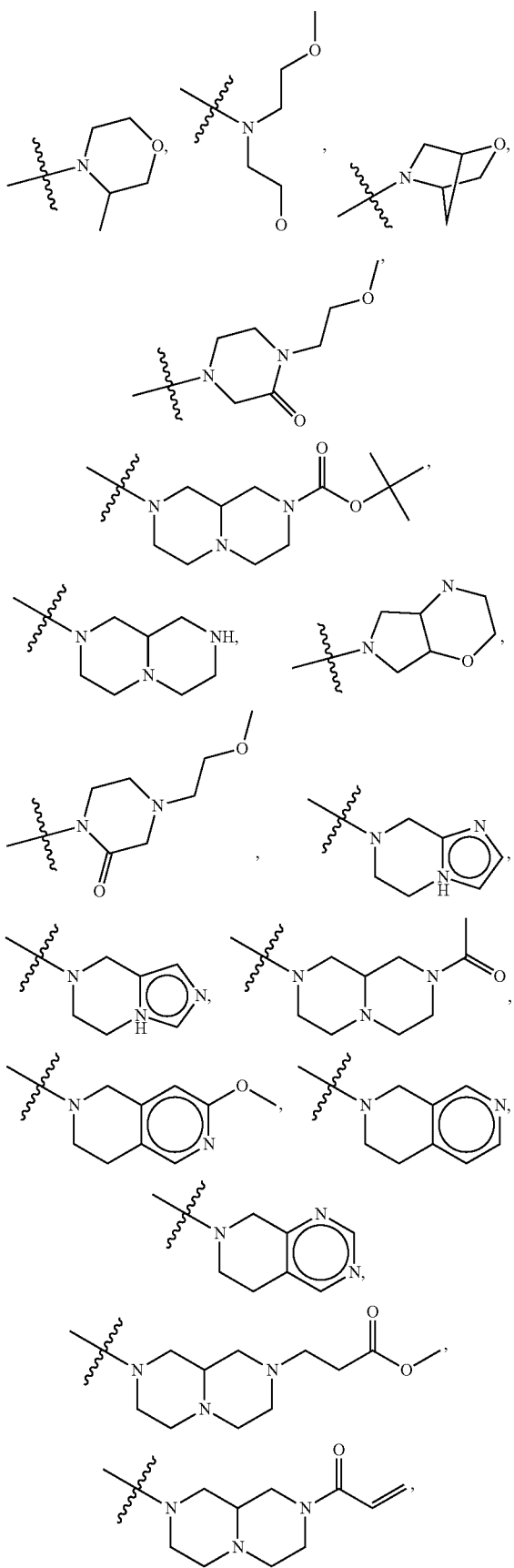

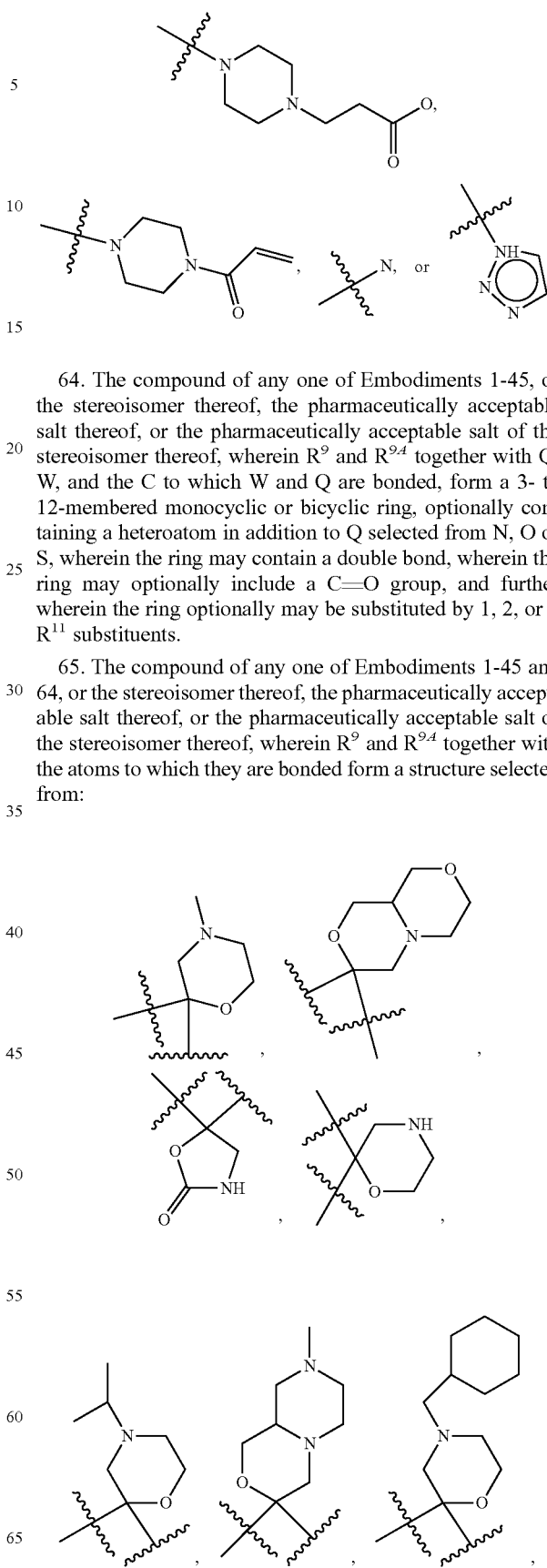

64. The compound of any one of Embodiments 1-45, or the stereoisomer thereof, the pharmaceutically acceptable salt thereof, or the pharmaceutically acceptable salt of the stereoisomer thereof, wherein $R^9$ and $R^{9A}$ together with Q, W, and the C to which W and Q are bonded, form a 3- to 12-membered monocyclic or bicyclic ring, optionally containing a heteroatom in addition to Q selected from N, O or S, wherein the ring may contain a double bond, wherein the ring may optionally include a C=O group, and further wherein the ring optionally may be substituted by 1, 2, or 3 $R^{11}$ substituents.

65. The compound of any one of Embodiments 1-45 and 64, or the stereoisomer thereof, the pharmaceutically acceptable salt thereof, or the pharmaceutically acceptable salt of the stereoisomer thereof, wherein $R^9$ and $R^{9A}$ together with the atoms to which they are bonded form a structure selected from:

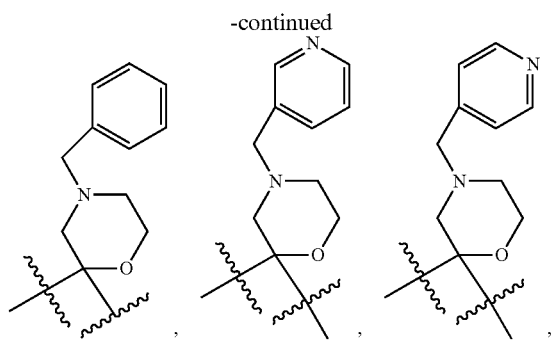

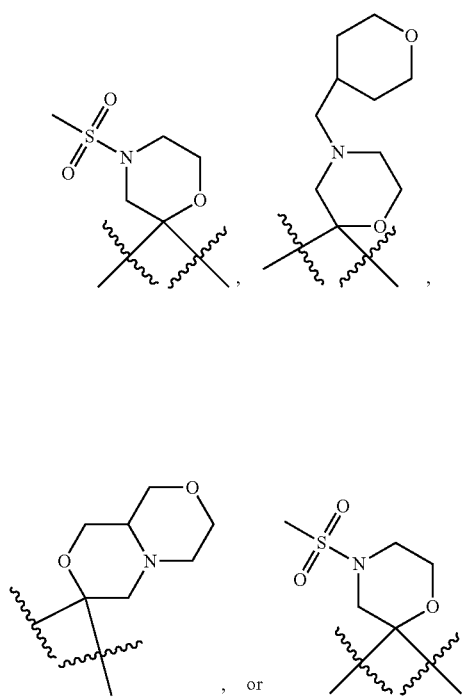

66. The compound of any one of Embodiments 1-9, 12-52 or 64, or the stereoisomer thereof, the pharmaceutically acceptable salt thereof, or the pharmaceutically acceptable salt of the stereoisomer thereof, wherein when W is C=O, then $R^{9A}$ is

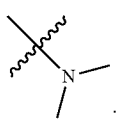

67. The compound of any one of Embodiments 1-11 or 14-66, or the stereoisomer thereof, the pharmaceutically acceptable salt thereof, or the pharmaceutically acceptable salt of the stereoisomer thereof, wherein $R^1$ is H.

68. Another embodiment of the present invention comprises the compound of Embodiment 1, wherein the compound of Formula I' has Formula II':

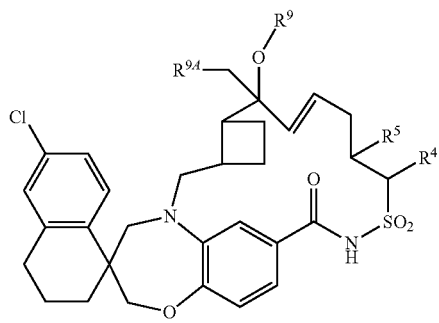

or the stereoisomer thereof, the pharmaceutically acceptable salt thereof, or the pharmaceutically acceptable salt of the stereoisomer thereof.

69. Another embodiment of the present invention comprises the compound of any one of Embodiments 1, 2, or 68, wherein the compound of Formula I' has Formula II'a:

(II'a)

or the stereoisomer thereof, the pharmaceutically acceptable salt thereof, or the pharmaceutically acceptable salt of the stereoisomer thereof.

70. The compound of any one of Embodiments 1, 2, 68, or 69, or the stereoisomer thereof, the pharmaceutically acceptable salt thereof, or the pharmaceutically acceptable salt of the stereoisomer thereof, wherein $R^4$ is independently selected from H, —$C_{1-6}$alkyl, —$C_{1-6}$alkylhalo, —$C_{1-6}$alkyl-O—$C_{1-6}$alkyl, or —$(CH_2CH_2O)_nR^a$, wherein the —$C_{1-6}$alkyl is unsubstituted or substituted with —OH, (=O), phenyl, —O—$SiR^aR^bR^c$, —$NR^aR^b$, a 3- to 12-membered cycloalkyl, or a 3- to 12-membered monocyclic or bicyclic heterocycloalkyl having 1, 2, 3, or 4 heteroatoms independently selected from O, N or S.

71. The compound of any one of Embodiments 1, 2, 68-69, or 70, or the stereoisomer thereof, the pharmaceutically acceptable salt thereof, or the pharmaceutically acceptable salt of the stereoisomer thereof, wherein $R^4$ is —$CH_3$.

72. The compound of any one of Embodiments 1, 2, 68-69, or 70, or the stereoisomer thereof, the pharmaceutically acceptable salt thereof, or the pharmaceutically acceptable salt of the stereoisomer thereof, wherein $R^4$ is —$CH_2CH_2OCH_3$.

73. The compound of any one of Embodiments 1, 2, 68-71 or 72, or the stereoisomer thereof, the pharmaceutically acceptable salt thereof, or the pharmaceutically acceptable salt of the stereoisomer thereof, wherein $R^5$ is H or —$C_{1-6}$alkyl.

74. The compound of any one of Embodiments 1, 2, 68-71 or 72, or the stereoisomer thereof, the pharmaceutically acceptable salt thereof, or the pharmaceutically acceptable salt of the stereoisomer thereof, wherein $R^5$ is —$CH_3$.

75. The compound of any one of Embodiments 1, 2, 68-71 or 72, or the stereoisomer thereof, the pharmaceutically acceptable salt thereof, or the pharmaceutically acceptable salt of the stereoisomer thereof, wherein $R^5$ is H.

76. The compound of any one of Embodiments 1, 2, 68-74 or 75, or the stereoisomer thereof, the pharmaceutically acceptable salt thereof, or the pharmaceutically acceptable salt of the stereoisomer thereof, wherein $R^6$ is H or —$C_{1-6}$alkyl.

77. The compound of any one of Embodiments 1, 2, 68-75 or 76, or the stereoisomer thereof, the pharmaceutically acceptable salt thereof, or the pharmaceutically acceptable salt of the stereoisomer thereof, wherein $R^6$ is —$CH_3$.

78. The compound of any one of Embodiments 1, 2, 68-75 or 76, or the stereoisomer thereof, the pharmaceutically acceptable salt thereof, or the pharmaceutically acceptable salt of the stereoisomer thereof, wherein $R^6$ is H.

79. The compound of any one of Embodiments 1, 2, 68-77 or 78 or the stereoisomer thereof, the pharmaceutically acceptable salt thereof, or the pharmaceutically acceptable salt of the stereoisomer thereof, wherein $R^9$ is independently selected from H, —$C_{1-6}$haloalkyl, —$C_{1-6}$alkyl, —$C_{2-6}$alkenyl, —$C_{2-6}$alkynyl, —$(CH_2CH_2O)_nR^a$, —$C(\!=\!O)R^a$, —$C(\!=\!O)OR^a$, —$C(\!=\!O)NR^aR^b$, —$C_{1-6}$alkyl-O—$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$.

80. The compound of any one of Embodiments 1, 2, 68-78 or 79, or the stereoisomer thereof, the pharmaceutically acceptable salt thereof, or the pharmaceutically acceptable salt of the stereoisomer thereof, wherein $R^9$ is —$CH_3$.

81. The compound of any one of Embodiments 1, 2, 68-78 or 79, or the stereoisomer thereof, the pharmaceutically acceptable salt thereof, or the pharmaceutically acceptable salt of the stereoisomer thereof, wherein $R^9$ is —$CH_2CH_3$.

82. The compound of any one of Embodiments 1, 2, 68-80 or 81, or the stereoisomer thereof, the pharmaceutically acceptable salt thereof, or the pharmaceutically acceptable salt of the stereoisomer thereof, wherein $R^{9A}$ is independently selected from H, $C_{1-6}$haloalkyl, $C_{1-6}$alkyl, —$C_{2-6}$alkenyl, —$C_{2-6}$alkynyl-$(CH_2CH_2O)_nR^a$, —$SO_2R^a$, —$C(\!=\!O)R^a$, —$C(\!=\!O)OR^a$, —$C(\!=\!O)NR^aR^b$, —$NR^aR^b$, —N=N=N, —$C_{1-6}$alkyl-O—$C_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$.

83. The compound of any one of Embodiments 1, 2, 68-81 or 82, or the stereoisomer thereof, the pharmaceutically acceptable salt thereof, or the pharmaceutically acceptable salt of the stereoisomer thereof, wherein $R^{9A}$ is —$C_{1-6}$alkyl.

84. The compound of any one of Embodiments 1, 2, 68-81 or 82, or the stereoisomer thereof, the pharmaceutically acceptable salt thereof, or the pharmaceutically acceptable salt of the stereoisomer thereof, wherein $R^{9A}$ is —$C(\!=\!O)R^a$.

85. The compound of any one of Embodiments 1, 2, 68-81 or 82, or the stereoisomer thereof, the pharmaceutically acceptable salt thereof, or the pharmaceutically acceptable salt of the stereoisomer thereof, wherein $R^{9A}$ is a 3- to 12-membered monocyclic or bicyclic heterocycloalkyl group, wherein the heterocycloalkyl group has 1, 2, 3 or 4 heteroatoms independently selected from O, N or S.

86. The compound of any one of Embodiments 1, 2, 68-82 or 85, or the stereoisomer thereof, the pharmaceutically acceptable salt thereof, or the pharmaceutically acceptable salt of the stereoisomer thereof, wherein $R^{9A}$ is a 3- to 12-membered monocyclic heterocycloalkyl group, wherein the heterocycloalkyl group has 1, 2, 3 or 4 heteroatoms independently selected from O or N.

87. The compound of any one of Embodiments 1, 2, 68-82 or 85-86, or the stereoisomer thereof, the pharmaceutically acceptable salt thereof, or the pharmaceutically acceptable salt of the stereoisomer thereof, wherein the 3- to 12-membered monocyclic heterocycloalkyl $R^{9A}$ group can be unsubstituted or substituted with 1, 2, 3 or 4 $R^{10}$ substituents independently selected from OH, halo, —$NR^cR^d$, —$C_{1-6}$alkyl, —$C_{2-6}$alkenyl, —$C_{2-6}$alkynyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —$C(\!=\!O)NR^cR^d$, —$C(\!=\!O)R^c$, —$OC(\!=\!O)R^a$, —$C(\!=\!O)OR^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$.

88. The compound of any one of Embodiments 1, 2, 68-82 or 85-86, or the stereoisomer thereof, the pharmaceutically acceptable salt thereof, or the pharmaceutically acceptable salt of the stereoisomer thereof, wherein the 1, 2, 3 or 4 $R^{10}$ substituents are independently selected from —$C_{1-6}$alkyl or a 3- to 12-membered monocyclic heterocycloalkyl group, wherein the heterocycloalkyl group has 1, 2, 3 or 4 heteroatoms independently selected from O, N or S.

89. The compound of any one of Embodiments 1, 2, 68-82 or 85-88, or the stereoisomer thereof, the pharmaceutically acceptable salt thereof, or the pharmaceutically acceptable salt of the stereoisomer thereof, wherein $R^{10}$ is —$C_{1-6}$alkyl.

90. The compound of any one of Embodiments 1, 2, 68-82 or 85-88, or the stereoisomer thereof, the pharmaceutically acceptable salt thereof, or the pharmaceutically acceptable salt of the stereoisomer thereof, wherein $R^{10}$ is a 3- to 12-membered monocyclic heterocycloalkyl group, wherein the heterocycloalkyl group has 1, 2, 3 or 4 heteroatoms independently selected from O, N or S.

91. The compound of any one of Embodiments 1, 2, 68-82 or 85, or the stereoisomer thereof, the pharmaceutically acceptable salt thereof, or the pharmaceutically acceptable salt of the stereoisomer thereof, wherein $R^{9A}$ is a 5- to 12-membered bicyclic heterocycloalkyl group, wherein the heterocycloalkyl group has 1, 2, 3 or 4 heteroatoms independently selected from O or N.

92. The compound of any one of Embodiments 1, 2, or 68-82, or the stereoisomer thereof, the pharmaceutically acceptable salt thereof, or the pharmaceutically acceptable salt of the stereoisomer thereof, wherein $R^{9A}$ is independently selected from:

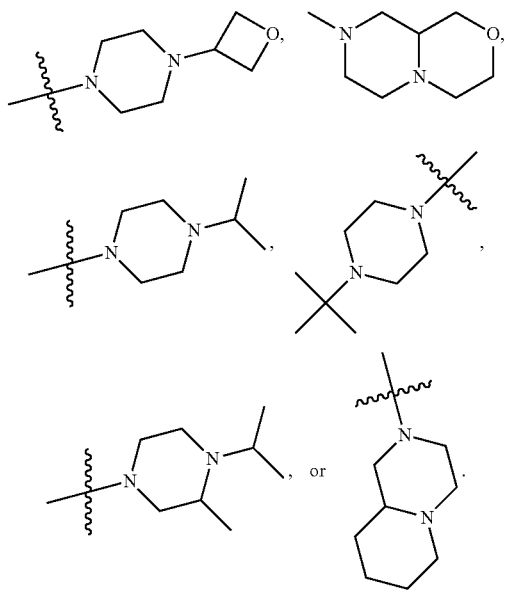

93. Another embodiment of the present invention comprises the compound of Embodiment 1, wherein the compound of Formula I' has Formula III':

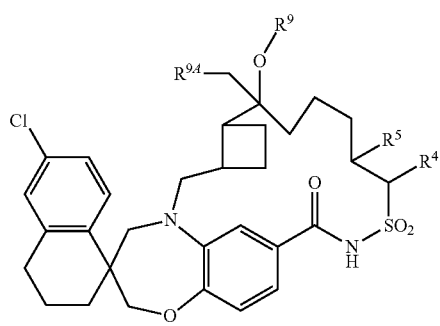

(III')

or the stereoisomer thereof, the pharmaceutically acceptable salt thereof, or the pharmaceutically acceptable salt of the stereoisomer thereof, wherein $R^4$, $R^5$, $R^9$ and $R^{9A}$ are as defined above.

94. Another embodiment of the present invention comprises the compound of Embodiment 1, 2, or 93, wherein the compound of Formula I' has Formula III'a:

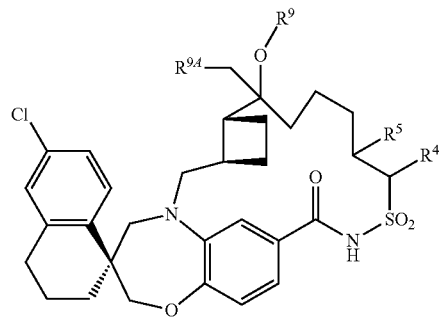

(III'a)

or the stereoisomer thereof, the pharmaceutically acceptable salt thereof, or the pharmaceutically acceptable salt of the stereoisomer thereof.

95. The compound of any one of Embodiments 1, 2, or 93-94, or the stereoisomer thereof, the pharmaceutically acceptable salt thereof, or the pharmaceutically acceptable salt of the stereoisomer thereof, wherein $R^4$ is independently selected from H, —$C_{1-6}$alkyl, —$C_{1-6}$alkylhalo, —$C_{1-6}$alkyl-O—$C_{1-6}$alkyl, or —$(CH_2CH_2O)_nR^a$, wherein the —$C_{1-6}$alkyl is unsubstituted or substituted with —OH, —(=O), phenyl, —O—$SiR^aR^bR^c$, —$NR^aR^b$, a 3- to 12-membered cycloalkyl, or a 3- to 12-membered monocyclic or bicyclic heterocycloalkyl having 1, 2, 3, or 4 heteroatoms independently selected from O, N or S.

96. The compound of any one of Embodiments 1, 2, or 93-95, or the stereoisomer thereof, the pharmaceutically acceptable salt thereof, or the pharmaceutically acceptable salt of the stereoisomer thereof, wherein $R^4$ is —$CH_3$.

97. The compound of any one of Embodiments 1, 2, or 93-95, or the stereoisomer thereof, the pharmaceutically acceptable salt thereof, or the pharmaceutically acceptable salt of the stereoisomer thereof, wherein $R^4$ is —$CH_2CH_2OCH_3$.

98. The compound of any one of Embodiments 1, 2 or 93-97, or the stereoisomer thereof, the pharmaceutically acceptable salt thereof, or the pharmaceutically acceptable salt of the stereoisomer thereof, wherein $R^5$ is H or —$C_{1-6}$alkyl.

99. The compound of any one of Embodiments 1, 2 or 93-98, or the stereoisomer thereof, the pharmaceutically acceptable salt thereof, or the pharmaceutically acceptable salt of the stereoisomer thereof, wherein $R^5$ is —$CH_3$.

100. The compound of any one of Embodiments 1, 2 or 93-98, or the stereoisomer thereof, the pharmaceutically acceptable salt thereof, or the pharmaceutically acceptable salt of the stereoisomer thereof, wherein $R^5$ is H.

101. The compound of any one of Embodiments 1, 2 or 93-100, or the stereoisomer thereof, the pharmaceutically acceptable salt thereof, or the pharmaceutically acceptable salt of the stereoisomer thereof, wherein $R^6$ is H or —$C_{1-6}$alkyl.

102. The compound of any one of Embodiments 1, 2 or 93-101, or the stereoisomer thereof, the pharmaceutically acceptable salt thereof, or the pharmaceutically acceptable salt of the stereoisomer thereof, wherein $R^6$ is —$CH_3$.

103. The compound of any one of Embodiments 1, 2 or 93-101, or the stereoisomer thereof, the pharmaceutically acceptable salt thereof, or the pharmaceutically acceptable salt of the stereoisomer thereof, wherein $R^6$ is H.

104. The compound of any one of Embodiments 1, 2 or 93-103, or the stereoisomer thereof, the pharmaceutically acceptable salt thereof, or the pharmaceutically acceptable salt of the stereoisomer thereof, wherein $R^9$ is independently selected from H, —$C_{1-6}$haloalkyl, —$C_{1-6}$alkyl, —$C_{2-6}$alkenyl, —$C_{2-6}$alkynyl, —(CH$_2$CH$_2$O)$_n$R$^a$, —C(=O)R$^a$, —C(=O)OR$^a$, —C(=O)NR$^a$R$^b$, —$C_{1-6}$alkyl-O—$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$.

105. A compound of any one of Embodiments 1, 2 or 93-104, or the stereoisomer thereof, the pharmaceutically acceptable salt thereof, or the pharmaceutically acceptable salt of the stereoisomer thereof, wherein $R^9$ is —CH$_3$.

106. A compound of any one of Embodiments 1, 2 or 93-104, or the stereoisomer thereof, the pharmaceutically acceptable salt thereof, or the pharmaceutically acceptable salt of the stereoisomer thereof, wherein $R^9$ is —CH$_2$CH$_3$.

107. A compound of any one of Embodiments 1, 2 or 93-104, or the stereoisomer thereof, the pharmaceutically acceptable salt thereof, or the pharmaceutically acceptable salt of the stereoisomer thereof, wherein $R^9$ is —H.

108. A compound of any one of Embodiments 1, 2 or 93-107, or the stereoisomer thereof, the pharmaceutically acceptable salt thereof, or the pharmaceutically acceptable salt of the stereoisomer thereof, wherein $R^{9A}$ is independently selected from H, $C_{1-6}$haloalkyl, $C_{1-6}$alkyl, —$C_{2-6}$alkenyl-(CH$_2$CH$_2$O)$_n$R$^a$, —SO$_2$R$^a$, —C(=O)R$^a$, —C(=O)OR$^a$, —C(=O)NR$^a$R$^b$, —NR$^a$R$^b$, —N=N=N, —$C_{1-6}$alkyl-O—$C_{1-6}$alkyl, a 6- to 12-membered aryl, a 6- to 12-membered heteroaryl, a 5- to 10-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$.

109. The compound of any one of Embodiments 1, 2 or 93-108, or the stereoisomer thereof, the pharmaceutically acceptable salt thereof, or the pharmaceutically acceptable salt of the stereoisomer thereof, wherein $R^{9A}$ is —$C_{1-6}$alkyl.

110. The compound of any one of Embodiments 1, 2 or 93-108, or the stereoisomer thereof, the pharmaceutically acceptable salt thereof, or the pharmaceutically acceptable salt of the stereoisomer thereof, wherein $R^{9A}$ is —C(=O)R$^a$.

111. The compound of any one of Embodiments 1, 2 or 93-108, or the stereoisomer thereof, the pharmaceutically acceptable salt thereof, or the pharmaceutically acceptable salt of the stereoisomer thereof, wherein $R^{9A}$ is a 3- to 12-membered monocyclic or bicyclic heterocycloalkyl group, wherein the heterocycloalkyl group has 1, 2, 3 or 4 heteroatoms independently selected from O, N or S.

112. The compound of any one of Embodiments 1, 2, 93-108 or 111, or the stereoisomer thereof, the pharmaceutically acceptable salt thereof, or the pharmaceutically acceptable salt of the stereoisomer thereof, wherein $R^{9A}$ is a 3- to 12-membered monocyclic heterocycloalkyl group, wherein the heterocycloalkyl group has 1, 2, 3 or 4 heteroatoms independently selected from O or N.

113. The compound of any one of Embodiments 1, 2, 93-108 or 112, or the stereoisomer thereof, the pharmaceutically acceptable salt thereof, or the pharmaceutically acceptable salt of the stereoisomer thereof, wherein the 3- to 12-membered monocyclic heterocycloalkyl $R^{9A}$ group can be unsubstituted or substituted with from 1, 2, 3 or 4 $R^{10}$ substituents independently selected from OH, halo, —NR$^c$R$^d$, —$C_{1-6}$alkyl, —$C_{2-6}$alkenyl, —$C_{2-6}$alkynyl, —OC$_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$.

114. The compound of any one of Embodiments 1, 2, 93-108 or 112-113, or the stereoisomer thereof, the pharmaceutically acceptable salt thereof, or the pharmaceutically acceptable salt of the stereoisomer thereof, wherein the 1, 2, 3 or 4 $R^{10}$ substituents are independently selected from —$C_{1-6}$alkyl or a 3- to 12-membered monocyclic heterocycloalkyl group, wherein the heterocycloalkyl group has 1, 2, 3 or 4 heteroatoms independently selected from O, N or S.

115. The compound of any one of Embodiments 1, 2, 93-108 and 112-114, or the stereoisomer thereof, the pharmaceutically acceptable salt thereof, or the pharmaceutically acceptable salt of the stereoisomer thereof, wherein $R^{10}$ is —$C_{1-6}$alkyl.

116. The compound of any one of Embodiments 1, 2, 93-108 or 112-113, or the stereoisomer thereof, the pharmaceutically acceptable salt thereof, or the pharmaceutically acceptable salt of the stereoisomer thereof, wherein $R^{10}$ is a 3- to 12-membered monocyclic heterocycloalkyl group, wherein the heterocycloalkyl group has from 1, 2, 3 or 4 heteroatoms independently selected from O, N or S.

117. The compound of any one of Embodiments 1, 2, 93-108 or 111, or the stereoisomer thereof, the pharmaceutically acceptable salt thereof, or the pharmaceutically acceptable salt of the stereoisomer thereof, wherein $R^{9A}$ is a 5- to 12-membered bicyclic heterocycloalkyl group, wherein the heterocycloalkyl group has 1, 2, 3 or 4 heteroatoms independently selected from O or N.

118. The compound of any one of Embodiments 1, 2, or 93-108, or the stereoisomer thereof, the pharmaceutically acceptable salt thereof, or the pharmaceutically acceptable salt of the stereoisomer thereof, wherein $R^{9A}$ is independently selected from:

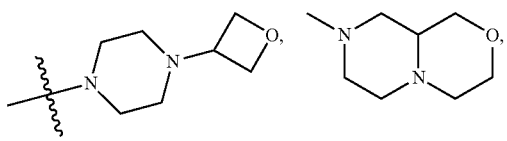

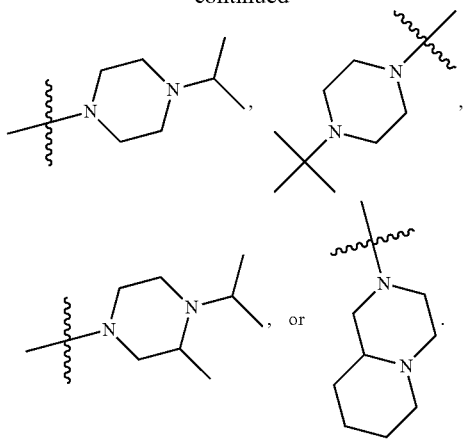

119. Another embodiment of the present invention comprises the compound of Embodiment 1, wherein the compound of Formula I' has Formula IV':

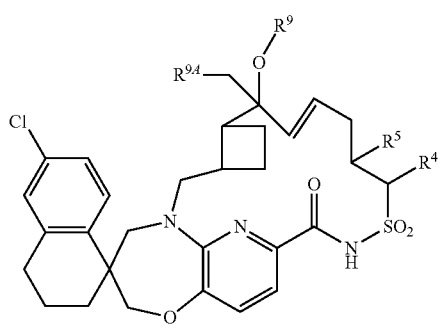

or the stereoisomer thereof, the pharmaceutically acceptable salt thereof, or the pharmaceutically acceptable salt of the stereoisomer thereof, wherein $R^4$, $R^5$, $R^9$ and $R^{9A}$ are as defined above.

120. Another embodiment of the present invention comprises the compound of Embodiment 1, 2 or 119, wherein the compound of Formula I' has Formula IV'a:

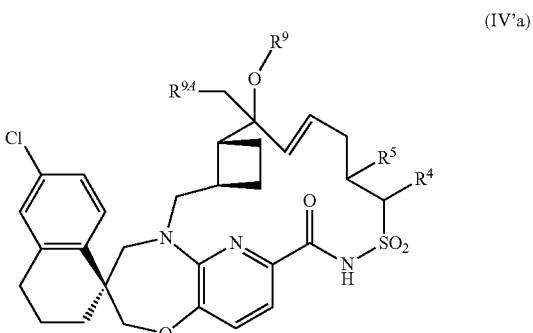

or a stereoisomer thereof, a pharmaceutically acceptable salt thereof, or a pharmaceutically acceptable salt of the stereoisomer thereof.

121. The compound of any one of Embodiments 1, 2, or 119-120, or the stereoisomer thereof, the pharmaceutically acceptable salt thereof, or the pharmaceutically acceptable salt of the stereoisomer thereof, wherein $R^4$ is independently selected from H, —$C_{1-6}$alkyl, —$C_{1-6}$alkylhalo, —$C_{1-6}$alkyl-O—$C_{1-6}$alkyl, or —$(CH_2CH_2O)_nR^a$, wherein the —$C_{1-6}$alkyl is unsubstituted or substituted with —OH, —(=O), phenyl, —O—$SiR^aR^bR^c$, —$NR^aR^b$, a 3- to 12-membered cycloalkyl, or a 3- to 12-membered monocyclic or bicyclic heterocycloalkyl having 1, 2, 3, or 4 heteroatoms independently selected from O, N or S.

122. The compound of any one of Embodiments 1, 2, or 119-121, or the stereoisomer thereof, the pharmaceutically acceptable salt thereof, or the pharmaceutically acceptable salt of the stereoisomer thereof, wherein $R^4$ is —$CH_3$.

123. The compound of any one of Embodiments 1, 2, or 119-121, or the stereoisomer thereof, the pharmaceutically acceptable salt thereof, or the pharmaceutically acceptable salt of the stereoisomer thereof, wherein $R^4$ is —$CH_2CH_2OCH_3$.

124. The compound of any one of Embodiments 1, 2, or 119-123, or the stereoisomer thereof, the pharmaceutically acceptable salt thereof, or the pharmaceutically acceptable salt of the stereoisomer thereof, wherein $R^5$ is H or —$C_{1-6}$alkyl.

125. The compound of any one of Embodiments 1, 2, or 119-124, or the stereoisomer thereof, the pharmaceutically acceptable salt thereof, or the pharmaceutically acceptable salt of the stereoisomer thereof, wherein $R^5$ is —$CH_3$.

126. The compound of any one of Embodiments 1, 2, or 119-125, or the stereoisomer thereof, the pharmaceutically acceptable salt thereof, or the pharmaceutically acceptable salt of the stereoisomer thereof, wherein $R^5$ is H.

127. The compound of any one of Embodiments 1, 2, or 119-126, or the stereoisomer thereof, the pharmaceutically acceptable salt thereof, or the pharmaceutically acceptable salt of the stereoisomer thereof, wherein $R^6$ is H or —$C_{1-6}$alkyl.

128. The compound of any one of Embodiments 1, 2, or 119-127, or the stereoisomer thereof, the pharmaceutically acceptable salt thereof, or the pharmaceutically acceptable salt of the stereoisomer thereof, wherein $R^6$ is —$CH_3$.

129. The compound of any one of Embodiments 1, 2, or 119-127, or the stereoisomer thereof, the pharmaceutically acceptable salt thereof, or the pharmaceutically acceptable salt of the stereoisomer thereof, wherein $R^6$ is H.

130. The compound of any one of Embodiments 1, 2, or 119-129, or the stereoisomer thereof, the pharmaceutically acceptable salt thereof, or the pharmaceutically acceptable salt of the stereoisomer thereof, wherein $R^9$ is independently selected from H, —$C_{1-6}$haloalkyl, —$C_{1-6}$alkyl, —$C_{2-6}$alkenyl, —$(CH_2CH_2O)_nR^a$, —$C(=O)R^a$, —$C(=O)OR^a$, —$C(=O)NR^aR^b$, —$C_{1-6}$alkyl-O—$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$.

131. The compound of any one of Embodiments 1, 2, or 119-130, or the stereoisomer thereof, the pharmaceutically acceptable salt thereof, or the pharmaceutically acceptable salt of the stereoisomer thereof, wherein $R^9$ is —$CH_3$.

132. The compound of any one of Embodiments 1, 2, or 119-130, or the stereoisomer thereof, the pharmaceutically acceptable salt thereof, or the pharmaceutically acceptable salt of the stereoisomer thereof, wherein $R^9$ is —$CH_2CH_3$.

133. The compound of any one of Embodiments 1, 2, or 119-132, or the stereoisomer thereof, the pharmaceutically acceptable salt thereof, or the pharmaceutically acceptable salt of the stereoisomer thereof, wherein $R^{9A}$ is independently selected from H, $C_{1-6}$haloalkyl, $C_{1-6}$alkyl, —$C_{2-6}$alkenyl-$(CH_2CH_2O)_nR^a$, —$SO_2R^a$, —$C(=O)R^a$, —$C(=O)OR^a$, —$C(=O)NR^aR^b$, —$NR^aR^b$, —N=N=N, —$C_{1-6}$alkyl-O—$C_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl group have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$.

134. The compound of any one of Embodiments 1, 2, 119-133, or the stereoisomer thereof, the pharmaceutically acceptable salt thereof, or the pharmaceutically acceptable salt of the stereoisomer thereof, wherein $R^{9A}$ is —$C_{1-6}$alkyl.

135. The compound of any one of Embodiments 1, 2, or 119-113, or the stereoisomer thereof, the pharmaceutically acceptable salt thereof, or the pharmaceutically acceptable salt of the stereoisomer thereof, wherein $R^{9A}$ is —$C(=O)R^a$.

136. The compound of any one of Embodiments 1, 2, or 119-133, or the stereoisomer thereof, the pharmaceutically acceptable salt thereof, or the pharmaceutically acceptable salt of the stereoisomer thereof, wherein $R^{9A}$ is a 3- to 12-membered monocyclic or bicyclic heterocycloalkyl group, wherein the heterocycloalkyl group has 1, 2, 3 or 4 heteroatoms independently selected from O, N or S.

137. The compound of any one of Embodiments 1, 2, 119-133 or 136, or the stereoisomer thereof, the pharmaceutically acceptable salt thereof, or the pharmaceutically acceptable salt of the stereoisomer thereof, wherein $R^{9A}$ is a 3- to 12-membered monocyclic heterocycloalkyl group, wherein the heterocycloalkyl group has 1, 2, 3 or 4 heteroatoms independently selected from O or N.

138. The compound of any one of Embodiments 1, 2, 119-133, or 136-137, or the stereoisomer thereof, the pharmaceutically acceptable salt thereof, or the pharmaceutically acceptable salt of the stereoisomer thereof, wherein the 3- to 12-membered monocyclic heterocycloalkyl $R^{9A}$ group can be unsubstituted or substituted with 1, 2, 3 or 4 $R^{10}$ substituents independently selected from OH, halo, —$NR^cR^d$, —$C_{1-6}$alkyl, —$C_{2-6}$alkenyl, —$C_{2-6}$alkynyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —$C(=O)NR^cR^d$, —$C(=O)R^c$, —$OC(=O)R^a$, —$C(=O)OR^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$.

139. The compound of any one of Embodiments 1, 2, 119-133, or 136-138, or the stereoisomer thereof, the pharmaceutically acceptable salt thereof, or the pharmaceutically acceptable salt of the stereoisomer thereof, wherein the 1, 2, 3 or 4 $R^{10}$ substituents are independently selected from —$C_{1-6}$alkyl or a 3- to 12-membered monocyclic heterocycloalkyl group, wherein the heterocycloalkyl group has 1, 2, 3 or 4 heteroatoms independently selected from O, N or S.

140. The compound of any one of Embodiments 1, 2, 119-133, or 136-139, or the stereoisomer thereof, the pharmaceutically acceptable salt thereof, or the pharmaceutically acceptable salt of the stereoisomer thereof, wherein $R^{10}$ is —$C_{1-6}$alkyl.

141. The compound of any one of Embodiments 1, 2, 119-133, or 136-139, or the stereoisomer thereof, the pharmaceutically acceptable salt thereof, or the pharmaceutically acceptable salt of the stereoisomer thereof, wherein $R^{10}$ is a 3- to 12-membered monocyclic heterocycloalkyl group, wherein the heterocycloalkyl group has 1, 2, 3 or 4 heteroatoms independently selected from O, N or S.

142. The compound of any one of Embodiments 1, 2, 119-133, or 136, or the stereoisomer thereof, the pharmaceutically acceptable salt thereof, or the pharmaceutically acceptable salt of the stereoisomer thereof, wherein $R^{9A}$ is a 5- to 12-membered bicyclic heterocycloalkyl group, wherein the heterocycloalkyl group has 1, 2, 3 or 4 heteroatoms independently selected from O or N.

143. The compound of any one of Embodiments 68-70, or the stereoisomer thereof, the pharmaceutically acceptable salt thereof, or the pharmaceutically acceptable salt of the stereoisomer thereof, wherein $R^{9A}$ is independently selected from:

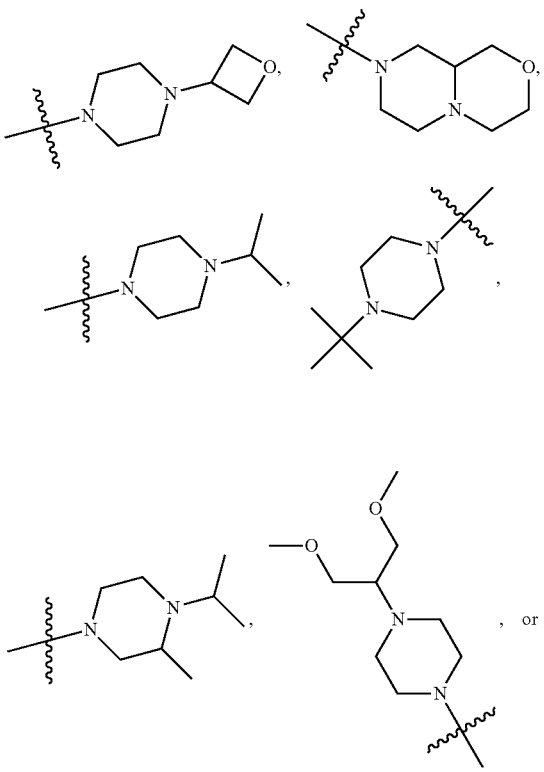

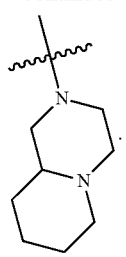
144. Another embodiment of the present invention comprises the compound of Embodiment 1, wherein the compound is selected from:
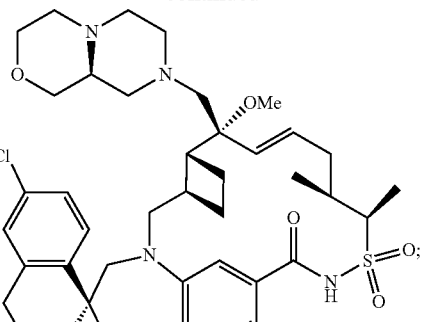
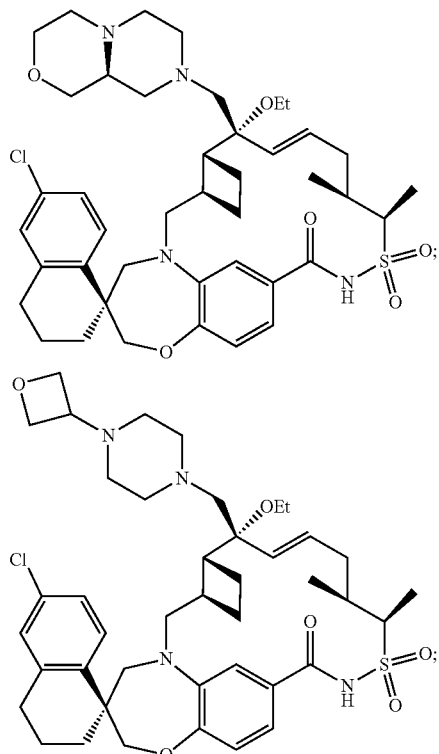
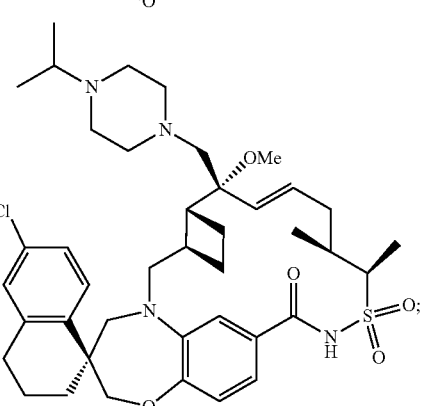
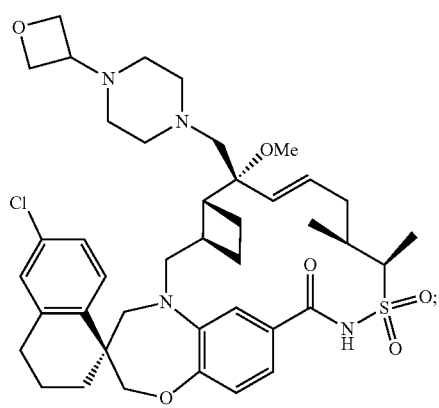
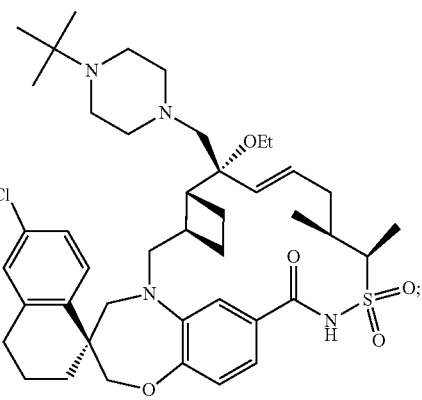

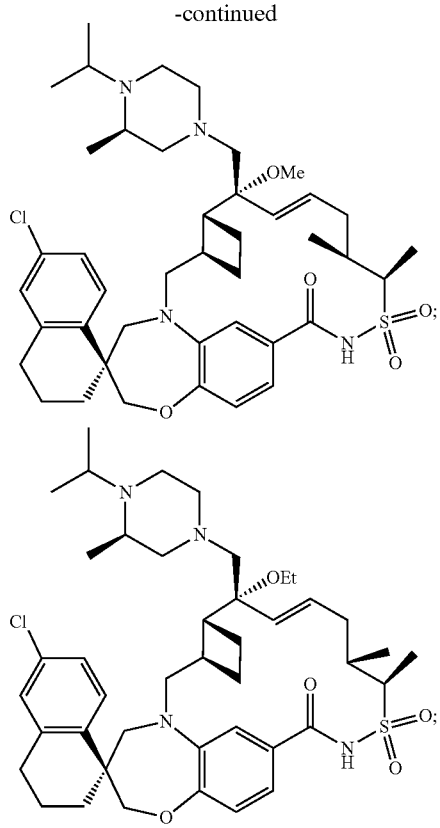
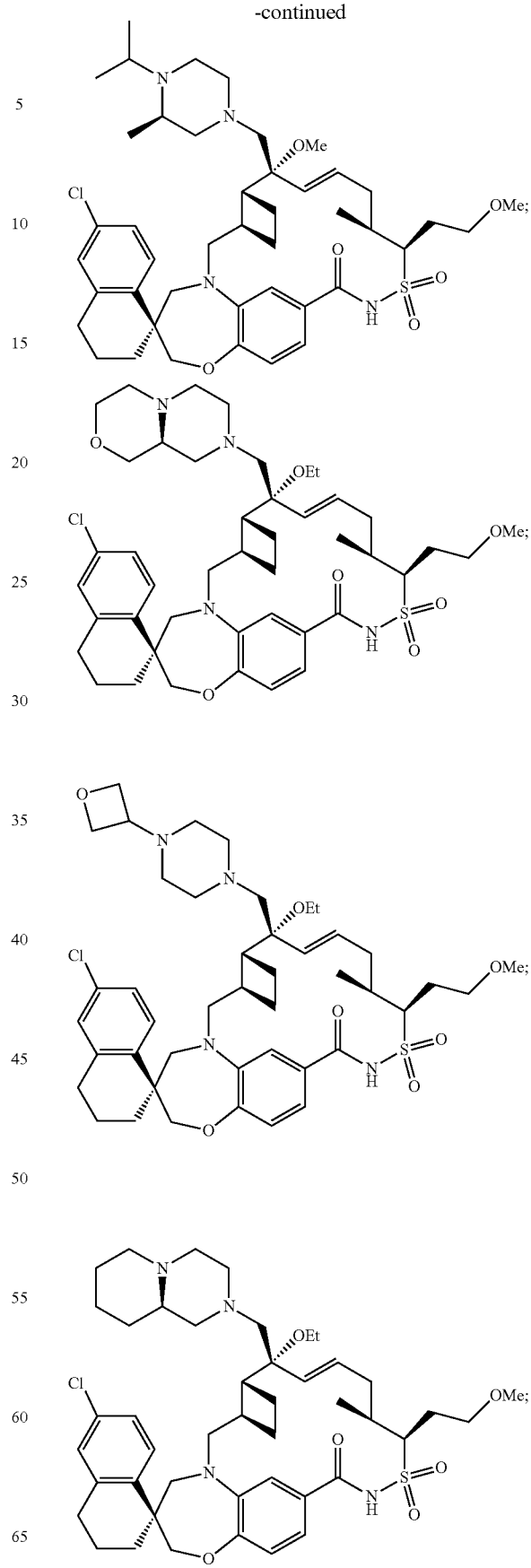

-continued
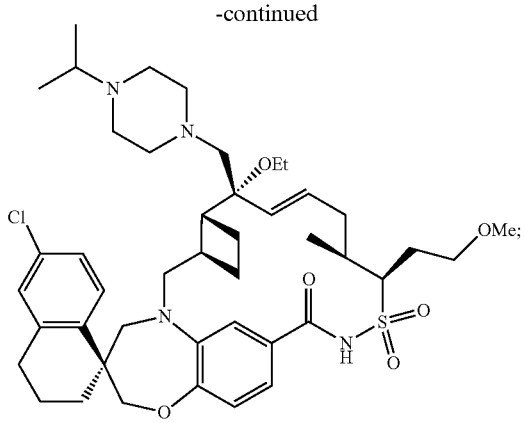
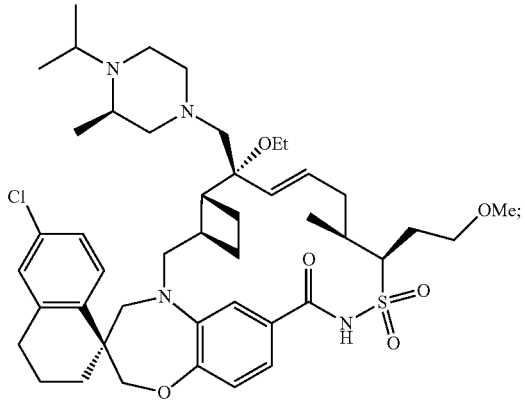
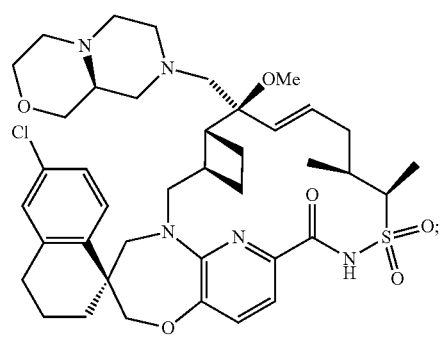
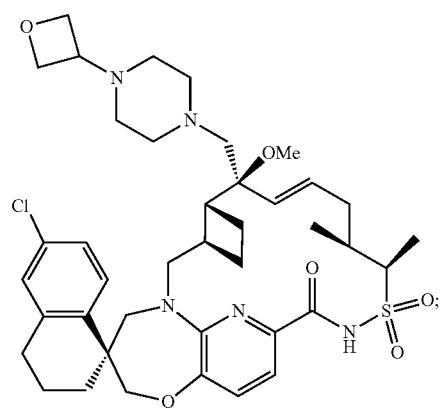
-continued
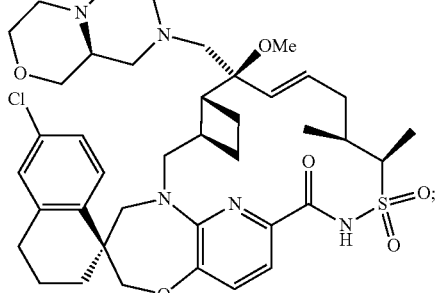
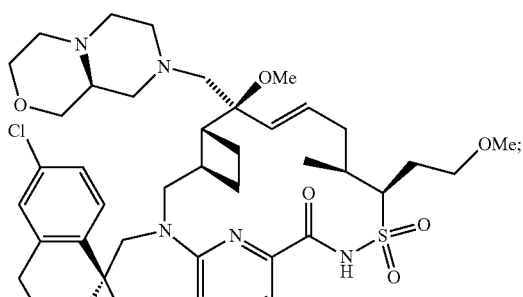
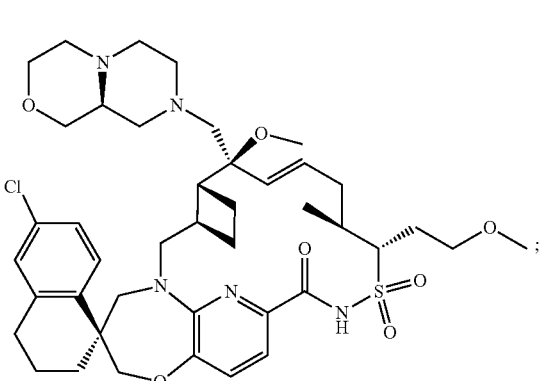
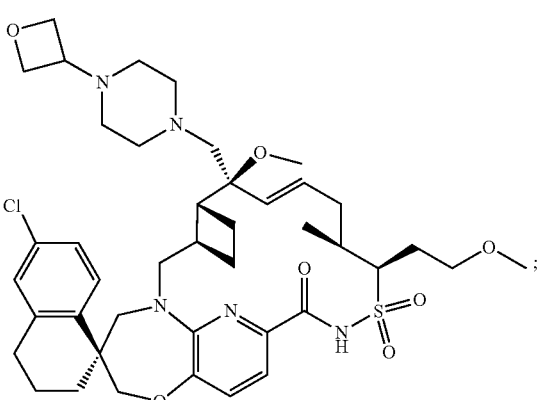

53
-continued
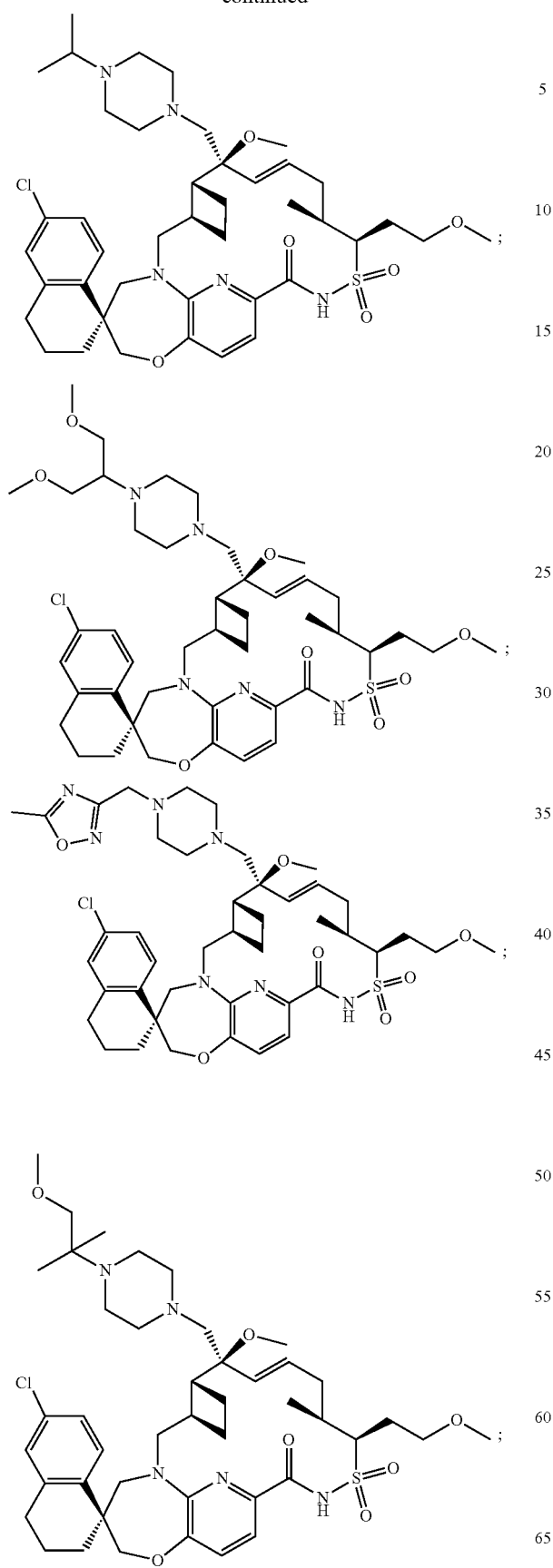
54
-continued
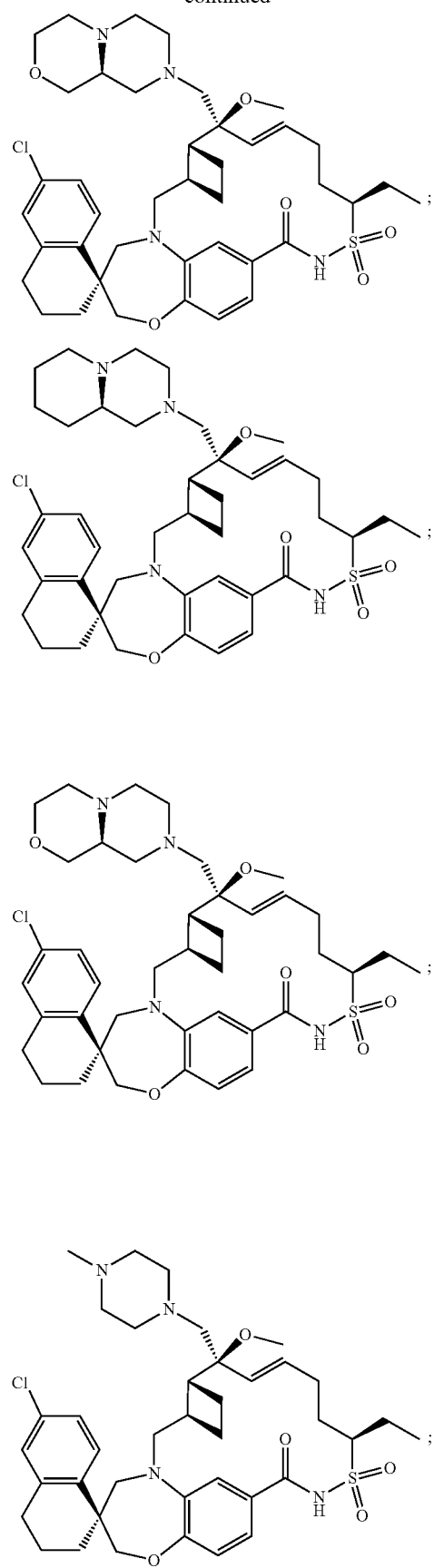

55
-continued
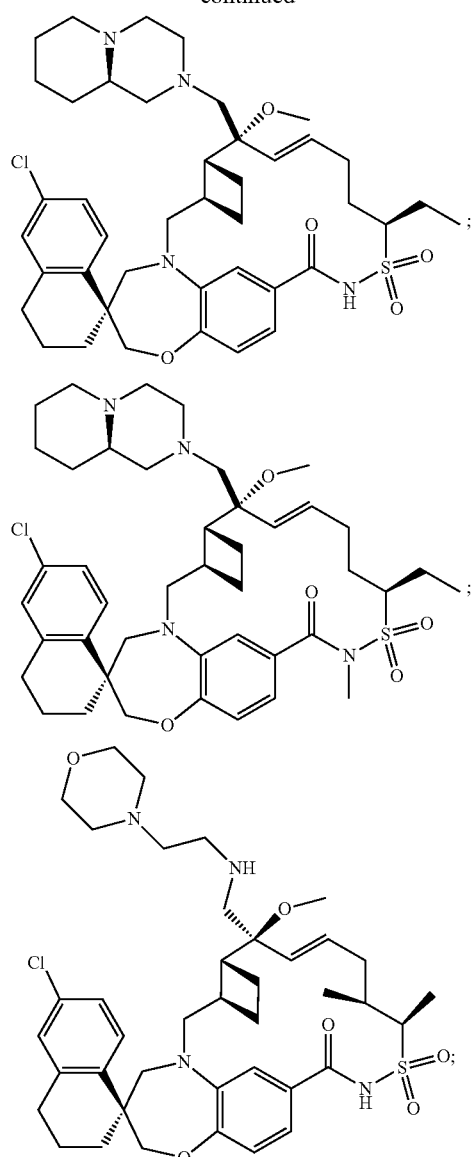
56
-continued
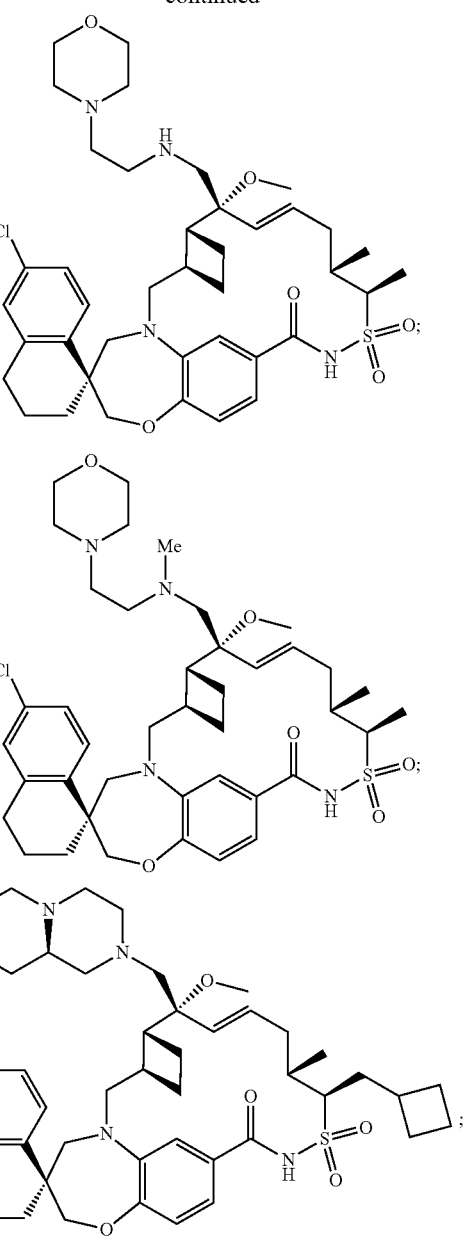
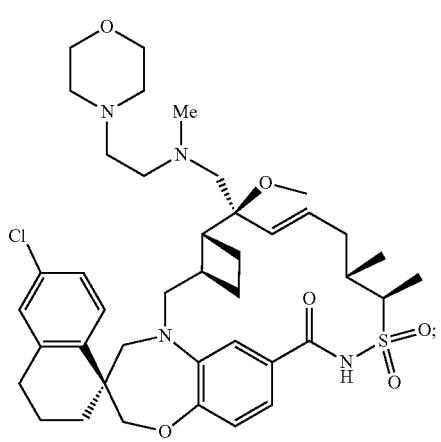

57
-continued
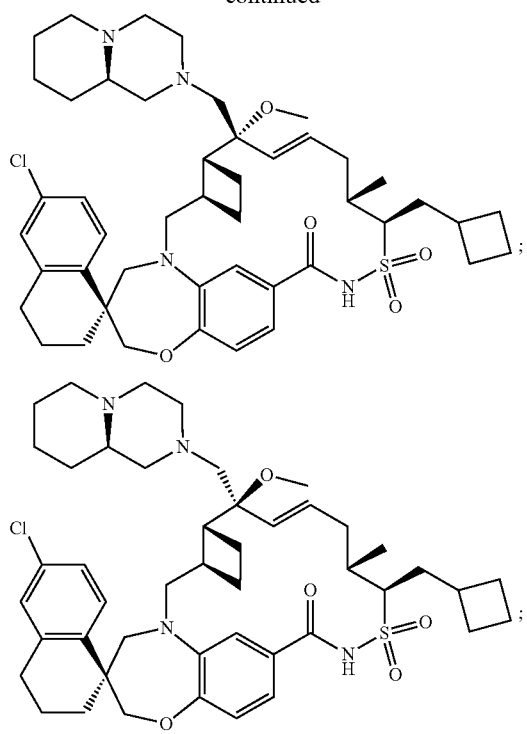
58
-continued
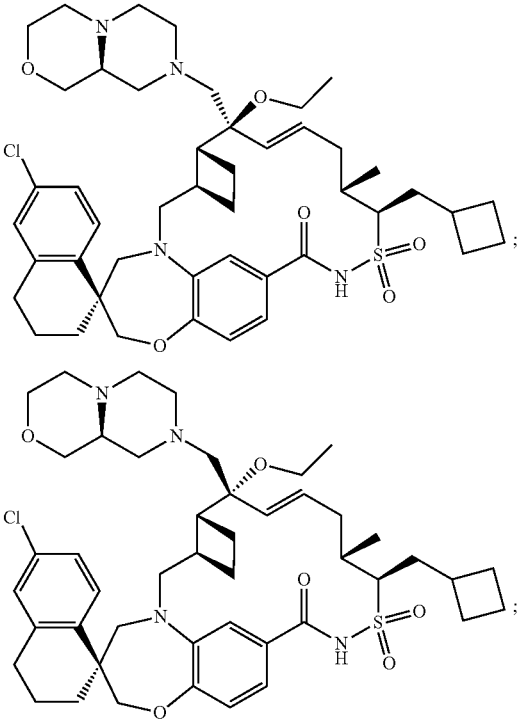
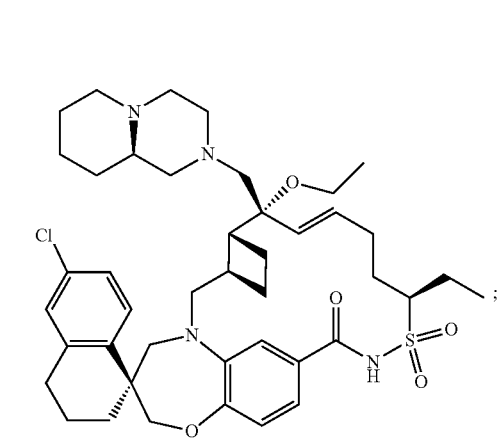
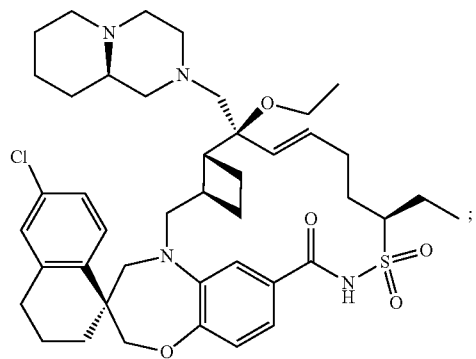
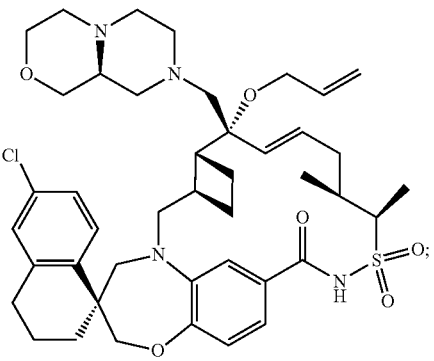
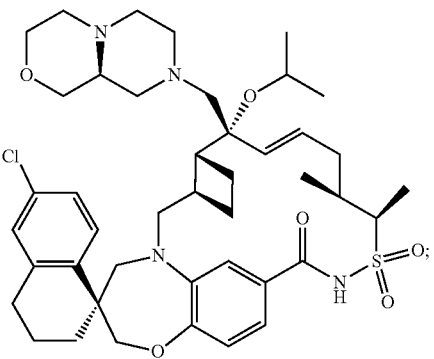

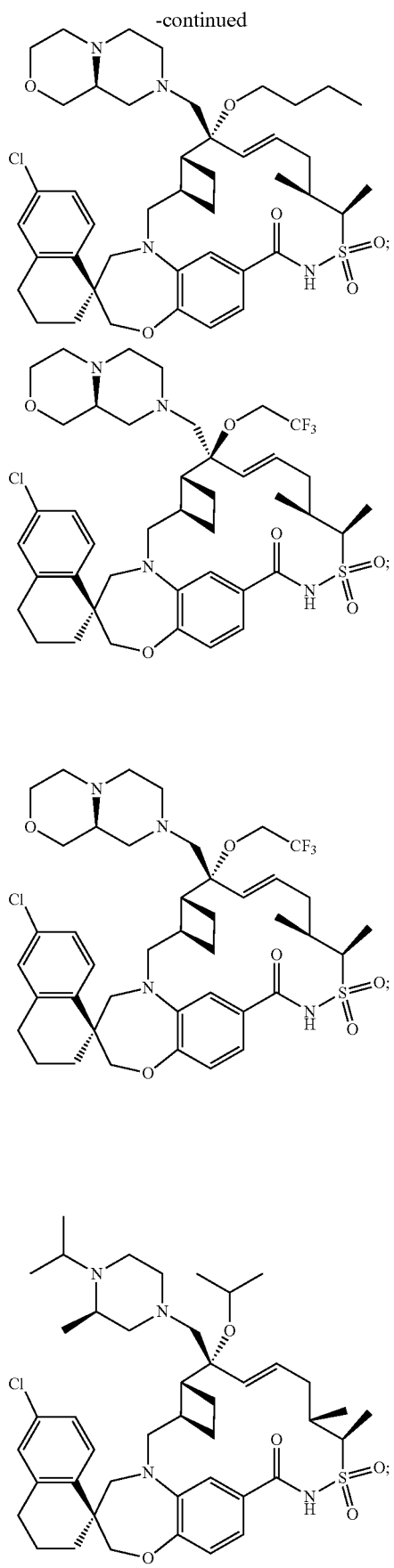
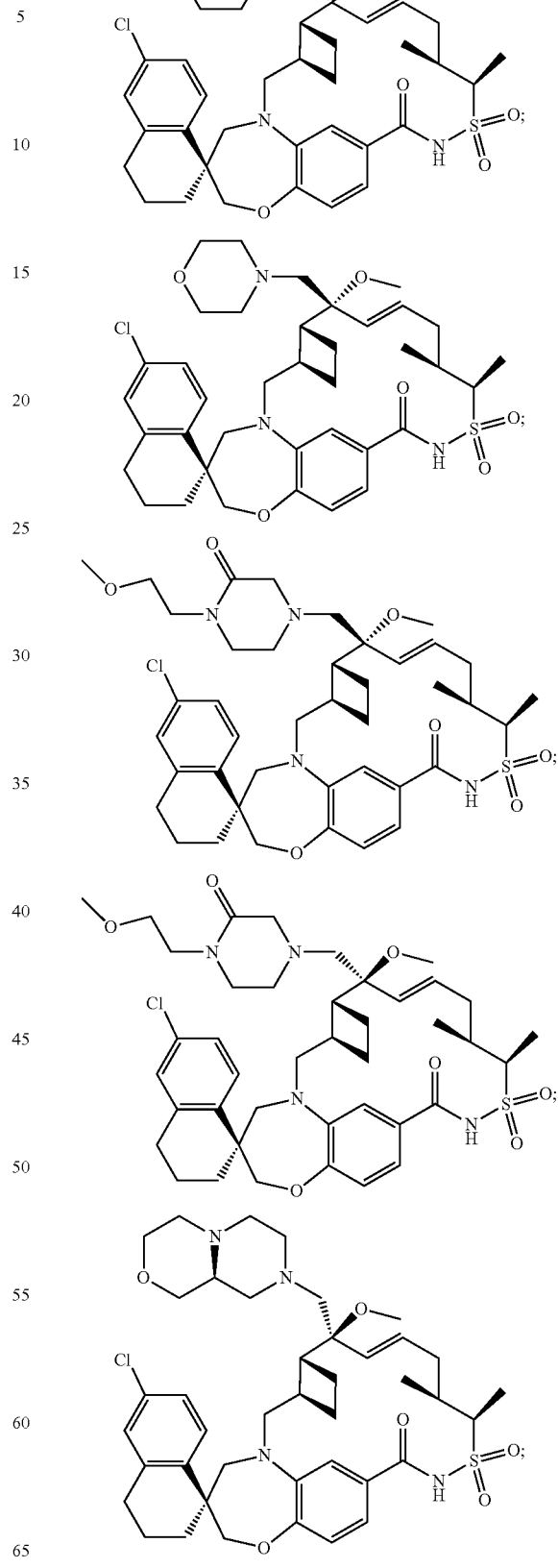

61
-continued
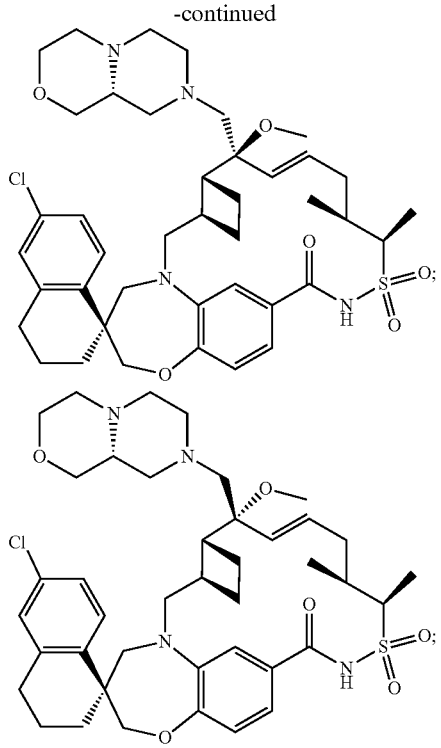
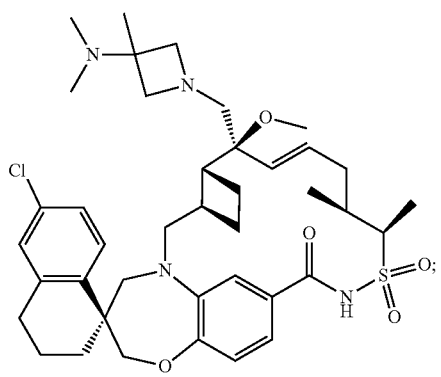
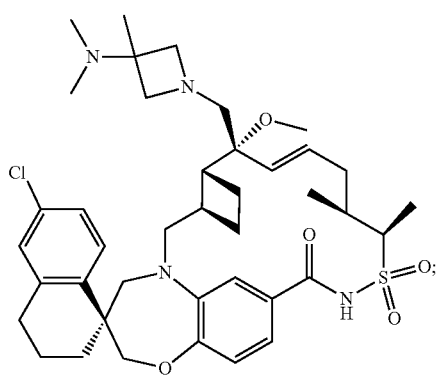
62
-continued
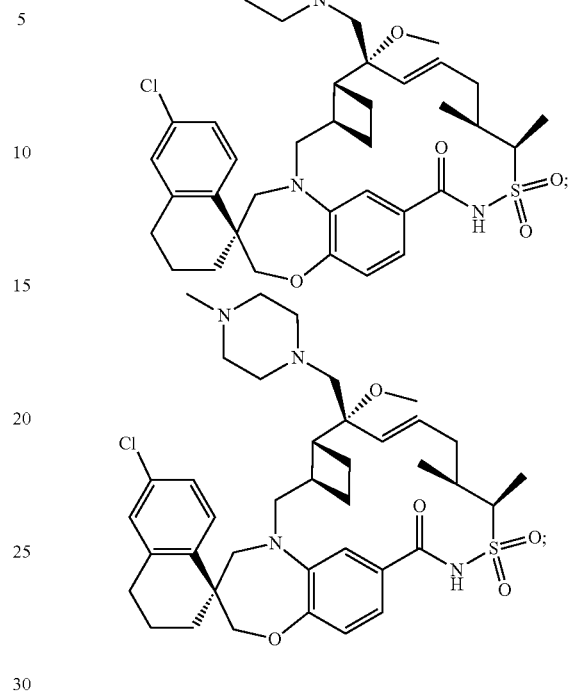
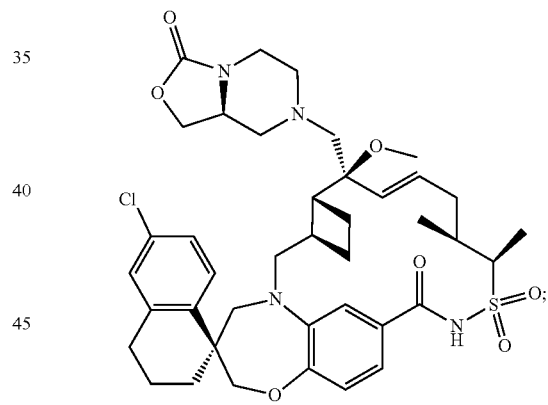
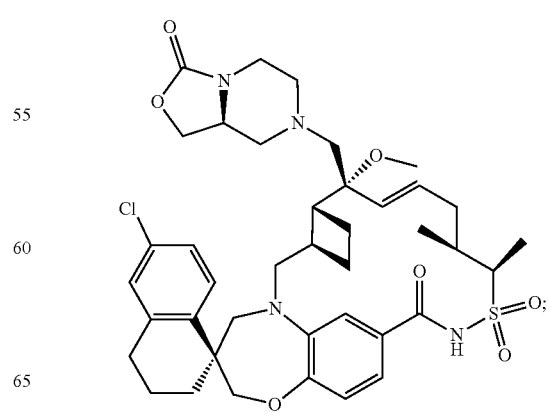

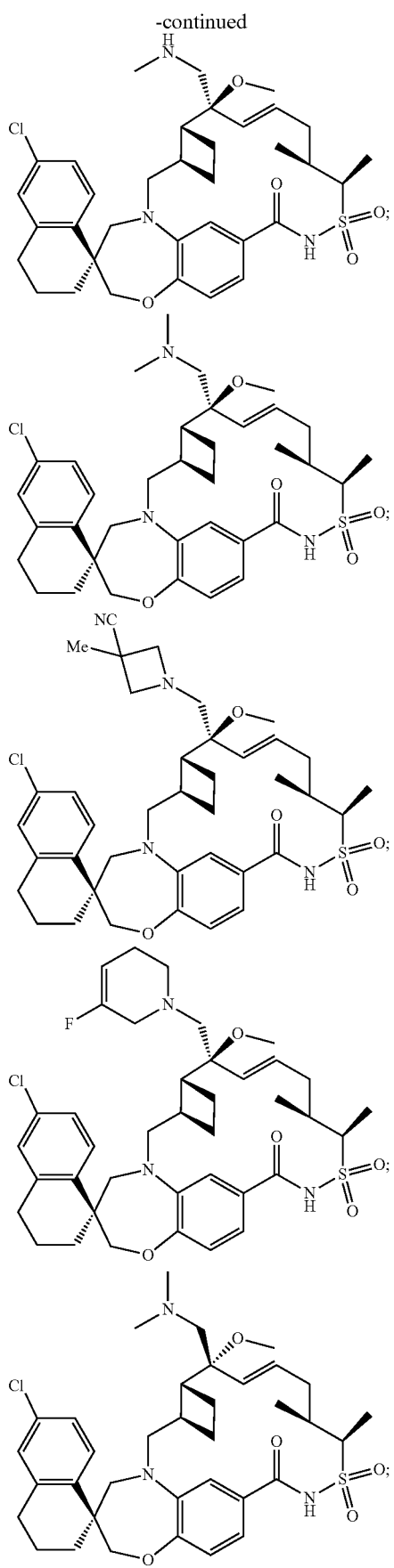
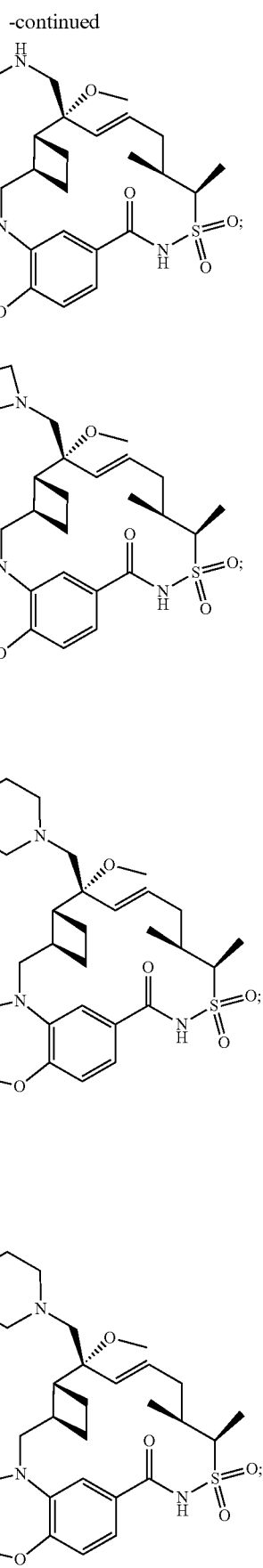

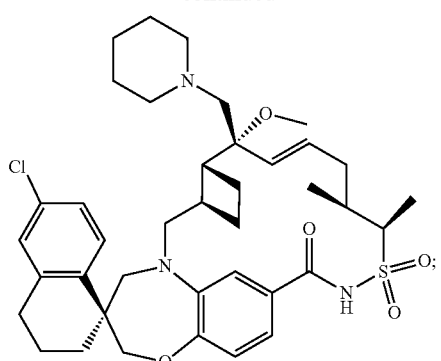
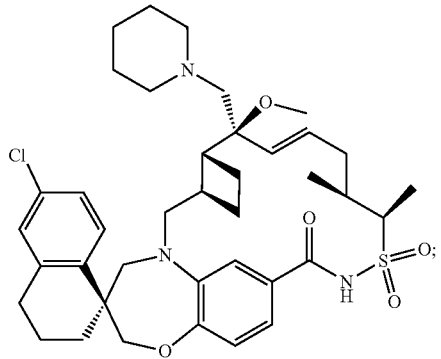
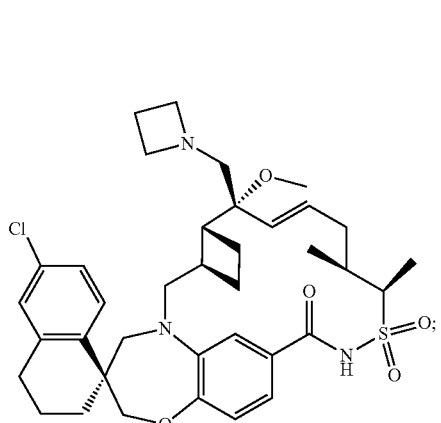
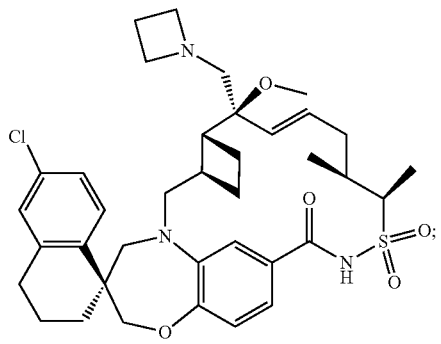
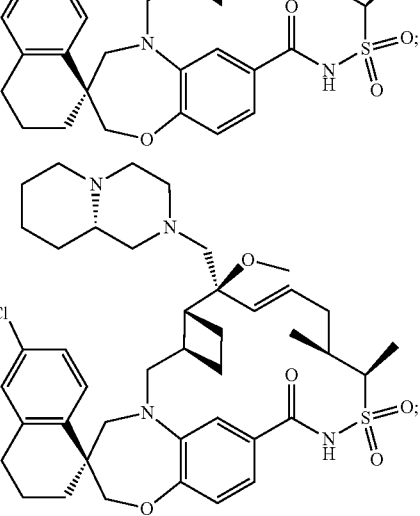
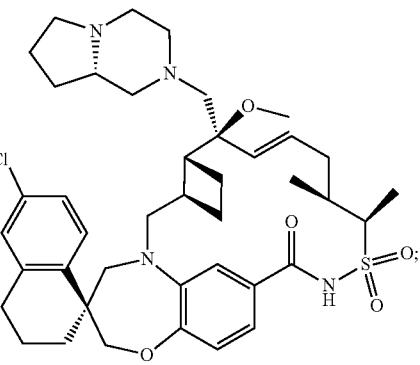

-continued
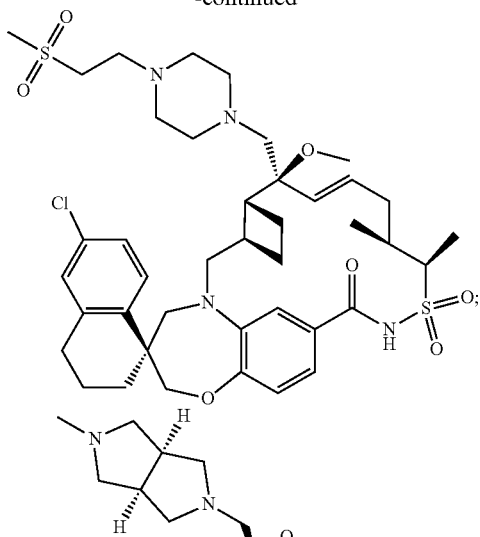
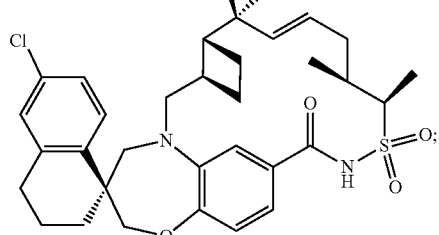
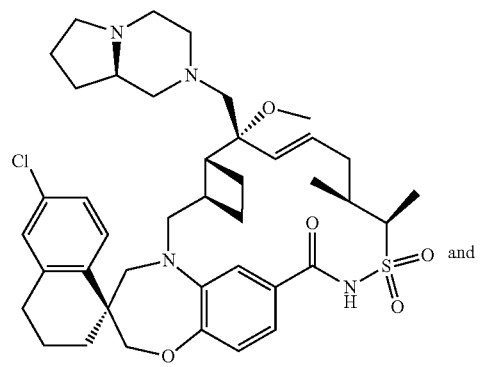
and
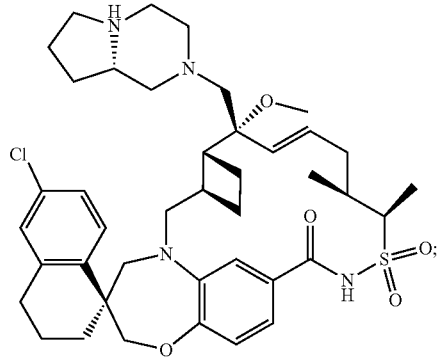
-continued
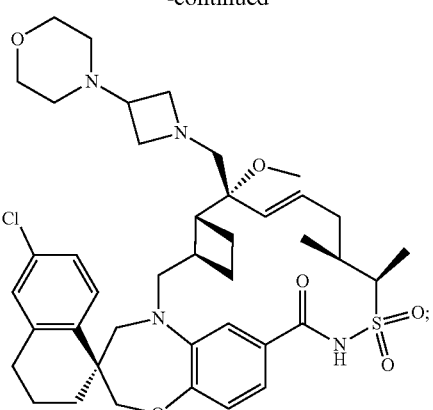
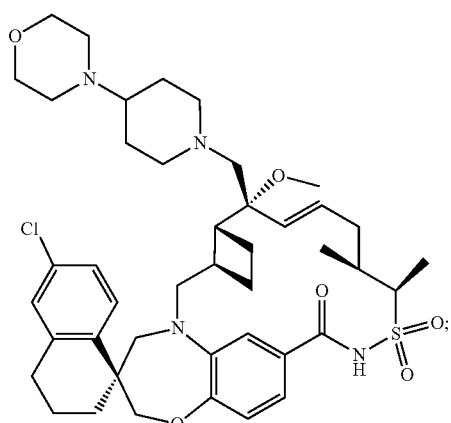
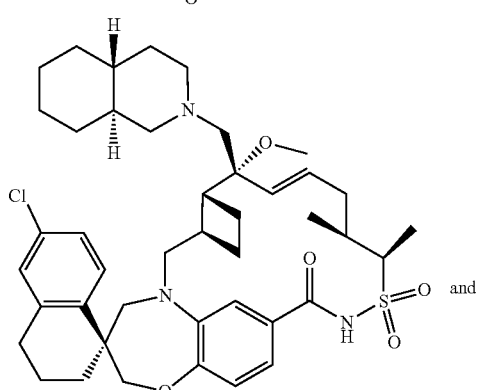
and
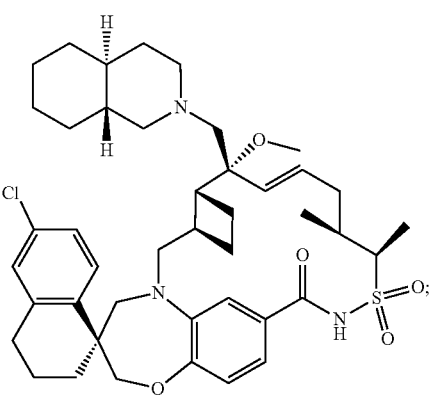

69
-continued
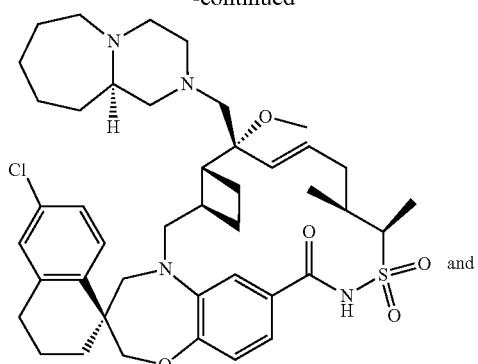
and
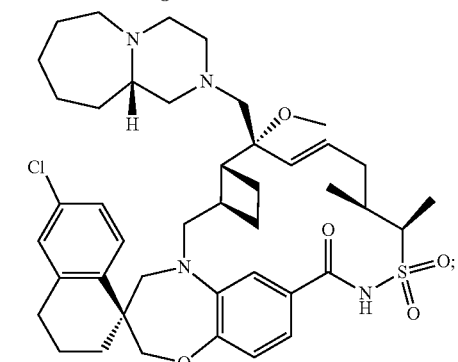
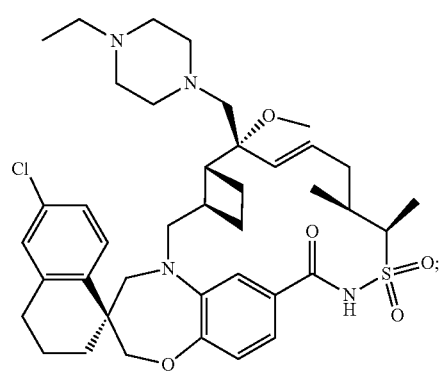
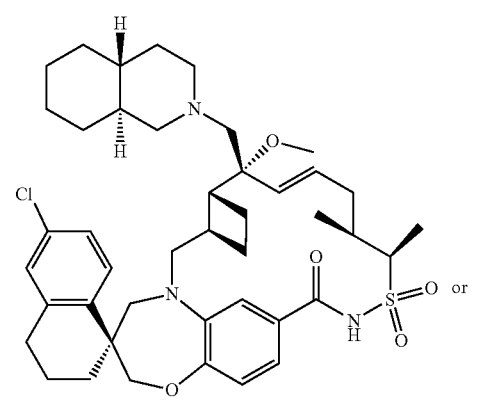
or
70
-continued
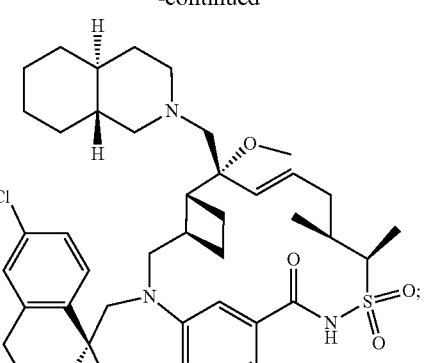
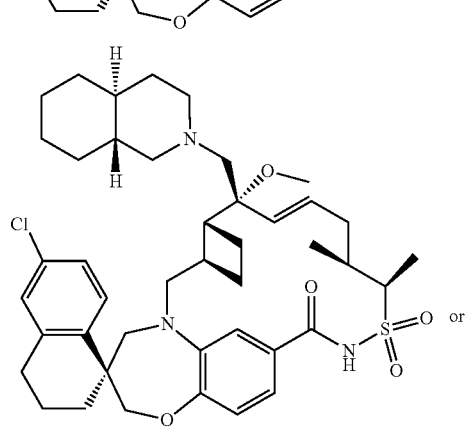
or
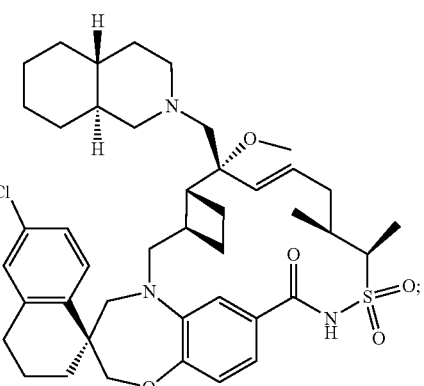
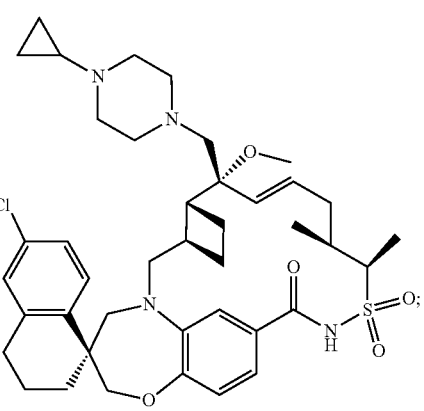

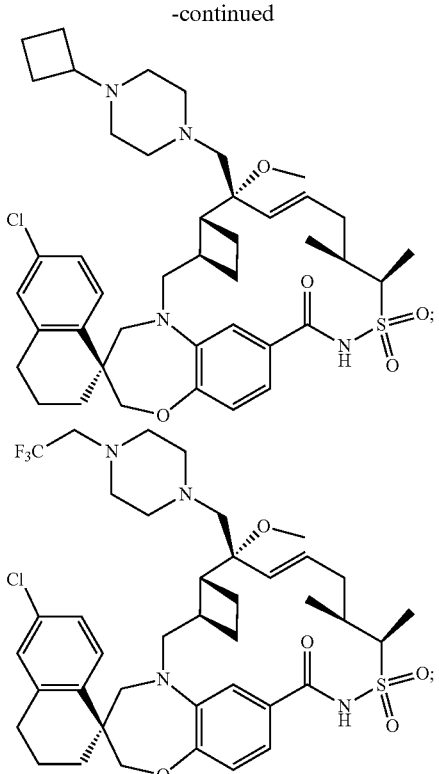
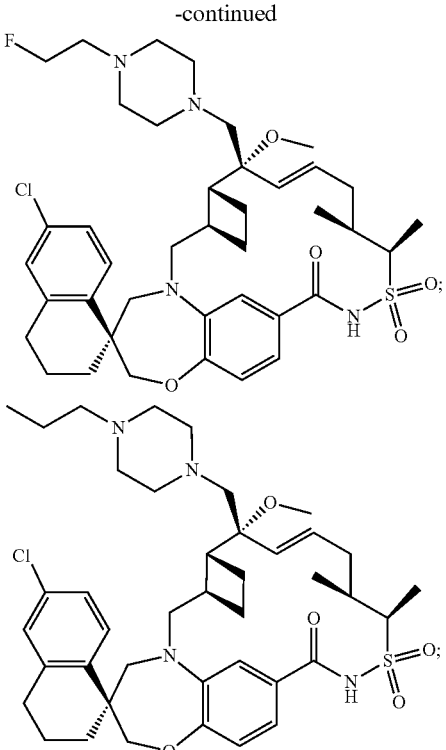

73
-continued
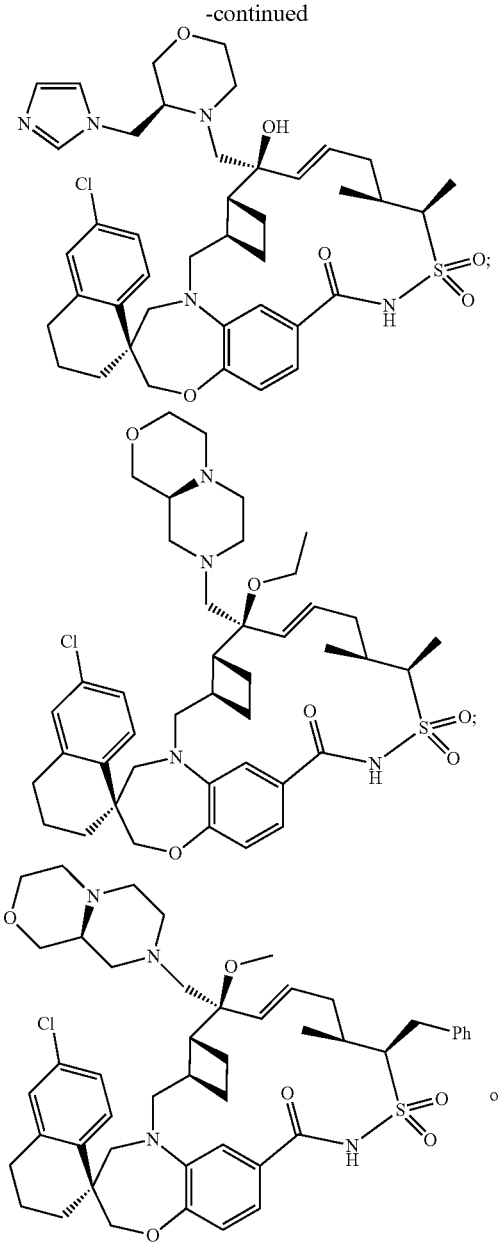
74
-continued
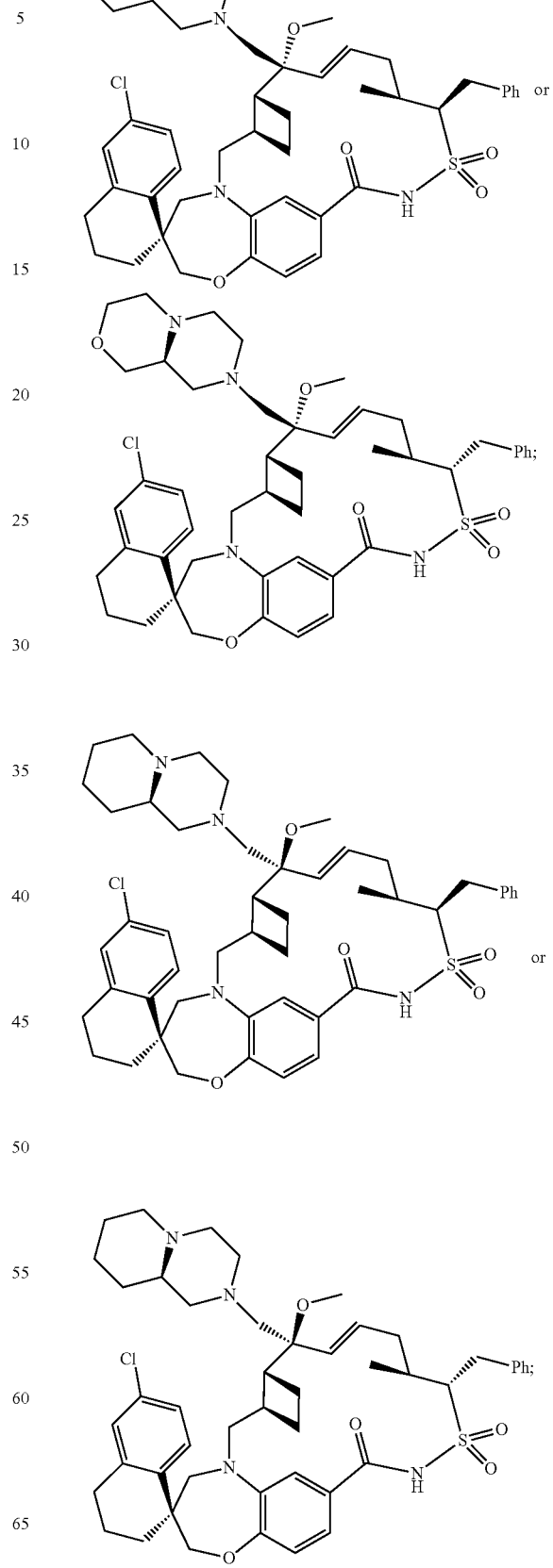

75
-continued
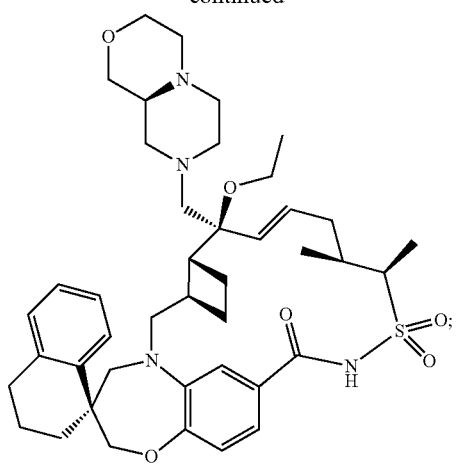
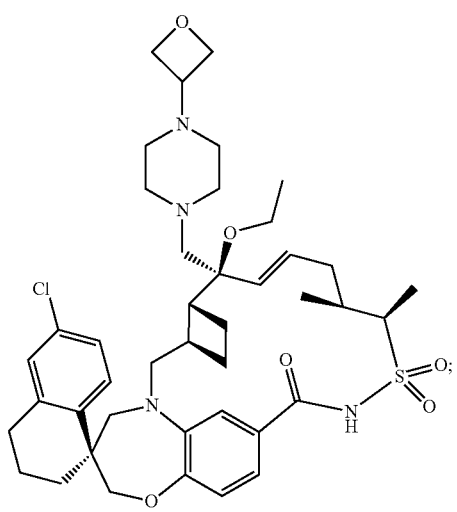
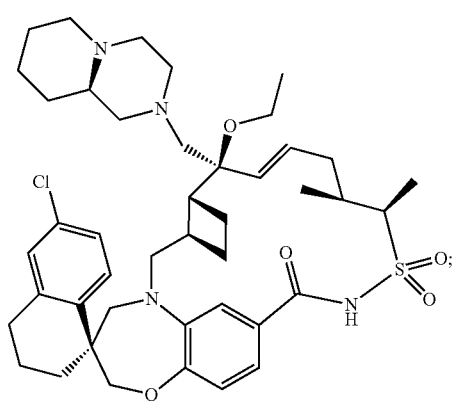
76
-continued
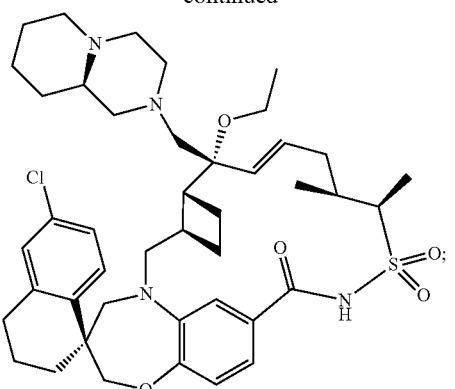
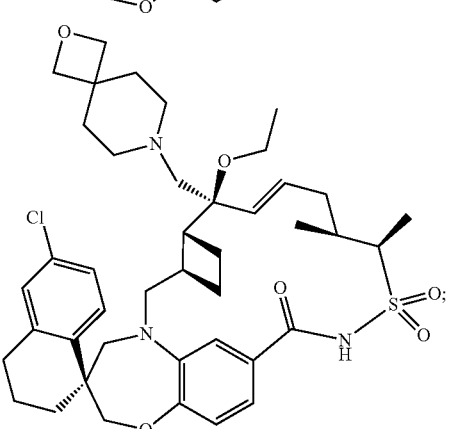
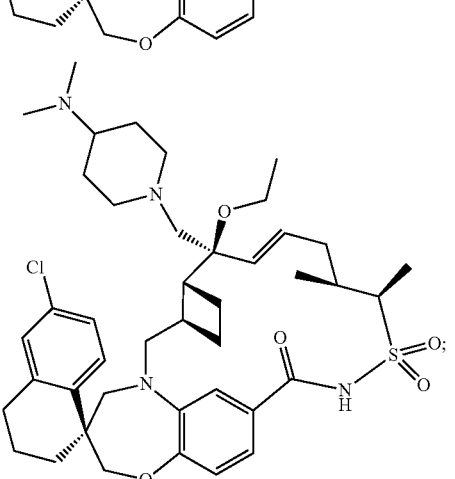
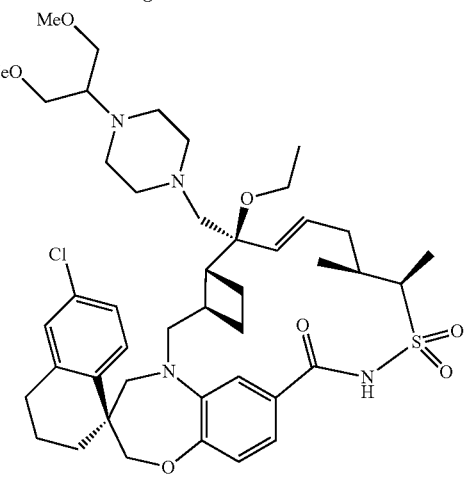

-continued
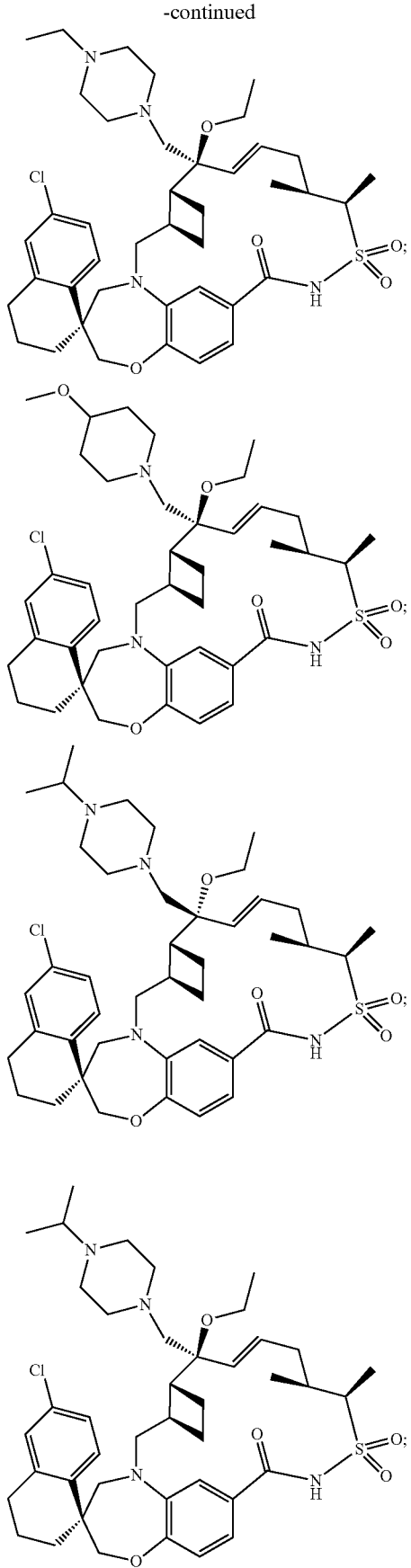
-continued
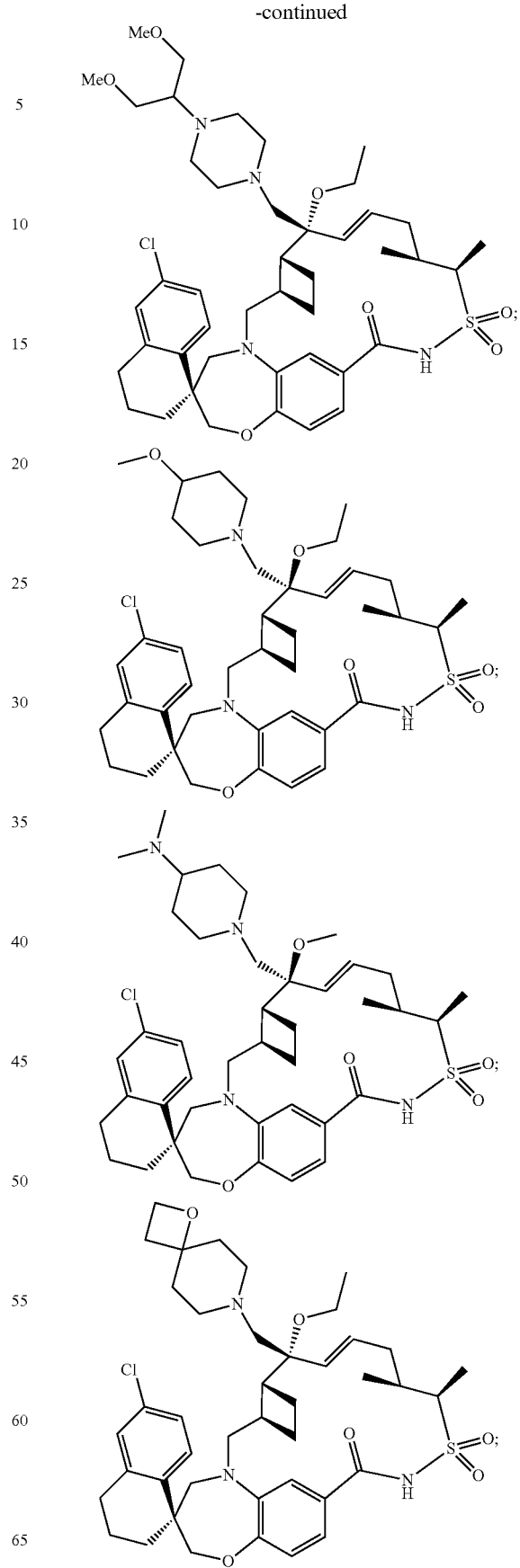

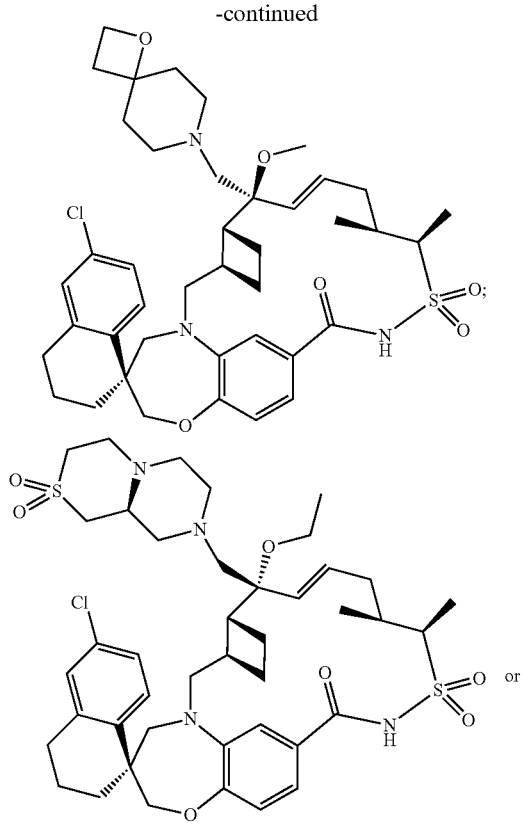
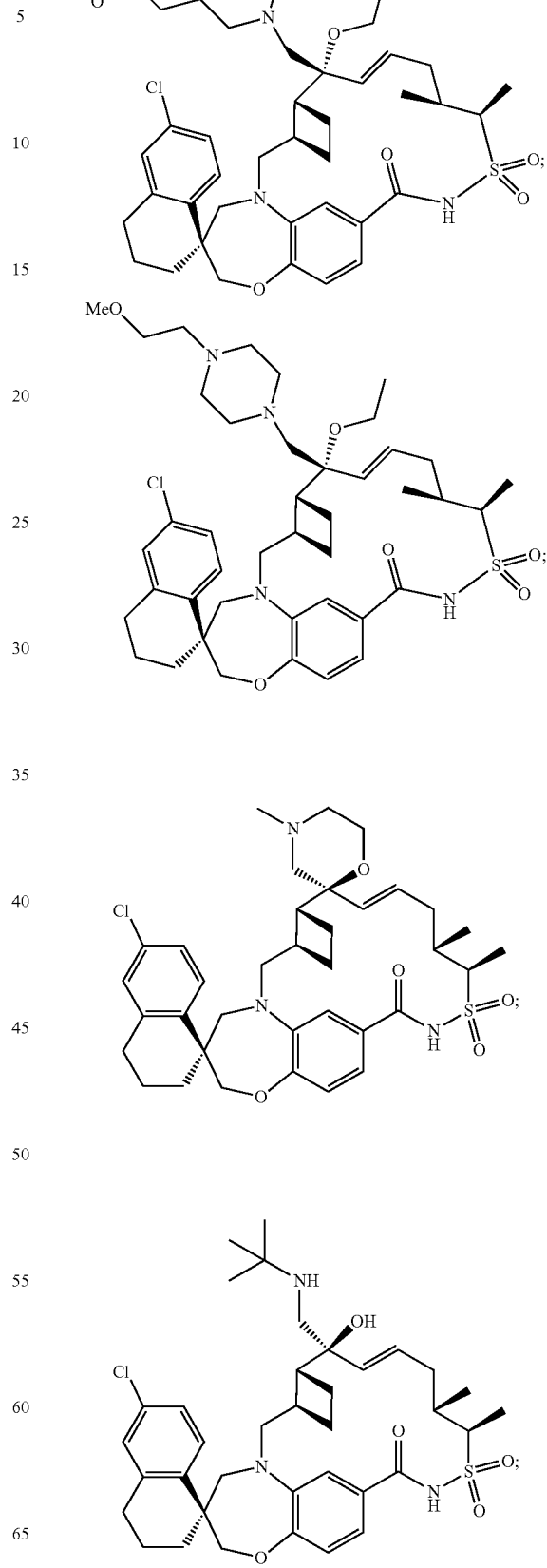

81
-continued
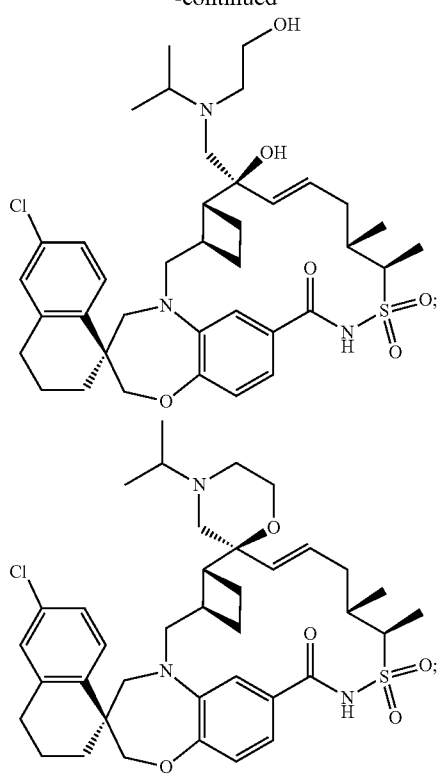
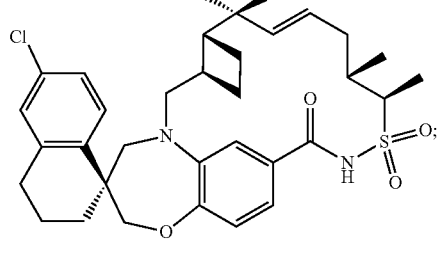
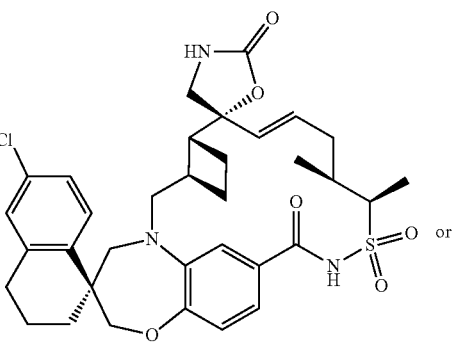
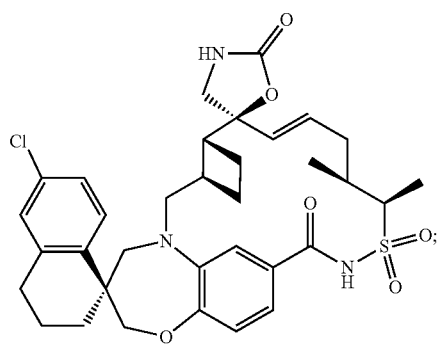
82
-continued
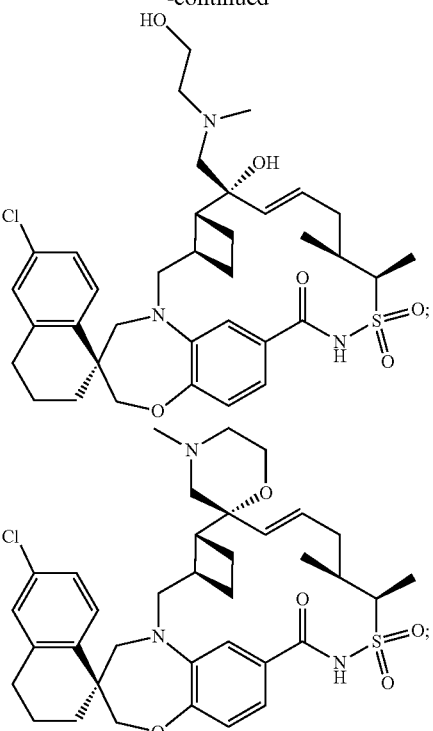

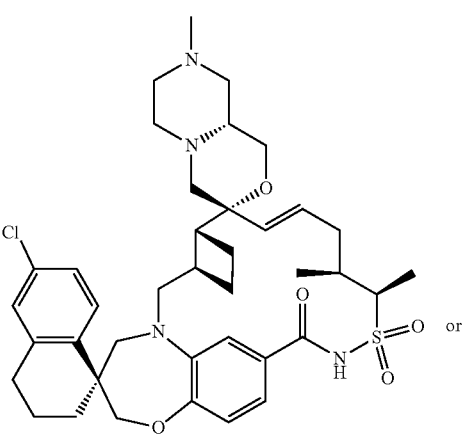

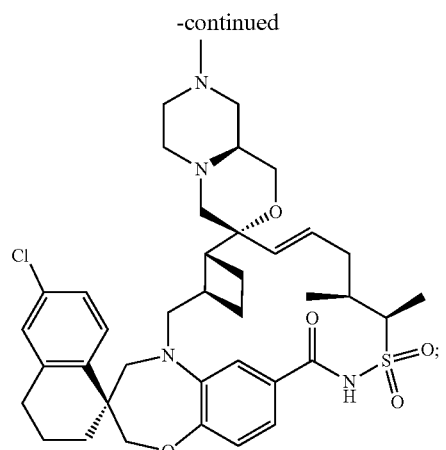
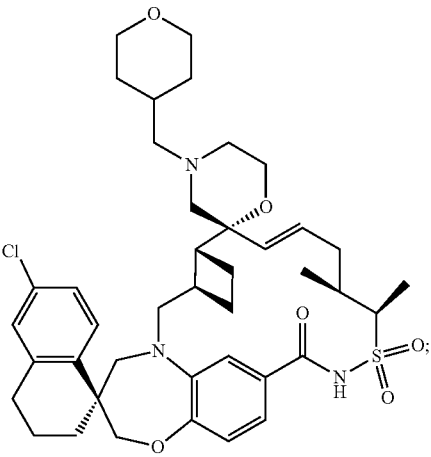
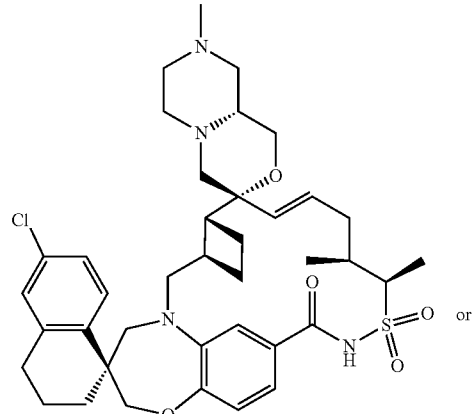
or
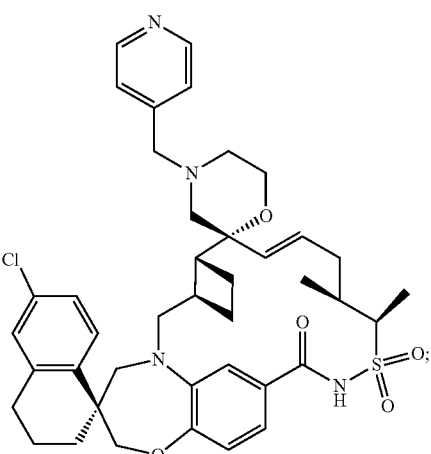
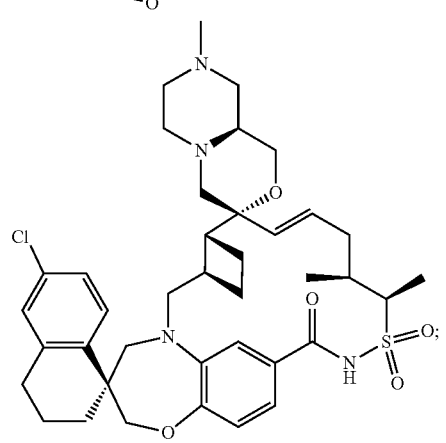
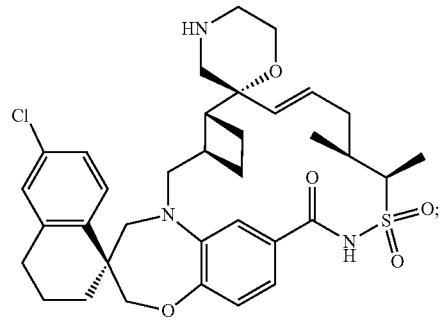
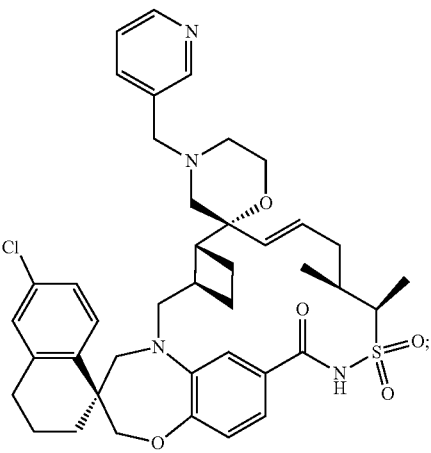

85
-continued
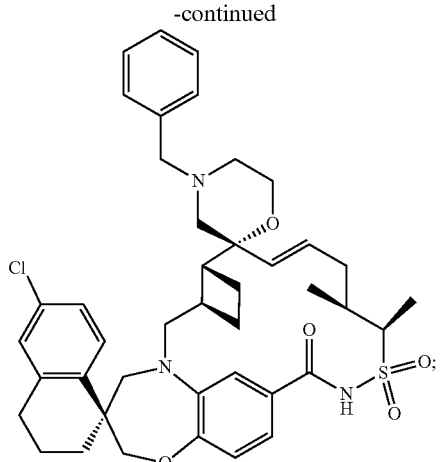
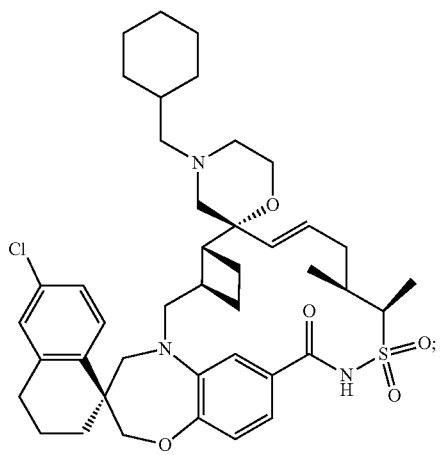
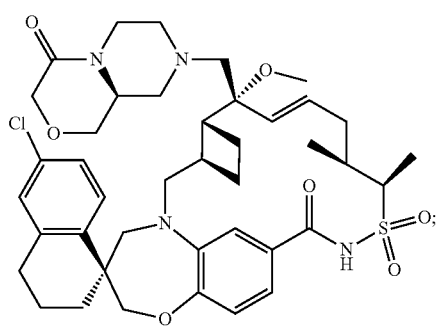
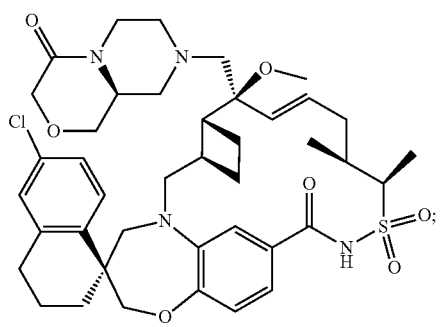
86
-continued
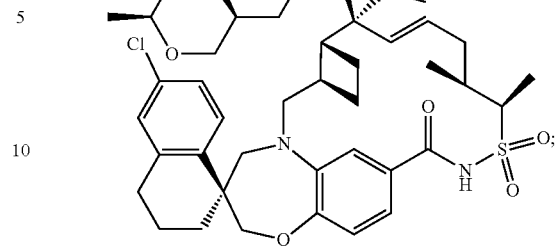
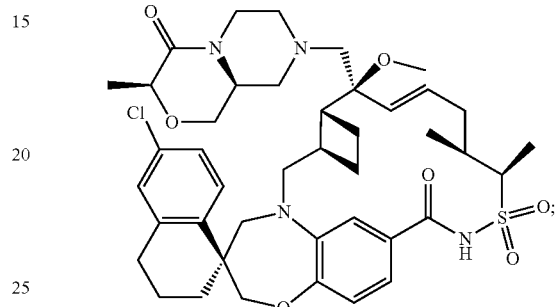
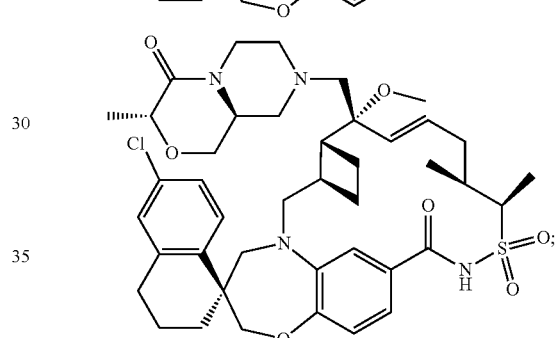
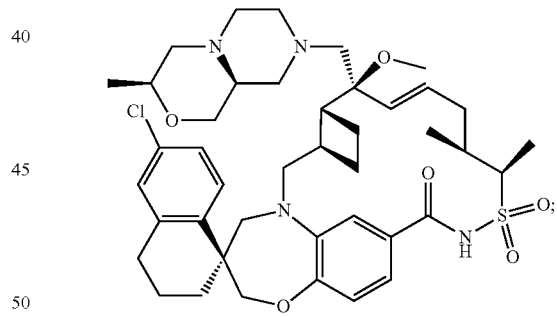

87
-continued
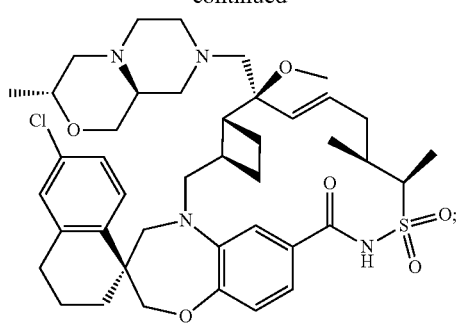
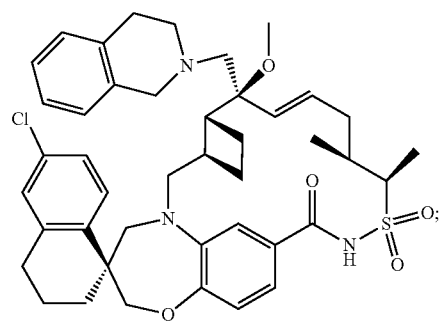
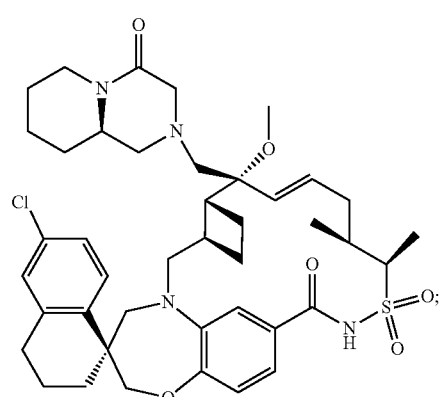
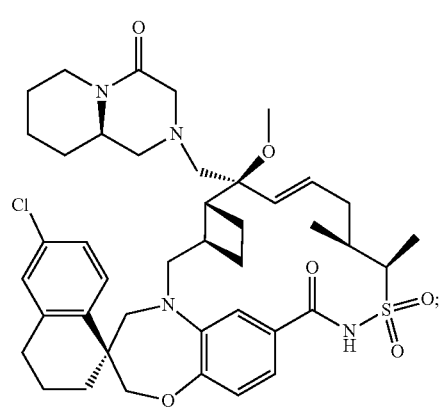
88
-continued
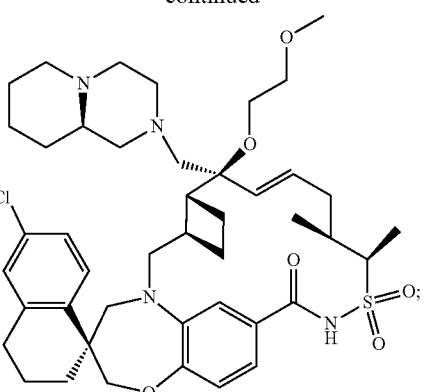
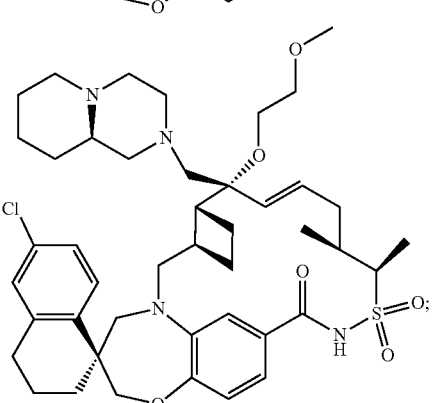
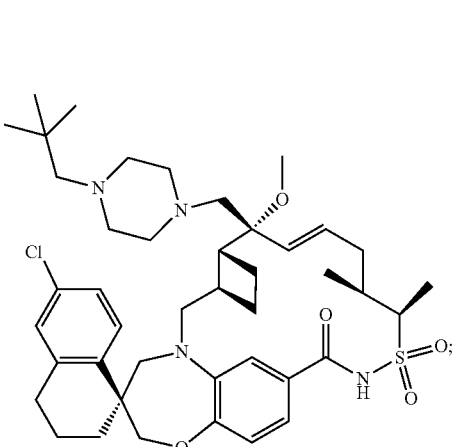
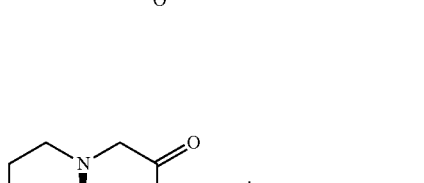
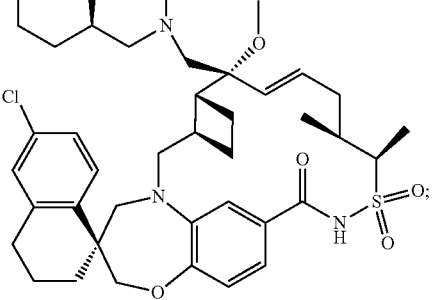

89
-continued
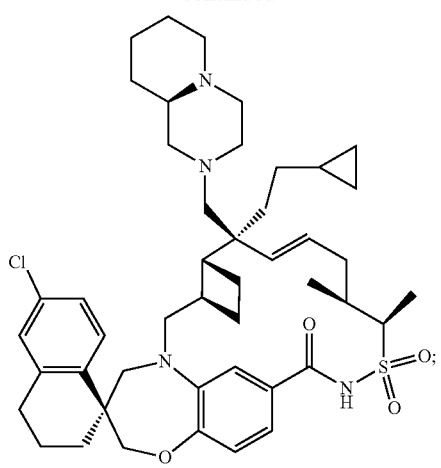
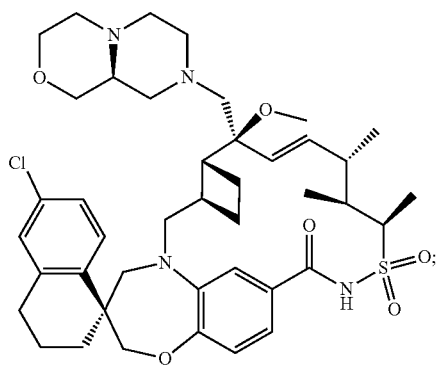
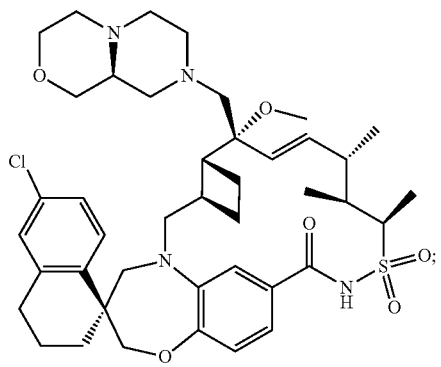
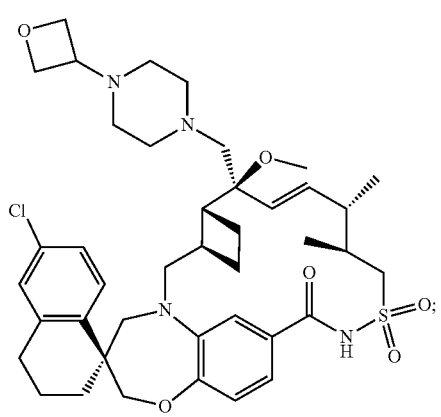
90
-continued
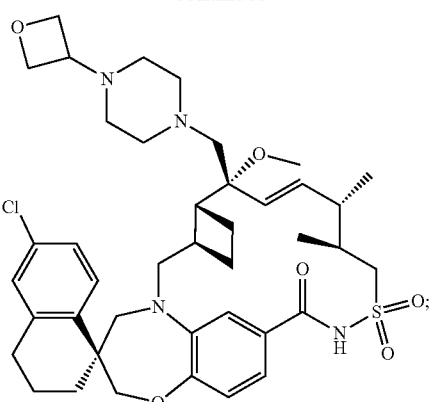
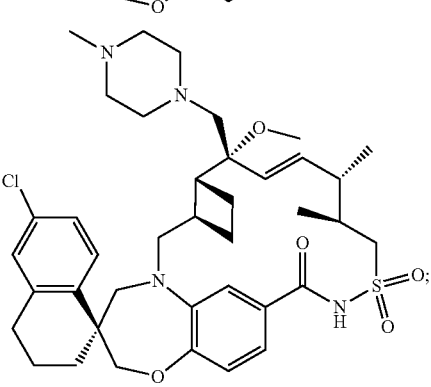
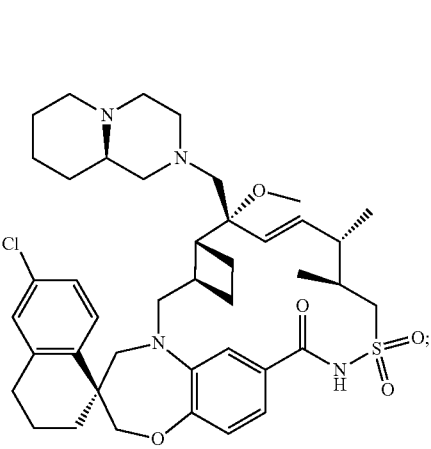
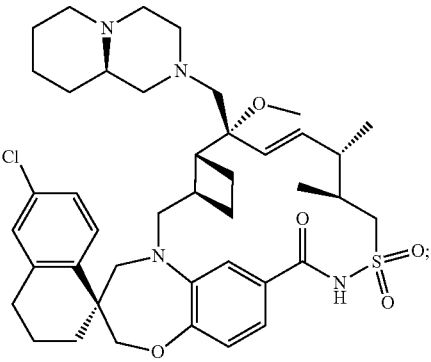
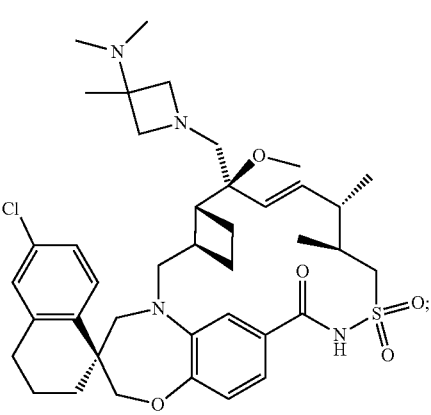

91
-continued
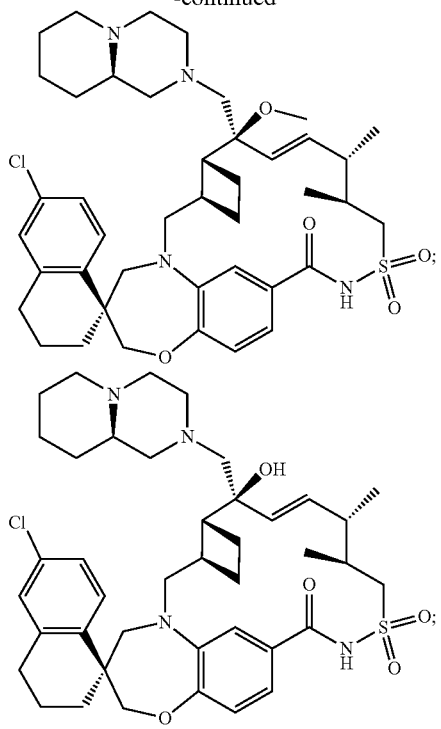
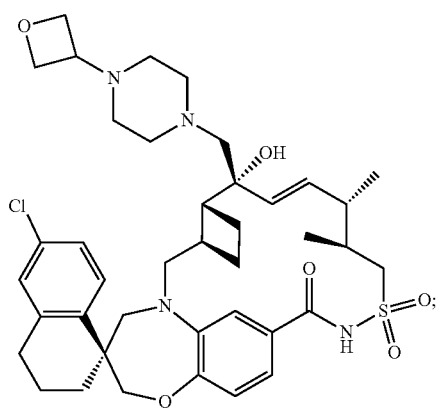
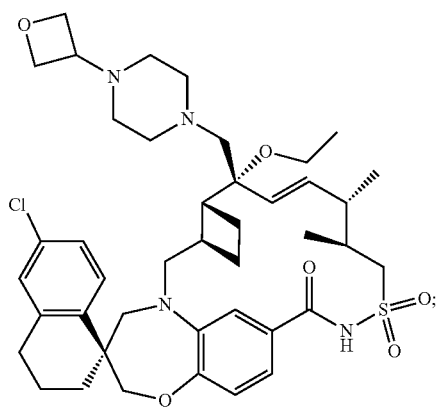
92
-continued
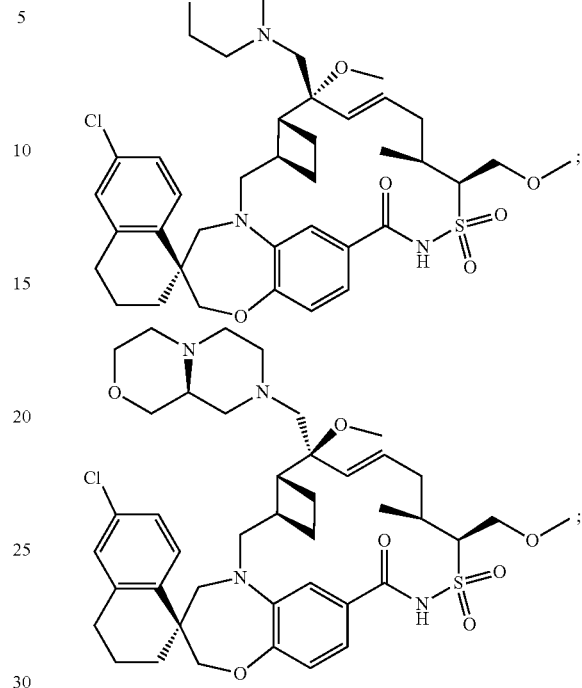
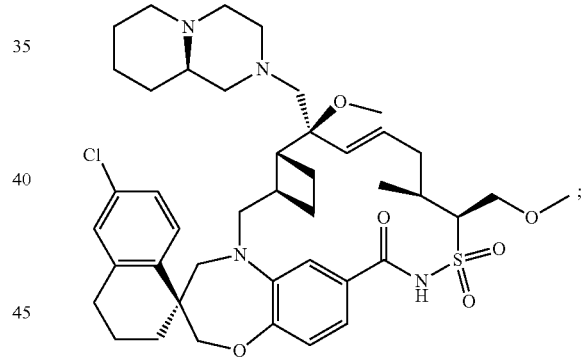
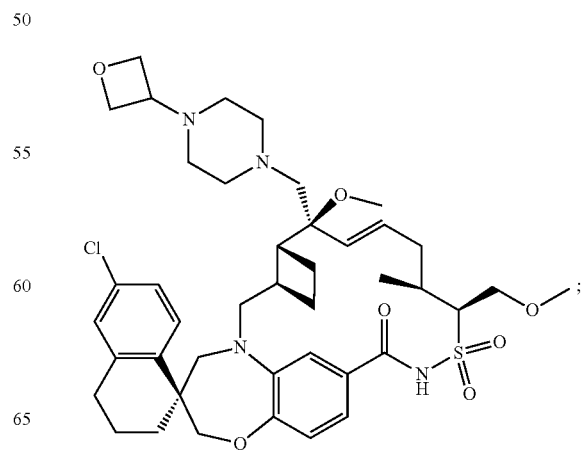

93
-continued
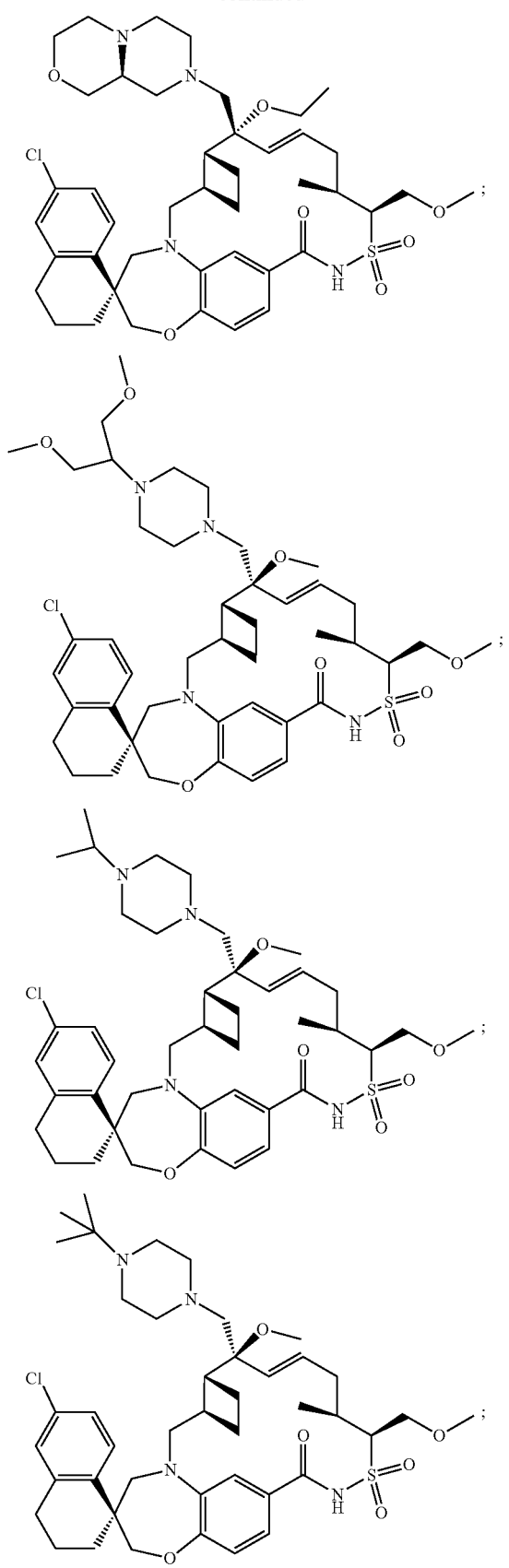
94
-continued
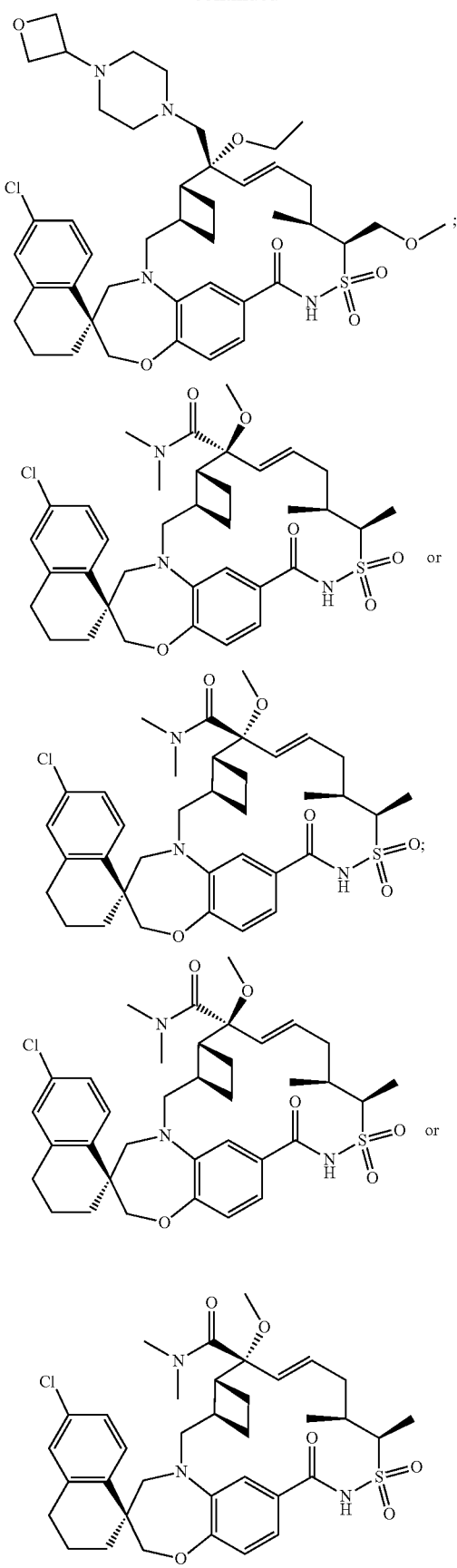

95
-continued
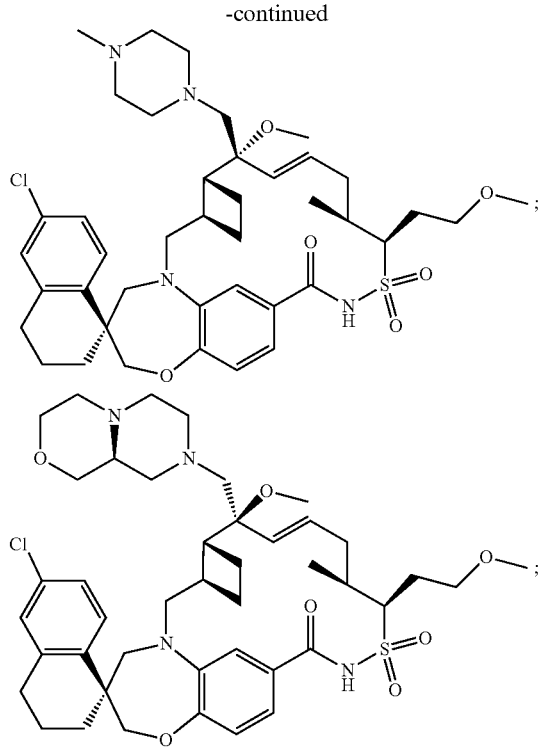
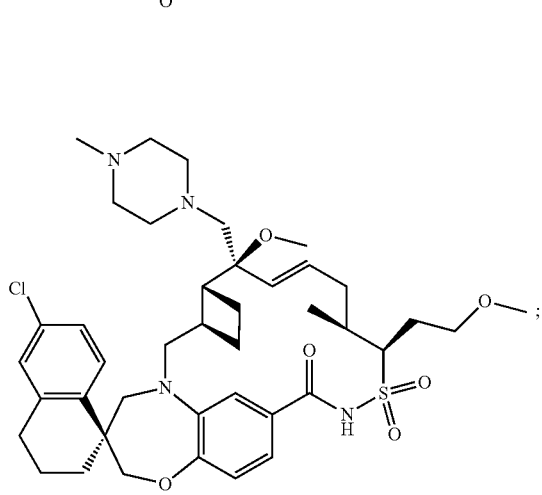
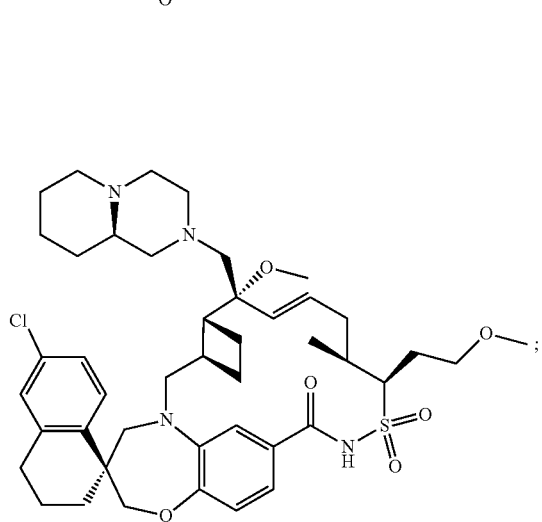
96
-continued
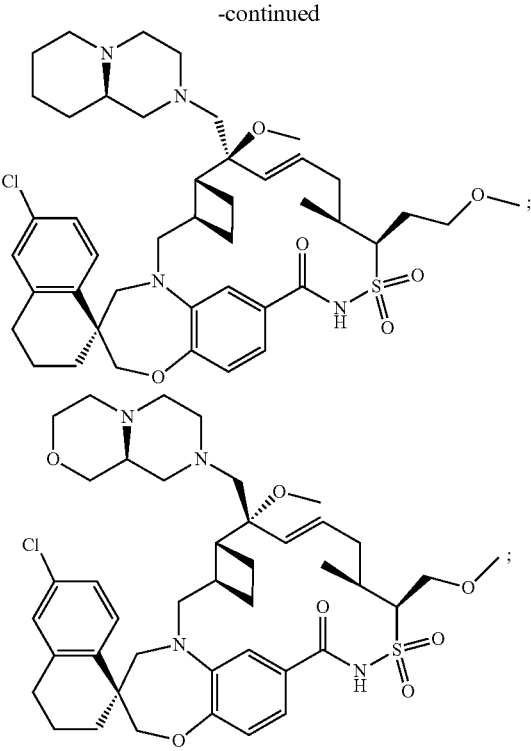
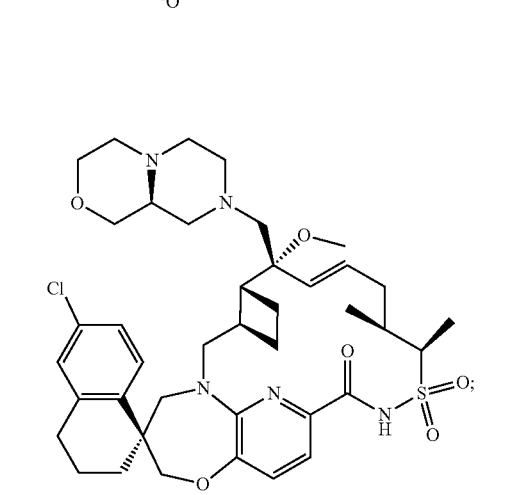
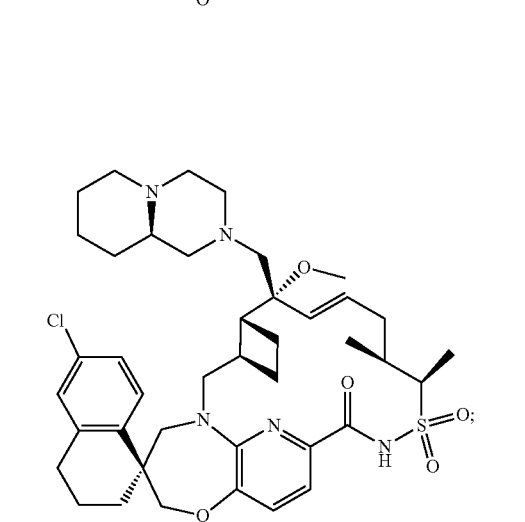

97
-continued
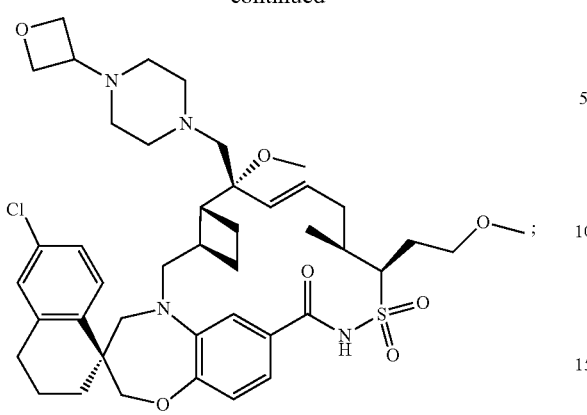
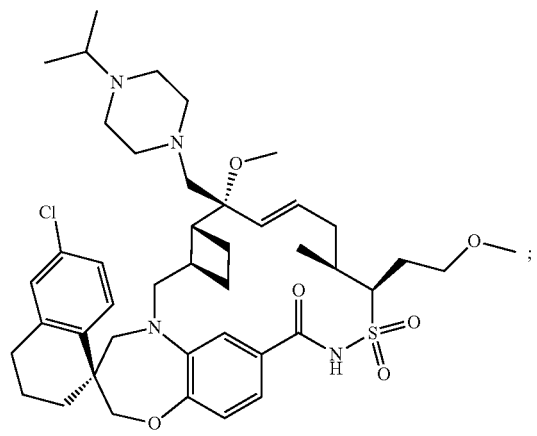
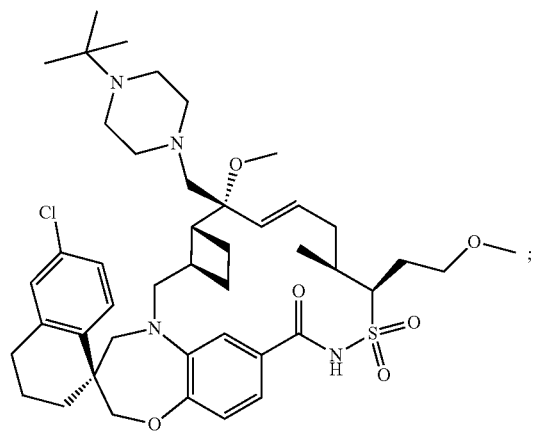
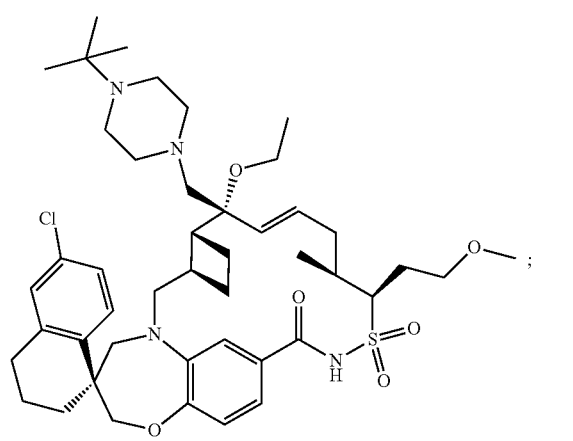
98
-continued
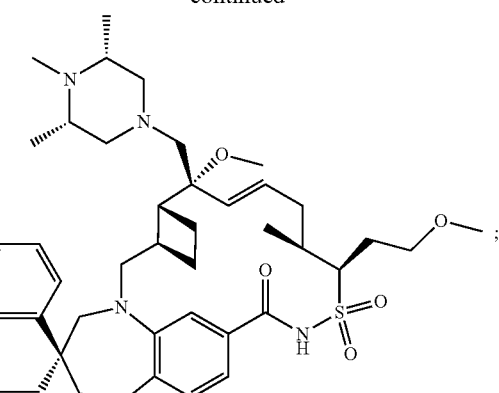
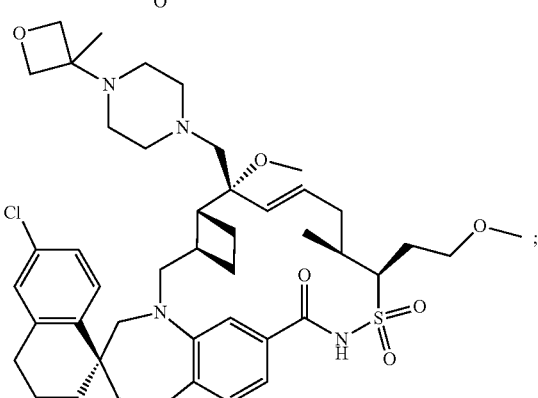
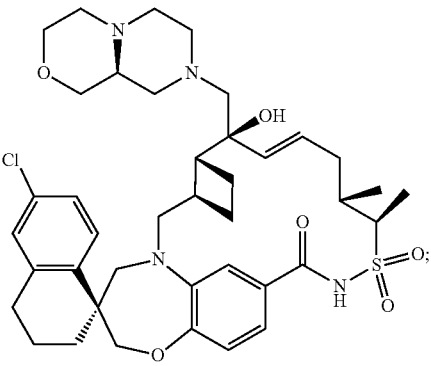
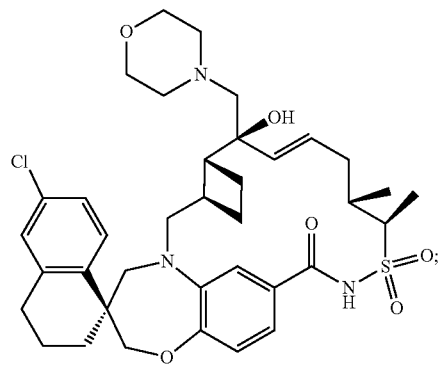

99
-continued
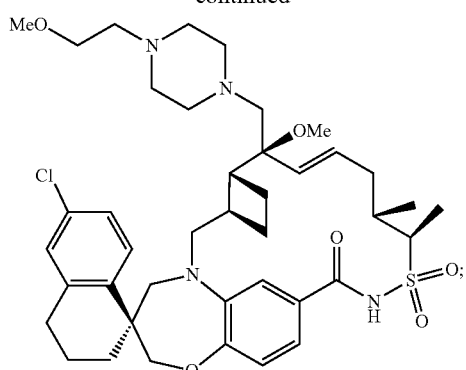
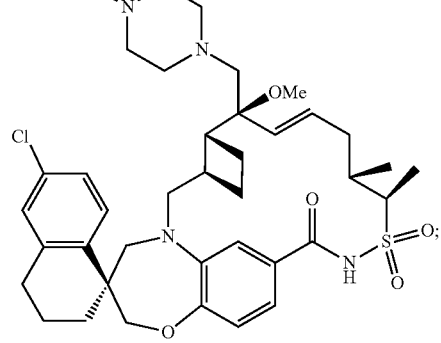
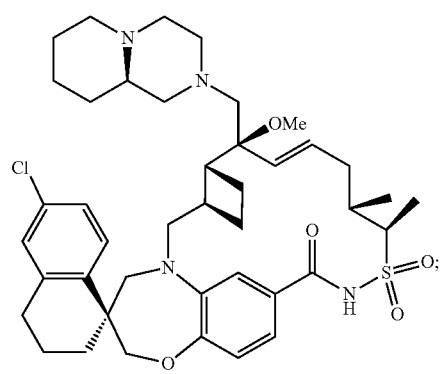
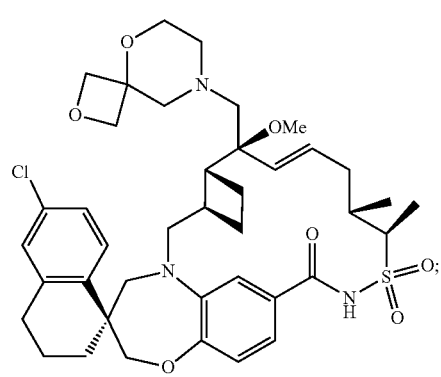
100
-continued
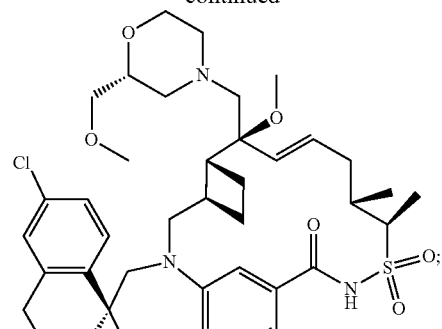
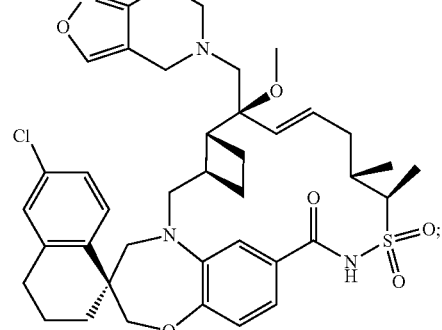
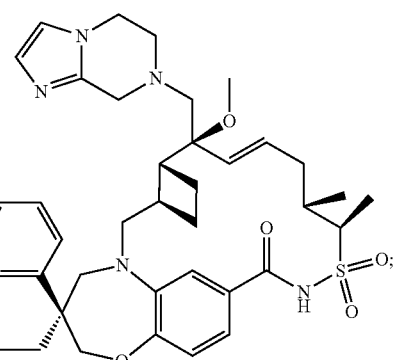
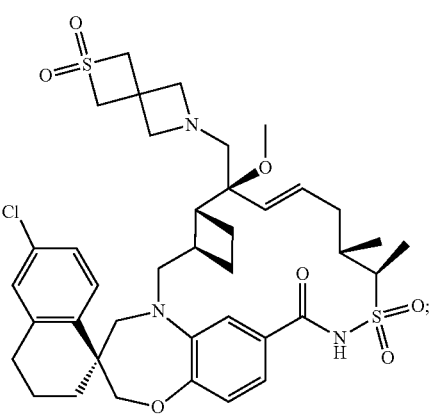

-continued
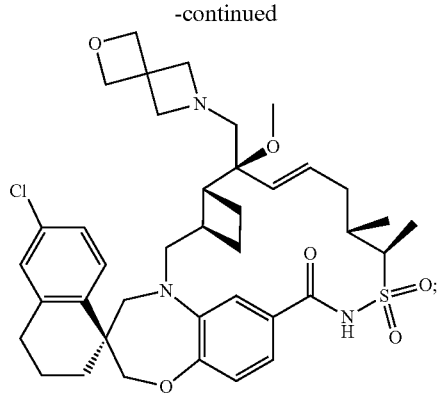
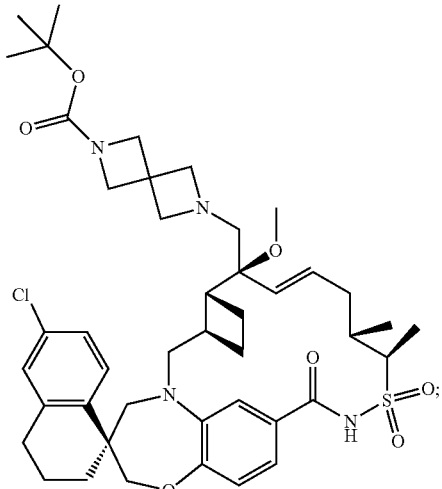
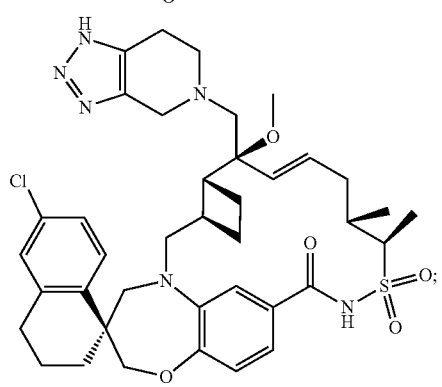
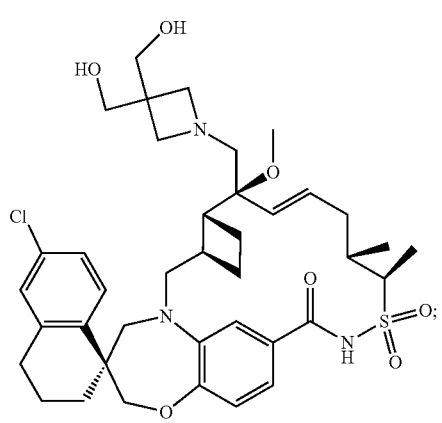
-continued
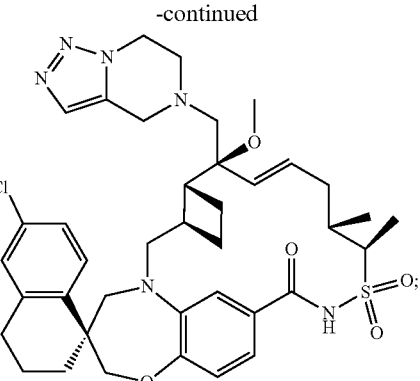
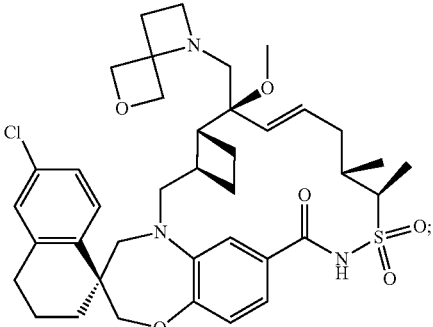
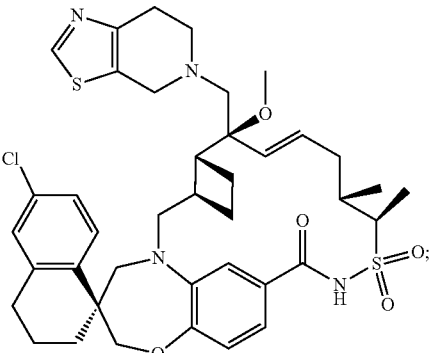
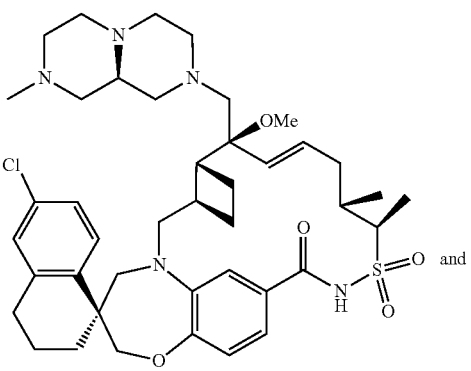
and

103
-continued
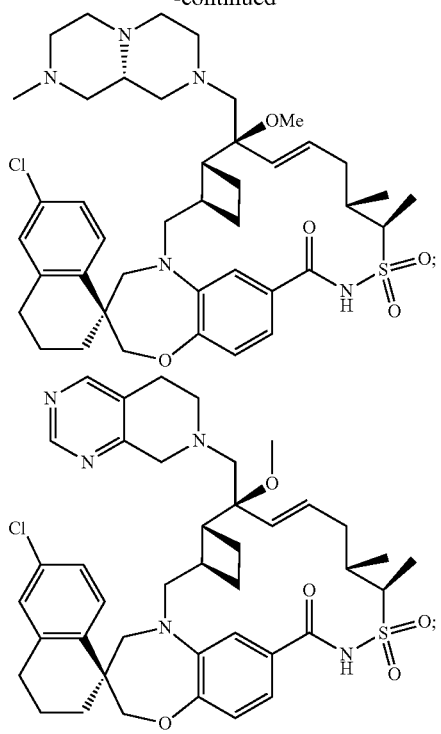
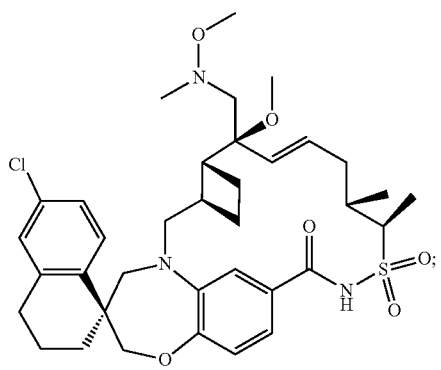
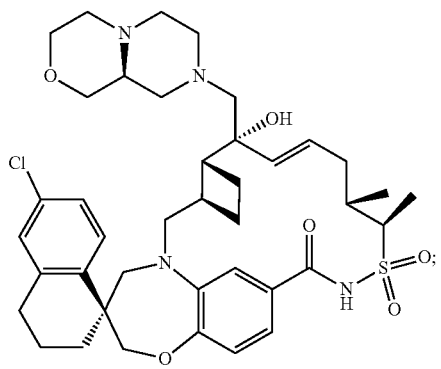
104
-continued
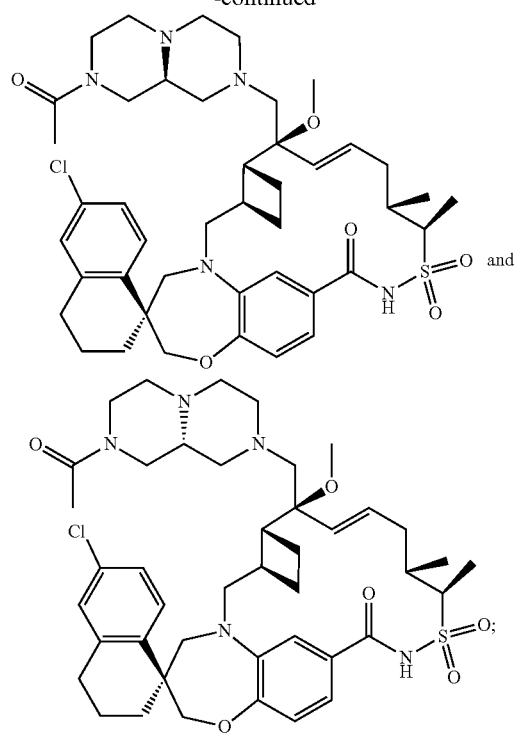
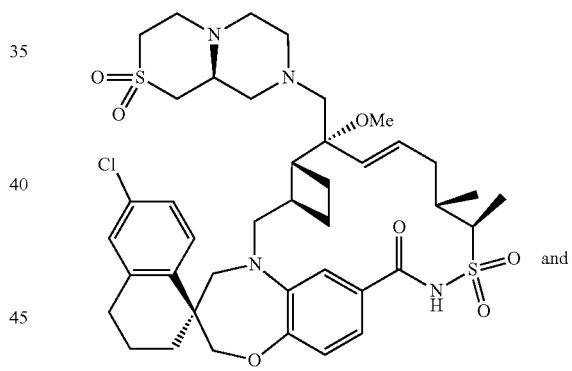
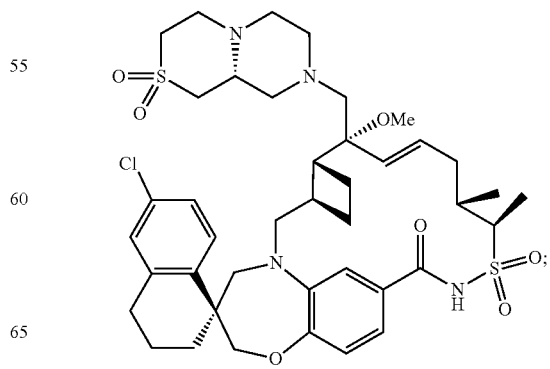

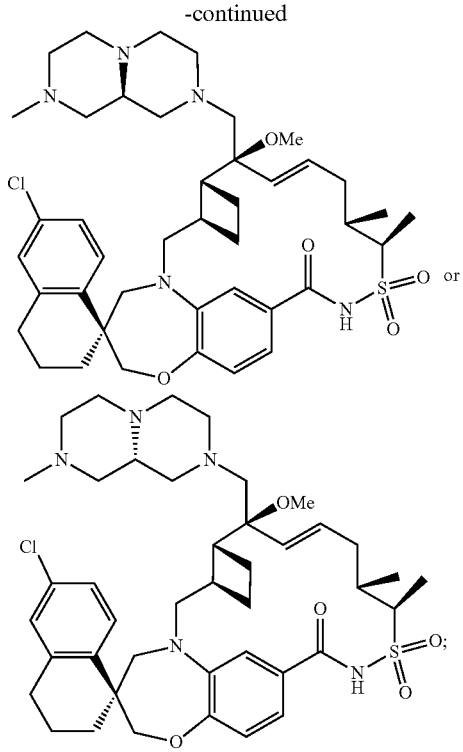
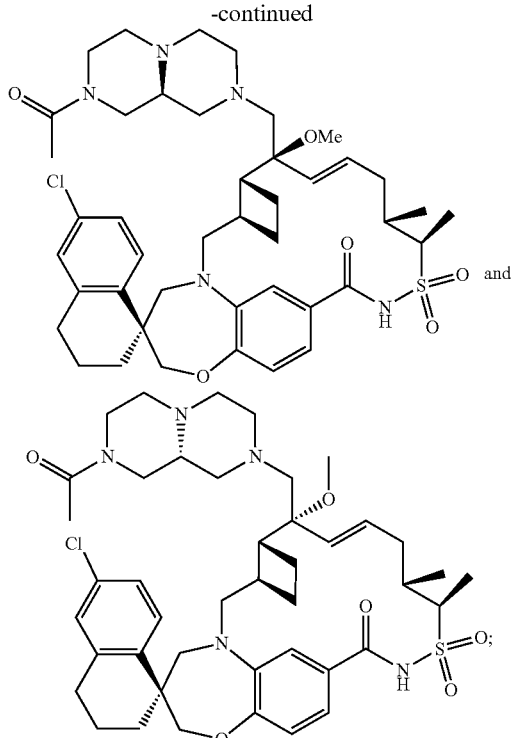
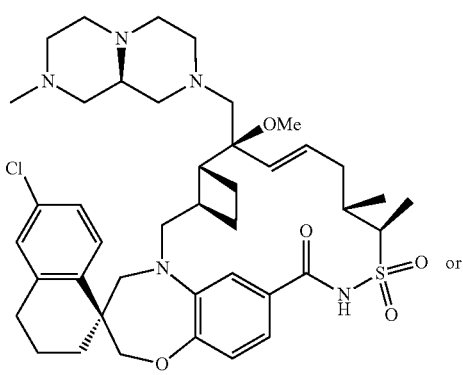
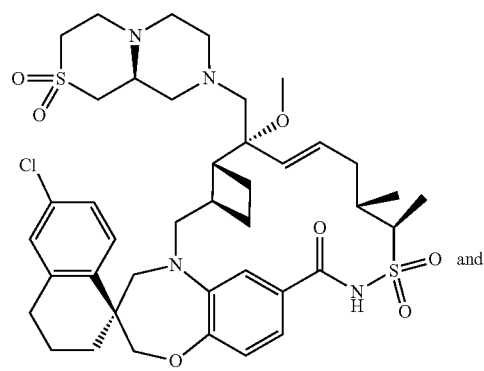
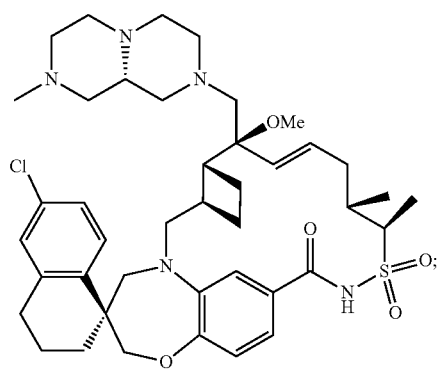
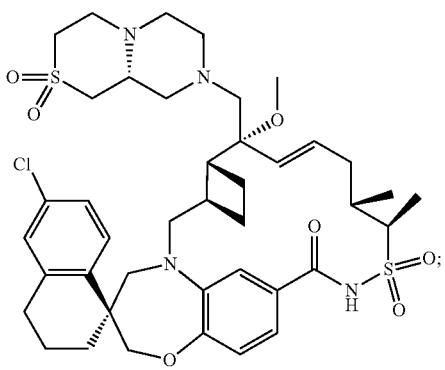

107
-continued
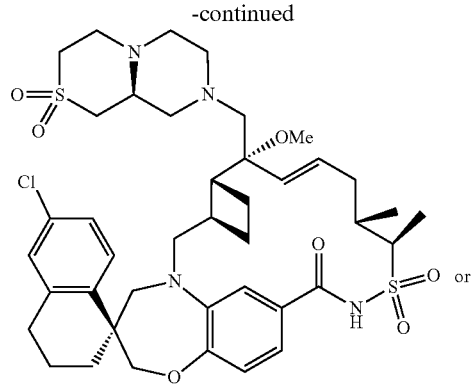
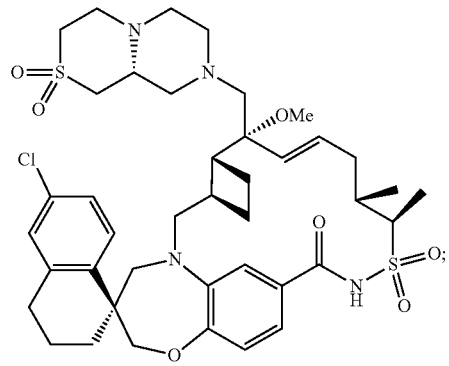
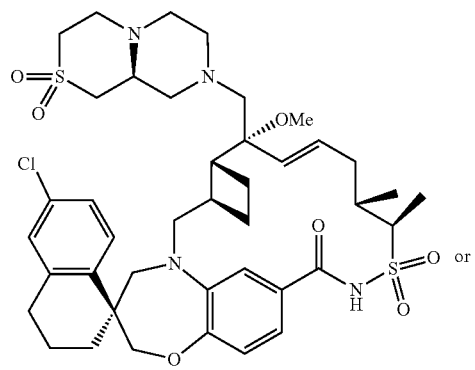
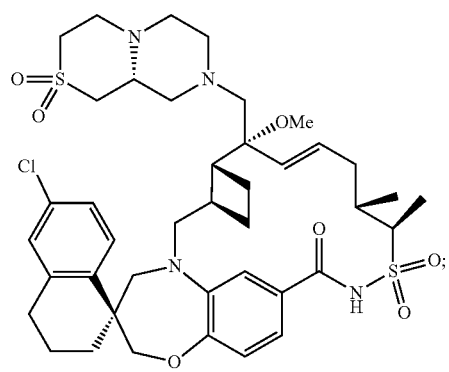
108
-continued
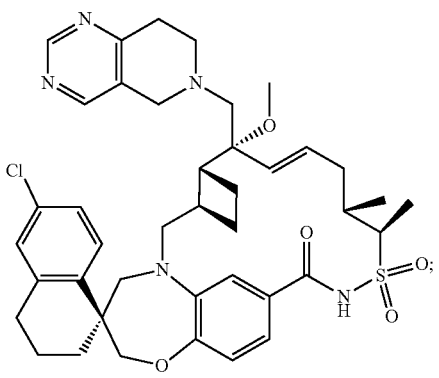
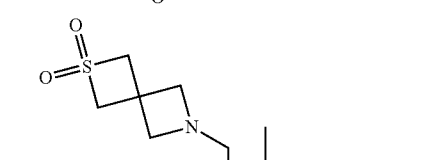
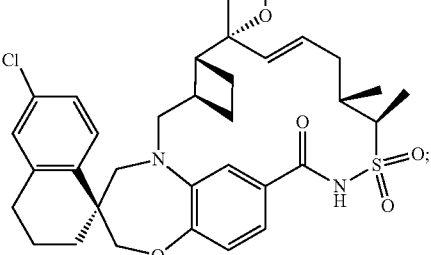
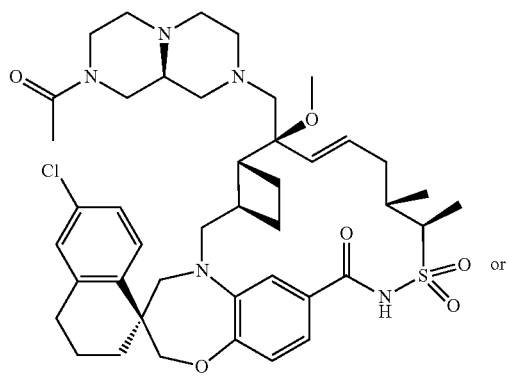

109
-continued
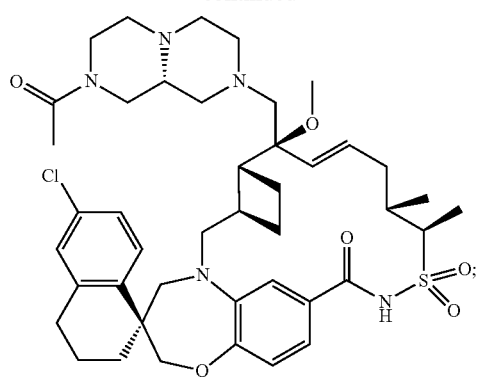
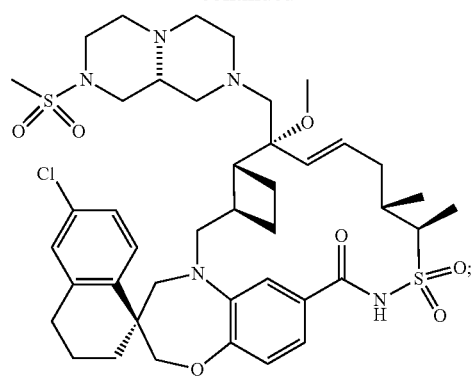
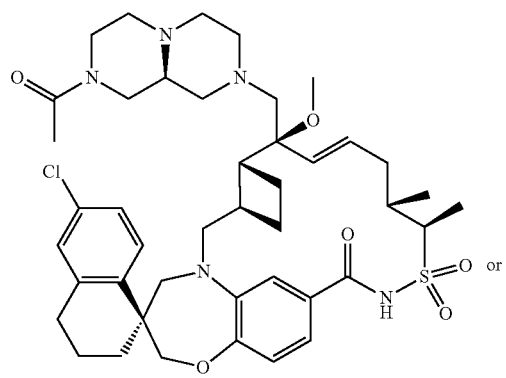
or
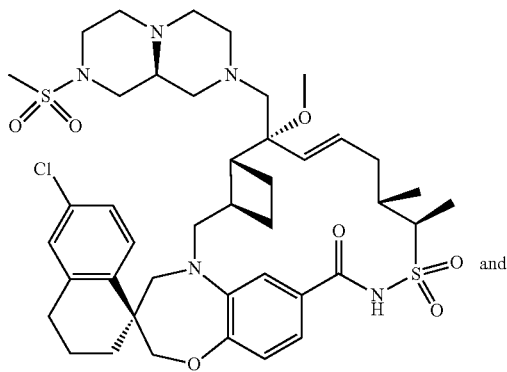
and
110
-continued
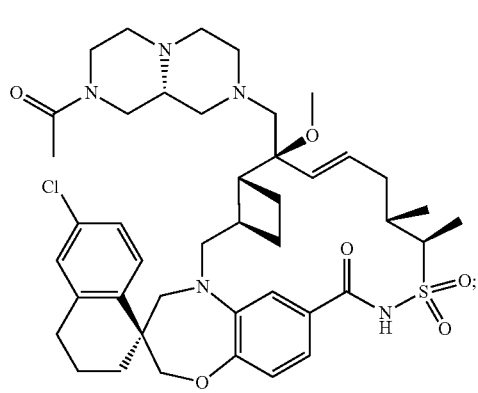
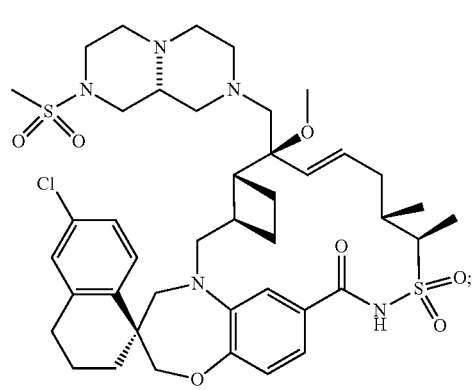
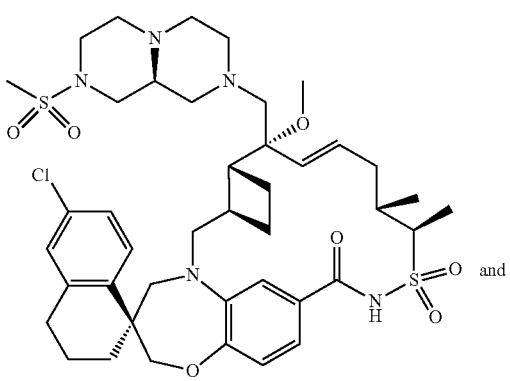
and
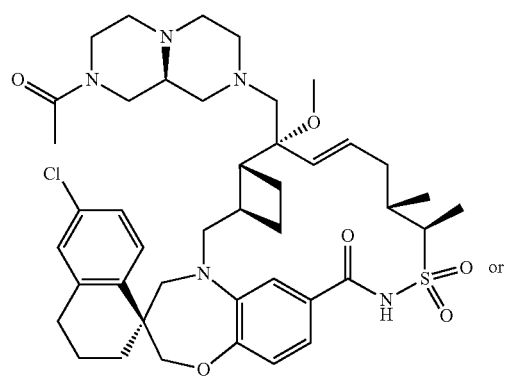
or

111
-continued
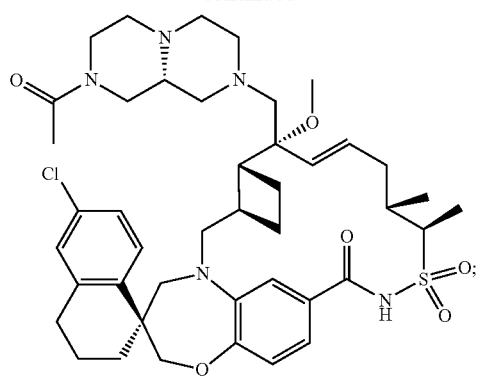
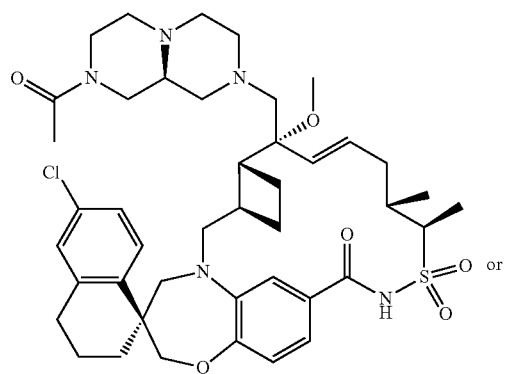
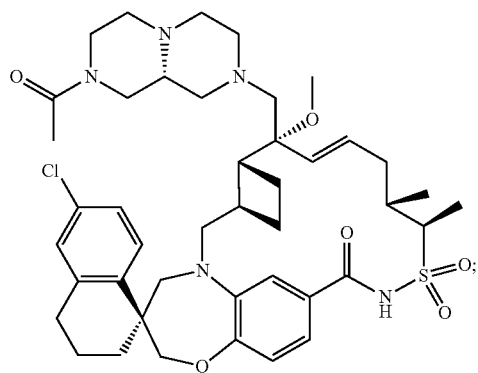
or
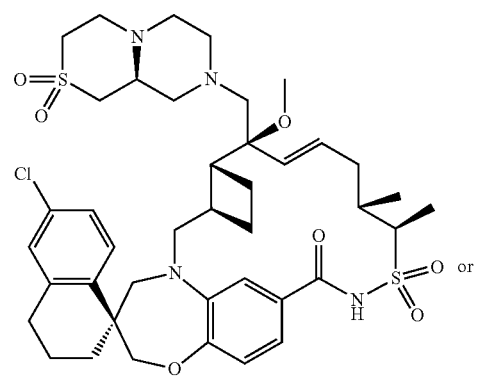
or
112
-continued
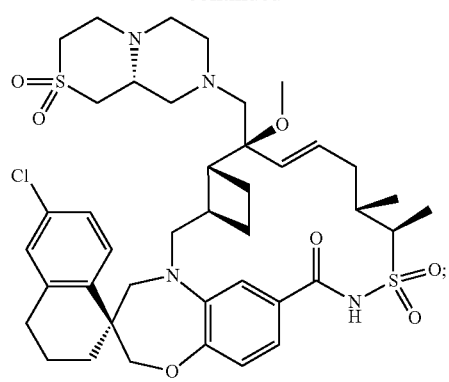
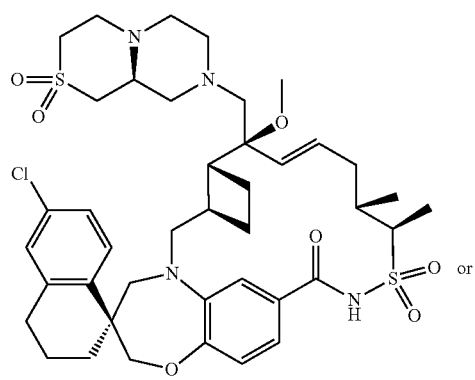
or
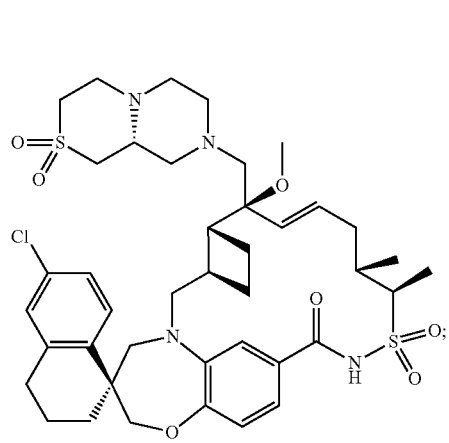
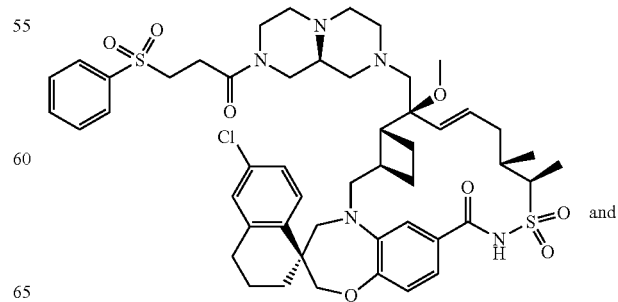
and

113
-continued
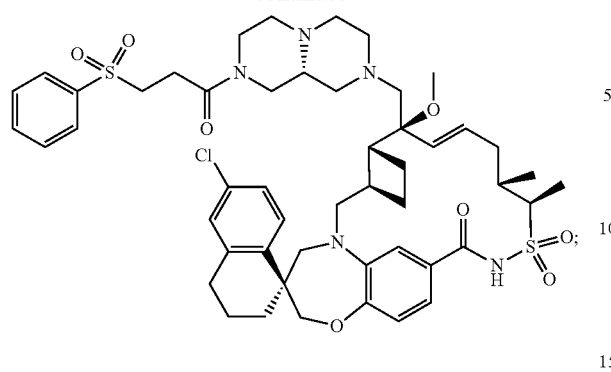
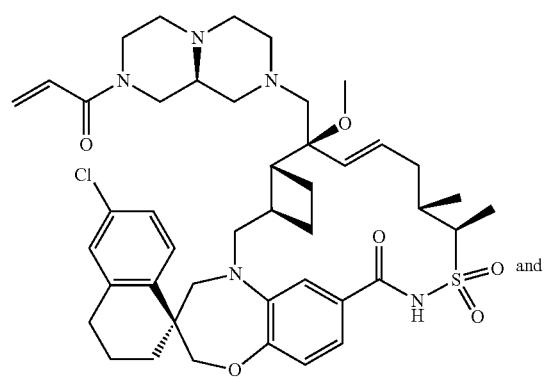
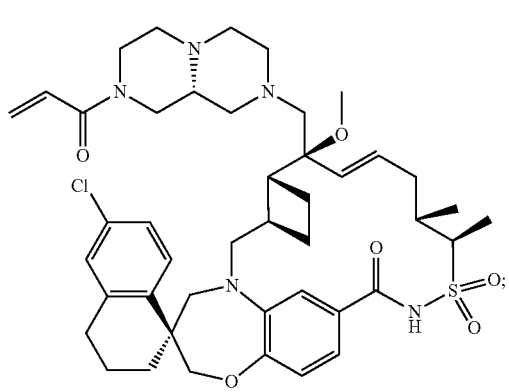
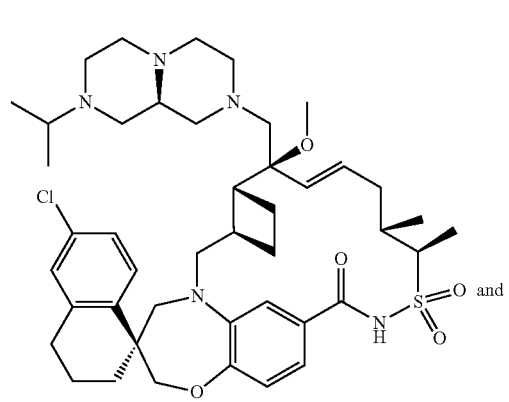
114
-continued
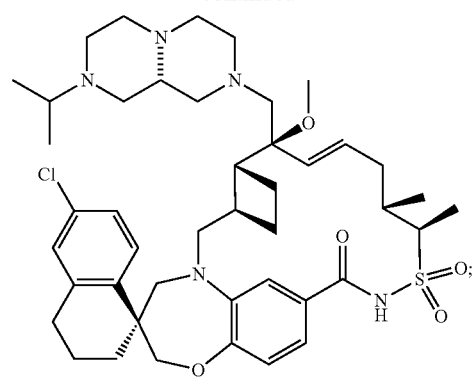
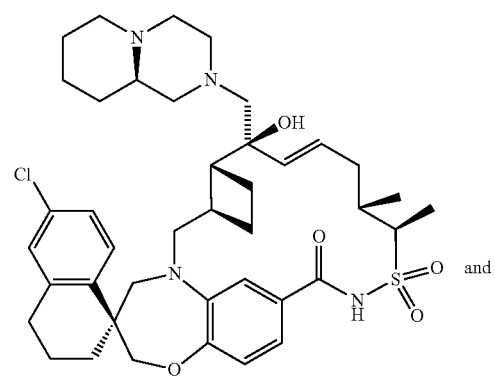
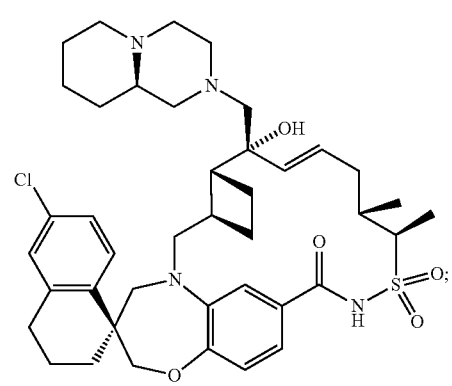
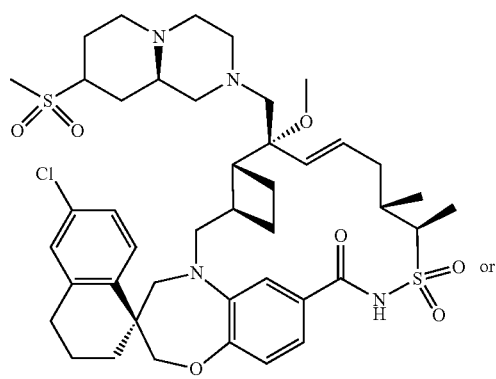

115
-continued
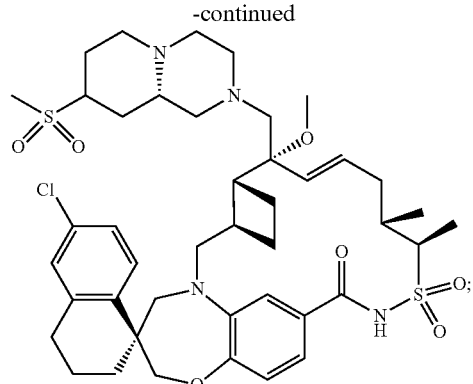
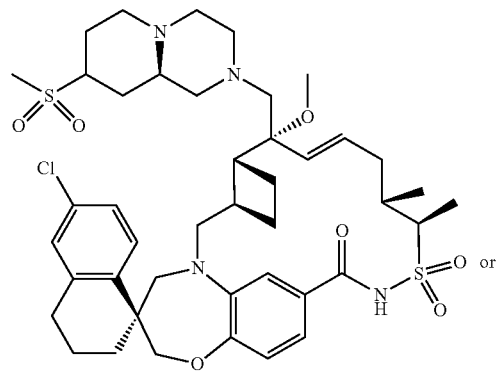
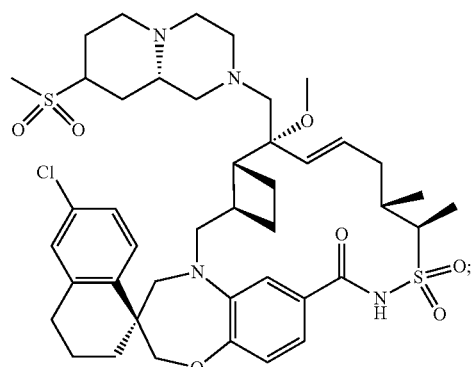
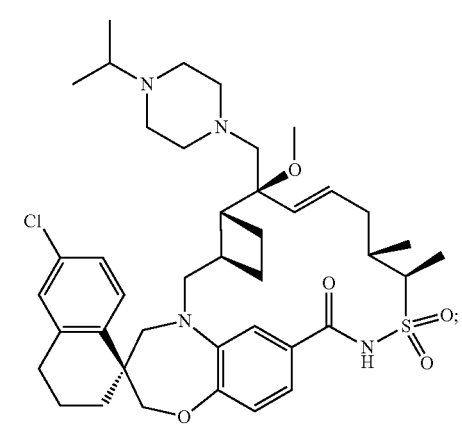
116
-continued
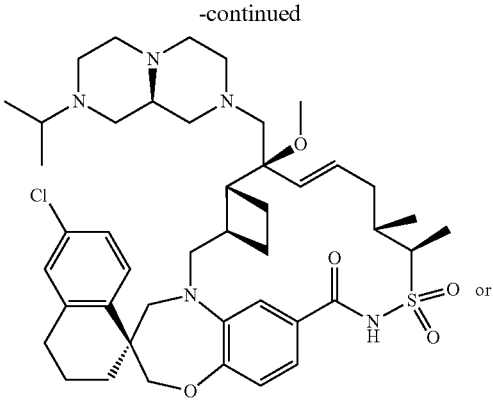
or
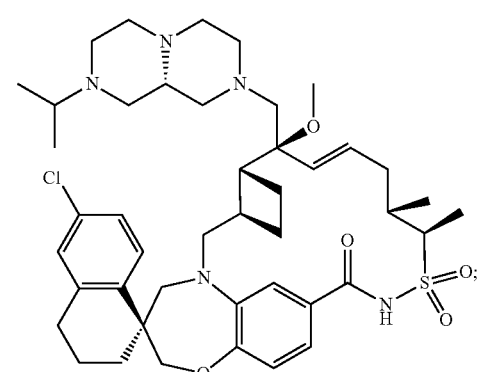
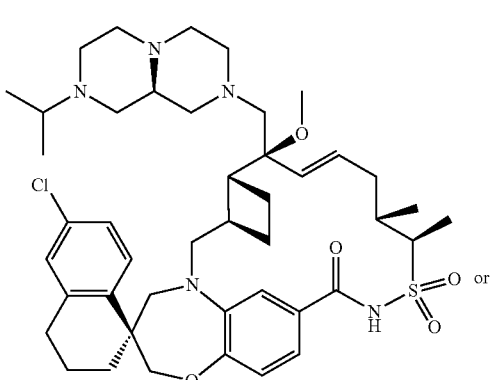
or
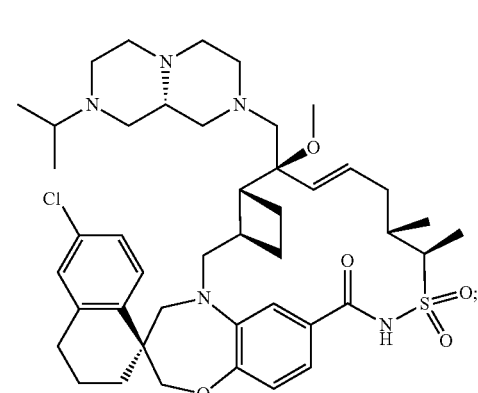

117
-continued
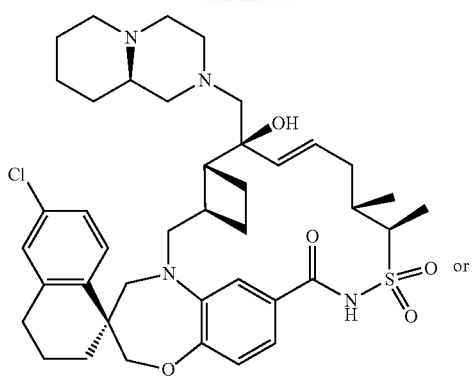
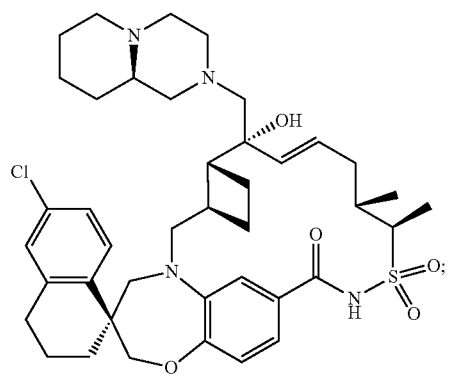
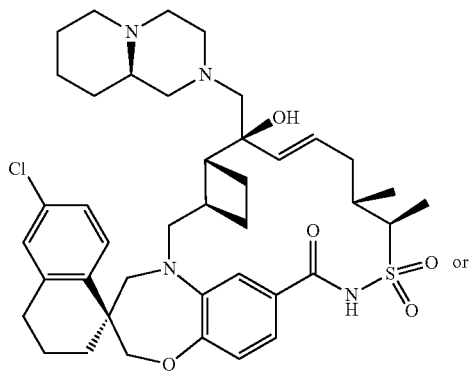
or
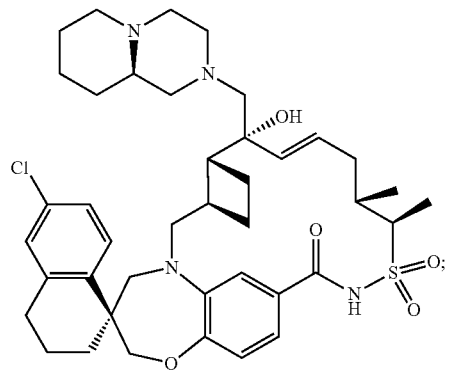
;
118
-continued
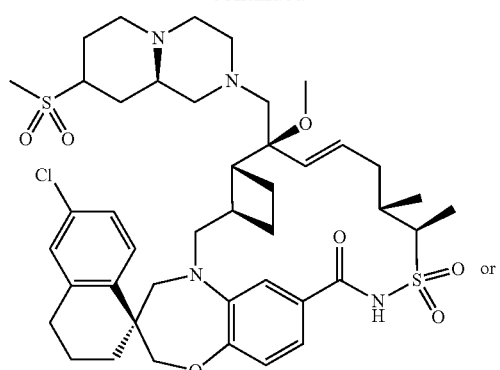
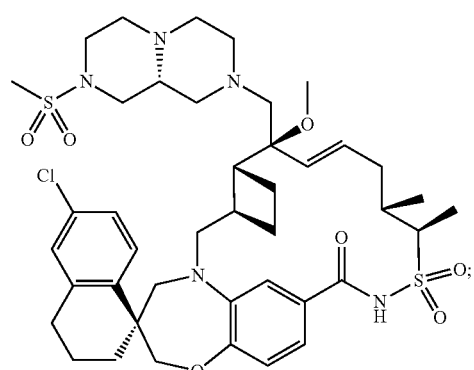
or
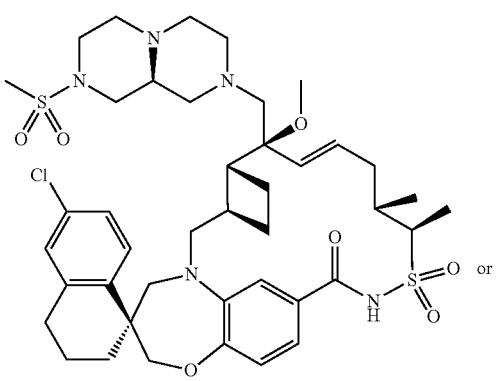
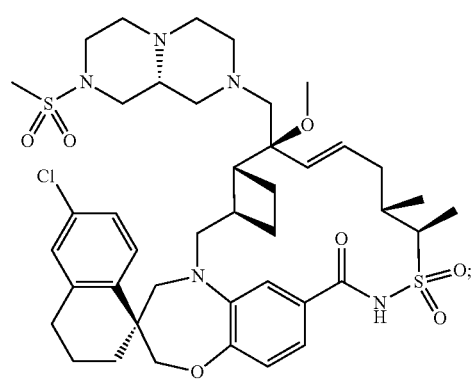
or
;

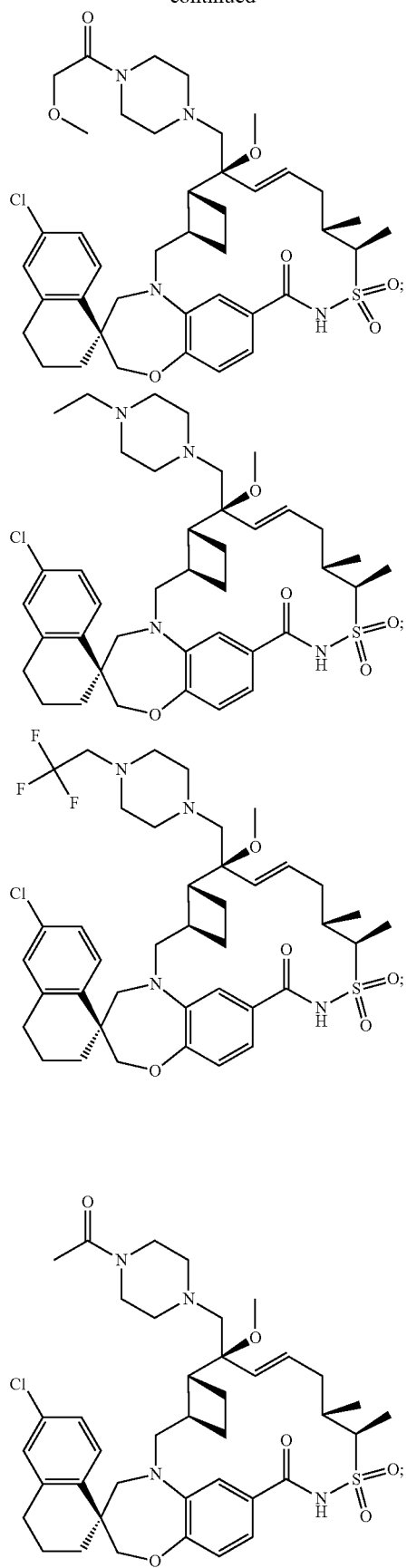
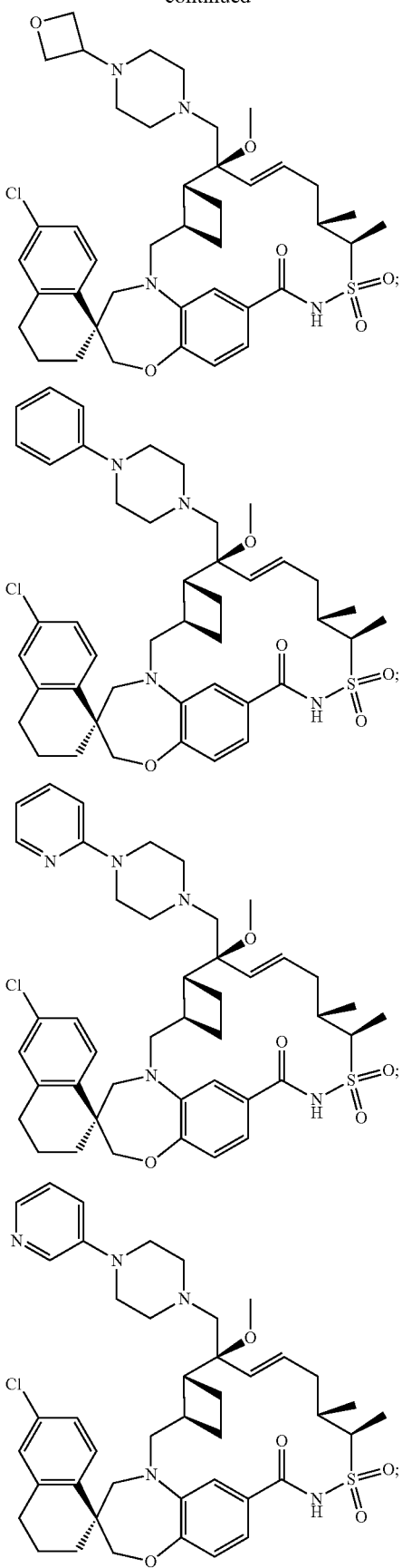

121
-continued
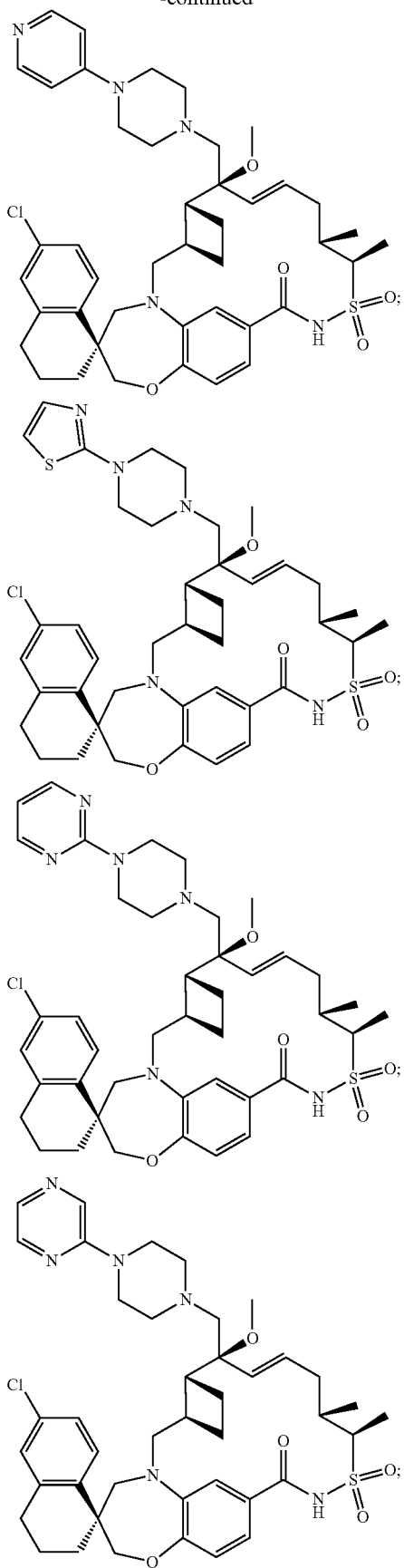
122
-continued
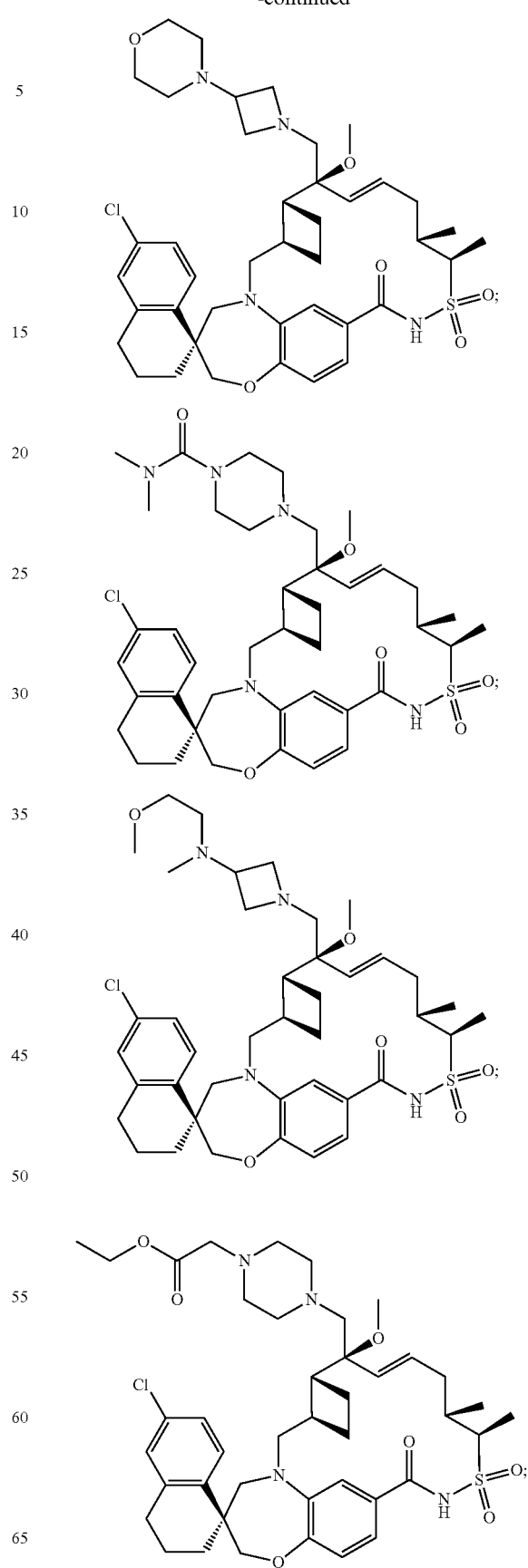

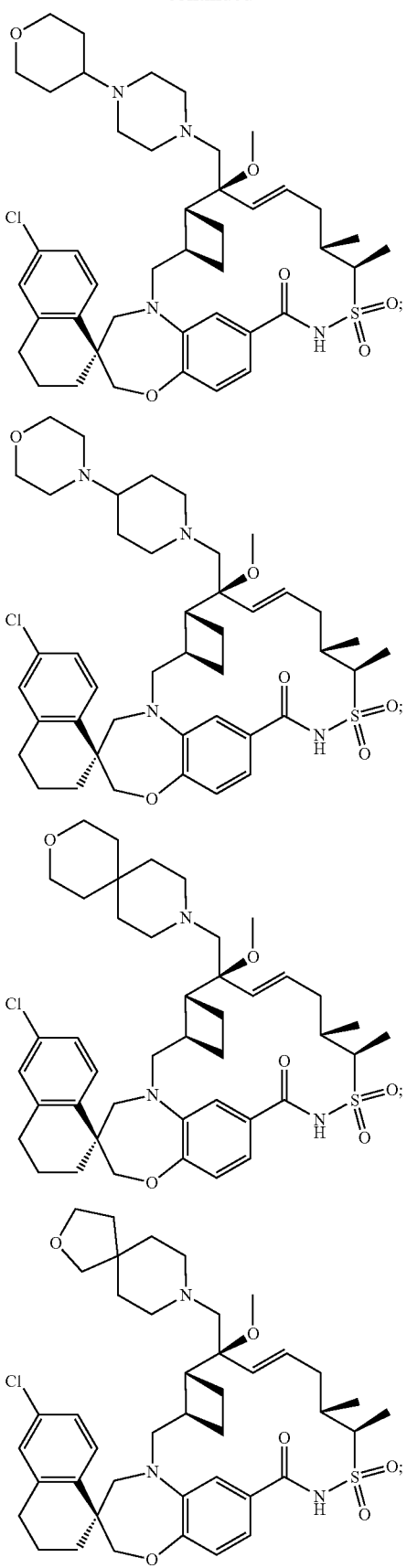
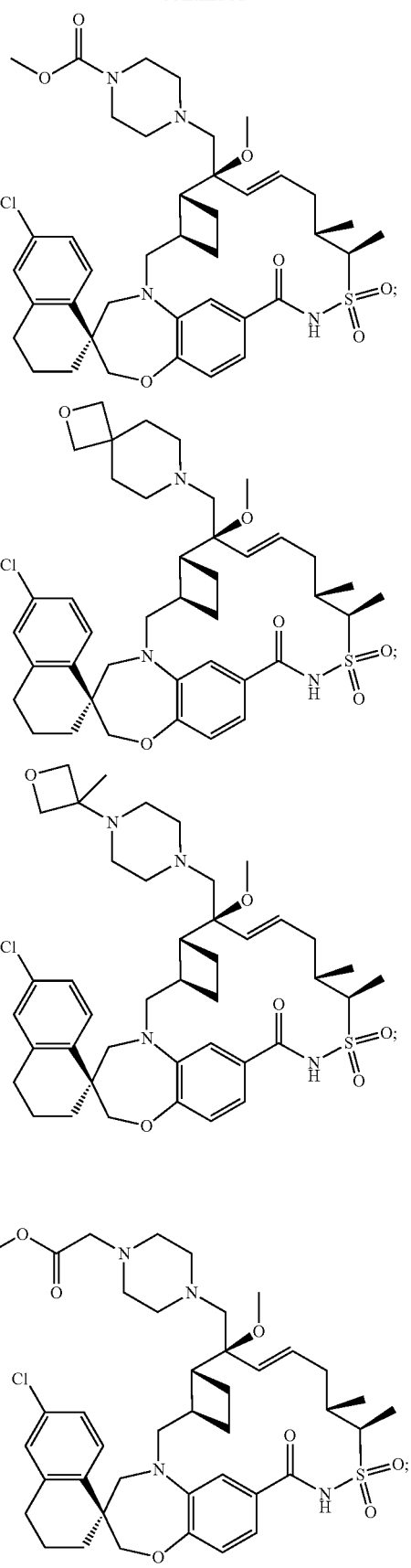

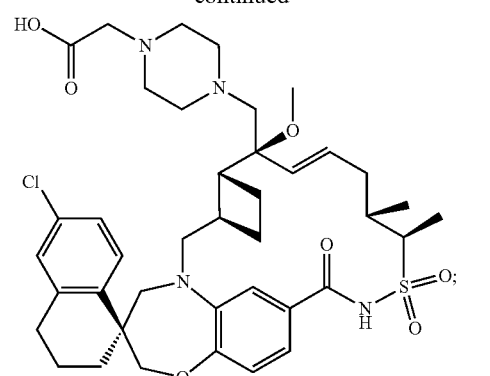
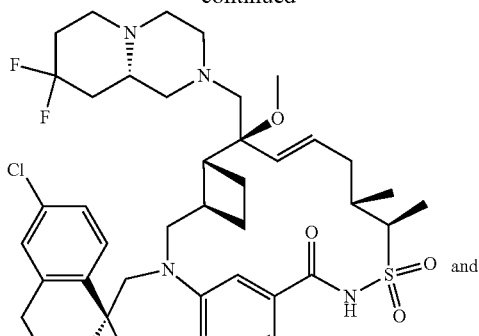

127
-continued
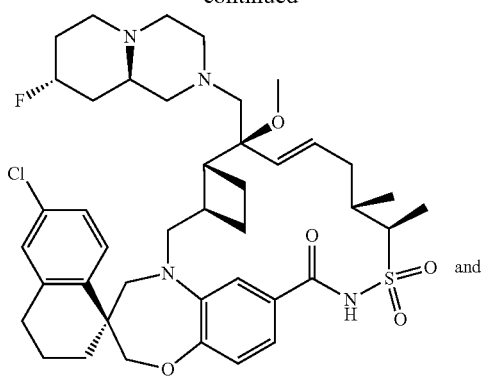
and
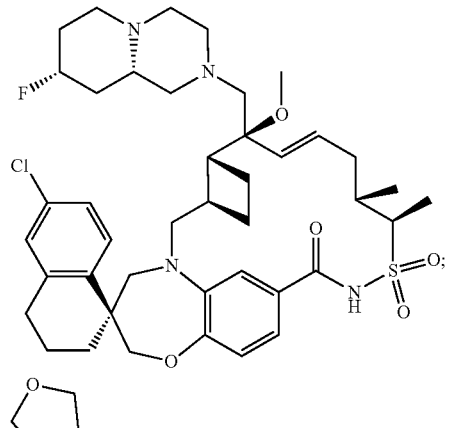
;
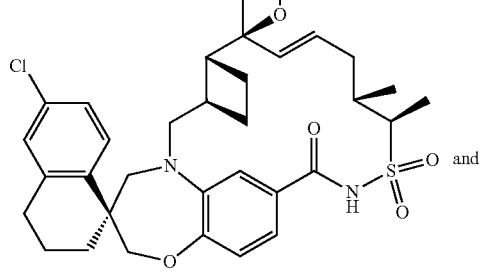
and
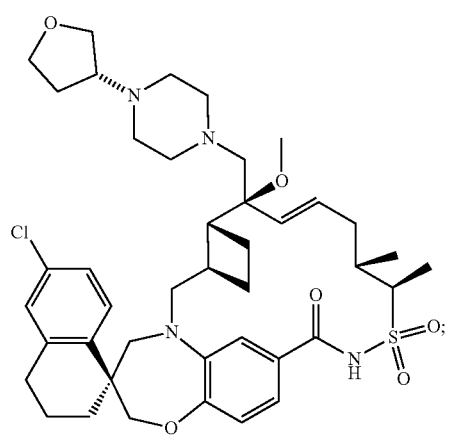
;
128
-continued
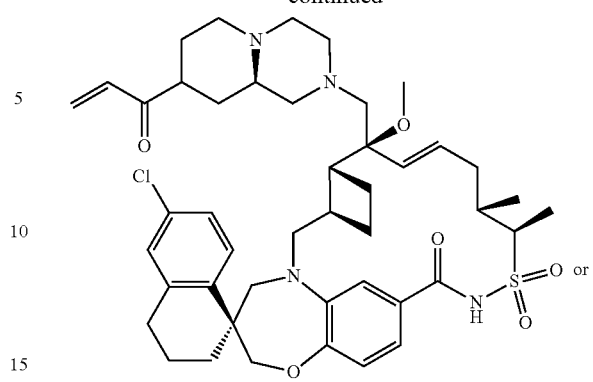
or
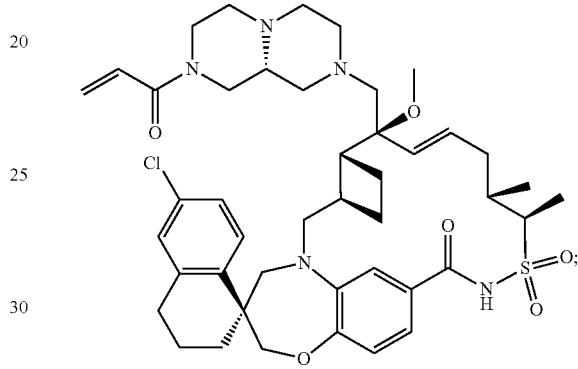
;
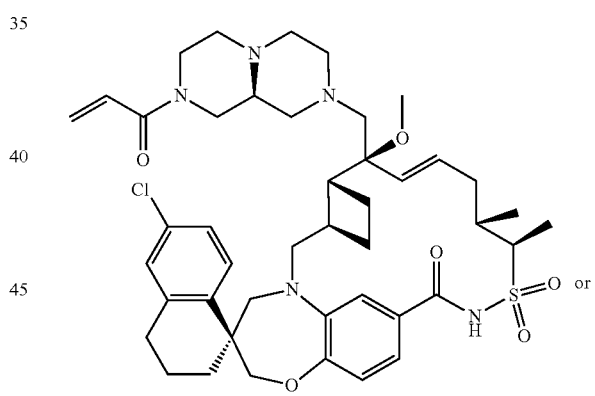
or
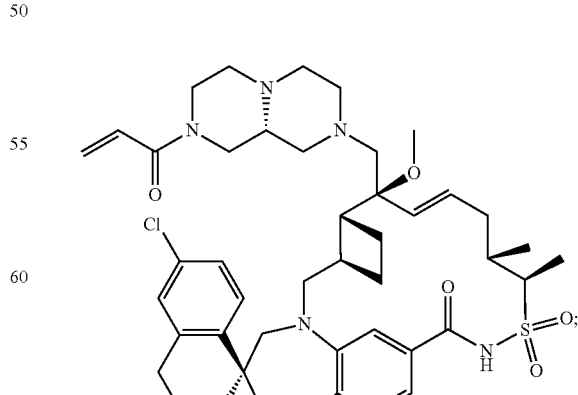
;

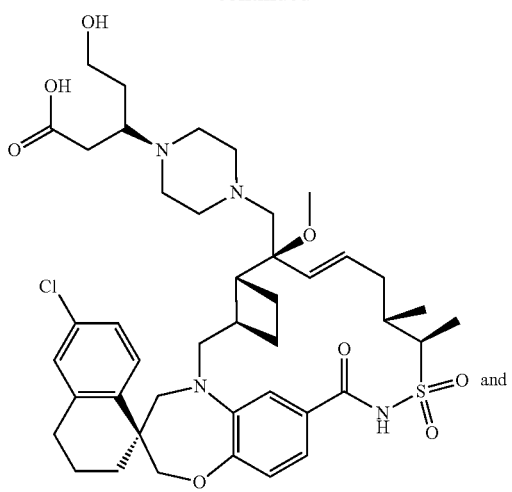
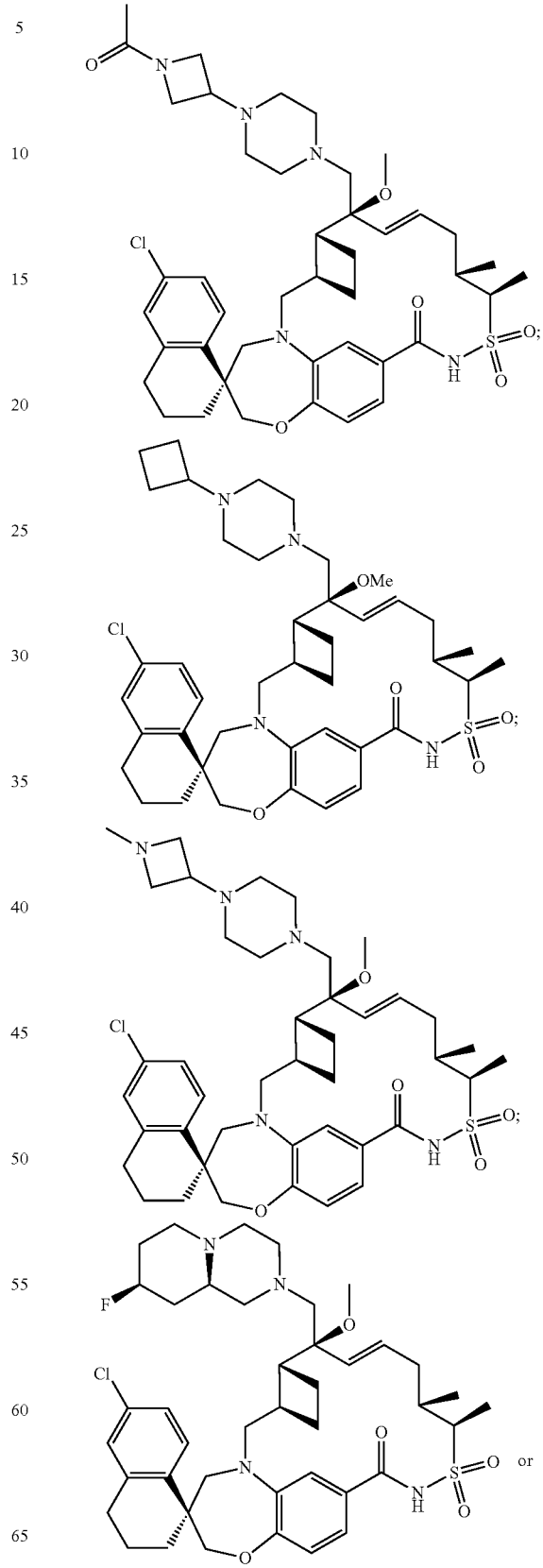

131
-continued
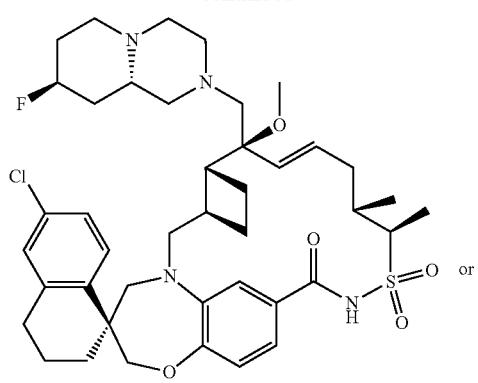
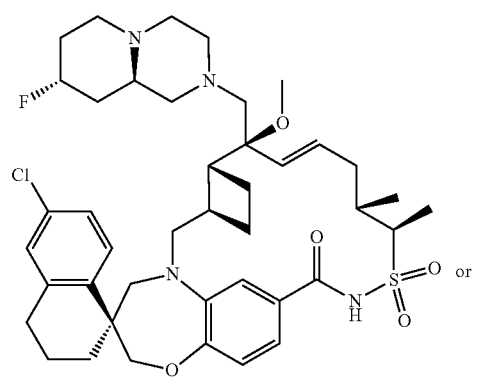
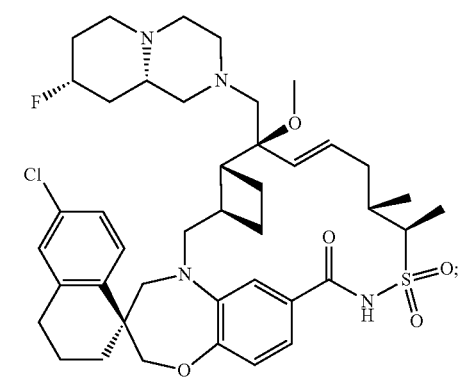
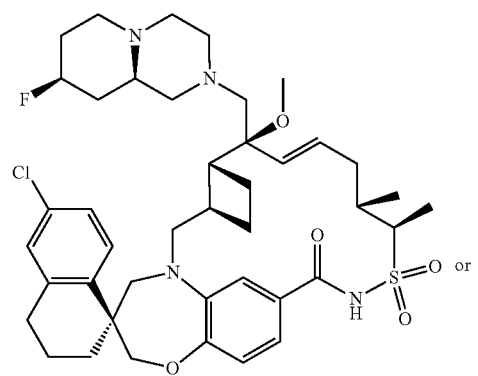
132
-continued
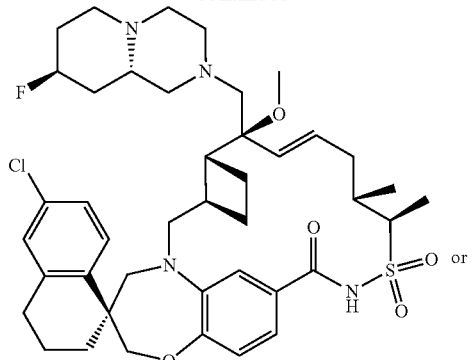
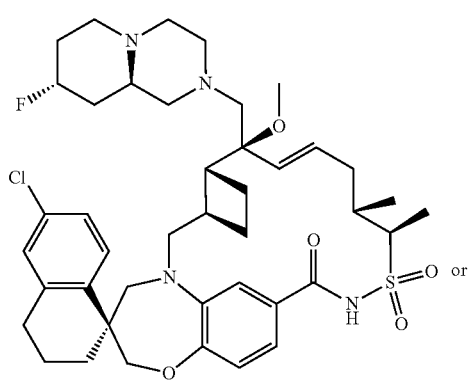
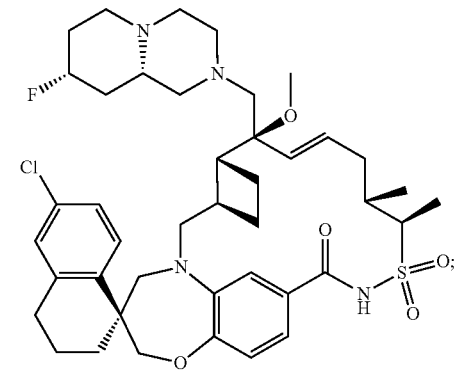
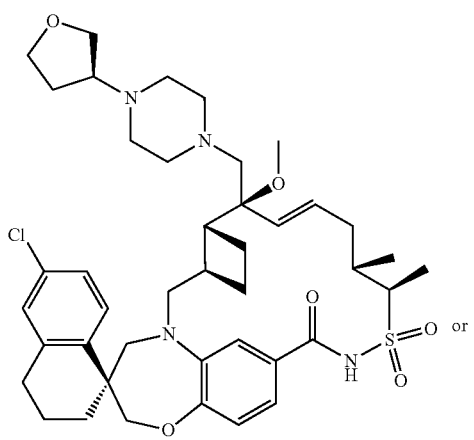

133
-continued
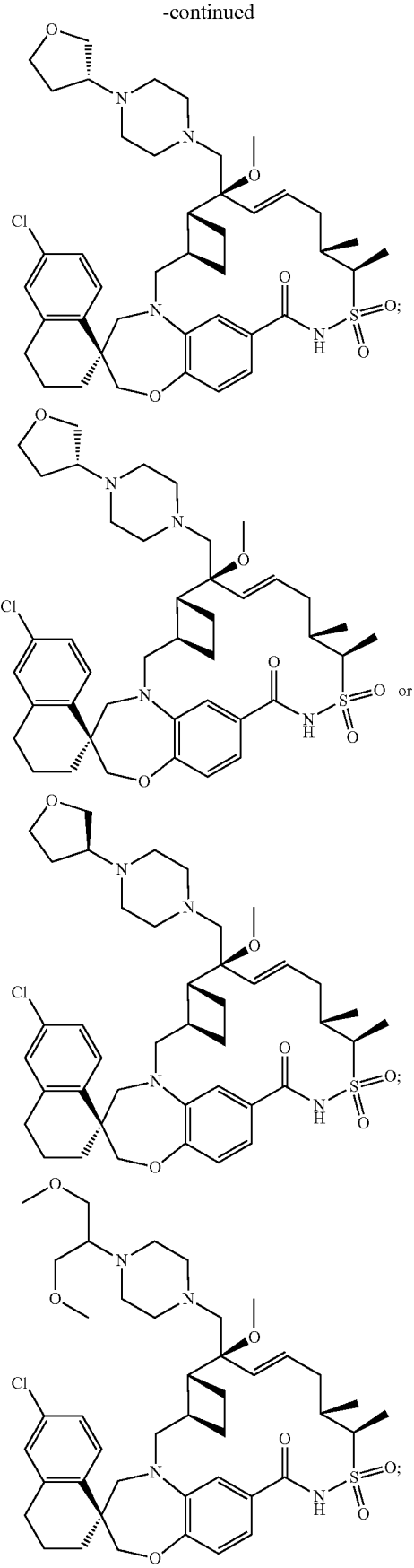
134
-continued
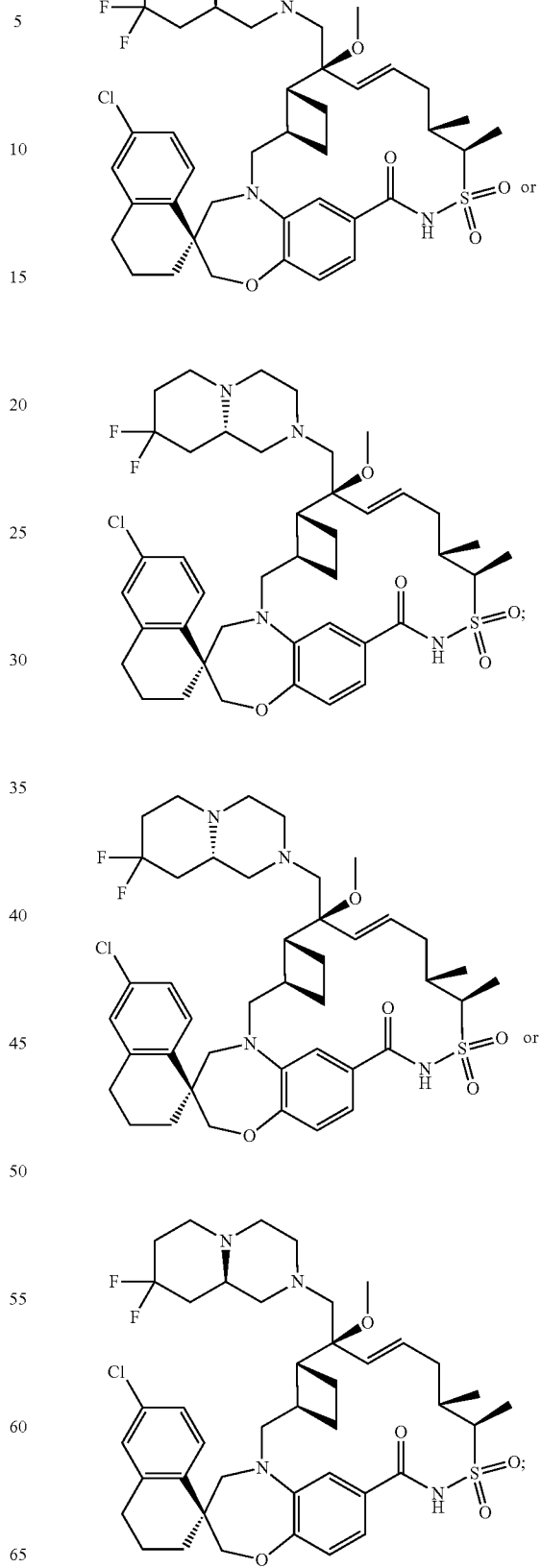

135
-continued
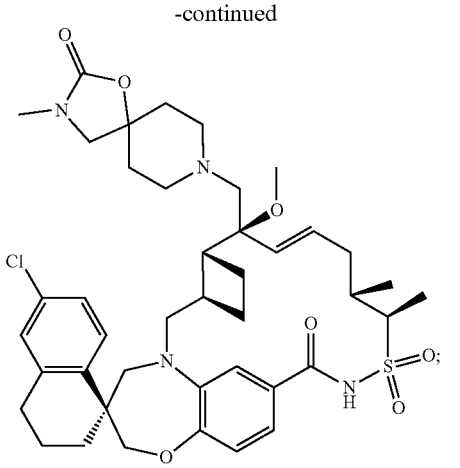
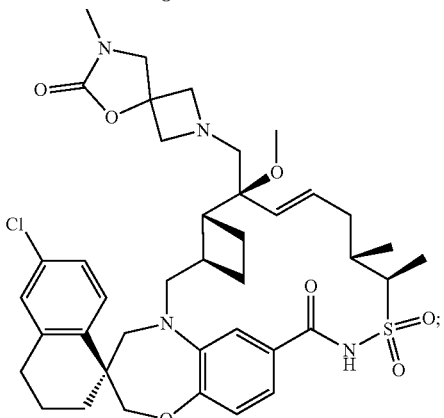
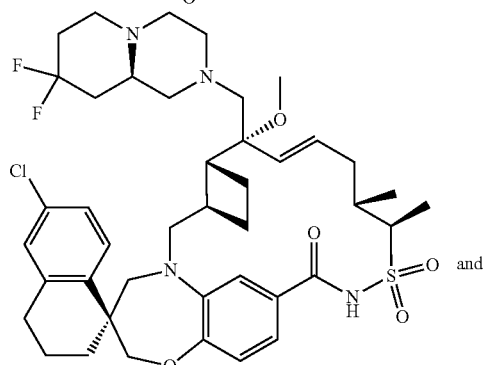 and
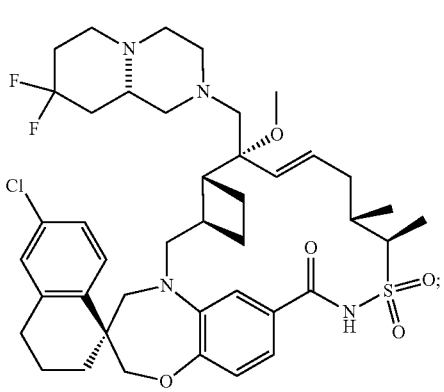
136
-continued
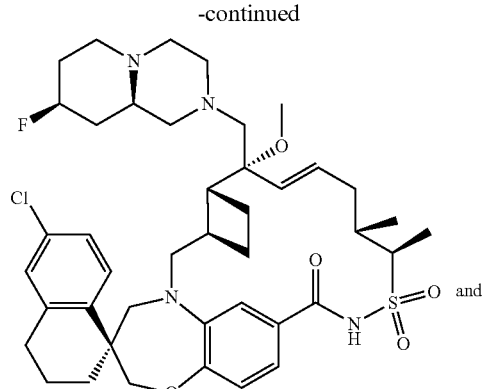 and
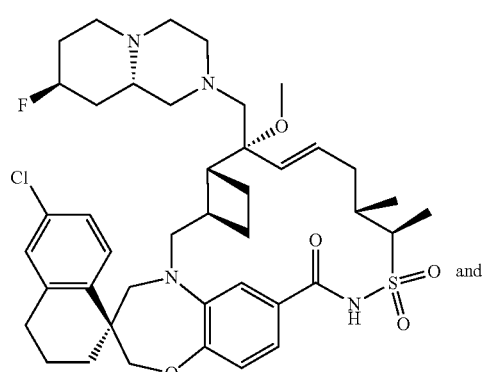 and
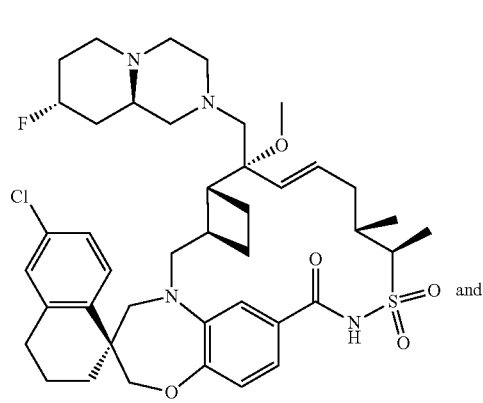 and
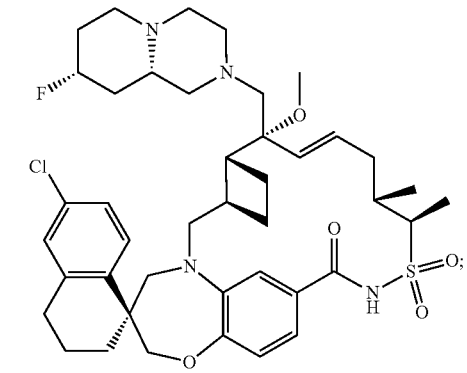

137
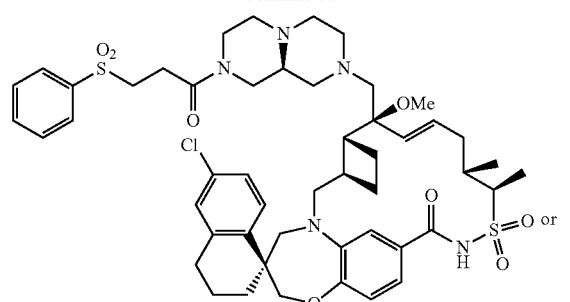
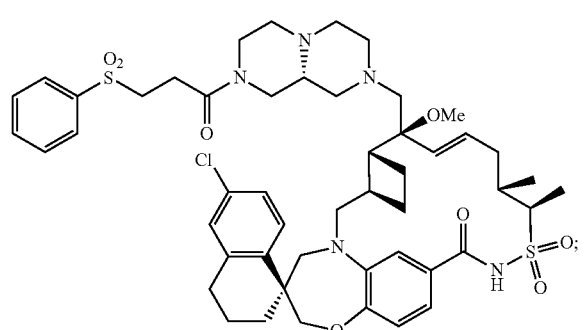
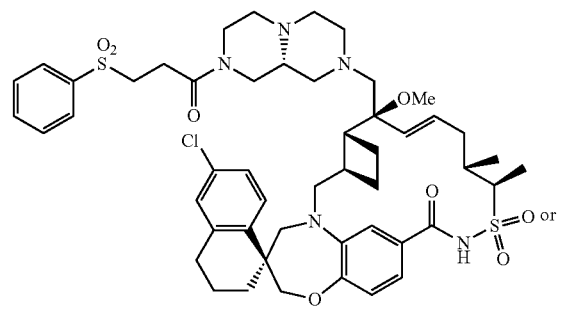
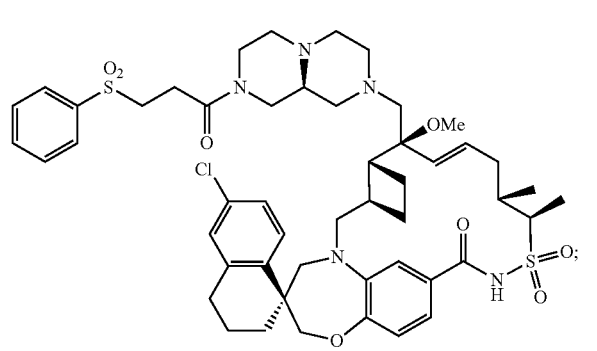
138
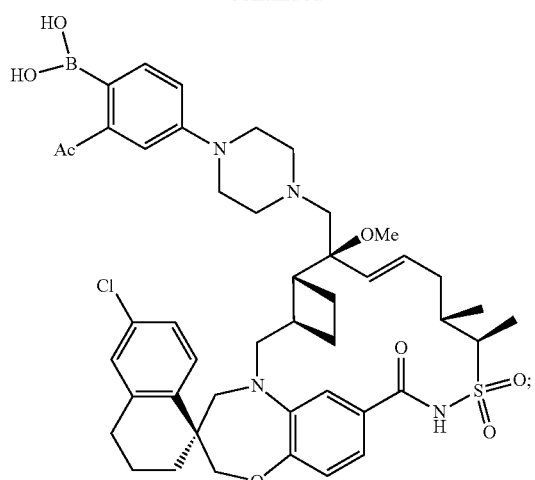
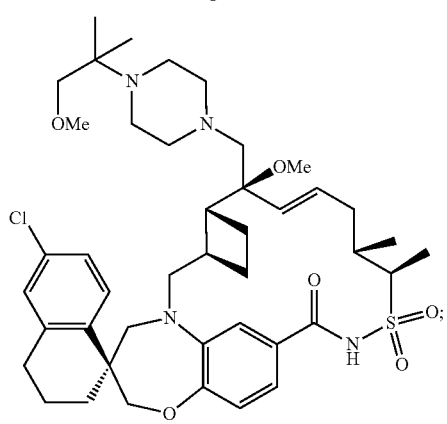
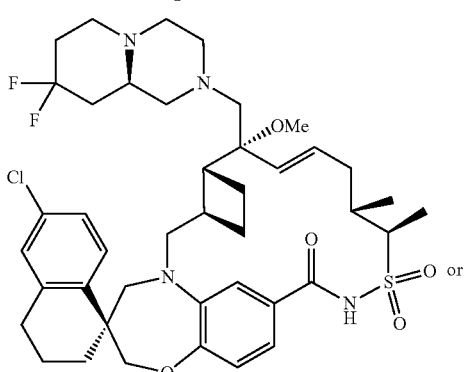
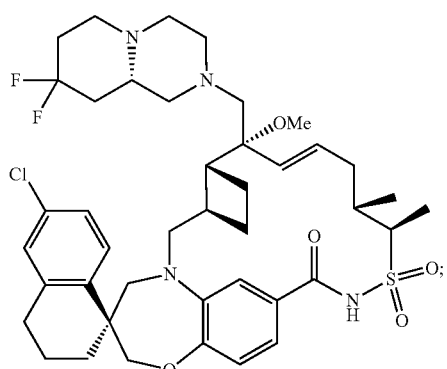

139
-continued
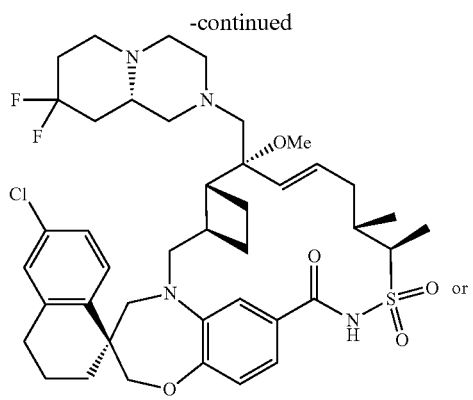
or
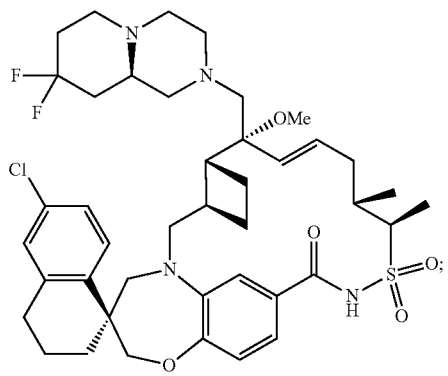
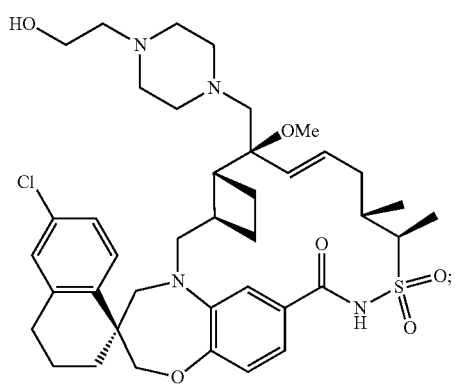
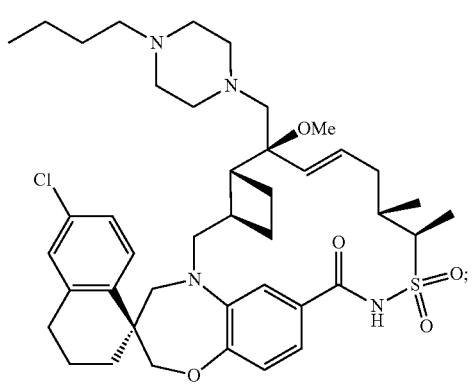
140
-continued
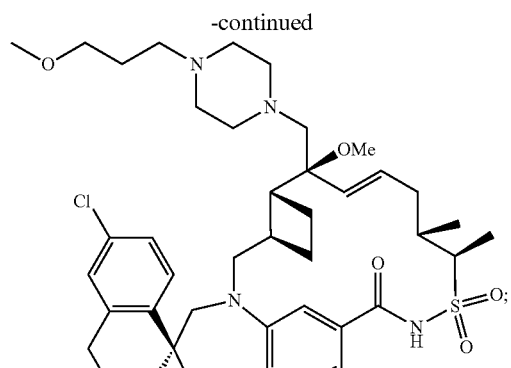
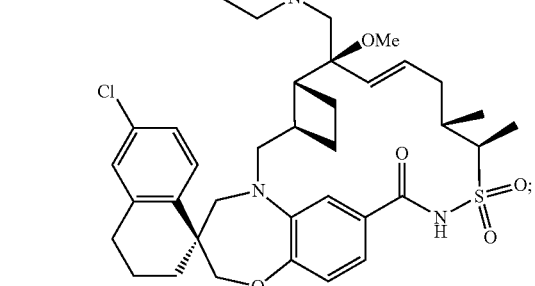
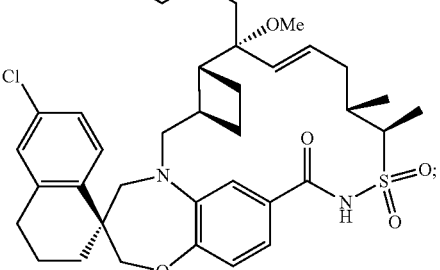
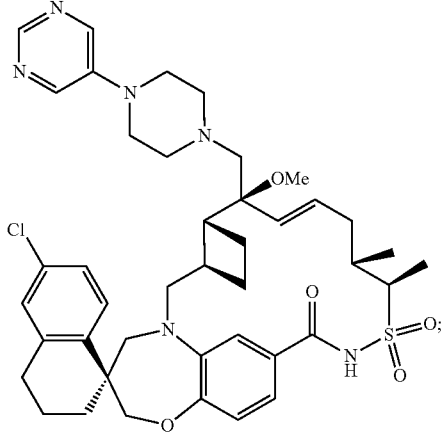

141     142
-continued    -continued
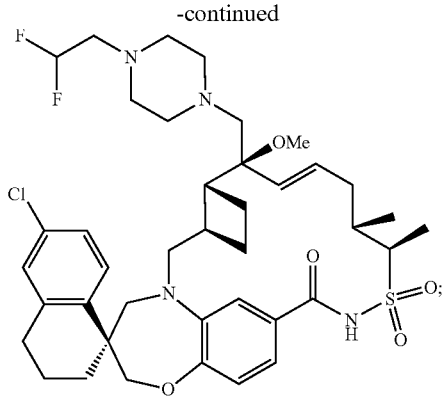
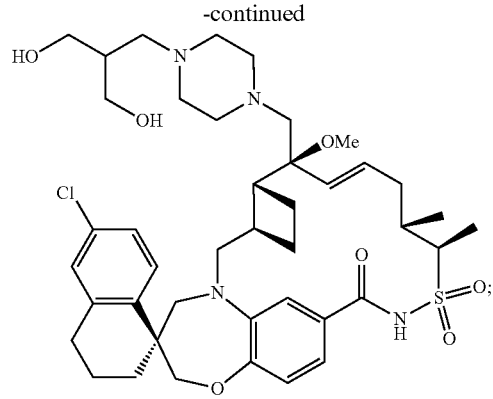
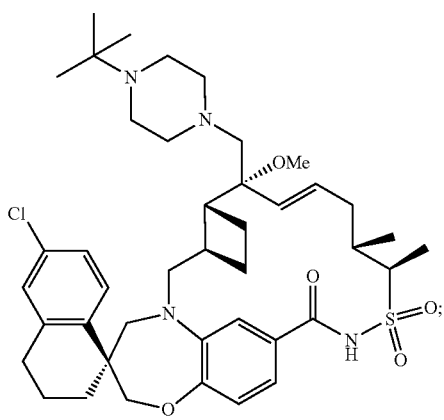
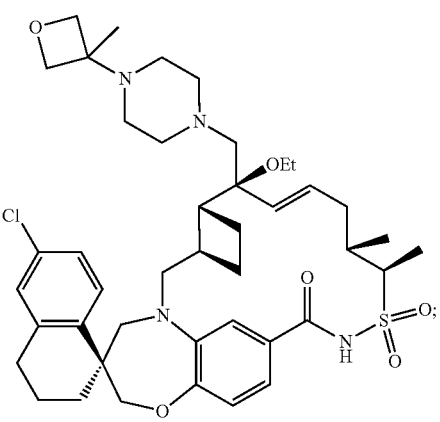
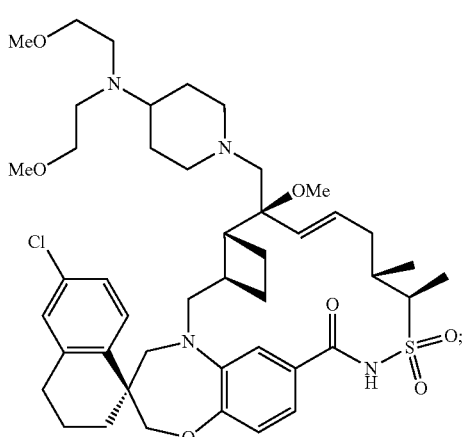
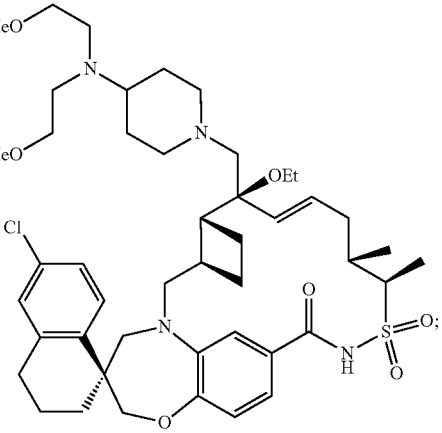
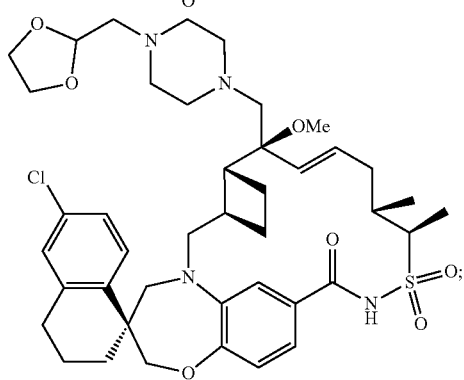
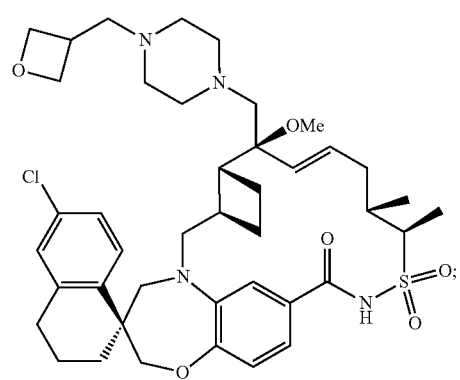

143
-continued
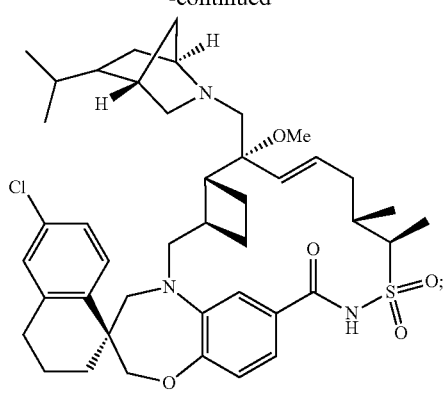
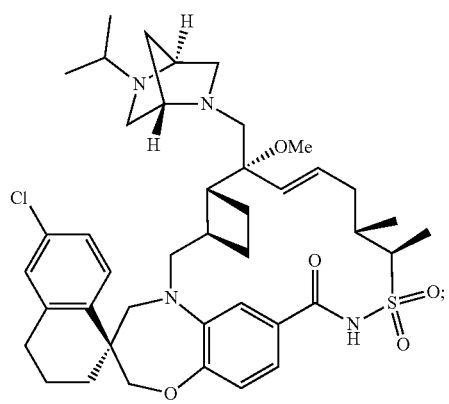
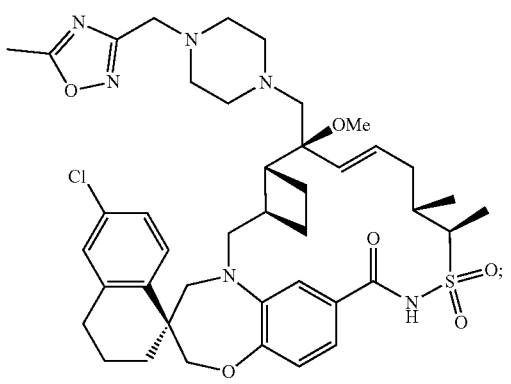
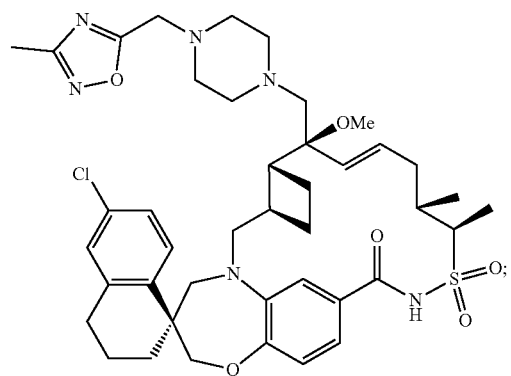
144
-continued
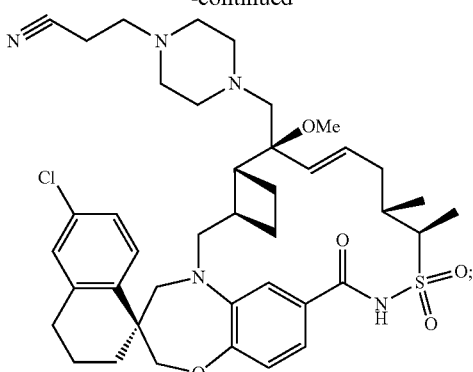
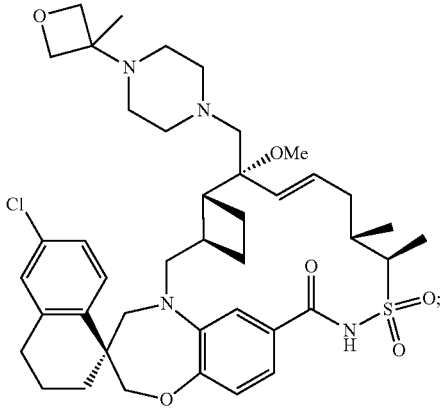
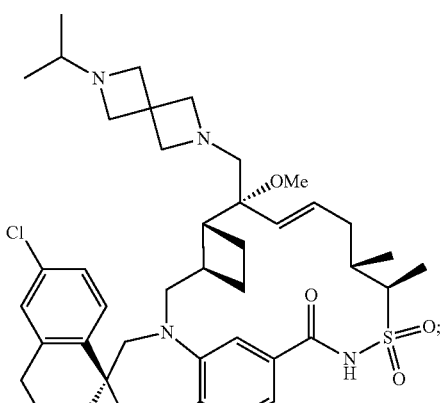
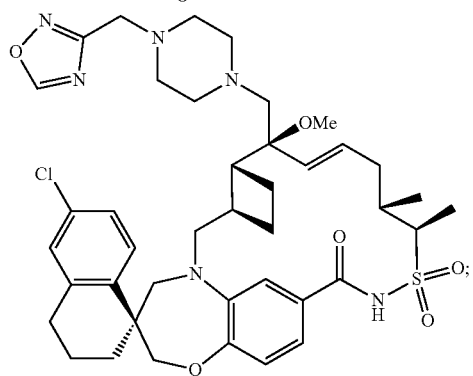

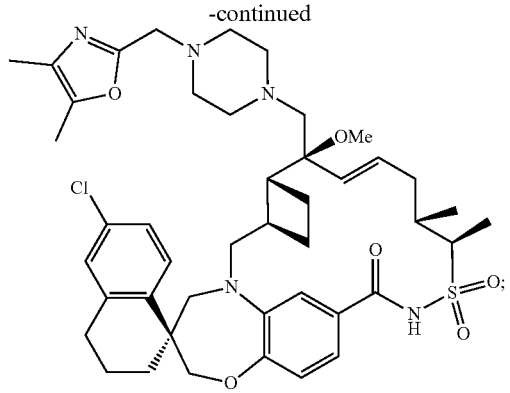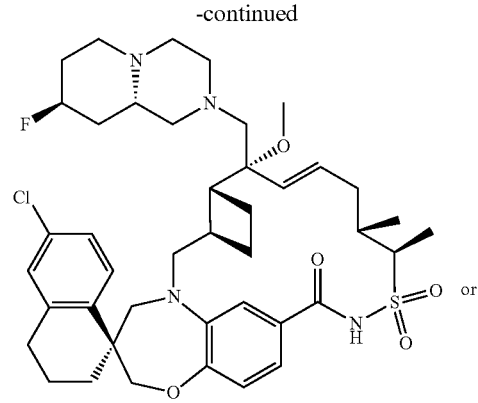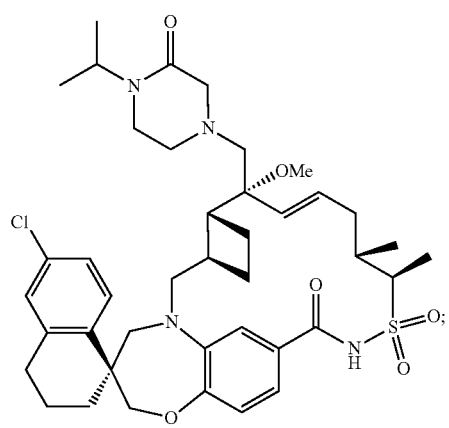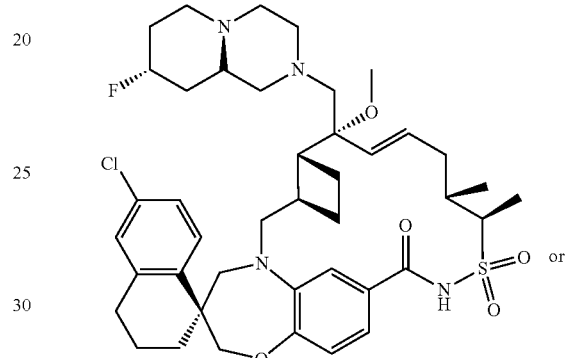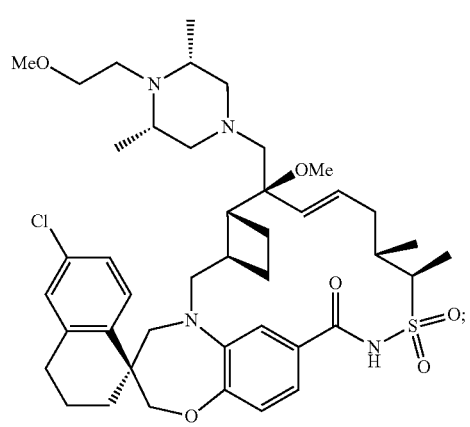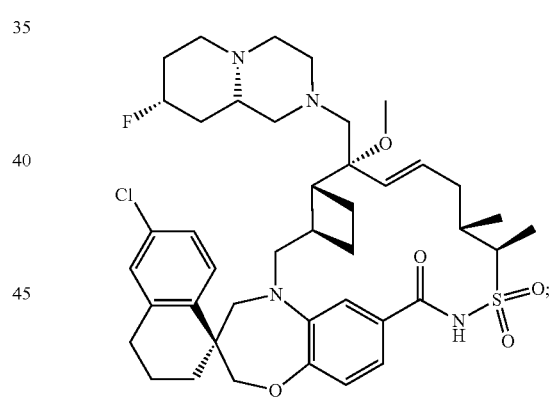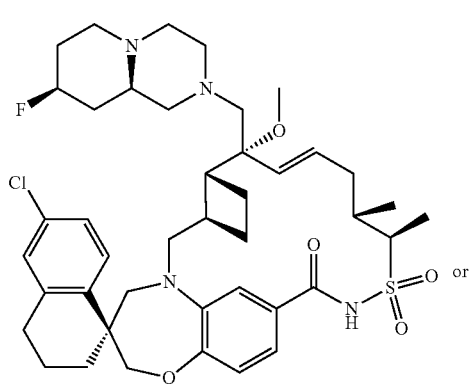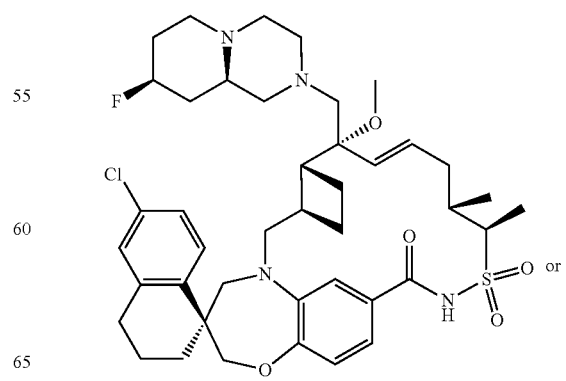

147
-continued
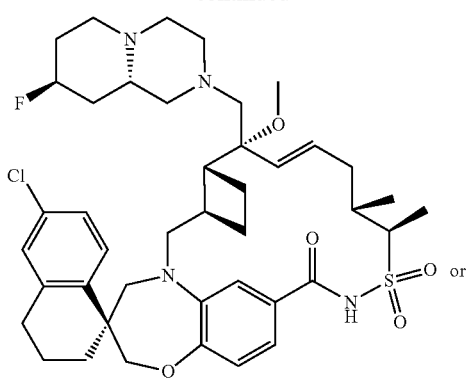
or
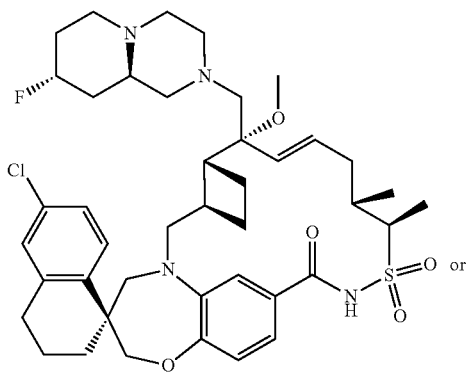
or
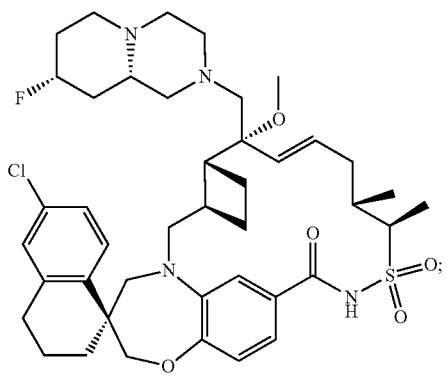
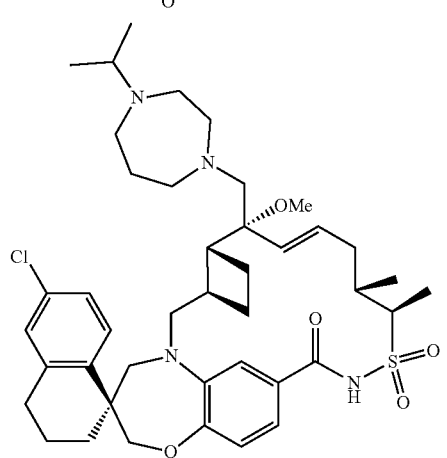
148
-continued
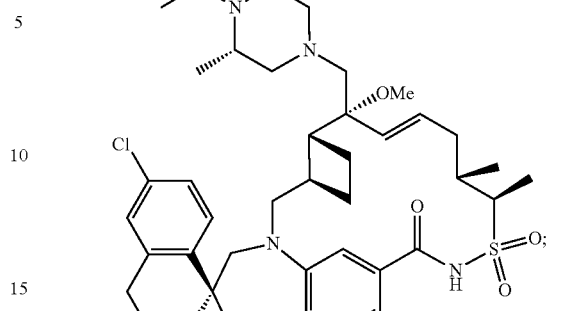
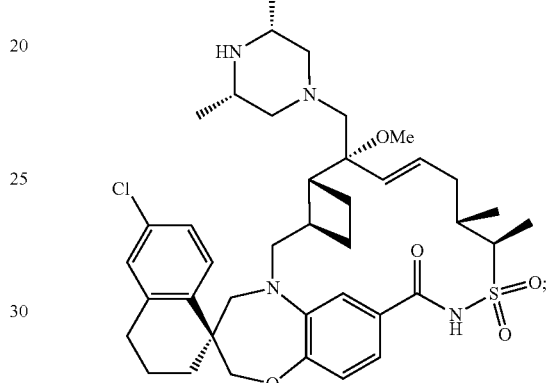
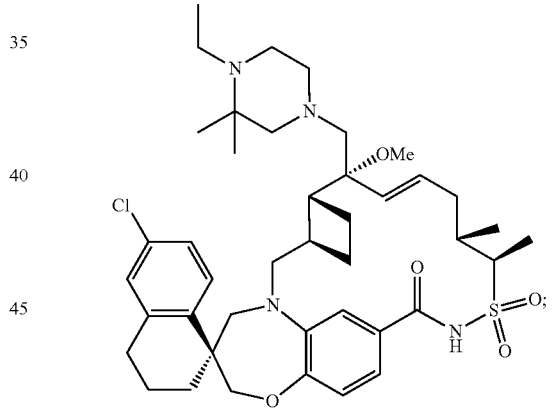
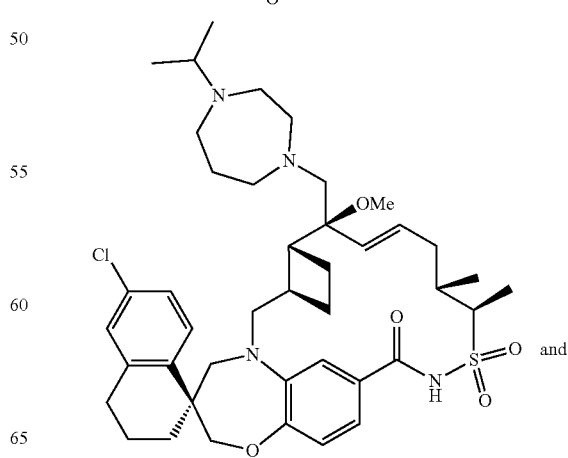
and 149
-continued
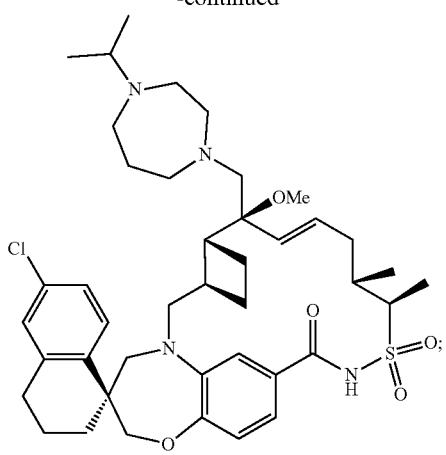
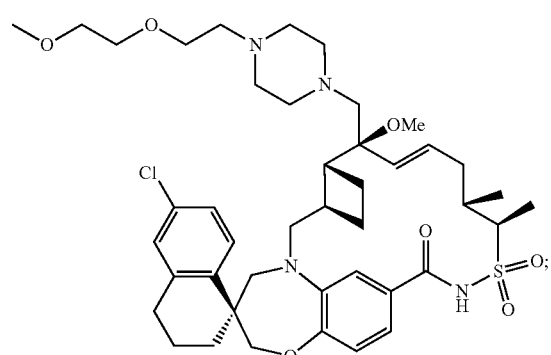
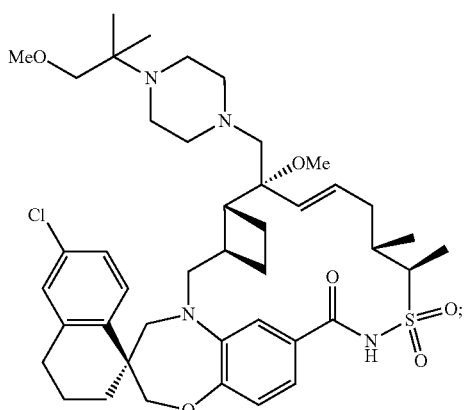
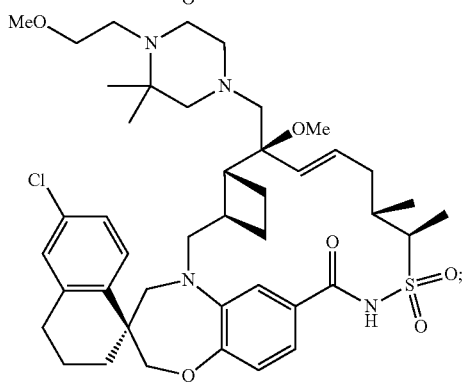
150
-continued
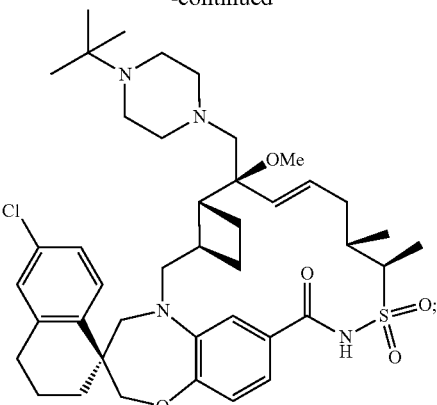
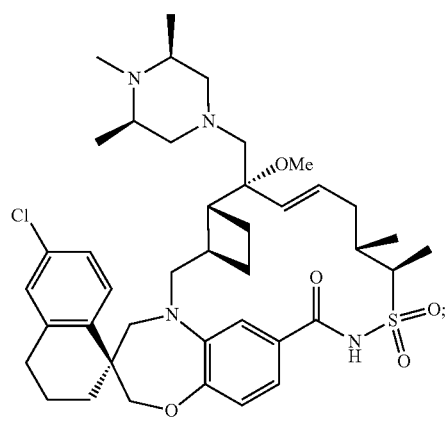
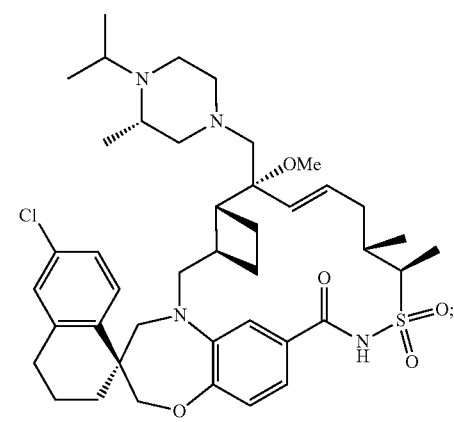
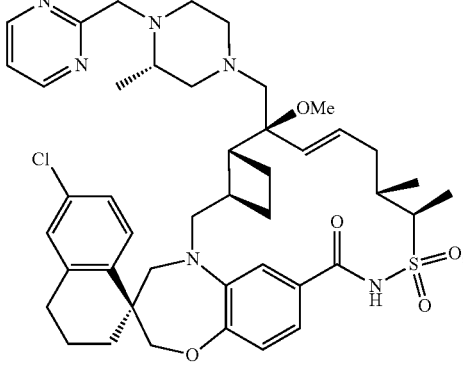

151
-continued
152
-continued
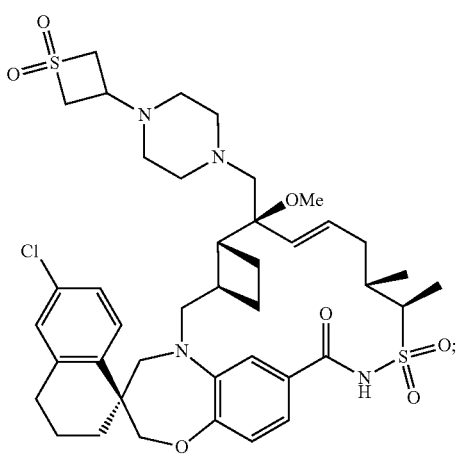
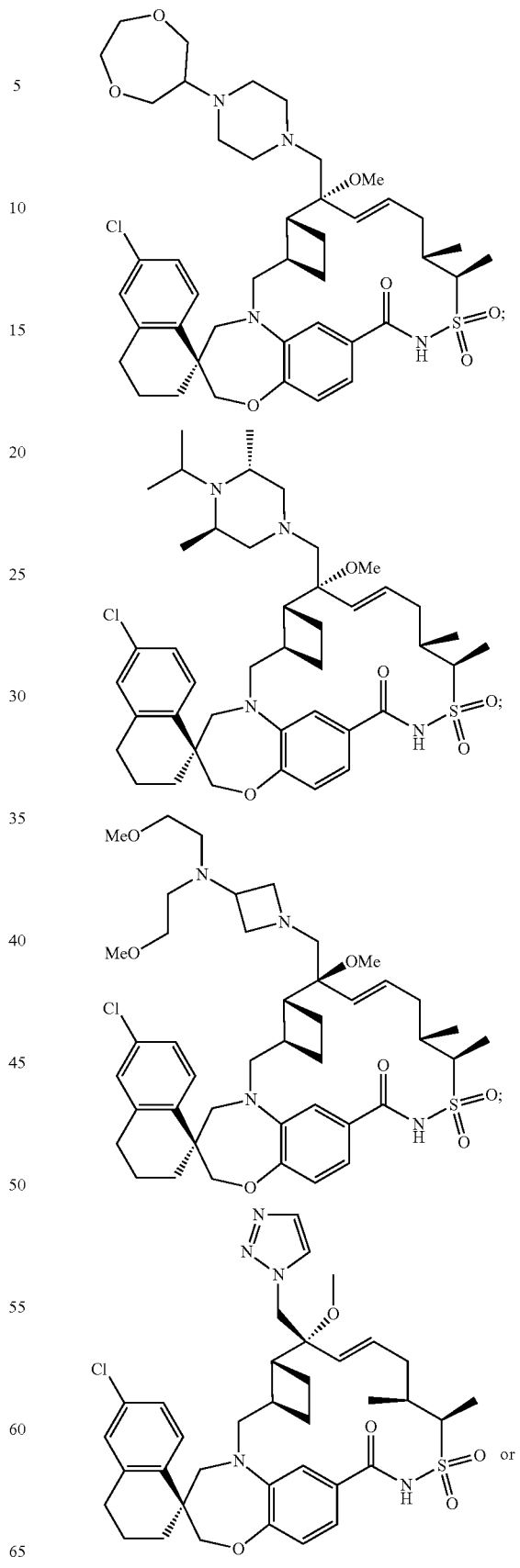

-continued

155
-continued
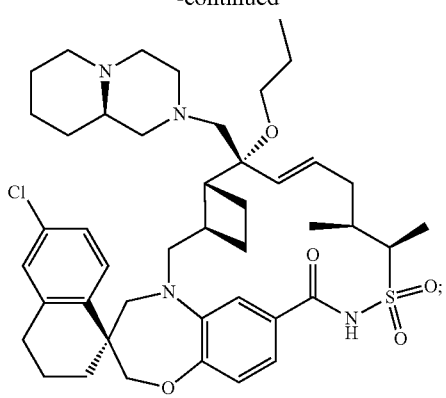
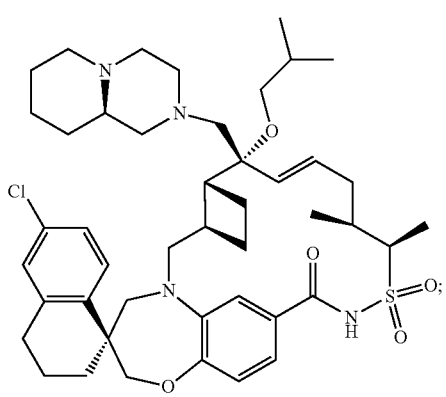
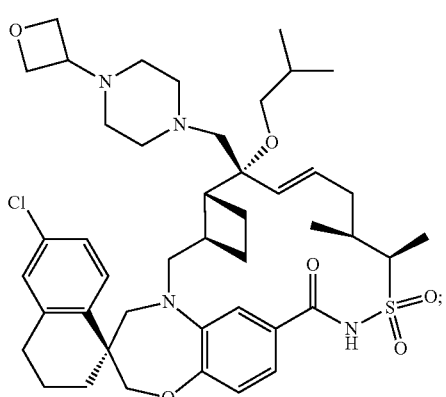
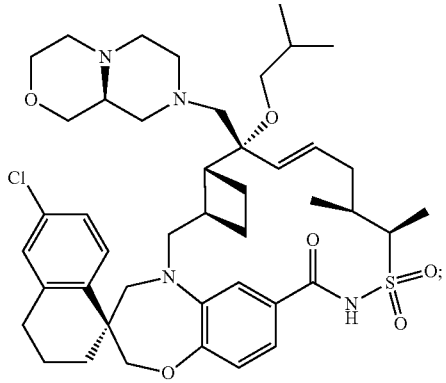
156
-continued
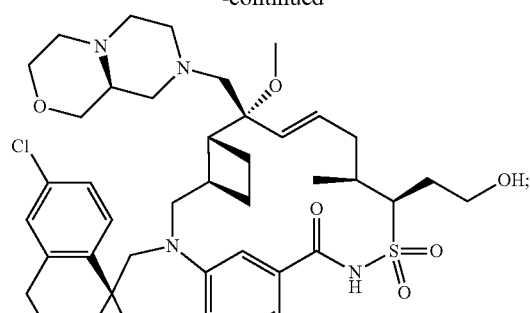
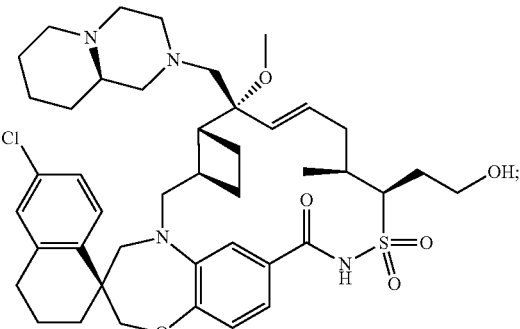
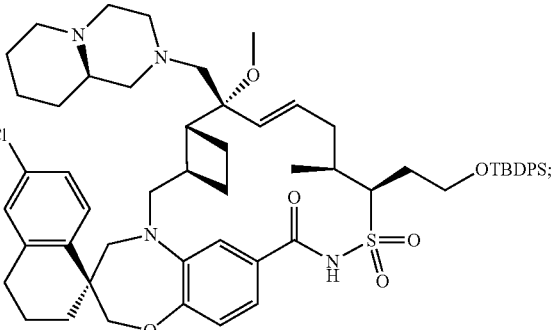
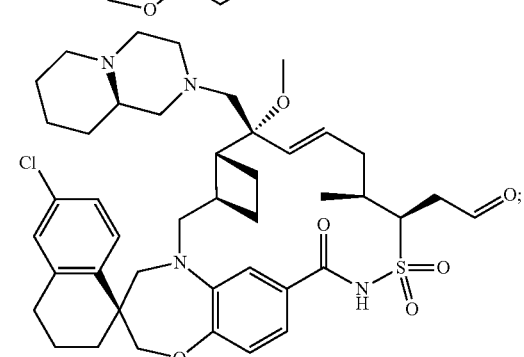
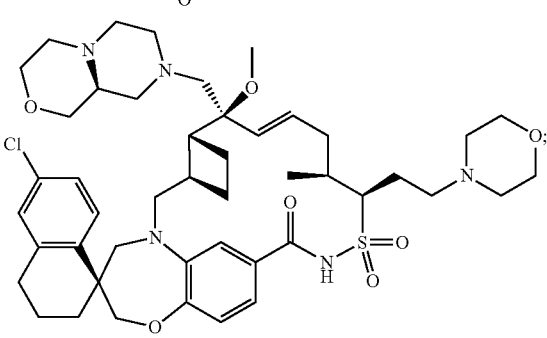

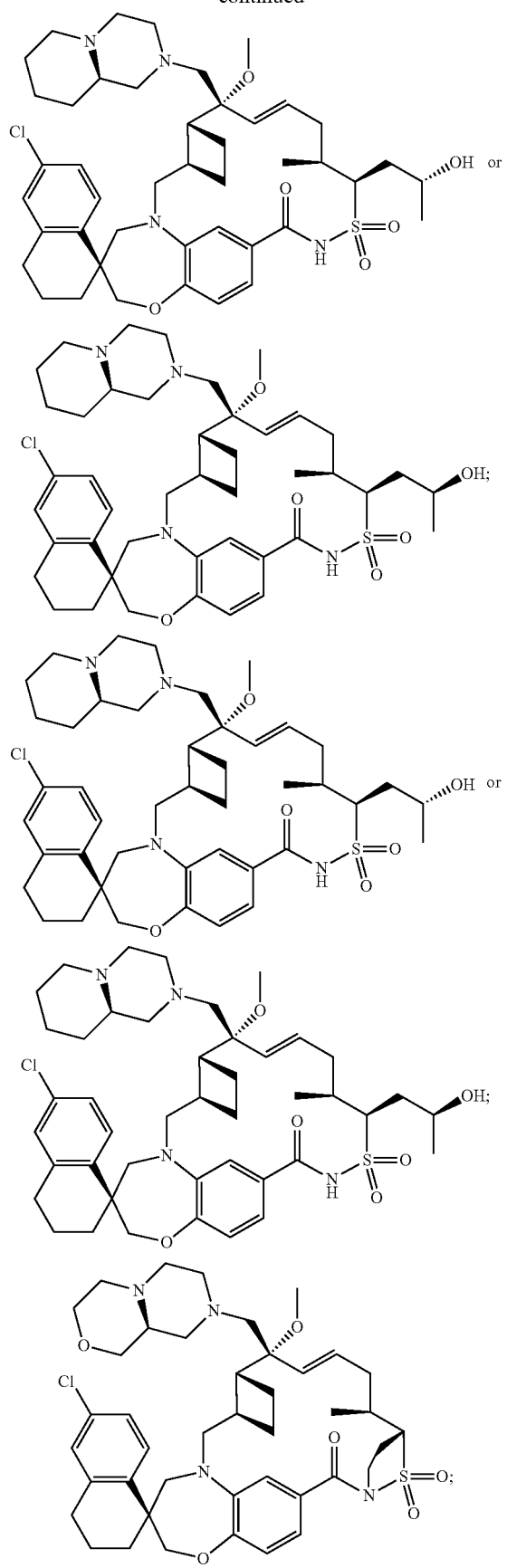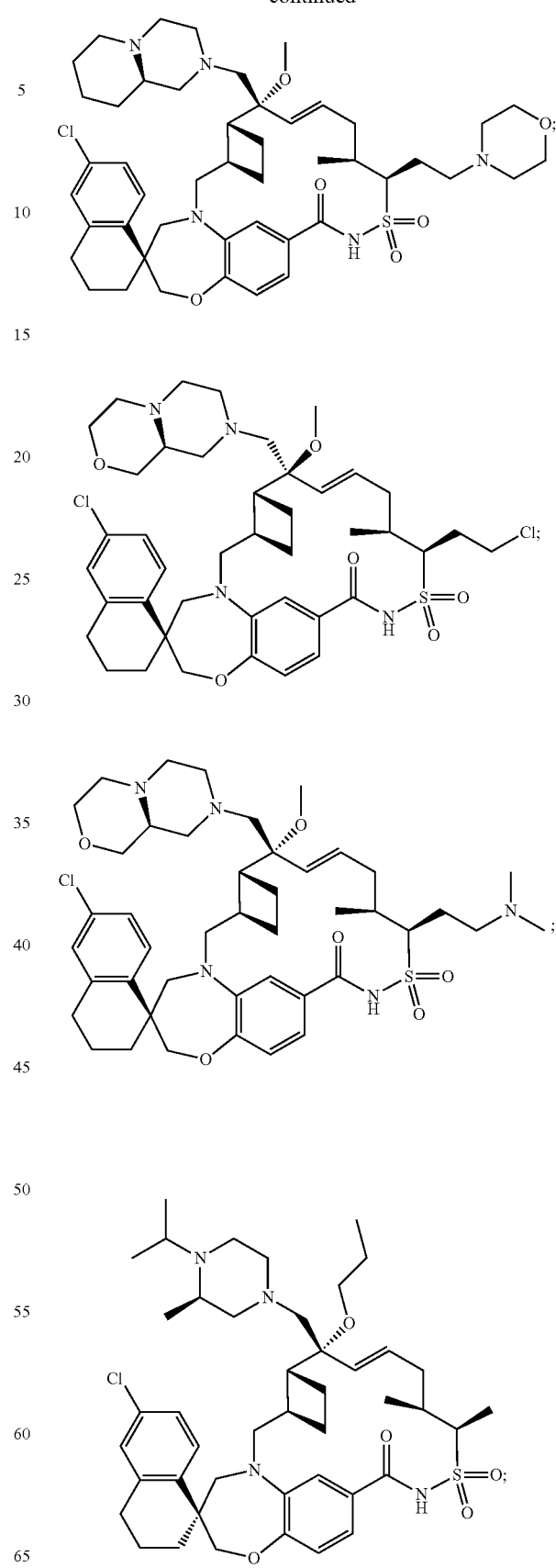

159
-continued
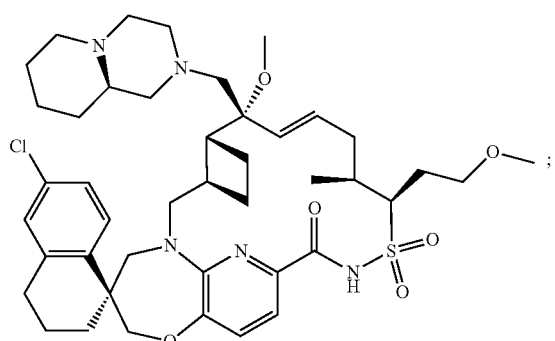
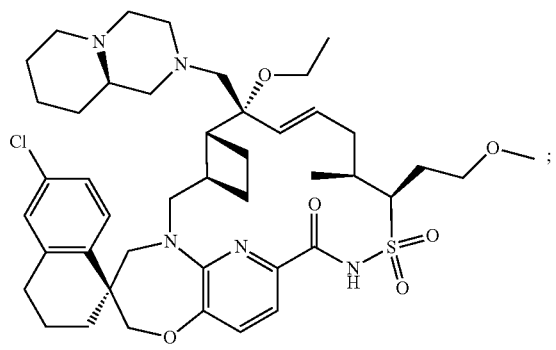
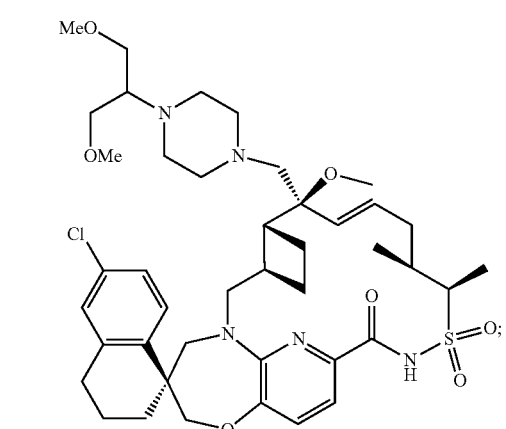
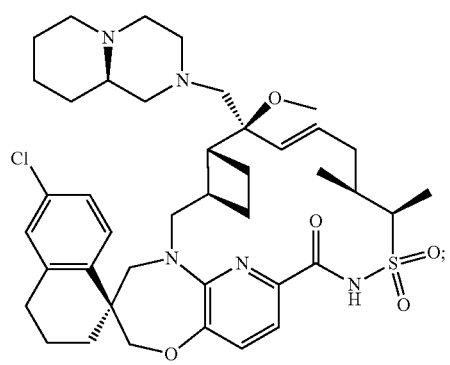
160
-continued
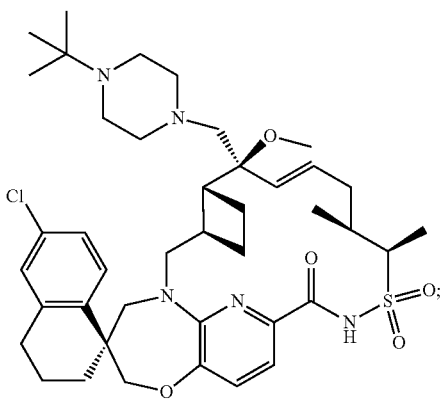
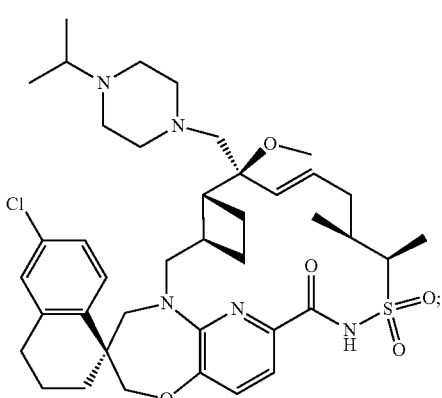
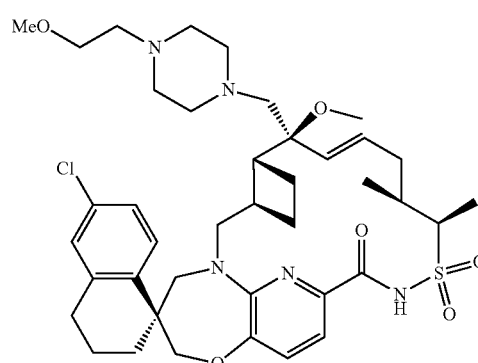
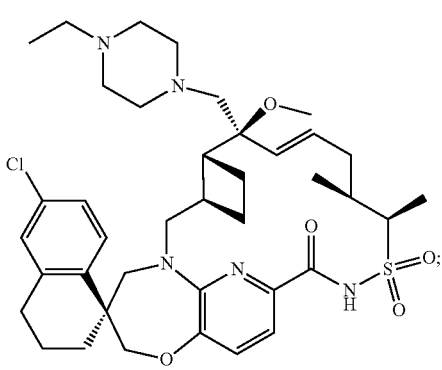

161
-continued
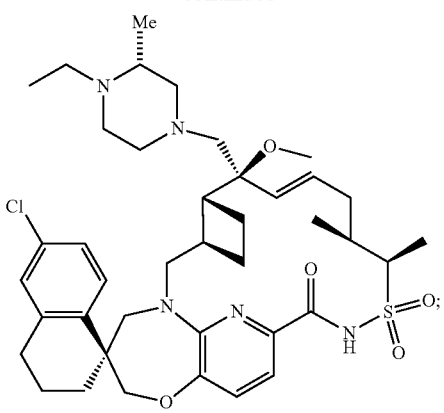
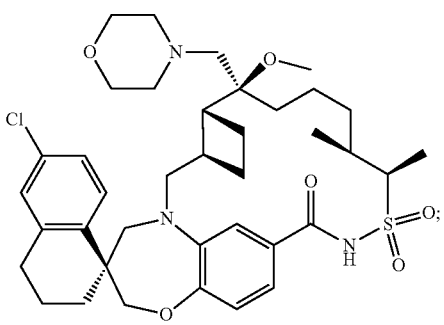
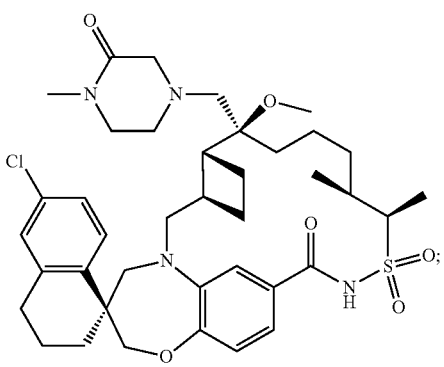
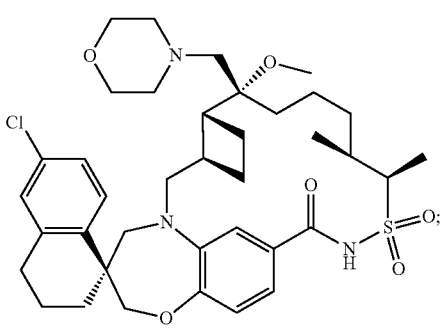
162
-continued
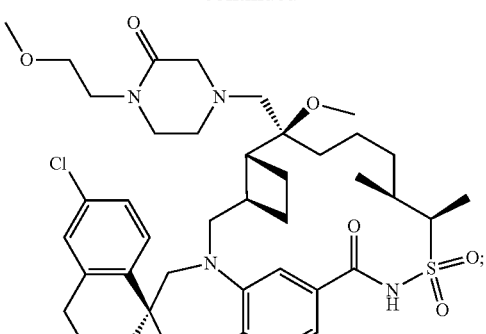
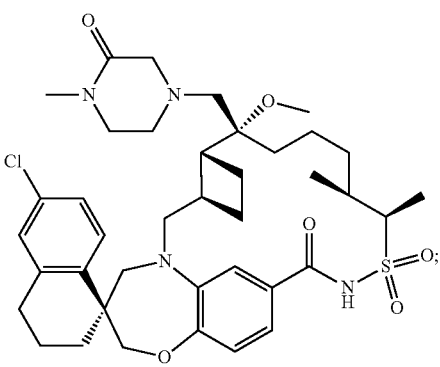
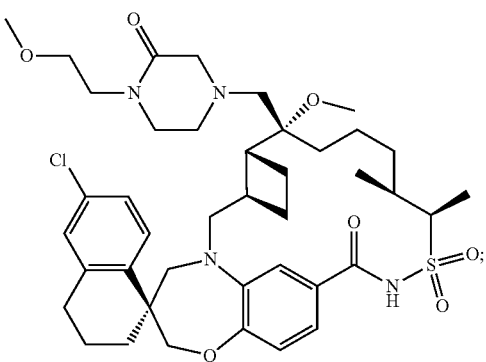
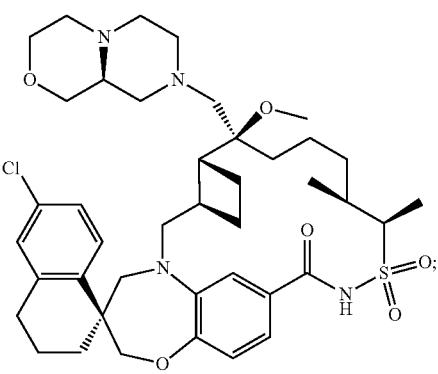

163
-continued
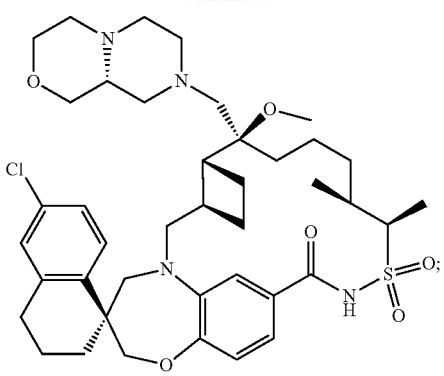
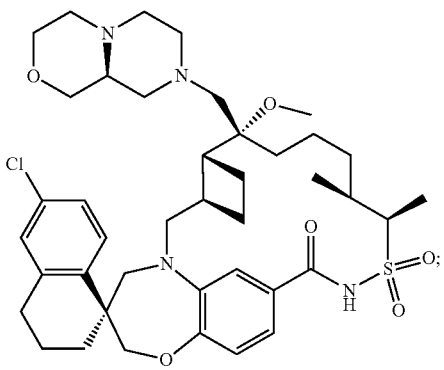
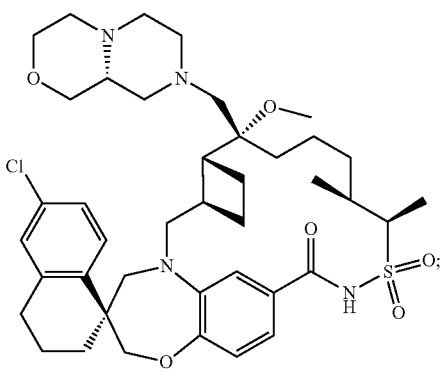
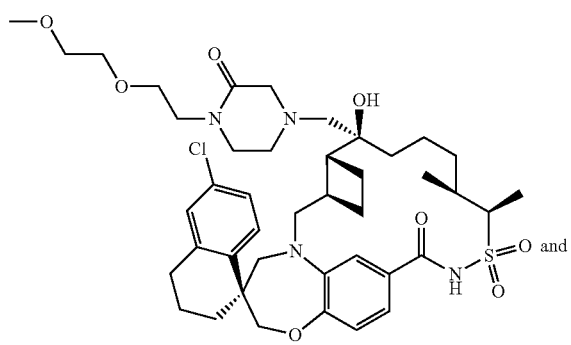
164
-continued
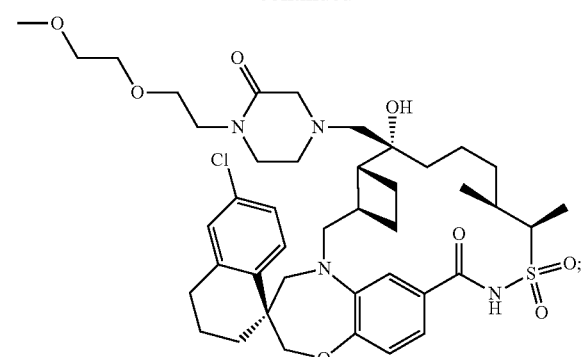
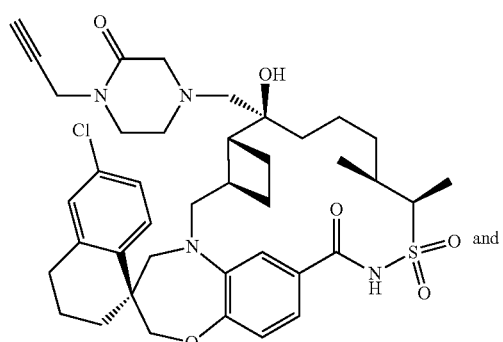
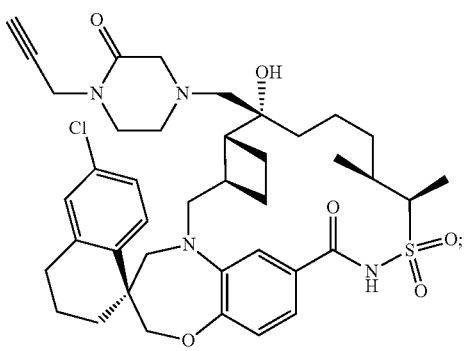
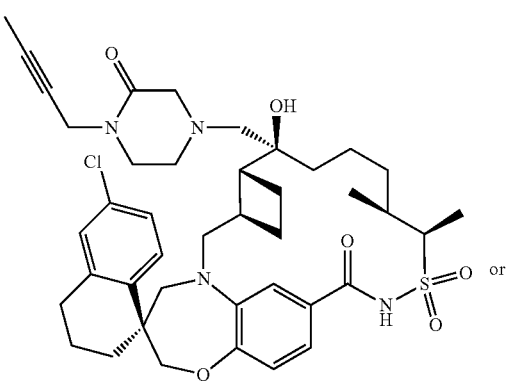

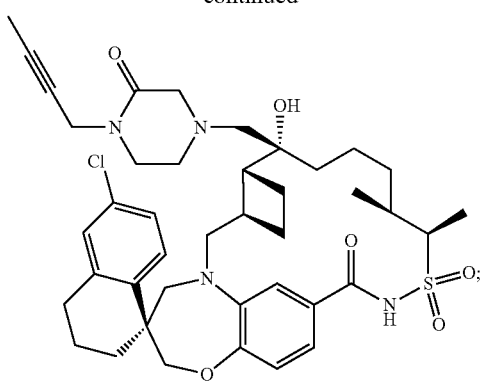
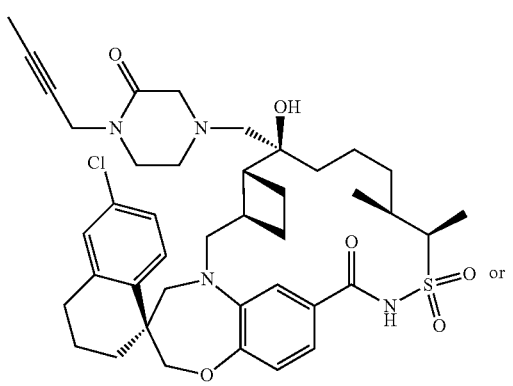
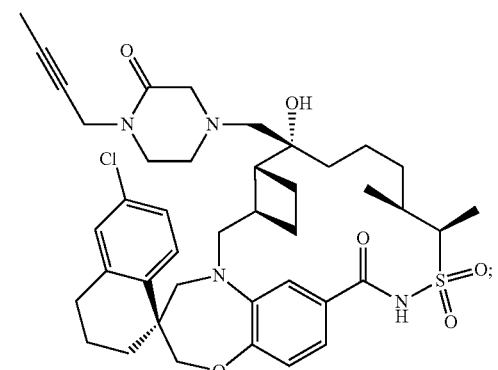
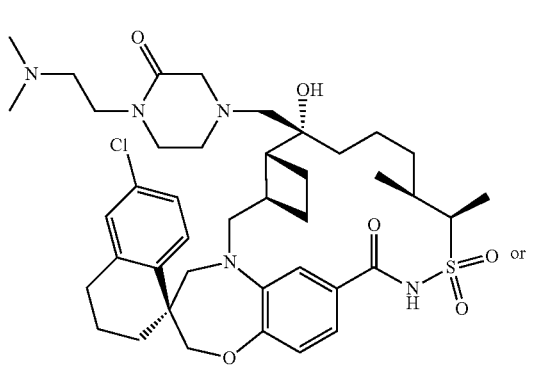
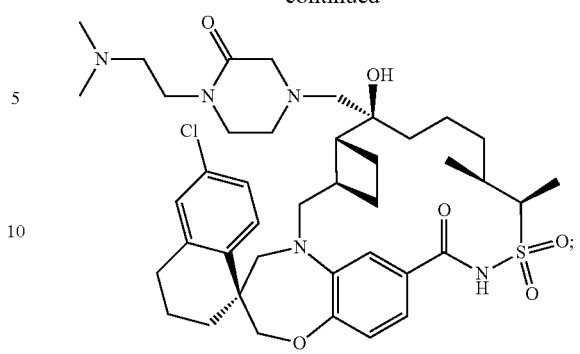
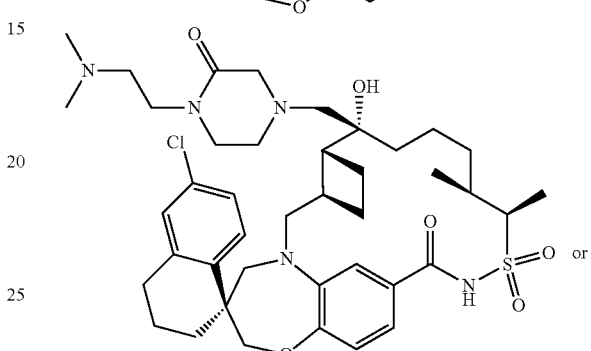

-continued
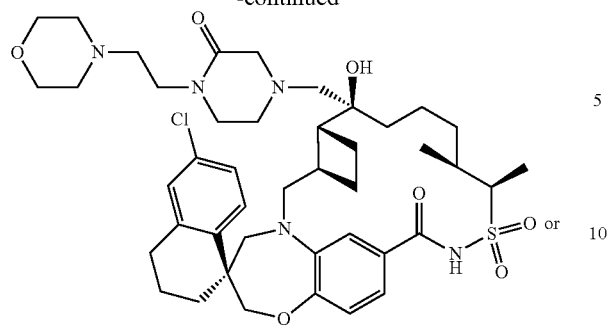
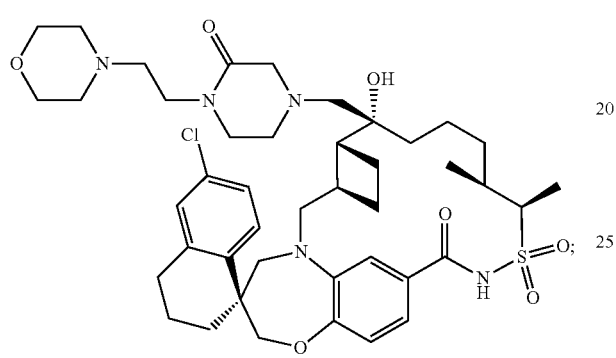
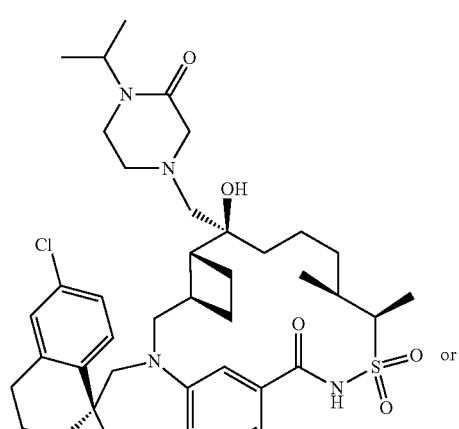
or
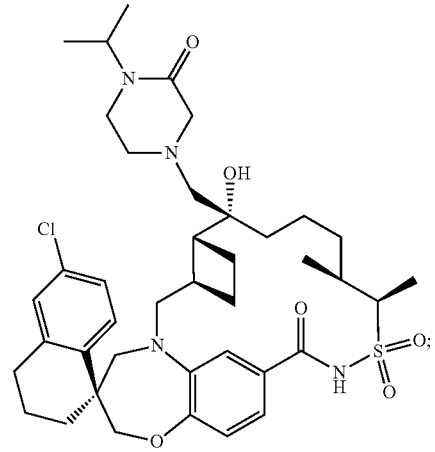
;
-continued
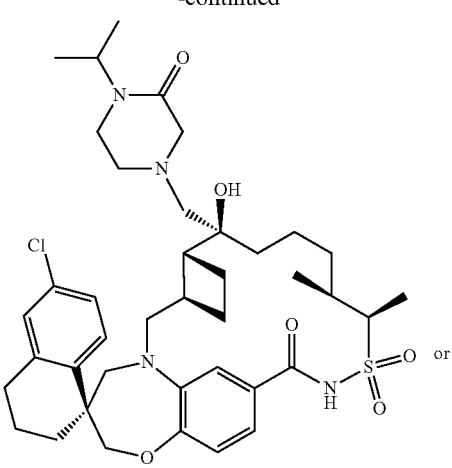
or
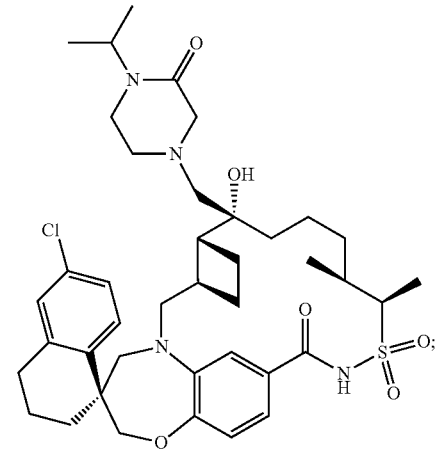
;
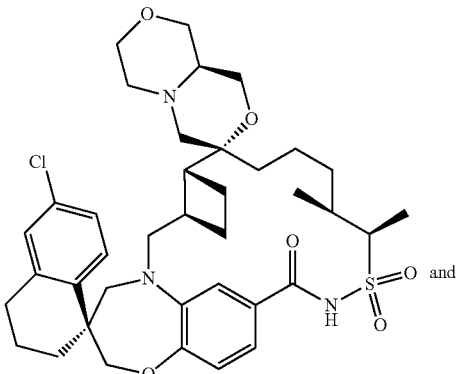
and
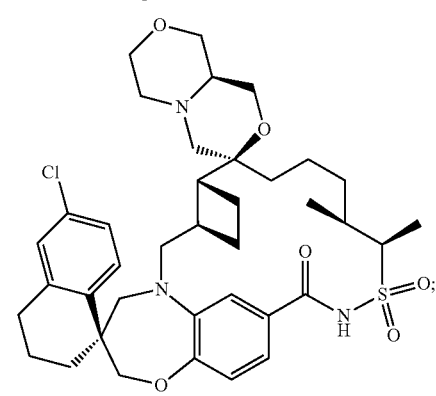
;

169
-continued
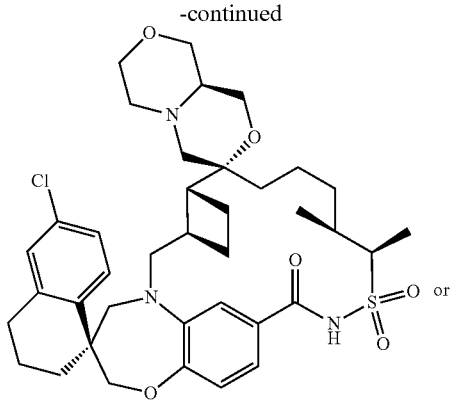
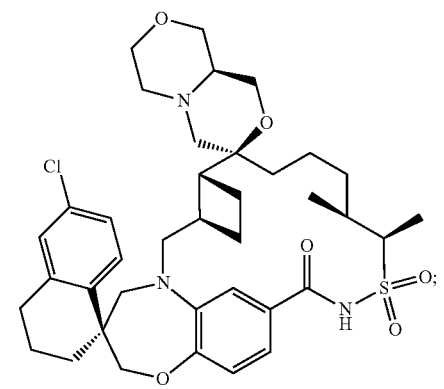
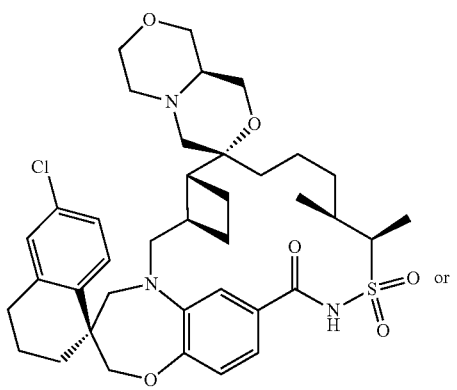
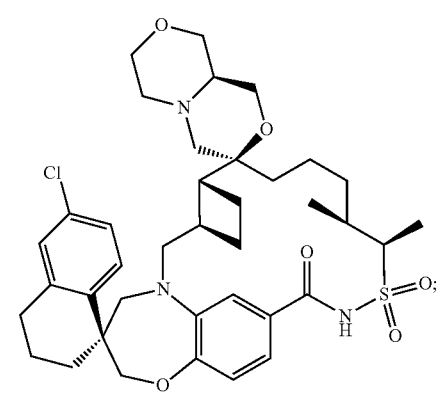
170
-continued
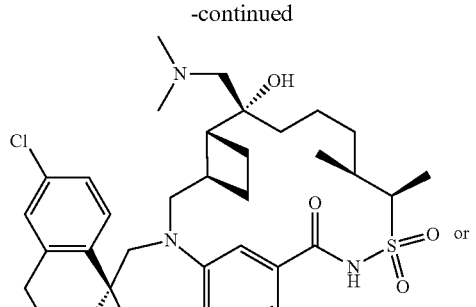
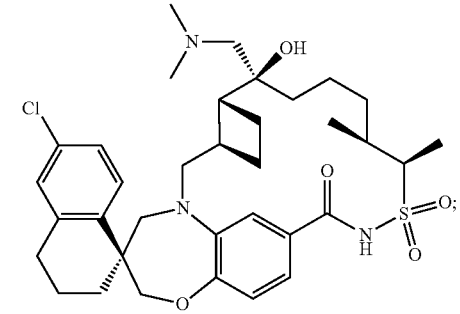
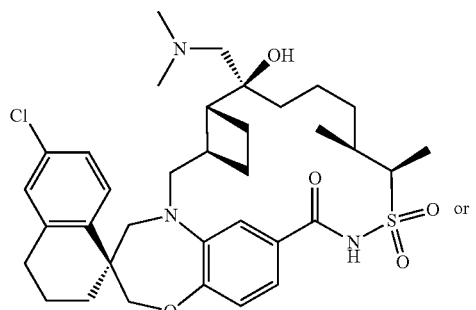
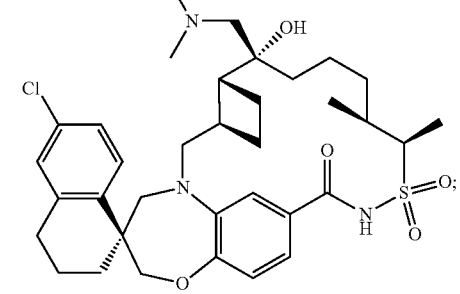
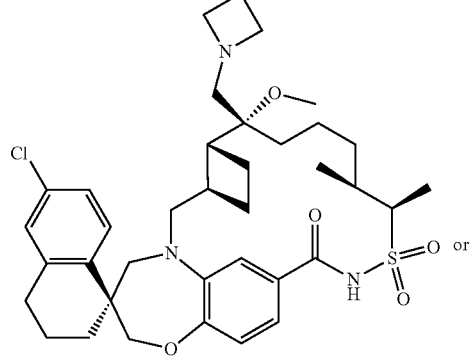

171
-continued
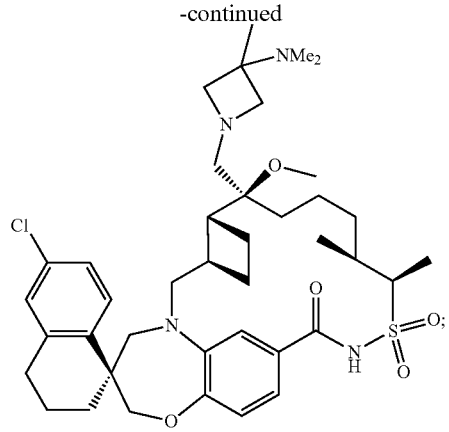
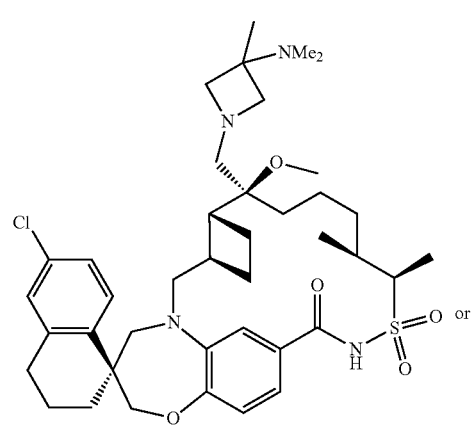
or
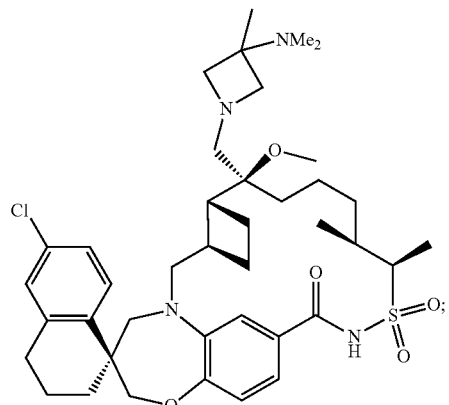
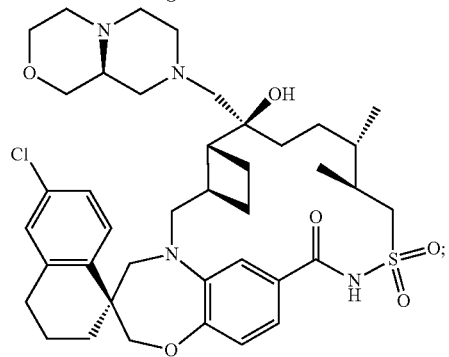
172
-continued
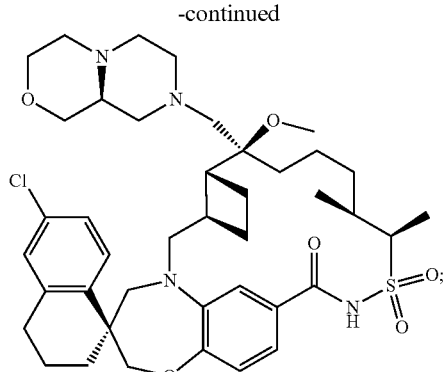
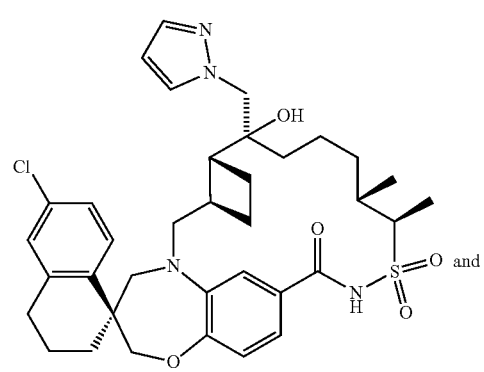
and
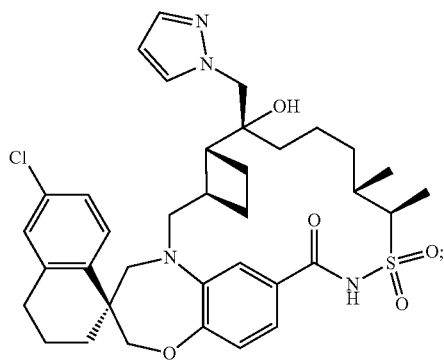
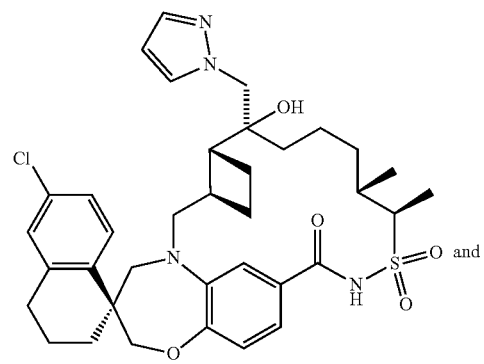
and 173
-continued
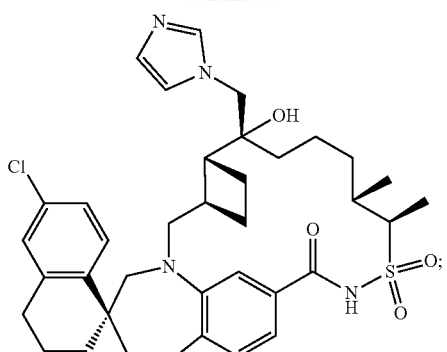
and
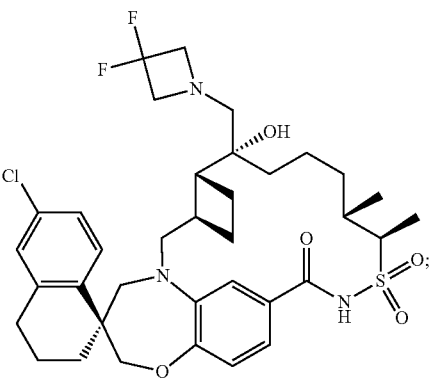
or
174
-continued
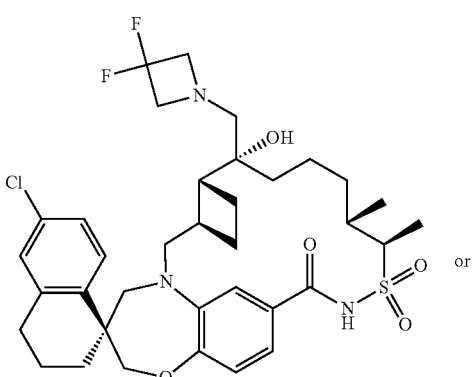
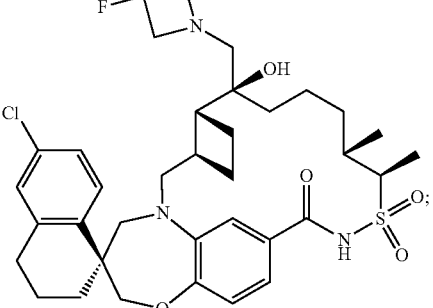
or
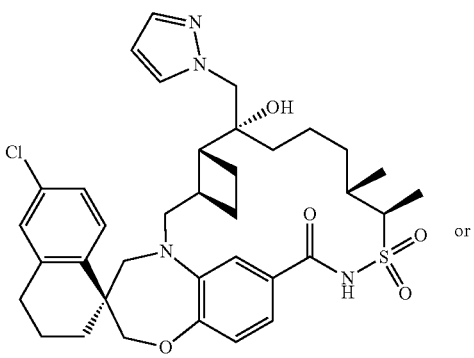
or 175
-continued 176
-continued 177
-continued
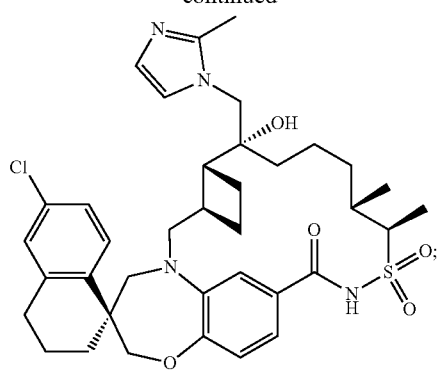
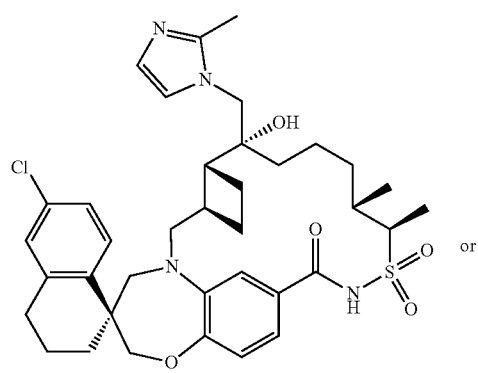
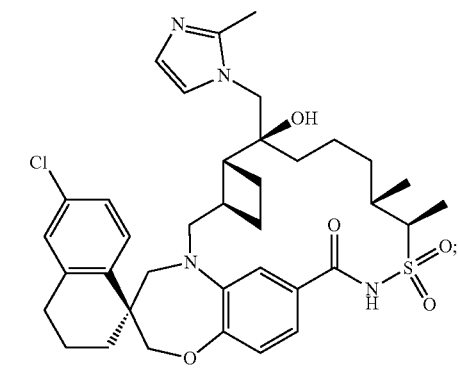
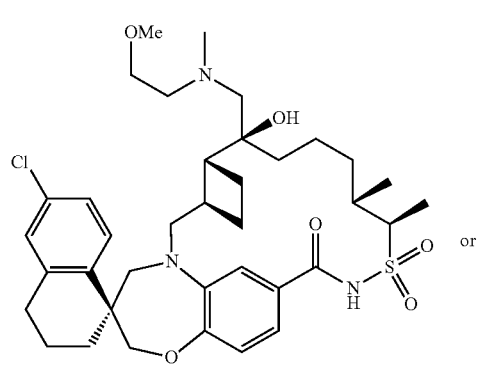
178
-continued
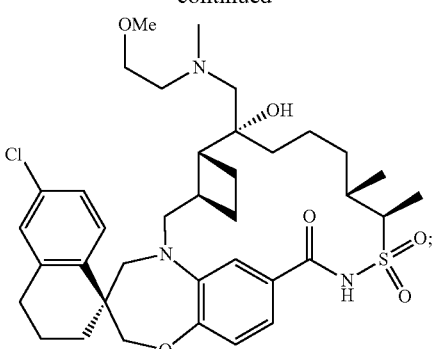
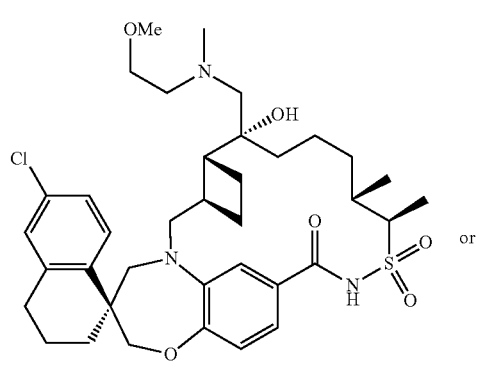
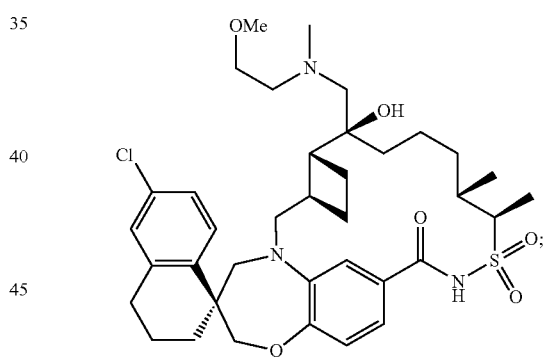
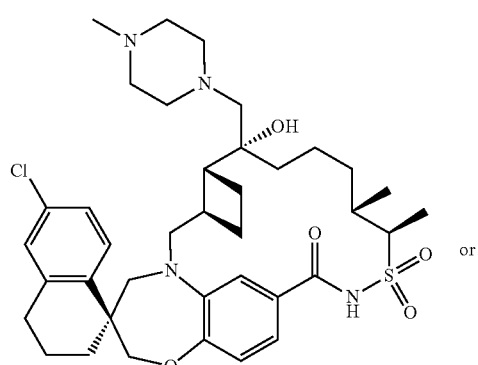

179
-continued
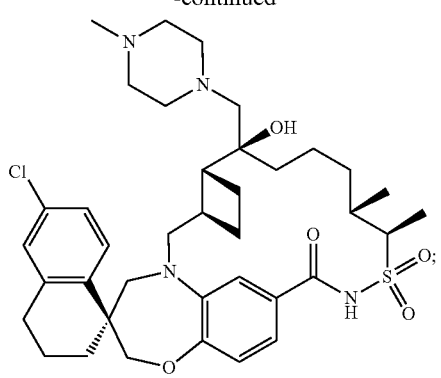
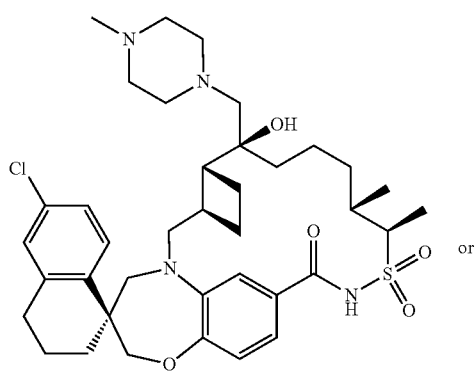
or
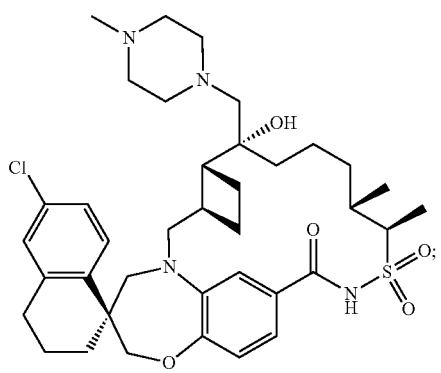
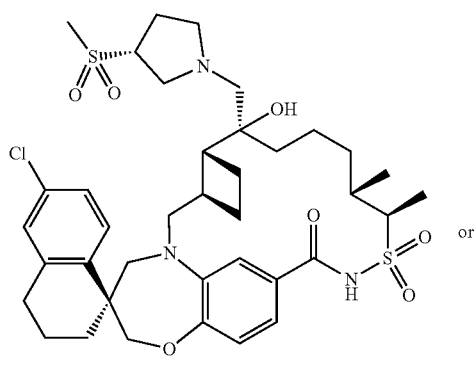
or
180
-continued
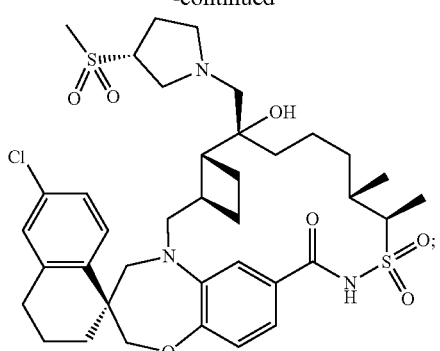
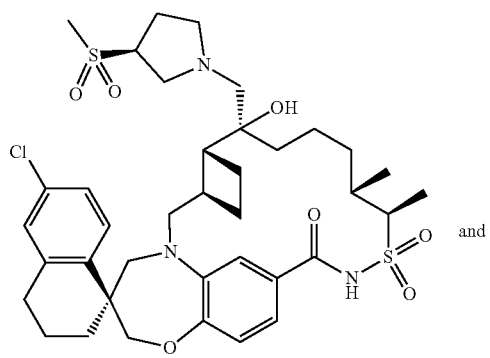
and
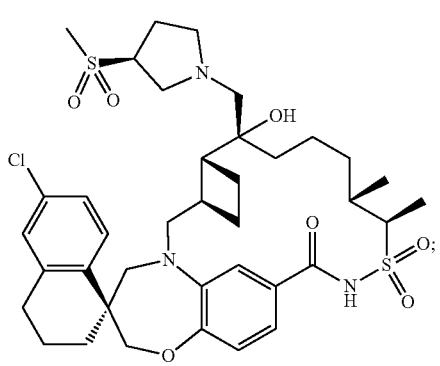
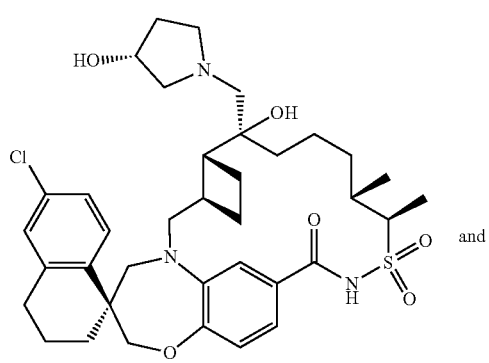
and

181
-continued
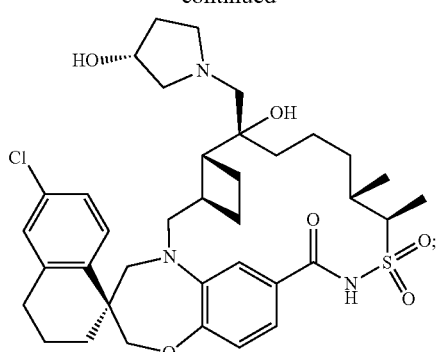
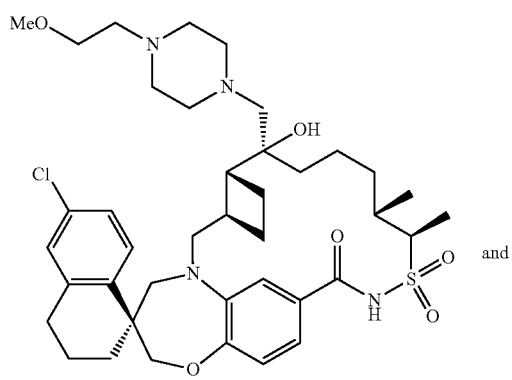
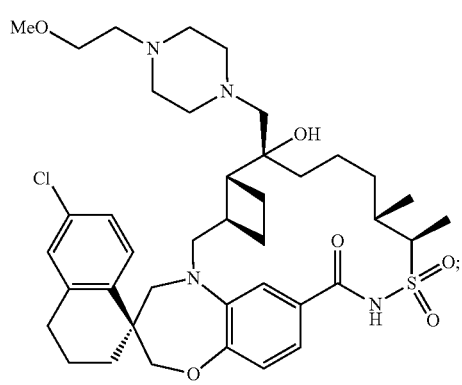
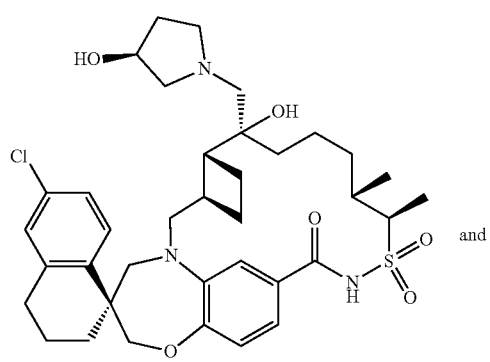
182
-continued
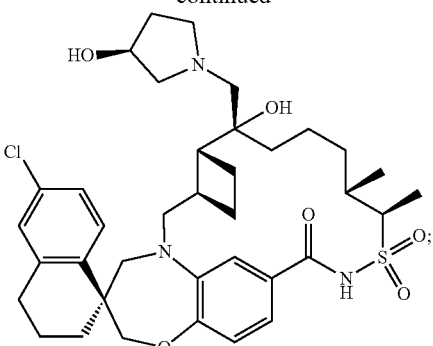
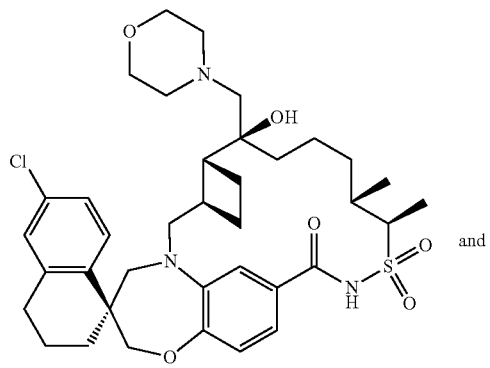
and
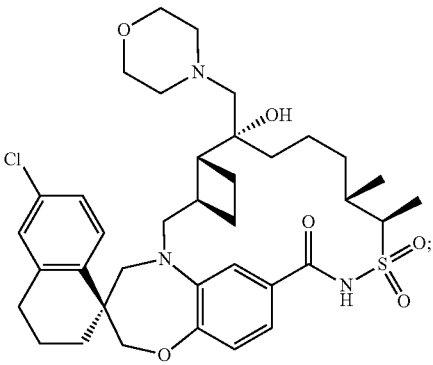
and
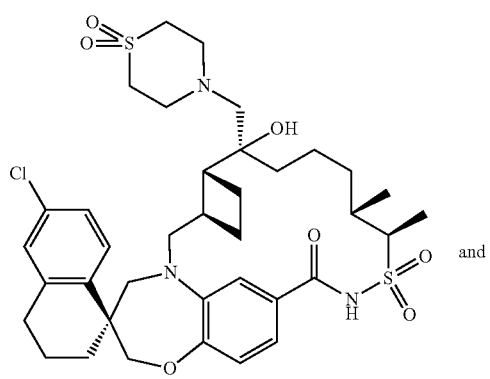
and

183
-continued
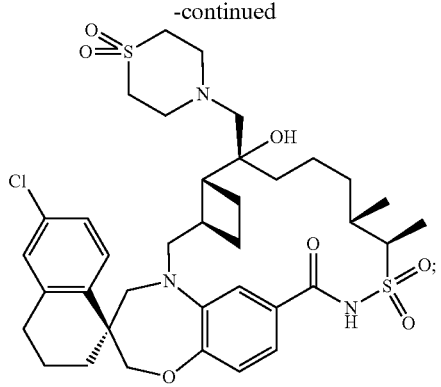
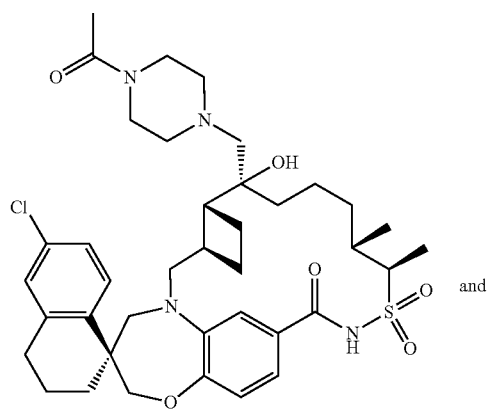
and
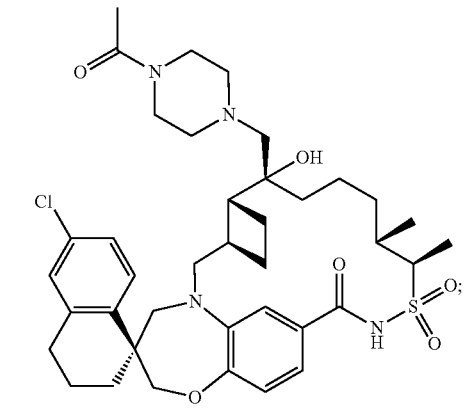
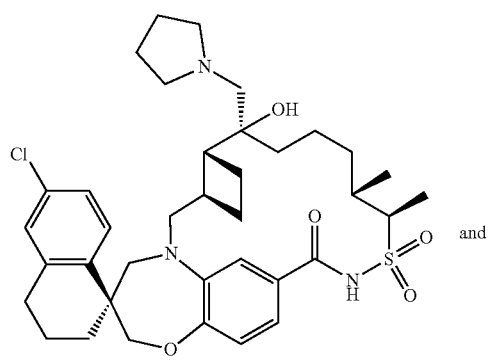
and
184
-continued
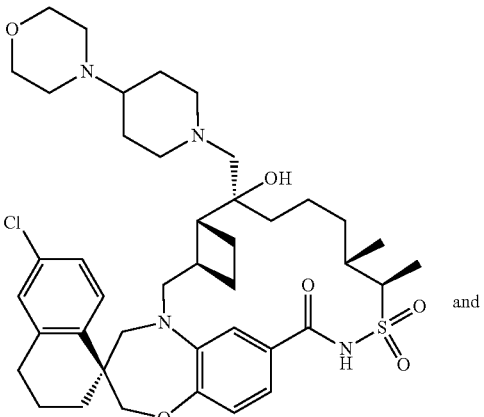
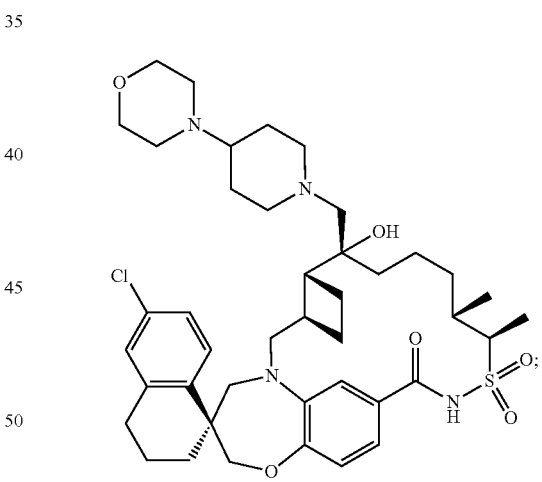
and
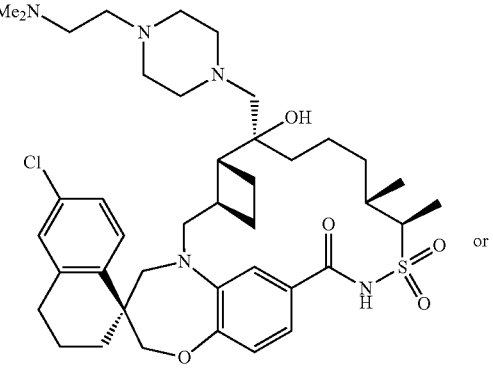
or 185
-continued
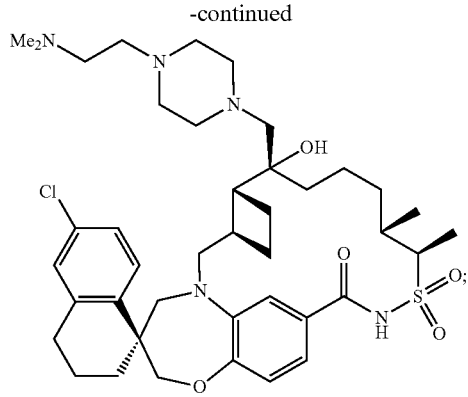
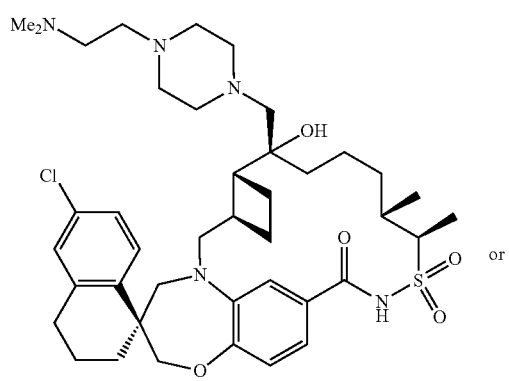
or
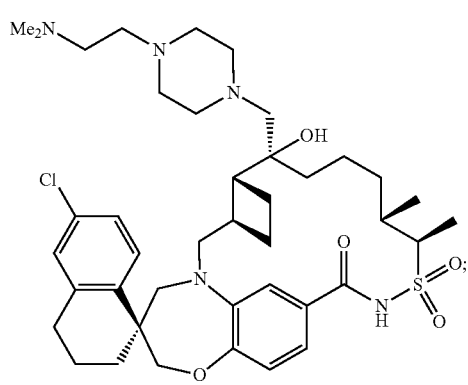
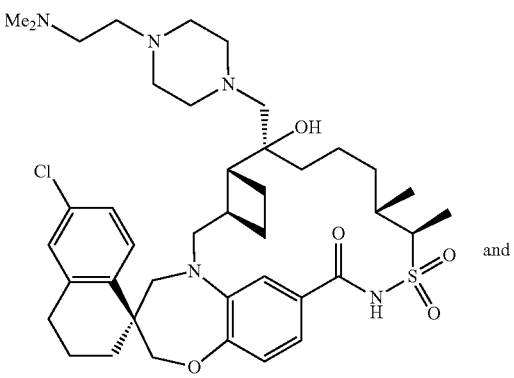
and
186
-continued
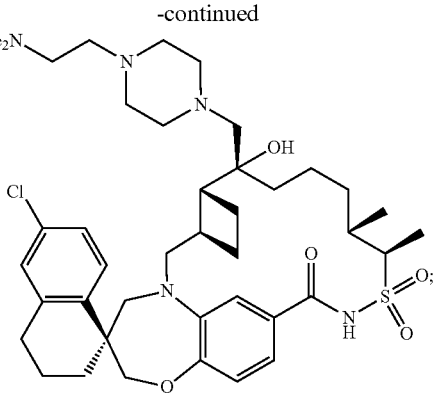
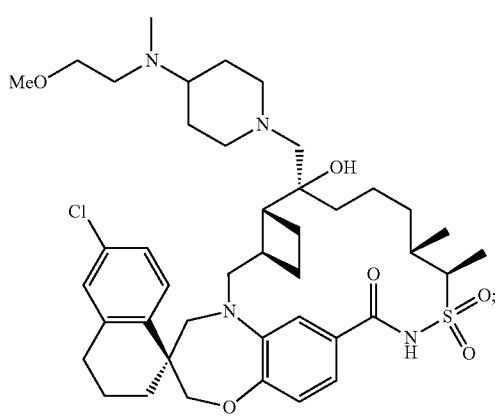
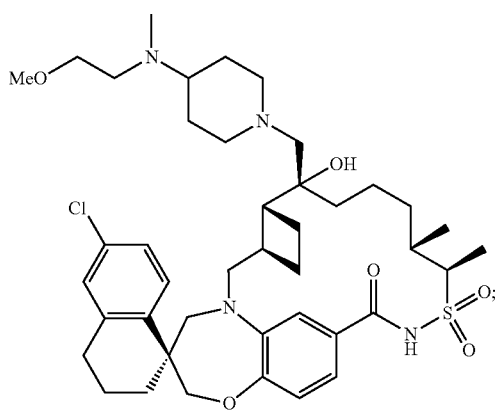
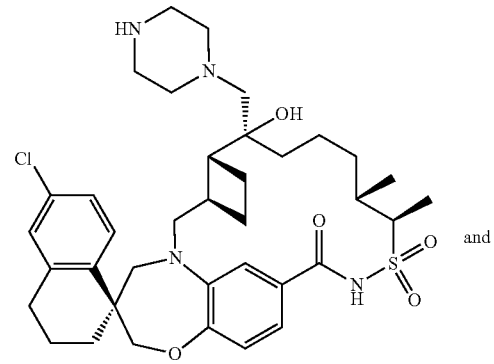
and 187
-continued
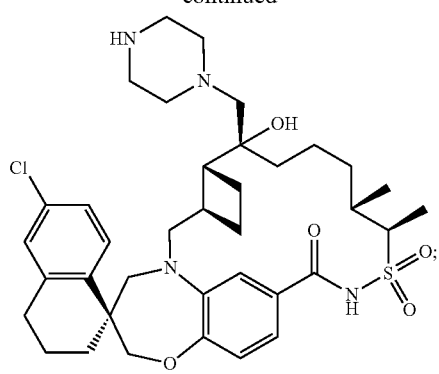
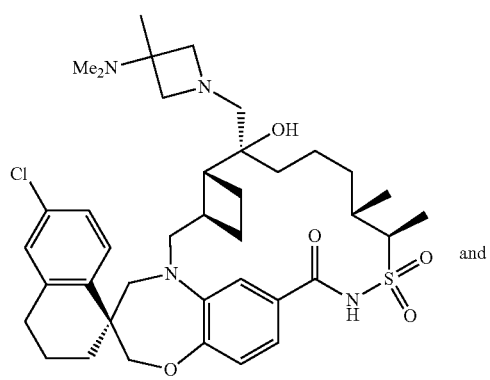
and
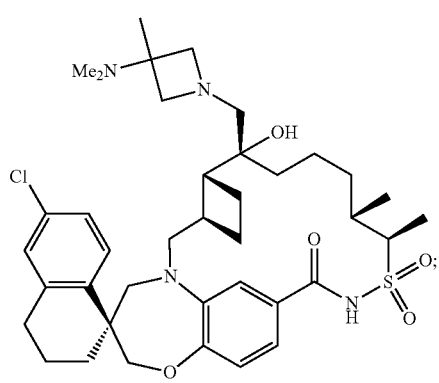
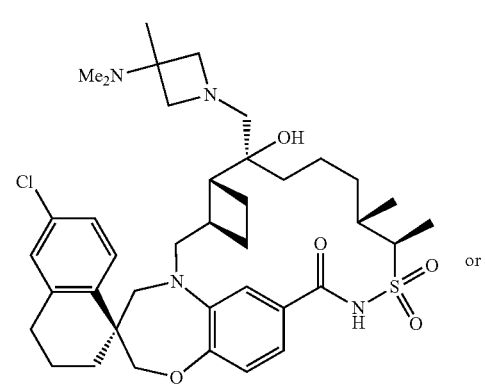
or
188
-continued
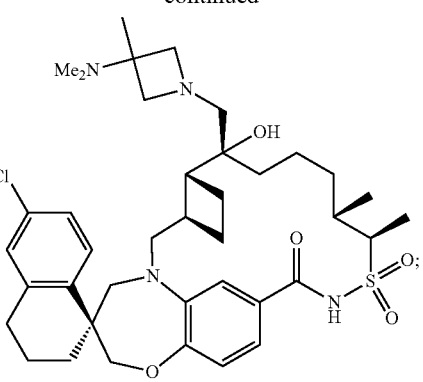
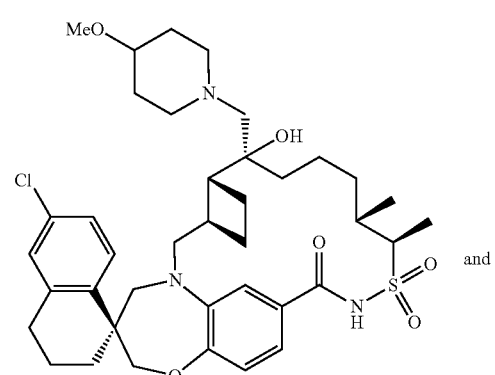
and
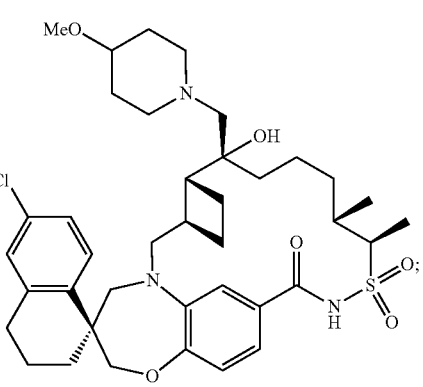
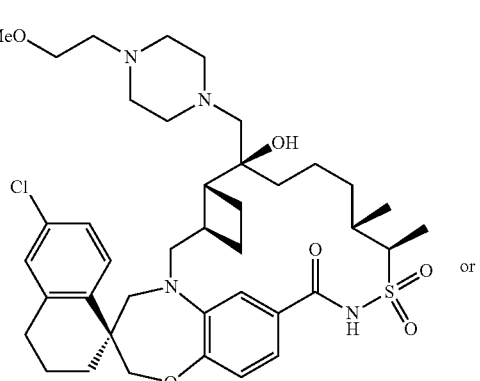
or

189
-continued
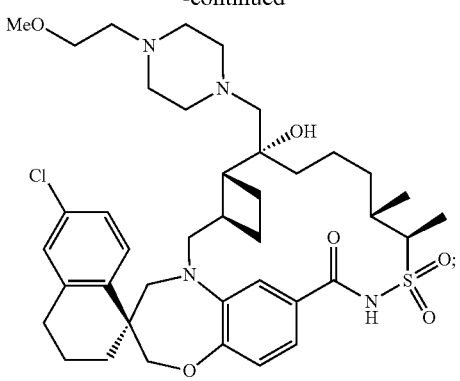
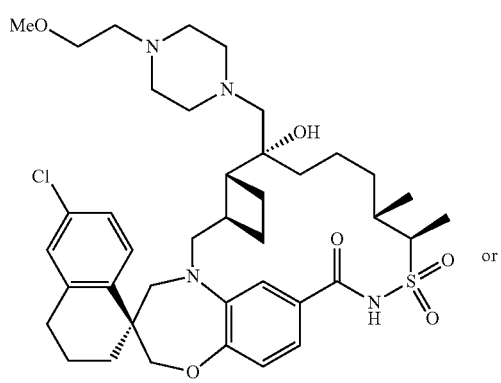
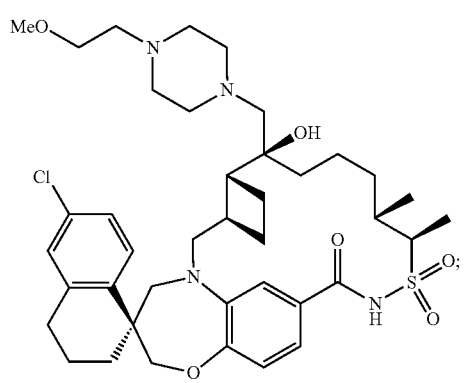
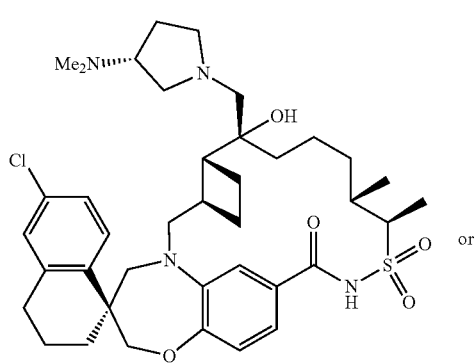
190
-continued
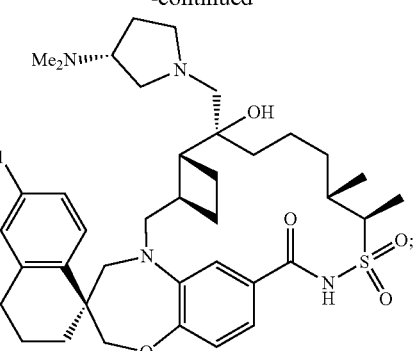
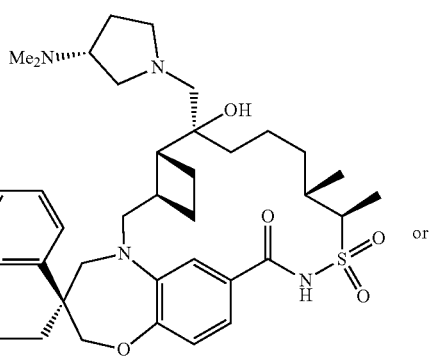
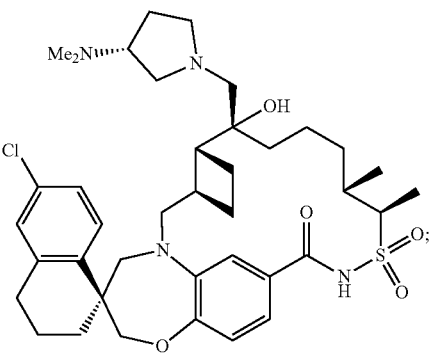
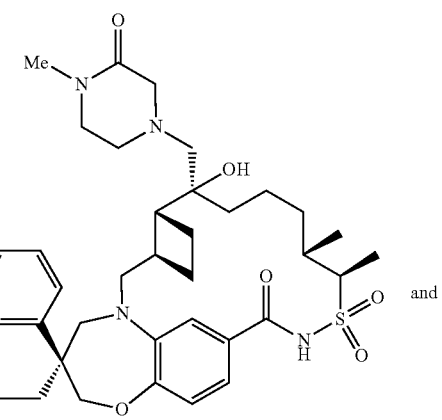

191
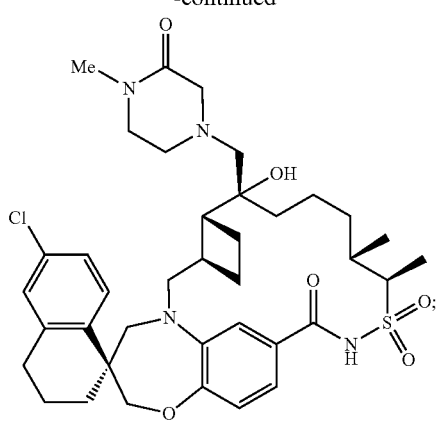
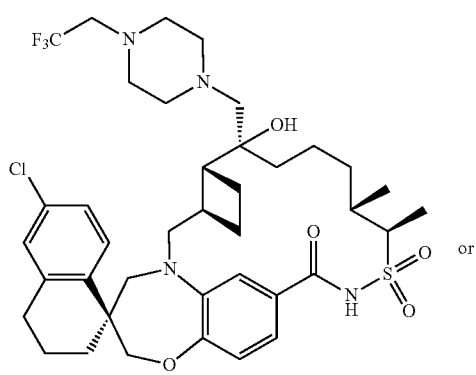
or
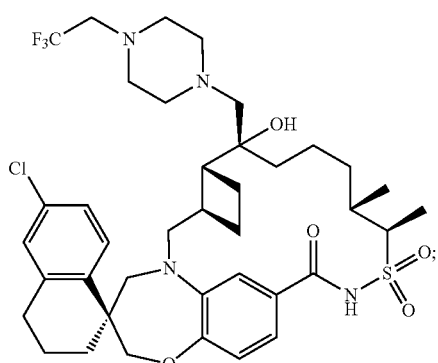
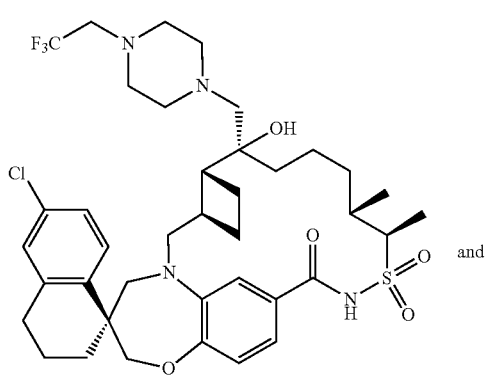
and
192
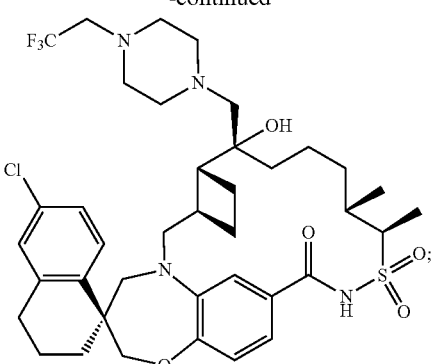
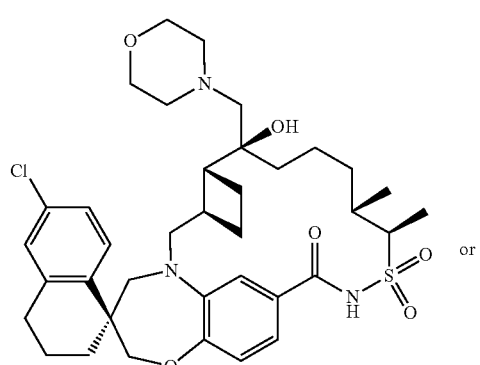
or
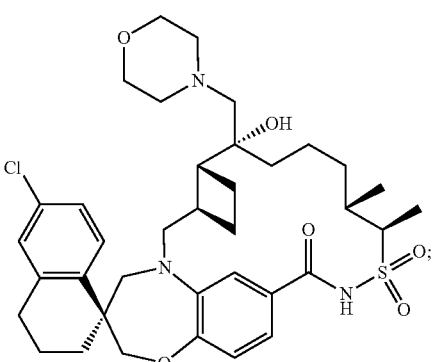
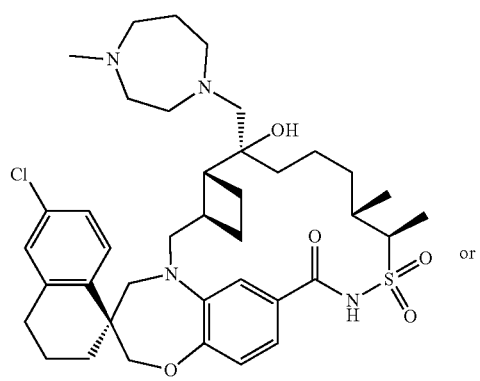
or 193
-continued
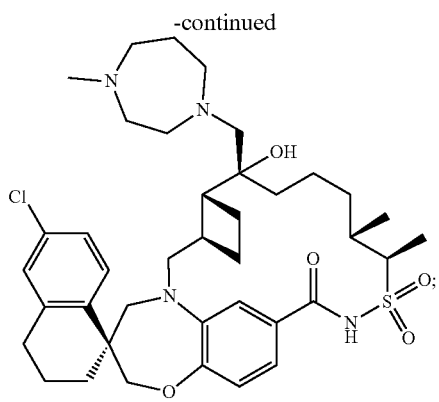
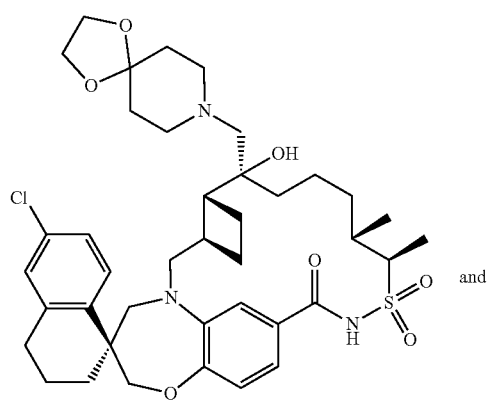
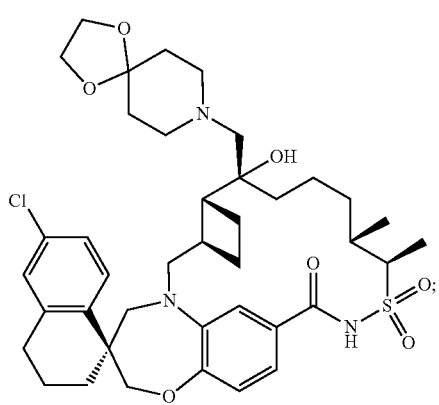
and
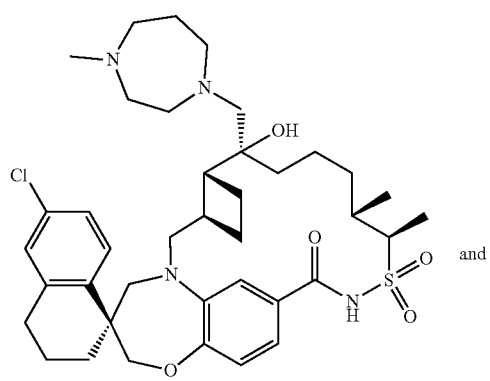
and
194
-continued
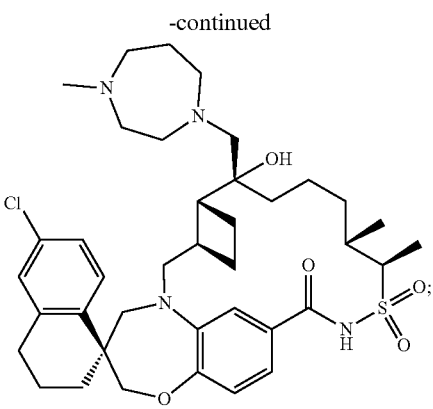
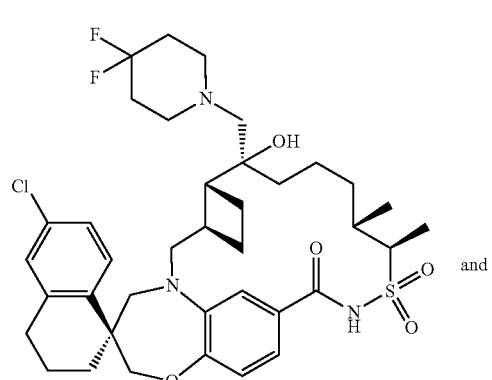
and
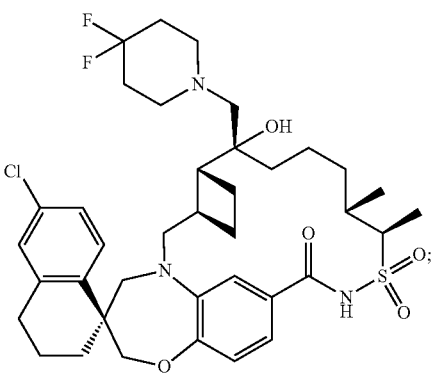
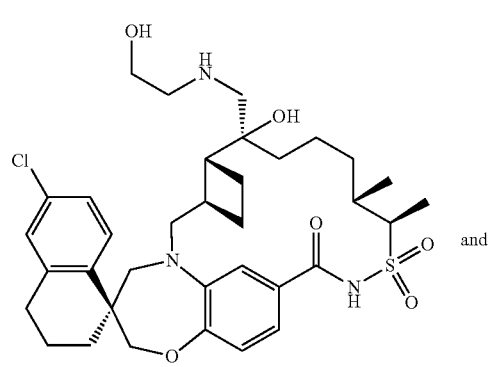
and

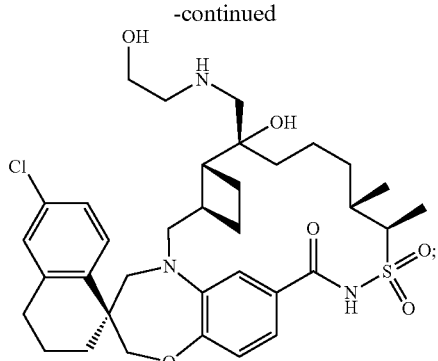
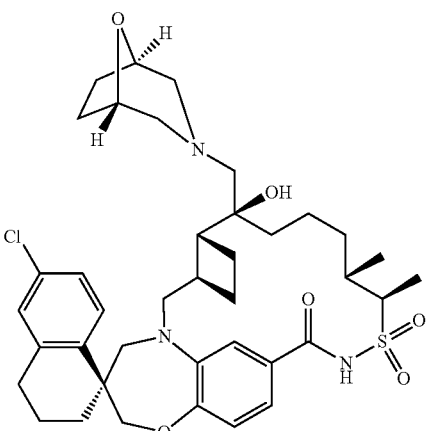 and
 or
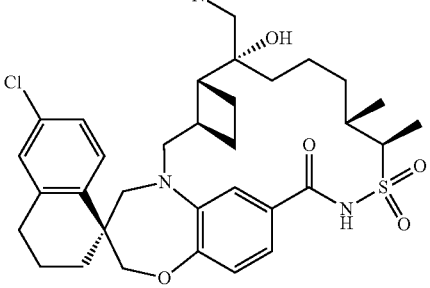 or

197
-continued
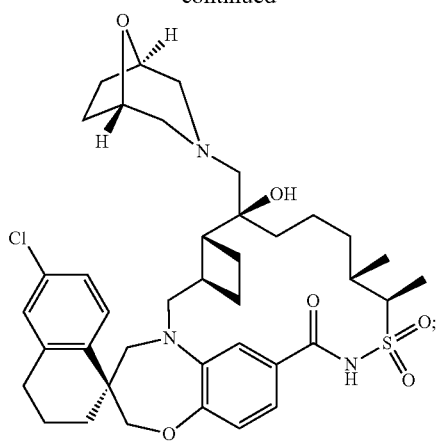
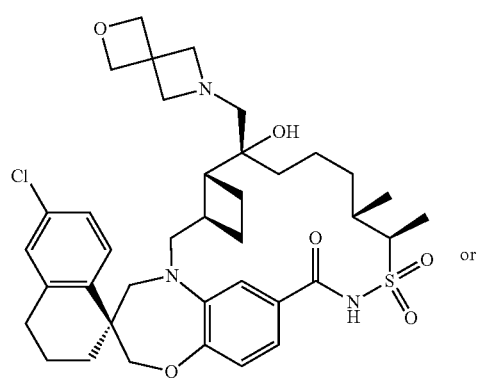
or
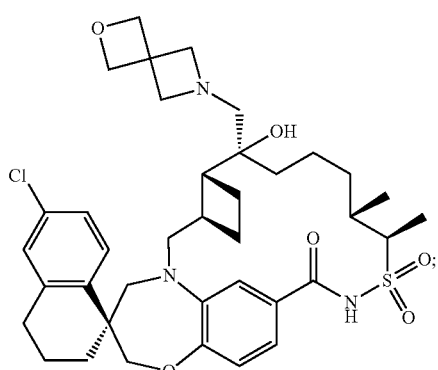
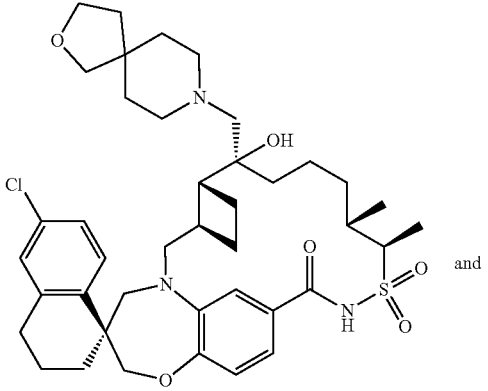
and
198
-continued
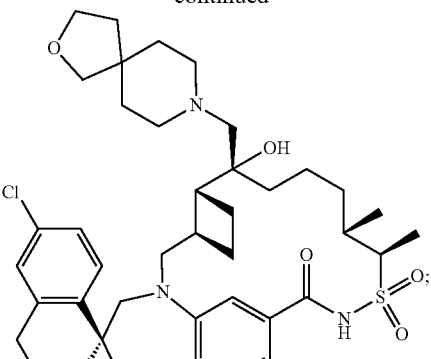
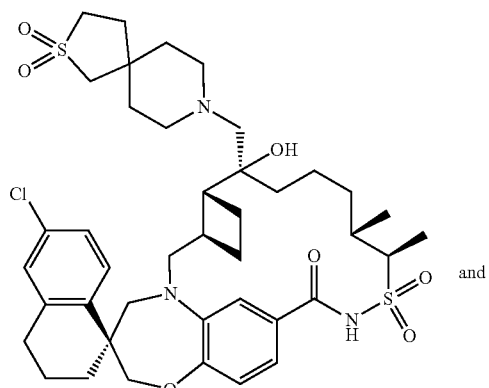
and
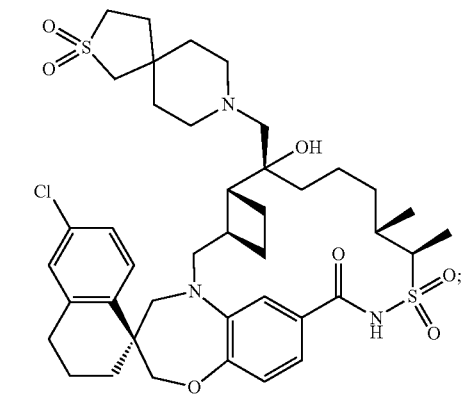
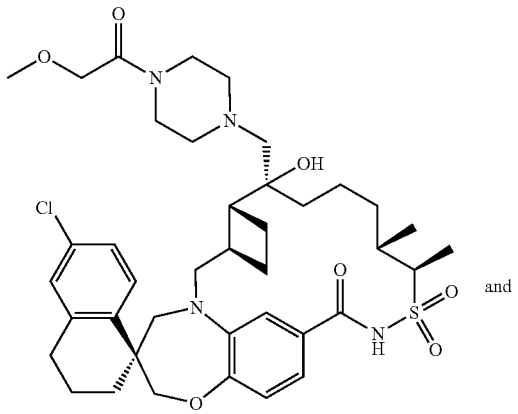
and

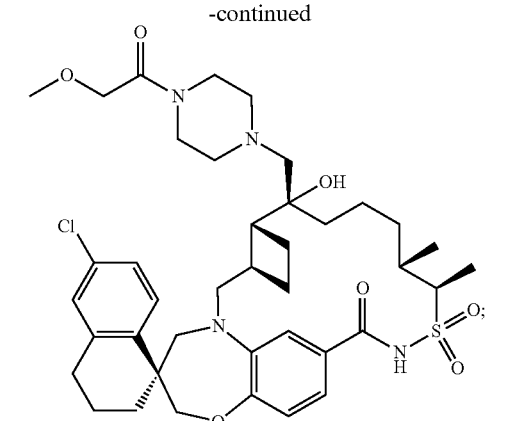
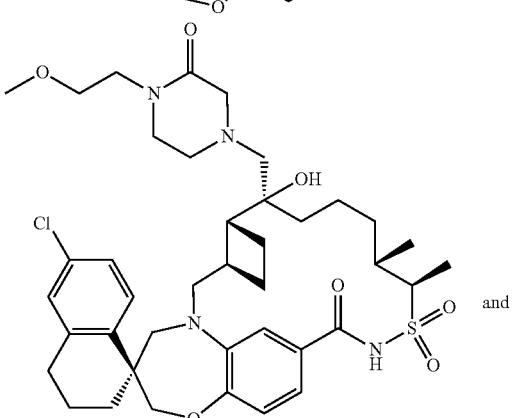
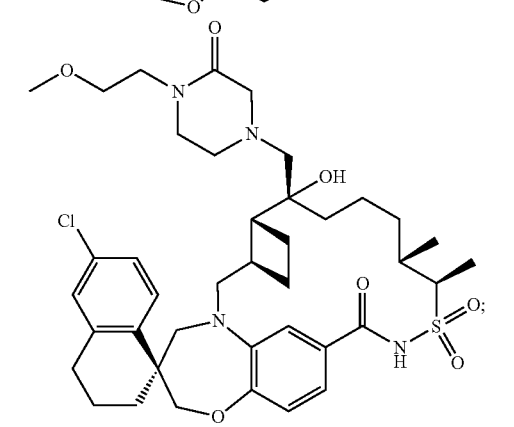
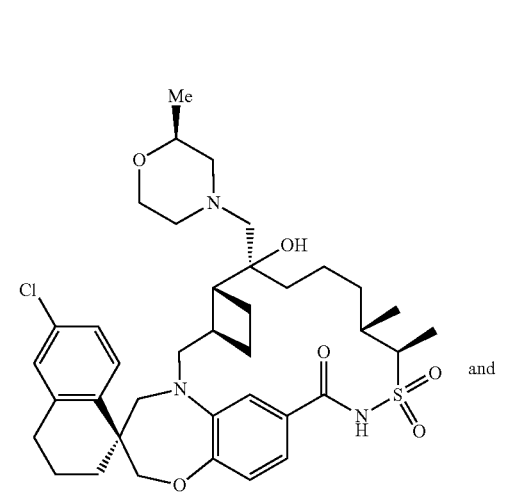
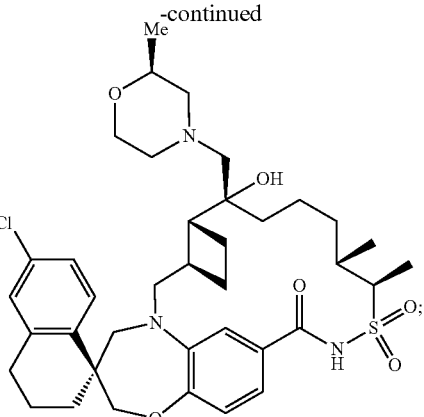
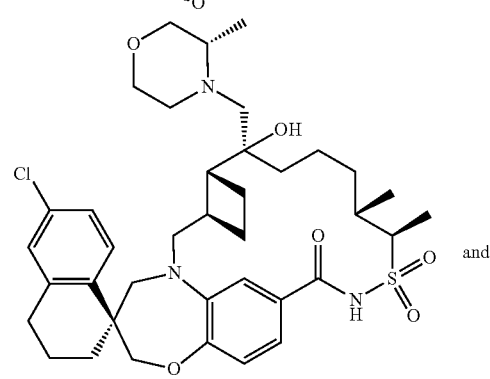
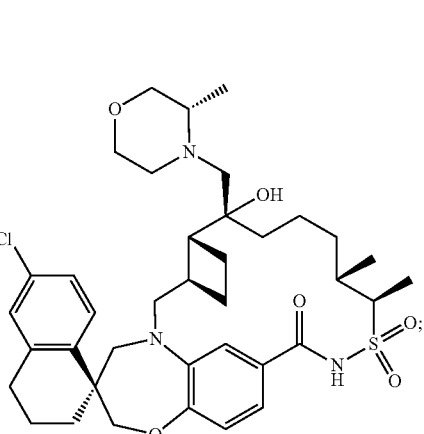
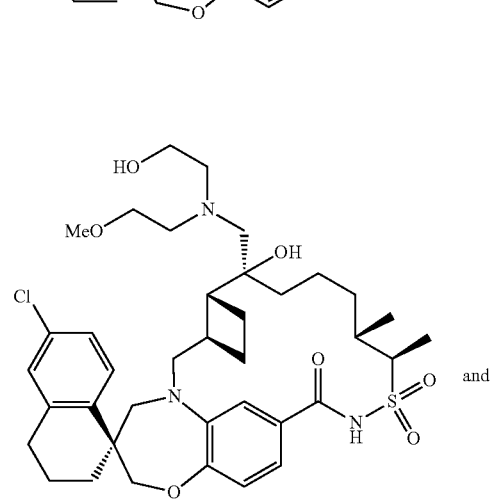

201
-continued

202
-continued

203
-continued
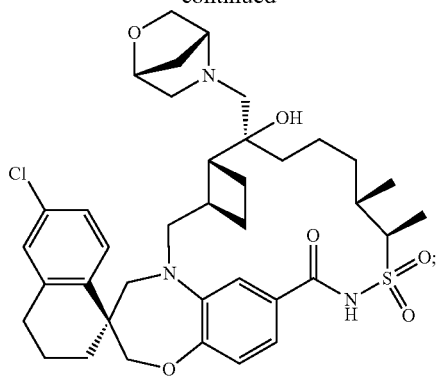
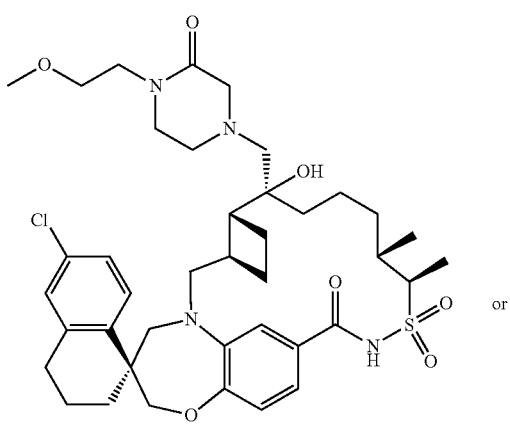
or
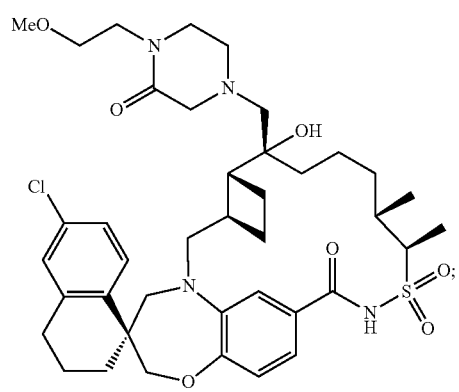
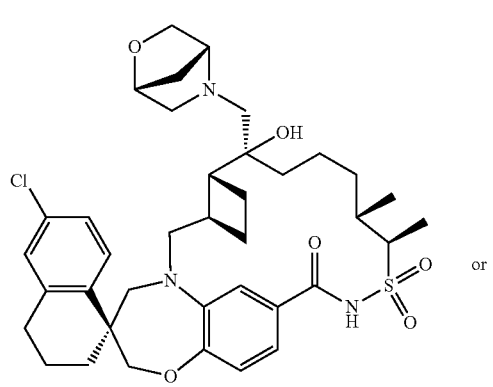
or
204
-continued
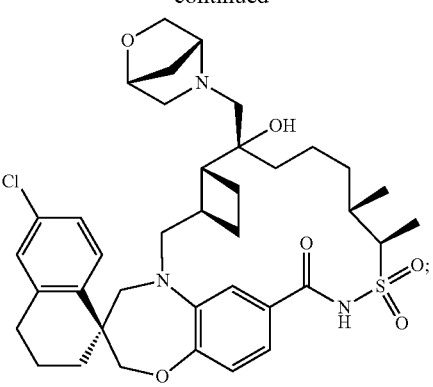
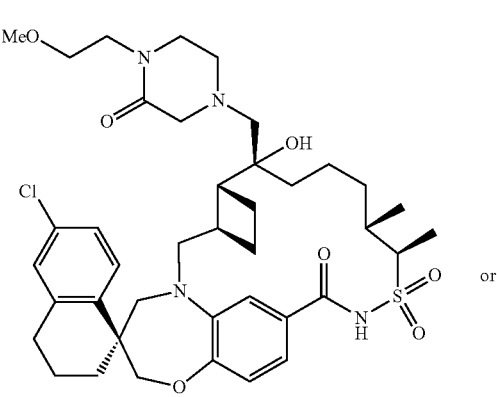
or
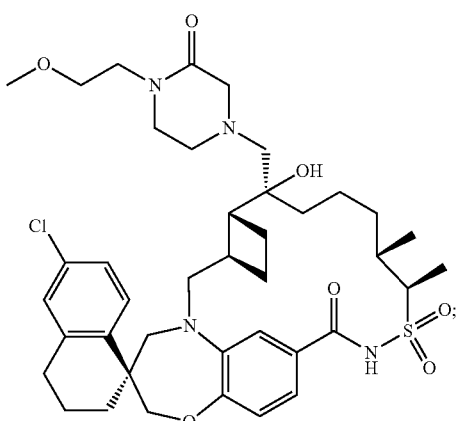
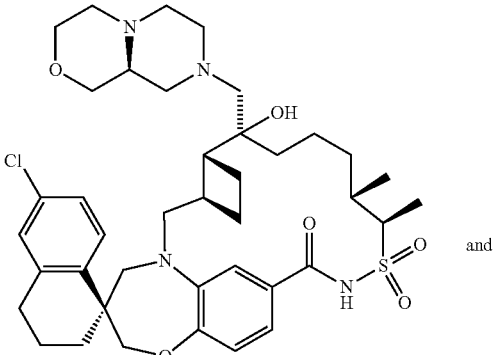
and

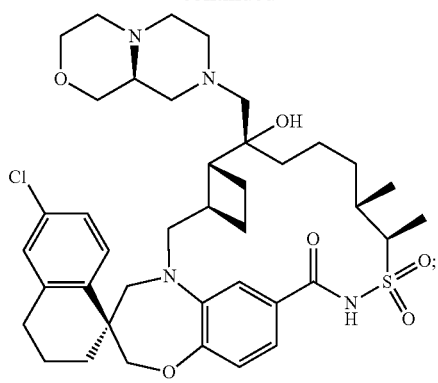
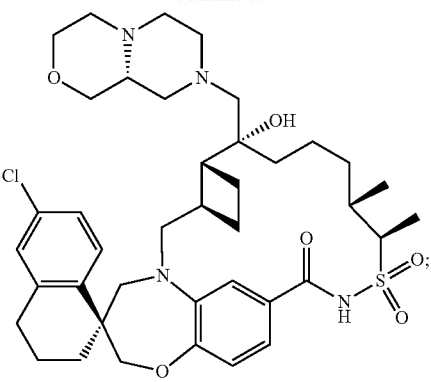
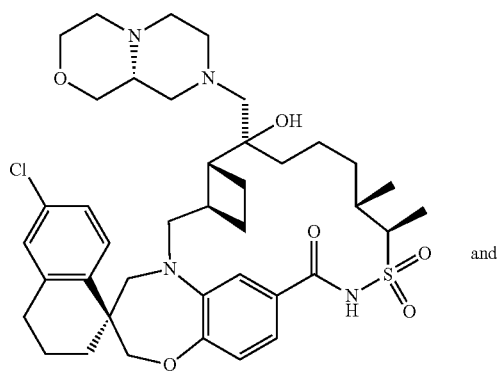 and
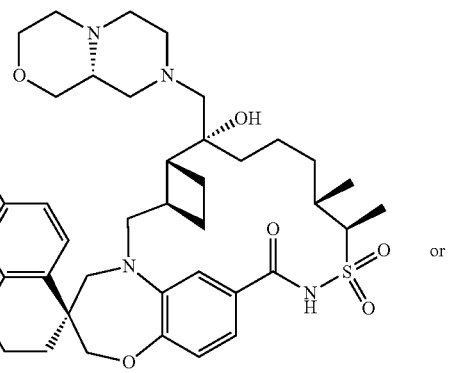 or
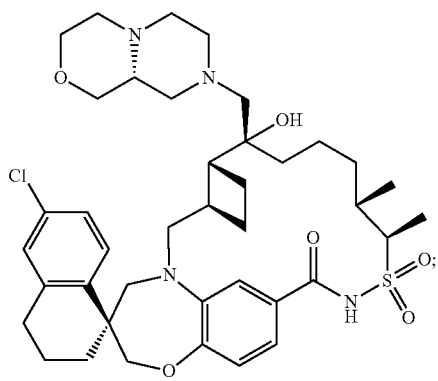
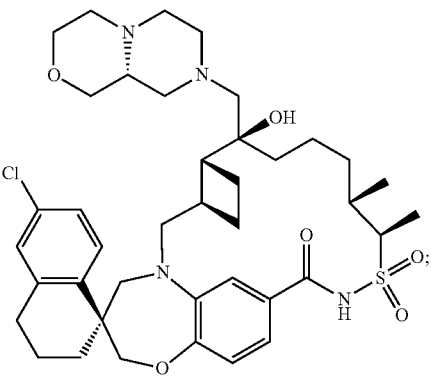
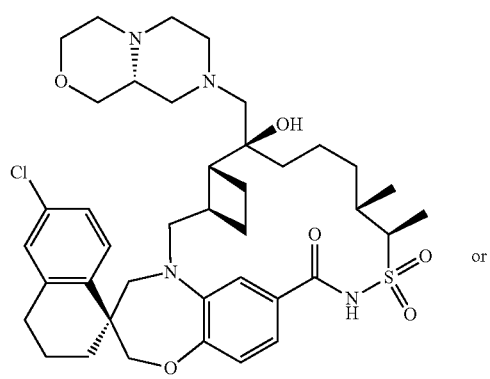 or
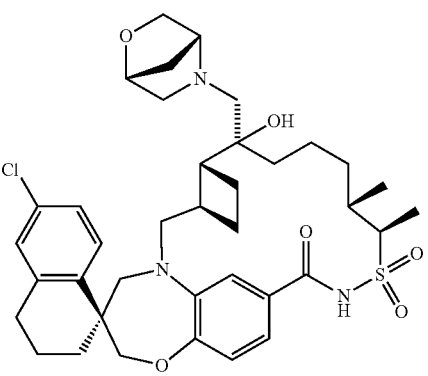

207
-continued
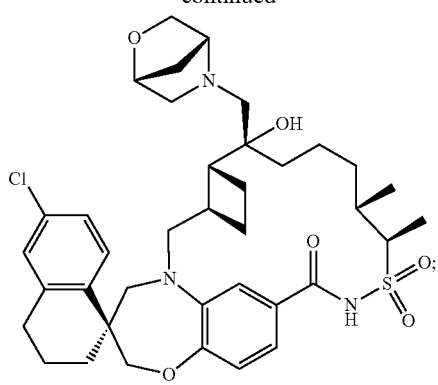
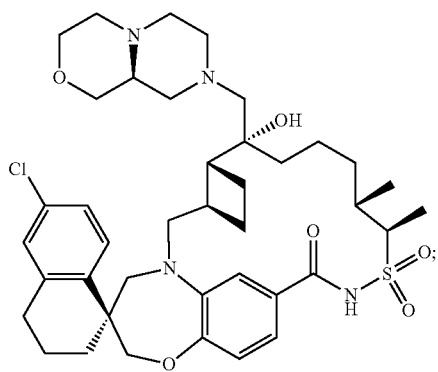
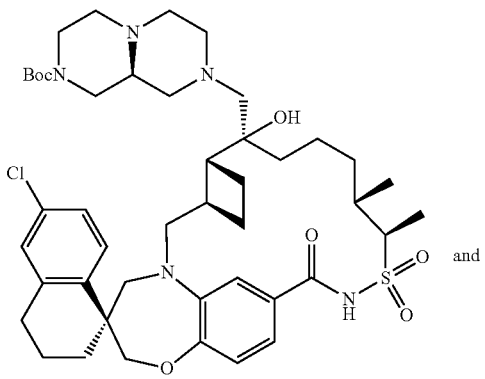
and

and
208
-continued
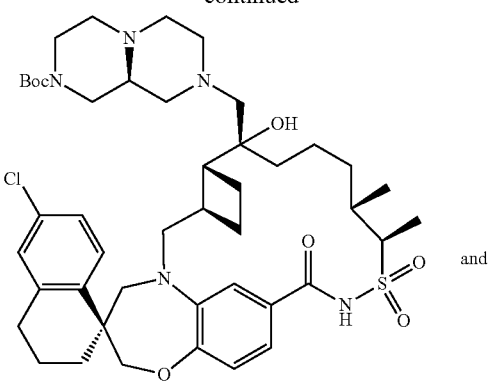
and
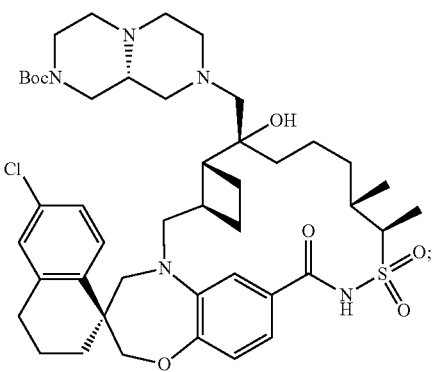
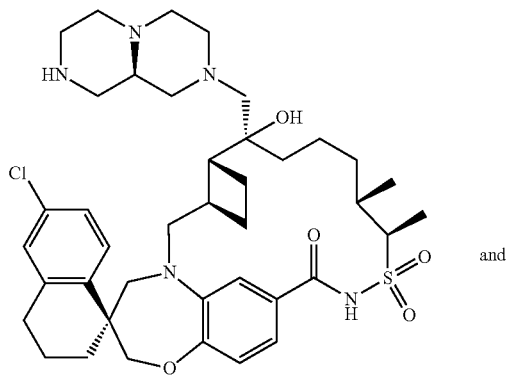
and
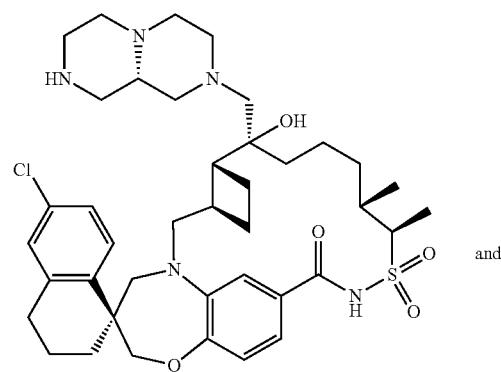
and 209
-continued
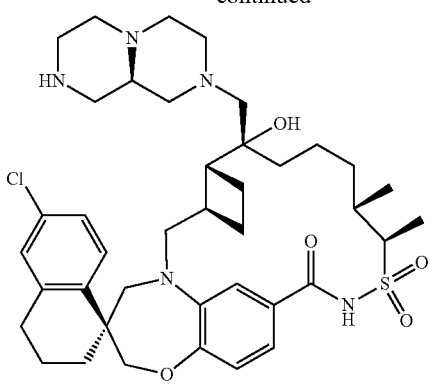
and
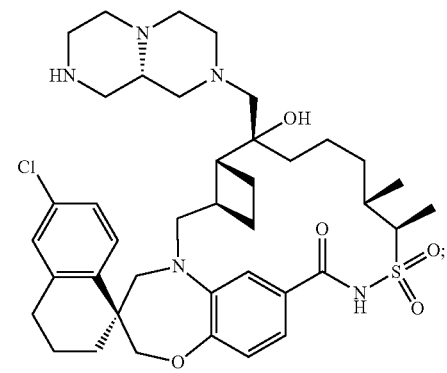
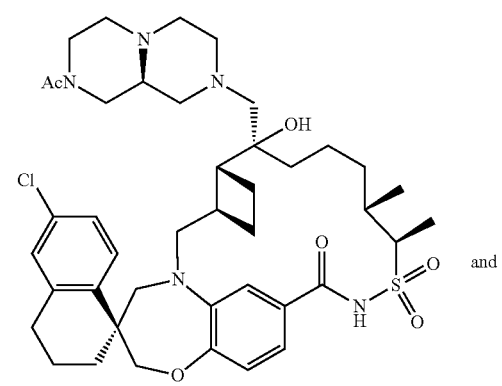
and
210
-continued
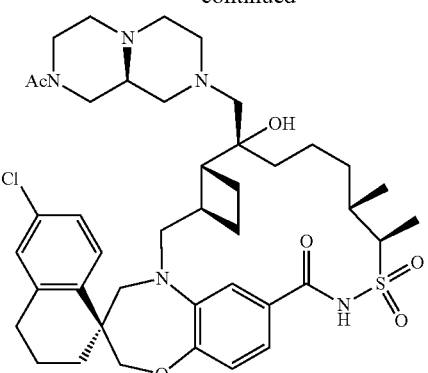
and
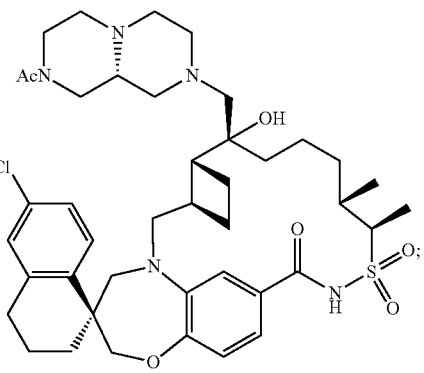
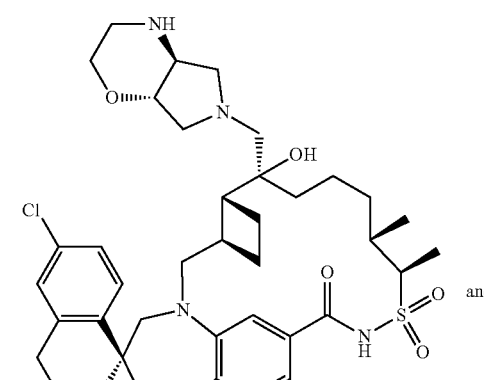
and
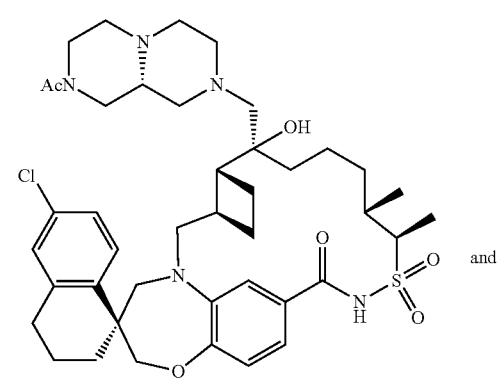
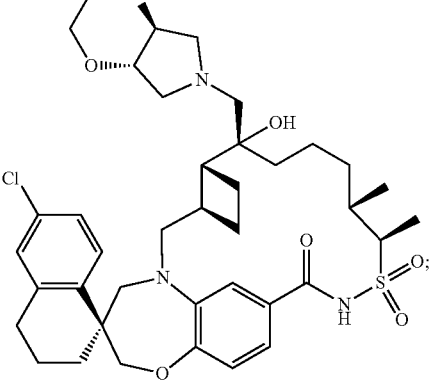

211
-continued
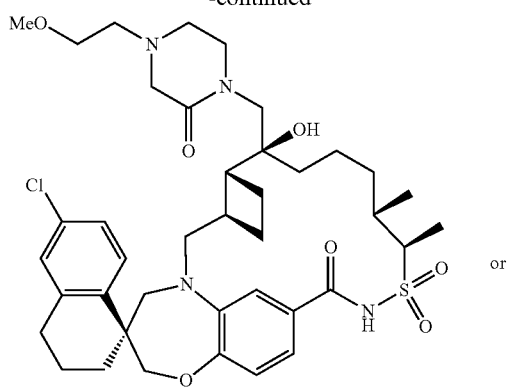
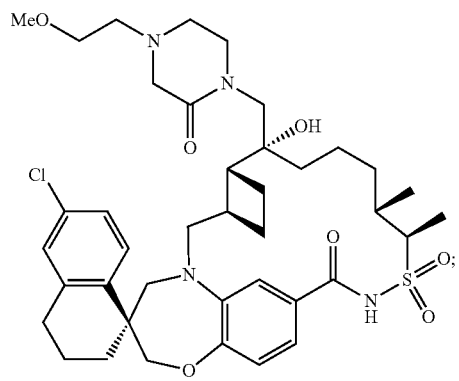
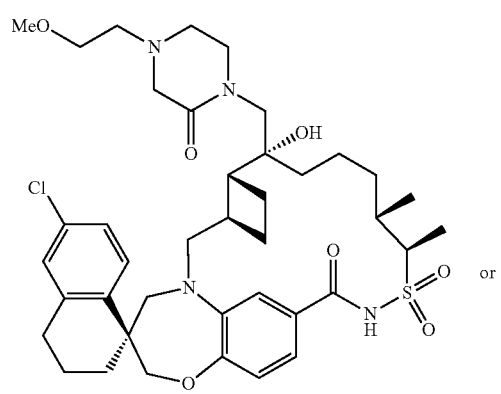
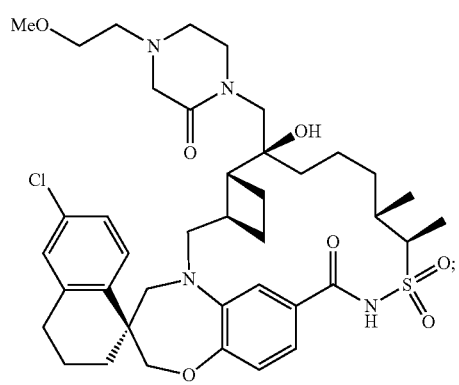
212
-continued
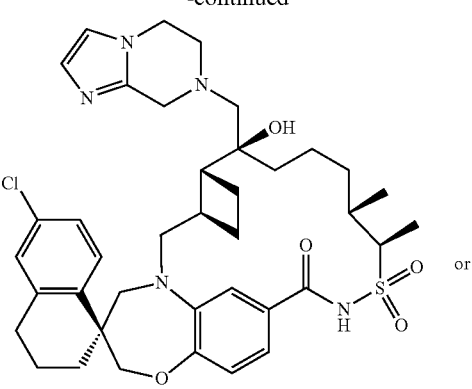
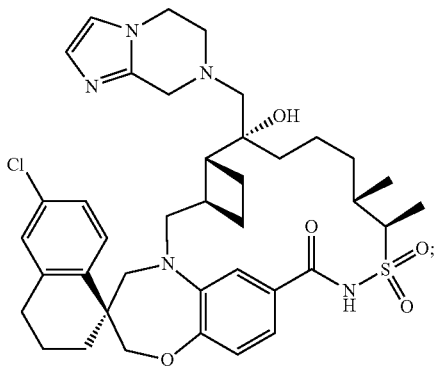
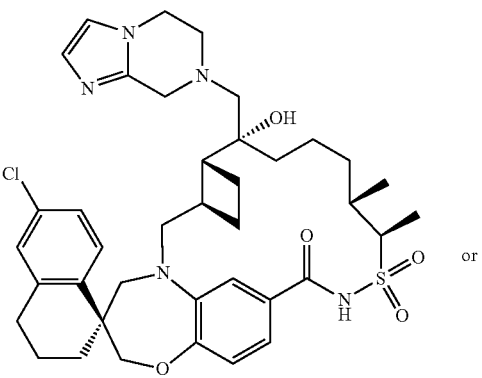
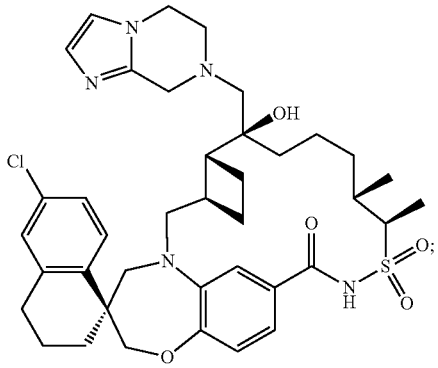

213
-continued
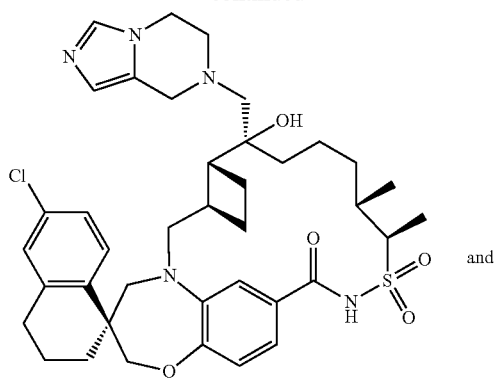
and
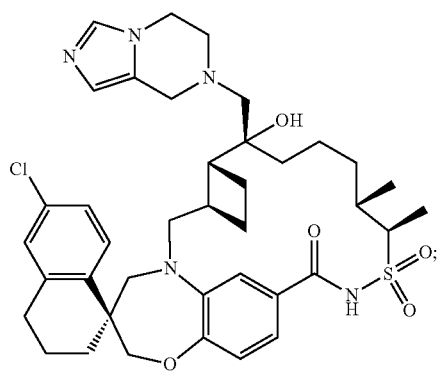
;
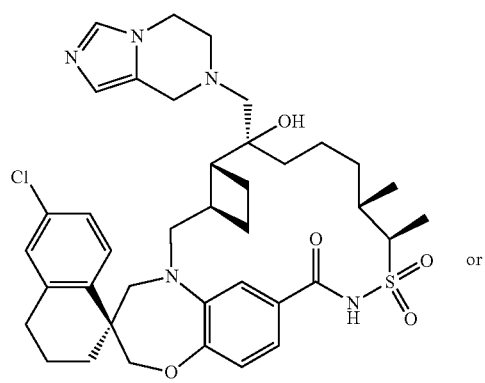
or
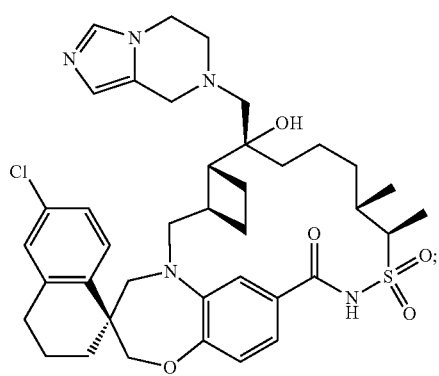
;
214
-continued
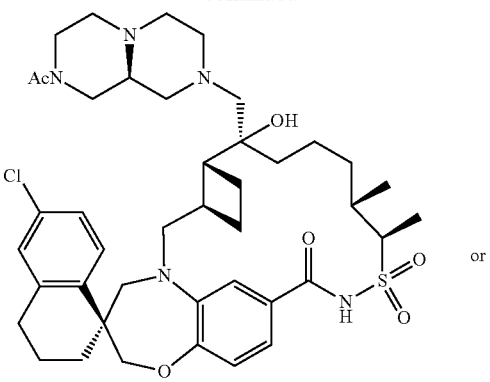
or
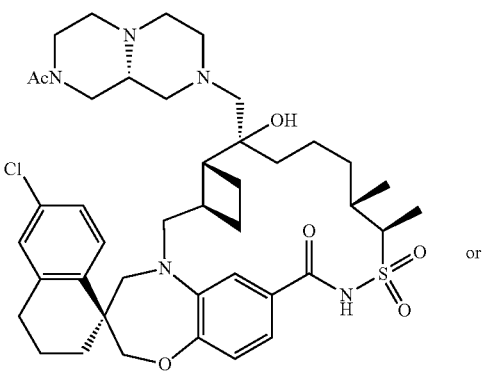
or
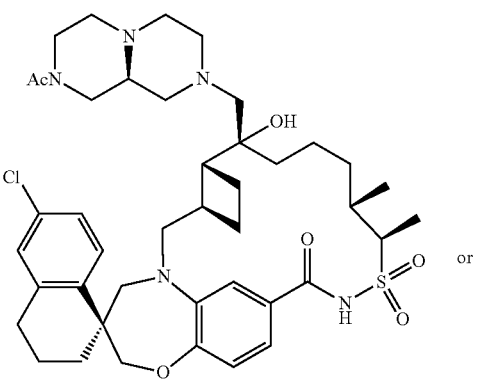
or
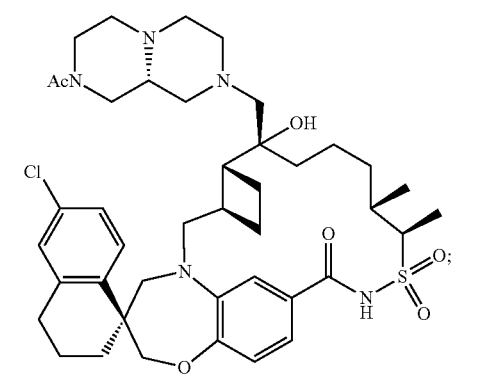
;

215
-continued

or
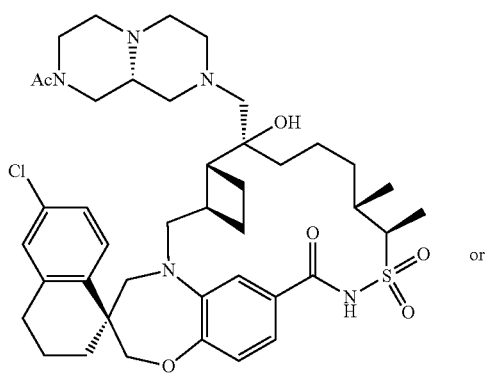
or
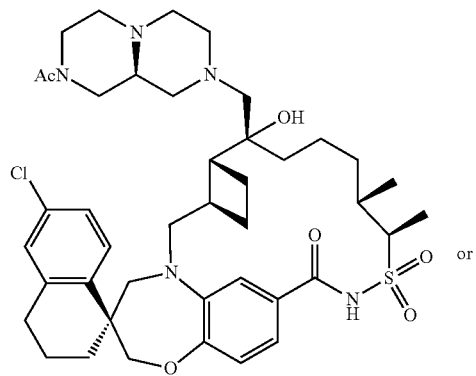
or
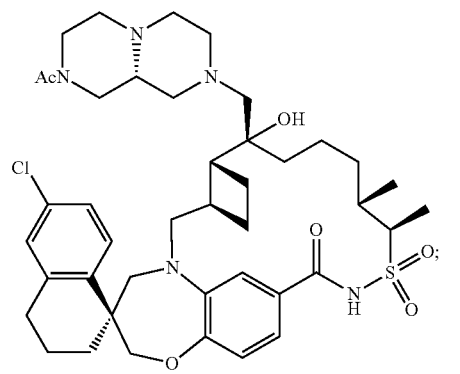
216
-continued

or
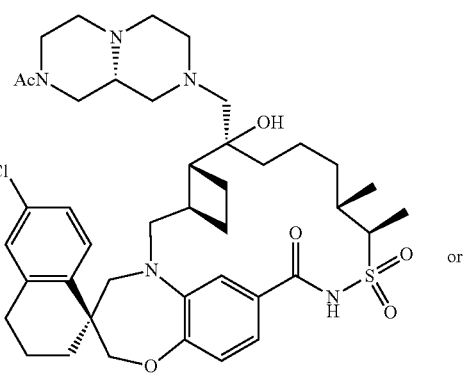
or
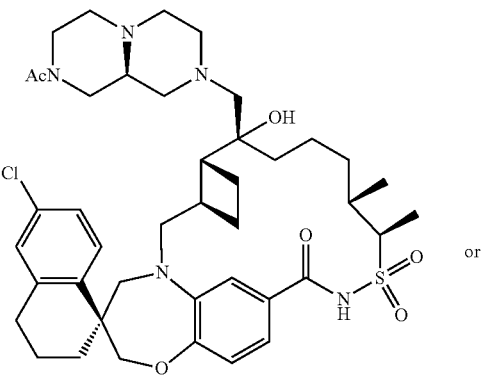
or
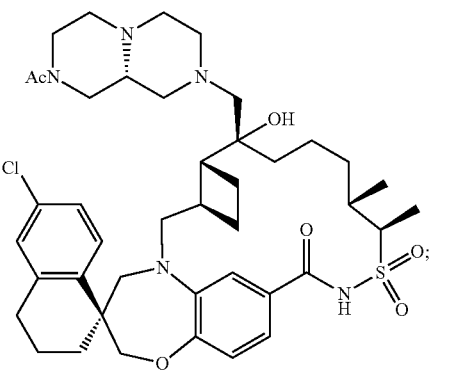;

217
-continued
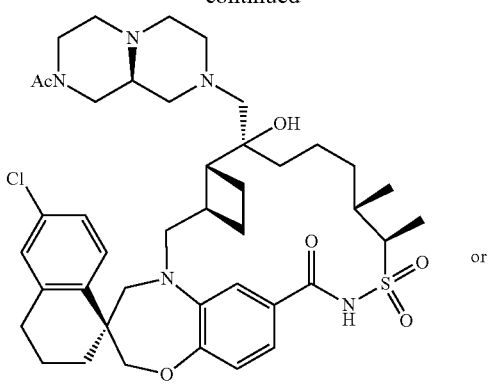
or
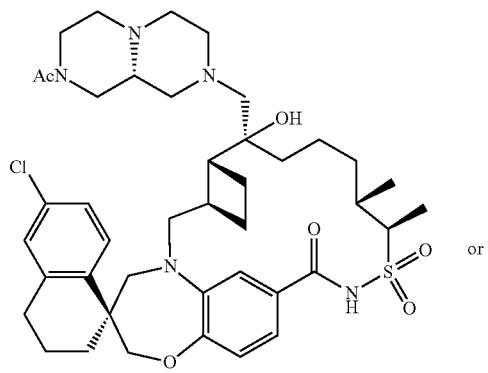
or
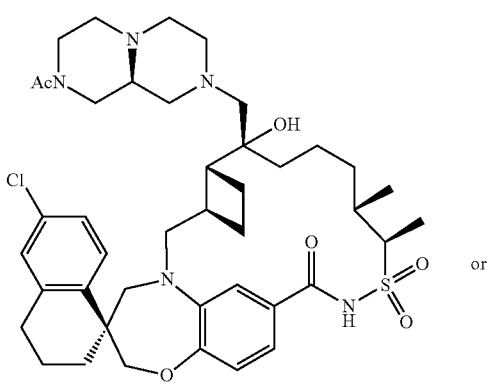
or
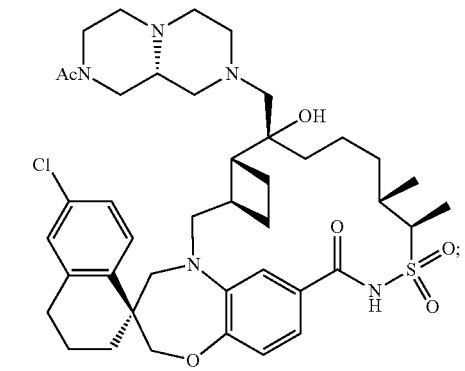
;
218
-continued
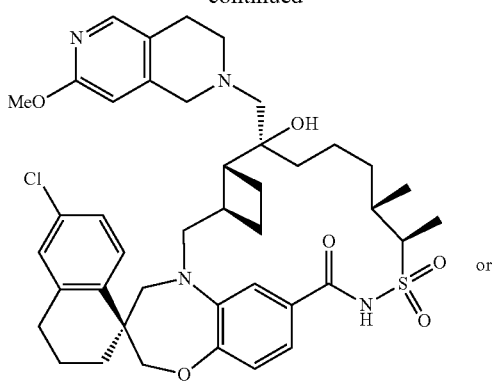
or
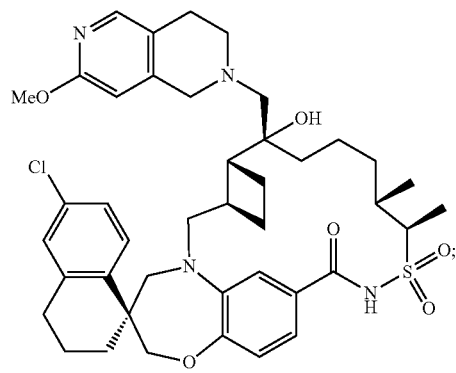
;
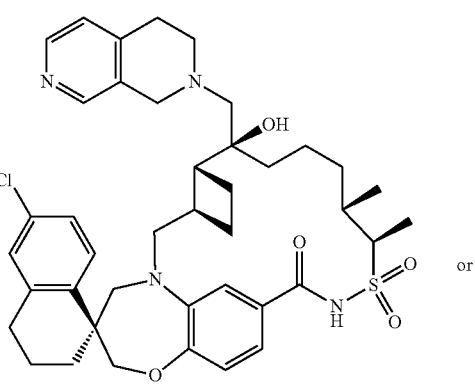
or
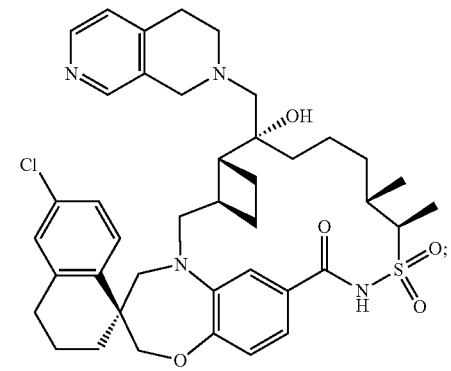
;

219
-continued
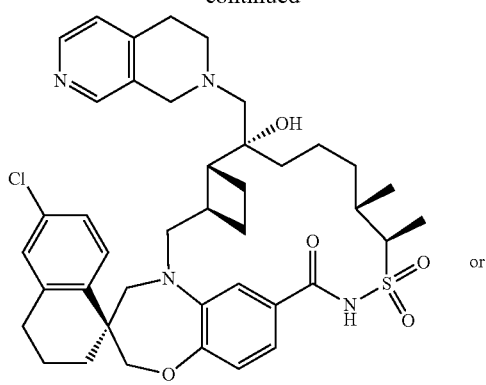
or
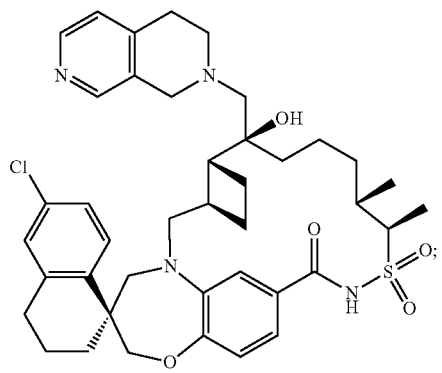
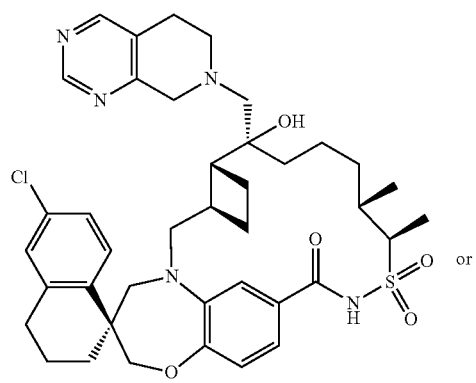
or
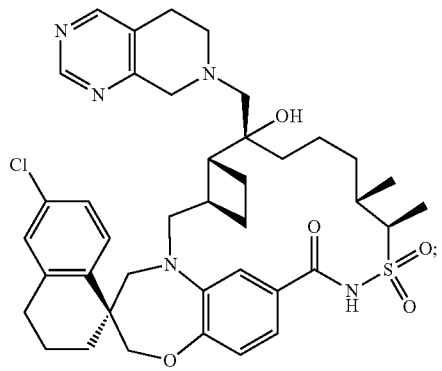
220
-continued
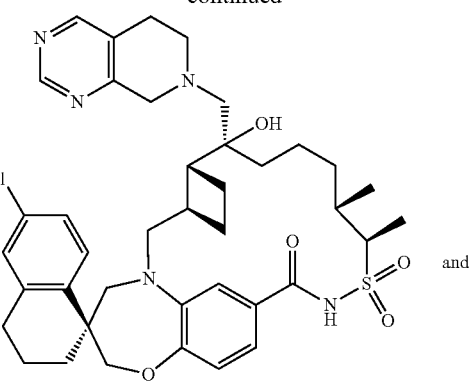
and
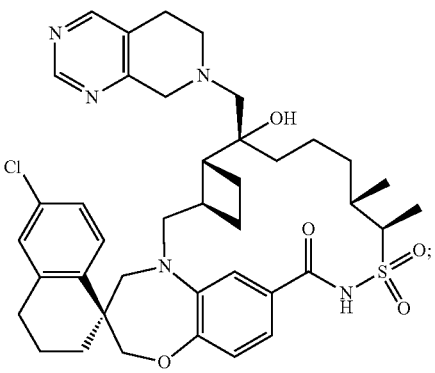
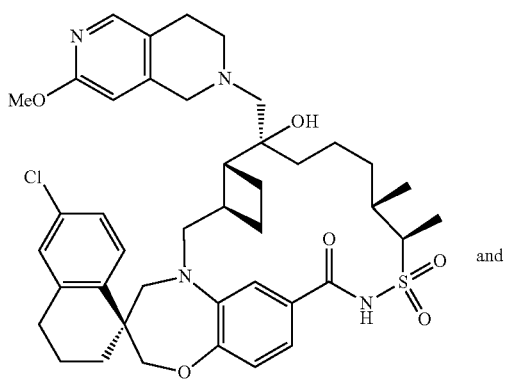
and
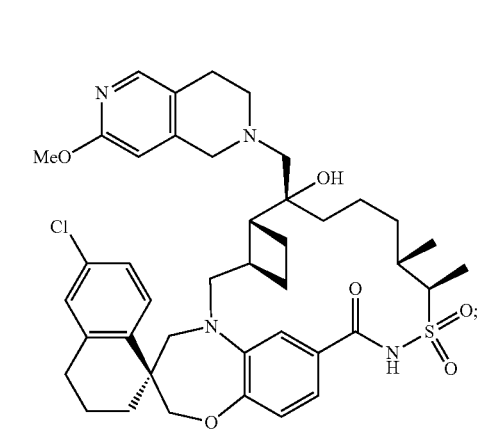

221
-continued
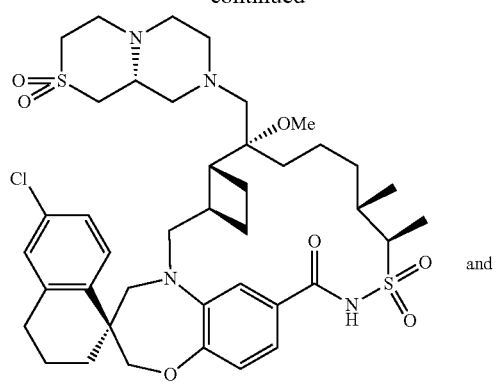
and
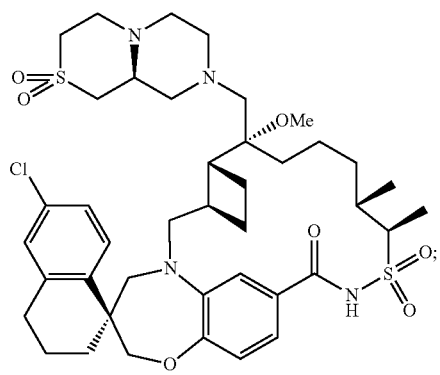
;
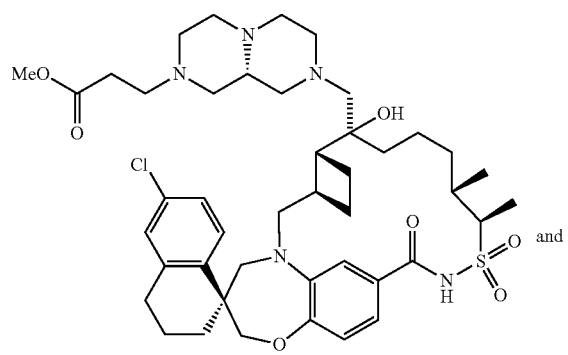
and
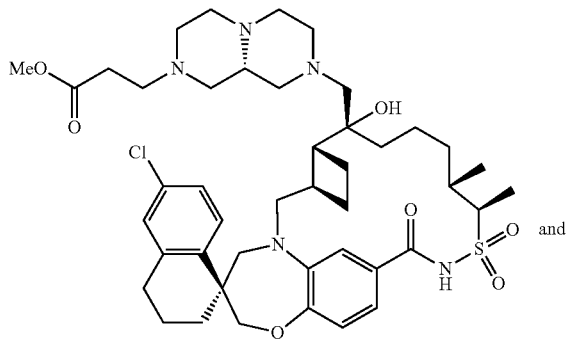
and
222
-continued
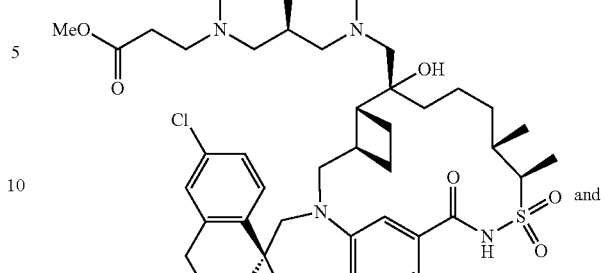

223
-continued
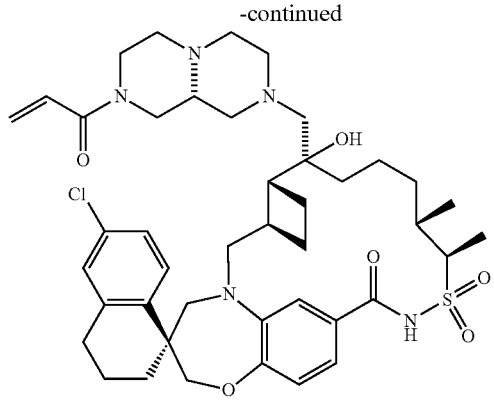
and
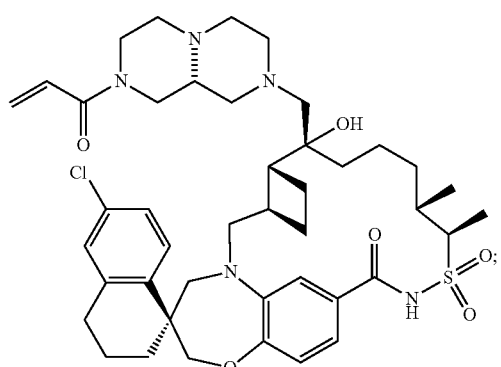
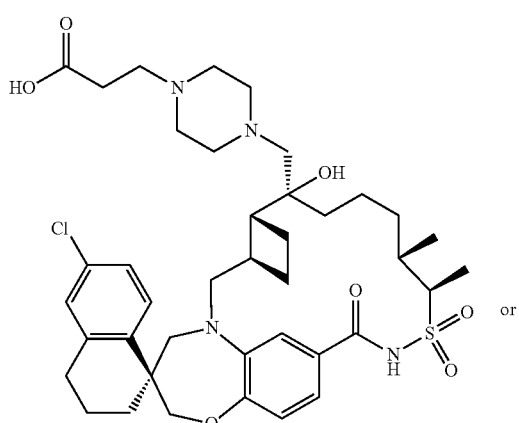
or
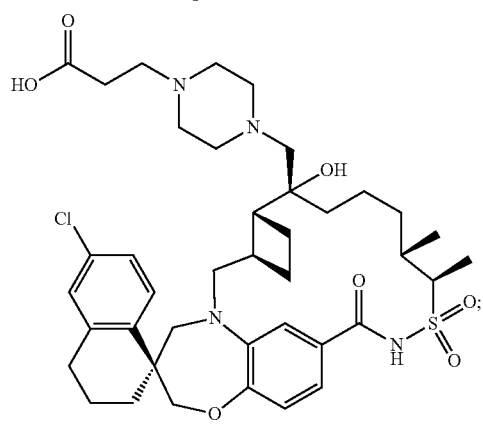
224
-continued
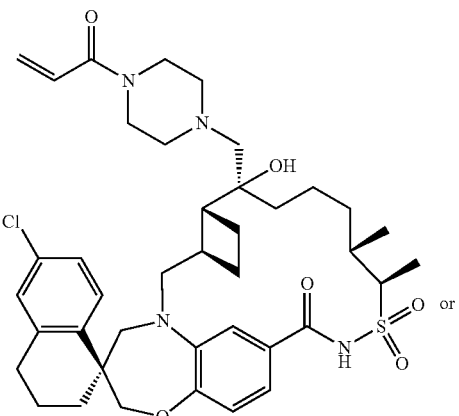
or
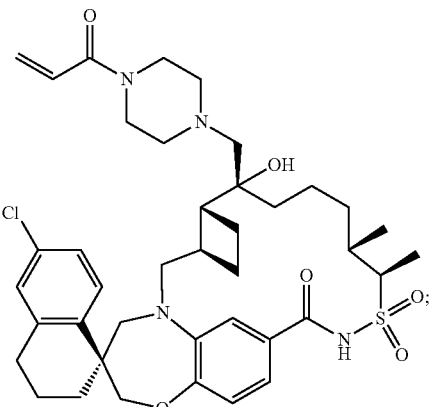
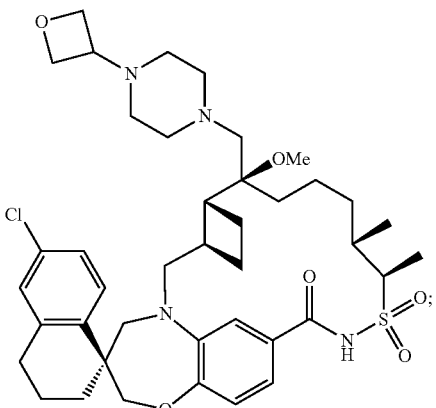
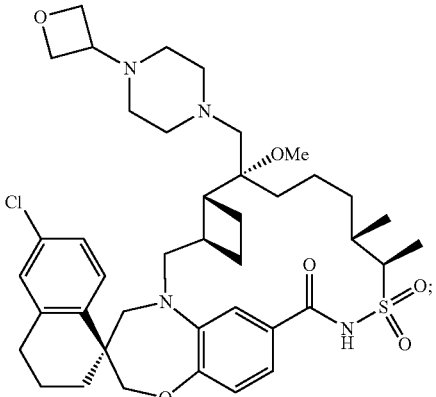

225
-continued
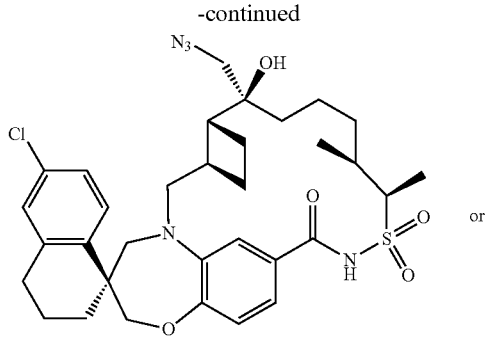
or
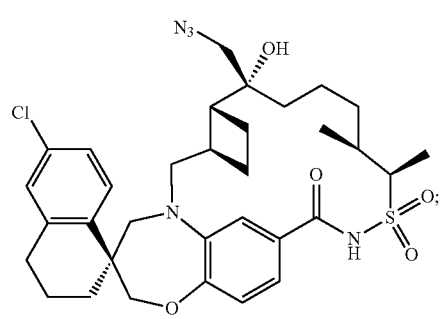
;
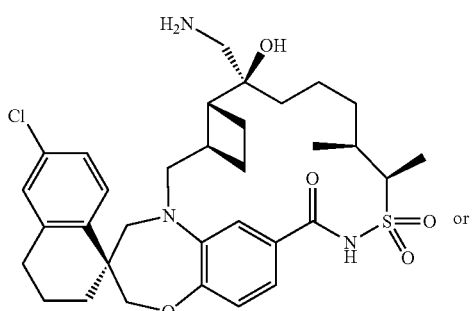
or
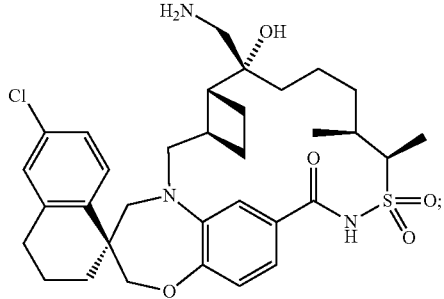
;
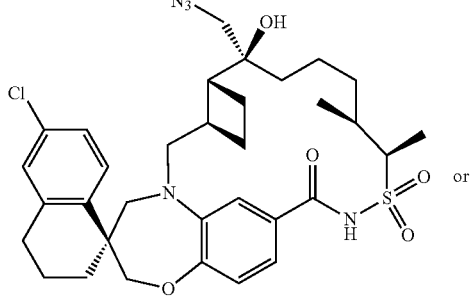
or
226
-continued
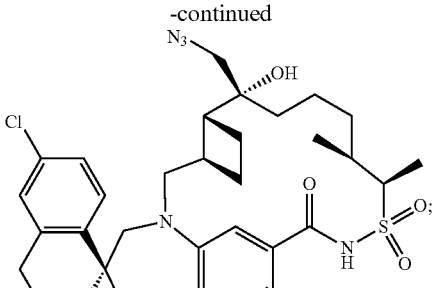
;
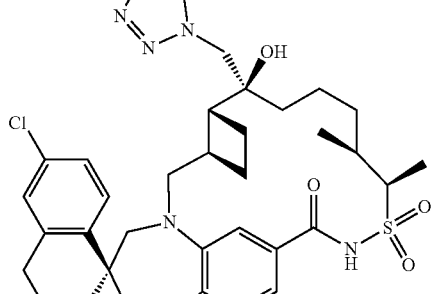
or
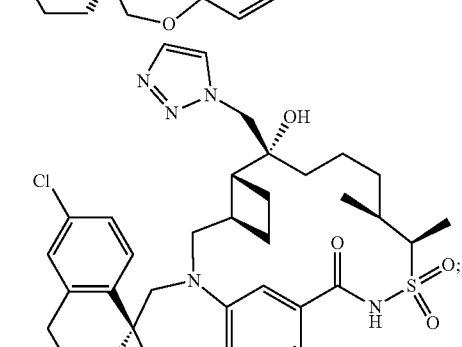
;
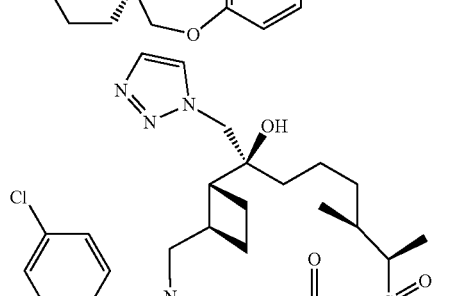
or
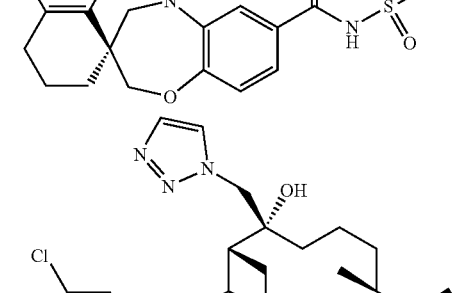
;
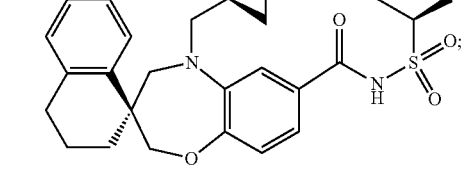

227
-continued
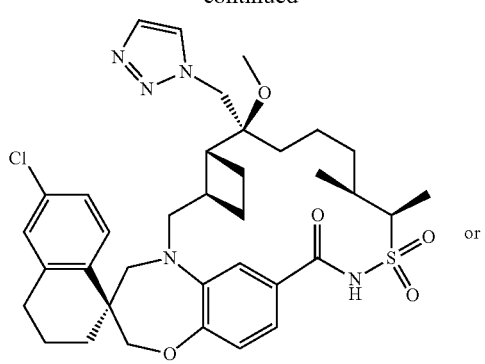
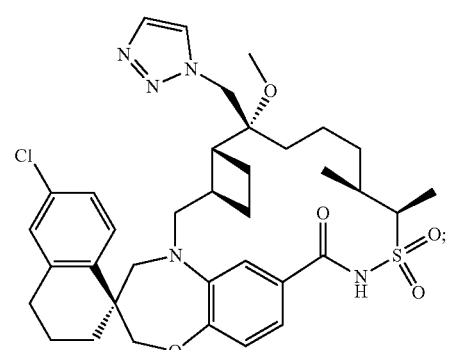
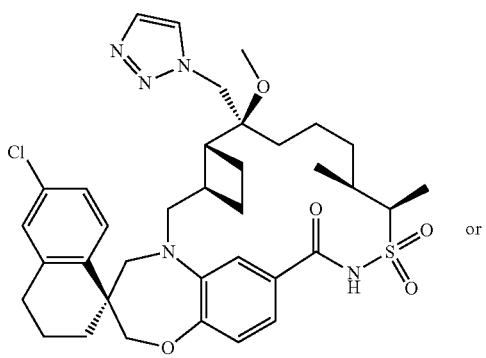
or
or
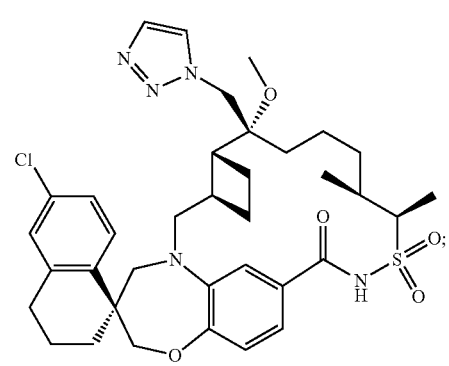
228
-continued
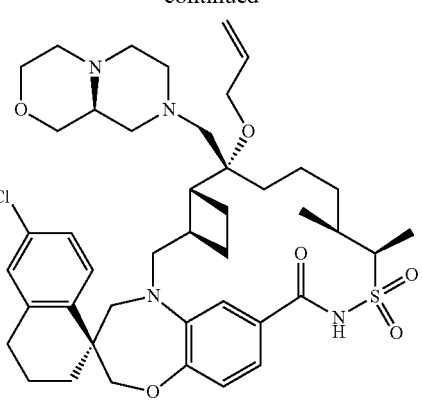
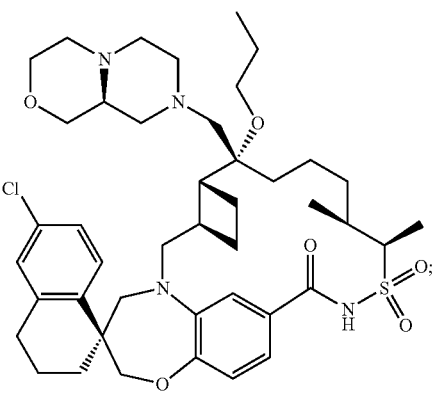
or
;

229
-continued
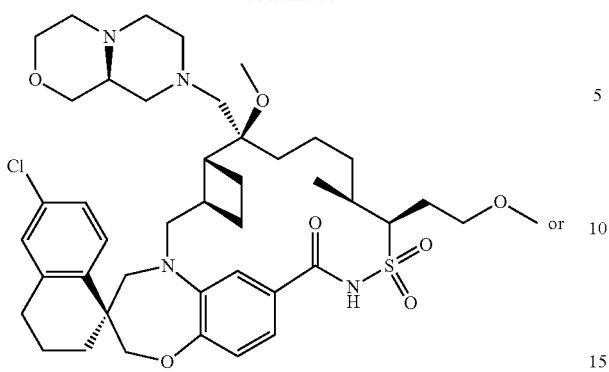
or
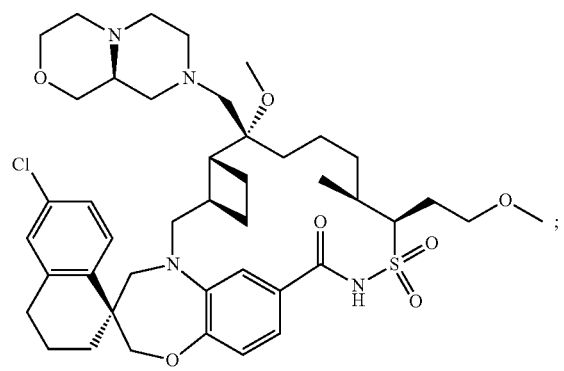

230
-continued
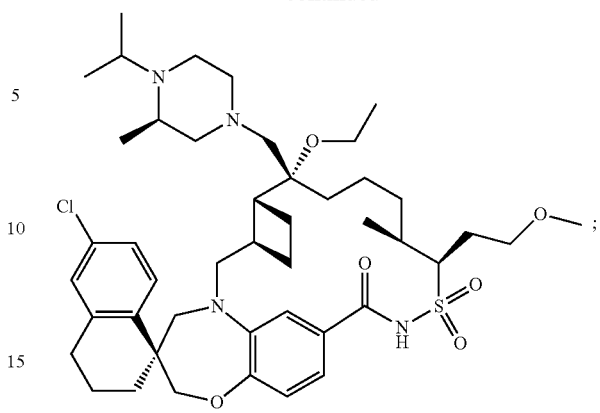
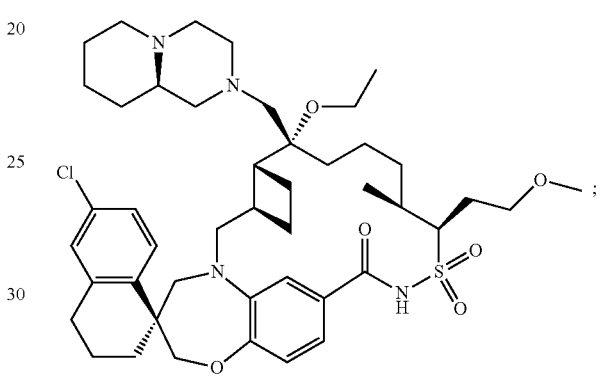
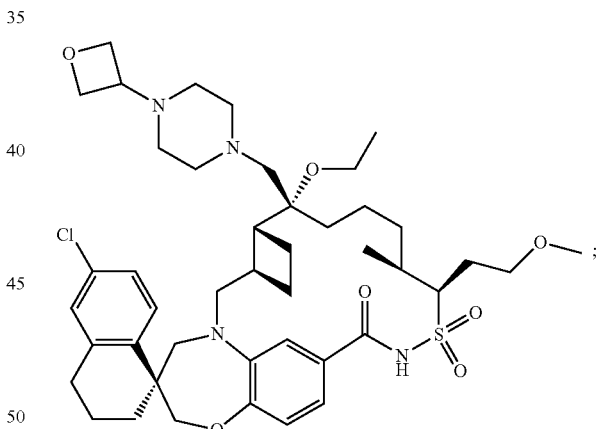
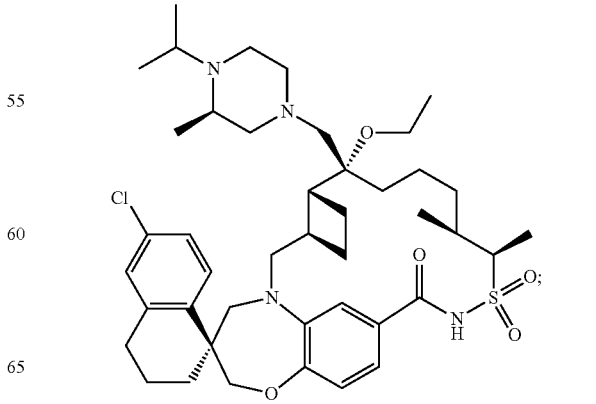

231
-continued
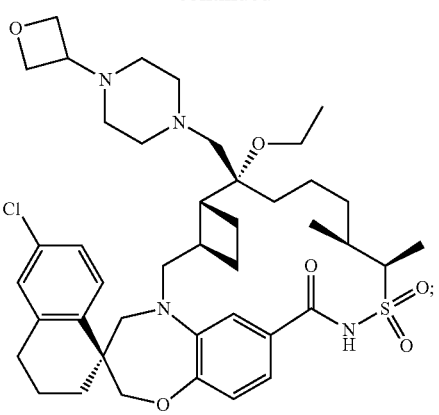
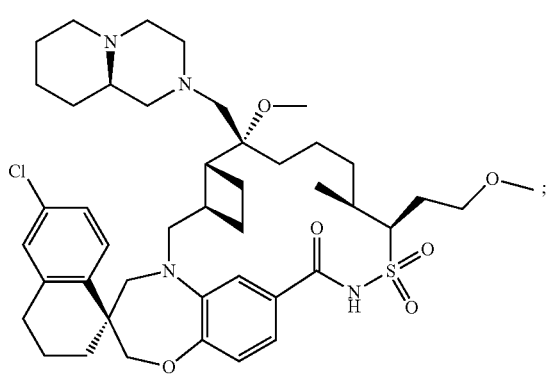
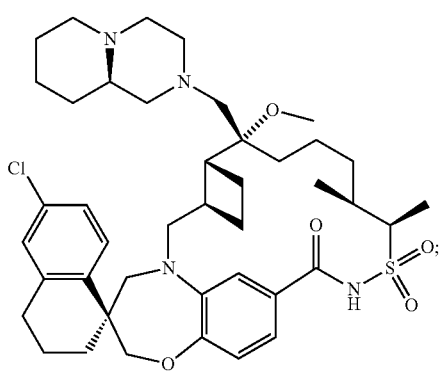
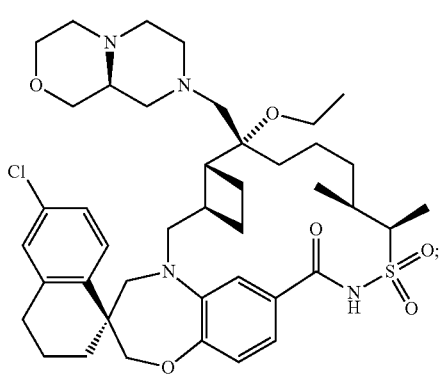
232
-continued
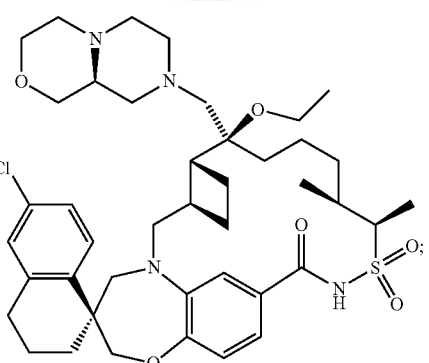
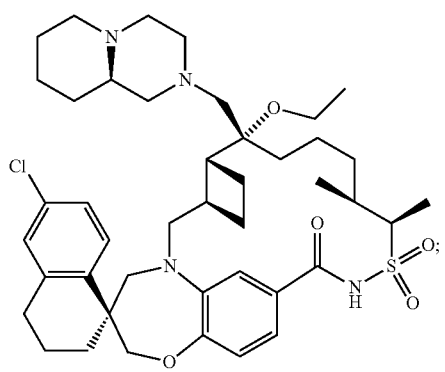
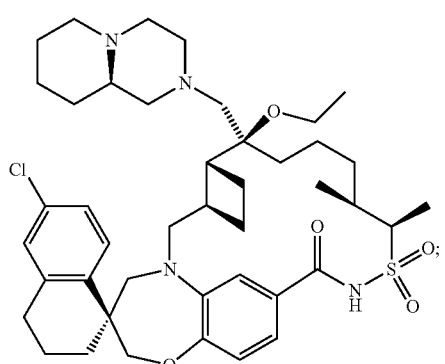
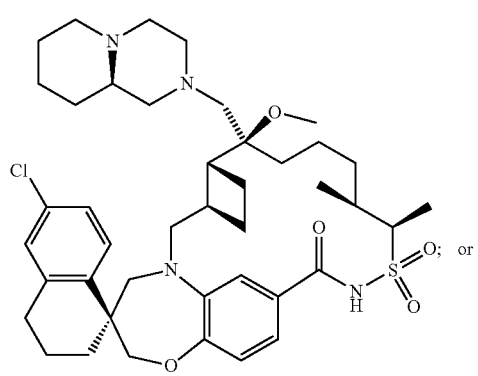

or the stereoisomer thereof, the pharmaceutically acceptable salt thereof, or the pharmaceutically acceptable salt of the stereoisomer thereof.
145. The compound of embodiment 144 or the pharmaceutically acceptable salt thereof.
146. Another embodiment of the present invention comprises the compound of Embodiment 1, wherein the compound is selected from:
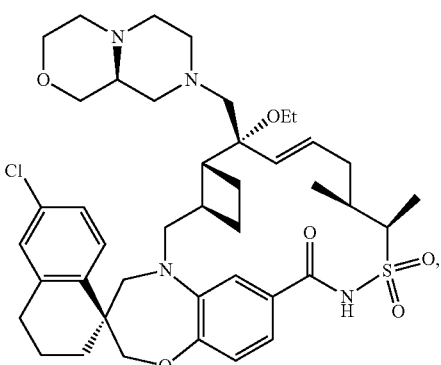
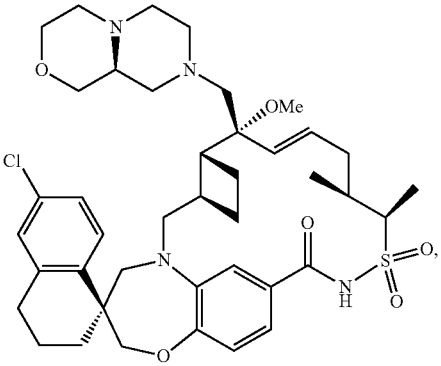
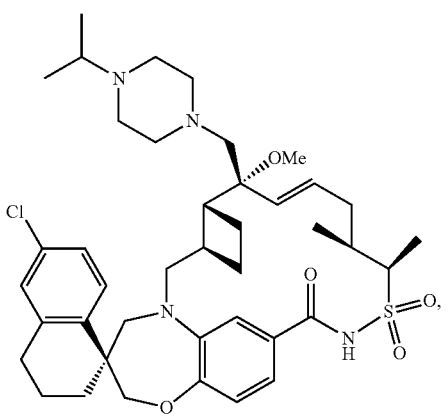
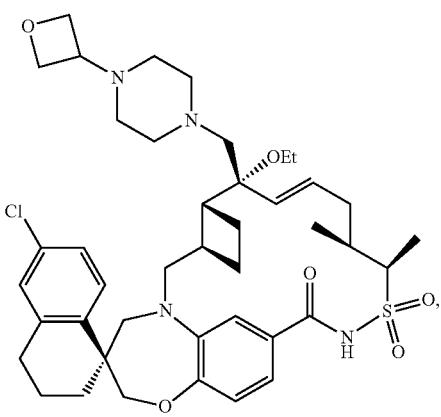
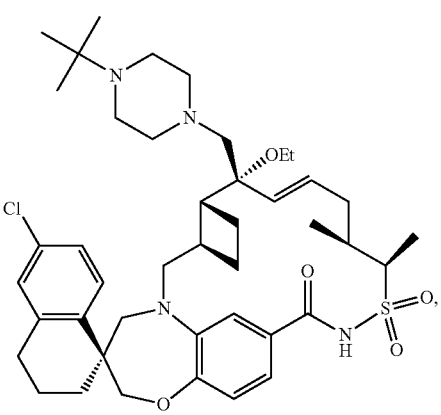

235
-continued
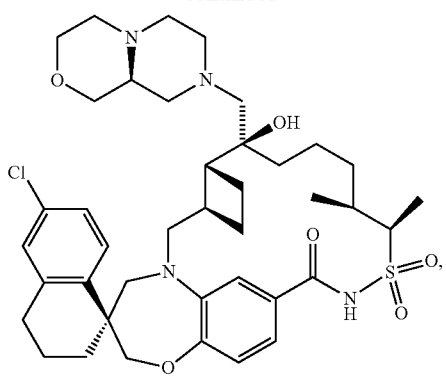
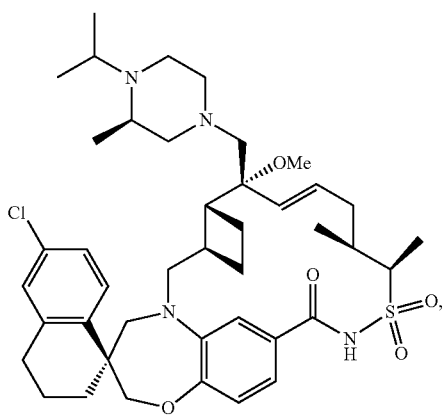
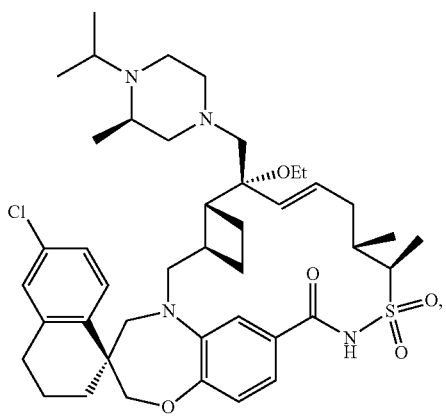
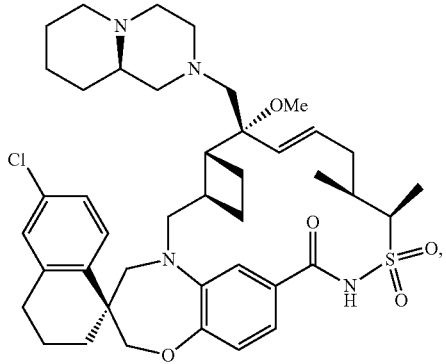
236
-continued
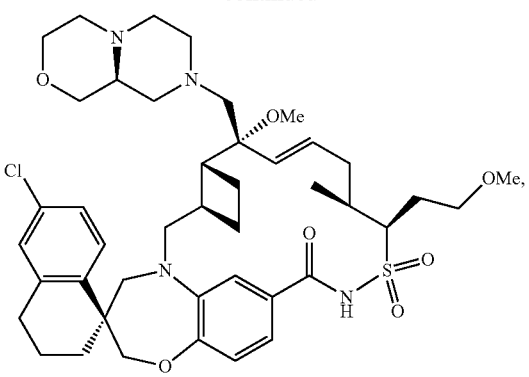
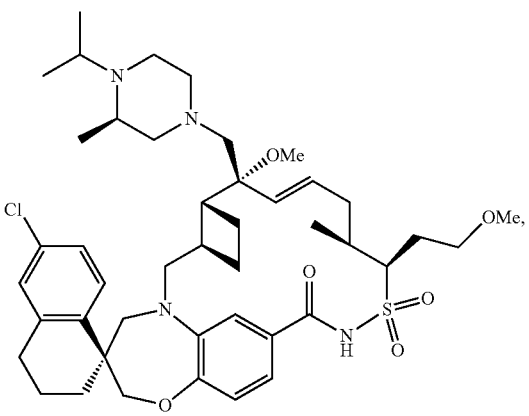
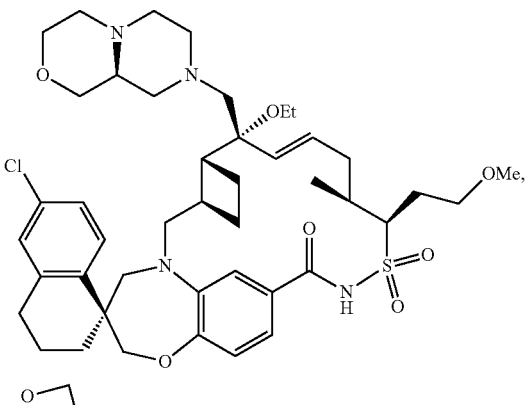
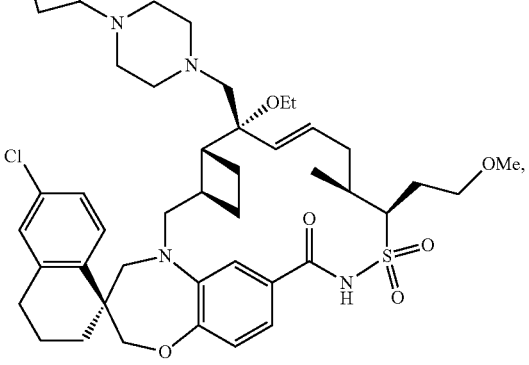

-continued

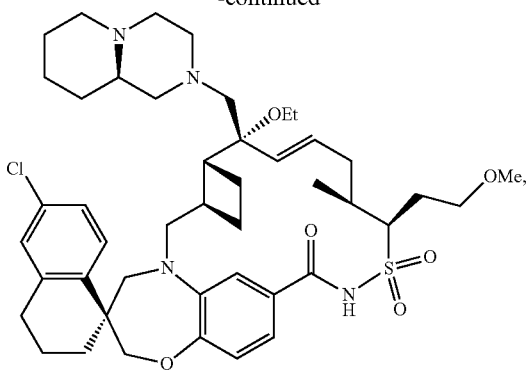

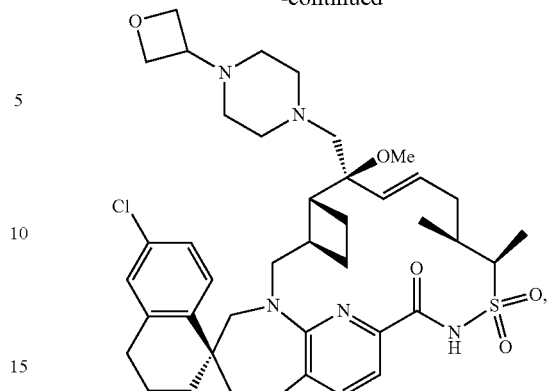

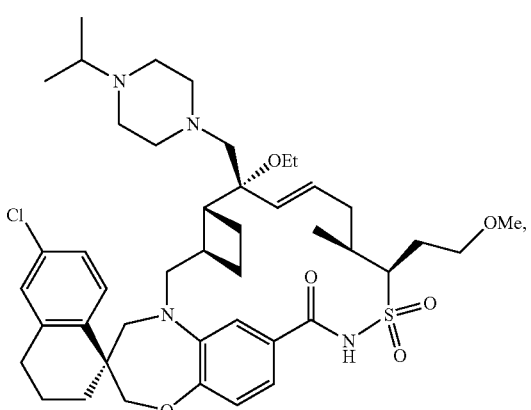

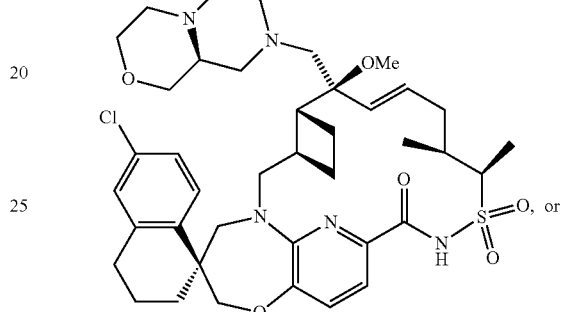

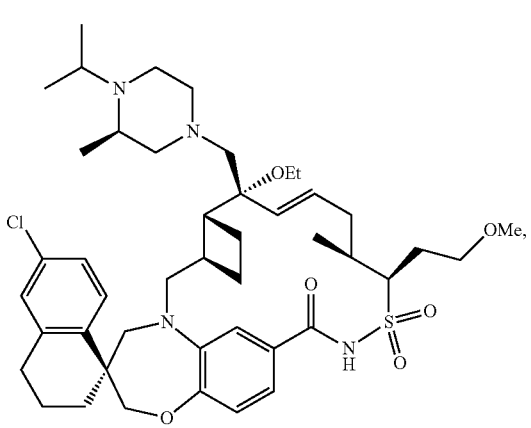

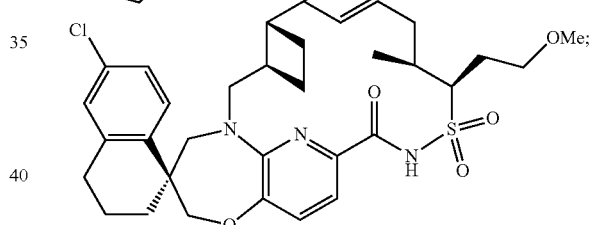

or the stereoisomer thereof, the pharmaceutically acceptable salt thereof, or the pharmaceutically acceptable salt of the stereoisomer thereof.

147. The compound of embodiment 146 or the pharmaceutically acceptable salt thereof.

148. Another embodiment of the present invention comprises a pharmaceutical composition comprising the compound of any one of Embodiments 1-147 or the pharmaceutically acceptable salt thereof, and a pharmaceutically acceptable carrier or diluent.

149. Another embodiment of the present invention comprises a method of treating cancer, the method comprising: administering to a patient in need thereof a therapeutically effective amount of the compound of any of Embodiments 1-147 or the pharmaceutically acceptable salt thereof.

150. The method of Embodiment 149, wherein the cancer is a hematologic malignancy.

151. The method of Embodiment 149, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

152. The method of Embodiment 149, wherein the cancer is multiple myeloma.

153. The method of Embodiment 149, further comprising administering to the patient in need thereof a therapeutically effective amount of an additional pharmaceutically active compound.

154. The method of Embodiment 153, wherein the additional pharmaceutically active compound is carfilzomib.

155. The method of Embodiment 153, wherein the additional pharmaceutically active compound is venetoclax.

156. The method of Embodiment 153, wherein the additional pharmaceutically active compound is cytarabine.

157. Another embodiment of the present invention comprises the use of a compound according to any one of Embodiments 1-147 for treating cancer in a subject.

158. Another embodiment of the present invention comprises the compound according to any one of Embodiments 1-147 in the preparation of a medicament for treating cancer.

159. The compound according to Embodiment 158, wherein the cancer is a hematologic malignancy.

160. The compound according to Embodiment 158, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

161. The compound according to Embodiment 158, wherein the cancer is multiple myeloma.

162. The compound according to Embodiment 158, wherein the cancer is acute myelogenous leukemia.

163. The compound according to Embodiment 158, wherein the cancer is non-Hodgkin's lymphoma.

Embodiments B

The embodiments listed below are presented in numbered form for convenience and for ease and clarity of reference in referring back to multiple embodiments.

In a first embodiment, the present invention comprises a compound of Formula I:

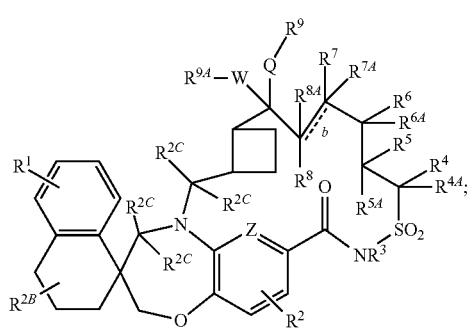

(I)

a stereoisomer thereof, a pharmaceutically acceptable salt thereof, or a pharmaceutically acceptable salt of the stereoisomer thereof,
wherein:
Z is C or N;
Q is O, S, $CR^{WA}R^{WB}$, or $NR^aR^b$;
W is $CR^{WA}R^{WB}$, —C=O, or is absent;
$R^{WA}$ and $R^{WB}$ are independently selected from H, —$C_{1-3}$alkyl, —$C_{2-3}$alkenyl, —$C_{2-3}$alkynyl, halo, —OH, or —O—$C_{1-3}$alkyl;

b, represented by the symbol ====, is a single or double chemical bond which may be cis or trans;
$R^1$ is independently selected from H, halo, $C_{1-6}$alkylhalo, $C_{1-6}$alkyl, $C_{2-6}$alkenyl, —$(CH_2CH_2O)_nR^a$, —$SO_2R^a$, —C(=O)$R^a$, —C(=O)O$R^a$, or —C(=O)NR$^a$R$^b$;
$R^2$ is selected from H, halo, $C_{1-6}$haloalkyl, $C_{1-6}$alkyl, O—$C_{1-6}$alkyl, $C_{2-6}$alkenyl, $C_{1-6}$alkenylene, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, —C(=O)NR$^a$R$^b$, a 6- to 12-membered aryl or heteroaryl, a 5- to 12-membered spirocycloalkyl or spiroheterocycloalkyl, or a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl or heterocycloalkyl group have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$;
$R^3$ is selected from H, —$C_{1-6}$alkylhalo, —$C_{1-6}$alkyl, —$C_{2-6}$alkenyl, —$(CH_2CH_2O)_nR^a$, —C(=O)$R^a$, —C(=O)O$R^a$, or —C(=O)NR$^a$R$^b$;
each of $R^{2B}$, $R^{2C}$, $R^4$, $R^5$, $R^6$, $R^7$, and $R^8$ is independently selected from H, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, —C(=O)NR$^a$R$^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
alternatively $R^3$ and $R^4$ together with the atoms to which they are bonded may form a 5- to 12-membered ring, optionally containing a heteroatom selected from a N, O or S atom, in addition to the S and N atoms present in the ring, wherein the ring may optionally contain at least one double bond; and the ring may be substituted with 0, 1, 2, or 3 $R^{3A}$ substituents;
wherein $R^{3A}$ is selected from H, halo, —OH, $C_{1-6}$haloalkyl, $C_{1-6}$alkyl, O—$C_{1-6}$alkyl, $C_{2-6}$alkenyl, —$C_{1-6}$alkyl-O—$C_{1-6}$alkyl, —$(CH_2CH_2O)_nR^a$, —$SO_2R^a$, —C(=O)$R^a$, —C(=O)O$R^a$, —OC(=O)$R^a$, or —C(=O)NR$^a$R$^b$;
each of $R^{4A}$, $R^{5A}$, $R^{6A}$, $R^{7A}$, and $R^{8A}$ is independently selected from H, OH, halo, or —$C_{1-6}$alkyl;
$R^{7A}$ and $R^{8A}$ are absent when b is a double chemical bond;
alternatively $R^7$ and $R^8$ together with the atoms to which they are bonded may form a 3- to 12-membered ring, wherein the ring may optionally contain at least one double bond;
$R^9$ is independently selected from H, OH, —(=O), —$C_{1-6}$ haloalkyl, —$C_{1-6}$alkyl, —$C_{1-6}$alkenylene, —$(CH_2CH_2O)_nR^a$, —C(=O)$R^a$, —C(=O)O$R^a$, —C(=O) NR$^a$R$^b$, —$C_{1-6}$alkyl-O—$C_{1-6}$alkyl, cyano, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl or heterocycloalkyl groups have 1, 2, 3 or 4 heteroatoms independently selected from O, N or S, and the cycloalkyl, spirocycloalkyl, spiroheterocycloalkyl, and heterocycloalkyl group may include a C=O group, and further wherein the spiroheterocycloalkyl, and heterocycloalkyl groups may include a S=O or $SO_2$;

$R^{9A}$ is independently selected from H, —OH, halo, cyano, —$C_{1-6}$haloalkyl, —$C_{1-6}$alkyl, —$C_2$-$C_6$ alkenyl, —$C_2$-$C_6$ alkynyl, —$C_{1-6}$alkenylene, —$(CH_2CH_2O)_nR^a$, —P(=O)OR$^a$OR$^b$, —CSR$^a$, —CS(=O)R$^a$, —SR$^a$, —SOR$^a$, —OSO$_2$R$^a$, —SO$_2$R$^a$, —(CH$_2$CH$_2$O)$_n$CH$_3$, —(=O), —C(=O), —C(=O)R$^a$, —C(=O)OR$^a$, —C(=O)NR$^a$R$^b$, —CH$_2$—NR$^a$R$^b$, —NR$^a$R$^b$, —$C_{1-6}$alkyl-O—$C_{1-6}$alkyl, —OC$_{1-6}$alkyl, —O—$C_{1-6}$alkyl-O—$C_{1-6}$alkyl, phenyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may contain a double bond and may contain a C=O group, and further wherein the spiroheterocycloalkyl, and heterocycloalkyl groups may include a S=O or $SO_2$;

wherein $R^{9A}$ is not H when W is absent;

wherein the aryl, heteroaryl, cycloalkyl, heterocycloalkyl, spirocycloalkyl and spiroheterocycloalkyl groups of the $R^{9A}$ substituent can be unsubstituted or substituted with 1, 2, 3 or 4 $R^{10}$ substituents independently selected from OH, halo, —NR$^c$R$^d$, —$C_{1-6}$alkyl, —$C_2$-$C_6$ alkenyl, —$C_2$-$C_6$alkynyl, —OC$_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

alternatively $R^7$ and $R^{9A}$ together with the atoms to which they are bonded may form a 3- to 12-membered ring, wherein the ring may optionally contain at least one double bond;

alternatively $R^9$ and $R^{9A}$ together with Q, W, and the C to which W and Q are bonded, may form a 3- to 12-membered monocyclic or bicyclic ring, optionally containing a heteroatom in addition to Q that is selected from N, O or S, wherein the ring may contain a double bond, wherein the ring may optionally include a C=O group, and further wherein the ring optionally may be substituted by 1, 2, or 3 $R^{11}$ substituents;

$R^{11}$ is independently selected from H, —OH, halo, —$C_{1-6}$alkyl, —OC$_{1-6}$alkyl, —$C_{1-6}$alkyl-OH, —$C_{1-6}$alkyl-O—$C_{1-6}$alkyl, —$C_{1-6}$haloalkyl, —O-halo$C_{1-6}$alkyl, —SO$_2$R$^c$, —CN, —NR$^c$R$^d$, —C(=O)NR$^c$R$^d$, —C(=O)R$^c$, —OC(=O)R$^c$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3 or 4 heteroatoms independently selected from O, N or S, wherein the cycloalkyl, spirocycloalkyl, spiroheterocycloalkyl, and heterocycloalkyl group may include a double bond, and wherein the cycloalkyl, spirocycloalkyl, spiroheterocycloalkyl, and heterocycloalkyl group may include a C=O group, and further wherein the spiroheterocycloalkyl, and heterocycloalkyl groups may include a S=O or $SO_2$;

wherein the $C_{1-6}$alkyl, $C_{2-6}$ alkenyl, $C_{2-6}$ alkynyl and the —OC$_{1-6}$alkyl of any of the $R^1$, $R^2$, $R^3$, $R^4$, $R^5$, $R^6$, $R^7$, $R^8$, $R^9$, $R^{10}$, $R^{11}$, $R^{4A}$, $R^{5A}$, $R^{6A}$, $R^{7A}$, $R^{8A}$, $R^{9A}$, $R^{WA}$ and $R^{WB}$ substituents is unsubstituted or substituted by 1, 2 or 3 $R^{12}$ substituents independently selected from OH, —OC$_{1-6}$alkyl, —$C_{1-6}$alkyl-O—$C_{1-6}$alkyl, halo, —O-halo$C_{1-6}$alkyl, —CN, —NR$^a$R$^b$, —(NR$^a$R$^b$R$^c$)$_n$, —OSO$_2$R$^a$, —SO$_2$R$^a$, —(CH$_2$CH$_2$O)$_n$CH$_3$, —(=O), —C(=O), —C(=O)R$^a$, —OC(=O)R$^a$, —C(=O)OR$^a$, —C(=O)NR$^a$R$^b$, —O—SiR$^a$R$^b$R$^c$, —SiR$^a$R$^b$R$^c$, —O-(3- to 10-membered heterocycloakyl), a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$;

wherein the aryl, heteroaryl, cycloalkyl, heterocycloalkyl, spirocycloalkyl and spiroheterocycloalkyl group of any of the $R^2$, $R^4$, $R^5$, $R^6$, $R^7$, $R^8$, $R^9$, $R^{9A}$, $R^{10}$, $R^{11}$, $R^{12}$, $R^{WA}$ and $R^{WB}$ substituents can be unsubstituted or substituted with 1, 2, 3 or 4 $R^{13}$ substituents independently selected from OH, halo, —NR$^c$R$^d$, —$C_{1-6}$alkyl, —OC$_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups of $R^{13}$ have 1, 2, 3 or 4 heteroatoms independently selected from O, N or S, wherein the cycloalkyl, spirocycloalkyl, and spiroheterocycloalkyl groups of $R^{13}$ or the heterocycloalkyl group of $R^{13}$ may include a C=O group, and further wherein the spiroheterocycloalkyl and heterocycloalkyl groups may include a S=O or $SO_2$;

wherein each $R^a$, $R^b$, $R^c$, and $R^d$ is independently hydrogen, OH, —$C_{1-6}$alkyl, —$C_{2-6}$alkenyl, —$C_{2-6}$alkynyl, —$C_{1-6}$alkyl-NR$^{14}$R$^{14}$, —NR$^{14}$R$^{14}$, —SO$_2$R$^{14}$, —(CH$_2$CH$_2$O)$_n$CH$_3$, —(=O), —C(=O)R$^{14}$, —OC(=O)R$^{14}$, —C(=O)OR$^{14}$, —C(=O)NR$^{14}$R$^{14}$, —$C_{1-6}$haloalkyl, —O-halo$C_{1-6}$alkyl, —$C_{1-6}$alkyl-O—$C_{1-6}$alkyl, benzyl, phenyl, —$C_{1-6}$alkyl-C(=O)OH, —$C_{1-6}$alkyl-C(=O)—O—$C_{1-6}$alkyl, —$C_{1-6}$alkyl-cycloalkyl, —$C_{1-6}$alkyl-heterocycloalkyl, —$C_{1-6}$alkyl-6- to 10-membered aryl, —$C_{1-6}$alkyl-6- to 10-membered heteroaryl, a 6- to 12-membered aryl or heteroaryl, a 5- to 12-membered spirocycloalkyl or spiroheterocycloalkyl, or a 3- to 12-membered cycloalkenyl, a 3- to 12-membered monocyclic or bicyclic cycloalkyl, or a 3- to 12-membered monocyclic or bicyclic heterocycloalkyl group, where the heteroaryl, spiroheterocycloalkyl, heterocycloalkyl group or the —C$_{1-6}$alkyl-heterocycloalkyl groups have 1, 2, 3 or 4 heteroatoms independently selected from O, N or S, and the cycloalkyl, spirocycloalkyl, spiroheterocycloalkyl, heterocycloalkyl, group of R$^a$, R$^b$, R$^c$, and R$^d$ or the heterocycloalkyl group or the —C$_{1-6}$alkyl-heterocycloalkyl group may include a double bond and may contain a C═O group, and the spiroheterocycloalkyl, or heterocycloalkyl may include a S═O or SO$_2$;

the alkyl, aryl, heteroaryl, spirocycloalkyl, spiroheterocycloalkyl, cycloalkyl, or heterocycloalkyl group of R$^a$, R$^b$, R$^c$, and R$^d$ and the heterocycloalkyl group of the —C$_{1-6}$alkyl-heterocycloalkyl group of R$^a$, R$^b$, R$^c$, and R$^d$ can be unsubstituted or substituted with 1, 2, 3, or 4 R$^{14}$ substituents, wherein each R$^{14}$ is independently selected from H, —OH, —N═N═N, halo, —C$_{1-6}$alkyl, —C$_{1-6}$haloalkyl, —OC$_{1-6}$alkyl, —C$_{1-6}$alkyl-O—C$_{1-6}$alkyl, —C$_{1-6}$haloalkyl, —O-haloC$_{1-6}$alkyl, phenyl, tolyl, —C(═O)C$_{1-6}$alkyl, —C(═O)O—C$_{1-6}$alkyl, N(CH$_3$)$_2$ or —SO$_2$—N(CH$_3$)$_2$; and wherein n is independently in each instance an integer of 1, 2, 3 or 4.

2. Another embodiment of the present invention comprises the compound of embodiment 1, wherein the compound has the Formula II:

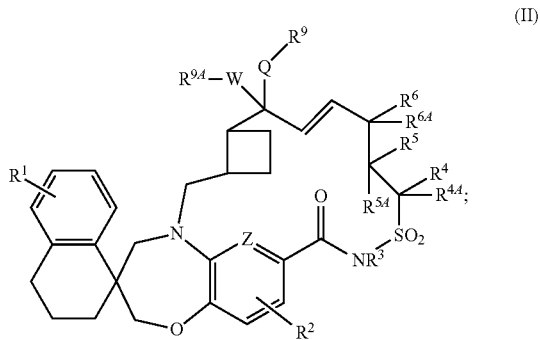

(II)

or the stereoisomer thereof, the pharmaceutically acceptable salt thereof, or the pharmaceutically acceptable salt of the stereoisomer thereof.

3. Another embodiment of the present invention comprises a compound of any of embodiments 1 or 2, wherein the compound has the Formula IIa:

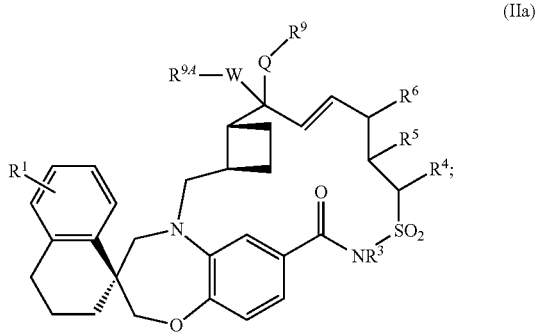

(IIa)

or the stereoisomer thereof, the pharmaceutically acceptable salt thereof, or the pharmaceutically acceptable salt of the stereoisomer thereof.

4. The compound of any one of embodiments 1-3, or the stereoisomer thereof, the pharmaceutically acceptable salt thereof, or the pharmaceutically acceptable salt of the stereoisomer thereof, wherein Q is O, NR$^a$NR$^b$, or S.

5. The compound of any one of embodiments 1-4, or the stereoisomer thereof, the pharmaceutically acceptable salt thereof, or the pharmaceutically acceptable salt of the stereoisomer thereof, wherein Q is O.

6. The compound of any one of embodiments 1-5, or the stereoisomer thereof, the pharmaceutically acceptable salt thereof, or the pharmaceutically acceptable salt of the stereoisomer thereof, wherein W is CR$^{WA}$R$^{WB}$, —C═O, or is absent.

7. The compound of embodiment 5, or the stereoisomer thereof, the pharmaceutically acceptable salt thereof, or the pharmaceutically acceptable salt of the stereoisomer thereof, wherein W is CR$^{WA}$R$^{WB}$.

8. The compound of embodiment 5, or the stereoisomer thereof, the pharmaceutically acceptable salt thereof, or the pharmaceutically acceptable salt of the stereoisomer thereof, wherein W is absent.

9. The compound of any one of embodiments 1-7, or the stereoisomer thereof, the pharmaceutically acceptable salt thereof, or the pharmaceutically acceptable salt of the stereoisomer thereof, wherein R$^{WA}$ and R$^{WB}$ are independently selected from H, (═O), —C$_{1-3}$alkyl, —C$_{2-3}$alkenyl, —C$_{2-3}$alkynyl, halo, —OH, or —O—C$_{1-3}$alkyl.

10. The compound of embodiment 9, or the stereoisomer thereof, the pharmaceutically acceptable salt thereof, or the pharmaceutically acceptable salt of the stereoisomer thereof, wherein R$^{WA}$ and R$^{WB}$ are both H.

11. The compound of embodiment 9, or the stereoisomer thereof, the pharmaceutically acceptable salt thereof, or the pharmaceutically acceptable salt of the stereoisomer thereof, wherein R$^{WA}$ is —CH$_3$.

12. The compound of embodiment 9, or the stereoisomer thereof, the pharmaceutically acceptable salt thereof, or the pharmaceutically acceptable salt of the stereoisomer thereof, wherein R$^{WB}$ is —CH$_3$.

13. The compound of embodiment 9, or the stereoisomer thereof, the pharmaceutically acceptable salt thereof, or the pharmaceutically acceptable salt of the stereoisomer thereof, wherein R$^{WA}$ is —OH and R$^{WB}$ is H.

14. The compound of any one of embodiments 1-13, or the stereoisomer thereof, the pharmaceutically acceptable salt thereof, or the pharmaceutically acceptable salt of the stereoisomer thereof, wherein R$^1$ is halo.

15. The compound of embodiment 14, or the stereoisomer thereof, the pharmaceutically acceptable salt thereof, or the pharmaceutically acceptable salt of the stereoisomer thereof, wherein R$^1$ is Cl.

16. The compound of any one of embodiments 1-15, or the stereoisomer thereof, the pharmaceutically acceptable salt thereof, or the pharmaceutically acceptable salt of the stereoisomer thereof, wherein R$^3$ is selected from H and —C$_{1-6}$alkyl.

17. The compound of embodiment 16, or the stereoisomer thereof, the pharmaceutically acceptable salt thereof, or the pharmaceutically acceptable salt of the stereoisomer thereof, wherein R$^3$ is H.

18. The compound of any one of embodiments 1-17, or the stereoisomer thereof, the pharmaceutically acceptable salt thereof, or the pharmaceutically acceptable salt of the stereoisomer thereof, wherein R$^4$ is independently selected from H, —C$_{1-6}$alkyl, —C$_{1-6}$alkyl-O—C$_{1-6}$alkyl, —C$_{1-6}$alkyl-OH, —C$_{1-6}$alkyl-OSO$_2$CH$_3$, —C$_{1-6}$alkyl-phenyl, or —C$_{1-6}$alkyl-(5-6 membered heterocycloalkyl, having one or two heteroatoms independently selected from N or O).

19. The compound of any one of embodiments 1-18, or the stereoisomer thereof, the pharmaceutically acceptable salt thereof, or the pharmaceutically acceptable salt of the stereoisomer thereof, wherein $R^4$ is independently selected from H, —$CH_3$, —$CH_2CH_3$,

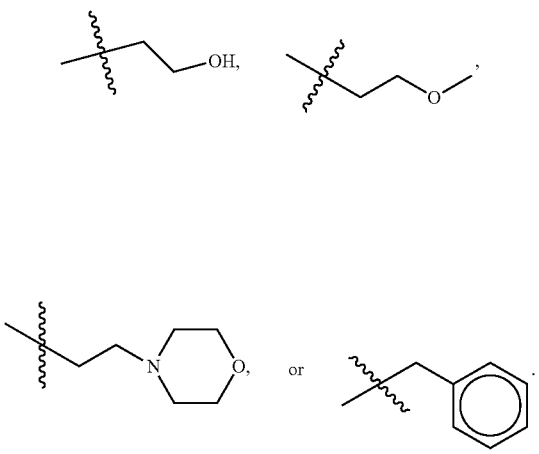

20. The compound of embodiment 19, or the stereoisomer thereof, the pharmaceutically acceptable salt thereof, or the pharmaceutically acceptable salt of the stereoisomer thereof, wherein $R^4$ is —$CH_3$.

21. The compound of any one of embodiments 1-20, or the stereoisomer thereof, the pharmaceutically acceptable salt thereof, or the pharmaceutically acceptable salt of the stereoisomer thereof, wherein $R^5$ is selected from H or —$C_{1-6}$alkyl.

22. The compound of embodiment 21, or the stereoisomer thereof, the pharmaceutically acceptable salt thereof, or the pharmaceutically acceptable salt of the stereoisomer thereof, wherein $R^5$ is —$CH_3$.

23. The compound of any one of embodiments 1-22, or the stereoisomer thereof, the pharmaceutically acceptable salt thereof, or the pharmaceutically acceptable salt of the stereoisomer thereof, wherein $R^6$ is selected from H or —$C_{1-6}$alkyl.

24. The compound of embodiment 23, or the stereoisomer thereof, the pharmaceutically acceptable salt thereof, or the pharmaceutically acceptable salt of the stereoisomer thereof, wherein $R^6$ is H.

25. The compound of any one of embodiments 1-24, or the stereoisomer thereof, the pharmaceutically acceptable salt thereof, or the pharmaceutically acceptable salt of the stereoisomer thereof, wherein $R^9$ is independently selected from H, —$C_{1-6}$alkyl, —$C_{1-6}$haloalkyl, —$C_{1-6}$alkyl-O—$C_{1-6}$alkyl, —$C_{1-6}$alkyl-(5-6 membered heterocycloalkyl), wherein the heterocycloalkyl has one or two heteroatoms independently selected from N or O, or —$C_{1-6}$alkyl-phenyl, wherein the phenyl of the —$C_{1-6}$alkyl-phenyl of the $R^9$ groups is unsubstituted or substituted with 1 or 2 $R^{13}$ substituents selected from halo or —$C_{1-6}$alkyl-O—$C_{1-6}$alkyl.

26. The compound of embodiment 25, or the stereoisomer thereof, the pharmaceutically acceptable salt thereof, or the pharmaceutically acceptable salt of the stereoisomer thereof, wherein $R^9$ is independently selected from H, —$CH_3$, —$CH_2CH_3$, —$CH_2CH_2CH_3$, $CH_2CH_2OCH_3$, $CH_2CF_3$,

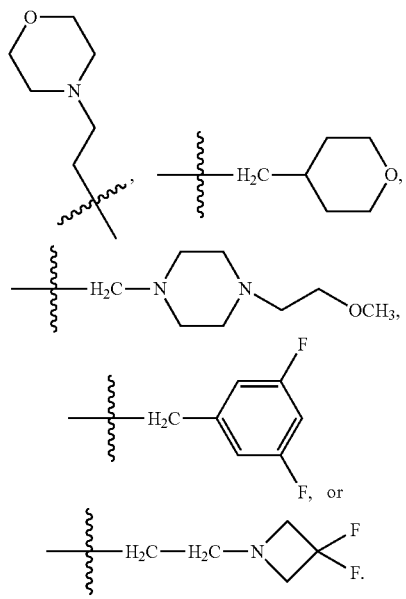

27. The compound of embodiment 26, or the stereoisomer thereof, the pharmaceutically acceptable salt thereof, or the pharmaceutically acceptable salt of the stereoisomer thereof, wherein $R^9$ is H.

28. The compound of embodiment 26, or the stereoisomer thereof, the pharmaceutically acceptable salt thereof, or the pharmaceutically acceptable salt of the stereoisomer thereof, wherein $R^9$ is —$C_{1-6}$alkyl.

29. The compound of embodiment 26, or the stereoisomer thereof, the pharmaceutically acceptable salt thereof, or the pharmaceutically acceptable salt of the stereoisomer thereof, wherein $R^9$ is —$CH_3$.

30. The compound of embodiment 26, wherein $R^9$ is

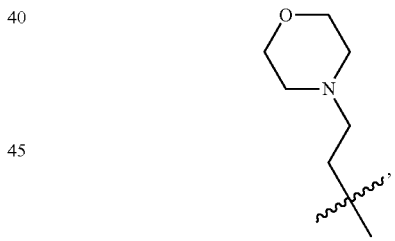

or the stereoisomer thereof, the pharmaceutically acceptable salt thereof, or the pharmaceutically acceptable salt of the stereoisomer thereof.

31. The compound of any one of embodiments 1-24, or the stereoisomer thereof, the pharmaceutically acceptable salt thereof, or the pharmaceutically acceptable salt of the stereoisomer thereof, wherein alternatively $R^9$ and $R^{9A}$ together with Q, W, and the C to which W and Q are bonded, may form a 3- to 12-membered monocyclic or bicyclic ring, optionally containing a heteroatom in addition to Q that is selected from N, O or S, wherein the ring may contain a double bond, wherein the ring may optionally include a C=O group.

32. The compound of embodiment 31, or the stereoisomer thereof, the pharmaceutically acceptable salt thereof, or the pharmaceutically acceptable salt of the stereoisomer thereof, wherein $R^9$ and $R^{9A}$ together with Q, W and the C to which Q and W are bonded form

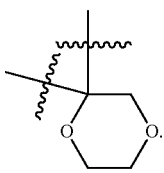 [SMILES: *C1(*)COCCO1]

33. The compound of any one of embodiments 1-30, or the stereoisomer thereof, the pharmaceutically acceptable salt thereof, or the pharmaceutically acceptable salt of the stereoisomer thereof, wherein $R^{9A}$ is independently selected from H, OH, —$C_{1-6}$alkyl, —$C_2$-$C_6$ alkenyl, —$C_{2-6}$alkynyl; —$OC_{1-6}$alkyl, —$CH_2$—$NR^aR^b$, —$C(=O)NR^aR^b$, —(=O), —$C(=O)$, $C(=O)OR^a$, —$C(=O)R^a$, cyano, —$C_{1-6}$haloalkyl, —$C_{1-6}$alkyl-O—$C_{1-6}$alkyl, —O—$C_{1-6}$alkyl-O—$C_{1-6}$ alkyl, —$P(=O)OR^aOR^b$, —$SR^a$, —$OSO_2R^a$, —$SOR^a$, —$SO_2R^a$, a 6- to 12-membered aryl or heteroaryl, a 3- to 12-membered monocyclic or bicyclic cycloalkyl, or a 3- to 12-membered unsubstituted monocyclic or bicyclic heterocycloalkyl group, wherein the aryl, heteroaryl, or heterocycloalkyl group can have from 1, 2, 3 or 4 heteroatoms independently selected from O, N or S, wherein the cycloalkyl and the heterocycloalkyl group may contain a double bond and further wherein the cycloalkyl and the heterocycloalkyl group may contain a C=O group;

wherein the aryl, heteroaryl, cycloalkyl, heterocycloalkyl, group of the $R^{9A}$ substituent can be unsubstituted or substituted with from 1, 2, 3 or 4 $R^{10}$ substituents independently selected from OH, halo, —$NR^cR^d$, —$C_{1-6}$alkyl, —$C_{1-6}$ alkyl-OH, —$C_{1-6}$alkyl-O—$C_{1-6}$alkyl, cyano, —$C(=O)OR^c$, a 6- to 10-membered aryl, or —$SO_2R^c$;

wherein the $C_{1-6}$alkyl, $C_{2-6}$ alkenyl, $C_{2-6}$ alkynyl, and the —$OC_{1-6}$alkyl of any of the $R^{9A}$ and $R^{10}$ substituents is unsubstituted or substituted by 1, 2 or 3 $R^{12}$ substituents independently selected from OH, halo, —(=O), —$OC_{1-6}$alkyl, —$C_{1-6}$alkyl, —$NR^aR^b$, —$SiR^aR^bR^c$, a 6- to 12-membered aryl or heteroaryl, a 3- to 12-membered monocyclic or bicyclic cycloalkyl, or a 3- to 12-membered monocyclic or bicyclic heterocycloalkyl group, wherein the heteroaryl, or heterocycloalkyl groups have 1, 2, 3 or 4 heteroatoms independently selected from O, N or S, wherein the cycloalkyl or heterocycloalkyl groups may include a C=O group, and further wherein the heterocycloalkyl group may include a S=O or $SO_2$;

wherein the —$C_{1-6}$alkyl groups of the $R^{10}$ substituents is unsubstituted or substituted by 1, 2 or 3 $R^{12}$ substituents of —$OC_{1-6}$alkyl;

wherein the heterocycloalkyl groups of $R^{12}$ substituents can be unsubstituted or substituted with from 1, 2, 3 or 4 $R^{13}$ substituents independently selected from —$NR^cR^d$, or —$C_{1-6}$ alkyl;

wherein each $R^a$, $R^b$, $R^c$ and $R^d$ is independently hydrogen, OH, —$C_{1-6}$alkyl, —$(CH_2CH_2O)_nCH_3$, —$NR^{14}R^{14}$, —$C_{1-6}$alkyl-$NR^{14}R^{14}$, phenyl, —$C_{1-6}$alkyl-$C(=O)OH$, —$C_{1-6}$alkyl-$C(=O)$—O—$C_{1-6}$alkyl, —$C_{1-6}$alkyl-3- to 12-membered cycloalkyl, —$C_{1-6}$alkyl-3- to 12-membered heterocycloalkyl, —$C_{1-6}$alkyl-6- to 12-membered heteroaryl, a 6- to 12-membered aryl or heteroaryl, a 3- to 12-membered monocyclic or bicyclic cycloalkyl, or a 3- to 12-membered monocyclic or bicyclic heterocycloalkyl group, wherein the heteroaryl group, heterocycloalkyl groups of $R^a$, $R^b$, $R^c$, and $R^d$ or the heterocycloalkyl group of the —$C_{1-6}$alkyl-heterocycloalkyl group of $R^a$, $R^b$, $R^c$, and $R^d$ has from 1, 2, 3, or 4 heteroatoms independently selected from O, N or S, wherein the cycloalkyl and heterocycloalkyl groups of $R^a$, $R^b$, $R^c$, and $R^d$ and the heterocycloalkyl group of the —$C_{1-6}$alkyl-heterocycloalkyl groups of $R^a$, $R^b$, $R^c$, and $R^d$ may include a double bond, and further wherein the cycloalkyl and heterocycloalkyl groups of $R^a$, $R^b$, $R^c$, and $R^d$ and the heterocycloalkyl group of the —$C_{1-6}$alkyl-heterocycloalkyl groups of $R^a$, $R^b$, $R^c$, and $R^d$ may contain a C=O group;

the alkyl, aryl, heteroaryl, cycloalkyl, heterocycloalkyl groups of $R^a$, $R^b$, $R^c$, and $R^d$ or the heterocycloalkyl groups of the —$C_{1-6}$alkyl-heterocycloalkyl groups of $R^a$, $R^b$, $R^c$, and $R^d$ can be unsubstituted or substituted with from 1, 2, 3, or 4 $R^{14}$ substituents, wherein each $R^{14}$ is independently selected from H, OH, halo, —$C_{1-6}$alkyl, $N(CH_3)_2$, —$C_{1-6}$ haloalkyl, $C(=O)CH_3$, —$C(=O)OCH_3$, or —$C_{1-6}$alkyl-O—$C_{1-6}$alkyl;

alternatively $R^a$ and $R^b$ together with the atoms to which they are bonded may form a 4- to 12-membered monocyclic or bicyclic ring, optionally containing a heteroatom selected from N, O or S atom, which may contain a double bond; and wherein n is independently in each instance an integer from 1, 2, 3 or 4.

34. The compound of any one of embodiments 1-23, or the stereoisomer thereof, the pharmaceutically acceptable salt thereof, or the pharmaceutically acceptable salt of the stereoisomer thereof, wherein $R^{9A}$ is independently selected from H, —$CH_3$, OH,

-continued

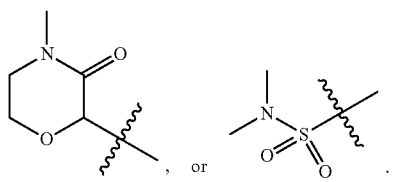, or

35. The compound of embodiment 34, or the stereoisomer thereof, the pharmaceutically acceptable salt thereof, or the pharmaceutically acceptable salt of the stereoisomer thereof, wherein $R^{9A}$ is H.

36. The compound of embodiment 34, or the stereoisomer thereof, the pharmaceutically acceptable salt thereof, or the pharmaceutically acceptable salt of the stereoisomer thereof, wherein $R^{9A}$ is —$CH_3$.

37. The compound of embodiment 34, or the stereoisomer thereof, the pharmaceutically acceptable salt thereof, or the pharmaceutically acceptable salt of the stereoisomer thereof, wherein $R^{9A}$ is —OH.

38. The compound of embodiment 34, or the stereoisomer thereof, the pharmaceutically acceptable salt thereof, or the pharmaceutically acceptable salt of the stereoisomer thereof, wherein $R^{9A}$ is

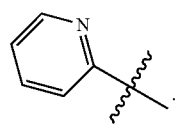

39. The compound of embodiment 34, or the stereoisomer thereof, the pharmaceutically acceptable salt thereof, or the pharmaceutically acceptable salt of the stereoisomer thereof, wherein $R^{9A}$ is

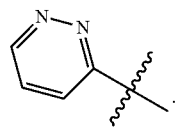

40. The compound of embodiment 34, or the stereoisomer thereof, the pharmaceutically acceptable salt thereof, or the pharmaceutically acceptable salt of the stereoisomer thereof, wherein $R^{9A}$ is

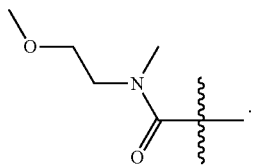 [SMILES: *C(=O)N(C)CCOC]

41. The compound of embodiment 34, or the stereoisomer thereof, the pharmaceutically acceptable salt thereof, or the pharmaceutically acceptable salt of the stereoisomer thereof, wherein $R^{9A}$ is

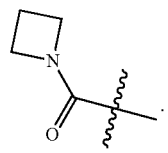 [SMILES: *C(=O)N1CCC1]

42. The compound of embodiment 34, or the stereoisomer thereof, the pharmaceutically acceptable salt thereof, or the pharmaceutically acceptable salt of the stereoisomer thereof, wherein $R^{9A}$ is

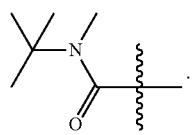 [SMILES: *C(=O)N(C)C(C)(C)C]

43. The compound of embodiment 34, or the stereoisomer thereof, the pharmaceutically acceptable salt thereof, or the pharmaceutically acceptable salt of the stereoisomer thereof, wherein $R^{9A}$ is

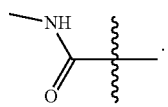 [SMILES: *C(=O)NC]

44. The compound of embodiment 34, or the stereoisomer thereof, the pharmaceutically acceptable salt thereof, or the pharmaceutically acceptable salt of the stereoisomer thereof, wherein $R^{9A}$ is

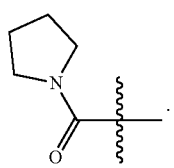 [SMILES: *C(=O)N1CCCC1]

45. The compound of embodiment 34, or the stereoisomer thereof, the pharmaceutically acceptable salt thereof, or the pharmaceutically acceptable salt of the stereoisomer thereof, wherein $R^{9A}$ is

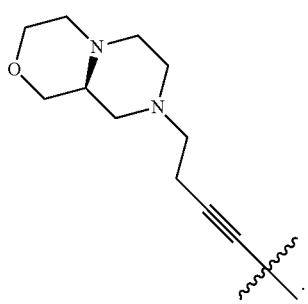 [SMILES: *C#CCCN1CCN2CCOC[C@@H]2C1]

46. The compound of embodiment 34, or the stereoisomer thereof, the pharmaceutically acceptable salt thereof, or the pharmaceutically acceptable salt of the stereoisomer thereof, wherein $R^{9A}$ is

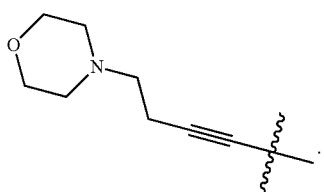 [SMILES: *C#CCCN1CCOCC1]

47. The compound of embodiment 34, or the stereoisomer thereof, the pharmaceutically acceptable salt thereof, or the pharmaceutically acceptable salt of the stereoisomer thereof, wherein $R^{9A}$ is

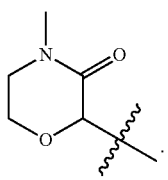 [SMILES: *C1OCCN(C)C1=O]

48. The compound of embodiment 34, or the stereoisomer thereof, the pharmaceutically acceptable salt thereof, or the pharmaceutically acceptable salt of the stereoisomer thereof, wherein $R^{9A}$ is

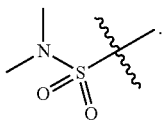 [SMILES: *S(=O)(=O)N(C)C]

49 Another embodiment of the present invention comprises a compound of embodiment 1, wherein the compound has the Formula III:

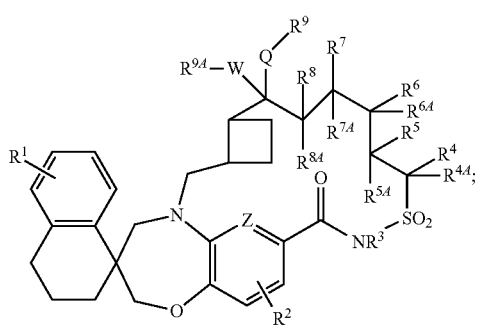

(III)

or the stereoisomer thereof, the pharmaceutically acceptable salt thereof, or the pharmaceutically acceptable salt of the stereoisomer thereof.

50. Another embodiment of the present invention comprises a compound of any one of embodiments 1 or 49, wherein the compound has the Formula IIIa:

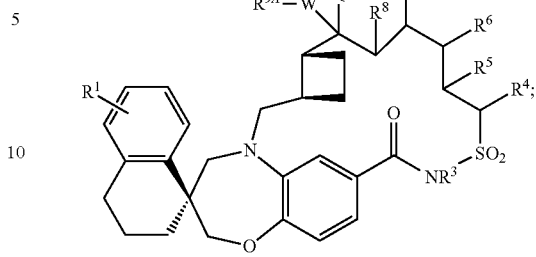

(IIIa)

or the stereoisomer thereof, the pharmaceutically acceptable salt thereof, or the pharmaceutically acceptable salt of the stereoisomer thereof.

51. The compound of any one of embodiments 1, or 49-50, or the stereoisomer thereof, the pharmaceutically acceptable salt thereof, or the pharmaceutically acceptable salt of the stereoisomer thereof, wherein Q is O, —$CR^aR^b$, or —$NR^aR^b$.

52. The compound of embodiment 51, or the stereoisomer thereof, the pharmaceutically acceptable salt thereof, or the pharmaceutically acceptable salt of the stereoisomer thereof, wherein Q is O.

53. The compound of embodiment 52, or the stereoisomer thereof, the pharmaceutically acceptable salt thereof, or the pharmaceutically acceptable salt of the stereoisomer thereof, wherein Q is —$CH_2$.

54. The compound of embodiment 52, or the stereoisomer thereof, the pharmaceutically acceptable salt thereof, or the pharmaceutically acceptable salt of the stereoisomer thereof, wherein Q is —$NR^aR^b$.

55. The compound of any one of embodiments 1, or 49-54, or the stereoisomer thereof, the pharmaceutically acceptable salt thereof, or the pharmaceutically acceptable salt of the stereoisomer thereof, wherein W is $CR^{WA}R^{WB}$, —C=O, or is absent.

56. The compound of embodiment 55, or the stereoisomer thereof, the pharmaceutically acceptable salt thereof, or the pharmaceutically acceptable salt of the stereoisomer thereof, wherein W is $CR^{WA}R^{WB}$.

57. The compound of embodiment 55, or the stereoisomer thereof, the pharmaceutically acceptable salt thereof, or the pharmaceutically acceptable salt of the stereoisomer thereof, wherein W is absent.

58. The compound of any one of embodiments 1, or 49-56, or the stereoisomer thereof, the pharmaceutically acceptable salt thereof, or the pharmaceutically acceptable salt of the stereoisomer thereof, wherein $R^{WA}$ and $R^{WB}$ are independently selected from H, —$C_{1-3}$alkyl, —$C_{1-3}$alkenyl, —$C_{1-3}$alkynyl, halo, —OH, or —O—$C_{1-3}$alkyl.

59. The compound of embodiment 58, or the stereoisomer thereof, the pharmaceutically acceptable salt thereof, or the pharmaceutically acceptable salt of the stereoisomer thereof, wherein $R^{WA}$ and $R^{WB}$ are both H.

60. The compound of embodiment 58, or the stereoisomer thereof, the pharmaceutically acceptable salt thereof, or the pharmaceutically acceptable salt of the stereoisomer thereof, wherein $R^{WA}$ is —$CH_3$.

61. The compound of embodiment 58, or the stereoisomer thereof, the pharmaceutically acceptable salt thereof, or the pharmaceutically acceptable salt of the stereoisomer thereof, wherein at least one of $R^{WA}$ and $R^{WB}$ is H.

62. The compound of embodiment 58, or the stereoisomer thereof, the pharmaceutically acceptable salt thereof, or the pharmaceutically acceptable salt of the stereoisomer thereof, wherein $R^{WA}$ is —OH and $R^{WB}$ is H.

63. The compound of any one of embodiments 1, or 49-62, or the stereoisomer thereof, the pharmaceutically acceptable salt thereof, or the pharmaceutically acceptable salt of the stereoisomer thereof, wherein $R^1$ is halo.

64. The compound of embodiment 63, or the stereoisomer thereof, the pharmaceutically acceptable salt thereof, or the pharmaceutically acceptable salt of the stereoisomer thereof, wherein $R^1$ is Cl.

65. The compound of any one of embodiments 1, or 49-64, or the stereoisomer thereof, the pharmaceutically acceptable salt thereof, or the pharmaceutically acceptable salt of the stereoisomer thereof, wherein $R^3$ is H.

66. The compound of any one of embodiments 1, or 49-65, or the stereoisomer thereof, the pharmaceutically acceptable salt thereof, or the pharmaceutically acceptable salt of the stereoisomer thereof, wherein $R^4$ is independently selected from H or —$C_{1-6}$alkyl.

67. The compound of embodiment 66, or the stereoisomer thereof, the pharmaceutically acceptable salt thereof, or the pharmaceutically acceptable salt of the stereoisomer thereof, wherein $R^4$ is —$CH_3$.

68. The compound of any one of embodiments 1, or 49-67, or the stereoisomer thereof, the pharmaceutically acceptable salt thereof, or the pharmaceutically acceptable salt of the stereoisomer thereof, wherein $R^5$ is selected from H or —$C_{1-6}$alkyl.

69. The compound of embodiment 68, or the stereoisomer thereof, the pharmaceutically acceptable salt thereof, or the pharmaceutically acceptable salt of the stereoisomer thereof, wherein $R^5$ is —$CH_3$.

70. The compound of any one of embodiments 1, or 49-69, or the stereoisomer thereof, the pharmaceutically acceptable salt thereof, or the pharmaceutically acceptable salt of the stereoisomer thereof, wherein $R^6$ is H.

71. The compound of any one of embodiments 1, or 49-70, or the stereoisomer thereof, the pharmaceutically acceptable salt thereof, or the pharmaceutically acceptable salt of the stereoisomer thereof, wherein $R^7$ is selected from H or —$NR^aR^b$.

72. The compound of embodiment 71, or the stereoisomer thereof, the pharmaceutically acceptable salt thereof, or the pharmaceutically acceptable salt of the stereoisomer thereof, wherein $R^7$ is H.

73. The compound of any one of embodiments 1, or 49-73, or the stereoisomer thereof, the pharmaceutically acceptable salt thereof, or the pharmaceutically acceptable salt of the stereoisomer thereof, wherein $R^8$ is selected from H or —$C_{1-6}$alkyl.

74. The compound of embodiment 73, or the stereoisomer thereof, the pharmaceutically acceptable salt thereof, or the pharmaceutically acceptable salt of the stereoisomer thereof, wherein $R^8$ is H.

75. The compound of any one of embodiments 1, or 49-70, or the stereoisomer thereof, the pharmaceutically acceptable salt thereof, or the pharmaceutically acceptable salt of the stereoisomer thereof, wherein alternatively $R^7$ and $R^8$ together with the atoms to which they are bonded may form a 3- to 12-membered ring.

76. The compound of any one of embodiments 1, 49-70, or the stereoisomer thereof, the pharmaceutically acceptable salt thereof, or the pharmaceutically acceptable salt of the stereoisomer thereof, wherein alternatively $R^7$ and $R^{9A}$ together with the atoms to which they are bonded may form a 3- to 12-membered ring, wherein the ring may optionally contain at least one double bond.

77. The compound of any one of embodiments 1, 49-76, or the stereoisomer thereof, the pharmaceutically acceptable salt thereof, or the pharmaceutically acceptable salt of the stereoisomer thereof, wherein $R^9$ is independently selected from H, —OH, —(=O), —$C_{1-6}$alkyl, cyano, —C(=O)—$C_{1-6}$alkyl, —C(=O)-phenyl, —$C_{1-6}$alkyl-O— $C_{1-6}$alkyl, —$C_{1-6}$alkyl-(5-10 membered mono or bicyclic heterocycloalkyl), wherein the heterocycloalkyl may contain one, two, three or four heteroatoms independently selected from N or O.

78. The compound of any one of embodiments 1, or 49-75, or the stereoisomer thereof, the pharmaceutically acceptable salt thereof, or the pharmaceutically acceptable salt of the stereoisomer thereof, wherein alternatively $R^9$ and $R^{9A}$ together with Q, W and the C to which Q and W are bonded, may form a 3- to 12-membered monocyclic or bicyclic ring, optionally containing a heteroatom in addition to Q selected from N, O or S atom, the ring may contain a double bond, the ring may optionally include a C=O group, and the ring optionally may be substituted with 0, 1, 2, or 3 $R^{11}$ substituents;

wherein $R^{11}$ is selected from H, halo, —OH, —$C_{1-6}$ haloalkyl, —$C_{1-6}$alkyl, —$C_{1-6}$alkyl, —O—$C_{1-6}$alkyl, —C(=O)$R^c$, —C(=O)$NR^cR^d$, —$NR^cR^d$, a 3- to 12-membered monocyclic or bicyclic heterocycloalkyl group, where the heterocycloalkyl groups have 1, 2, 3 or 4 heteroatoms independently selected from O, N or S, wherein the heterocycloalkyl groups may include a double bond, and wherein the heterocycloalkyl groups may contain a C=O group; and further wherein the heterocycloalkyl groups may be unsubstituted or substituted with one or more —$C_{1-6}$alkyl.

79. The compound of any one of embodiments 1, 49-75 or 77, or the stereoisomer thereof, the pharmaceutically acceptable salt thereof, or the pharmaceutically acceptable salt of the stereoisomer thereof, wherein $R^{9A}$ is independently selected from H, —OH, —$C_{1-6}$alkyl, —$C_{2-6}$ alkenyl, —$C_{2-6}$ alkynyl, —$C_{1-6}$alkyl, —C(=O), —(=O), —C(=O)$R^a$, cyano, —$C_{1-6}$alkyl-O— $C_{1-6}$alkyl, —O— $C_{1-6}$alkyl-O—$C_{1-6}$alkyl, —$OR^a$, —$CSR^a$, —$CS(=O)R^a$, —$SOR^a$, —$NR^aR^b$, —C(=O)$NR^aR^b$, phenyl, a 6- to 12-membered aryl or heteroaryl, a 5- to 12-membered spirocycloalkyl or spiroheterocycloalkyl, or a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl and heterocycloalkyl groups have 1, 2, 3 or 4 heteroatoms independently selected from O, N or S, and the cycloalkyl and heterocycloalkyl groups may contain a double bond and wherein the cycloalkyl and heterocycloalkyl groups may contain a C=O group, and further wherein the heterocycloalkyl groups may include a S=O or $SO_2$;

wherein the aryl, heteroaryl, cycloalkyl, and heterocycloalkyl groups of the $R^{9A}$ substituent can be unsubstituted or substituted with from 1, 2, 3 or 4 $R^{10}$ substituents independently selected from halo, —$NR^cR^d$, or —$C_{1-6}$alkyl;

wherein the $C_{1-6}$alkyl, $C_{2-6}$ alkenyl, $C_{2-6}$ alkynyl, and the —$OC_{1-6}$alkyl of any of the $R^{9A}$ and $R^{10}$ substituents is unsubstituted or substituted by 1, 2 or 3 $R^{12}$ substituents independently selected from OH, halo, —(=O), —$OC_{1-6}$ alkyl, —$C_{1-6}$alkyl, —$NR^aR^b$, —$SiR^aR^bR^c$, a 6- to 12-membered aryl or heteroaryl, or a 3- to 12-membered monocyclic or bicyclic heterocycloalkyl group, where the heteroaryl or heterocycloalkyl groups have 1, 2, 3 or 4 heteroatoms independently selected from O, N or S, and the heterocycloalkyl groups may include a C=O group.

80. The compound of any one of embodiments 1, 49-76, or the stereoisomer thereof, the pharmaceutically acceptable salt thereof, or the pharmaceutically acceptable salt of the stereoisomer thereof, wherein $R^9$ is independently selected from H, —OH, —$CH_3$, —$CH_2CH_3$, —C(=O)$CH_3$, —$CH_2$C(=O)O$CH_2CH_3$,

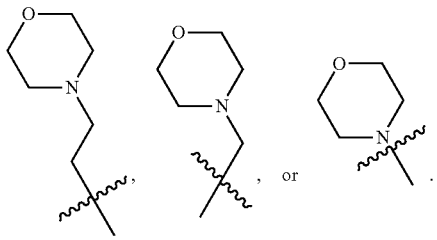

81. The compound of embodiment 80, or the stereoisomer thereof, the pharmaceutically acceptable salt thereof, or the pharmaceutically acceptable salt of the stereoisomer thereof, wherein $R^9$ is H.

82. The compound of embodiment 80, or the stereoisomer thereof, the pharmaceutically acceptable salt thereof, or the pharmaceutically acceptable salt of the stereoisomer thereof, wherein $R^9$ is —$CH_3$.

83. The compound of any one of embodiments 1, 49-75, or 77-80, or the stereoisomer thereof, the pharmaceutically acceptable salt thereof, or the pharmaceutically acceptable salt of the stereoisomer thereof, wherein $R^{9A}$ is independently selected from H, —OH, —$CH_3$, —$CH_2CH_3$, —O$CH_2$C(=O)O$CH_2CH_3$,

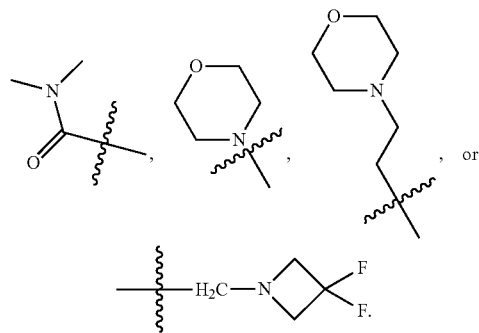

84. The compound of embodiment 83, or the stereoisomer thereof, the pharmaceutically acceptable salt thereof, or the pharmaceutically acceptable salt of the stereoisomer thereof, wherein $R^{9A}$ is H.

85. The compound of embodiment 83, or the stereoisomer thereof, the pharmaceutically acceptable salt thereof, or the pharmaceutically acceptable salt of the stereoisomer thereof, wherein $R^{9A}$ is —$C_{1-6}$alkyl.

86. The compound of embodiment 83, or the stereoisomer thereof, the pharmaceutically acceptable salt thereof, or the pharmaceutically acceptable salt of the stereoisomer thereof, wherein $R^{9A}$ is —$CH_3$.

87. The compound of embodiment 83, or the stereoisomer thereof, the pharmaceutically acceptable salt thereof, or the pharmaceutically acceptable salt of the stereoisomer thereof, wherein $R^{9A}$ is

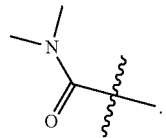 [SMILES: *C(=O)N(C)C]

88. The compound of any one of embodiments 1, 49-75 and 78, or the stereoisomer thereof, the pharmaceutically acceptable salt thereof, or the pharmaceutically acceptable salt of the stereoisomer thereof, wherein alternatively $R^9$ and $R^{9A}$ together with the atoms to which they are bonded may form a 5- to 12-membered monocyclic or bicyclic ring, optionally containing a heteroatom in addition to Q selected from N, O or S atom, further wherein the 5-12 membered ring may contain a double bond.

89. The compound of embodiment 88, or the stereoisomer thereof, the pharmaceutically acceptable salt thereof, or the pharmaceutically acceptable salt of the stereoisomer thereof, wherein $R^9$ and $R^{9A}$ together with Q, W and the C to which Q and W are bonded form

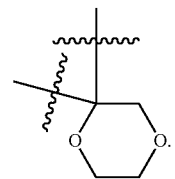 [SMILES: *C1(*)COCCO1]

90. Another embodiment of the present invention comprises a compound, wherein the compound has a structure selected from:

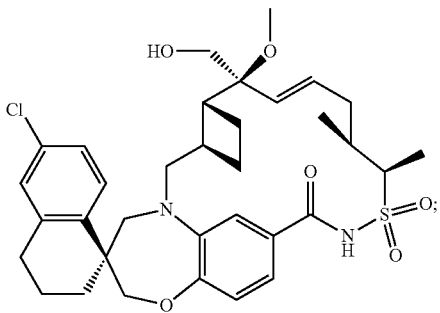

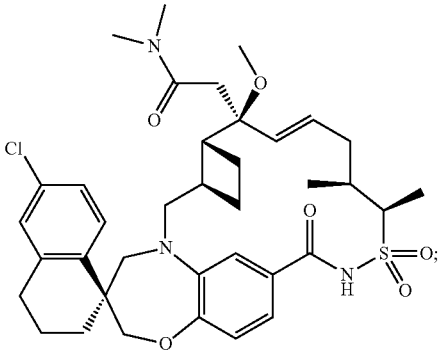

257
-continued
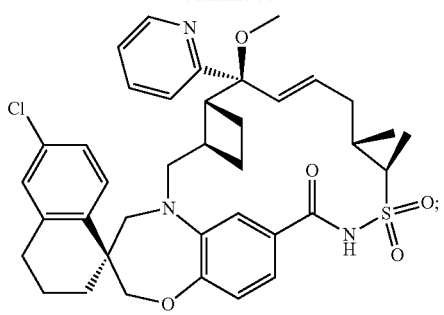
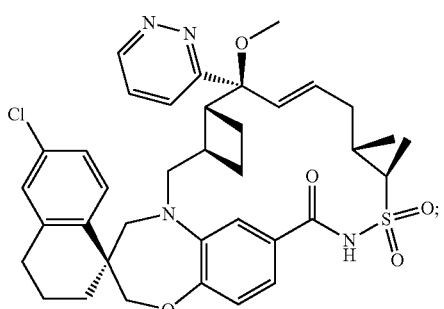
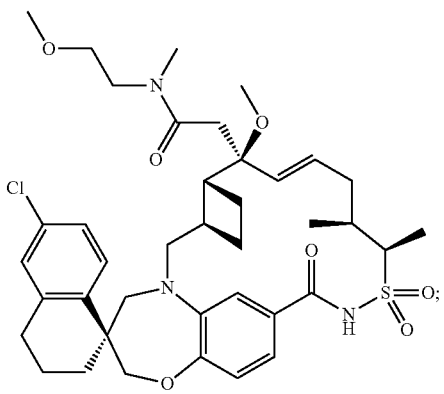
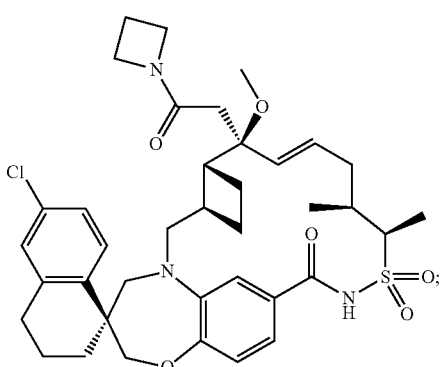
258
-continued
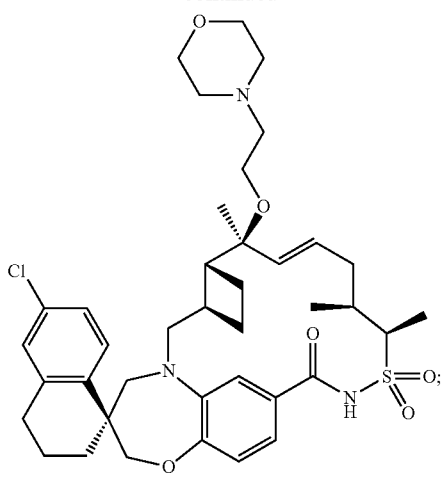
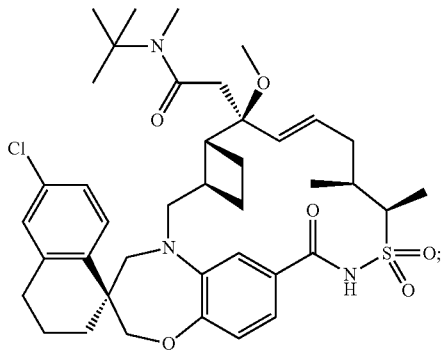
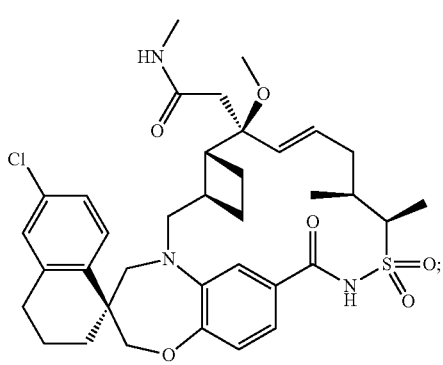
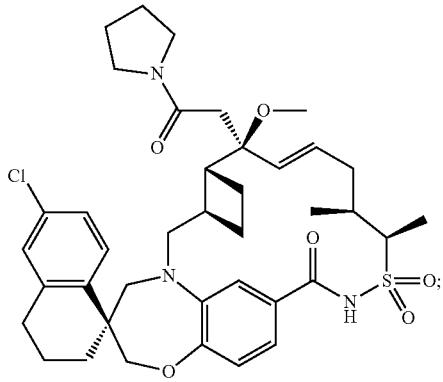

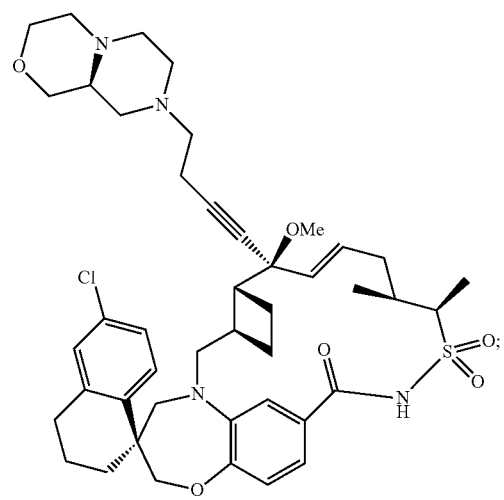
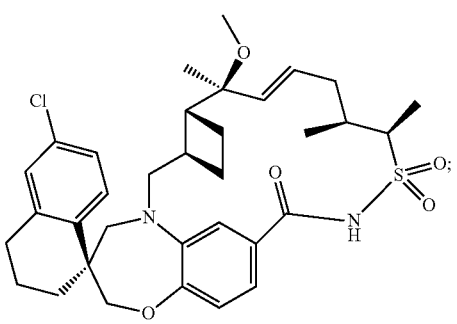
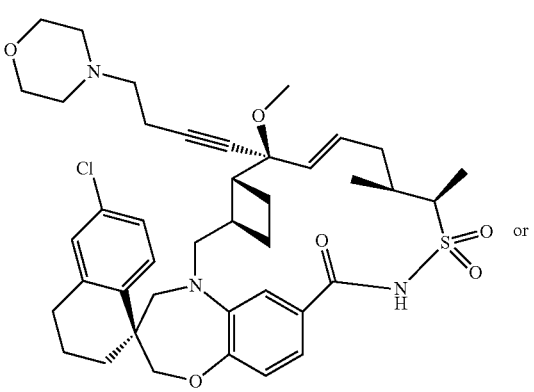
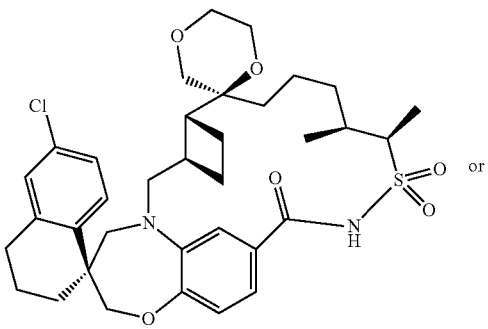
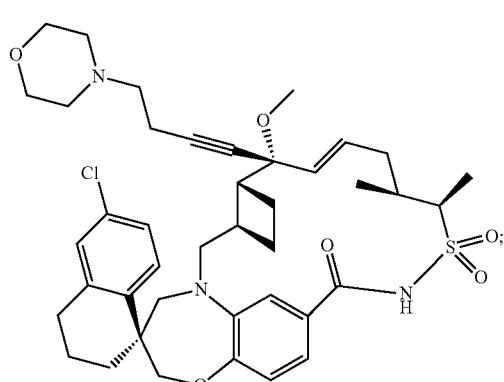
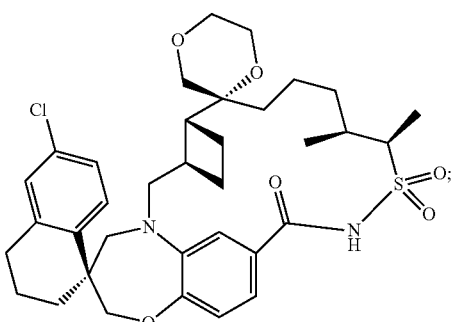
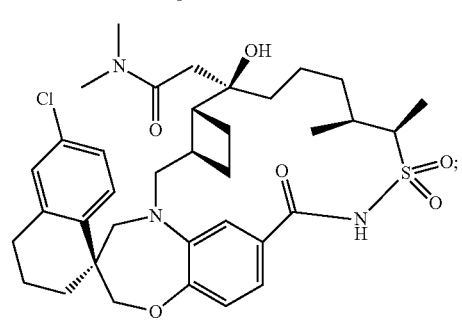
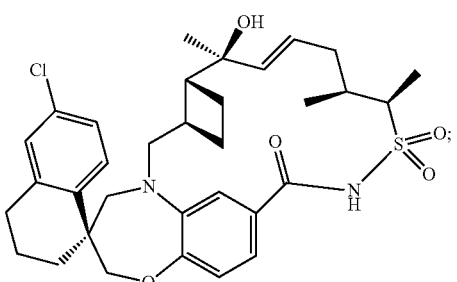
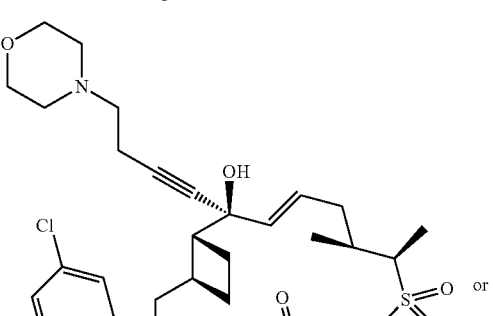

261
-continued
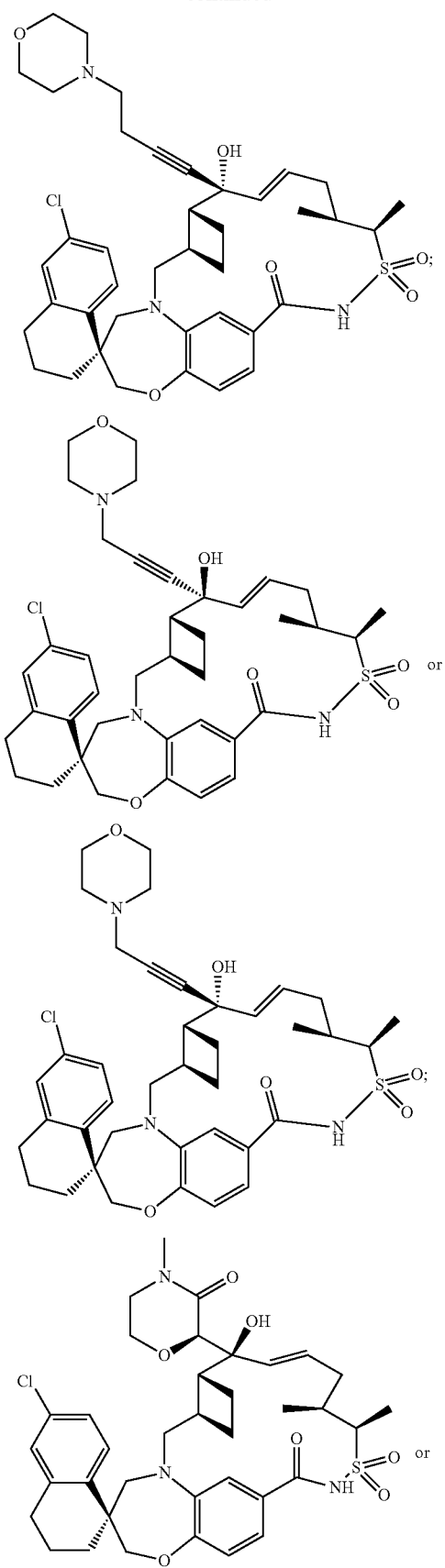
262
-continued
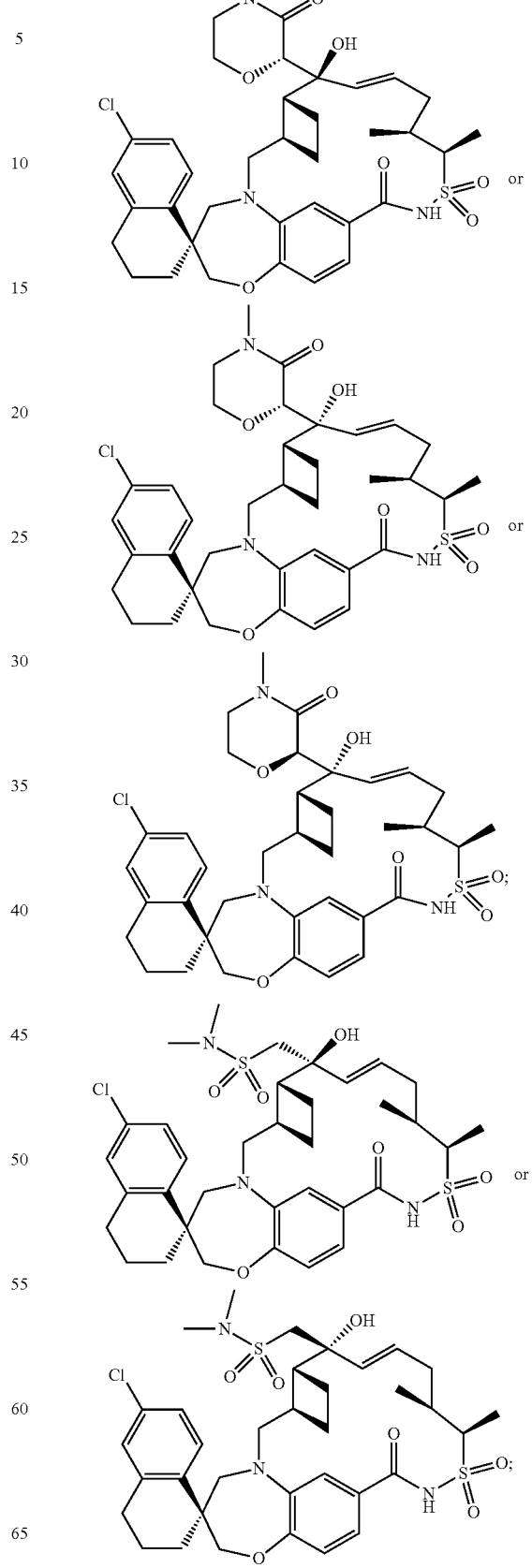

263
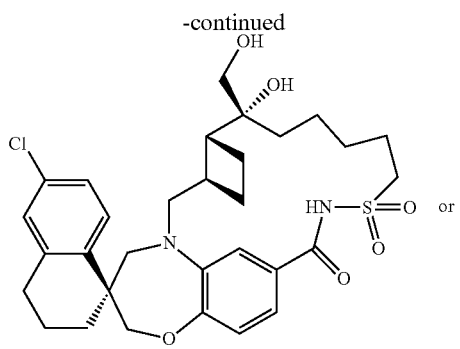
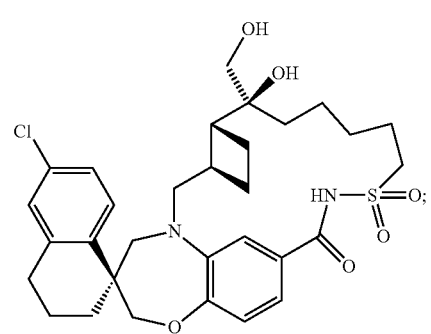
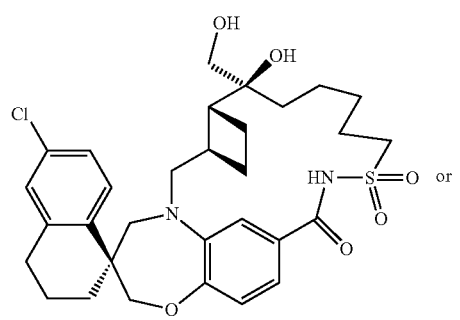
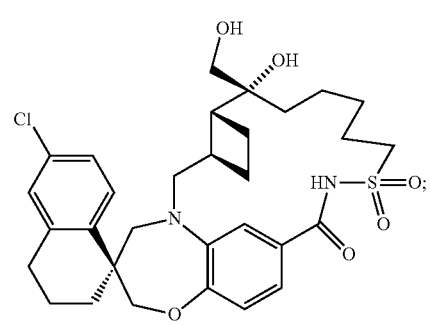
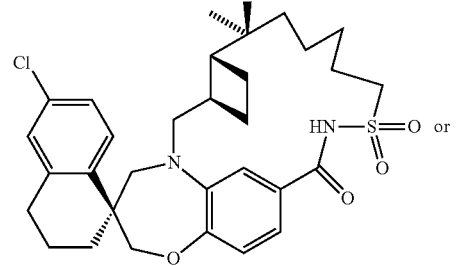
264
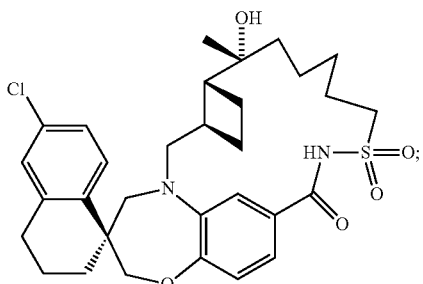
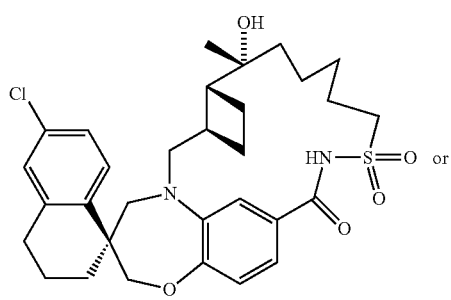
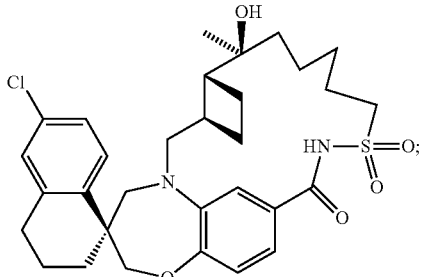
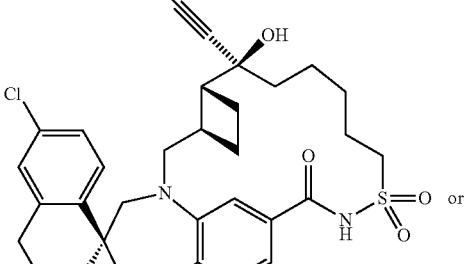
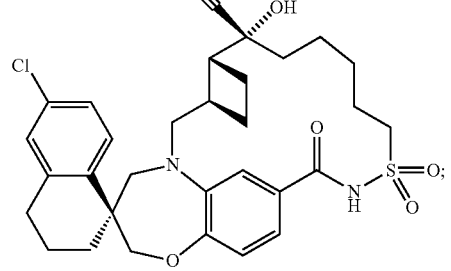

265
-continued
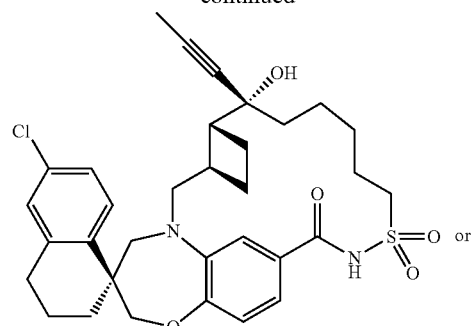
or
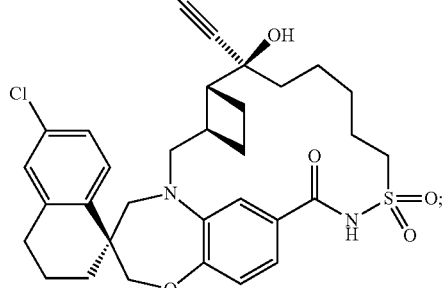
;
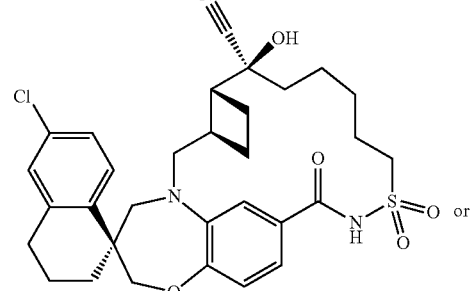
or
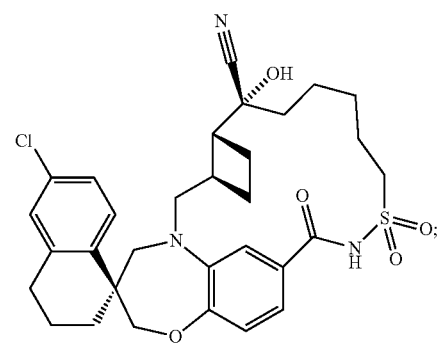
;
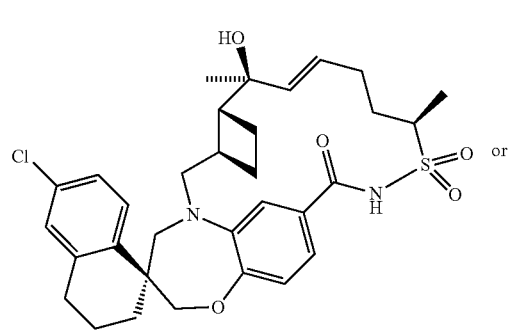
or
266
-continued
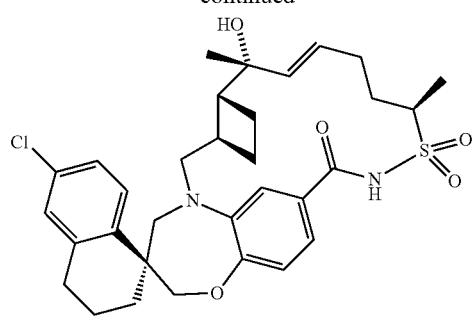
or
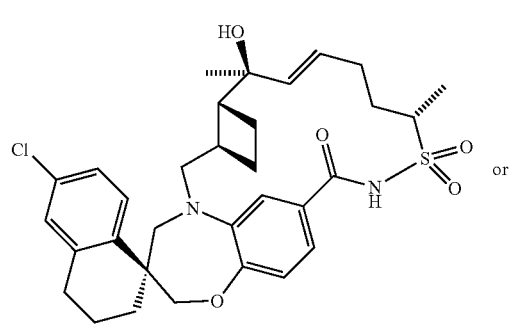
or
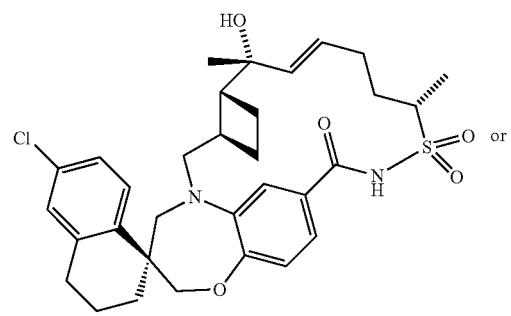
or

or
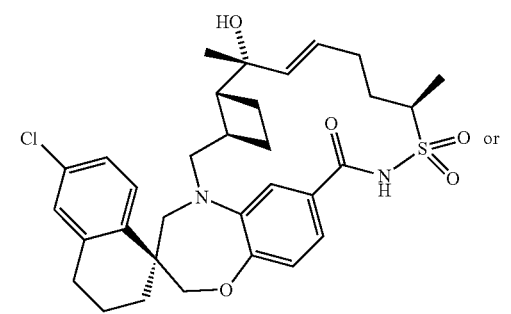
or 267
-continued
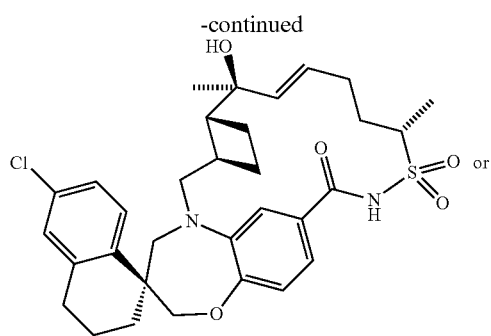
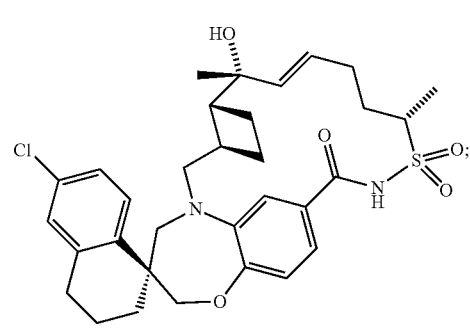
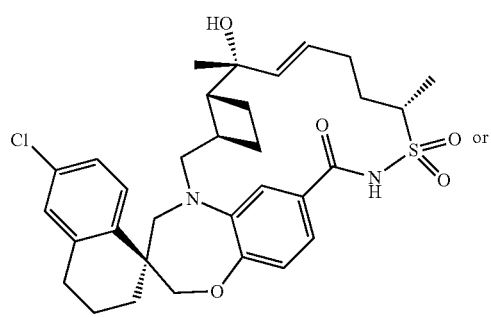
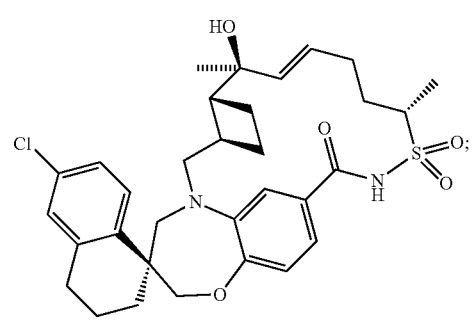
268
-continued
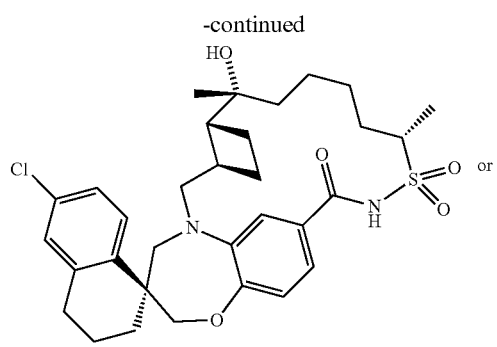
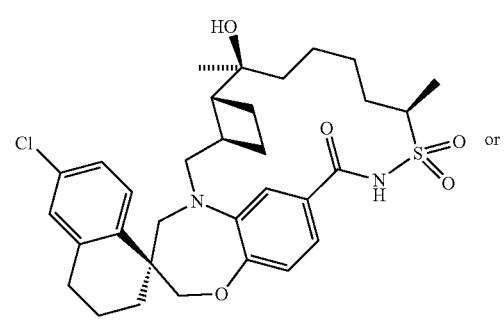
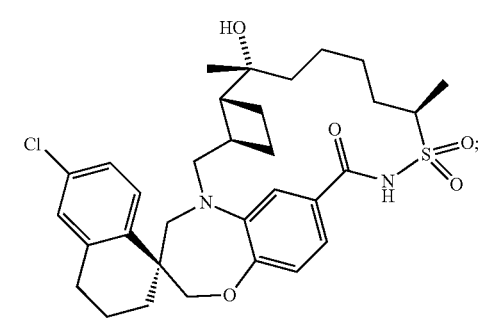

269
-continued

or
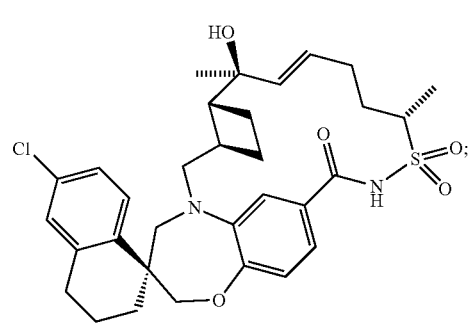
;
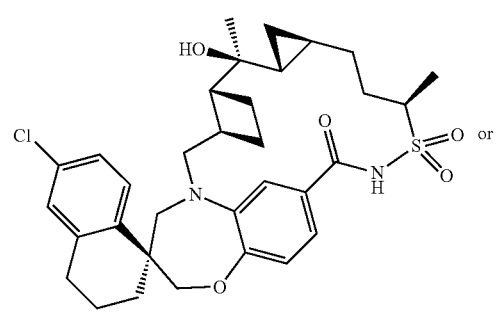
or
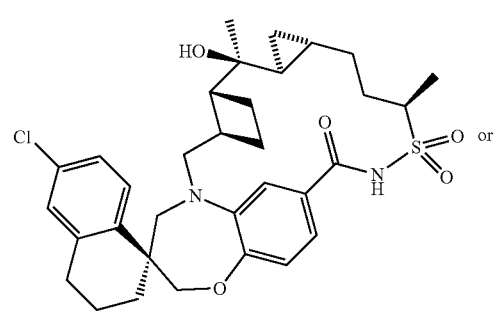
or
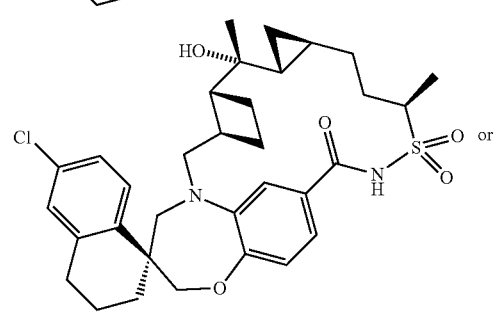
or
270
-continued

;
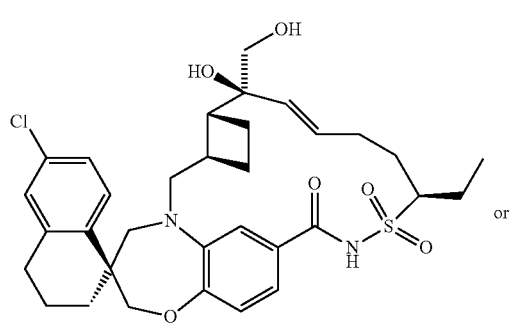
or
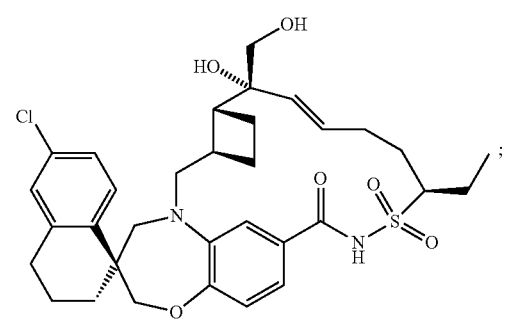
;
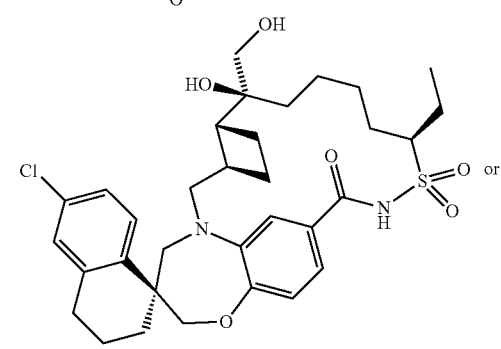
or
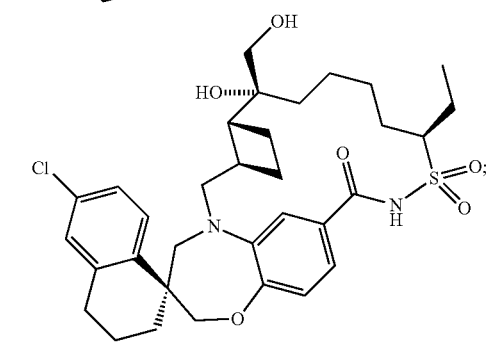
;

-continued
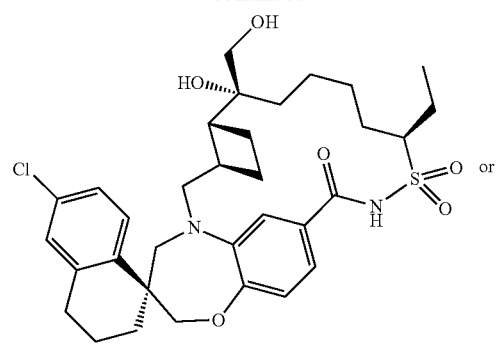 or
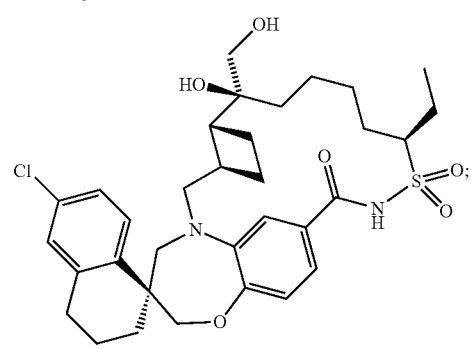;
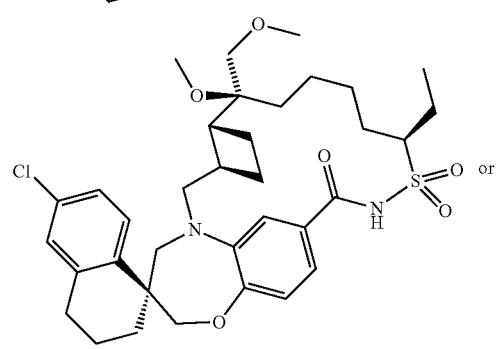 or
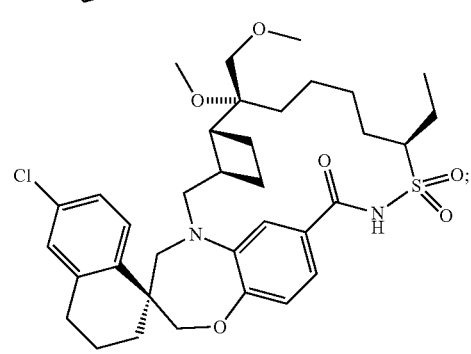;
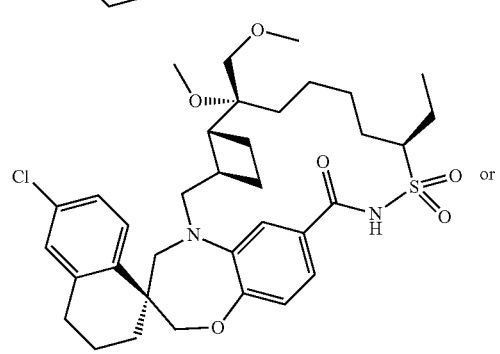 or
-continued
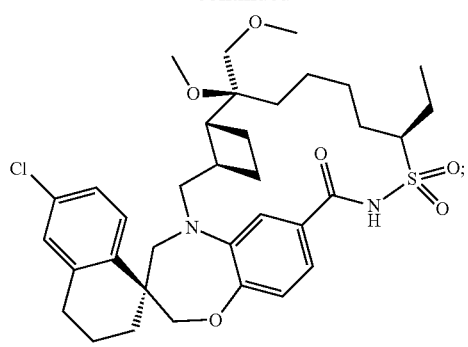;
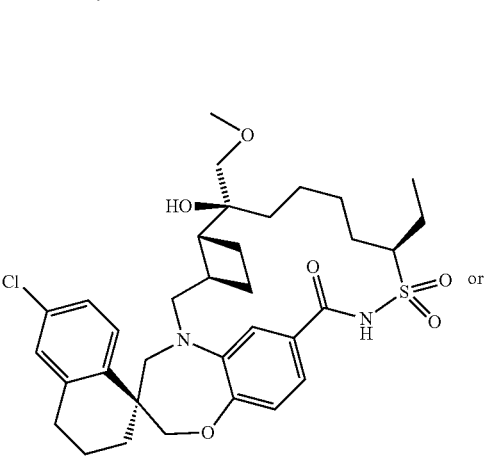 or
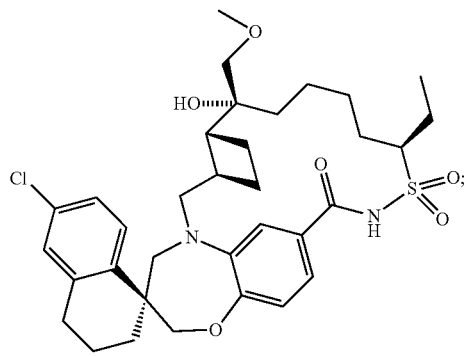;
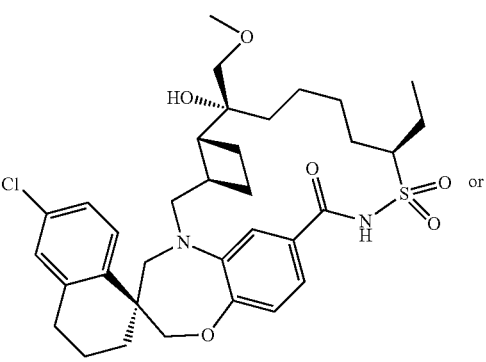 or

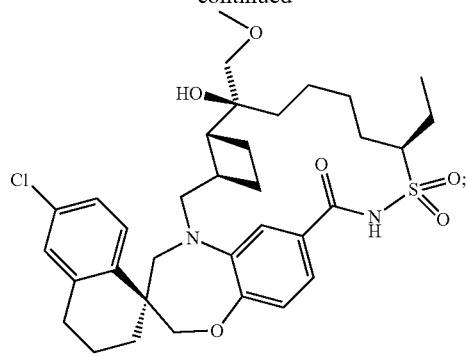
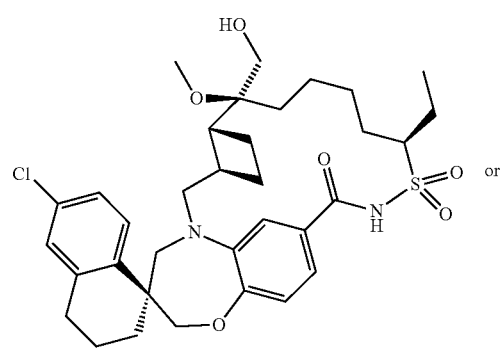
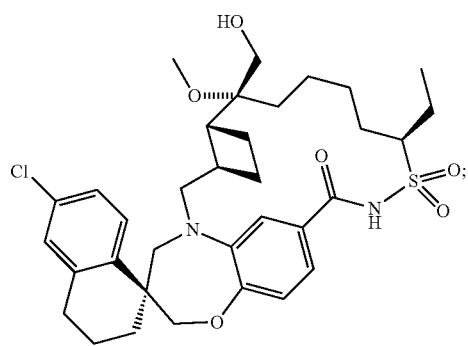
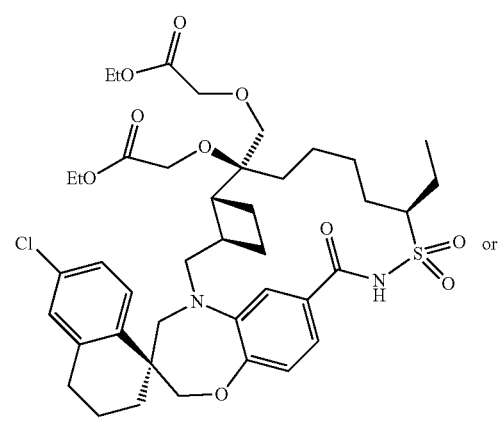
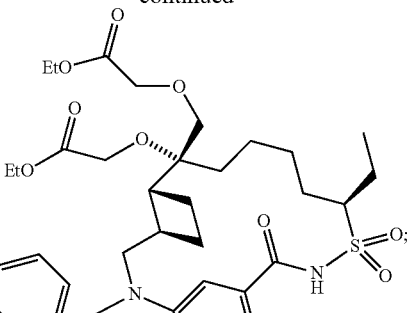
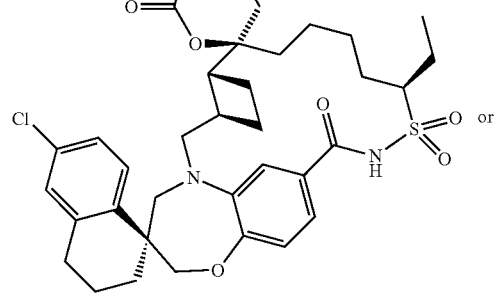
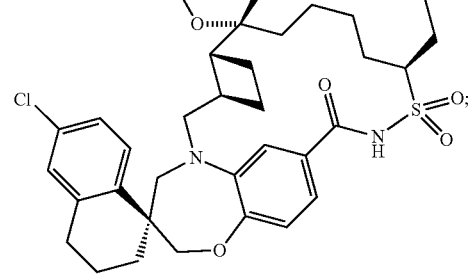
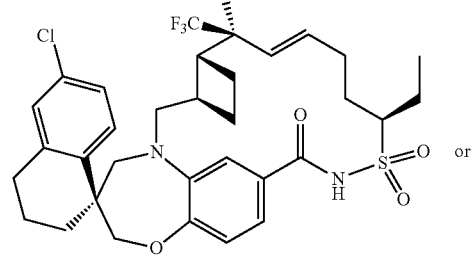
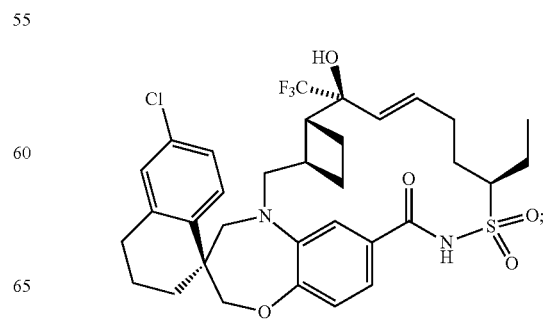

275
-continued
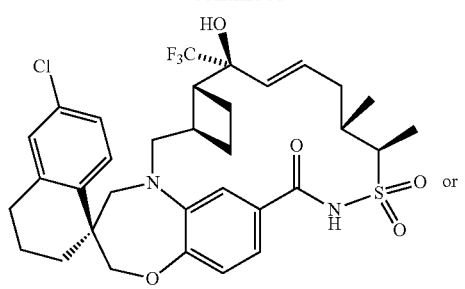
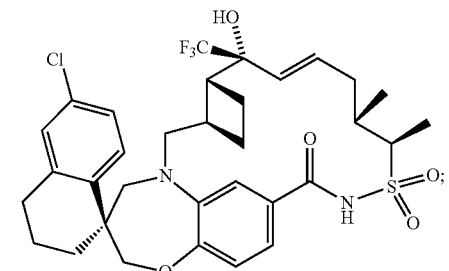
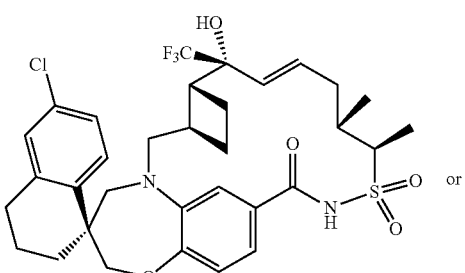
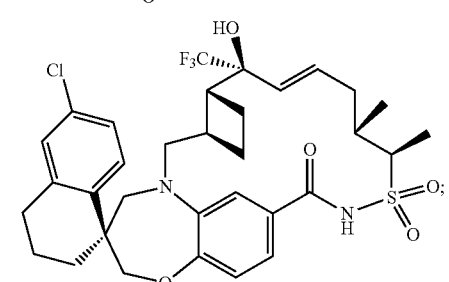
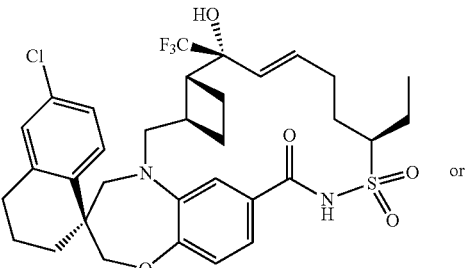
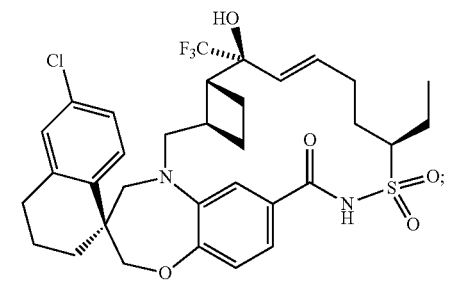
276
-continued
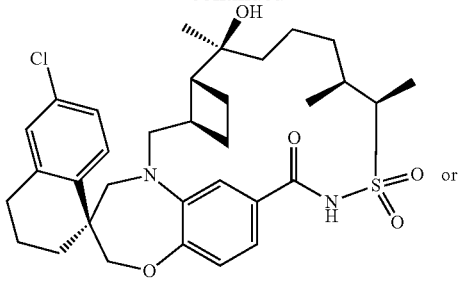
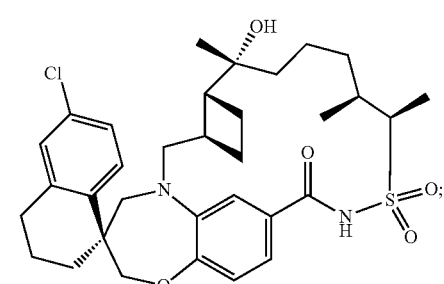
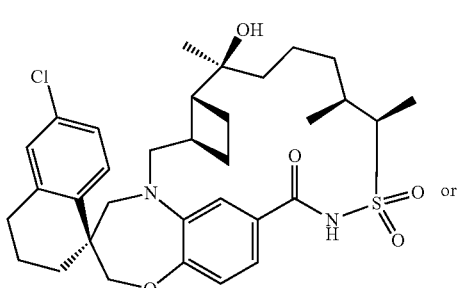
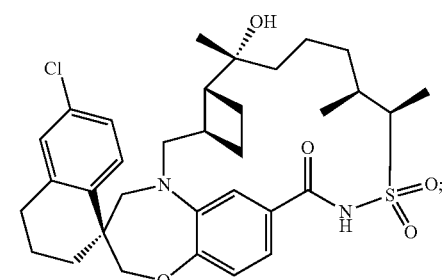
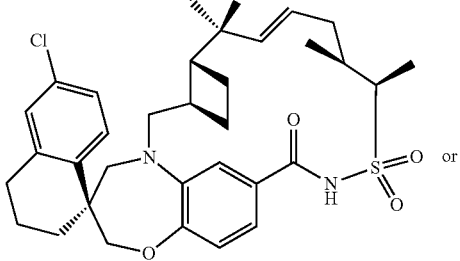

277
-continued
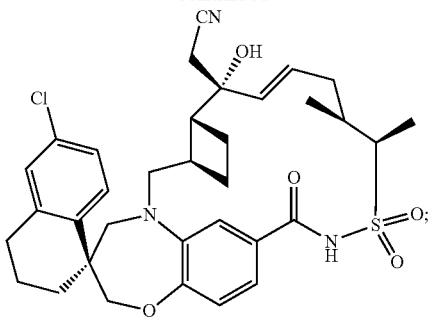
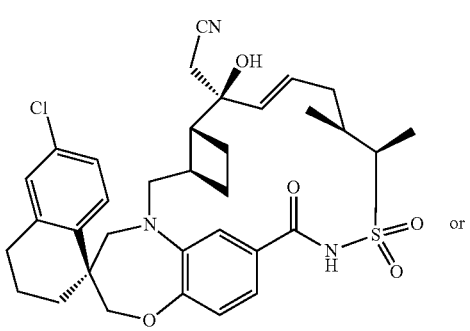
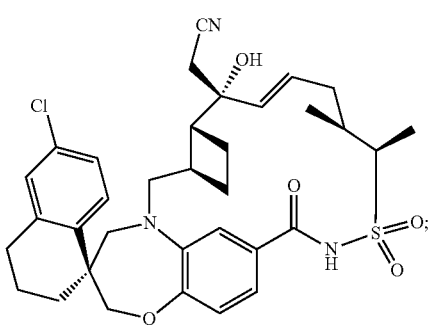
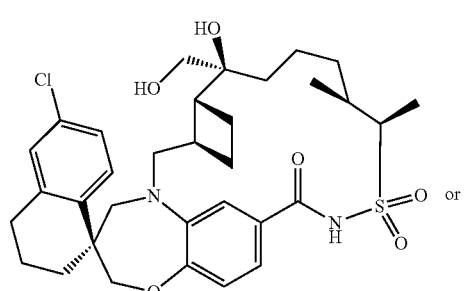
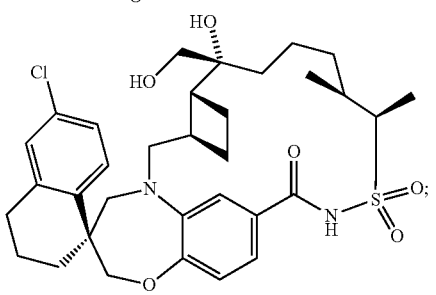
278
-continued
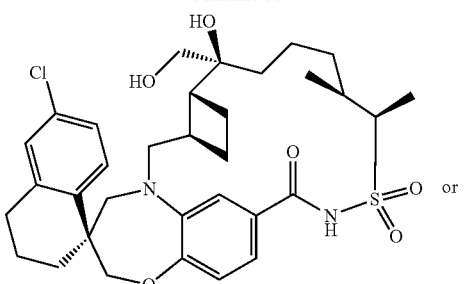
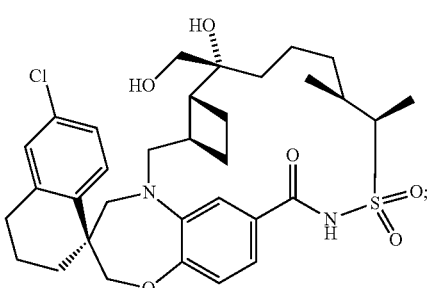
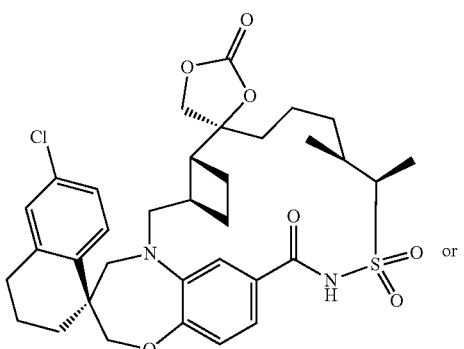
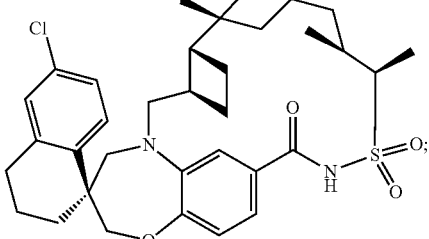
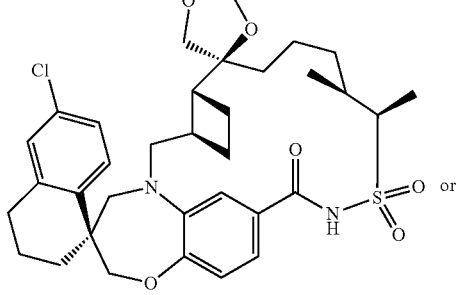

279
-continued
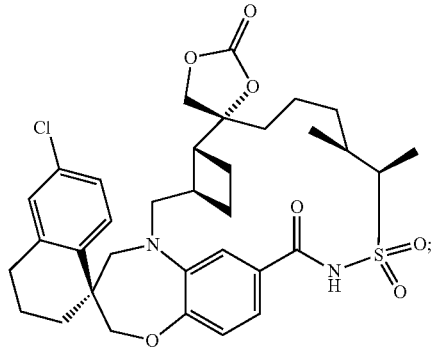
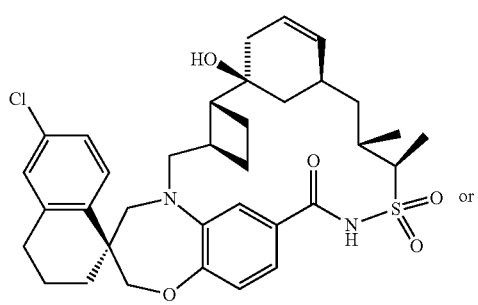
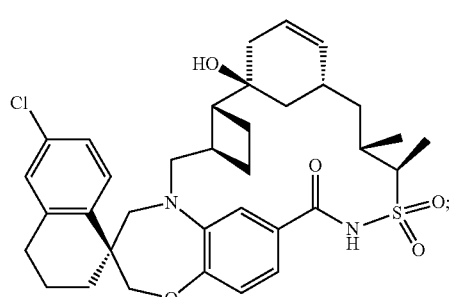
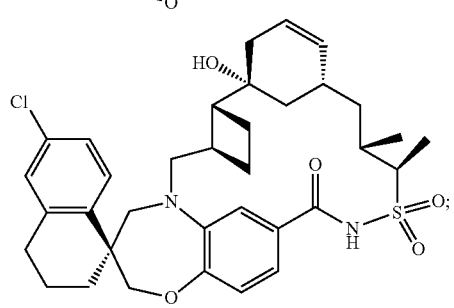
280
-continued
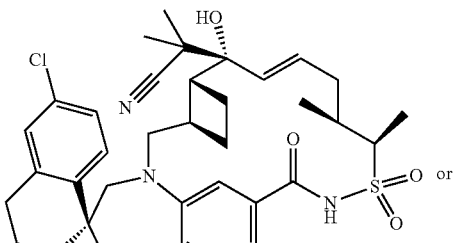
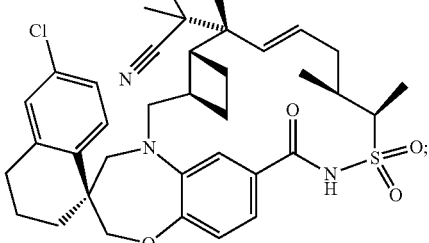
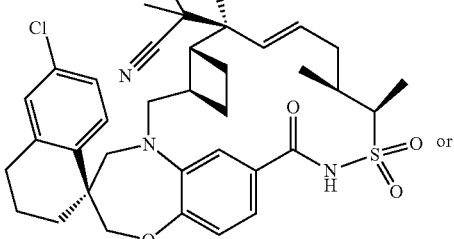
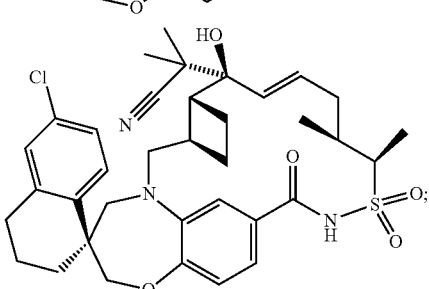
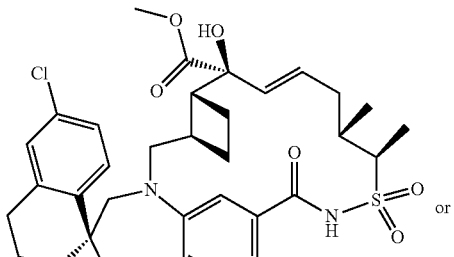

281
-continued
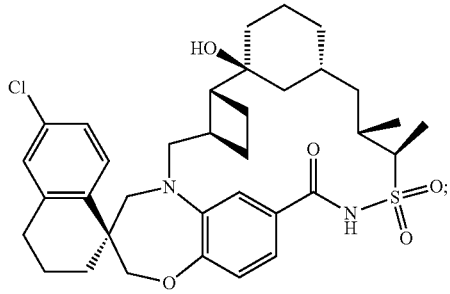
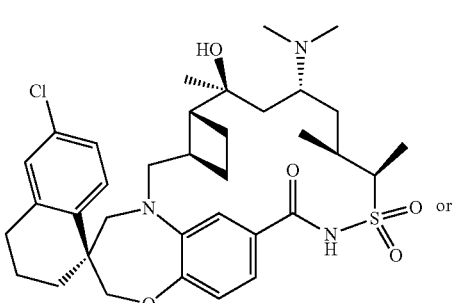
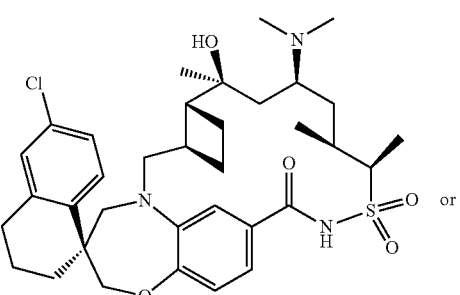
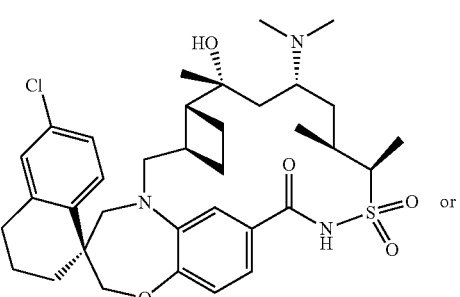
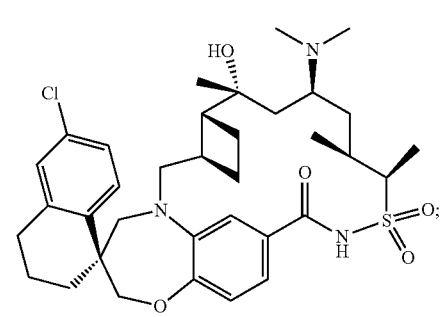
282
-continued
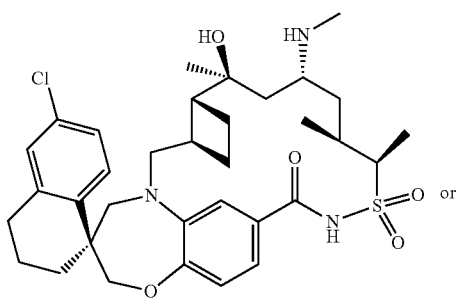
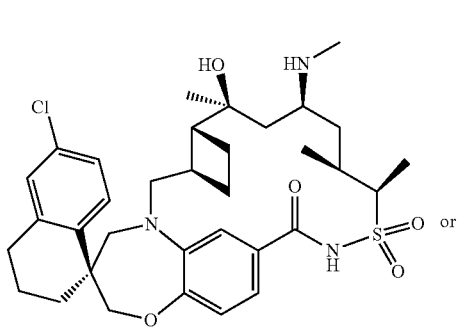
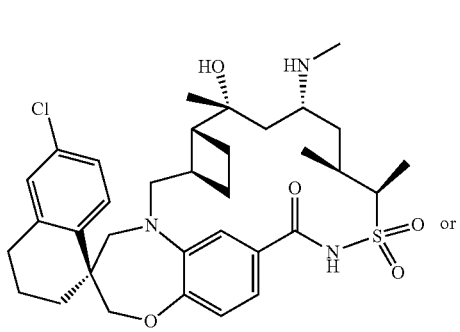
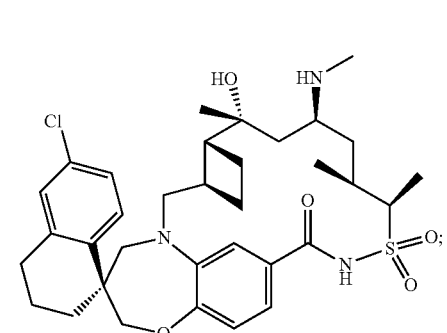

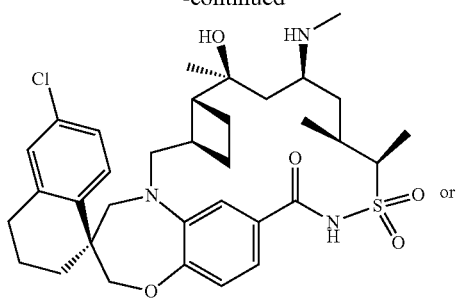
or
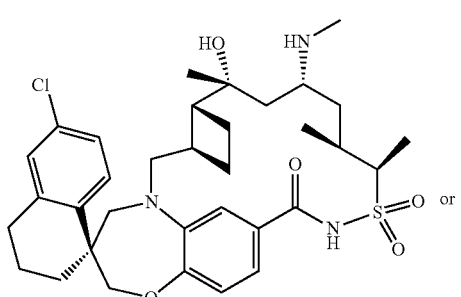
or
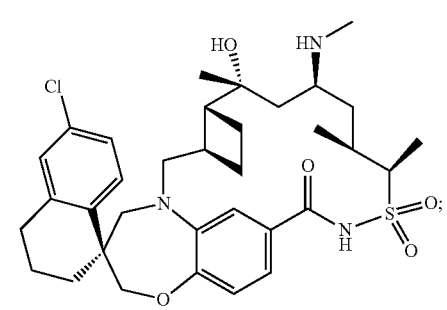
;
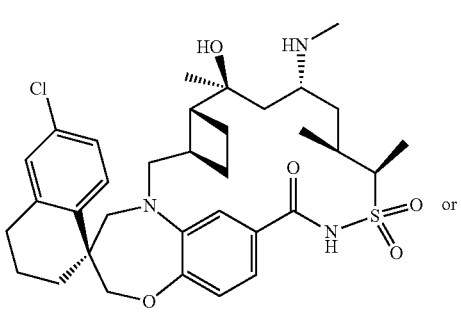
or
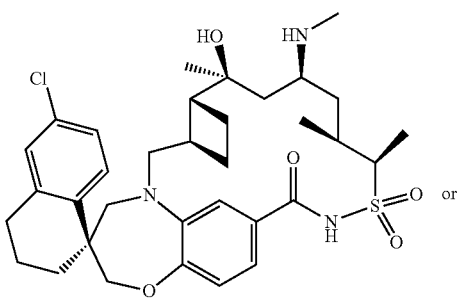
or
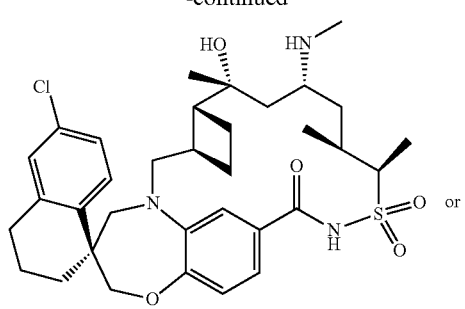
or
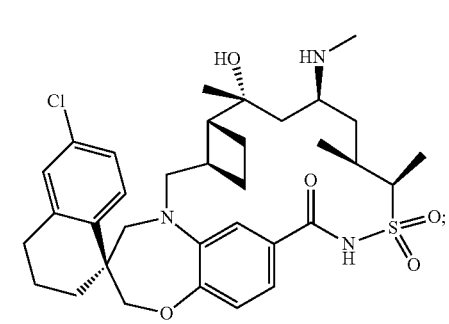
;
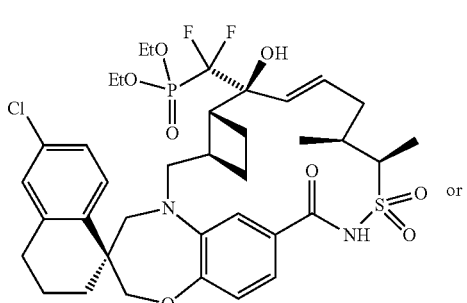
or
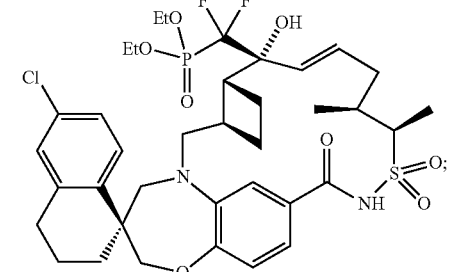
;
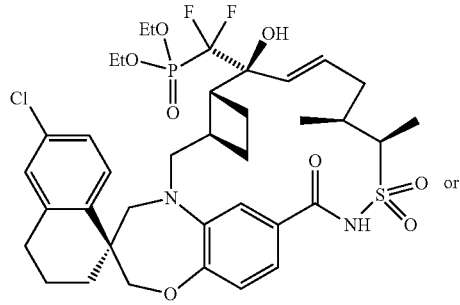
or

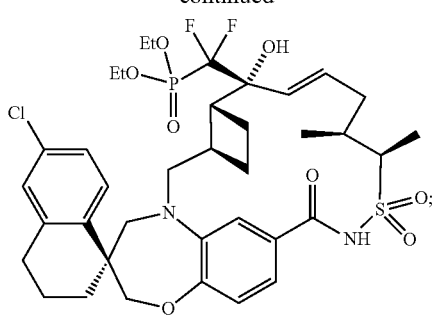
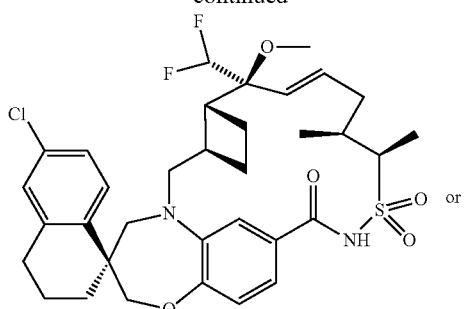
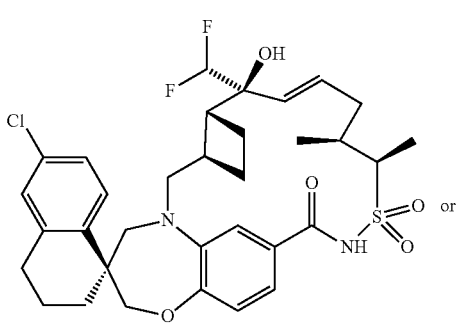
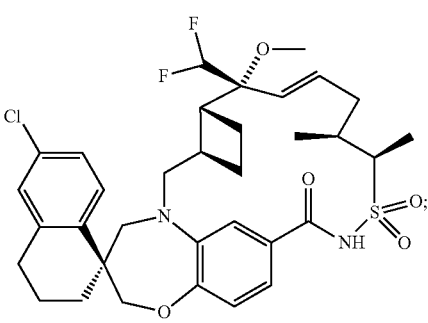
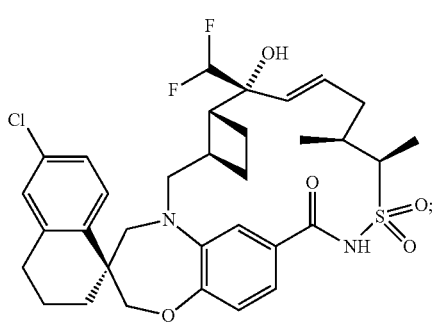
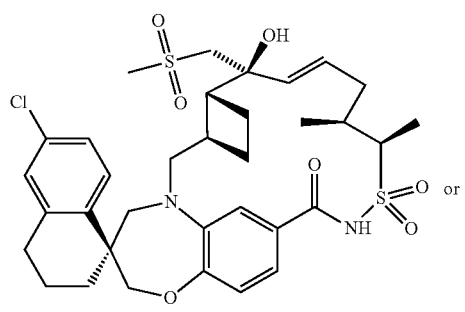
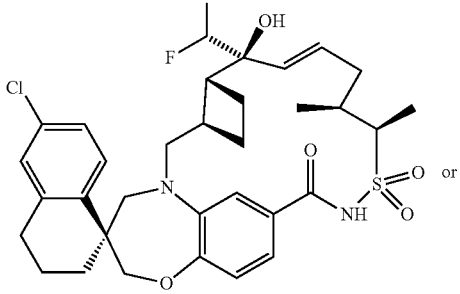
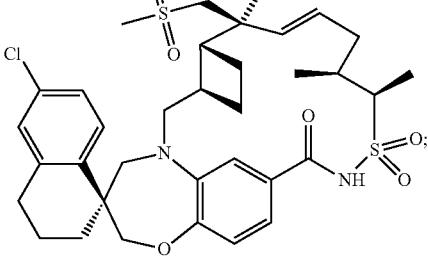
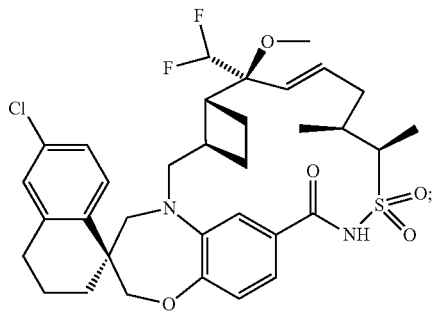
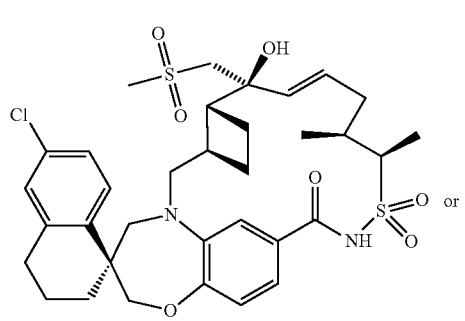

287
-continued
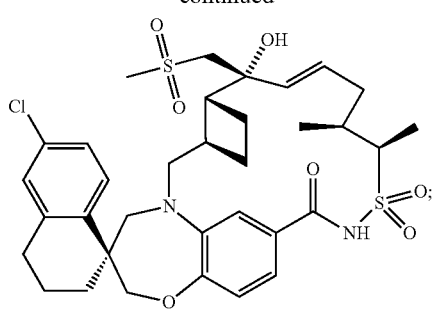
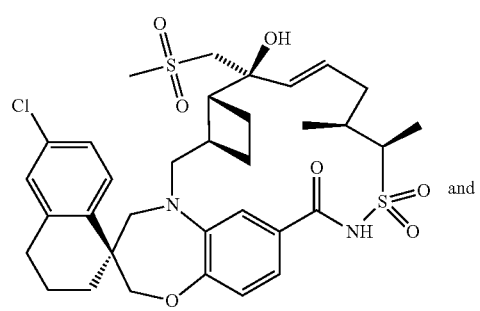
and
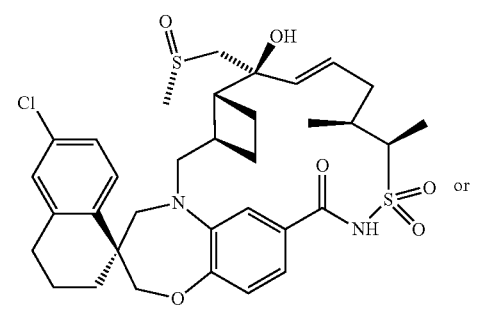
or
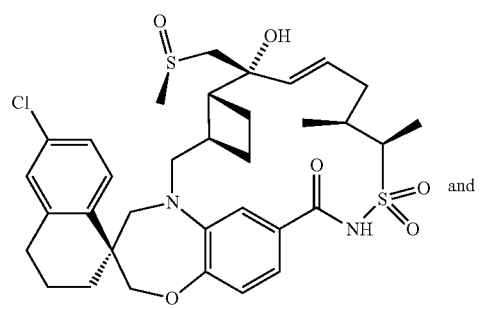
and
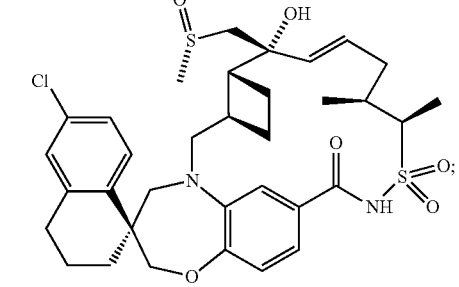
;
288
-continued
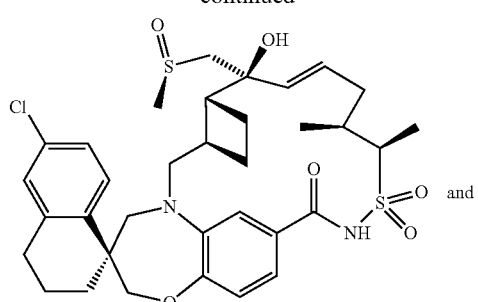
and
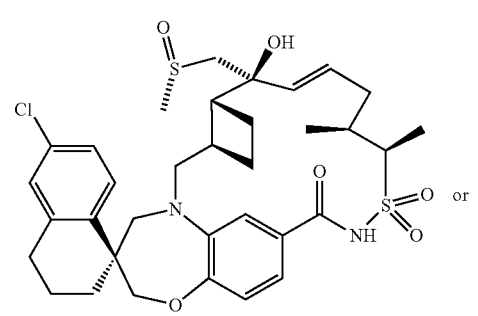
or
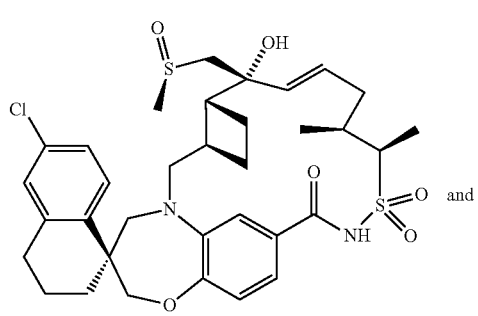
and
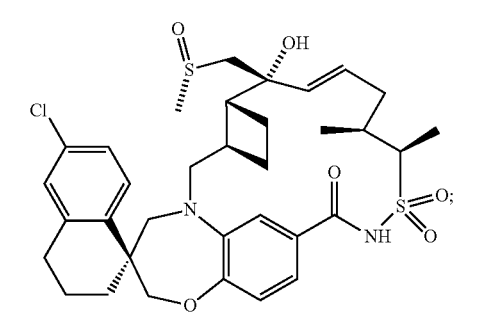
;
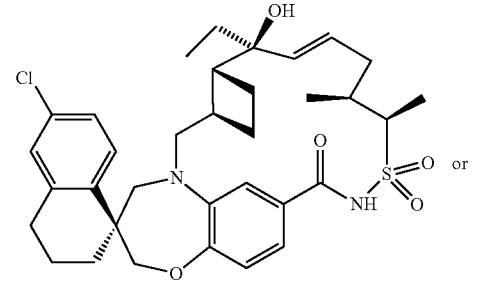
or 289
-continued
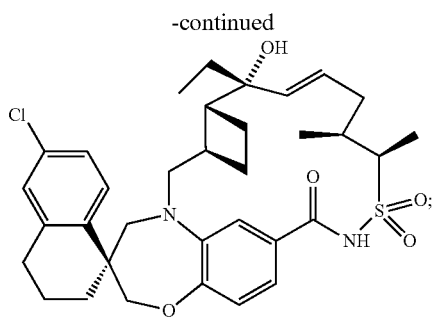
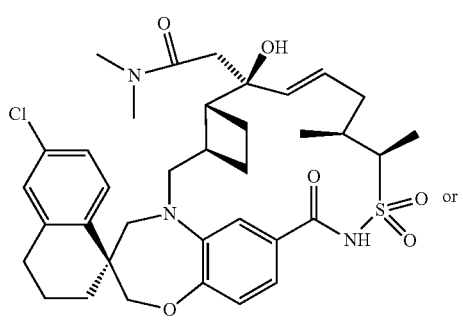
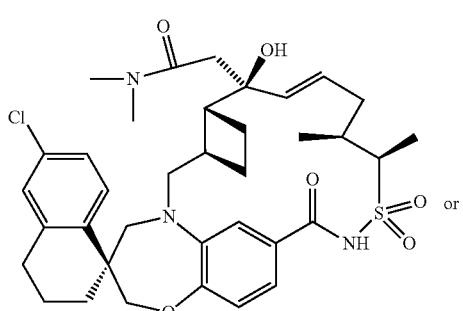
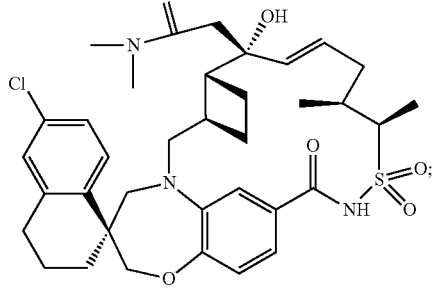
290
-continued
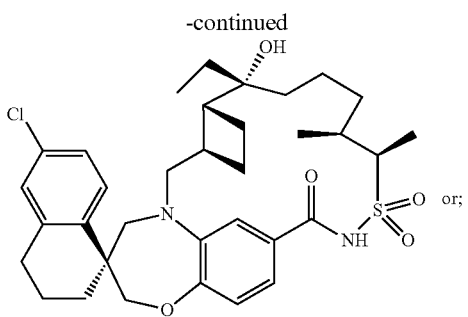
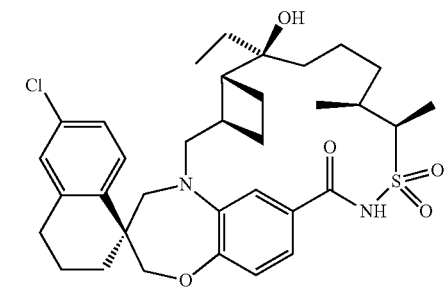
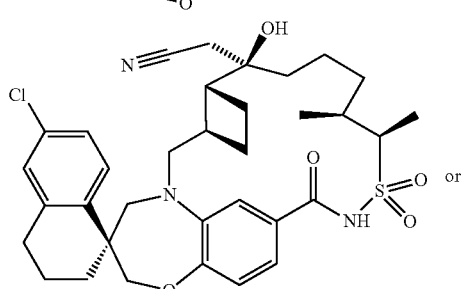
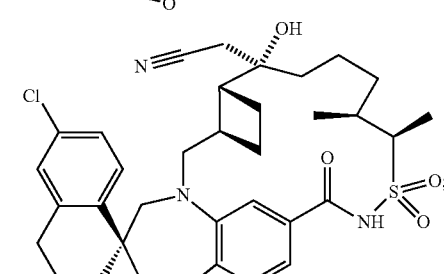
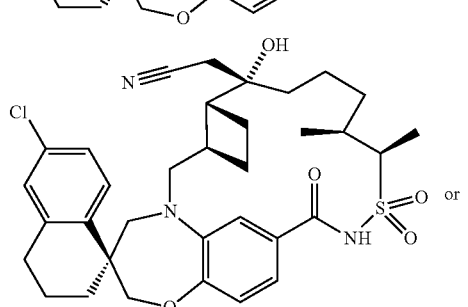
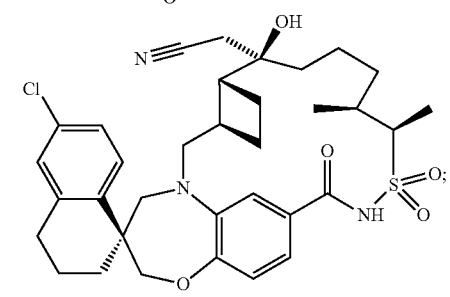

291
-continued
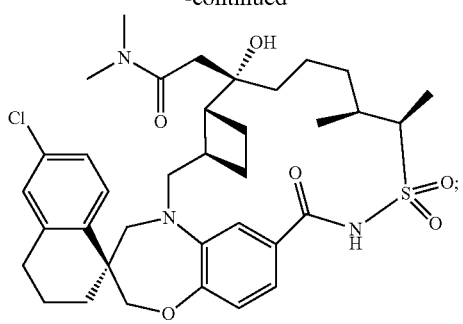
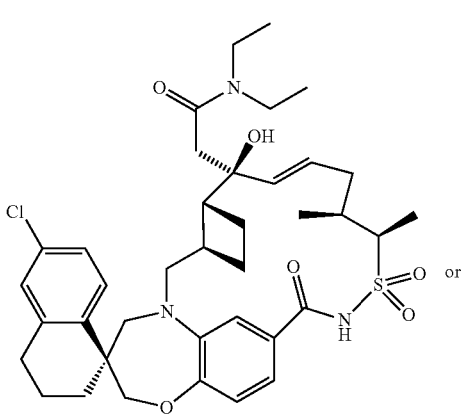
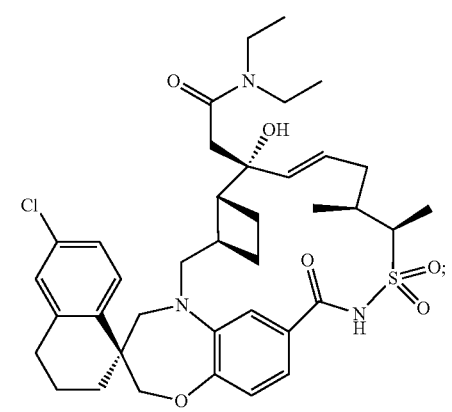
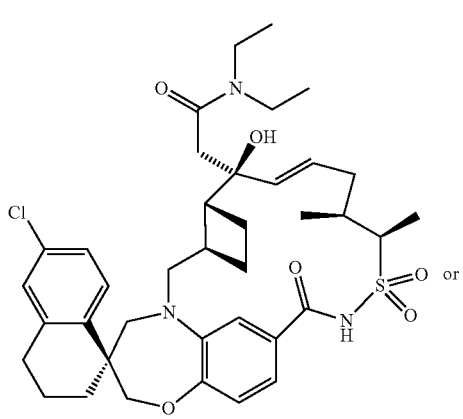
292
-continued
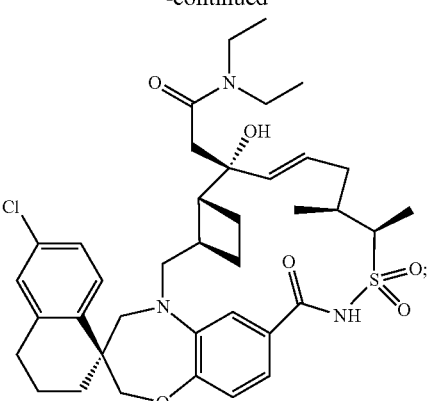
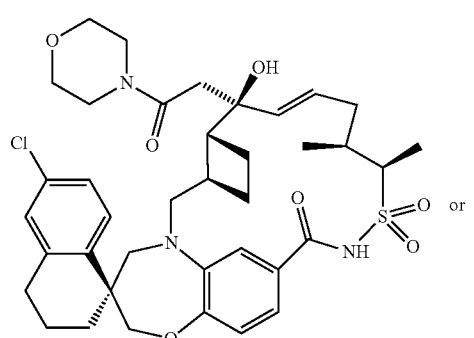
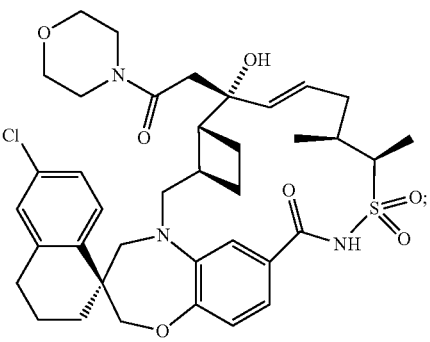
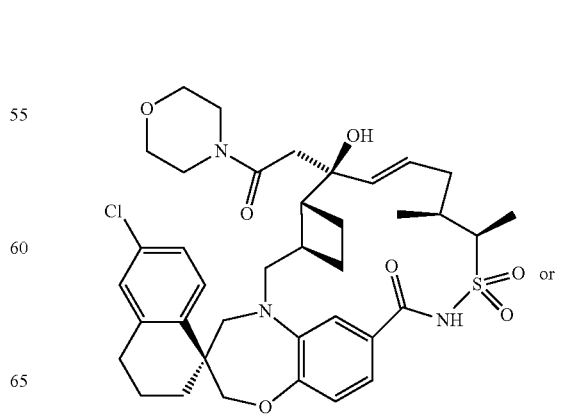

293
-continued
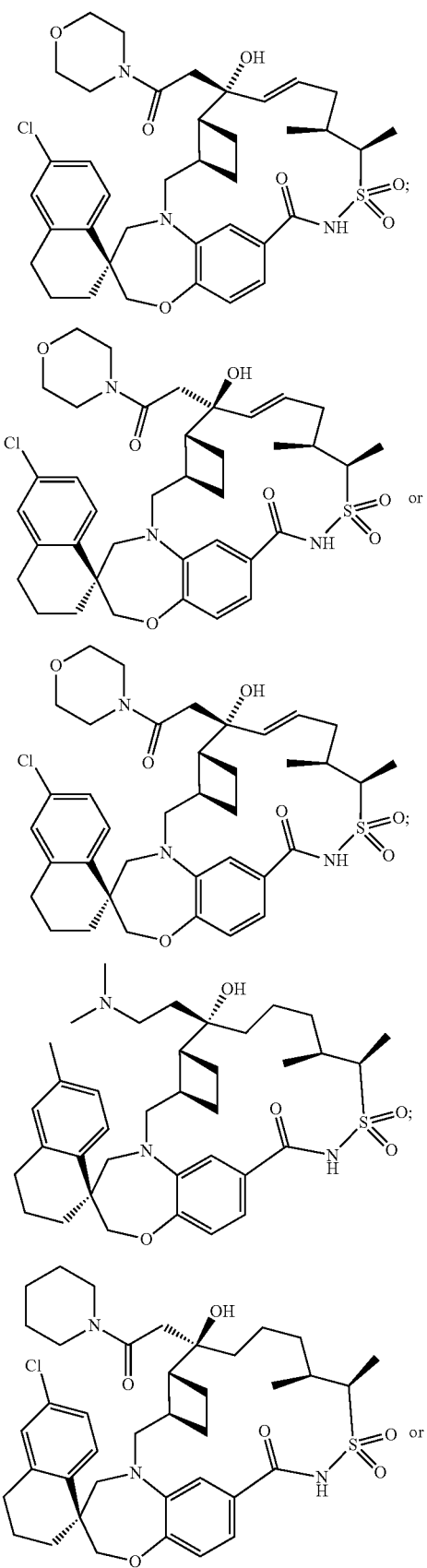
294
-continued
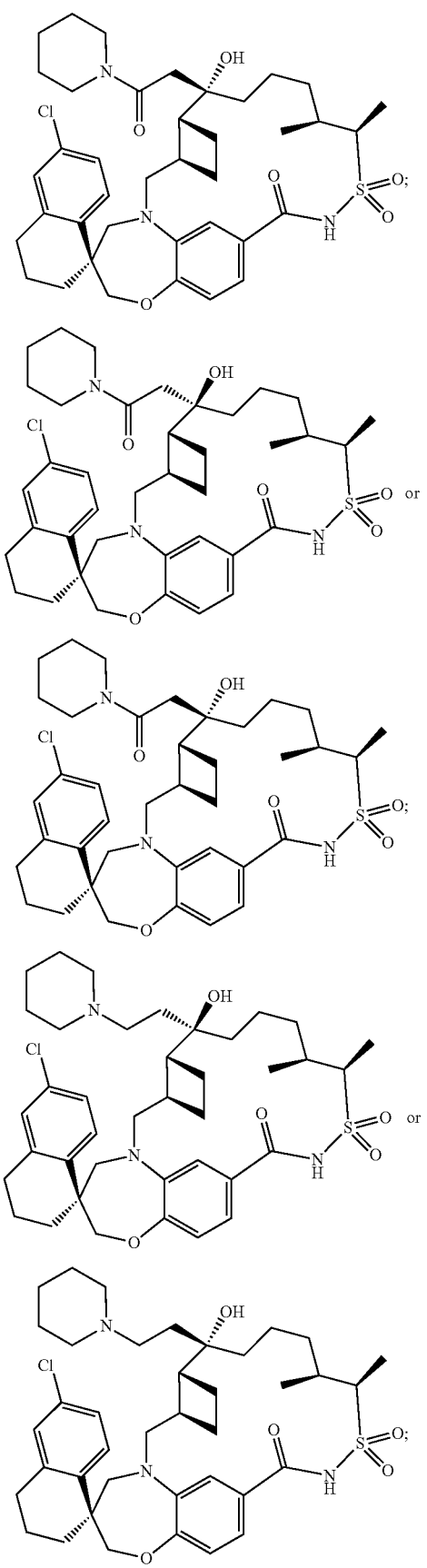

295
-continued
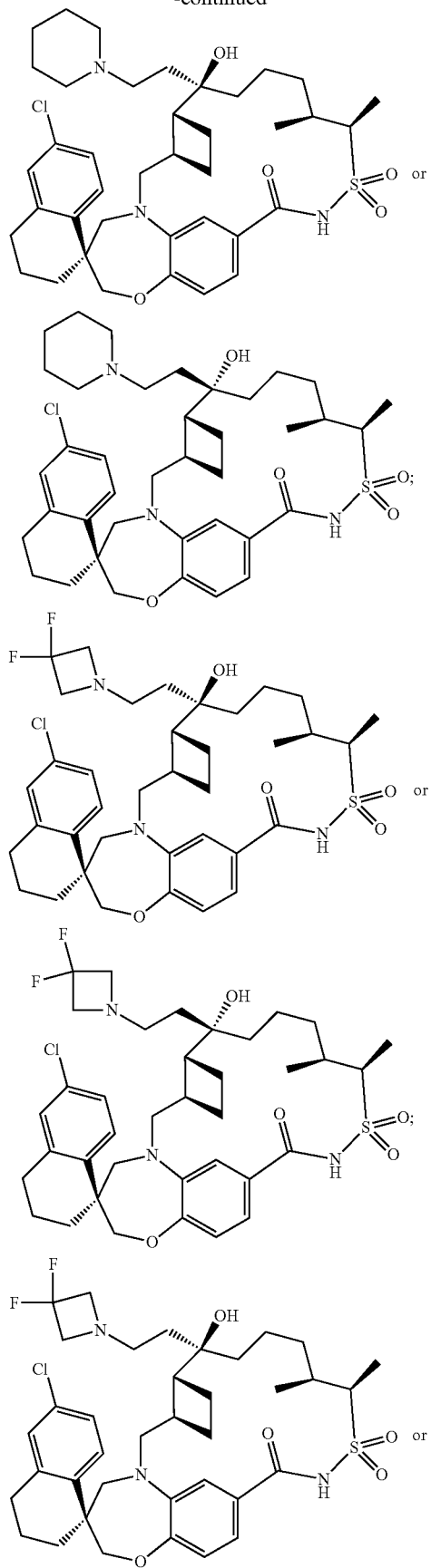
296
-continued
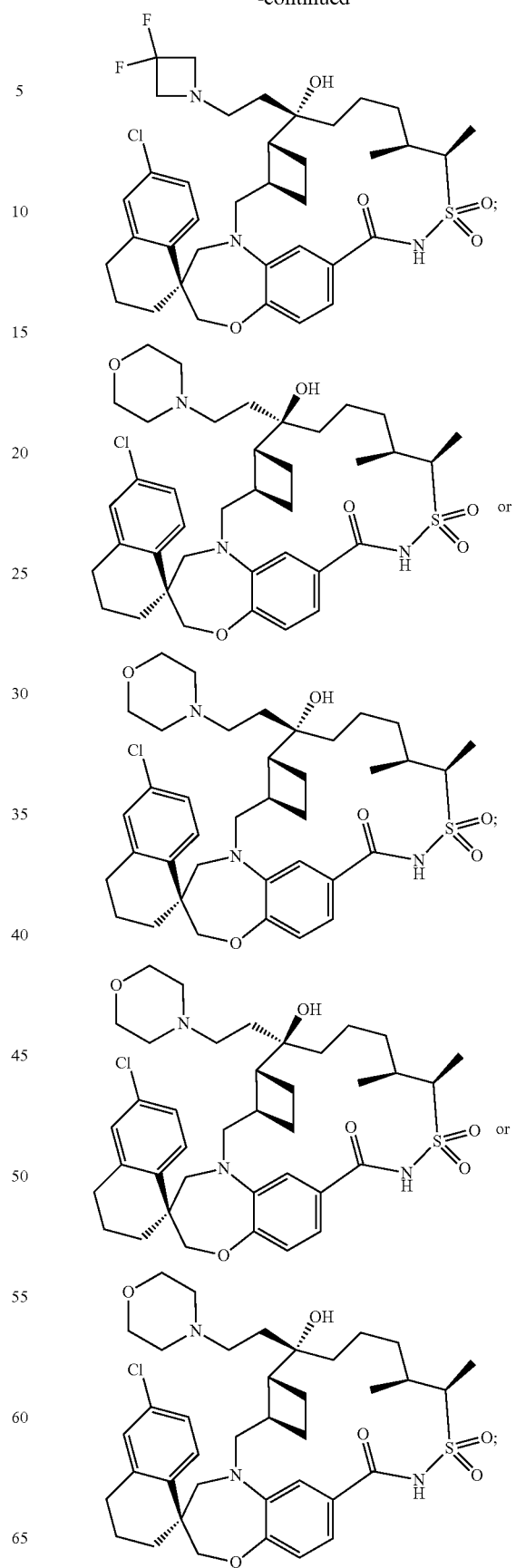

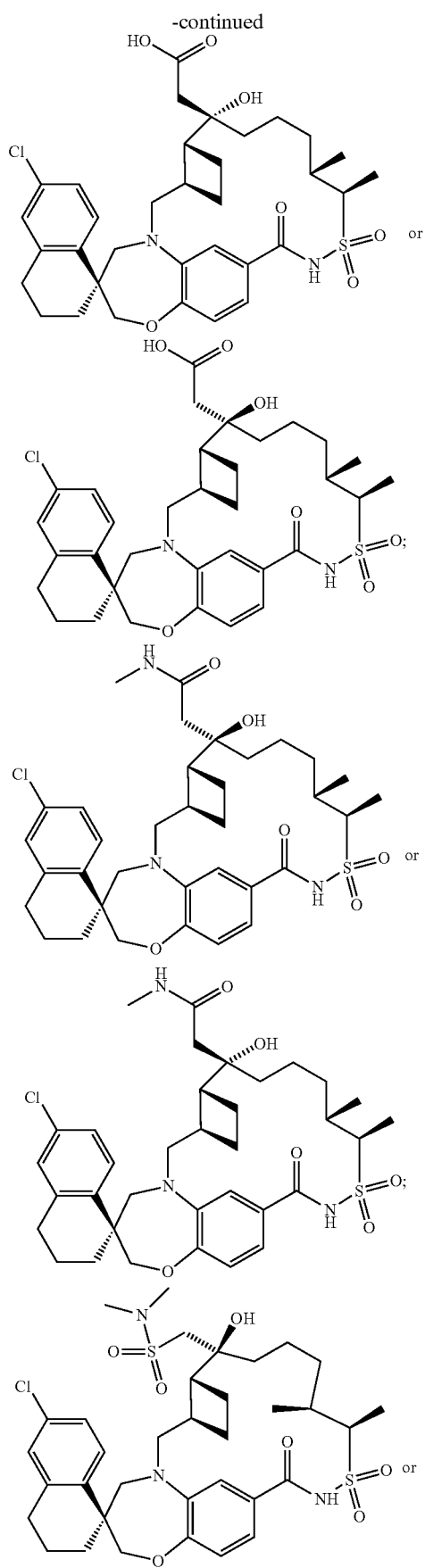
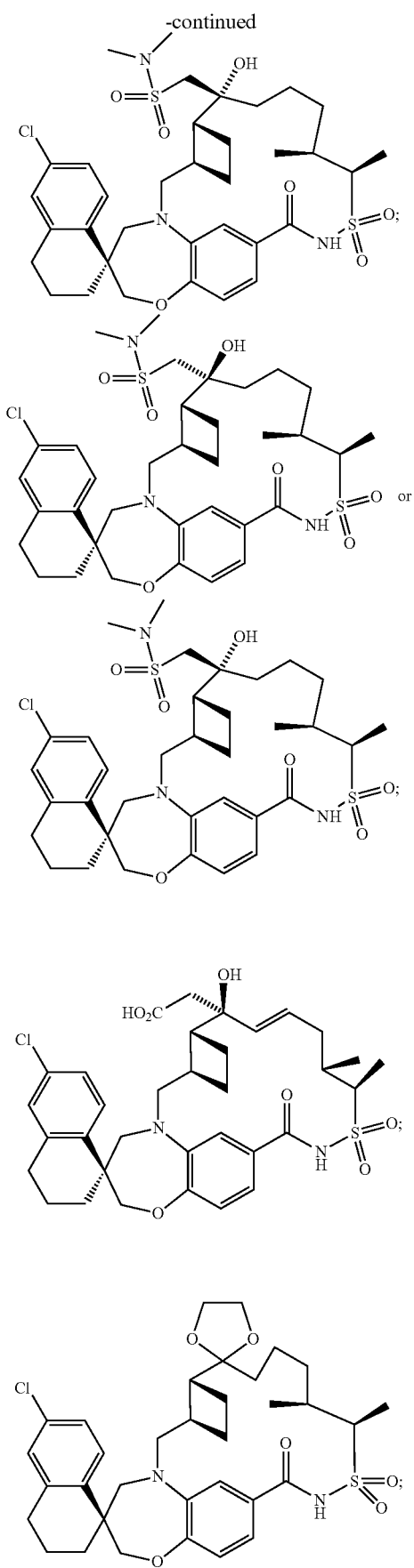

299
-continued
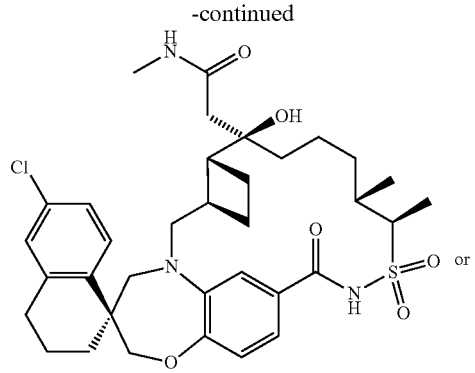
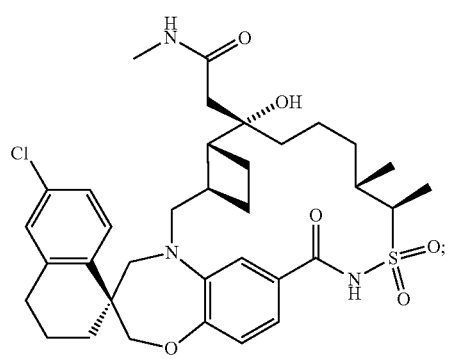
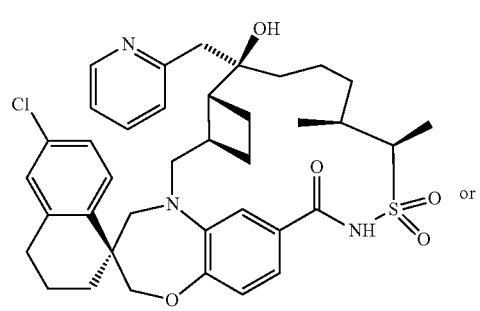
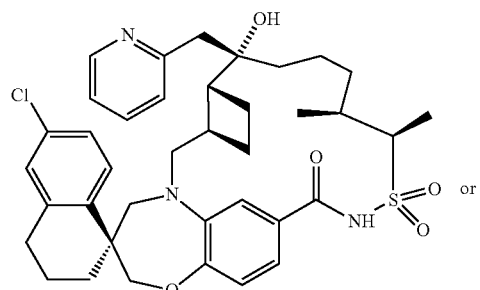
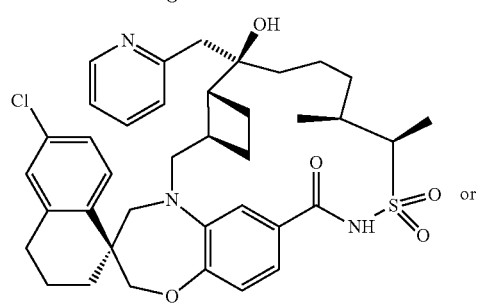
300
-continued
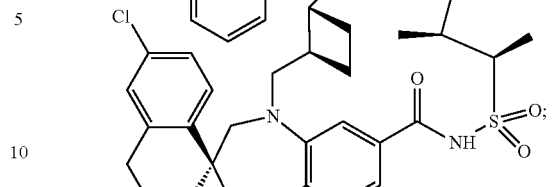
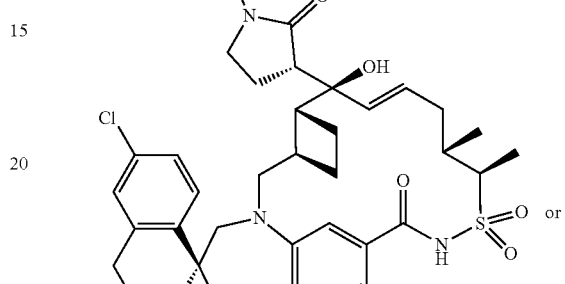
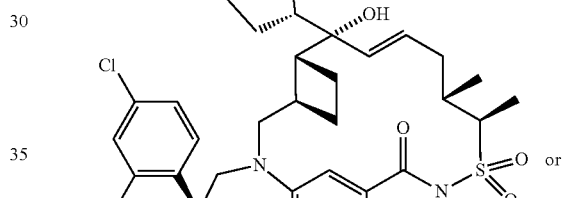
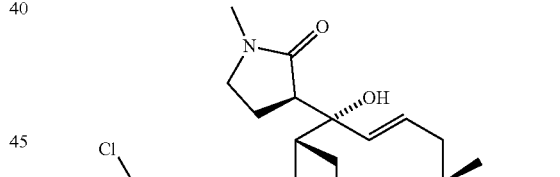
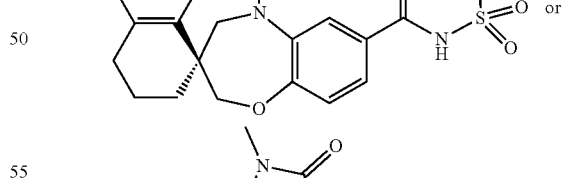
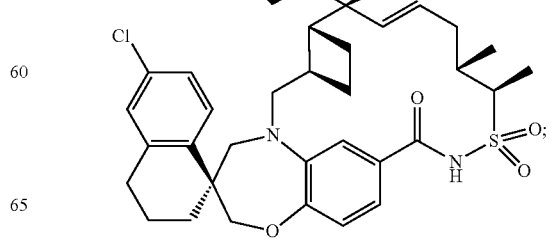

301
-continued
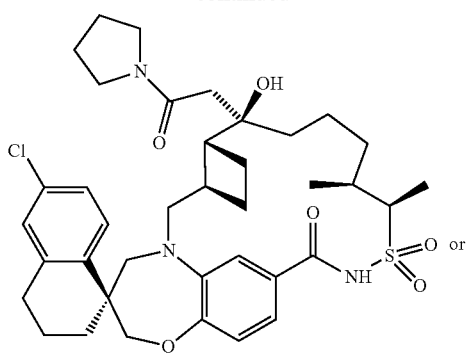
or
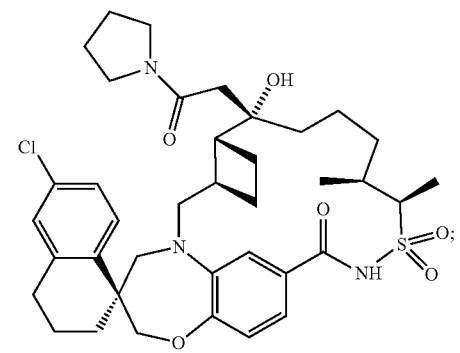
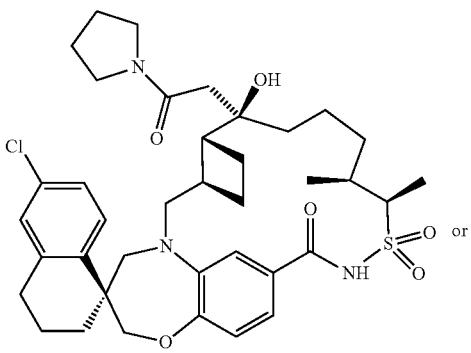
or
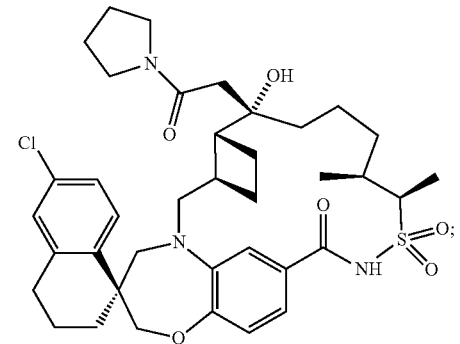
302
-continued
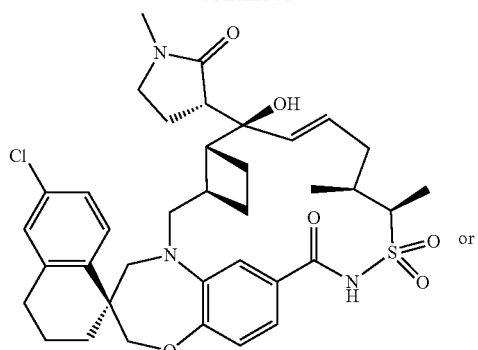
or
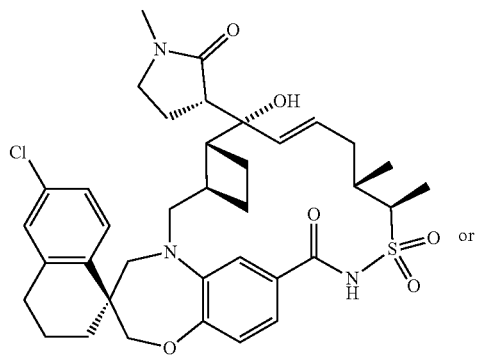
or

or
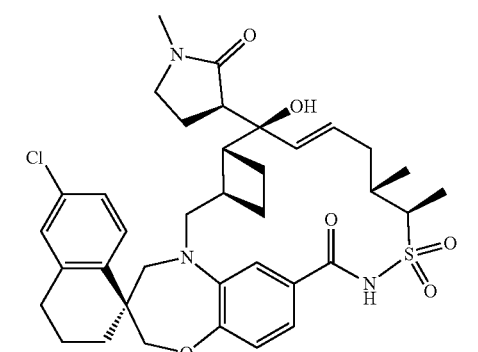

303
-continued
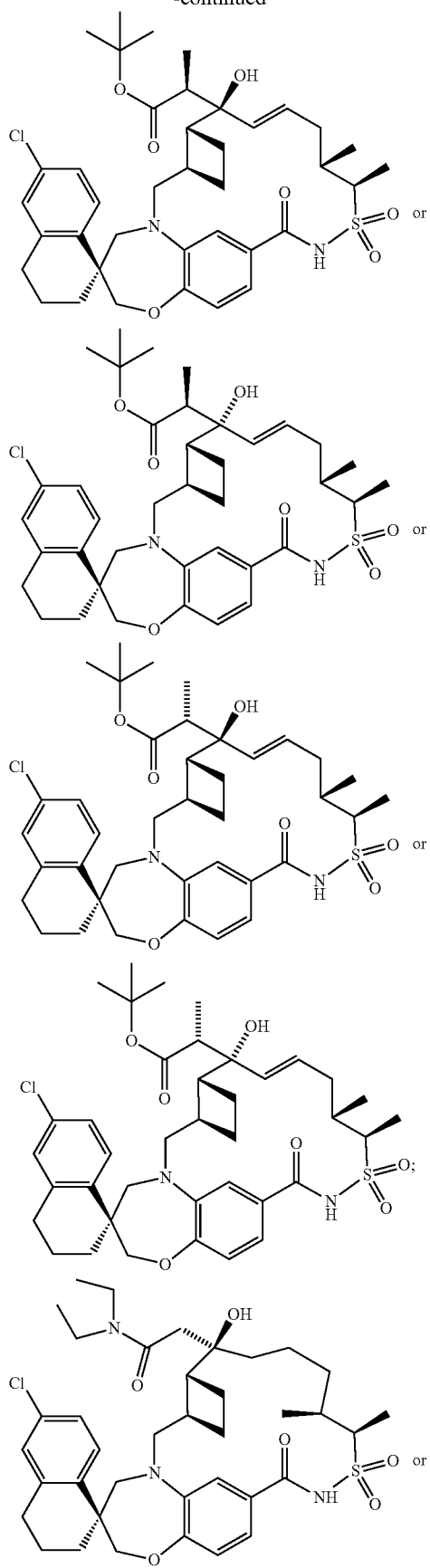
304
-continued
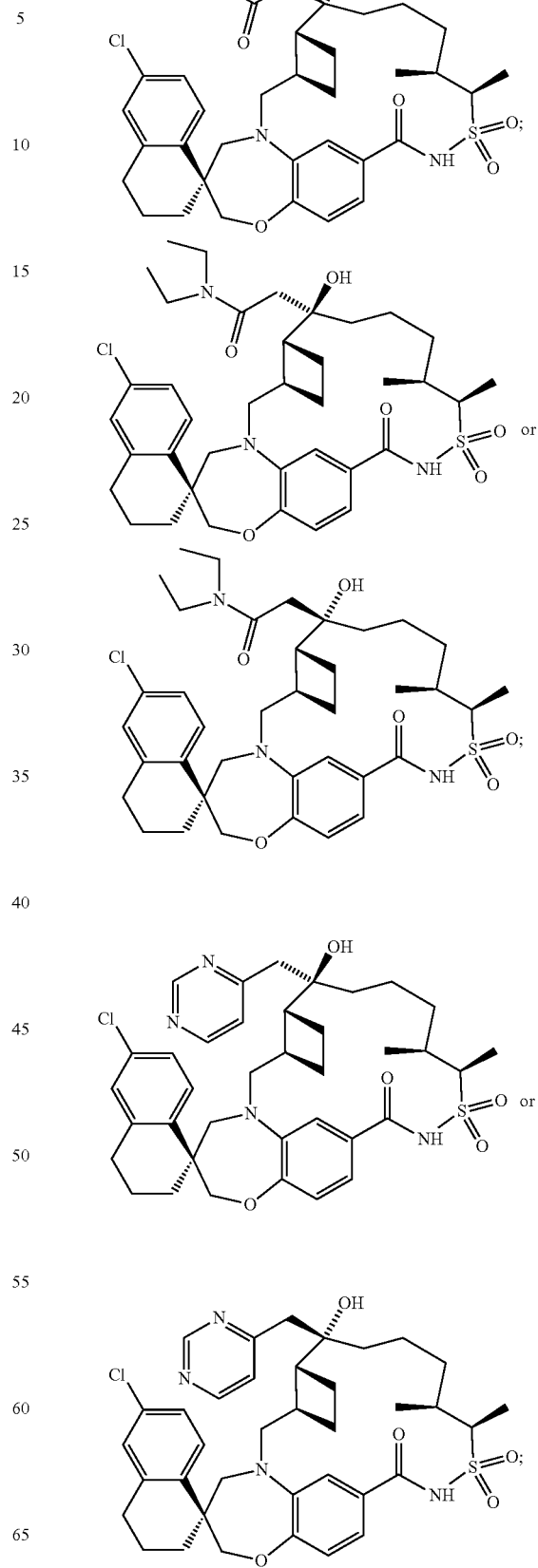

305
-continued
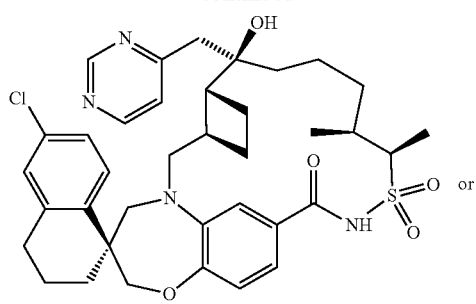
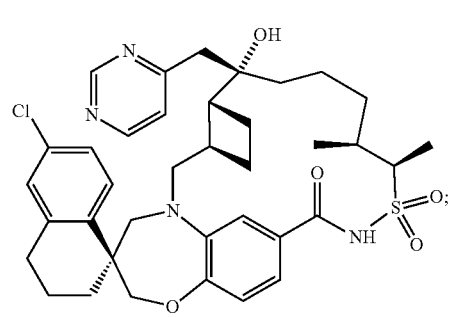

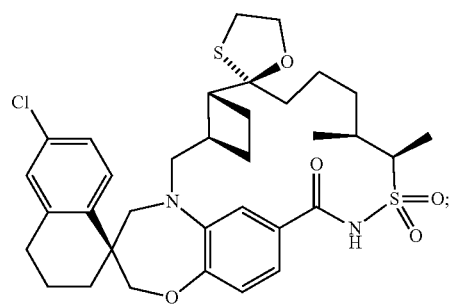
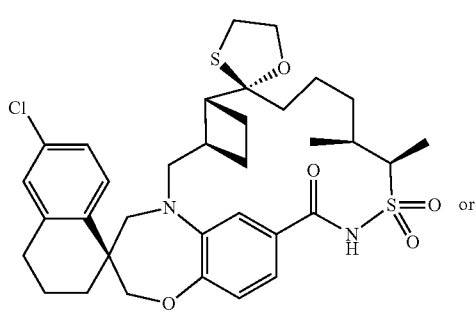
306
-continued
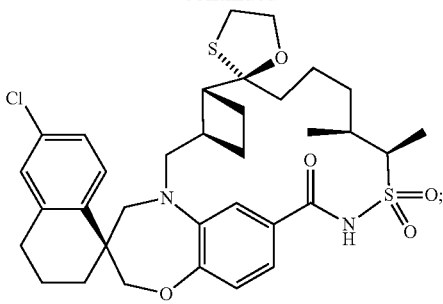
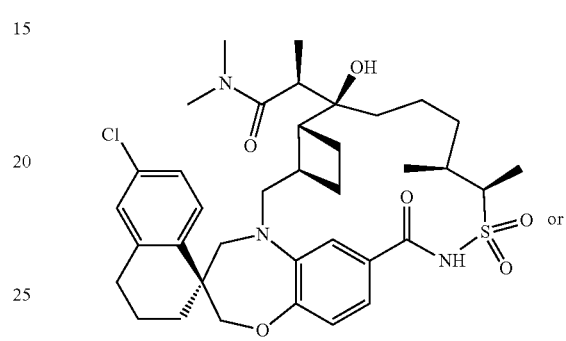
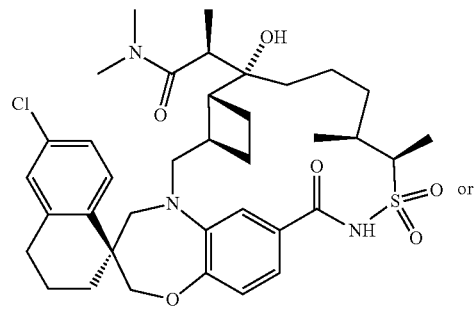
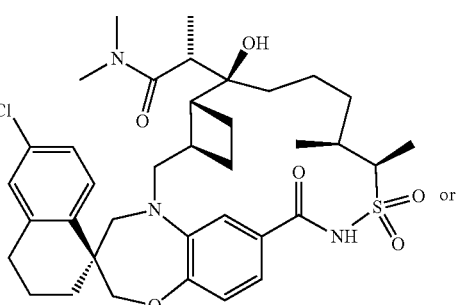
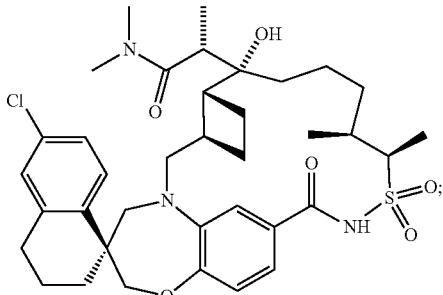

307
-continued
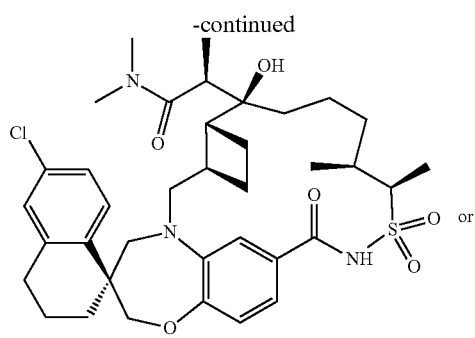
or
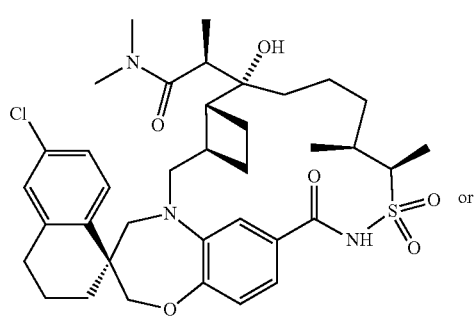
or
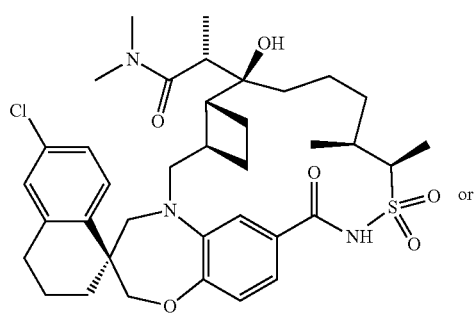
or
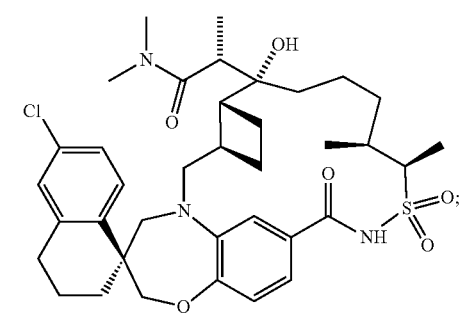
or
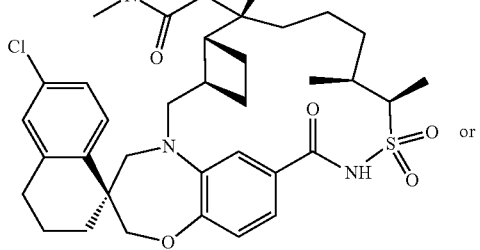
or
308
-continued
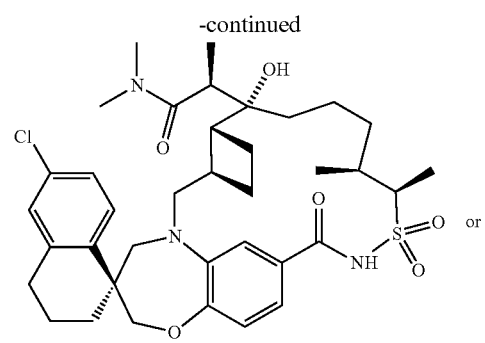
or
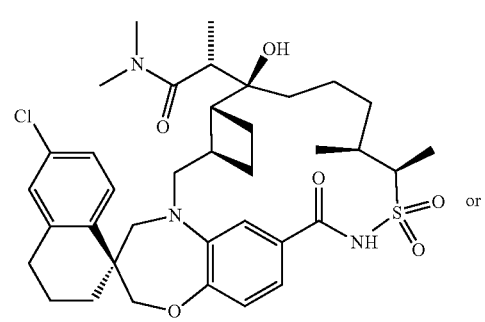
or
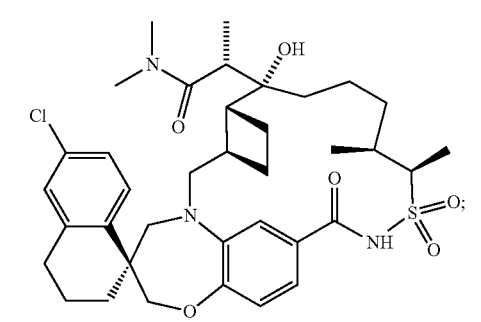
;
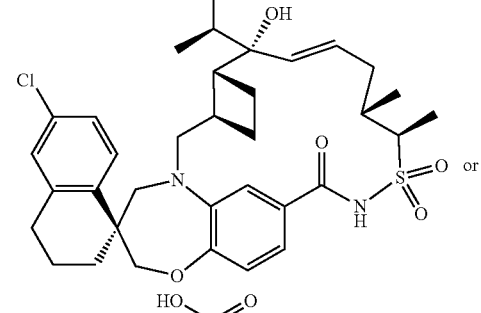
or
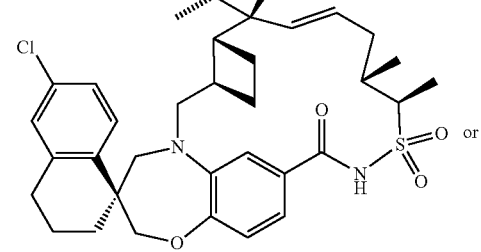
or

309
-continued
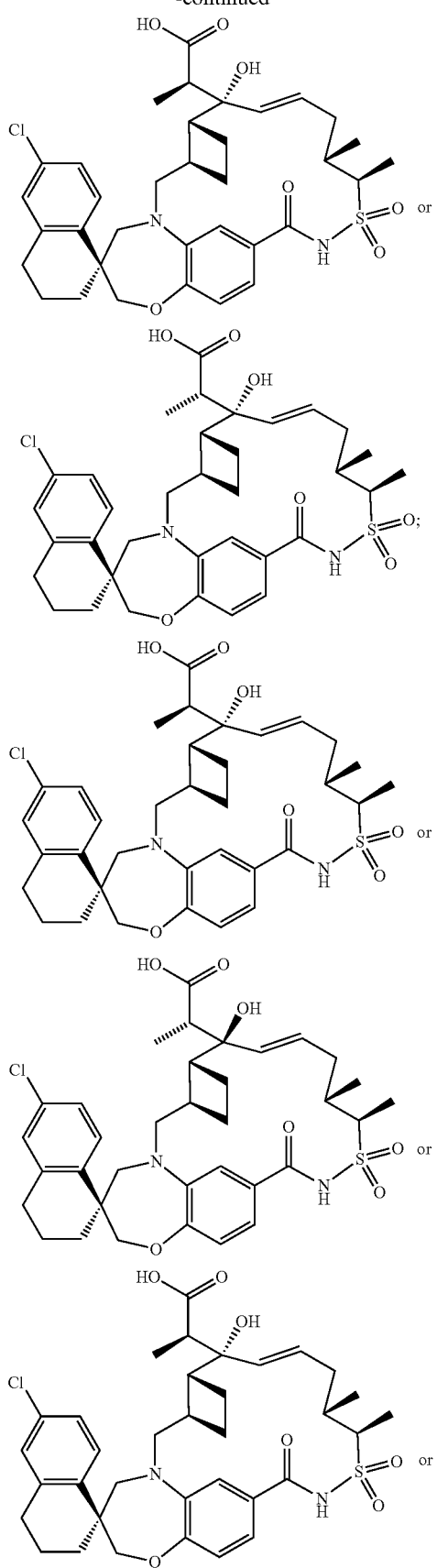
310
-continued
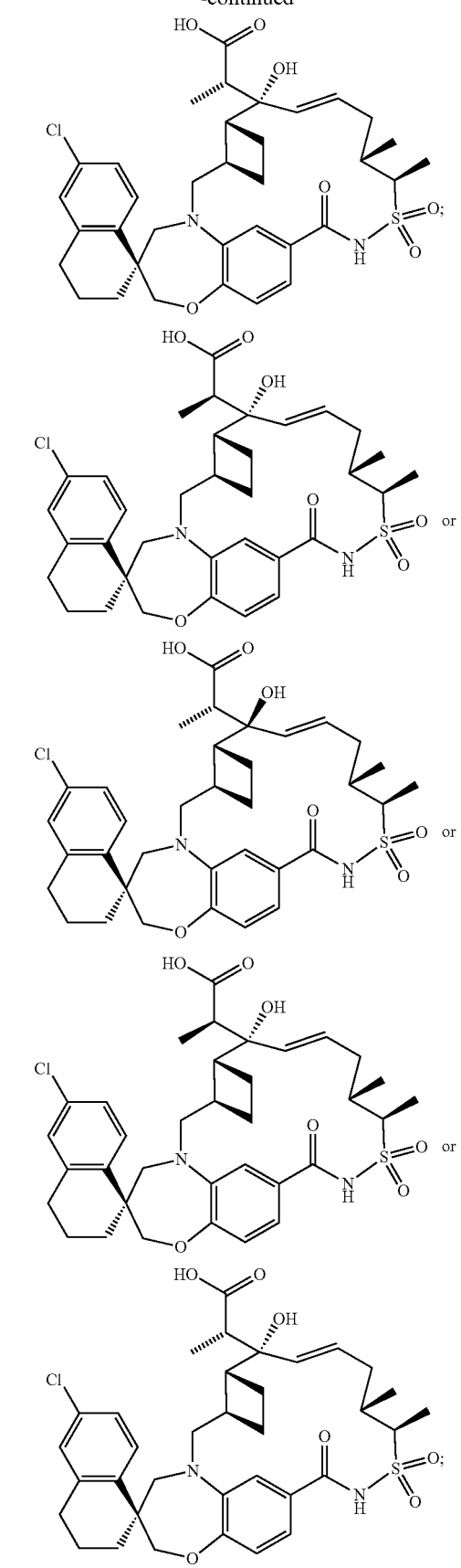

311
-continued
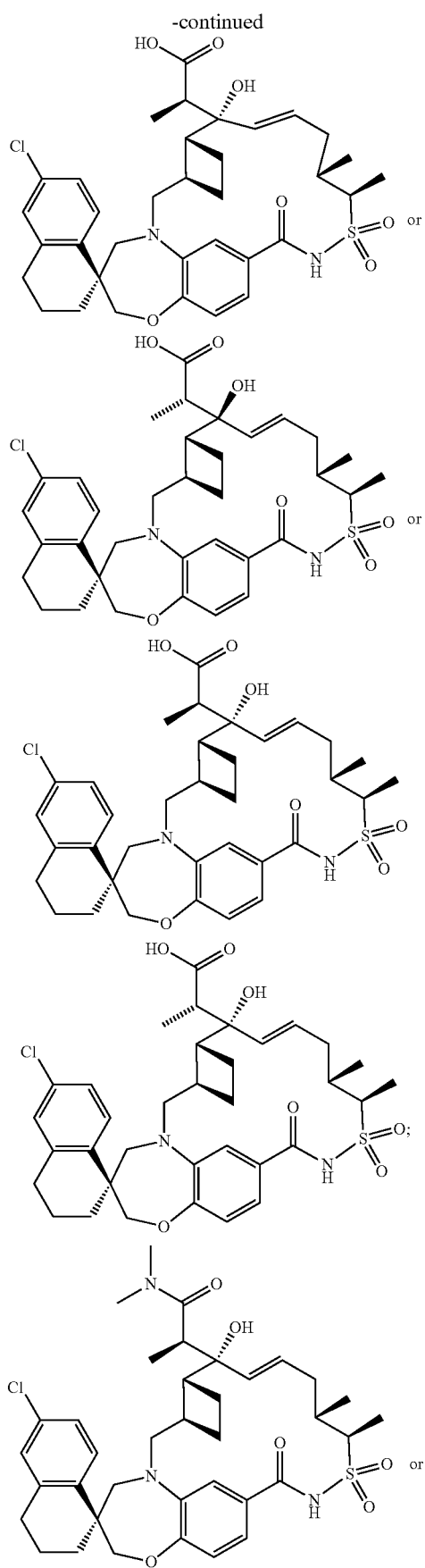
312
-continued
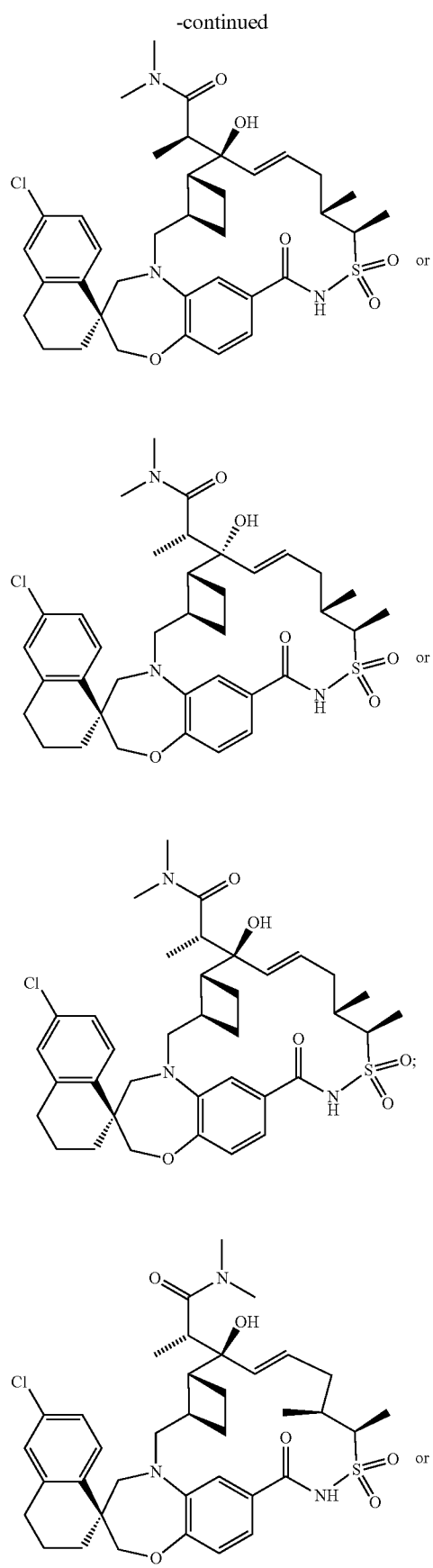

313
-continued
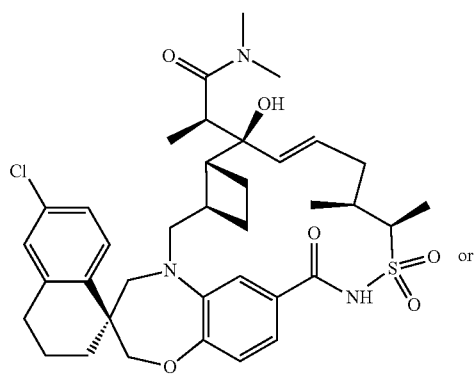
or
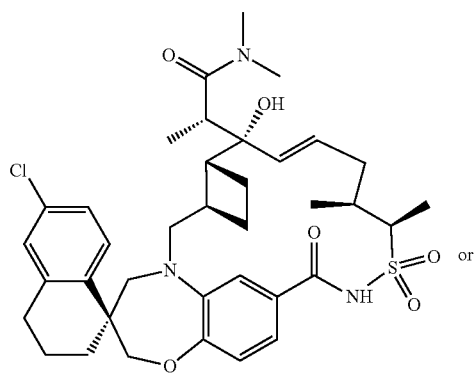
or
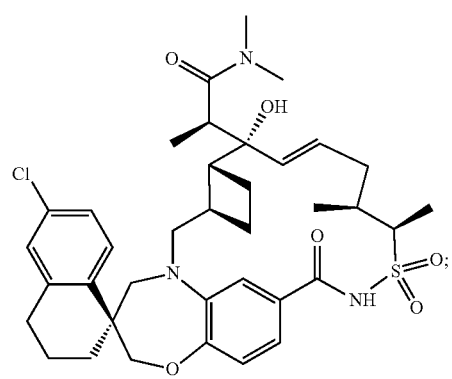
or
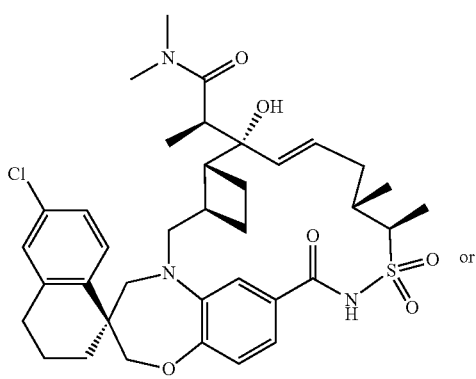
or
314
-continued
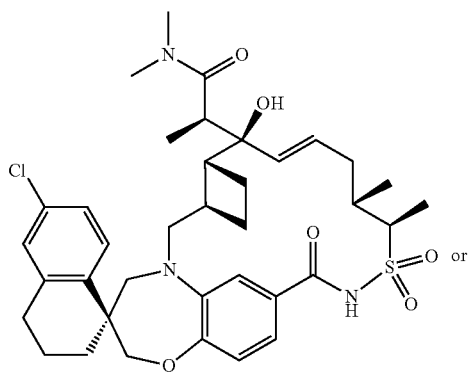
or
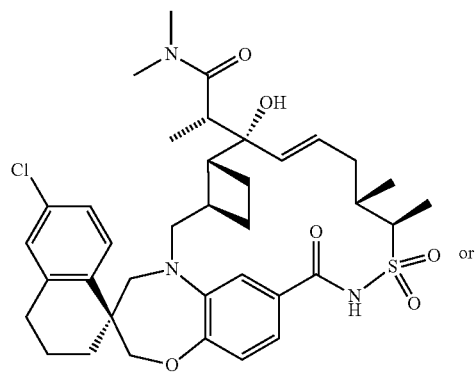
or
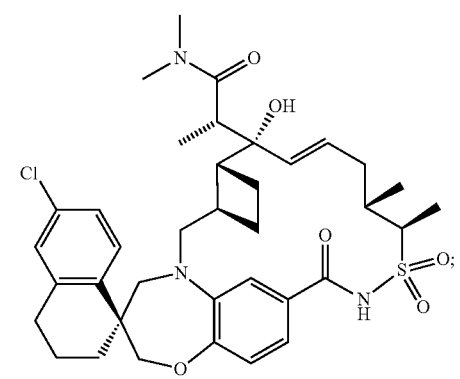
;
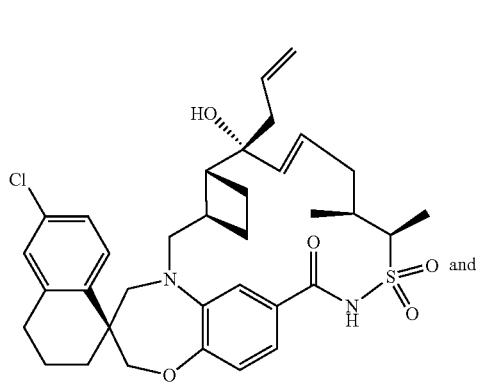
and

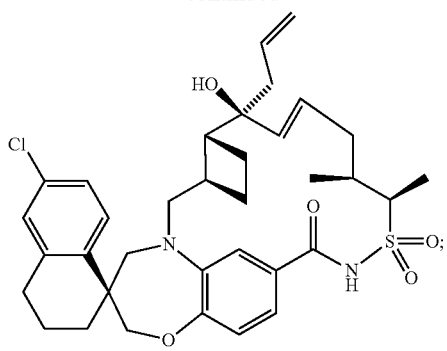
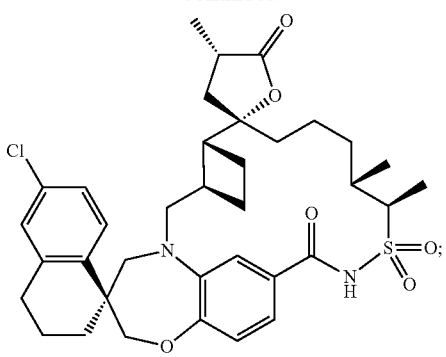
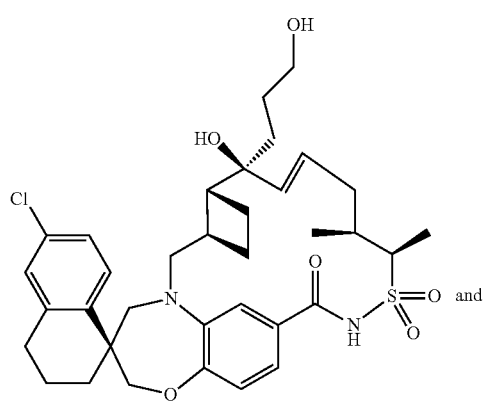
and
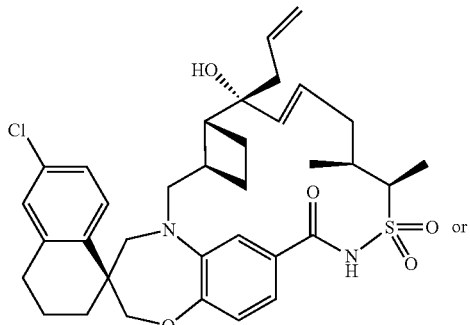
or
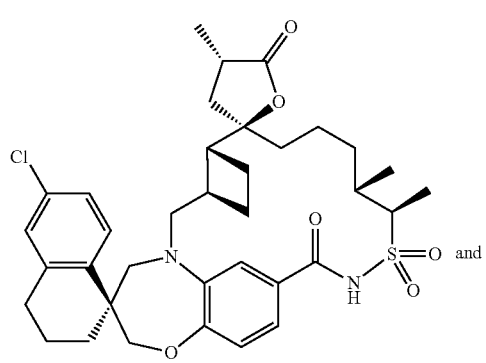
and

317
-continued
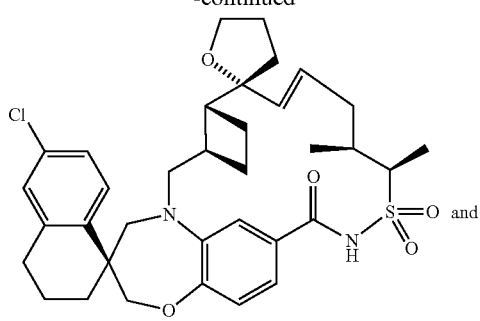 and
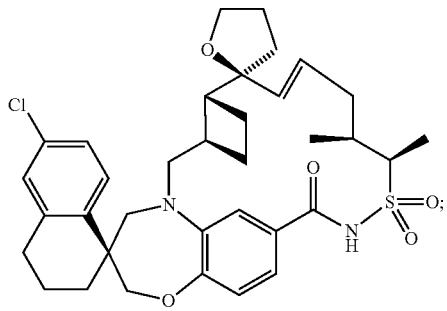;
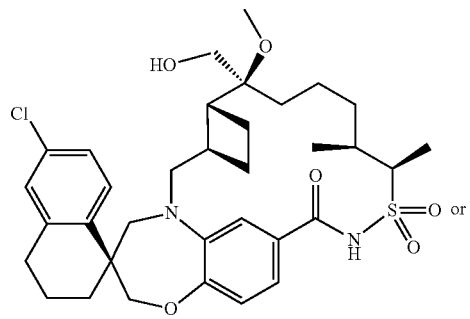 or
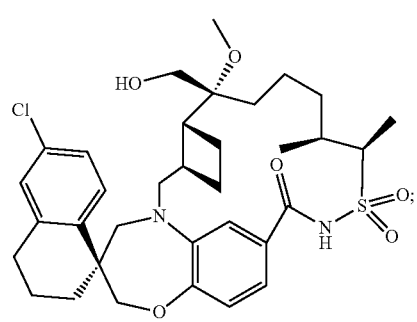;
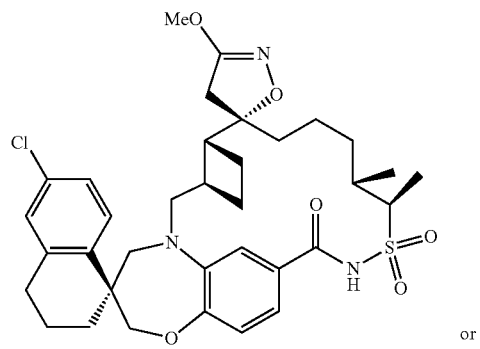 or
318
-continued
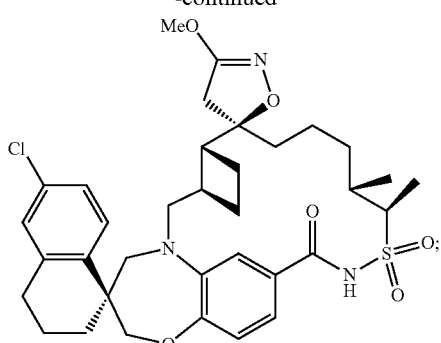;
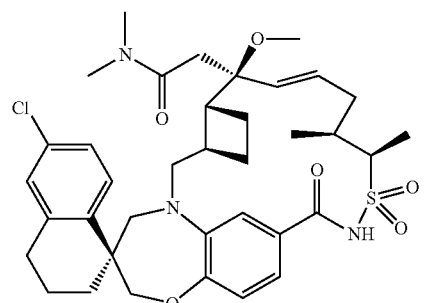 or
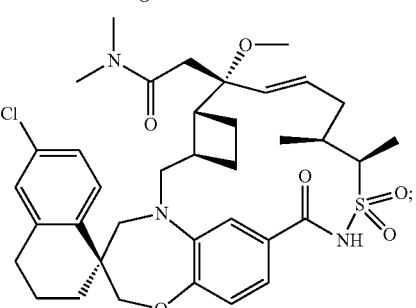
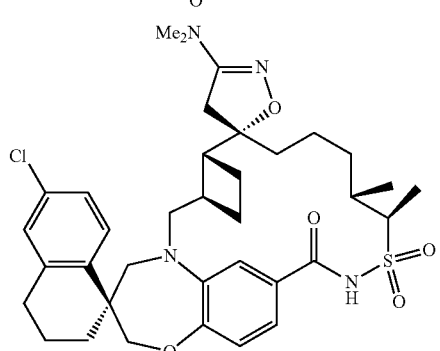 or
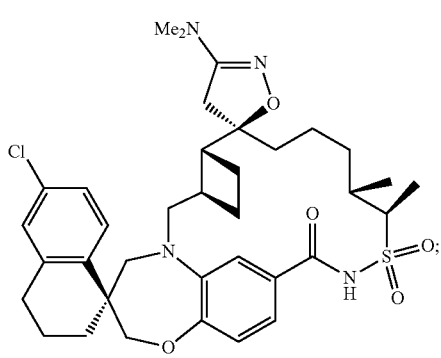;

319
-continued
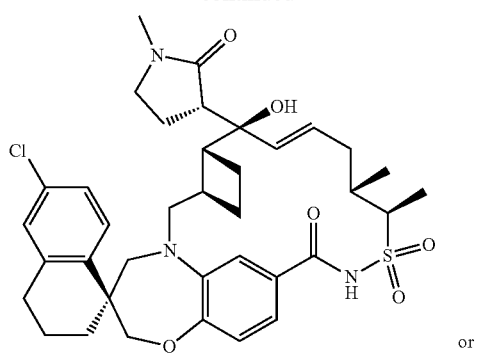
or
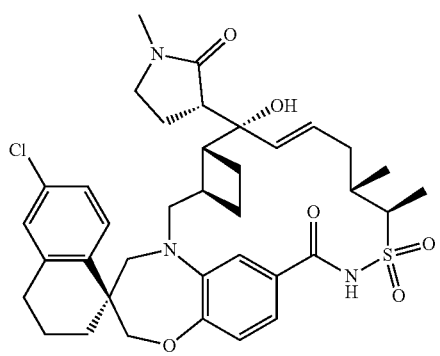
or
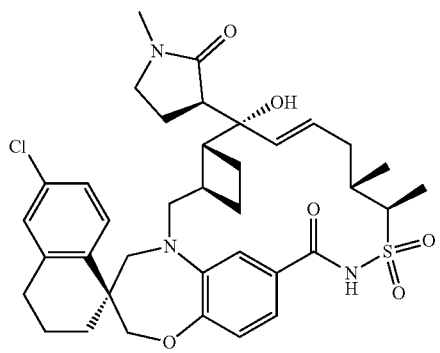
or
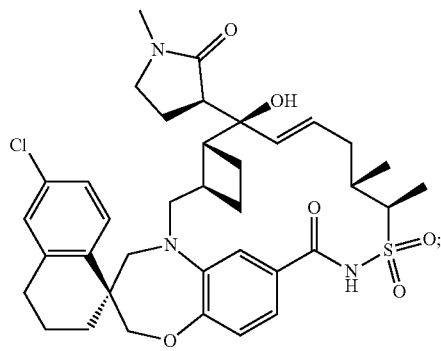
320
-continued
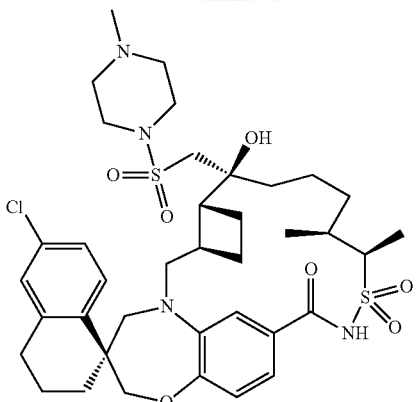
or
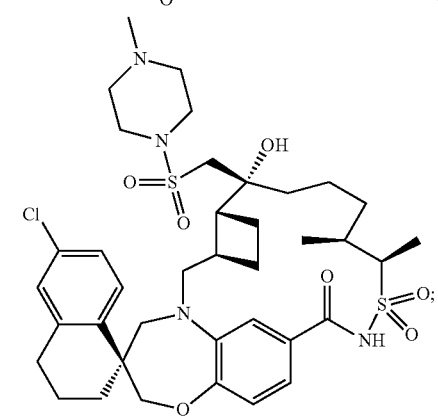
or
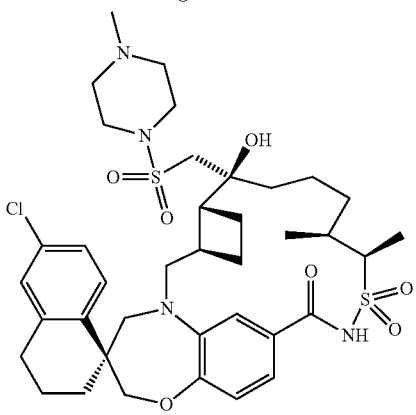
or
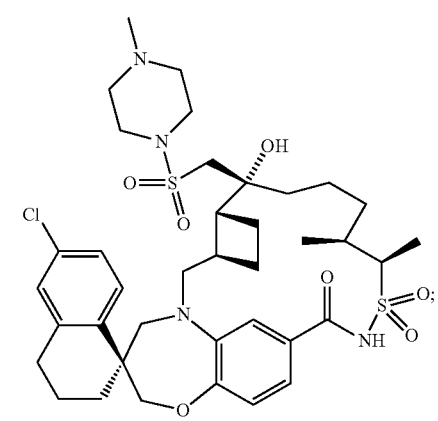

321
-continued
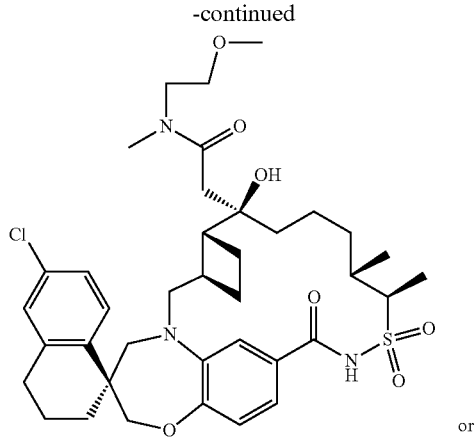
or
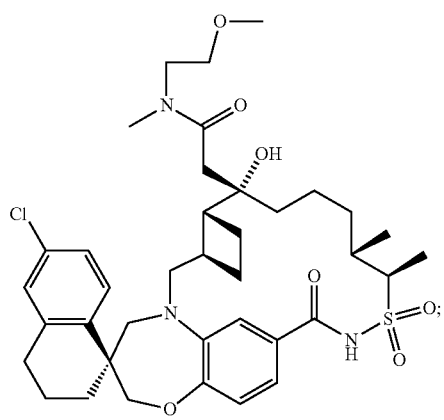
or
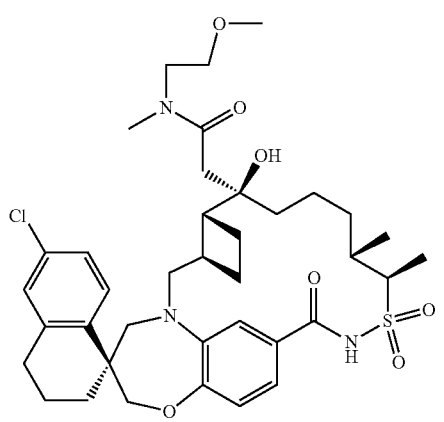
or
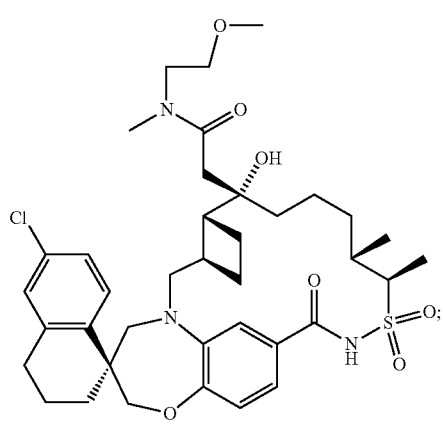
322
-continued
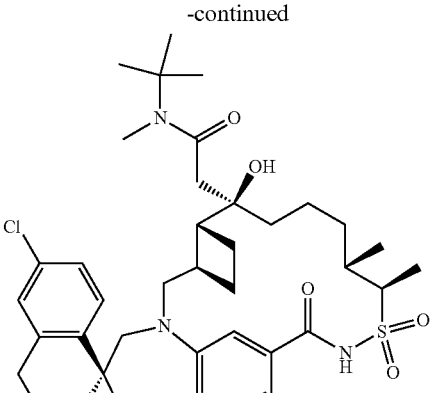
or
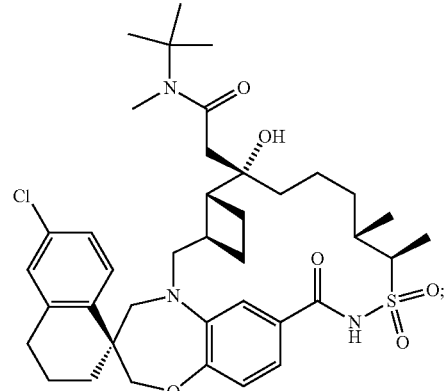
or
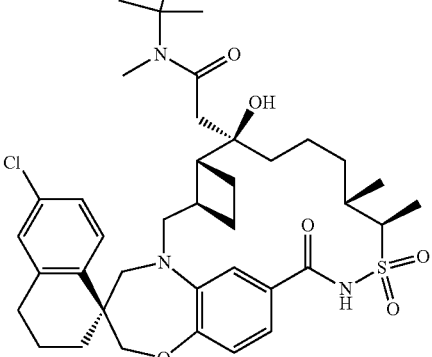
or
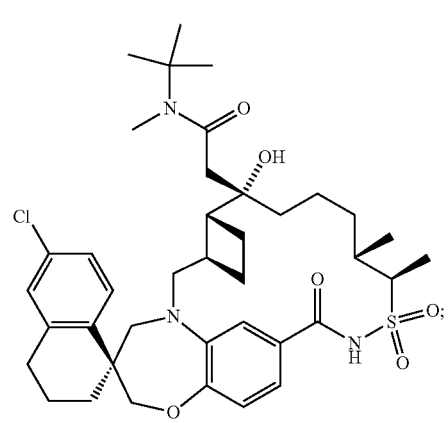

323
-continued
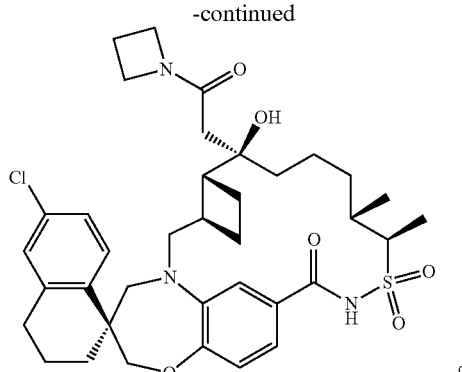
or
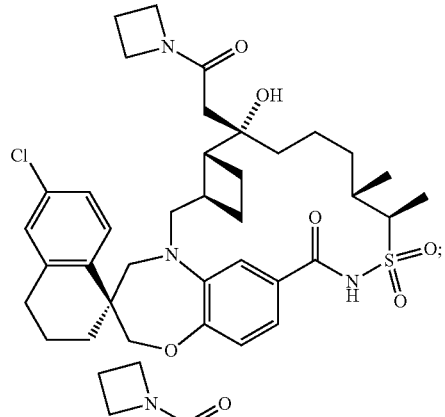
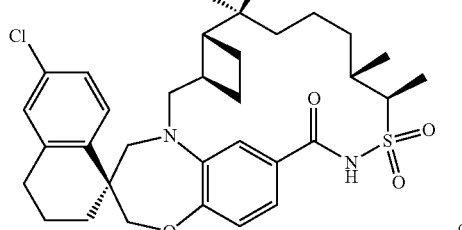
or
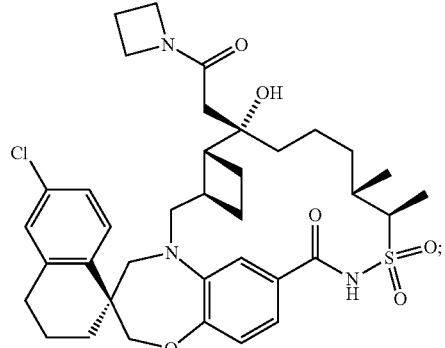
or
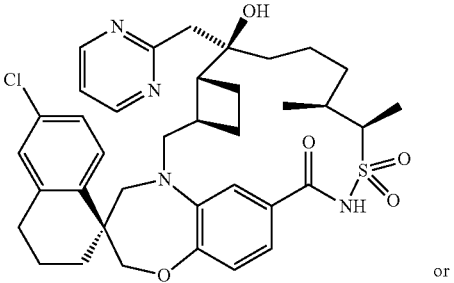
or
324
-continued
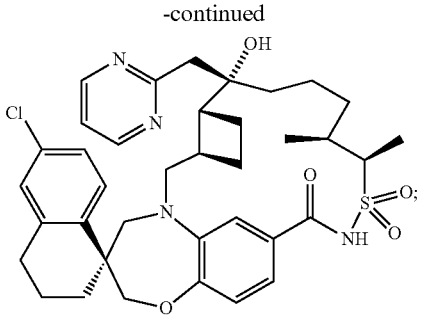
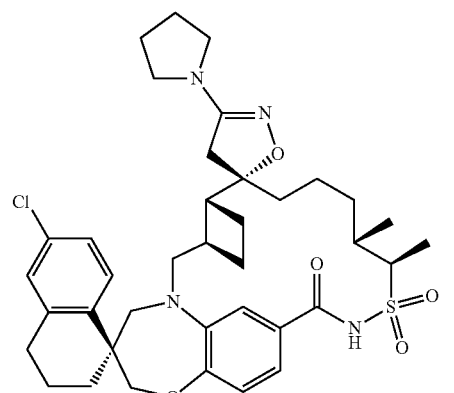
or
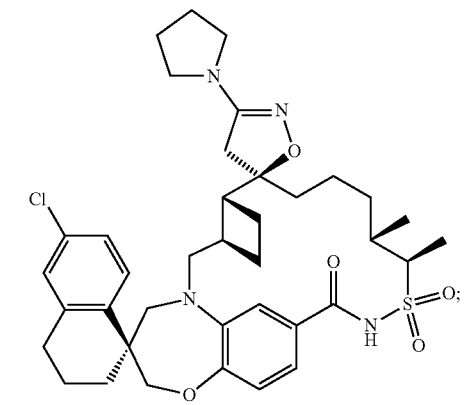
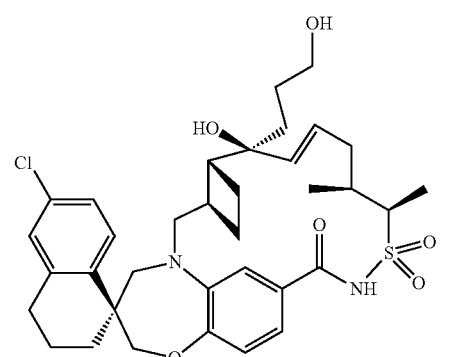
or 325
-continued
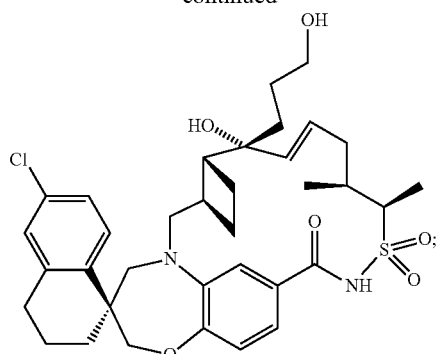
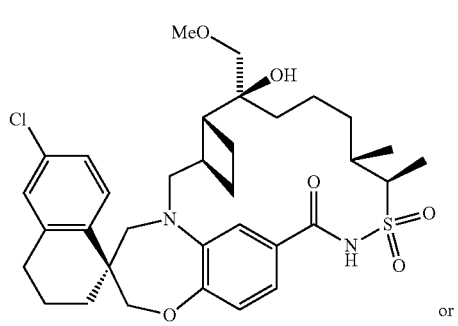
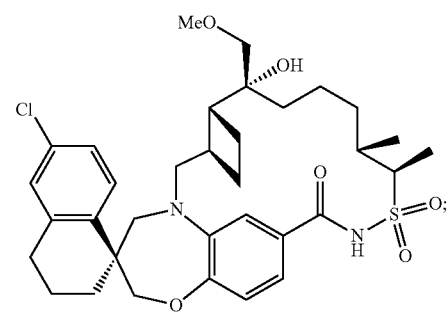
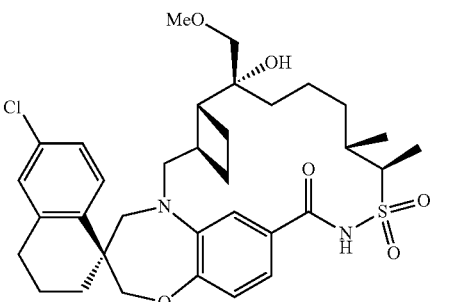
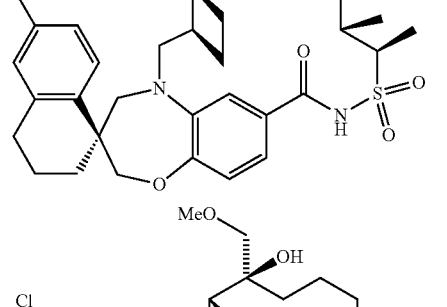
or
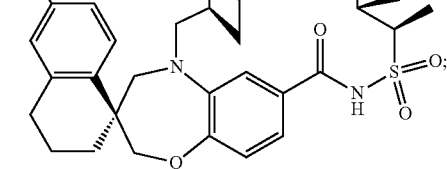
326
-continued
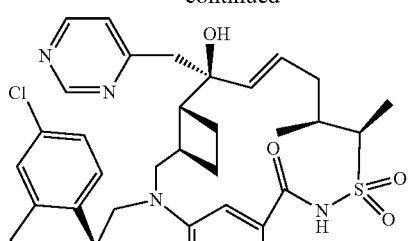
or
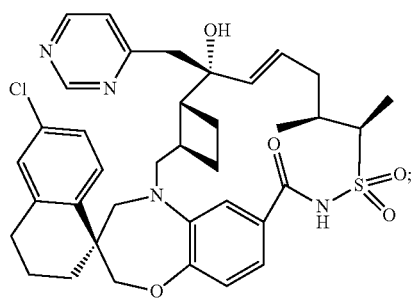
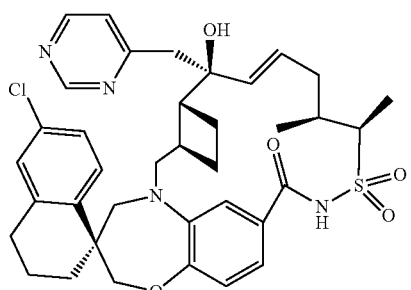
or
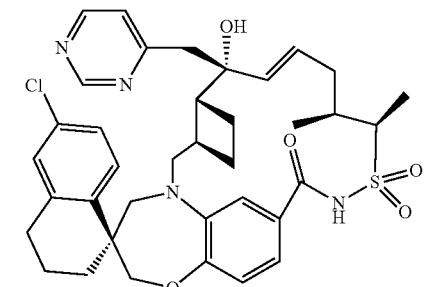
or
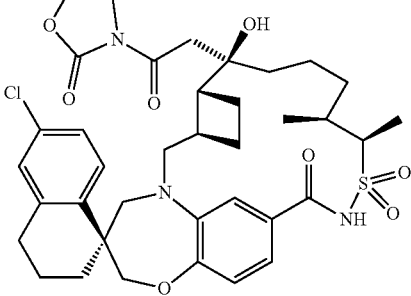
or 327
-continued
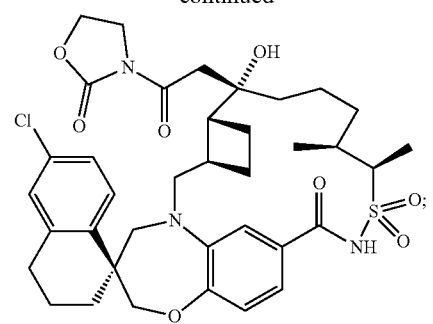
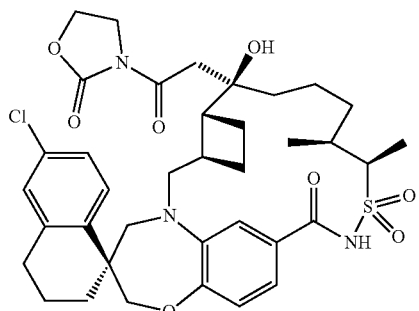
or
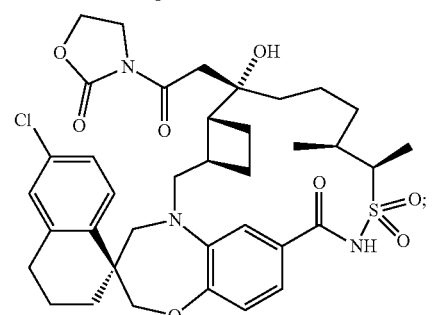
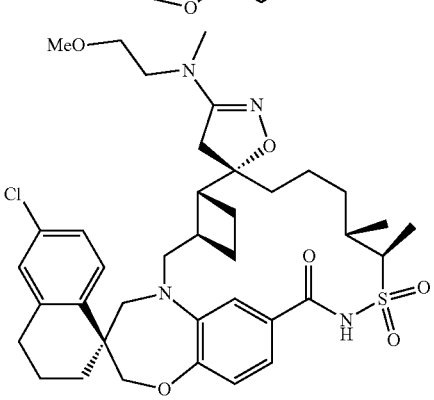
or
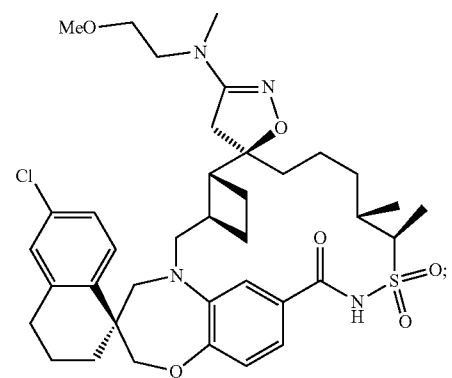
328
-continued
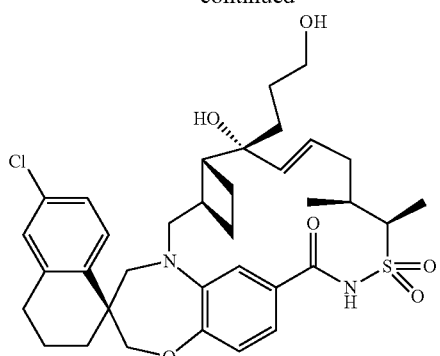
or
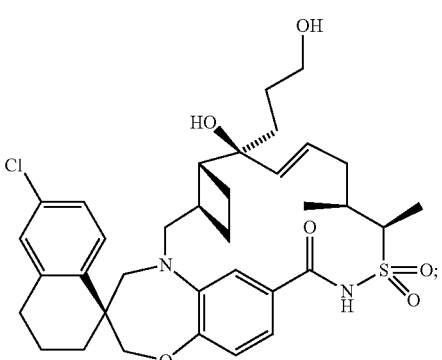
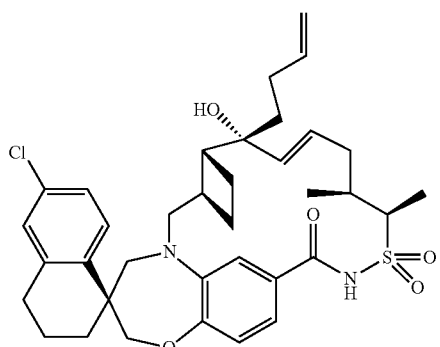
or
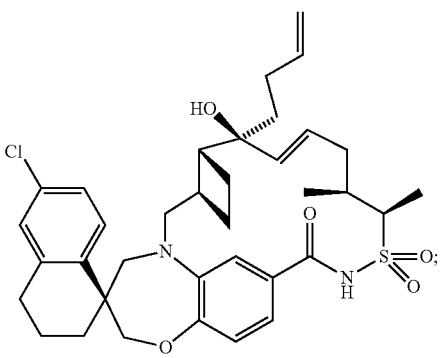

329
-continued
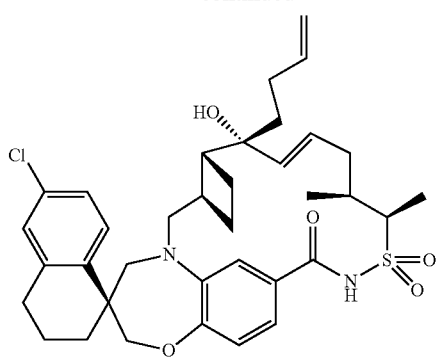
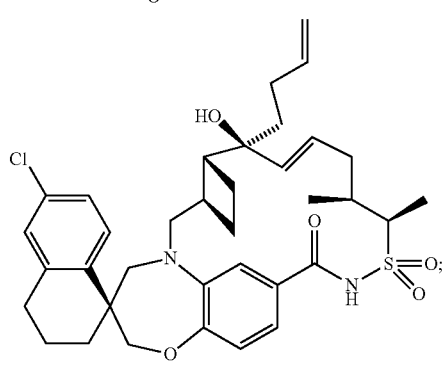
or
330
-continued
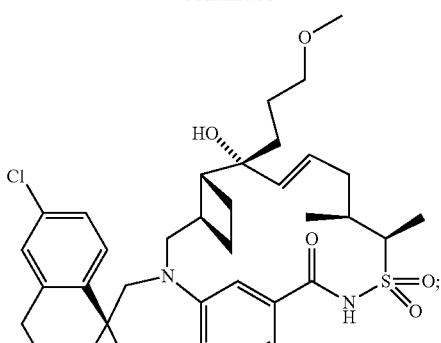
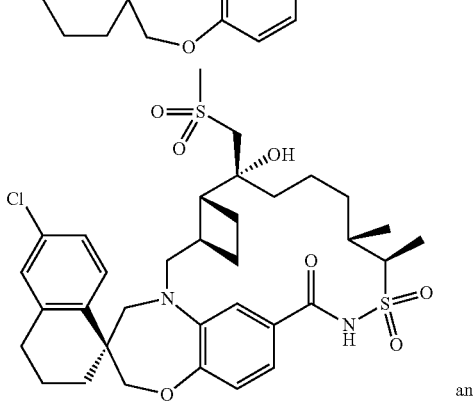
and
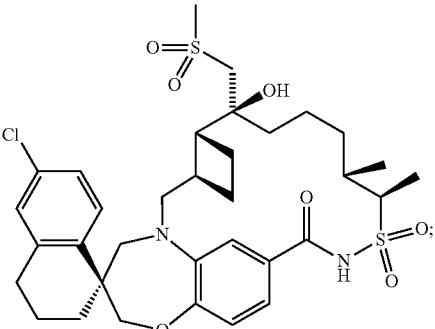
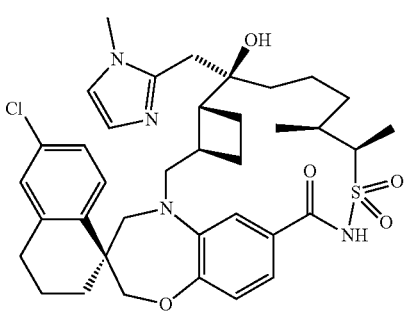
or
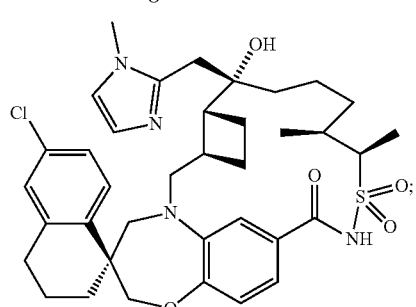

331
-continued
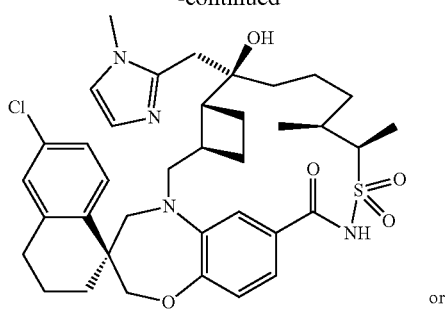
or
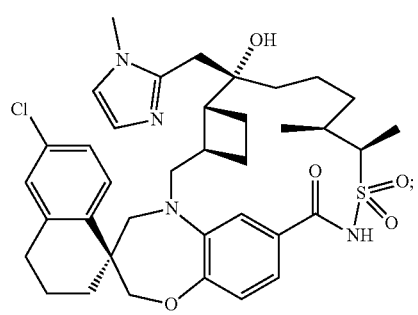
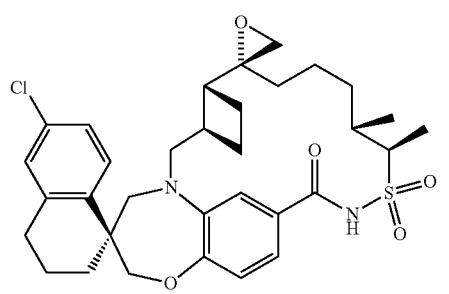
and
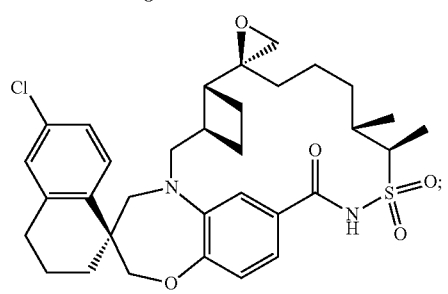
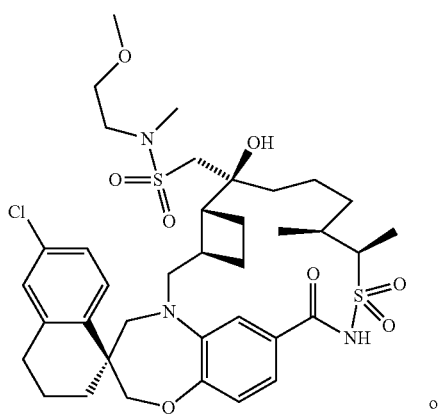
or
332
-continued
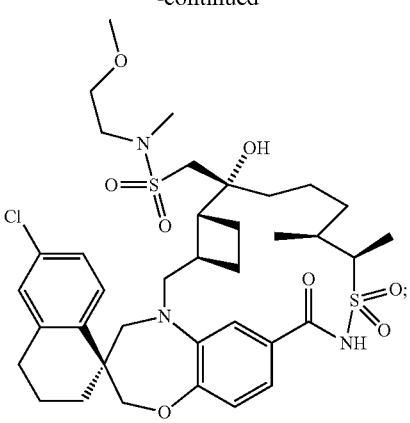
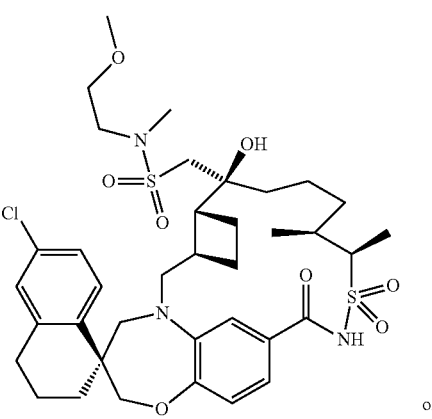
or
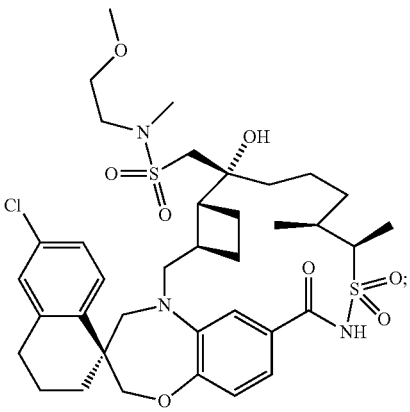
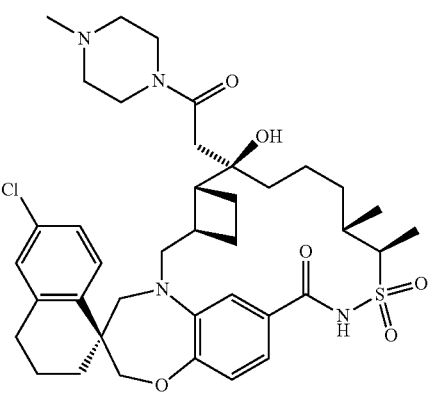
or 333
-continued
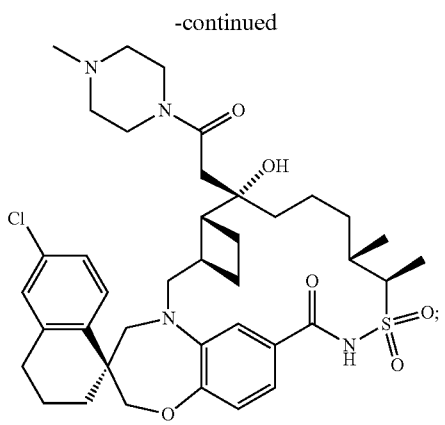
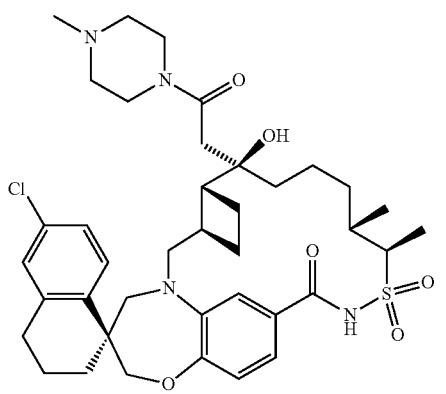
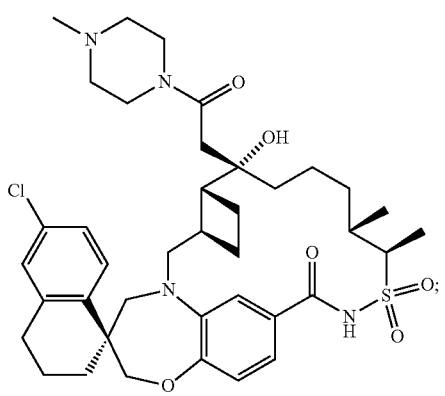
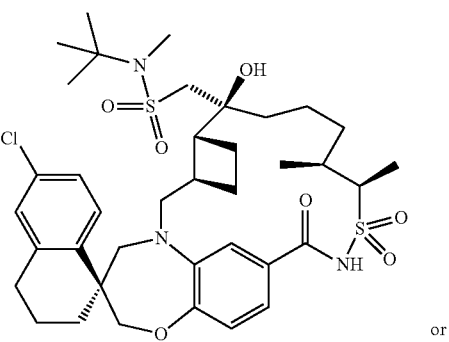
or
334
-continued
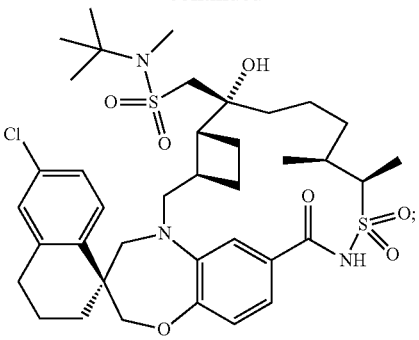
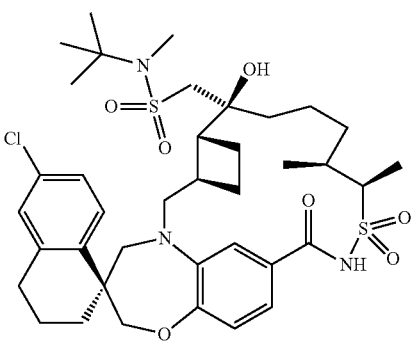
or
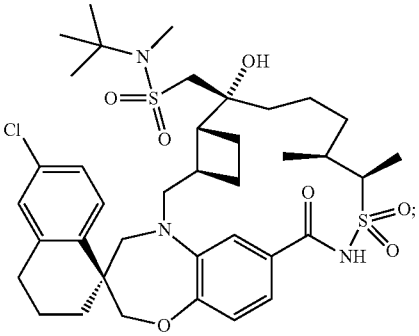
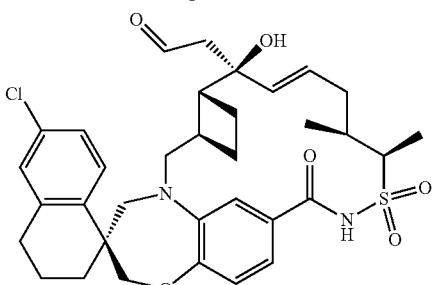
or
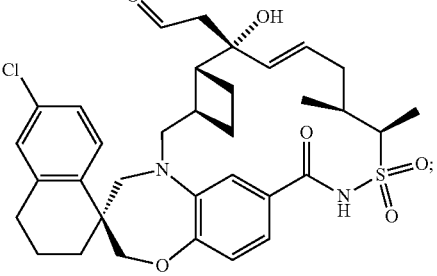

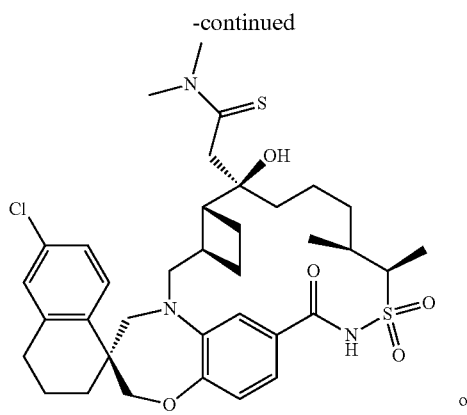
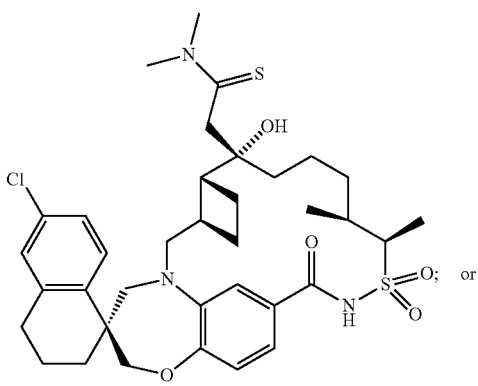
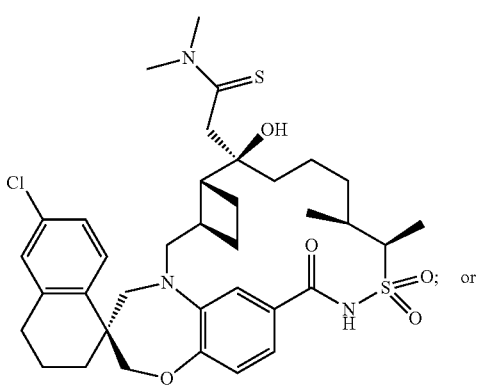
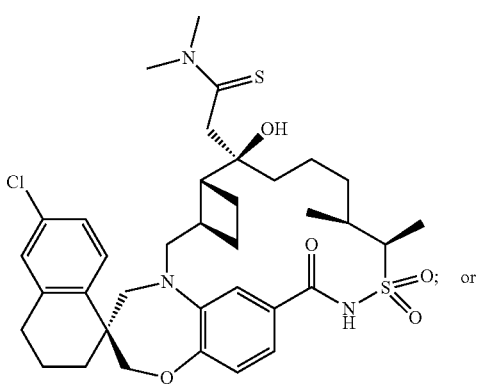
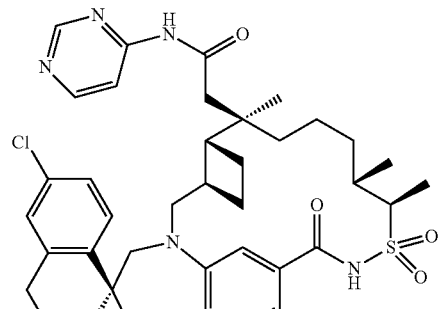
or
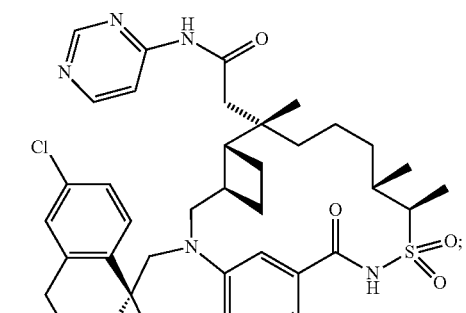
or
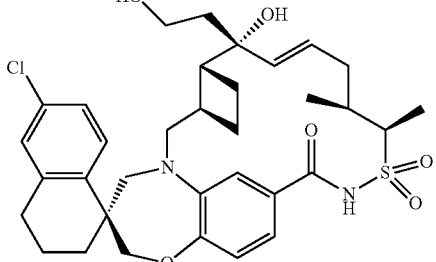
or
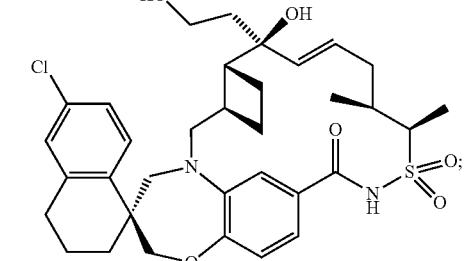
or
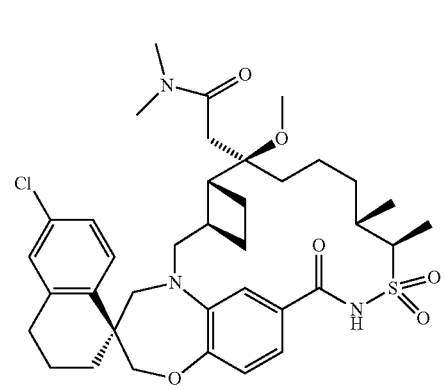
or 337 -continued
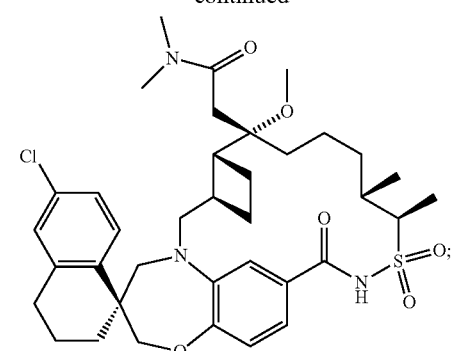
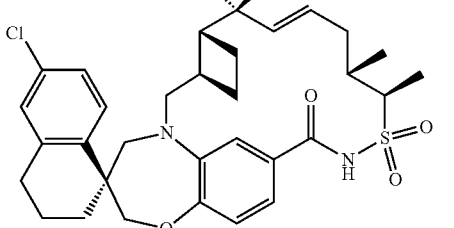
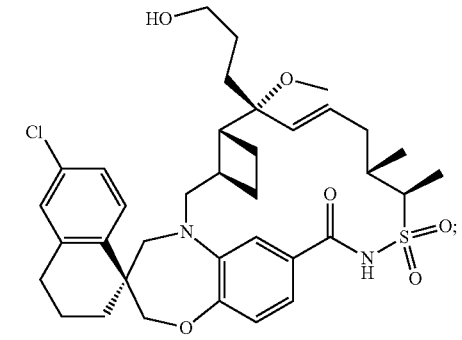
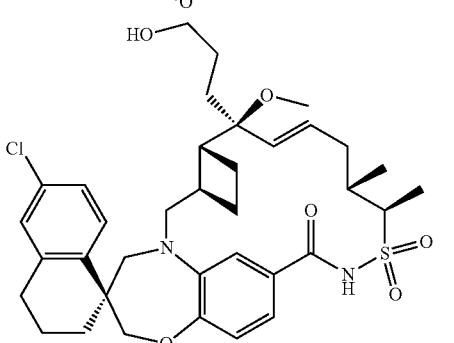
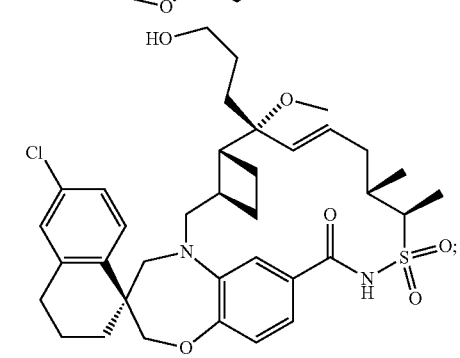
338 -continued
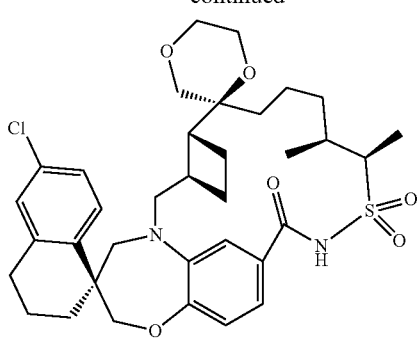
or
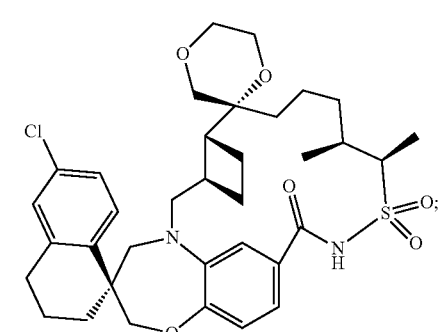
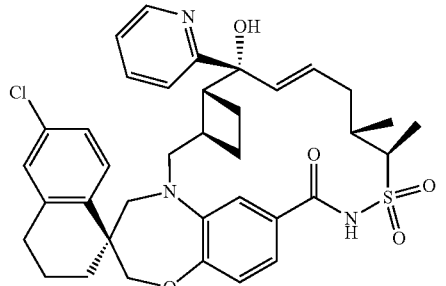
or
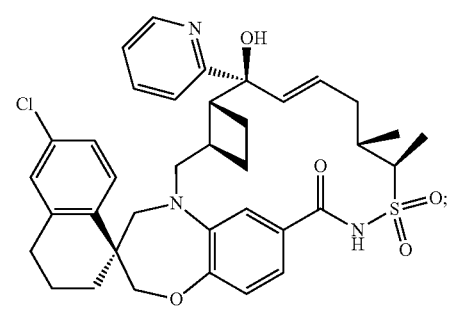
or
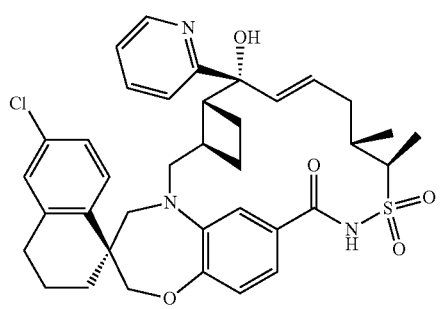
or

339
-continued
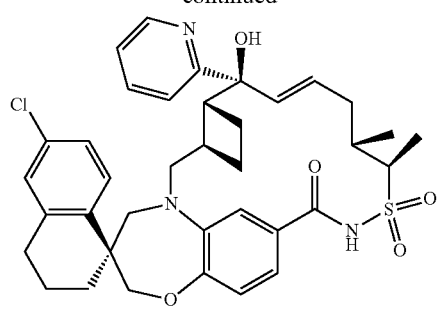
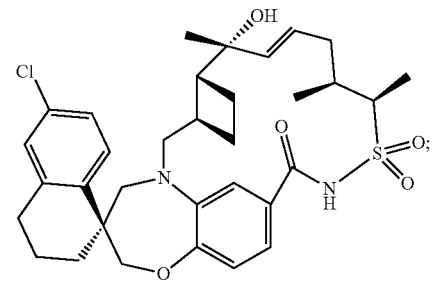
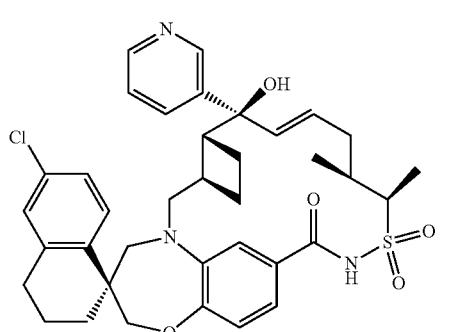
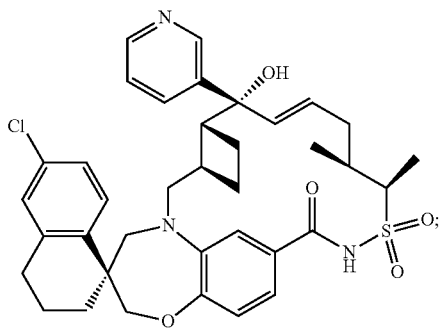
or
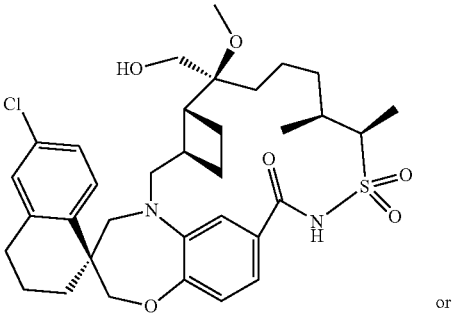
or
340
-continued
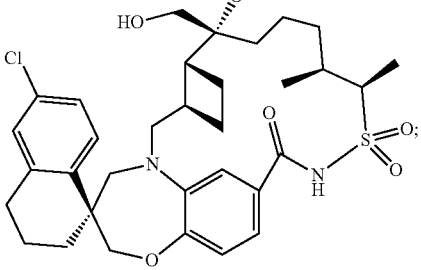
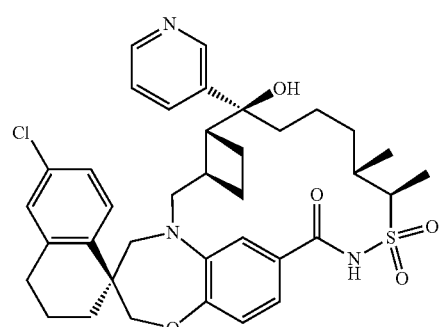
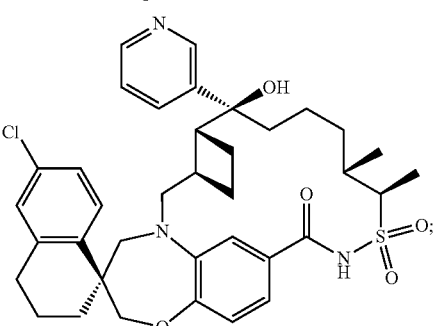
or
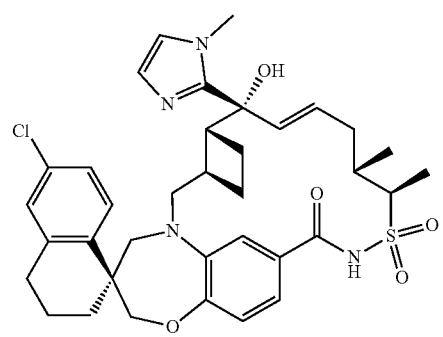
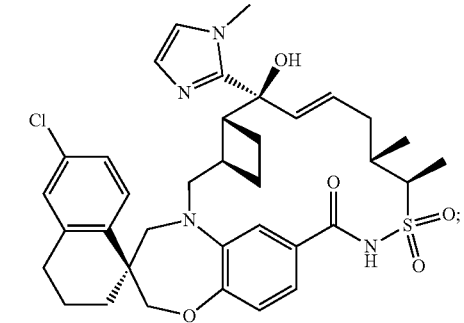
or

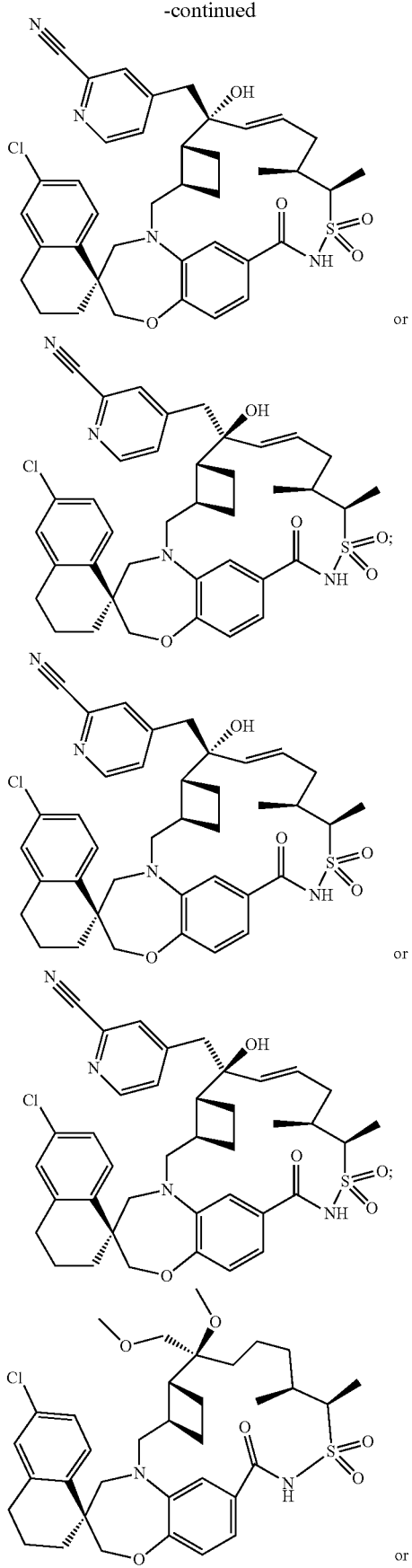
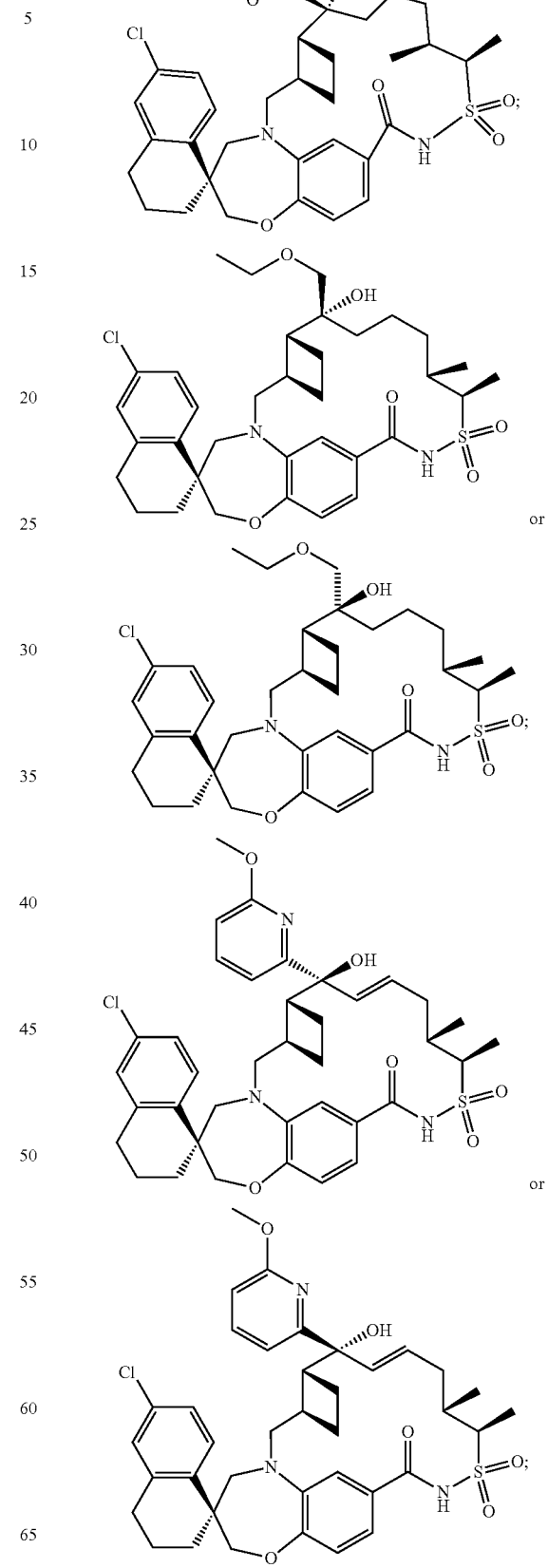

343
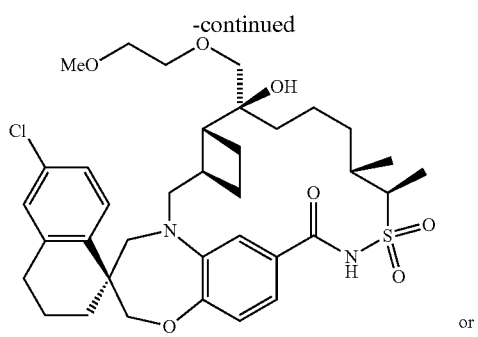
or
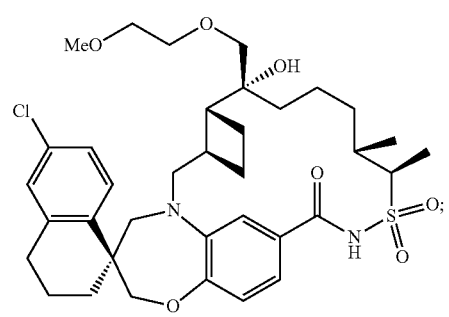
or
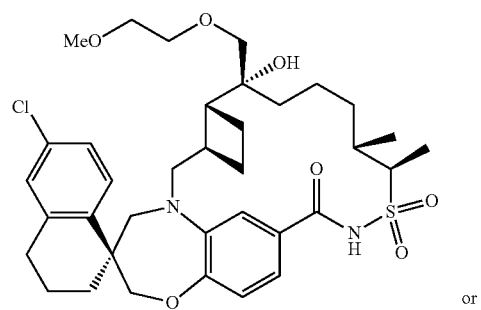
or
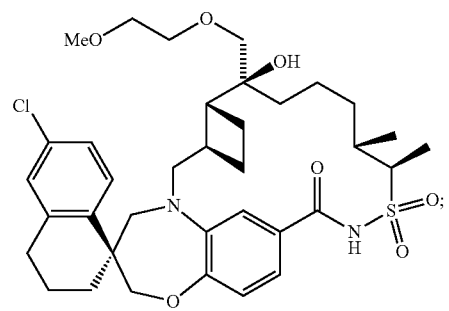
or
344
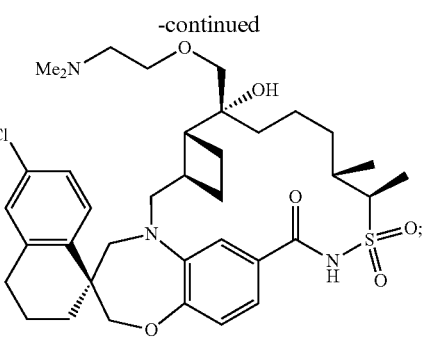
or
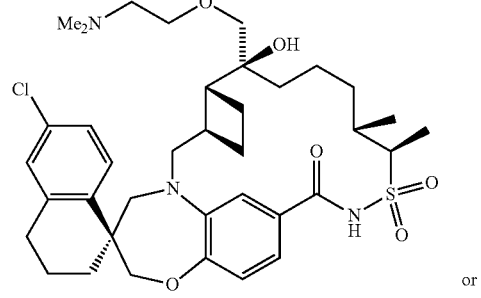

345
-continued
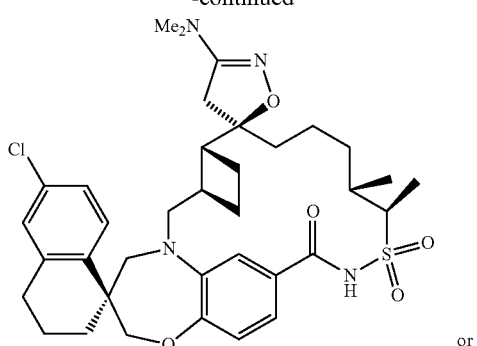
or
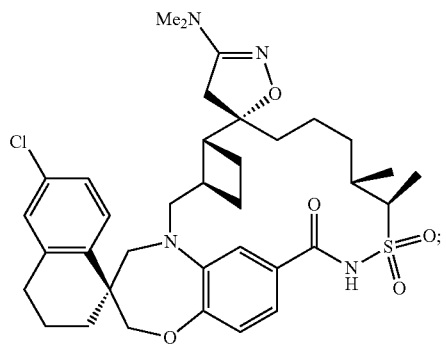
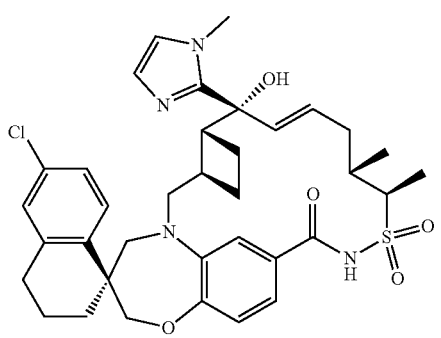
or
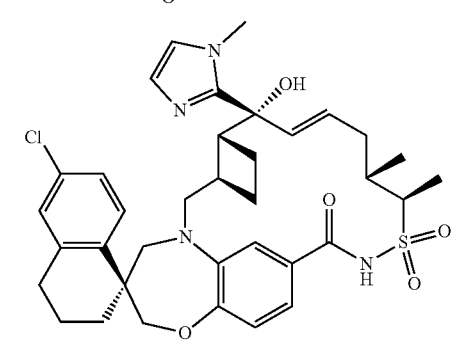
or
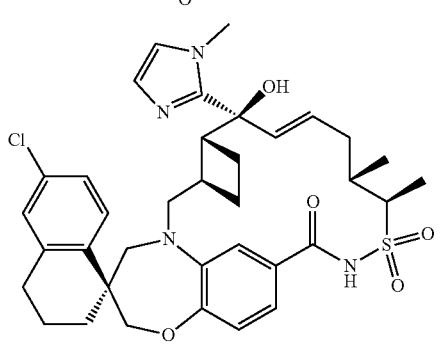
or
346
-continued
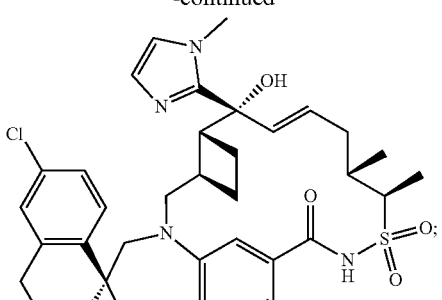
or
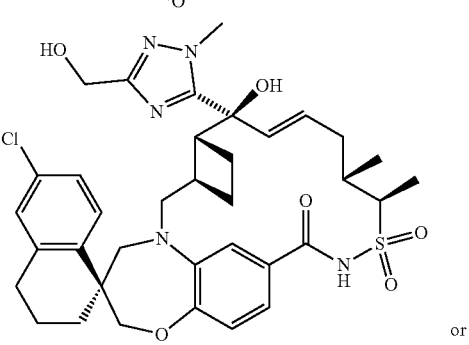
or
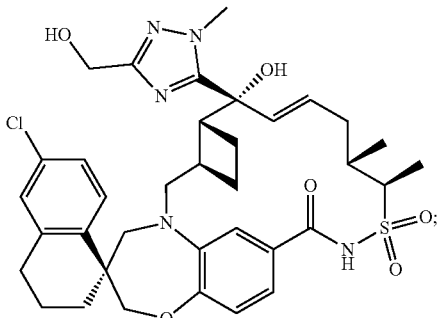
or
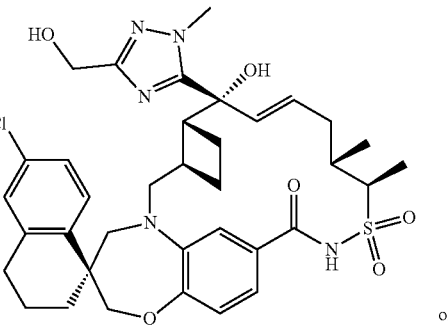
or
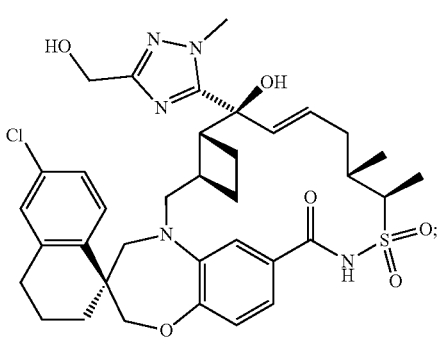

347
-continued
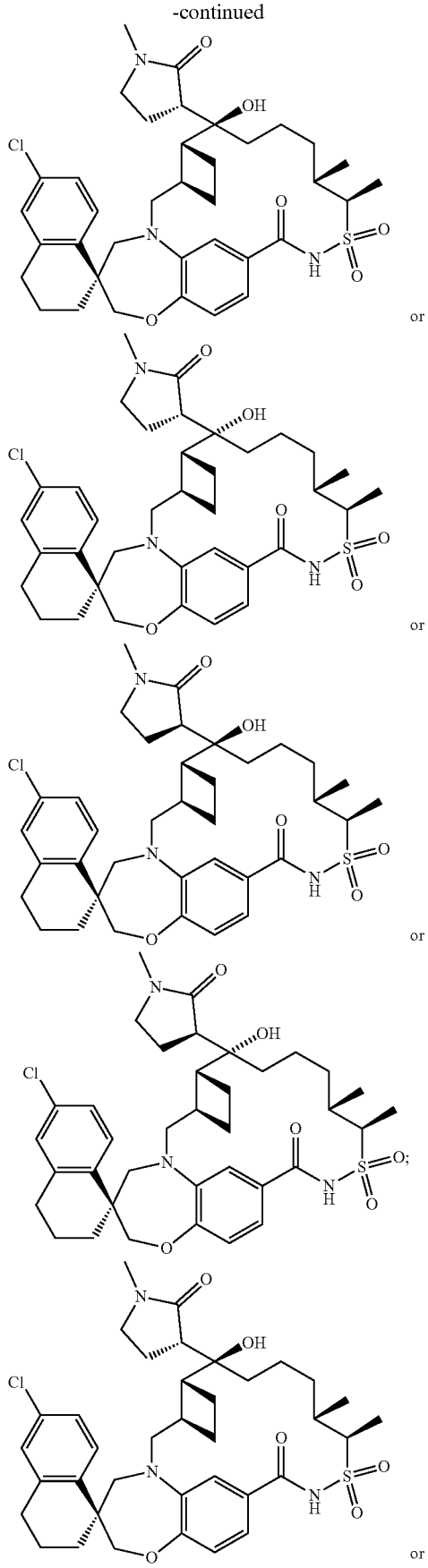
or
348
-continued
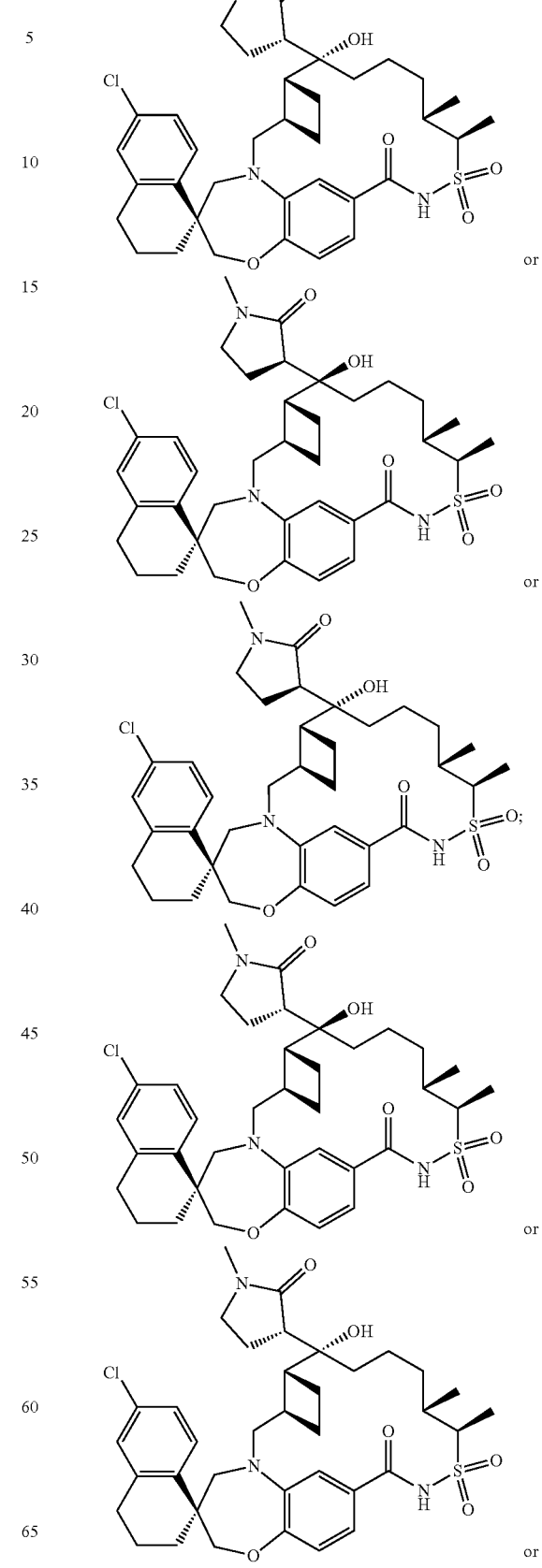
or

349
-continued
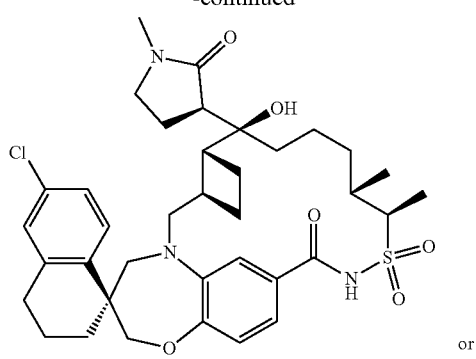
or
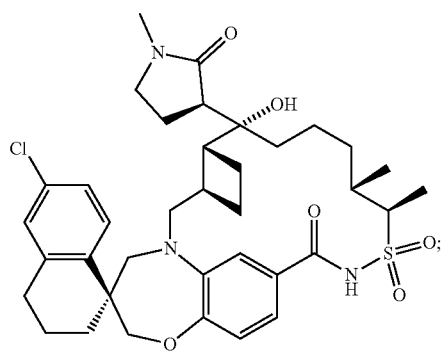
or
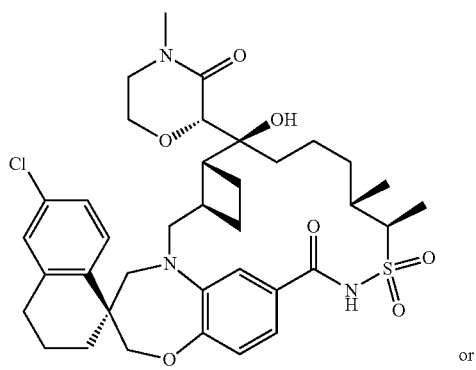
or
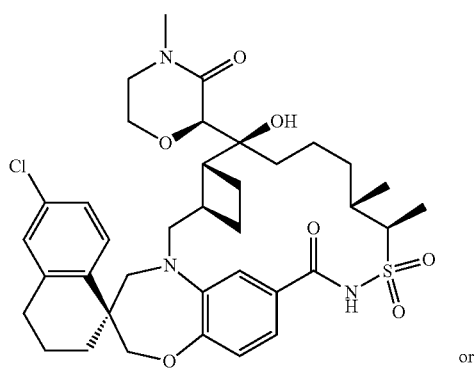
or
350
-continued
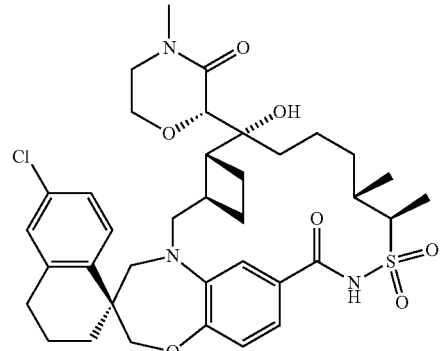
or
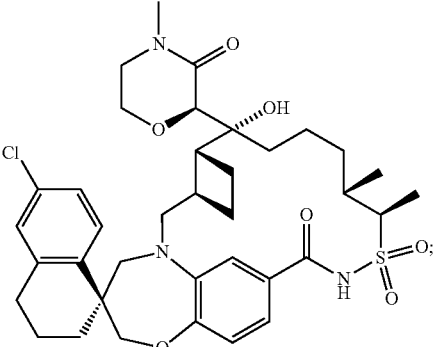
or
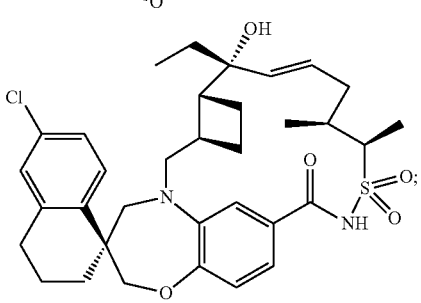
or
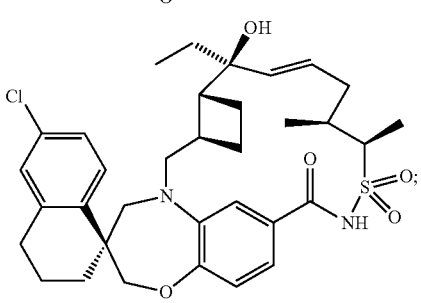
or
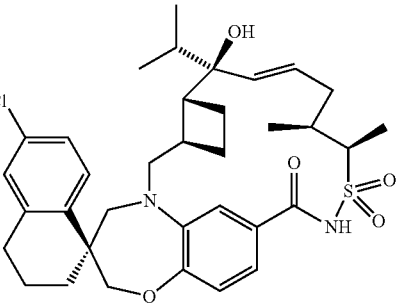
or -continued
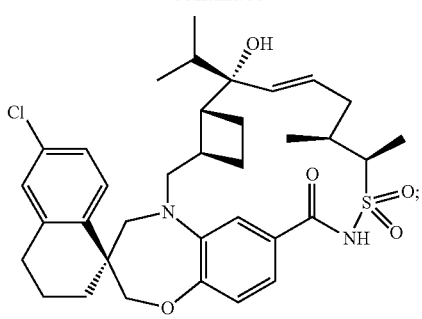
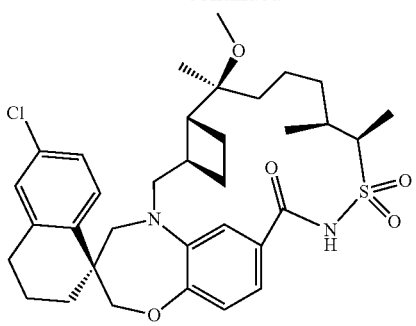
or
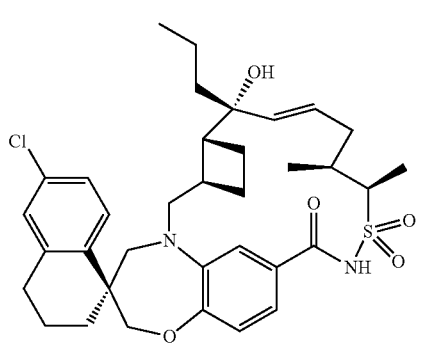
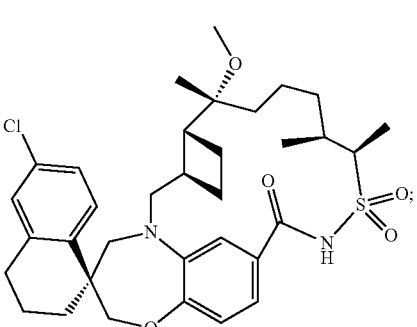
or
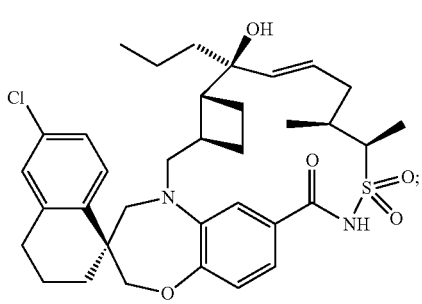
or
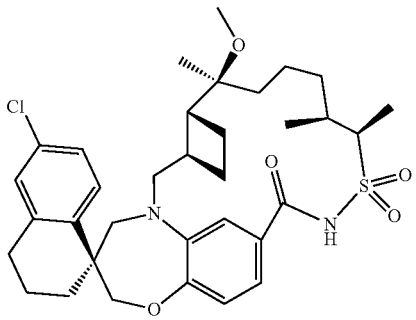
or
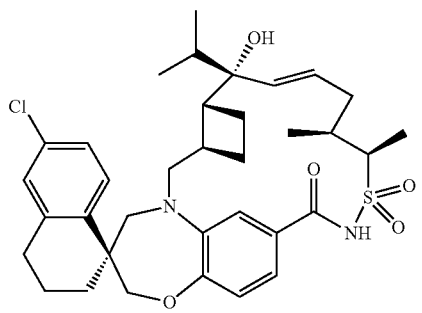
or
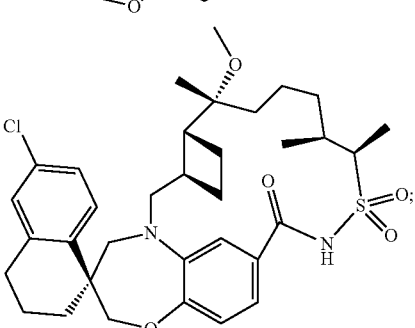
or
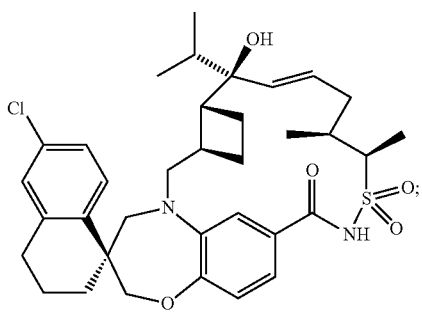
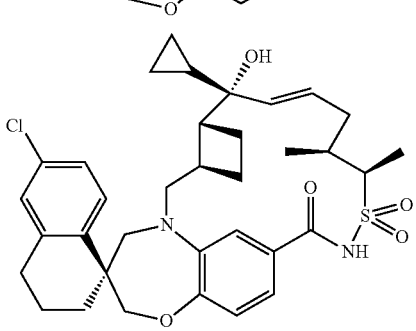
or

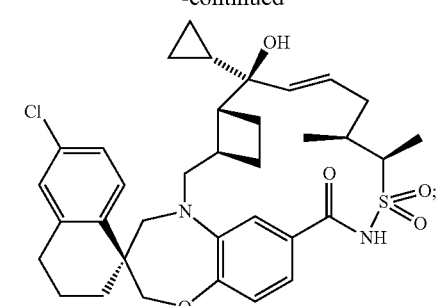
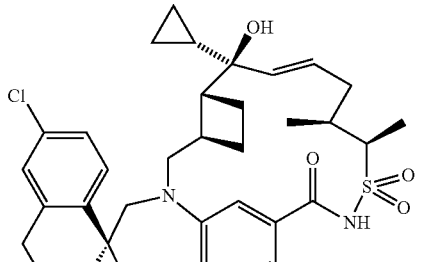

or
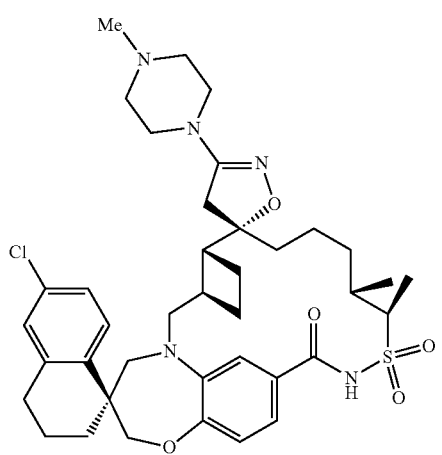
or
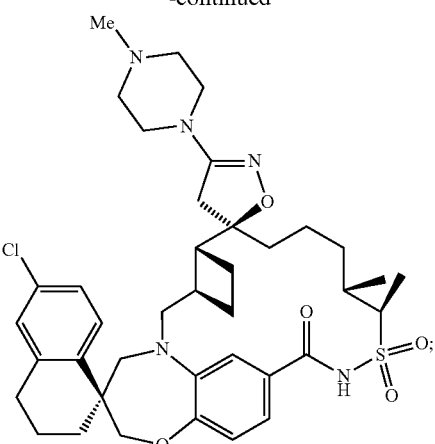
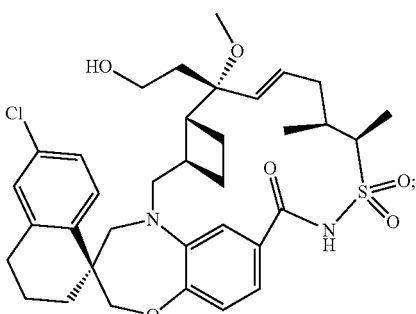
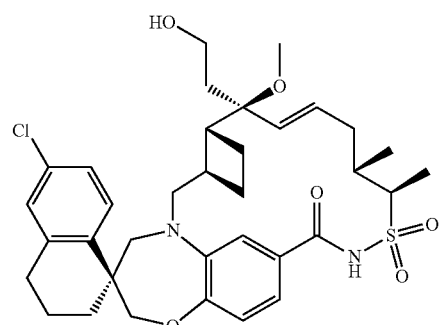
or
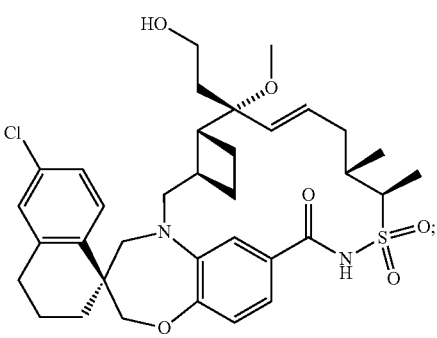
or 355
-continued
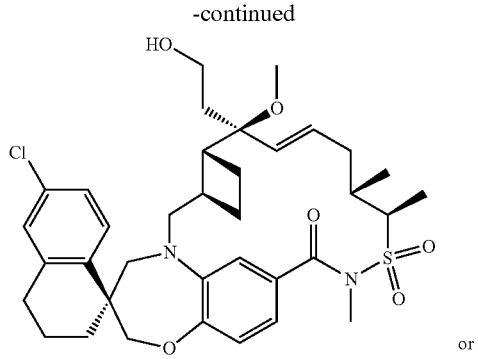
or
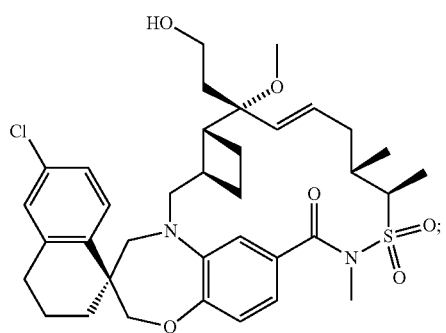
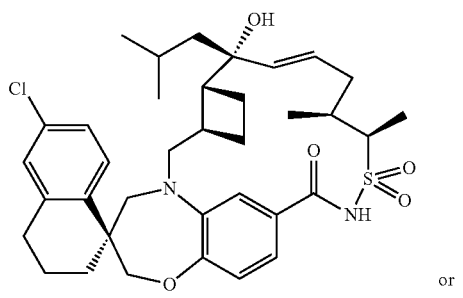
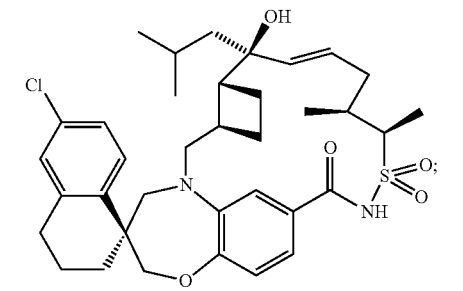
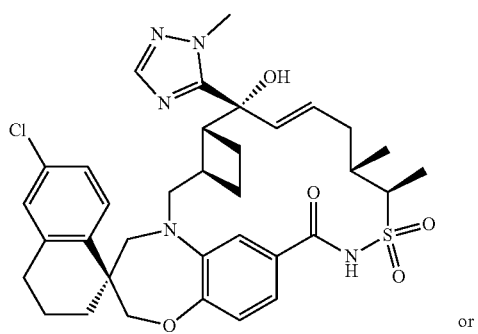
or
356
-continued
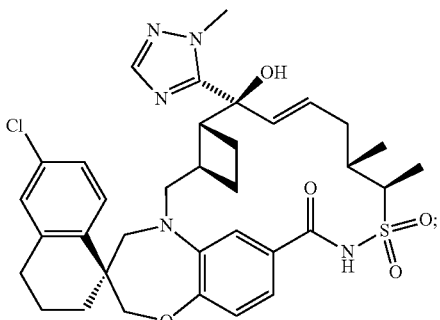
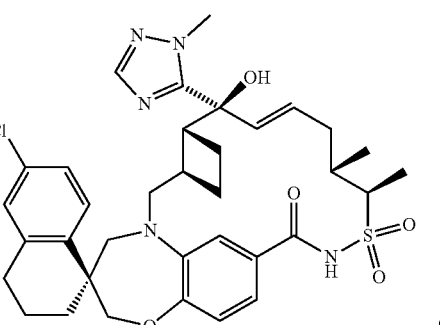
or
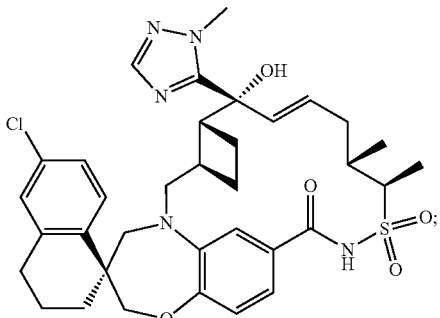
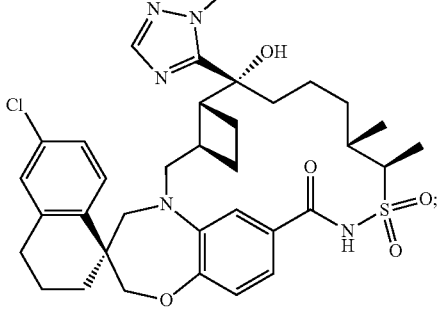
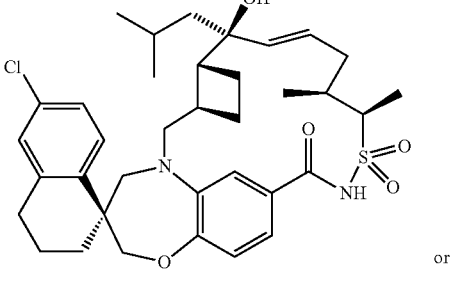
or

357
-continued
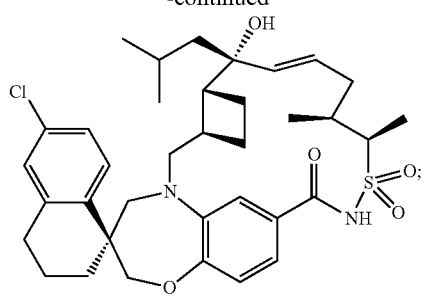
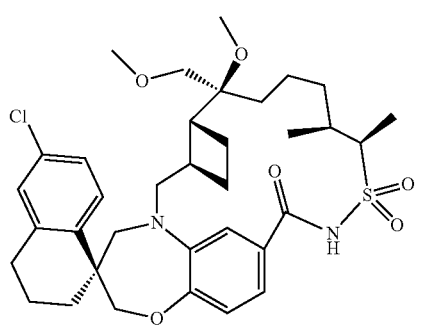
or
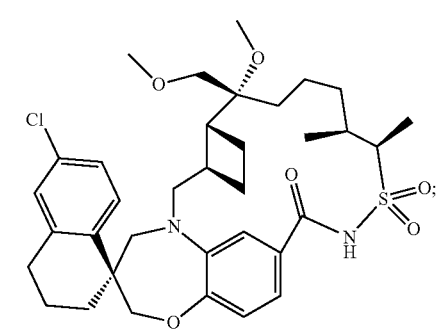
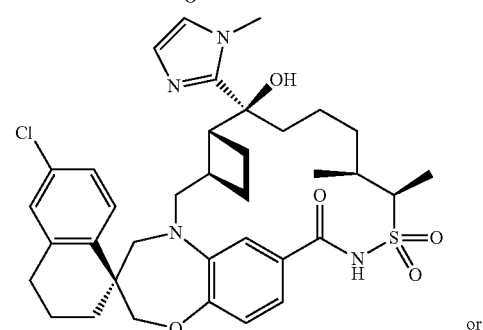
or
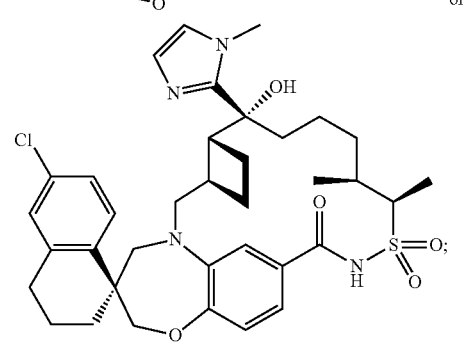
358
-continued
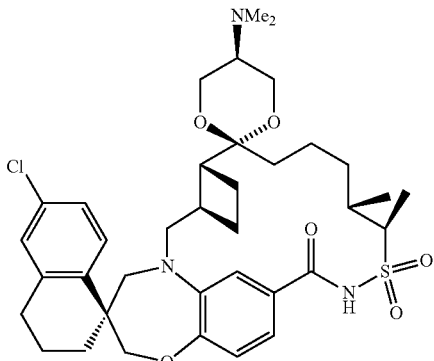
and
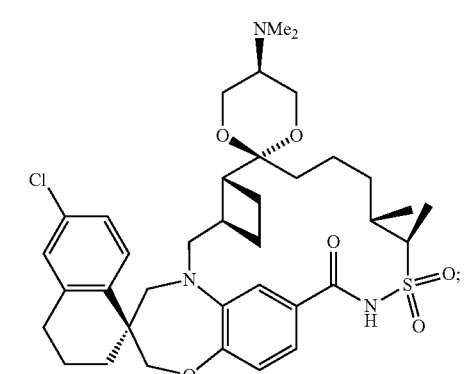
or
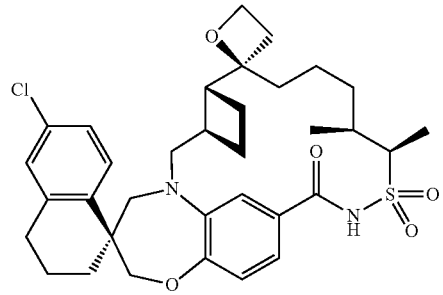
or
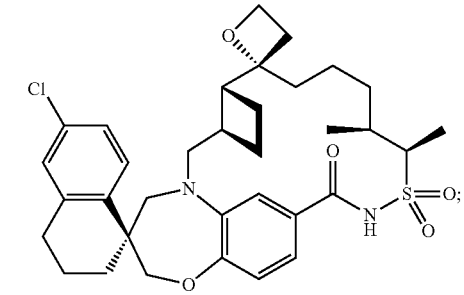
or
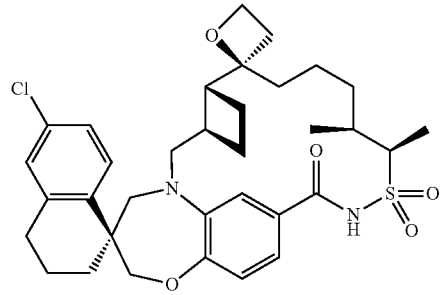
or 359
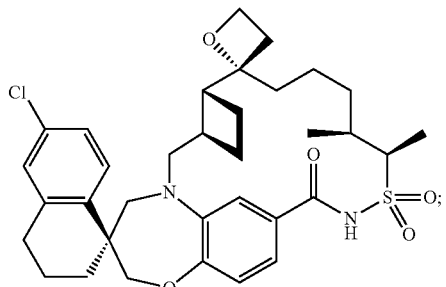
or
360
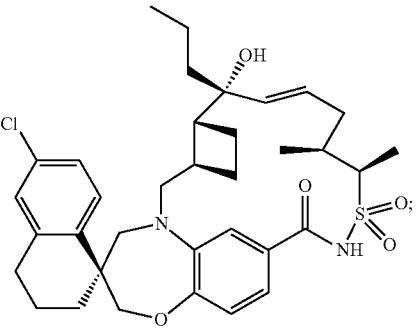
or
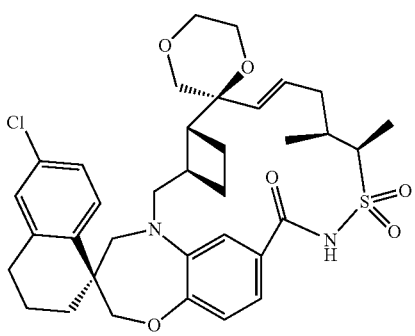
or
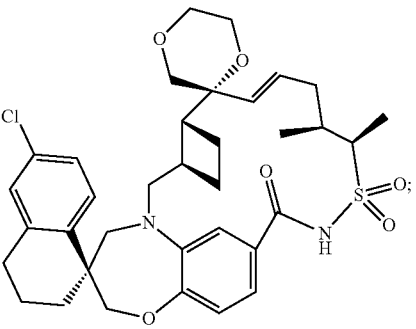
or
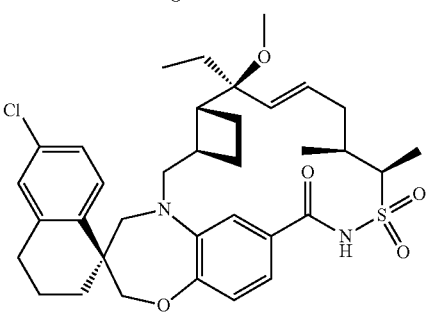
or
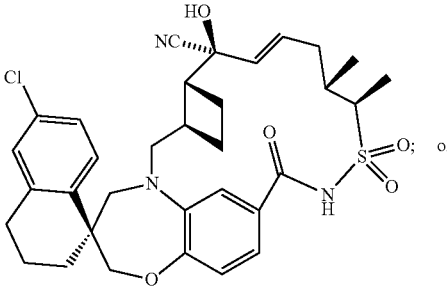
or

361
-continued
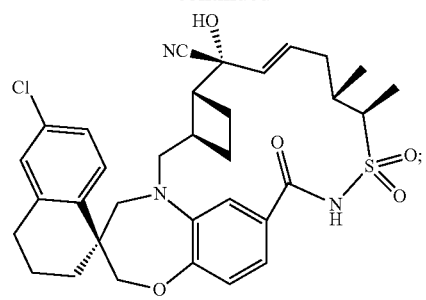
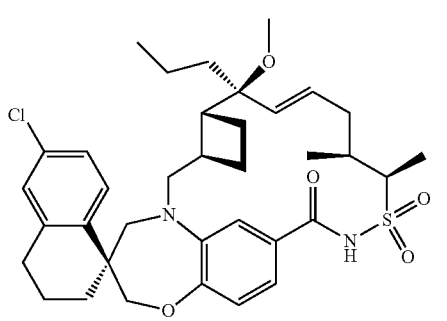
or
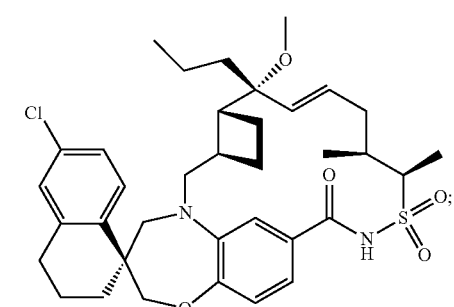
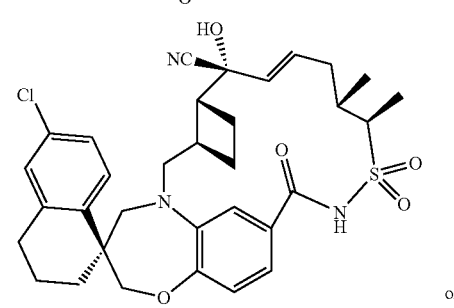
or
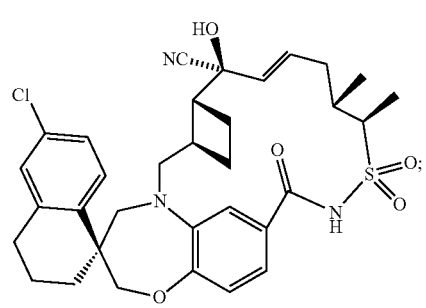
362
-continued
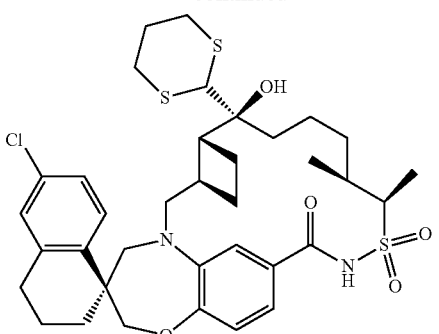
or
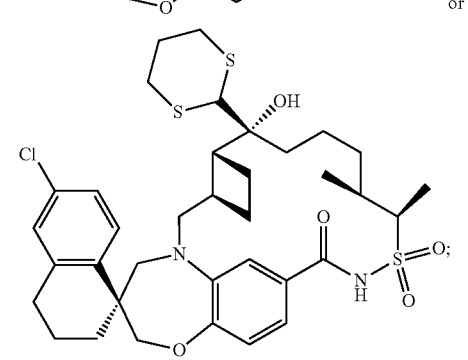
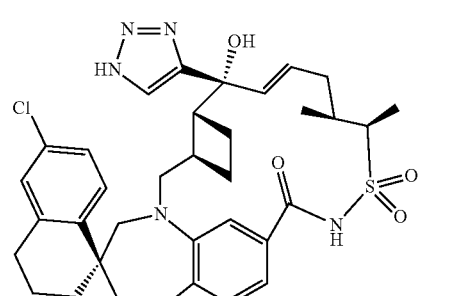
or
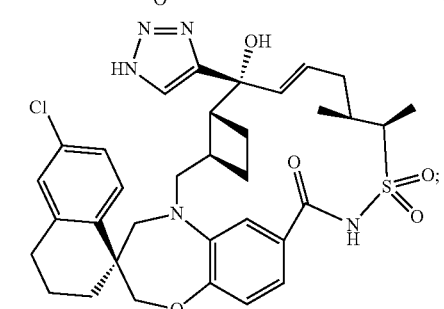
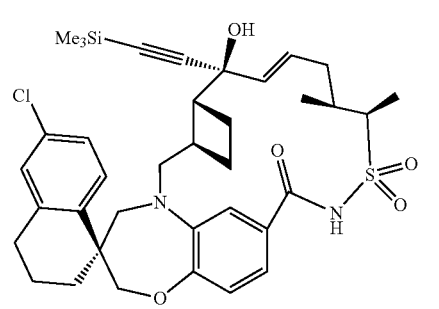
or

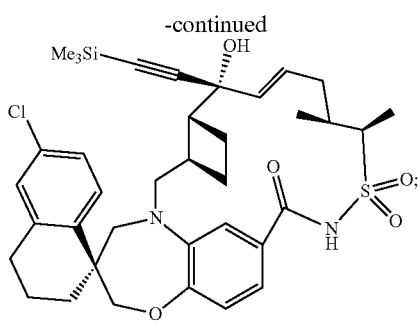
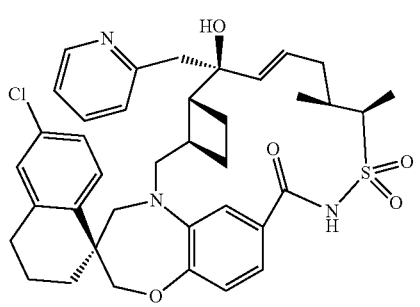
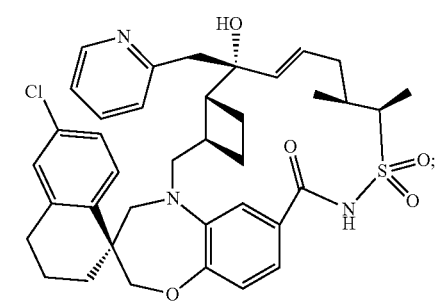
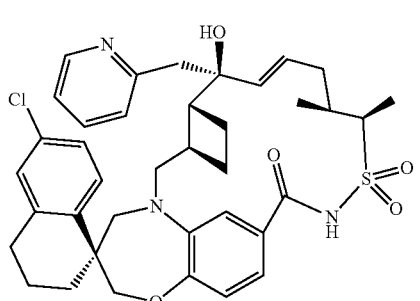
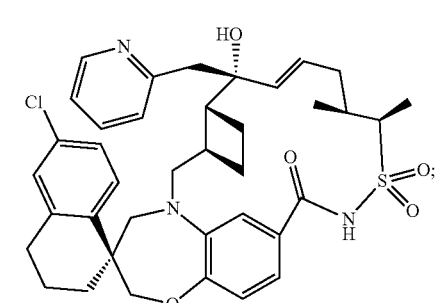
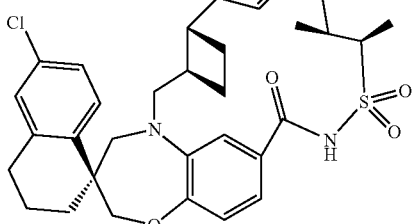
or
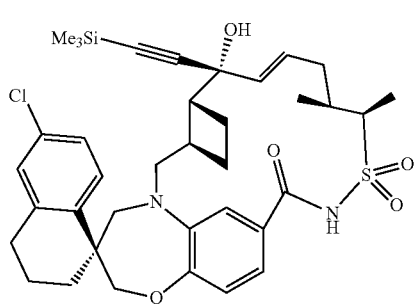
or
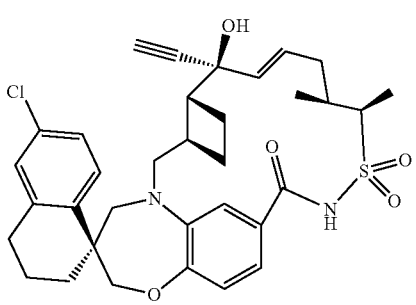
or
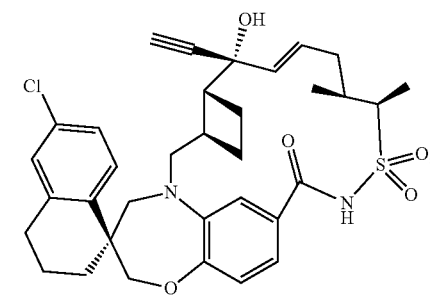
or
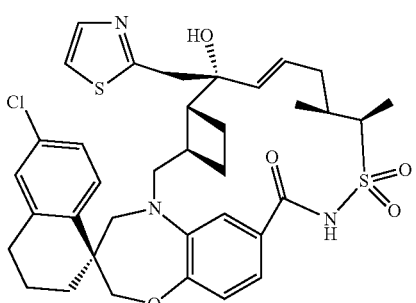
or 365
-continued
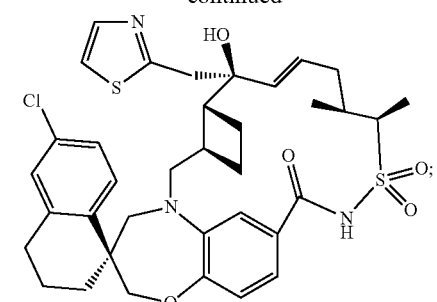
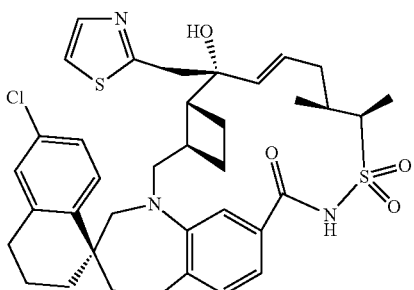
or
366
-continued
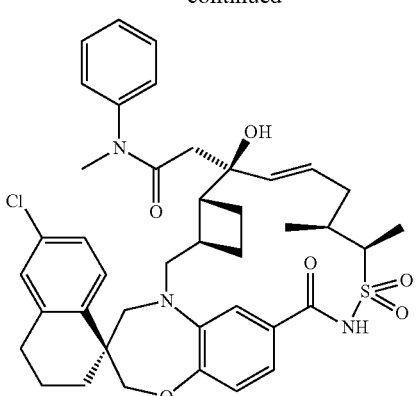
or
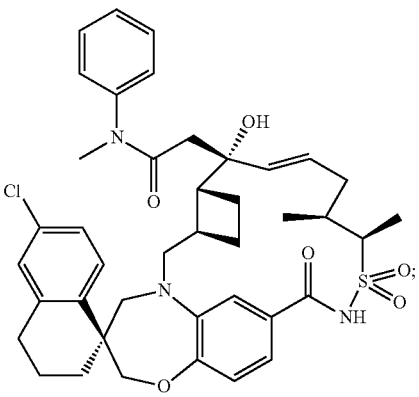
or
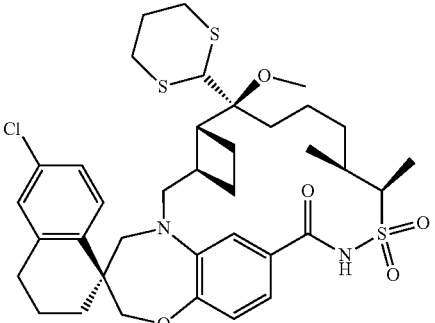
or
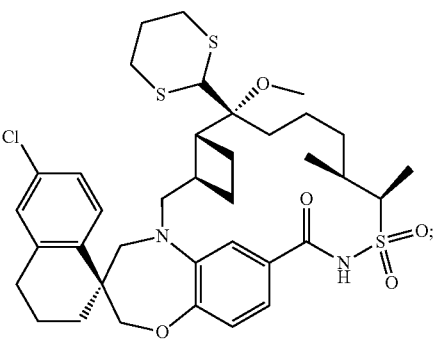

367
-continued
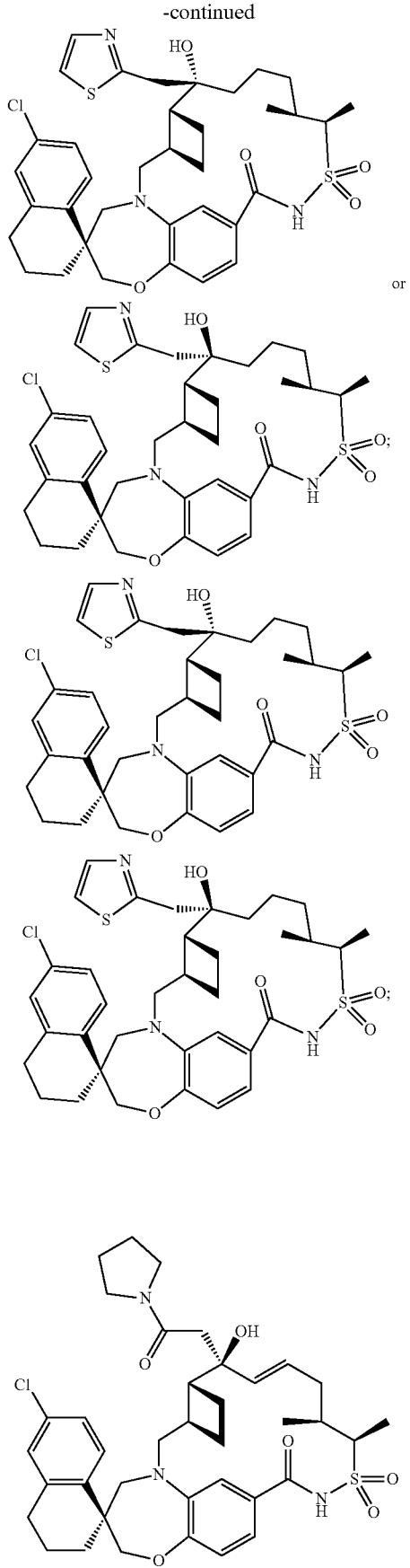
or
368
-continued
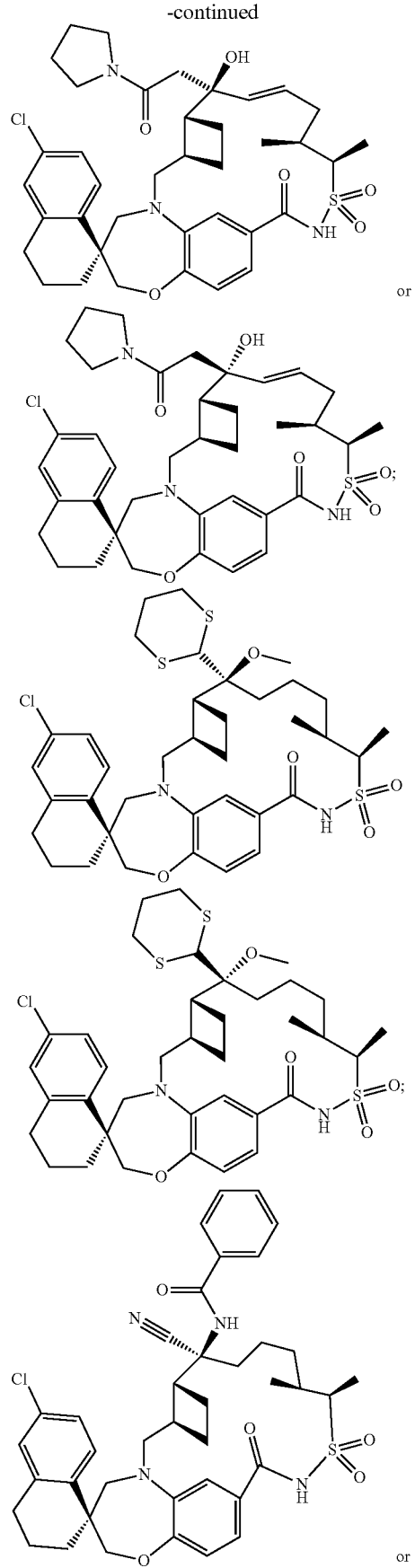
or

369
-continued
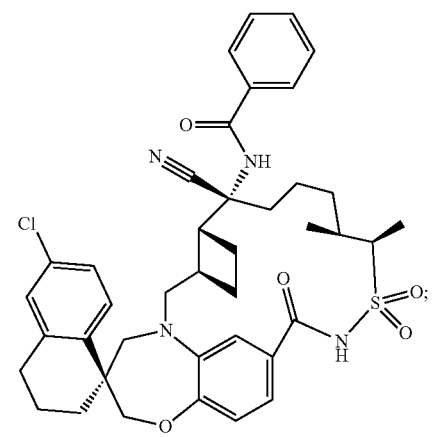
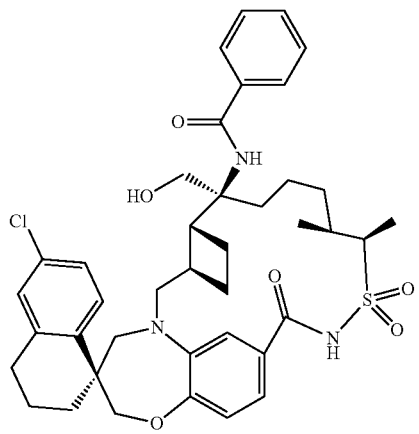
or
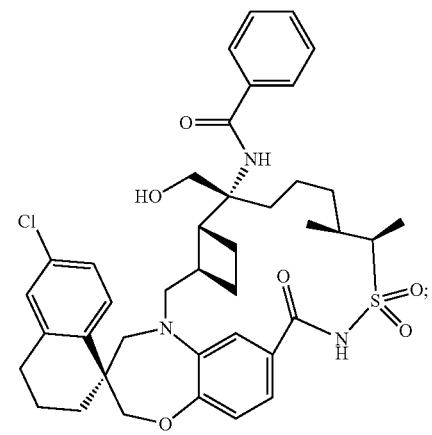
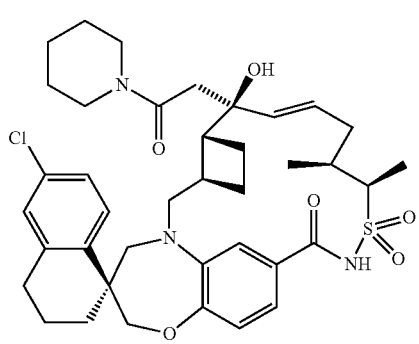
or
370
-continued
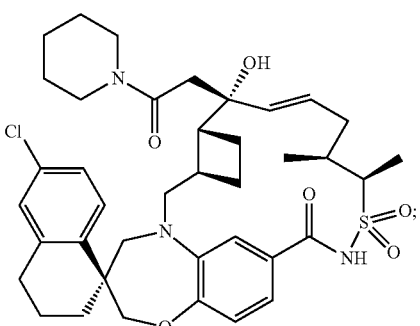
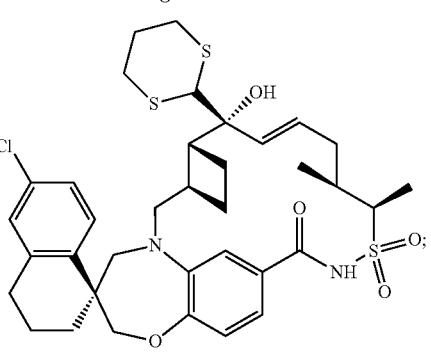
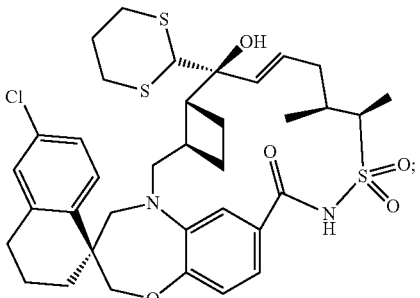
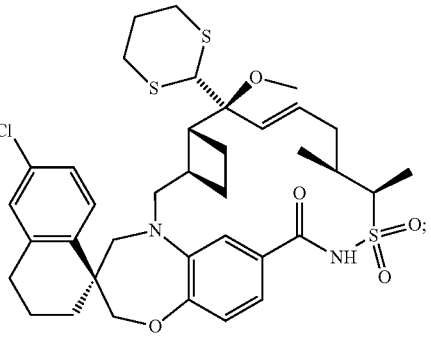
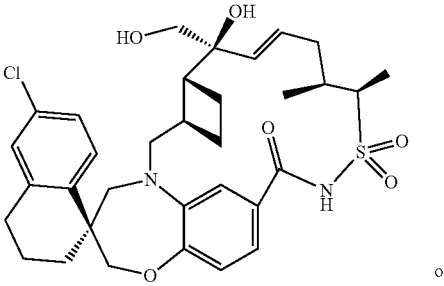
or 371
-continued
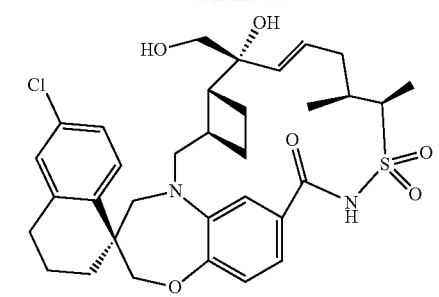
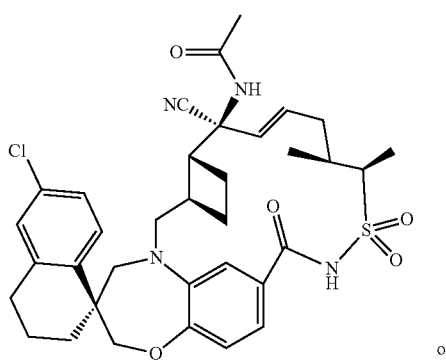
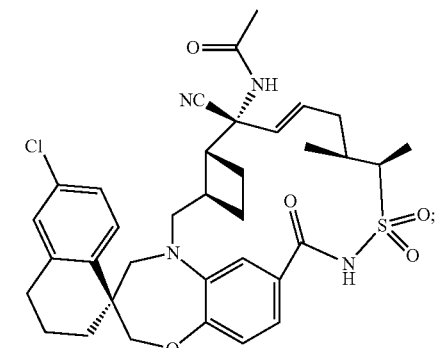
or
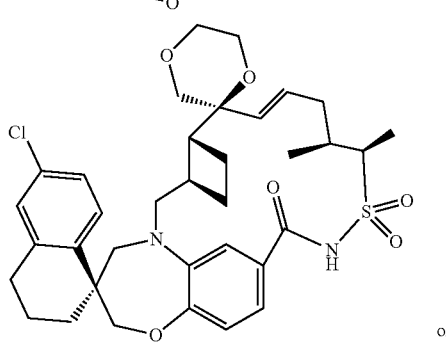
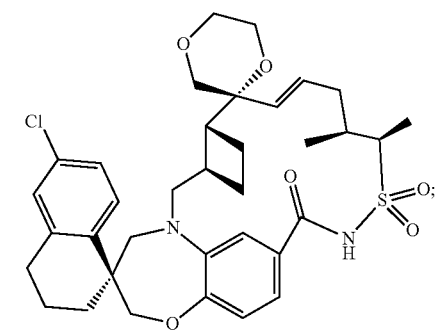
372
-continued
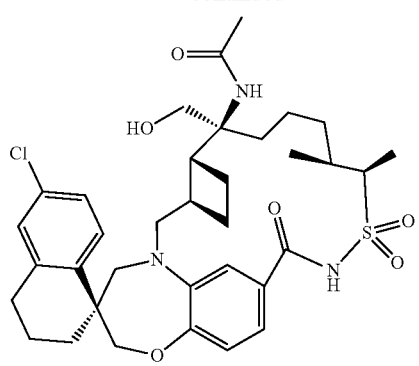
or
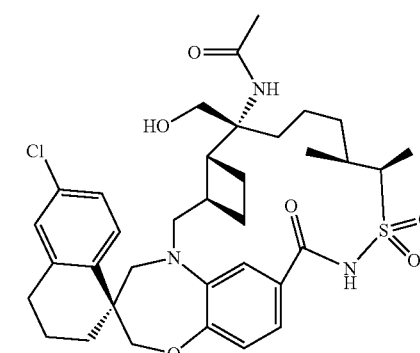
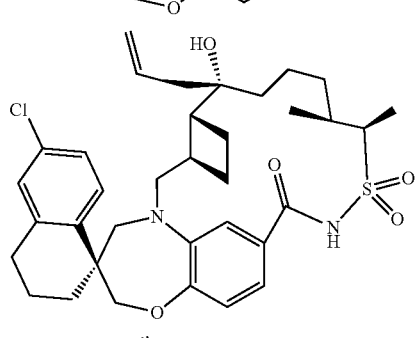
or
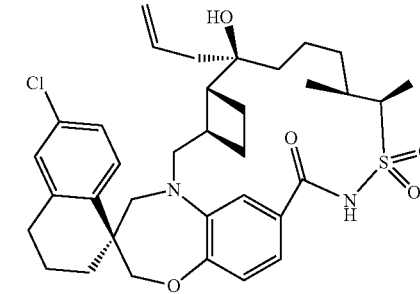
or
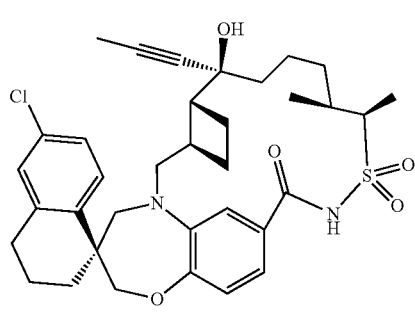
or 373
-continued
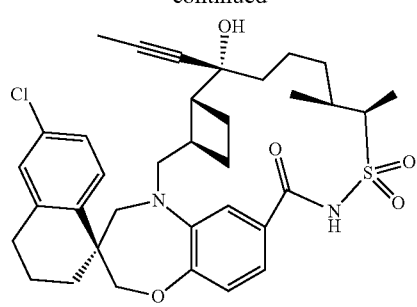
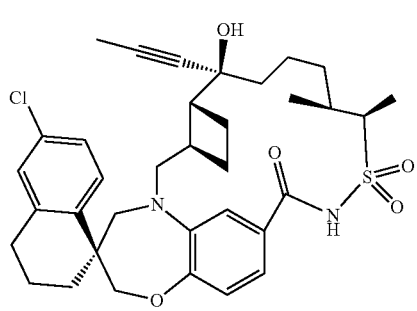
or
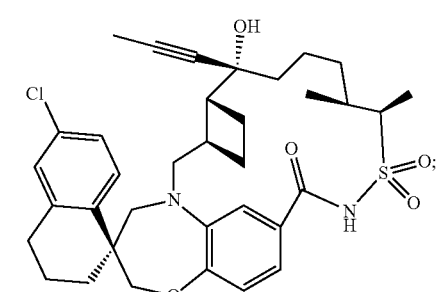
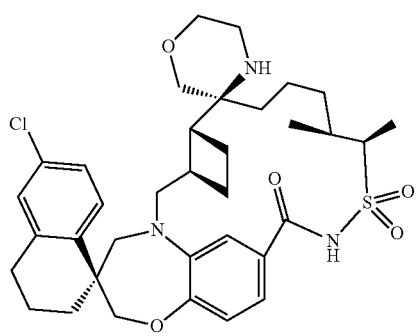
or
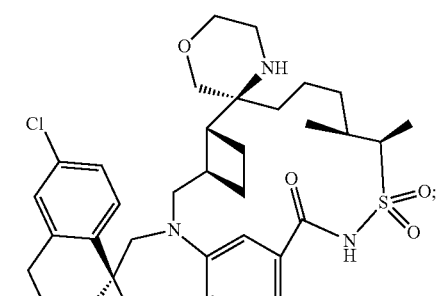
374
-continued
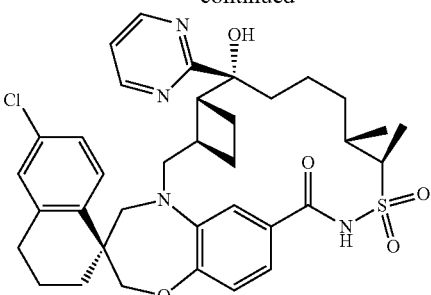
and
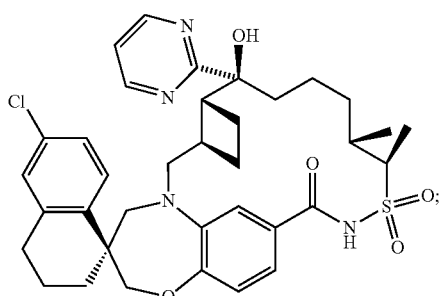
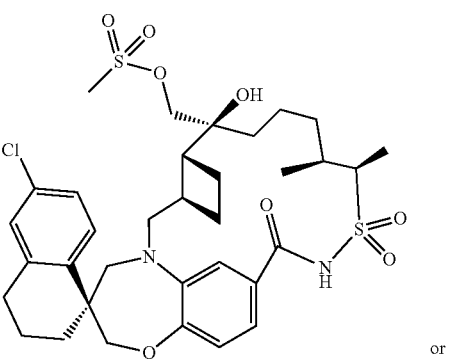
or
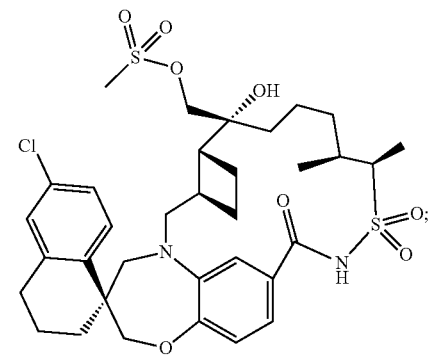

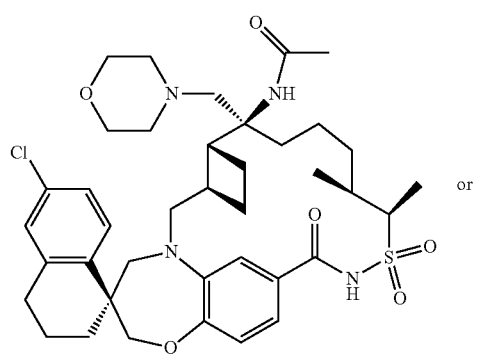
or
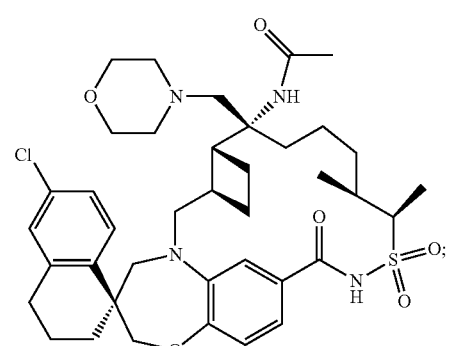
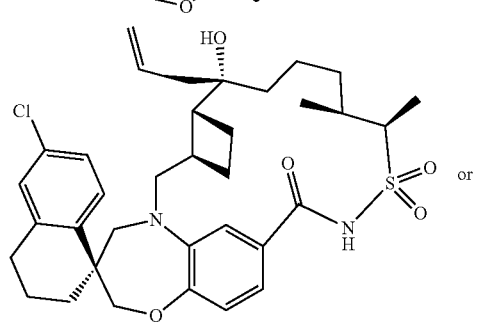
or
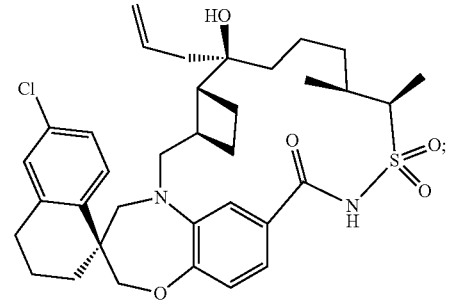
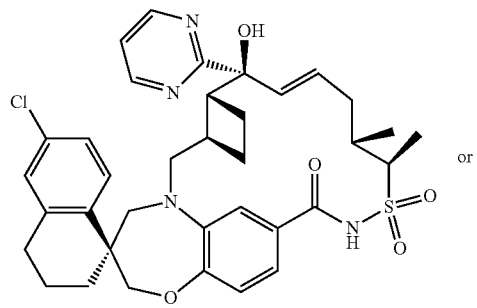
or
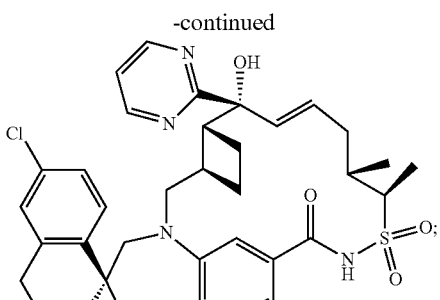
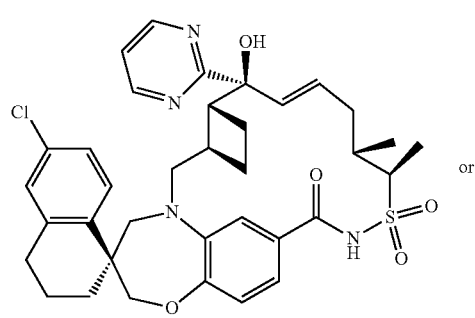
or
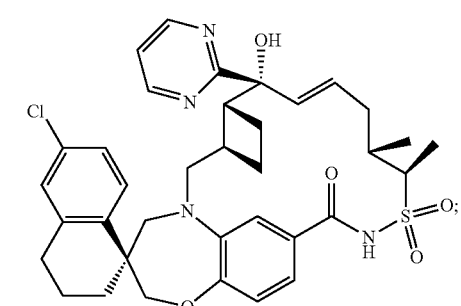
or
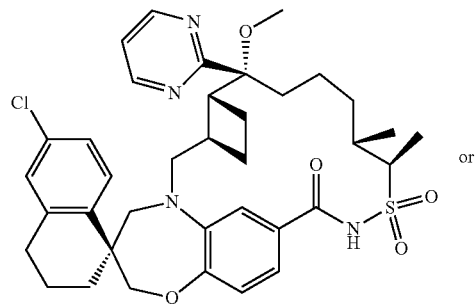
or
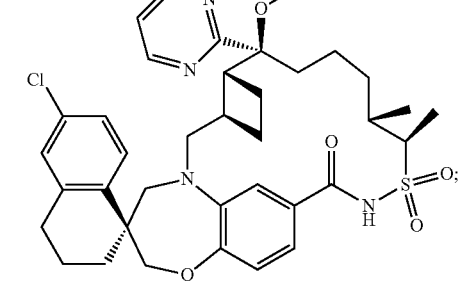

377
-continued
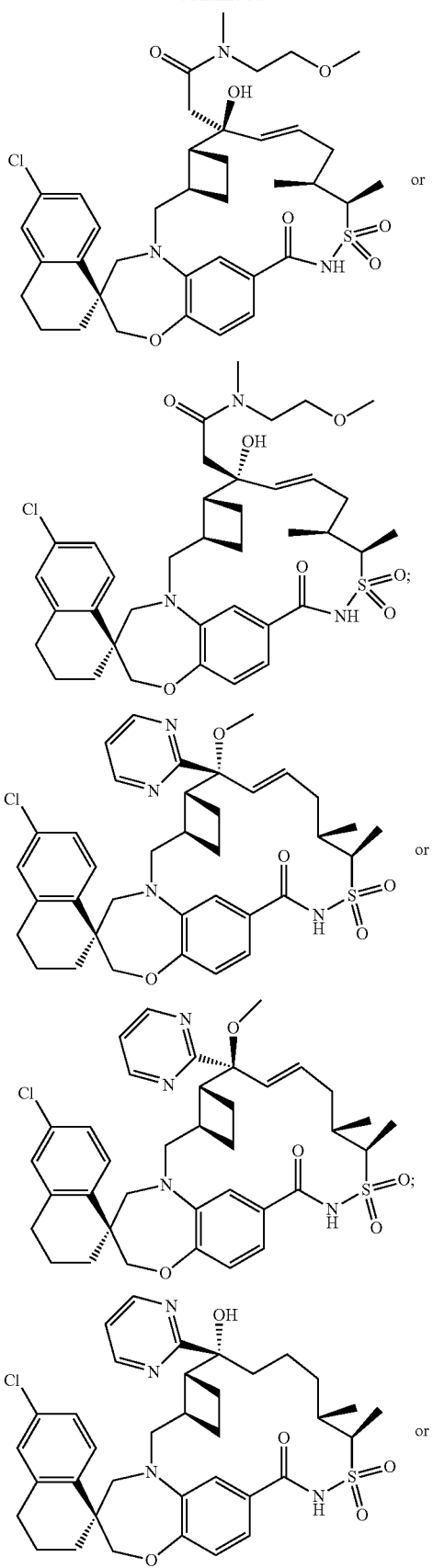
378
-continued
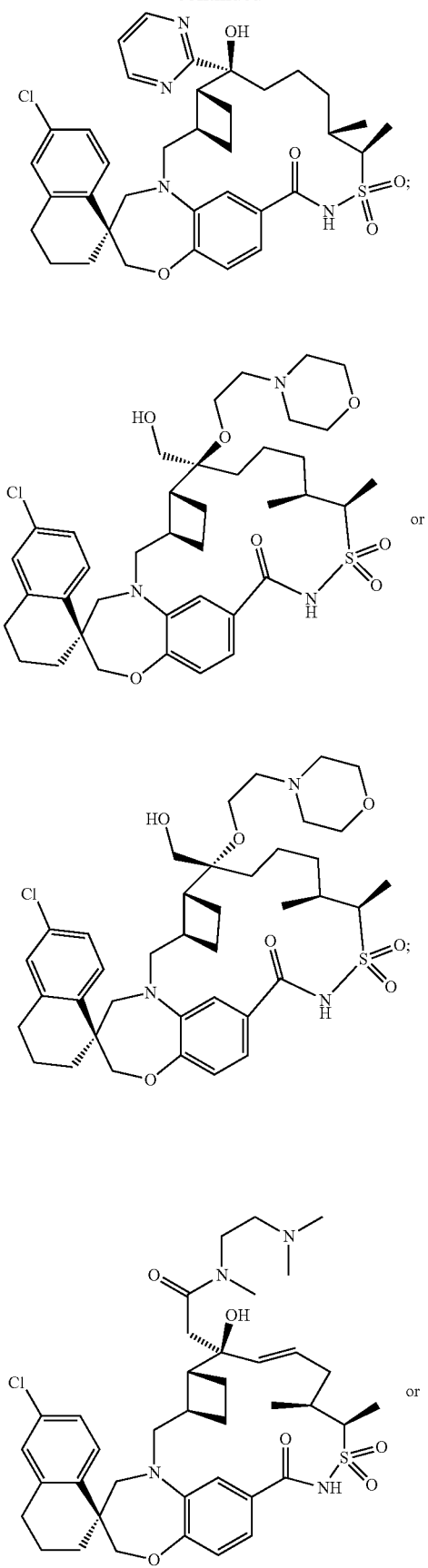

379
-continued
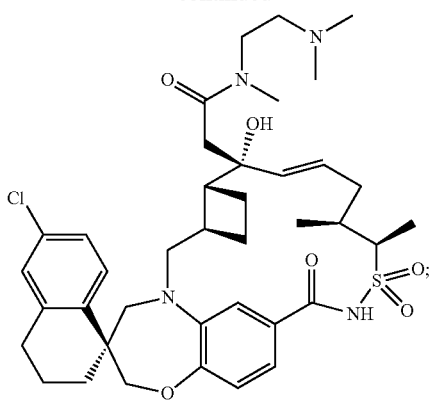
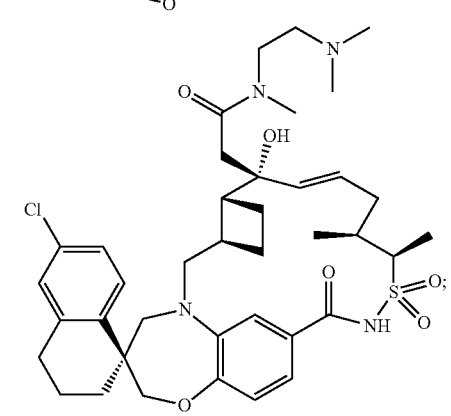
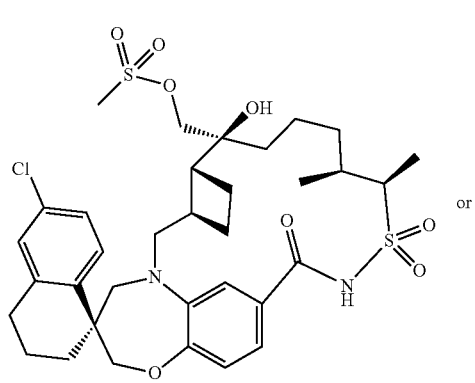
380
-continued
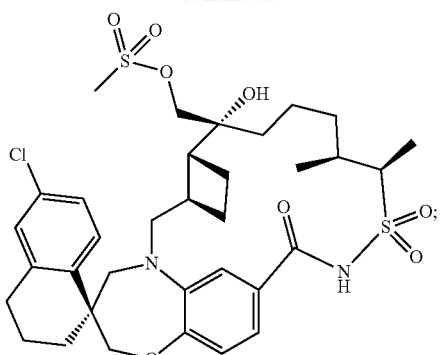
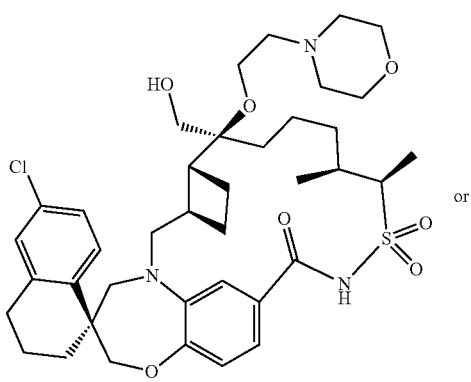
or
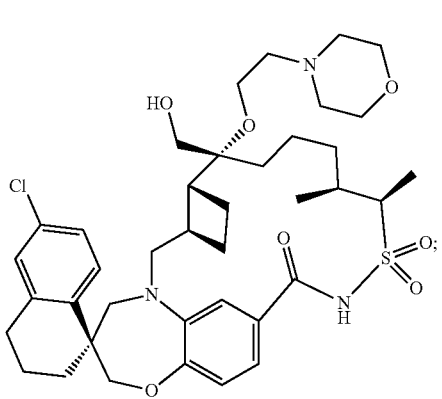
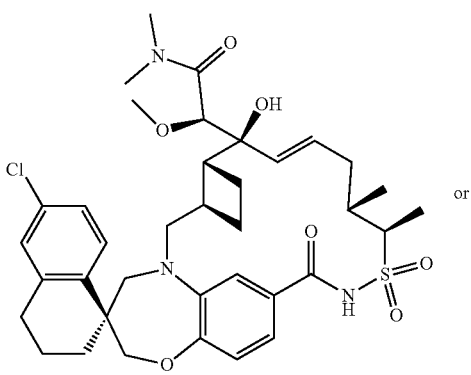
or 381
-continued
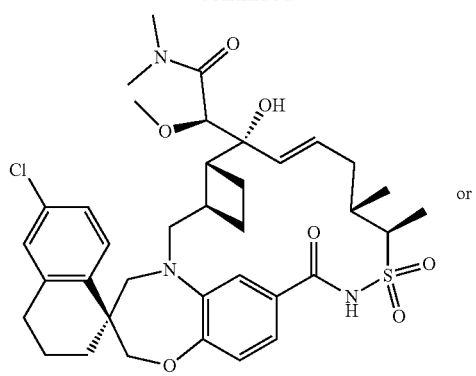
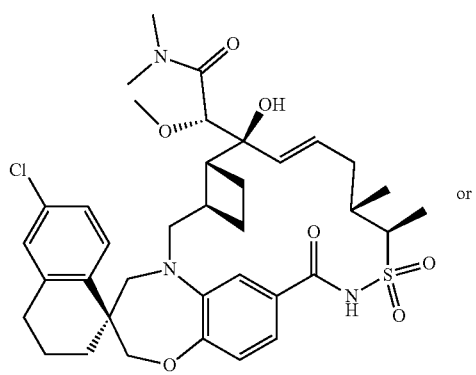
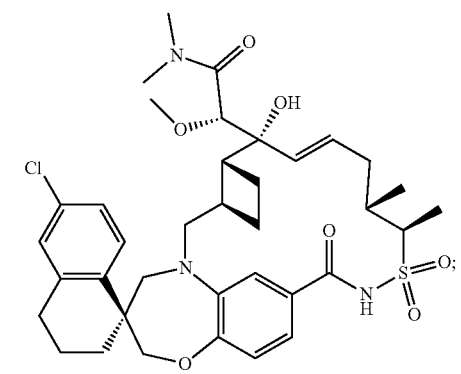
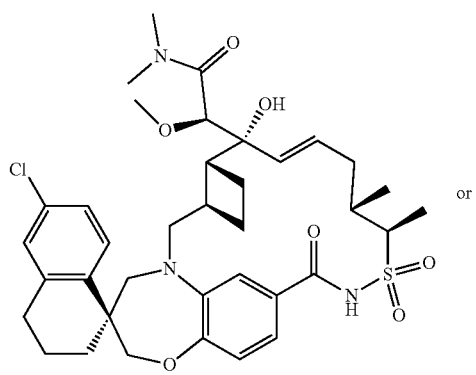
or
or
or;
or
382
-continued
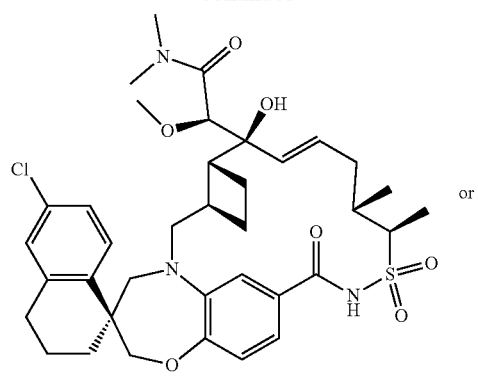
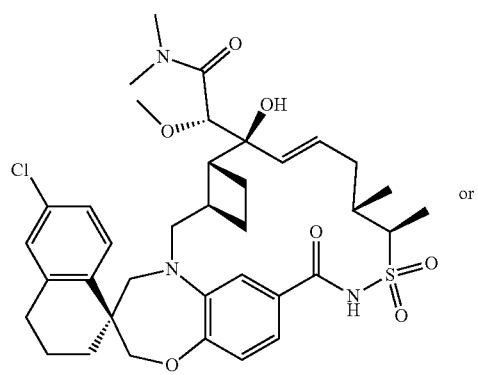
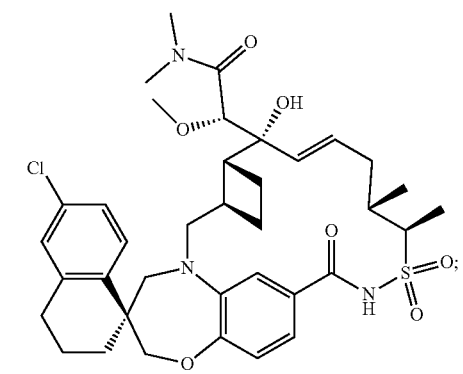
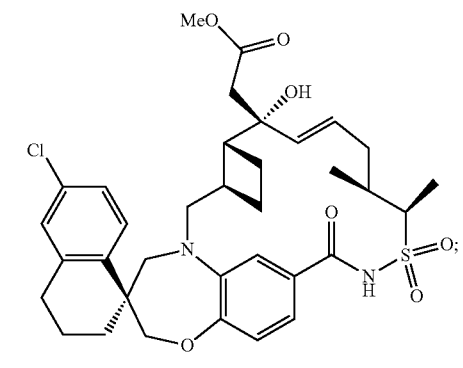
or
or
or;

383
-continued
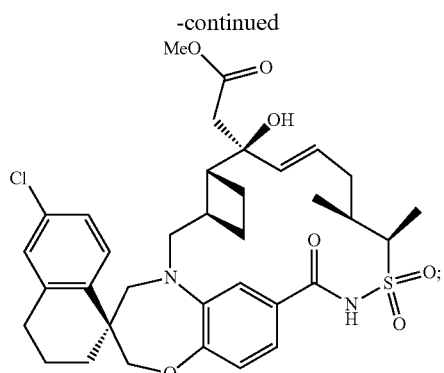
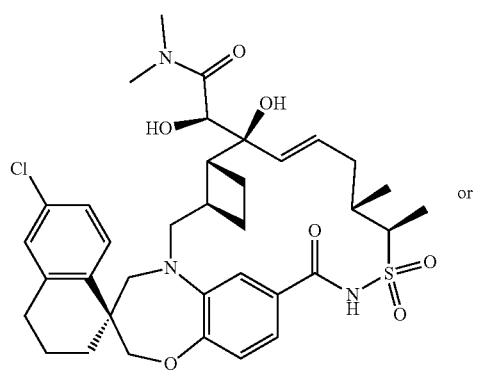
or
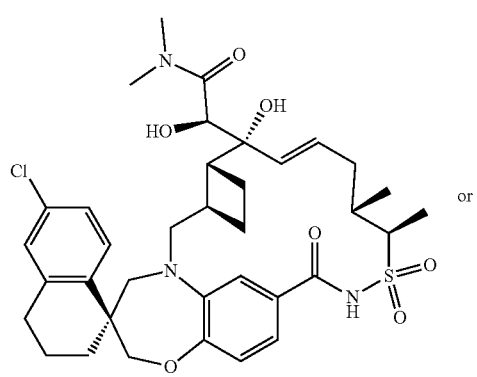
or
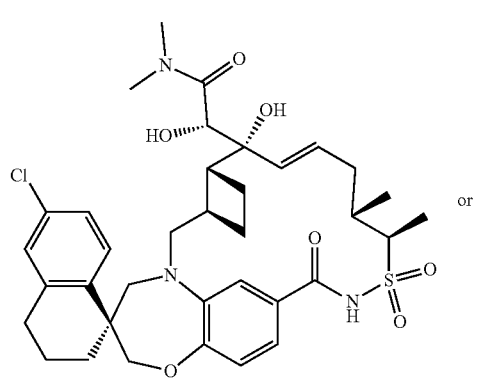
or
384
-continued
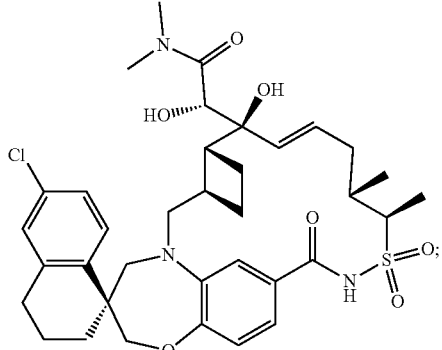
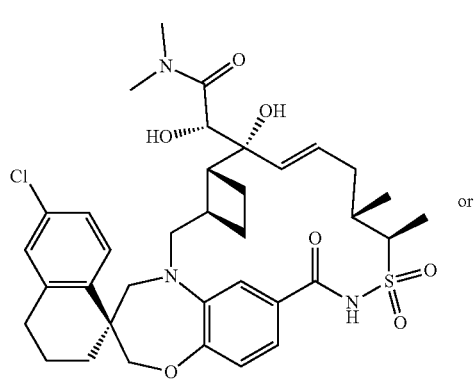
or
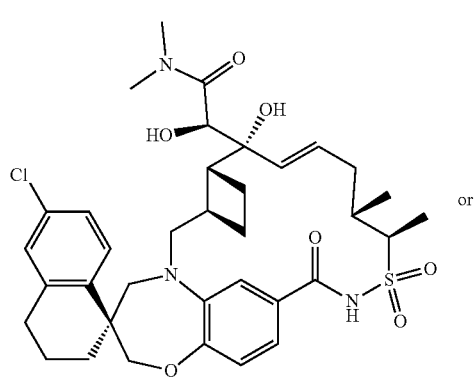
or
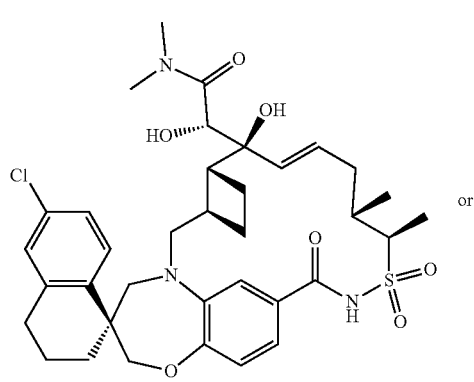
or 385
-continued
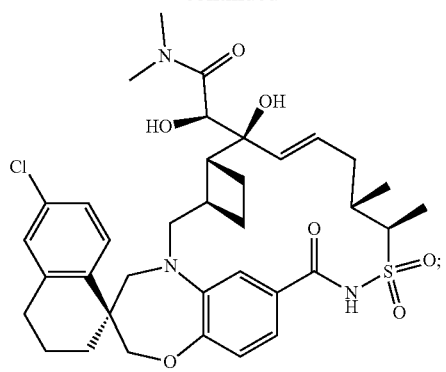
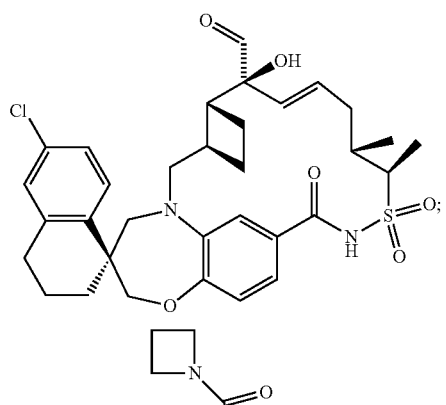
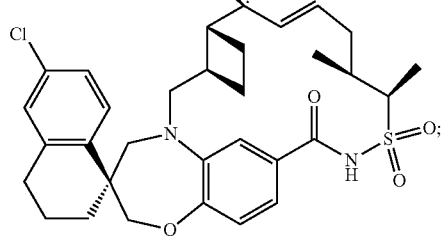
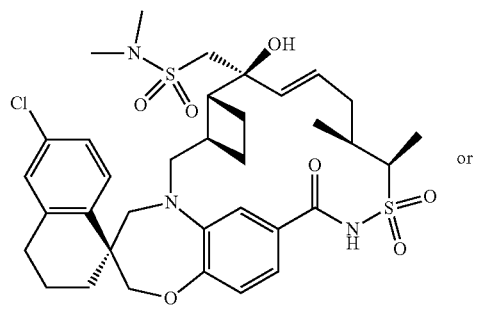
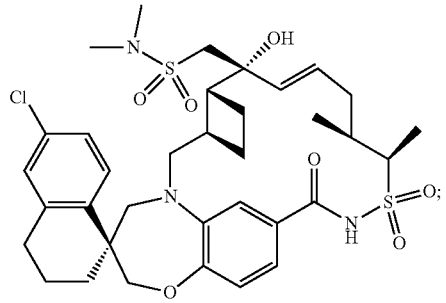
386
-continued
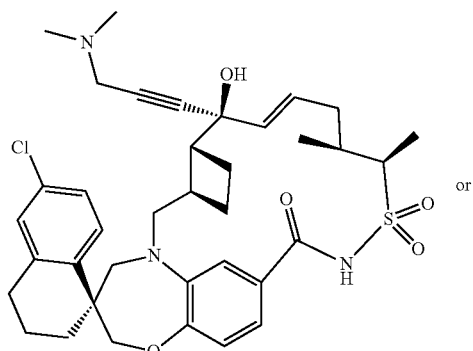
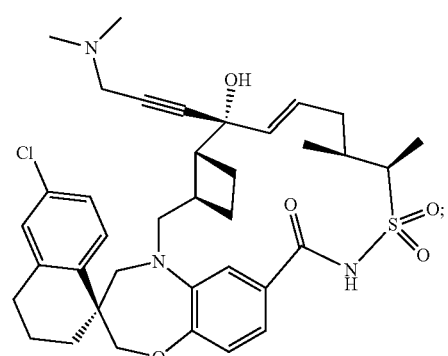
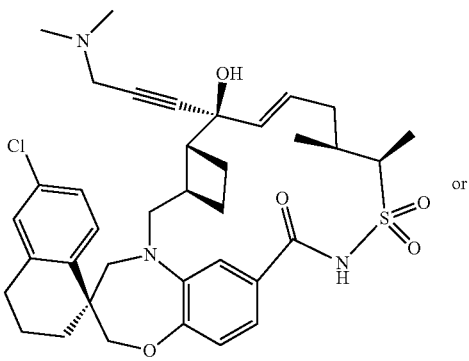
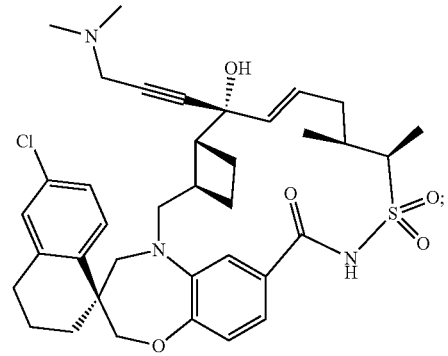

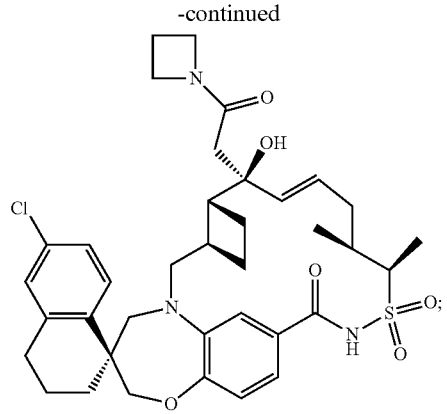
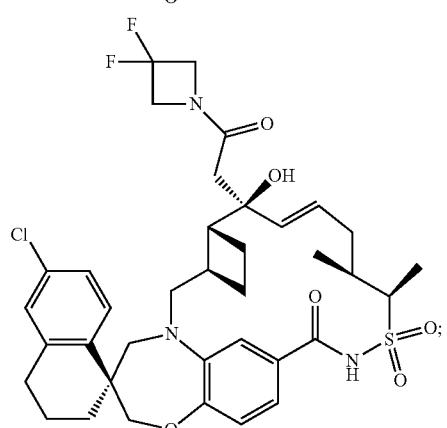
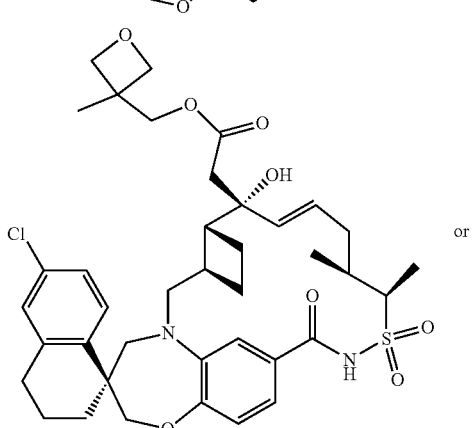
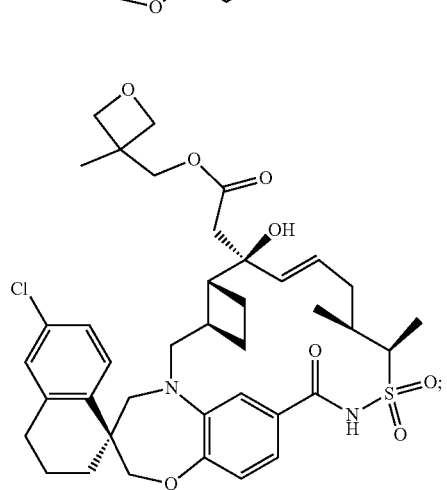
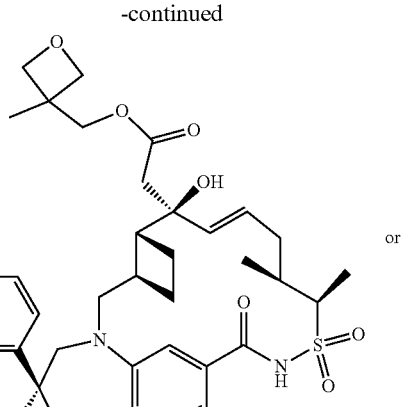
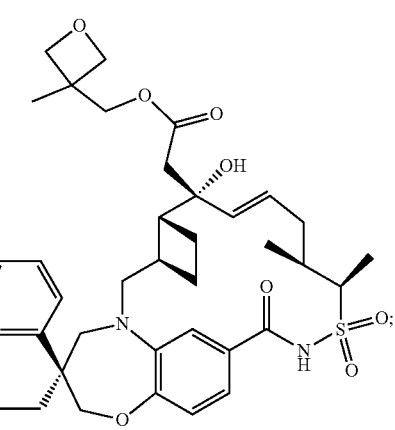
or
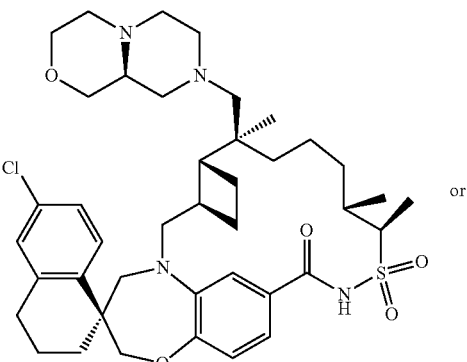
or
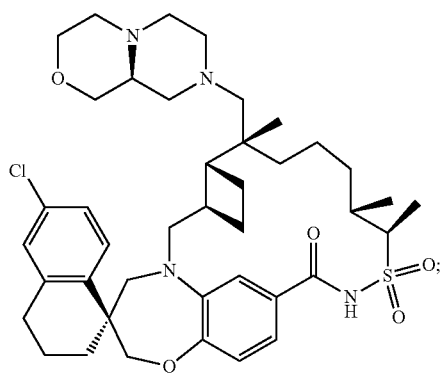

389
-continued
390
-continued
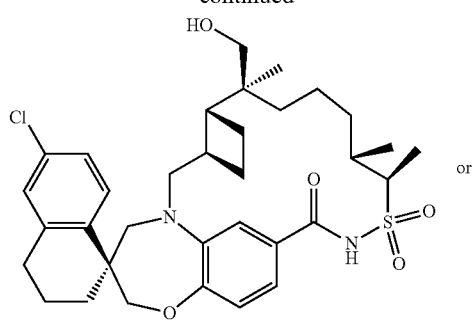
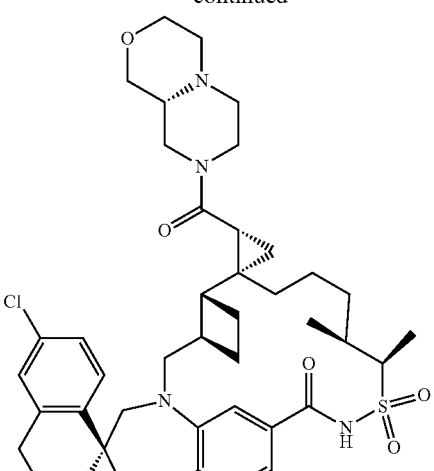
or
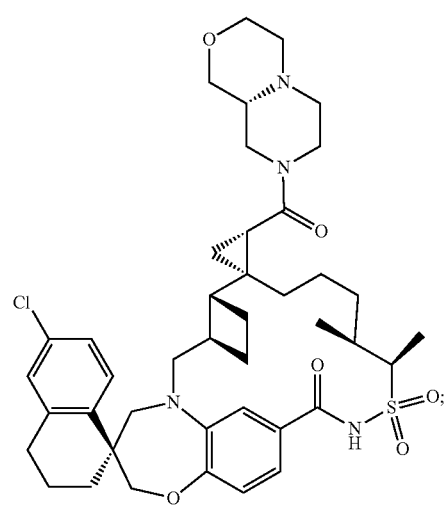
or
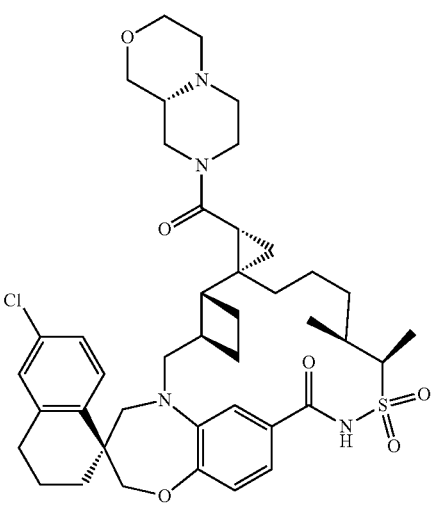
or 391
-continued
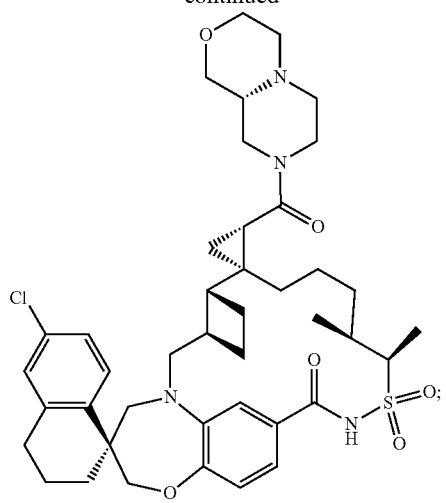
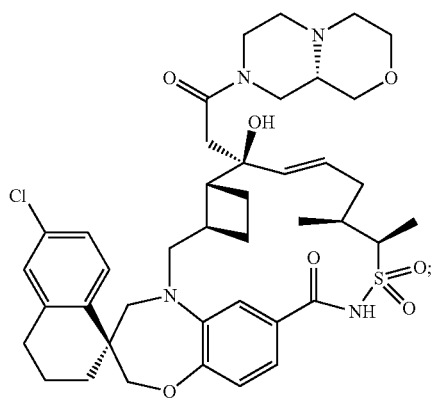
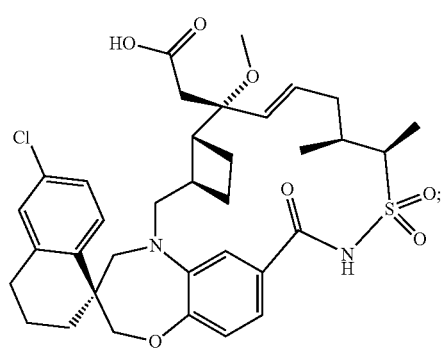
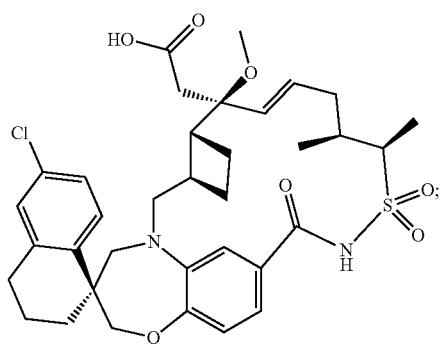
392
-continued
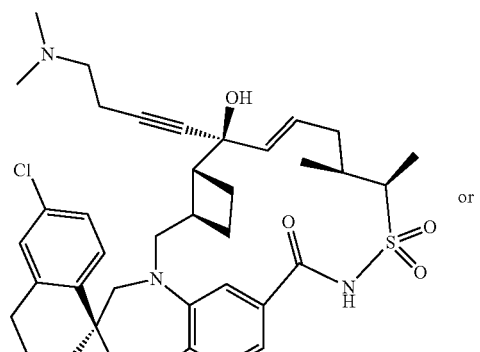
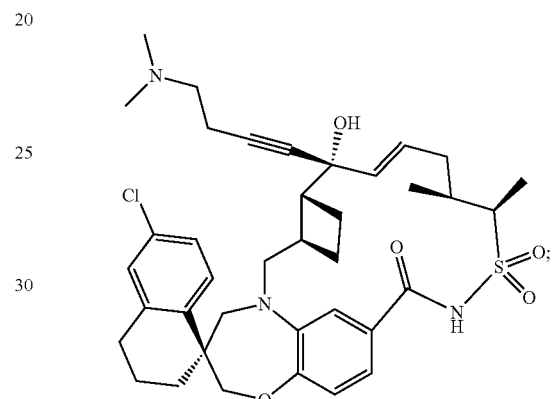
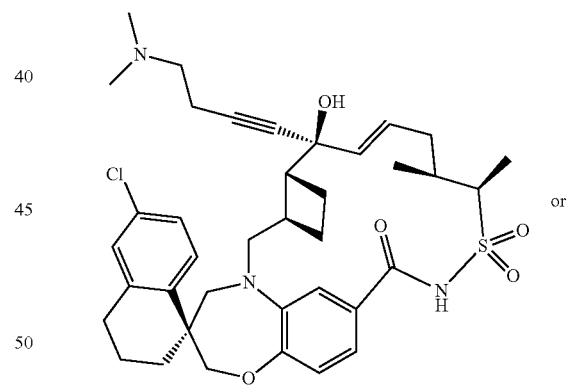
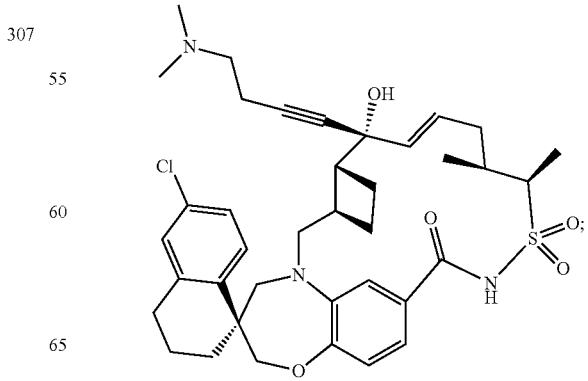
or 393
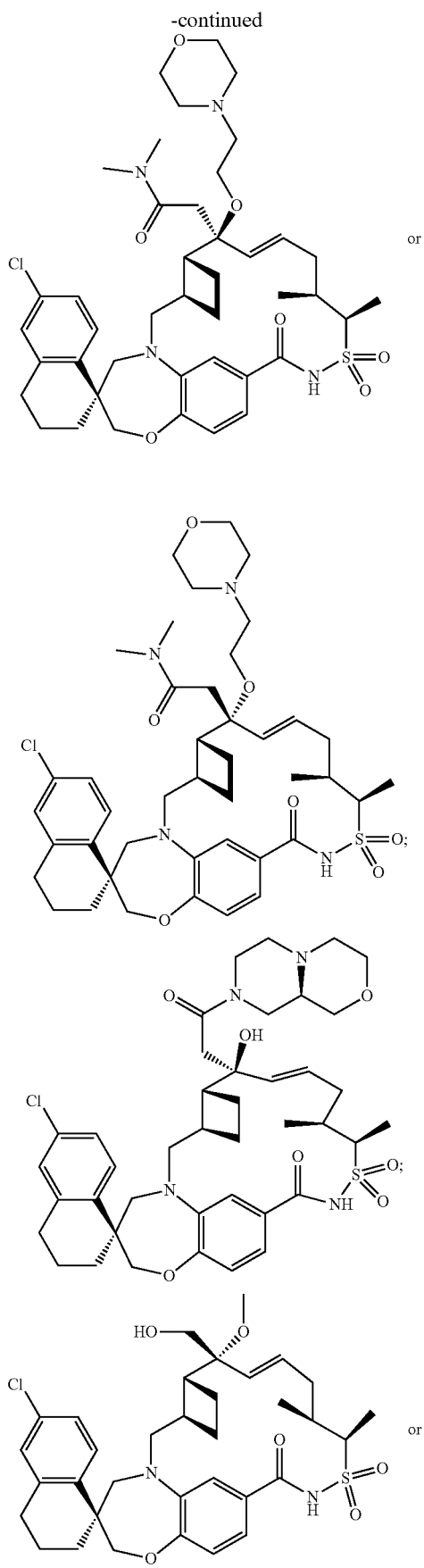
394
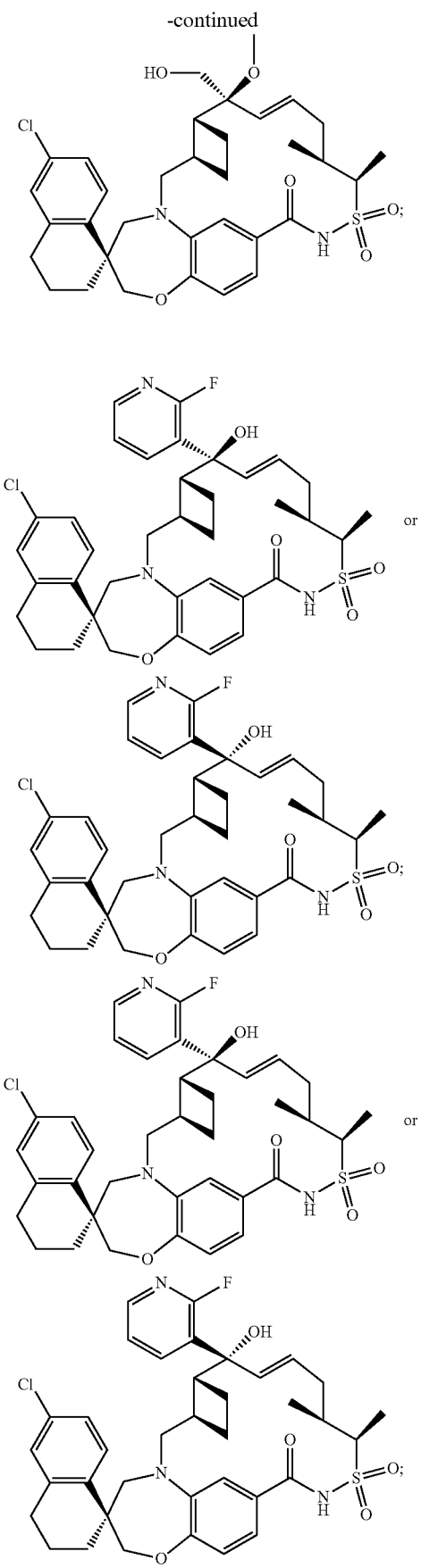

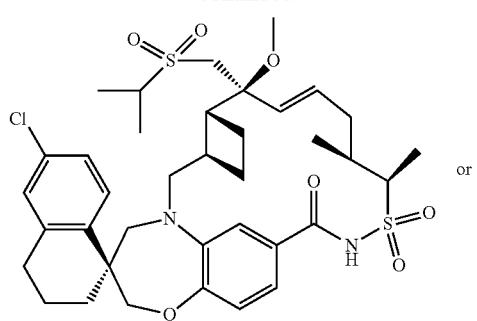
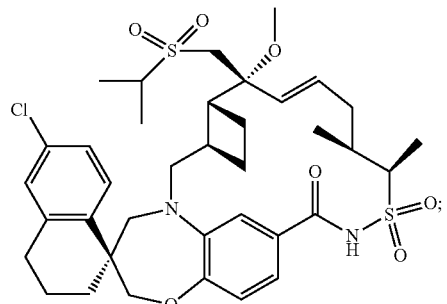
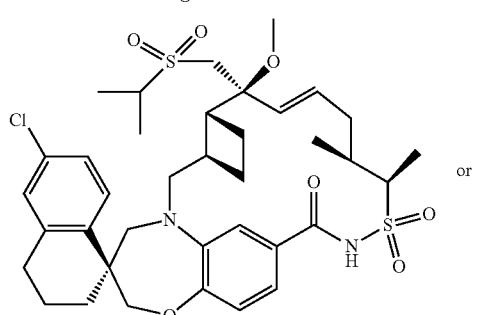
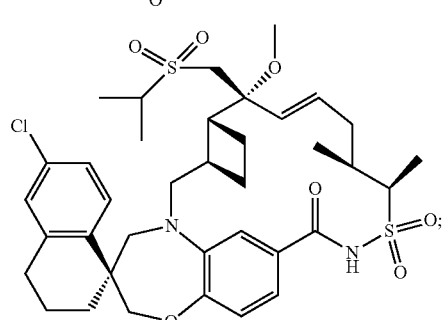
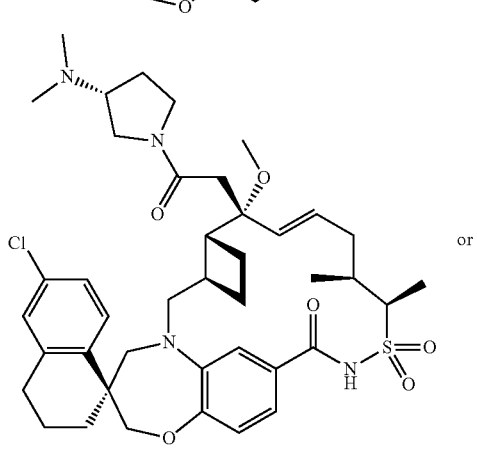
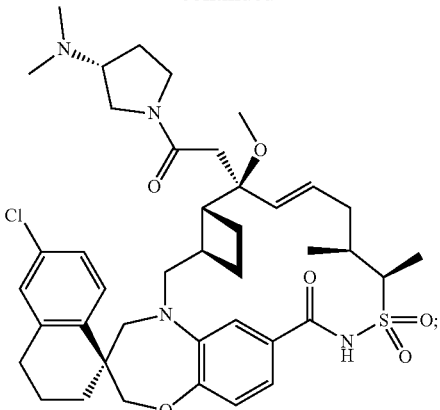
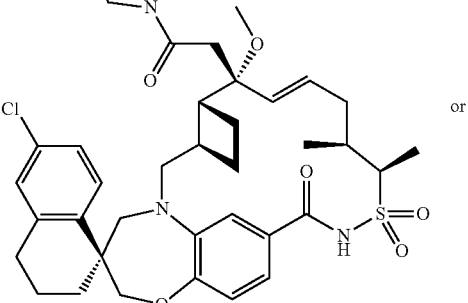

397
-continued
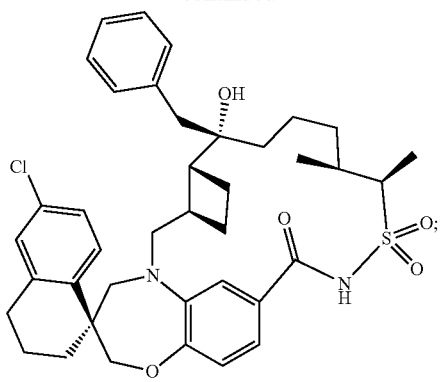
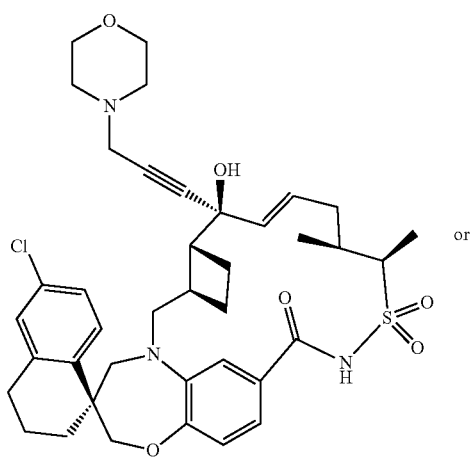
or
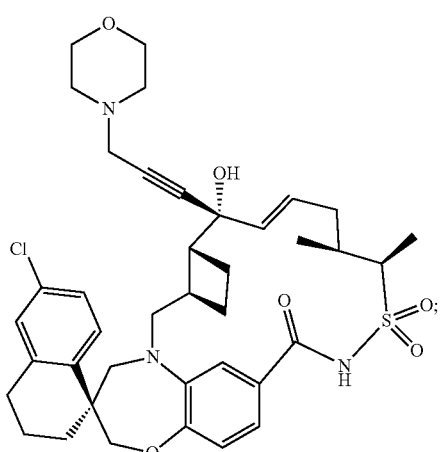
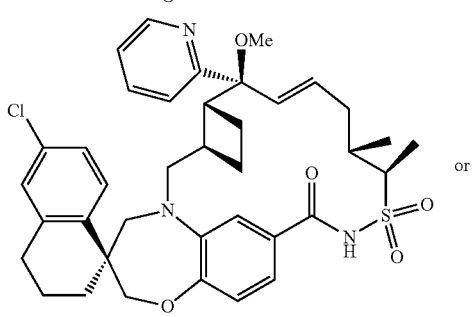
or
398
-continued
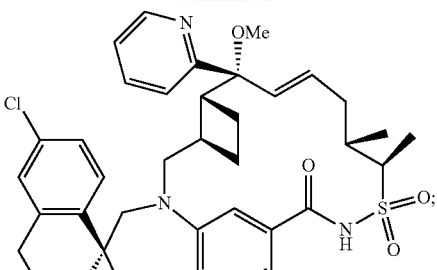
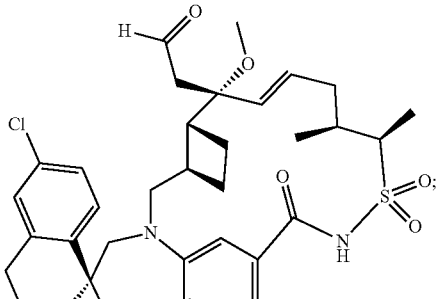
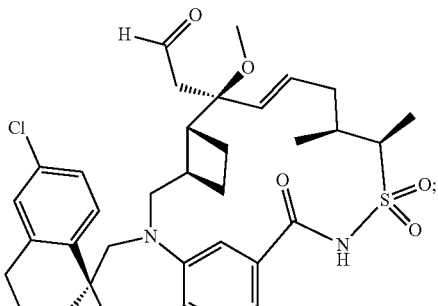
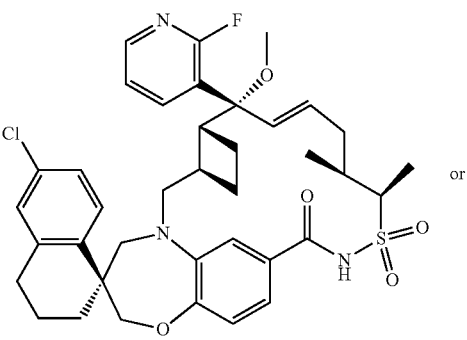
or
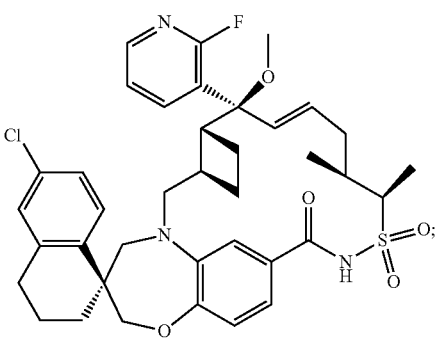

399
-continued
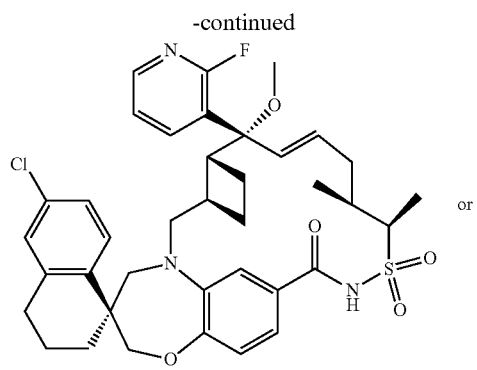
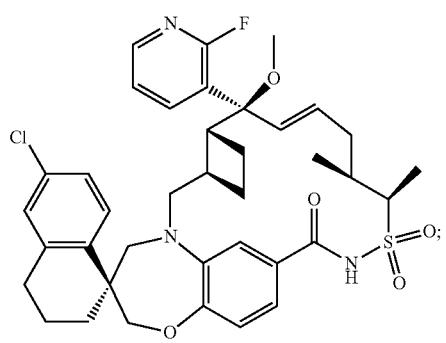
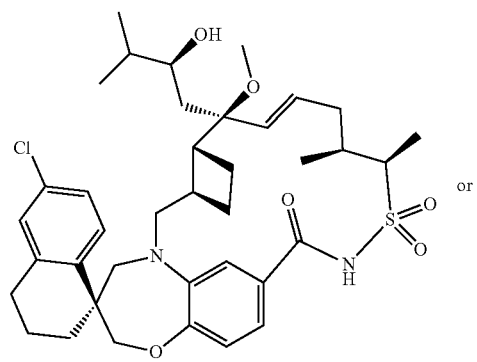
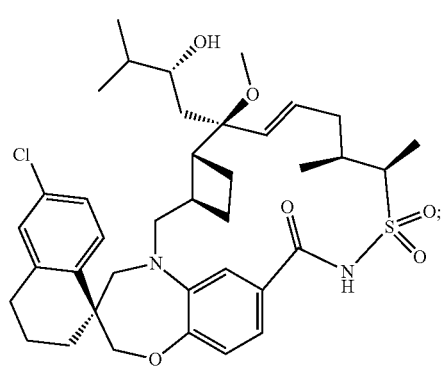
400
-continued
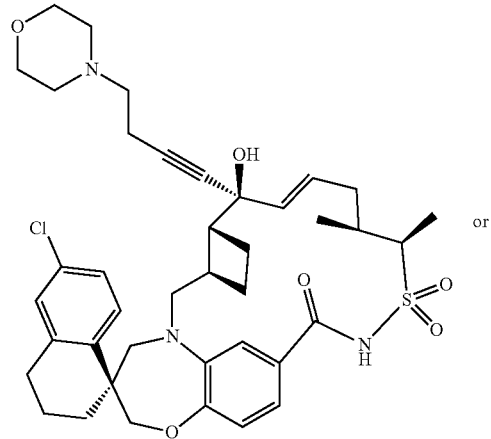
or
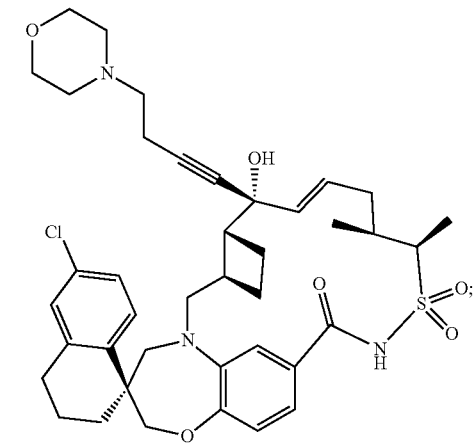
;
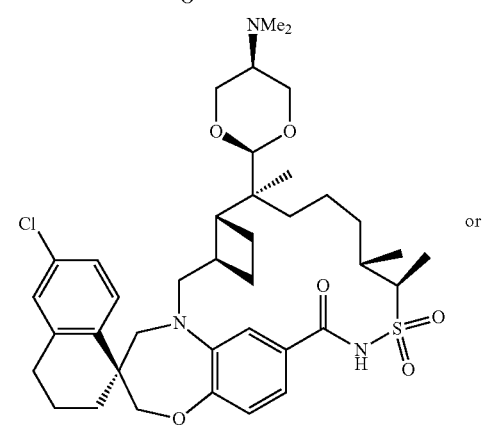
or
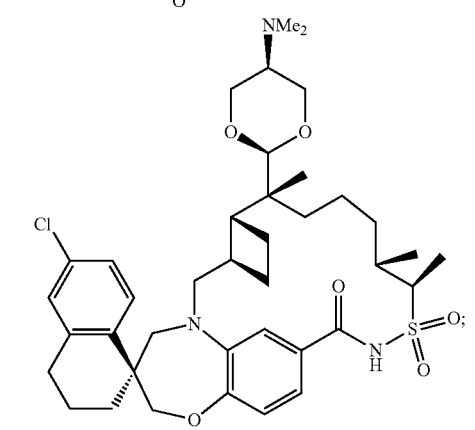
;

401
-continued
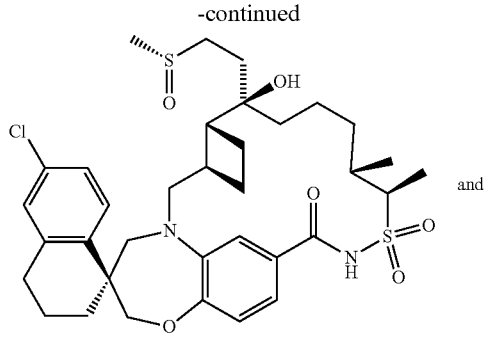
and
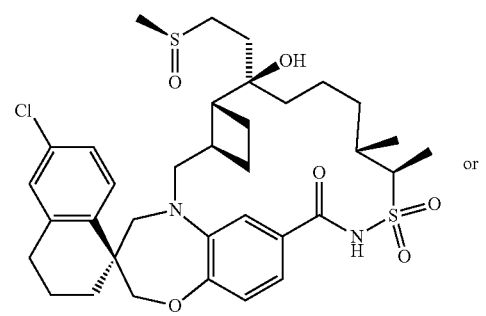
or
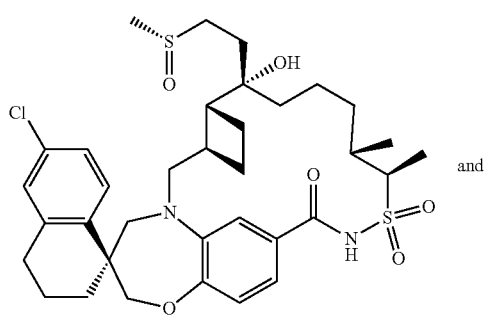
and
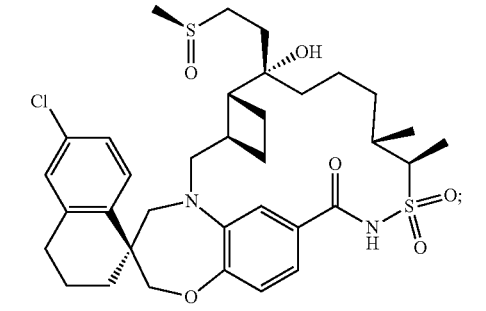
;
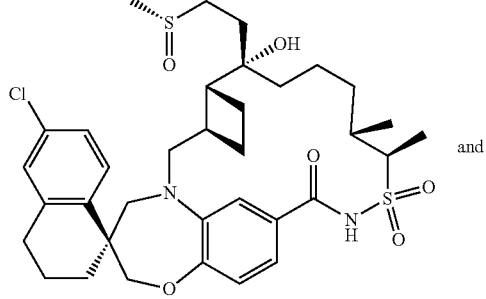
and
402
-continued
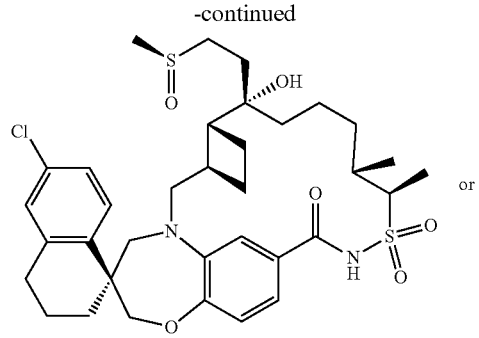
or
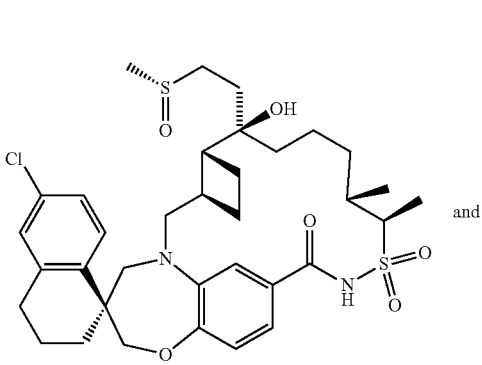
and
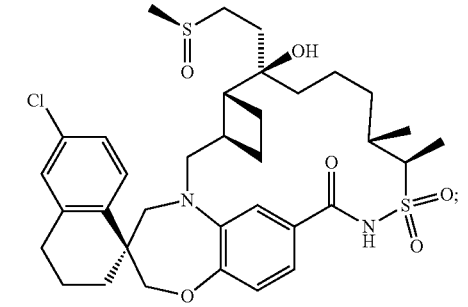
;
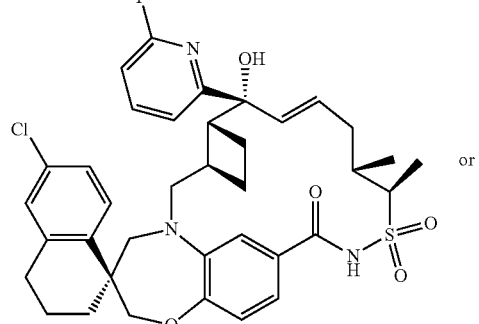
or
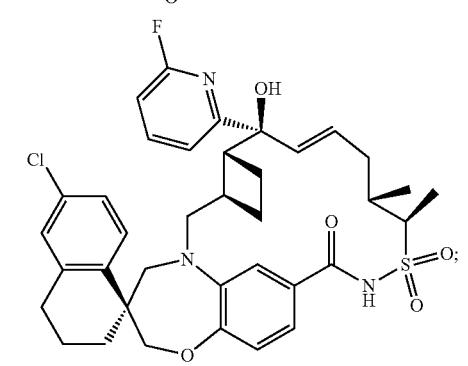
;

403
-continued
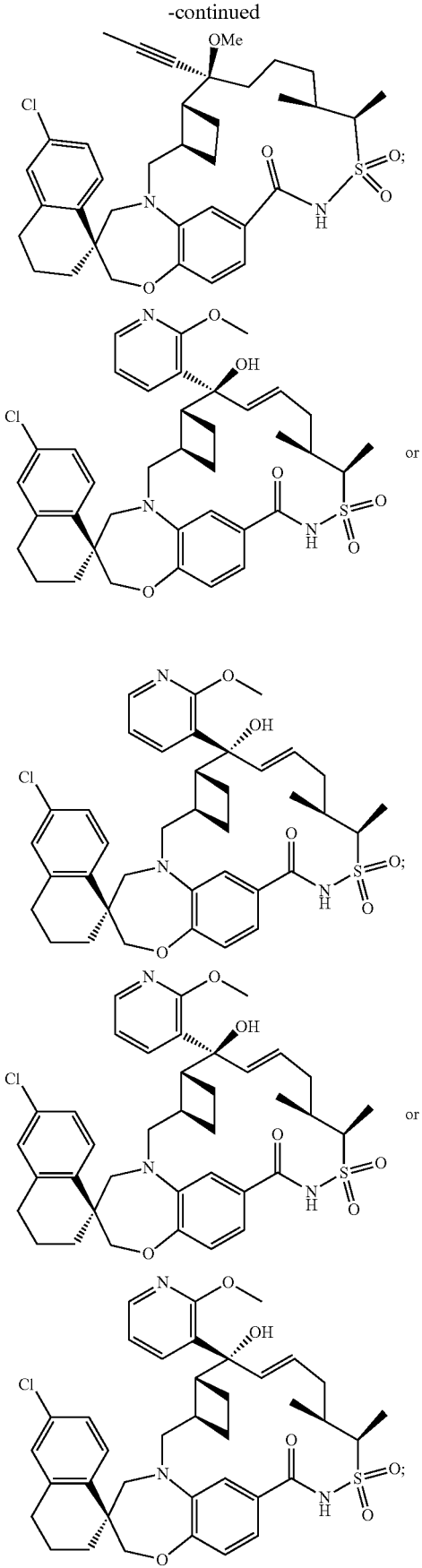
404
-continued
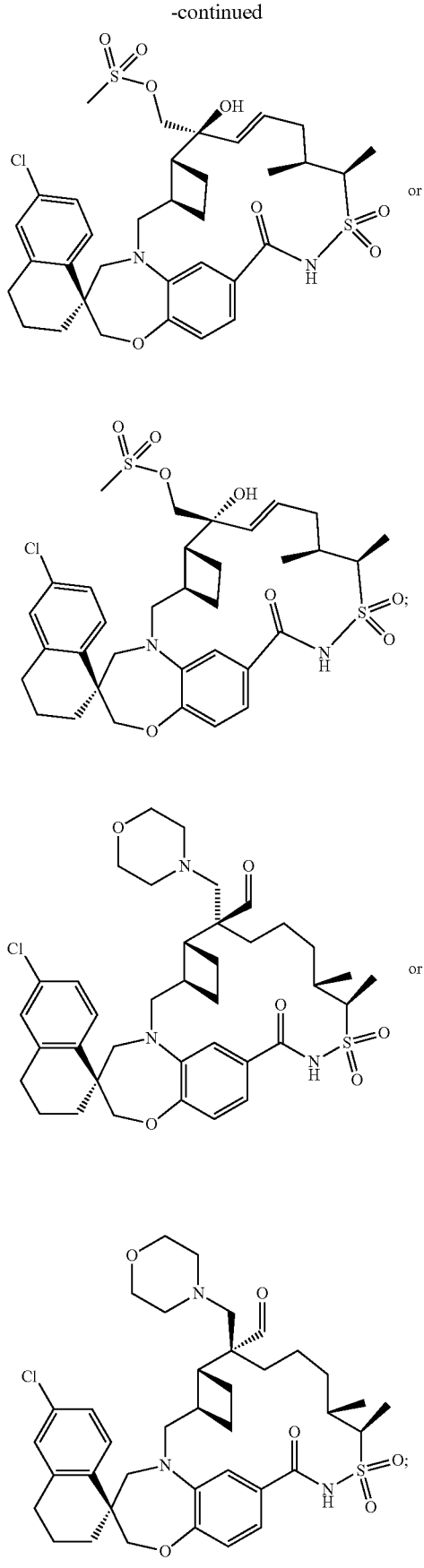

405
-continued

406
-continued

407
-continued
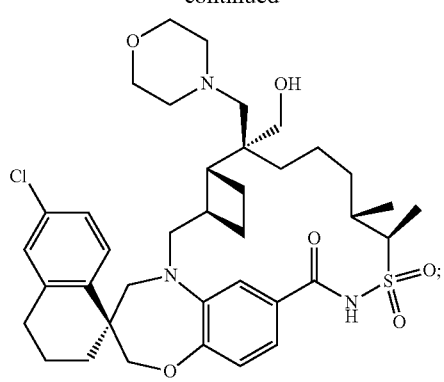
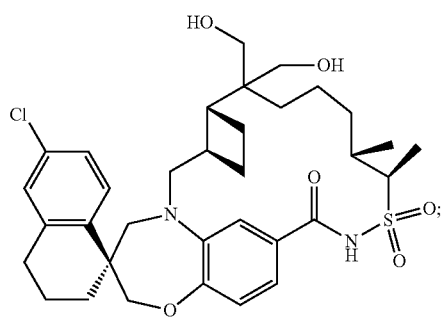
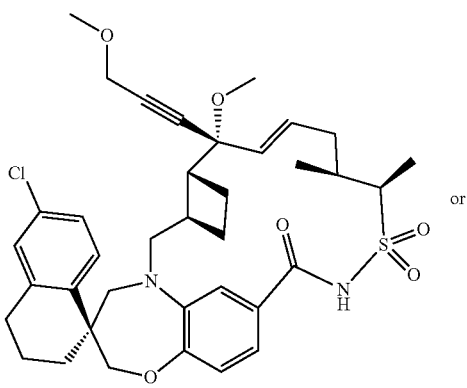
or
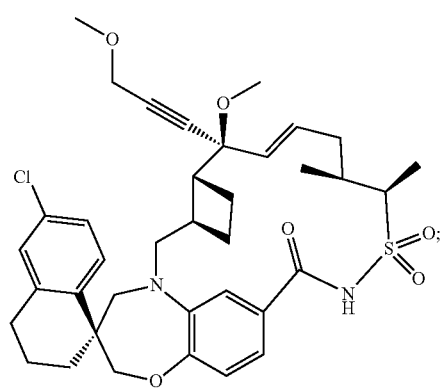
408
-continued
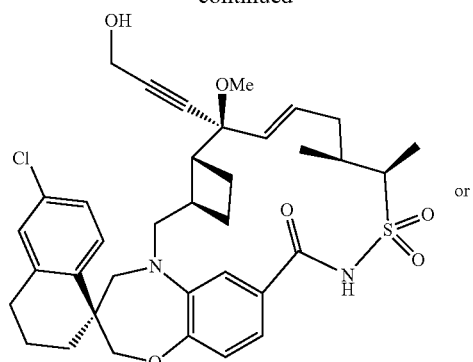
or
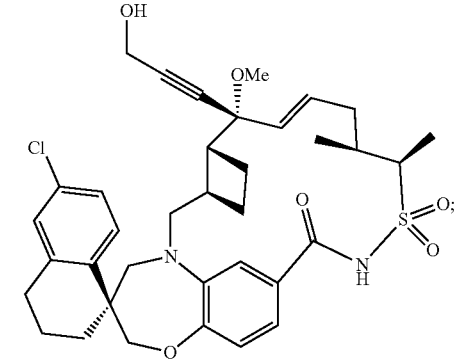
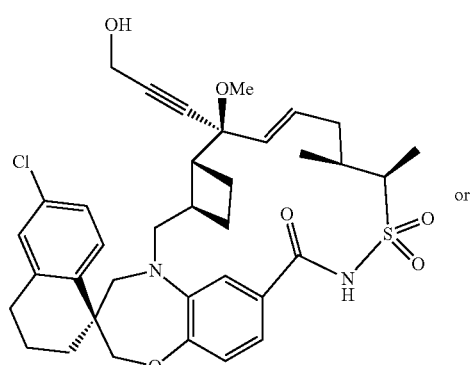
or
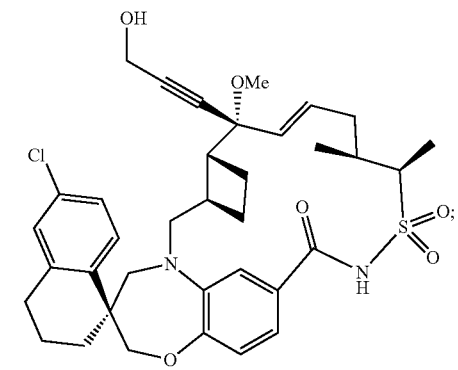

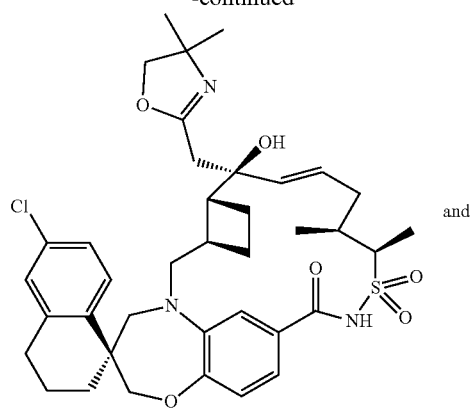
and
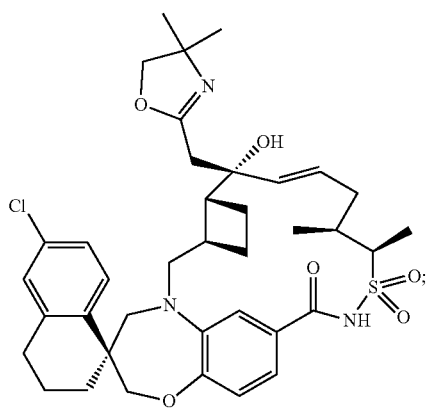
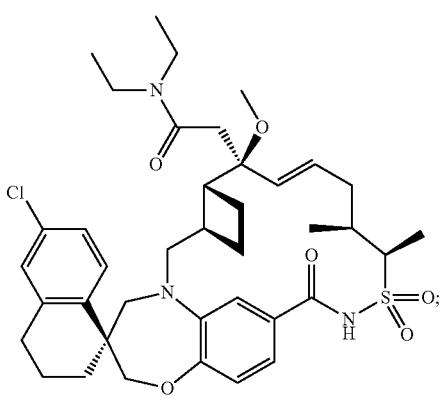
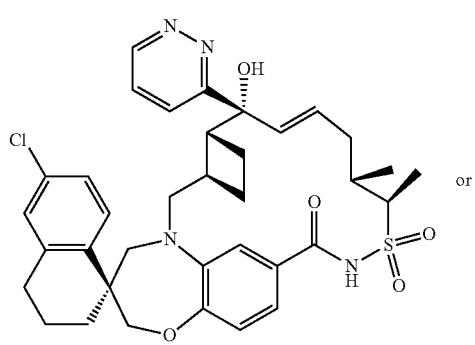
or
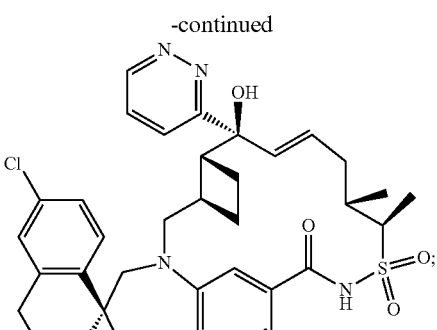
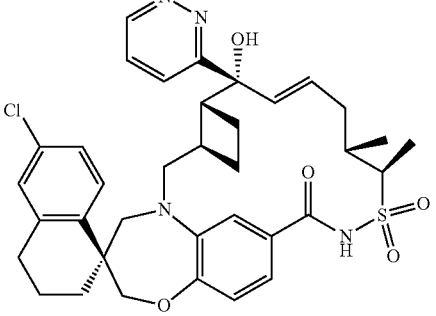
or
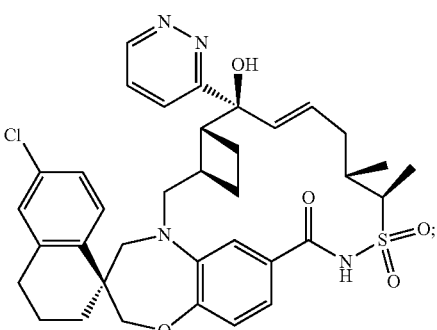
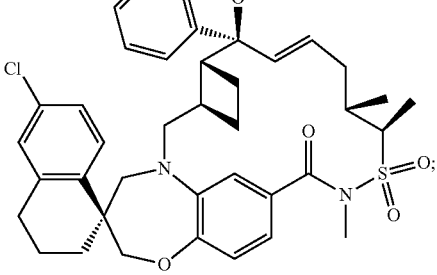
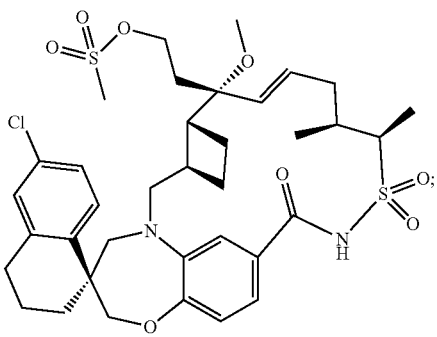

411
-continued
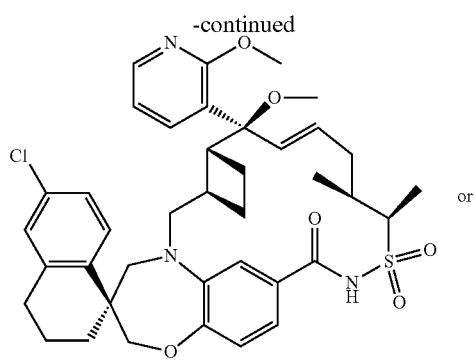
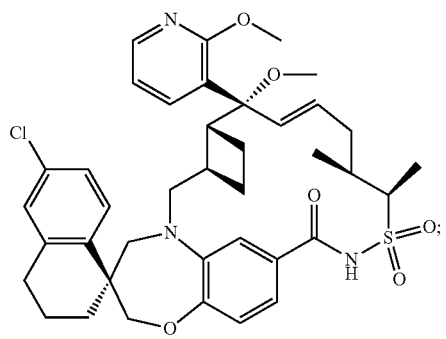
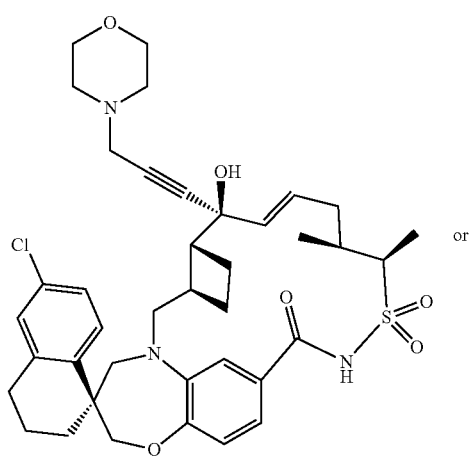
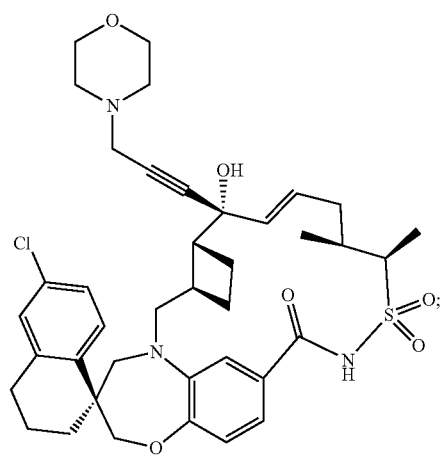
412
-continued
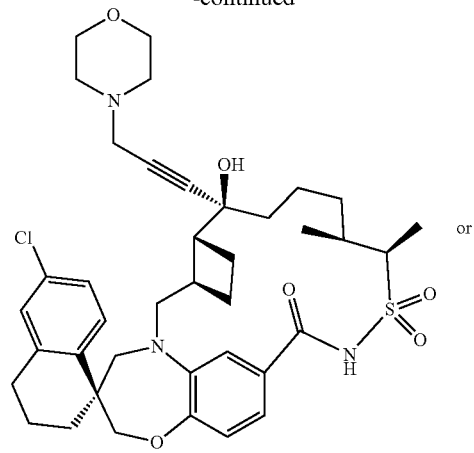
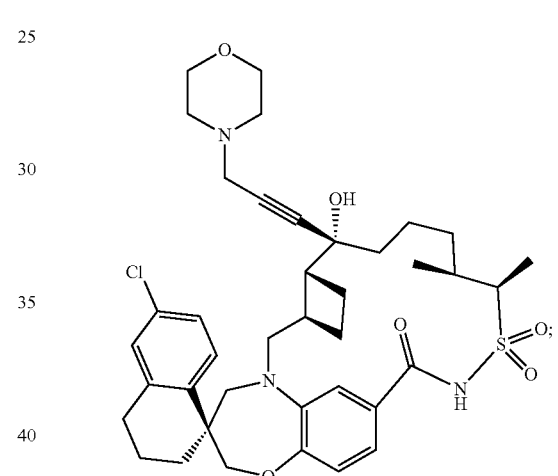
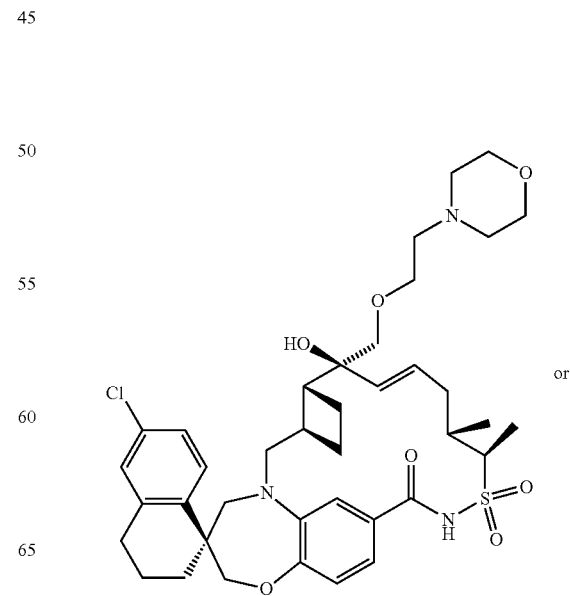
or
or
or 413
-continued
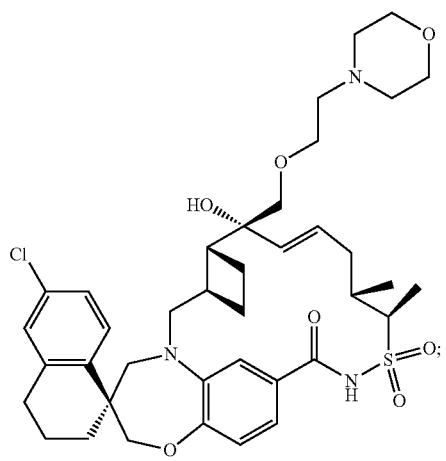
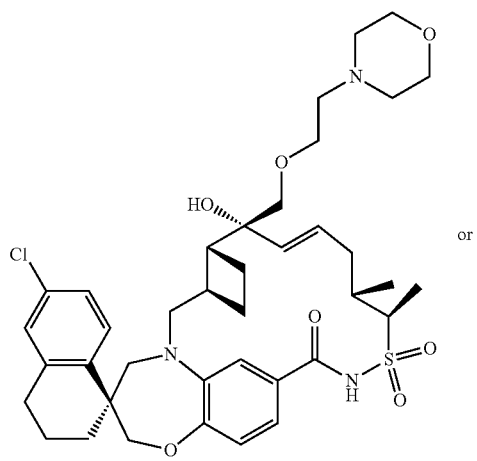
or
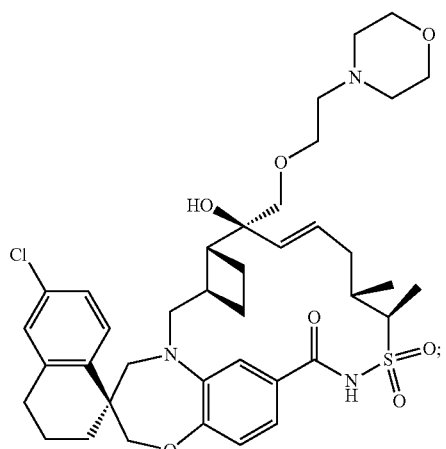
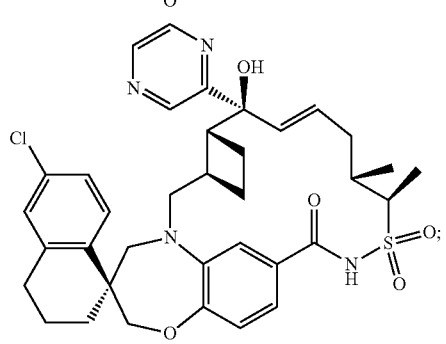
414
-continued
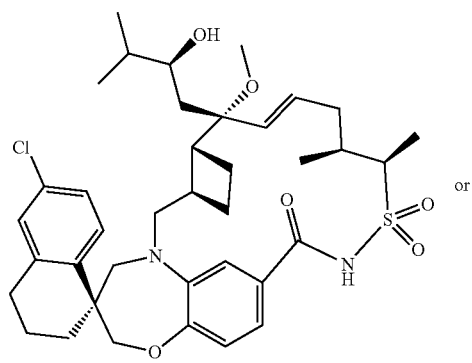
or
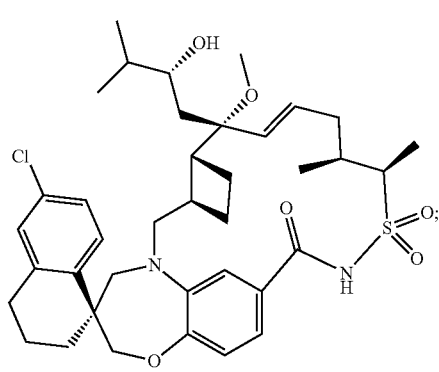
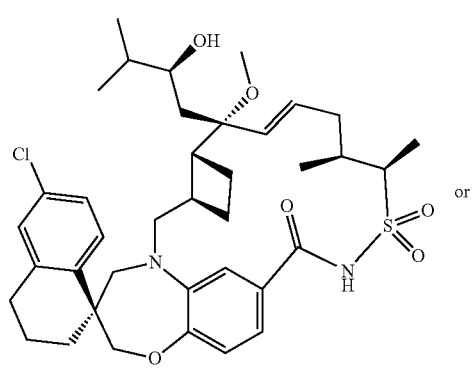
or
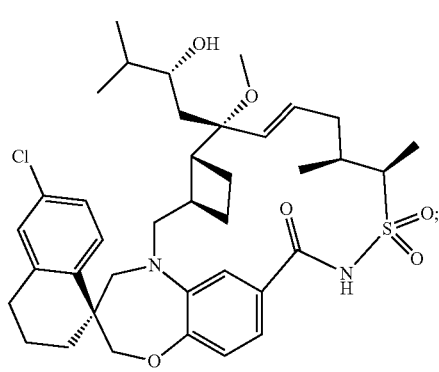

415
-continued
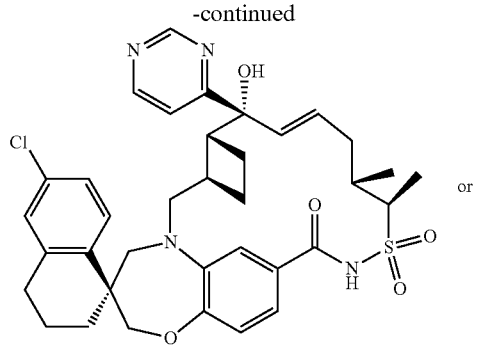
or
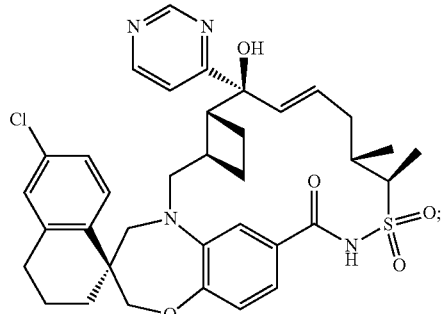
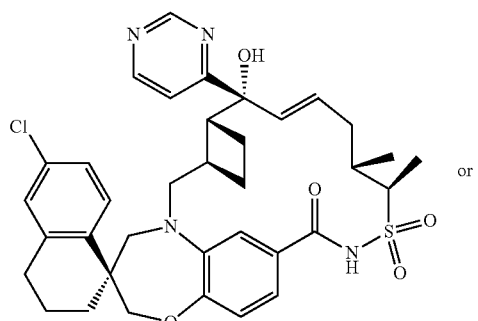
or
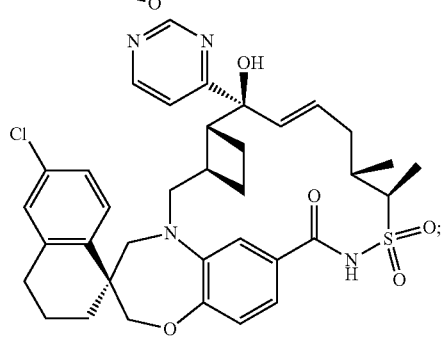
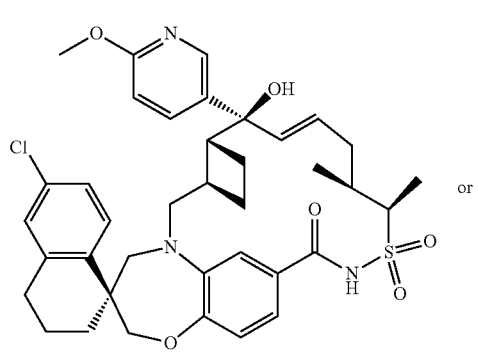
or
416
-continued
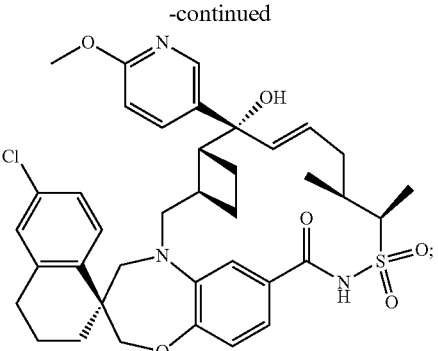
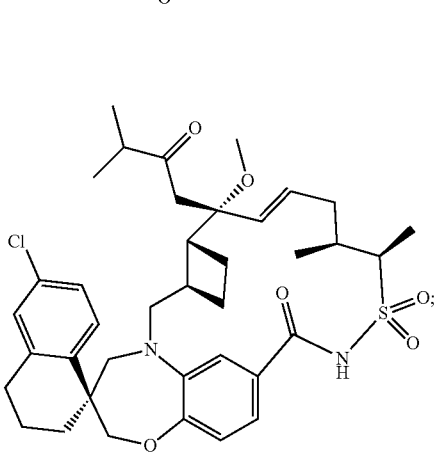
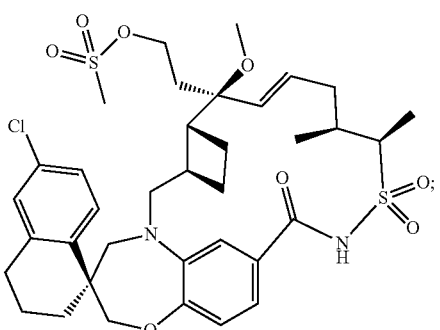
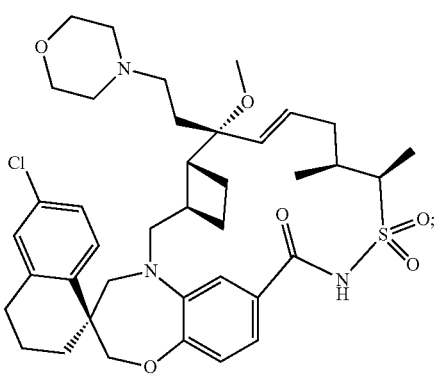

417
-continued
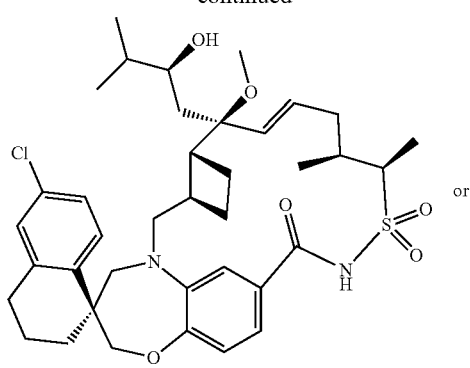
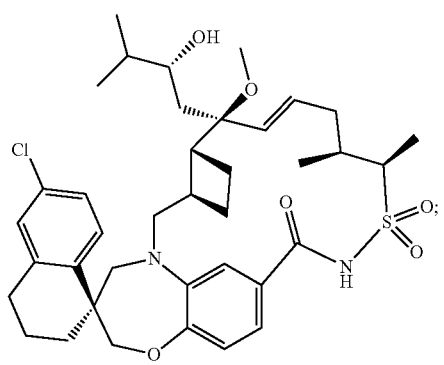
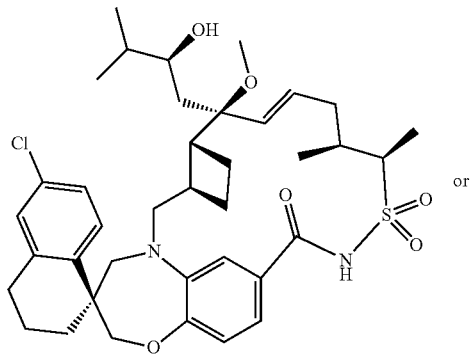
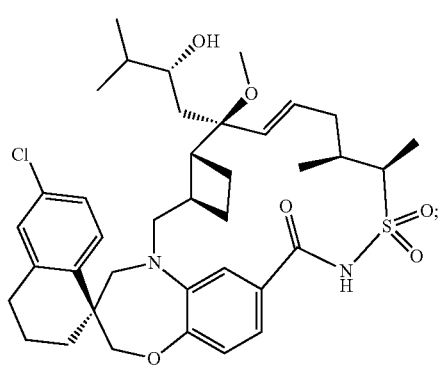
418
-continued
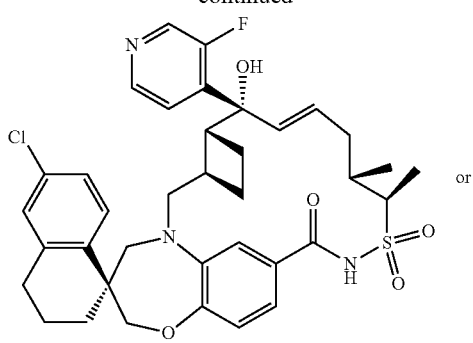
or
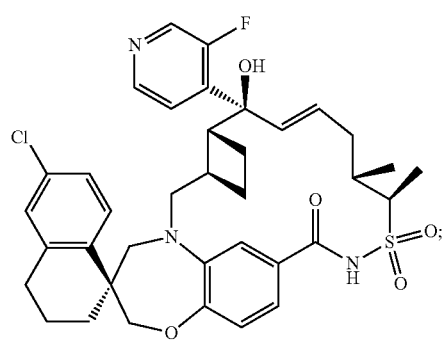
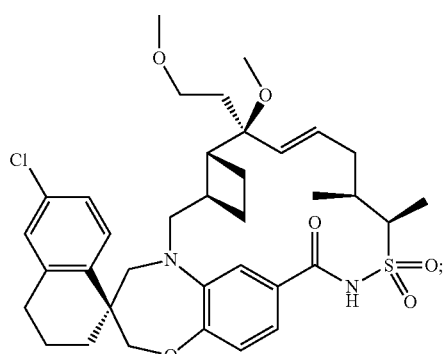
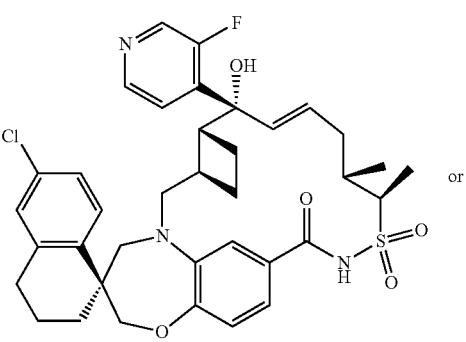
or
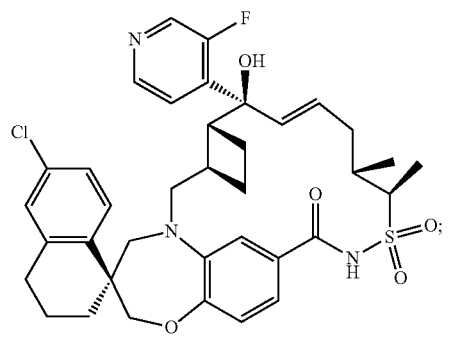

419
-continued
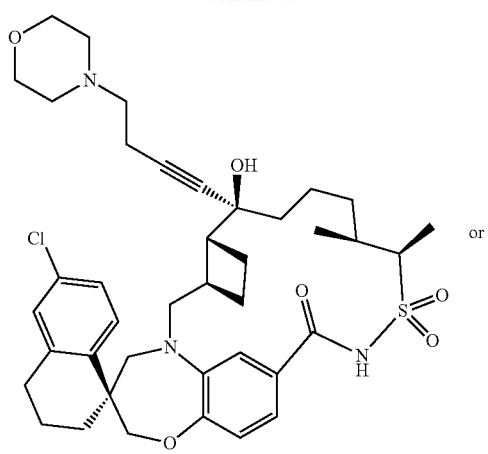
420
-continued
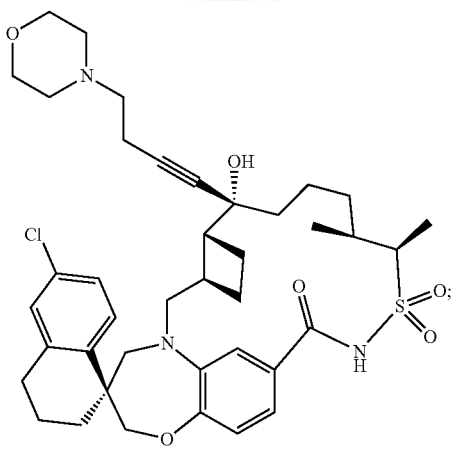
or
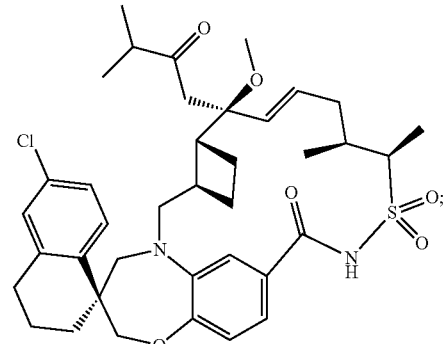
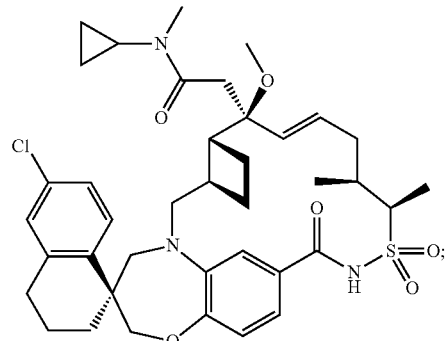
or
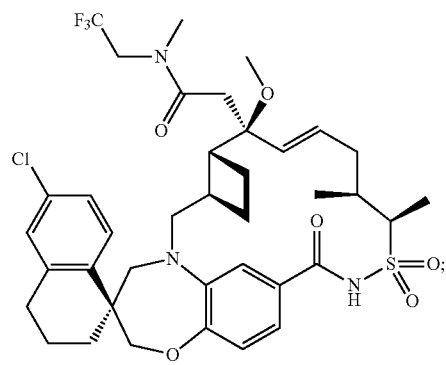

421
-continued
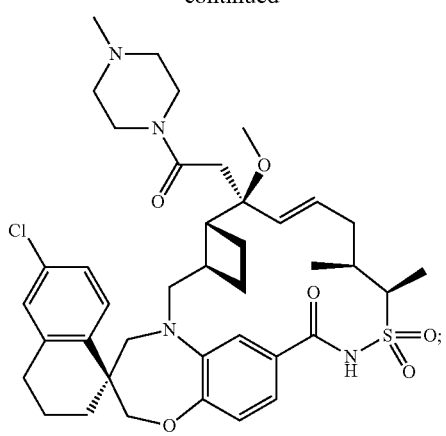
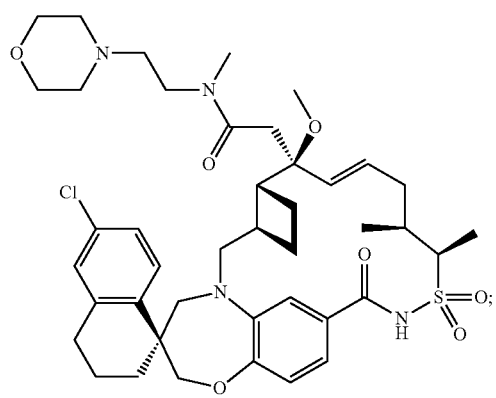
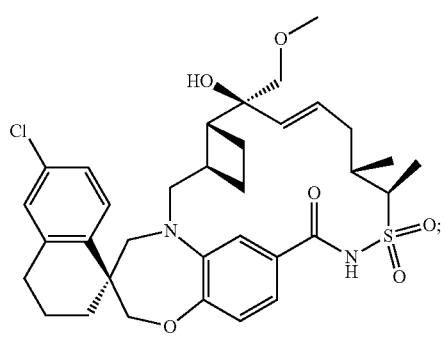
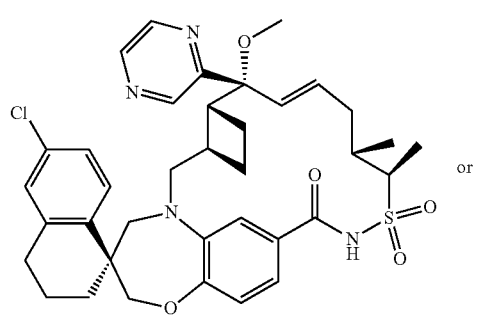
or
422
-continued
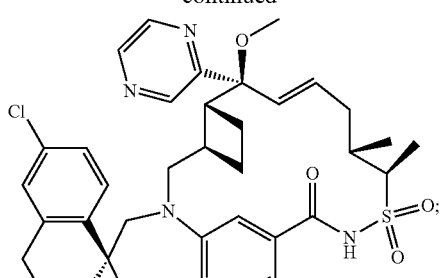
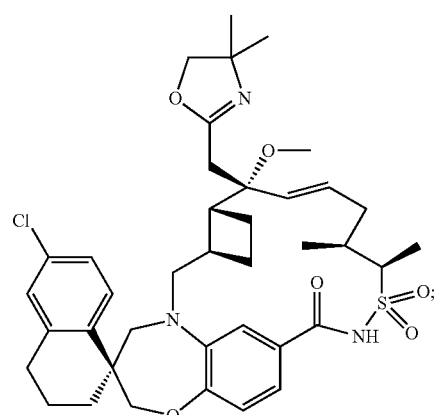
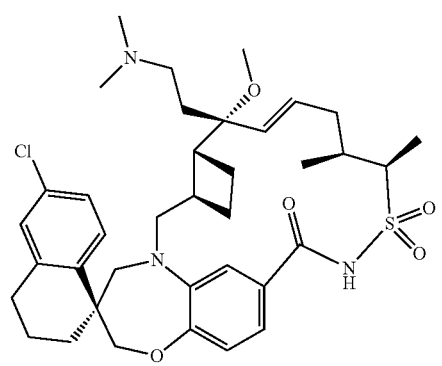
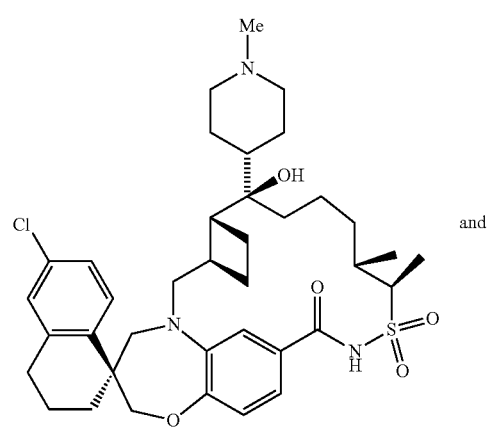
and

423
-continued
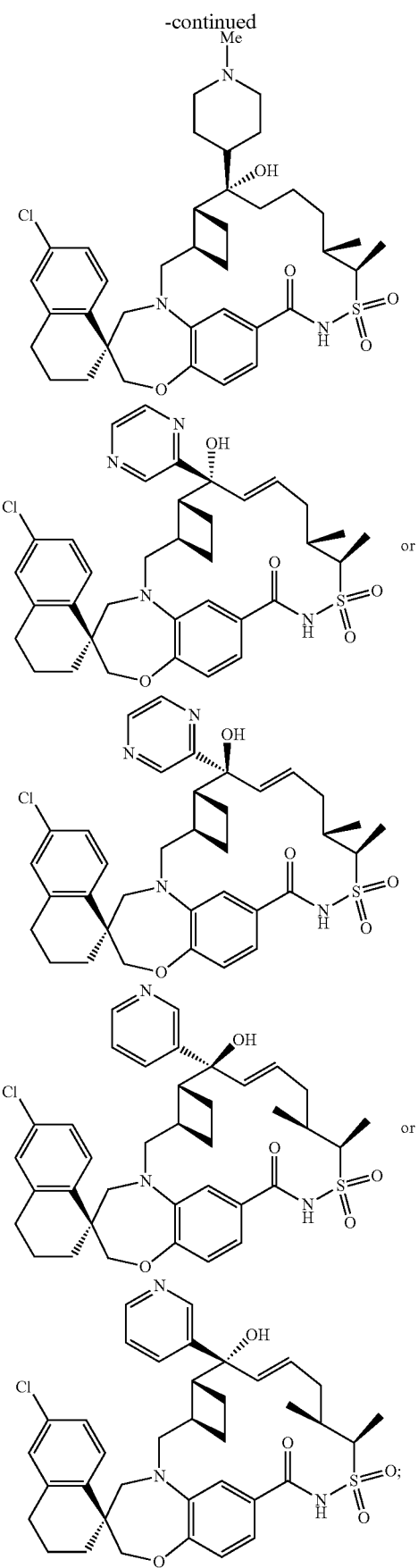
424
-continued
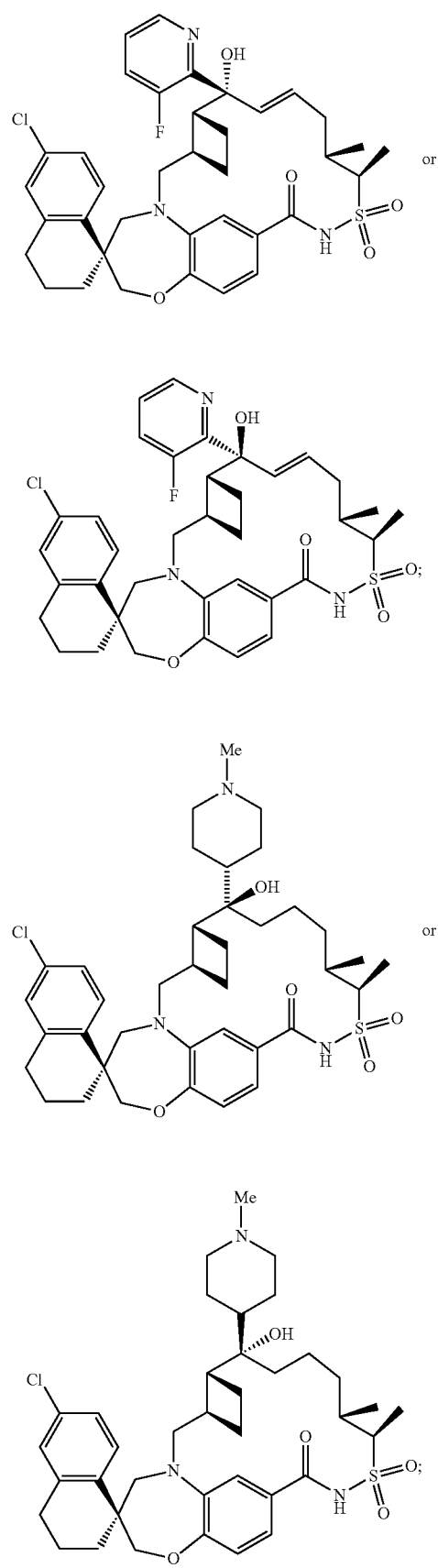 [SMILES: C[C@@H]1[C@@H](C)C/C=C/[C@](O)(c2ncccc2F)[C@@H]2CC[C@H]2CN2C[C@@]3(CCCc4cc(Cl)ccc43)COc3ccc(cc32)C(=O)NS1(=O)=O ; C[C@@H]1[C@@H](C)C/C=C/[C@@](O)(c2ncccc2F)[C@@H]2CC[C@H]2CN2C[C@@]3(CCCc4cc(Cl)ccc43)COc3ccc(cc32)C(=O)NS1(=O)=O ; C[C@@H]1[C@@H](C)CCC[C@@](O)(C2CCN(C)CC2)[C@@H]2CC[C@H]2CN2C[C@@]3(CCCc4cc(Cl)ccc43)COc3ccc(cc32)C(=O)NS1(=O)=O ; C[C@@H]1[C@@H](C)CCC[C@](O)(C2CCN(C)CC2)[C@@H]2CC[C@H]2CN2C[C@@]3(CCCc4cc(Cl)ccc43)COc3ccc(cc32)C(=O)NS1(=O)=O]

425
-continued
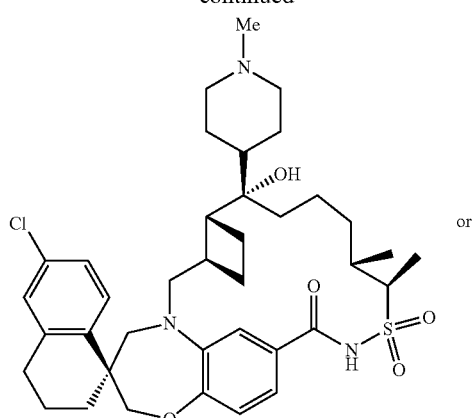
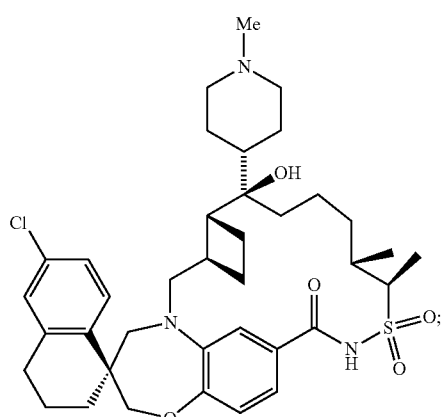
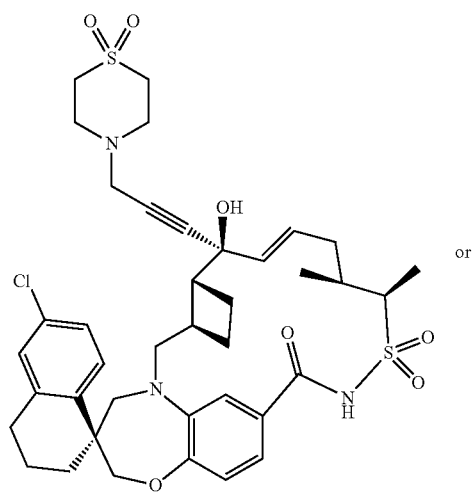
426
-continued
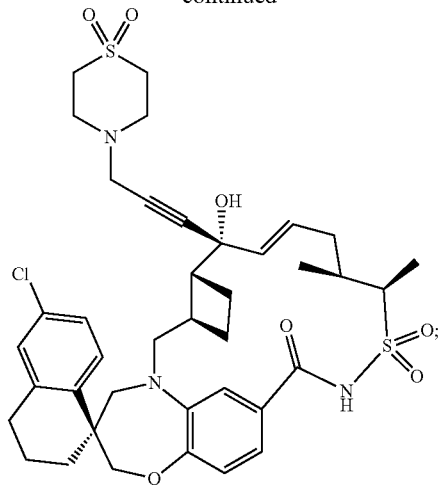
or
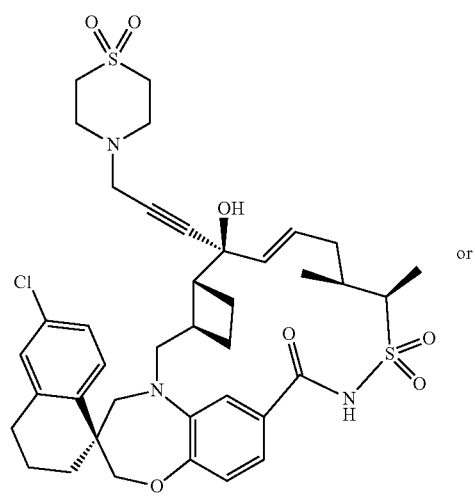
or
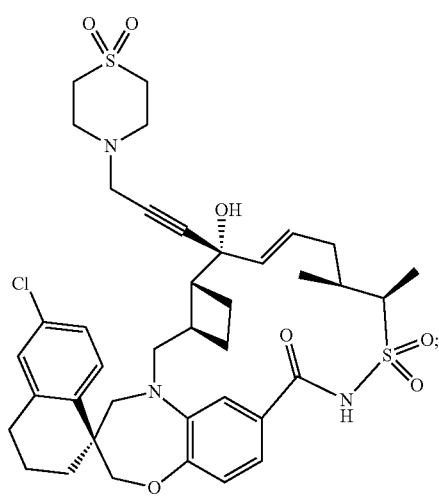

427
-continued
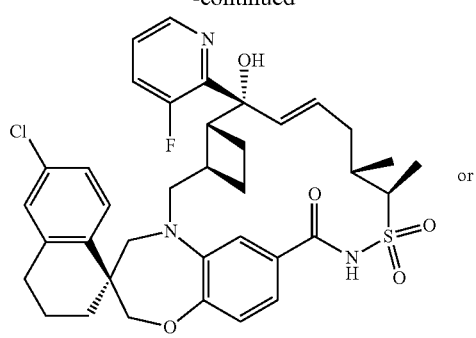
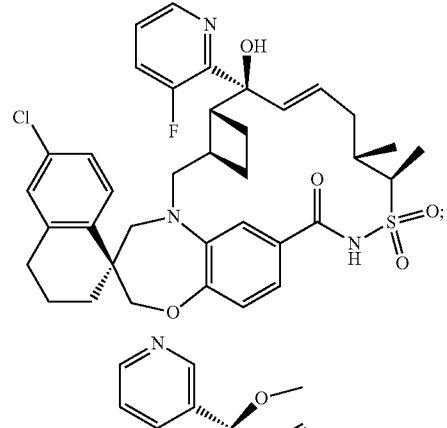
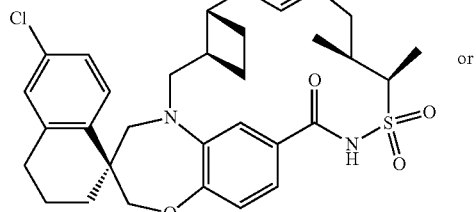
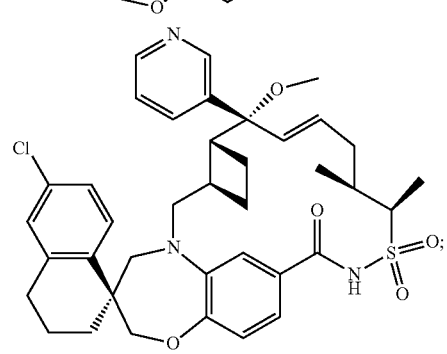
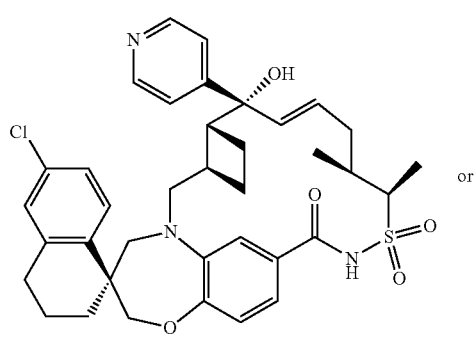
or
428
-continued
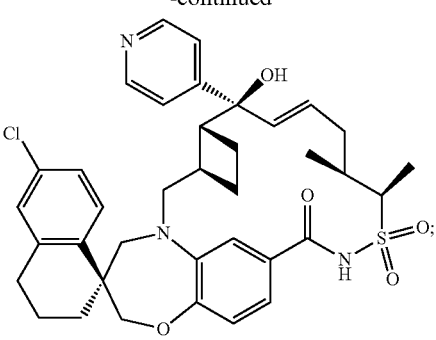
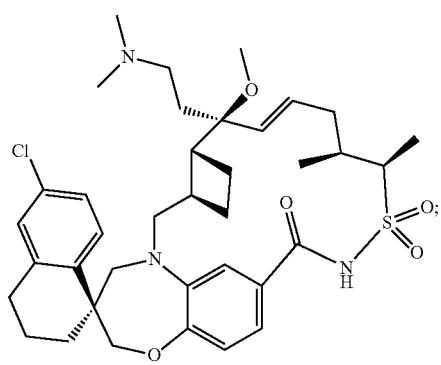
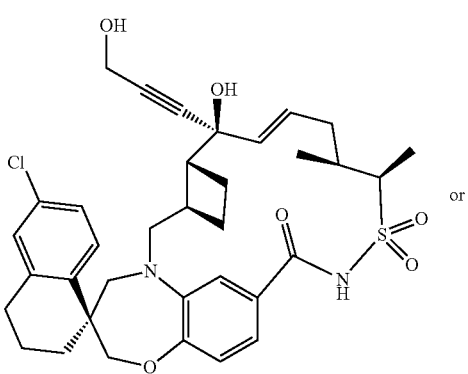
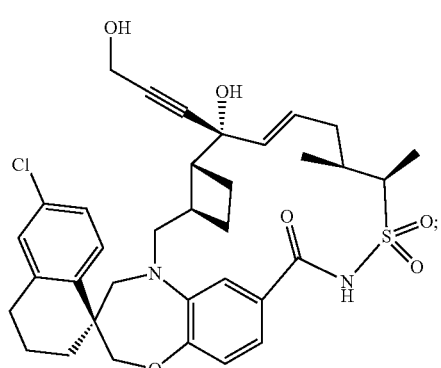
or

| 429 -continued | 430 -continued |
|---|---|
| 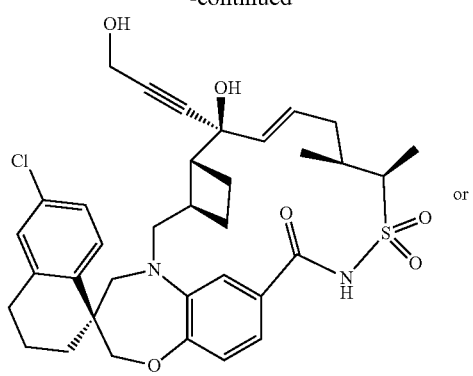 | 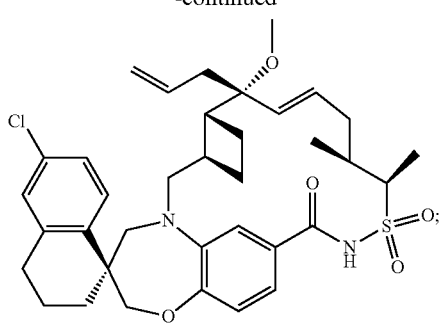 |
| or | ; |
| 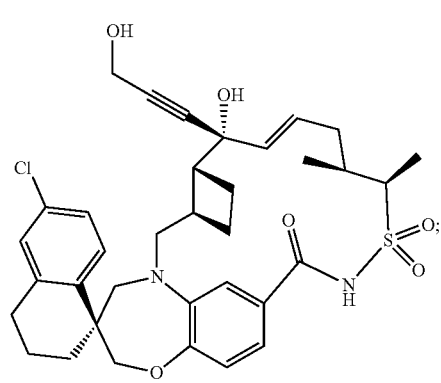 | 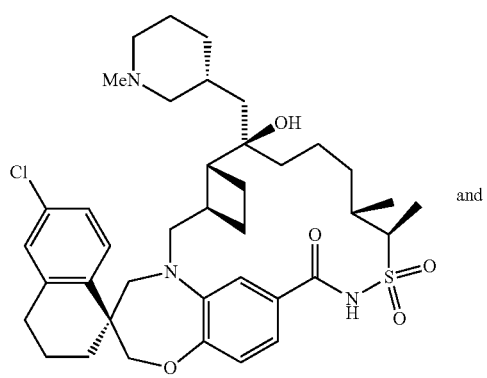 |
| ; | and |
| 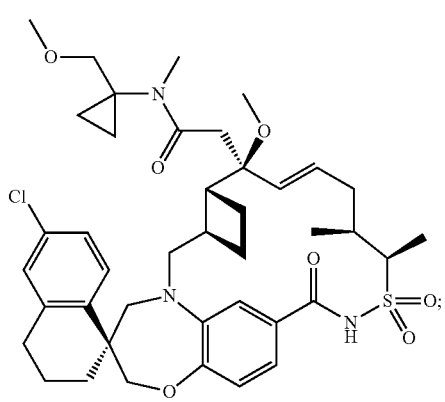 | 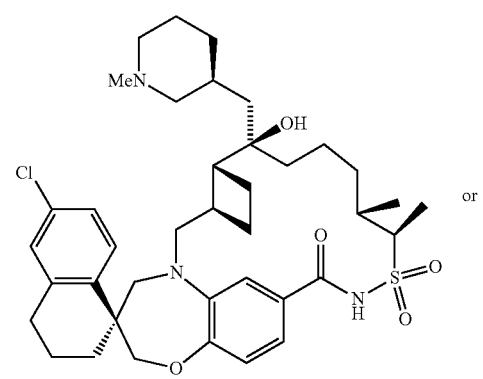 |
| ; | or |
| 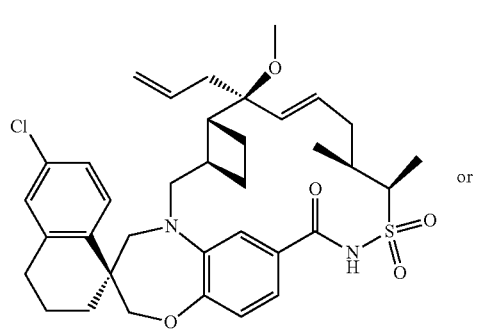 | 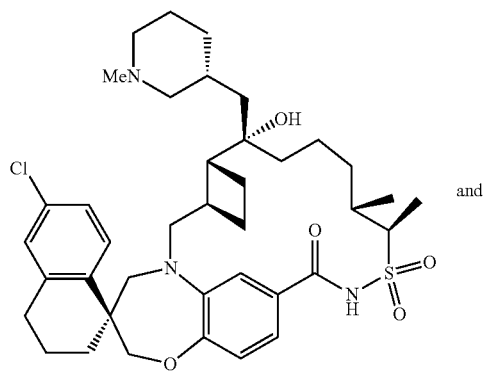 |
| or | and |

431
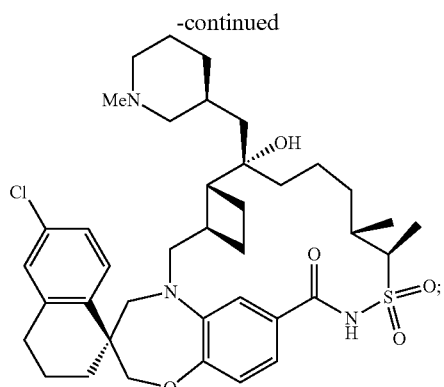

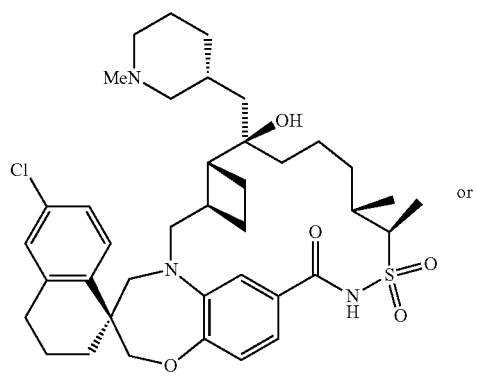
432
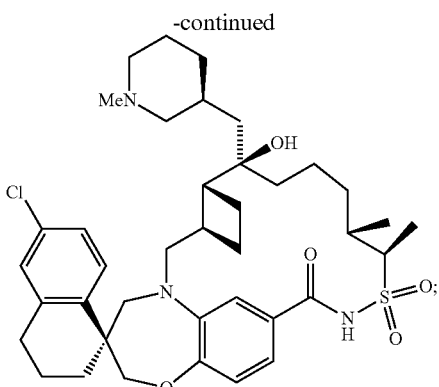
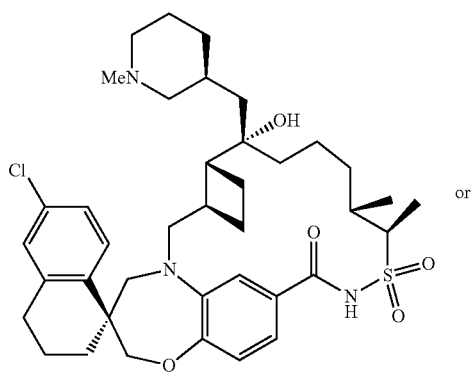
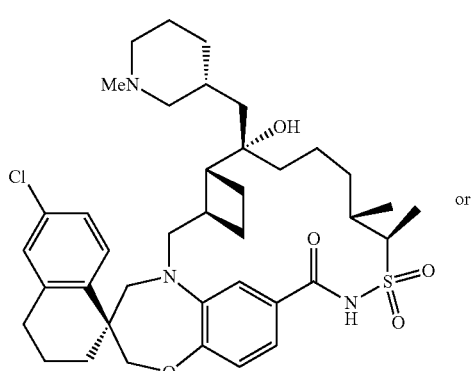
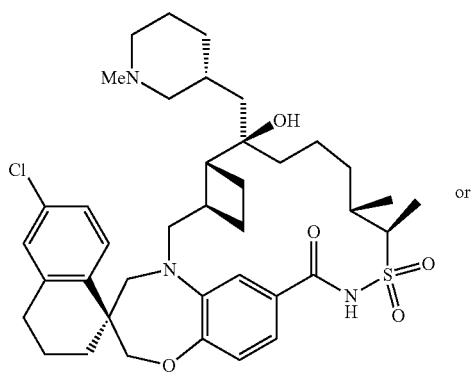

433
-continued
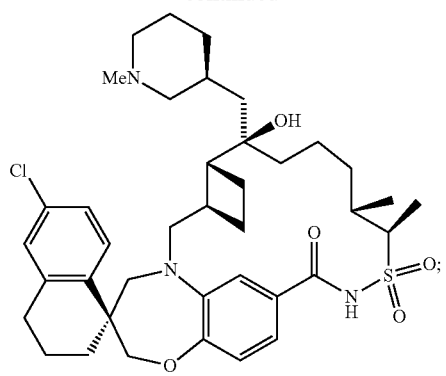
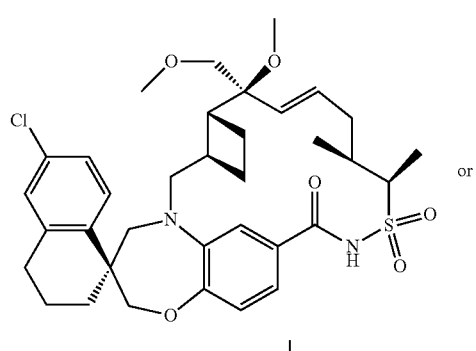
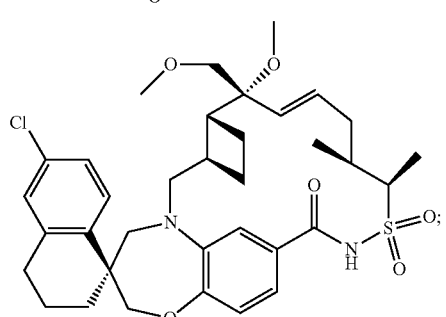
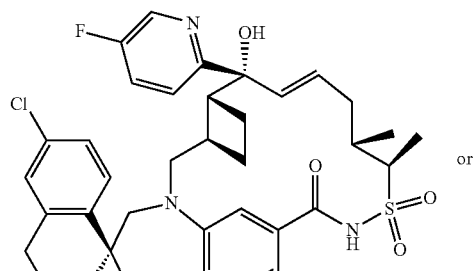
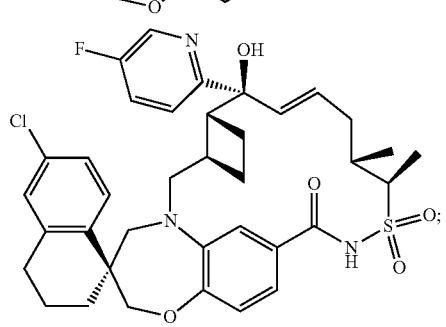
434
-continued
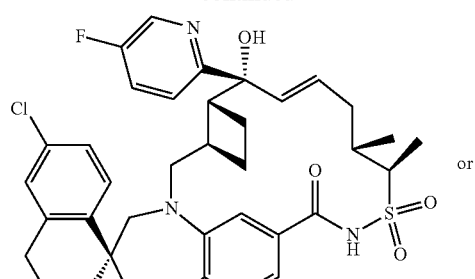
or
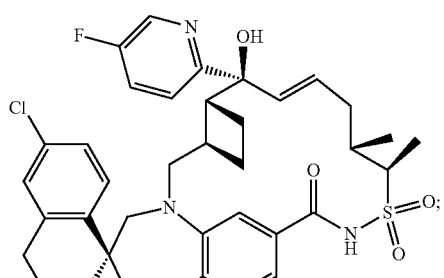
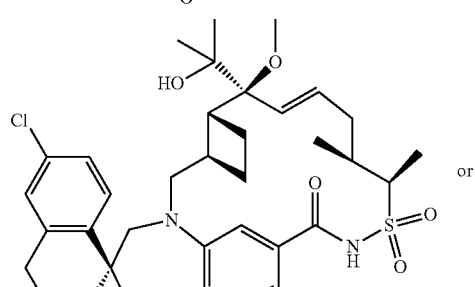
or
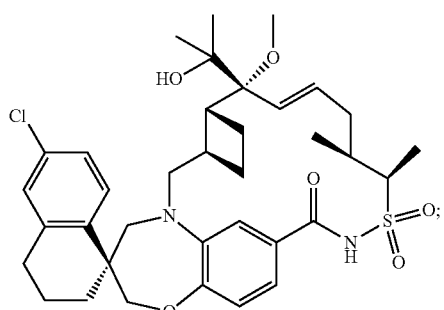
or
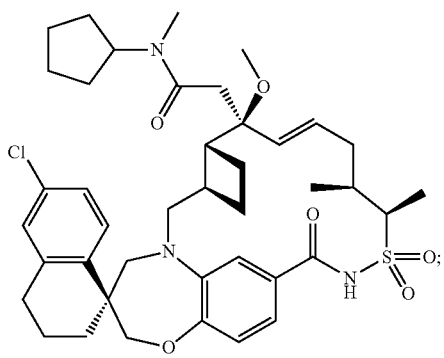

435
-continued
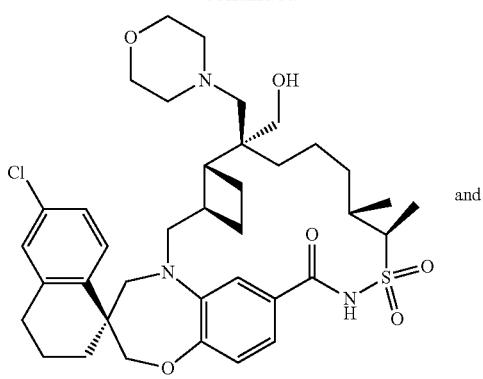
and
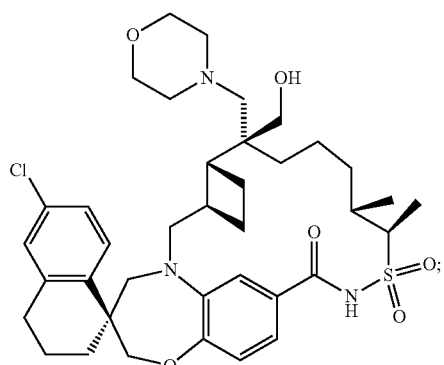
;
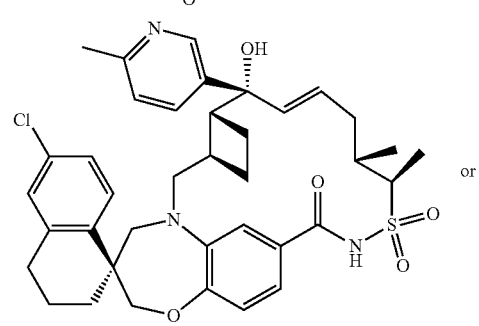
or
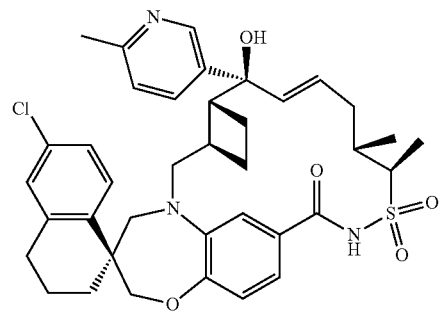
or
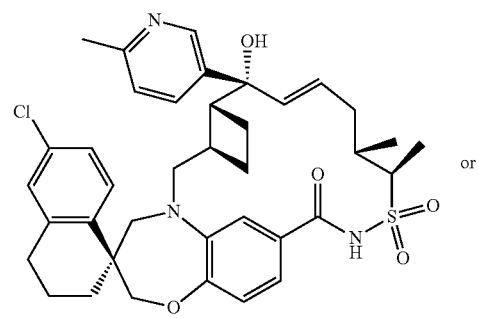
or
436
-continued
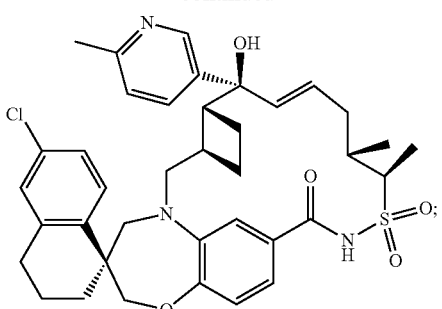
;
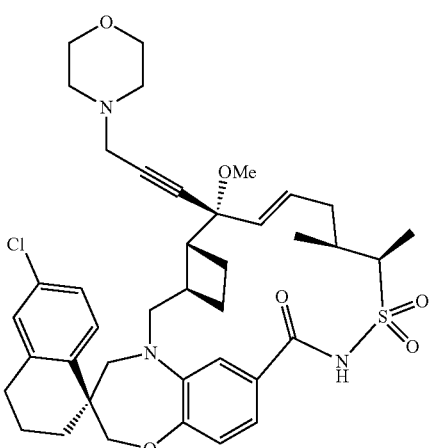
or
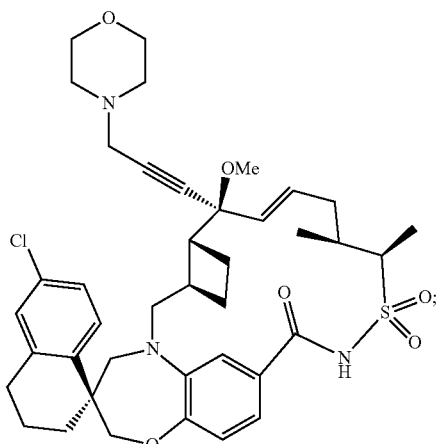
or
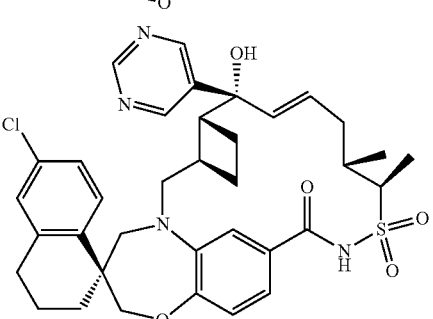
or 437
-continued
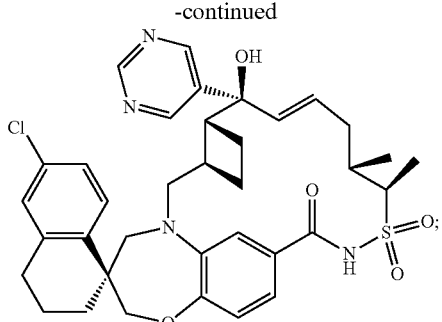
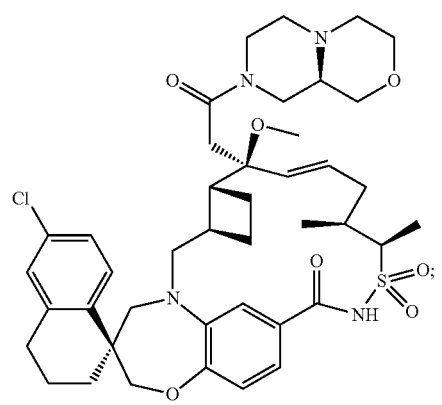
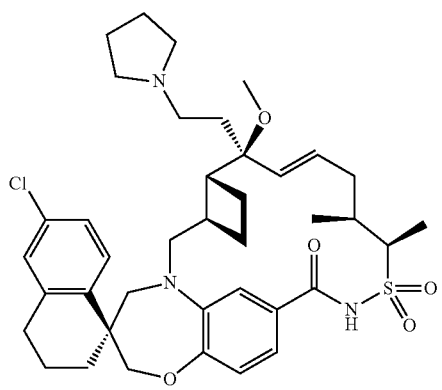
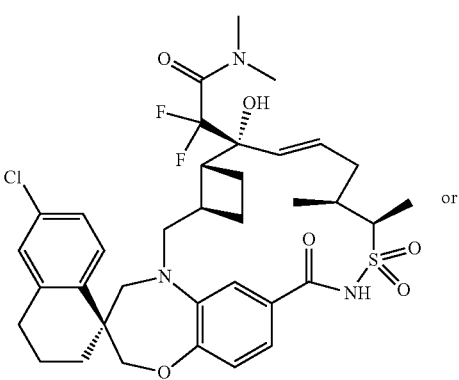
438
-continued
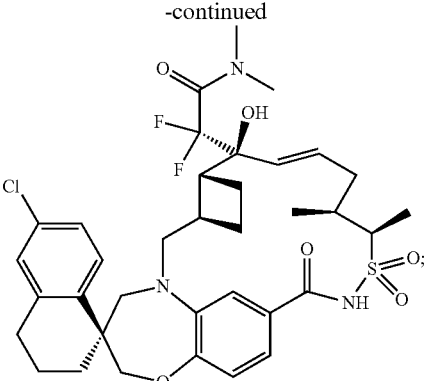
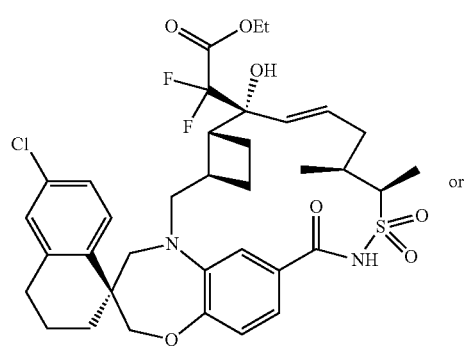
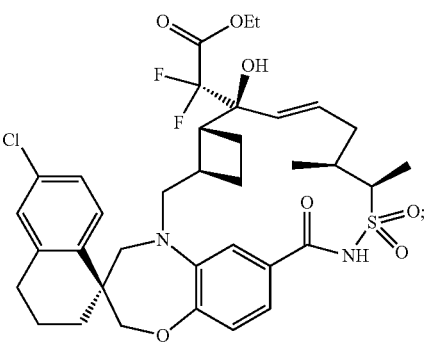
or
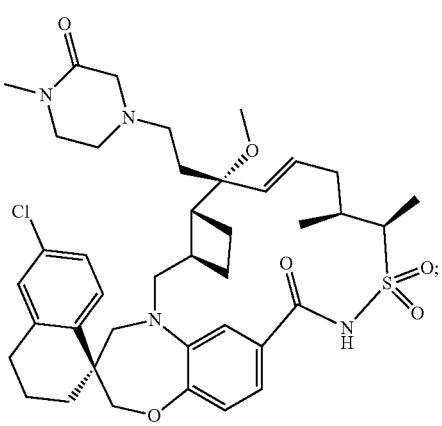

439
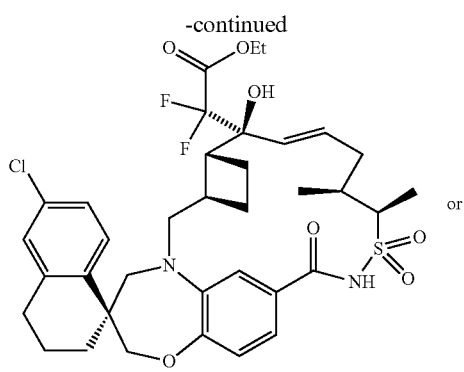
-continued
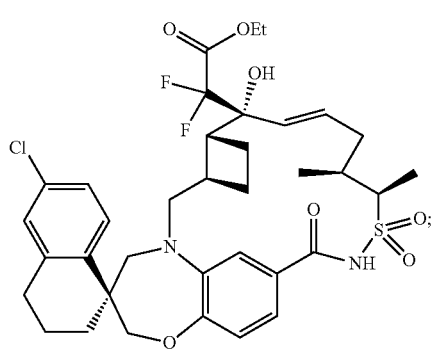
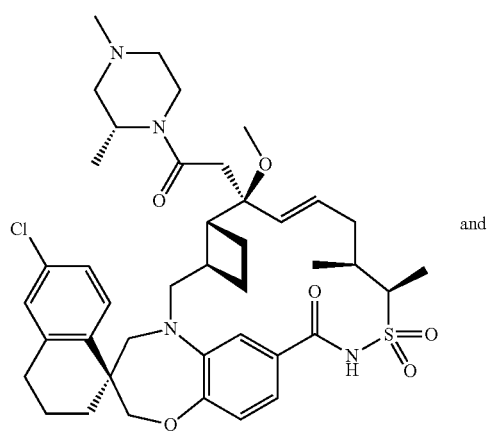
and
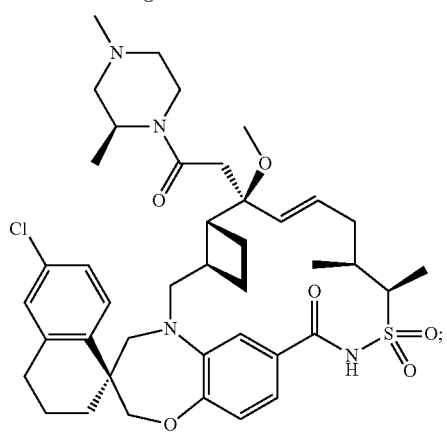
440
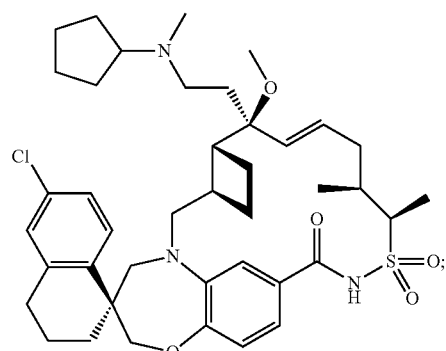
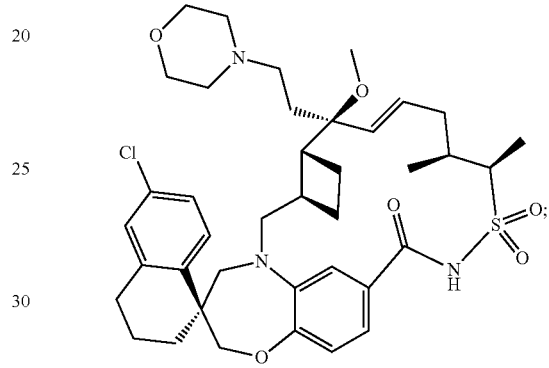
;
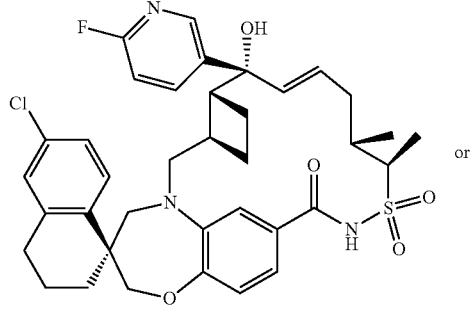
or
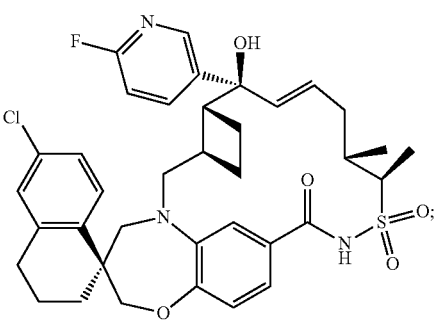
;

441
-continued
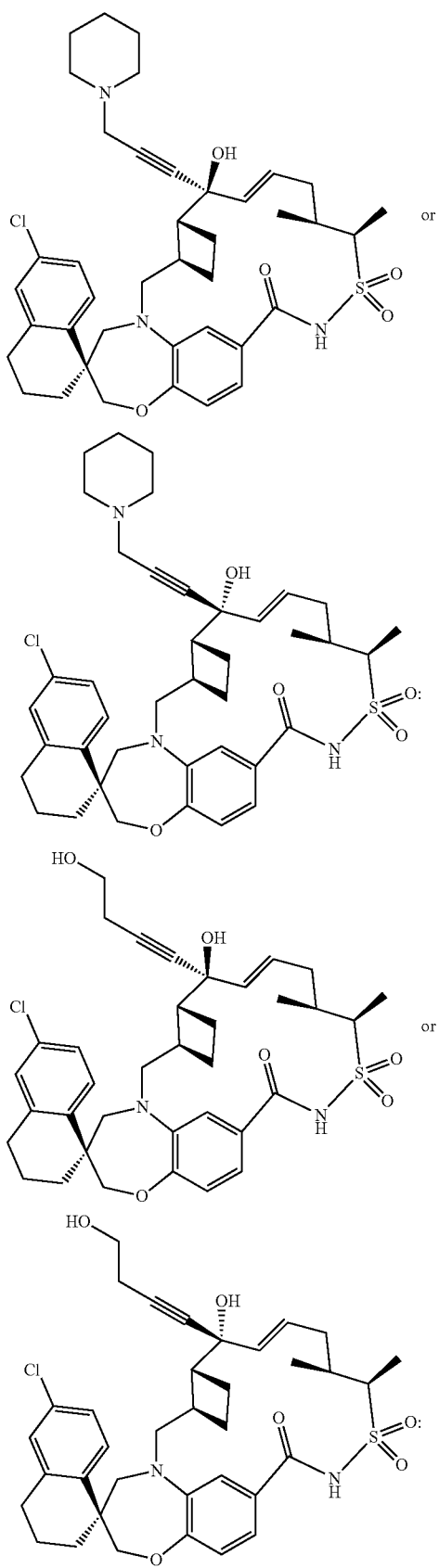
442
-continued
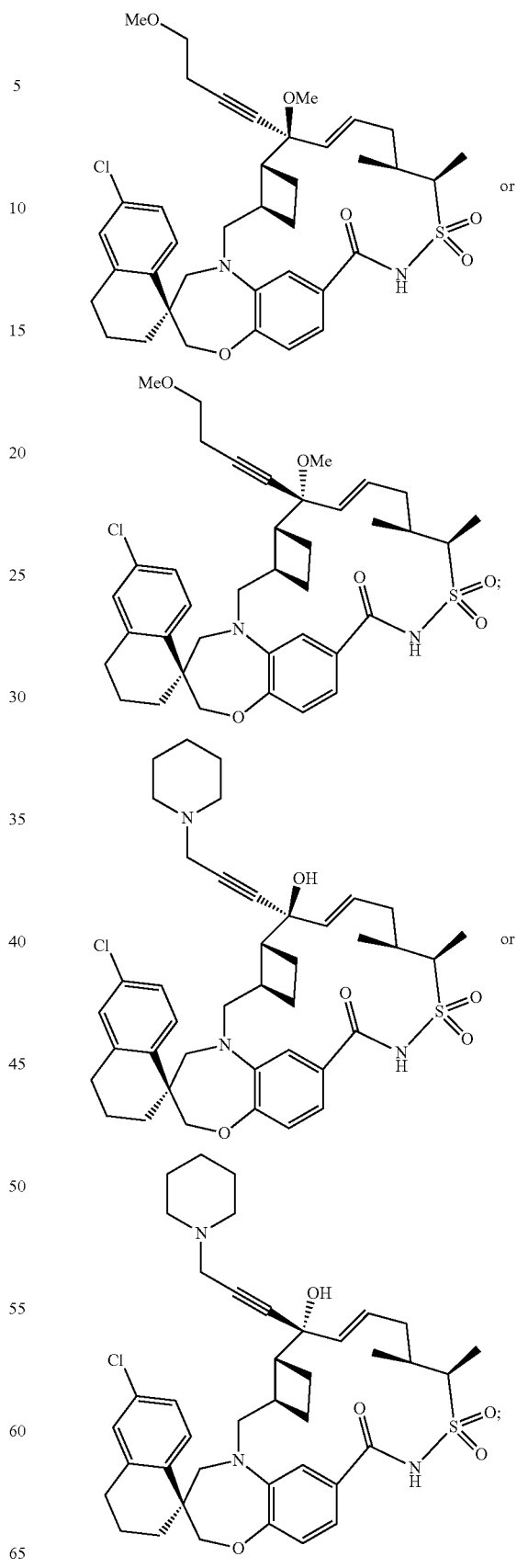

443
-continued
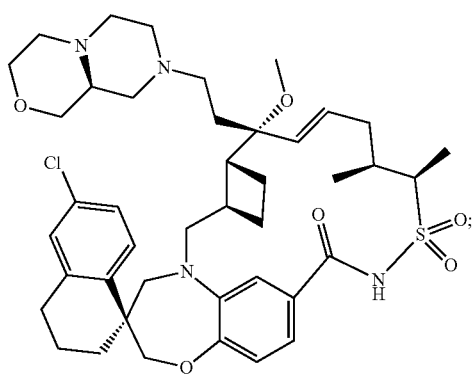
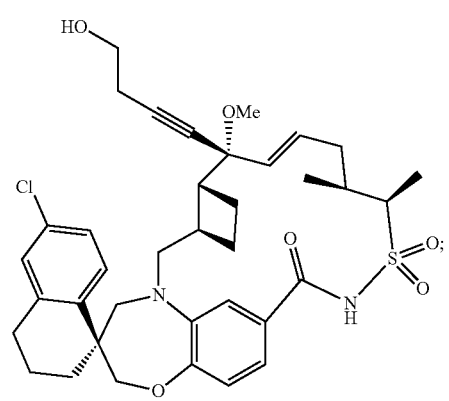
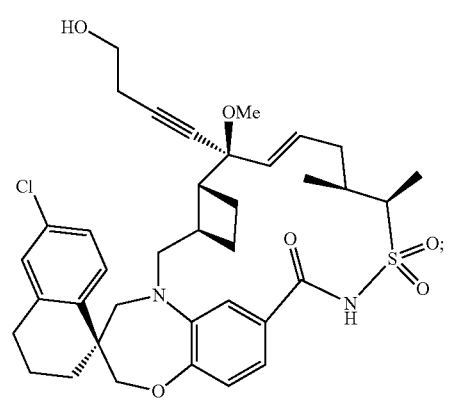
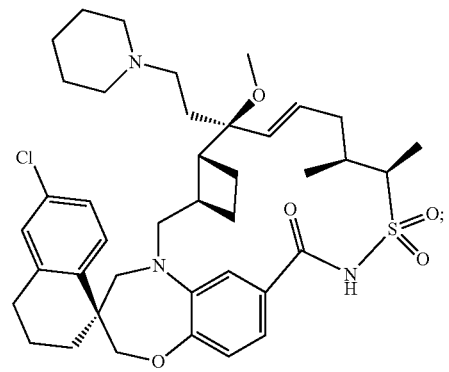
444
-continued
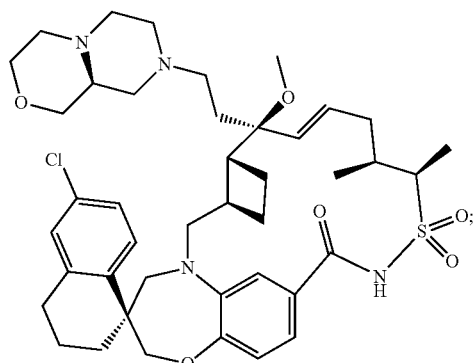
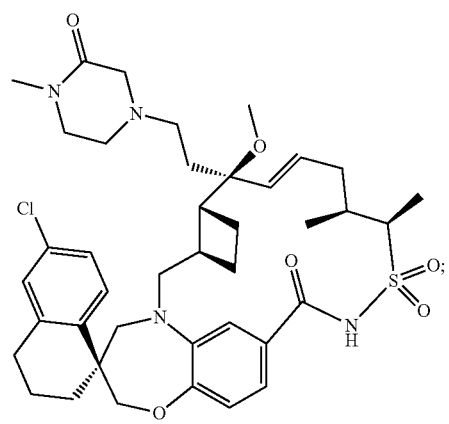
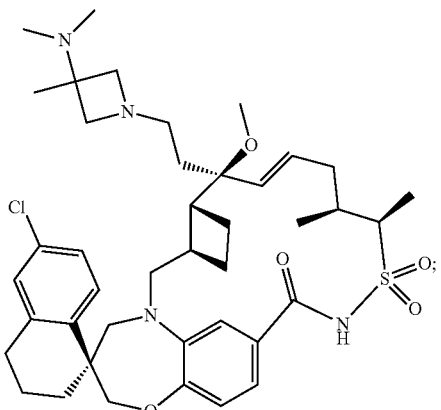
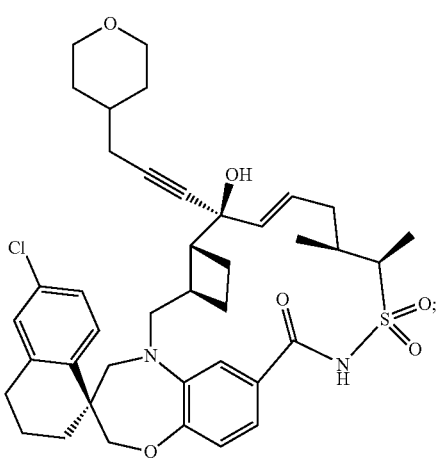

445
-continued
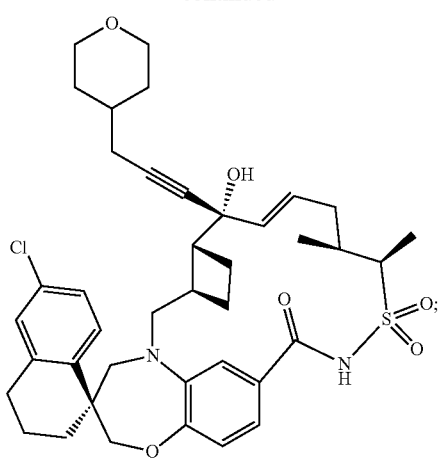
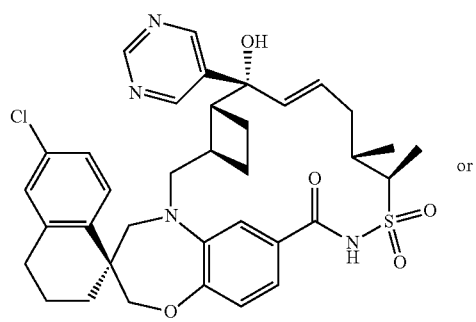
or
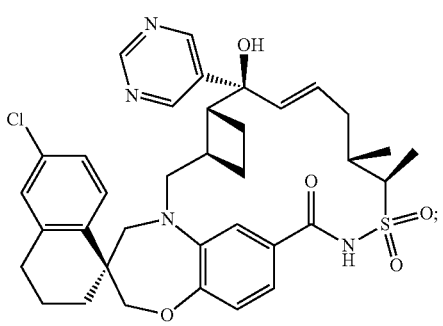
or
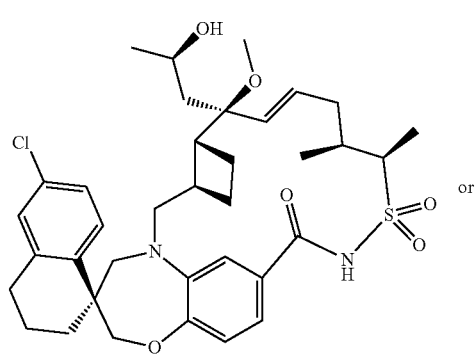
or
446
-continued
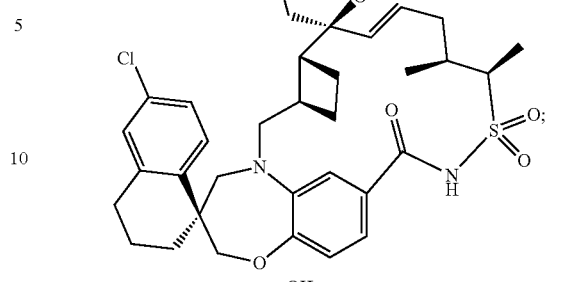
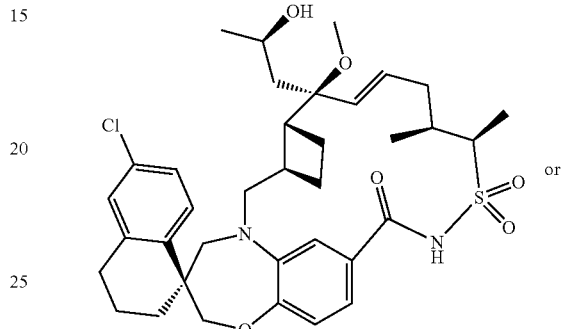
or
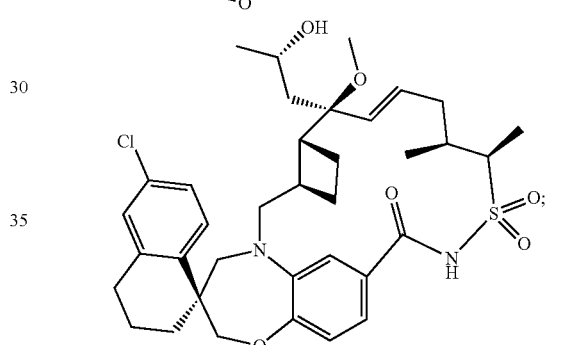
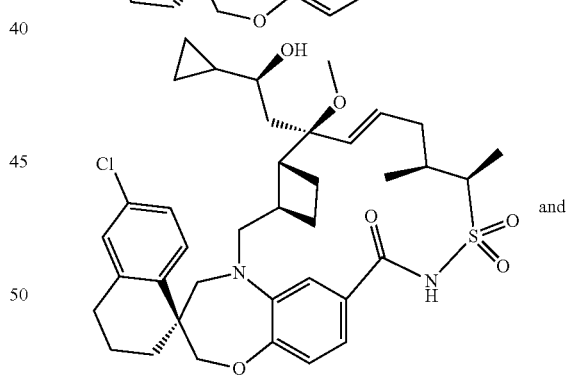
and
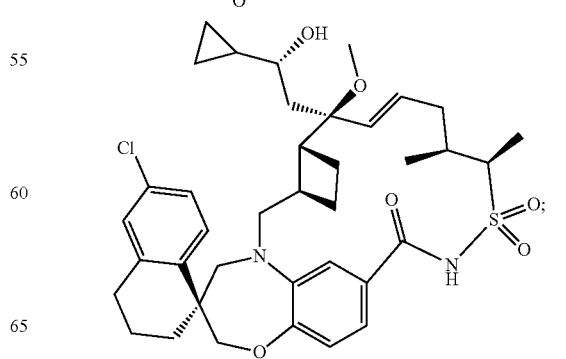

447
-continued
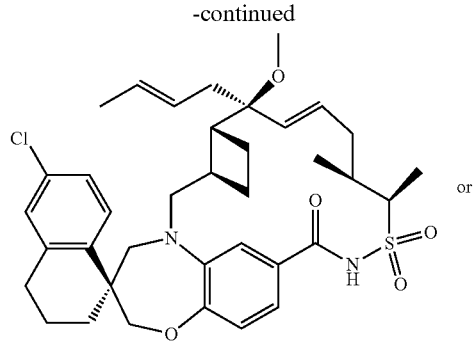
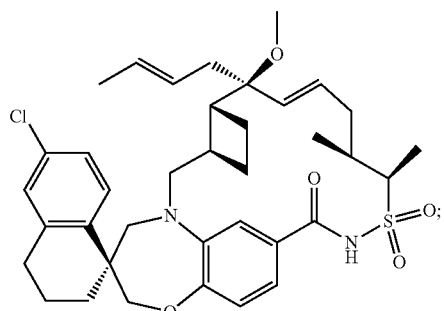
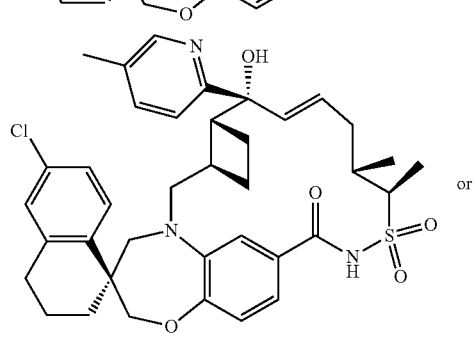
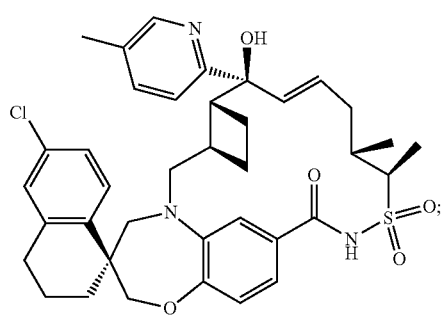
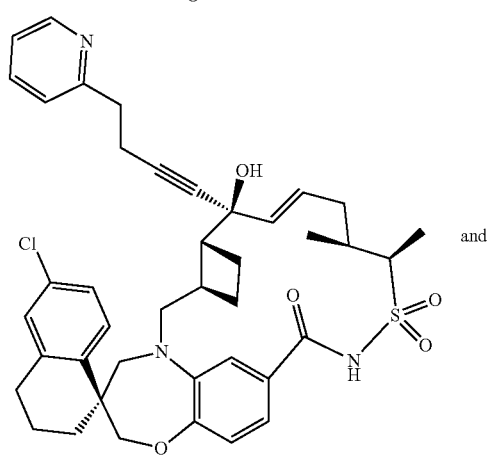
448
-continued
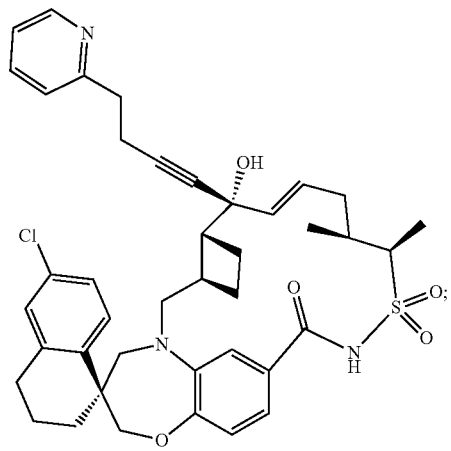
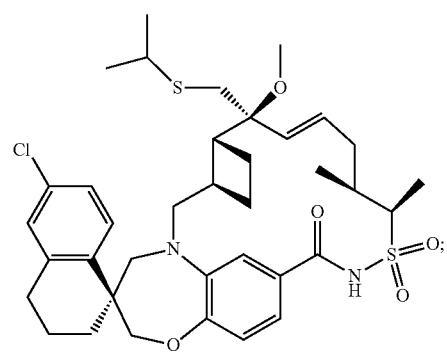
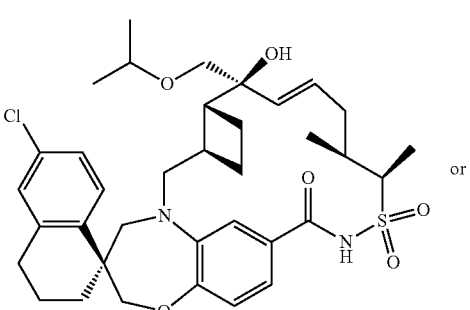
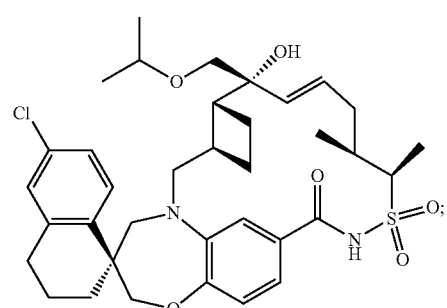

449
-continued
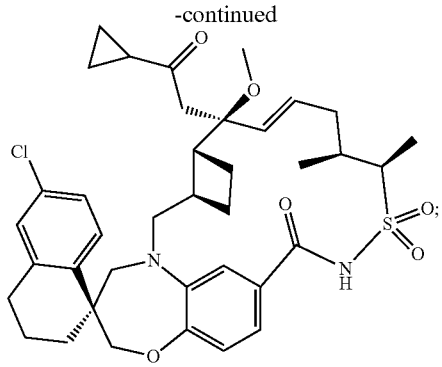
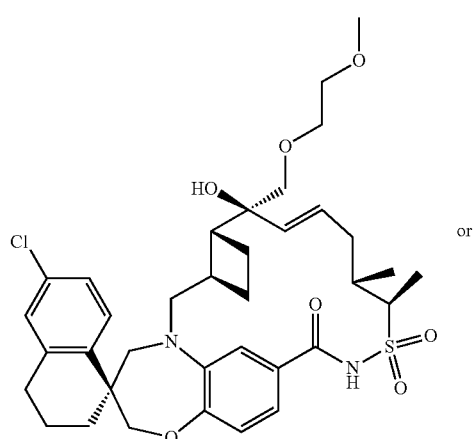
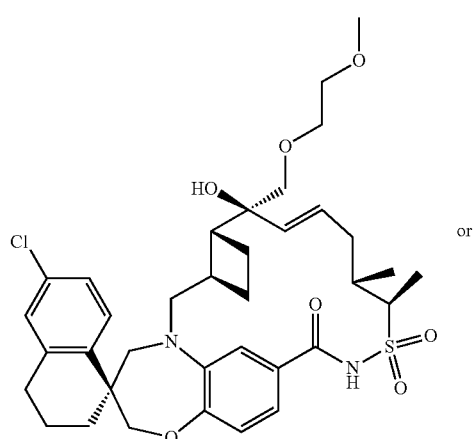
or
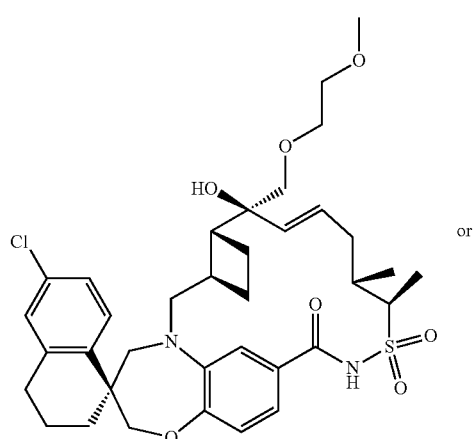
or
450
-continued
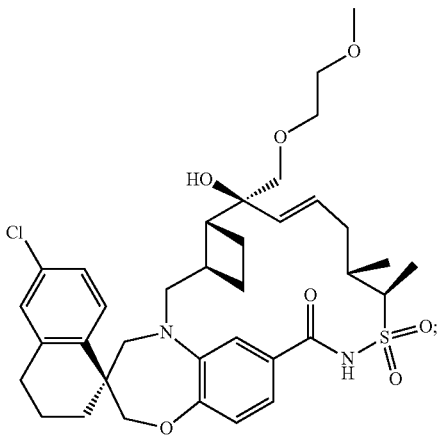
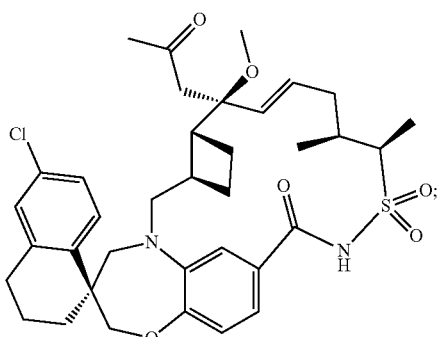
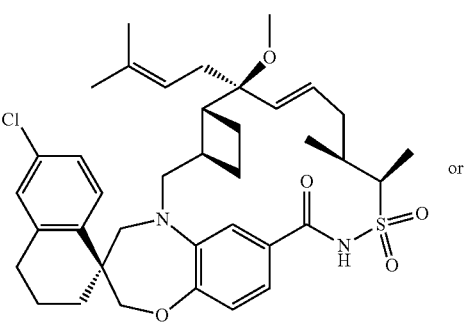
or
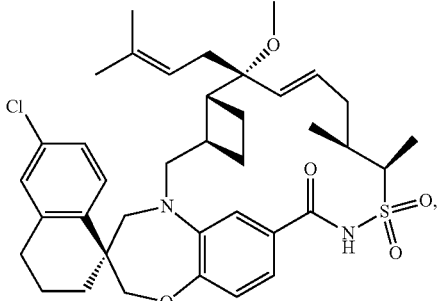

451
-continued
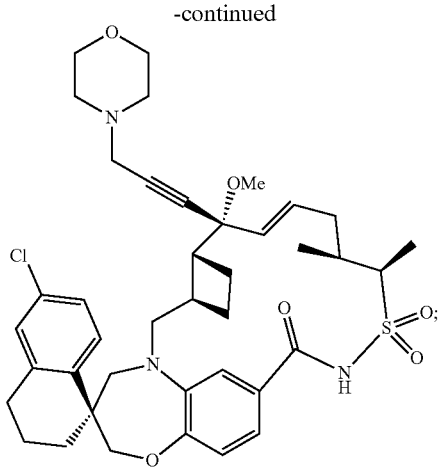
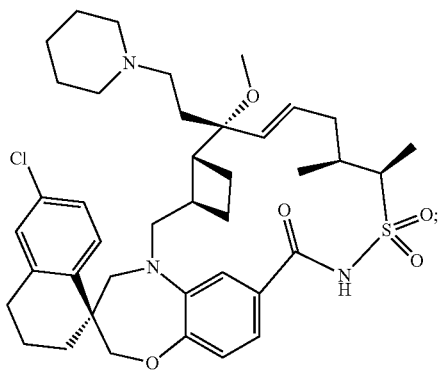
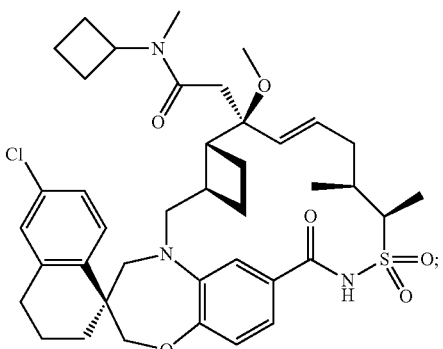
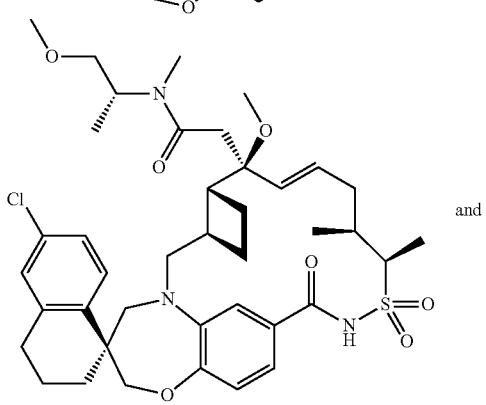
and
452
-continued
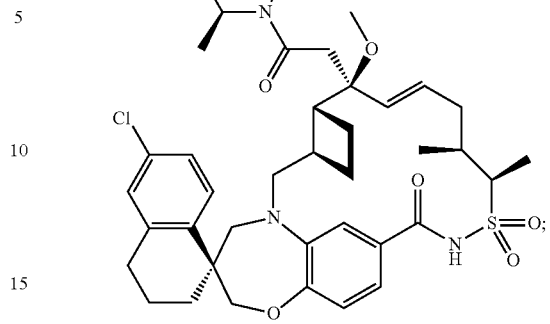
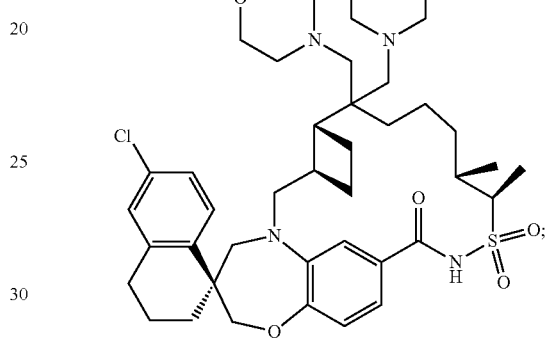
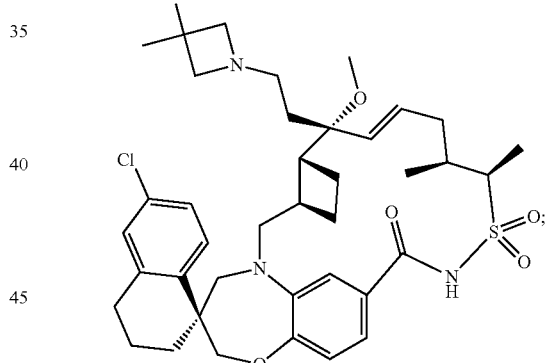
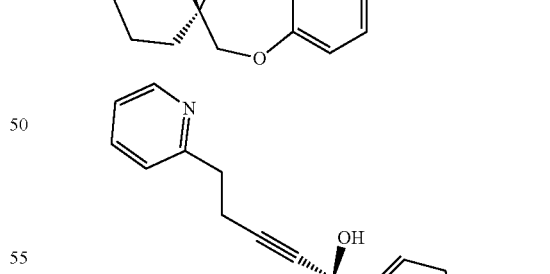
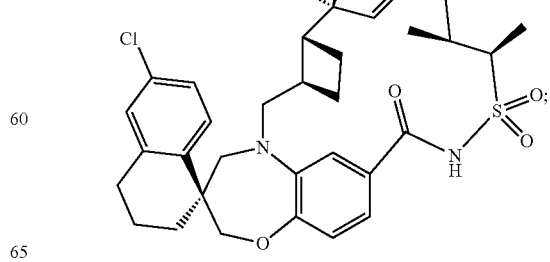

453
-continued
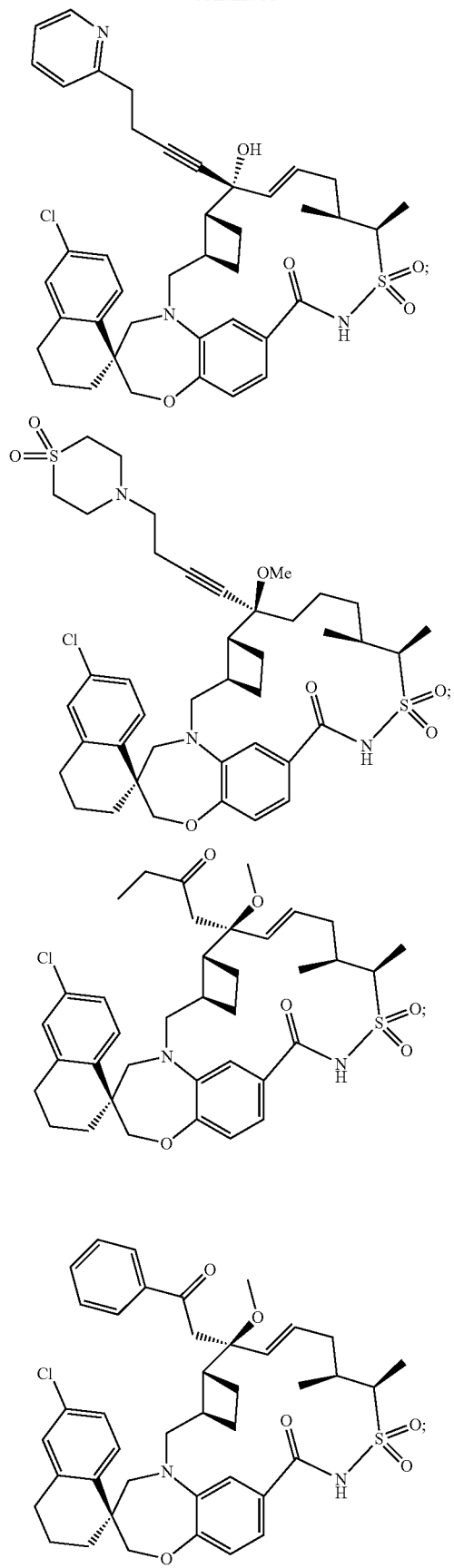
454
-continued
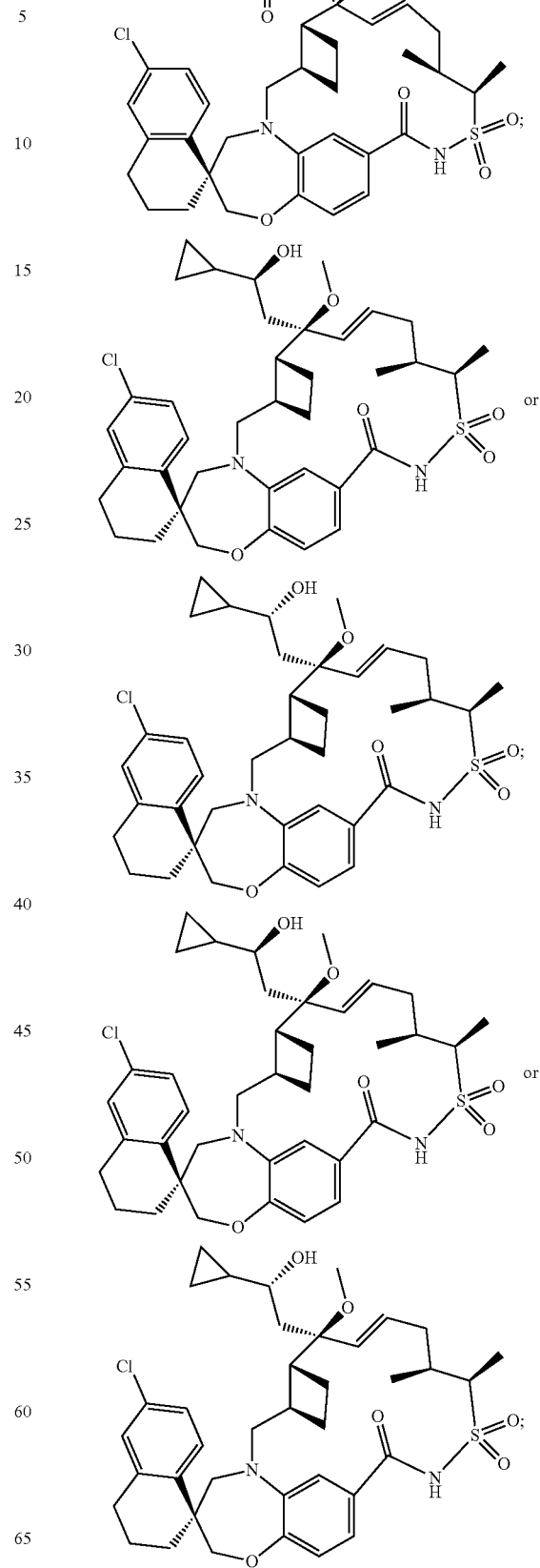

455
-continued

456
-continued or

457
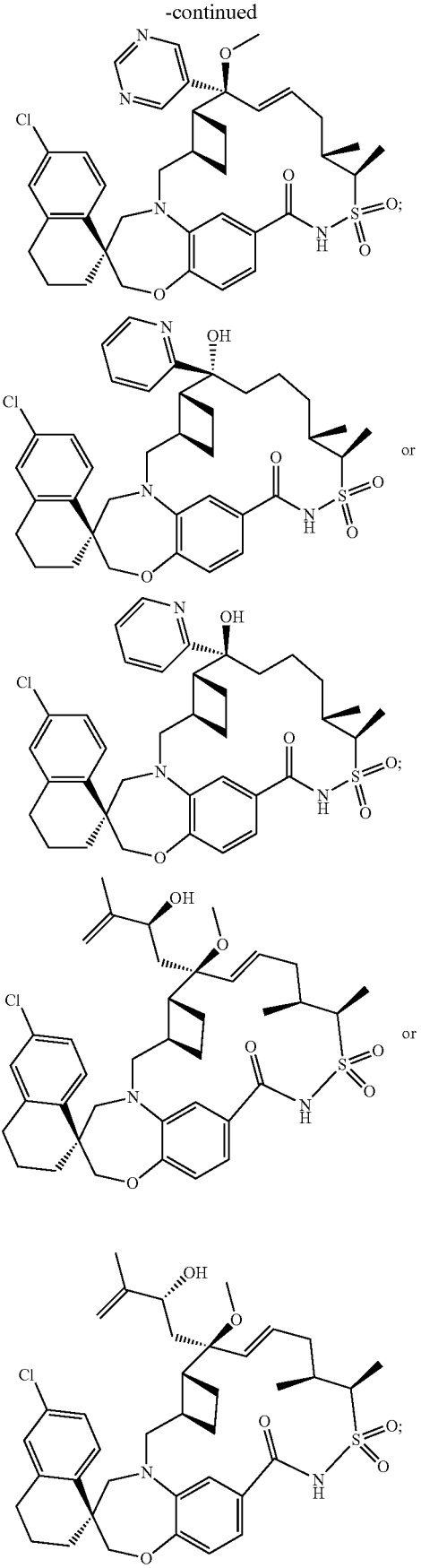
458
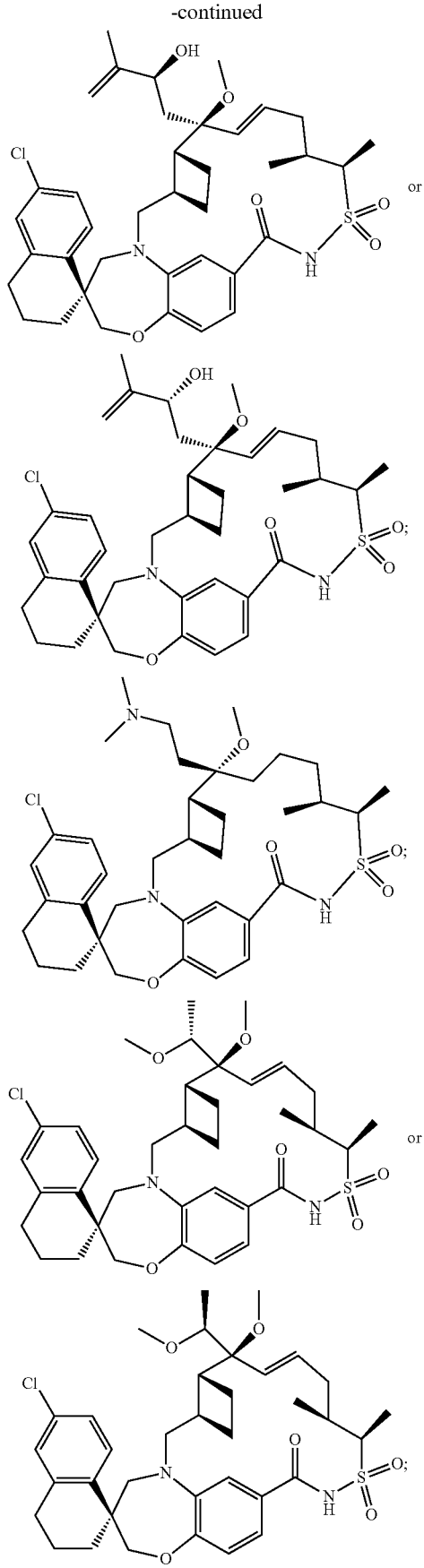

459
-continued
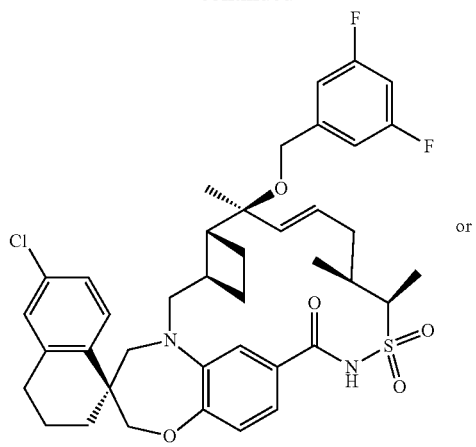
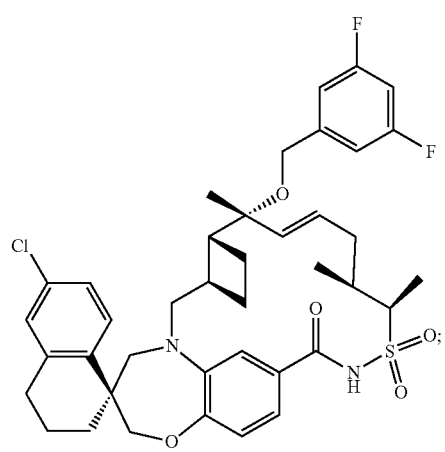
or
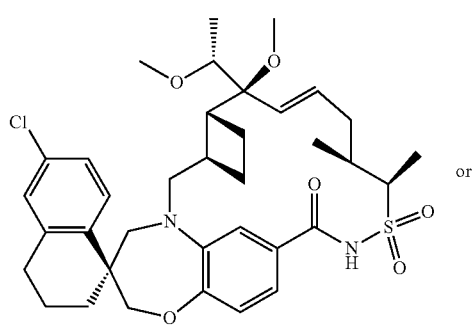
or
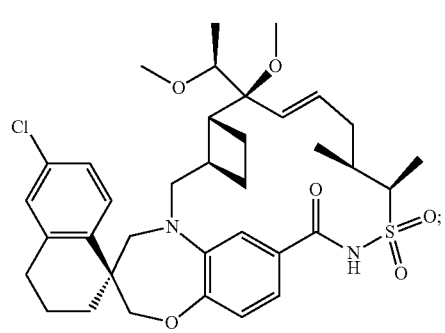
460
-continued
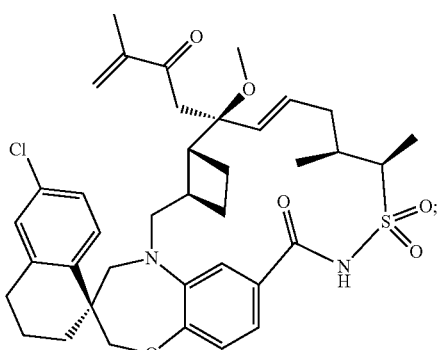
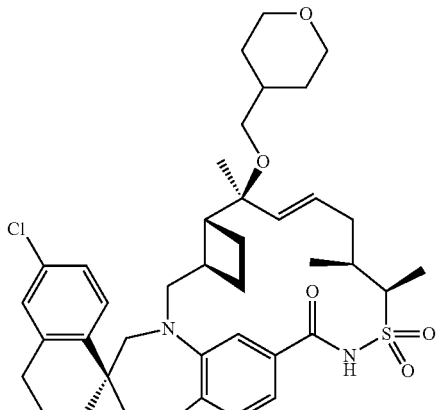
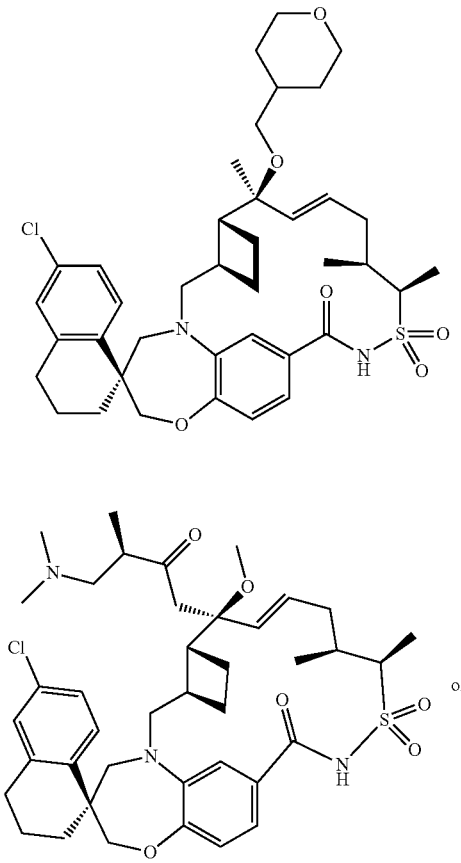
or
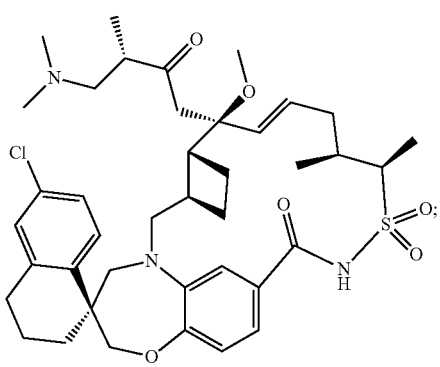

461
-continued
462
-continued
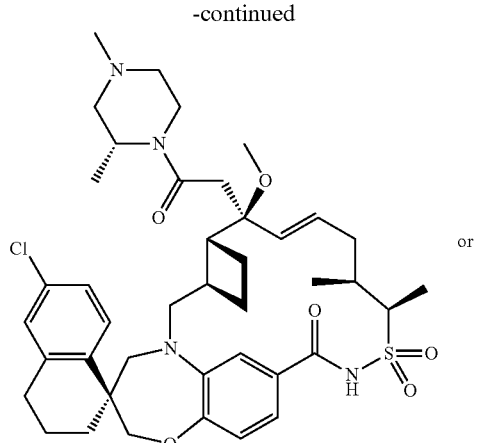
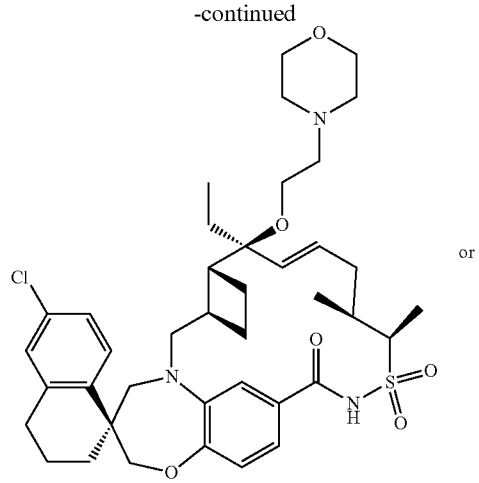

463
-continued
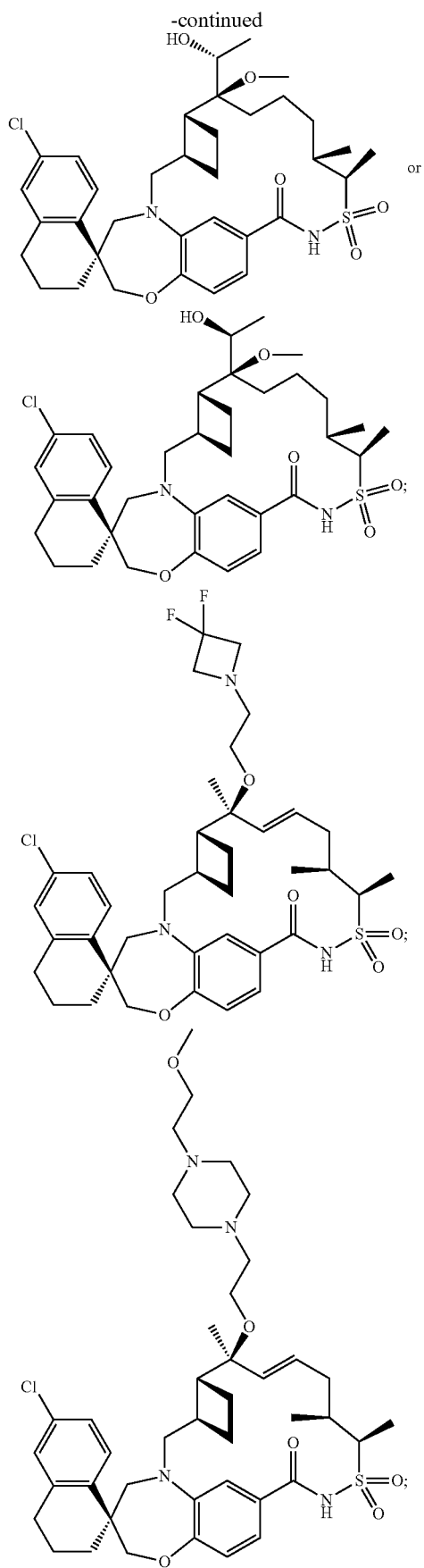
464
-continued
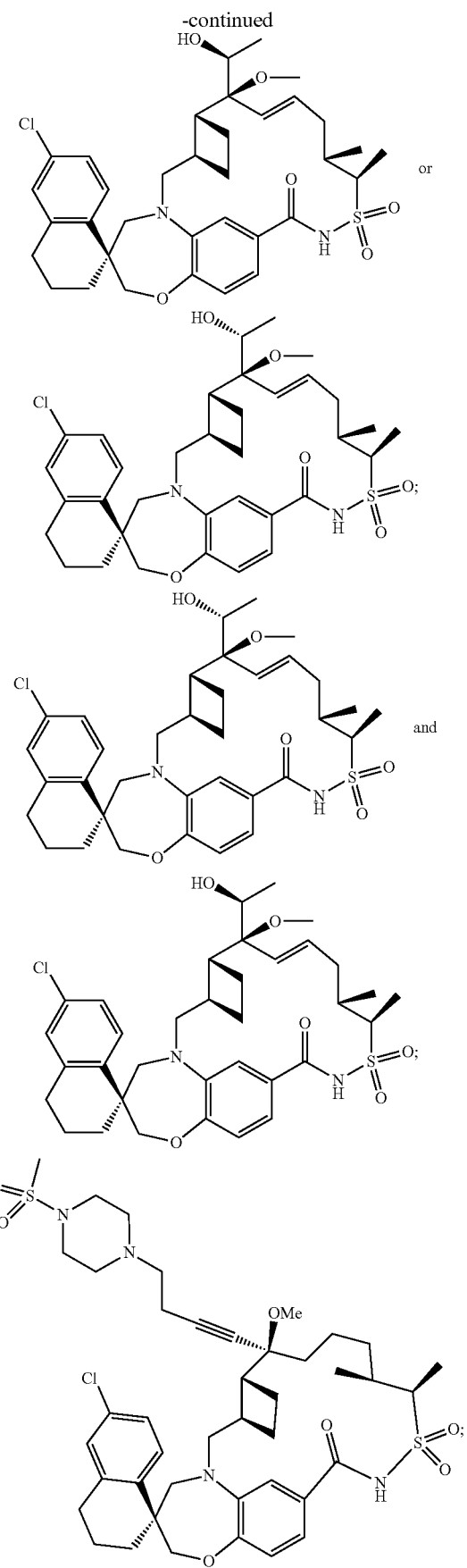

465
-continued
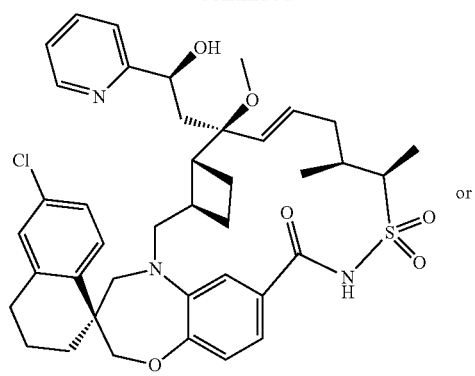
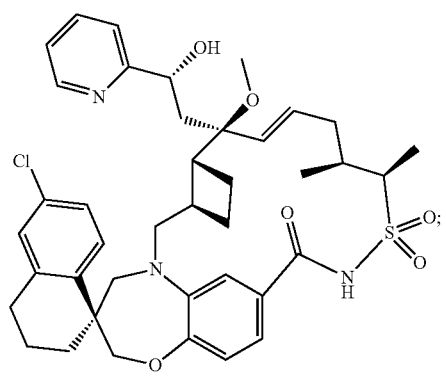
or
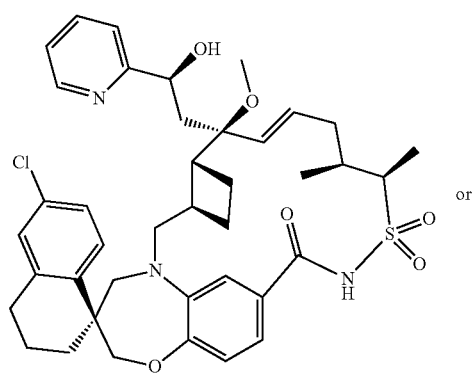
or
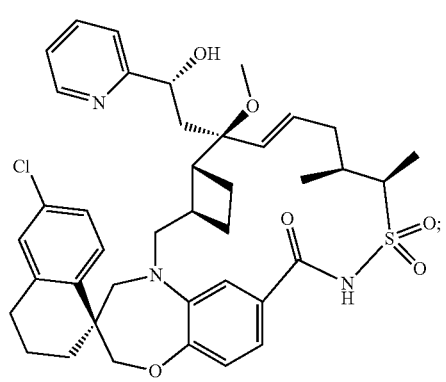
466
-continued
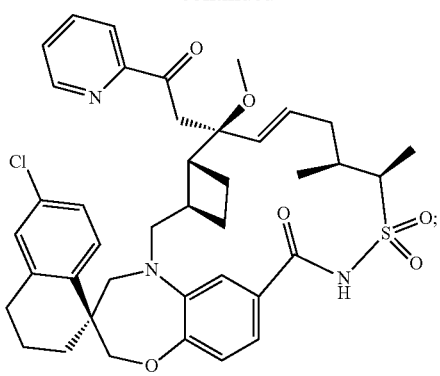
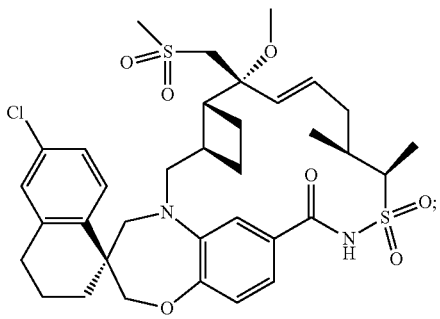
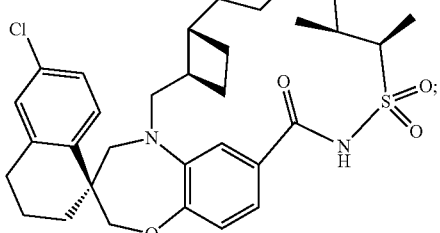
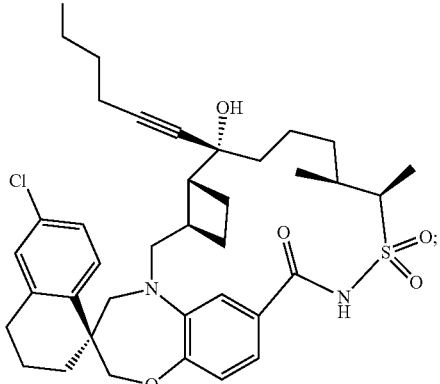

467
-continued
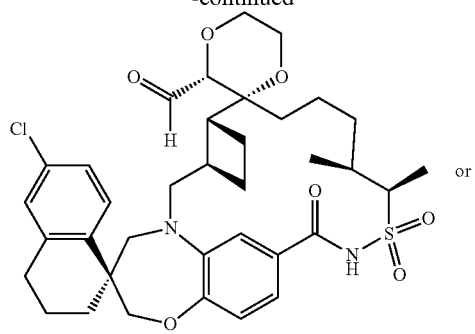
or
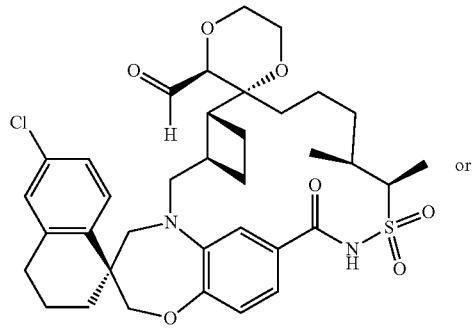
or
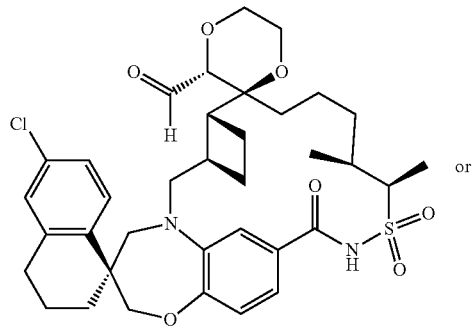
or
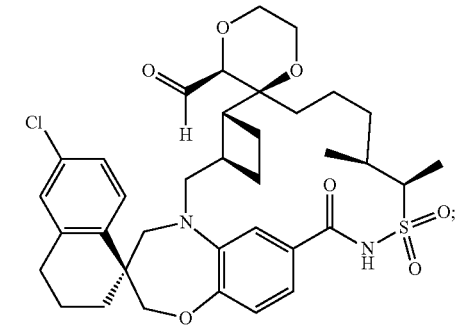
or
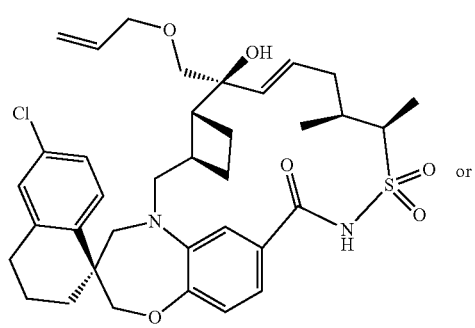
or
468
-continued
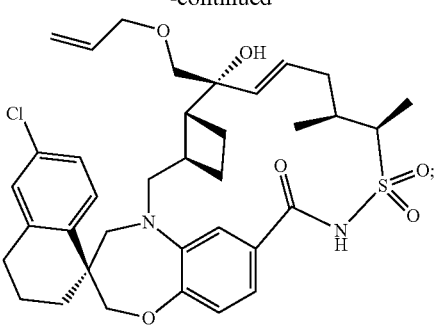
or
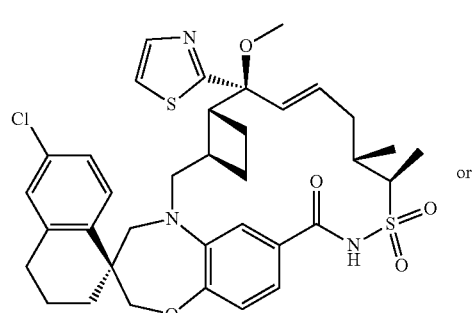
or
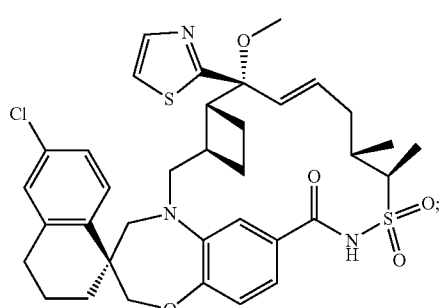
or
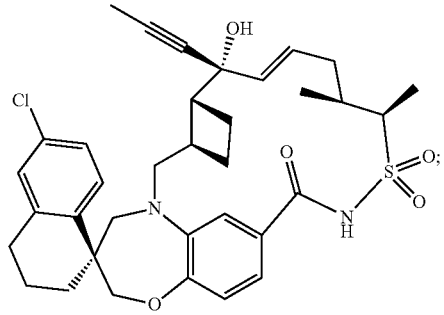
or
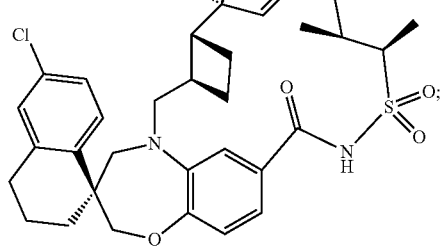

469
-continued
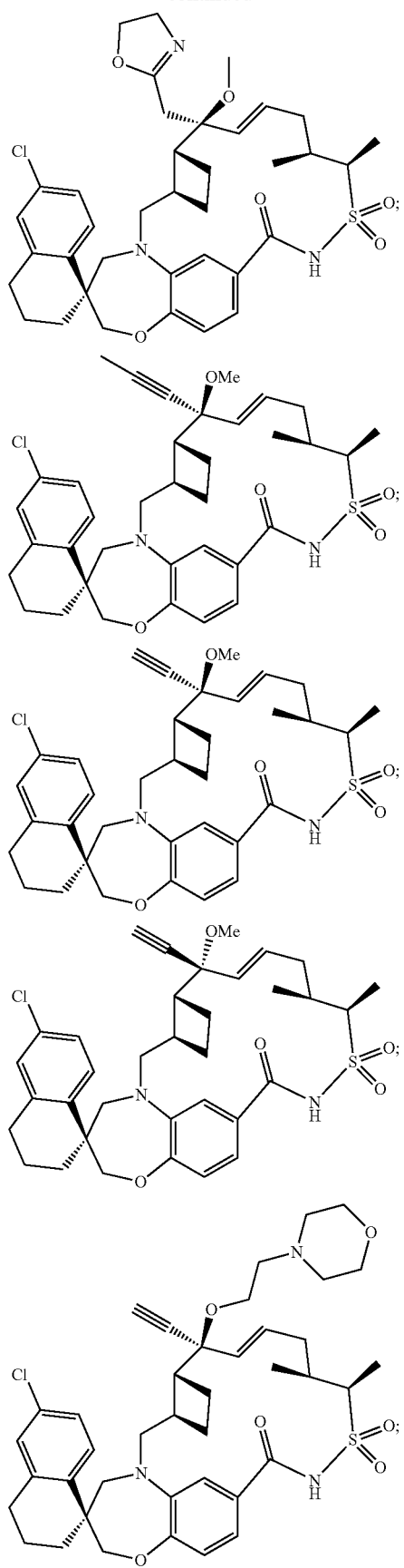
470
-continued
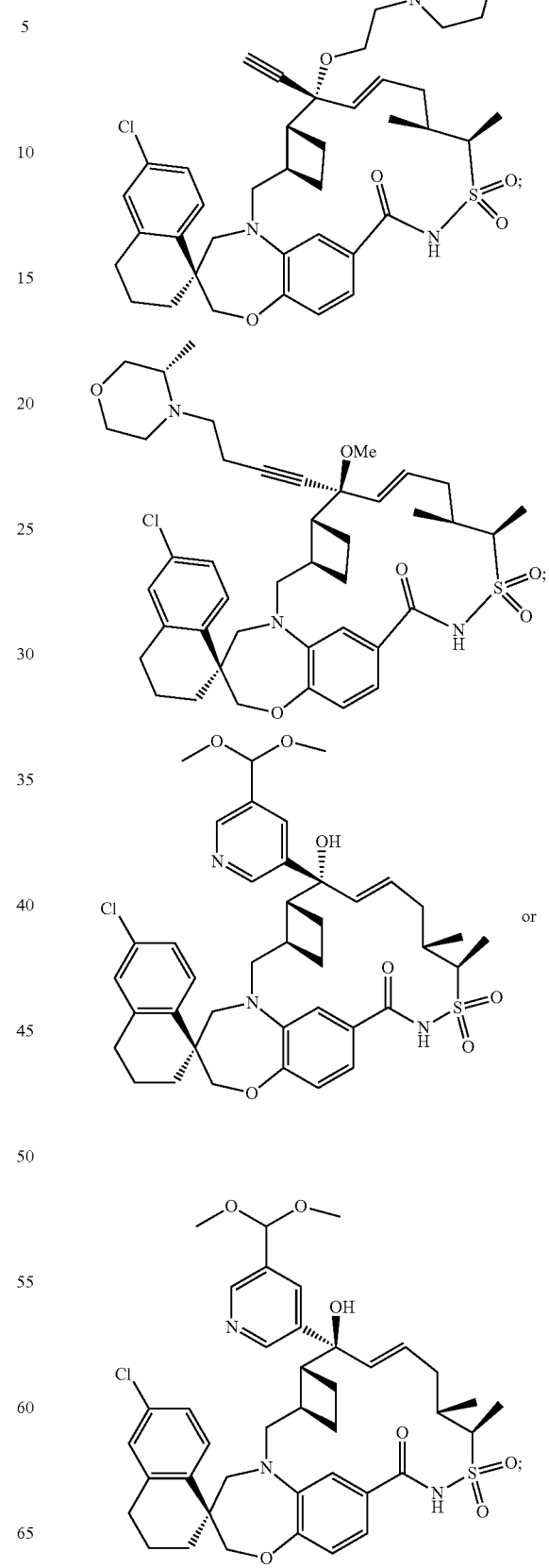
or

471
-continued
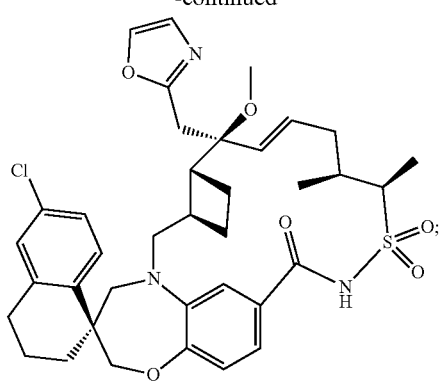
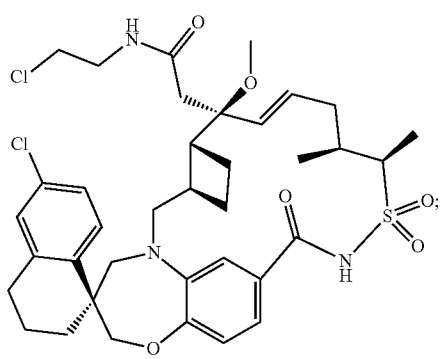
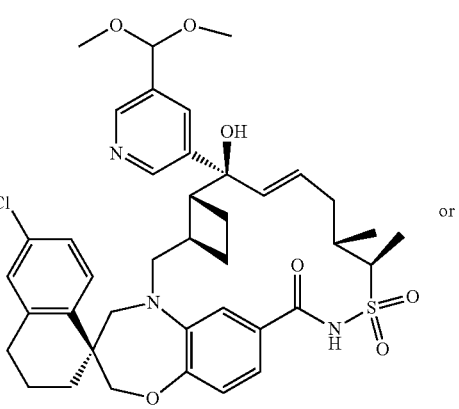
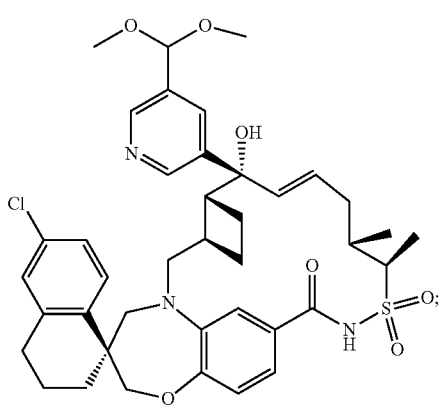
472
-continued
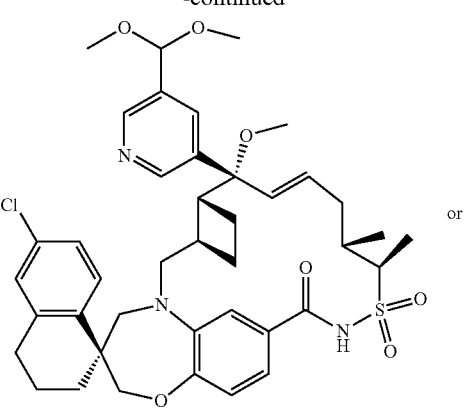
or
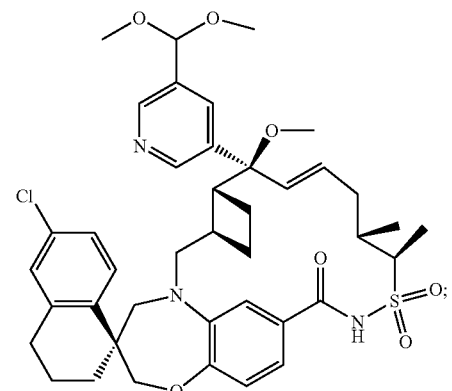
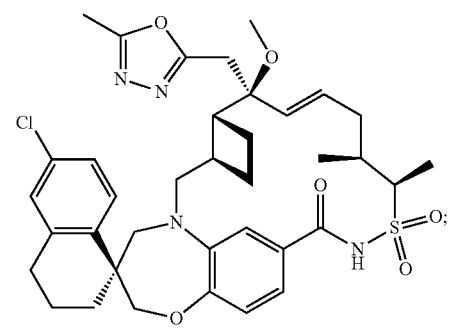
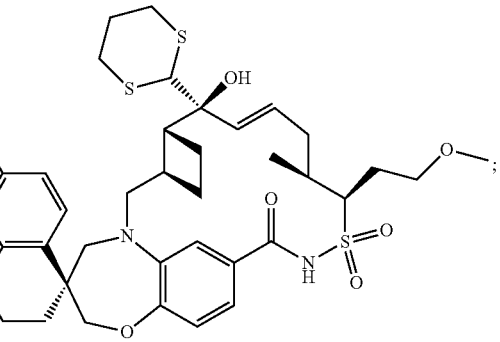

473
-continued
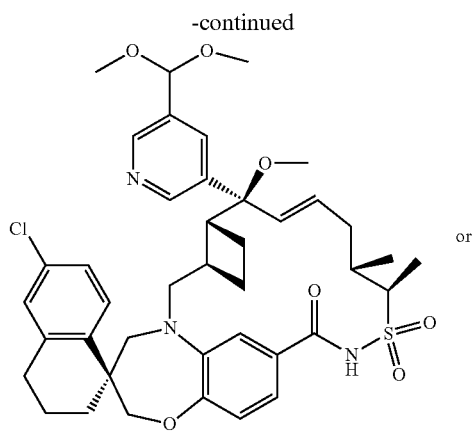
or
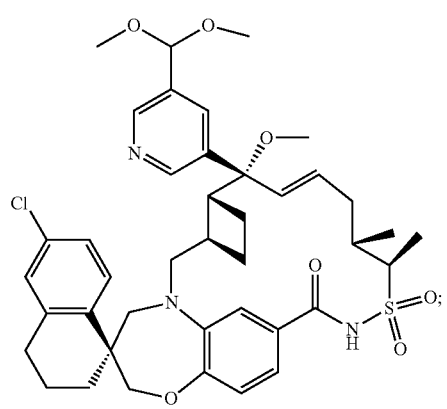
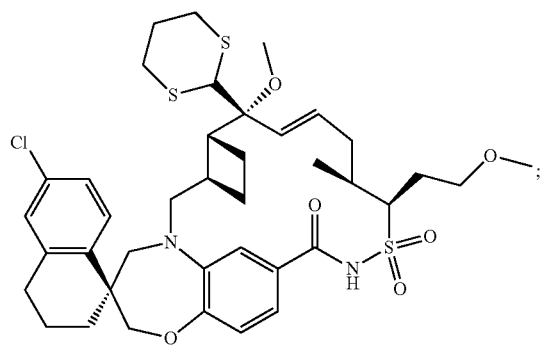
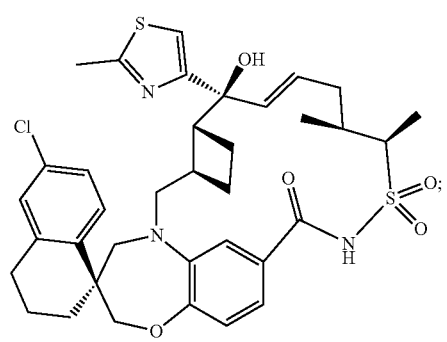
474
-continued
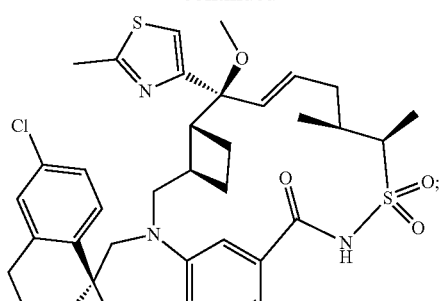
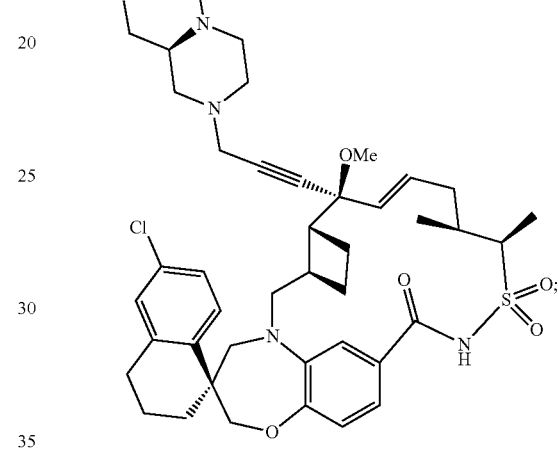
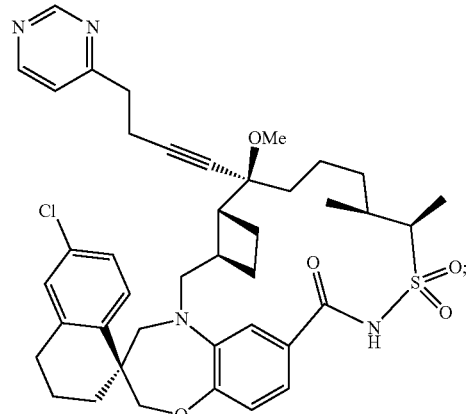
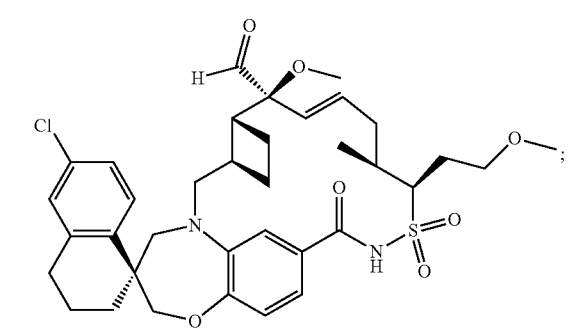

475
-continued
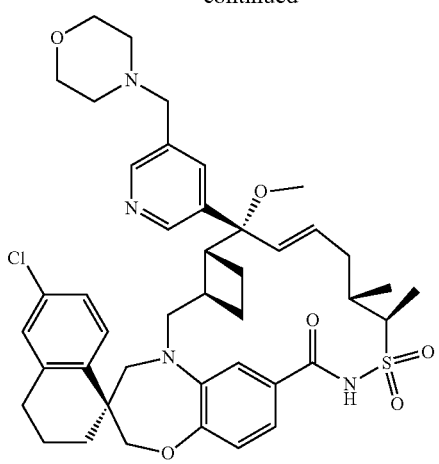
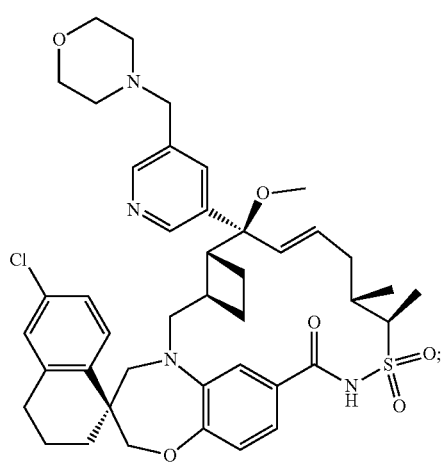
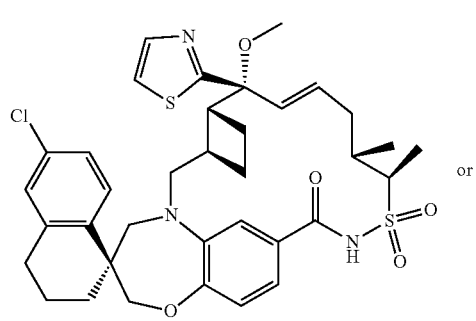
or
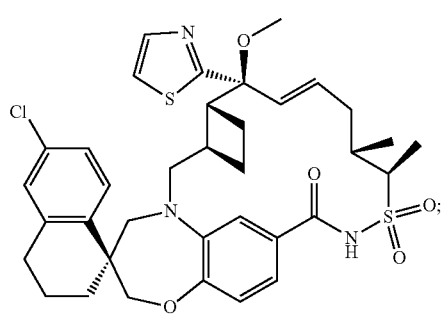
476
-continued
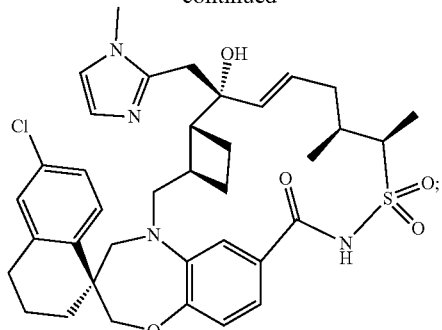
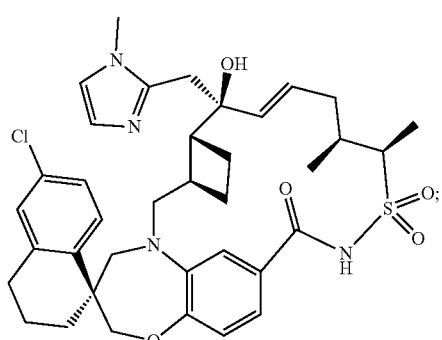
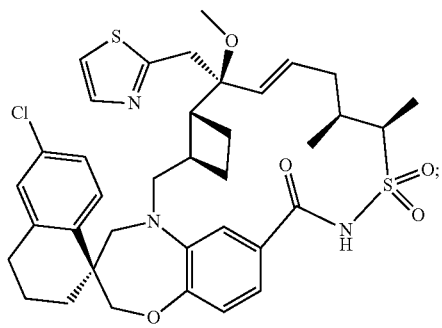
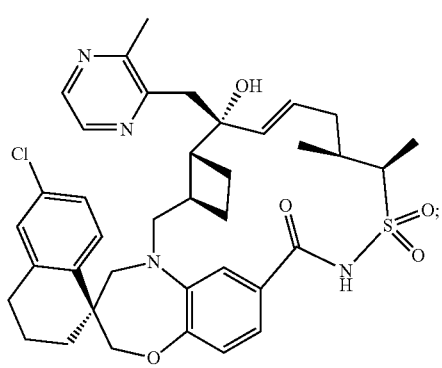
and 477
-continued
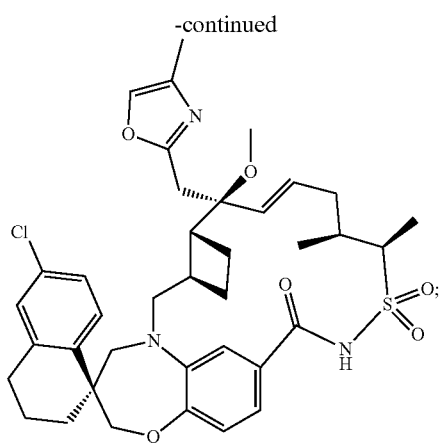
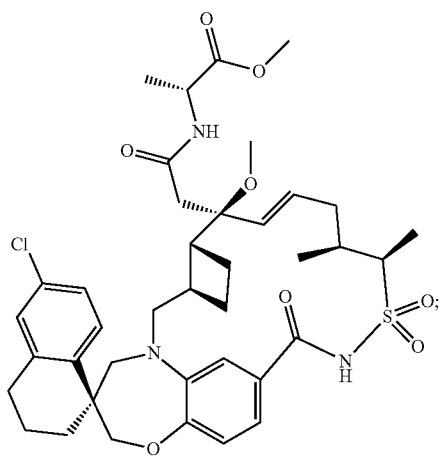
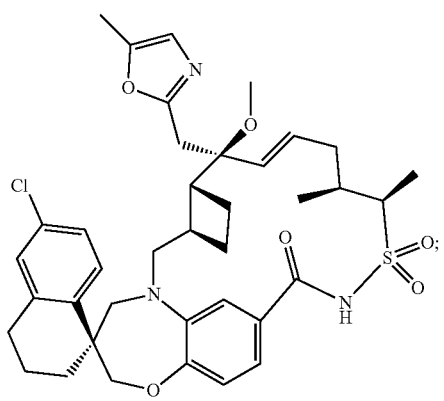
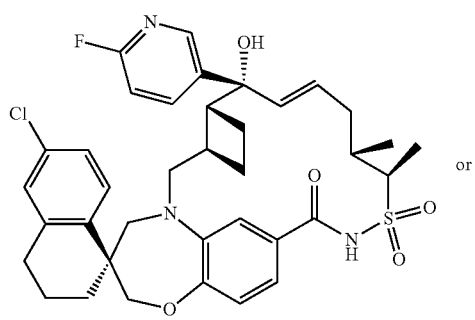
or
478
-continued
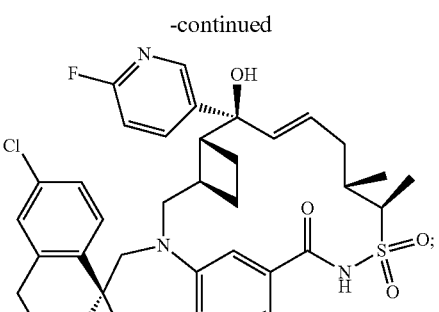
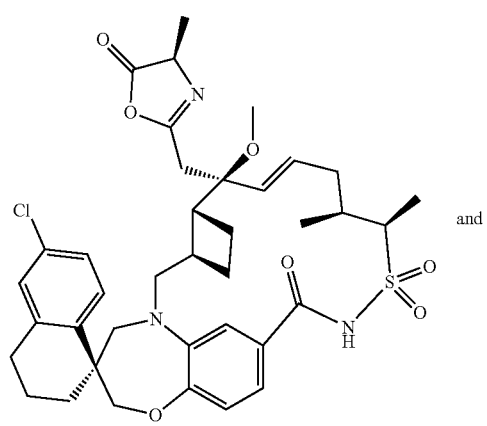
and
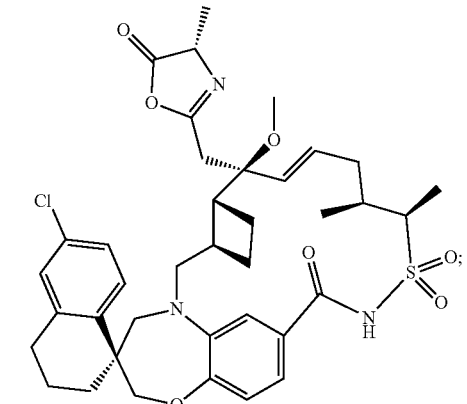
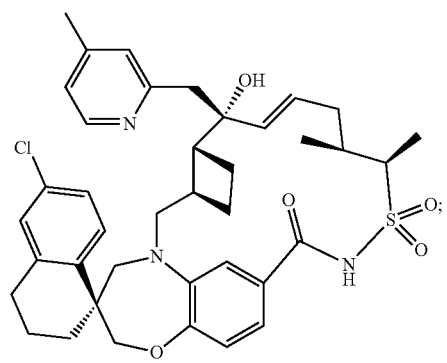

479
-continued
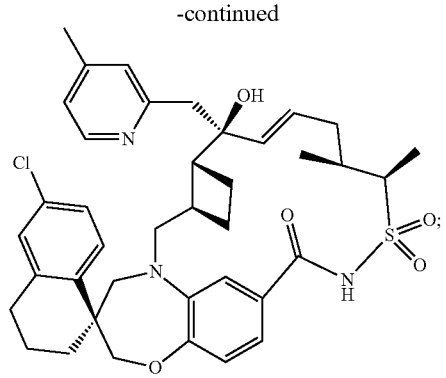
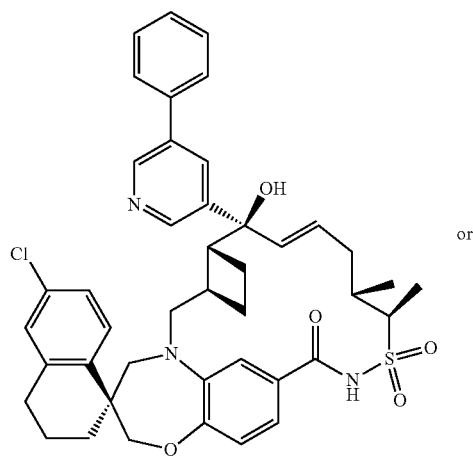
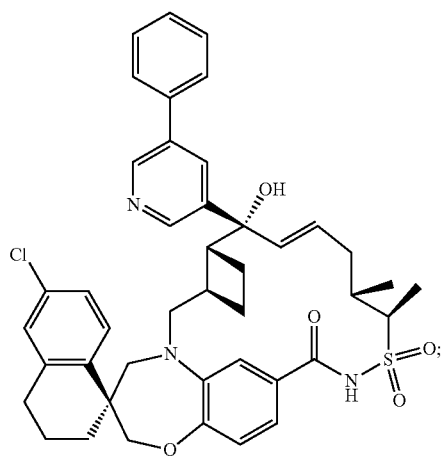
or
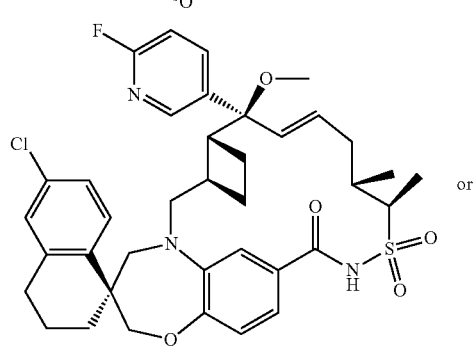
or
480
-continued
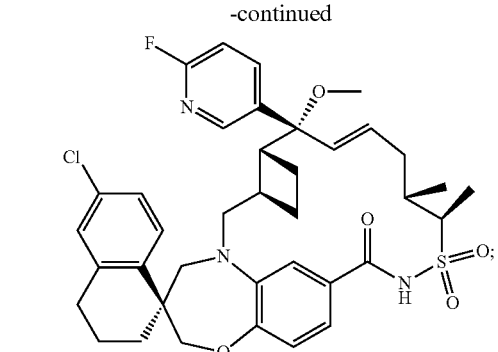
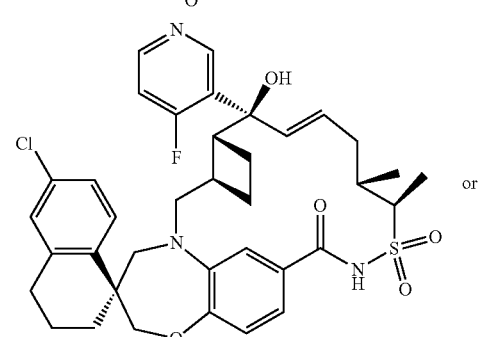
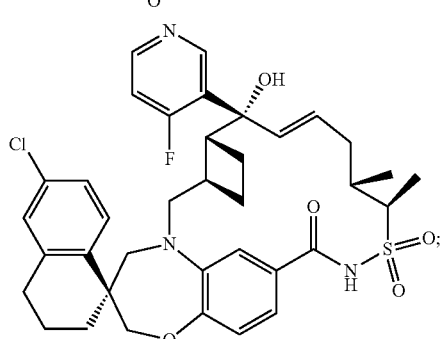
or
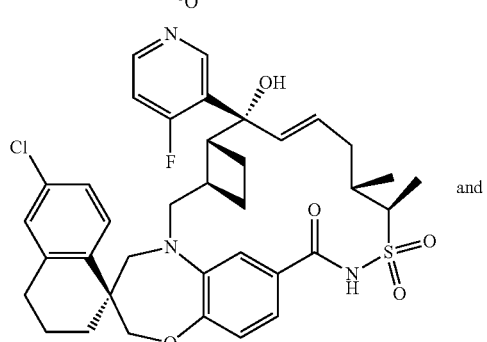
and
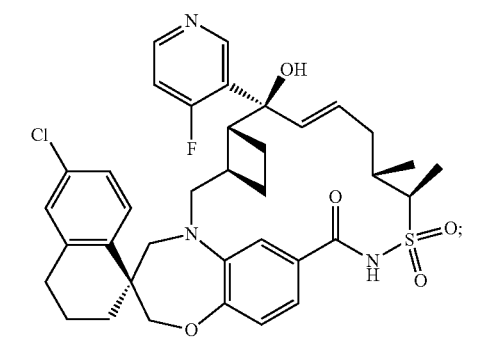

481
-continued
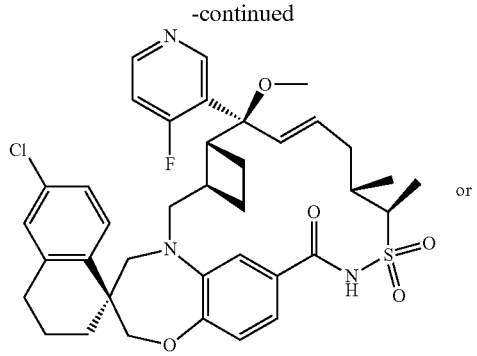
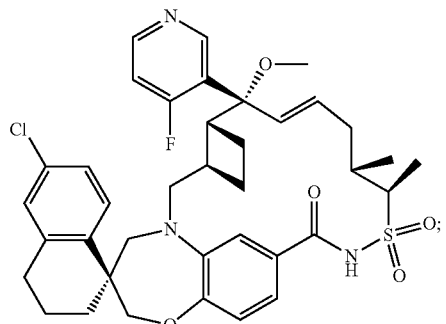
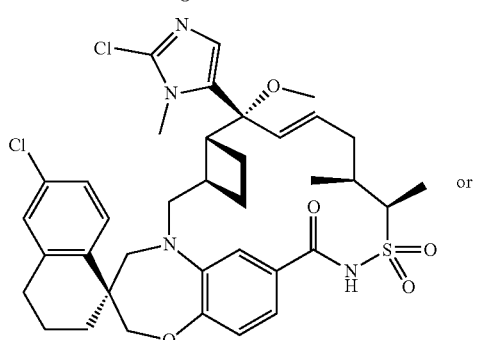
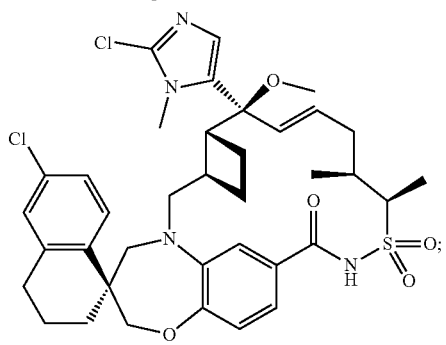
or
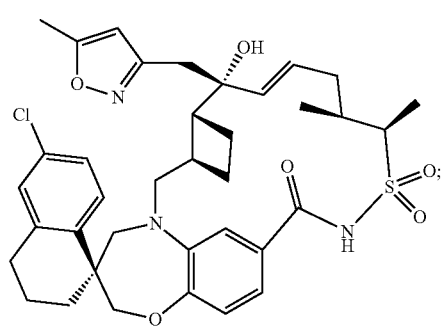
482
-continued
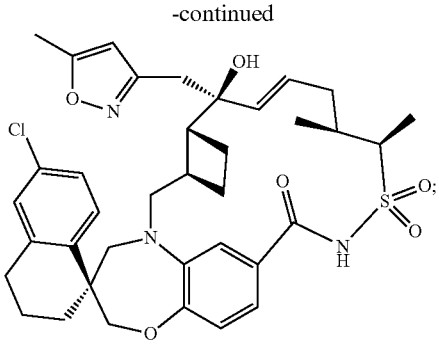
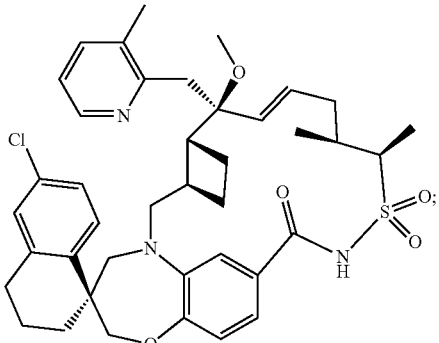
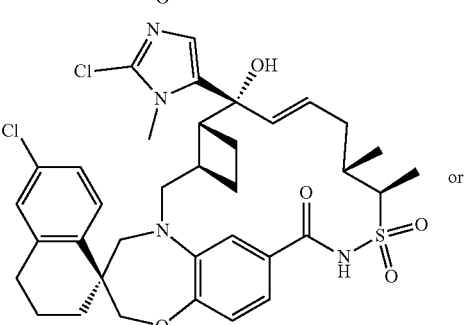
or
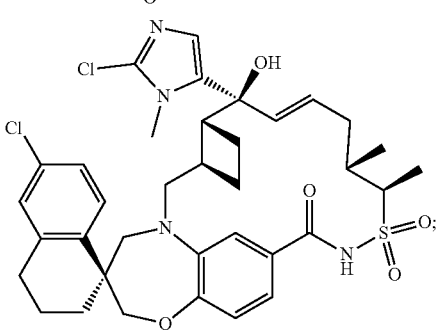
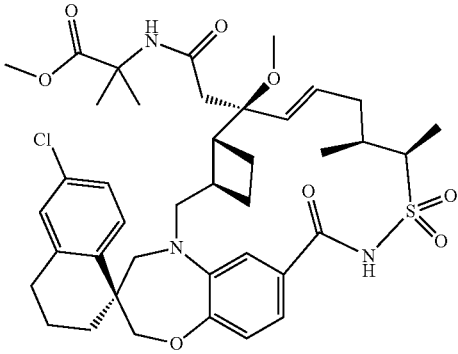

483
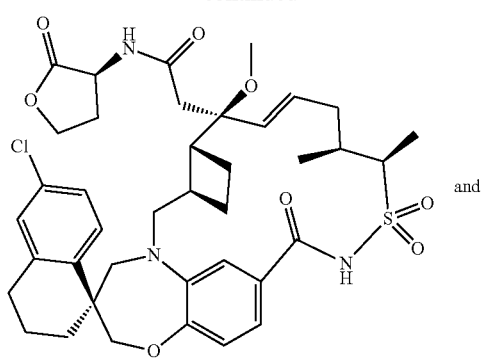
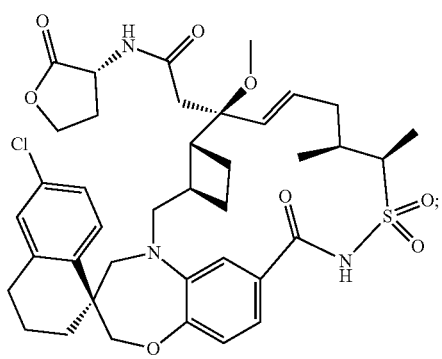
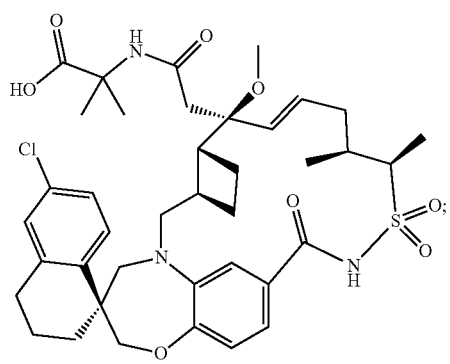
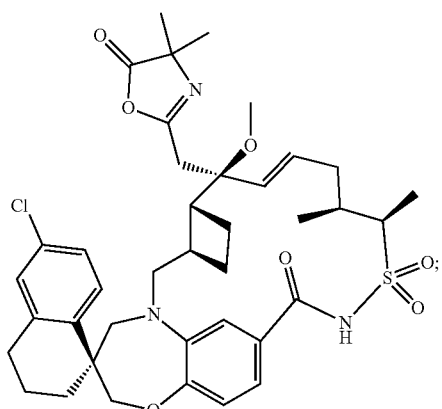
484
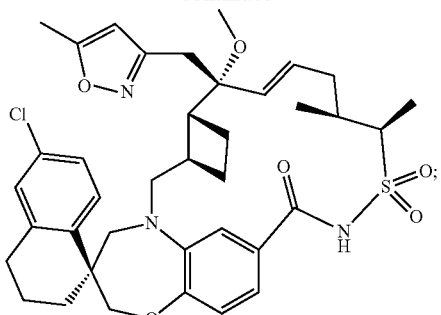
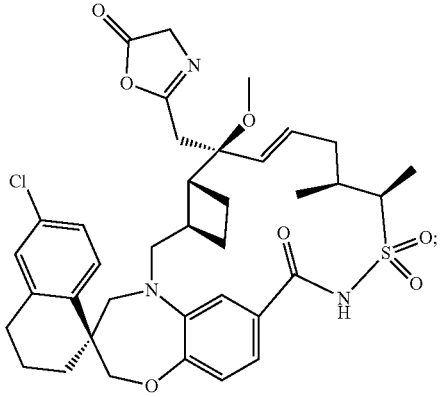
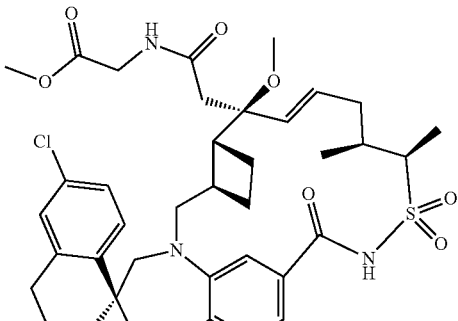
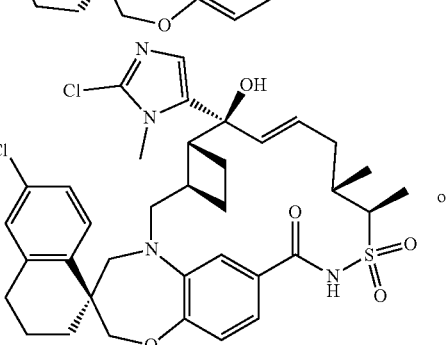
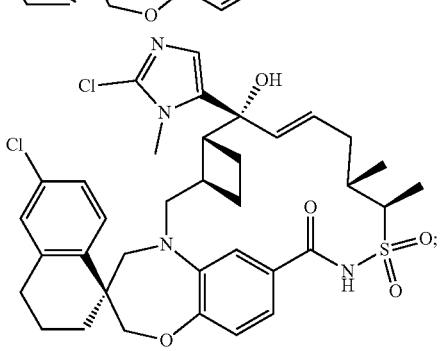

485
-continued
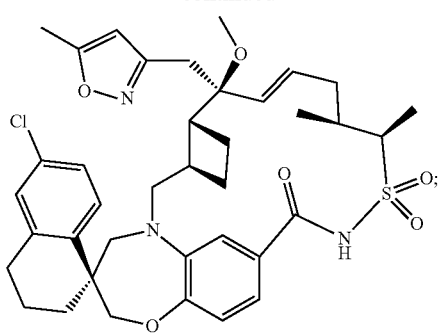
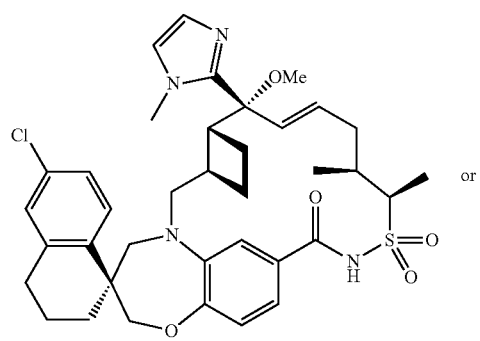
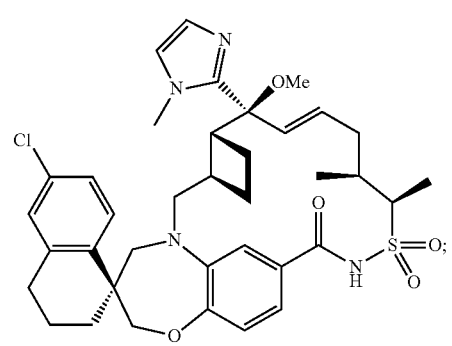
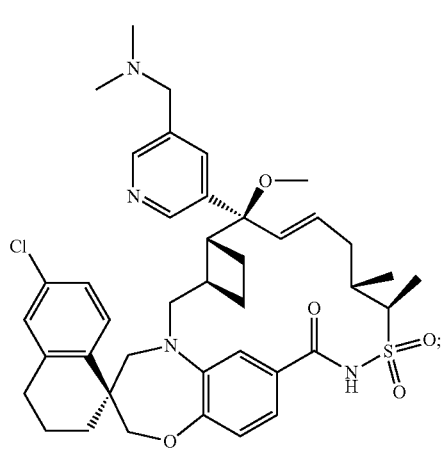
486
-continued
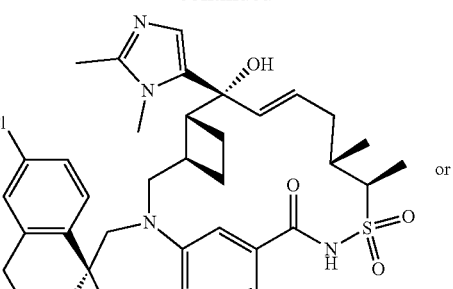
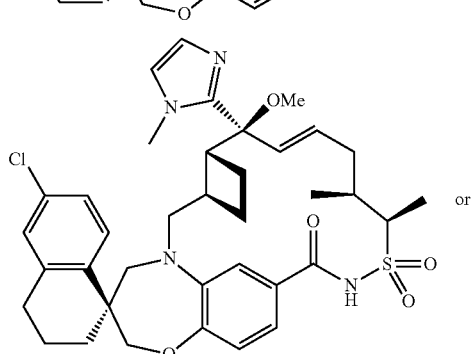
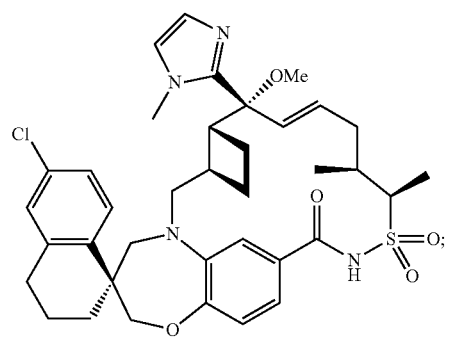
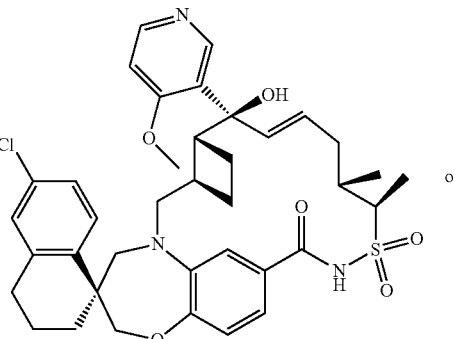
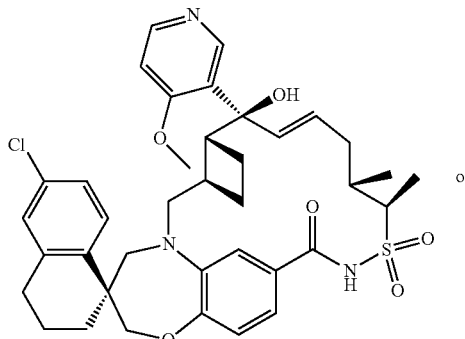

487
-continued
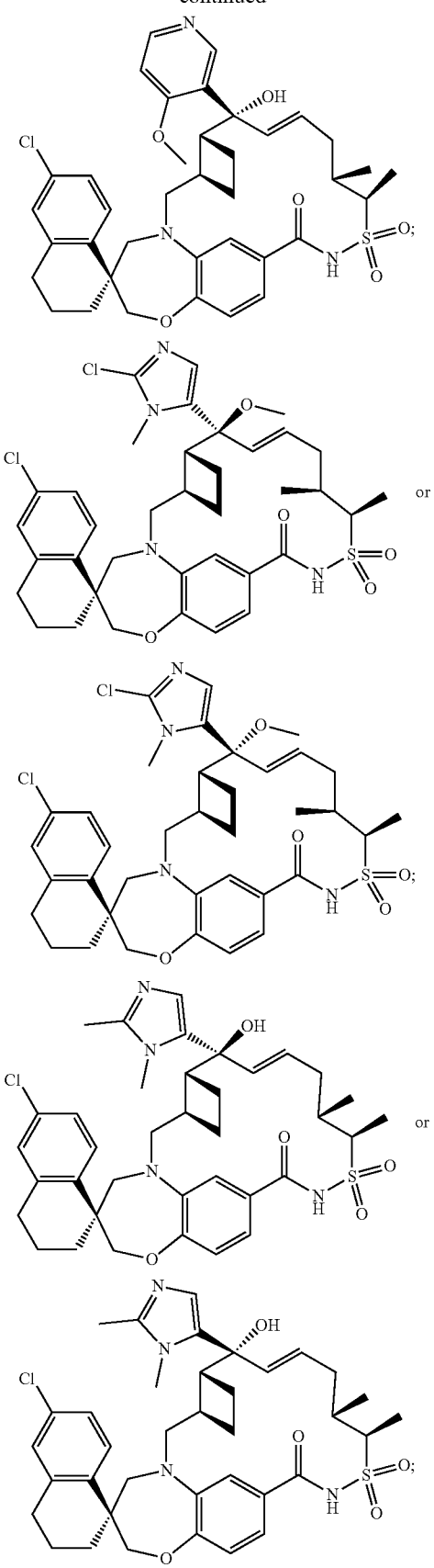
488
-continued
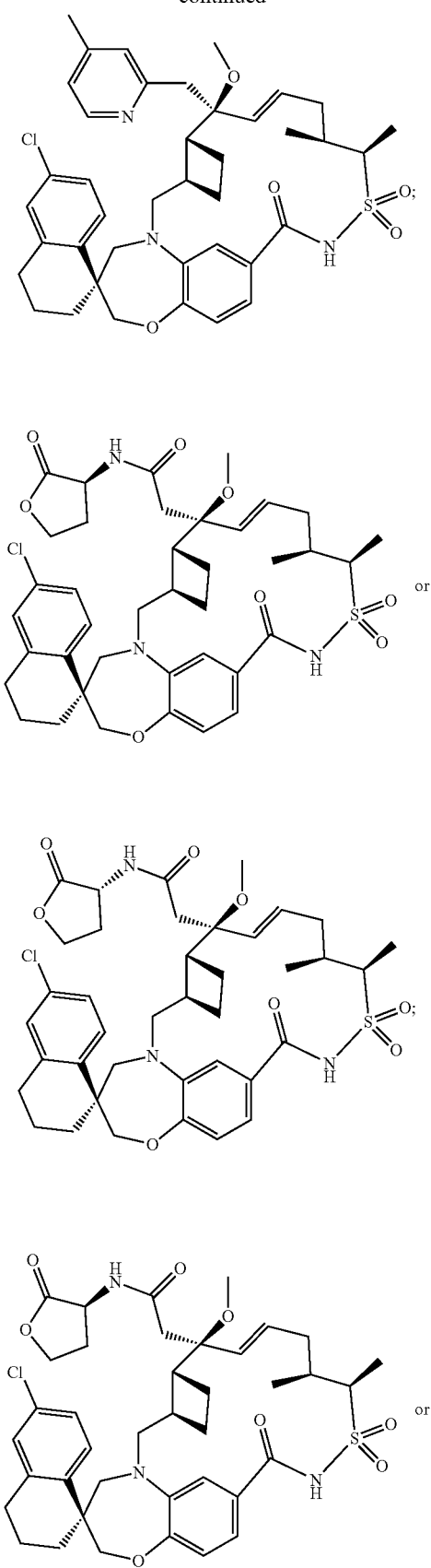

489
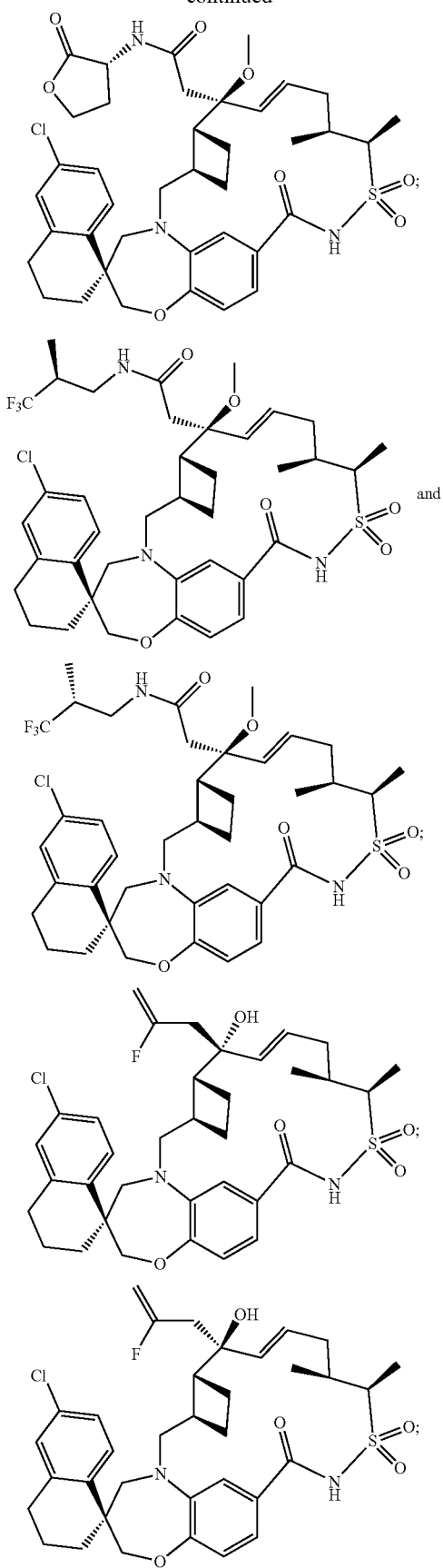
490
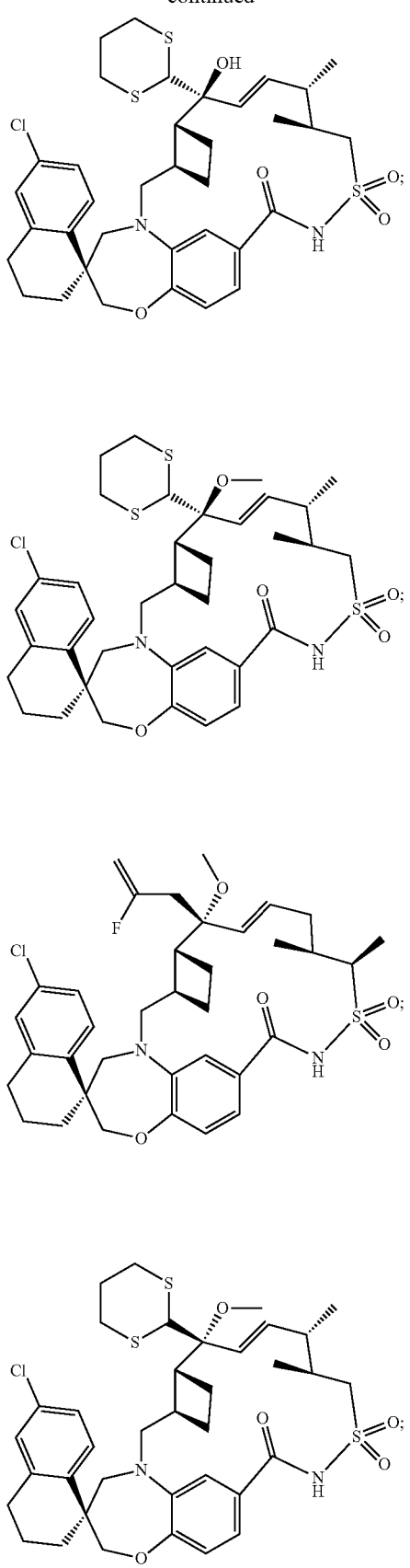

491
-continued
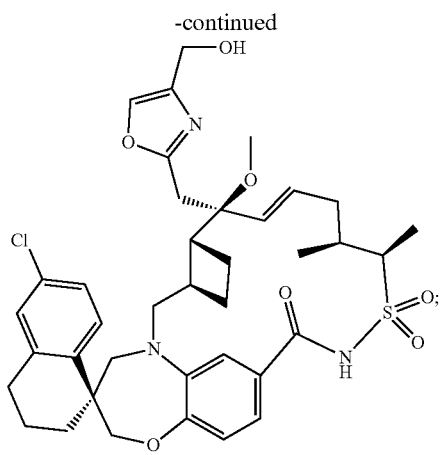
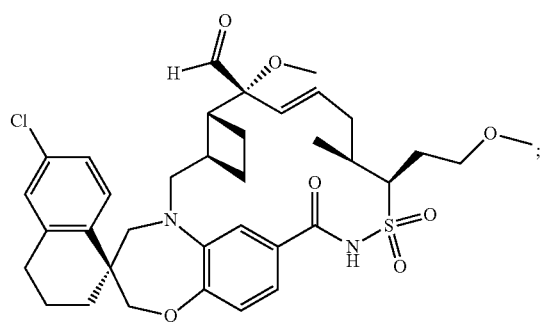
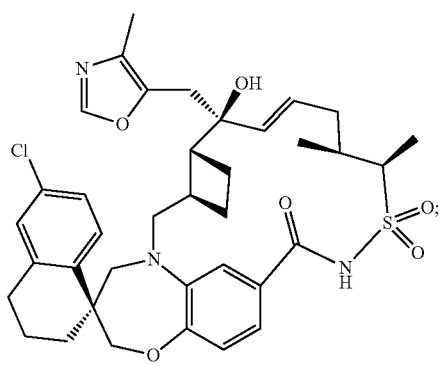
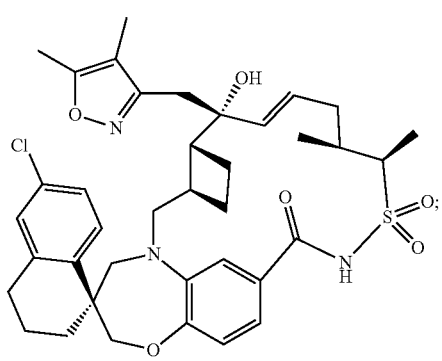
492
-continued
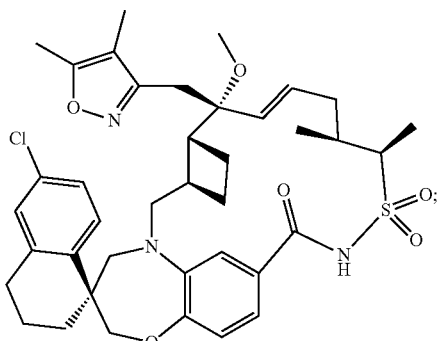
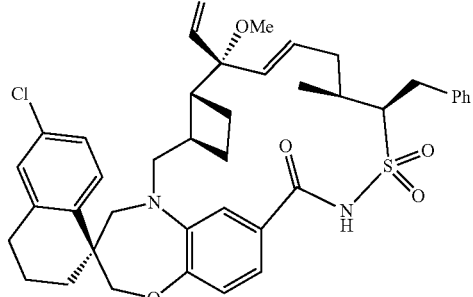
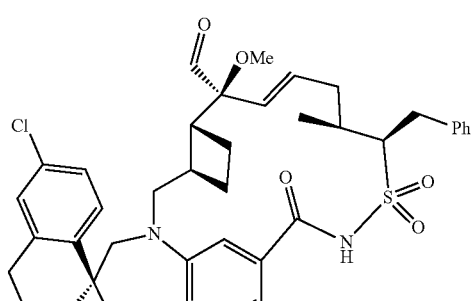 or
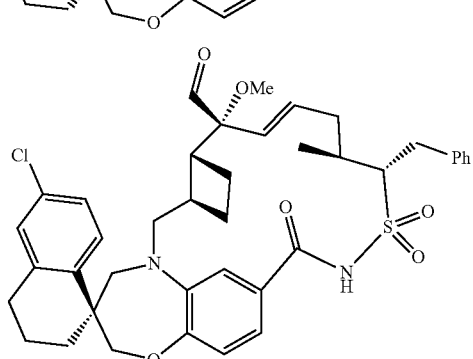 or
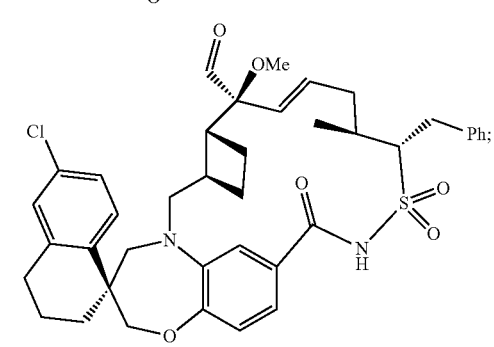

493
-continued
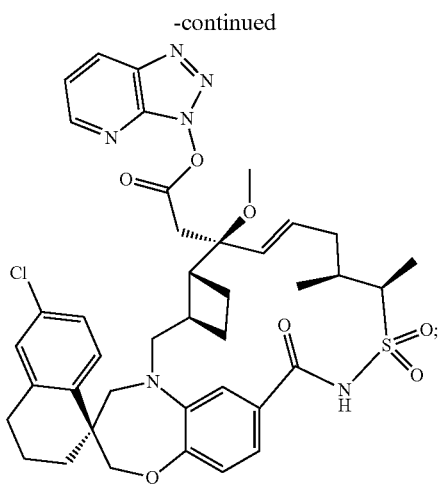
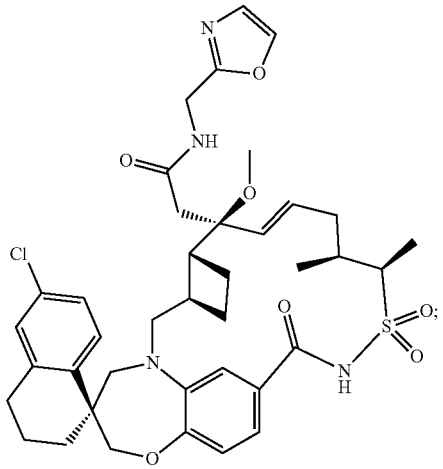
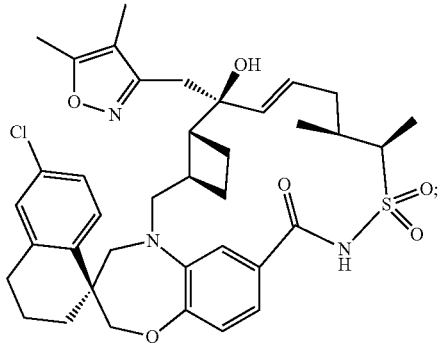
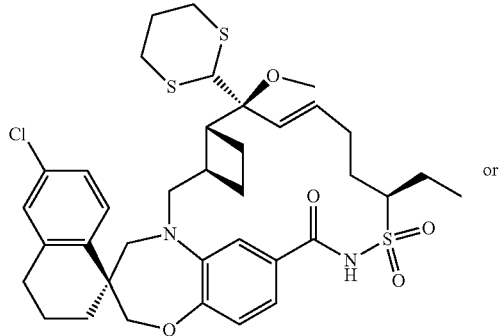
or
494
-continued
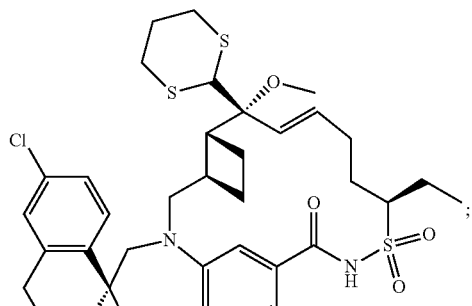
;
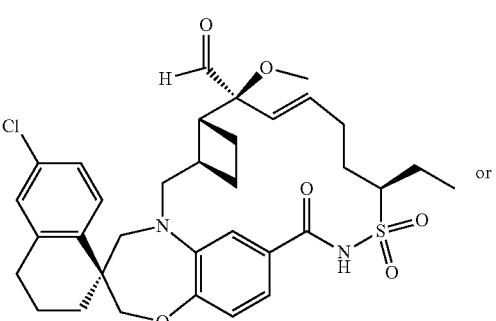
or
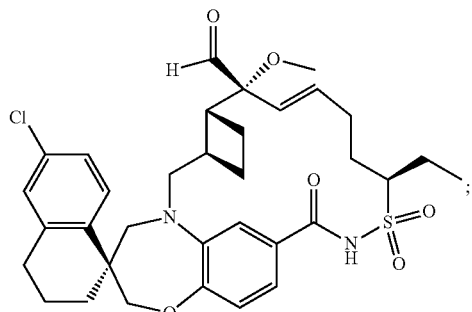
;
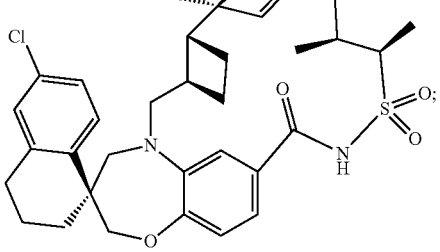

495
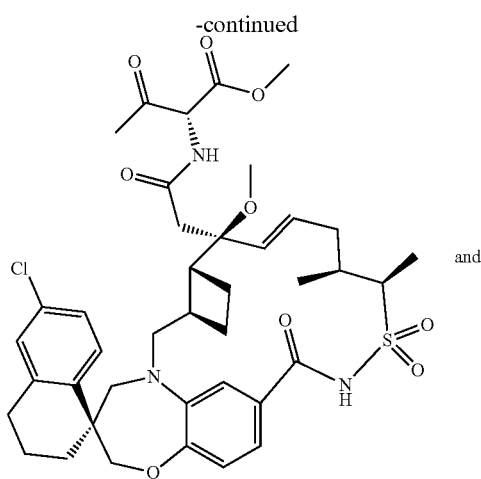
and
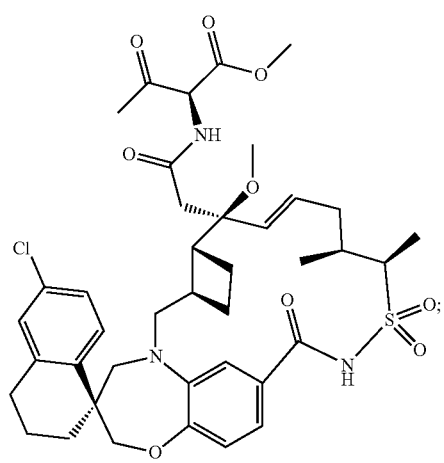
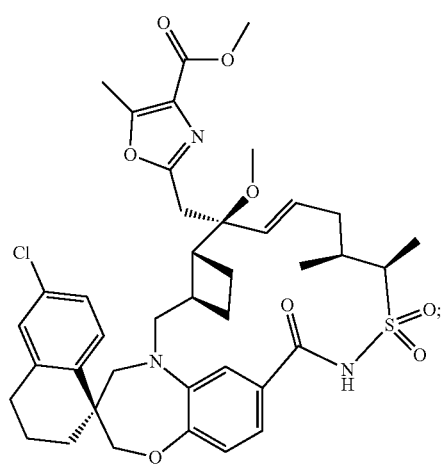
496
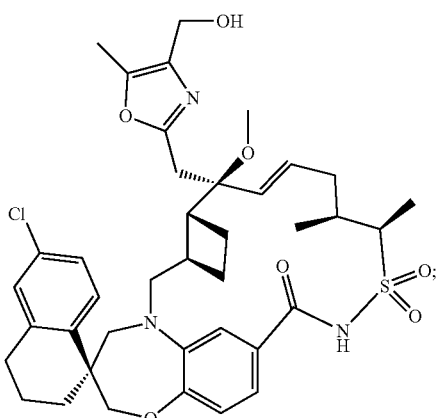
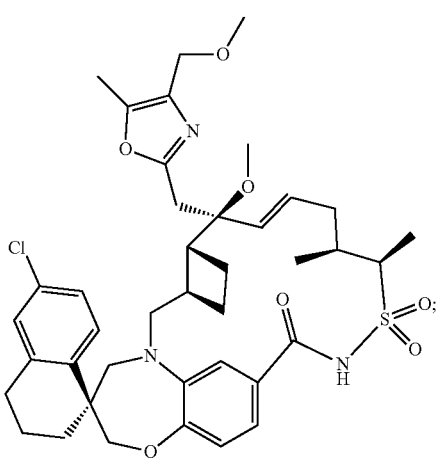
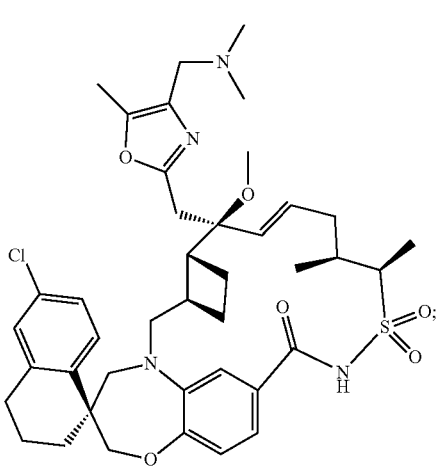

497
-continued
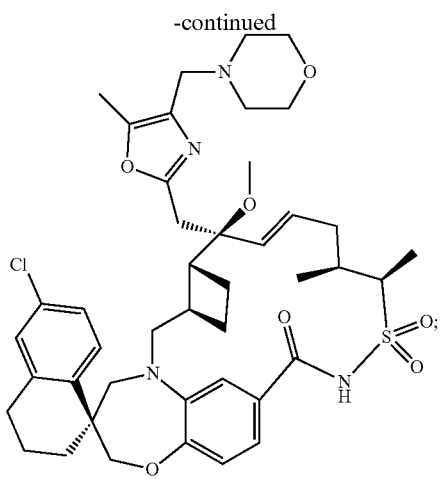
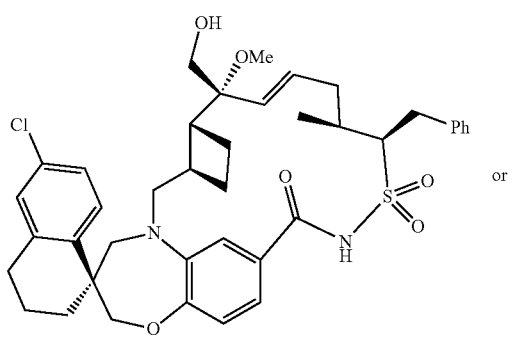
or
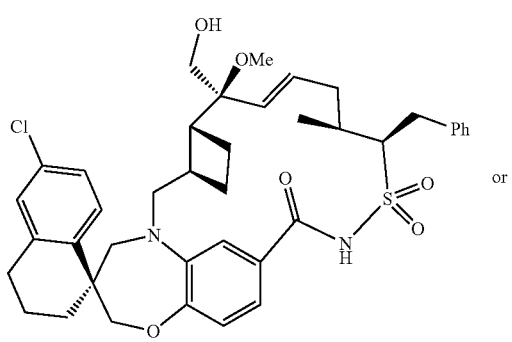
or
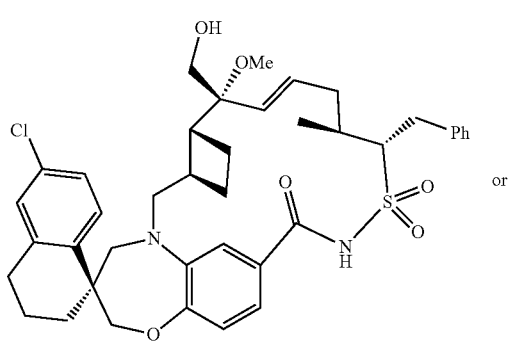
or
498
-continued
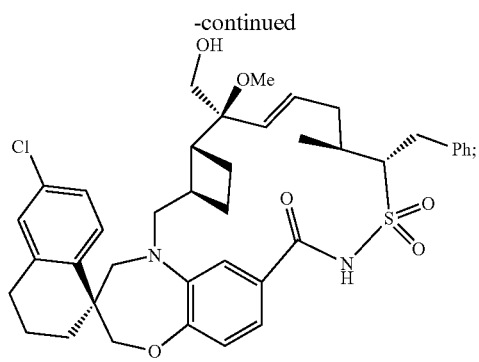
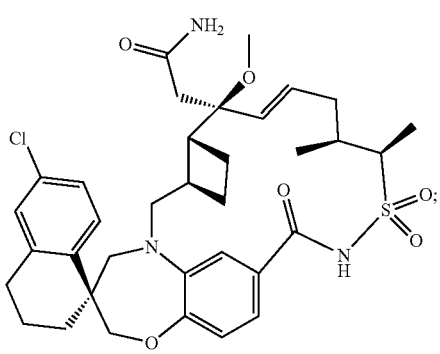
or
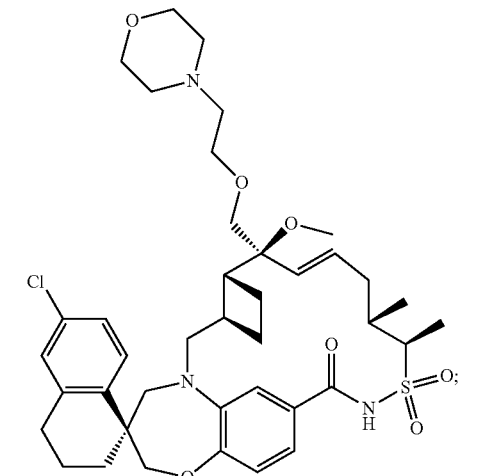

499
-continued
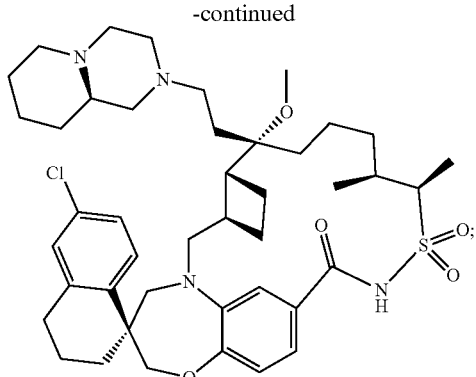
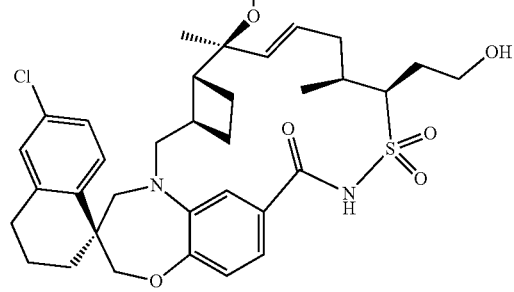
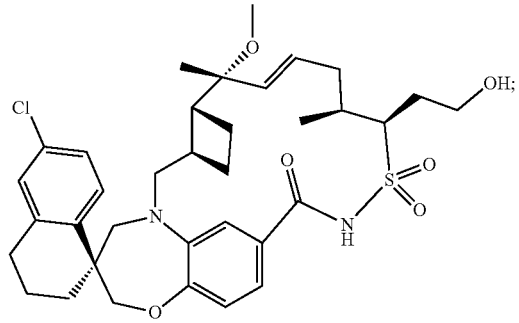
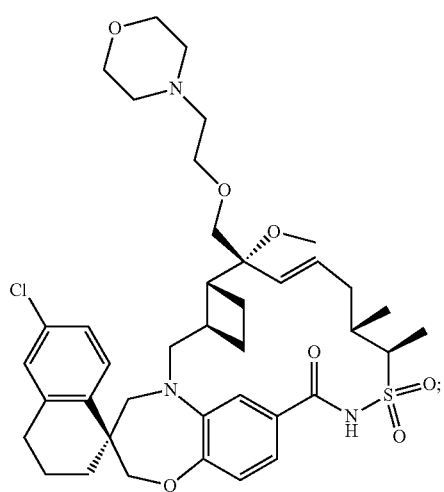
500
-continued
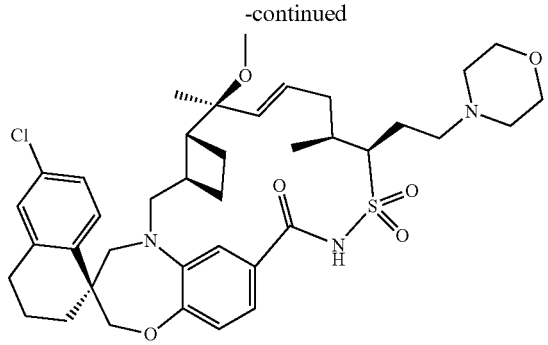
or
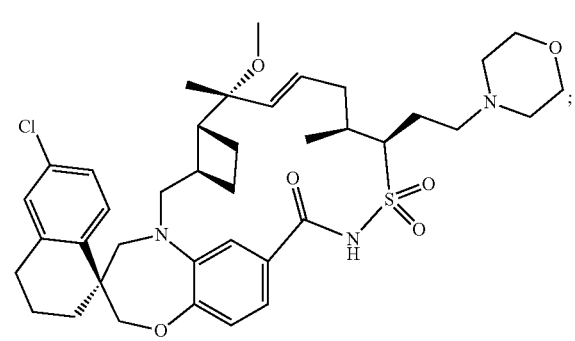
;
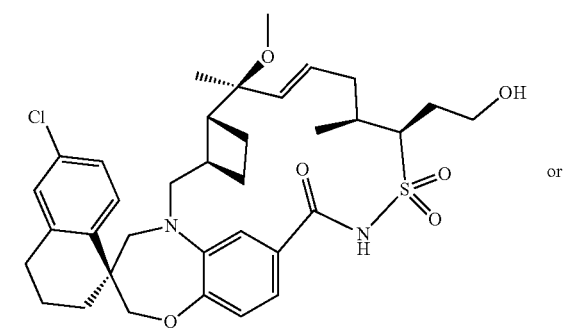
or
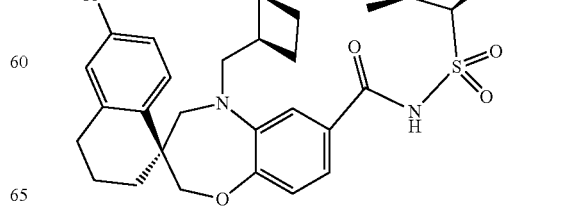

501
-continued
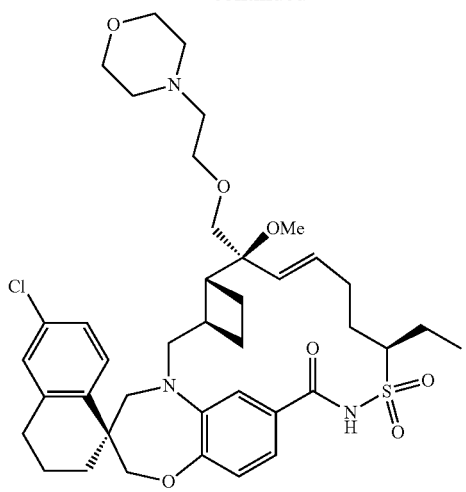
or
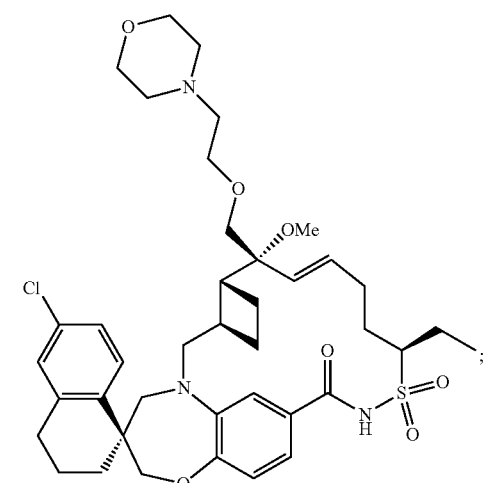
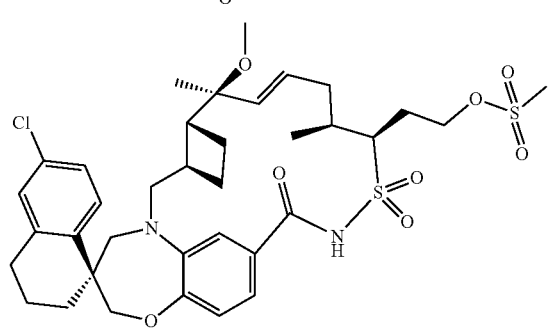
or
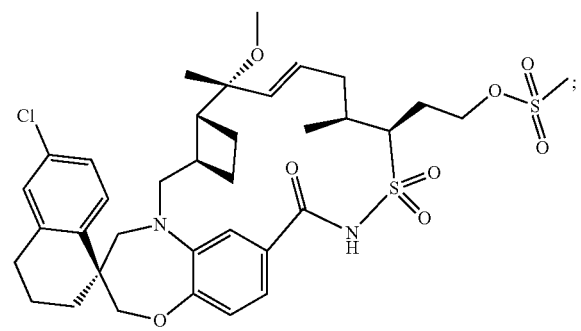
502
-continued
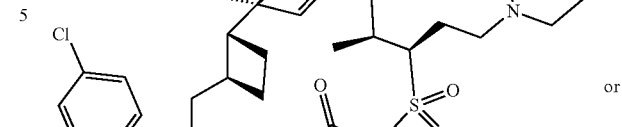
or
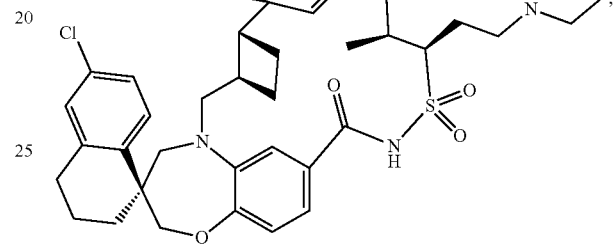
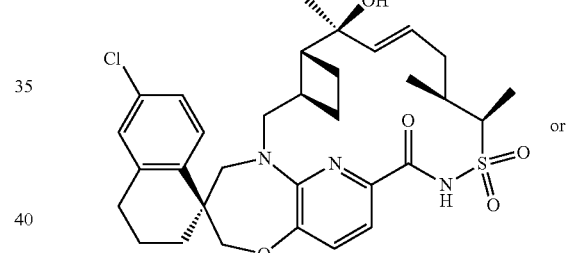
or
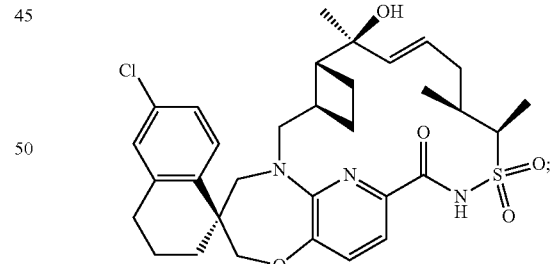
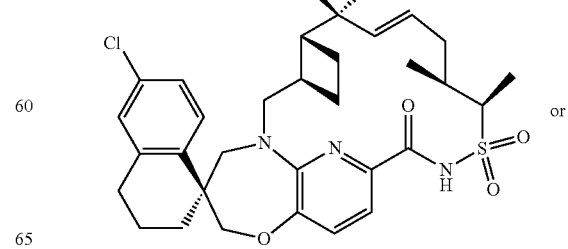
or

503
-continued
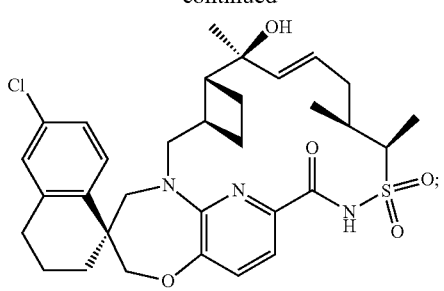
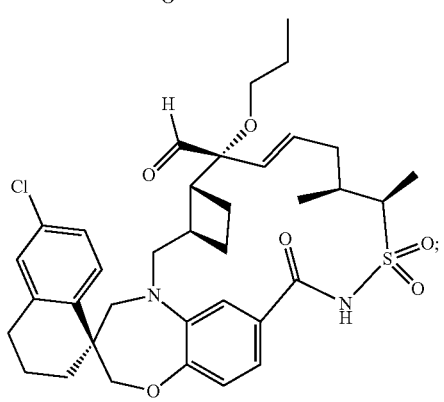
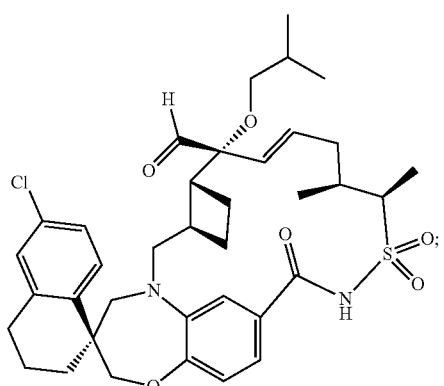
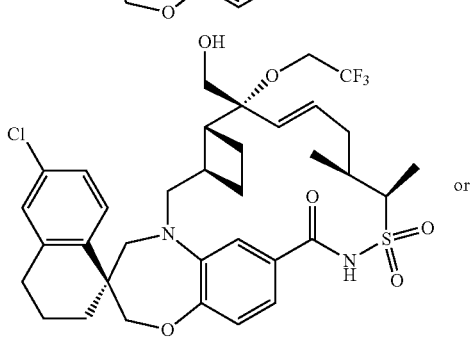
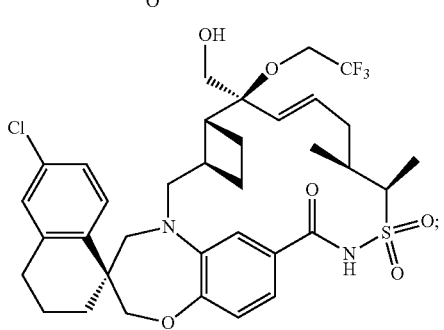
504
-continued
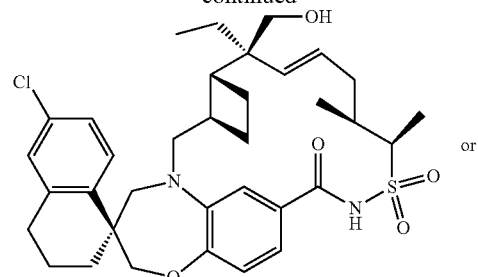
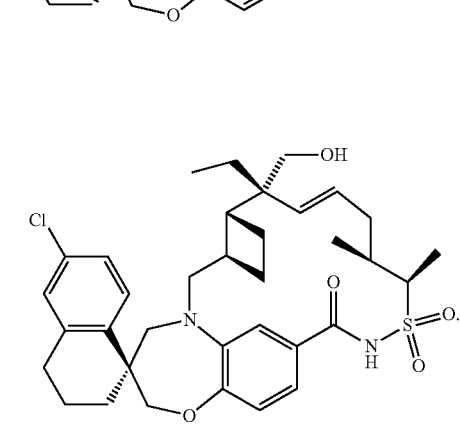
or a stereoisomer thereof; a pharmaceutically acceptable salt thereof, a pharmaceutically acceptable salt of the stereoisomer thereof.
91. Another embodiment of the present invention comprises a compound, wherein the compound has a structure selected from.
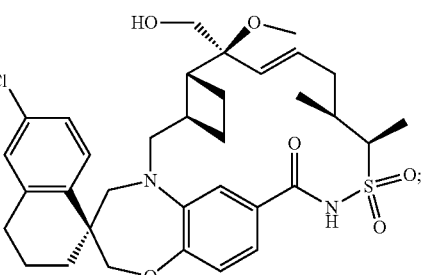
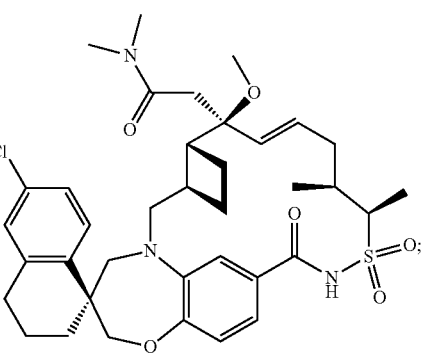

505
-continued
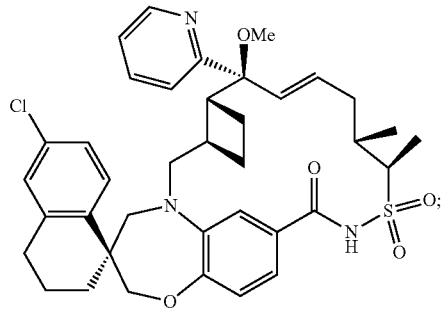
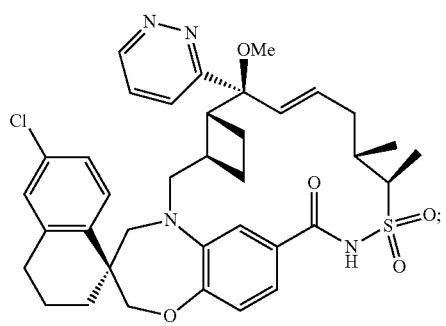
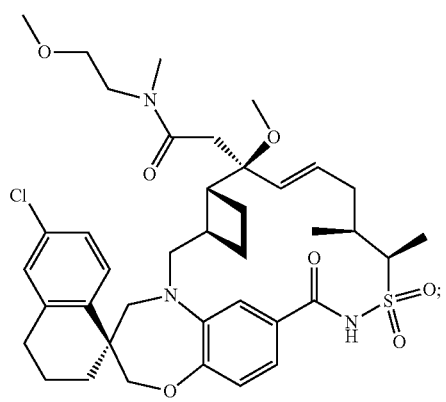
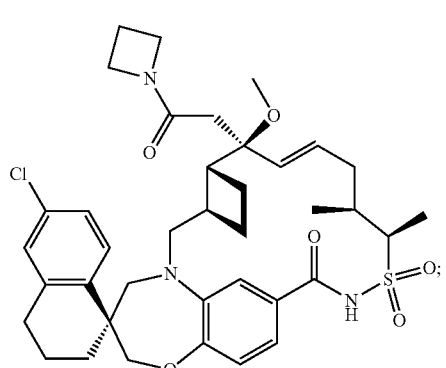
506
-continued
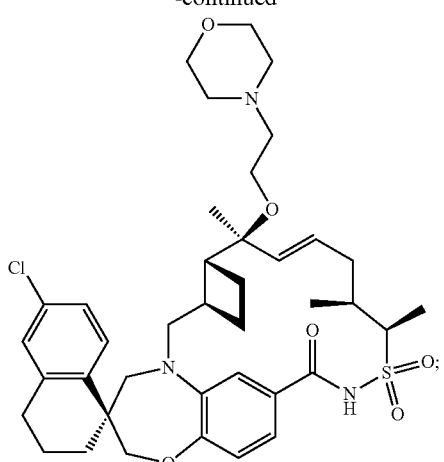
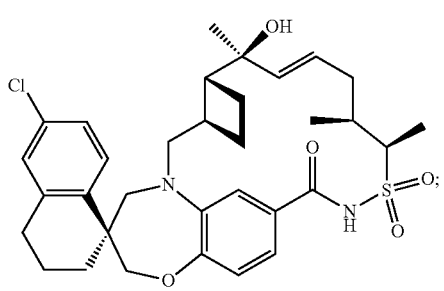
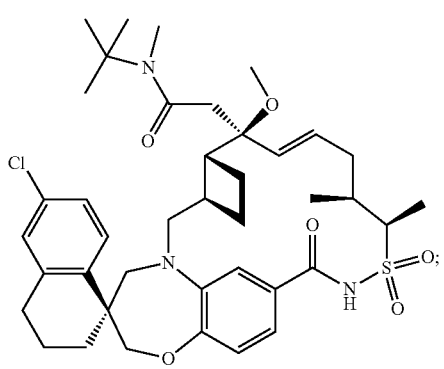
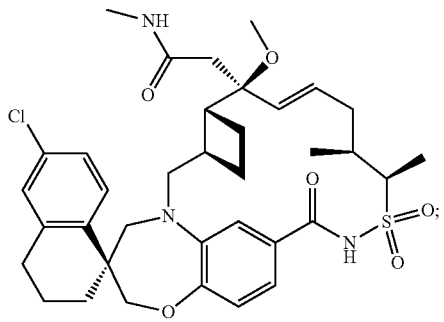

507
-continued
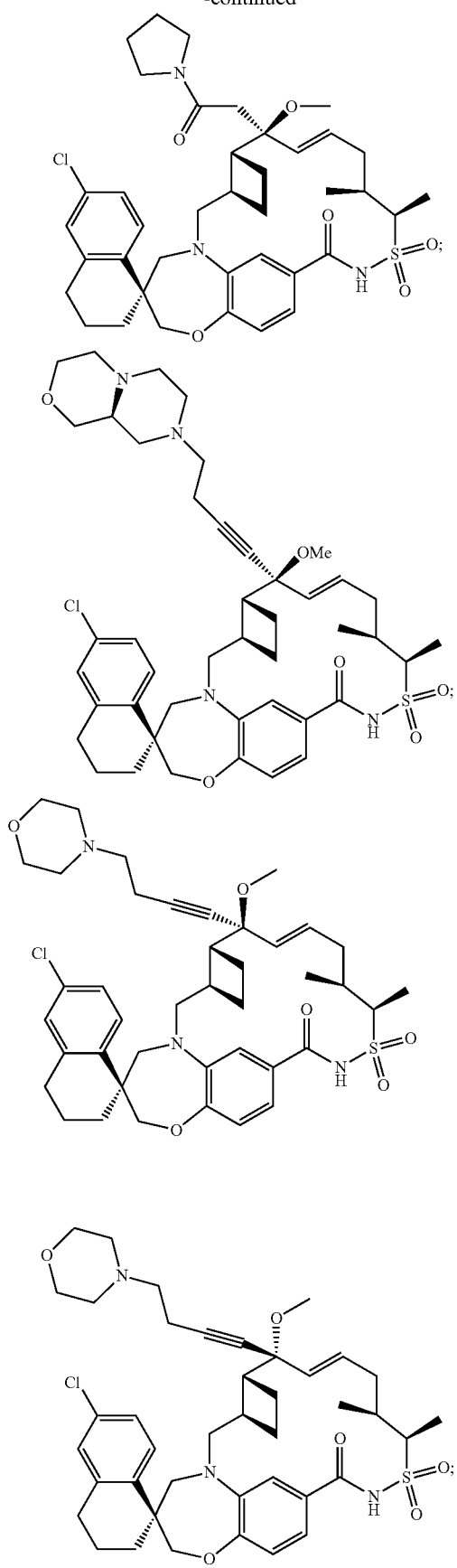
508
-continued
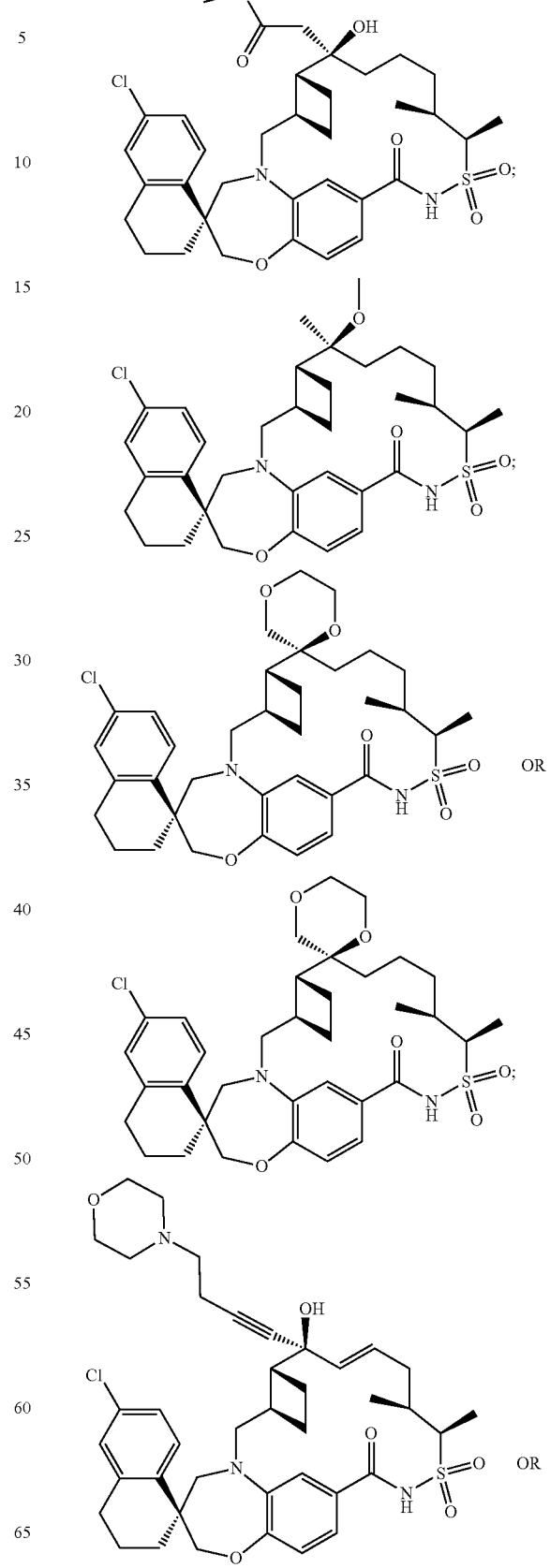

509
-continued

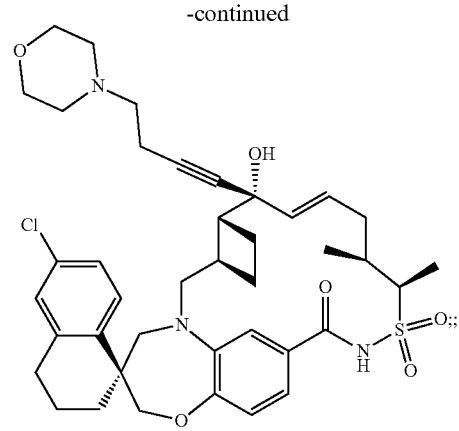

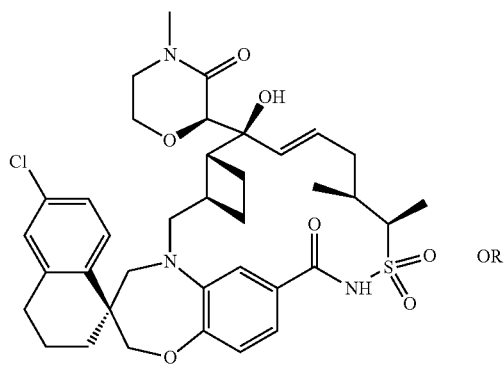
OR

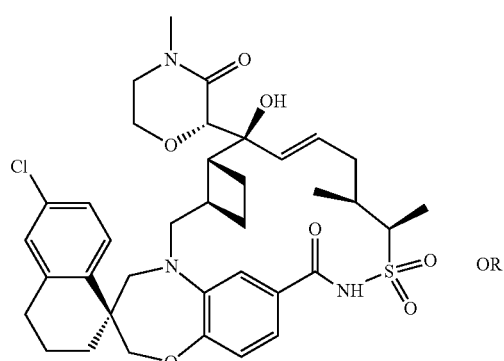
OR

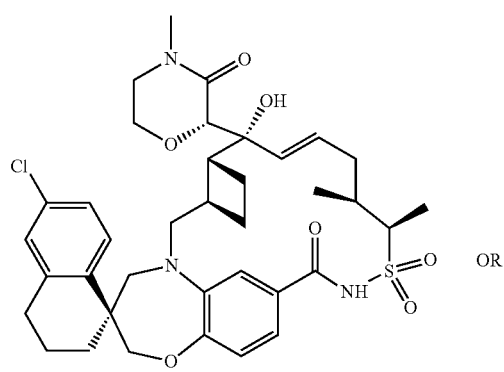
OR

510
-continued

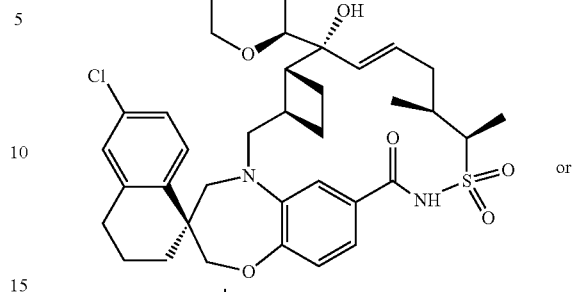
or

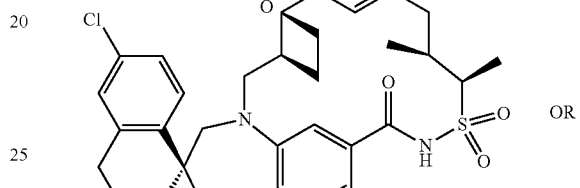
OR

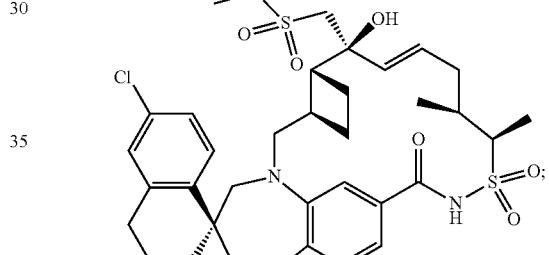

or a stereoisomer thereof; a pharmaceutically acceptable salt thereof, a pharmaceutically acceptable salt of the stereoisomer thereof.

92. The compound of embodiment 91 or the pharmaceutically acceptable salt thereof.

93. Another embodiment of the present invention comprises a pharmaceutical composition comprising the compound of any one of embodiments 1-92 or the pharmaceutically acceptable salt thereof, and a pharmaceutically acceptable carrier or diluent.

94. Another embodiment of the present invention comprises a method of treating cancer, the method comprising: administering to a patient in need thereof a therapeutically effective amount of the compound of any of embodiments 1-92 or a pharmaceutically acceptable salt thereof.

95. The method of embodiment 94, wherein the cancer is a hematologic malignancy.

96. The method of embodiment 94, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

97. The method of embodiment 94, wherein the cancer is multiple myeloma.

98. The method of embodiment 94, further comprising administering to the patient in need thereof a therapeutically effective amount of an additional pharmaceutically active compound.

99. The method of embodiment 98, wherein the additional pharmaceutically active compound is carfilzomib.

100. The method of embodiment 98, wherein the additional pharmaceutically active compound is venetoclax.

101. The method of embodiment 98, wherein the additional pharmaceutically active compound is cytarabine.

102. Another embodiment of the present invention comprises a use of a compound according to any one of Embodiments 1-92 for treating cancer in a subject.

103. Another embodiment of the present invention comprises a compound according to any one of Embodiments 1-92 in the preparation of a medicament for treating cancer.

104. The compound according to Embodiment 103, wherein the cancer is a hematologic malignancy.

105. The compound according to embodiment 102, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

106. The compound according to Embodiment 102, wherein the cancer is multiple myeloma.

107. The compound according to Embodiment 102, wherein the cancer is acute myelogenous leukemia.

108. The compound according to Embodiment 102, wherein the cancer is non-Hodgkin's lymphoma. Another embodiment of the present invention is directed to a method of inhibiting myeloid cell leukemia 1 protein (Mcl-1) of a cell comprising contacting the cell with the compound of Formula I in an effective amount to inhibit the Mcl-1, in conjunction with any of the above or below embodiments. In one embodiment, the contacting is in vitro. In another embodiment, the contacting is in vivo. In one embodiment, the contacting comprises administering the compound to a subject. In one embodiment, the administering is oral, parenteral, via injection, via inhalation, transdermal, or transmucosal. In one embodiment, the subject suffers from cancer.

One embodiment of the present invention is directed to a method of the treatment of cancer, comprising administering to a patient in need thereof a therapeutically effective amount of the compound of Formula I or a pharmaceutical composition comprising the compound of Formula I, or pharmaceutically acceptable salt thereof, and a pharmaceutically acceptable excipient, in conjunction with any of the above or below embodiments. In one embodiment, the cancer is a hematologic malignancy. In one embodiment, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In one embodiment, the cancer is multiple myeloma. In another embodiment, the method further comprises the step of administering to the patient in need thereof a therapeutically effective amount of at least one additional pharmaceutically active compound. In one embodiment, the additional pharmaceutically active compound is carfilzomib, in conjunction with any of the above embodiments.

The methods provided herein include the manufacture and use of pharmaceutical compositions, which include one or more of the compounds provided herein. Also included are the pharmaceutical compositions themselves.

In some Claims, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxida Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. The dose of the compound or composition can be varied over time. All combinations, delivery methods and administration sequences are contemplated.

The compounds of the present invention and in some Claims, other additional pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof, (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In one Claim, the IV formulation consists of a composition containing hydroxypropyl beta cyclodextrin within a pH range between 8-10 as a buffered or unbuffered solution. The IV formulation can be formulated as a sterile solution ready for injection, a sterile solution ready for dilution into an IV admixture or a sterile solid for reconstitution. The API in the IV formulation may exist as a free acid/base or an in situ salt.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant (e.g., a gas such as carbon dioxide) or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some Claims, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one claim, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially (e.g., from Alza Corporation and Nova Pharmaceuticals, Inc). Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety for all purposes.

The compounds of the present invention are used in the treatment of diseases, disorders or symptoms mediated by Mcl-1 inhibition. Examples of diseases, disorders or symptoms mediated by Mcl-1 inhibition include, but are not limited to, cancers. Non-limiting examples of cancers include breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

The cancers can include carcinomas (originating in the outer layer of cells of the skin and internal membranes, e.g., breasts, kidneys, lungs, skin); sarcomas (arising from connective tissue such as bone, muscle, cartilage, and blood vessels), and hematologic malignancies (e.g., lymphomas and leukemias, which arise in the blood or blood-forming organs such as the spleen, lymph nodes, and bone marrow). Cancer cells can include, for example, tumor cells, neoplastic cells, malignant cells, metastatic cells, and hyperplastic cells.

In an Claim, the disease, disorder or symptom is a hyperproliferative disorder, e.g., a lymphoma, leukemia, carcinoma (e.g., renal, breast, lung, skin), multiple myeloma, or a sarcoma. In one Claim, the leukemia is acute myeloid leukemia. In one Claim, the hyperproliferative disorder is a relapsed or refractory cancer.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The specific dosage and dosage range depends on a number of factors, including the requirements of the patient, the severity of the condition or disease being treated, the pharmacokinetic characteristics of the compound(s) employed, and the route of administration. In some Claims, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain about 0.001%-100% active ingredient, in one Claim from about 0.1 to about 95%, in another Claim from about 75 to about 85%. Although the dosage will vary depending on the symptoms, age and body weight of the patient, the nature and severity of the disorder to be treated or prevented, the route of administration and the form of the drug, in general, a daily dosage of from about 0.01 to about 3,000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the Claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing The compounds of the present invention can be administered alone, in combination with other compounds of the present invention, or with other pharmaceutically active compounds or agents. The other pharmaceutically active compounds/agents can be intended to treat the same disease or condition as the compounds of the present invention or a different disease or condition. If the patient is to receive or is receiving multiple pharmaceutically active compounds or agents, the compounds can be administered simultaneously, or sequentially.

The compounds of the present invention, or pharmaceutically acceptable salts thereof, may be used in combination with one or more additional pharmaceutically active compounds/agents. One or more additional pharmaceutically active compounds or agents may be administered separately, as part of a multiple dose regimen, from the compound of Formula I (e.g., sequentially, e.g., on different overlapping schedules with the administration of one or more compounds of Formula I (including any subgenera or specific compounds thereof). In other Claims, the one or more additional compounds/agents may be part of a single dosage form, mixed together with the compound of Formula I in a single composition. In still another Claim, the one or more additional compounds/agents can be given as a separate dose that is administered at about the same time that one or more compounds of Formula I are administered (e.g., simultaneously with the administration of one or more compounds of Formula I (including any subgenera or specific compounds thereof). Both the compound of Formula I and the one or more additional compounds/agents can be present at dosage levels of between about 1 to 100%, and more preferably between about 5 to 95% of the dosage normally administered in a monotherapy regimen.

In a particular claim, the additional pharmaceutically active compound/agent is a compound or agent that can be used to treat a cancer. For example, the additional pharmaceutically active compound/agent can be selected from antineoplastic agents, anti-angiogenic agents, chemotherapeutic agents, and peptidal cancer therapy agents. In another Claim, the antineoplastic agents are selected from antibiotic-type agents, alkylating agents, antimetabolite agents, hormonal agents, immunological agents, interferon-type agents, kinase inhibitors, proteasome inhibitors, and combinations thereof. It is noted that the additional pharmaceutically active compound/agent may be a traditional small organic chemical molecule or can be a macromolecule such as a protein, antibody, peptibody, DNA, RNA or a fragment of such macromolecules.

Examples of additional pharmaceutically active compounds/agents that can be used in the treatment of cancers and that can be used in combination with one or more compounds of the present invention include: acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; cytarabine; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; 243rimethyl polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; trametinib; tumor necrosis factor alpha natural; ubenimex; bladder cancer vaccine; Maruyama vaccine; melanoma lysate vaccine; valrubicin; venetoclax; verteporfin; virulizin; zinostatin stimalamer; abarelix; AE 941 (Aetema); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (Mab) (Biomira); cancer Mab (Japan Pharmaceutical Development); HER-2 and Fc Mab (Medarex); idiotypic 105AD7 Mab (CRC Technology); idiotypic CEA Mab (Trilex); LYM-1-iodine 131 Mab (Techniclone); polymorphic epithelial mucin-yttrium 90 Mab (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine; melanoma oncolysate vaccine; viral melanoma cell lysates vaccine; valspodarl; fluorouracil; 5-fluorouracil; 244rimethyla; imatinib; altretamine; cladribine; cyclophosphamine; decarazine; irinotecan; mitosmycin; mitoxane; topotecan; vinorelbine; 244rimethyla; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; 244rimethylam; oprozomib; vorinostat; capecitabine; zoledronic acid; anastrozole; sunitinib; aprepitant and nelarabine, or a pharmaceutically acceptable salt thereof.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain claims, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNTO328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), inhibitors of KRAS including covalent inhibitors of KRAS G12C, MEK inhibitor, including trametinib, HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zamestra™), anti-CD138 (e.g., BT062), Torc1/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain claims, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular Claim, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some Claims, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, 247rimethylamine, ethylamine, and the like. See, for example, S. M. Berge, et al., "Pharmaceutical Salts," J Pharm Sci, 66: 1-19 (1977).

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The compounds of the present invention may exist in various solid states including crystalline states and as an amorphous state. The different crystalline states, also called polymorphs, and the amorphous states of the present compounds are contemplated as part of this invention.

EXAMPLES

The examples presented below illustrate specific Claims of the present invention. These examples are meant to be representative and are not intended to limit the scope of the Claims in any manner.

The following abbreviations may be used herein:

~ about
Ac acetate
Ac$_2$O acetic anhydride
AcOH acetic acid
Al$_2$O$_3$ aluminum oxide
br broad
Boc tert-butyloxycarbonyl
B(OiPr)$_3$ triisopropyl borate
B(Oallyl)$_3$ triallyl borate
B(OCH$_2$CF$_3$)$_3$ tris(2,2,2-trifluoroethyl) borate
B(On-Bu)$_3$ tri-n-butyl borate
Calcd calculated
CO$_2$ carbon dioxide
CSA 10-camphorsulfonic acid
d day or doublet
DBU 1,8-diazabicyclo[5.4.0]undec-7-ene
DCE dichloroethane
DCM dichloromethane
DEA diethylamine
Dess-Martin periodinane 1,1,1-triacetoxy-1,1-dihydro-1,2-benziodoxol-3-(1H)-one
DIPEA or DIEA diisopropylethylamine
DMA N,N-dimethylacetamide
DMF N,N-dimethylformamide
DMSO dimethyl sulfoxide
EDC N-ethyl-N'-(3-dimethylaminopropyl)carbodiimide
ee or e.e. enantiomeric excess
ELISA enzyme-linked immunosorbent assay
eq or equiv equivalent
ESI or ES electrospray ionization
Et ethyl
Et$_2$O diethyl ether
EtOAc ethyl acetate
Et$_3$N triethylamine
EtOH ethyl alcohol
EtI ethyl iodide
g gram(s)
GC gas chromatography
h hour(s)
H$_2$ hydrogen gas
HCl hydrochloric acid
$^1$H NMR proton nuclear magnetic resonance spectroscopy
HATU 1-[Bis(dimethylamino)methylene]-1H-1,2,3-triazolo[4,5-b]pyridinium 3-oxid hexafluorophosphate
H$_2$O water
HPLC high performance liquid chromatography
H$_2$SO$_4$ sulfuric acid
Hz Hertz
IP intraperitoneal IPA isopropyl alcohol
$K_2CO_3$ potassium carbonate
KF Karl Fischer titration
KHMDS potassium hexamethyldisilazide
KOAc potassium acetate
KOH potassium hydroxide
$K_3PO_4$ potassium phosphate
KOtBu potassium tert-butoxide
L liter
LAH lithium aluminium hydride
LCMS, LC-MS, or LC/MS liquid chromatography mass spectrometry
LHMDS lithium hexamethyldisilazide
m multiplet
mm millimeter
M molar (mol/L) or mass
Me methyl
MeCN acetonitrile
MeI iodomethane
MeOH methyl alcohol
MeTHF 2-methyltetrahydrofuran
$Me_3SI$ trimethylsulfonium iodide
$MeNH_2$ methylamine
$Me_2NH$ dimethylamine
mg milligram(s)
$MgSO_4$ magnesium sulphate
MHz megahertz
μm micrometer
μL microliter
min minute(s)
mL milliliter(s)
mm millimeter(s)
mol mole
MS mass spectrometry
MSA methanesulfonic acid
MsCl methanesulfonyl chloride
MTBE methyl tert-butyl ether
m/z mass-to-charge ratio
N Normality (Eq/L)
$N_2$ nitrogen gas
nBuLi n-butyllithium
NaCl sodium chloride
$Na_2CO_3$ sodium carbonate
$NaHCO_3$ sodium bicarbonate
$NaH_2PO_4$ sodium dihydrogen phosphate
$NaNO_2$ sodium nitrite
NaOH sodium hydroxide
NaOtBu sodium tert-butoxide
$Na_2SO_4$ sodium sulfate
$Na_2S_2O_3$ sodium thiosulfate
$NH_3$ ammonia, azane
$NH_4Cl$ ammonium chloride
$NH_4OH$ ammonium hydroxide
NMP 1-methyl-2-pyrrolidinone
NMR nuclear magnetic resonance spectroscopy
OMe methoxy
PO per oral
+ve positive
Ph phenyl
PhMe toluene
PMB p-methoxybenzyl
$POCl_3$ phosphoryl chloride
ppm parts per million
prep preparative
psi pounds per square inch
q quartet
QD once daily
QNMR quantitative NMR
Rac racemic
RBF round-bottomed flask
RT, rt, or r.t. room temperature
s singlet
sat. or satd or sat'd saturated
SFC supercritical fluid chromatography
SIMes 1,3-bis(2,4,6-trimethylphenyl)-4,5-dihydroimidazol-2-ylidene
$SiO_2$ silica
$SOCl_2$ thionyl chloride
t triplet
TBDPS tert-butyldiphenylsilyl
TBS tert-butyldimethylsilyl
TEMPO (2,2,6,6-tetramethylpiperidin-1-yl)oxidanyl
t-BuOH tert-butanol
TFA triflouroacetic acid
THF tetrahydrofuran
$Ti(OiPr)_4$ titanium isopropoxide
TLC thin layer chromatography
TsOH toluene sulfonic acid
UV ultraviolet
v/v volume per volume
wt % weight percent It is noted that when a percent (%) is used with regard to a liquid, it is a percent by volume with respect to the solution. When used with a solid, it is the percent with regard to the solid composition.

General Synthetic Schemes

Unless otherwise stated, starting materials and reagents used in preparing these compounds are either available from commercial suppliers such as Aldrich Chemical Co., (Milwaukee, Wis.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989).

The starting materials for the following synthetic methods can be found in the General Methods and General Synthesis for Intermediates. The synthesis of some of the starting materials and the intermediates are disclosed in U.S. Pat. No. 9,562,061 and PCT/US17/19336, respectively, herein incorporated by reference in their entireties for all purposes. These synthetic methods are merely illustrative of some methods by which the compounds of this invention can be synthesized, and various modifications to these methods can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 22° C.

IUPAC names were generated using either ACD/Name v2015 or ChemBioDraw Ultra 12.
General Method 1: Enone Synthesis
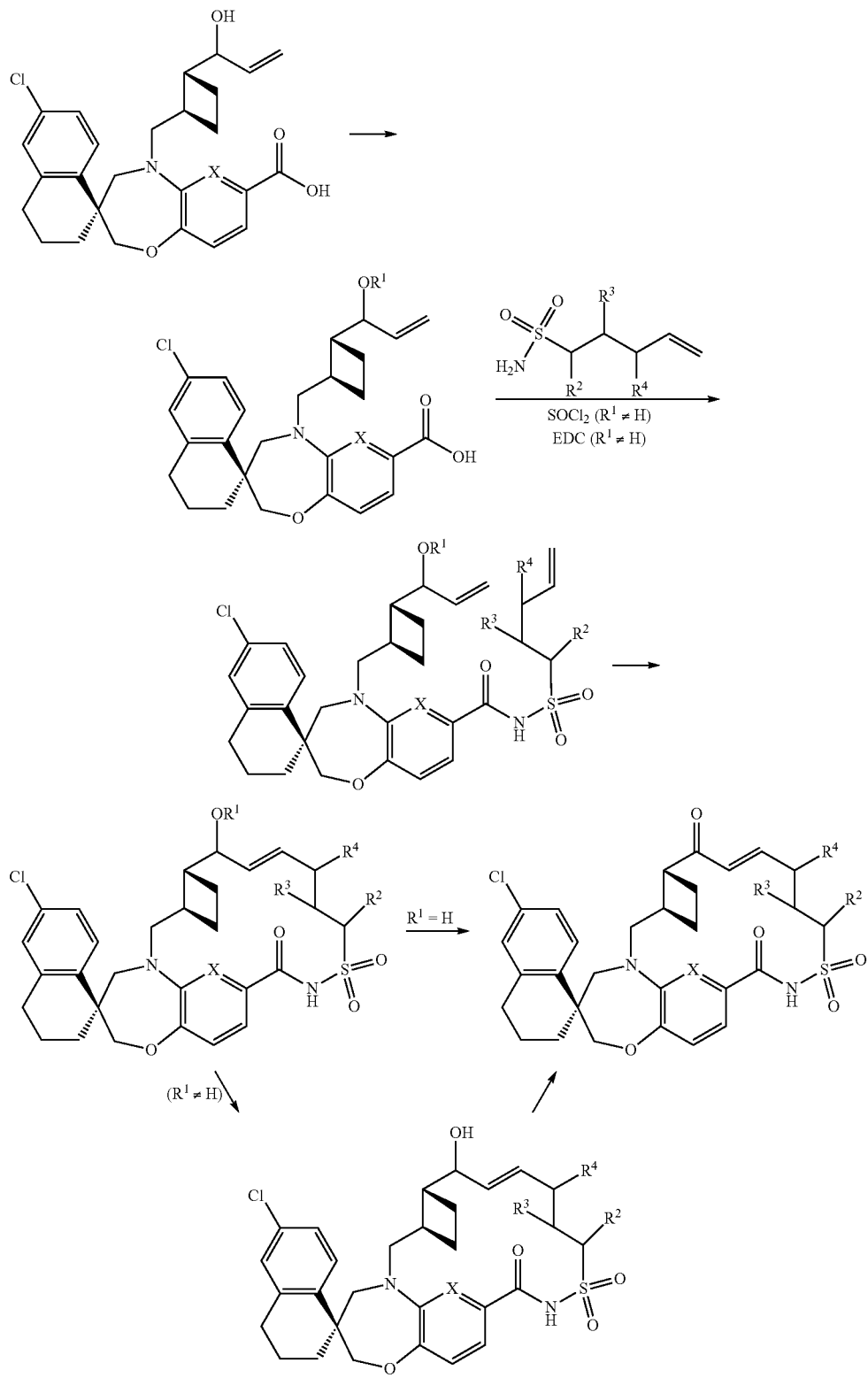

529
General Method 2: Enone Synthesis
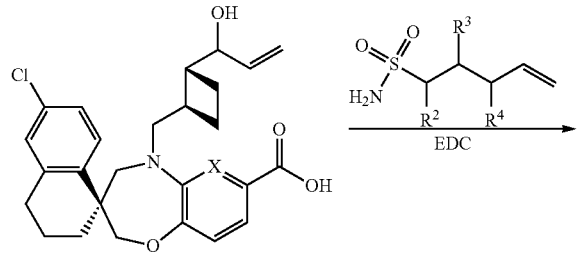
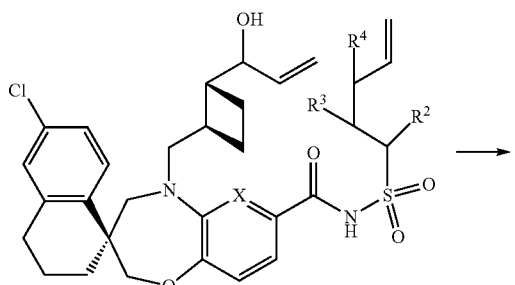
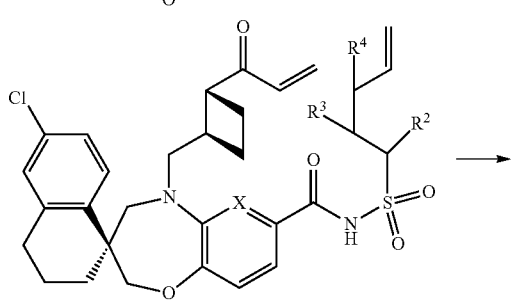
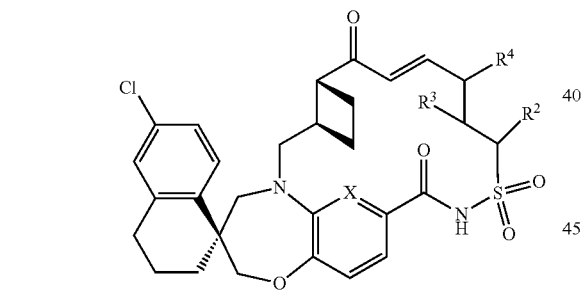
General Method 3: Conversion of Enone to Aldehyde Via Epoxide
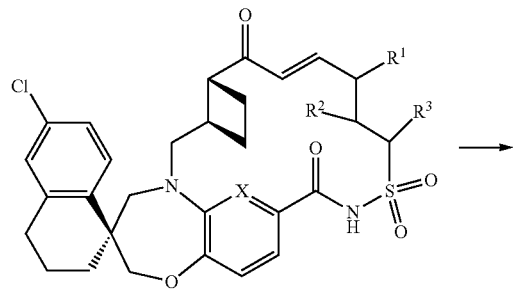
530
-continued
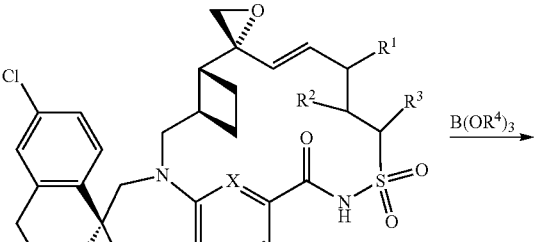
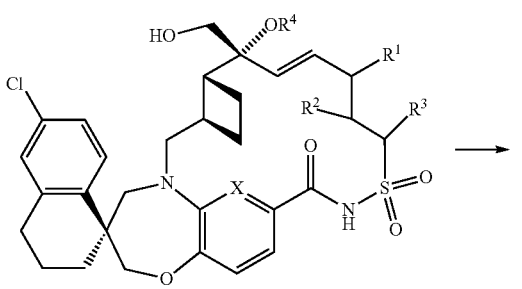
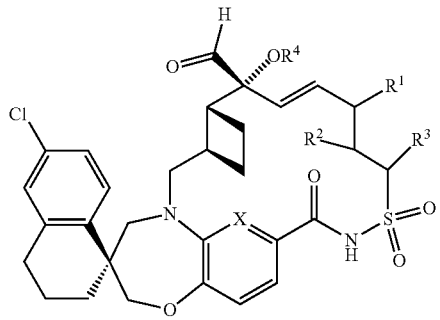
General Method 4: Conversion of Ketone to Aldehyde Via Epoxide
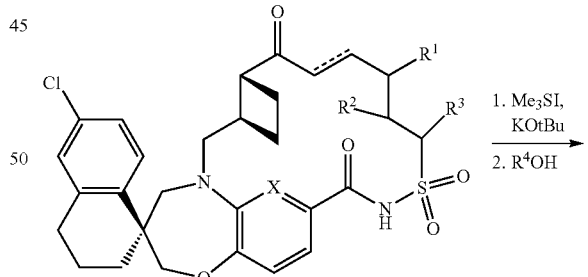
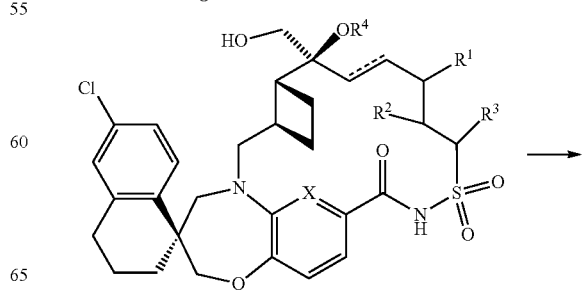

531
-continued
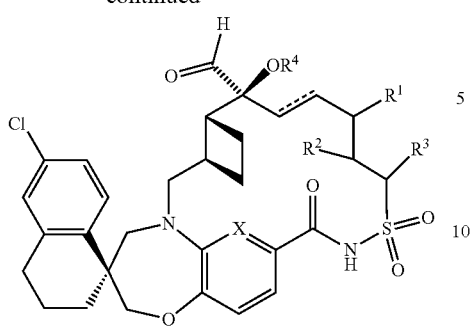
532
-continued
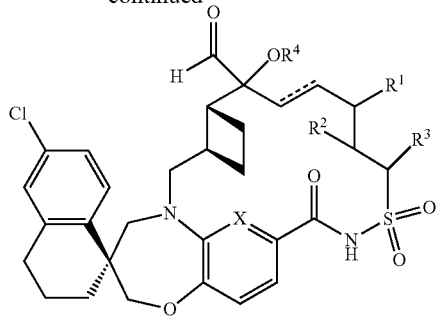
General Method 5: Conversion of Ketone to Aldehyde Via Dithiane
General Method 6: Conversion of Ketone to Amino Alcohol Via Epoxide
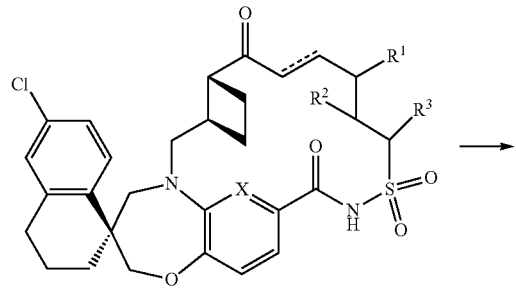
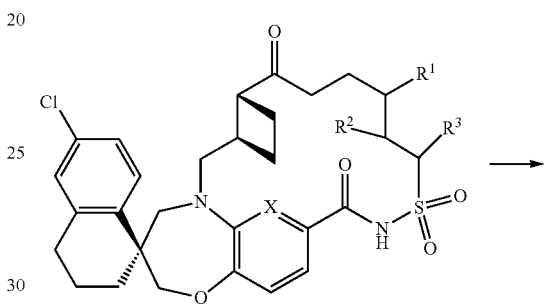
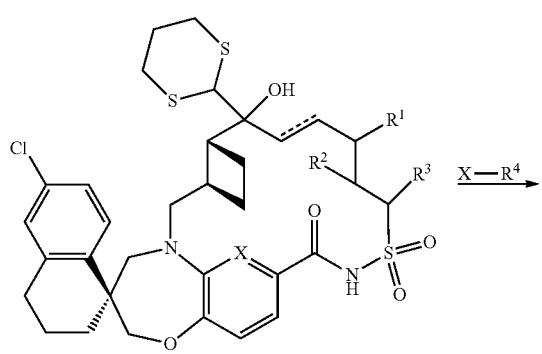
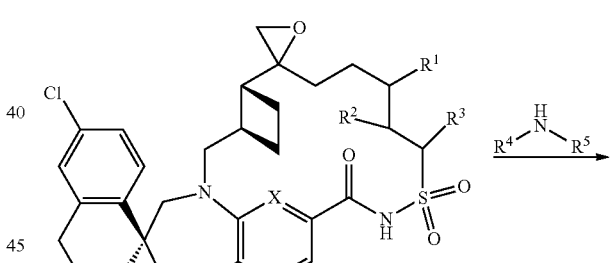
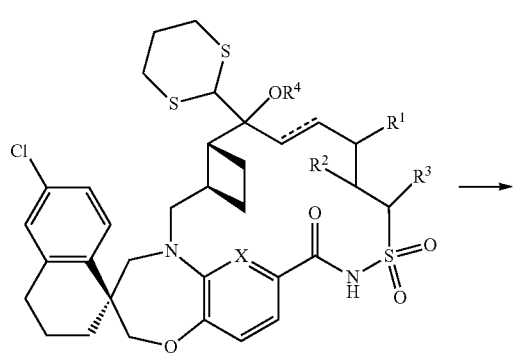
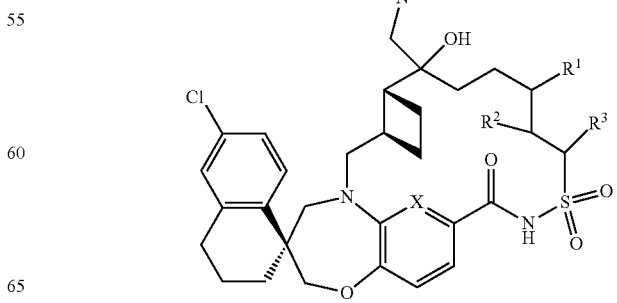

533
General Method 7: Conversion of Enone to Amino Ether
534
General Methods 8: Reductive Amination with NaBH(OAc)$_3$
General Methods 9: Reductive Amination with NaBH$_4$, Ti(OiPr)$_4$, and Amine Salt
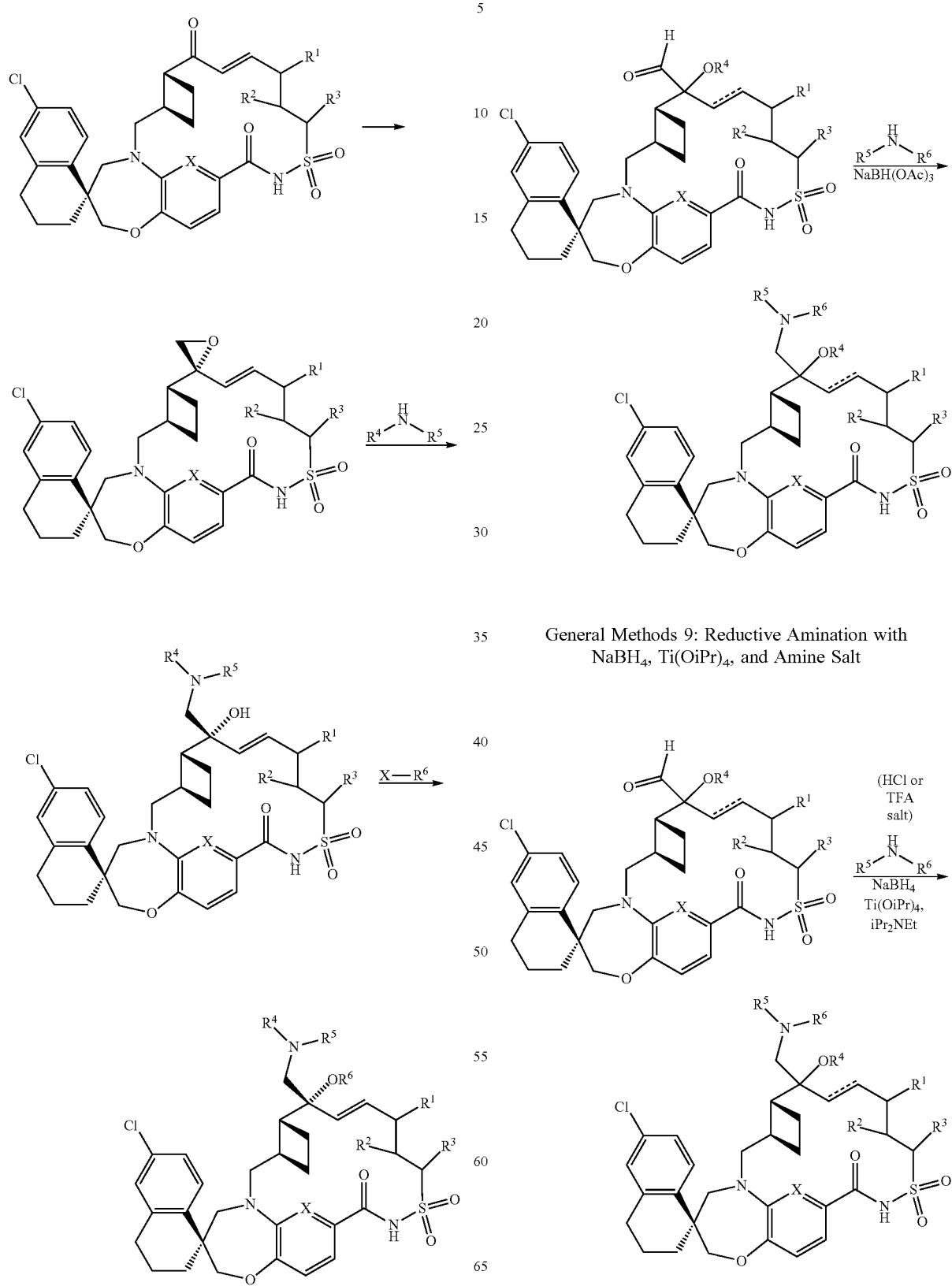

535
General Methods 10: Reductive Amination with NaBH(OAc)$_3$ and Amine Salt
General Methods 11: Reductive Amination with NaBH(OAc)$_3$, Ti(OiPr)$_4$, and Amine Salt
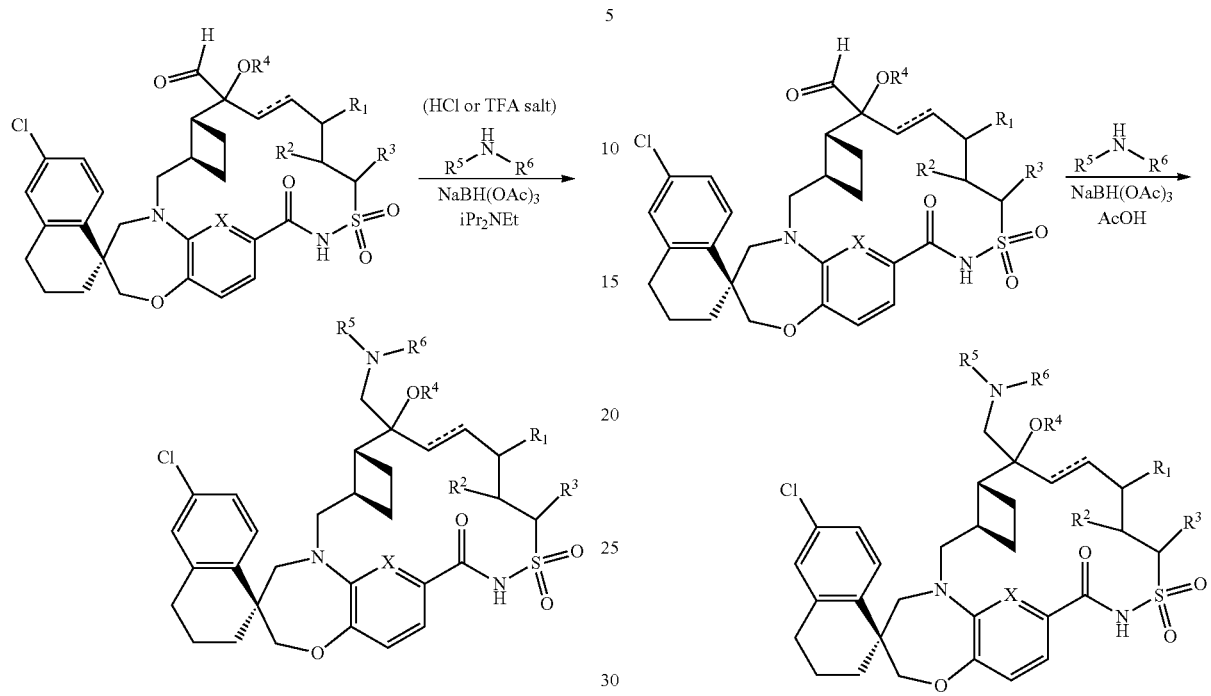
536
General Methods 12: Reductive Amination with NaBH(OAc)$_3$ and AcOH
General Methods 13: Reductive Amination with NaBH$_3$CN and AcOH
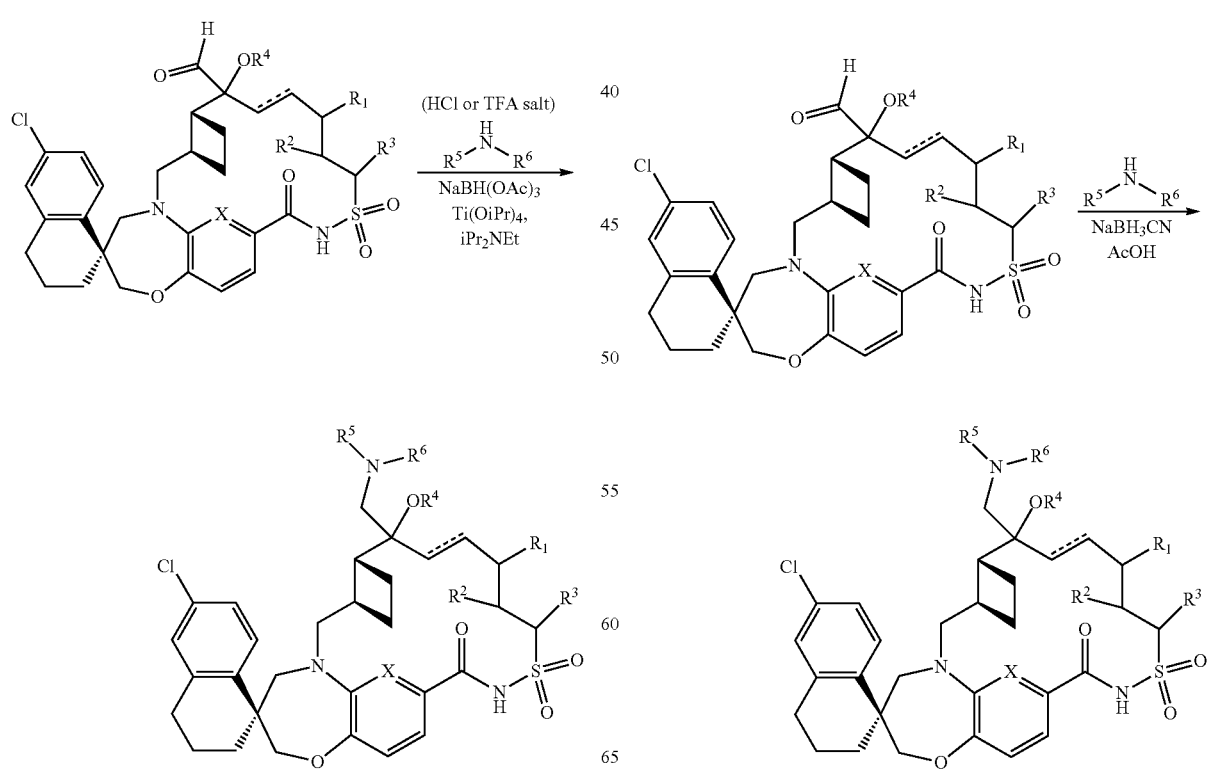

537

Example 1

(1S,3'R,6'R,7'R,8'E,11'S,12'R)-6-chloro-7'-ethoxy-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide General Method 3 (Steps 1-3), General Method 7 (Step 1), General Method 8 (Step 4)

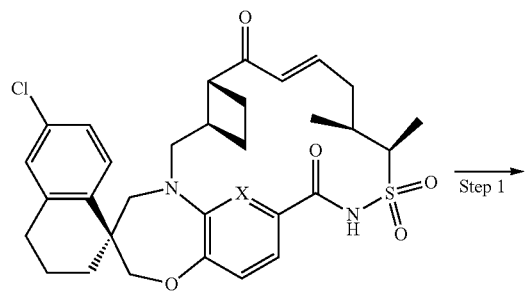

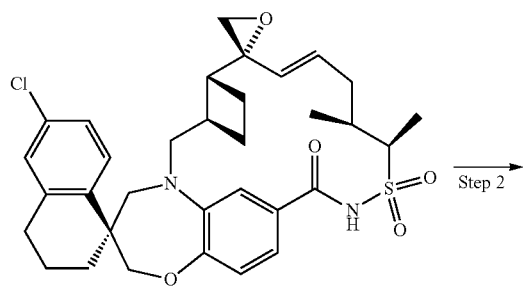

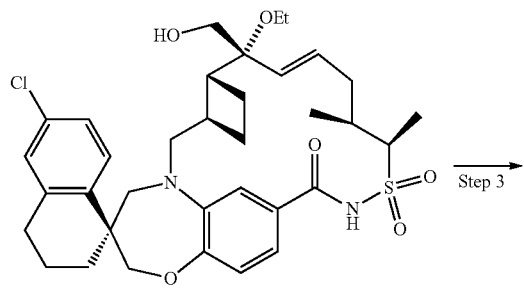

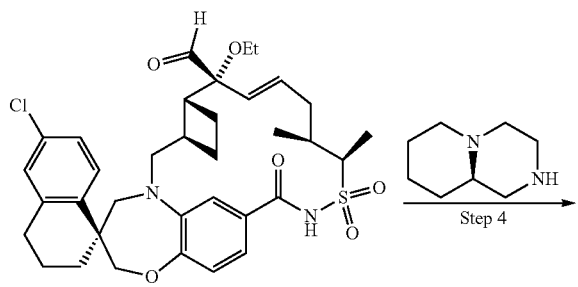

538

-continued

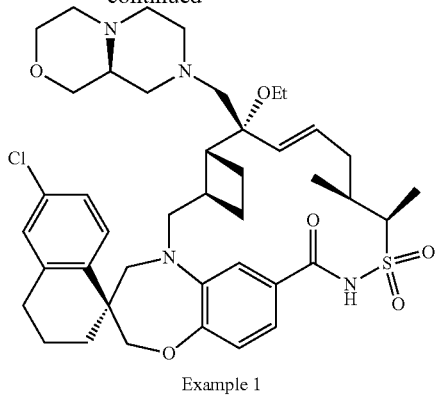

Example 1

Step 1: (1S,3'R,6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2'-oxiran]-15'-one 13',13'-dioxide A 250 mL 3-neck, equipped with a thermocouple, nitrogen inlet and septum, was charged with (1S,3'R,6'R,8'E,11'S,12'R)-6-chloro-11',12'-dimethyl-3,4-dihydro-2H,7'H,15'H-spiro[naphthalene-1,22' [20]oxa[13]thia[1,14]diazatetracyclo[14.7.2.0~3,6~.0~19,24~]pentacosa[8,16,18,24]tetraene]-7',15'-dione 13',13'-dioxide (10.05 g, 15.48 mmol) and trimethylsulfonium iodide (4.79 g, 23.47 mmol). Dimethyl sulfoxide (80 mL) and tetrahydrofuran (20 mL) were added and the reaction was cooled to 5° C. using an ice-water bath. The reaction was treated with 1 M potassium t-butoxide in THF (39.0 mL, 39.0 mmol) via syringe over a period of 20 min. The reaction was quenched with glacial acetic acid (2.20 mL, 38.1 mmol) and stirred for 1 min. The mixture was poured into isopropyl acetate (200 mL) and washed with water (200 mL). The aqueous layer was extracted with isopropyl acetate (100 mL) and the combined organic layers were washed with water (3×200 mL), brine (60 mL) and dried over Na$_2$SO$_4$. The solution was filtered and the filtrate was concentrated under reduced pressure. The residue was azeotrope with DCM (2×200 mL) then dissolved in DCM (40 mL). Heptane (400 mL) was added dropwise over a period of 1 h and the mixture was then stirred for 30 min. The solids were filtered and dried with nitrogen purge on the frit for 3 h to give 8.60 g of (1S,3'R,6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-oxiran]-15'-one 13',13'-dioxide as a white solid. $^1$H NMR (400 MHz, DICHLOROMETHANE-d$_2$) δ ppm 8.08 (s, 1H), 7.72 (d, J=8.41 Hz, 1H), 7.22 (d, J=0.98 Hz, 1H), 7.19 (dd, J=8.41, 2.35 Hz, 1H), 7.09 (d, J=2.15 Hz, 1H), 6.83-6.95 (m, 2H), 5.73-5.91 (m, 1H), 5.60 (d, J=15.26 Hz, 1H), 4.20 (q, J=7.24 Hz, 1H), 4.01-4.14 (m, 2H), 3.92 (dd, J=15.45, 4.50 Hz, 1H), 3.73 (br d, J=14.28 Hz, 1H), 3.20 (d, J=14.28 Hz, 1H), 2.96 (dd, J=15.55, 6.55 Hz, 1H), 2.65-2.85 (m, 2H), 2.47 (d, J=5.48 Hz, 1H), 2.25-2.43 (m, 2H), 1.73-2.08 (m, 9H), 1.60-1.72 (m, 1H), 1.33-1.44 (m, 4H), 1.03 (br d, J=5.87 Hz, 3H).

Step 2: (1S,3'R,6'R,7'R,8'E,11'S,12'R)-6-chloro-7'-ethoxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A 1 L 3-neck, equipped with a thermocouple, nitrogen adapter and septum, was charged with (1S,3'R,6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-oxiran]-15'-one 13',13'-dioxide (10.22 g, 16.72 mmol) and 2-methyltetrahydrofuran (300 mL). Triethyl borate (50 mL, 291 mmol) was added via syringe and the reaction was placed on a heat block preheated to 65° C. After 12 h the reaction was cooled to room temperature overnight. The reaction mixture was quenched with saturated $NaHCO_3$ (100 mL) and stirred for 10 min. The aqueous layer was extracted with EtOAc (3×50 mL) and the combined organic layers were washed with brine (50 mL), dried over $Na_2SO_4$ and filtered. The filtrate was evaporated onto silica gel and purified by flash chromatography (Isco (330 gram)) eluting with 0.3% AcOH in EtOAc:0.3% AcOH in heptane (0:1→1:1) to afford 6.27 g of (1S,3'R,6'R,7'R,8'E,11'S,12'R)-6-chloro-7'-ethoxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide. MS (ESI, +ve ion) m/z 657.3 $(M+1)^+$.

Step 3: (1S,3'R,6'R,7'R,8'E,11'S,12'R)-6-chloro-7'-ethoxy-11',12'-dimethyl-15'-oxo-3,4-dihydro-2H-spiro[naphthalene-1,22'-[20]oxa[13]thia[1,14]diazatetracyclo [14.7.2.0~3,6~.0~19,24~]pentacosa[8,16,18,24]tetraene]-7'-carbaldehyde 13',13'-dioxide A 250 mL 3-neck, equipped with a thermocouple, nitrogen adapter and septum, was charged with the starting (1S,3'R,6'R,7'R,8'E,11'S,12'R)-6-chloro-7'-ethoxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (6.27 g, 7.54 mmol), DCM (50 mL) and dimethyl sulfoxide (20 mL). The solution was cooled (0° C.) in an ice bath, and N,N-diisopropylethylamine was added (6.6 mL, 37.8 mmol) followed by sulfur trioxide pyridine complex (3.02 g, 18.97 mmol), portion wise over 15 min. The ice bath was removed and allowed to warm to room temperature for 2 h. The reaction mixture was poured into isopropyl acetate (200 mL) and the solution was washed with water (200 mL). The aqueous layer was extracted with EtOAc (1×100 mL) and the combined organic layers were washed with 50% saturated $NH_4Cl$ (2×100 mL), water (50 mL), brine (50 mL) and dried over $Na_2SO_4$. The solution was filtered and the filtrate was concentrated under reduced pressure to give a light-yellow solid. The solid was dissolved in EtOAc, evaporated onto silica gel and purified by flash chromatography (Isco (220 gram)) eluting with 0.3% AcOH in EtOAc:0.3% AcOH in heptane (0:1-1:1) to give 4.44 g of (1S,3'R,6'R,7'R,8'E,11'S,12'R)-6-chloro-7'-ethoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide as a white solid. MS (ESI, +ve ion) m/z 655.3 $(M+1)^+$.

Step 4: (1S,3'R,6'R,7'R,8'E,11'S,12'R)-6-chloro-7'-ethoxy-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Preparation of amine free base: To a room temperature suspension of (S)-octahydropiperazino[2,1-c]morpholine dihydrochloride (7.04 g, 32.7 mmol; Synthonix, Wake Forest, N.C.) in DCM (100 mL) was added sodium methoxide (25 wt % solution in methanol, 15 mL, 65.6 mmol) and the reaction was stirred for 2 h. The solvent was removed under reduced pressure and the residue was stirred over EtOAc (100 mL) for 1 h. The solution was filtered and the filtrate was concentrated under reduced pressure to give (S)-octahydropyrazino[2,1-c][1,4]oxazine (4.33 g) as a light-yellow oil. $^1$H NMR (400 MHz, DICHLOROMETHANE-$d_2$) δ ppm 3.70-3.82 (m, 1H), 3.61-3.67 (m, 1H), 3.52-3.60 (m, 1H), 3.15 (t, J=10.47 Hz, 1H), 2.79-2.93 (m, 2H), 2.60-2.71 (m, 2H), 2.55 (br d, J=11.54 Hz, 1H), 2.27-2.39 (m, 2H), 2.05-2.21 (m, 2H).

To a room temperature solution of (1S,3'R,6'R,7'R,8'E,11'S,12'R)-6-chloro-7'-ethoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (4.44 g, 6.51 mmol) in 1,2-dichloroethane (40 mL) was added a solution of (S)-octahydropyrazino[2,1-c][1,4]oxazine (2.91 g, 18.01 mmol) in 1,2-dichloroethane (5 mL) and the reaction was stirred for 2 h. To the reaction was added sodium triacetoxyborohydride (0.350 g, 1.651 mmol) was added as a solid. Additional sodium triacetoxyborohydride (0.350 g, 1.651 mmol) was added until the reaction was complete. The reaction was quenched with saturated $NH_4Cl$ (40 mL) and the layers were separated. The aqueous layer was extracted with DCM (2×) and the combined organic layers were washed with 1 M $KH_2PO_4$ (40 mL). The organic layer was dried over $Na_2SO_4$, filtered and the filtrate was concentrated under reduced pressure and stored in the freezer. The residual material was dissolved in DCM, evaporated onto silica gel, and purified by flash chromatography (Isco (330 gram)) eluting with EtOAc:heptane:MeOH:DCM (0:1:0:0→3:2:0:0→0:0:1:49→0:0:3:47) to give 3.63 g (70%) of an off-white solid. The material was stirred over MeOH (15 mL) for 1 h. To the thick slurry was added MeOH (30 mL) to maintain good stirring. After another 1 h the solvent was removed under reduced pressure and the residue was dried in vacuo. The solid was dried under nitrogen purge/vacuum for 24 h to give 3.10 g of (1S,3'R,6'R,7'R,8'E,11'S,12'R)-6-chloro-7'-ethoxy-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid. MS (ESI, +ve ion) m/z 781.3 $(M+1)^+$. $^1$H NMR (400 MHz, DICHLOROMETHANE-$d_2$) δ ppm 7.72 (d, J=8.41 Hz, 1H), 7.23 (s, 1H), 7.17 (dd, J=8.41, 1.96 Hz, 1H), 7.09 (d, J=1.96 Hz, 1H), 6.89 (s, 2H), 5.58-5.75 (m, 1H), 5.43 (br d, J=15.85 Hz, 1H), 4.15 (q, J=6.85 Hz, 1H), 4.07 (s, 2H), 4.01 (br d, J=15.45 Hz, 1H), 3.74-3.82 (m, 1H), 3.71 (br d, J=14.08 Hz, 1H), 3.54-3.66 (m, 3H), 3.43-3.52 (m, 1H), 3.27 (d, J=14.28 Hz, 1H), 3.17 (br t, J=10.37 Hz, 1H), 2.89-3.03 (m, 2H), 2.72-2.85 (m, 2H), 2.58-2.71 (m, 2H), 2.54 (m, 2H), 2.48 (br d, J=14.28 Hz, 1H), 2.20-2.40 (m, 5H), 2.03-2.20 (m, 4H), 1.65-2.00 (m, 6H), 1.54-1.64 (m, 2H), 1.41 (d, J=7.24 Hz, 3H), 1.30-1.38 (m, 4H), 1.01 (br d, J=5.67 Hz, 3H).

Example 2

(1S,3'R,6'R,7'R,8'E,11'S,12'R)-6-chloro-7'-ethoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

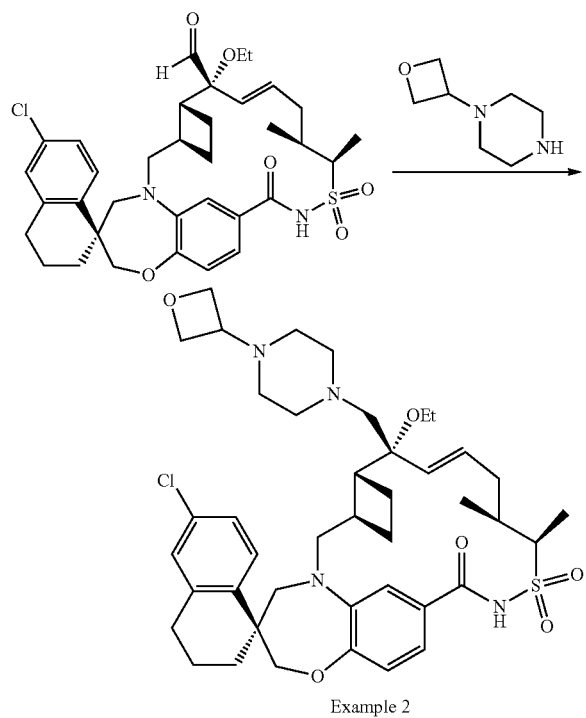

Example 2

To a room temperature solution of (1S,3'R,6'R,7'R,8'E,11'S,12'R)-6-chloro-7'-ethoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.050 g, 0.076 mmol) in 1,2-dichloroethane (1 mL) was added 1-(oxetan-3-yl)piperazine (0.100 mL, 0.823 mmol, Astatech, Inc., Bristol Pa.) via syringe and the reaction was stirred for 1 h. To the reaction was added sodium triacetoxyborohydride (0.050 g, 0.236 mmol) as a solid and the reaction was stirred overnight. The reaction was quenched with pH 7 buffer and the layers were separated. The aqueous layer was extracted with DCM (3×) and the combined organic layers were concentrated under reduced pressure. The residue was dissolved in MeOH and purified by reverse-phase HPLC (Gilson; Gemini-NX 10 m C18 110 Å AXIA, 100×50 mm column) eluting with 0.1% TFA-H$_2$O:0.1% TFA CH$_3$CN (7:3→5:95). The fractions containing the desired product were combined, treated with pH 7 buffer (1 M KH$_2$PO$_4$/1 M K$_2$HPO$_4$; 5 mL) and the layers were separated. The aqueous layer was extracted with EtOAc (3×) and the combined organic layers were washed with brine and dried over Na$_2$SO$_4$. The solution was filtered and concentrated under reduced pressure to give (1S,3'R,6'R,7'R,8'E,11'S,12'R)-6-chloro-7'-ethoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (47 mg, 79%) as a white crystalline solid. MS (ESI, +ve ion) m/z 781.2 (M+1)$^+$. $^1$H NMR (400 MHz, DICHLOROMETHANE-d$_2$) δ ppm 8.07 (br s, 1H), 7.71 (d, J=8.41 Hz, 1H), 7.23 (s, 1H), 7.17 (dd, J=8.51, 2.25 Hz, 1H), 7.08 (d, J=2.15 Hz, 1H), 6.82-6.93 (m, 2H), 5.61-5.78 (m, 1H), 5.45 (br d, J=15.85 Hz, 1H), 4.56-4.66 (m, 2H), 4.44-4.54 (m, 2H), 4.15 (br d, J=7.04 Hz, 1H), 4.03-4.10 (m, 2H), 3.99 (br d, J=14.67 Hz, 1H), 3.70 (br d, J=14.28 Hz, 1H), 3.61 (quin, J=7.24 Hz, 1H), 3.35-3.52 (m, 2H), 3.26 (d, J=14.28 Hz, 1H), 2.95 (br dd, J=14.87, 9.98 Hz, 1H), 2.72-2.85 (m, 2H), 2.59-2.71 (m, 2H), 2.46-2.57 (m, 4H), 2.24-2.41 (m, 4H), 2.02-2.19 (m, 4H), 1.78-1.98 (m, 3H), 1.70 (br s, 1H), 1.57 (br d, J=6.26 Hz, 4H), 1.29-1.45 (m, 7H), 1.00 (br d, J=5.09 Hz, 3H).

Example 3

(1S,3'R,6'R,7'R,8'E,11'S,12'R)-6-chloro-7'-methoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide General Method 5 (Steps 1-3)

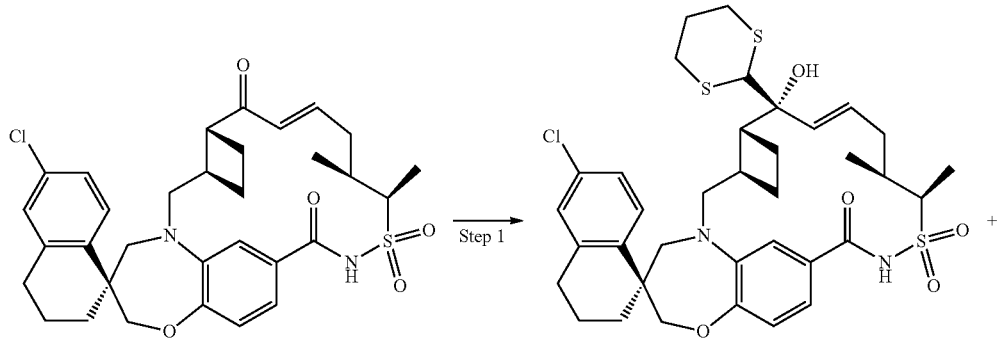

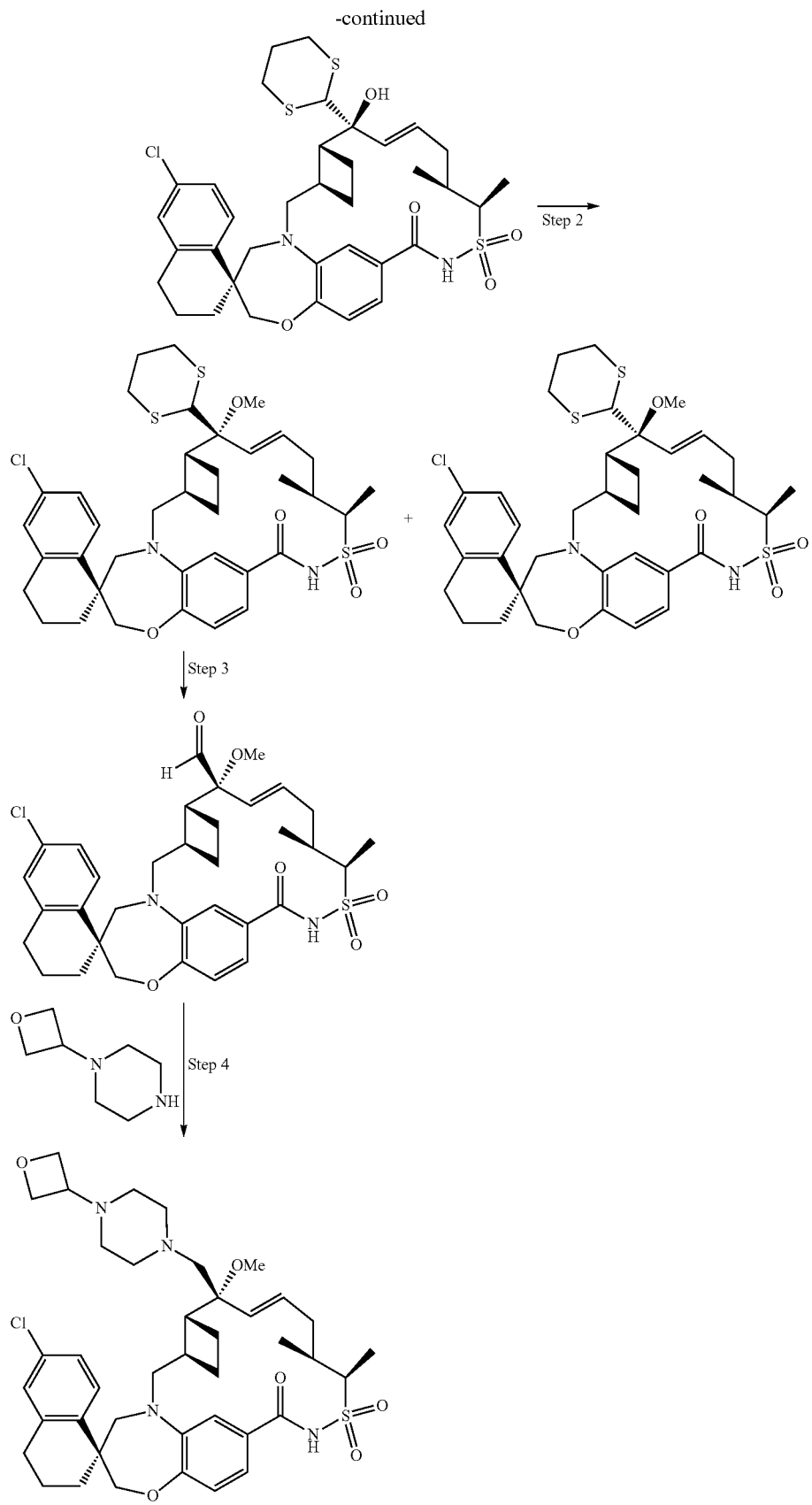
-continued
Example 3

Step 1: (1S,3'R,6'R,7'R,8'E,11'S,12'R)-6-CHLORO-7'-(1,3-DITHIAN-2-YL)-7'-HYDROXY-11',12'-DIMETHYL-3,4-DIHYDRO-2H,15'H-SPIRO [NAPHTHALENE-1,22'-[20]OXA[13]THIA[1,14] DIAZATETRACYCLO[14.7.2.0~3,6~.0~19,24~] PENT ACOSA[8,16,18,24]TETRAEN]-15'-ONE 13',13'-DIOXIDE AND (1S,3'R,6'R,7'S,8'E,11'S, 12'R)-6-CHLORO-7'-(1,3-DITHIAN-2-YL)-7'-HYDROXY-11',12'-DIMETHYL-3,4-DIHYDRO-2H, 15'H-SPIRO[NAPHTHALENE-1,22'-[20]OXA[13] THIA[1,14]DIAZATETRACYCLO[14.7.2.0~3, 6~.0~19,24~]PENT ACOSA[8,16,18,24] TETRAEN]-15'-ONE 13',13'-DIOXIDE To a 250 mL round-bottomed flask was added 1,3-dithiane (4.79 g, 39.8 mmol) and THF (100 mL). The mixture was cooled to −78° C. and n-butyllithium (1.6 M solution in hexane, 22.5 mL, 36.1 mmol) was added over 8 min. The solution was stirred in the −78° C. bath for 30 min. In a separate 100 mL flask was added (1S,3'R,6'R,8'E,11'S,12'R)-6-chloro-11',12'-dimethyl-3,4-dihydro-2H,7'H,15'H-spiro [naphthalene-1,22'-[20]oxa[13]thia[1,14]diazatetracyclo [14.7.2.0~3,6~.0~19,24~]pentacosa[8,16,18,24]tetraene]-7', 15'-dione 13',13'-dioxide and THF (5 mL). To this was added lanthanum(III) chloride bis(lithium chloride) complex solution (0.6 M in THF, 60.1 mL, 36.1 mmol) and this was stirred for 5 min at room temperature. The solution was then cooled to −78° C. and added via cannula to the dithiane solution. After 2.5 h at −78° C., the solution was treated with sat NH$_4$Cl and water. The pH of the solution was adjusted to pH=4 with aqueous 10% citric acid and aqueous NaHCO$_3$. The solution was extracted with EtOAc and the combined extracts were filtered through Celite. The filtrate was washed with water and brine and then dried (Na$_2$SO$_4$) and concentrated to afford a mixture of (1S,3'R,6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13] thia[1,14]diazatetracyclo[14.7.2.0~3,6~.0~19,24~] pentacosa[8,16,18,24]tetraen]-15'-one 13',13'-dioxide and (1S,3'R,6'R,7'S,8'E,11'S,12'R)-6-chloro-7'-(1,3-dithian-2-yl)-7'-hydroxy-11',12'-dimethyl-3,4-dihydro-2H,15'H-spiro [naphthalene-1,22'-[20]oxa[13]thia[1,14]diazatetracyclo [14.7.2.0~3,6~.0~19,24~]pentacosa[8,16,18,24]tetraen]-15'-one 13',13'-dioxide as a brown oil which was carried on directly to next step. MS (ESI, +ve ion) m/z 717.5 (M+H)$^+$.

Step 2: (1S,3'R,6'R,7'R,8'E,11'S,12'R)-6-CHLORO-7'-(1,3-DITHIAN-2-YL)-7'-METHOXY-11',12'-DIMETHYL-3,4-DIHYDRO-2H,15'H-SPIRO [NAPHTHALENE-1,22'-[20]OXA[13]THIA[1,14] DIAZATETRACYCLO[14.7.2.0~3,6~.0~19,24~] PENT ACOSA[8,16,18,24]TETRAEN]-15'-ONE 13',13'-DIOXIDE AND (1S,3'R,6'R,7'S,8'E,11'S, 12'R)-6-CHLORO-7'-(1,3-DITHIAN-2-YL)-7'-METHOXY-11',12'-DIMETHYL-3,4-DIHYDRO-2H,15'H-SPIRO[NAPHTHALENE-1,22'-[20]OXA [13]THIA[1,14]DIAZATETRACYCLO[14.7.2.0~3, 6~.0~19,24~]PENT ACOSA[8,16,18,24] TETRAEN]-15'-ONE 13',13'-DIOXIDE To a resealable vial was added the mixture of (1S,3'R, 6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo [14.7.2.0~3,6~.0~19,24~]pentacosa[8,16,18,24]tetraen]-15'-one 13',13'-dioxide and (1S,3'R,6'R,7'S,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13] thia[1,14]diazatetracyclo[14.7.2.0~3,6~.0~19,24~] pentacosa[8,16,18,24]tetraen]-15'-one 13',13'-dioxide (6.81 g, 9.49 mmol) and THF (100 mL). The mixture was cooled to 0° C. and potassium bis(trimethylsilyl)amide (1 M in THF, 38.0 mL, 38.0 mmol) was added over 10 min. The solution was stirred at 0° C. for 5 min and then iodomethane (2.36 mL, 38.0 mmol) was added over 3 min. After 2.5 h at 0° C., the solution was poured into saturated NH$_4$Cl and the pH was adjusted to 4 with 1 M citric acid. The solution was extracted with EtOAc and the combined extracts were washed with brine, dried (Na$_2$SO$_4$) and concentrated onto silica. Purification by silica gel chromatography (0% to 35% EtOAc/heptane, both with 0.3% AcOH v/v, 330 g Redi-Sep Gold column) afforded: (1S,3'R,6'R,7'R,8'E,11'S,12'R)-6-chloro-7'-(1,3-dithian-2-yl)-7'-methoxy-11',12'-dimethyl-3, 4-dihydro-2H,15'H-spiro[naphthalene-1,22'-[20]oxa[13] thia[1,14]diazatetracyclo[14.7.2.0~3,6~.0~19,24~] pentacosa[8,16,18,24]tetraen]-15'-one 13',13'-dioxide (1.66 g, 2.27 mmol, 24% yield). MS (ESI, +ve ion) m/z 731.5 (M+H)$^+$ and (1S,3'R,6'R,7'S,8'E,11'S,12'R)-6-chloro-7'-(1, 3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18, 24]tetraen]-15'-one 13',13'-dioxide (4.69 g, 6.41 mmol, 68% yield). MS (ESI, +ve ion) m/z 731.5 (M+H)$^+$.

Step 3: (1S,3'R,6'R,7'R,8'E,11'S,12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16, 18,24]tetraene]-7'-carbaldehyde 13',13'-dioxide To a 250 mL round-bottomed flask equipped with a reflux condenser was added (1S,3'R,6'R,7'R,8'E,11'S,12'R)-6-chloro-7'-(1,3-dithian-2-yl)-7'-methoxy-11',12'-dimethyl-3, 4-dihydro-2H,15'H-spiro[naphthalene-1,22'-[20]oxa[13] thia[1,14]diazatetracyclo[14.7.2.0~3,6~.0~19,24~] pentacosa[8,16,18,24]tetraen]-15'-one 13',13'-dioxide (1.63 g, 2.23 mmol), acetonitrile (40 mL) and water (10 mL). The mixture was heated to 50° C. and calcium carbonate (1.12 g, 11.1 mmol) and iodomethane (1.38 mL, 22.3 mmol) were added. After 23 h at 50° C., the solution was poured into sat NH$_4$Cl and water and then extracted with EtOAc. The combined extracts were washed with brine and then dried (Na$_2$SO$_4$) and concentrated onto silica. Purification by silica gel chromatography (0% to 40% EtOAc/heptane (both with 0.3% AcOH), Silicycle HP 120 g column) afforded (1S,3'R, 6'R,7'R,8'E,11'S,12'R)-6-chloro-7'-methoxy-11',12'-dimethyl-15'-oxo-3,4-dihydro-2H-spiro[naphthalene-1,22'-[20] oxa[13]thia[1,14]diazatetracyclo[14.7.2.0~3,6~.0~19,24~] pentacosa[8,16,18,24]tetraene]-7'-carbaldehyde 13',13'-dioxide (1.34 g, 2.09 mmol, 94% yield) as a white solid. MS (ESI, +ve ion) m/z 641.3 (M+H)$^+$.

Step 4: (1S,3'R,6'R,7'R,8'E,11'S,12'R)-6-CHLORO-7'-METHOXY-11',12'-DIMETHYL-7'-((4-(3-OXETANYL)-1-PIPERAZINYL)METHYL)-3,4-DIHYDRO-2H,15'H-SPIRO[NAPHTHALENE-1,22'-[20]OXA[13]THIA[1,14]DIAZATETRACYCLO [14.7.2.0~3,6~.0~19,24~]PENTACOSA[8,16,18,24] TETRAEN]-15'-ONE 13',13'-DIOXIDE To a resealable vial was added (1S,3'R,6'R,7'R,8'E,11'S, 12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18, 24]tetraene]-7'-carbaldehyde 13',13'-dioxide (0.135 g, 0.211 mmol), 1,2-dichloroethane (2.0 mL) and 1-(oxetan-3-yl)piperazine (0.090 g, 0.632 mmol, AstaTech, Inc.). The solution was stirred at room temperature for 1 h. To this solution was added sodium triacetoxyborohydride (0.011 g, 0.053 mmol). After stirring overnight at room temperature, additional portions of sodium triacetoxyborohydride (0.011 g, 0.053 mmol) were added until the reaction was complete. The reaction was carefully quenched with MeOH stirred for 1 h and then filtered for Prep-HPLC purification. The solution was purified by prep-HPLC (Column: Phenomenex Luna 5μ C18, 100 Å, 150×20 mm; Solvent: A=water (0.1% TFA), B=(R) (0.1% TFA), 30 mL/min, 30% B to 100% B over 18 min then 2 min at 100% B) and the fractions containing product were treated with aqueous pH 7 buffer ($KH_2PO_4/K_2HPO_4$ based) and extracted with EtOAc. The combined extracts were washed with brine, and then dried ($Na_2SO_4$), filtered and concentrated to afford (1S,3'R,6'R,7'R,8'E,11'S,12'R)-6-chloro-7'-methoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid (0.101 g, 0.132 mmol, 63% yield). $^1$H NMR (400 MHz, DICHLOROMETHANE-$d_2$) δ ppm 7.72 (d, J=9.8 Hz, 1H), 7.25 (br s, 1H), 7.16 (br d, J=8.6 Hz, 1H), 7.09 (s, 1H), 6.89 (s, 2H), 5.62 (br s, 1H), 5.37 (br d, J=14.9 Hz, 1H), 4.56-4.66 (m, 2H), 4.52 (br t, J=5.9 Hz, 2H), 4.12 (br d, J=6.5 Hz, 1H), 4.06 (s, 2H), 3.98 (br d, J=14.9 Hz, 1H), 3.70 (br d, J=14.1 Hz, 1H), 3.40-3.52 (m, 1H), 3.36 (s, 3H), 3.19-3.30 (m, 1H), 2.90-3.03 (m, 1H), 2.64-2.85 (m, 4H), 2.45-2.63 (m, 5H), 2.26-2.41 (m, 4H), 2.15-2.25 (m, 1H), 2.02-2.15 (m, 3H), 1.78-1.99 (m, 4H), 1.66-1.76 (m, 1H), 1.49-1.64 (m, 2H), 1.40 (br d, J=7.2 Hz, 4H), 1.01 (br d, J=5.7 Hz, 3H). MS (ESI, +ve ion) m/z 767.3 (M+H)$^+$.

Example 4

(1S,3'R,6'R,7'R,8'E,11'S,12'R)-6-CHLORO-7'-((9AS)-HEXAHYDROPYRAZINO[2,1-C][1,4]OXAZIN-8(1H)-YLMETHYL)-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE

General Method 9

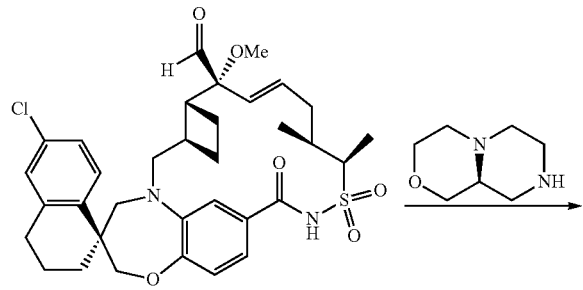

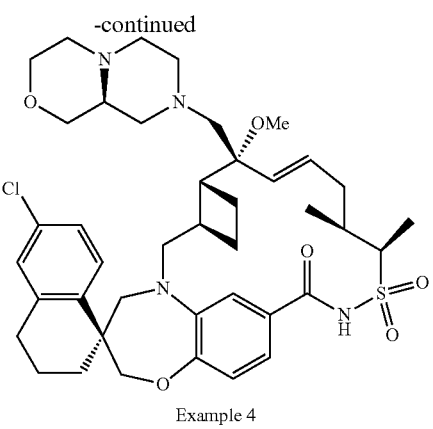

Example 4

To a 100 mL 3-neck flask was added (1S,3'R,6'R,7'R,8'E,11'S,12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.486 g, 0.758 mmol), DCM (20 mL) and ethanol (8.0 mL). To this solution was added (9aS)-octahydropiperazino[2,1-c]morpholine dihydrochloride (1.96 g, 9.10 mmol) followed by N,N-diisopropylethylamine (4.0 mL, 22.7 mmol). To the solution was added titanium(iv) isopropoxide (2.24 mL, 7.58 mmol). The solution was stirred at room temperature for 17 h. To this solution was added sodium borohydride (0.143 g, 3.79 mmol) in 3 portions. The reaction mixture was stirred at room temperature. After 18 h, additional sodium borohydride (35 mg) was added and stirring was continued at room temperature for an additional 24 h. The reaction was carefully quenched with sat. $NH_4Cl$ and then diluted with aqueous pH 7 buffer ($KH_2PO_4/K_2HPO_4$ based), filtered through Celite, and extracted with EtOAc. The combined extracts were washed with brine, dried ($Na_2SO_4$), filtered and concentrated to afford a white solid. The solid was purified by prep-HPLC (Column: Phenomenex Gemini C18 110 Å, 100×50 mm; Solvent: A=water (0.1% TFA), B=(R) (0.1% TFA), 100 mL/min, 10% B to 100% B over 11 min then 2 min at 100% B) and the fractions containing product were treated with aqueous pH 7 buffer ($KH_2PO_4/K_2HPO_4$ based), concentrated to remove the acetonitrile, and extracted with EtOAc. The combined extracts were washed with brine, dried ($Na_2SO_4$), filtered and concentrated to afford (1S,3'R,6'R,7'R,8'E,11'S,12'R)-6-chloro-7'-((9aS)-hexahydropyrazino[2,1-c][1,4]oxazin-8(1H)-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid (0.478 g, 0.622 mmol, 82% yield). $^1$H NMR (400 MHz, DICHLOROMETHANE-$d_2$) δ ppm 7.72 (d, J=8.6 Hz, 1H), 7.26 (s, 1H), 7.17 (dd, J=8.5, 2.2 Hz, 1H), 7.09 (d, J=2.3 Hz, 1H), 6.85-6.93 (m, 2H), 5.57-5.68 (m, 1H), 5.35 (s, 1H), 4.08-4.17 (m, 1H), 4.07 (s, 2H), 3.96-4.04 (m, 1H), 3.78 (br d, J=9.6 Hz, 1H), 3.70 (br d, J=14.3 Hz, 1H), 3.59 (br d, J=10.8 Hz, 2H), 3.35 (s, 3H), 3.25 (d, J=14.3 Hz, 1H), 3.17 (br s, 1H), 2.88-3.06 (m, 2H), 2.72-2.81 (m, 2H), 2.58-2.67 (m, 2H), 2.45-2.54 (m, 3H), 2.30-2.37 (m, 2H), 2.17-2.27 (m, 3H), 2.07-2.14 (m, 2H), 2.03-2.07 (m, 1H), 1.90-1.99 (m, 2H), 1.81-1.90 (m, 2H), 1.66-1.75 (m, 1H), 1.48-1.65 (m, 4H), 1.36-1.44 (m, 4H), 1.02 (d, J=6.1 Hz, 3H) MS (ESI, +ve ion) m/z 767.7 (M+H)$^+$.

Example 5

(1S,3'R,6'R,7'R,8'E,11'S,12'R)-6-CHLORO-7'-METHOXY-11',12'-DIMETHYL-7'-((4-(1-METHY-LETHYL)-1-PIPERAZINYL)METHYL)-3,4-DI-HYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE

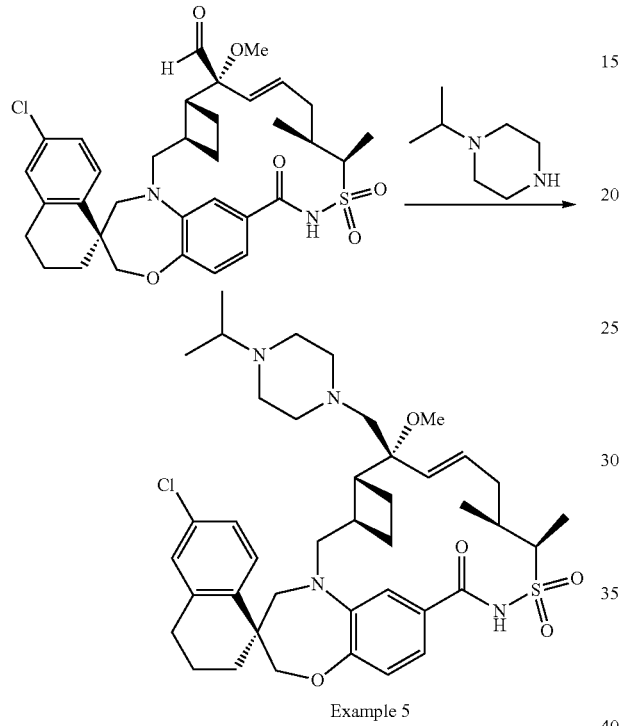

Example 5

To a resealable vial was added (1S,3'R,6'R,7'R,8'E,11'S,12'R)-6-chloro-7'-methoxy-11',12'-dimethyl-15'-oxo-3,4-di-hydro-2H-spiro[naphthalene-1,22'-[20]oxa[13]thia[1,14]di-azatetracyclo[14.7.2.0~3,6~.0~19,24~]pentacosa[8,16,18,24]tetraene]-7'-carbaldehyde 13',13'-dioxide (0.135 g, 0.211 mmol), 1,2-dichloroethane (2 mL) and 1-isopropylpipera-zine (0.090 mL, 0.632 mmol, Across Organics). The solution was stirred at room temperature for 1 h. To this solution was added sodium triacetoxyborohydride (0.011 g, 0.053 mmol). After 2 h at room temperature, additional 0.25 eq. portions of sodium triacetoxyborohydride were added (4 total) until the reaction was complete. The reaction mixture was carefully quenched with MeOH, stirred for 1 h, and then filtered for Prep-HPLC purification. The solution was purified by prep-HPLC (Column: Phenomenex Luna C18, 100 Å, 150× 21.20 mm; Solvent: A=water (0.1% TFA), B=(R) (0.1% TFA), 30 mL/min, 30% B to 100% B over 18 min then 2 min at 100% B) and the fractions containing product were treated with aqueous pH 7 buffer ($KH_2PO_4/K_2HPO_4$ based) and extracted with EtOAc. The combined extracts were washed with brine, and then dried ($Na_2SO_4$), filtered and concentrated to afford (1S,3'R,6'R,7'R,8'E,11'S,12'R)-6-chloro-7'-methoxy-11',12'-dimethyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid (0.0855 g, 0.113 mmol, 54% yield). $^1$H NMR (400 MHz, DICHLOROMETHANE-$d_2$) δ ppm 7.76 (d, J=8.6 Hz, 1H), 7.30 (s, 1H), 7.20 (br d, J=8.4 Hz, 1H), 7.13 (s, 1H), 7.00 (d, J=8.2 Hz, 1H), 6.92 (d, J=9.0 Hz, 1H), 5.63-5.74 (m, 1H), 5.49 (d, J=15.8 Hz, 1H), 4.10 (s, 2H), 3.96-4.05 (m, 2H), 3.74 (br d, J=14.3 Hz, 1H), 3.46 (s, 1H), 3.38-3.43 (m, 1H), 3.37 (s, 3H), 3.30 (br d, J=14.3 Hz, 1H), 2.96-3.04 (m, 2H), 2.85-2.94 (m, 2H), 2.77-2.84 (m, 2H), 2.54-2.68 (m, 3H), 2.36-2.43 (m, 1H), 2.23-2.35 (m, 2H), 2.14-2.23 (m, 2H), 2.06-2.14 (m, 2H), 1.83-2.03 (m, 4H), 1.50-1.76 (m, 4H), 1.35-1.47 (m, 10H), 1.05 (d, J=6.7 Hz, 3H). MS (ESI, +ve ion) m/z 753.2 (M+H)$^+$.

Example 6

(1S,3'R,6'R,7'R,8'E,11'S,12'R)-7'-((4-TERT-BUTYL-1-PIPERAZINYL)METHYL)-6-CHLORO-7'-ETHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE

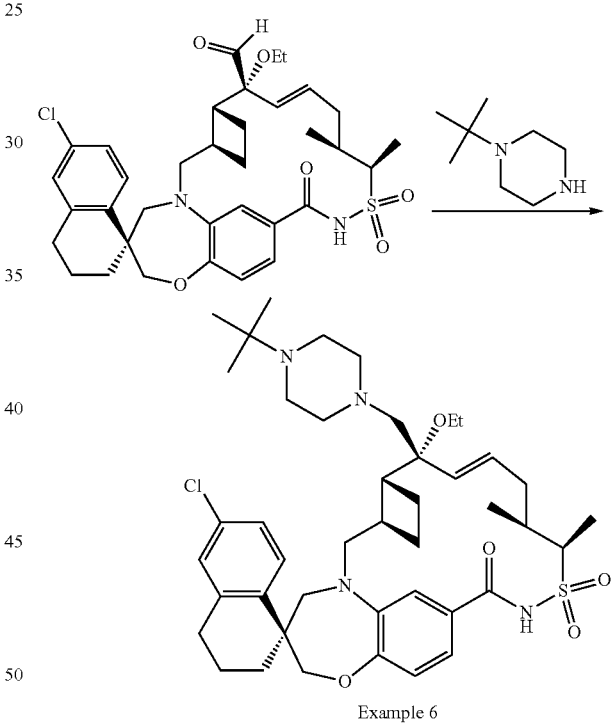

Example 6

To a resealable vial was added (1S,3'R,6'R,7'R,8'E,11'S,12'R)-6-chloro-7'-ethoxy-11',12'-dimethyl-15'-oxo-3,4-di-hydro-2H-spiro[naphthalene-1,22'-[20]oxa[13]thia[1,14]di-azatetracyclo[14.7.2.0~3,6~.0~19,24~]pentacosa[8,16,18,24]tetraene]-7'-carbaldehyde 13',13'-dioxide, 0.035 g, 0.053 mmol), 1,2-dichloroethane (0.7 mL) and N-t-butylpipera-zine (0.026 mL, 0.160 mmol, Oakwood Products, Inc.). The solution was stirred at room temperature for 30 min. To this solution was added sodium triacetoxyborohydride (2.83 mg, 0.013 mmol.). The reaction was stirred at room temperature. After 1 h, additional portions of sodium triacetoxyborohy-dride (2.83 mg, 0.013 mmol) were added every 1 h until the reaction was complete. The reaction was carefully quenched with MeOH, stirred for 30 min and then concentrated.

Purification by silica gel chromatography (0% to 10% MeOH/CH$_2$Cl$_2$) afforded (1S,3'R,6'R,7'R,8'E,11'S,12'R)-7'-((4-tert-butyl-1-piperazinyl)methyl)-6-chloro-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid (0.0284 g, 0.036 mmol, 68% yield). $^1$H NMR (400 MHz, DICHLOROMETHANE-d$_2$) δ ppm 7.73 (d, J=8.6 Hz, 1H), 7.31 (s, 1H), 7.16 (dd, J=8.5, 2.2 Hz, 1H), 7.08 (d, J=2.2 Hz, 1H), 7.02 (br d, J=8.0 Hz, 1H), 6.84 (d, J=8.2 Hz, 1H), 5.55-5.74 (m, 2H), 3.96-4.10 (m, 3H), 3.79 (br s, 1H), 3.69 (br d, J=14.5 Hz, 1H), 3.50-3.65 (m, 1H), 3.34-3.45 (m, 1H), 3.30 (d, J=14.3 Hz, 1H), 2.94-3.04 (m, 1H), 2.73-2.80 (m, 2H), 2.58-2.68 (m, 3H), 2.45-2.57 (m, 3H), 2.29-2.35 (m, 1H), 2.03-2.18 (m, 4H), 1.90-1.98 (m, 2H), 1.81-1.90 (m, 2H), 1.55-1.70 (m, 3H), 1.45-1.53 (m, 1H), 1.34-1.44 (m, 1H), 1.24-1.31 (m, 9H), 1.17-1.24 (m, 9H), 1.00 (d, J=6.8 Hz, 3H). MS (ESI, +ve ion) m/z 781.3 (M+H)$^+$.

Example 7

(1S,3'R,6'R,7'S,11'S,12'R)-6-CHLORO-7'-((9AS)-HEXAHYDROPYRAZINO [2,1-C][1,4]OXAZIN-8(1H)-YLMETHYL)-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-15'-ONE 13',13'-DIOXIDE

General Method 6 (Steps 1-2)

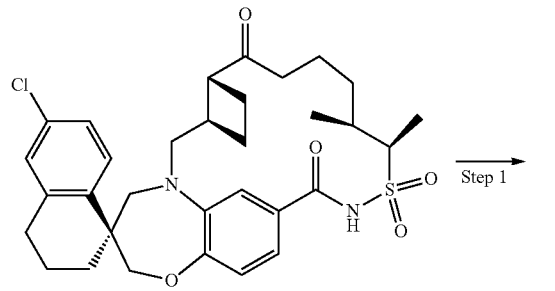

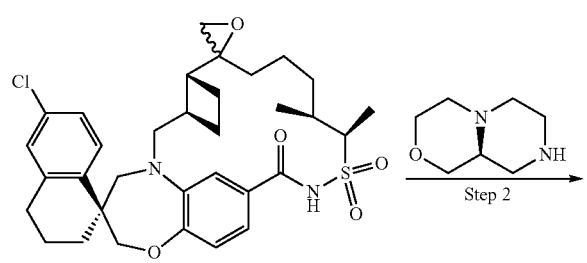

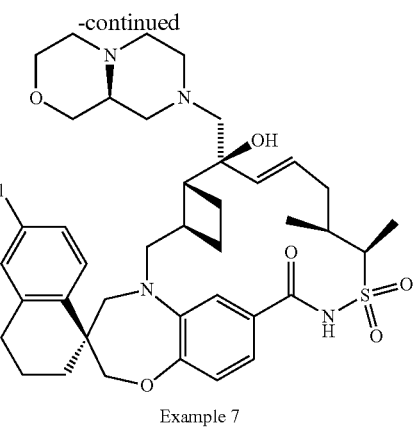

Example 7

Step 1: (1S,3'R,6'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2"-oxiran]-15'-one 13',13'-dioxide To a stirred solution of (1S,3'R,6'R,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[16,18,24]triene]-7',15'-dione 13',13'-dioxide (100 mg, 0.167 mmol) and trimethylsulfoxonium iodide (38.6 mg, 0.175 mmol) in DMSO (1.5 mL) was added potassium hydroxide (33.0 mg, 0.501 mmol) at room temperature. The resulting mixture was stirred at room temperature for a period of 18 h. The mixture was poured into saturated ammonium chloride aqueous solution and extracted with EtOAc (2×). The combined organics were dried over anhydrous sodium sulfate. The residue was subjected to combi-flash column chromatography on a 12 g ISCO gold column eluting with 10% to 100% EtOAc/hexanes to give (1S,3'R,6'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2"-oxiran]-15'-one 13',13'-dioxide (72 mg, 0.117 mmol, 70% yield) as a mixture of diastereomers. MS (ESI, +ve ion) m/z 613.1 (M+H)$^+$.

Step 2: (1S,3'R,6'R,7'S,11'S,12'R)-6-chloro-7'-((9aS)-hexahydropyrazino[2,1-c][1,4]oxazin-8(1H)-ylmethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide A mixture of (1S,3'R,6'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2"-oxiran]-15'-one 13',13'-dioxide (840 mg, 1.37 mmol), (S)-octahydropyrazino[2,1-c][1,4]oxazine dihydrochloride (1.47 g, 6.85 mmol), and triethylamine (3.00 mL, 21.6 mmol) in EtOH (6.0 mL) in a sealed microwave reaction vessel was subjected to microwave reaction condition (24 h, 90° C.). The crude mixture was directly loaded onto a silica gel precolumn (25 g) and subjected to combi-flash column chromatography on a 12 g ISCO gold column eluting with 0% to 20% MeOH/DCM to give an impure mixture of two epimeric beta-hydroxylamine products, which was subjected to separation by SFC (Column: MSA, Mobile Phase: 65:35 (A:B) isocratic, A: Liquid $CO_2$, B: methanol (20 mM $NH_3$), Flow Rate: 70 g/min, Column/Oven temp.: 40° C., Detection: UV at 240 nm). The epimer first eluting on both the reverse-phase prep-HPLC and the SFC column was collected and subjected to combi-flash column chromatography on a 12 g ISCO gold column eluting with 0 to 20% MeOH/DCM to give (1S,3'R,6'R,7'S,11'S,12'R)-6-chloro-7'-((9aS)-hexahydropyrazino[2,1-c][1,4]oxazin-8(1H)-ylmethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (340 mg, 0.45 mmol, 33% yield) as a white solid. $^1$H NMR (400 MHz, DICHLOROMETHANE-$d_2$) δ 7.72 (d, J=8.61 Hz, 1H), 7.17 (dd, J=2.15, 8.41 Hz, 1H), 7.09 (d, J=2.15 Hz, 1H), 7.01 (s, 1H), 6.91-6.99 (m, 2H), 4.04-4.15 (m, 3H), 3.87 (br d, J=15.06 Hz, 1H), 3.78 (dd, J=2.93, 11.15 Hz, 1H), 3.69 (br d, J=14.28 Hz, 1H), 3.56-3.65 (m, 2H), 3.16-3.27 (m, 2H), 3.00 (br dd, J=8.71, 15.16 Hz, 1H), 2.87 (br d, J=9.98 Hz, 1H), 2.59-2.79 (m, 7H), 2.44-2.54 (m, 3H), 2.23-2.41 (m, 4H), 1.98-2.12 (m, 3H), 1.87-1.96 (m, 2H), 1.80-1.86 (m, 1H), 1.69-1.78 (m, 2H), 1.55 (br dd, J=9.29, 13.79 Hz, 3H), 1.20-1.44 (m, 9H), 0.98 (d, J=6.65 Hz, 3H). MS (ESI, +ve ion) m/z 755.3 (M+H)$^+$.

Example 8

(1S,3'R,6'R,7'R,8'E,11'S,12'R)-6-CHLORO-7'-METHOXY-11',12'-DIMETHYL-7'-(((3R)-3-METHYL-4-(1-METHYLETHYL)-1-PIPERAZINYL)METHYL)-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE

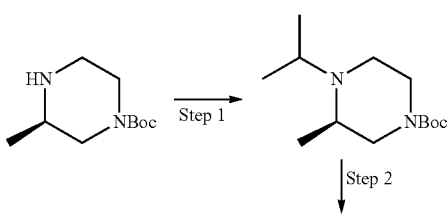

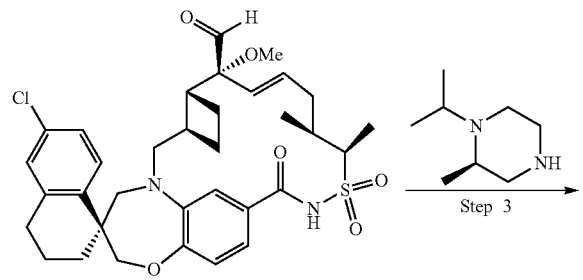

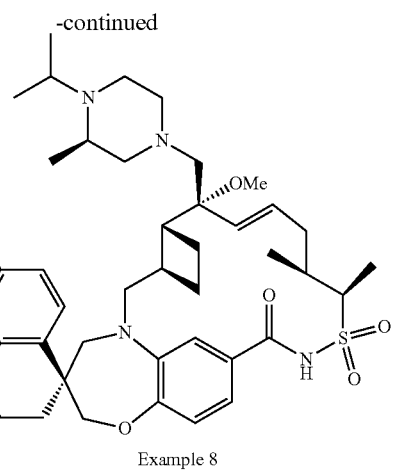

Example 8

Step 1: (R)-TERT-BUTYL 4-ISOPROPYL-3-METHYLPIPERAZINE-1-CARBOXYLATE

A mixture of (R)-1-boc-3-methyl-piperazine (630 mg, 3.15 mmol) and acetone (3.0 mL, 40.9 mmol) in DCM (4.0 mL) was stirred for 10 min before sodium triacetoxyborohydride (1333 mg, 6.29 mmol) was added in one portion as a solid. The resulting mixture was stirred at room temperature for 2.5 days. MeOH (0.5 mL) was added to the reaction and the mixture was stirred for 5 min and then directly loaded onto a silica gel precolumn (25 g) and subjected to combi-flash column chromatography on a 24 g ISCO gold column eluting with 2% to 20% MeOH/DCM to give (R)-tert-butyl 4-isopropyl-3-methylpiperazine-1-carboxylate (0.72 g, 2.97 mmol, 94% yield) as a colorless oil. $^1$H NMR (400 MHz, DICHLOROMETHANE-$d_2$) δ 3.54-3.90 (m, 2H), 3.25 (td, J=6.41, 13.01 Hz, 1H), 3.02 (br s, 1H), 2.64-2.84 (m, 2H), 2.52-2.63 (m, 1H), 2.19-2.34 (m, 1H), 1.43 (s, 9H), 1.10 (d, J=6.65 Hz, 3H), 1.04 (d, J=6.26 Hz, 3H), 0.90 (d, J=6.65 Hz, 3H). MS (ESI, +ve ion) m/z 243.2 (M+H)$^+$.

Step 2: (R)-1-ISOPROPYL-2-METHYLPIPERAZINE BIS-TFA SALT

To a stirred solution of (R)-tert-butyl 4-isopropyl-3-methylpiperazine-1-carboxylate (670 mg, 2.76 mmol) in DCM (10 mL) was added trifluoroacetic acid (3.0 mL, 40 mmol) at room temperature. The resulting mixture was stirred at room temperature for 40 min. The volatiles were removed and the residue was subjected to high vacuum to give (R)-1-isopropyl-2-methylpiperazine bis-TFA salt as an off-white solid. $^1$H NMR (400 MHz, DICHLOROMETHANE-$d_2$) δ 11.33-12.07 (m, 2H), 10.45-11.02 (m, 1H), 3.88-4.10 (m, 3H), 3.72-3.86 (m, 2H), 3.49-3.65 (m, 3H), 1.46 (dd, J=6.46, 12.91 Hz, 6H), 1.31 (d, J=6.65 Hz, 3H). MS (ESI, +ve ion) m/z 143.2 (M+H)$^+$.

Step 3: (1S,3'R,6'R,7'R,8'E,11'S,12'R)-6-Chloro-7'-methoxy-11',12'-dimethyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a stirred mixture of (1S,3'R,6'R,7'R,8'E,11'S,12'R)-6-chloro-7'-methoxy-11',12'-dimethyl-15'-oxo-3,4-dihydro- 2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (20 mg, 0.031 mmol) and (R)-1-isopropyl-2-methylpiperazine bis-TFA salt (76.2 mg, 0.206 mmol) in DCM (1.5 mL) was added N,N-diisopropylethylamine (0.50 mL, 2.9 mmol). The resulting mixture was stirred at room temperature for 10 min before sodium triacetoxyborohydride (26.4 mg, 0.125 mmol) was added in one portion as a solid. The resulting mixture was stirred at room temperature for 25 h. The reaction mixture was concentrated in vacuo and the residue was dissolved and taken up in MeOH and subjected to preparative reverse-phase HPLC (Gemini™ Prep Cis 10 µm column; Phenomenex, Torrance, Calif.; gradient elution of 35 to 90% MeCN in water, where both solvents contain 0.1% TFA, 15-min gradient in a 24 min method) to give, after lyophilization, (1S,3'R,6'R,7'R,8'E,11'S,12'R)-6-Chloro-7'-methoxy-11',12'-dimethyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (17.6 mg, 0.020 mmol, 64% yield) as a TFA salt as a white solid. $^1$H NMR (400 MHz, DICHLOROMETHANE-$d_2$) δ 8.08 (br s, 1H), 7.71 (d, J=8.61 Hz, 1H), 7.11-7.20 (m, 2H), 7.09 (d, J=1.76 Hz, 1H), 6.90 (s, 2H), 5.78-5.96 (m, 1H), 5.47 (br d, J=15.65 Hz, 1H), 4.13-4.26 (m, 1H), 4.07 (s, 2H), 3.82-3.99 (m, 2H), 3.58-3.77 (m, 2H), 3.20-3.51 (m, 9H), 2.92-3.04 (m, 1H), 2.74-2.82 (m, 3H), 2.51-2.62 (m, 2H), 2.02-2.18 (m, 6H), 1.85-1.97 (m, 3H), 1.72-1.79 (m, 1H), 1.55-1.68 (m, 2H), 1.35-1.45 (m, 10H), 1.24 (d, J=6.85 Hz, 3H), 1.02 (d, J=6.65 Hz, 3H). MS (ESI, +ve ion) m/z 767.2 (M+H)$^+$.

Example 9

(1S,3'R,6'R,7'R,8'E,11'S,12'R)-6-CHLORO-7'-ETHOXY-11',12'-DIMETHYL-7'-(((3R)-3-METHYL-4-(1-METHYLETHYL)-1-PIPERAZINYL)METHYL)-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE

General Method 10

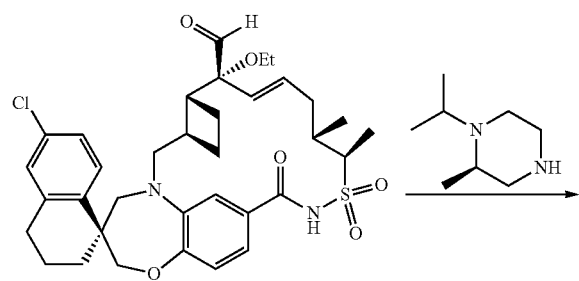

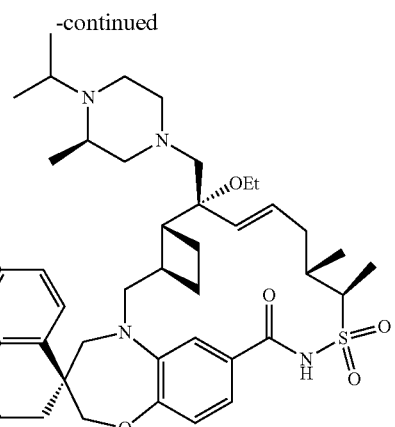

Example 9

To an 1-dram vial was placed (1S,3'R,6'R,7'R,8'E,11'S,12'R)-6-chloro-7'-ethoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (12 mg, 0.018 mmol) followed by a solution of (R)-1-isopropyl-2-methylpiperazine 2,2,2-trifluoroacetate (46.9 mg, 0.126 mmol) in DCM (1.5 mL) and N,N-diisopropylethylamine (0.60 mL, 3.5 mmol). The resulting mixture was stirred at room temperature for 10 min before sodium triacetoxyborohydride (16 mg, 0.073 mmol) was added in one portion as a solid. The resulting mixture was stirred at room temperature for 58 h. The reaction mixture was concentrated in vacuo and the residue was dissolved and taken up in MeOH and subjected to preparative reverse-phase HPLC (Gemini™ Prep C18 10 µm column; Phenomenex, Torrance, Calif.; gradient elution of 20% to 90% MeCN in water, where both solvents contain 0.1% TFA, 15-min gradient in a 24 min method) to give, after lyophilization, (1S,3'R,6'R,7'R,8'E,11'S,12'R)-6-Chloro-7'-ethoxy-11',12'-dimethyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (11.2 mg, 0.013 mmol, 70% yield) as a TFA salt as a white solid. $^1$H NMR (400 MHz, DICHLOROMETHANE-$d_2$) δ 8.05 (br s, 1H), 7.71 (d, J=8.61 Hz, 1H), 7.17 (dd, J=2.25, 8.51 Hz, 1H), 7.08-7.13 (m, 2H), 6.90 (s, 2H), 5.94-6.08 (m, 1H), 5.55-5.64 (m, 1H), 4.20-4.29 (m, 1H), 4.08 (s, 2H), 3.85-3.92 (m, 2H), 3.70-3.83 (m, 2H), 3.62-3.68 (m, 1H), 3.46-3.58 (m, 3H), 3.33 (br d, J=4.50 Hz, 2H), 3.26 (d, J=14.28 Hz, 1H), 2.99 (br dd, J=10.07, 14.57 Hz, 2H), 2.73-2.87 (m, 3H), 2.57 (br dd, J=7.92, 14.18 Hz, 2H), 2.11-2.18 (m, 3H), 2.06 (br d, J=13.89 Hz, 2H), 1.86-1.98 (m, 4H), 1.79 (br d, J=8.02 Hz, 1H), 1.67 (br d, J=4.89 Hz, 2H), 1.37-1.45 (m, 13H), 1.24 (d, J=6.65 Hz, 3H), 1.01 (d, J=6.65 Hz, 3H). MS (ESI, +ve ion) m/z 781.2 (M+H)$^+$.

Example 10

(1S,3'R,6'R,7'R,8'E,11'S,12'R)-6-CHLORO-7'-METHOXY-11',12'-DIMETHYL-7'-((9AR)-OCTAHYDRO-2H-PYRIDO[1,2-A]PYRAZIN-2-YLMETHYL)-3,4-DIHYDRO-2H,15'H-SPIRO[NAPHTHALENE-1,22'-[20]OXA[13]THIA[1,14]DIAZATETRACYCLO [14.7.2.0~3,6~.0~19,24~]PENTACOSA[8,16,18,24]TETRAEN]-15'-ONE 13',13'-DIOXIDE

General Method 7 (Steps 1-2)

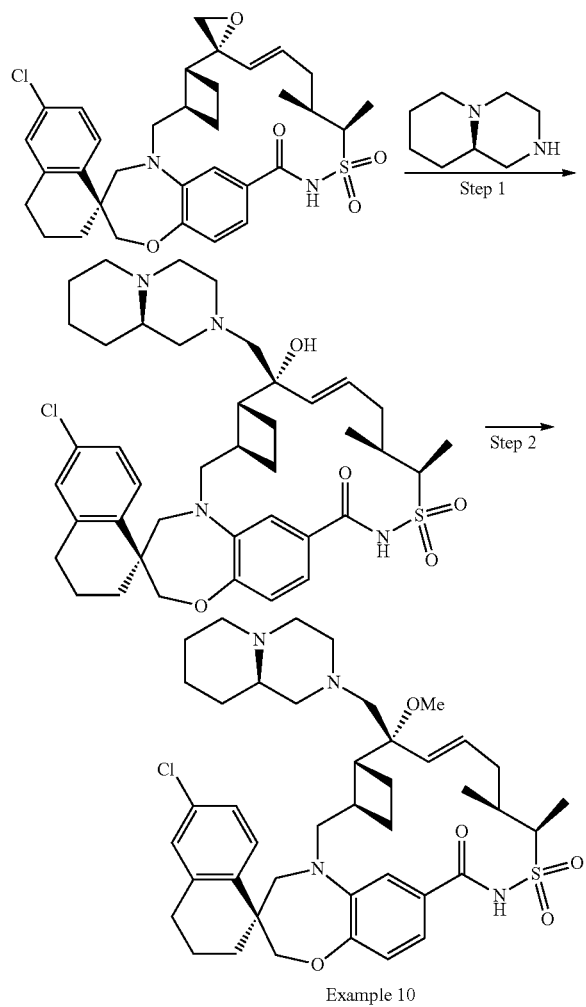

Example 10

Step 1: (1S,3'R,6'R,7'R,8'E,11'S,12'R)-6-CHLORO-7'-HYDROXY-11',12'-DIMETHYL-7'-((9AR)-OCTAHYDRO-2H-PYRIDO[1,2-A]PYRAZIN-2-YLMETHYL)-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE Preparation of amine free base: To a 150 mL round bottomed flask was added (R)-octahydro-1H-pyrido[1,2-a]pyrazine dihydrochloride (5.0 g, 23.5 mmol, WuXi) and methanol (30 mL). To the solution at room temperature was added sodium methoxide (25 wt % solution in methanol, 14.0 mL, 58.6 mmol) over 2 min. The solution was stirred at room temperature for 10 min and then concentrated. The material was treated with 2-methyltetrahydrofuran to form a suspension and then filtered. The filtrate was concentrated to form a viscous brown oil. The oil was treated with 2-methyltetrahydrofuran and heptane, filtered through a syringe filter and then concentrated to afford (R)-octahydro-1H-pyrido[1,2-a]pyrazine (3.4 g) as a brown semi-solid.

To a 250 mL 3-neck flask was added (1S,3'R,6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2'-oxiran]-15'-one 13',13'-dioxide (4.75 g, 7.77 mmol), sodium tert-butoxide (1.49 g, 15.5 mmol), and 2-methyltetrahydrofuran (40 mL). To the solution was added (R)-octahydro-1H-pyrido[1,2-a]pyrazine (1.64 g, 11.7 mmol). The reaction mixture was then heated at 65° C. for 1 d. The solution was allowed to cool to room temperature and treated with pH 7 buffer ($K_2HPO_4/KH_2PO_4$ based). The solution was extracted with DCM (3×) and the combined extracts were washed with water and brine, dried over $Na_2SO_4$, and concentrated. The crude product, (1S,3'R,6'R,7'R,8'E,11'S,12'R)-6-chloro-7'-hydroxy-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide, was carried on directly.

Step 2: (1S,3'R,6'R,7'R,8'E,11'S,12'R)-6-CHLORO-7'-METHOXY-11',12'-DIMETHYL-7'-((9AR)-OCTAHYDRO-2H-PYRIDO[1,2-A]PYRAZIN-2-YLMETHYL)-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE To a 250 mL flask containing (1S,3'R,6'R,7'R,8'E,11'S,12'R)-6-chloro-7'-hydroxy-1',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo [14.7.2.0~3,6~.0~19,24~]pentacosa[8,16,18,24]tetraen]-15'-one 13',13'-dioxide (5.8 g, 7.7 mmol) was added 2-methyltetrahydrofuran (80 mL). The solution was cooled to 0° C. and potassium bis(trimethylsilyl)amide (1 M in THF, 19.3 mL, 19.3 mmol) was added over 5 min. After stirring for 10 min at 0° C., iodomethane (1.44 mL, 23.2 mmol) was added in one portion. The solution was stirred at 0° C. for 2 h and then additional potassium bis(trimethylsilyl)amide (4 mL) was added, stirred for 10 min and then additional iodomethane (0.48 mL) was added. The solution was stirred for 1 h at 0° C. and then aqueous pH 7 buffer ($KH_2PO_4/K_2HPO_4$ based) was added and the reaction mixture was allowed to warm to room temperature. The solution was extracted with DCM (3×) and the combined extracts were washed with brine, dried over $Na_2SO_4$, and concentrated onto silica. Purification by silica gel chromatography (10% to 60% EtOAc/heptane and then 5% to 10% MeOH/$CH_2Cl_2$) afforded (1S,3'R,6'R,7'R,8'E,11'S,12'R)-6-chloro-7'-methoxy-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as an off-white solid

559

(3.30 g, 4.31 mmol, 56% yield). $^1$H NMR (400 MHz, DICHLOROMETHANE-$d_2$) δ ppm 7.72 (d, J=8.6 Hz, 1H), 7.26 (d, J=1.4 Hz, 1H), 7.17 (dd, J=8.6, 2.2 Hz, 1H), 7.09 (d, J=2.0 Hz, 1H), 6.92-6.99 (m, 1H), 6.89 (d, J=8.0 Hz, 1H), 5.64 (dt, J=15.7, 5.3 Hz, 1H), 5.42 (br d, J=16.4 Hz, 1H), 4.07 (s, 2H), 4.03 (br d, J=7.2 Hz, 1H), 3.98 (br d, J=14.9 Hz, 1H), 3.70 (br d, J=14.3 Hz, 1H), 3.34 (s, 3H), 3.23-3.30 (m, 1H), 3.06-3.22 (m, 2H), 2.90-3.01 (m, 1H), 2.74-2.81 (m, 2H), 2.65-2.73 (m, 2H), 2.52-2.62 (m, 4H), 2.28-2.35 (m, 1H), 2.16-2.26 (m, 2H), 2.03-2.15 (m, 3H), 1.81-1.99 (m, 6H), 1.71-1.79 (m, 2H), 1.57-1.71 (m, 4H), 1.47-1.56 (m, 2H), 1.34-1.44 (m, 5H), 1.02 (d, J=6.7 Hz, 3H). MS (ESI, +ve ion) m/z 765.3 (M+H)$^+$.

560

Example 11

(1S,3'R,6'R,7'R,8'E,11'S,12'R)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide General Method 1 (Steps 3-7) and General Method 11 (Step 11)

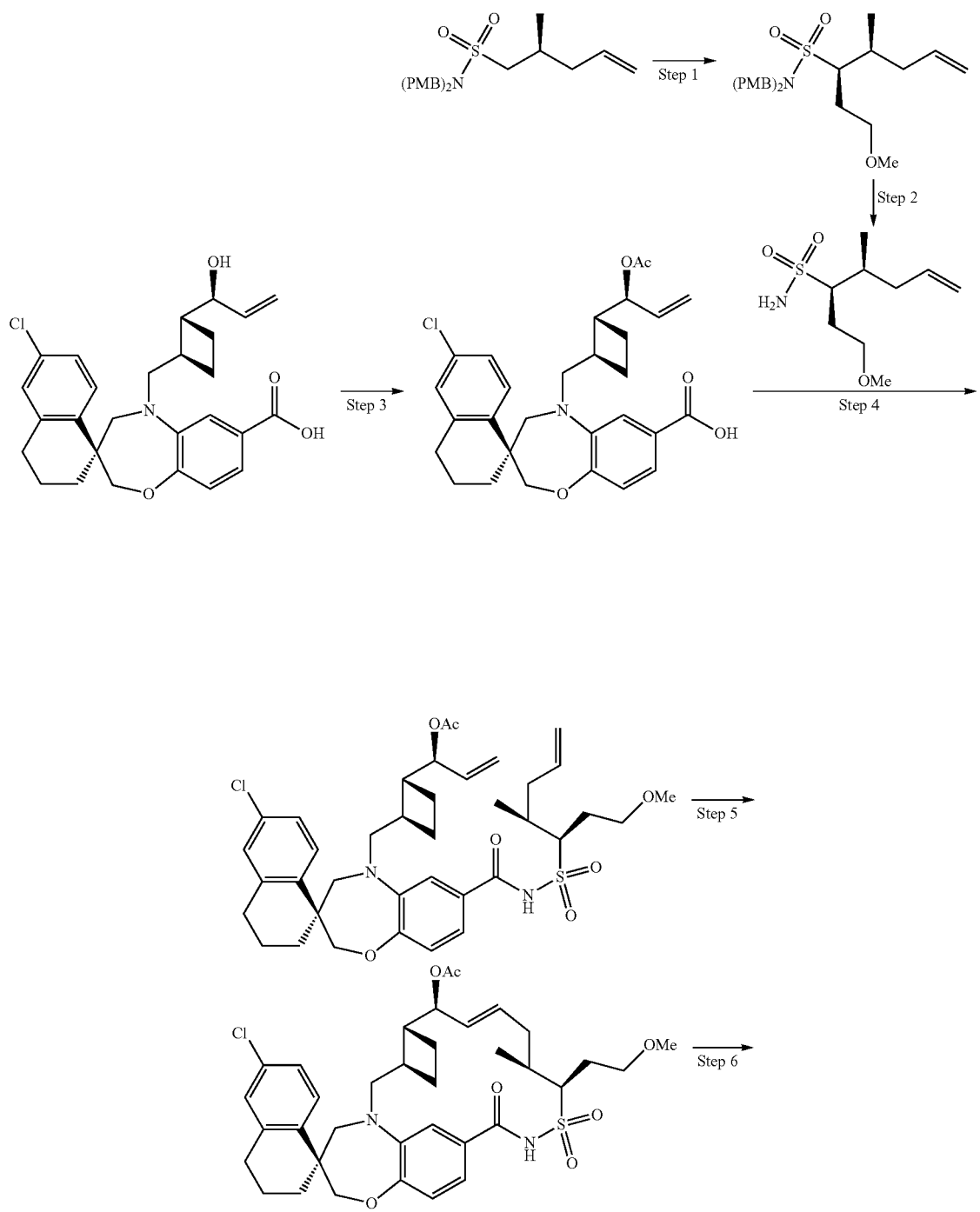

-continued
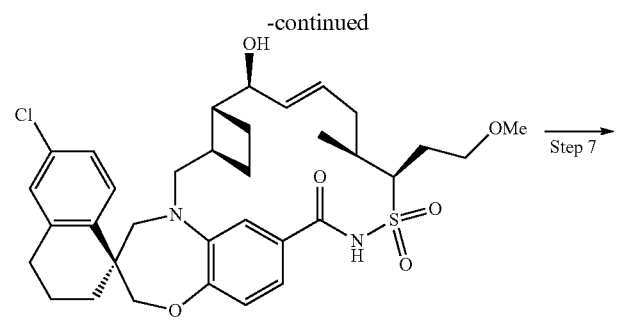
Step 7
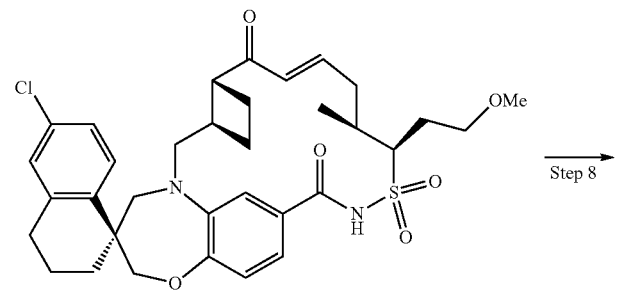
Step 8
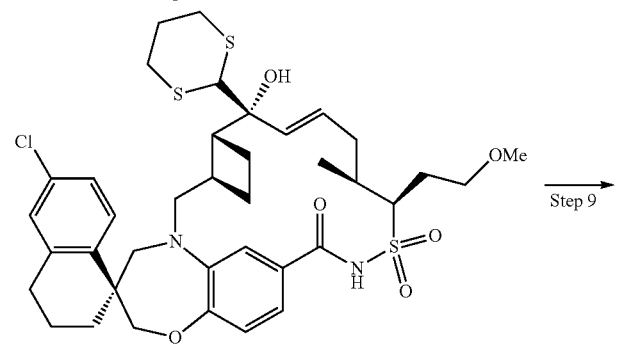
Step 9
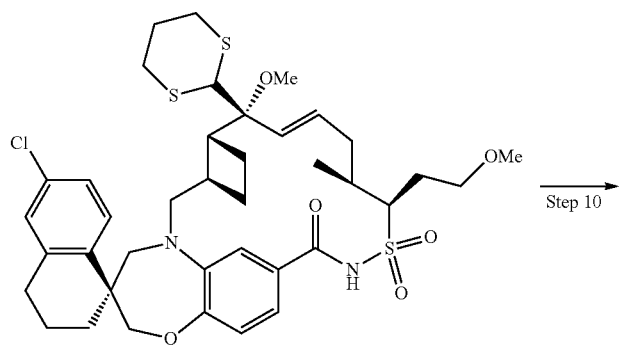
Step 10
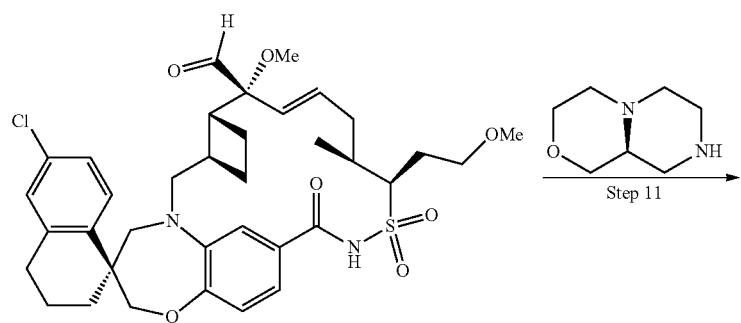
Step 11

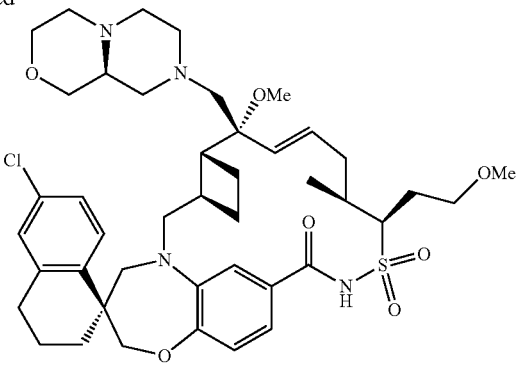

Example 11

Step 1: (3R,4S)-1-methoxy-N,N-bis(4-methoxybenzyl)-4-methylhept-6-ene-3-sulfonamide A dry 2 L three neck flask with a thermo couple and magnetic stir bar under nitrogen was charged with (S)—N,N-bis(4-methoxybenzyl)-2-methylpent-4-ene-1-sulfonamide (54 g, 134 mmol) and 300 mL of dry toluene. Cooled solution to −76° C. internal temperature (acetone/dry ice bath). Added n-butyllithium solution (1.6 M in hexanes, 100 mL, 161 mmol) slowly via cannula under a positive pressure of nitrogen. The mixture was stirred at −78° C. for 1 hour. Then 2-bromoethyl methyl ether (18.88 mL, 201 mmol) was slowly via syringe. After the addition, the −78° C. bath was replaced with an ice water bath. After a total of 105 minutes reaction time, the reaction was quenched with saturated ammonium chloride at 0° C. The mixture was diluted with water and EtOAc and warmed to room temperature with stirring. The layers were separated and extracted with additional EtOAc. The combined organic layers were washed with water and brine, dried over sodium sulfate, filtered, and concentrated in vacuo. The crude products were further separated to give 20.4 g of (3R,4S)-1-methoxy-N,N-bis(4-methoxybenzyl)-4-methylhept-6-ene-3-sulfonamide (44.2 mmol, 55% yield). MS (ESI, +ve ion) m/z 484.0 (M+Na)$^+$.

Step 2: (3R,4S)-1-methoxy-4-methylhept-6-ene-3-sulfonamide

At 0° C., trifluoroacetic acid (164 mL, 2210 mmol) was added dropwise via addition funnel to a solution of (3R,4S)-1-methoxy-N,N-bis(4-methoxybenzyl)-4-methylhept-6-ene-3-sulfonamide (20.4 g, 44.2 mmol) and anisole (48.0 mL, 442 mmol) in DCM (221 mL). The solution was allowed to come to room temperature and stirred overnight. The reaction was concentrated in vacuo. The remaining material was partitioned between DCM and saturated aqueous sodium bicarbonate. The layers were separated and the aqueous layer was extracted with DCM. The combined organic extracts were washed with saturated aqueous sodium chloride and dried over sodium sulfate. The solution was filtered and concentrated in vacuo to give the crude material. Purification by flash column chromatography on silica gel (eluted with 0% to 100% EtOAc in heptane) gave (3R,4S)-1-methoxy-4-methylhept-6-ene-3-sulfonamide (9.85 g, 44.5 mmol, 101% yield) as a light yellow oil. MS (ESI, +ve ion) m/z 243.9 (M+Na)$^+$.

Step 3: (S)-5-(((1R,2R)-2-((S)-1-acetoxyallyl)cyclobutyl)methyl)-6'-chloro-3',4,4',5-tetrahydro-2H,2'H-spiro[benzo[b][1,4]oxazepine-3,1'-naphthalene]-7-carboxylic acid To a nitrogen inerted 3-neck 1 L flask equipped with a thermometer and a magnetic stir bar at room temperature was added 4-(dimethylamino) pyridine (0.821 g, 6.72 mmol), 2-methyltetrahydrofuran (80 mL), triethylamine (7.02 mL, 50.4 mmol), acetic anhydride (4.76 mL, 50.4 mmol), and a solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (15.72 g, 33.6 mmol) in 2-methyltetrahydrofuran (80 mL) was added via cannula over 20 min (internal temperature increased from 20° C. to 25° C. during the addition). The reaction mixture was stirred at room temperature for 1.5 h. Water (40 mL) was added (internal temperature increased from 23° C. to 26° C.) followed by 1 M Na$_2$HPO$_4$ (60 mL). Sodium hydroxide (1 M, 20 mL, 220 mmol) was added until the pH reached 9. The mixture was stirred at room temperature for 19 h and the pH was adjusted to 3 with 2 M HCl (80 mL). The mixture was diluted with PhMe (150 mL) and transferred to a separatory funnel. The aqueous layer was discarded and the organic phase was washed with water (75 mL), 20% brine (75 mL), and concentrated under reduced pressure. The concentrate was diluted with PhMe (100 mL) and the PhMe was removed under reduced pressure. This was repeated three times to give (S)-5-(((1R,2R)-2-((S)-1-acetoxyallyl)cyclobutyl)methyl)-6'-chloro-3',4,4',5-tetrahydro-2H,2'H-spiro[benzo[b][1,4]oxazepine-3,1'-naphthalene]-7-carboxylic acid as an orange oil that was used without further purification. MS (ESI, +ve ion) m/z 510.2 (M+H)$^+$.

Step 4: (S)-1-((1R,2R)-2-(((S)-6'-chloro-7-((((3R,4S)-1-methoxy-4-methylhept-6-en-3-yl)sulfonyl)carbamoyl)-3',4'-dihydro-2H,2'H-spiro[benzo[b][1,4]oxazepine-3,1'-naphthalen]-5(4H)-yl)methyl)cyclobutyl)allyl acetate To a 1 L 3-neck flask was charged (S)-5-(((1R,2R)-2-((S)-1-acetoxyallyl)cyclobutyl)methyl)-6'-chloro-3',4,4',5-tetrahydro-2H,2'H-spiro[benzo[b][1,4]oxazepine-3,1'-naphthalene]-7-carboxylic acid (28.73 g, 35.8 mmol) as a solution in toluene (228 mL). DMF (0.277 mL, 3.58 mmol) was added followed by slow addition of thionyl chloride (2.74 mL, 37.6 mmol) via syringe. The reaction was stirred at room temperature for 4 h and additional thionyl chloride (0.50 mL) was added and the reaction was stirred for 1 h. In a separate flask (3R,4S)-1-methoxy-4-methylhept-6-ene-3-sulfonamide (9.85 g, 42.5 mmol) and 4-(dimethylamino)pyridine (0.437 g, 3.58 mmol) were combined and azetroped by concentration in vacuo with PhMe (80 mL) and then taken up in 100 mL of PhMe. The resulting solution was added to the acid chloride solution described above via cannula. The solution was cooled in an ice bath for 10 min before triethylamine (17.41 mL, 125 mmol) was added dropwise via addition funnel. After the addition, the reaction was warmed to room temperature and stirred overnight. The reaction was quenched with saturated ammonium chloride. To the mixture was added 0.1 M aqueous HCl and then the mixture was extracted with EtOAc (3×). The combined organic layers were washed with brine, dried with sodium sulfate, filtered, and concentrate in vacuo. Purification by flash column chromatography on silica gel (eluted with 0% to 100% EtOAc in heptane) gave (S)-1-((1R,2R)-2-(((S)-6'-chloro-7-((((3R,4S)-1-methoxy-4-methylhept-6-en-3-yl)sulfonyl)carbamoyl)-3',4'-dihydro-2H,2'H-spiro[benzo[b][1,4]oxazepine-3,1'-naphthalen]-5(4H)-yl)methyl)cyclobutyl)allyl acetate (28.11 g, 39.4 mmol) as an orange foam that was used in the next step without further purification. MS (ESI, +ve ion) m/z 713.0 (M+H)$^+$.

Step 5: (1S,3'R,6'R,7'S,8'E,11'S,12'R)-6-chloro-12'-(2-methoxyethyl)-11'-methyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl acetate To a 5 L reactor equipped with mechanical stirrer, thermocouple, nitrogen sparge tube, condenser, was charged 3.6 L of toluene. The PhMe was heated at 79° C. with sparging of nitrogen through the solution. In a separate flask, (S)-1-((1R,2R)-2-(((S)-6'-chloro-7-((((3R,4S)-1-methoxy-4-methylhept-6-en-3-yl)sulfonyl)carbamoyl)-3',4'-dihydro-2H,2'H-spiro[benzo[b][1,4]oxazepine-3,1'-naphthalen]-5(4H)-yl)methyl)cyclobutyl)allyl acetate (25.14 g, 32.0 mmol) was azetroped with 300 mL of toluene and then dissolved in 1.2 L PhMe which was added via syringe pump over 2 h. Simultaneously, 4 charges of Umicore M73 SIMes (4×238 mg) (Umicore AG & Co. KG, Precious Metals Chemistry, Rodenbacher Chaussee 4, 63457 Hanau-Wolfgang, Germany) was added as a slurry in 5 mL PhMe. Each charge was added at intervals of 40 min. After 4 h, the reaction was cooled to 30° C. and di(ethylene glycol) vinyl ether (0.350 mL, 2.56 mmol) was added and the solution was stirred overnight with the sparge replaced with a nitrogen inlet. The reactor was drained and the volume of the reaction was reduced to 1 L. SilaMetS Thiol (70 g) (SiliCycle Inc. 2500, Parc-Technologique Blvd Quebec City, Quebec, Canada) was added and the mixture was stirred overnight. The mixture was filtered and the SilaMetS Thiol was washed with EtOAc and the filtrate was concentrated. Purification by flash column chromatography on silica gel (330 g Gold Rf, eluted with 0% to 100% EtOAc in heptane) gave (1S,3'R,6'R,7'S,8'E,11'S,12'R)-6-chloro-12'-(2-methoxyethyl)-11'-methyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl acetate (19.76 g, 28.8 mmol, 90% yield) as an orange oil. MS (ESI, +ve ion) m/z 685.0 (M+H)$^+$.

Step 6: (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Sodium methoxide (25% solution in methanol, 11.35 mL, 49.7 mmol) was added to a solution of (1S,3'R,6'R,7'S,8'E,11'S,12'R)-6-chloro-12'-(2-methoxyethyl)-11'-methyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl acetate (19.76 g, 24.83 mmol) in toluene (100 mL) and methanol (20.00 mL) at room temperature. After 45 min, the reaction was quenched with citric acid (2 M aqueous solution, 37.2 mL, 74.5 mmol) and diluted with EtOAc and water. The layers were separated and the aqueous layer was extracted with EtOAc. The combined organic extracts were washed with 2× water, saturated aqueous sodium chloride, and dried over sodium sulfate. The mixture was filtered and concentrated in vacuo and dried overnight to give (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as an orange oil. MS (ESI, +ve ion) m/z 643.0 (M+H)$^+$.

Step 7: (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide To a 1 L flask containing (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (19.1 g, 29.7 mmol), prepared in the previous step, was added DCM (300 mL). The solution was cooled in an ice bath for 20 min. Dess-Martin periodinane (15.11 g, 35.6 mmol) was added in one portion and the reaction was stirred while cooled in the ice bath for 40 min. The reaction was removed from the ice bath and stirred for 1.5 h at room temperature. Sodium thiosulfate was added followed by water and the mixture was stirred vigorously for 20 min. The reaction was diluted with saturated aqueous sodium bicarbonate and extracted with EtOAc (3×). The combined organic layers were washed with water and brine, dried with sodium sulfate, filtered, and concentrated. Purification by silica gel chromatography (eluted with 0% to 60% EtOAc in heptane) gave (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (14.29 g, 22.3 mmol, 75% yield) as a light yellow solid. MS (ESI, +ve ion) m/z 640.8 (M+H)$^+$.

Step 8: (1S,3'R,6'R,7'R,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a 100 mL round-bottomed flask was added 1,3-dithiane (2.025 g, 16.84 mmol) in THF (42.1 mL). At −78° C., n-butyllithium (2.5 M solution in hexane, 5.90 mL, 14.7 mmol) was added to the solution. The solution was stirred for 15 min and then (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (2.70 g, 4.21 mmol) in 10 mL of THF was added slowly. The mixture was stirred for 1 h and 10 mL of saturated ammonium chloride was added to quench the reaction. The mixture was diluted with 1 N HCl (20 mL) and extracted with EtOAc (3×40 mL). The organic extracts were washed with saturated NaCl (40 mL) and dried over MgSO$_4$. The solution was filtered and concentrated in vacuo. The material was purified by chromatography through a Redi-Sep pre-packed silica gel column (80 g), eluting with a gradient of 0% to 60% EtOAc (with 0.1% HOAc) in heptane to give (1S,3'R,6'R,7'R,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1.6 g, 2.1 mmol, 50% yield). MS (ESI, +ve ion) m/z 761.1 (M+H)$^+$.

Step 9: (1S,3'R,6'R,7'R,8'E,11'S,12'R)-6-chloro-7'-(1,3-dithian-2-yl)-7'-methoxy-12'-(2-methoxy ethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a 100 mL round-bottomed flask was added (1S,3'R,6'R,7'R,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1.6 g, 2.1 mmol) and iodomethane (1.044 mL, 16.81 mmol) in THF (21 mL). At 0° C., sodium hydride (0.504 g, 21.0 mmol) was added portion wise. The reaction W was stirred at room temperature for 5 h. The reaction mixture was diluted with saturated NH$_4$Cl (20 mL) and extracted with EtOAc (2×20 mL). The combined organic extracts were washed with saturated NaCl (15 mL) and dried over MgSO$_4$. The solution was filtered and concentrated in vacuo. Purification by chromatography through a Redi-Sep pre-packed silica gel column (40 g), eluting with a gradient of 0% to 60% EtOAc (with 0.1% HOAc) in heptane gave (1S,3'R,6'R,7'R,8'E,11'S,12'R)-6-chloro-7'-(1,3-dithian-2-yl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.93 g, 1.2 mmol, 57% yield) as an off-white solid. MS (ESI, +ve ion) m/z 775.1 (M+H)$^+$.

Step 10: (1S,3'R,6'R,7'R,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide To a resealable vial was added (1S,3'R,6'R,7'R,8'E,11'S,12'R)-6-chloro-7'-(1,3-dithian-2-yl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.93 g, 1.2 mmol), acetonitrile (9.6 mL) and water (2.4 mL). To the mixture was added calcium carbonate (0.600 g, 6.00 mmol) and iodomethane (0.745 mL, 12.0 mmol). The mixture was heated at 45° C. overnight. The solution was poured into saturated NH$_4$Cl and water and then extracted with EtOAc. The combined extracts were washed with brine and then dried over Na$_2$SO$_4$ and concentrated. Purification by silica gel chromatography (eluted with 0% to 60% EtOAc in heptane (with 0.1% AcOH) gave (1S,3'R,6'R,7'R,8'E,11'S,12'R)-6-chloro-7'-methoxy-12'-(2-methoxyethyl)-1'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.70 g, 1.021 mmol, 85% yield) as a white solid. MS (ESI, +ve ion) m/z 685.1 (M+H)$^+$.

Step 11: (1S,3'R,6'R,7'R,8'E,11'S,12'R)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a 100 mL round-bottomed flask was added (1S,3'R,6'R,7'R,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (450 mg, 0.657 mmol), (S)-octahydropyrazino[2,1-c][1,4]oxazine HCl salt (1130 mg, 5.25 mmol) and N,N-diisopropylethylamine (2.341 mL, 13.13 mmol) in DCM (13.1 mL). Titanium(IV) isopropoxide (0.770 mL, 2.63 mmol) was added to the solution slowly. The reaction was stirred at room temperature overnight. Sodium triacetoxyborohydride (278 mg, 1.31 mmol) was added to the reaction portion wise and the mixture was stirred overnight. The reaction was diluted with saturated NaCl (20 mL). The white precipitate was removed by filtration through Celite. The filtrate was concentrated and diluted with 1 N HCl (20 mL) and extracted with EtOAc (3×50 mL). The combined organic extracts were washed with saturated NaCl (50 mL) and dried over MgSO$_4$. The solution was filtered and concentrated in vacuo. The concentrate was absorbed onto a plug of silica gel and purified by chromatography through a Redi-Sep pre-packed silica gel column (40 g, with a layer of sodium bicarbonate on top). Elution with a gradient of 0% to 10% methanol in DCM gave (1S,3'R,6'R,7'R,8'E,11'S,12'R)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (420 mg, 0.518 mmol, 79% yield) as a white solid. MS (ESI, +ve ion) m/z 811.0 (M+H)$^+$. 1H NMR (400 MHz, dichloromethane-d$_2$) δ ppm 0.91-1.10 (m, 3H), 1.33-1.72 (m, 10H, with water residue), 1.81-1.97 (m, 5H), 2.03-2.39 (m, 10H), 2.41-2.69 (m, 6H), 2.71-2.83 (m, 2H), 2.90-3.08 (m, 2H), 3.12-3.27 (m, 2H), 3.33 (s, 3H), 3.37 (s, 3H), 3.53-3.83 (m, 6H), 3.95-4.09 (m, 3H), 4.11-4.22 (m, 1H), 5.23-5.29 (m, 1H), 5.55-5.62 (m, 1H), 6.80-6.93 (m, 2H), 7.09 (s, 1H), 7.13-7.22 (m, 1H), 7.30 (s, 1H), 7.72 (d, J=8.41 Hz, 1H).

Example 12

(1S,3'R,6'R,7'R,8'E,11'S,12'R)-6-chloro-7'-methoxy-12'-(2-methoxyethyl)-11'-methyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

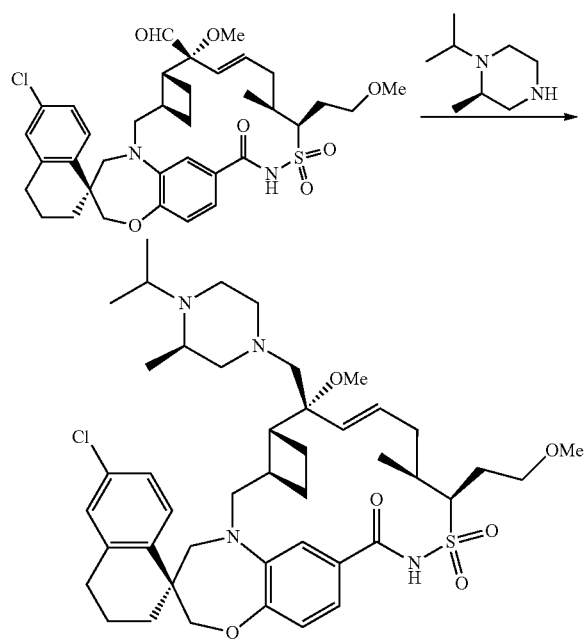

Example 12

To a 25 mL flask was added (1S,3'R,6'R,7'R,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (80 mg, 0.117 mmol), (R)-1-isopropyl-2-methylpiperazine bis(2,2,2-trifluoroacetate) (330 mg, 0.891 mmol), N,N-diisopropylethylamine (366 µL, 2.10 mmol) and titanium(IV) isopropoxide (137 µL, 0.467 mmol) in DCM (2335 µL). The solution was stirred at room temperature overnight. To this solution was added sodium triacetoxyborohydride (99 mg, 0.47 mmol). The reaction was stirred for 24 h. The reaction mixture was diluted with 1 N HCl (10 mL) and extracted with DCM (2×20 mL). The organic solvent was concentrated. The residue was purified by prep-HPLC to give (1S,3'R,6'R,7'R,8'E,11'S,12'R)-6-chloro-7'-methoxy-12'-(2-methoxyethyl)-11'-methyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a TFA salt. MS (ESI, +ve ion) m/z 811.2 (M+H)$^+$. $^1$H NMR (400 MHz, MeOH-d$_4$) δ ppm 1.06 (d, J=6.06 Hz, 3H), 1.25-1.48 (m, 10H), 1.49-2.30 (m, 12H), 2.42-2.84 (m, 8H), 2.94-3.27 (m, 4H), 3.35 (s, 3H), 3.42 (s, 4H), 3.51-3.74 (m, 5H), 3.91-4.10 (m, 3H), 4.14-4.25 (m, 1H), 5.35 (d, J=16.04 Hz, 1H), 5.69-5.82 (m, 1H), 6.86-6.94 (m, 1H), 7.01 (dd, J=8.02, 1.76 Hz, 1H), 7.10 (d, J=1.96 Hz, 1H), 7.16 (dd, J=8.41, 2.15 Hz, 1H), 7.26 (d, J=1.37 Hz, 1H), 7.73 (d, J=8.61 Hz, 1H).

Example 13

(1S,3'R,6'R,7'R,8'E,11'S,12'R)-6-chloro-7'-ethoxy-7'-(((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

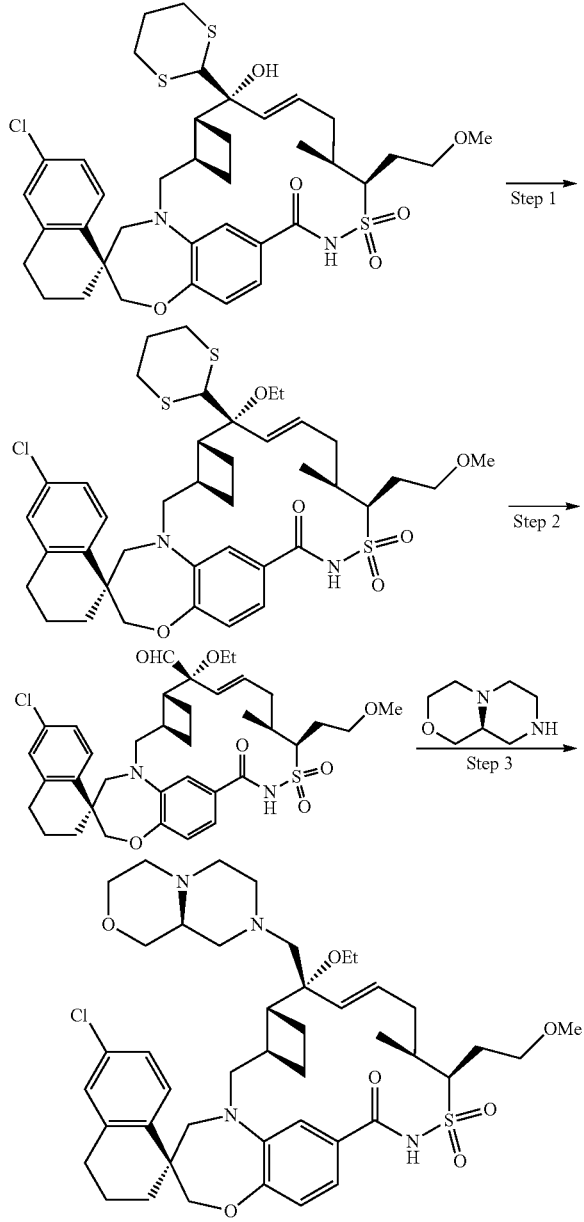

Example 13

Step 1: (1S,3'R,6'R,7'R,8'E,11'S,12'R)-6-chloro-7'-(1,3-dithian-2-yl)-7'-ethoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a 100 mL round-bottomed flask was added (1S,3'R,6'R,7'R,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.62 g, 0.814 mmol) and iodoethane (0.655 mL, 8.14 mmol) in N, N-dimethylformamide (8.14 mL). At 0° C., potassium bis(trimethylsilyl)amide (1 M in THF, 8.14 mL, 8.14 mmol) was added slowly. The reaction was stirred overnight. The reaction mixture was diluted with 1 N HCl (15 mL) and extracted with EtOAc (3×15 mL). The organic extract was washed with saturated NaCl (15 mL) and dried over $MgSO_4$. The solution was filtered and concentrated in vacuo. The concentrate was absorbed onto a plug of silica gel and purified by chromatography through a 24 g ISCO gold column, eluted with a gradient of 0% to 40% EtOAc (with 0.1% of HOAc) in heptane, to provide (1S,3'R,6'R,7'R,8'E,11'S,12'R)-6-chloro-7'-(1,3-dithian-2-yl)-7'-ethoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.24 g, 0.304 mmol, 37% yield). MS (ESI, +ve ion) m/z 789.1 $(M+H)^+$.

Step 2: (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide To a resealable vial was added (1S,3'R,6'R,7'R,8'E,11'S,12'R)-6-chloro-7'-(1,3-dithian-2-yl)-7'-ethoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (510 mg, 0.646 mmol), acetonitrile (5168 µL) and water (1292 µL). To the mixture was added calcium carbonate (323 mg, 3.23 mmol) and iodomethane (401 µL, 6.46 mmol). The mixture was heated at 45° C. overnight. The reaction was diluted with saturated $NH_4Cl$ (10 mL) and extracted with EtOAc (3×15 mL). The combined organic extracts were washed with saturated NaCl (20 mL) and dried over $MgSO_4$. The solution was filtered and concentrated in vacuo. The concentrate was absorbed onto a plug of silica gel and purified by chromatography through a Redi-Sep pre-packed silica gel column (40 g), eluting with a gradient of 0% to 60% EtOAc (with 0.1% of HOAc), to provide (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (230 mg, 0.329 mmol, 50.9% yield) as a white solid. MS (ESI, +ve ion) m/z 699.1 $(M+H)^+$.

Step 3: (1S,3'R,6'R,7'R,8'E,11'S,12'R)-6-chloro-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a 50-mL round-bottomed flask was added (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (150 mg, 0.215 mmol), (S)-octahydropyrazino[2,1-c][1,4]oxazine HCl salt (277 mg, 1.29 mmol) and N,N-diisopropylethylamine (574 µL, 3.22 mmol) in DCM (4290 µL). The reaction was stirred at room temperature overnight. Sodium triacetoxyborohydride (182 mg, 0.858 mmol) was added to the reaction mixture. The reaction was stirred for 8 h. The reaction mixture was diluted with 1 N HCl (20 mL) and extracted with DCM (2×20 mL). The organic layer was fully concentrated. The residue was further purified by prep-HPLC. The solution after pre-HPLC was washed with pH 7 solution and extracted with EtOAc (2×20 mL). The organic extract was washed with saturated NaCl (20 mL) and dried over $MgSO_4$. The solution was filtered and concentrated in vacuo to give (1S,3'R,6'R,7'R,8'E,11'S,12'R)-6-chloro-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid. MS (ESI, +ve ion) m/z 825.2 $(M+H)^+$. $^1H$ NMR (400 MHz, dichloromethane-$d_2$) δ ppm 1.01 (d, J=6.26 Hz, 3H), 1.35 (t, J=6.85 Hz, 3H), 1.44-1.74 (m, 7H), 1.77-2.01 (m, 5H), 2.04-2.38 (m, 9H), 2.41-2.65 (m, 5H), 2.70-2.83 (m, 2H), 2.86-3.08 (m, 2H), 3.27 (d, J=14.28 Hz, 1H), 3.35 (s, 3H), 3.40-3.49 (m, 1H), 3.52-3.83 (m, 7H), 3.99-4.10 (m, 3H), 4.12-4.28 (m, 1H), 5.35-5.42 (m, 1H), 5.57-5.76 (m, 1H), 6.85-6.92 (m, 2H), 7.09 (d, J=2.15 Hz, 1H), 7.13-7.20 (m, 1H), 7.24 (s, 1H), 7.72 (d, J=8.41 Hz, 1H).

Example 14

(1S,3'R,6'R,7'R,8'E,11'S,12'R)-6-chloro-7'-ethoxy-12'-(2-methoxyethyl)-11'-methyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide General Method 12

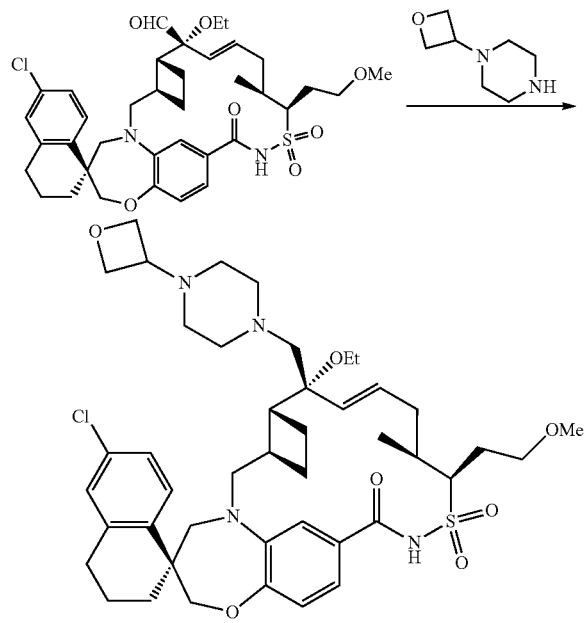

Example 14

To a 25 mL flask was added (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (130 mg, 0.186 mmol) in DCM (3718 μL). To this solution was added 1-(oxetan-3-yl)piperazine (159 mg, 1.12 mmol) and a drop of acetic acid. The mixture was stirred for 8 h and sodium triacetoxyborohydride (158 mg, 0.744 mmol) was added. The reaction was stirred for 2 h and diluted with 1 N HCl (10 mL) and extracted with DCM (3×15 mL). The organic layer was concentrated. The concentrate was purified by prep-HPLC. The solution from prep-HPLC was washed with pH 7 buffer and extracted with EtOAc. The organic layer was concentrated to give (1S,3'R,6'R,7'R,8'E,11'S,12'R)-6-chloro-7'-ethoxy-12'-(2-methoxyethyl)-11'-methyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white solid. MS (ESI, +ve ion) m/z 825.2 (M+H)⁺. ¹H NMR (400 MHz, dichloromethane-d₂) δ ppm 0.98 (br s, 3H), 1.29-1.43 (m, 4H), 1.47-2.24 (m, 12H), 2.24-2.41 (m, 4H), 2.45-2.84 (m, 9H), 2.87-3.07 (m, 1H), 3.27 (br d, J=14.09 Hz, 1H), 3.34 (s, 3H), 3.39-3.52 (m, 2H), 3.57-3.76 (m, 4H), 3.95-4.20 (m, 4H), 4.45-4.55 (m, 2H), 4.57-4.65 (m, 2H), 5.38-5.51 (m, 1H), 5.59-5.74 (m, 1H), 6.89 (s, 2H), 7.09 (d, J=1.96 Hz, 1H), 7.13-7.19 (m, 1H), 7.21-7.28 (m, 1H), 7.72 (d, J=8.41 Hz, 1H).

Example 15

(1S,3'R,6'R,7'R,8'E,11'S,12'R)-6-chloro-7'-ethoxy-12'-(2-methoxyethyl)-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

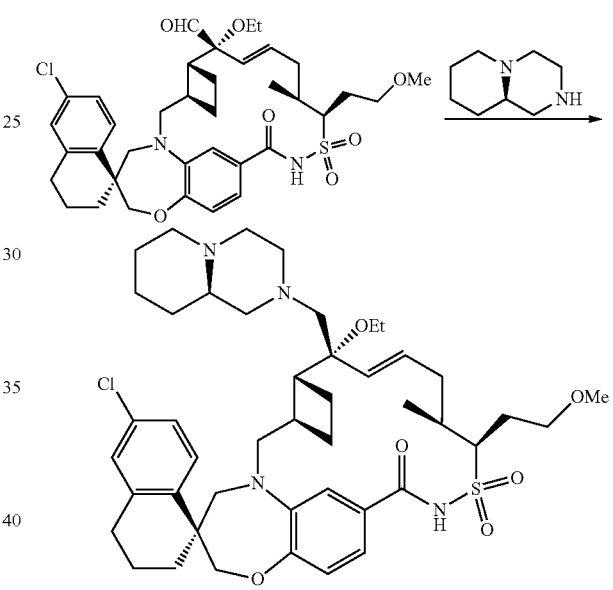

Example 15

To a 25 mL flask was added (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (60 mg, 0.086 mmol) and (9ar)-octahydro-2h-pyrido[1,2-a]pyrazine (120 mg, 0.858 mmol) in DCM (1716 μL). A drop of acetic acid was added. The solution was stirred at room temperature overnight. To this solution was added sodium triacetoxyborohydride (73 mg, 0.34 mmol). The reaction was stirred for 8 h and diluted with 1 N HCl (10 mL) and extracted with DCM (2×10 mL). The solvent was removed under reduced pressure. The concentrate was purified by prep-HPLC to give (1S,3'R,6'R,7'R,8'E,11'S,12'R)-6-chloro-7'-ethoxy-12'-(2-methoxyethyl)-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a TFA salt. MS (ESI, +ve ion) m/z 823.2 (M+H)⁺. ¹H NMR (400 MHz, MeOH-d₄) δ ppm 1.05 (d, J=6.46 Hz, 3H), 1.37 (t, J=6.85 Hz, 3H), 1.41-2.02 (m, 14H), 2.04-2.26 (m, 5H), 2.30-2.51 (m, 2H), 2.51-2.87 (m, 6H), 2.92-3.08 (m, 3H), 3.11-3.26 (m, 2H), 3.35-3.54 (m, 7H), 3.60-3.78 (m, 4H), 3.94-4.11 (m, 3H), 4.18-4.29 (m, 1H), 5.43 (d, J=16.04 Hz, 1H), 5.67-5.89 (m, 1H), 6.87-6.94 (m, 1H), 6.95-7.03 (m, 1H), 7.10 (d, J=1.96 Hz, 1H), 7.14-7.19 (m, 1H), 7.24 (d, J=1.56 Hz, 1H), 7.73 (d, J=8.61 Hz, 1H).

Example 16

(1S,3'R,6'R,7'R,8'E,11'S,12'R)-6-chloro-7'-ethoxy-12'-(2-methoxyethyl)-11'-methyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (s, 4H), 3.45-3.57 (m, 3H), 3.59-3.78 (m, 4H), 3.95-4.11 (m, 3H), 4.20-4.33 (m, 1H), 5.45 (d, J=15.85 Hz, 1H), 5.77-5.91 (m, 1H), 6.84-6.94 (m, 1H), 6.96-7.02 (m, 1H), 7.10 (d, J=1.96 Hz, 1H), 7.16 (br d, J=8.41 Hz, 1H), 7.23 (d, J=1.57 Hz, 1H), 7.73 (d, J=8.41 Hz, 1H).

Example 17

(1S,3'R,6'R,7'R,8'E,11'S,12'R)-6-chloro-7'-ethoxy-12'-(2-methoxyethyl)-11'-methyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

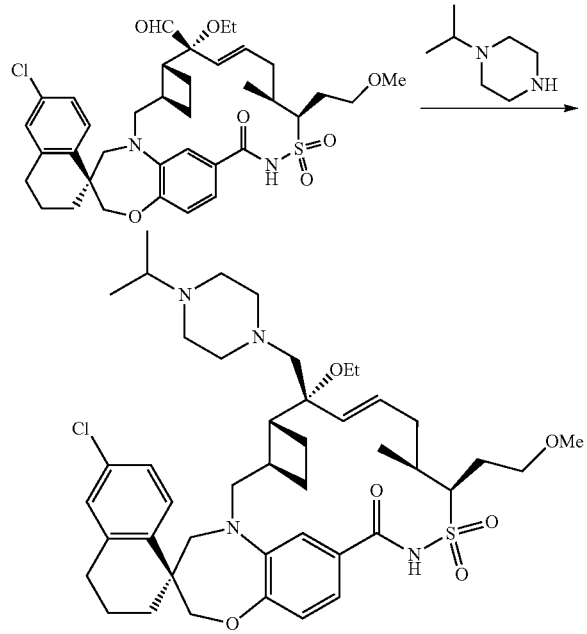

Example 16

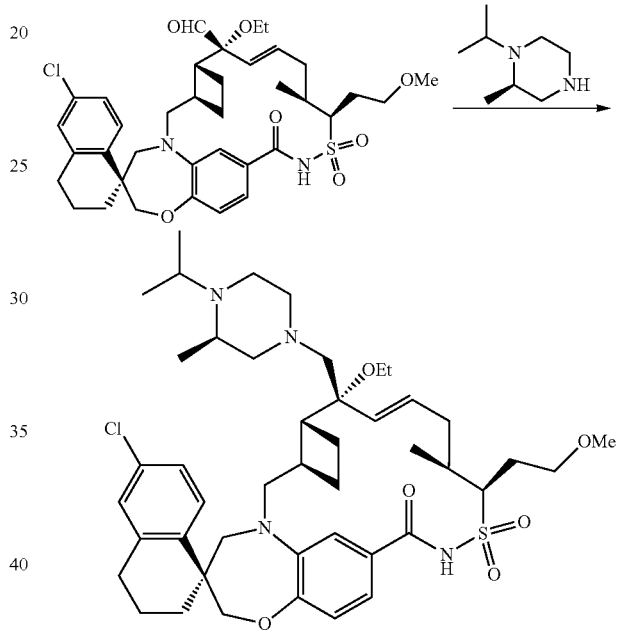

Example 17

To a 10 mL flask was added 1-isopropylpiperazine (123 µL, 0.858 mmol) and (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (60 mg, 0.086 mmol) in DCM (1716 µL). A drop of acetic acid was added and the reaction was stirred overnight. Sodium triacetoxyborohydride (72.7 mg, 0.343 mmol) was added to the reaction mixture. The reaction was stirred at room temperature for 8 h. The reaction mixture was diluted with 1 N HCl (5 mL) and extracted with DCM (2×10 mL). The organic layer was concentrated. The concentrate was purified by prep-HPLC to give (1S,3'R,6'R,7'R,8'E,11'S,12'R)-6-chloro-7'-ethoxy-12'-(2-methoxyethyl)-11'-methyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a TFA salt. MS (ESI, +ve ion) m/z 811.2 (M+H)+. 1H NMR (400 MHz, MeOH-d4) δ ppm 1.05 (d, J=6.46 Hz, 3H), 1.29-1.47 (m, 10H), 1.52-2.30 (m, 12H), 2.51-2.87 (m, 8H), 2.93-3.11 (m, 2H), 3.38

To a 25 mL flask was added (1S,3'R,6'R,7'R,8'E,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (80 mg, 0.11 mmol), (R)-1-isopropyl-2-methylpiperazine bis(2,2,2-trifluoroacetate) (254 mg, 0.686 mmol), N,N-diisopropylethylamine (408 µL, 2.29 mmol) and titanium(IV) isopropoxide (134 µL, 0.458 mmol) in DCM (2288 µL). The solution was stirred at room temperature for 8 h. To this solution was added sodium triacetoxyborohydride (97 mg, 0.46 mmol). The reaction was stirred overnight. The reaction mixture was diluted with 1 N HCl (10 mL) and extracted with DCM (2×10 mL). The solvent was concentrated. The residue was purified by prep-HPLC to give (1S,3'R,6'R,7'R,8'E,11'S,12'R)-6-chloro-7'-ethoxy-12'-(2-methoxyethyl)-11'-methyl-7'-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a TFA salt. MS (ESI, +ve ion) m/z 825.4 (M+H)+. 1H NMR (400 MHz, MeOH-d₄) δ ppm 1.05 (d, J=6.46 Hz, 3H), 1.21-1.49 (m, 13H), 1.51-2.28 (m, 12H), 2.37-2.87 (m, 8H), 2.92-3.20 (m, 3H), 3.36-3.57 (m, 7H), 3.60-3.79 (m, 4H), 3.97-4.07 (m, 3H) 4.20-4.31 (m, 1H), 5.43 (d, J=16.04 Hz, 1H), 5.75-5.90 (m, 1H), 6.87-6.94 (m, 1H), 6.98-7.01 (m, 1H), 7.10 (d, J=1.37 Hz, 1H), 7.14-7.19 (m, 1H), 7.24 (d, J=1.37 Hz, 1H), 7.73 (d, J=8.61 Hz, 1H).
Example 18
(1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11',12'-dimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide
General Method 2 (Steps 10-12) and General Method 4 (Steps 13-14)
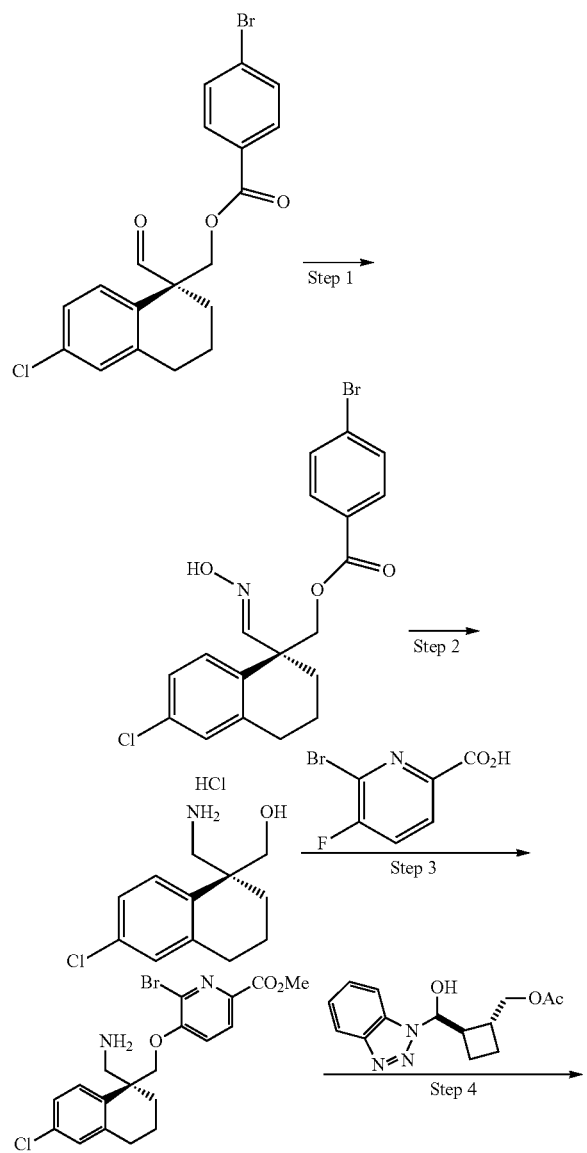
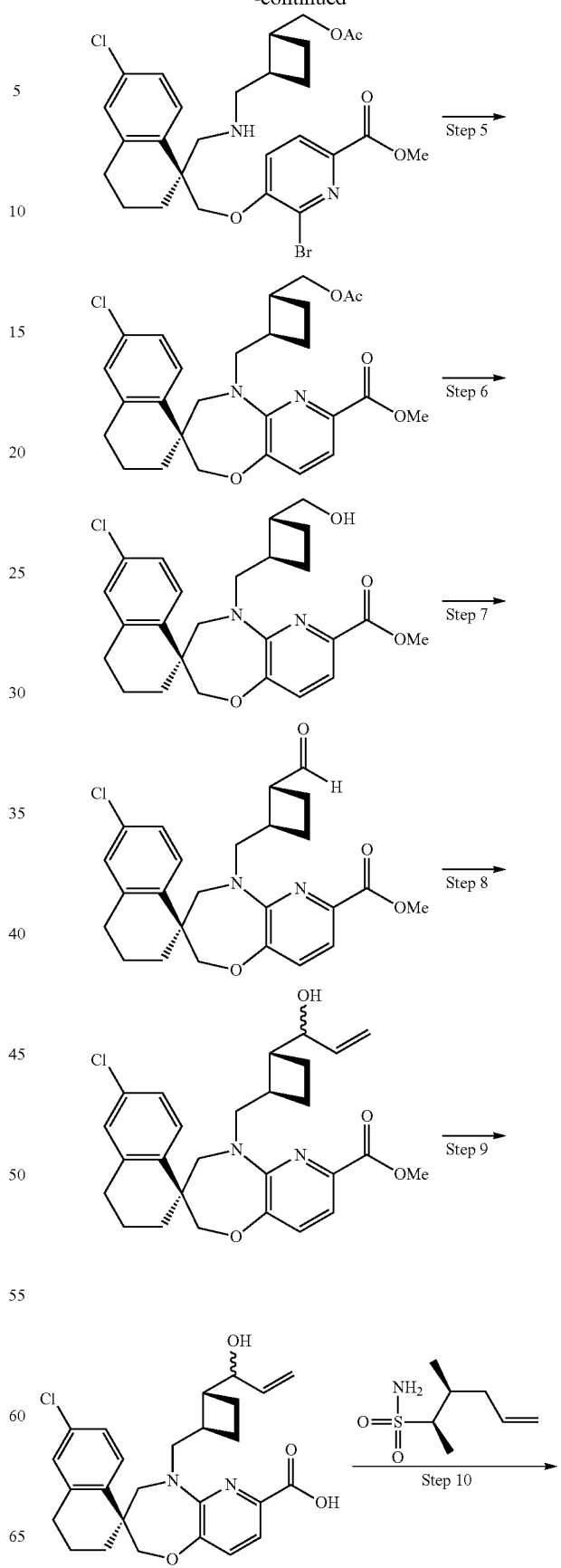

-continued

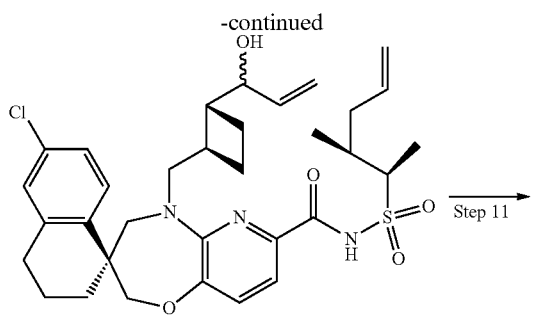

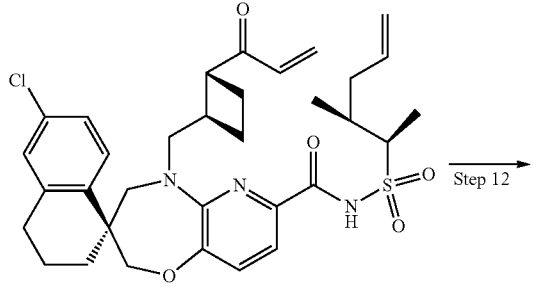

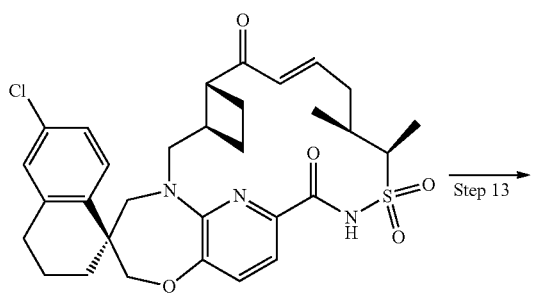

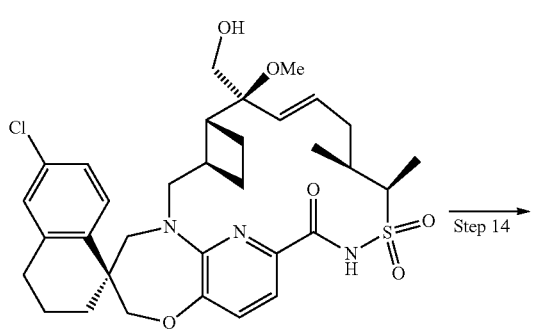

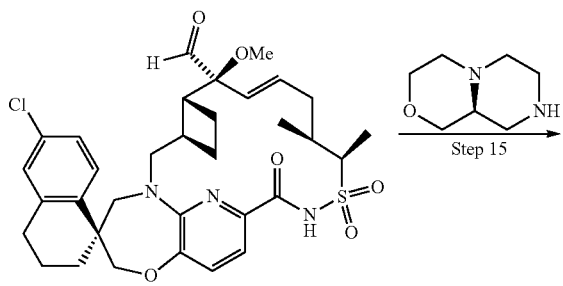

-continued

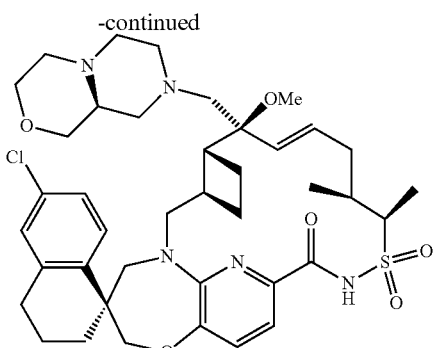

Example 18

Step 1: (S,E)-(6-chloro-1-((hydroxyimino)methyl)-1,2,3,4-tetrahydronaphthalen-1-yl)methyl 4-bromobenzoate To a stirred solution of (R)-(6-chloro-1-formyl-1,2,3,4-tetrahydronaphthalen-1-yl)methyl 4-bromobenzoate (425 g, 1042 mmol) in DCM (5100 mL) and MeOH (5100 mL) under a nitrogen atmosphere was added pyridine (337 mL, 4170 mmol) followed by hydroxylamine hydrochloride (145 g, 2085 mmol). The reaction mixture was stirred at room temperature for 3 h. The reaction was diluted with DCM (2.0 L) and the organic layer was washed with water (2.0 L). The organic layer was dried over sodium sulfate, filtered, and concentrated under reduced pressure to yield (S,E)-(6-chloro-1-((hydroxyimino)methyl)-1,2,3,4-tetrahydronaphthalen-1-yl)methyl 4-bromobenzoate as yellow liquid. The material was used in the next step without further purification. $^1$H NMR (400 MHz, Chloroform-d) δ 7.85-7.80 (dd, J=8.7, 2.1 Hz, 2H), 7.58-7.55 (m, 2H), 7.51 (s, 1H), 7.23-7.26 (m, 1H), 7.14-7.16 (m, 2H), 4.66-4.64 (d, J=11.3 Hz, 1H), 4.56-4.53 (d, J=11.2 Hz, 1H), 2.84-2.81 (t, J=6.3 Hz, 2H), 2.14-2.02 (dddd, J=14.8, 13.2, 7.1, 3.8 Hz, 2H), 1.96-1.83 (dddt, J=13.9, 11.8, 5.9, 3.7 Hz, 2H).

Step 2: (S)-(1-(aminomethyl)-6-chloro-1,2,3,4-tetrahydronaphthalen-1-yl)methanol hydrochloride (S,E)-(6-Chloro-1-((hydroxyimino)methyl)-1,2,3,4-tetrahydronaphthalen-1-yl)methyl 4-bromobenzoate (425 g, 1005 mmol), prepared in the previous step, was dissolved in THF (5160 mL) under a nitrogen atmosphere. The reaction mixture was cooled to 0° C. and lithium aluminum hydride (1.0 M in THF, 3519 mL, 3519 mmol) was added drop-wise. The ice-bath was removed and the reaction mixture was stirred at room temperature for 3 h. The reaction was cooled to 0° C. and water (160 mL) was added slowly, followed by 15% aqueous NaOH solution (160 mL) and water (500 mL). The mixture was allowed to stir for 10 min at room temperature and the reaction was filtered. The residual solids were washed with hot ethyl acetate (3×4.0 L). The combined filtrate was concentrated under reduced pressure to yield a yellow oil. The residue was dissolved in DCM (5160 mL) and the solution was cooled to 0° C. A solution of HCl (4.0 M in dioxane, 65 mL) was added drop-wise and mixture was allowed to stir for 15 min at room temperature. The precipitate was collected by filtration. The solid was washed with ice-cold DCM (100 mL) and dried to afford (S)-(1-(aminomethyl)-6-chloro-1,2,3,4-tetrahydronaphthalen-1-yl)methanol hydrochloride (192 g, 72.8% yield). $^1$H NMR (400

MHz, Methanol-d₄) δ 7.38-7.36 (d, J=8.2 Hz, 1H), 7.23-7.20 (m, 2H), 3.81-3.78 (m, 1H), 3.69-3.68 (dd, J=10.9, 1.3 Hz, 1H), 3.48-3.45 (d, J=13.1 Hz, 1H), 3.23-3.20 (d, J=13.2 Hz, 1H), 2.83-2.81 (d, J=6.3 Hz, 2H), 2.17-2.11 (m, 1H), 1.91-1.85 (m, 2H), 1.83-1.74 (m, 1H); exchangeable protons not observed.

Step 3: (S)-methyl 5-((1-(aminomethyl)-6-chloro-1,2,3,4-tetrahydronaphthalen-1-yl)methoxy)-6-bromopicolinate To a stirred solution of (S)-(1-(aminomethyl)-6-chloro-1,2,3,4-tetrahydronaphthalen-1-yl)methanol hydrochloride (150 g, 572 mmol) was dissolved in dry DMSO (2250 mL) under a nitrogen atmosphere at room temperature. The solution was treated with 6-bromo-5-fluoropicolinic acid (151 g, 687 mmol) and the resulting solution was treated with potassium 2-methylpropan-2-olate (218 g, 1945 mmol) at room temperature. The reaction mixture was stirred for 2 h at room temperature and quenched by addition of acetic acid (~170 mL) at room temperature, followed by water (1.5 L) which resulted in precipitation of a solid. The solid was collected by filtration, washed with water (1.0 L), and dried. The solid was added to a pre-mixed solution of MeOH/H₂SO₄ (10:1, v/v, 5400 mL) and stirred at 80° C. for 3 h. The mixture was cooled to room temperature and solid K₂CO₃ (600 g) was slowly added to quench the sulfuric acid. The mixture was suspended in water (2 L) and ethyl acetate (2 L). The layers were separated. The aqueous layer was extracted with ethyl acetate (2×2.5 L). The combined organic extracts were washed with brine (2.0 L), dried over Na₂SO₄, and filtered. The filtrate was concentrated under reduced pressure. Purification by column chromatography on silica gel (60-120 mesh, eluted with 0% to 5% MeOH in DCM) gave (S)-methyl 5-((1-(aminomethyl)-6-chloro-1,2,3,4-tetrahydronaphthalen-1-yl)methoxy)-6-bromopicolinate (170 g, 67.6% yield) as off-white solid. MS (ESI, +ve ion) m/z 439.0 (M+1). ¹H NMR (400 MHz, Chloroform-d) δ 8.06-8.04 (dd, J=8.4, 1.0 Hz, 1H), 7.51-7.49 (d, J=8.4 Hz, 1H), 7.18-7.14 (m, 3H), 4.18-4.11 (m, 2H), 3.93 (s, 3H), 3.25-3.17 (m, 2H), 2.80-2.76 (m, 2H), 2.06-1.97 (m, 2H), 1.94-1.85 (tdd, J=9.5, 6.7, 4.2 Hz, 2H); exchangeable protons not observed.

Step 4: methyl 5-(((S)-1-(((((1R,2R)-2-(acetoxymethyl)cyclobutyl)methyl)amino)methyl)-6-chloro-1,2,3,4-tetrahydronaphthalen-1-yl)methoxy)-6-bromopicolinate To a stirred solution of (S)-methyl 5-((1-(aminomethyl)-6-chloro-1,2,3,4-tetrahydronaphthalen-1-yl)methoxy)-6-bromopicolinate (170 g, 387 mmol) in dry DCM (1.7 L) and acetic acid (1105 mL) under a nitrogen atmosphere was added ((1R,2S)-2-((S)-(1H-benzo[d][1,2,3]triazol-1-yl)(hydroxy)methyl)cyclobutyl)methyl acetate (128 g, 464 mmol) followed by sodium cyanoborohydride (31.6 g, 503 mmol) at 0° C. The reaction was maintained at 0° C. for 2 h. The reaction was poured slowly into cold 10% sodium bicarbonate solution. The aqueous phase was extracted with ethyl acetate (2×2.0 L). The combined organic layer was washed with brine (1.0 L) and dried over sodium sulfate and concentrated under reduced pressure. Purification by column chromatography on silica gel (60-120 mesh, eluted with 2% to 5% MeOH in DCM) gave methyl 5-(((S)-1-(((((1R,2R)-2-(acetoxymethyl)cyclobutyl)methyl)amino)methyl)-6-chloro-1,2,3,4-tetrahydronaphthalen-1-yl)methoxy)-6-bromopicolinate (149 g, 66.5% yield) as yellow liquid. MS (ESI, +ve ion) m/z 579.1 (M+1). ¹H NMR (400 MHz, Chloroform-d) δ 8.08-8.06 (dt, J=8.4, 1.3 Hz, 1H), 7.55-7.53 (dd, J=8.3, 1.6 Hz, 1H), 7.19-7.13 (m, 3H), 4.13 (s, 2H), 4.10-4.00 (t, J=2.3 Hz, 2H), 3.98 (d, J=1.4 Hz, 3H), 3.05-2.98 (m, 2H), 2.79-2.78 (m, 2H), 2.69-2.58 (m, 2H), 2.18-2.11 (dd, J=8.9, 4.9 Hz, 2H), 2.09-2.06 (dq, J=9.7, 4.8, 3.1 Hz, 1H), 2.00 (t, J=1.3 Hz, 3H), 1.97-1.82 (m, 6H), 1.65-1.61 (d, J=9.2 Hz, 1H), 1.59-1.51 (q, J=8.9 Hz, 1H).

Step 5: (S)-methyl 5'-(((1R,2R)-2-(acetoxymethyl)cyclobutyl)methyl)-6-chloro-3,4,4',5'-tetrahydro-2H,2'H-spiro[naphthalene-1,3'-pyrido[3,2-b][1,4]oxazepine]-7'-carboxylate A solution of methyl 5-(((S)-1-(((((1R,2R)-2-(acetoxymethyl)cyclobutyl)methyl)amino)methyl)-6-chloro-1,2,3,4-tetrahydronaphthalen-1-yl)methoxy)-6-bromopicolinate (36 g, 62.1 mmol) and N-ethyl-N-isopropylpropan-2-amine (161 mL, 933 mmol) in N-methyl-2-pyrrolidinone (360 mL) was stirred at 130° C. under a nitrogen atmosphere for 16 h. The reaction was cooled to room temperature and diluted with ethyl acetate (1.0 L). The mixture was washed with water (5×400 mL). The organic layer was dried with sodium sulfate, filtered, and concentrated under reduced pressure. Purification by column chromatography on silica gel (60-120 mesh, 0% to 10% EtOAc in hexane) gave (S)-methyl 5'-(((1R,2R)-2-(acetoxymethyl)cyclobutyl)methyl)-6-chloro-3,4,4',5'-tetrahydro-2H,2'H-spiro[naphthalene-1,3'-pyrido[3,2-b][1,4]oxazepine]-7'-carboxylate (16 g, 51.7% yield) as yellow liquid. MS (ESI, +ve ion) m/z 499.1 (M+1). ¹H NMR (400 MHz, Chloroform-d) δ 7.72-7.70 (d, J=8.5 Hz, 1H), 7.46-7.44 (dd, J=7.9, 1.1 Hz, 1H), 7.21-7.20 (dd, J=8.5, 2.2 Hz, 1H), 7.18-7.11 (m, 2H), 4.18-4.15 (d, J=12.2 Hz, 1H), 4.05-3.98 (m, 3H), 3.95-3.93 (d, J=4.5 Hz, 1H), 3.91-3.89 (d, J=1.0 Hz, 3H), 3.74-3.70 (d, J=14.5 Hz, 1H), 3.42-3.32 (m, 2H), 2.79-2.76 (dt, J=9.0, 5.1 Hz, 2H), 2.55-2.49 (dt, J=15.5, 7.4 Hz, 2H), 1.98-1.85 (m, 8H), 1.76-1.74 (t, J=9.4 Hz, 1H), 1.62-1.61 (d, J=1.1 Hz, 1H), 1.50-1.49 (d, J=1.1 Hz, 1H).

Step 6: (S)-methyl 6-chloro-5'-(((1R,2R)-2-(hydroxymethyl)cyclobutyl)methyl)-3,4,4',5'-tetrahydro-2H,2'H-spiro[naphthalene-1,3'-pyrido[3,2-b][1,4]oxazepine]-7'-carboxylate To a stirred solution of (S)-methyl 5'-(((1R,2R)-2-(acetoxymethyl)cyclobutyl)methyl)-6-chloro-3,4,4',5'-tetrahydro-2H,2'H-spiro[naphthalene-1,3'-pyrido[3,2-b][1,4]oxazepine]-7'-carboxylate (68 g, 136 mmol) in THF (680 mL) and water (680 mL) was added lithium hydroxide monohydrate (22.87 g, 545 mmol) at room temperature. The reaction was allowed to stir at room temperature for 12 h. The reaction was concentrated under reduced pressure and the residue was taken up in MTBE (1.0 L), 10% citric acid monohydrate solution (500 mL) was added and the solution was stirred for 10 min. The layers were separated and the organic layer was washed with brine (500 mL), dried over sodium sulfate, and concentrated under reduced pressure. The concentrate was dissolved in dry methanol (600 mL) and cooled to 0° C. Thionyl chloride (14.92 mL, 204 mmol) was added and the reaction was heated at 60° C. for 12 h. The reaction was cooled to 0° C. and quenched by slow addition of 10% sodium bicarbonate solution (500 mL) and extracted with ethyl acetate (2×500 mL). The combined organic layer was washed with brine (300 mL), dried over sodium sulfate, and concentrated under reduced pressure. The concentrate was suspended in acetonitrile (140 mL) and water (140 mL) was added. The mixture was stirred for 10 min. The solid was collected by filtration and dried to give (S)-methyl 6-chloro-5'-(((1R,2R)-2-(hydroxymethyl)cyclobutyl)methyl)-3,4,4',5'-tetrahydro-2H,2'H-spiro[naphthalene-1,3'-pyrido[3,2-b][1,4]oxazepine]-7'-carboxylate (58 g, 93% yield). MS (ESI, +ve ion) m/z 457.1 (M+1). $^1$H NMR (400 MHz, Chloroform-d) δ 7.73-7.72 (d, J=8.5 Hz, 1H), 7.47-7.45 (d, J=7.9 Hz, 1H), 7.21-7.19 (dd, J=8.5, 2.3 Hz, 1H), 7.14-7.11 (m, 2H), 4.44-4.40 (m, 1H), 4.16-4.13 (d, J=12.1 Hz, 1H), 4.06-4.03 (d, J=12.1 Hz, 1H), 3.95 (s, 3H), 3.84-3.80 (d, J=14.4 Hz, 1H), 3.75-3.68 (m, 1H), 3.57-3.56 (ddt, J=14.1, 9.3, 4.2 Hz, 2H), 3.37-3.36 (d, J=14.5 Hz, 1H), 2.96-2.90 (dd, J=14.0, 9.1 Hz, 1H), 2.82-2.76 (m, 2H), 2.58-2.54 (m, 1H), 2.32 (td, J=12.2, 10.4, 6.3 Hz, 1H), 2.02-1.95 (m, 3H), 1.88-1.83 (m, 2H), 1.67-1.55 (m, 2H), 1.49-1.43 (m, 1H).

Step 7: (S)-methyl 6-chloro-5'-(((1R,2R)-2-formylcyclobutyl)methyl)-3,4,4',5'-tetrahydro-2H,2'H-spiro[naphthalene-1,3'-pyrido[3,2-b][1,4]oxazepine]-7'-carboxylate A 1 L 3-neck flask equipped with a mechanical stir bar and a temperature probe was charged with DCM (220 mL, 5V) followed by oxalyl chloride (10.16 mL, 116 mmol). The solution was cooled to −73° C. in a dry-ice acetone bath. DMSO (17.15 mL, 242 mmol) was added via syringe over 7 min (internal temperature increased from −74° C. to −60° C. during the addition). The mixture was held for 14 min and a solution of (S)-methyl 6-chloro-5'-(((1R,2R)-2-(hydroxymethyl)cyclobutyl)methyl)-3,4,4',5'-tetrahydro-2H,2'H-spiro [naphthalene-1,3'-pyrido[3,2-b][1,4]oxazepine]-7'-carboxylate (44.2 g, 97 mmol) in DCM (220 mL, 5V) cooled in a dry-ice acetone bath was added via cannula over 12 min (internal temperature increased from −75° C. to −72° C. during the addition). The solution was stirred for 17 min and triethylamine (67.4 mL, 484 mmol) was added over 7 min (internal temperature increased from −76° C. to −65° C. during the addition). After the addition of the Et$_3$N, the reaction was held in the dry ice acetone bath for 5 min then warmed to 7° C. over 4 h and quenched with water (220 mL, 5V) (internal temperature increased from 7° C. to 15° C. during the quench). The mixture was transferred to a separatory funnel and the aqueous layer was discarded. The bottom layer was washed with saturated NH$_4$Cl (220 mL, 5V), 1:1 water:saturated NaHCO$_3$ (220 mL, 5V), and 1:1 water:brine (220 mL, 5V). The bottom organic layer was dried over MgSO$_4$, filtered through a fine frit, and concentrated under reduced pressure to give an off white foam. The foam was dissolved in 1:1 EtOAc/DCM (100 mL) and filtered through a 2 cm pad of silica (eluted with 400 mL of 1:1 EtOAc/DCM). The solution was concentrated under reduced pressure, diluted with PhMe (100 mL) and concentrated. This was repeated twice more and the product (S)-methyl 6-chloro-5'-(((1R,2R)-2-formylcyclobutyl)methyl)-3,4,4',5'-tetrahydro-2H,2'H-spiro[naphthalene-1,3'-pyrido[3,2-b][1,4]oxazepine]-7'-carboxylate was used without further purification. MS (ESI, +ve ion) m/z 454.9 (M+H)$^+$.

Step 8: (1S)-methyl 6-chloro-5'-(((1R,2R)-2-(1-hydroxyallyl)cyclobutyl)methyl)-3,4,4',5'-tetrahydro-2H,2'H-spiro[naphthalene-1,3'-pyrido[3,2-b][1,4]oxazepine]-7'-carboxylate To a 2 L jacketed reactor was charged (−)-cinchonidine (5.69 g, 19.34 mmol) followed by PhMe (220 mL, 5V) and THF (220 mL, 5V). The solution was cooled to −23° C. (internal temperature) and zinc chloride (1.9 M in 2-methyltetrahydrofuran, 81 mL, 155 mmol) was added over 3 min (internal temperature increased from −23° C. to −19° C. during the addition). The solution was stirred for 5 min and vinylmagnesium chloride (1.6 M solution in THF, 206 mL, 329 mmol) was added via an addition funnel over 24 min (internal temperature increased from −21° C. to −13° C. during the addition). The solution was stirred for 20 min (internal temperature decreased to −22° C.) and a solution of (S)-methyl 6-chloro-5'-(((1R,2R)-2-formylcyclobutyl)methyl)-3,4,4',5'-tetrahydro-2H,2'H-spiro[naphthalene-1,3'-pyrido[3,2-b][1,4]oxazepine]-7'-carboxylate, prepared in the previous step, in PhMe (220 mL, 5V) cooled in an ice-water bath was added via cannula over 8 min (internal temperature increased from −22° C. to −16° C. during the addition). The reaction was stirred at −20° C. for 1 h and warmed to 0° C. After 45 min, the reaction was cooled to −8° C. and quenched with saturated NH$_4$Cl (350 mL, 8V). Water (88 mL, 2V) was added. Ammonium hydroxide (20 mL, 0.45V) was added and the solids dissolved. The aqueous phase was discarded. The organic phase was washed with saturated NH$_4$Cl (220 mL, 5 V), 1 M citric acid (4×88 mL, 2V), 1:1 water:brine (440 mL, 10V), dried over MgSO$_4$, filtered, and concentrated to give a yellow oil. MeOH (200 mL) was added and removed under reduced pressure. This was repeated a second time and the product (1S)-methyl 6-chloro-5'-(((1R,2R)-2-(1-hydroxyallyl)cyclobutyl)methyl)-3,4,4',5'-tetrahydro-2H,2'H-spiro[naphthalene-1,3'-pyrido[3,2-b][1,4]oxazepine]-7'-carboxylate was used without further purification as a mixture of diastereomers. MS (ESI, +ve ion) m/z 483.0 (M+H)$^+$.

Step 9: (1S)-6-chloro-5'-(((1R,2R)-2-(1-hydroxyallyl)cyclobutyl)methyl)-3,4,4',5'-tetrahydro-2H,2'H-spiro[naphthalene-1,3'-pyrido[3,2-b][1,4]oxazepine]-7'-carboxylic acid To a 2 L jacketed reactor was charged a solution of (1S)-methyl 6-chloro-5'-(((1R,2R)-2-(1-hydroxyallyl)cyclobutyl)methyl)-3,4,4',5'-tetrahydro-2H,2'H-spiro[naphthalene-1,3'-pyrido[3,2-b][1,4]oxazepine]-7'-carboxylate, prepared in the previous step, in MeOH (234 mL, 5V) and THF (234 mL, 5V). Lithium hydroxide monohydrate (16.23 g, 387 mmol) was added and the reaction was stirred at room temperature for 17 h. Citric acid (1 M in water, 180 mL) was added followed by water (187 mL, 4V) and EtOAc (234 mL, 5V). All the solids dissolved. The mixture was drained from the reactor into a 3 L flask and the mixture was concentrated to half the original volume. EtOAc (234 mL, 5V) was added and the mixture was transferred to a separatory funnel. The pH of the aqueous layer was 5. The aqueous layer was discarded. The organic layer was washed with 1:1 water:brine (235 mL, 5V), dried over MgSO$_4$, filtered, and concentrated to give 47.0 g of a yellow solid that was 79 wt % (1S)-6-chloro-5'-(((1R,2R)-2-(1-hydroxyallyl)cyclobutyl)methyl)-3,4,4',5'-tetrahydro-2H,2'H-spiro[naphthalene-1,3'-pyrido[3,2-b][1,4]oxazepine]-7'-carboxylic acid (37.1 g, 79 mmol, 82% yield) and a mixture of diastereomers. MS (ESI, +ve ion) m/z 469.0 (M+H)$^+$.

Step 10: (1S)-6-chloro-5'-(((1R,2R)-2-(1-hydroxyallyl)cyclobutyl)methyl)-N-(((2R,3 S)-3-methylhex-5-en-2-yl)sulfonyl)-3,4,4',5'-tetrahydro-2H,2'H-spiro[naphthalene-1,3'-pyrido[3,2-b][1,4]oxazepine]-7'-carboxamide To a mixture of (1S)-6-chloro-5'-(((1R,2R)-2-(1-hydroxyallyl)cyclobutyl)methyl)-3,4,4',5'-tetrahydro-2H,2'H-spiro

[naphthalene-1,3'-pyrido[3,2-b][1,4]oxazepine]-7'-carboxylic acid (34.7 g, 58.5 mmol), 4-(dimethylamino)pyridine (21.42 g, 175 mmol), and (2R,3S)-3-methylhex-5-ene-2-sulfonamide (21.41 g, 117 mmol) in a 500 mL 1-neck flask was added PhMe (100 mL). The PhMe was removed under reduced pressure and the concentrate was diluted with DCM (347 mL, 10V) and transferred to a 3-neck 1 L flask equipped with a temperature probe and a magnetic stirrer. Triethylamine (24.44 mL, 175 mmol) and 1-(3-dimethylaminopropyl)-3-ethylcarbodiimide HCl (22.41 g, 117 mmol) were added and the reaction was stirred at room temperature. After 43 h, the reaction was diluted with water (240 mL, 7V) and transferred to a separatory funnel. The pH of the aqueous phase was adjusted to 4 with 1 M citric acid (240 mL, 7V) and the aqueous phase was discarded. The organic phase was washed with 1:1 brine:water (240 mL, 7V), dried over $MgSO_4$, filtered, and concentrated. Purification by flash column chromatography on silica gel (330 g silica, eluted with 50% to 100% DCM in heptane) gave (1S)-6-chloro-5'-(((1R,2R)-2-(1-hydroxyallyl)cyclobutyl)methyl)-N-(((2R,3 S)-3-methylhex-5-en-2-yl)sulfonyl)-3,4,4',5'-tetrahydro-2H,2'H-spiro[naphthalene-1,3'-pyrido[3,2-b][1,4]oxazepine]-7'-carboxamide (24.7 g, 39.3 mmol, 67% yield) as a pale yellow foam and a mixture of diastereomers. MS (ESI, +ve ion) m/z 628.0 $(M+H)^+$.

Step 11: (S)-5'-(((1R,2R)-2-acryloylcyclobutyl)methyl)-6-chloro-N-(((2R,3S)-3-methylhex-5-en-2-yl)sulfonyl)-3,4,4',5'-tetrahydro-2H,2'H-spiro[naphthalene-1,3'-pyrido[3,2-b][1,4]oxazepine]-7'-carboxamide A solution of (1S)-6-chloro-5'-(((1R,2R)-2-(1-hydroxyallyl)cyclobutyl)methyl)-N-(((2R,3 S)-3-methylhex-5-en-2-yl)sulfonyl)-3,4,4',5'-tetrahydro-2H,2'H-spiro[naphthalene-1,3'-pyrido[3,2-b][1,4]oxazepine]-7'-carboxamide (2.82 g, 4.49 mmol) in DCM (28 mL, 10V) in a 100 mL 1-neck flask equipped with a temperature probe and magnetic stir bar was cooled to 2° C. in an ice-water bath and Dess-Martin periodinane (2.094 g, 4.94 mmol) was added in one portion. The reaction was warmed to room temperature over 20 min and stirred at room temperature for 30 min. The solution was cooled to 2° C. in a water-ice bath and quenched with a solution of sodium thiosulfate (2.4 g) in water (8.4 mL, 3V) followed by saturated $NaHCO_3$ (20 mL, 7V). The internal temperature increased from 2° C. to 7° C. during the quench. The reaction was removed from the water-ice bath, warmed to room temperature, and stirred for 30 min. The mixture was transferred to a separatory funnel. The pH was adjusted to 7 with 1 M citric acid. The aqueous layer was discarded. The organic phase was washed with 1:1 water:brine (28 mL, 10V), dried over $MgSO_4$, filtered, and concentrated to give a yellow foam. The concentrate was dissolved in 10% EtOAc in DCM (~50 mL) and filtered through a 1 cm pad of silica gel (eluted with ~100 mL of 10% EtOAc in DCM). The filtrate was concentrated to give (S)-5'-(((1R,2R)-2-acryloylcyclobutyl)methyl)-6-chloro-N-(((2R,3 S)-3-methylhex-5-en-2-yl)sulfonyl)-3,4,4',5'-tetrahydro-2H,2'H-spiro[naphthalene-1,3'-pyrido[3,2-b][1,4]oxazepine]-7'-carboxamide as a pale yellow foam that was used without further purification. MS (ESI, +ve ion) m/z 625.8 $(M+H)^+$. $^1$H NMR (400 MHz, CHLOROFORM-d) δ ppm 1.14 (d, J=6.85 Hz, 3H), 1.45 (d, J=7.04 Hz, 3H), 1.48-1.56 (m, 1H), 1.81-2.05 (m, 6H), 2.10-2.19 (m, 2H), 2.27 (q, J=8.80 Hz, 1H), 2.62 (qd, J=7.14, 2.45 Hz, 1H), 2.73-2.87 (m, 2H), 3.04-3.17 (m, 1H), 3.30 (q, J=8.80 Hz, 1H), 3.36-3.43 (m, 1H), 3.43-3.47 (m, 1H), 3.78 (d, J=14.48 Hz, 1H), 3.89-4.07 (m, 3H), 4.20 (d, J=12.32 Hz, 1H), 5.07-5.15 (m, 2H), 5.74-5.87 (m, 2H), 6.15-6.32 (m, 2H), 7.12 (d, J=2.15 Hz, 1H), 7.18-7.22 (m, 2H), 7.58 (d, J=7.83 Hz, 1H), 7.69 (d, J=8.41 Hz, 1H), 9.90 (s, 1H).

Step 12: (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14,25]triazatetracyclo [14.7.2.0~3,6~.0~19,24~]pentacosa[8,16, 18,24] tetraene]-7',15'-dione 13',13'-dioxide To a 4-neck flask equipped with a magnetic stir bar, a temperature probe, and an air cooled condenser was charged PhMe (1.8 L, 250V). The solvent was heated to 80° C. and a gas dispersion tube was immersed into the solvent. Nitrogen gas was bubbled through the solvent via the gas dispersion tube. A solution of (S)-5'-(((1R,2R)-2-acryloylcyclobutyl)methyl)-6-chloro-N-(((2R,3S)-3-methylhex-5-en-2-yl)sulfonyl)-3,4,4',5'-tetrahydro-2H,2'H-spiro [naphthalene-1,3'-pyrido[3,2-b][1,4]oxazepine]-7'-carboxamide (8.93 g, 80 wt %, 11.41 mmol) in PhMe (65 mL) was added via an addition funnel over 2 h. During the addition of the diene, Umicore M73 SIMes (Umicore AG & Co. KG, Precious Metals Chemistry, Rodenbacher Chaussee 4, 63457 Hanau-Wolfgang, Germany) was added in four equal portions (total amount of catalyst was 0.346 g, 0.456 mmol) as a suspension in PhMe (4 mL) via syringe at: t=0 min, t=30 min, t=60 min, and t=90 min. After the addition of the diene was complete, the reaction was stirred for an additional 1 h at 80° C. The reaction was cooled to room temperature and 2-(2-(vinyloxy)ethoxy)ethanol (0.125 mL, 0.913 mmol) and SilaMetS Thiol (SiliCycle Inc. 2500, Parc-Technologique Blvd Quebec City, Quebec, Canada) (7.71 g) were added. The mixture was stirred at room temperature for 18 h and the SilaMetS Thiol was removed by filtration and washed with EtOAc and concentrated to give a tan color solid. MeOH (~50 mL) was added and removed under reduced pressure. MeOH (107 mL, 15V) was added and the slurry was stirred at room temperature for 3 d and collected by filtration. The solid was washed with MeOH (1×40 mL) and dried on a frit under a vacuum with a positive flow of nitrogen to give 6.39 g of an off white solid that was 66 wt % (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14,25]triazatetracyclo[14.7.2.0~3, 6~.0~19,24~]pentacosa[8,16, 18,24]tetraene]-7',15'-dione 13',13'-dioxide (4.22 g, 7.0 mmol, 62% yield). MS (ESI, +ve ion) m/z 598.1 $(M+H)^+$.

Step 13: (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa [13]thia[1,14,25]triazatetracyclo[14.7.2.0~3, 6~.0~19,24~]pentacosa[8,16, 18,24]tetraen]-15'-one 13',13'-dioxide To a 3-neck flask equipped with temperature probe, septum, and nitrogen inlet was charged (1S,3'R,6'R,8'E,11'S, 12'R)-6-chloro-11',12'-dimethyl-3,4-dihydro-2H,7'H,15'H-spiro[naphthalene-1,22'-[20]oxa[13]thia[1,14,25]triazatetracyclo[14.7.2.0~3,6~.0~19,24~]pentacosa[8,16, 18,24] tetraene]-7',15'-dione 13',13'-dioxide (6.33 g, 66 wt %, 6.98 mmol) and trimethylsulfonium iodide (2.138 g, 10.48 mmol). DMSO (35 mL) and THF (8.75 mL) were added and the mixture was stirred at room temperature for 20 min until the solids dissolved. The solution was cooled in an ice-water bath. When the internal temperature reached 6.5° C., potassium tert-butoxide (1.0 M solution in THF, 17.46 mL, 17.46 mmol) was added slowly via syringe. After 40 min, a small amount of trimethylsulfonium iodide was added followed by potassium tert-butoxide (1 M solution in THF, 1.2 mL, 1.2 mmol). After 15 minutes, zinc(II) trifluoromethanesulfonate (0.5 M in MeOH, 84 mL, 41.9 mmol) was added over 5 min. After addition, the reaction was warmed to room temperature, stirred for 2 h and quenched with saturated ammonium chloride (~150 mL). Water and EtOAc were added. The aqueous phase was extracted with EtOAc (3×). The combined organic extracts were concentrated. The concentrate was dissolved in EtOAc, washed with water (2×), brine (1×), dried over $Na_2SO_4$, filtered, and concentrated. The material was absorbed onto silica gel. Purification by flash column chromatography (330 g silica, eluted with 10% to 80% EtOAc (2% AcOH) in heptane) gave 5.17 g of a light yellow solid that was 57 wt % (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide (2.93 g, 4.55 mmol, 65% yield). MS (ESI, +ve ion) m/z 644.0 (M+H)⁺.

Step 14: (1S,3'R,6'R,7'S,8'E,11'S,12'R)-6-chloro-7'-methoxy-11',12'-dimethyl-15'-oxo-3,4-dihydro-2H-spiro[naphthalene-1,22'-[20]oxa[13]thia[1,14,25]triazatetracyclo[14.7.2.0~3,6~.0~19,24~]pentacosa[8,16, 18,24]tetraene]-7'-carbaldehyde 13',13'-dioxide To a solution of (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide (79 wt %, 7.4 g, 9.07 mmol) in DCM (60 mL) and DMSO (30 mL) was added N,N-diisopropylethylamine (7.92 mL, 45.4 mmol). The solution was cooled in an ice water bath and pyridine-sulfur trioxide complex (3.61 g, 22.69 mmol) was added. After 40 min, the reaction was quench with saturated ammonium chloride and diluted water and EtOAc. The organic phase was washed with water. The combined aqueous phase was extracted with EtOAc (2×). The combined organic phase was washed with 50% saturated ammonium chloride (2×), brine, dried over $Na_2SO_4$, filtered, and concentrated to give (1S,3'R,6'R,7'S,8'E,11'S,12'R)-6-chloro-7'-methoxy-11',12'-dimethyl-15'-oxo-3,4-dihydro-2H-spiro[naphthalene-1,22'-[20]oxa[13]thia[1,14,25]triazatetracyclo[14.7.2.0~3,6~.0~19,24~]pentacosa[8,16, 18,24]tetraene]-7'-carbaldehyde 13',13'-dioxide which was used without further purification. MS (ESI, +ve ion) m/z 641.9 (M+H)⁺.

Step 15: (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11',12'-dimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide To a solution of (1S,3'R,6'R,7'S,8'E,11'S,12'R)-6-chloro-7'-methoxy-11',12'-dimethyl-5'-oxo-3,4-dihydro-2H-spiro[naphthalene-1,22'-[20]oxa[13]thia[1,14,25]triazatetracyclo[14.7.2.0~3,6~.0~19,24~]pentacosa[8,16, 18,24]tetraene]-7'-carbaldehyde 13',13'-dioxide (5.28 g, 8.22 mmol) and (S)-octahydropyrazino[2,1-c][1,4]oxazine (3.51 g, 24.67 mmol) in DCM (82 mL) at room temperature was added acetic acid (0.475 mL, 8.22 mmol). The mixture was stirred at room temperature for 1 h and sodium triacetoxyborohydride (2.091 g, 9.87 mmol) was added slowly over 1 min. After 1 h, additional sodium triacetoxyborohydride (300 mg) was added. The reaction was stirred for 30 min and quenched with saturated $NH_4Cl$. The aqueous phase was extracted with DCM (3×). The combined organic extracts were washed with saturated $NH_4Cl$ (1×), brine (1×), dried over $Na_2SO_4$, filtered, and concentrated. Purification by flash column chromatography (330 g silica, eluted with 0% to 10% MeOH in DCM) gave (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11',12'-dimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide (6.02 g, 7.83 mmol, 95% yield) as off-white solid. MS (ESI, +ve ion) m/z 768.2 (M+H)⁺. ¹H NMR (400 MHz, CHLOROFORM-d) δ ppm 1.17 (d, J=6.85 Hz, 3H), 1.46 (d, J=7.04 Hz, 3H), 1.48-1.63 (m, 4H), 1.68-2.09 (m, 8H), 2.19 (br d, J=17.22 Hz, 1H), 2.49 (br s, 3H), 2.33 (br s, 3H), 2.42 (br s, 1H), 2.55-2.70 (m, 2H), 2.77-3.04 (m, 6H), 3.08 (s, 3H), 3.15 (br s, 1H), 3.54 (br s, 1H), 3.66 (br s, 1H), 3.74-3.96 (m, 2H), 3.95-3.95 (m, 1H), 4.02 (d, J=12.32 Hz, 1H), 4.09-4.21 (m, 2H), 5.51 (br d, J=17.02 Hz, 1H), 5.64 (br d, J=16.82 Hz, 1H), 7.11-7.17 (m, 2H), 7.21 (dd, J=8.51, 2.25 Hz, 1H), 7.38 (d, J=7.82 Hz, 1H), 7.67 (d, J=8.61 Hz, 1H), 9.12 (br s, 1H).

Example 19

(1S,3'R,6'R,7'S,8'E,11'S,12'R)-6-chloro-7'-methoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide General Method 13

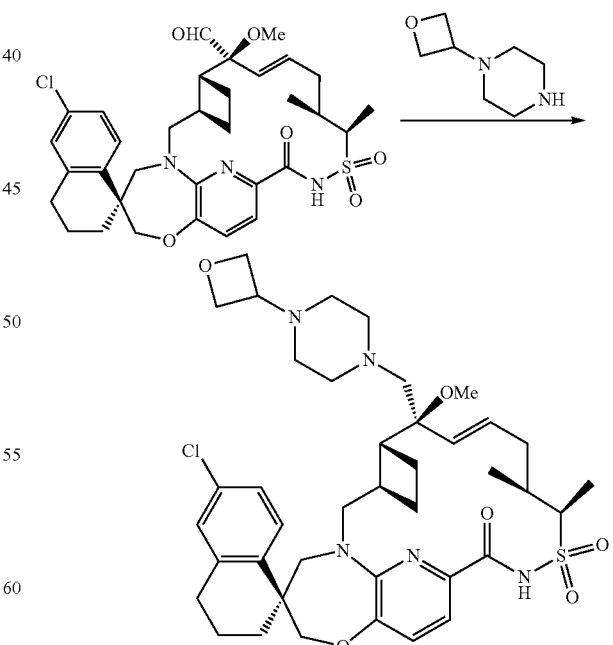

Example 19

To a solution of (1S,3'R,6'R,7'S,8'E,11'S,12'R)-6-chloro-7'-methoxy-11',12'-dimethyl-15'-oxo-3,4-dihydro-2H-spiro

[naphthalene-1,22'-[20]oxa[13]thia[1,14,25]triazatetracyclo[14.7.2.0~3,6~.0~19,24~]pentacosa[8,16, 18,24]tetraene]-7'-carbaldehyde 13',13'-dioxide (12 mg, 0.019 mmol) and 1-(oxetan-3-yl)piperazine (26.6 mg, 0.187 mmol) in DCM (374 μL) at room temperature was added a few drop of titanium (IV) isopropoxide. The mixture was stirred at room temperature for 8 h and sodium triacetoxyborohydride (15.84 mg, 0.075 mmol) was added slowly over 1 min. The reaction was stirred for overnight and quenched with 5 mL of 1 N HCl solution. The aqueous phase was extracted with DCM (3×). The combined organic extracts were concentrated. The residue was purified by prep-HPLC to give (1S,3'R,6'R,7'S,8'E,11'S,12'R)-6-chloro-7'-methoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide as a TFA salt. MS (ESI, +ve ion) m/z 768.2 (M+H)+. 1H NMR (400 MHz, MeOH-d4) δ ppm 1.11 (d, J=6.65 Hz, 3H), 1.39 (d, J=7.24 Hz, 3H), 1.44-1.58 (m, 1H,) 1.64-2.01 (m, 6H), 2.03-2.27 (m, 2H), 2.29-2.43 (m, 2H), 2.45-2.56 (m, 1H), 2.32-3.04 (m, 7H), 3.35-3.67 (m, 6H), 3.35-3.65 (m, 6H), 3.72-3.93 (m, 4H), 4.03-4.10 (m, 1H), 4.12-4.28 (m, 2H), 4.61 (t, J=6.16 Hz, 2H), 4.69-4.77 (m, 2H), 5.78-5.90 (m, 2H), 7.12 (d, J=1.96 Hz, 1H), 7.15-7.20 (m, 1H), 7.21-7.26 (m, 2H), 7.70 (d, J=8.41 Hz, 1H).

Example 20

(1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide

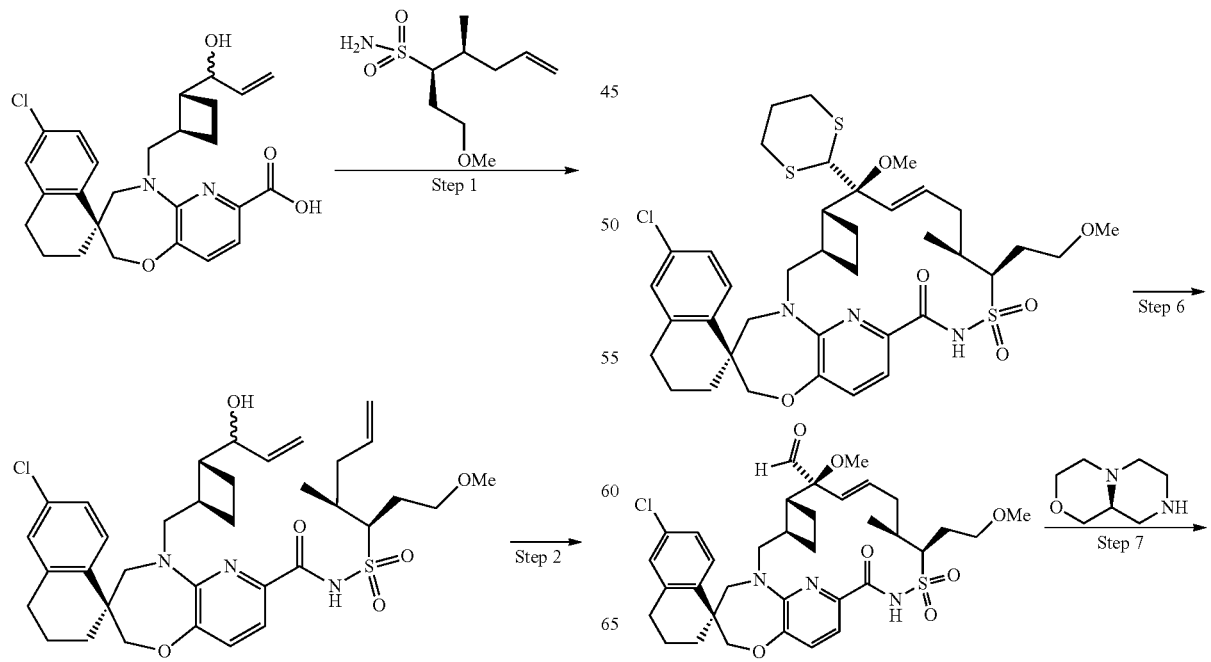

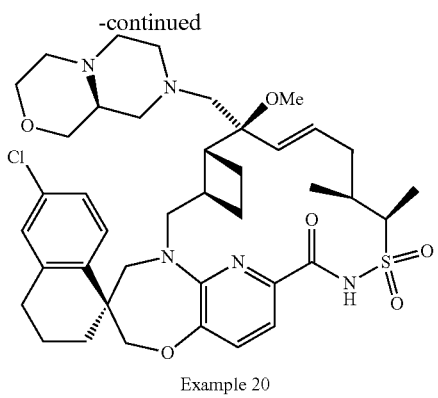

Example 20

Step 1: (1S)-6-chloro-5'-(((1R,2R)-2-(1-hydroxyallyl)cyclobutyl)methyl)-N-(((3R,4S)-1-methoxy-4-methylhept-6-en-3-yl)sulfonyl)-3,4,4',5'-tetrahydro-2H,2'H-spiro[naphthalene-1,3'-pyrido[3,2-b][1,4]oxazepine]-7'-carboxamide To a solution of (3R,4S)-1-methoxy-4-methylhept-6-ene-3-sulfonamide (4.94 g, 22.34 mmol) in DCM (80 mL) was added (1S)-6-chloro-5'-(((1R,2R)-2-(1-hydroxyallyl)cyclobutyl)methyl)-3,4,4',5'-tetrahydro-2H,2'H-spiro[naphthalene-1,3'-pyrido[3,2-b][1,4]oxazepine]-7'-carboxylic acid (6.8 g, 11.5 mmol), 4-(dimethylamino) pyridine (4.20 g, 34.4 mmol), triethylamine (3.2 mL, 23.0 mmol), and 1-(3-dimethylaminopropyl)-3-ethylcarbodiimide HCl (6.6 g, 34.4 mmol). The resulting mixture was stirred at room temperature under nitrogen for 20 h. The reaction was quenched with 2 N HCl (5 mL) and diluted with water (30 mL). The aqueous layer was extracted with DCM (2×40 mL). The combined organic layers were dried over MgSO$_4$, filtered, and concentrated. The crude product was purified by column chromatography (330 g of silica, 0% to 40% acetone in heptane) to obtain (1S)-6-chloro-5'-(((1R,2R)-2-(1-hydroxyallyl)cyclobutyl)methyl)-N-(((3R,4S)-1-methoxy-4-methylhept-6-en-3-yl)sulfonyl)-3,4,4',5'-tetrahydro-2H,2'H-spiro[naphthalene-1,3'-pyrido[3,2-b][1,4]oxazepine]-7'-carboxamide as light brown solid (6.1 g). $^1$H NMR (DICHLOROMETHANE-d$_2$) δ 10.43 (br. S., 1H), 7.70 (d, J=8.4 Hz, 1H), 7.52 (d, J=7.8 Hz, 1H), 7.19 (d, J=7.8 Hz, 2H), 7.10 (s, 1H), 5.67-5.87 (m, 2H), 5.19 (d, J=17.2 Hz, 1H), 5.01-5.12 (m, 3H), 4.60 (d, J=13.7 Hz, 1H), 4.10-4.20 (m, 1H), 3.96-4.07 (m, 3H), 3.89 (d, J=14.7 Hz, 1H), 3.53 (t, J=6.4 Hz, 1H), 3.43-3.50 (m, 1H), 3.34-3.42 (m, 1H), 3.19-3.25 (m, 2H), 3.13 (s, 1H), 2.82-2.92 (m, 1H), 2.73-2.82 (m, 2H), 2.55-2.69 (m, 1H), 2.37-2.48 (m, 1H), 2.33 (br. S., 1H), 2.04-2.22 (m, 3H), 1.91-2.01 (m, 4H), 1.76-1.91 (m, 2H), 1.62-1.74 (m, 1H), 1.54-1.61 (m, 1H), 1.41 (t, J=12.8 Hz, 1H), 1.07 (dd, J=11.2, 7.0 Hz, 3H). MS (ESI, +ve ion) m/z 672.4 (M+H)$^+$.

Step 2: (S)-5'-(((1R,2R)-2-acryloylcyclobutyl)methyl)-6-chloro-N-(((3R,4S)-1-methoxy-4-methylhept-6-en-3-yl)sulfonyl)-3,4,4',5'-tetrahydro-2H,2'H-spiro[naphthalene-1,3'-pyrido[3,2-b][1,4]oxazepine]-7'-carboxamide To a solution of (1S)-6-chloro-5'-(((1R,2R)-2-(1-hydroxyallyl)cyclobutyl)methyl)-N-(((3R,4S)-1-methoxy-4-methylhept-6-en-3-yl)sulfonyl)-3,4,4',5'-tetrahydro-2H,2'H-spiro[naphthalene-1,3'-pyrido[3,2-b][1,4]oxazepine]-7'-carboxamide (6.1 g, 9.07 mmol) in DCM (70 mL) at 0° C. was added Dess-Martin periodinane (4.5 g, 10.61 mmol). After the addition, the ice bath was removed and the resulting mixture was warmed up to room temperature and stirred for 20 h. The reaction was quenched with 10% sodium thiosulfate (5 mL) and stirred for 30 min. The resulting mixture was washed with saturated NaHCO$_3$ (30 mL). The aqueous layer was extracted with DCM (2×50 mL). The combined organic layers were dried over MgSO$_4$, filtered, and concentrated. The crude product was purified by column chromatography (330 g of silica, 0% to 40% acetone in heptane) to obtain (S)-5'-(((1R,2R)-2-acryloylcyclobutyl)methyl)-6-chloro-N-(((3R,4S)-1-methoxy-4-methylhept-6-en-3-yl)sulfonyl)-3,4,4',5'-tetrahydro-2H,2'H-spiro[naphthalene-1,3'-pyrido[3,2-b][1,4]oxazepine]-7'-carboxamide as light brown foam. $^1$H NMR (DICHLOROMETHANE-d$_2$) δ 9.25-9.54 (m, 1H), 7.70-7.76 (m, 1H), 7.44-7.51 (m, 1H), 7.14-7.21 (m, 1H), 7.03-7.13 (m, 2H), 5.85-6.03 (m, 2H), 4.13-4.22 (m, 1H), 4.01-4.12 (m, 2H), 3.85-3.99 (m, 1H), 3.72-3.81 (m, 1H), 3.58-3.70 (m, 2H), 3.29-3.33 (m, 7H), 3.17-3.27 (m, 6H), 2.94-3.04 (m, 3H), 2.83-2.93 (m, 4H), 2.73-2.80 (m, 2H), 2.51-2.64 (m, 1H), 2.32-2.41 (m, 1H), 2.23-2.31 (m, 1H), 2.05-2.12 (m, 2H), 1.97-2.05 (m, 1H), 1.87-1.96 (m, 2H), 1.76-1.87 (m, 2H), 1.61-1.70 (m, 2H), 1.51-1.59 (m, 5H), 1.40-1.51 (m, 2H), 1.04-1.11 (m, 5H), 0.96-1.02 (m, 3H). MS (ESI, +ve ion) m/z 670.2 (M+H)$^+$.

Step 3: (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14,25]triazatetracyclo[14.7.2.0~3,6~.0~19,24~]pentacosa[8,16, 18,24]tetraene]-7',15'-dione 13',13'-dioxide To a solution of (S)-5'-(((1R,2R)-2-acryloylcyclobutyl)methyl)-6-chloro-N-(((3R,4S)-1-methoxy-4-methylhept-6-en-3-yl)sulfonyl)-3,4,4',5'-tetrahydro-2H,2'H-spiro[naphthalene-1,3'-pyrido[3,2-b][1,4]oxazepine]-7'-carboxamide (2.2 g, 3.28 mmol) in 1,2-dichloroethane (1200 mL) under nitrogen was added Hoveyda-Grubbs catalyst 2$^{nd}$ generation (0.206 g, 0.328 mmol). The resulting mixture was heated at 55° C. for 20 h. The reaction was cooled to room temperature and concentrated. The crude product was purified by column chromatography (220 g of silica, 0% to 30% acetone in heptane) to obtain (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14,25]triazatetracyclo[14.7.2.0~3,6~.0~19,24~]pentacosa[8,16, 18,24]tetraene]-7',15'-dione 13',13'-dioxide as pale yellow solid (1.5 g). $^1$H NMR (DICHLOROMETHANE-d$_2$) δ 8.69 (s, 1H), 7.72 (d, J=8.4 Hz, 1H), 7.20 (d, J=8.4 Hz, 1H), 7.08-7.18 (m, 3H), 6.71-6.82 (m, 1H), 5.86-5.96 (m, 1H), 4.44 (dd, J=14.1, 8.4 Hz, 1H), 4.14 (d, J=12.1 Hz, 1H), 3.99 (d, J=12.1 Hz, 1H), 3.92 (d, J=15.3 Hz, 1H), 3.85-3.89 (m, 1H), 3.73-3.82 (m, 1H), 3.70 (dd, J=8.0, 5.1 Hz, 1H), 3.59-3.66 (m, 1H), 3.42 (s, 3H), 3.39 (d, J=14.7 Hz, 1H), 2.94 (dd, J=14.0, 3.8 Hz, 1H), 2.82-2.90 (m, 1H), 2.72-2.82 (m, 2H), 2.35-2.45 (m, 1H), 2.26-2.34 (m, 1H), 2.09-2.19 (m, 3H), 1.97-2.06 (m, 2H), 1.75-1.94 (m, 5H), 1.37-1.48 (m, 1H), 1.18 (d, J=6.8 Hz, 3H). MS (ESI, +ve ion) m/z 642.2 (M+H)$^+$.

Step 4: (1S,3'R,6'R,7'S,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide An oven dry 50 mL 3-neck flask, which was equipped with stir bar and temperature probe, was added 1,3-dithiane (0.890 g, 7.40 mmol) and THF (15 mL). The resulting mixture was cooled between −20 to −30° C. and n-butyllithium solution (2.5 M in hexanes, 2.7 mL, 6.75 mmol) was added dropwise via syringe. The resulting mixture was stirred at −20° C. for 30 min, cooled below −70° C. and stirred for 20 min. To this reaction was added lanthanum(III) chloride lithium chloride complex (0.6 M in THF, 5.6 mL, 3.36 mmol, Strem Chemical, Newbury Port, Mass.) dropwise via syringe (internal temperature was kept below −70° C.). After 10 min, (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14,25]triazatetracyclo[14.7.2.0~3,6~.0~19,24~]pentacosa[8,16, 18,24]tetraene]-7',15'-dione 13',13'-dioxide (0.430 g, 0.670 mmol) in THF (5 mL) was added dropwise via syringe (internal temperature was kept below −70° C.). The reaction was stirred at −70° C. for 15 min after the addition. The reaction was quenched with saturated NH$_4$Cl (3 mL), warmed to room temperature and partitioned between EtOAc (60 mL) and water (30 mL). The organic layer was dried over MgSO$_4$, filtered, and concentrated. Purification by column chromatography (80 g of silica, 0% to 30% acetone in heptane) gave (1S,3'R,6'R,7'S,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide as white solid (0.350 g). $^1$H NMR (DICHLOROMETHANE-d$_2$) δ 9.24 (br. S., 1H), 7.65-7.73 (m, 1H), 7.35-7.41 (m, 1H), 7.19 (d, J=7.8 Hz, 2H), 7.11 (s, 1H), 5.76-5.87 (m, 1H), 5.60-5.71 (m, 1H), 4.61 (dd, J=13.5, 4.9 Hz, 1H), 4.12-4.22 (m, 2H), 3.94-4.03 (m, 2H), 3.89 (d, J=14.5 Hz, 1H), 3.53-3.63 (m, 2H), 3.44 (d, J=14.5 Hz, 1H), 3.32 (s, 3H), 2.94-3.04 (m, 2H), 2.85-2.93 (m, 4H), 2.73-2.84 (m, 3H), 2.54-2.70 (m, 2H), 2.17-2.33 (m, 2H), 2.04-2.13 (m, 4H), 1.87-2.00 (m, 3H), 1.71-1.83 (m, 3H), 1.64 (dt, J=18.6, 9.5 Hz, 1H), 1.47 (d, J=14.9 Hz, 1H), 1.15 (d, J=6.8 Hz, 3H). MS (ESI, +ve ion) m/z 762.2 (M+H)$^+$.

Step 5: (1S,3'R,6'R,7'S,8'E,11'S,12'R)-6-chloro-7'-(1,3-dithian-2-yl)-7'-methoxy-12'-(2-methoxy ethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide To a 15 mL flask was added (1S,3'R,6'R,7'S,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide (0.350 g, 0.459 mmol) and THF (15.0 mL). The mixture was cooled to 0° C. and sodium hydride (60 weight percent in oil, 0.165 g, 4.13 mmol) was added. The ice bath was removed after the addition and the mixture was stirred at room temperature for 20 min then iodomethane (0.520 mL, 8.37 mmol) was added. The mixture was stirred at room temperature for 2 h then quenched with water (5 mL). The resulting mixture was partitioned between EtOAc (50 mL) and water (20 ml). The organic layers was dried over MgSO$_4$, filtered, and concentrated. Purification by column chromatography (40 g of silica, 0% to 30% acetone in heptane) gave (1S,3'R,6'R,7'S,8'E,11'S,12'R)-6-chloro-7'-(1,3-dithian-2-yl)-7'-methoxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide as white solid. $^1$H NMR (DICHLOROMETHANE-d$_2$) δ 9.20 (br. S., 1H), 7.69 (d, J=8.4 Hz, 1H), 7.36 (d, J=7.8 Hz, 1H), 7.16-7.22 (m, 2H), 7.11 (s, 1H), 5.73-5.86 (m, 1H), 5.49-5.60 (m, 1H), 4.82 (dd, J=14.0, 5.0 Hz, 1H), 4.37 (s, 1H), 4.09-4.20 (m, 2H), 3.99 (d, J=12.3 Hz, 1H), 3.91 (d, J=14.5 Hz, 1H), 3.56-3.71 (m, 2H), 3.40-3.50 (m, 1H), 3.33 (s, 3H), 3.22 (s, 3H), 3.09 (br. S., 1H), 2.92-3.00 (m, 1H), 2.83-2.91 (m, 4H), 2.75-2.83 (m, 2H), 2.66-2.74 (m, 1H), 2.63 (br. S., 1H), 2.17-2.33 (m, 2H), 2.04-2.14 (m, 3H), 1.91 (td, J=11.7, 3.6 Hz, 4H), 1.71-1.80 (m, 1H), 1.62-1.70 (m, 2H), 1.54-1.62 (m, 1H), 1.39-1.49 (m, 1H), 1.15 (d, J=6.8 Hz, 3H). MS (ESI, +ve ion) m/z 776.2 (M+H)$^+$.

Step 6: (1S,3'R,6'R,7'S,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14,25]triazatetracyclo[14.7.2.0~3,6~.0~19, 24~]pentacosa[8,16, 18,24]tetraene]-7'-carbaldehyde 13',13'-dioxide To a solution of (1S,3'R,6'R,7'S,8'E,11'S,12'R)-6-chloro-7'-(1,3-dithian-2-yl)-7'-methoxy-12'-(2-methoxyethyl)-11'-methyl-3,4-dihydro-2H,15'H-spiro[naphthalene-1,22'-[20]oxa[13]thia[1,14,25]triazatetracyclo [14.7.2.0~3,6~.0~19,24~]pentacosa[8,16,18,24]tetraen]-15'-one 13',13'-dioxide (0.250 g, 0.322 mmol) in acetonitrile (12.0 mL) was added calcium carbonate (0.161 g, 1.610 mmol), water (3.00 mL), and iodomethane (0.250 mL, 4.02 mmol). The resulting mixture was heated at 40° C. for 20 h. The reaction was partitioned between water (20 mL) and DCM (50 mL). The aqueous layer was extracted with DCM (30 mL). The combined organic layers were dried over MgSO$_4$, filtered, and concentrated. The purification by column chromatography (24 g of silica, 0% to 30% acetone in heptane) gave (1S,3'R,6'R,7'S,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14,25]triazatetracyclo[14.7.2.0~3,6~.0~19,24~]pentacosa[8,16,18,24]tetraene]-7'-carbaldehyde 13',13'-dioxide as white solid (0.130 g). $^1$H NMR (DICHLOROMETHANE-d$_2$) δ 9.74 (s, 1H), 9.50 (s, 1H), 7.72 (d, J=8.4 Hz, 1H), 7.47 (d, J=7.8 Hz, 1H), 7.21 (d, J=8.0 Hz, 2H), 7.12 (d, J=2.2 Hz, 1H), 5.69 (d, J=16.2 Hz, 1H), 5.38-5.47 (m, 1H), 4.42 (dd, J=14.0, 8.5 Hz, 1H), 4.19 (d, J=12.3 Hz, 1H), 4.04 (d, J=12.1 Hz, 1H), 3.87 (d, J=14.7 Hz, 1H), 3.60 (td, J=8.7, 4.9 Hz, 1H), 3.46-3.54 (m, 1H), 3.38-3.45 (m, 1H), 3.31 (s, 3H), 3.06 (s, 3H), 2.96 (dd, J=14.1, 5.9 Hz, 1H), 2.74-2.90 (m, 4H), 2.46 (ddd, J=11.2, 7.1, 3.7 Hz, 1H), 2.21-2.28 (m, 1H), 2.11-2.20 (m, 1H), 1.97-2.08 (m, 2H), 1.81-1.96 (m, 5H), 1.67-1.79 (m, 1H), 1.55-1.66 (m, 1H), 1.40-1.50 (m, 1H), 1.14 (d, J=6.8 Hz, 3H). MS (ESI, +ve ion) m/z 686.2 (M+H)$^+$.

Step 7: (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide To a solution of (1S,3'R,6'R,7'S,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14,25]triazatetracyclo[14.7.2.0~3,6~.0~19,24~]pentacosa[8, 16, 18,24]tetraene]-7'-carbaldehyde 13',13'-dioxide (0.080 g, 0.117 mmol) in DCM (4.0 mL) was added (S)-octahydropyrazino[2,1-c][1,4]oxazine (0.093 g, 0.653 mmol) in DCM (4.0 mL) and acetic acid (1 drop). The mixture was stirred at room temperature under nitrogen for 1 h. Sodium triacetoxyborohydride (0.100 g, 0.472 mmol) was added and the mixture was stirred at room temperature for 1 h. The reaction was partitioned between water (10 mL) and DCM (20 mL). The aqueous layer was extracted with DCM (20 mL). The combined organic layers were dried over MgSO$_4$, filtered, and concentrated. Purification by column chromatography (24 g of silica, 0% to 10% MeOH in DCM) gave (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-12'-(2-methoxy ethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide as white solid (0.066 g). $^1$H NMR (DICHLOROMETHANE-d$_2$) δ 7.70 (d, J=8.4 Hz, 1H), 7.40 (d, J=7.8 Hz, 1H), 7.19 (d, J=8.4 Hz, 1H), 7.08-7.16 (m, 2H), 5.53-5.66 (m, 2H), 4.13-4.19 (m, 1H), 4.02-4.12 (m, 2H), 3.74-3.83 (m, 2H), 3.65-3.73 (m, 1H), 3.53-3.63 (m, 3H), 3.46 (d, J=14.7 Hz, 1H), 3.32 (s, 4H), 2.98-3.10 (m, 7H), 2.74-2.85 (m, 2H), 2.72 (d, J=6.1 Hz, 1H), 2.52-2.64 (m, 3H), 2.46 (d, J=16.8 Hz, 3H), 2.23-2.37 (m, 2H), 2.06-2.15 (m, 1H), 1.96-2.03 (m, 2H), 1.85-1.94 (m, 4H), 1.72-1.81 (m, 2H), 1.45-1.63 (m, 6H), 1.08 (d, J=6.8 Hz, 3H). One exchangeable proton was not observed. MS (ESI, +ve ion) m/z 812.4 (M+H)$^+$.

Example 21

(1S,3'R,6'R,7'S,8'E,11'S,12'R)-6-chloro-7'-methoxy-12'-(2-methoxyethyl)-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide dihydro-2H-spiro[naphthalene-1,22'-[20]oxa[13]thia[1,14,25]triazatetracyclo[14.7.2.0~3,6~.0~19,24~]pentacosa[8,16, 18,24]tetraene]-7'-carbaldehyde 13',13'-dioxide (0.140 g, 0.204 mmol) in DCM (5.0 mL) was added (R)-octahydro-1H-pyrido[1,2-a]pyrazine (0.160 g, 1.141 mmol) in DCM (1 mL) and AcOH (2 drops). The mixture was stirred at room temperature under nitrogen for 1 h then treated with sodium triacetoxyborohydride (0.173 g, 0.816 mmol). The resulting mixture was stirred for 1 h then partitioned between water (10 mL) and DCM (20 mL). The aqueous layer was extracted with DCM (20 mL). The combined organic layers were dried over MgSO$_4$, filtered, and concentrated. Purification by column chromatography (24 g of silica, 0% to 10% MeOH in DCM) gave (1S,3'R,6'R,7'S,8'E,11'S,12'R)-6-chloro-7'-methoxy-12'-(2-methoxyethyl)-11'-methyl-7'-((9aR)-octahydro-2H-pyrido[1,2-a]pyrazin-2-ylmethyl)-3, 4-dihydro-2H, 15'H-spiro[naphthalene-1,22'-[20]oxa[13]thia[1,14,25]triazatetracyclo[14.7.2.0~3,6~.0~19,24~]pentacosa[8,16, 18,24]tetraen]-15'-one 13',13'-dioxide as white solid (0.120 g). $^1$H NMR (DICHLOROMETHANE-d$_2$) δ 7.69-7.76 (m, 1H), 7.42-7.50 (m, 1H), 7.18 (dd, J=8.5, 2.1 Hz, 1H), 7.04-7.14 (m, 2H), 5.77 (br. S., 2H), 4.17 (d, J=12.9 Hz, 1H), 4.00-4.13 (m, 2H), 3.77 (d, J=14.5 Hz, 1H), 3.64-3.73 (m, 1H), 3.57 (d, J=9.2 Hz, 2H), 3.35-3.47 (m, 1H), 3.21-3.34 (m, 5H), 3.09 (br. S., 3H), 2.99 (br. S., 1H), 2.83-2.95 (m, 2H), 2.65-2.82 (m, 5H), 2.55 (br. S., 2H), 2.25-2.44 (m, 3H), 2.09-2.21 (m, 1H), 1.97-2.08 (m, 3H), 1.89 (d, J=19.2 Hz, 4H), 1.61-1.73 (m, 4H), 1.38-1.51 (m, 4H), 1.29-1.35 (m, 1H), 1.17 (br. S., 2H), 1.02 (d, J=6.8 Hz, 4H). One exchangeable proton was not observed. MS (ESI, +ve ion) m/z 810.4 (M+H)$^+$.

Example 33

(1S,3'R,6'R,7'R,8'E,12'R)-6-chloro-12'-ethyl-7'-methoxy-14'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

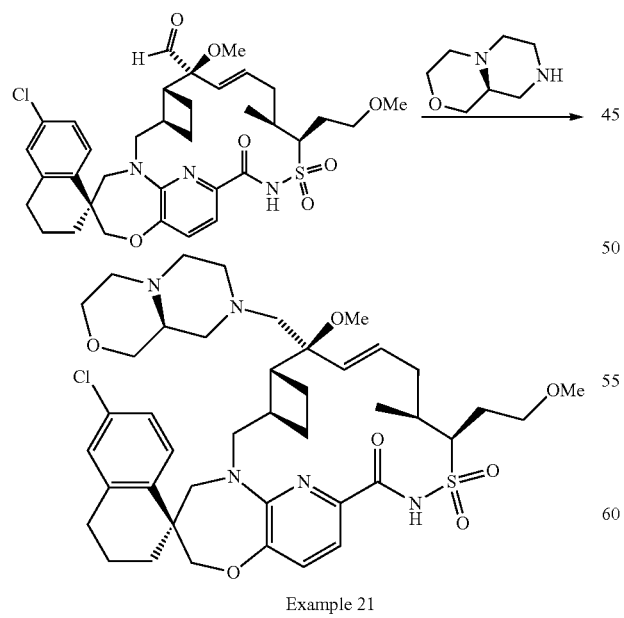

Example 21

To a solution of (1S,3'R,6'R,7'S,8'E,11'S,12'R)-6-chloro-7'-methoxy-12'-(2-methoxyethyl)-11'-methyl-15'-oxo-3,4-

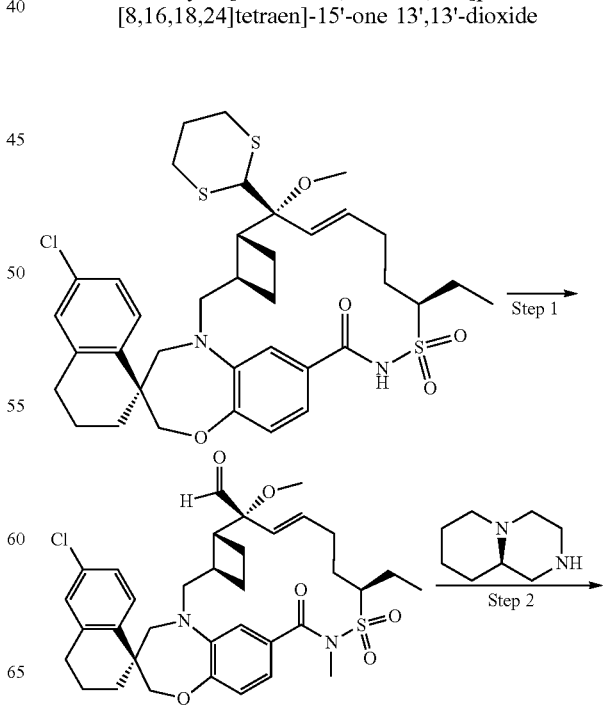

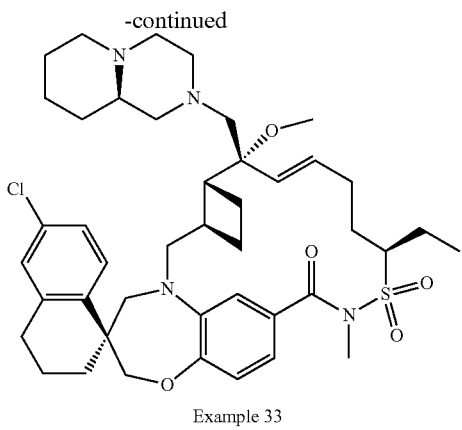

Example 33

Step 1: (1S,3'R,6'R,7'R,8'E,12'R)-6-chloro-12'-ethyl-7'-methoxy-14'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide A 2-dram vial was charged with (1S,3'R,6'R,7'R,8'E,12'R)-6-chloro-7'-(1,3-dithian-2-yl)-12'-ethyl-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (27 mg, 0.037 mmol; Accessed via General Methods 1 (R¹=H, using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid and (R)-hept-6-ene-3-sulfonamide) and General Methods 5 (using MeI)), a magnetic stir bar, acetonitrile (820 μL) and water (205 μL). To the resulting suspension was added calcium carbonate (18.5 mg, 0.185 mmol) and iodomethane (23 μL, 0.37 mmol). The vial was sealed and the mixture stirred at 45° C. Additional iodomethane (10 equiv) was added after 2.5 h, 19 h, 23 h, and 27 h. After a 51 h reaction time, the reaction was quenched by adding saturated aqueous ammonium chloride (1 mL) and water (1 mL). The mixture was extracted with EtOAc (3×2 mL) and the combined organic extracts were washed with brine, dried over magnesium sulfate, filtered, and concentrated under reduced pressure to afford a mixture of (1S,3'R,6'R,7'R,8'E,12'R)-6-chloro-12'-ethyl-7'-methoxy-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide and (1S,3'R,6'R,7'R,8'E,12'R)-6-chloro-12'-ethyl-7'-methoxy-14'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide in a 3:1 ratio that was carried forward in the next step without purification.

Step 2: (1S,3'R,6'R,7'R,8'E,12'R)-6-chloro-12'-ethyl-7'-methoxy-14'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A 1 mL vial was charged with a 3:1 mixture of (1S,3'R,6'R,7'R,8'E,12'R)-6-chloro-12'-ethyl-7'-methoxy-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide and (1S,3'R,6'R,7'R,8'E,12'R)-6-chloro-12'-ethyl-7'-methoxy-14'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.022 g, 0.034 mmol), (R)-octahydro-1H-pyrido[1,2-a]pyrazine (26.5 mg, 0.189 mmol; Aurum Pharmatech, Franklin Park, N.J.), a magnetic stir bar, and 1,2-dichloroethane (343 μL). The resulting mixture was stirred for 1 h before the addition of sodium triacetoxyborohydride (3.6 mg, 0.017 mmol). After 45 min, a second portion of sodium triacetoxyborohydride (3.6 mg, 0.017 mmol) was added and the reaction was continued for an additional 2 h before a third portion of sodium triacetoxyborohydride (3.6 mg, 0.017 mmol) was added. After an additional 3 h, the reaction was quenched by adding methanol. (1S,3'R,6'R,7'R,8'E,12'R)-6-chloro-12'-ethyl-7'-methoxy-14'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide was isolated as the corresponding TFA salt after purification via RP-HPLC (Column: Phenomenex Luna, C18, 150×21 mm; Solvent: A=water (0.1% TFA), B=(R) (0.1% TFA), 30 mL/min, 30% B to 100% B over 18 min then 2 min at 100% B): 5.2 mg (0.006 mmol, 17% yield); MS (ESI, +ve ion) m/z 779.3 (M+H)⁺.

Example 34

(1S,3'R,6'R,7'S,8'E,11'S,12'R)-6-chloro-7'-methoxy-11',12'-dimethyl-7'-(((2-(4-morpholinyl)ethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide General Method 13

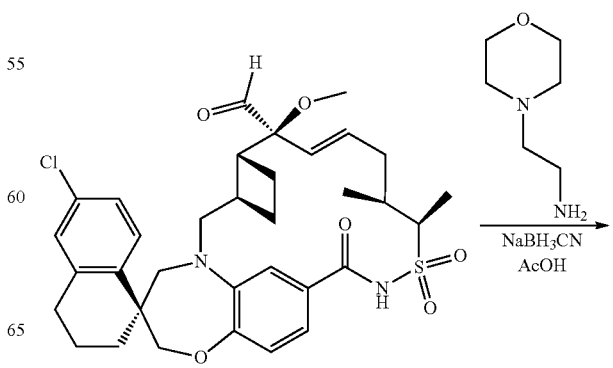

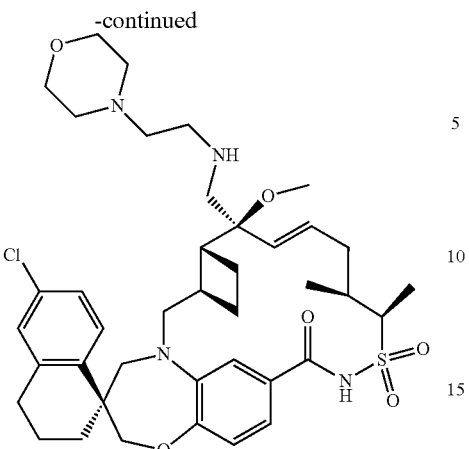

Example 34

A solution of (1S,3'R,6'R,7'S,8'E,11'S,12'R)-6-chloro-11', 12'-dimethyl-15'-oxo-7'-methoxy-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (52 mg, 0.081 mmol) and 2-morpholinoethanamine (106 µL, 0.811 mmol) in THF (810 µL) was stirred at ambient temperature for 90 min. Sodium cyanotrihydroborate (25.5 mg, 0.405 mmol) and acetic acid (93 µL, 1.6 mmol) were added and the reaction mixture was stirred at ambient temperature for 1 h. The reaction mixture was diluted with EtOAc (2 mL) and washed with saturated aqueous sodium bicarbonate (5 mL); the layers were partitioned and the aqueous layer was washed with EtOAc (2×5 mL). The organic extracts were combined, dried over anhydrous MgSO$_4$, filtered, and concentrated in vacuo to afford an off-white solid. (1S,3'R,6'R,7'S,8'E,11'S,12'R)-6-chloro-7'-methoxy-11',12'-dimethyl-7'-(((2-(4-morpholinyl)ethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide was isolated as the corresponding TFA salt after purification via RP-HPLC (Column: Phenomenex Luna, C18, 150×21 mm; Solvent: A=water (0.1% TFA), B=(R) (0.1% TFA), 30 mL/min, 30% B to 100% B over 18 min then 2 min at 100% B): 41.8 mg (0.048 mmol, 59% yield); MS (ESI, +ve ion) m/z 755.2 (M+H)$^+$.

Example 99

(1S,3'R,6'R,7'S,8'E,9a"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[8,16,18,24]tetraene-7',3"-[1,4]oxazino[3,4-c][1,4]oxazin]-15'-one 13',13'-dioxide

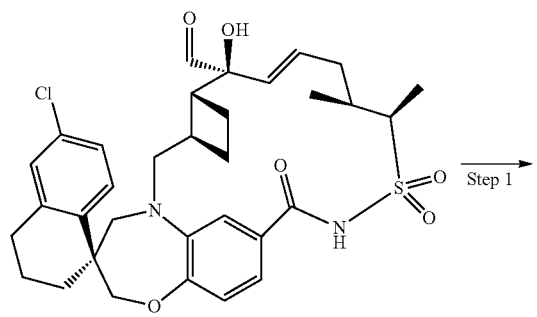

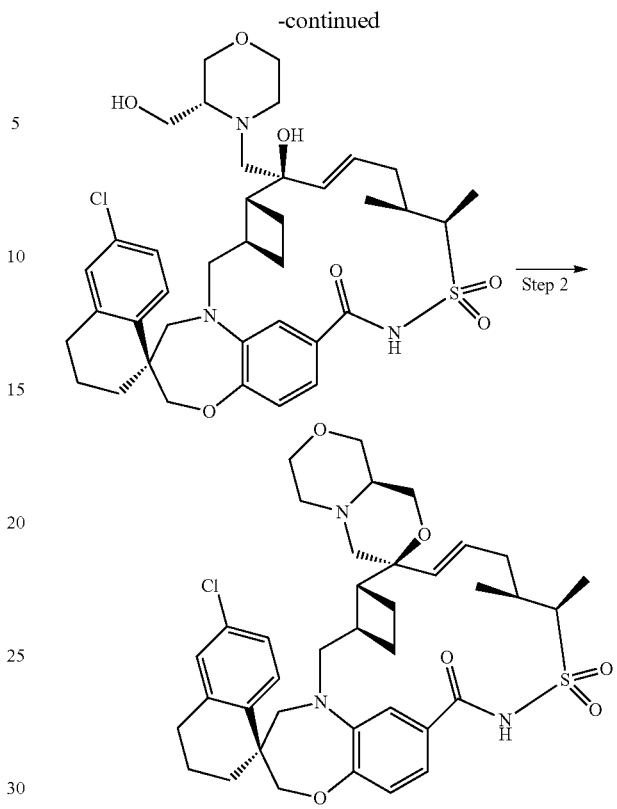

Example 99

Step 1: (1S,3'R,6'R,7'S,8'E,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a room temperature mixture of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.050 g, 0.080 mmol) and (R)-morpholin-3-ylmethanol hydrochloride (0.124 g, 0.807 mmol; J&W Pharmlab, Levittown, Pa.) was added N,N-diisopropylethylamine (0.230 mL, 1.32 mmol) via syringe. After 30 min, 1.0 M sodium cyanoborohydride in tetrahydrofuran (0.400 mL, 0.400 mmol) and acetic acid (0.100 mL, 1.73 mmol) were added and the reaction was allowed to stir at room temperature overnight. The reaction mixture was quenched with satd NH$_4$Cl and the aqueous layer was extracted with DCM (3×). The combined organic layers were evaporated onto silica gel and purified by flash chromatography (Isco, (4 gram HP)) eluting with 0% to 100% 2 M NH$_3$ in MeOH in DCM to give 70 mg of (1S,3'R,6'R,7'S,8'E,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a white crystalline solid. (ESI, +ve ion) m/z 728.3 (M+1)+.

Step 2: (1S,3'R,6'R,7'S,8'E,9a"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[8,16,18,24]tetraene-7',3"-[1,4]oxazino[3,4-c][1,4]oxazin]-15'-one 13',13'-dioxide To a room temperature solution of (1S,3'R,6'R,7'S,8'E,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide in tetrahydrofuran (0.3 mL) was added 60% sodium hydride in mineral oil (0.011 g, 0.275 mmol) as a solid. After 30 min the mixture was cooled (0° C.) and treated with 1-(p-toluenesulfonyl)imidazole (0.064 g, 0.288 mmol) and the reaction was allowed to warm to room temperature overnight. The reaction mixture was quenched with saturated NH₄Cl and the aqueous layer was extracted with EtOAc (3×). The combined organic layers were evaporated onto silica gel and purified by flash chromatography (Isco, (4 gram HP)) eluting with 2 M NH₃ in MeOH:CH₂Cl2 (0:1-1:9) to afford (1S,3'R,6'R,7'S,8'E,9a"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[8,16,18,24]tetraene-7',3"-[1,4]oxazino[3,4-c][1,4]oxazin]-15'-one 13',13'-dioxide (2.1 mg, 9%) as a tan crystalline solid. MS (ESI, +ve ion) m/z 710.3 (M+1)⁺.

Example 100

(1S,3'R,6'R,7'S,8'E,11'S,12'R)-6-chloro-7'-hydroxy-7'-(((3S)-3-(1H-imidazol-1-ylmethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

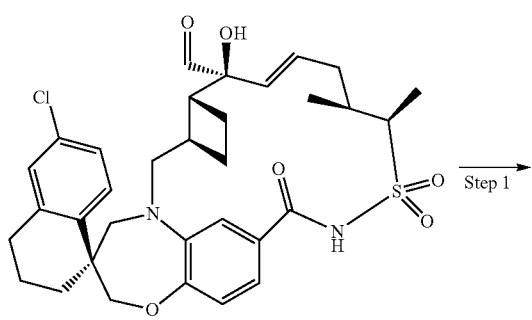

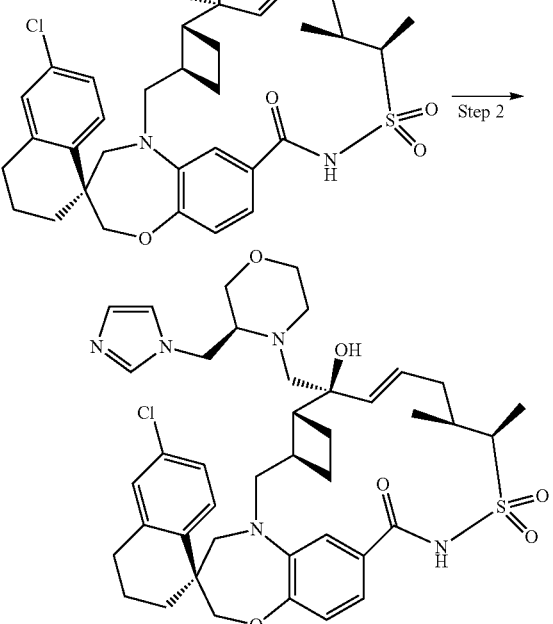

Example 100

Step 1: (1S,3'R,6'R,7'S,8'E,11'S,12'R)-6-chloro-7'-hydroxy-7'-(((3S)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a room temperature mixture of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.052 g, 0.083 mmol) and 3(S)-hydroxymethylmorpholine (0.099 g, 0.845 mmol; J&W Pharmlab, Levittown, Pa.) in tetrahydrofuran (2 mL) was added N,N-diisopropylethylamine (0.250 mL, 1.437 mmol). After 1 h, 1.0 M sodium cyanoborohydride in tetrahydrofuran (0.450 mL, 0.450 mmol) and acetic acid (0.100 mL, 1.73 mmol) were added and the reaction was stirred overnight. The reaction mixture was quenched with pH 7 buffer and the aqueous layer was extracted with DCM (3×). The combined organic layers were evaporated onto silica gel and purified by flash chromatography (Isco (4 g)) eluting with 25% EtOH/EtOAc:heptane (0:1-1:1) to give (1S,3'R,6'R,7'S,8'E,11'S,12'R)-6-chloro-7'-hydroxy-7'-(((3S)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19, 24~]pentacosa[8,16,18,24]tetraen]-15'-one 13',13'-dioxide (46 mg, 76%) as a white crystalline solid. (ESI, +ve ion) m/z 728.2 (M+1)$^+$.

Step 2: (1S,3'R,6'R,7'S,8'E,11'S,12'R)-6-chloro-7'-hydroxy-7'-(((3S)-3-(1H-imidazol-1-ylmethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~] pentacosa[8,16,18,24]tetraen]-15'-one 13',13'-dioxide To a room temperature solution of (1S,3'R,6'R,7'S,8'E,11'S,12'R)-6-chloro-7'-hydroxy-7'-(((3S)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide in tetrahydrofuran (1 mL) was added sodium hydride (0.020 g, 0.51 mmol) as a solid. After 30 min the reaction was cooled (0° C.) and treated with 1-(p-toluenesulfonyl)imidazole (0.112 g, 0.505 mmol). After stirring overnight the reaction mixture was quenched with pH 7 buffer and the aqueous layer was extracted with DCM (3×). The combined organic layers were evaporated onto silica gel and purified by flash chromatography (Isco (4 g)) eluting with 25% EtOH/EtOAc:heptane (0:1-1:0) to give (1S,3'R,6'R,7'S,8'E,11'S,12'R)-6-chloro-7'-hydroxy-7'-(((3S)-3-(1H-imidazol-1-ylmethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (27 mg, 55%) as a white crystalline solid. (ESI, +ve ion) m/z 778.3 (M+1)$^+$.

Example 105

(1S,3'R,6'R,7'S,8'E,11'S,12'R)-7'-ethoxy-7'-((9aS)-hexahydropyrazino[2,1-c][1,4]oxazin-8(1H)-ylmethyl)-11',12'-dimethyl-3,4-dihydro-2H,15'H-spiro [naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

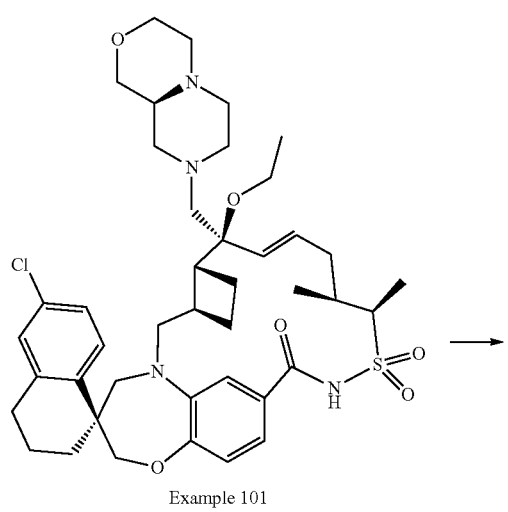

Example 101

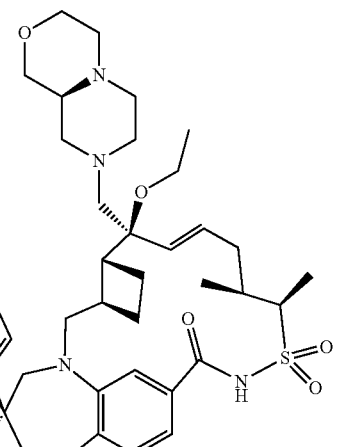

Example 105

A mixture of (1S,3'R,6'R,7'S,8'E,11'S,12'R)-6-chloro-7'-ethoxy-7'-((9aS)-hexahydropyrazino[2,1-c][1,4]oxazin-8(1H)-ylmethyl)-11',12'-dimethyl-3,4-dihydro-2H,15'H-spiro [naphthalene-1,22'-[20]oxa[13]thia[1,14]diazatetracyclo [14.7.2.0~3,6~.0~19,24~]pentacosa[8,16,18,24]tetraen]-15'-one 13',13'-dioxide (0.010 g, 0.013 mmol) and palladium, 10 wt. % (dry basis) on activated carbon, wet, degussa type (0.005 g, 2.3 μmol) in EtOAc (1 mL) was stirred at room temperature under hydrogen (18 psig) overnight. The reaction was filtered through a pad of Celite and the pad was washed with EtOAc. The filtrate was concentrated under reduced pressure, diluted with MeOH and purified by reverse-phase HPLC (Gilson; Gemini-NX C18 AXIA, 100×50 mm column) eluting with 0.1% TFA-H$_2$O: 0.1% TFA CH$_3$CN (9:1-1:9). The fractions containing the desired product were combined and partitioned between pH 7 buffer (1 M K$_2$HPO$_4$/KH$_2$PO$_4$)/EtOAc. The aqueous layer was extracted with EtOAc (3×) and the combined organic layers were washed with brine, dried over Na$_2$SO$_4$ and filtered. The filtrate was concentrated under reduced pressure to give (1S,3'R,6'R,7'S,8'E,11'S,12'R)-7'-ethoxy-7'-((9aS)-hexahydropyrazino[2,1-c][1,4]oxazin-8(1H)-ylmethyl)-11',12'-dimethyl-3,4-dihydro-2H,15'H-spiro [naphthalene-1,22'-[20]oxa[13]thia[1,14]diazatetracyclo [14.7.2.0~3,6~.0~19,24~]pentacosa[8,16,18,24]tetraen]-15'-one 13',13'-dioxide (6.5 mg, 68%) as a white crystalline solid. (ESI, +ve ion) m/z: 747.3 (M+1)$^+$.

Example 124

(1S,3'R,6'R,7'S,8'E,11'S,12'R)-6-chloro-4'',11',12'-trimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-[1,4]oxazinan]-15'-one 13',13'-dioxide

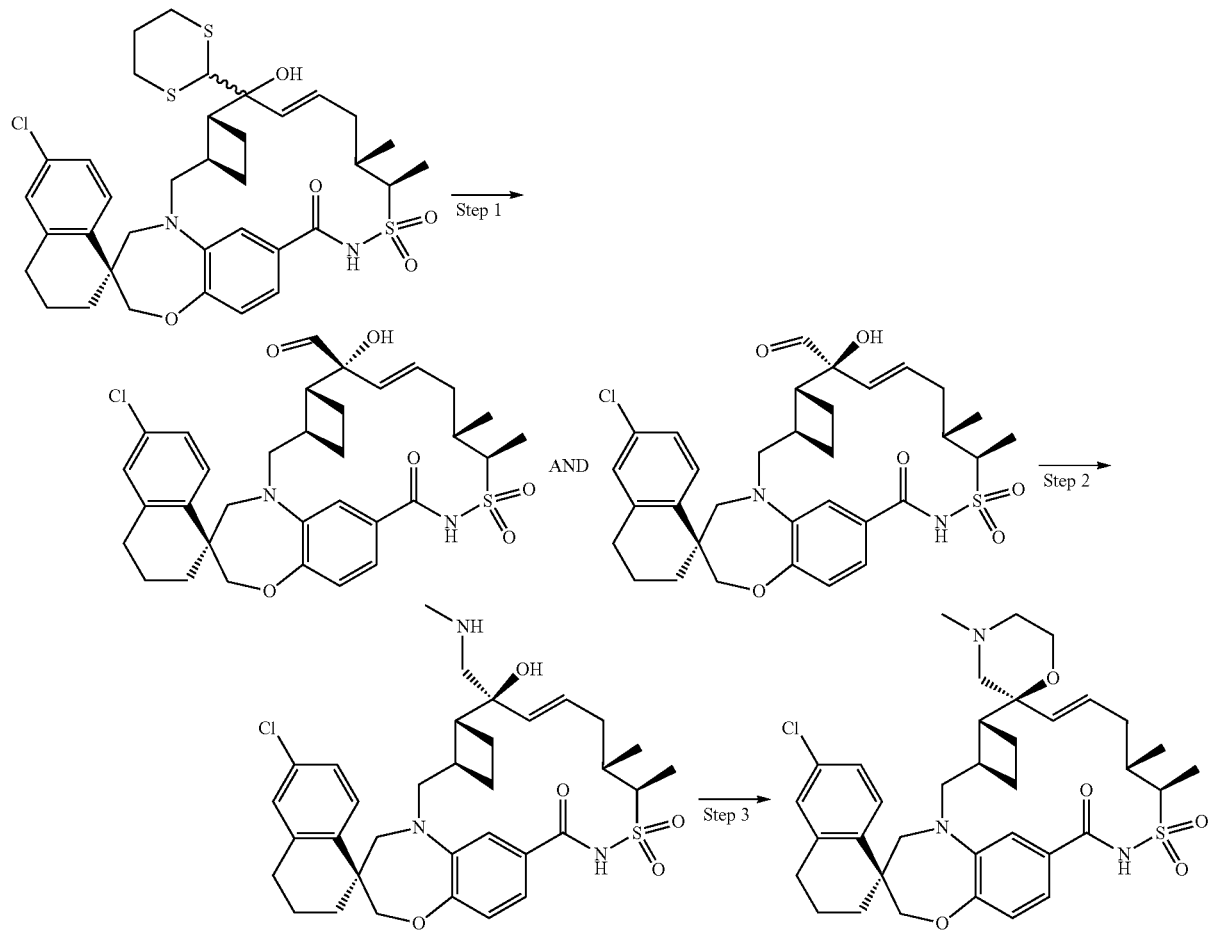

Example 124

Step 1: (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide and (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide Calcium carbonate (2.60 g, 18.5 mmol) and iodomethane (1 M in TBME; 18.5 mL, 37.1 mmol) were sequentially added to a solution of (1S,3'R,6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'S,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (2.66 g, 3.71 mmol) in acetonitrile (44 mL)/water (6.5 mL) at 50° C.; the reaction mixture was stirred at 50° C. for 16 h. The slurry was filtered to remove any excess calcium carbonate, and the filtrate was concentrated. The solid was diluted with EtOAc (150 mL); the milky mixture was poured off; the remaining solid was diluted with DCM/IPA (3:2, 200 mL), and the combined organics were partitioned with sat. aq. NH4Cl (100 mL). The organic layer was separated, solubilized with MeOH, dried over Na2SO4, filtered, and concentrated in vacuo. The crude product was adsorbed onto silica gel and was purified via automated flash chromatography (silica gel, 0% to 50% EtOAc/heptane w/0.3% AcOH) to give (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8, 16,18,24]tetraene]-7'-carbaldehyde 13',13'-dioxide (396 mg, 0.631 mmol, 17% yield) and (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (0.810, 1.29 mmol, 35% yield), both as white solids. MS (ESI, +ve) m/z 627.2 (M+1)+ for both.

Step 2: (1S,3'R,6'R,7'S,8'E,11'S,12'R)-6-chloro-7'-hydroxy-11',12'-dimethyl-7'-((methylamino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A mixture of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (48 mg, 0.077 mmol), methanamine hydrochloride (91 mg, 1.3 mmol), and DIPEA (227 µL, 1.30 mmol) in DCM (383 µL)/MeOH (580 µL) was stirred at room temperature for 15 min; sodium cyanotrihydroborate (14 mg, 0.23 mmol) was then added. The slurry was stirred at room temperature for 30 min. The reaction mixture was diluted with DCM (50 mL), added to a separatory funnel, and washed with water (50 mL); the organic layer was separated, dried over anhydrous Na$_2$SO$_4$, and concentrated in vacuo. The crude product was adsorbed onto silica gel and was purified via automated flash chromatography (silica gel, 0% to 20% MeOH/DCM) to give (1S,3'R,6'R,7'S,8'E,11'S,12'R)-6-chloro-7'-hydroxy-11',12'-dimethyl-7'-((methylamino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (14 mg, 0.022 mmol, 29% yield) as a white film. MS (ESI, +ve) m/z 642.2 (M+1)+.

Step 3: (1S,3'R,6'R,7'S,8'E,11'S,12'R)-6-chloro-4'',11',12'-trimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-[1,4]oxazinan]-15'-one 13',13'-dioxide Cesium carbonate (85 mg, 0.26 mmol) was added to a solution of (1S,3'R,6'R,7'S,8'E,11'S,12'R)-6-chloro-7'-hydroxy-11',12'-dimethyl-7'-((methylamino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (14 mg, 0.022 mmol) and 1,2-dibromoethane (8 µL, 0.09 mmol) in DMF (0.22 mL) at ambient temperature. The reaction mixture was stirred at 70° C. for 16 h. 1-Tosyl-1H-imidazole (4.8 mg, 0.022 mmol) and sodium hydride (60% in mineral oil; 0.5 mg, 0.02 mmol) were added to the reaction mixture which was then stirred at ambient temperature for 20 min. The reaction mixture was diluted with EtOAc (50 mL), added to a separatory funnel, and washed with saturated, aqueous sodium bicarbonate (2×50 mL); the organic layer was separated, dried over anhydrous Na$_2$SO$_4$, and concentrated in vacuo. The crude product was adsorbed onto silica gel and was purified via automated flash chromatography (silica gel, 0% to 10% MeOH/DCM) to give (1S,3'R,6'R,7'S,8'E,11'S,12'R)-6-chloro-4'',11',12'-trimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-[1,4]oxazinan]-15'-one 13',13'-dioxide (2 mg, 3 µmol, 14% yield) as a light yellow oil. MS (ESI, +ve) m/z 668.3 (M+1)+.

Example 125

(1S,3'R,6'R,7'S,8'E,11'S,12'R)-7'-((tert-butylamino)methyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

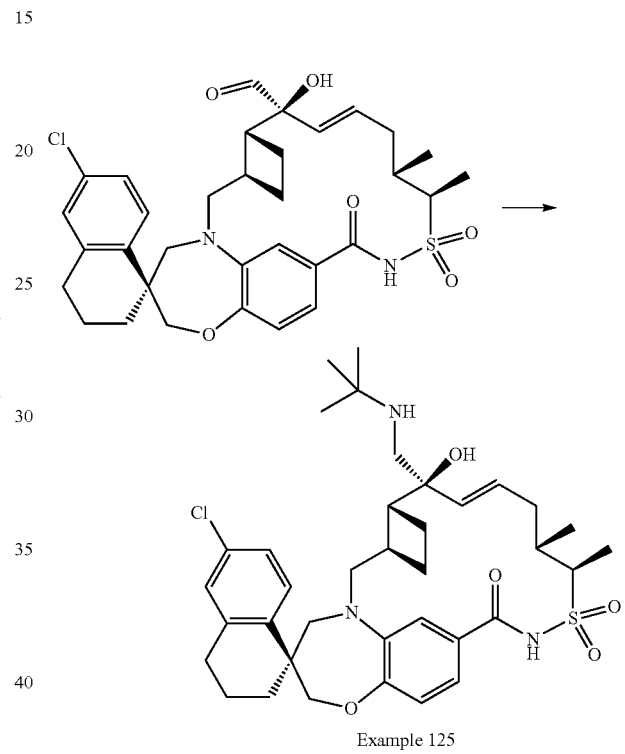

Example 125

A solution of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (99 mg, 0.16 mmol) and 2-methylpropan-2-amine (115 mg, 1.58 mmol) in THF (1.6 mL) was stirred at ambient temperature for 1.5 h; sodium cyanotrihydroborate (50 mg, 0.79 mmol) and acetic acid (181 µL, 3.16 mmol) were added, and the reaction mixture was stirred at ambient temperature for 1 h. The reaction mixture was diluted with EtOAc (75 mL), added to a separatory funnel, and washed with saturated, aqueous sodium bicarbonate (100 mL); the organic layer was separated, dried over anhydrous Na$_2$SO$_4$, and concentrated in vacuo. The crude product was adsorbed onto silica gel and was purified via automated flash chromatography (silica gel, 0% to 10% MeOH/DCM) to give (1S,3'R,6'R,7'S,8'E,11'S,12'R)-7'-((tert-butylamino)methyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (53 mg, 0.077 mmol, 49% yield) as a white solid. MS (ESI, +ve) m/z 684.3 (M+1)+.

Example 126

(1S,3'R,6'R,7'S,8'E,11'S,12'R)-6-chloro-7'-hydroxy-7'-(((2-hydroxyethyl)(1-methylethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

Example 127

(1S,3'R,6'R,7'S,8'E,11'S,12'R)-6-chloro-11',12'-dimethyl-4''-(1-methylethyl)-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-[1,4]oxazinan]-15'-one 13',13'-dioxide

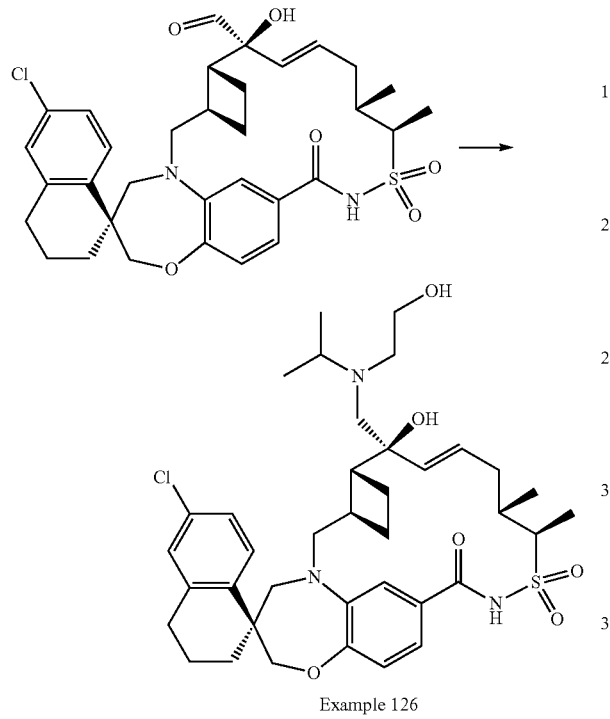

Example 126

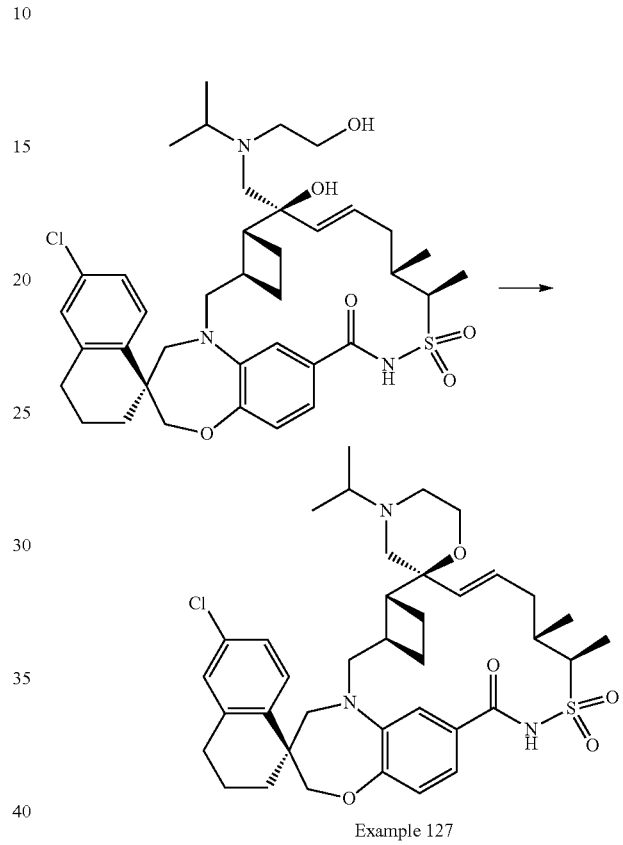

Example 127

A solution of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (68 mg, 0.11 mmol) and 2-(isopropylamino)ethanol (Enamine, Monmouth Jct, N.J.; 112 mg, 1.08 mmol) in THF (1.1 mL) was stirred at ambient temperature for 2.5 h; sodium cyanotrihydroborate (34 mg, 0.54 mmol) and acetic acid (0.1 mL, 2.2 mmol) were added, and the reaction mixture was stirred at ambient temperature for 1 h. The reaction mixture was diluted with EtOAc (75 mL), added to a separatory funnel, and washed with saturated, aqueous sodium bicarbonate (100 mL); the organic layer was separated, dried over anhydrous $Na_2SO_4$, and concentrated in vacuo. The crude product was adsorbed onto silica gel and was purified via automated flash chromatography (silica gel, 0% to 8% MeOH/DCM) to give (1S,3'R,6'R,7'S,8'E,11'S,12'R)-6-chloro-7'-hydroxy-7'-(((2-hydroxyethyl)(1-methylethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (20 mg, 0.028 mmol, 26% yield) as a white solid. MS (ESI, +ve) m/z 714.2 $(M+1)^+$.

Sodium hydride (60% in mineral oil; 3 mg, 0.07 mmol) was added to a solution of (1S,3'R,6'R,7'S,8'E,11'S,12'R)-6-chloro-7'-hydroxy-7'-(((2-hydroxyethyl)(1-methylethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (17 mg, 0.024 mmol) and 1-tosyl-1H-imidazole (6.9 mg, 0.031 mmol) in THF (0.24 mL) at 0° C.; the reaction mixture was stirred at 0° C. for 15 min. The reaction mixture was diluted with EtOAc (75 mL), added to a separatory funnel, and washed with saturated, aqueous ammonium chloride (100 mL); the organic layer was separated, dried over anhydrous $Na_2SO_4$, and concentrated in vacuo. A solution of the crude product in DCM was loaded onto the column and was purified via automated flash chromatography (silica gel, 0% to 6% MeOH/DCM) to give (1S,3'R,6'R,7'S,8'E,11'S,12'R)-6-chloro-11',12'-dimethyl-4''-(1-methylethyl)-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2''-[1,4]oxazinan]-15'-one 13',13'-dioxide (6 mg, 9 μmol, 36% yield) as a white solid. MS (ESI, +ve) m/z: 696.3 $(M+1)^+$.

Example 128
(1S,3'R,6'R,7'R,8'E,11'S,12'R)-6-chloro-11',12'-dimethyl-3,4-dihydro-2H,2"H,15'H-dispiro[naphthalene-1,22'-[20]oxa[13]thia[1,14]diazatetracyclo[14.7.2.0~3,6~.0~19,24~]pentacosa[8,16,18,24]tetraene-7',5"-[1,3]oxazolidine]-2",15'-dione 13',13'-dioxide OR (1S,3'R,6'R,7'S,8'E,11'S,12'R)-6-chloro-11',12'-dimethyl-3,4-dihydro-2H,2"H,15'H-dispiro[naphthalene-1,22'-[20]oxa[13]thia[1,14]diazatetracyclo[14.7.2.0~3,6~.0~19,24~]pentacosa[8,16,18,24]tetraene-7',5"-[1,3]oxazolidine]-2",15'-dione 13',13'-dioxide
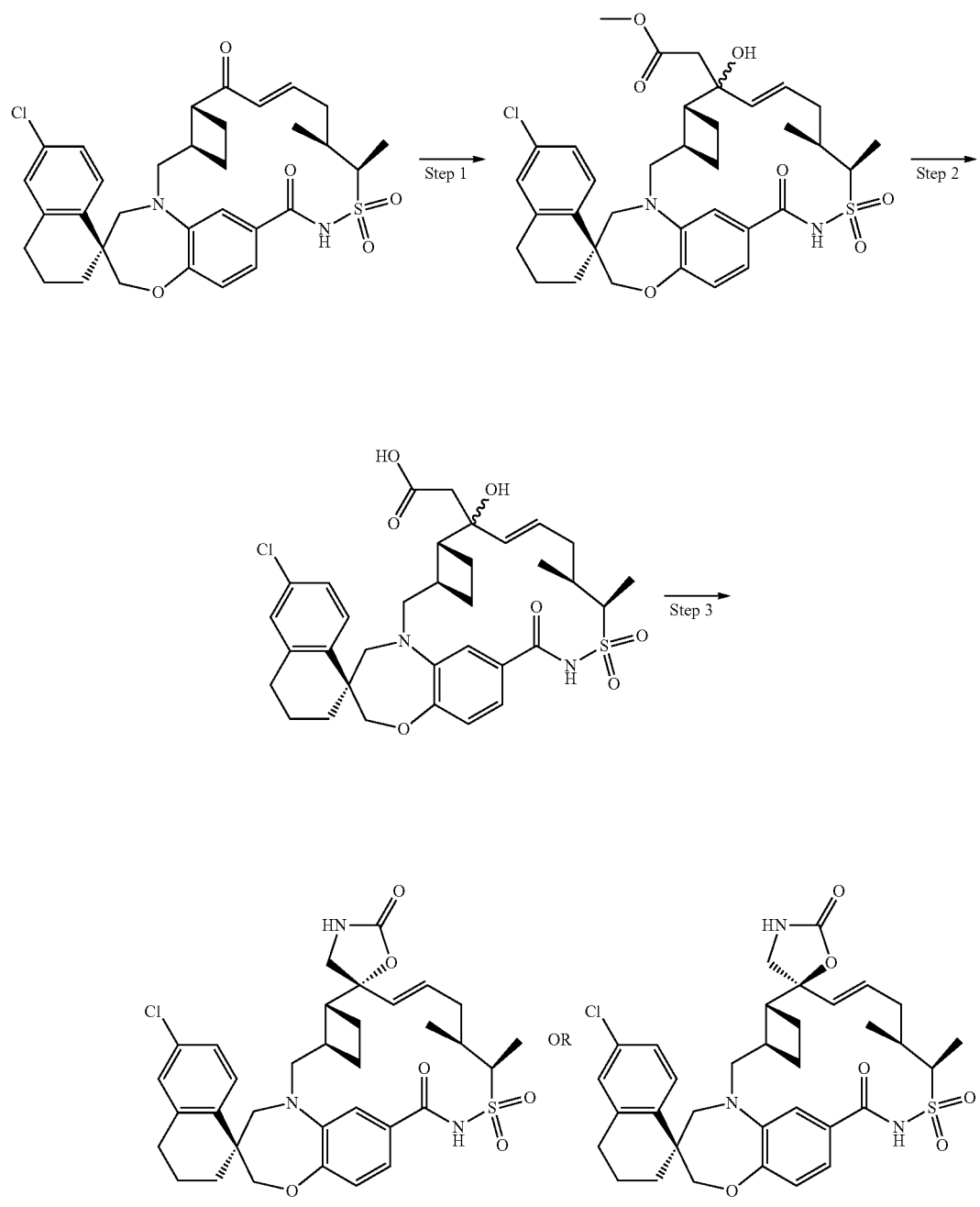
Example 128

Step 1: methyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate and methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate A solution of methyl acetate (0.172 mL, 2.17 mmol) in THF (1 mL) was added dropwise to a stirred solution of lithium diisopropylamide (1.0 M solution in hexanes/tetrahydrofuran, 2.17 mL, 2.17 mmol) in THF (1 mL) at −78° C. The mixture was stirred at −78° C. for 0.5 h before a solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (216 mg, 0.362 mmol) in THF (2 mL) was added slowly via syringe. The reaction mixture was stirred at −78° C. for 1.5 h before being allowed to warm to room temperature and quenched with water (15 mL). The mixture was extracted with EtOAc (25 mL). The organic layer was separated, washed with 1 M aqueous HCl (15 mL), washed with brine (15 mL), dried over MgSO$_4$, filtered, and concentrated in vacuo to give a crude mixture of methyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate and methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate (246 mg, 0.366 mmol, 101% yield) as a yellow solid that was used directly in the next step. MS (ESI, +ve ion) m/z 671.3 (M+H)$^+$.

Step 2: ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid and ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid Lithium hydroxide (2.0 M aqueous, 0.453 mL, 0.905 mmol) was added to a stirred solution of methyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate and methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate (243 mg, 0.362 mmol) in tetrahydrofuran (7 mL). The reaction mixture was stirred at room temperature for 16 h. The reaction mixture was quenched with saturated aqueous NH$_4$Cl (30 mL) and extracted three times with EtOAc (50 mL). The combined organic layers were washed with brine (50 mL), dried over MgSO$_4$, filtered, and concentrated in vacuo. Chromatographic purification of the residue (silica gel, 0% to 100% EtOAc with 0.3% AcOH as a modifier in heptane) gave the desired product contaminated with AcOH. The isolated product was azeotroped with toluene to give a mixture of ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid and ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (66 mg, 0.100 mmol, 27.7% yield) as a white solid. MS (ESI, +ve ion) m/z 657.2 (M+H)$^+$.

Step 3: (1S,3'R,6'R,7'R,8'E,11'S,12'R)-6-chloro-11',12'-dimethyl-3,4-dihydro-2H,2''H,15'H-dispiro[naphthalene-1,22'-[20]oxa[13]thia[1,14]diazatetracyclo[14.7.2.0~3,6~.0~19,24~]pentacosa[8,16,18,24]tetraene-7',5''-[1,3]oxazolidine]-2'',15'-dione 13',13'-dioxide or (1S,3'R,6'R,7'S,8'E,11'S,12'R)-6-chloro-11',12'-dimethyl-3,4-dihydro-2H,2''H,15'H-dispiro[naphthalene-1,22'-[20]oxa[13]thia[1,14]diazatetracyclo[14.7.2.0~3,6~.0~19,24~]pentacosa[8,16,18,24]tetraene-7',5''-[1,3]oxazolidine]-2'',15'-dione 13',13'-dioxide A mixture of ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid and ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (66 mg, 0.100 mmol), triethylamine (0.031 mL, 0.221 mmol), and diphenylphosphoryl azide (0.024 mL, 0.110 mmol) in tert-butanol (2 mL) was refluxed for 2.5 h. The reaction mixture was concentrated in vacuo. Chromatographic purification of the residue (silica gel, 0% to 100% EtOAc with 0.3% AcOH as a modifier in heptane) provided (1S,3'R,6'R,7'R,8'E,11'S,12'R)-6-chloro-11',12'-dimethyl-3,4-dihydro-2H,2''H,15'H-dispiro[naphthalene-1,22'-[20]oxa[13]thia[1,14]diazatetracyclo[14.7.2.0~3,6~.0~19,24~]pentacosa[8,16,18,24]tetraene-7',5''-[1,3]oxazolidine]-2'',15'-dione 13',13'-dioxide or (1S,3'R,6'R,7'S,8'E,11'S,12'R)-6-chloro-11',12'-dimethyl-3,4-dihydro-2H,2''H,15'H-dispiro[naphthalene-1,22'-[20]oxa[13]thia[1,14]diazatetracyclo[14.7.2.0~3,6~.0~19,24~]pentacosa[8,16,18,24]tetraene-7',5''-[1,3]oxazolidine]-2'',15'-dione 13',13'-dioxide (30 mg, 0.046 mmol, 45.7% yield) as a white solid. MS (ESI, +ve ion) m/z 654.2 (M+H)$^+$.

Example 138

(1S,3'R,6'R,7'R,8'E,11'S,12'R)-4"-benzyl-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2"-[1,4]oxazinan]-15'-one 13',13'-dioxide

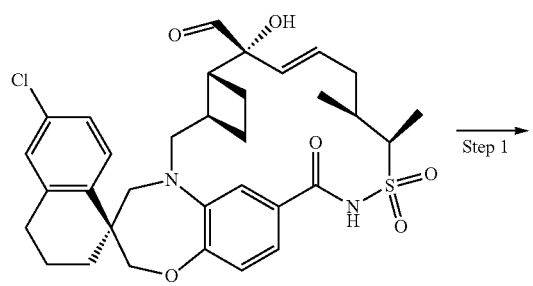

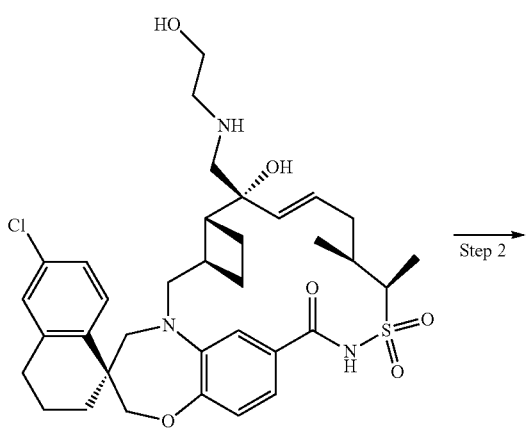

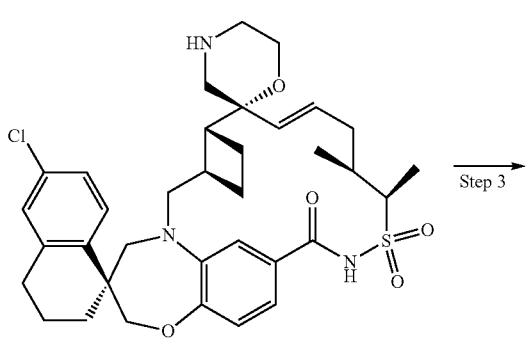

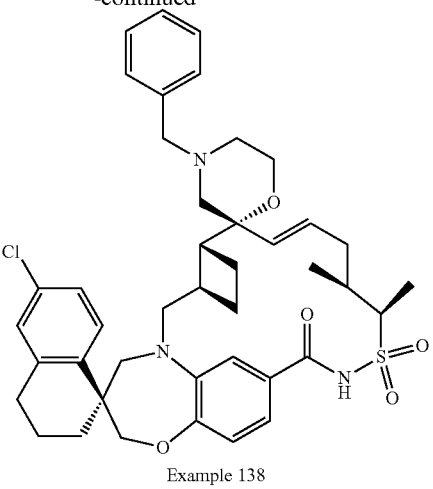

Example 138

Step 1: (1S,3'R,6'R,7'R,8'E,11'S,12'R)-6-chloro-7'-hydroxy-7'-(((2-hydroxyethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A mixture of (1S,3'R,6'R,7'R,8'E,11'S,12'R)-6-chloro-7'-hydroxy-11',12'-dimethyl-5'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (199 mg, 0.317 mmol) and 2-aminoethanol (322 mg, 5.27 mmol) was stirred in dichloromethane (6 mL) for 20 min before acetic acid (0.366 mL, 6.35 mmol) and sodium cyanoborohydride (59.8 mg, 0.952 mmol) were added. The reaction mixture was stirred at room temperature for 17 h. The reaction mixture was quenched with saturated aqueous NH$_4$Cl (40 mL) and extracted with EtOAc (50 mL). The organic layer was separated, washed with brine (30 mL), dried over MgSO$_4$, filtered, and concentrated in vacuo. Chromatographic purification of the residue (silica gel, 0% to 10% 2 M ammonia in MeOH in DCM) provided (1S,3'R,6'R,7'R,8'E,11'S,12'R)-6-chloro-7'-hydroxy-7'-(((2-hydroxyethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (115 mg, 0.171 mmol, 53.9% yield) as a white solid. MS (ESI, +ve ion) m/z 672.2 (M+H)$^+$.

Step 2: (1S,3'R,6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7',2"-[1,4]oxazinan]-15'-one 13',13'-dioxide Sodium hydride (60% dispersion in mineral oil, 20.5 mg, 0.513 mmol) was added to a stirred suspension of (1S,3'R,6'R,7'R,8'E,11'S,12'R)-6-chloro-7'-hydroxy-7'-(((2-hydroxyethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (115 mg, 0.171 mmol) in tetrahydrofuran (5 mL) at room temperature. The mixture was stirred for 20 min before being cooled to 0° C., followed by addition of 1-(p-toluenesulfonyl)imidazole (38.0 mg, 0.171 mmol). The reaction mixture was stirred at 0° C. for 5 h. The reaction mixture was quenched with saturated aqueous NH₄Cl (20 mL) and extracted with EtOAc (30 mL). The organic layer was separated, washed with brine (20 mL), dried over MgSO₄, filtered, and concentrated in vacuo. Chromatographic purification of the residue (silica gel, 0% to 10% 2 M ammonia in MeOH in DCM) provided (1S,3'R, 6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[8, 16,18,24]tetraene-7',2'-[1,4]oxazinan]-15'-one 13',13'-dioxide (67 mg, 0.102 mmol, 60% yield) as a white solid. MS (ESI, +ve ion) m/z 654.2 (M+H)⁺.

Step 3: (1S,3'R,6'R,7'R,8'E,11'S,12'R)-4''-benzyl-6-chloro-11',12'-dimethyl-3,4-dihydro-2H,15'H-dispiro [naphthalene-1,22'-[20]oxa[13]thia[1,14]diazatetracyclo[14.7.2.0~3,6~.0~19,24~]pentacosa[8,16,18, 24]tetraene-7',2''-[1,4]oxazinan]-15'-one 13',13'-dioxide (1S,3'R,6'R,7'R,8'E,11'S,12'R)-6-Chloro-11',12'-dimethyl-3,4-dihydro-2H,15'H-dispiro[naphthalene-1,22'-[20] oxa[13]thia[1,14]diazatetracyclo[14.7.2.0~3,6~.0~19,24~] pentacosa[8,16,18,24]tetraene-7',2''-[1,4]oxazinan]-15'-one 13',13'-dioxide (17 mg, 0.026 mmol), (bromomethyl)benzene (3.40 µl, 0.029 mmol), and triethylamine (7.95 µl, 0.057 mmol) were mixed in acetonitrile (0.25 mL). The reaction mixture was stirred at room temperature for 2 h. The reaction mixture was quenched with saturated aqueous NH₄Cl (10 mL) and extracted with EtOAc (15 mL). The organic layer was separated, washed with brine (10 mL), dried over MgSO₄, filtered, and concentrated in vacuo. Chromatographic purification of the residue (silica gel, 0 to 10% 2 M ammonia in MeOH in DCM) provided (1S,3'R, 6'R,7'R,8'E,11'S,12'R)-4''-benzyl-6-chloro-11',12'-dimethyl-3,4-dihydro-2H,15'H-dispiro[naphthalene-1,22'-[20]oxa [13]thia[1,14]diazatetracyclo[14.7.2.0~3,6~.0~19,24~] pentacosa[8,16,18,24]tetraene-7',2''-[1,4]oxazinan]-15'-one 13',13'-dioxide (9 mg, 0.012 mmol, 47% yield) as a white solid. MS (ESI, +ve ion) m/z 744.3 (M+H)⁺.

Example 151

(1S,3'R,6'R,7'S,8'E,11'S,12'R)-6-chloro-7'-(2-methoxyethoxy)-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa [13]thia[1,14]diazatetracyclo[14.7.2.0~3,6~.0~19, 24~]pentacosa[8,16,18,24]tetraen]-15'-one 13',13'-dioxide

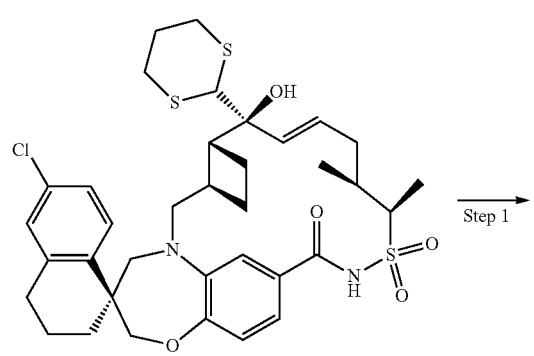

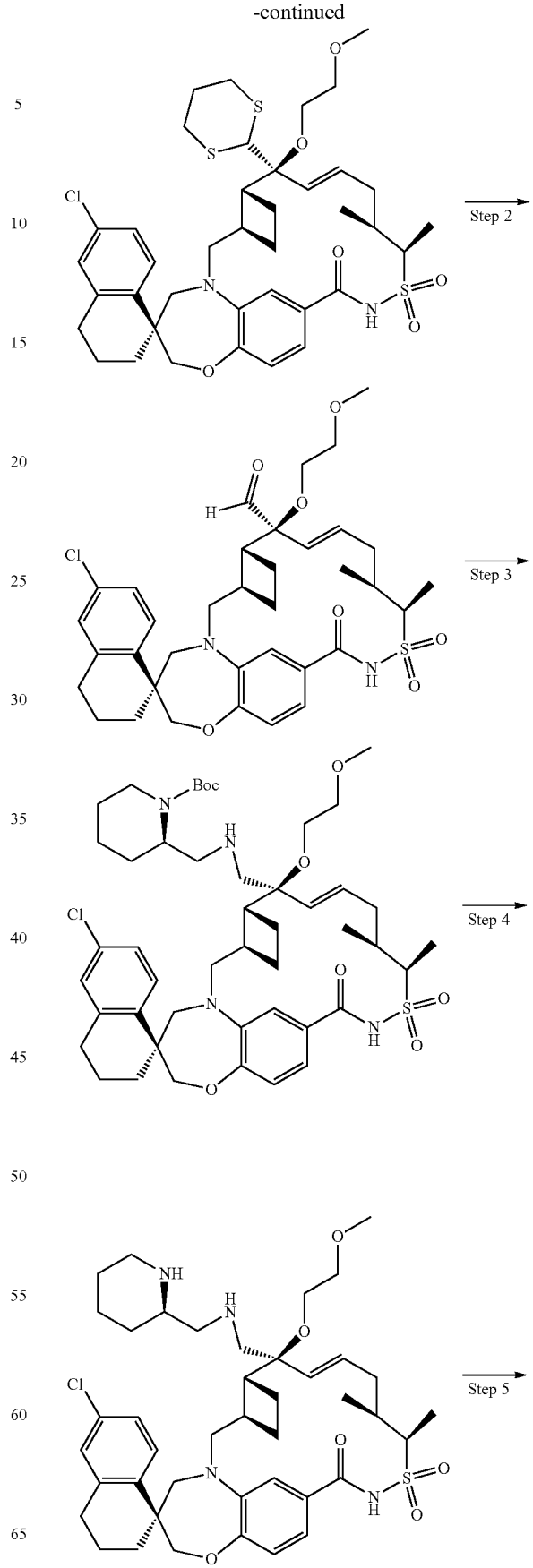

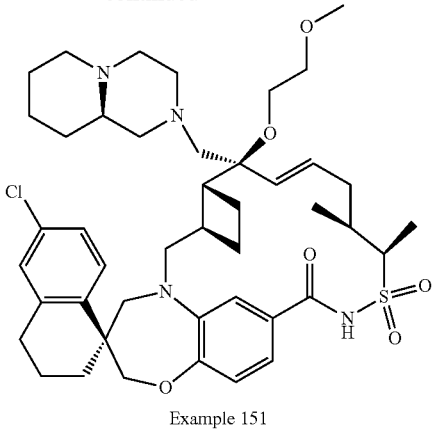

Example 151

Step 1: (1S,3'R,6'R,7'S,8E,11'S,12'R)-6-chloro-7'-(1,3-dithian-2-yl)-7'-(2-methoxyethoxy)-11',12'-dimethyl-3,4-dihydro-2H,15'H-spiro[naphthalene-[20]oxa[13]thia[1,14]diazatetracyclo[14.7.2.0~3,6~.0~19,24~]pentacosa[8,16,18,24]tetraen]-15'-one 13',13'-dioxide To a solution of (1S,3'R,6'R,7'S,8E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (460 mg, 0.641 mmol) in tetrahydrofuran (8 mL) was added sodium hydride, 60% dispersion in mineral oil (679 mg, 19.24 mmol) in portions. After addition, the mixture was then stirred at room temperature under nitrogen for 10 min, then 2-bromoethyl methyl ether (1.809 mL, 19.24 mmol) was added. The resulting mixture was stirred at room temperature for 14 h. The mixture was quenched with saturated NH$_4$Cl (150 mL) and was extracted with EtOAc (2×200 mL). The combined organic extracts were dried over MgSO$_4$ and concentrated in vacuo. Chromatographic purification of the residue (silica gel, 0% to 100% EtOAc/heptane) provided (1S,3'R,6'R,7'S,8'E,11'S,12'R)-6-chloro-7'-(1,3-dithian-2-yl)-7'-(2-methoxyethoxy)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (391 mg, 0.504 mmol, 79% yield) as a light yellow solid. MS (ESI, +ve ion) m/z 699.2, 755.3 (M+H)$^+$.

Step 2: (1S,3'R,6'R,7'S,8'E,11'S,12'R)-6-chloro-7'-(2-methoxyethoxy)-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide A solution of (1S,3'R,6'R,7'S,8'E,11'S,12'R)-6-chloro-7'-(1,3-dithian-2-yl)-7'-(2-methoxyethoxy)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (391 mg, 0.504 mmol) in acetonitrile (10 mL) and water (2.500 mL) was added methyl iodide (0.313 mL, 5.04 mmol) and calcium carbonate (252 mg, 2.52 mmol). The resulting mixture was then stirred at 50° C. for 14 h. The mixture was quenched with saturated NH$_4$Cl and was extracted with EtOAc (2×100 mL). The combined organic extracts were then dried over MgSO$_4$ and concentrated in vacuo. Chromatographic purification of the residue (silica gel, 0% to 100% EtOAc/heptane) provided (1S,3'R,6'R,7'S,8'E,11'S,12'R)-6-chloro-7'-(2-methoxyethoxy)-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (233 mg, 0.340 mmol, 67.4% yield) as a light yellow solid. MS (ESI, +ve ion) m/z 685.3 (M+H)$^+$.

Step 3: 2-methyl-2-propanyl (2R)-2-(((((1S,3'R,6'R,7'S,8'E,11'S,12'R)-6-chloro-7'-(2-methoxyethoxy)-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)amino)methyl)-1-piperidinecarboxylate A solution of (1S,3'R,6'R,7'S,8'E,11'S,12'R)-6-chloro-7'-(2-methoxyethoxy)-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (55 mg, 0.080 mmol) and (R)-tert-butyl 2-(aminomethyl)piperidine-1-carboxylate (172 mg, 0.803 mmol) in 1,2-dichloroethane (0.8 mL) was stirred at room temperature for 14 h. Sodium triacetoxyborohydride (0.059 mL, 0.401 mmol) was added to the mixture and the mixture was then stirred at room temperature for 1 h. The mixture was diluted with MeOH (5 mL) and silica gel was added. The mixture was concentrated and dried in vacuo. The solid mixture was then purified by silica gel column chromatography (solid loading, 0% to 100% EtOAc/heptane) provided 2-methyl-2-propanyl (2R)-2-(((((1S,3'R,6'R,7'S,8'E,11'S,12'R)-6-chloro-7'-(2-methoxyethoxy)-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)amino)methyl)-1-piperidinecarboxylate (64 mg, 0.072 mmol, 90% yield) as a light yellow solid. MS (ESI, +ve ion) m/z 883.5 (M+H)$^+$.

Step 4: (1S,3'R,6'R,7'S,8'E,11'S,12'R)-6-chloro-7'-(2-methoxyethoxy)-11',12'-dimethyl-7'-((((2R)-2-piperidinylmethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a solution of 2-methyl-2-propanyl (2R)-2-(((((1S,3'R,6'R,7'S,8'E,11'S,12'R)-6-chloro-7'-(2-methoxyethoxy)-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)amino)methyl)-1-piperidinecarboxylate (58 mg, 0.066 mmol) in dichloromethane (0.5 mL) was added trifluoroacetic acid (0.098 mL, 1.3 mmol). The resulting mixture was then stirred at room temperature for 2 h. The mixture was cooled to 0° C. and iPr$_2$Net (0.457 mL, 2.63 mmol) was added followed by 1,2-dibromoethane (0.023 mL, 0.263 mmol) and DMA (0.1 mL). The resulting mixture was then stirred at room temperature for 72 h and at 50° C. for 1 h. The mixture was concentrated in vacuo and chromatographic purification of the residue (silica gel, 0% to 100% EtOAc/heptane) provided (1S,3'R,6'R,7'S,8'E,11'S,12'R)-6-chloro-7'-(2-methoxyethoxy)-11',12'-dimethyl-7'-

(((((2R)-2-piperidinylmethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a colorless oil, which was used in the next step. MS (ESI, +ve ion) m/z 783.3 (M+H)⁺.

Step 5: (1S,3'R,6'R,7'S,8'E,11'S,12'R)-6-chloro-7'-(2-methoxyethoxy)-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a solution of (1S,3'R,6'R,7'S,8'E,11'S,12'R)-6-chloro-7'-(2-methoxyethoxy)-11',12'-dimethyl-7'-((((2R)-2-piperidinylmethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (51.4 mg, 0.066 mmol) in N,N-dimethylacetamide (0.4 mL) was added iPr₂Net (0.057 mL, 0.328 mmol) and 1,2-dibromoethane (0.028 mL, 0.328 mmol). The resulting mixture was then stirred at room temperature for 14 h. Then, 1,2-dibromoethane (0.2 mL) was added and the mixture was stirred at room temperature for 14 h then at 55° C. for 72 h. The mixture was purified by silica gel column chromatography (0% to 10% MeOH/DCM) provided (1S,3'R,6'R,7'S,8'E,11'S,12'R)-6-chloro-7'-(2-methoxyethoxy)-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (17 mg, 0.021 mmol, 32.0% yield) as a light yellow solid. MS (ESI, +ve ion) m/z 809.2 (M+H)⁺.

Example 154

(1S,3'R,6'R,7'R,8'E,11'S,12'R)-6-chloro-7'-methoxy-11',12'-dimethyl-7'-(((9aR)-3-oxooctahydro-2H-pyrido[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

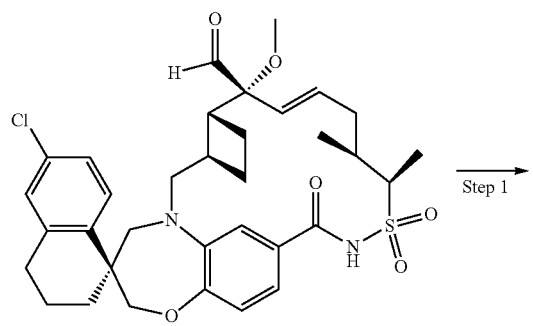

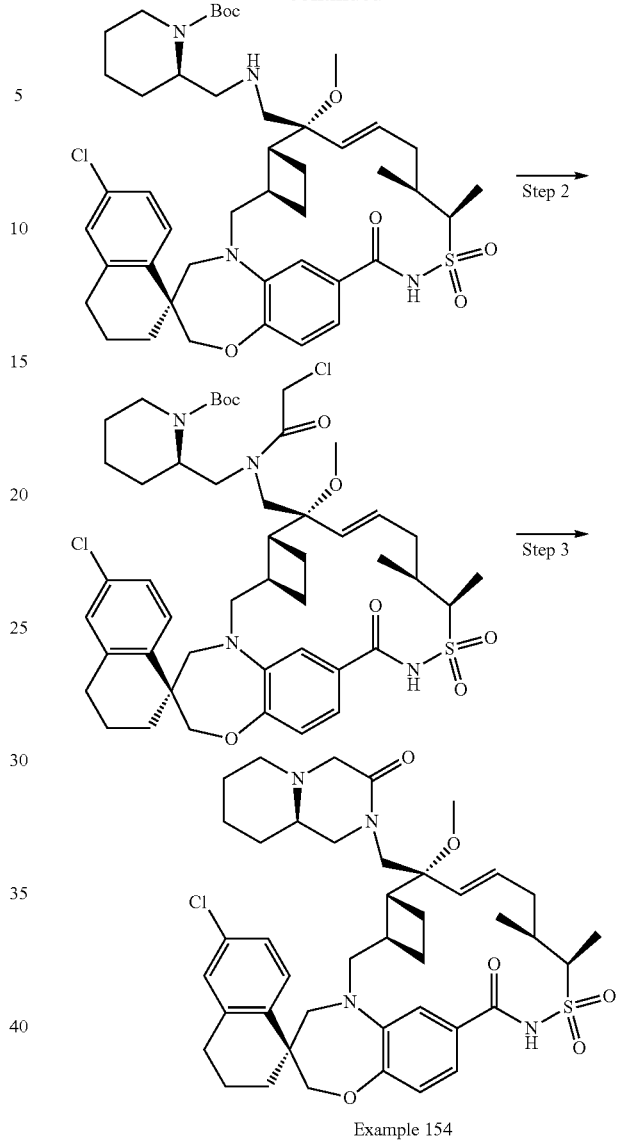

Example 154

Step 1: 2-methyl-2-propanyl (2R)-2-(((((1S,3'R,6'R,7'R,8E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)amino)methyl)-1-piperidinecarboxylate To a solution of (1S,3'R,6'R,7'R,8'E,11'S,12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (44 mg, 0.069 mmol) in 1,2-dichloroethane (1 mL) was added (R)-tert-butyl 2-(aminomethyl)piperidine-1-carboxylate (147 mg, 0.686 mmol). The resulting mixture was then stirred at room temperature for 1 h. Then, sodium triacetoxyborohydride (73 mg, 0.343 mmol) was added in portions. After addition, the mixture was then stirred at room temperature for 3 d. The mixture was purified by silica gel column chromatography (0% to 20% MeOH/DCM) to provide 2-methyl-2-propanyl (2R)-2-(((((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)amino)methyl)-1-piperidinecarboxylate (57.6 mg, 0.069 mmol, 100% yield) as a light yellow solid, which was used in the next step. MS (ESI, +ve ion) m/z 839.4 (M+H)+.

Step 2: 2-methyl-2-propanyl (2R)-2-(((chloroacetyl) (((1S,3'R,6'R,7'R,8'E,11'S,12'R)-6-chloro-7'-methoxy-11',12'-dimethyl-13',13'-dioxido-15'-oxo-3, 4-dihydro-2H-spiro[naphthalene-1,22'-[20]oxa[13] thia[1,14]diazatetracyclo[14.7.2.0~3,6~.0~19,24~] pentacosa[8,16,18,24]tetraen]-7'-yl)methyl)amino) methyl)-1-piperidinecarboxylate To a solution of 2-methyl-2-propanyl (2R)-2-(((((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo [14.7.2.0~3,6~.0~19,24~]pentacosa[8,16,18,24]tetraen]-7'-yl)methyl)amino)methyl)-1-piperidinecarboxylate (57.6 mg, 0.069 mmol) in dichloromethane (1.5 mL) at −78° C. under nitrogen was added chloroacetyl chloride (10.92 µL, 0.137 mmol) followed by iPr2Net (0.036 mL, 0.206 mmol). After addition, the mixture was then stirred at −78° C. for 1.5 h. Chloroacetyl chloride (0.022 mL) was added and the mixture was stirred at −25° C. for 1 h and placed in a −20° C. freezer for 16 h. The mixture was quenched with MeOH (2 mL) and concentrated in vacuo. Chromatographic purification (silica gel, 0% to 100% EtOAc/heptane) provided 2-methyl-2-propanyl (2R)-2-(((chloroacetyl)(((1S,3'R,6'R, 7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3, 6~.0~19,24~]pentacosa[8,16,18,24]tetraen]-7'-yl)methyl) amino)methyl)-1-piperidinecarboxylate (62.8 mg, 0.069 mmol, 100% yield) as a light yellow solid. MS (ESI, +ve ion) m/z 937.3, 939.2 (M+Na)+.

Step 3: (1S,3'R,6'R,7'R,8'E,11'S,12'R)-6-chloro-7'-methoxy-11',12'-dimethyl-7'-(((9aR)-3-oxooctahydro-2H-pyrido[1,2-a]pyrazin-2-yl)methyl)-3,4-dihydro-2H,15'H-spiro[naphthalene-1,22'-[20]oxa [13]thia[1,14]diazatetracyclo[14.7.2.0~3,6~.0~19, 24~]pentacosa[8,16,18,24]tetraen]-15'-one 13',13'-dioxide To a solution of 2-methyl-2-propanyl (2R)-2-(((chloroacetyl)(((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14] diazatetracyclo[14.7.2.0~3,6~.0~19,24~]pentacosa[8,16,18, 24]tetraen]-7'-yl)methyl)amino)methyl)-1-piperidinecarboxylate (61.8 mg, 0.067 mmol) in dichloromethane (1 mL) was added trifluoroacetic acid (0.251 mL, 3.37 mmol). After addition, the mixture was then stirred at room temperature for 17 min. The mixture was cooled to −78° C. and iPrNEt (0.704 mL, 4.05 mmol) was added dropwise. After addition, the mixture was stirred at room temperature for 14 h. The mixture was purified by silica gel column chromatography (0% to 20% MeOH/DCM) followed by preparative HPLC (Phenomenex Gemini C18 column, 150×30 mm, 10% to 100% 0.1% TFA in MeCN/H2O) provided a desired product in a solution of MeCN/H2O 0.1% TFA. The pH was adjusted to 7 with buffer (KH2PO4/K2HPO4) and extracted with EtOAc (2×10 mL). The combined extracts were washed with brine, dried (Na2SO4), concentrated, and dried in vacuo to provide (1S,3'R,6'R,7'R,8'E,11'S,12'R)-6-chloro-7'-methoxy-11',12'-dimethyl-7'-(((9aR)-3-oxooctahydro-2H-pyrido[1,2-a]pyrazin-2-yl)methyl)-3,4-dihydro-2H,15'H-spiro[naphthalene-1,22'-[20]oxa[13]thia[1,14]diazatetracyclo[14.7.2.0~3, 6~.0~19,24~]pentacosa[8,16,18,24]tetraen]-15'-one 13',13'-dioxide (33 mg, 0.042 mmol, 62.8% yield) as an off white solid. MS (ESI, +ve ion) m/z 779.3 (M+H)+.

Examples 176 and 177

(1S,3'R,6'R,7'S,8'E,11'S,12'R)-6-chloro-7'-methoxy-N,N,11',12'-tetramethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16, 18,24]tetraene]-7'-carboxamide 13',13'-dioxide AND (1S,3'R,6'R,7'R,8'E,11'S,12'R)-6-chloro-7'-methoxy-N,N,11',12'-tetramethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16, 18,24]tetraene]-7'-carboxamide 13',13'-dioxide

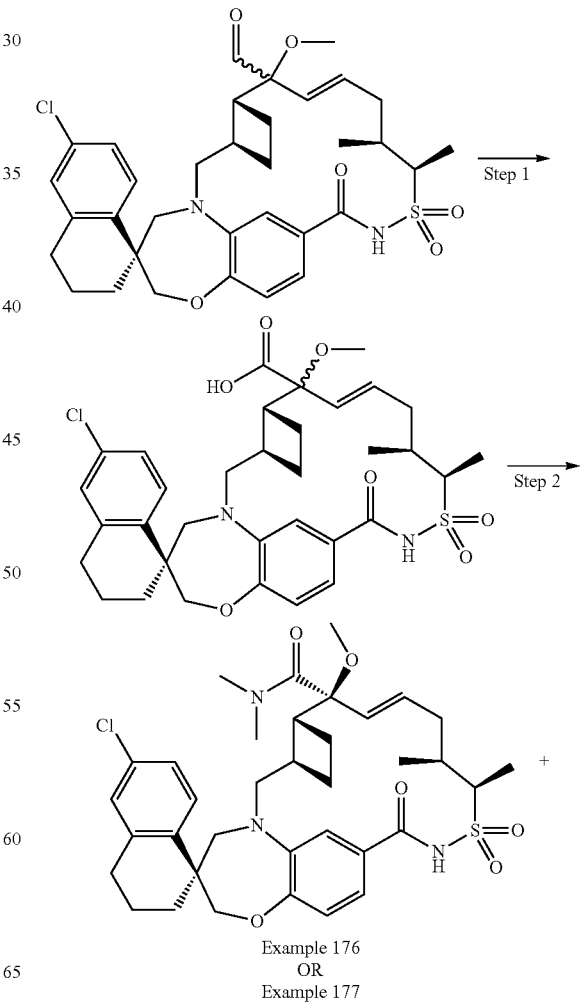

Example 176
OR
Example 177

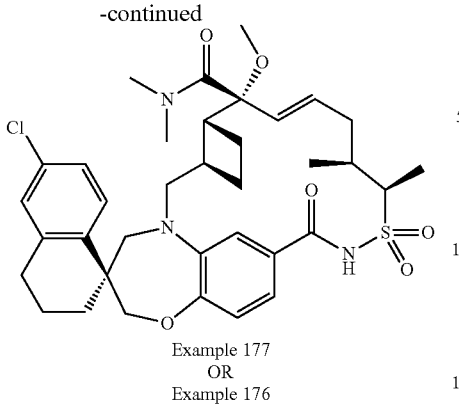

Example 177
OR
Example 176

Step 1: (1S,3'R,6'R,8'E,11'S,12'R)-6-chloro-11',12'-dimethyl-15'-oxo-7'-methyoxy-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carboxylic acid 13',13'-dioxide To a 15-mL round-bottomed flask was added (1S,3'R,6'R,8'E,11'S,12'R)-6-chloro-11',12'-dimethyl-15'-oxo-7'-methoxy-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (18 mg, 0.028 mmol, a mixture of two epimers) and 2-methyl-2-butene (149 µL, 1.404 mmol) in tert-butanol (281 µL) and water (281 µL). Potassium phosphate monobasic (38.2 mg, 0.281 mmol) and sodium chlorite (25.4 mg, 0.281 mmol) was added to the solution. The solution was stirred at room temperature for 1 h. The reaction mixture was diluted with saturated Na₂SO₃ (5 mL) and extracted with DCM (3×10 mL). The organic extract was washed with saturated NaCl (10 mL) and dried over MgSO₄. The solution was filtered and concentrated in vacuo to give an off-white solid. The material was used in the next step without further purification. MS (ESI, +ve ion) m/z 657.2 (M+H)⁺.

Step 2: (1S,3'R,6'R,7'S,8'E,11'S,12'R)-6-chloro-7'-methoxy-N,N,11',12'-tetramethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carboxamide 13',13'-dioxide AND (1S,3'R,6'R,7'R,8'E,11'S,12'R)-6-chloro-7'-methoxy-N,N, 11',12'-tetramethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carboxamide 13',13'-dioxide To a 5-mL round-bottomed flask was added (1S,3'R,6'R,8'E,11'S,12'R)-6-chloro-11',12'-dimethyl-15'-oxo-7'-methyoxy-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carboxylic acid 13',13'-dioxide (13 mg, 0.020 mmol, a mixture of two epimers) and diethylamine (2 M in THF, 39.6 µL, 0.079 mmol) in DCM (396 µL). 1-Propanephosphonic acid cyclic anhydride (50 wt. % solution in ethyl acetate, 62.9 µL, 0.099 mmol) was added at room temperature. The solution was stirred at room temperature for 2 h. The reaction mixture was diluted with saturated NaHCO₃ (5 mL) and extracted with EtOAc (2×10 mL). The organic layer was concentrated. The crude material was further purified by prep-HPLC to give two products. The first peak collected was assigned to be Example 176 and the second peak was assigned to be Example 177. MS (ESI, +ve ion) m/z 684.2 (M+H)⁺ for both isomers.

Examples 193 and 213

(1S,3'R,6'R,7'S,8'E,11'S,12'R)-6-chloro-7'-((9aS)-hexahydropyrazino[2,1-c][1,4]oxazin-8(1H)-ylmethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-((9aS)-hexahydropyrazino[2,1-c][1,4]oxazin-8(1H)-ylmethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

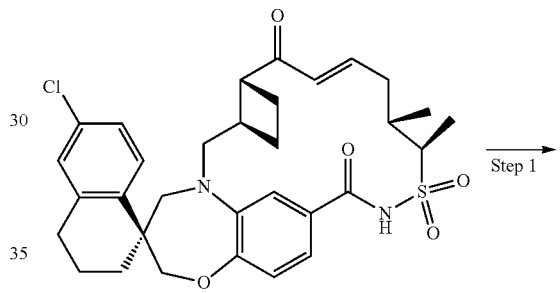

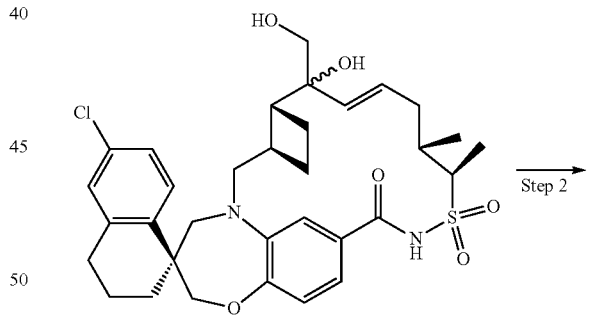

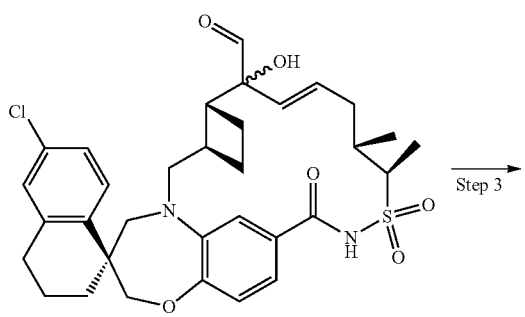

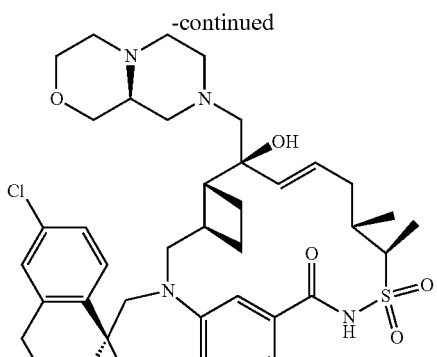

Example 193

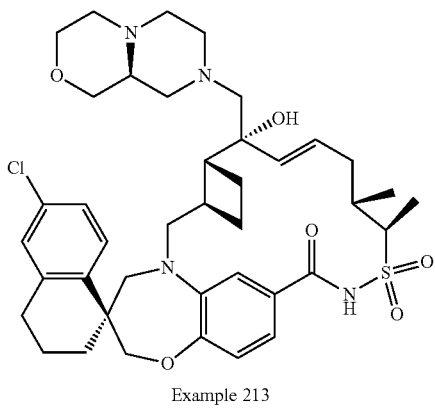

Example 213

Step 1: (1S,3'R,6'R,7'S,8'E,11'S,12'R)-6-CHLORO-7'-HYDROXY-7'-(HYDROXYMETHYL)-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE AND (1S,3'R,6'R,7'R,8'E,11'S,12'R)-6-CHLORO-7'-HYDROXY-7'-(HYDROXYMETHYL)-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE To a stirred ice-cooled solution of (1S,3'R,6'R,8'E,11'S, 12'R)-6-chloro-11',12'-dimethyl-3,4-dihydro-2H,7'H,15'H-spiro[naphthalene-1,22' [20]oxa[13]thia[1,14]diazatetracyclo[14.7.2.0~3,6~.0~19,24~]pentacosa[8,16,18,24]tetraene]-7',15'-dione 13',13'-dioxide (1.015 g, 1.700 mmol) and trimethylsulfonium iodide (0.364 g, 1.785 mmol) in dimethyl sulfoxide (4.0 mL) was dropwise added potassium tert-butoxide, 1.0 M solution in tetrahydrofuran (4.25 mL, 4.25 mmol) under argon. The resulting mixture was stirred in the ice bath for 5 min and at ambient temperature for 30 min. The crude reaction mixture was directly loaded onto a silica gel precolumn (25 g) previously covered with a layer of ammonium chloride and subjected to combi-flash column chromatography on a 24 g ISCO gold column eluting with 0% to 100% EtOAc/Hexanes followed by 5% to 20% MeOH/DCM to give an approximately 3:1 mixture of (1S, 3'R,6'R,7'S,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.82 g, 1.3 mmol, 79% yield) as a white solid. MS (ESI, +ve ion) m/z 629.2 (M+1)$^+$.

Step 2: (1S,3'R,6'R,7'S,8'E,11'S,12'R)-6-CHLORO-7'-HYDROXY-11',12'-DIMETHYL-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAENE]-7'-CARBALDEHYDE 13',13'-DIOXIDE AND (1S,3'R,6'R,7'R,8'E,11'S,12'R)-6-CHLORO-7'-HYDROXY-11',12'-DIMETHYL-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAENE]-7'-CARBALDEHYDE 13',13'-DIOXIDE To a stirred ice-cooled solution of a mixture of (1S,3'R,6'R,7'S,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (180 mg, 0.286 mmol) in DCM (5.0 mL) was added under argon Dess-Martin periodinane (121 mg, 0.286 mmol) in one portion as a solid. The resulting mixture was stirred under argon at 0° C. for 10 min and at ambient temperature for a period of 3 h. The crude mixture was directly loaded onto a silica gel precolumn (25 g) and subjected to combi-flash column chromatography on a 12 g ISCO gold column eluting with 0% to 20% MeOH/DCM to give 180 mg of an impure mixture of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide and (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide as an off-white solid. It was taken onto the next step without further purification. MS (ESI, +ve ion) m/z 627.2 (M+1)$^+$.

Step 3: (1S,3'R,6'R,7'S,8'E,11'S,12'R)-6-CHLORO-7'-((9AS)-HEXAHYDROPYRAZINO[2,1-C][1,4]OXAZIN-8(1H)-YLMETHYL)-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE AND (1S,3'R,6'R,7'R,8'E,11'S,12'R)-6-CHLORO-7'-((9AS)-HEXAHYDROPYRAZINO [2,1-C][1,4]OXAZIN-8(1H)-YLMETHYL)-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE The title compounds were prepared from a mixture of (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide and (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide according to General Method 10. (1S,3'R,6'R,7'S,8'E,11'S,12'R)-6-chloro-7'-((9aS)-hexahydropyrazino[2,1-c][1,4]oxazin-8(1H)-ylmethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 193) was the second eluting epimer off the silica gel column. MS (ESI, +ve ion) m/z 753.3 (M+1)+.

(1S,3'R,6'R,7'R,8'E,11'S,12'R)-6-chloro-7'-((9aS)-hexahydropyrazino[2,1-c][1,4]oxazin-8(1H)-ylmethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 213) was the first eluting epimer off the silica gel column. MS (ESI, +ve ion) m/z 753.3 (M+1)+.

Example 194

(1S,3'R,6'R,7'S,8'E,11'S,12'R)-6-CHLORO-7'-HYDROXY-11',12'-DIMETHYL-7'-(4-MORPHOLINYLMETHYL)-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE

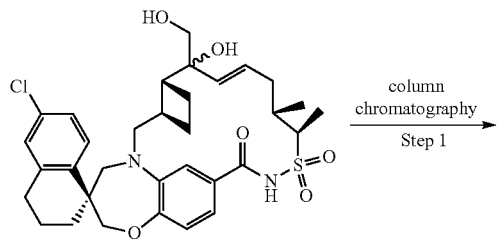

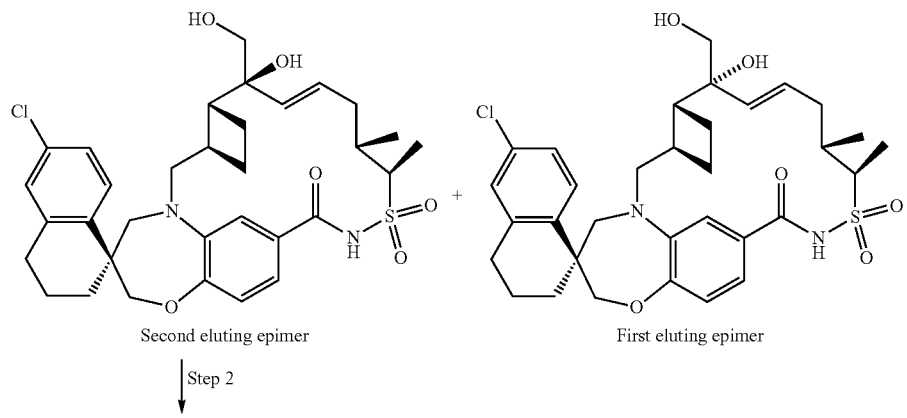

Second eluting epimer · First eluting epimer

Step 2

631

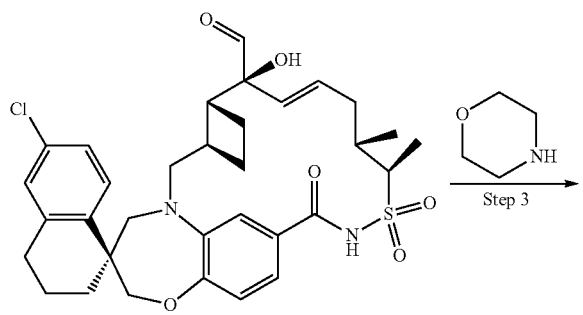

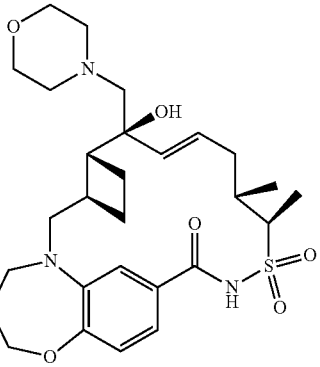

Example 194

Step 1: (1S,3'R,6'R,7'S,8'E,11'S,12'R)-6-CHLORO-7'-HYDROXY-7'-(HYDROXYMETHYL)-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE The title compound was obtained as a single stereoisomer from a silica gel column chromatography separation of an epimeric mixture of (1S,3'R,6'R,7'S,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide eluting with 1% to 20% MeOH/DCM. The title compound was the second eluting epimer off the silica gel column. MS (ESI, +ve ion) m/z 629.3 (M+1)+.

Step 2: (1S,3'R,6'R,7'S,8'E,11'S,12'R)-6-CHLORO-7'-HYDROXY-11',12'-DIMETHYL-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAENE]-7'-CARBALDEHYDE 13',13'-DIOXIDE The title compound was synthesized from (1S,3'R,6'R,7'S,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide according to the protocol in Example 193 (Step 2). MS (ESI, +ve ion) m/z 627.4 (M+1)+.

632

-continued

Step 3: (1S,3'R,6'R,7'S,8'E,11'S,12'R)-6-CHLORO-7'-HYDROXY-11',12'-DIMETHYL-7'-(4-MORPHOLINYLMETHYL)-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-15'-ONE 13',13'-DIOXIDE The title compound was synthesized from (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide according to General Method 10. MS (ESI, +ve ion) m/z 698.5 (M+1)+.

Example 270

(4-(((1S,3'R,6'R,7'S,8'E,11'S,12'R)-6-CHLORO-7'-METHOXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[8,16,18,24]TETRAEN]-7'-YL)METHYL)-1-PIPERAZINYL)ACETIC ACID

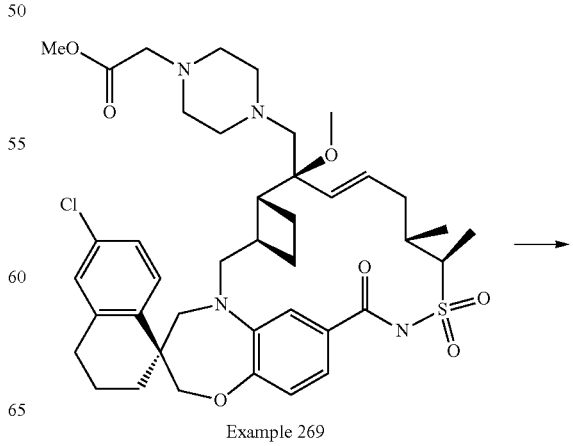

Example 269

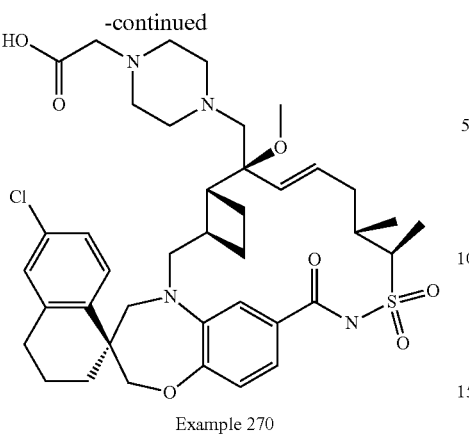

Example 270

To a stirred solution of methyl (4-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinyl) acetate (Example 269) (15 mg, 0.019 mmol) in MeOH (1.5 mL) and water (0.5 mL) was added lithium hydroxide hydrate (8.0 mg, 0.19 mmol). The resulting mixture was stirred at room temperature for 3 h. The residue was taken up in MeOH and subjected to preparative reverse-phase HPLC (Gemini™ Prep C18 10 μm column; Phenomenex, Torrance, Calif.; gradient elution of 20 to 90% MeCN in water, where both solvents contain 0.1% TFA, a 15-min gradient in a 24-min method) to give, after lyophilization, 11 mg of (4-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinyl)acetic acid as a white solid. MS (ESI, +ve ion) m/z 769.7 (M+1)+.

Example 276

(1S,3'R,6'R,7'S,8'E,11'S,12'R)-7'-(((9AS)-8-ACRYLOYLOCTAHYDRO-2H-PYRAZINO[1,2-A]PYRAZIN-2-YL)METHYL)-6-CHLORO-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE OR (1S,3'R,6'R,7'S,8'E,11'S,12'R)-7'-(((9AR)-8-ACRYLOYLOCTAHYDRO-2H-PYRAZINO[1,2-A]PYRAZIN-2-YL)METHYL)-6-CHLORO-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE

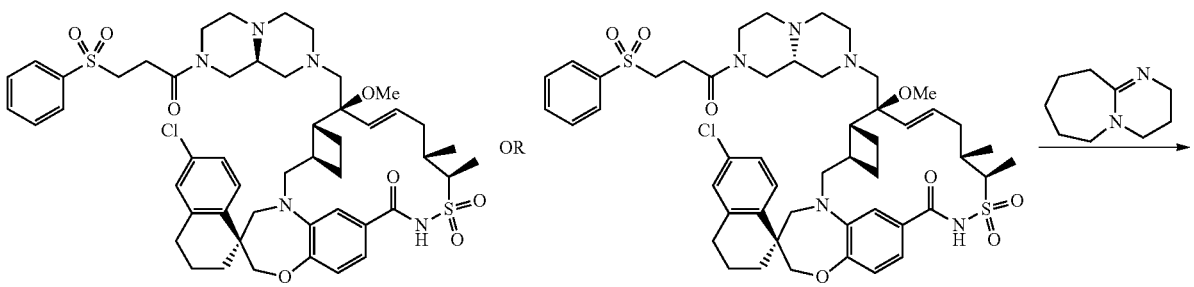

Example 294

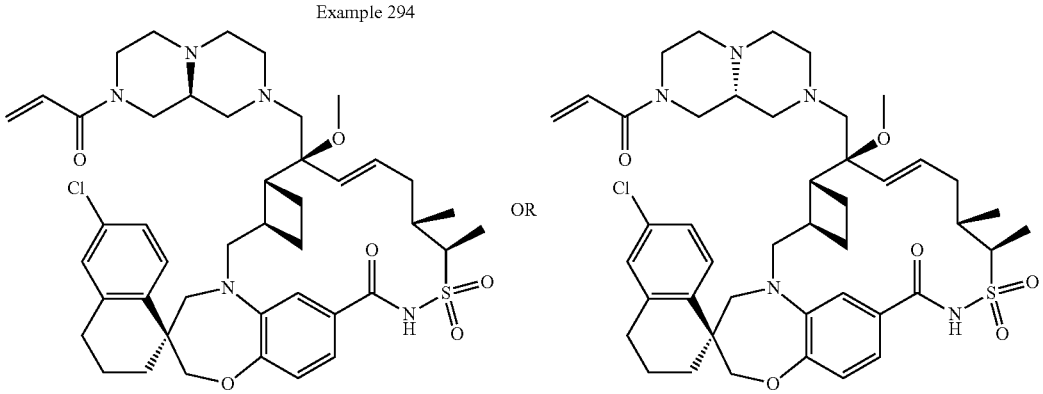

Example 276

A solution of (1S,3'R,6'R,7'S,8'E,11'S,12'R)-6-chloro-7'-methoxy-11',12'-dimethyl-7'-(((9aS)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-(((9aR)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (15 mg, 0.016 mmol) and 1,8-diazabicyclo-[5.4.0]undec-7-ene (0.15 mL, 1.0 mmol) in pyridine (0.30 mL) in a microwave reaction vessel was subjected to microwave irradiation for 50 min at 75° C. The crude mixture was taken up in MeOH and subjected to preparative reverse-phase HPLC (Gemini™ Prep C18 10 μm column; Phenomenex, Torrance, Calif.; gradient elution of 20 to 90% MeCN in water, where both solvents contain 0.1% TFA, a 15-min gradient in a 24-min method) to give, after lyophilization, 7.5 mg of (1S,3'R,6'R, 7'S,8'E,11'S,12'R)-7'-(((9AS)-8-ACRYLOYLOCTA-HYDRO-2H-PYRAZINO[1,2-A]PYRAZIN-2-YL) METHYL)-6-CHLORO-7'-METHOXY-11',12'-DIMETHYL-3,4-DIHYDRO-2H,15'H-SPIRO [NAPHTHALENE-1,22'-[20]OXA[13]THIA[1,14] DIAZATETRACYCLO[14.7.2.0~3,6~.0~19,24~]PENT ACOSA[8,16,18,24]TETRAEN]-15'-ONE 13',13'-DIOX-IDE OR (1S,3'R,6'R,7'S,8'E,11'S,12'R)-7'-(((9AR)-8-ACRYLOYLOCTAHYDRO-2H-PYRAZINO[1,2-A] PYRAZIN-2-YL)METHYL)-6-CHLORO-7'-METHOXY-11',12'-DIMETHYL-3,4-DIHYDRO-2H,15'H-SPIRO [NAPHTHALENE-1,22'-[20]OXA[13]THIA[1,14] DIAZATETRACYCLO[14.7.2.0~3,6~.0~19,24~]PENT ACOSA[8,16,18,24]TETRAEN]-15'-ONE 13',13'-DIOX-IDE. MS (ESI, +ve ion) m/z 821.0 (M+1)+.

Example 345

(1S,3'R,6'R,7'R,8'E,11'S,12'R)-6-chloro-7'-methoxy-11',12'-dimethyl-7'-(1H-1,2,3-triazol-1-ylmethyl)-3, 4-dihydro-2H,15'H-spiro[naphthalene-1,22'-[20]oxa [13]thia[1,14]diazatetracyclo[14.7.2.0~3,6~.0~19, 24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-(1H-1,2,3-triazol-1-ylmethyl)-3,4-dihydro-2H,15'H-spiro[naphthalene-1, 22'-[20]oxa[13]thia[1,14]diazatetracyclo[14.7.2.0~3, 6~.0~19,24~]pentacosa[8,16,18,24]tetraen]-15'-one 13',13'-dioxide

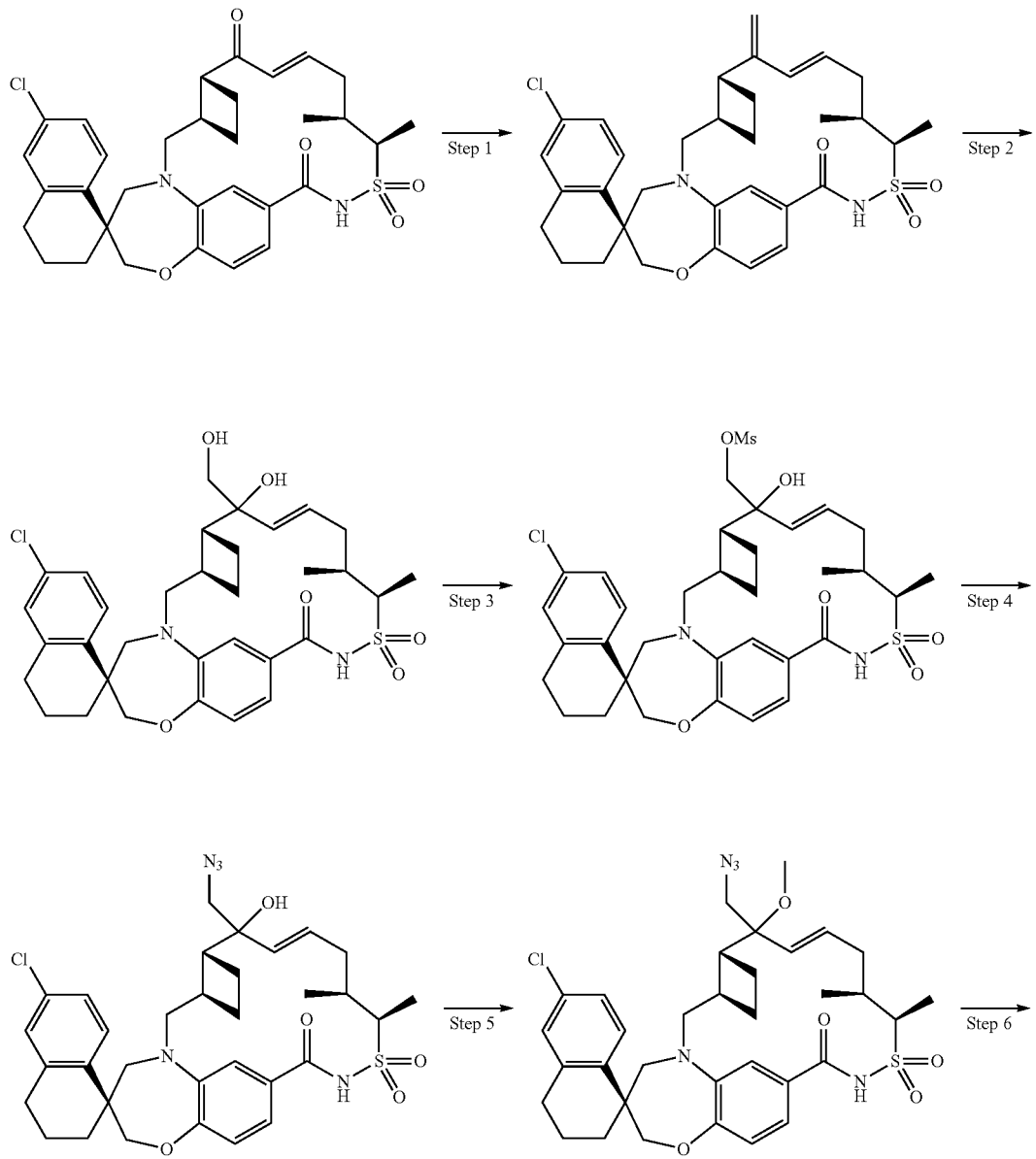

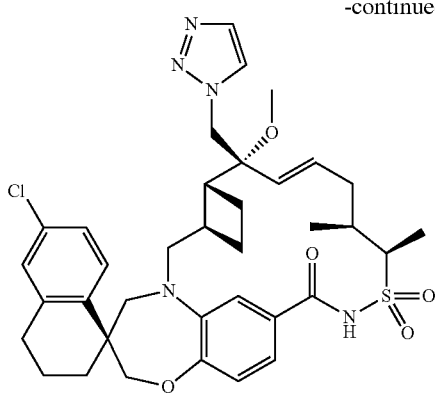 OR 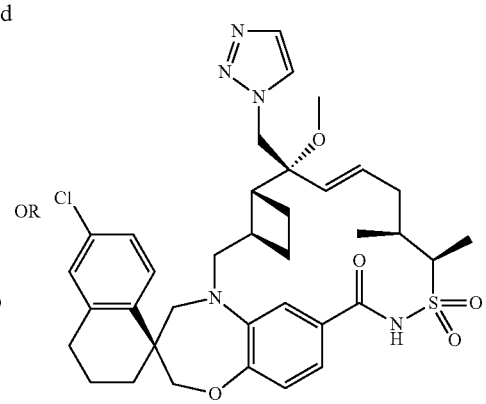

Example 345

Step 1: (1S,3'R,6'R,8'E,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A solution of methyltriphenylphosphonium bromide (1.80 g, 5.0 mmol) in THF (15 mL) was cooled to 0° C. n-butyllithium solution (2.5 M in hexanes, 1.8 mL, 4.5 mmol) was added dropwise and it was stirred at 0° C. for 10 min. The bromide solution was added dropwise to a solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (0.30 g, 0.50 mmol) in THF (6.0 mL) (cooled in ice bath) until the yellow color persisted. It was stirred at 0° C. for 12 min. The reaction mixture was added to stirred ice water (20 mL). It was acidified with 1 N HCl to pH 2-4. The organic phase was separated and the aqueous was extracted with EtOAc (50 mL). The organic phase was washed with brine and dried over magnesium sulfate. The filtrate was concentrated to give crude product. The compound was purified by medium pressure chromatography (silica, 0% to 50% EtOAc (+0.3% HOAc:Hexanes) to give (1S,3'R,6'R,8'E,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (290 mg, 0.49 mmol, 97% yield). MS (ESI, +ve ion) m/z 595.2 (M+H)+.

Step 2: (1S,3'R,6'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide The AD-Mix-alpha mixture (640 mg, 0.43 mmol) was dissolved in a 20 mL of a 1:1 mixture of tert-butanol (10.0 mL) and water (10.0 mL) and cooled to 0° C. The (1S,3'R,6'R,8'E,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (255 mg, 0.428 mmol) was added and the reaction mixture was warmed slowly to room temperature overnight. Another 5.0 mL of t-BuOH was added to homogenize the mixture. The reaction was stirred overnight. Another 320 mg of AD-Mix-alpha mixture was added and the reaction was stirred for an additional 3 d. The reaction was quenched by adding 575 mg of sodium sulfite at 0° C. and stirring for 45 minutes. The mixture was then extracted with EtOAc (2×25 mL). The combined organic layers were washed with brine (1×20 mL) and dried over sodium sulfate. The crude product was then purified by medium pressure chromatography (silica, 0% to 100% EtOAc (+0.3% HOAc):heptanes) to give (1S,3'R,6'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (31 mg, 0.049 mmol, 12% yield). MS (ESI, +ve ion) m/z 629.2 (M+H)+.

Step 3: ((1S,3'R,6'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl methanesulfonate (1S,3'R,6'R,8'E,11'S,12'R)-6-Chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (25.0 mg, 0.040 mmol) was dissolved in DCM (800 µL) and cooled to 0° C. Triethylamine (17 µL, 0.12 mmol) was added followed by mesyl chloride (6.50 µL, 0.083 mmol) addition and the reaction was stirred for 1.5 h. The reaction was then diluted with DCM (15 mL) and the mixture was washer with water (2×10 mL) and dried over sodium sulfate. The crude product was then purified by medium pressure chromatography (silica, 0% to 70% EtOAc (+0.3% HOAc):heptanes) to give ((1S,3'R,6'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl methanesulfonate. MS (ESI, +ve ion) m/z 707.2 (M+H)+.

Step 4: (1S,3'R,6'R,8'E,11'S,12'R)-7'-(azidomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide ((1S,3'R,6'R,8'E,11'S,12'R)-6-Chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl methanesulfonate (10 mg, 0.014 mmol) was dissolved in 0.36 mL of a 5:1 DMF:water mixture. To the solution was added sodium azide (2.1 mg, 3.2 µmol). The mixture was heated to 70° C. and stirred overnight. The reaction was diluted with water and extracted with EtOAc. The organic layer was dried over sodium sulfate and the crude product was purified by medium pressure chromatography (silica, 0% to 60% EtOAc (+0.3% HOAc):heptanes) to give (1S,3'R,6'R,8'E,11'S,12'R)-7'-(azidomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (2.1 mg, 3.2 µmol, 23% yield). MS (ESI, +ve ion) m/z 654.2 (M+H)⁺.

Step 5: (1S,3'R,6'R,8'E,11'S,12'R)-7'-(azidomethyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1S,3'R,6'R,8'E,11'S,12'R)-7'-(Azidomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (2.0 mg, 3.1 µmol) was dissolved in 2-methyltetrahydrofuran (1.0 mL) and sodium hydride (60% dispersion) (0.73 mg, 0.031 mmol) was added followed by methyl iodide (0.956 µL, 0.015 mmol). The reaction was then stirred overnight to completion. The reaction was quenched with dropwise addition of water and extracted with EtOAc. The organic layers were then washed with brine and dried over magnesium sulfate to give (1S,3'R,6'R,8'E,11'S,12'R)-7'-(azidomethyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (3.0 mg) that was used directly in the next reaction without any further purification. MS (ESI, +ve ion) m/z 668.2 (M+H)⁺.

Step 6: (1S,3'R,6'R,7'R,8'E,11'S,12'R)-6-chloro-7'-methoxy-11',12'-dimethyl-7'-(1H-1,2,3-triazol-1-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-(1H-1,2,3-triazol-1-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1S,3'R,6'R,8'E,11'S,12'R)-7'-(Azidomethyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (20 mg, 0.030 mmol) was slurried in 3.0 mL of a 1:1:1 t-BuOH:water:DMF solution. To the solution was added copper (II) sulfate (2.9 mg, 0.018 mmol), (+)-sodium 1-ascorbate (12.0 mg, 0.061 mmol) and (trimethylsilyl)acetylene (65 µL, 0.46 mmol). The solution was then heated in a microwave reactor at 120° C. for 2 h. The reaction was then diluted with water and EtOAc. The mixture was extracted with EtOAc (2×25 mL). The combined organic layers were washed with 1 N lithium chloride solution (1×15 mL) and brine (1×15 mL) then dried over magnesium sulfate. The residue was then purified by medium pressure chromatography (silica, 25% to 100% EtOAc (+0.3% HOAc):heptanes) to give (1S,3'R,6'R,7'R,8'E,11'S,12'R)-6-chloro-7'-methoxy-11',12'-dimethyl-7'-(1H-1,2,3-triazol-1-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-(1H-1,2,3-triazol-1-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide. MS (ESI, +ve ion) m/z 694.3 (M+H)⁺.

Example 348

(1S,3'R,6'R,7'S,8'E,11'S,12'R)-6-chloro-11',12'-dimethyl-7'-(2-methylpropoxy)-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

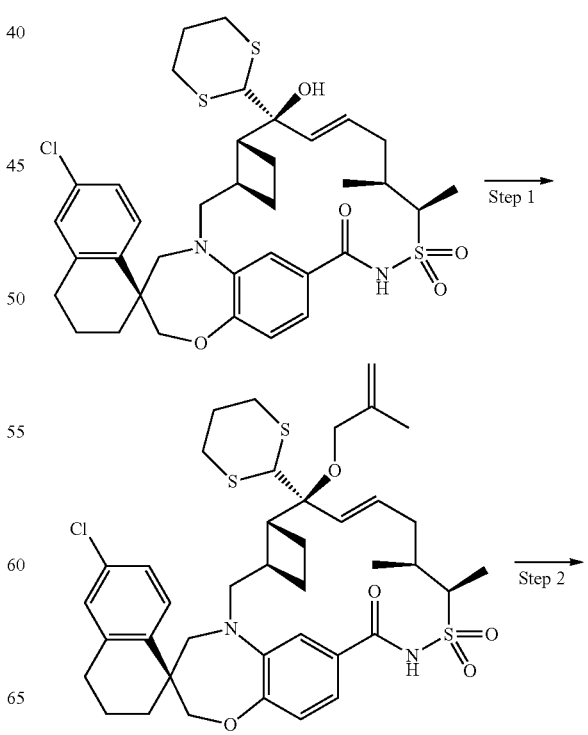

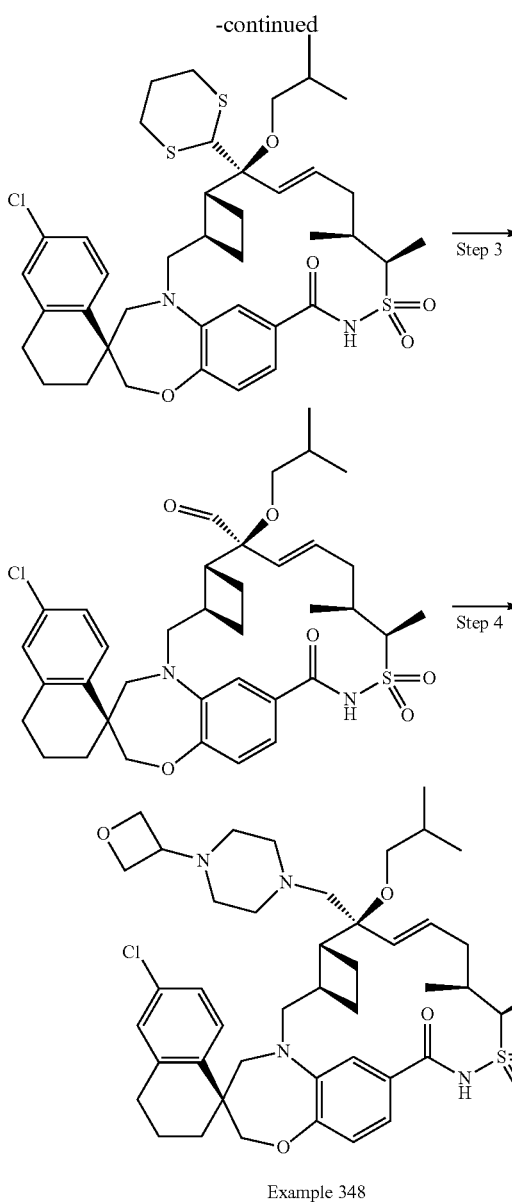

Example 348

Step 1: (1S,3'R,6'R,7'S,8'E,11'S,12'R)-6-chloro-7'-(1,3-dithian-2-yl)-11',12'-dimethyl-7'-((2-methyl-2-propen-1-yl)oxy)-3,4-dihydro-2H,15'H-spiro[naphthalene-1,22'-[20]oxa[13]thia[1,14]diazatetracyclo[14.7.2.0~3,6~.0-19,24~]pentacosa[8,16,18,24]tetraen]-15'-one 13',13'-dioxide The reaction was performed following the procedure for general method 5, step 2. MS (ESI, +ve ion) m z 771.2 (M+H)+.

Step 2: (1S,3'R,6'R,7'S,8'E,11'S,12'R)-6-chloro-7'-(1,3-dithian-2-yl)-11',12'-dimethyl-7'-(2-methylpropoxy)-3,4-dihydro-2H,15'H-spiro[naphthalene-1,22'-[20]oxa[13]thia[1,14]diazatetracyclo[14.7.2.0~3,6~.0-19,24~]pentacosa[8,16,18,24]tetraen]-15'-one 13',13'-dioxide The (1S,3'R,6'R,7'S,8'E,11'S,12'R)-6-chloro-7'-(1,3-dithian-2-yl)-11',12'-dimethyl-7'-((2-methyl-2-propen-1-yl)oxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (200 mg, 0.26 mmol) was dissolved in EtOAc (5.0 mL) and platinum (IV) oxide (180 mg, 0.78 mmol) was added. The vessel was then pressurized to 40 psi with hydrogen and stirred for 3.5 h to completion. The black slurry was then filtered through a pad of Celite and washed with EtOAc. The filtrate was then concentrated to give (1S,3'R,6'R,7'S,8'E,11'S,12'R)-6-chloro-7'-(1,3-dithian-2-yl)-11',12'-dimethyl-7'-(2-methylpropoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (200 mg, 0.26 mmol, 100% yield). MS (ESI, +ve ion) m/z 773.2 (M+H)+.

Step 3: (1S,3'R,6'R,7'S,8'E,11'S,12'R)-6-chloro-11',12'-dimethyl-7'-(2-methylpropoxy)-15'-oxo-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide The reaction was performed following the procedure for general method 5, step 3. MS (ESI, +ve ion) m/z 683.3 (M+H)+.

Step 4: (1S,3'R,6'R,7'S,8'E,11'S,12'R)-6-chloro-11',12'-dimethyl-7'-(2-methylpropoxy)-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide The reaction was performed following the procedure for general method 8. MS (ESI, +ve ion) m/z 809.2 (M+H)+.

Examples 362 and 363

(1S,3'R,6'R,7'R,8'E,11'S,12'R)-6-chloro-12'-((2S)-2-hydroxypropyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-12'-((2R)-2-hydroxypropyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

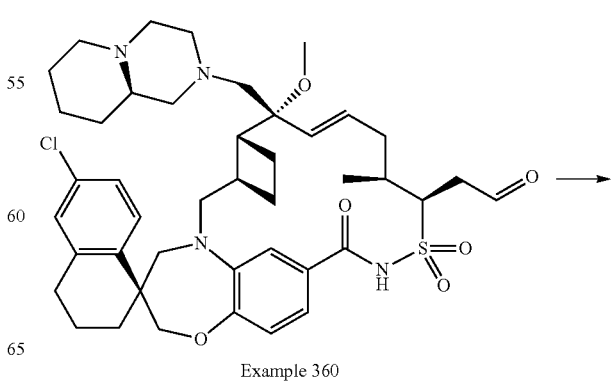

Example 360

-continued

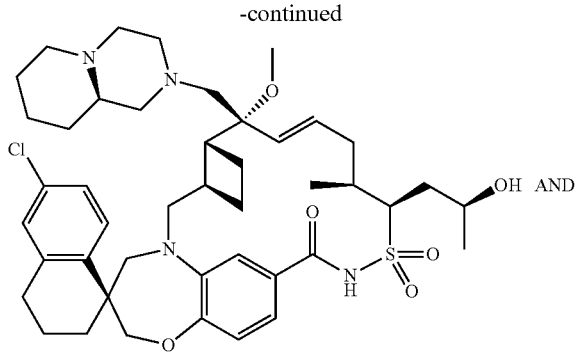

Example 362
OR
Example 363

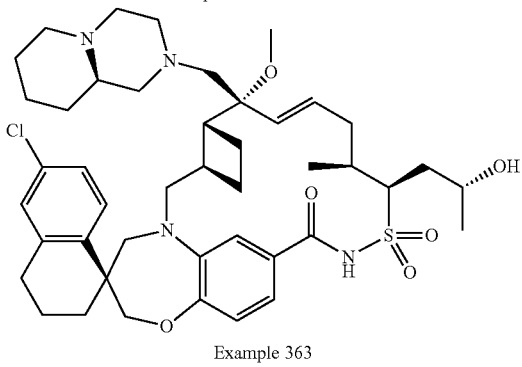

Example 363
OR
Example 362

((1S,3'R,6'R,7'R,8'E,11'S,12'R)-6-Chloro-7'-methoxy-11'-methyl-7'-((9aR)-octahydro-2H-pyrido[1,2-a]pyrazin-2-ylmethyl)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)acetaldehyde (Example 360) (32 mg, 0.040 mmol) was dissolved in THF (2.0 mL) and cooled to 0° C. Methylmagnesium bromide (3.4 M in 2-MeTHF, 0.12 mL, 0.40 mmol) was added dropwise and stirred for 45 min. The reaction was quenched with saturated ammonium chloride solution (15 mL) and the mixture was extracted with EtOAc (2×30 mL). The combined organic layers were washed with brine (1×20 mL) and then dried over sodium sulfate. The mixture was then purified by preparatory SCF chromatography (4FBSA, 250 mm×21 mm column, Phenomenex, Torrance, Calif.; 28 g/minute MeOH (+20 mM $NH_3$)+42 g/minute $CO_2$ on Thar 200 SFC; outlet pressure=100 bar; temperature=40° C.; wavelength=220 nm; used 1.1 mL injections of 28 mg/3 mL (9.3 mg/mL) sample solution of MeOH (3 mL) to give (1S,3'R,6'R,7'R,8'E,11'S,12'R)-6-chloro-12'-((2S)-2-hydroxypropyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-12'-((2R)-2-hydroxypropyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 362, first eluting isomer, $t_R$=3.19 minutes on analytical SFC; 4FBSA; 40% MeOH (+20 mM $NH_3$ in $CO_2$) with >99.5% de) (6.2 mg, 7.7 μmol, 19% yield). MS (ESI, +ve ion) m/z 809.4 $(M+H)^+$. And (1S,3'R,6'R,7'R,8'E,11'S,12'R)-6-chloro-12'-((2S)-2-hydroxypropyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-12'-((2R)-2-hydroxypropyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 363, second eluting isomer, $t_R$=6.49 minutes on analytical SFC; 4FBSA; 40% MeOH (+20 mM $NH_3$ in $CO_2$) with >99.5% de) (13 mg, 0.016 mmol, 39% yield). MS (ESI, +ve ion) m/z 809.4 $(M+H)^+$.

Examples 364 and 366

(1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11'-methyl-3,4-dihydro-2H,16'H-spiro[naphthalene-1,23'-[21]oxa[27]thia[1,15]diazapentacyclo[15.7.2.1~12,15~.0~3,6~.0~20,25~]heptacosa[8,17,19,25]tetraen]-16'-one 27',27'-dioxide AND (1S,3'R,6'R,7'S,8'E,11'S,12'R)-6-chloro-12'-(2-chloroethyl)-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

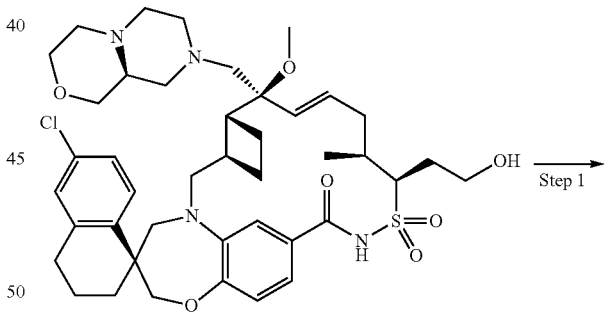

Example 346

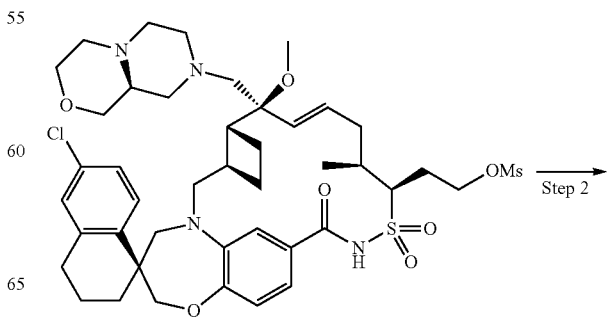

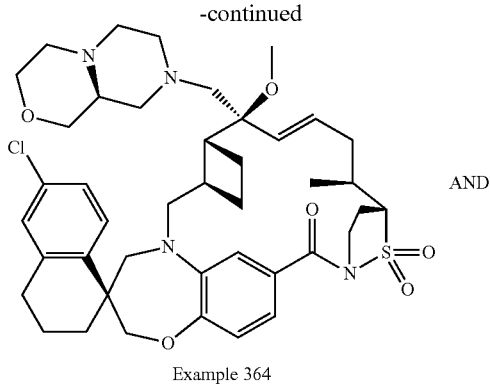

Example 364

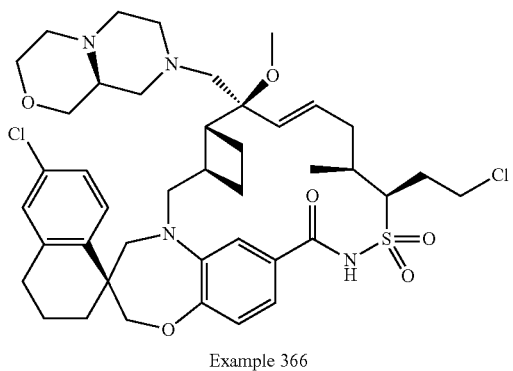

Example 366

Step 1: 2-((1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate (1S,3'R,6'R,7'S,8'E,11'S,12'R)-6-Chloro-7'-((9aS)-hexahydropyrazino[2,1-c][1,4]oxazin-8(1H)-ylmethyl)-12'-(2-hydroxyethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 346) (15 mg, 0.018 mmol) was dissolved in DCM (1.0 mL) and the Hunig's base (0.011 mL, 0.064 mmol) and mesyl chloride (3.7 µL, 0.048 mmol) were added. The reaction mixture was stirred for 1.5 h to near completion. The mixture was then diluted with DCM (20 mL) and water (15 mL). The layers were separated and the organic layer was dried over sodium sulfate. The filtrate was concentrated to dryness under vacuum to give 2-((1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate (16 mg, 0.018 mmol, 100% yield) that was used directly in the next reaction. MS (ESI, +ve ion) m/z 875.3 (M+H)$^+$.

Step 2: (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11'-methyl-3,4-dihydro-2H,16'H-spiro[naphthalene-1,23'-[21]oxa[27]thia[1,15]diazapentacyclo[15.7.2.1~12,15~.0~3,6~.0~20,25~]heptacosa[8,17,19,25]tetraen]-16'-one 27',27'-dioxide AND (1S,3'R,6'R,7'S,8'E,11'S,12'R)-6-chloro-12'-(2-chloroethyl)-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide 2-((1S,3'R,6'R,7'S,8'E,11'S,12'R)-6-Chloro-7'-((9aS)-hexahydropyrazino[2,1-c][1,4]oxazin-8(1H)-ylmethyl)-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate (16 mg, 0.018 mmol) was dissolved in acetonitrile (1.0 mL) and tetrabutylammonium difluoro-triphenylsilicate (59 mg, 0.11 mmol) was added. The reaction was then heated at 75° C. to completion. The reaction was then cooled to room temperature and then diluted with EtOAc (25 mL) and water (20 mL). The layers were separated and the organic layer was washed again with water (1×20 mL) and brine (1×20 mL) and dried over sodium sulfate. The crude product was then purified by medium pressure chromatography (silica, 0% to 100% (10% 2 M ammonia in MeOH):DCM) to give two products, (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11'-methyl-3,4-dihydro-2H,16'H-spiro[naphthalene-1,23'-[21]oxa[27]thia[1,15]diazapentacyclo[15.7.2.1~12,15~.0~3,6~.0~20,25~]heptacos a[8,17,19,25]tetraen]-16'-one 27',27'-dioxide (Example 364) (4.9 mg, 6.3 µmol, 34% yield), MS (ESI, +ve ion) m/z 779.3 (M+H)$^+$ AND (1S,3'R,6'R,7'S,8'E,11'S,12'R)-6-chloro-12'-(2-chloroethyl)-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 366) (3.5 mg, 4.29 µmol, 23% yield), MS (ESI, +ve ion) m/z 815.3 (M+H)$^+$.

Examples 358, 359, and 367

(1S,3'R,6'R,7'R,8'E,11'S,12'R)-6-chloro-12'-(2-hydroxyethyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 358) AND (1S,3'R,6'R,7'R,8'E,11'S,12'R)-6-chloro-7'-methoxy-11'-methyl-12'-(2-(((2-methyl-2-propanyl)(diphenyl)silyl)oxy)ethyl)-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 359) AND (1S,3'R,6'R,7'R,8'E,11'S,12'R)-6-chloro-12'-(2-(dimethylamino)ethyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 367)

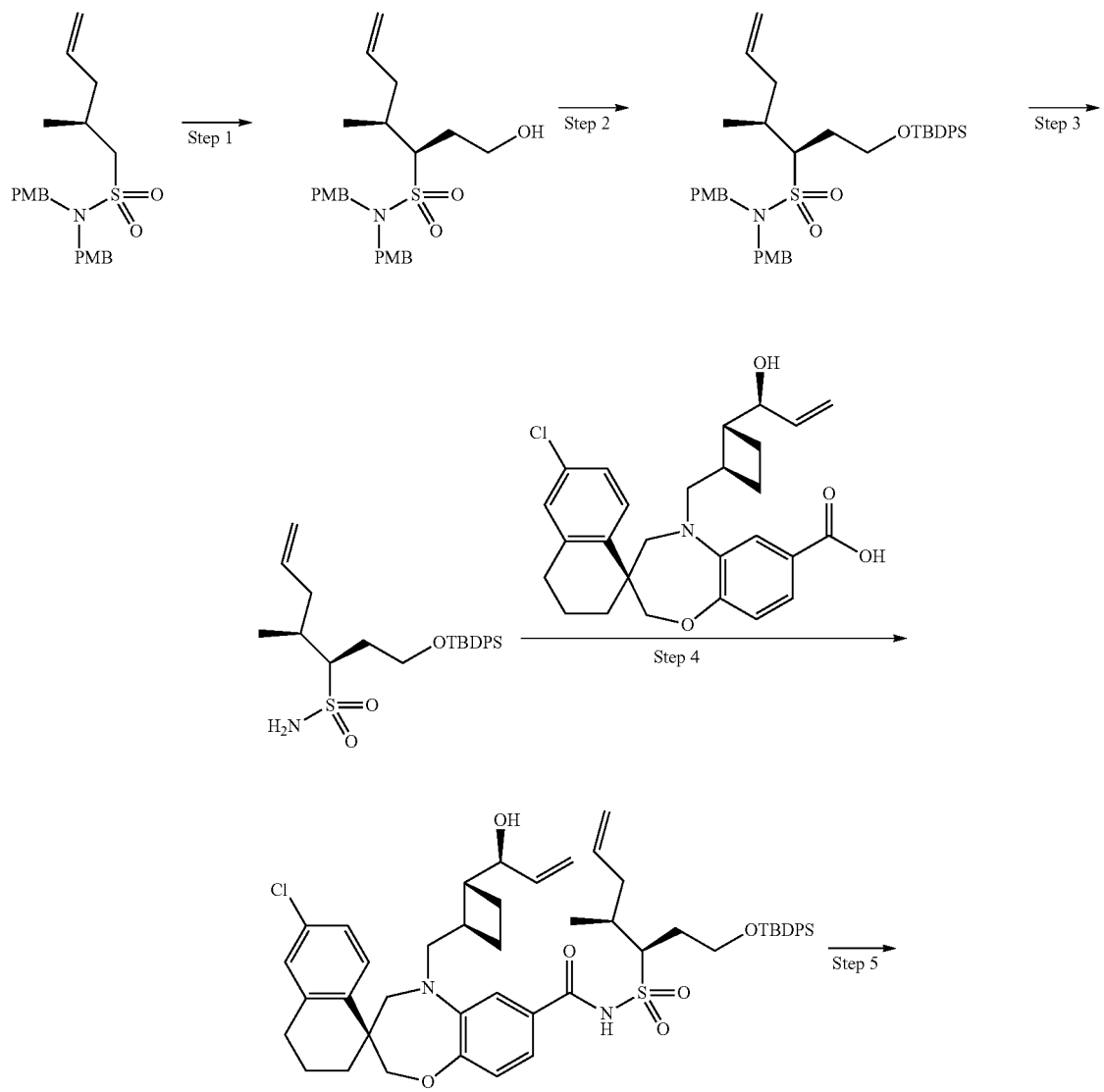

-continued
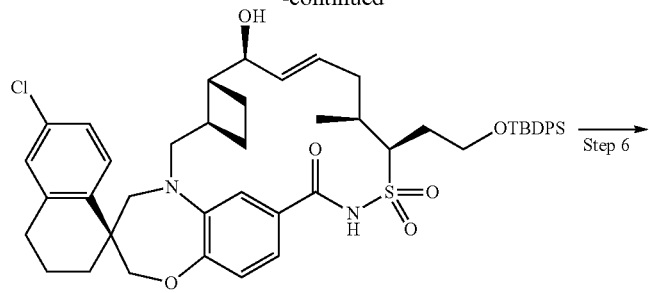
Step 6
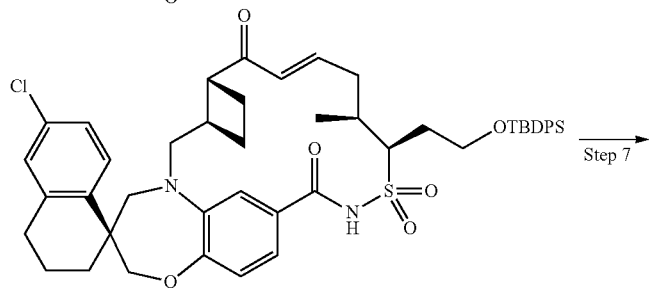
Step 7
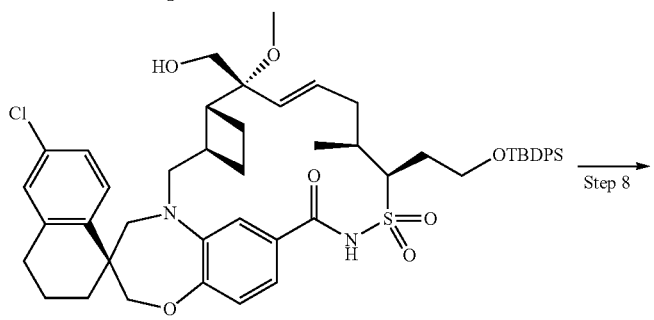
Step 8
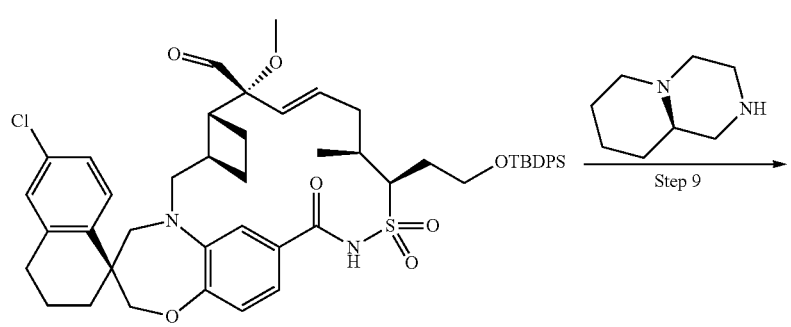
Step 9
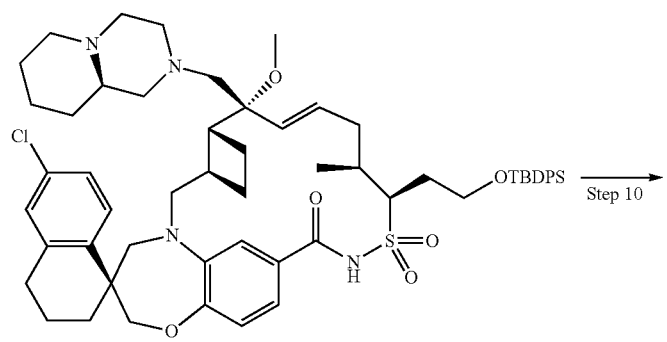
Step 10
Example 359

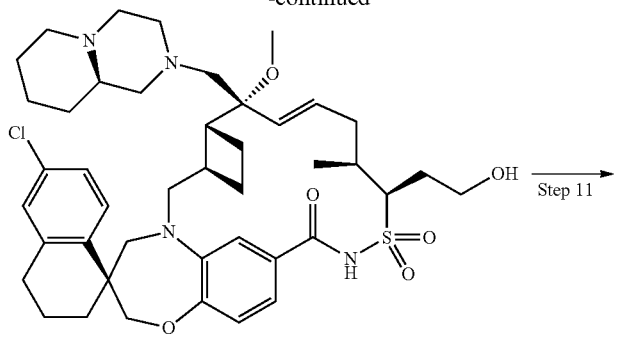

Example 358

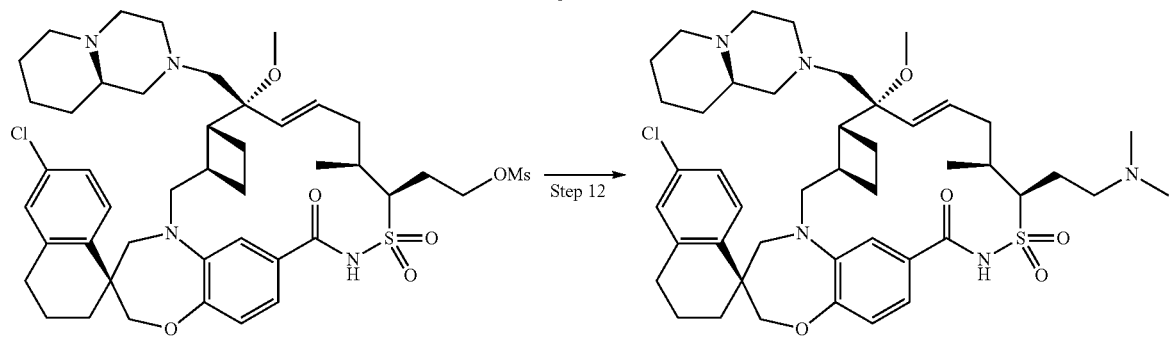

Example 367 (right)

Step 1: (3R,4S)-1-HYDROXY-N,N-BIS(4-METHOXYBENZYL)-4-METHYL-6-HEPTENE-3-SULFONAMIDE To a solution of (S)—N,N-bis(4-methoxybenzyl)-2-methylpent-4-ene-1-sulfonamide (2.8 g, 6.9 mmol) in THF (15 mL) was added n-butyllithium (2.5 M in hexanes, 3.1 mL, 7.6 mmol) at −78° C. dropwise. The mixture was stirred at −78° C. for 5 min, and ethylene oxide (2.5 M in THF, 5.6 mL, 14 mmol) was then added. The mixture was allowed to warm up to ambient temperature and stirred for 18 h. The mixture was quenched with saturated aqueous $NH_4Cl$, and extracted with EtOAc (2×). The organic layer was washed with brine, dried ($MgSO_4$), and filtered. The filtrate was concentrated and the resulting residue was chromatographed (silica gel, 20% to 60%, EtOAc/Hexane) to afford a diastereomeric mixture of the title compound. The mixture was then purified by preparatory SFC chromatography (ChiralPak IC-H 250 mm×30 mm column, Phenomenex, Torrance, Calif.; 35 g/minute MeOH+105 g/minute $CO_2$ on Thar 200 SFC; outlet pressure=100 bar; temperature=22° C.; wavelength=215 nm; used 1.0 mL injections of 25,000 mg/50 mL (500 mg/mL) sample solution of MeOH (50 mL) to provide (3R,4S)-1-hydroxy-N,N-bis(4-methoxybenzyl)-4-methyl-6-heptene-3-sulfonamide as the slower eluting isomer as a yellow liquid ($t_R$=2.51 minutes on analytical SFC; IC-H column; 25% MeOH in $CO_2$) with 100% de. $^1H$ NMR (400 MHz, DICHLOROMETHANE-$d_2$) δ ppm 7.24 (d, J=8.61 Hz, 4H), 6.90 (d, J=8.61 Hz, 4H), 5.62 (ddt, J=16.75, 10.20, 7.07, 7.07 Hz, 1H), 5.08 (s, 1H), 5.05 (br d, J=7.83 Hz, 1H), 4.39 (d, J=15.26 Hz, 2H), 4.23 (d, J=15.26 Hz, 2H), 3.83 (s, 6H), 3.66-3.81 (m, 2H), 3.00-3.16 (m, 1H), 1.97-2.23 (m, 3H), 1.79-1.96 (m, 3H), 1.06 (d, J=6.85 Hz, 3H). MS (ESI, +ve ion) m/z 470.2 (M+Na)$^+$.

Step 2: (3R,4S)—N,N-bis(4-methoxybenzyl)-4-methyl-1-(((2-methyl-2-propanyl)(diphenyl)silyl)oxy)-6-heptene-3-sulfonamide (3R,4S)-1-Hydroxy-N,N-bis(4-methoxybenzyl)-4-methylhept-6-ene-3-sulfonamide (6.4 g, 14 mmol) was dissolved in DMF (34 mL). Imidazole (1.7 g, 24 mmol) and tert-butyldiphenylsilyl chloride (6.3 mL, 24 mmol) were added and the mixture was stirred for 45 min. The reaction was then quenched with saturated ammonium chloride solution (150 mL) and extracted with EtOAc (1×300 mL). The layers were separated and the organic was washed (1×100 mL) with 1 N LiCl solution (1×100 mL), 1 N HCl solution and (1×100 mL) of brine and then dried over magnesium sulfate. The crude product was then purified by medium pressure chromatography (silica, 5% to 100% EtOAc:Heptanes) to give (3R,4S)—N,N-bis(4-methoxybenzyl)-4-methyl-1-(((2-methyl-2-propanyl)(diphenyl)silyl)oxy)-6-heptene-3-sulfonamide (9.70 g, 14.14 mmol, 98% yield). $^1H$ NMR (400 MHz, CHLOROFORM-d) δ 7.67 (dt, J=1.5, 7.3 Hz, 4H), 7.47-7.35 (m, 6H), 7.16 (d, J=8.8 Hz, 4H), 6.79-6.78 (m, 1H), 6.81 (d, J=8.6 Hz, 3H), 5.56 (tdd, J=7.0, 10.1, 17.0 Hz, 1H), 4.97 (dd, J=1.8, 10.0 Hz, 1H), 4.91 (dd, J=1.6, 17.0 Hz, 1H), 4.31-4.10 (m, 4H), 3.84-3.80 (m, 1H), 3.78 (s, 6H), 3.77-3.72 (m, 1H), 3.09 (ddd, J=1.6, 4.2, 7.4 Hz, 1H), 2.22-2.07 (m, 2H), 1.98-1.79 (m, 3H), 1.07 (s, 9H), 1.02 (d, J=6.8 Hz, 3H). MS (ESI, +ve ion) m/z 708.3 (M+Na)$^+$.

Step 3: (3R,4S)-4-methyl-1-(((2-methyl-2-propanyl)(diphenyl)silyl)oxy)-6-heptene-3-sulfonamide To a 1000 mL flask cooled to 0° C., was added (3R,4S)—N,N-bis(4-methoxybenzyl)-4-methyl-1-(((2-methyl-2-propanyl)(diphenyl)silyl)oxy)-6-heptene-3-sulfonamide (9.4 g, 14 mmol), DCM (290 mL), anisole (7.5 mL, 69 mmol) and then trifluoroacetic acid (49 mL). The reaction was allowed to warm to room temperature overnight to completion. The reaction mixture was then concentrated on the rotovap to a volume of ~25 mL. The crude product was then purified by medium pressure chromatography (silica, 10% to 50% EtOAc:heptanes) to give (3R,4S)-4-methyl-1-(((2-methyl-2-propanyl)(diphenyl)silyl)oxy)-6-heptene-3-sulfonamide (2.7 g, 6.1 mmol, 44% yield). $^1$H NMR (400 MHz, CHLOROFORM-d) δ 7.67 (ddd, J=1.5, 5.8, 7.2 Hz, 4H), 7.49-7.37 (m, 6H), 5.72 (tdd, J=6.9, 10.1, 17.0 Hz, 1H), 5.06-4.94 (m, 2H), 4.41 (br s, 2H), 3.93-3.80 (m, 2H), 3.23-3.16 (m, 1H), 2.46 (m, 1H), 2.13-2.06 (m, 1H), 2.05-2.01 (m, 1H), 1.91 (dtd, J=3.7, 7.1, 14.7 Hz, 2H), 1.07 (s, 9H), 1.02 (d, J=7.0 Hz, 3H). MS (ESI, +ve ion) m/z 468.2 (M+Na)$^+$.

Step 4: (3 S)-6'-chloro-5-(((1R,2R)-2-((1S)-1-hydroxy-2-propen-1-yl)cyclobutyl)methyl)-N-(((3R,4S)-4-methyl-1-(((2-methyl-2-propanyl)(diphenyl)silyl)oxy)-6-hepten-3-yl)sulfonyl)-3',4,4',5-tetrahydro-2'H-spiro[1,5-benzoxazepine-3,1'-naphthalene]-7-carboxamide The reaction was performed following the procedure for general method 1 (R$^1$═H). MS (ESI, +ve ion) m/z 895.3 (M+H)$^+$.

Step 5: (1S,3'R,6'R,7'S,8'E,11'S,12'R)-6-chloro-7'-hydroxy-11'-methyl-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide The reaction was performed following the procedure for general method 1 (R$^1$═H). MS (ESI, +ve ion) m/z 867.3 (M+H)$^+$.

Step 6: (1S,3'R,6'R,8'E,11'S,12'R)-6-chloro-11'-methyl-12'-(2-(((2-methyl-2-propanyl)(diphenyl)silyl)oxy)ethyl)-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide The reaction was performed following the procedure for general method 1 (R$^1$═H). MS (ESI, +ve ion) m/z 865.3 (M+H)$^+$.

Step 7: (1S,3'R,6'R,7'R,8'E,11'S,12'R)-6-chloro-7'-(hydroxymethyl)-7'-methoxy-11'-methyl-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide The reaction was performed following the procedure for general method 3 (R$^4$═Me). MS (ESI, +ve ion) m/z 911.4 (M+H)$^+$.

Step 8: (1S,3'R,6'R,7'R,8'E,11'S,12'R)-6-chloro-7'-methoxy-11'-methyl-12'-(2-(((2-methyl-2-propanyl)(diphenyl)silyl)oxy)ethyl)-5'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide The reaction was performed following the procedure for general method 3 (R$^4$═Me). MS (ESI, +ve ion) m/z 909.3 (M+H)$^+$.

Step 9: (1S,3'R,6'R,7'R,8'E,11'S,12'R)-6-chloro-7'-methoxy-11'-methyl-12'-(2-(((2-methyl-2-propanyl)(diphenyl)silyl)oxy)ethyl)-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 359)

The reaction was performed following the procedure for general method 8. MS (ESI, +ve ion) m/z 1033.3 (M+H)$^+$.

Step 10: (1S,3'R,6'R,7'R,8'E,11'S,12'R)-6-chloro-12'-(2-hydroxyethyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 358)

(1S,3'R,6'R,7'R,8'E,11'S,12'R)-6-Chloro-7'-methoxy-11'-methyl-12'-(2-(((2-methyl-2-propanyl)(diphenyl)silyl)oxy)ethyl)-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 359) (38 mg, 0.037 mmol) was dissolved in THF (1.0 mL). Tetrabutylammonium fluoride (1.0 M in THF, 1.1 mL, 1.1 mmol) was then added and the reaction was stirred for 24 h to completion. The reaction mixture was then diluted with DCM and then loaded directly on a column to purify by medium pressure chromatography (silica, 0% to 100% (hold) (10% 2 M ammonia in MeOH:DCM):DCM) to give product that was contaminated with tetrabutylammonium fluoride. This material was then diluted with water (50 mL) and EtOAc (20 mL). The layers were then separated and the organic layer was then washed again with water (1×50 mL) to remove the residual tetrabutylammonium fluoride. The organic layer was then extracted with brine (1×15 mL) and dried over sodium sulfate. The slurry was filtered and the filtrate was concentrated to give (1S,3'R,6'R,7'R,8'E,11'S,12'R)-6-chloro-12'-(2-hydroxyethyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 358) (150 mg, 0.18 mmol, 61% yield). MS (ESI, +ve ion) m/z 795.3 (M+H)$^+$.

Step 11: 2-((1S,3'R,6'R,7'R,8'E,11'S,12'R)-6-chloro-7'-methoxy-11'-methyl-7'-((9aR)-octahydro-2H-pyrido[1,2-a]pyrazin-2-ylmethyl)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate (1S,3'R,6'R,7'R,8'E,11'S,12'R)-6-Chloro-12'-(2-hydroxyethyl)-7'-methoxy-11'-methyl-7'-((9aR)-octahydro-2H- pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 358) (50 mg, 0.063 mmol) was dissolved in DCM (3.0 mL) and the Hunig's Base (66 µL, 0.38 mmol) and mesyl chloride (21 µL, 0.26 mmol) were added. The reaction mixture was stirred for 1.5 h to completion. The mixture was then diluted with DCM (20 mL) and water (25 mL). The layers were separated and the organic layer was washed again with water (25 mL) and then was dried over sodium sulfate. The filtrate was concentrated to dryness under vacuum to give 2-((1S,3'R,6'R,7'R,8'E,11'S,12'R)-6-chloro-7'-methoxy-11'-methyl-7'-((9aR)-octahydro-2H-pyrido[1,2-a]pyrazin-2-ylmethyl)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate (63 mg). MS (ESI, +ve ion) m/z 873.3 (M+H)+.

Step 12: (1S,3'R,6'R,7'R,8'E,11'S,12'R)-6-chloro-12'-(2-(dimethylamino)ethyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 367)

2-((1S,3'R,6'R,7'R,8'E,11'S,12'R)-6-Chloro-7'-methoxy-11'-methyl-7'-((9aR)-octahydro-2H-pyrido[1,2-a]pyrazin-2-ylmethyl)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate (30 mg, 0.34 mmol), dimethylamine (2 M in THF, 0.17 mL, 0.34 mmol), potassium carbonate (95 mg, 0.69 mmol) and a catalytic amount of potassium iodide was dissolved in acetonitrile (1.0 mL) in a vial and sealed with a pressure cap. The reaction mixture was then heated to 65° C. for 40 min to completion. The reaction was then diluted with DCM and filtered through a fine glass frit. The filtrate was then concentrated and the residue was then purified by preparatory SFC chromatography (Kromasil Cyano 250 mm×21 mm column 17.5 g/minute MeOH (+20 mM ammonia)+52.5 g/minute CO2 on Thar 200 SFC; outlet pressure=100 bar; temperature=22° C.; wavelength=215 nm; used 1.0 mL injections of 31 mg/4 mL (7.8 mg/mL) sample solution of MeOH (4 mL) to give (1S,3'R,6'R,7'R,8'E,11'S,12'R)-6-chloro-12'-(2-(dimethylamino)ethyl)-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 367) (4.7 mg, 5.7 mmol, 17% yield) as the slower eluting peak ($t_R$=2.90 minutes on analytical SFC; Kromasil Cyano column 25% MeOH in CO2) with 97.8% purity. MS (ESI, +ve ion) m/z 822.3 (M+H)+.

Examples 399 and 400

(1S,3'R,6'R,7'R,9"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[16,18,24]triene-7',3"-[1,4]oxazino[3,4-c][1,4]oxazin]-15'-one 13',13'-dioxide AND (1S,3'R,6'R,7'S,9a"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[16,18,24]triene-7',3"-[1,4]oxazino[3,4-c][1,4]oxazin]-15'-one 13',13'-dioxide

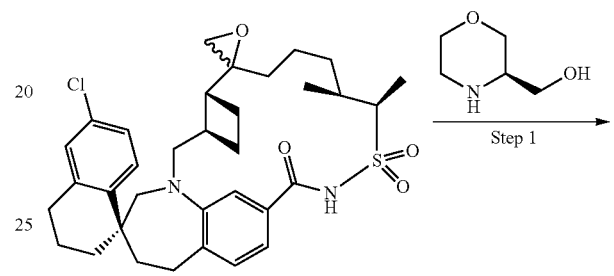

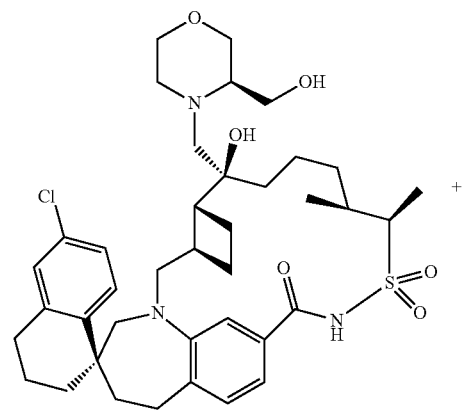

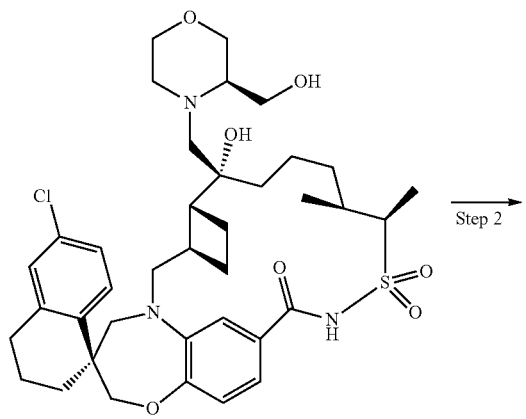

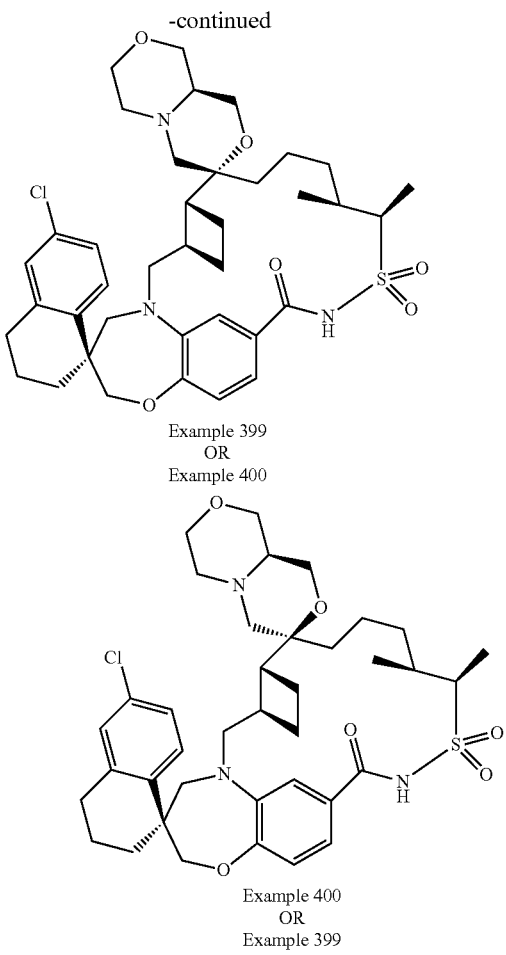

Example 399
OR
Example 400

Example 400
OR
Example 399

Step 1: (1S,3'R,6'R,7'R,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND (1S,3'R,6'R,7'S,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide A glass microwave reaction vessel was charged with (1S,3'R,6'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2"-oxiran]-15'-one 13',13'-dioxide (0.300 g, 0.489 mmol) and 3(R)-hydroxymethylmorpholine (0.650 g, 5.55 mmol; Matrix Sci., Elgin, S.C.). Ethanol (3 mL) and triethylamine (1.8 mL, 12.9 mmol) were added, the reaction mixture was sealed under argon, and heated in an Initiator microwave reactor at 90° C. for a total of 27 h. The reaction was heated at 90° C. in the microwave for another 16 h. The reaction mixture was purified by reverse-phase HPLC (Gilson; Gemini-NX 10 μm, C18, AXIA, 100×50 mm column) eluting with 0.1% TFA-H₂O:0.1% TFA CH₃CN (9:1-1:9). The fractions containing the desired product were combined and partitioned between pH 7 buffer (1 M K₂HPO₄/KH₂PO₄)/EtOAc. The aqueous layer was extracted with EtOAc (3×) and the combined organic layers were washed with brine, dried over Na₂SO₄ and filtered. The filtrate was concentrated under reduced pressure to give a mixture of (1S,3'R,6'R,7'R,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide and (1S,3'R,6'R,7'S,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (177 mg, 50%) as a white crystalline solid.

Step 2: (1S,3'R,6'R,7'R,9a"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[16,18,24]triene-7',3"-[1,4]oxazino[3,4-c][1,4]oxazin]-15'-one 13',13'-dioxide AND (1S,3'R,6'R,7'S,9a"S,11'S,12'R)-6-chloro-11',12'-dimethyl-3,4,6",7",9",9a"-hexahydro-1"H,2H,15'H-dispiro[naphthalene-1,22'-[20]oxa[13]thia[1,14]diazatetracyclo[14.7.2.0~3,6~.0~19,24~]pentacosa[16,18,24]triene-7',3"-[1,4]oxazino[3,4-c][1,4]oxazin]-15'-one 13',13'-dioxide To a room temperature mixture of (1S,3'R,6'R,7'R,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide and (1S,3'R,6'R,7'S,11'S,12'R)-6-chloro-7'-hydroxy-7'-(((3R)-3-(hydroxymethyl)-4-morpholinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (0.136 g, 0.186 mmol) in tetrahydrofuran (4 mL) was added sodium hydride, 60% dispersion in mineral oil (0.050 g, 1.250 mmol) and the reaction was stirred for 30 min. To the reaction was added p-toluenesulfonic anhydride (0.250 g, 0.766 mmol) and the reaction was stirred for 5.5 h. To the reaction was added sodium hydride, 60% dispersion in mineral oil (0.050 g, 1.250 mmol) and the reaction was stirred overnight. To the reaction was added p-toluenesulfonic anhydride (0.180 g) and the reaction was stirred for 24 h. To the reaction was added sodium hydride, 60% dispersion in mineral oil (0.050 g, 1.25 mmol) and the reaction was stirred for another 24 h. The reaction was quenched with pH 7 buffer (1 M K₂HPO₄/KH₂PO₄) and the aqueous layer was extracted with EtOAc (3×). The combined organic layers were washed with brine and the filtrate was purified by reverse-phase HPLC (Gilson; Gemini-NX 10 μm, C18, AXIA, 100×50 mm column) eluting with 0.1% TFA-H₂O:0.1% TFA CH₃CN (9:1→1:9). The fractions containing the desired product were combined and partitioned between pH 7 buffer (1 M K₂HPO₄/KH₂PO₄)/EtOAc. The aqueous layer was extracted with EtOAc (3×) and the combined organic layers were washed with brine, dried over Na₂SO₄ and filtered. The filtrate was concentrated under reduced pressure to give 118 mg (89%) of a white solid. The material was purified by achiral SFC chromatography to give (1S,3'R,6'R,7'R,9a"S,11'S,12'R)-6-chloro-11',12'-dimethyl-3,4,6",7",9",9a"-hexahydro-1"H, 2H,15'H-dispiro[naphthalene-1,22'-[20]oxa[13]thia[1,14]
diazatetracyclo[14.7.2.0~3,6~.0~19,24~]pentacosa[16,18,
24]triene-7',3"-[1,4]oxazino[3,4-c][1,4]oxazin]-15'-one 13',
13'-dioxide OR (1S,3'R,6'R,7'S,9a"S,11'S,12'R)-6-chloro-
11',12'-dimethyl-3,4,6",7",9",9a"-hexahydro-1"H,2H,15'H-
dispiro[naphthalene-1,22'-[20]oxa[13]thia[1,14]
diazatetracyclo[14.7.2.0~3,6~.0~19,24~]pentacosa[16,18,
24]triene-7',3"-[1,4]oxazino[3,4-c][1,4]oxazin]-15'-one 13',
13'-dioxide (10 mg, 8%, first eluted peak) as a white
crystalline solid. m/z (ESI, +ve ion) 712.7 (M+1)⁺. A second
eluting compound was isolated as (1S,3'R,6'R,7'R,9a"S,
11'S,12'R)-6-chloro-11',12'-dimethyl-3,4,6",7",9",9a"-hexa-
hydro-1"H,2H,15'H-dispiro[naphthalene-1,22'-[20]oxa[13]
thia[1,14]diazatetracyclo[14.7.2.0~3,6~.0~19,24~]
pentacosa[16,18,24]triene-7',3"-[1,4]oxazino[3,4-c][1,4]
oxazin]-15'-one 13',13'-dioxide OR (1S,3'R,6'R,7'S,9a"S,
11'S,12'R)-6-chloro-11',12'-dimethyl-3,4,6",7",9",9a"-
hexahydro-1"H,2H,15'H-dispiro[naphthalene-1,22'-[20]oxa
[13]thia[1,14]diazatetracyclo[14.7.2.0~3,6~.0~19,24~]
pentacosa[16,18,24]triene-7',3"-[1,4]oxazino[3,4-c][1,4]
oxazin]-15'-one 13',13'-dioxide (12 mg, 9%, second eluted
peak) as a white crystalline solid. (ESI, +ve ion) m/z 712.6
(M+1)⁺.

Example 405

(1S,3'R,6'R,7'S,10'S,11'S)-6-chloro-7'-((9aS)-hexa-
hydropyrazino[2,1-c][1,4]oxazin-8(1H)-ylmethyl)-
7'-hydroxy-10',11'-dimethyl-3,4-dihydro-2H,15'H-
spiro[naphthalene-1,22'-[20]oxa[13]thia[1,14]
diazatetracyclo[14.7.2.0~3,6~.0~19,24~]pentacosa
[16,18,24]trien]-15'-one 13',13'-dioxide

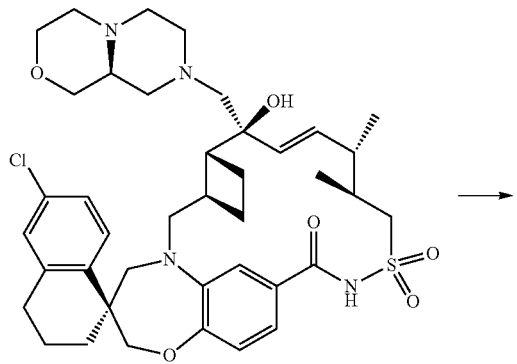

A vial was charged with (1S,3'R,6'R,7'S,8'E,10'S,11'S)-
6-chloro-7'-((9aS)-hexahydropyrazino[2,1-c][1,4]oxazin-8
(1H)-ylmethyl)-7'-hydroxy-10',11'-dimethyl-3,4-dihydro-
2H,15'H-spiro[naphthalene-1,22'-[20]oxa[13]thia[1,14]
diazatetracyclo[14.7.2.0~3,6~.0~19,24~]pentacosa[8,16,18,
24]tetraen]-15'-one 13',13'-dioxide (0.012 g, 0.016 mmol)
and platinum (IV) oxide (0.4 mg, 1.6 μmol). Ethanol (2 mL)
and methanol (0.3 mL) were added. The reaction was
flushed with nitrogen for 5 min then evacuated/backfilled
with hydrogen three times. The reaction was stirred under 20
psi hydrogen at room temperature overnight. The reaction
was flushed with nitrogen. Methanol (5 mL) and DCM (5
mL) were added. The reaction was flushed with nitrogen
then evacuated/backfilled with hydrogen three times. The
reaction was stirred under 20 psi hydrogen at room tem-
perature for 24 h. The reaction was flushed with nitrogen and
filtered through celite rinsing with ethyl acetate. The filtrate
was concentrated under reduced pressure and purified by
silica gel flash chromatography using a gradient of 0% to
10% MeOH in DCM to afford the title compound (0.007 g,
9 μmol, 58% yield). MS (ESI, +ve ion) m/z 755.2 (M+H)⁺.

Example 466

(1S,3'R,6'R,7'R,11'S,12'R)-6-CHLORO-11',12'-DI-
METHYL-4'-(METHYLSULFONYL)-3,4-DI-
HYDRO-2H,15'H-DISPIRO[NAPHTHALENE-1,
22'-[20]OXA[13]THIA[1,14]
DIAZATETRACYCLO[14.7.2.0~3,6~.0~19,24~]
PENTACOSA[16,18,24]TRIENE-7',2"-[1,4]
OXAZINAN]-15'-ONE 13',13'-DIOXIDE AND
(1S,3'R,6'R,7'S,11'S,12'R)-6-CHLORO-11',12'-DIM-
ETHYL-4"-(METHYLSULFONYL)-3,4-DI-
HYDRO-2H,15'H-DISPIRO[NAPHTHALENE-1,
22'-[20]OXA[13]THIA[1,14]
DIAZATETRACYCLO[14.7.2.0~3,6~.0~19,24~]
PENTACOSA[16,18,24]TRIENE-7',2"-[1,4]
OXAZINAN]-15'-ONE 13',13'-DIOXIDE

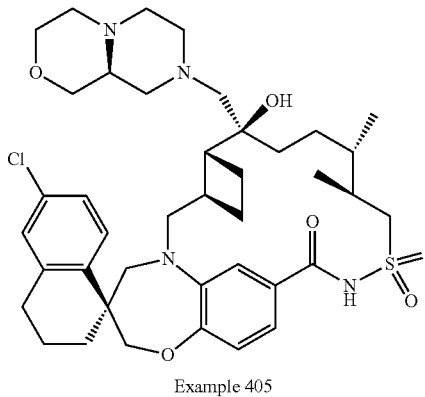

Example 405

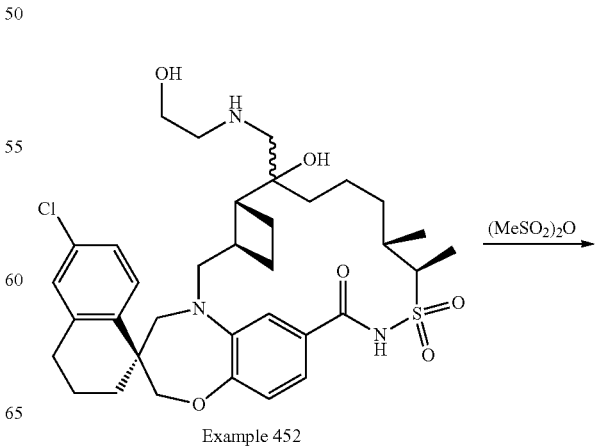

Example 452

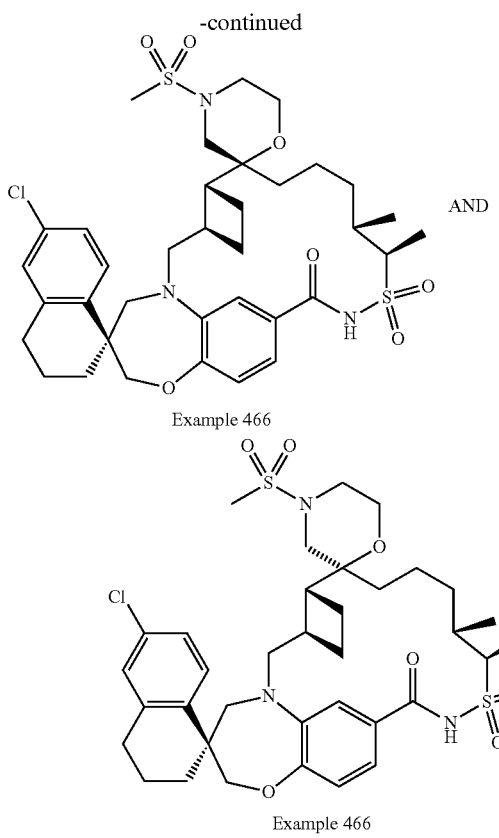

Example 466

Example 466

To a stirred solution of (1S,3'R,6'R,7'R,11'S,12'R)-6-chloro-7'-hydroxy-7'-(((2-hydroxyethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND (1S,3'R,6'R,7'S,11'S,12'R)-6-chloro-7'-hydroxy-7'-(((2-hydroxyethyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (Example 452) (34 mg, 0.043 mmol) in THF (1.5 mL) in a microwave reaction vessel was added at room temperature, diisopropylethylamine (0.075 mL, 0.431 mmol) under argon followed by methanesulfonic anhydride (37.6 mg, 0.216 mmol). The resulting mixture was stirred at room temperature for 5 min during which the color of the mixture changed from colorless to light greenish yellow. The vessel was capped and subjected to microwave reaction irradiation (3 h at 70° C.). 4-(Dimethylamino) pyridine (15.81 mg, 0.129 mmol) was then added followed by more methanesulfonic anhydride (18 mg, 0.11 mmol). The vessel was sealed and again subjected to microwave irradiation (4 h at 70° C.). The volatiles were removed and the concentrate was dissolved in DMSO and purified by preparative reverse-phase HPLC (Gemini™ Prep C18 5 µm column; Phenomenex, Torrance, Calif.; gradient elution of 30% to 95% MeCN in water, where both solvents contain 0.1% TFA, 25 min method) to provide, after lyophilization, 4.0 mg of (1S,3'R,6'R,7'R,11'S,12'R)-6-chloro-11',12'-dimethyl-4''-(methylsulfonyl)-3,4-dihydro-2H,15'H-dispiro[naphthalene-1,22'-[20]oxa[13]thia[1,14]diazatetracyclo[14.7.2.0~3,6~.0~19,24~]pentacosa[16,18,24 ]triene-7',2''-[1,4]oxazinan]-15'-one 13',13'-dioxide AND (1S,3'R,6'R,7'S,11'S,12'R)-6-chloro-11',12'-dimethyl-4''-(methylsulfonyl)-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-[1,4]oxazinan]-15'-one 13',13'-dioxide as a white solid. MS (ESI, +ve ion) m/z 734.2 (M+1)⁺.

Examples 499 and 500

METHYL 3-((9AR)-8-(((1S,3'R,6'R,7'R,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-7'-YL)METHYL)OCTAHYDRO-2H-PYRAZINO[1,2-A]PYRAZIN-2-YL)PROPANOATE AND METHYL 3-((9AR)-8-(((1S,3'R,6'R,7'S,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-7'-YL)METHYL)OCTAHYDRO-2H-PYRAZINO[1,2-A]PYRAZIN-2-YL)PROPANOATE AND METHYL 3-((9AS)-8-(((1S,3'R,6'R,7'R,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-7'-YL)METHYL)OCTAHYDRO-2H-PYRAZINO[1,2-A]PYRAZIN-2-YL)PROPANOATE AND METHYL 3-((9AS)-8-(((1S,3'R,6'R,7'S,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-7'-YL)METHYL)OCTAHYDRO-2H-PYRAZINO[1,2-A]PYRAZIN-2-YL)PROPANOATE (Example 499) AND (1S,3'R,6'R,7'R,11'S,12'R)-7'-(((9AR)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-15'-ONE 13',13'-DIOXIDE AND (1S,3'R,6'R,7'S,11'S,12'R)-7'-(((9AS)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-15'-ONE 13',13'-DIOXIDE AND (1S,3'R,6'R,7'S,11'S,12'R)-7'-(((9AR)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENT ACOSA[16,18,24]TRIEN]-15'-ONE 13',13'-DIOXIDE AND (1S,3'R,6'R,7'S,11'S,12'R)-7'-(((9AS)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]

PENTACOSA[16,18,24]TRIEN-15'-ONE 13',13'-DIOXIDE (Example 500)
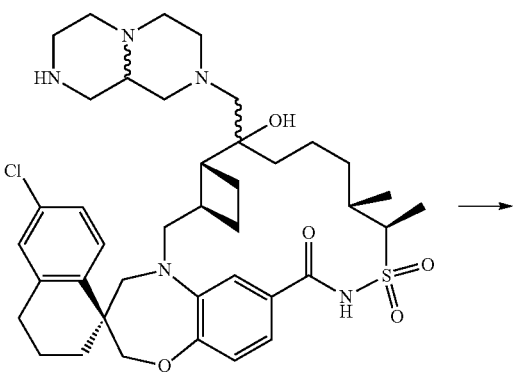
Example 479
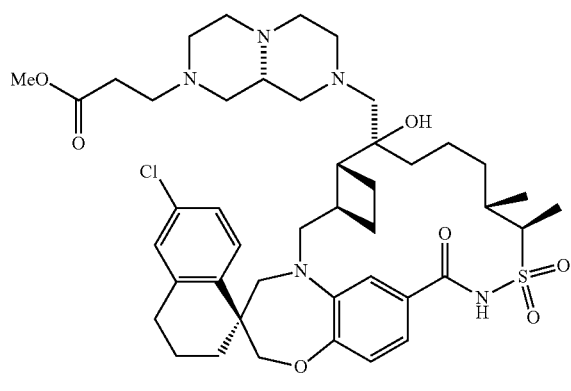
AND
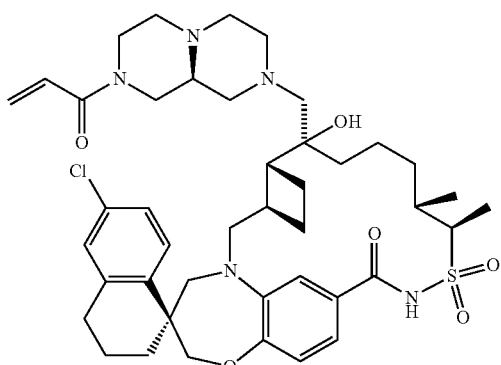
AND
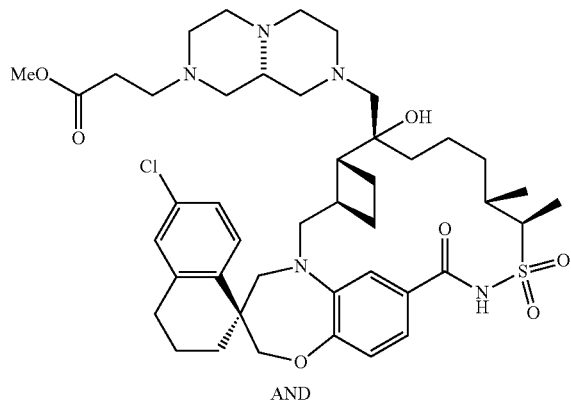
AND
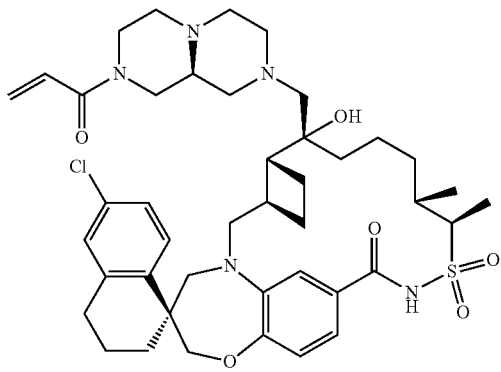
AND
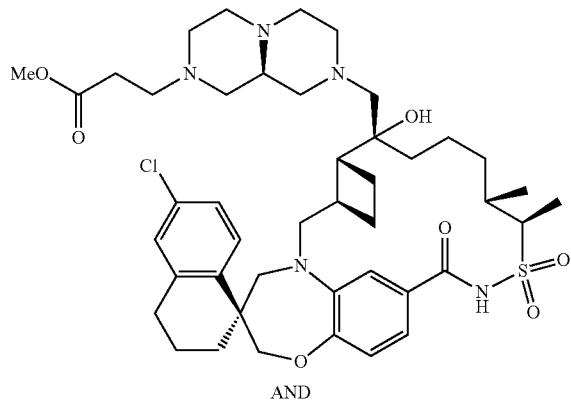
AND
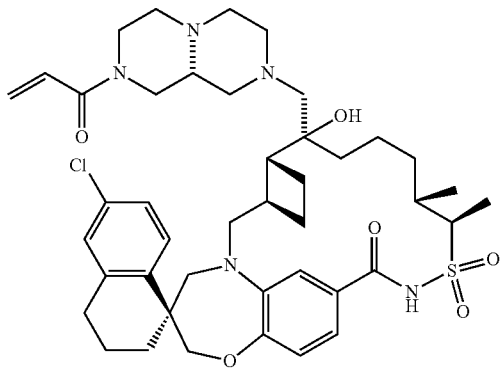
AND

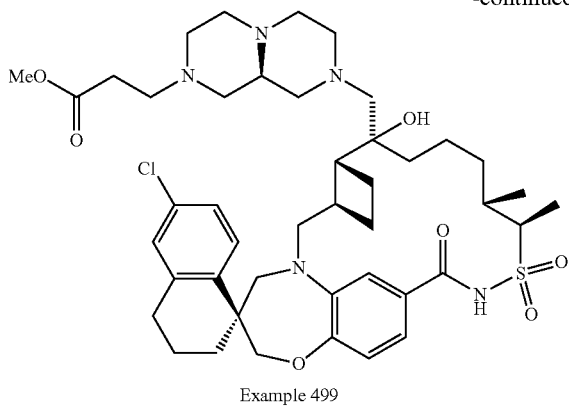

Example 499

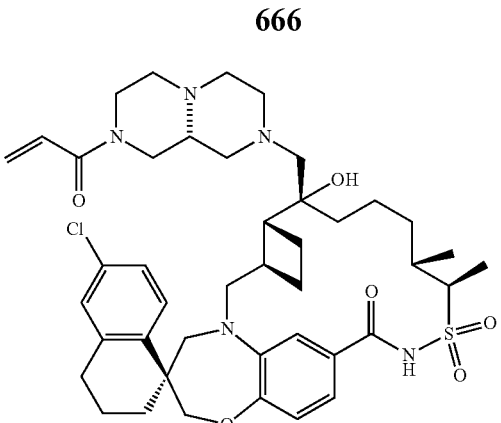

Example 500

To a stirred solution of (1S,3'R,6'R,7'R,11'S,12'R)-6-chloro-7'-hydroxy-11',12'-dimethyl-7'-((9aR)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (1S,3'R,6'R,7'R,11'S,12'R)-6-chloro-7'-hydroxy-11',12'-dimethyl-7'-((9aS)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (1S,3'R,6'R,7'S,11'S,12'R)-6-chloro-7'-hydroxy-11',12'-dimethyl-7'-((9aR)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo [14.7.2.0~3,6~.0~19,24~]pentacosa[16,18,24]trien]-15'-one 13',13'-dioxide (1S,3'R,6'R,7'S,11'S,12'R)-6-chloro-7'-hydroxy-11',12'-dimethyl-7'-((9aS)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (Example 479) (0.15 g, 0.199 mmol) and diisopropylethylamine (1.5 mL, 8.62 mmol) in DCM (10 mL) was added at room temperature acrylic acid n-hydroxysuccinimide ester (0.303 g, 1.789 mmol) in one portion as a solid. The resulting mixture was stirred at room temperature for 3 h. MeOH (8 mL) was added to the reaction mixture. The resulting mixture was stirred at room temperature for 20 min before concentrated in vacuo. The crude residue was directly loaded onto a silica gel precolumn (25 g) and subjected to combi-flash column chromatography on a 12 g ISCO gold column eluting with 1% to 20% MeOH/DCM to give 30 mg of impure product mixture, which was subjected to preparative reverse-phase HPLC (Gemini™ Prep C18 10 μm column; Phenomenex, Torrance, Calif.; gradient elution of 20% to 90% MeCN in water, where both solvents contain 0.1% TFA, a 15-min gradient in a 24-min method) to give, after lyophilization, 18.5 mg of METHYL 3-((9AR)-8-(((1S,3'R,6'R,7'R,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-7'-YL)METHYL)OCTAHYDRO-2H-PYRAZINO[1,2-A]PYRAZIN-2-YL)PROPANOATE AND METHYL 3-((9AR)-8-(((1S,3'R,6'R,7'S,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO [14.7.2.0~3,6~.0~19,24~] PENTACOSA[16,18,24]TRIEN]-7'-YL)METHYL) OCTAHYDRO-2H-PYRAZINO[1,2-A]PYRAZIN-2-YL) PROPANOATE AND METHYL 3-((9AS)-8-(((1S,3'R,6'R,7'R,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-7'-YL)METHYL)OCTAHYDRO-2H-PYRAZINO[1,2-A]PYRAZIN-2-YL)PROPANOATE AND METHYL 3-((9AS)-8-(((1S,3'R,6'R,7'S,11'S,12'R)-6-CHLORO-7'-HYDROXY-11',12'-DIMETHYL-13',13'-DIOXIDO-15'-OXO-3,4-DIHYDRO-2H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-7'-YL)METHYL)OCTAHYDRO-2H-PYRAZINO[1,2-A]PYRAZIN-2-YL)PROPANOATE (EXAMPLE 499) in an approximately 1-to-1-to-1-to-1 epimeric mixture. MS (ESI, +ve ion) m/z 841.0 (M+1)⁺. In addition, (1S,3'R,6'R,7'R,11'S,12'R)-7'-(((9AR)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-15'-ONE 13',13'-DIOXIDE AND (1S,3'R,6'R,7'R,11'S,12'R)-7'-(((9AS)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-15'-ONE 13',13'-DIOXIDE AND (1S,3'R,6'R,7'S,11'S,12'R)-7'-(((9AR)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-15'-ONE 13',13'-DIOXIDE AND (1S,3'R,6'R,7'S,11'S,12'R)-7'-(((9AS)-8-ACRYLOYLOCTAHYDRO-2H-PYRAZINO[1,2-A]PYRAZIN-2-YL)METHYL)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[16,18,24]TRIEN]-15'-ONE 13',13'-DIOXIDE (EXAMPLE 500) was isolated as a white solid in a 1-to-1-to-1-to-1 epimeric mixture. MS (ESI, +ve ion) m/z 808.8 (M+1)⁺.

Example 507

(1S,3'R,6'R,7'S,11'S,12'R)-7'-(aminomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'S,11'S,12'R)-7'-(aminomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide

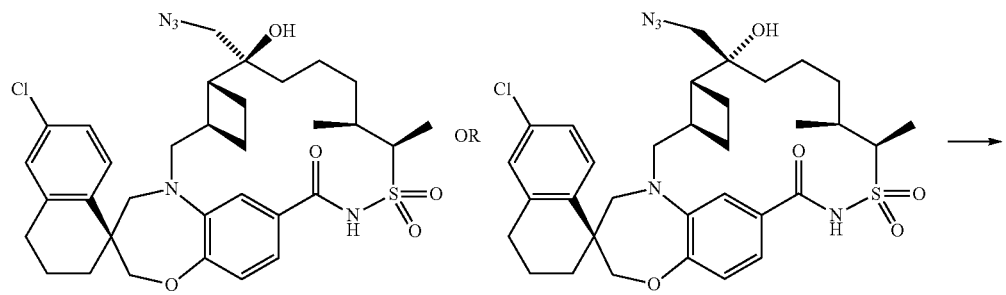

Example 506

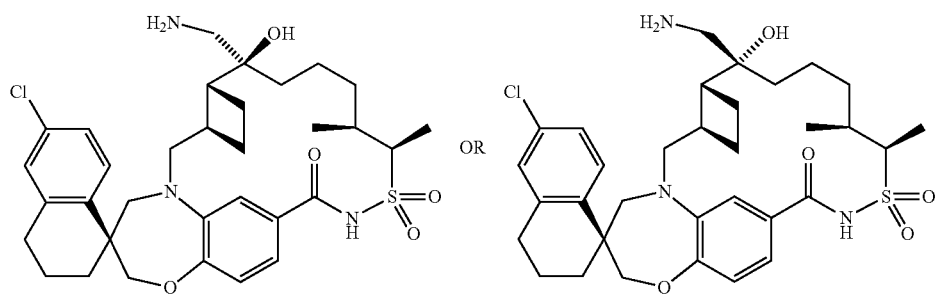

Example 507

(1S,3'R,6'R,7'S,11'S,12'R)-7'-(Azidomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'S,11'S,12'R)-7'-(azidomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (Example 506) (36.0 mg, 0.055 mmol) was dissolved in ethyl acetate (5.0 mL) and platinum(IV) oxide (2.49 mg, 11.0 μmol) was added. The reaction vessel was filled with hydrogen to 15 psi and stirred vigorously for 2.5 h. MeOH (1.5 mL) was added and the reaction vessel was again filled with hydrogen (15 psi) and stirred overnight. The slurry was filtered and the precipitate was washed with DMSO to ensure that no product was remaining on the catalyst. The filtrate was concentrated. The crude material was purified by reverse-phase preparative HPLC using a Phenomenex Gemini column, 10 μm, C18, 100 Å, 150×30 mm, 0.1% TFA in $CH_3CN/H_2O$, gradient 20% to 85% over 30 min to provide (1S,3'R,6'R,7'S,11'S,12'R)-7'-(aminomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'S,11'S,12'R)-7'-(aminomethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (32 mg, 0.037 mmol, 68% yield) as a di-TFA salt. MS (ESI, +ve ion) m/z 630.2 $(M+H)^+$.

Examples 517 and 518

(1S,3'R,6'R,7'R,11'S,12'R)-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND (1S,3'R,6'R,7'R,11'S,12'R)-6-chloro-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide

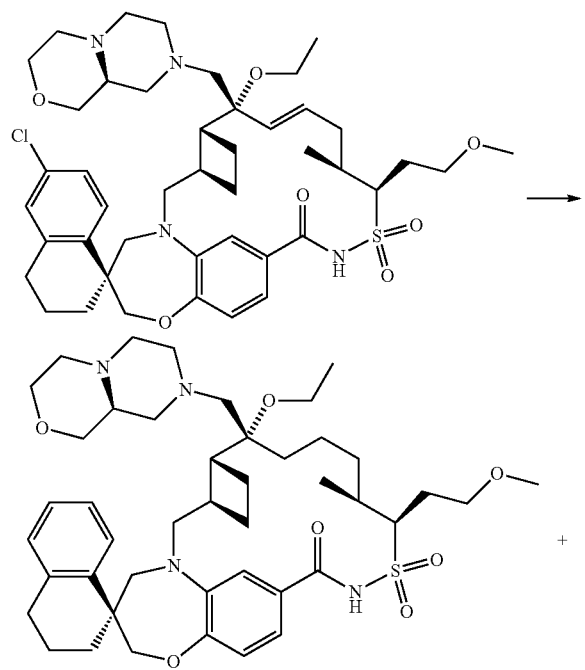

Example 517

Example 518

A reaction vessel was charged with platinum (IV) oxide (18.6 mg, 0.082 mmol), then placed in a Biotage Endeavor and treated with a solution of (1S,3'R,6'R,7'R,8'E,11'S,12'R)-6-chloro-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (128 mg) in EtOAc (3 mL). The vessel was purged with Ar (3×), then pressurized to 200 psi with $H_2$ and stirred (250 RPM) at 80° C. for 20 h. The vessel was cooled to room temperature and purged with Ar (3×), then filtered through a celite pad that was rinsed liberally with EtOAc. The filtrate was concentrated in vacuo and purified by reverse-phase preparative HPLC (Shimadzu) on a Phenomenex Luna column (5 μm, C18, 110 Å, Axia, 150 mm×21.2 mm) eluting at 30 mL/min with a linear gradient of 25% to 100% MeCN (0.1% TFA) in water (0.1% TFA) over 20 min. The desired fractions were poured into 10% $Na_2CO_3$ and extracted with DCM (2×5 mL). The combined organic layers were dried over $MgSO_4$ and concentrated in vacuo to afford (1S,3'R,6'R,7'R,11'S,12'R)-6-chloro-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (Example 518) (32.8 mg, 0.040 mmol, 13% yield) as a white solid. MS (ESI, +ve ion) m/z 827.2 (M+H)+. In addition, (1S,3'R,6'R,7'R,11'S,12'R)-7'-ethoxy-7'-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (Example 517) was isolated as an earlier eluting peak (12.9 mg, 0.016 mmol, 6% yield) as a white solid. MS (ESI, +ve ion) m/z 793.3 (M+H)+.

Example 519

(1S,3'R,6'R,7'R,11'S,12'R)-6-chloro-7'-ethoxy-12'-(2-methoxyethyl)-11'-methyl-7'-(((3R)-3-methyl-4-(2-propanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide

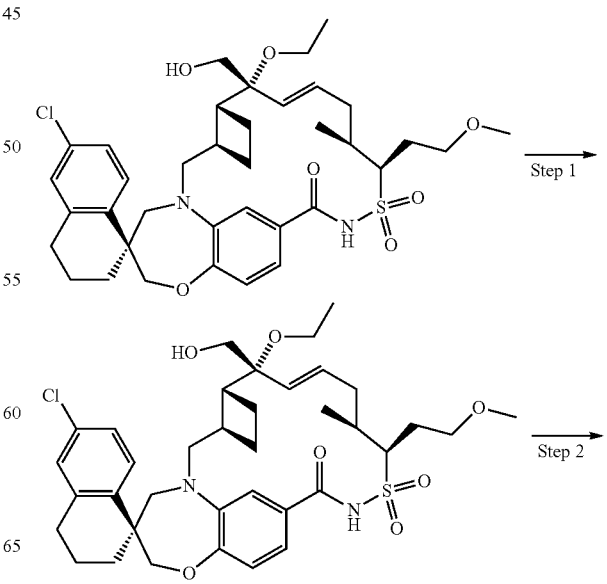

-continued

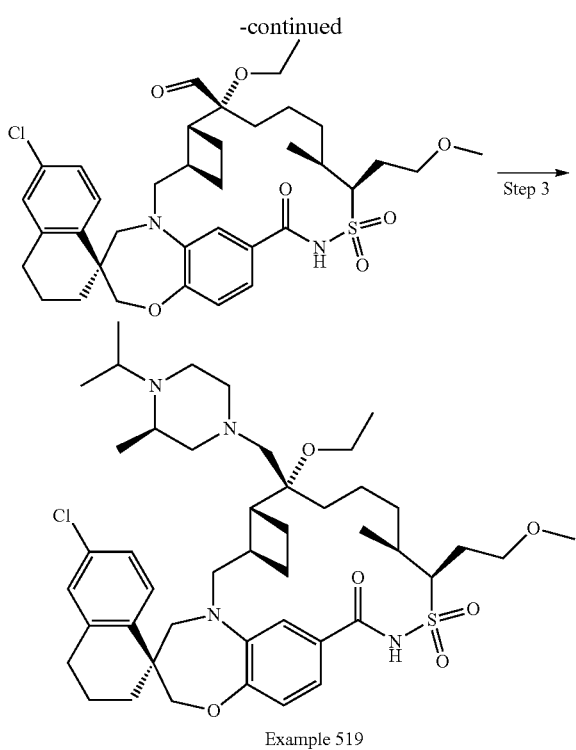

Example 519

Step 1: (1S,3'R,6'R,7'R,11'S,12'R)-6-chloro-7'-ethoxy-7'-(hydroxymethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide A reaction vessel was charged with sulfided Pt on carbon (5% wt %, 54.2 mg, 0.295 mmol), then placed in the Biotage Endeavor and treated with a solution of (1S,3'R,6'R,7'R,8'E,11'S,12'R)-6-chloro-7'-ethoxy-7'-(hydroxymethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide [derived from methods analogous to General Method 3, steps 1-2 using (1S,3'R,6'R,8'E,11'S,12'R)-6-chloro-12'-(2-methoxyethyl)-11'-methyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide] (207 mg, 0.295 mmol) in EtOAc (3.25 mL). The vessel was purged with Ar (3×), then pressurized to 200 psi with H$_2$ and stirred (250 RPM) at 80° C. for 20 h. The vessel was cooled to room temperature and purged with Ar (3×), then filtered through a celite pad that was rinsed liberally with EtOAc. The filtrate was concentrated in vacuo to afford (1S,3'R,6'R,7'R,11'S,12'R)-6-chloro-7'-ethoxy-7'-(hydroxymethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (196 mg, 0.279 mmol, 94% yield) as a white solid. MS (ESI, +ve ion) m/z 703.3 (M+H)$^+$.

Step 2: (1S,3'R,6'R,7'R,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide To an ice bath cooled solution of (1S,3'R,6'R,7'R,11'S,12'R)-6-chloro-7'-ethoxy-7'-(hydroxymethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (161 mg, 0.229 mmol) in DCM (10 mL) was added 0.3 M Dess-Martin Periodinane in DCM (1.0 mL, 0.300 mmol) dropwise over 2 min. After 1.5 h, LC-MS suggests about 60% conversion, the reaction was treated with another 0.9 mL of 0.3 M Dess-Martin Periodinane in DCM dropwise over 1 min. After a further 2.5 h, LC-MS suggests complete conversion. The reaction was treated with 5 mL of saturated sodium bisulfite and stirred for 20 min. The reaction was poured into water (15 mL) and the organic layer separated. The aqeuous layer was extracted with DCM (1×5 mL). The combined organic layers were concentrated in vacuo and adsorbed onto a plug of silica gel and chromatographed through a Redi-Sep® pre-packed silica gel column (Gold, 12 g), eluting with 0% to 25% EtOAc in heptanes, to afford (1S,3'R,6'R,7'R,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide (105 mg, 0.150 mmol, 65.4% yield) as a white solid. MS (ESI, +ve ion) m/z 701.2 (M+H)$^+$.

Step 3: (1S,3'R,6'R,7'R,11'S,12'R)-6-chloro-7'-ethoxy-12'-(2-methoxyethyl)-11'-methyl-7'-(((3R)-3-methyl-4-(2-propanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide To a round bottom flask was charged the TFA salt of (R)-1-isopropyl-2-methylpiperazine (68.2 mg, 0.285 mmol) and (1S,3'R,6'R,7'R,11'S,12'R)-6-chloro-7'-ethoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide (50 mg, 0.071 mmol) in DCE (2 mL) and N,N-diisopropylethylamine (0.1 mL, 0.574 mmol). After 1.5 h, the solution was treated with sodium triacetoxyborohydride (6 mg). After a further 3 h, the reaction was treated with more sodium triacetoxyborohydride (7 mg). After a further 16 h, the reaction was again treated with sodium triacetoxy borohydride (6 mg). The reaction was monitored by LC-MS and sodium triacetoxyborohydride added in 5-10 mg portions until reaction was judged complete. After a further 24 h, the reaction was diluted with DCE (3 mL). After 4 d, the reaction was treated with acetic acid (12 µL, 0.208 mmol). After a further 24 h, more acetic acid (18 µL) was added. After a further 24 h, the reaction was treated with another 30 mg of amine. After a further 96 h, the reaction was treated with larger portions of sodium triacetoxyborohydride to drive reaction to desired product or the alcohol resulting from reduced aldehyde. LC-MS suggests no further progress, the reaction was quenched with water and the aqeuous layer extracted with DCM (2×10 mL). The combined DCM layers were concentrated in vacuo and adsorbed onto a plug of silica gel and chromatographed through a Redi-Sep® pre-packed silica gel column (Gold, 12 g), eluting with 0% to 80% EtOAc:EtOH (3:1) in heptanes, to afford (1S,3'R,6'R,7'R,11'S,12'R)-6-chloro-7'-ethoxy-12'-(2-methoxyethyl)-11'-methyl-7'-(((3R)-3-methyl-4-(2-propanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (24.2 mg, 0.029 mmol, 41.0% yield) as a white solid. MS (ESI, +ve ion) m/z 827.4 (M+H)$^+$.

Table 1 lists compounds prepared by the General Methods outlined in the present specification

TABLE 1

Examples Prepared by the General Methods

| Example Number | Starting Materials | General Method | Product Structure | Product Name | MS Data (M + 1)+ |
|---|---|---|---|---|---|
| 22 | | 5, 12 | | (1S,3'R,6'R,7'S,8'E,11'S,12'S)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 812.4 |
| 23 | | 5, 12 | | (1S,3'R,6'R,7'S,8'E,11'S,12'R)-6-chloro-7'-methoxy-12'-(2-methoxyethyl)-11'-methyl-7'-((4-(3-oxetanyl)-1-piperazinyl)methyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one | 812.2 |

TABLE 1-continued

Examples Prepared by the General Methods

| Example Number | Starting Materials | General Method | Product Structure | Product Name | MS Data (M + 1)+ |
|---|---|---|---|---|---|
| 24 | 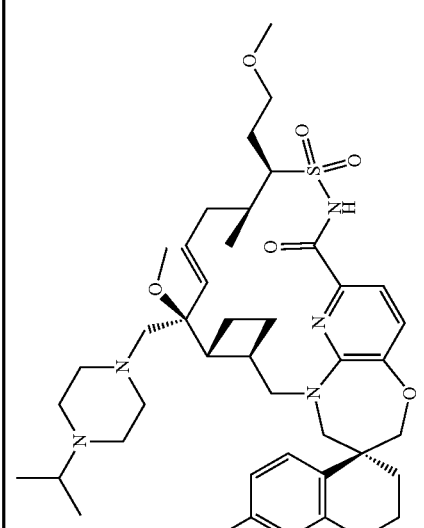 MeI <br> (Combi-Blocks) | 5, 12 | 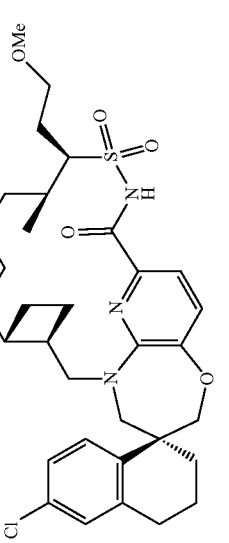 | (1S,3'R,6R,7S,8E,11S,12'R)-6-chloro-7'-methoxy-12'-(2-methoxyethyl)-11'-methyl-7'-((4-(1-methylethyl)-1-piperazinyl)methyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 798.2 |

TABLE 1-continued

Examples Prepared by the General Methods

| Example Number | Starting Materials | General Method | Product Structure | Product Name | MS Data (M + 1)+ |
|---|---|---|---|---|---|
| 25 | 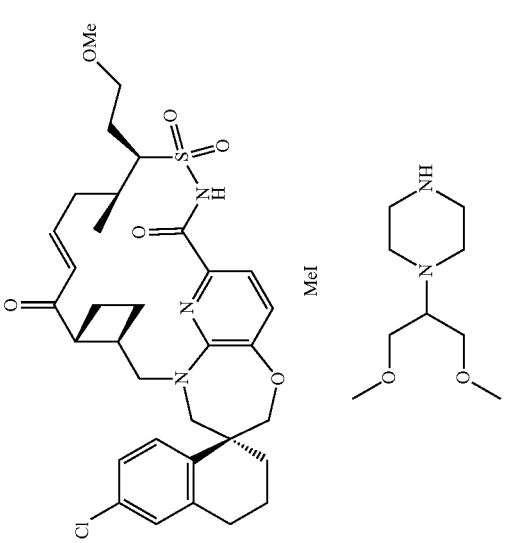 (FCH Group) | 5, 12 | 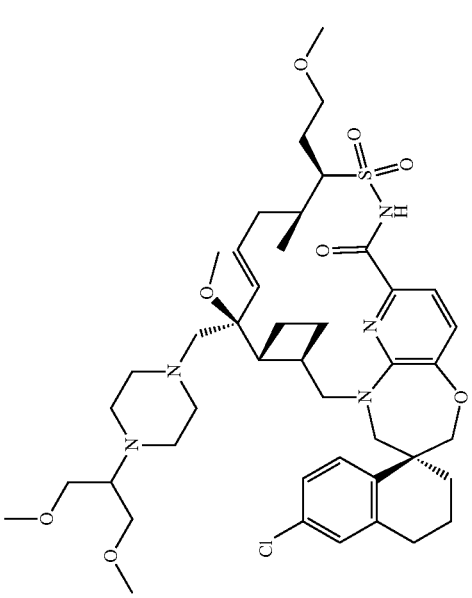 | (1S,3'R,6'R,7S,8'E,11'S,12'R)-6-chloro-7'-methoxy-12'-(2-methoxyethyl)-7'-((4-(2-methoxy-1-(methoxymethyl)ethyl)-1-piperazinyl)methyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 858.4 |

TABLE 1-continued

Examples Prepared by the General Methods

| Example Number | Starting Materials | General Method | Product Structure | Product Name | MS Data (M + 1)+ |
|---|---|---|---|---|---|
| 26 |  MeI (Enamine) | 5, 12 |  | (1S,3'R,6'R,7S,8'E,11'S,12'R)-6-chloro-7'-methoxy-12'-(2-methoxyethyl)-11'-methyl-7'-((4-((5-methyl-1,2,4-oxadiazol-3-yl)methyl)-1-piperazinyl)methyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 852.4 |

TABLE 1-continued

Examples Prepared by the General Methods

| Example Number | Starting Materials | General Method | Product Structure | Product Name | MS Data (M + 1)+ |
|---|---|---|---|---|---|
| 27 | | 5, 12 | | (1S,3R,6R,7S,8E,11S,12R)-6-chloro-7'-methoxy-7'-((4-(2-methoxy-1,1-dimethylethyl)-1-piperazinyl)methyl)-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 842.4 |
| 28 | | 1 (R¹ = H), 5, 8 | | (1S,3R,6R,7S,8E,12R)-6-chloro-12'-ethyl-7'-((9aS)-hexahydropyrazino[2,1-c][1,4]oxazin-8(1H)-ylmethyl)-7'-methoxy-3,4-dihydro-2H,15'H-spiro[naphthalene-1,22'-[20]oxa[13]thia[1,14]diazatetracyclo[14.7.2.0-3,6.0~19,24~]pentacosa[8,16,18,24]tetraen]-15'-one 13',13'-dioxide | 767.2 |

TABLE 1-continued

Examples Prepared by the General Methods

| Example Number | Starting Materials | General Method | Product Structure | Product Name | MS Data (M + 1)+ |
|---|---|---|---|---|---|
| 29 | | 1 (R¹ = H), 5, 8 | | (1S,3'R,6'R,7'S,8'E,12'R)-6-chloro-12'-ethyl-7'-methoxy-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.2 |

| Example Number | Starting Materials | General Method | Product Structure | Product Name | MS Data (M + 1)+ |
|---|---|---|---|---|---|
| 30 | 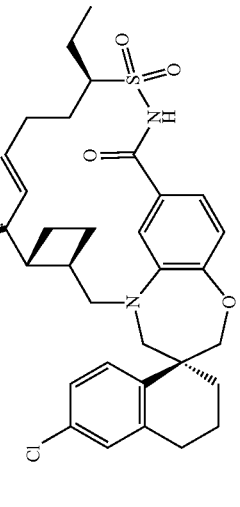 | 1 (R[1] = H), 5, 8 | 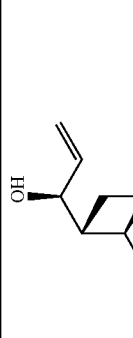 | (1S,3'R,6'R,7'R,8'E,12'R)-6-chloro-12'-ethyl-7'-((9aS)-hexahydropyrazino[2,1-c][1,4]oxazin-8(1H)-ylmethyl)-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued
Examples Prepared by the General Methods
| Example Number | Starting Materials | General Method | Product Structure | Product Name | MS Data (M + 1)+ |
|---|---|---|---|---|---|
| 31 | 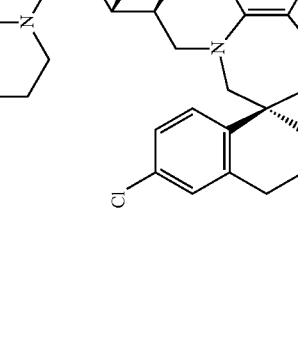 | 1 (R¹ = H), 5, 8 | 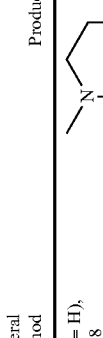 | (1S,3'R,6'R,7'S,8'E,12'R)-6-chloro-12'-ethyl-7'-methoxy-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen-15'-one 13',13'-dioxide | 725.2 |

TABLE 1-continued
Examples Prepared by the General Methods
| Example Number | Starting Materials | General Method | Product Structure | Product Name | MS Data (M + 1)+ |
|---|---|---|---|---|---|
| 32 | 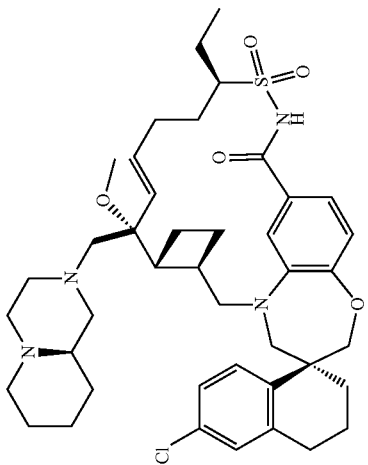 | 1 (R$^1$ = H), 5, 8 | 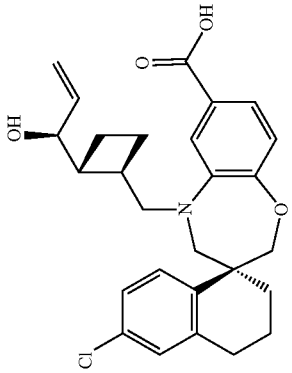 | (1S,3'R,6'R,7'R,8'E,12'R)-6-chloro-12'-ethyl-7'-methoxy-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.2 |

TABLE 1-continued

Examples Prepared by the General Methods

| Example Number | Starting Materials | General Method | Product Structure | Product Name | MS Data (M + 1)+ |
|---|---|---|---|---|---|
| 35 | | 5, 8 | | (1S,3'R,6R,7S,8E,11S,12'R)-6-chloro-7'-methoxy-11',12'-dimethyl-7'-((methyl(2-(4-morpholinyl)ethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.2 |

TABLE 1-continued

Examples Prepared by the General Methods

| Example Number | Starting Materials | General Method | Product Structure | Product Name | MS Data (M + 1)+ |
|---|---|---|---|---|---|
| 36 | | 5, 13 | | (1S,3'R,6R,7R,8E,11'S,12'R)-6-chloro-7'-methoxy-11',12'-dimethyl-7'-(((2-(4-morpholinyl)ethyl)amino)methyl)-3,4-dihydro-2H,15'H-spiro[naphtlalene-1,22'-[20]oxa[13]thia[1,14]diazatetracyclo[14.7.2.0~3,6~.0~19,24~]pentacosa[8,16,18,24]tetraen]-15'-one 13',13'-dioxide | 755.2 |

TABLE 1-continued

Examples Prepared by the General Methods

| Example Number | Starting Materials | General Method | Product Structure | Product Name | MS Data (M + 1)+ |
|---|---|---|---|---|---|
| 37 | (structure); MeI; (morpholine-ethyl-methylamine structure) | 5, 13 | (structure) | (1S,3'R,6R,7R,8E,11'S,12'R)-6-chloro-7'-methoxy-11',12'-dimethyl-7'-((methyl(2-(4-morpholinyl)ethyl)amino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.2 |

TABLE 1-continued
Examples Prepared by the General Methods
| Example Number | Starting Materials | General Method | Product Structure | Product Name | MS Data (M + 1)+ |
|---|---|---|---|---|---|
| 38 | 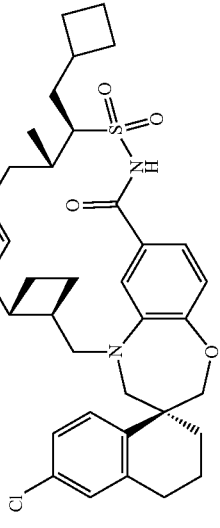 | 2, 5, 8 | 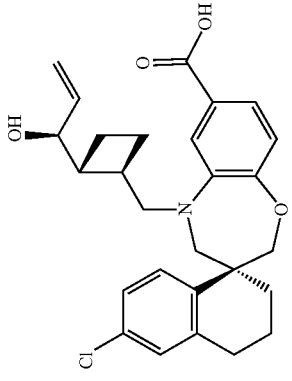 | (1S,3'R,6R,7R,7R,8E,11'S,12'R)-6-chloro-7'-(cyclobutylmethyl)-7-((9aS)-hexahydropyrazino[2,1-c][1,4]oxazin-8(1H)-ylmethyl)-7'-methoxy-11'-methyl-3,4-dihydro-2H,15'H-spiroonaphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 821.2 |

TABLE 1-continued

Examples Prepared by the General Methods

| Example Number | Starting Materials | General Method | Product Structure | Product Name | MS Data (M + 1)+ |
|---|---|---|---|---|---|
| 39 | 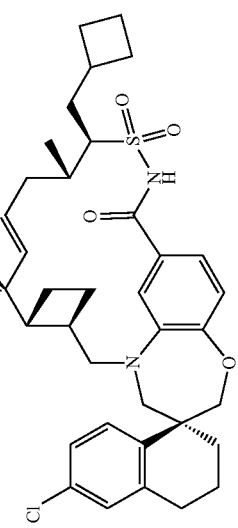 | 2, 5, 8 | 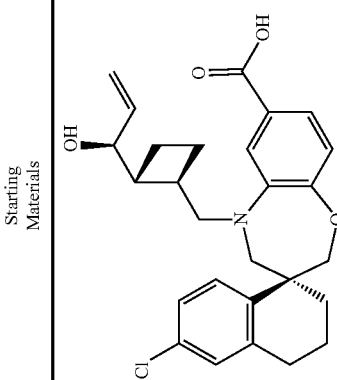 | (1S,3'R,6R,7S,8E,11S,12R)-6-chloro-12'-(cyclobutylmethyl)-7-((9aS)-hexahydropyrazino[2,1-c][1,4]oxazin-8(1H)-ylmethyl)-7-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 821.2 |

(Pharmablock)

TABLE 1-continued
Examples Prepared by the General Methods
| Example Number | Starting Materials | General Method | Product Structure | Product Name | MS Data (M + 1)+ |
|---|---|---|---|---|---|
| 40 | 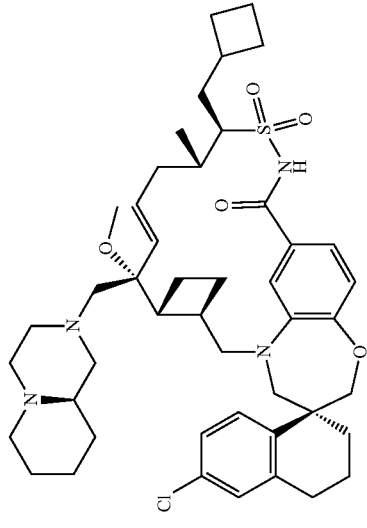 | 2, 5, 8 | 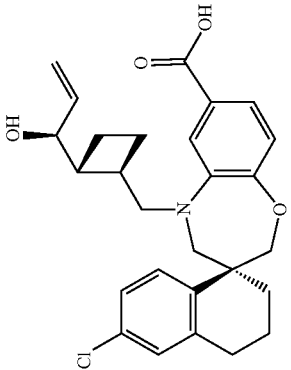 | (1S,3'R,6R,7R,8E,11'S,12'R)-6-chloro-12'-(cyclobutylmethyl)-7-methoxy-11'-methyl-7-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 819.2 |

TABLE 1-continued
Examples Prepared by the General Methods
| Example Number | Starting Materials | General Method | Product Structure | Product Name | MS Data (M + 1)+ |
|---|---|---|---|---|---|
| 41 | 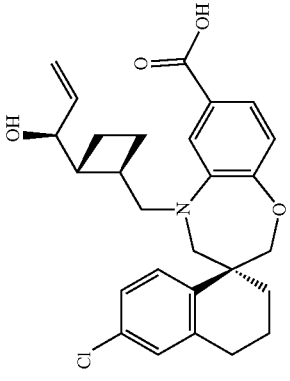 | 2, 5, 8 | 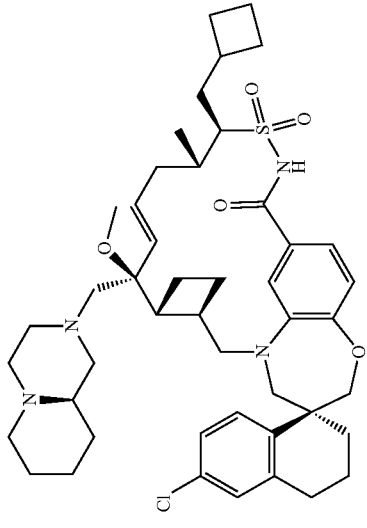 | (1S,3'R,6R,7S,8E,11'S,12'R)-6-chloro-12'-(cyclobutylmethyl)-7-methoxy-11'-methyl-7'-((9aR)-octahydro-2H-pyrido[1,2-a]pyrazin-2-ylmethyl)-3,4-dihydro-2H,15'H,spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 819.2 |

TABLE 1-continued
Examples Prepared by the General Methods
| Example Number | Starting Materials | General Method | Product Structure | Product Name | MS Data (M + 1)+ |
|---|---|---|---|---|---|
| 42 | 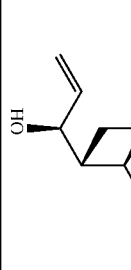 | 1 (R¹ = H), 5, 8 |  | (1S,3'R,6R,7R,8E,12R)-6-chloro-7'-ethoxy-12'-ethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.2 |

TABLE 1-continued

Examples Prepared by the General Methods

| Example Number | Starting Materials | General Method | Product Structure | Product Name | MS Data (M + 1)+ |
|---|---|---|---|---|---|
| 43 | | 1 (R¹ = H), 5, 8 | | (1S,3R,6R,7S,8E,12R)-6-chloro-7'-ethoxy-12'-ethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.2 |

TABLE 1-continued

Examples Prepared by the General Methods

| Example Number | Starting Materials | General Method | Product Structure | Product Name | MS Data (M + 1)+ |
|---|---|---|---|---|---|
| 44 | 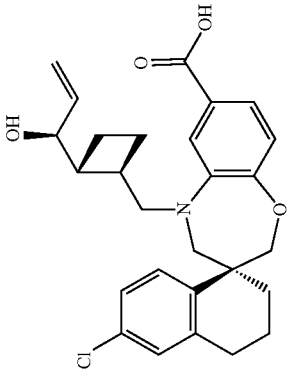 | 2, 5, 8 | 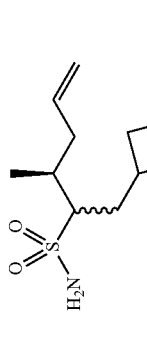 | (1S,3'R,6R,7S,8E,11S,12'R)-6-chloro-12'-(cyclobutylmethyl)-7-ethoxy-7'-((9aS)-hexahydropyrazino[2,1-c][1,4]oxazin-8(1H)-ylmethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 835.2 |

(Pharmablock)

| Example Number | Starting Materials | General Method | Product Structure | Product Name | MS Data (M + 1)+ |
|---|---|---|---|---|---|
| 45 | (structures shown; includes chloro-tetrahydronaphthalene-spiro-benzoxazepine carboxylic acid, sulfonamide with cyclobutyl and EtI, and hexahydropyrazino[2,1-c][1,4]oxazine (Pharmablock)) | 2, 5, 8 | (structure shown) | (1S,3'R,6R,7R,8E,11'S,12R)-6-chloro-12'-(cyclobutylmethyl)-7-ethoxy-7'-((9aS)-hexahydropyrazino[2,1-c][1,4]oxazin-8(1H)-ylmethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen-15'-one 13',13'-dioxide | 835.2 |

TABLE 1-continued

Examples Prepared by the General Methods

| Example Number | Starting Materials | General Method | Product Structure | Product Name | MS Data (M + 1)+ |
|---|---|---|---|---|---|
| 46 |  B(Oallyl)₃ <br> (Pharmablock) | 3, 8 |  | (1S,3'R,6R,7R,8E,11S,12R)-6-chloro-7'-(9aS)-hexahydropyrazino[2,1-c][1,4]oxazin-8(1H)-ylmethyl)-11',12'-dimethyl-7'-(2-propen-1-yloxy)-3,4-dihydro-2H,15'H-spiro[naphthalene-1,22'-[20]oxa[13]thia[1,14]diazatetracyclo[14.7.2.0-3,6-.0-19,24-]pentacosa[8,16,18,24]tetraen]-15'-one 13',13'-dioxide | 793.2 |
| 47 |  B(OiPr)₃ <br> (Pharmablock) | 3, 8 |  | (1S,3'R,6R,7R,8E,11S,12R)-6-chloro-7'-(9aS)-hexahydropyrazino[2,1-c][1,4]oxazin-8(1H)-ylmethyl)-11',12'-dimethyl-7'-(1-methylethoxy)-3,4-dihydro-2H,15'H-spiro[naphthalene-1,22'-[20]oxa[13]thia[1,14]diazatetracyclo[14.7.2.0-3,6-.0-19,24-]pentacosa[8,16,18,24]tetraen]-15'-one 13',13'-dioxide | 795.2 |

TABLE 1-continued

Examples Prepared by the General Methods

| Example Number | Starting Materials | General Method | Product Structure | Product Name | MS Data (M + 1)+ |
|---|---|---|---|---|---|
| 48 |  B(On-Bu)₃ (Pharmablock) | 3, 8 | 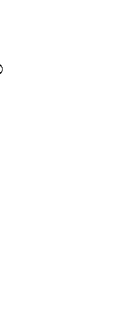 | (1S,3'R,6R,7R,8E,11'S,12R)-7'-butoxy-6-chloro-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.2 |
| 49 | 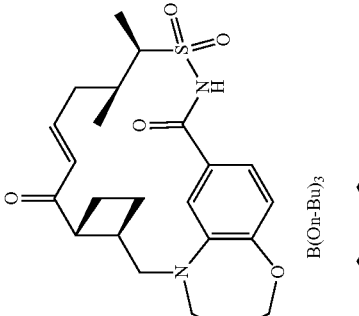 B(OCH₂CF₃)₃ (Pharmablock) | 3, 8 | 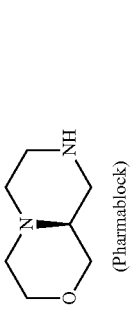 | (1S,3'R,6R,7S,8E,11'S,12R)-6-chloro-7'-((9aS)-hexahydropyrazino[2,1-c][1,4]oxazin-8(1H)-ylmethyl)-1-7'-(2,2,2-trifluoroethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 835.2 |

TABLE 1-continued

Examples Prepared by the General Methods

| Example Number | Starting Materials | General Method | Product Structure | Product Name | MS Data (M + 1)+ |
|---|---|---|---|---|---|
| 50 | (structure), B(OCH₂CF₃)₃, (Pharmablock structure) | 3, 8 | (structure) | (1S,3'R,6R,7R,8'E,11S,12R)-6-chloro-7'-((9aS)-hexahydropyrazino[2,1-c][1,4]oxazin-8(1H)-ylmethyl)-11',12'-dimethyl-7'-(2,2,2-trifluoroethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 835.2 |

TABLE 1-continued

Examples Prepared by the General Methods

| Example Number | Starting Materials | General Method | Product Structure | Product Name | MS Data (M + 1)+ |
|---|---|---|---|---|---|
| 51 | 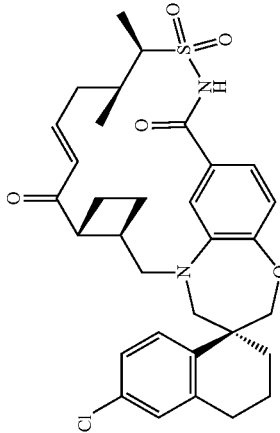 | 3, 10 | 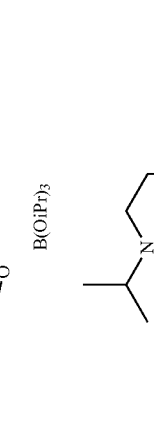 | (1S,3'R,6R,7R,8E,11'S,12'R)-6-chloro-11',12'-dimethyl-7'-(1-methylethoxy)-7-(((3R)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.2 |
| 52 | 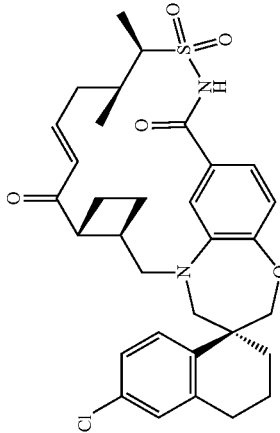 | 5, 12 | 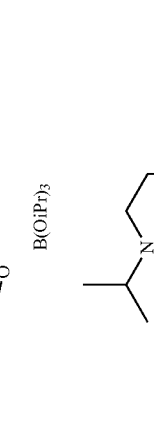 | (1S,3'R,6R,7S,8E,11'S,12'R)-6-chloro-7'-methoxy-11',12'-dimethyl-7-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 712.2 |

TABLE 1-continued

Examples Prepared by the General Methods

| Example Number | Starting Materials | General Method | Product Structure | Product Name | MS Data (M + 1)+ |
|---|---|---|---|---|---|
| 53 | | 12 | | (1S,3′R,6R,7R,8E,11S,12R)-6-chloro-7′-methoxy-11′,12′-dimethyl-7′-(4-morpholinylmethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 712.3 |
| 54 | (Enamine) | 12 | | (1S,3′R,6R,7R,8E,11S,12R)-6-chloro-7′-methoxy-7′-((4-(2-methoxyethyl)-3-oxo-1-piperazinyl)methyl)-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 783.2 |

TABLE 1-continued
Examples Prepared by the General Methods
| Example Number | Starting Materials | General Method | Product Structure | Product Name | MS Data (M + 1)+ |
|---|---|---|---|---|---|
| 55 |  MeI | 5, 12 |  | (1S,3R,6R,7S,8E,11S,12'R)-6-chloro-7'-methoxy-7'-((4-(2-methoxyethyl)-3-oxo-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.2 |

TABLE 1-continued

Examples Prepared by the General Methods

| Example Number | Starting Materials | General Method | Product Structure | Product Name | MS Data (M + 1)+ |
|---|---|---|---|---|---|
| 56 |  MeI<br>(HCl salt)<br>(Synthonix) | 5, 10 |  | (1S,3R,6R,7S,8E,11S,12R)-6-chloro-7'-((9aS)-hexahydropyrazino[2,1-c][1,4]oxazin-8(1H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |
| 57 |  MeI<br>(HCl salt)<br>(Synthonix) | 5, 10 |  | (1S,3R,6R,7S,8E,11S,12R)-6-chloro-7'-((9aR)-hexahydropyrazino[2,1-c][1,4]oxazin-8(1H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 58 |  (HCl salt) (Synthonix) | 10 |  | (1S,3'R,6'R,7'R,8'E,11'S,12'R)-6-chloro-7'-((9aR)-hexahydropyrazino[2,1-c][1,4]oxazin-8(1H)-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |
| 59 |  MeI (Matrix) | 5, 10 |  | (1S,3'R,6'R,7S,8'E,11'S,12'R)-6-chloro-7'-((3-(dimethylamino)-3-methyl-1-azetidinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 739.4 |

TABLE 1-continued

Examples Prepared by the General Methods

| Example Number | Starting Materials | General Method | Product Structure | Product Name | MS Data (M + 1)+ |
|---|---|---|---|---|---|
| 60 | (structure) (Matrix) | 10 | (structure) | (1S,3'R,6R,7R,8E,11'S,12'R)-6-chloro-7'-((3-(dimethylamino)-3-methyl-1-azetidinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 739.3 |
| 61 | (structure) | 10 | (structure) | (1S,3'R,6R,7R,8E,11'S,12'R)-6-chloro-7'-methoxy-7'-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.4 |

TABLE 1-continued

Examples Prepared by the General Methods

| Example Number | Starting Materials | General Method | Product Structure | Product Name | MS Data (M + 1)+ |
|---|---|---|---|---|---|
| 62 | | 12 | | (1S,3'R,6'R,7'R,8'E,11'S, 12'R)-6-chloro-7'-methoxy-11',12'-dimethyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 725.5 |
| 63 | | 5, 10 | | (1S,3'R,6'R,7'S,8'E,11'S, 12'R)-6-chloro-7'-methoxy-11',12'-dimethyl-7'-(((8aS)-3-oxotetrahydro[1,3]oxazolo[3,4-a]pyrazin-7(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 64 | (HCl salt) (Ark Pharm) | 10 | | (1S,3'R,6R,7R,8E,11'S,12'R)-6-chloro-7'-methoxy-11',12'-dimethyl-7-(((8aS)-3-oxotetrahydro[1,3]oxazolo[3,4-a]pyrazin-7(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |
| 65 | MeI MeNH$_2$·HCl | 5, 10 | | (1S,3'R,6R,7S,8E,11'S,12'R)-6-chloro-7'-methoxy-11',12'-dimethyl-7-((methylamino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 656.4 |

TABLE 1-continued

Examples Prepared by the General Methods

| Example Number | Starting Materials | General Method | Product Structure | Product Name | MS Data (M + 1)+ |
|---|---|---|---|---|---|
| 66 | MeI; Me₂NH·HCl | 5, 10 | | (1S,3'R,6'R,7'S,8'E,11'S,12'R)-6'-chloro-7'-((dimethylamino)methyl)-7'-methoxy-11',12'-dimethyl-3,4-dihydro-2H,15'H-spiro[naphthalene-1,22'-[20]oxa[13]thia[1,14]diazatetracyclo[14.7.2.0−3,6−.0−19,24−]pentacosa[8,16,18,24]tetraen]-15'-one 13',13'-dioxide | 670.3 |
| 67 | MeI; NC–(Me)–NH (HCl salt) (FSSI) | 5, 10 | | 1-((((1S,3'R,6'R,7'S,8'E,11'S,12'R)-6'-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0−3,6−.0−19,24−]pentacosa[8,16,18,24]tetraen]-7'-yl)methyl)-3-methyl-3-azetidinecarbonitrile | 721.3 |

TABLE 1-continued

Examples Prepared by the General Methods

| Example Number | Starting Materials | General Method | Product Structure | Product Name | MS Data (M + 1)+ |
|---|---|---|---|---|---|
| 68 | MeI (HCl salt) (FSSI) | 5, 10 | | (1S,3'R,6R,7R,7S,8E,11S,12R)-6-chloro-7'-((5-fluoro-3,6-dihydro-1(2H)-pyridinyl)methyl)-7'-methoxy-11',12'-dimethyl-3,4-dihydro-2H,15'H-[20]oxa[13]thia[1,14][20]oxa[13]thia[1,14]diazatetracyclo[14.7.2.0~3,6~.0~19,24~]pentacosa[8,16,18,24]tetraen]-15'-one 13',13'-dioxide | 726.3 |
| 69 | Me₂NH·HCl | 10 | | (1S,3'R,6R,7R,8E,11S,12R)-6-chloro-7'-((dimethylamino)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 670.2 |

TABLE 1-continued

Examples Prepared by the General Methods

| Example Number | Starting Materials | General Method | Product Structure | Product Name | MS Data (M + 1)+ |
|---|---|---|---|---|---|
| 70 | (structure) MeNH₂·HCl | 10 | (structure) | (1S,3'R,6R,7R,8E,11'S,12'R)-6-chloro-7'-methoxy-11',12'-dimethyl-7'-((methylamino)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 656.2 |
| 71 | (structure) (HCl salt) (FSSI) | 10 | (structure) | 1-(((1S,3'R,6R,7R,8E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-3-methyl-3-azetidinecarbonitrile | 721.3 |

TABLE 1-continued

Examples Prepared by the General Methods

| Example Number | Starting Materials | General Method | Product Structure | Product Name | MS Data (M + 1)+ |
|---|---|---|---|---|---|
| 72 | (structure with OMe, Cl, and FSSI piperazine-thiazole) | 10 | (product structure) | (1S,3'R,6R,7R,8E,11'S,12'R)-6-chloro-7'-methoxy-11',12'-dimethyl-7'-((4-(1,3-thiazol-4-ylmethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.2 |

TABLE 1-continued

Examples Prepared by the General Methods

| Example Number | Starting Materials | General Method | Product Structure | Product Name | MS Data (M + 1)+ |
|---|---|---|---|---|---|
| 73 |  | 10 |  | (1S,3'R,6R,7R,8E,11S,12R)-6-chloro-7'-methoxy-11',12'-dimethyl-7'-((4-(2-(methylsulfonyl)ethyl)-1-piperazinyl)methyl)-3,4-dihydro-2H,15H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 817.2 |
| 74 | 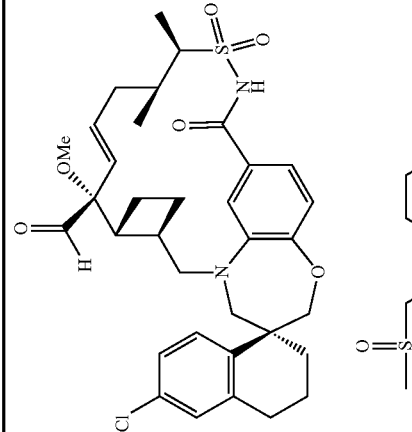 | 10 | 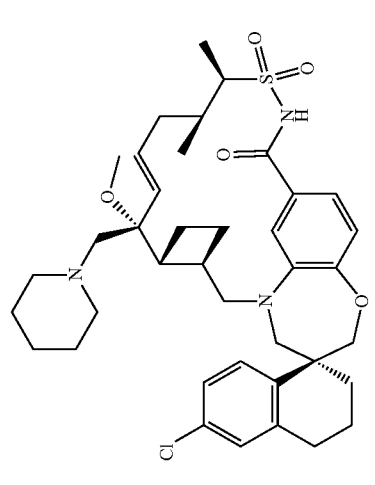 | (1S,3'R,6R,7R,8E,11S,12R)-6-chloro-7'-methoxy-11',12'-dimethyl-7'-((1-piperidinylmethyl)-3,4-dihydro-2H,15H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.3 |

TABLE 1-continued

Examples Prepared by the General Methods

| Example Number | Starting Materials | General Method | Product Structure | Product Name | MS Data (M + 1)+ |
|---|---|---|---|---|---|
| 75 | 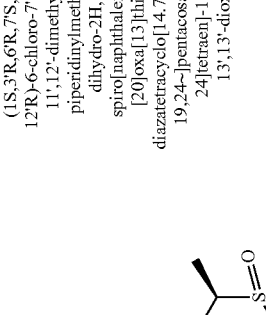 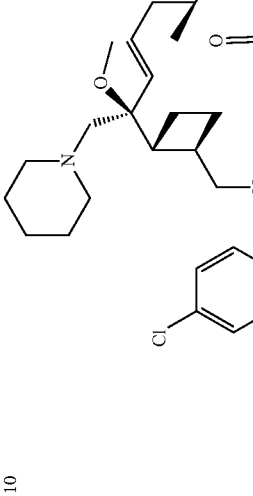 | 5, 10 | 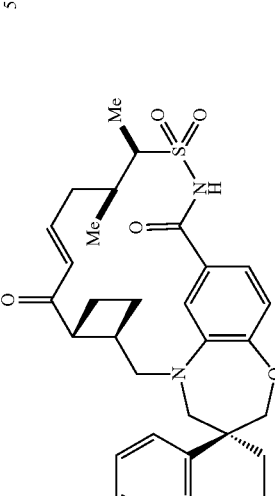 | (1S,3'R,6R,7S,8E,11S, 12'R)-6-chloro-7'-methoxy-11',12'-dimethyl-7-(1-piperidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.2 |
| 76 | 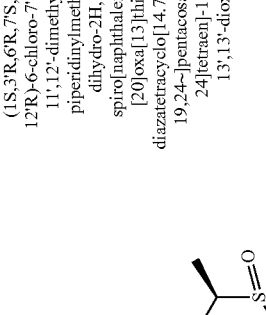 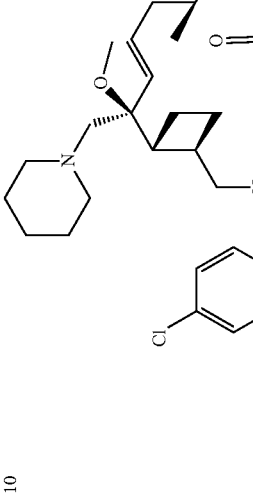 | 10 | 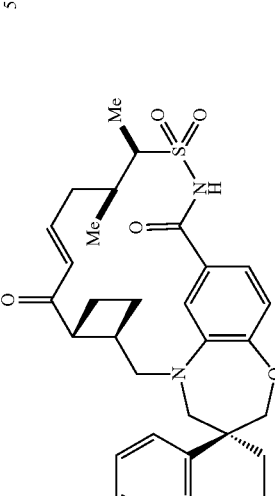 | (1S,3'R,6R,7S,8E,11S, 12'R)-7-(1-azetidinylmethyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 682.3 |

TABLE 1-continued

Examples Prepared by the General Methods

| Example Number | Starting Materials | General Method | Product Structure | Product Name | MS Data (M + 1)+ |
|---|---|---|---|---|---|
| 77 | | 5, 10 | | (1S,3'R,6'R,7'S,8'E,11'S,12'R)-7'-(1-azetidinylmethyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 682.3 |
| 78 | (J & W PharmLab) | 10 | | (1S,3'R,6'R,7'R,7'S,8'E,11'S,12'R)-6-chloro-7'-methoxy-11',12'-dimethyl-7'-((9aS)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.8 |

TABLE 1-continued

Examples Prepared by the General Methods

| Example Number | Starting Materials | General Method | Product Structure | Product Name | MS Data (M + 1)+ |
|---|---|---|---|---|---|
| 79 | | 5, 10 | | (1S,3′R,6R,7S,8E,11S,12′R)-6-chloro-7′-methoxy-11′,12′-dimethyl-7′-((9aS)-octahydro-2H-pyrido[1,2-a]pyrazin-2-ylmethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 765.8 |

MeI (J & W PharmLab)

TABLE 1-continued

Examples Prepared by the General Methods

| Example Number | Starting Materials | General Method | Product Name | MS Data (M + 1)+ |
|---|---|---|---|---|
| 80 | MeI, (FSSI) | 5, 10 | (1S,3'R,6'R,7S,8'E,11'S,12'R)-6-chloro-7'-((8aR)-hexahydropyrrolo[1,2-a]pyrazin-2(1H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7S,8'E,11'S,12'R)-6-chloro-7'-((8aS)-hexahydropyrrolo[1,2-a]pyrazin-2(1H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 751.8 |

TABLE 1-continued

Examples Prepared by the General Methods

| Example Number | Starting Materials | General Method | Product Structure | Product Name | MS Data (M + 1)+ |
|---|---|---|---|---|---|
| 81 | [structure with MeI and piperazine enamine HCl salt] | 5, 9 | [product structure] | (1S,3R,6R,7S,8E,11S,12'R)-6-chloro-7'-methoxy-11,12'-dimethyl-7'-((4-(2-(methylsulfonyl)ethyl)-1-piperazinyl)methyl)-3,4-dihydro-2H,15'H-spiro[naphthalene-1,22'-[20]oxa[13]thia[1,14]diazatetracyclo[14.7.2.0-3,6-.0-19,24-]pentacosa[8,16,18,24]tetraen]-15'-one 13,13'-dioxide | 818.0 |

TABLE 1-continued
Examples Prepared by the General Methods
| Example Number | Starting Materials | General Method | Product Structure | Product Name | MS Data $(M + 1)^+$ |
|---|---|---|---|---|---|
| 82 | 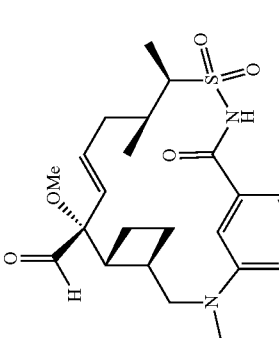 (Enamine) | 8 | 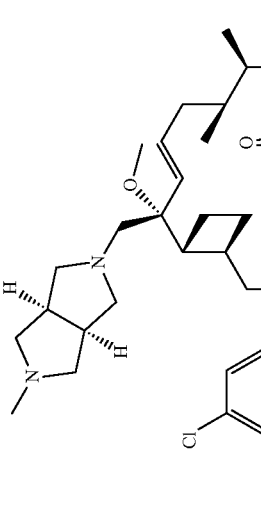 | (1S,3′R,6R,7R,8E,11′S,12′R)-6-chloro-7′-methoxy-11′,12′-dimethyl-7′-(((3aR,6aS)-5-methylhexahydropyrrolo[3,4-c]pyrrol-2(1H)-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 751.2 |

TABLE 1-continued

Examples Prepared by the General Methods

| Example Number | Starting Materials | General Method | Product Structure | Product Name | MS Data (M + 1)+ |
|---|---|---|---|---|---|
| 83 | 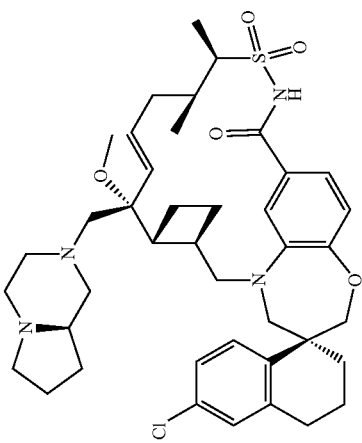 (Enamine) | 9 | 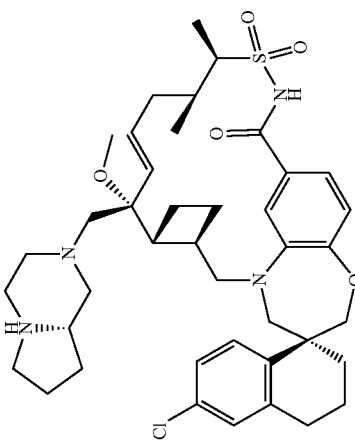 | (1S,3'R,6R,7R,8E,11'S,12'R)-6-chloro-7'-((8aR)-hexahydropyrrolo[1,2-a]pyrazin-2(1H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide(1S,3'R,6R,7R,8E,11'S,12'R)-6-chloro-7'-((8aS)-hexahydropyrrolo[1,2-a]pyrazin-2(1H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 751.2 |

TABLE 1-continued
Examples Prepared by the General Methods
| Example Number | Starting Materials | General Method | Product Structure | Product Name | MS Data (M + 1)+ |
|---|---|---|---|---|---|
| 84 | (HCl salt) (ChemBridge Corp.) | 9 | | (1S,3'R,6R,7R,7'R,8'E,11'S,12'R)-6-chloro-7'-methoxy-11',12'-dimethyl-7'-((3-(4-morpholinyl)-1-azetidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |
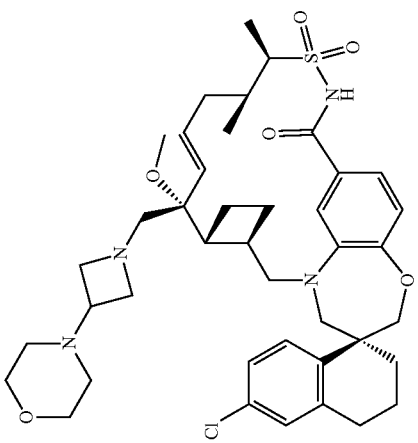

TABLE 1-continued

Examples Prepared by the General Methods

| Example Number | Starting Materials | General Method | Product Structure | Product Name | MS Data (M + 1)+ |
|---|---|---|---|---|---|
| 85 | | 8 | | (1S,3'R,6R,7R,8E,11'S,12'R)-6-chloro-7'-methoxy-11',12'-dimethyl-7'-((4-(4-morpholinyl)-1-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.9 |

TABLE 1-continued

Examples Prepared by the General Methods

| Example Number | Starting Materials | General Method | Product Structure | Product Name | MS Data (M + 1)+ |
|---|---|---|---|---|---|
| 86 | 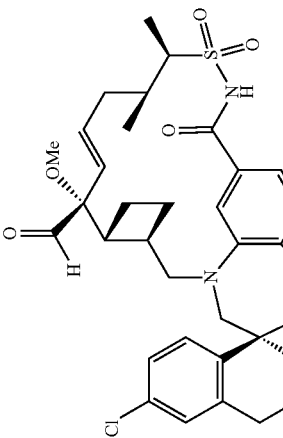 | 8 | 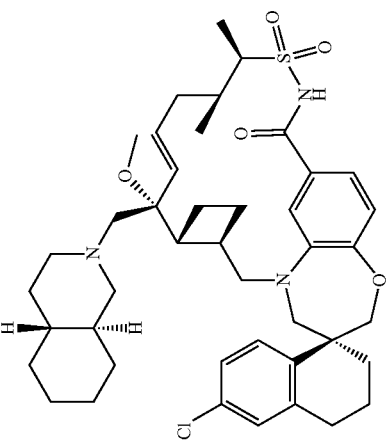 AND 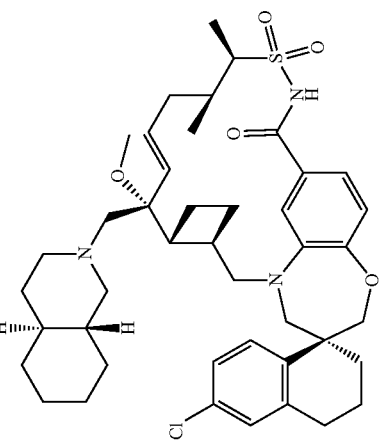 | (1S,3'R,6R,7R,8'E,11'S,12'R)-6-chloro-7'-methoxy-11',12'-dimethyl-7'-((4aR,8aS)-octahydro-2(1H)-isoquinolinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7R,8'E,11'S,12'R)-6-chloro-7'-methoxy-11',12'-dimethyl-7'-((4aS,8aR)-octahydro-2(1H)-isoquinolinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 764.8 |

TABLE 1-continued

Examples Prepared by the General Methods

| Example Number | Starting Materials | General Method | Product Structure | Product Name | MS Data (M + 1)+ |
|---|---|---|---|---|---|
| 87 | (Oakwood) | 8 | AND | (1S,3'R,6'R,7'R,8'E,11'S,12'R)-6-chloro-7'-methoxy-11',12'-dimethyl-7-((10aR)-octahydropyrazino[1,2-a]azepin-2(1H)-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-methoxy-11',12'-dimethyl-7-((10aS)-octahydropyrazino[1,2-a]azepin-2(1H)-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.8 |

TABLE 1-continued

Examples Prepared by the General Methods

| Example Number | Starting Materials | General Method | Product Structure | Product Name | MS Data (M + 1)+ |
|---|---|---|---|---|---|
| 88 | | 8 | | (1S,3'R,6R,7R,8E,11'S,12'R)-6-chloro-7'-((4-ethyl-1-piperazinyl)methyl)-7'-methoxy-11,12-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 739.8 |

TABLE 1-continued

Examples Prepared by the General Methods

| Example Number | Starting Materials | General Method | Product Structure | Product Name | MS Data (M + 1)+ |
|---|---|---|---|---|---|
| 89 |  | 8 | 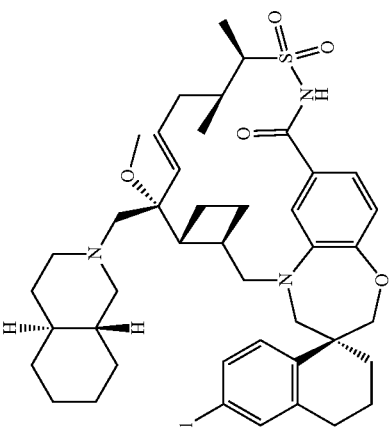 OR 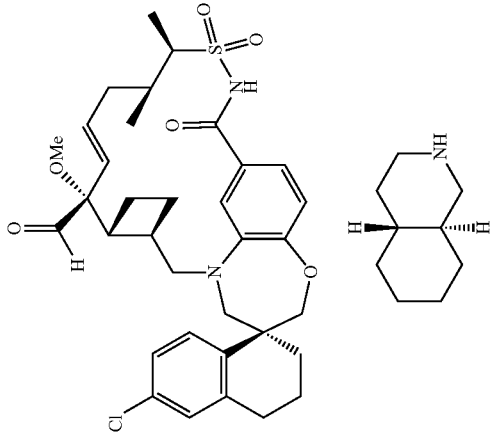 | (1S,3'R,6R,7R,8E,11S,12'R)-6-chloro-7'-methoxy-11',12'-dimethyl-7-((4aR,8aS)-octahydro-2(1H)-isoquinolinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,8E,11S,12'R)-6-chloro-7'-methoxy-11',12'-dimethyl-7-((4aS,8aR)-octahydro-2(1H)-isoquinolinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 764.2 |

TABLE 1-continued

Examples Prepared by the General Methods

| Example Number | Starting Materials | General Method | Product Structure | Product Name | MS Data (M + 1)+ |
|---|---|---|---|---|---|
| 90 | | 8 | | (1S,3'R,6R,7R,8'E,11'S,12'R)-6-chloro-7'-methoxy-11',12'-dimethyl-7-((4aS,8aR)-octahydro-2(1H)-isoquinolinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,8'E,11'S,12'R)-6-chloro-7'-methoxy-11',12'-dimethyl-7-((4aR,8aS)-octahydro-2(1H)-isoquinolinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 764.2 |

TABLE 1-continued

Examples Prepared by the General Methods

| Example Number | Starting Materials | General Method | Product Structure | Product Name | MS Data (M + 1)+ |
|---|---|---|---|---|---|
| 91 | (Combi-Blocks) | 8 | | (1S,3'R,6R,7R,8E,11'S,12'R)-6-chloro-7'-((4-cyclopropyl-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 751.8 |

TABLE 1-continued

Examples Prepared by the General Methods

| Example Number | Starting Materials | General Method | Product Structure | Product Name | MS Data (M + 1)+ |
|---|---|---|---|---|---|
| 92 | | 8 | | (1S,3'R,6R,7R,8E,11'S,12'R)-6-chloro-7'-((4-cyclobutyl-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.8 |

TABLE 1-continued
Examples Prepared by the General Methods
| Example Number | Starting Materials | General Method | Product Structure | Product Name | MS Data (M + 1)+ |
|---|---|---|---|---|---|
| 93 | | 8 | | (1S,3'R,6R,7R,8E,11'S,12'R)-6-chloro-7'-methoxy-11',12'-dimethyl-7'-((4-(2,2,2-trifluoroethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 794.0 |
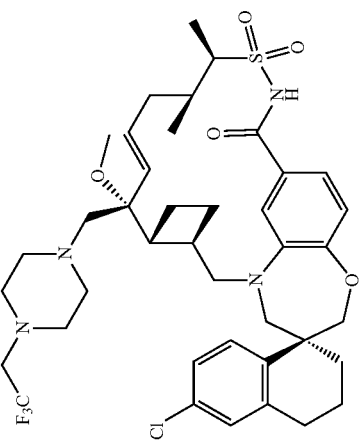

TABLE 1-continued

Examples Prepared by the General Methods

| Example Number | Starting Materials | General Method | Product Structure | Product Name | MS Data (M + 1)+ |
|---|---|---|---|---|---|
| 94 | (HCl salt) (Ryan Scientific) | 9 | | (1S,3'R,6'R,7'R,8'E,11'S,12'R)-6-chloro-7'-methoxy-7'-((3-((2-methoxyethyl)(methyl)amino)-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.8 |

TABLE 1-continued

Examples Prepared by the General Methods

| Example Number | Starting Materials | General Method | Product Structure | Product Name | MS Data (M + 1)+ |
|---|---|---|---|---|---|
| 95 | | 8 | | (1S,3'R,6'R,7'R,8'E,11'S,12'R)-6-chloro-7'-((4-(2,2-difluoroethyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 775.8 |
| 96 | (HCl salt) (Ark Pharm) | 9 | | (1S,3'R,6'R,7'R,8'E,11'S,12'R)-6-chloro-7'-((4-(2-fluoroethyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 757.2 |

| Example Number | Starting Materials | General Method | Product Structure | Product Name | MS Data $(M+1)^+$ |
|---|---|---|---|---|---|
| 97 | | 8 | | (1S,3′R,6′R,7′R,8′E,11′S,12′R)-6-chloro-7′-methoxy-11′,12′-dimethyl-7′-((4-propyl-1-piperazinyl)methyl)-3,4-dihydro-2H,15′H-spiro[naphthalene-1,22′-[20]oxa[13]thia[1,14]diazatetracyclo[14.7.2.0∼3,6∼.0∼19,24∼]pentacosa[8,16,18,24]tetraen]-15′-one 13′,13′-dioxide | 753.3 |
| 98 | | 8 | | (1S,3′R,6′R,7′R,8′E,11′S,12′R)-6-chloro-7′-ethoxy-11′,12′-dimethyl-7′-((4-propyl-1-piperazinyl)methyl)-3,4-dihydro-2H,15′H-spiro[naphthalene-1,22′-[20]oxa[13]thia[1,14]diazatetracyclo[14.7.2.0∼3,6∼.0∼19,24∼]pentacosa[8,16,18,24]tetraen]-15′-one 13′,13′-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 101 | (structure shown with dithiane, OH, chlorotetrahydronaphthalene spiro, sulfonamide, benzamide; and Et; and octahydropyrazino[2,1-c][1,4]oxazine·2HCl (Pharmablock)) | 5, 9 | (macrocyclic product structure shown) | (1S,3′R,6R,7R,8E,11S,12R)-6-chloro-7′-ethoxy-7′-((9aS)-hexahydropyrazino[2,1-c][1,4]oxazin-8(1H)-ylmethyl)-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 781.8 |

TABLE 1-continued

Examples Prepared by the General Methods

| Example Number | Starting Materials | General Method | Product Structure | Product Name | MS Data (M + 1)+ |
|---|---|---|---|---|---|
| 102 | 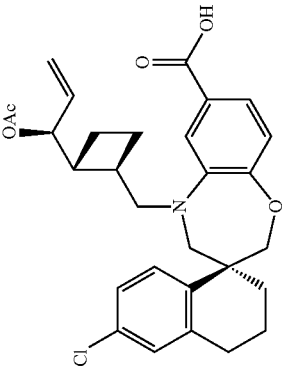 | 1, 5, 9 |  OR  | (1S,3'R,6'R,7'R,7'S,8'E,11'S,12'R)-12'-benzyl-6-chloro-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'S)-12'-benzyl-6-chloro-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 844.0 |

TABLE 1-continued

Examples Prepared by the General Methods

| Example Number | Starting Materials | General Method | Product Structure | Product Name | MS Data (M + 1)+ |
|---|---|---|---|---|---|
| 103 |  | 1, 5, 9 |  | (1S,3'R,6'R,7'R,8'E,11'S,12'R)-12'-benzyl-6-chloro-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'S)-12'-benzyl-6-chloro-7'-((9aS)-hexahydropyrazino[2,1-c][1,4]oxazin-8(1H)-ylmethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 844.0 |

TABLE 1-continued

Examples Prepared by the General Methods

| Example Number | Starting Materials | General Method | Product Structure | Product Name | MS Data (M + 1)+ |
|---|---|---|---|---|---|
| 104 | 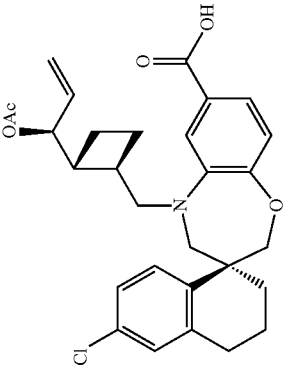 | 1, 5, 8 | 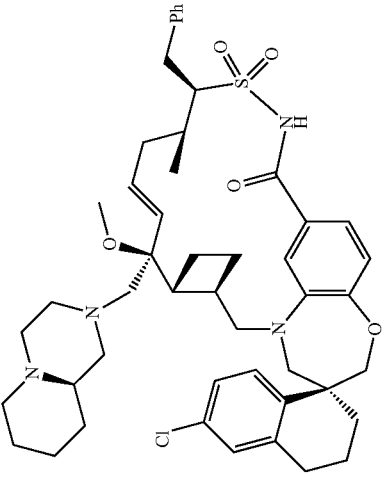 | (1S,3'R,6'R,7'R,8'E,11'S, 12'R)-12'-benzyl-6-chloro-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S, 12'S)-12'-benzyl-6-chloro-7'-methoxy-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 841.2 |

TABLE 1-continued

Examples Prepared by the General Methods

| Example Number | Starting Materials | General Method | Product Structure | Product Name | MS Data (M + 1)+ |
|---|---|---|---|---|---|
| 106 | | 5, 8 | | (1S,3'R,6'R,7S,8E,11'S,12'R)-6-chloro-7'-ethoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |

TABLE 1-continued

Examples Prepared by the General Methods

| Example Number | Starting Materials | General Method | Product Structure | Product Name | MS Data (M + 1)+ |
|---|---|---|---|---|---|
| 107 | | 5, 8 | | (1S,3R,6R,7S,8E,11S,12R)-6-chloro-7-ethoxy-11',12'-dimethyl-7-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.3 |

TABLE 1-continued

Examples Prepared by the General Methods

| Example Number | Starting Materials | General Method | Product Structure | Product Name | MS Data (M + 1)+ |
|---|---|---|---|---|---|
| 108 | | 5, 8 | | (1S,3R,6R,7S,8E,11S,12R)-6-chloro-7-ethoxy-11',12'-dimethyl-7-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.3 |

TABLE 1-continued

Examples Prepared by the General Methods

| Example Number | Starting Materials | General Method | Product Structure | Product Name | MS Data (M + 1)+ |
|---|---|---|---|---|---|
| 109 | | 5, 8 | | (1S,3'R,6'R,7'S,8'E,11'S,12'R)-6-chloro-7'-ethoxy-11',12'-dimethyl-7'-(2-oxa-7-azaspiro[3.5]non-7-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 766.3 |

TABLE 1-continued

Examples Prepared by the General Methods

| Example Number | Starting Materials | General Method | Product Structure | Product Name | MS Data (M + 1)+ |
|---|---|---|---|---|---|
| 110 | (structure with dithiane, OH, Et, chlorotetrahydronaphthalene-spiro-oxazepine, and 4-(dimethylamino)piperidine (Oakwood)) | 5, 8 | (macrocyclic product structure) | (1S,3'R,6R,7S,8E,11'S,12'R)-6-chloro-7'-((4-(dimethylamino)-1-piperidinyl)methyl)-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 111 | (structures shown: dithiane-containing macrocycle with chloro-tetrahydronaphthalene spiro system; EtI; 1-(1,3-dimethoxypropan-2-yl)piperazine (FCH Group Company)) | 5, 8 | (structure shown) | (1S,3'R,6'R,7S,7'S,8'E,11'S,12'R)-6'-chloro-7'-ethoxy-7-((4-(2-methoxy-1-(methoxymethyl)ethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 827.2 |

TABLE 1-continued

Examples Prepared by the General Methods

| Example Number | Starting Materials | General Method | Product Structure | Product Name | MS Data (M + 1)+ |
|---|---|---|---|---|---|
| 112 | (structure) | 5, 8 | (structure) | (1S,3R,6R,7S,8E,11S,12R)-6-chloro-7'-ethoxy-7'-((4-ethyl-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.3 |

TABLE 1-continued
Examples Prepared by the General Methods
| Example Number | Starting Materials | General Method | Product Structure | Product Name | MS Data (M + 1)+ |
|---|---|---|---|---|---|
| 113 | 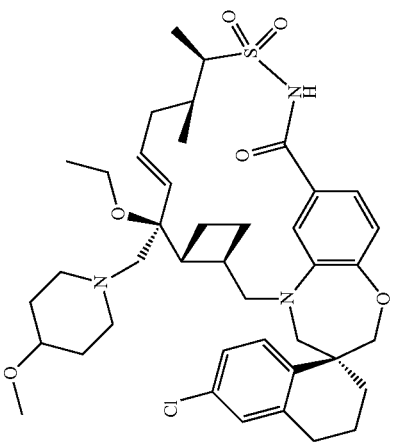 EtI (Combi-Blocks) | 5, 8 | 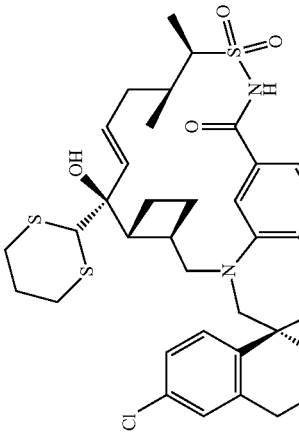 | (1S,3'R,6'R,7S,8E,11'S,12'R)-6-chloro-7'-ethoxy-7'-((4-methoxy-1-piperidinyl)methyl)-11',12'-dimethyl-3,4-dihydro-2H,15'H-spiro[naphthalene-1,22'-[20]oxa[13]thia[1,14]diazatetracyclo[14.7.2.0~3,6.0~19,24~]pentacosa[8,16,18,24]tetraen]-15'-one 13',13'-dioxide | 754.8 |

TABLE 1-continued

Examples Prepared by the General Methods

| Example Number | Starting Materials | General Method | Product Structure | Product Name | MS Data (M + 1)+ |
|---|---|---|---|---|---|
| 114 | (structure with dithiane, OH, Et, chlorotetrahydronaphthalene spiro, sulfonamide macrocycle) and 1-isopropylpiperazine (Acros Organics) | 5, 8 | (macrocyclic product structure with isopropylpiperazine) | (1S,3'R,6'R,7S,7'S,8'E,11'S,12'R)-6-chloro-7'-ethoxy-11',12'-dimethyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 115 | (Acros Organics) | 5, 8 | | (1S,3R,6R,7S,8E,11S,12R)-6-chloro-7-ethoxy-11'12'-dimethyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.8 |

TABLE 1-continued

Examples Prepared by the General Methods

| Example Number | Starting Materials | General Method | Product Structure | Product Name | MS Data (M + 1)+ |
|---|---|---|---|---|---|
| 116 | | 5, 8 | | (1S,3'R,6'R,7S,7'S,8'E,11'S,12'R)-6-chloro-7'-ethoxy-7-((4-(2-methoxy-1-(methoxymethyl)ethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 828.0 |

TABLE 1-continued
Examples Prepared by the General Methods
| Example Number | Starting Materials | General Method | Product Structure | Product Name | MS Data (M + 1)+ |
|---|---|---|---|---|---|
| 117 | 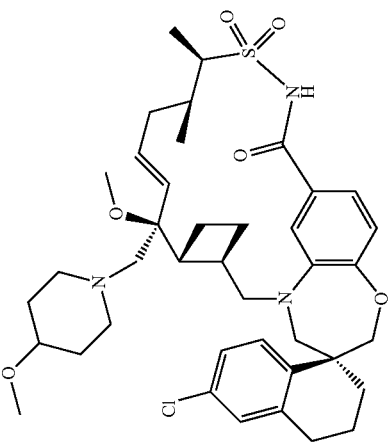 (Combi-Blocks) | 5, 8 | 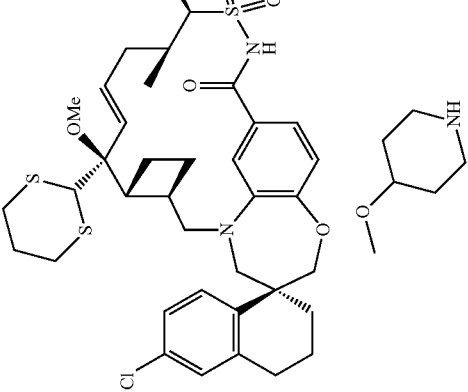 | (1S,3'R,6'R,7S,8'E,11'S,12'R)-6-chloro-7'-methoxy-7'-((4-methoxy-1-piperidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 740.7 |

TABLE 1-continued

Examples Prepared by the General Methods

| Example Number | Starting Materials | General Method | Product Structure | Product Name | MS Data (M + 1)+ |
|---|---|---|---|---|---|
| 118 | | 5, 8 | | (1S,3R,6R,7S,8E,11S,12R)-6-chloro-7'-((4-(dimethylamino)-1-piperidinyl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.7 |

| Example Number | Starting Materials | Examples Prepared by the General Methods | | | MS Data (M + 1)+ |
|---|---|---|---|---|---|
| | | General Method | Product Structure | Product Name | |
| 119 | 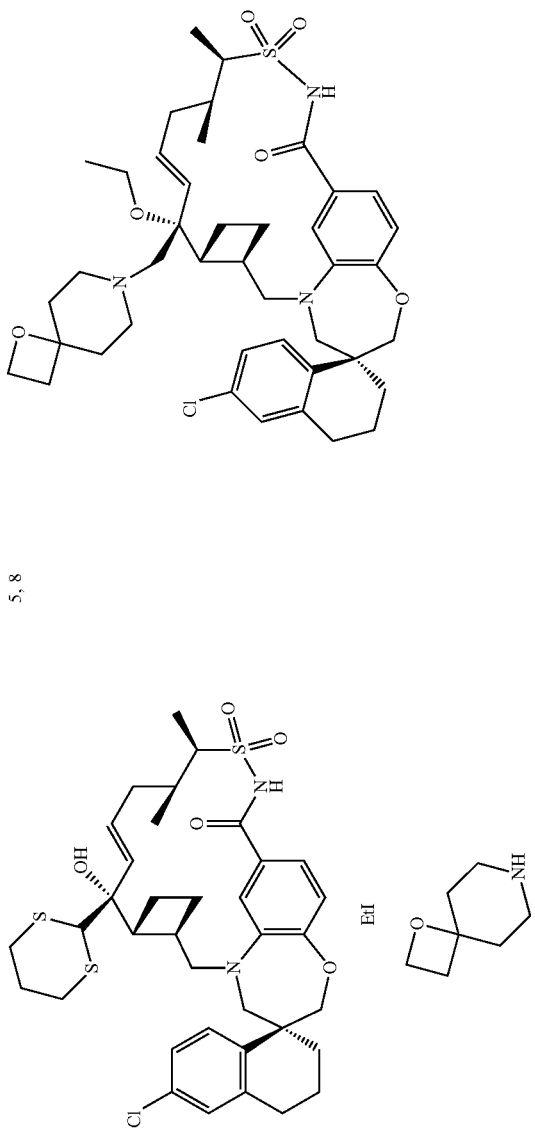 (Frontier Scientific) | 5, 8 | | (1S,3'R,6'R,7'R,8'E,11'S,12'R)-6-chloro-7'-ethoxy-11',12'-dimethyl-7'-(1-oxa-7-azaspiro[3.5]non-7-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 766.8 |

TABLE 1-continued

Examples Prepared by the General Methods

| Example Number | Starting Materials | General Method | Product Structure | Product Name | MS Data (M + 1)+ |
|---|---|---|---|---|---|
| 120 | (Oakwood) | 5, 8 | | (1S,3R,6R,7S,8E,11'S,12'R)-6-chloro-7'-methoxy-11',12'-dimethyl-7'-(1-oxa-7-azaspiro[3.5]non-7-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 752.8 |

TABLE 1-continued

Examples Prepared by the General Methods

| Example Number | Starting Materials | General Method | Product Structure | Product Name | MS Data (M + 1)+ |
|---|---|---|---|---|---|
| 121 | [structure]<br><br>EtI<br><br>[structure]<br><br>(after freebase the bis-HCl salt; FCH kGroup) | 5, 8 | [structure] OR [structure] | (1S,3'R,6R,7R,8E,11'S,12R)-6-chloro-7'-(((9aS)-2,2-dioxidohexahydropyrazino[2,1-c][1,4]thiazin-8(1H)-yl)methyl)-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR 1S,3'R,6R,7R,8E,11'S,12R)-6-chloro-7'-(((9aR)-2,2-dioxidohexahydropyrazino[2,1-c][1,4]thiazin-8(1H)-yl)methyl)-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 830.0 |

TABLE 1-continued

Examples Prepared by the General Methods

| Example Number | Starting Materials | General Method | Product Structure | Product Name | MS Data (M + 1)+ |
|---|---|---|---|---|---|
| 122 | (after freebase of bis-HCl salt; FCH Group) | 5, 8 | | (1S,3'R,6R,7R,8E,11'S,12'R)-6-chloro-7'-(((9aS)-2,2-dioxidohexahydropyrazino[2,1-c][1,4]thiazin-8(1H)-yl)methyl)-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR 1S,3'R,6R,7R,8E,11'S,12'R)-6-chloro-7'-(((9aR)-2,2-dioxidohexahydropyrazino[2,1-c][1,4]thiazin-8(1H)-yl)methyl)-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 830.0 |

TABLE 1-continued

Examples Prepared by the General Methods

| Example Number | Starting Materials | General Method | Product Structure | Product Name | MS Data (M + 1)+ |
|---|---|---|---|---|---|
| 123 | | 5, 8 | | (1S,3'R,6R,7R,8'E,11'S,12'R)-6-chloro-7'-ethoxy-7'-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.9 |
| 129 | | See Example 138 (Step 1) | | (1S,3'R,6R,7R,8'E,11'S,12'R)-6-chloro-7'-hydroxy-7'-(((2-hydroxyethyl)(methyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 686.3 |

TABLE 1-continued

Examples Prepared by the General Methods

| Example Number | Starting Materials | General Method | Product Structure | Product Name | MS Data (M + 1)+ |
|---|---|---|---|---|---|
| 130 | | See Example 138 (Step 2) | | (1S,3'R,6R,7R,8'E,11S,12R)-6-chloro-4'',11',12'-trimethyl-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,2''-[1,4]oxazinan]-15'-one 13',13'-dioxide | 668.3 |
| 131 | | See Example 138 (Step 1 with Net₃ due to HCl salt, Step 2) | | (1S,3'R,6R,7R,8'E,9a''R,11'S,12'R)-6-chloro-11',12'-dimethyl-3,4,6'',7'',9'',9a''-hexahydro-1''H,2H,15'H-dispiro[naphthalene-1,22'-[20]oxa[13]thia[1,14]diazatetracyclo[14.7.2.0~3,6~.0~19,24~]pentacosa[8,16,18,24]tetraene-7,3''-[1,4]oxazino[3,4-c][1,4]oxazin]-15'-one 13',13'-dioxide | 710.2 |

TABLE 1-continued

Examples Prepared by the General Methods

| Example Number | Starting Materials | General Method | Product Structure | Product Name | MS Data (M + 1)+ |
|---|---|---|---|---|---|
| 132 | 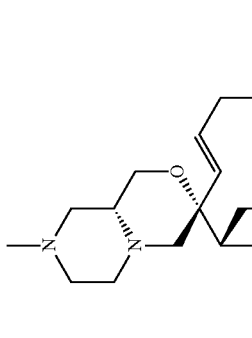 (ChemBridge) | See Example 138 (Steps 1-2) | 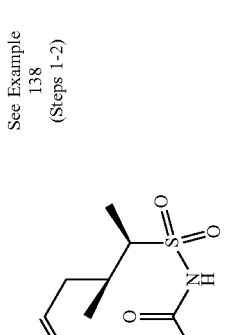 OR  | (1S,3R,6R,7R,8E,9a"R, 11'S,12'R-6-chloro-8",11',12'-trimethyl-1",3,4,6",7",8",9",9a"-octahydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,3'''-pyrazino[2,1-c][1,4]oxazin]-15'-one 13',13'-dioxide Or (1S,3R,6R,7R,8E,9a"S, 11'S,12'R)-6-chloro-8",11',12'-trimethyl-1",3,4,6",7",8",9",9a"-octahydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,3'''-pyrazino[2,1-c][1,4]oxazin]-15'-one 13',13'-dioxide | 723.3 |

| Example Number | Starting Materials | General Method | Product Structure | Product Name | MS Data (M + 1)+ |
|---|---|---|---|---|---|
| 133 | 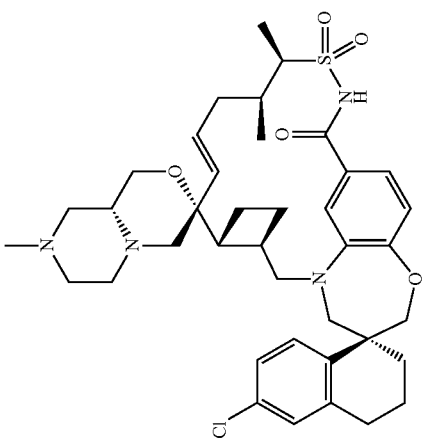 (ChemBridge) | See Example 138 (Steps 1-2) | 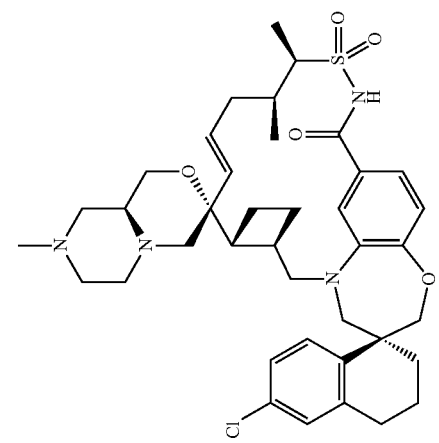 OR 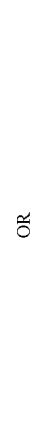 | (1S,3'R,6R,7R,8E,9a"R, 11'S,12'R-6-chloro-8",11',12'-trimethyl-1",3,4,6",7",8",9",9a"-octahydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,3"-pyrazino[2,1-c][[1,4]oxazin]-15'-one 13',13'-dioxide Or (1S,3'R,6R,7R,8E,9a"S, 11'S,12'R)-6-chloro-8",11',12'-trimethyl-1",3,4,6",7",8",9",9a"-octahydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,3"-pyrazino[2,1-c][[1,4]oxazin]-15'-one 13',13'-dioxide | 723.3 |

TABLE 1-continued

Examples Prepared by the General Methods

| Example Number | Starting Materials | General Method | Product Structure | Product Name | MS Data (M + 1)+ |
|---|---|---|---|---|---|
| 134 | | See Example 138 (Steps 1-2) | | (1S,3'R,6R,7R,8'E,11'S,12'R)-6-chloro-11',12'-dimethyl-3,4-dihydro-2H,15'H-dispiro[naphthalene-1,22"-[20]oxa[13]thia[1,14]diazatetracyclo[14.7.2.0~3,6~.0~19,24~]pentacosa[8,16,18,24]tetraene-7',2"-[1,4]oxazinan]-15'-one 13',13'-dioxide | 654.2 |
| 135 | (Combi-Blocks) | See Example 138 (Steps 1-3) | | (1S,3'R,6R,7R,8'E,11'S,12'R)-6-chloro-11',12'-dimethyl-4"-(tetrahydro-2H-pyran-4-ylmethyl)-3,4-dihydro-2H,15'H-dispiro[naphthalene-1,22"-[20]oxa[13]thia[1,14]diazatetracyclo[14.7.2.0~3,6~.0~19,24~]pentacosa[8,16,18,24]tetraene-7',2"-[1,4]oxazinan]-15'-one 13',13'-dioxide | 752.3 |

TABLE 1-continued

Examples Prepared by the General Methods

| Example Number | Starting Materials | General Method | Product Structure | Product Name | MS Data (M + 1)+ |
|---|---|---|---|---|---|
| 136 | | See Example 138 (Steps 1-3) | | (1S,3'R,6R,7R,8E,11'S,12'R)-6-chloro-11',12'-dimethyl-4'''-(4-pyridinylmethyl)-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,2''-[1,4]oxazinan]-15'-one 13',13'-dioxide | 745.3 |

TABLE 1-continued
Examples Prepared by the General Methods
| Example Number | Starting Materials | General Method | Product Structure | Product Name | MS Data (M + 1)+ |
|---|---|---|---|---|---|
| 137 | 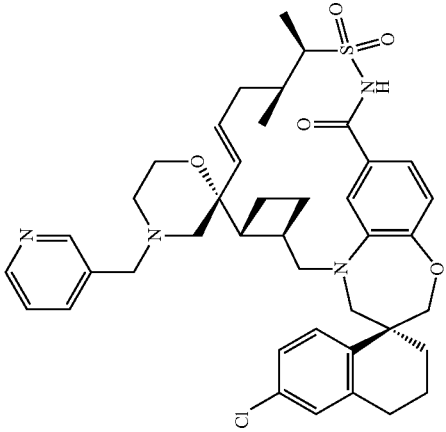 | See Example 138 (Steps 1-3) | 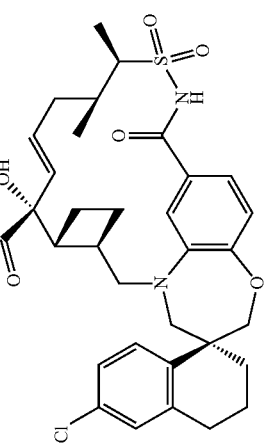 | (1S,3'R,6R,7R,8E,11'S,12'R)-6-chloro-11',12'-dimethyl-4''-(3-pyridinylmethyl)-3,4-dihydro-2H,15'H-dispiro[naphthalene-1,22'-[20]oxa[13]thia[1,14]diazatetracyclo[14.7.2.0~3,6~.0~19,24~]pentacosa[8,16,18,24]tetraene-7,2''-[1,4]oxazinan]-15'-one 13',13'-dioxide | 745.3 |

TABLE 1-continued
Examples Prepared by the General Methods
| Example Number | Starting Materials | General Method | Product Structure | Product Name | MS Data (M + 1)+ |
|---|---|---|---|---|---|
| 139 | 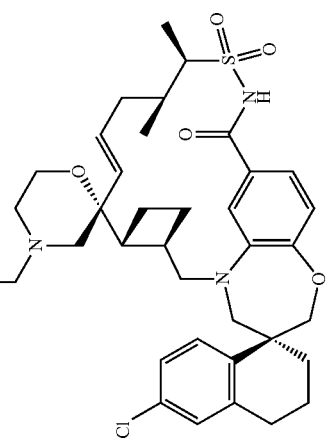 | See Example 138 (Steps 1-3) | 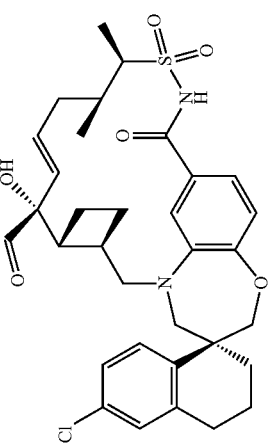 | (1S,3′R,6R,7R,8E,11′S,12′R)-6-chloro-4″-(cyclohexylmethyl)-11′,12′-dimethyl-3,4-dihydro-2H,15′H-dispiro[naphthalene-1,22′-[20]oxa[13]thia[1,14]diazatetracyclo[14.7.2.0~3,6~.0~19,24~]pentacosa[8,16,18,24]tetraene-7,2″-[1,4]oxazinan]-15′-one 13′,13′-dioxide | 750.3 |

TABLE 1-continued

Examples Prepared by the General Methods

| Example Number | Starting Materials | General Method | Product Structure | Product Name | MS Data (M + 1)+ |
|---|---|---|---|---|---|
| 140 | | 8 | | (1S,3'R,6R,7R,8E,11'S,12R)-6-chloro-7'-methoxsy-11',12'-dimethyl-7-(((9aS)-4-oxohexahydropyrazino[2,1-c][1,4]oxazin-8(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |

TABLE 1-continued

Examples Prepared by the General Methods

| Example Number | Starting Materials | General Method | Product Structure | Product Name | MS Data (M + 1)+ |
|---|---|---|---|---|---|
| 141 | 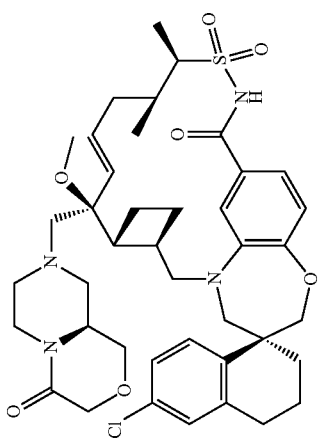 | 8 | 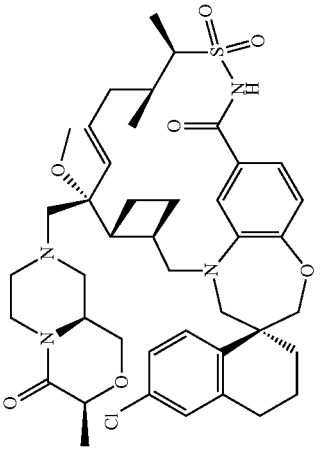 | (1S,3'R,6'R,7'R,8'E,11'S,12'R)-6-chloro-7'-methoxy-11',12'-dimethyl-7-(((9aS)-4-oxohexahydropyrazino[2,1-c][1,4]oxazin-8(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |
| 142 | 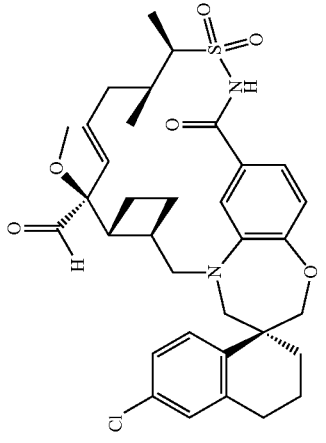 | 8 | 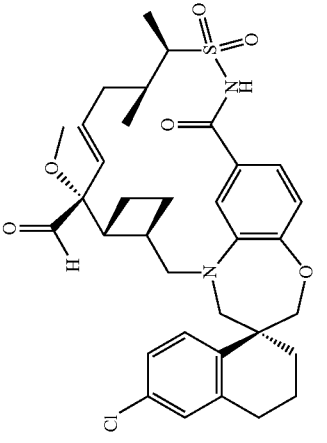 | (1S,3'R,6'R,7'R,8'E,11'S,12'R)-6-chloro-7'-methoxy-11',12'-dimethyl-7-(((3S,9aS)-3-methyl-4-oxohexahydropyrazino[2,1-c][1,4]oxazin-8(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.3 |

TABLE 1-continued

Examples Prepared by the General Methods

| Example Number | Starting Materials | General Method | Product Structure | Product Name | MS Data (M + 1)+ |
|---|---|---|---|---|---|
| 143 | 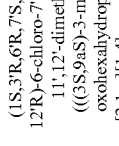 | 8 | 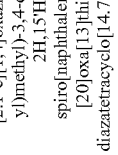 | (1S,3'R,6R,7R,7S,8E,11'S,12'R)-6-chloro-7'-methoxy-11',12'-dimethyl-7'-(((3S,9aS)-3-methyl-4-oxohexahydropyrazino[2,1-c][1,4]oxazin-8(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.2 |
| 144 | 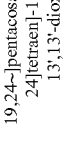 | 8 |  | (1S,3'R,6R,7R,8E,11'S,12'R)-6-chloro-7'-methoxy-11',12'-dimethyl-7'-(((3R,9aS)-3-methyl-4-oxohexahydropyrazino[2,1-c][1,4]oxazin-8(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.3 |

TABLE 1-continued

Examples Prepared by the General Methods

| Example Number | Starting Materials | General Method | Product Structure | Product Name | MS Data (M + 1)+ |
|---|---|---|---|---|---|
| 145 | | 8 | | (1S,3′R,6R,7S,8E,11′S,12′R)-6-chloro-7′-methoxy-11′,12′-dimethyl-7-(((3S,9aS)-3-methylhexahydropyrazino[2,1-c][1,4]oxazin-8(1H)-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 781.4 |
| 146 | | 8 | | (1S,3′R,6R,7R,8E,11′S,12′R)-6-chloro-7′-methoxy-11′,12′-dimethyl-7-(((3S,9aS)-3-methylhexahydropyrazino[2,1-c][1,4]oxazin-8(1H)-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 781.2 |

TABLE 1-continued

Examples Prepared by the General Methods

| Example Number | Starting Materials | General Method | Product Structure | Product Name | MS Data (M + 1)+ |
|---|---|---|---|---|---|
| 147 | | 8 | | (1S,3'R,6'R,7S,8E,11'S,12'R)-6-chloro-7'-methoxy-11',12'-dimethyl-7-(((3R,9aS)-3-methylhexahydropyrazino[2,1-c][1,4]oxazin-8(1H)-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |
| 148 | (Frontier Scientific) | 8 | | (1S,3'R,6'R,7S,8E,11'S,12'R)-6-chloro-7'-(3,4-dihydro-2(1H)-isoquinolinylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 758.3 |

TABLE 1-continued

Examples Prepared by the General Methods

| Example Number | Starting Materials | General Method | Product Structure | Product Name | MS Data (M + 1)+ |
|---|---|---|---|---|---|
| 149 | | 8 | | (1S,3'R,6'R,7'R,8'E,11'S,12'R)-6-chloro-7'-methoxy-11',12'-dimethyl-7'-(((9aR)-4-oxooctahydro-2H-pyrido[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.3 |

TABLE 1-continued

Examples Prepared by the General Methods

| Example Number | Starting Materials | General Method | Product Structure | Product Name | MS Data (M + 1)+ |
|---|---|---|---|---|---|
| 150 | | 8 | | (1S,3'R,6R,7S,8E,11S,12'R)-6-chloro-7'-methoxy-11',12'-dimethyl-7-(((9aR)-4-oxooctahydro-2H-pyrido[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.3 |

TABLE 1-continued

Examples Prepared by the General Methods

| Example Number | Starting Materials | General Method | Product Structure | Product Name | MS Data (M + 1)+ |
|---|---|---|---|---|---|
| 152 | | See example 151 | | (1S,3'R,6R,7R,8E,11'S, 12'R)-6-chloro-7'-(2-methoxyethoxy)-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.2 |

TABLE 1-continued

Examples Prepared by the General Methods

| Example Number | Starting Materials | General Method | Product Structure | Product Name | MS Data (M + 1)+ |
|---|---|---|---|---|---|
| 153 | | 8 | | (1S,3'R,6'R,7'R,8'E,11'S,12'R)-6-chloro-7'-((4-(2,2-dimethylpropyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.3 |

TABLE 1-continued
Examples Prepared by the General Methods
| Example Number | Starting Materials | General Method | Product Structure | Product Name | MS Data (M + 1)+ |
|---|---|---|---|---|---|
| 155 | 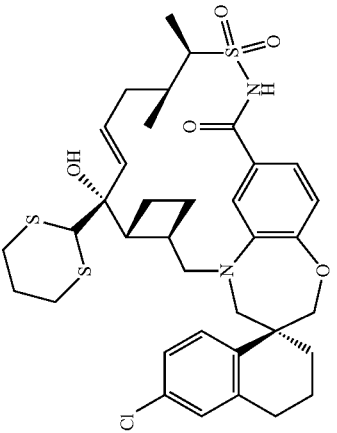 | 5, 8 | 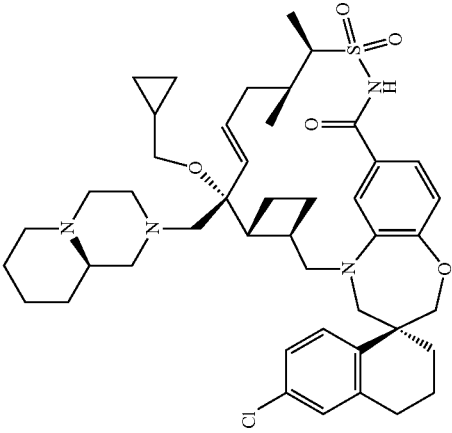 | (1S,3'R,6R,7R,8E,11'S,12'R)-6-chloro-7'-(cyclopropylmethoxy)-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 805.3 |

TABLE 1-continued
Examples Prepared by the General Methods
| Example Number | Starting Materials | General Method | Product Structure | Product Name | MS Data (M + 1)+ |
|---|---|---|---|---|---|
| 156 | 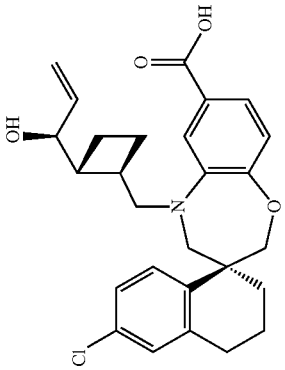 | 2, 5, 8 | 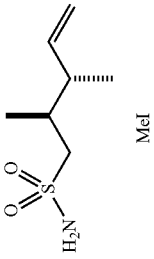 | (1S,3'R,6'R,7'S,8'E,10'S, 11'S)-6-chloro-7'-((9aS)- hexahydropyrazino[2,1- c][1,4]oxazin-8(1H)- ylmethyl)-7'-methoxy- 10', 11'-dimethyl-3,4- dihydro-2H,15'H- spiro[naphthalene-1,22'- [20]oxa[13]thia[1,14] diazatetracyclo[14.7.2.0~3,6~.0~ 19,24~]pentacosa[8,16,18, 24]tetraen]-15'-one 13',13'-dioxide | 767 |

TABLE 1-continued
Examples Prepared by the General Methods
| Example Number | Starting Materials | General Method | Product Structure | Product Name | MS Data (M + 1)+ |
|---|---|---|---|---|---|
| 157 | 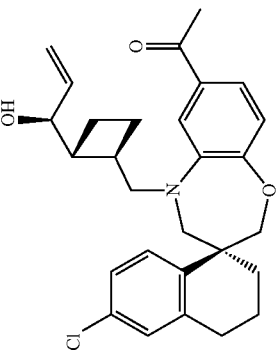 | 2, 5, 8 | 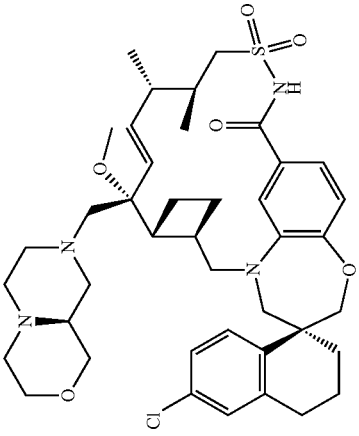 | (1S,3'R,6'R,7'R,8'E,10'S,11'S)-6-chloro-7'-((9aS)-hexahydropyrazino[2,1-c][1,4]oxazin-8(1H)-ylmethyl)-7'-methoxy-10,11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued
Examples Prepared by the General Methods
| Example Number | Starting Materials | General Method | Product Structure | Product Name | MS Data (M + 1)+ |
|---|---|---|---|---|---|
| 158 | 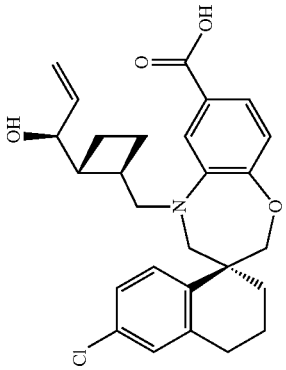 | 2, 5, 8 | 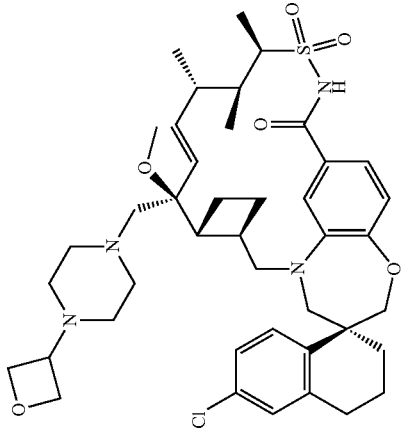 | (1S,3R,6R,7S,8E,10S,11'S)-6-chloro-7'-methoxy-10',11'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued

Examples Prepared by the General Methods

| Example Number | Starting Materials | General Method | Product Structure | Product Name | MS Data (M + 1)+ |
|---|---|---|---|---|---|
| 159 | | 2, 5, 8 | | (1S,3'R,6'R,7'R,8'E,10'S,11'S)-6-chloro-7'-methoxy-10',11'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued
Examples Prepared by the General Methods
| Example Number | Starting Materials | General Method | Product Structure | Product Name | MS Data (M + 1)+ |
|---|---|---|---|---|---|
| 160 | 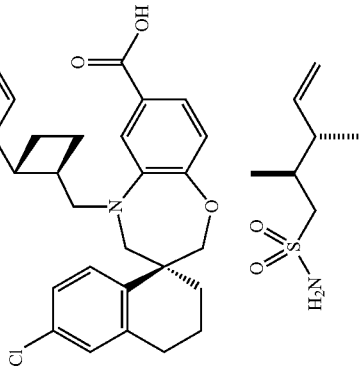 | 2, 5, 8 | 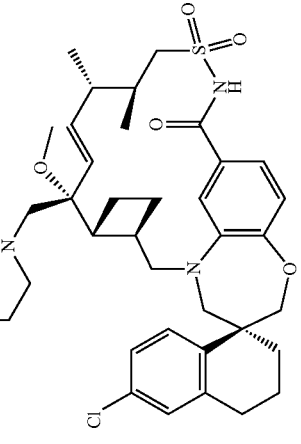 | (1S,3'R,6R,7R,8'E,10S,11'S)-6-chloro-7'-methoxy-10',11'-dimethyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 725.2 |

TABLE 1-continued

Examples Prepared by the General Methods

| Example Number | Starting Materials | General Method | Product Structure | Product Name | MS Data (M + 1)+ |
|---|---|---|---|---|---|
| 161 | (structures shown) | 2, 5, 8 | (structure shown) | (1S,3'R,6'R,7'R,8'E,10'S,11'S)-6-chloro-7'-methoxy-10,11'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.2 |

TABLE 1-continued
Examples Prepared by the General Methods
| Example Number | Starting Materials | General Method | Product Structure | Product Name | MS Data (M + 1)+ |
|---|---|---|---|---|---|
| 162 | 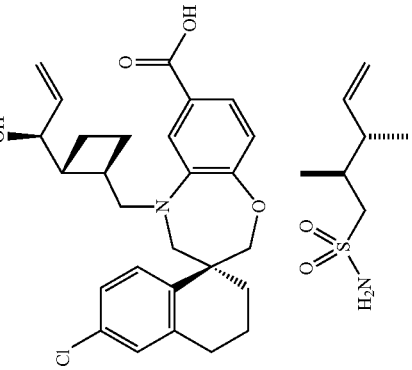 | 2, 5, 8 | 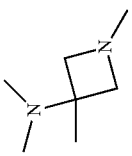 | (1S,3R,6R,7S,8E,10S,11'S)-6-chloro-7'-((3-(dimethylamino)-3-methyl-1-azetidinyl)methyl)-7-methoxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 739.2 |

TABLE 1-continued

Examples Prepared by the General Methods

| Example Number | Starting Materials | General Method | Product Structure | Product Name | MS Data (M + 1)+ |
|---|---|---|---|---|---|
| 163 | | 2, 5, 8 | | (1S,3R,6R,7S,8E,10S,11'S)-6-chloro-7'-methoxy-10',11'-dimethyl-7-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.2 |

TABLE 1-continued
Examples Prepared by the General Methods
| Example Number | Starting Materials | General Method | Product Structure | Product Name | MS Data (M + 1)+ |
|---|---|---|---|---|---|
| 164 | 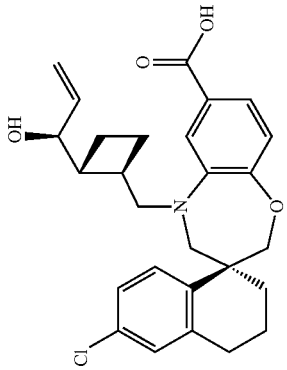 | 2, 5 (Step 1), 8 | 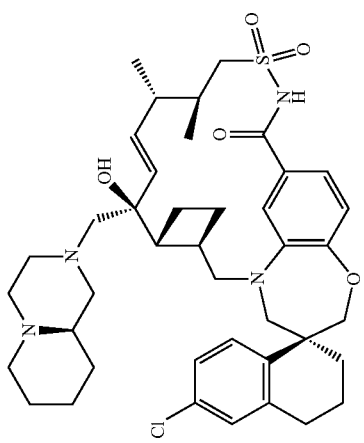 | (1S,3R,6R,7S,7S,8E,10S,11'S)-6-chloro-7'-((9aS)-hexahydropyrazino[2,1-c][1,4]oxazin-8(1H)-ylmethyl)-7-hydroxy-10,11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.2 |

TABLE 1-continued

Examples Prepared by the General Methods

| Example Number | Starting Materials | General Method | Product Structure | Product Name | MS Data (M + 1)+ |
|---|---|---|---|---|---|
| 165 | | 2 (Step 1), 5, 8 | | (1S,3'R,6R,7R,8E,10S,11'S)-6-chloro-7'-hydroxy-10',11'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.2 |

TABLE 1-continued
Examples Prepared by the General Methods
| Example Number | Starting Materials | General Method | Product Structure | Product Name | MS Data (M + 1)+ |
|---|---|---|---|---|---|
| 166 | 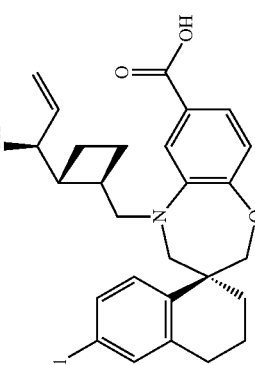 | 2, 5, 8 | 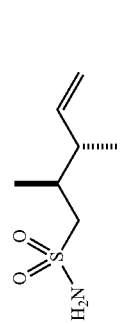 | (1S,3'R,6'R,7'R,8'E,10'S, 11'S)-6-chloro-7'-ethoxy-10',11'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |

TABLE 1-continued
Examples Prepared by the General Methods
| Example Number | Starting Materials | General Method | Product Structure | Product Name | MS Data (M + 1)+ |
|---|---|---|---|---|---|
| 167 | 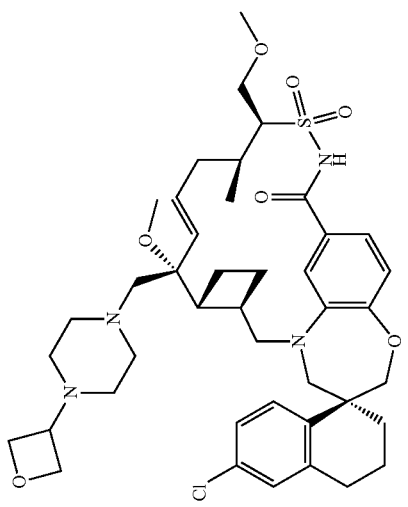 | 2, 5, 8 | 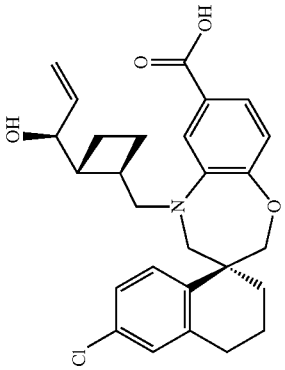 | (1S,3'R,6R,7R,8E,11'S,12'S)-6-chloro-7'-methoxy-12'-(methoxymethyl)-11'-methyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued
Examples Prepared by the General Methods
| Example Number | Starting Materials | General Method | Product Structure | Product Name | MS Data (M + 1)+ |
|---|---|---|---|---|---|
| 168 | 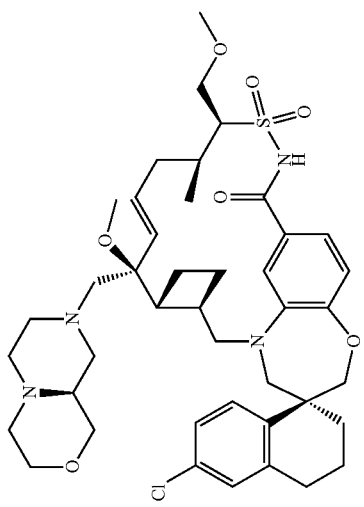 | 2, 5, 8 | 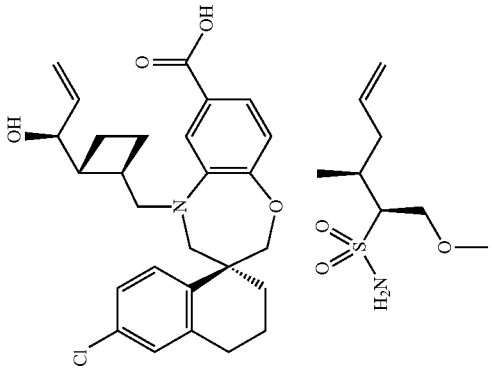 | (1S,3'R,6R,7S,8'E,11'S,12'S)-6-chloro-7'-((9aS)-hexahydropyrazino[2,1-c][1,4]oxazin-8(1H)-ylmethyl)-7'-methoxy-12'-(methoxymethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued
Examples Prepared by the General Methods
| Example Number | Starting Materials | General Method | Product Structure | Product Name | MS Data (M + 1)+ |
|---|---|---|---|---|---|
| 169 |  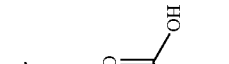 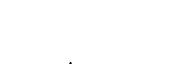 MeI | 2, 5, 8 | 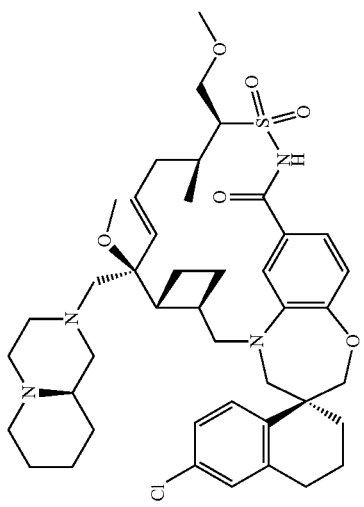 | (1S,3'R,6R,7R,8E,11'S,12'S)-6-chloro-7'-methoxy-12'-(methoxymethyl)-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14] diazatetracyclo[14.7.2.0~3,6~.0~19,24~]pentacosa[8,16,18,24]tetraen]-15'-one 13',13'-dioxide | 795.2 |

TABLE 1-continued

Examples Prepared by the General Methods

| Example Number | Starting Materials | General Method | Product Structure | Product Name | MS Data (M + 1)+ |
|---|---|---|---|---|---|
| 170 | | 2, 5, 8 | | (1S,3R,6R,7S,8E,11S,12′S)-6-chloro-7′-methoxy-12′-(methoxymethyl)-11′-methyl-7′-((4-(3-oxetanyl)-1-piperazinyl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 797.2 |

TABLE 1-continued
Examples Prepared by the General Methods
| Example Number | Starting Materials | General Method | Product Structure | Product Name | MS Data (M + 1)+ |
|---|---|---|---|---|---|
| 171 | 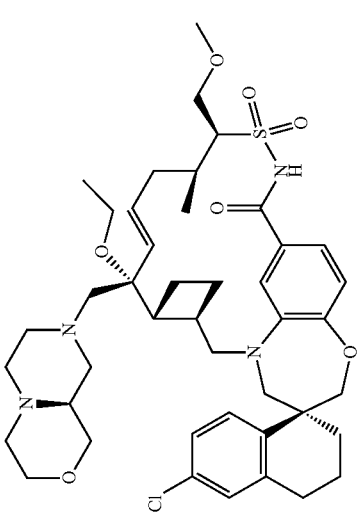 | 2, 5, 8 | 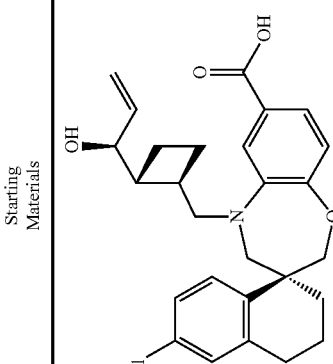 | (1S,3'R,6R,7R,8E,11'S,12'S)-6-chloro-7'-ethoxy-7'-((9aS)-hexahydropyrazino[2,1-c][1,4]oxazin-8(1H)-ylmethyl)-12'-(methoxymethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

TABLE 1-continued
Examples Prepared by the General Methods
| Example Number | Starting Materials | General Method | Product Structure | Product Name | MS Data (M + 1)+ |
|---|---|---|---|---|---|
| 172 | 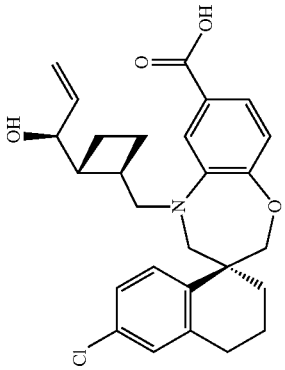 | 2, 5, 8 | 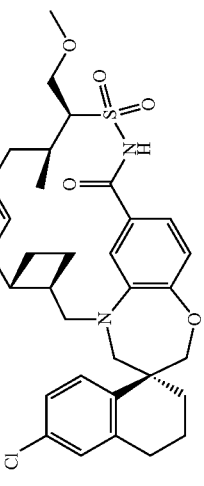 | (1S,3'R,6R,7S,8E,11S,12'S)-6-chloro-7-methoxy-7'-((4-(2-methoxy-1-(methoxymethyl)ethyl)-1-piperazinyl)methyl)-12'-(methoxymethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 843.2 |

TABLE 1-continued

Examples Prepared by the General Methods

| Example Number | Starting Materials | General Method | Product Structure | Product Name | MS Data (M + 1)+ |
|---|---|---|---|---|---|
| 173 | [structures] | 2, 5, 8 | [structure] | (1S,3'R,6R,7S,8'E,11'S,12'S)-6-chloro-7'-methoxy-12'-(methoxymethyl)-11'-methyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.4 |

TABLE 1-continued
Examples Prepared by the General Methods
| Example Number | Starting Materials | General Method | Product Structure | Product Name | MS Data (M + 1)+ |
|---|---|---|---|---|---|
| 174 | 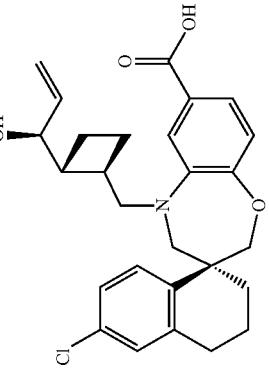 | 2, 5, 8 | 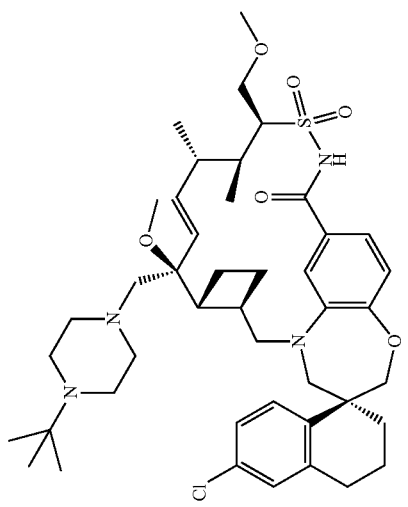 | (1S,3'R,6R,7S,8'E,11'S,12'S)-7'-((4-tert-butyl-1-piperazinyl)methyl)-6-chloro-7'-methoxy-12'-(methoxymethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued
Examples Prepared by the General Methods
| Example Number | Starting Materials | General Method | Product Structure | Product Name | MS Data (M + 1)+ |
|---|---|---|---|---|---|
| 175 | 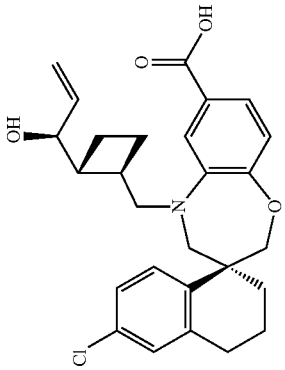 | 2, 5, 8 | 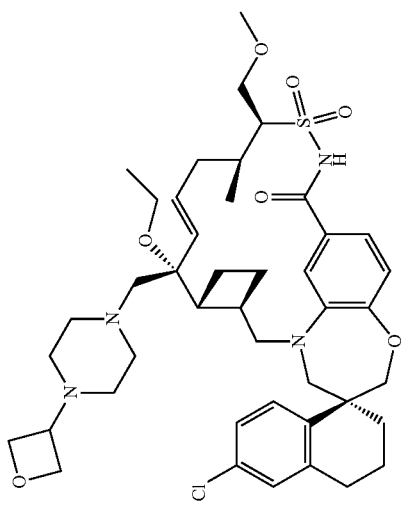 | (1S,3'R,6R,7R,8'E,11'S,12'S)-6-chloro-7'-ethoxy-12'-(methoxymethyl)-11'-methyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

TABLE 1-continued

Examples Prepared by the General Methods

| Example Number | Starting Materials | General Method | Product Structure | Product Name | MS Data (M + 1)+ |
|---|---|---|---|---|---|
| 178 | | 12 | | (1S,3'R,6'R,7'R,8'E,11'S,12'R)-6-chloro-7'-methoxy-12'-(2-methoxyethyl)-11'-methyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.2 |
| 179 | | 5, 10 | | (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

TABLE 1-continued

Examples Prepared by the General Methods

| Example Number | Starting Materials | General Method | Product Structure | Product Name | MS Data (M + 1)+ |
|---|---|---|---|---|---|
| 180 | | 5, 12 | | (1S,3'R,6'R,7'R,7S,8'E,11'S,12'R)-6-chloro-7'-methoxy-12'-(2-methoxyethyl)-11'-methyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.2 |
| 181 | | 12 | | (1S,3'R,6'R,7'R,8'E,11'S,12'R)-6-chloro-7'-methoxy-12'-(2-methoxyethyl)-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.0 |

TABLE 1-continued
Examples Prepared by the General Methods
| Example Number | Starting Materials | General Method | Product Structure | Product Name | MS Data (M + 1)+ |
|---|---|---|---|---|---|
| 182 | 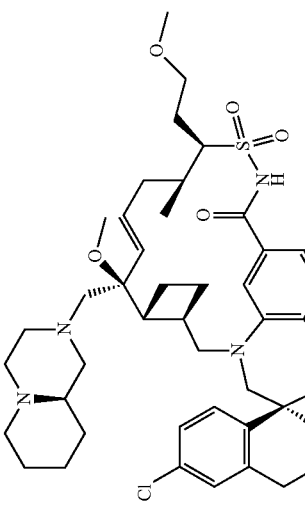 MeI | 5, 12 | 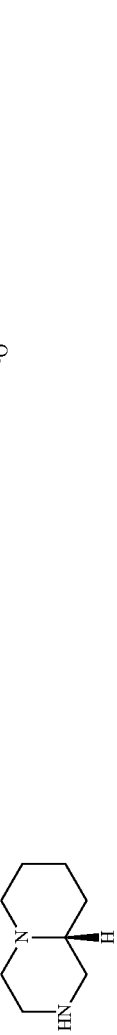 | (1S,3'R,6'R,7'S,8'E,11'S, 12'R)-6-chloro-7'-methoxy-12'-(2-methoxyethyl)-11'-methyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.2 |

TABLE 1-continued
Examples Prepared by the General Methods
| Example Number | Starting Materials | General Method | Product Structure | Product Name | MS Data (M + 1)+ |
|---|---|---|---|---|---|
| 184 | 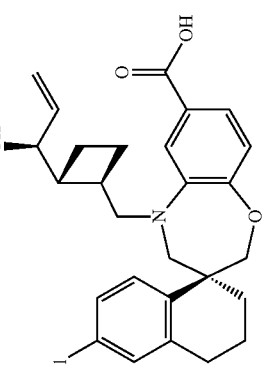 | 1, 5, 11 | 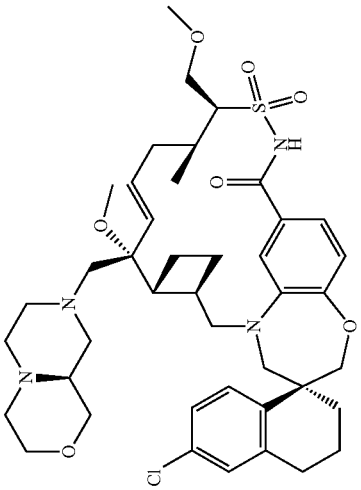 | (1S,3′R,6R,7R,7′R,8′E,11′S,12′S)-6-chloro-7′-((9aS)-hexahydropyrazino[2,1-c][1,4]oxazin-8(1H)-ylmethyl)-7′-methoxy-12′-(methoxymethyl)-11′-methyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 797.2 |

TABLE 1-continued

Examples Prepared by the General Methods

| Example Number | Starting Materials | General Method | Product Structure | Product Name | MS Data (M + 1)+ |
|---|---|---|---|---|---|
| 185 | 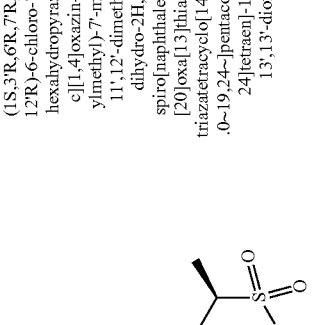 | 5, 11 | 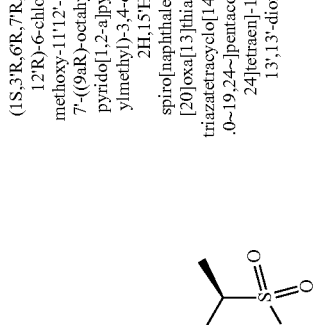 | (1S,3'R,6'R,7'R,8'E,11'S,12'R)-6-chloro-7'-((9aS)-hexahydropyrazino[2,1-c][1,4]oxazin-8(1H)-ylmethyl)-7'-methoxy-11',12'-dimethyl-3,4-dihydro-2H,15'H-spiro[naphthalene-1,22'-[20]oxa[13]thia[1,14,25]triazatetracyclo[14.7.2.0-3,6.0-19,24-]pentacosa[8,16,18,24]tetraen]-15'-one 13',13'-dioxide | 768.2 |
| 186 | 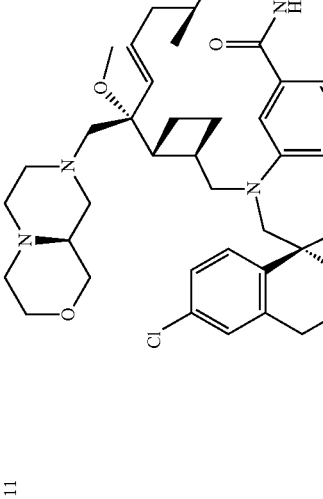 | 5, 11 | 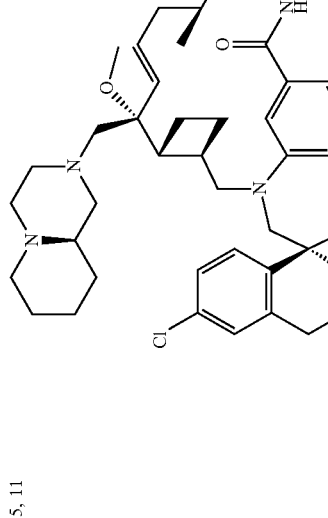 | (1S,3'R,6'R,7'R,8'E,11'S,12'R)-6-chloro-7'-methoxy-11'12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14,25]triazatetracyclo[14.7.2.0-3,6.0-19,24-]pentacosa[8,16,18,24]tetraen]-15'-one 13',13'-dioxide | 766.2 |

TABLE 1-continued
Examples Prepared by the General Methods
| Example Number | Starting Materials | General Method | Product Structure | Product Name | MS Data (M + 1)+ |
|---|---|---|---|---|---|
| 187 |  | 12 |  | (1S,3'R,6'R,7'R,8'E,11'S,12'R)-6-chloro-7'-methoxy-12'-(2-methoxyethyl)-11'-methyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

TABLE 1-continued

Examples Prepared by the General Methods

| Example Number | Starting Materials | General Method | Product Structure | Product Name | MS Data (M + 1)+ |
|---|---|---|---|---|---|
| 188 | | 12 | | (1S,3'R,6'R,7'R,8'E,11'S,12'R)-6-chloro-7'-methoxy-12'-(2-methoxyethyl)-11'-methyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued

Examples Prepared by the General Methods

| Example Number | Starting Materials | General Method | Product Structure | Product Name | MS Data (M + 1)+ |
|---|---|---|---|---|---|
| 189 | | 12 | | (1S,3'R,6R,7R,8'E,11'S,12'R)-7'-((4-tert-butyl-1-piperazinyl)methyl)-6-chloro-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

| Example Number | Starting Materials | General Method | Product Structure | Product Name | MS Data (M + 1)+ |
|---|---|---|---|---|---|
| 190 | | 12 | | (1S,3'R,6'R,7'R,8'E,11'S,12'R)-7'-((4-tert-butyl-1-piperazinyl)methyl)-6-chloro-7'-ethoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 825.2 |

TABLE 1-continued

Examples Prepared by the General Methods

| Example Number | Starting Materials | General Method | Product Structure | Product Name | MS Data (M + 1)+ |
|---|---|---|---|---|---|
| 191 | | 12 | | (1S,3'R,6R,7R,8E,11'S,12'R)-6-chloro-7'-methoxy-12'-(2-methoxyethyl)-1'-methyl-7'-(((3R,5S)-3,4,5-trimethyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued

Examples Prepared by the General Methods

| Example Number | Starting Materials | General Method | Product Structure | Product Name | MS Data (M + 1)+ |
|---|---|---|---|---|---|
| 192 | | 12 | | (1S,3'R,6'R,7'R,7S,8'E,11'S,12'R)-6'-chloro-7'-methoxy-12'-(2-methoxyethyl)-11'-methyl-7-((4-(3-methyl-3-oxetanyl))-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 825.2 |
| 195 | | 10 | | (1S,3'R,6'R,7'S,8'E,11'S,12'R)-6'-chloro-7'-methoxy-7-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.2 |

TABLE 1-continued

Examples Prepared by the General Methods

| Example Number | Starting Materials | General Method | Product Structure | Product Name | MS Data (M + 1)+ |
|---|---|---|---|---|---|
| 196 | 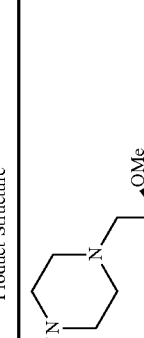 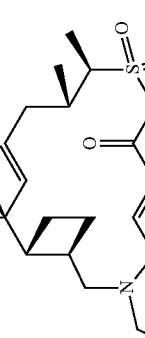 | 10 | 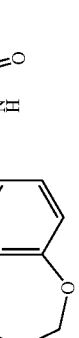 | (1S,3'R,6'R,7S,8'E,11'S,12'R)-6-chloro-7'-methoxy-11',12'-dimethyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 725.3 |
| 197 | 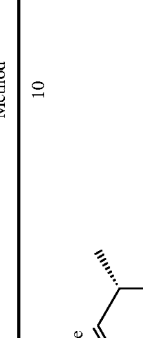  (J&W PharmLab) | 10 |  | (1S,3'R,6'R,7S,8'E,11'S,12'R)-6-chloro-7'-methoxy-11',12'-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.3 |

TABLE 1-continued
Examples Prepared by the General Methods
| Example Number | Starting Materials | General Method | Product Structure | Product Name | MS Data (M + 1)+ |
|---|---|---|---|---|---|
| 198 | 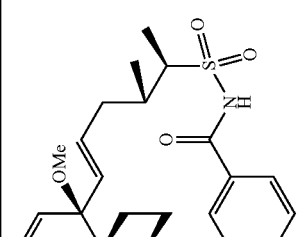 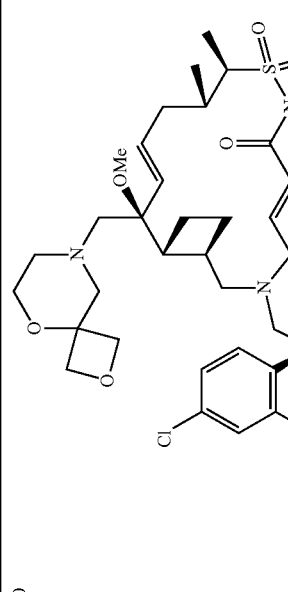 (A2Z Chemical) | 10 | 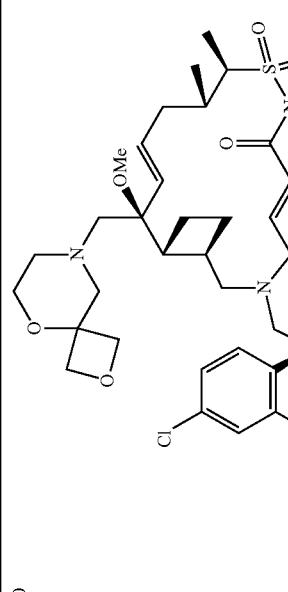 | (1S,3'R,6R,7S,8E,11'S, 12'R)-6-chloro-7'-(2,5-dioxa-8-azaspiro[3.5]non-8-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 754.4 |

TABLE 1-continued

Examples Prepared by the General Methods

| Example Number | Starting Materials | General Method | Product Structure | Product Name | MS Data $(M + 1)^+$ |
|---|---|---|---|---|---|
| 199 | (Ark Pharm, Inc.) | 10 | | (1S,3'R,6'R,7'S,8'E,11'S,12'R)-6-chloro-7'-methoxy-7'-(((2R)-2-(methoxymethyl)-4-morpholinyl)methyl)-11,12-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 756.3 |
| 200 | (Anichem) | 10 | | (1S,3'R,6'R,7'S,8'E,11'S,12'R)-6-chloro-7'-(6,7-dihydroisoxazolo[4,3-c]pyridin-5(4H)-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 749.3 |

TABLE 1-continued

Examples Prepared by the General Methods

| Example Number | Starting Materials | General Method | Product Structure | Product Name | MS Data (M + 1)+ |
|---|---|---|---|---|---|
| 201 | (Anichem) | 10 | | (1S,3'R,6'R,7'S,8'E,11'S,12'R)-6-chloro-7'-(5,6-dihydroimidazo[1,2-a]pyrazin-7(8H)-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 748.2 |
| 202 | (Synthonix) | 10 | | (1S,3'R,6'R,7'S,8'E,11'S,12'R)-6-chloro-7'-((2,2-dioxido-2-thia-6-azaspiro[3.3]hept-6-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 772.3 |

TABLE 1-continued
Examples Prepared by the General Methods
| Example Number | Starting Materials | General Method | Product Structure | Product Name | MS Data (M + 1)+ |
|---|---|---|---|---|---|
| 203 | 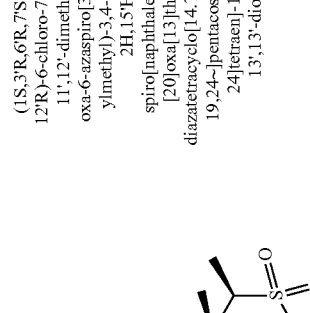 (Advanced ChemTech) | 10 | 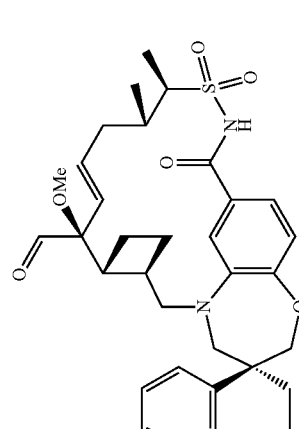 | (1S,3′R,6R,7′S,8′E,11′S,12′R)-6-chloro-7′-methoxy-11′,12′-dimethyl-7-(2-oxa-6-azaspiro[3.3]hept-6-ylmethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 724.3 |

TABLE 1-continued

Examples Prepared by the General Methods

| Example Number | Starting Materials | General Method | Product Structure | Product Name | MS Data (M + 1)+ |
|---|---|---|---|---|---|
| 204 | (Advanced ChemBlocks) | 10 | | tert-butyl 6-(1S,3R,6R,7S,8E,11S,12R)-6-chloro-7-methoxy-11′,12′-dimethyl-13′,13′-dioxido-15′-oxo-3,4-dihydro-2H-spiro[naphthalene-1,22′-[20]oxa[13]thia[1,14]diazatetracyclo[14.7.2.0~3,6~.0~19,24~]pentacosa[8,16,18,24]tetraen]-7′yl)methyl)-2,6-diazaspiro[3.3]heptane-2-carboxylate | 823.3 |
| 205 | (Enamine) | 10 | | (1S,3R,6R,7S,8E,11S,12R)-6-chloro-7-methoxy-11′,12′-dimethyl-7′-(1,4,6,7-tetrahydro-5H-[1,2,3]triazolo[4,5-c]pyridin-5-ylmethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 749.3 |

TABLE 1-continued

Examples Prepared by the General Methods

| Example Number | Starting Materials | General Method | Product Structure | Product Name | MS Data (M + 1)+ |
|---|---|---|---|---|---|
| 206 | | 10 (with in situ oxetane hydrolysis) | | (1S,3′R,6R,7S,8E,11′S,12′R)-7-((3,3-bis(hydroxymethyl)-1-azetidinyl)methyl)-6-chloro-7′-methoxy-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 742.3 |

| Example Number | Starting Materials | General Method | Product Structure | Product Name | MS Data (M + 1)+ |
|---|---|---|---|---|---|
| 207 | (Accela ChemBio, Inc.) | 10 | | (1S,3'R,6R,7S,8E,11'S, 12'R)-6-chloro-7'-(6,7-dihydro[1,2,3]triazolo[1,5-a]pyrazin-5(4H)-ylmethyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 749.5 |

TABLE 1-continued

Examples Prepared by the General Methods

| Example Number | Starting Materials | General Method | Product Structure | Product Name | MS Data (M + 1)+ |
|---|---|---|---|---|---|
| 208 | (Alfa Aesar, A Johnson-Matthey Company) | 10 | | (1S,3'R,6'R,7S,8E,11'S,12'R)-6'-chloro-7'-methoxy-11',12'-dimethyl-7'-(6-oxa-1-azaspiro[3.3]hept-1-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.4 |
| 209 | | 10 | | (1S,3'R,6'R,7S,8E,11'S,12'R)-6'-chloro-7'-(6,7-dihydro[1,3]thiazolo[5,4-c]pyridin-5(4H)-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.5 |

TABLE 1-continued

Examples Prepared by the General Methods

| Example Number | Starting Materials | General Method | Product Structure | Product Name | MS Data (M + 1)+ |
|---|---|---|---|---|---|
| 210 | 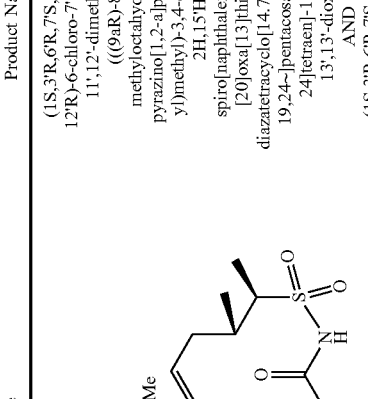 | 10 | 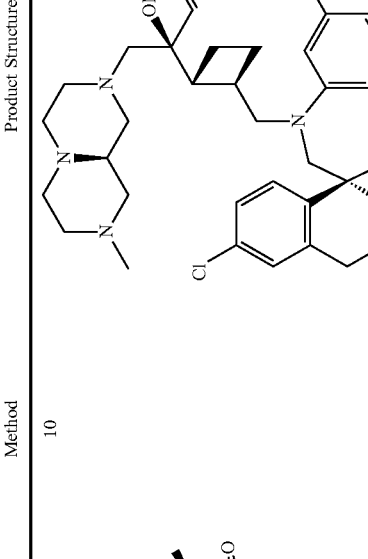 AND 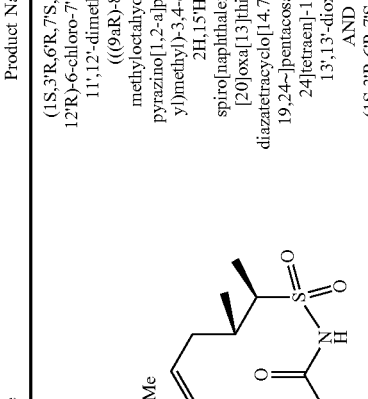 | (1S,3'R,6R,7S,8E,11'S,12'R)-6-chloro-7'-methoxy-11',12'-dimethyl-7-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7S,8E,11'S,12'R)-6-chloro-7'-methoxy-11',12'-dimethyl-7-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 780.5 |

TABLE 1-continued

Examples Prepared by the General Methods

| Example Number | Starting Materials | General Method | Product Structure | Product Name | MS Data (M + 1)+ |
|---|---|---|---|---|---|
| 211 | | 10 | | (1S,3'R,6'R,7S,8'E,11'S,12'R)-6-chloro-7'-(5,8-dihydropyrido[3,4-d]pyrimidin-7(6H)-yl methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 760.3 |
| 212 | | 10 | | (1S,3'R,6'R,7S,8'E,11'S,12'R)-6-chloro-7'-methoxy-7'-((methoxy(methyl)amino)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 686.5 |

TABLE 1-continued

Examples Prepared by the General Methods

| Example Number | Starting Materials | General Method | Product Structure | Product Name | MS Data (M + 1)+ |
|---|---|---|---|---|---|
| 214 | | 10 | | (1S,3'R,6'R,7'S,8'E,11'S, 12'R)-7'-(((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S, 12'R)-7'-(((9aR)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.3 |

TABLE 1-continued

Examples Prepared by the General Methods

| Example Number | Starting Materials | General Method | Product Name | Product Structure | MS Data (M + 1)+ |
|---|---|---|---|---|---|
| 215 | (FCH1267684) | 10 | (1S,3'R,6'R,7'S,8'E,11'S,12'R)-6'-chloro-7'-(((9aS)-2,2-dioxidohexahydropyrazino[2,1-c][1,4]thiazin-8(1H)-yl)methyl)-7'-methoxy-11',12',-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one AND (1S,3'R,6'R,7'S,8'E,11'S,12'R)-6'-chloro-7'-(((9aR)-2,2-dioxidohexahydropyrazino[2,1-c][1,4]thiazin-8(1H)-yl)methyl)-7'-methoxy-11',12',-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one | | 815.3 |

TABLE 1-continued

Examples Prepared by the General Methods

| Example Number | Starting Materials | General Method | Product Structure | Product Name | MS Data (M + 1)+ |
|---|---|---|---|---|---|
| 216 | 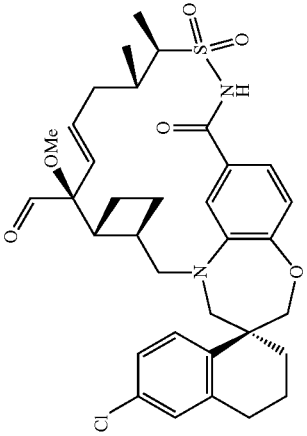 (ChemBridge) | 10 | 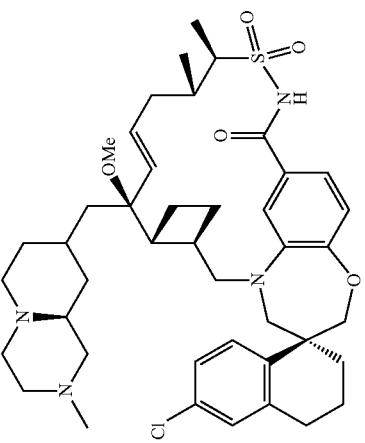 OR 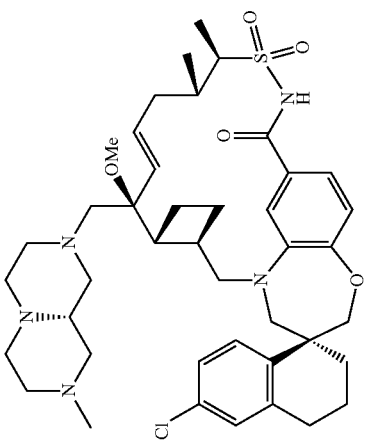 | (1S,3'R,6R,7S,8E,11'S,12'R)-6-chloro-7'-methoxy-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7S,8E,11'S,12'R)-6-chloro-7'-methoxy-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 780.5 |

TABLE 1-continued

Examples Prepared by the General Methods

| Example Number | Starting Materials | General Method | Product Structure | Product Name | MS Data (M + 1)+ |
|---|---|---|---|---|---|
| 217 | 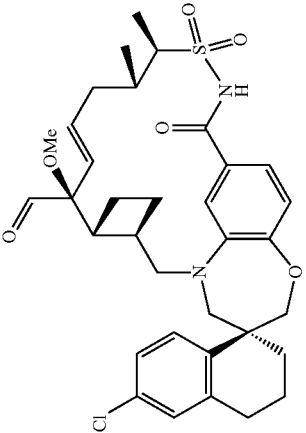 (ChemBridge) | 10 | 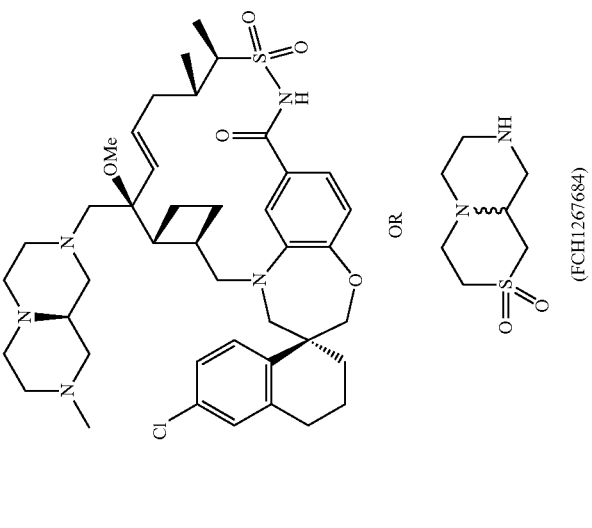 (FCH1267684) | (1S,3'R,6'R,7'S,8'E,11'S,12'R)-6-chloro-7'-methoxy-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 780.5 |

TABLE 1-continued

Examples Prepared by the General Methods

| Example Number | Starting Materials | General Method | Product Structure | Product Name | MS Data (M + 1)+ |
|---|---|---|---|---|---|
| 218 | | 10 | | (1S,3'R,6R,7S,8E,11S,12'R)-7-(((9aR)-8-acetyloctahydro-2H-pyrazino[1,2-a]pyrazin-2-yl)methyl)-6-chloro-7'-methoxy-11'12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7S,8E,11S,12'R)-7-(((9aR)-8-acetyloctahydro-2H-pyrazino[1,2-a]pyrazin-2-yl)methyl)-6-chloro-7'-methoxy-11'12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.3 |

TABLE 1-continued

Examples Prepared by the General Methods

| Example Number | Starting Materials | General Method | Product Structure | Product Name | MS Data (M + 1)+ |
|---|---|---|---|---|---|
| 219 | 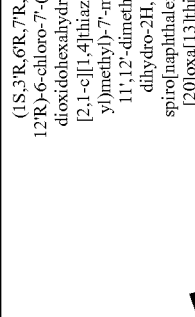 | 10 | 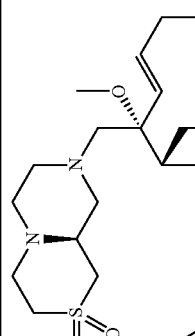 AND  | (1S,3R,6R,7R,8E,11S,12'R)-6-chloro-7'-(((9aR)-2,2-dioxidohexahydropyrazino[2,1-c][1,4]thiazin-8(1H)-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3R,6R,7R,8E,11S,12'R)-6-chloro-7'-(((9aS)-2,2-dioxidohexahydropyrazino[2,1-c][1,4]thiazin-8(1H)-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 815.2 |

TABLE 1-continued

Examples Prepared by the General Methods

| Example Number | Starting Materials | General Method | Product Structure | Product Name | MS Data (M + 1)+ |
|---|---|---|---|---|---|
| 220 | | 10 | | (1S,3'R,6R,7R,7R,8E,11'S, 12'R)-6-chloro-7'-(((9aS)-2,2-dioxidohexahydropyrazino[2,1-c][1,4]thiazin-8(1H)-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one OR (1S,3'R,6R,7R,7R,8E,11'S, 12'R)-6-chloro-7'-(((9aS)-2,2-dioxidohexahydropyrazino[2,1-c][1,4]thiazin-8(1H)-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 815.2 |

TABLE 1-continued

Examples Prepared by the General Methods

| Example Number | Starting Materials | General Method | Product Structure | Product Name | MS Data (M + 1)+ |
|---|---|---|---|---|---|
| 221 | | 10 | | (1S,3'R,6R,7R,8E,11'S,12'R)-6-chloro-7'-(((9aS)-2,2-dioxidohexahydropyrazino[2,1-c][1,4]thiazin-8(1H)-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one OR (1S,3'R,6R,7R,8E,11'S,12'R)-6-chloro-7'-(((9aR)-2,2-dioxidohexahydropyrazino[2,1-c][1,4]thiazin-8(1H)-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 815.2 |

TABLE 1-continued

Examples Prepared by the General Methods

| Example Number | Starting Materials | General Method | Product Structure | Product Name | MS Data (M + 1)+ |
|---|---|---|---|---|---|
| 222 | | 8 | | (1S,3'R,6R,7R,8'E,11'S,12'R)-6-chloro-7'-(7,8-dihydropyrido[4,3-d]pyrimidin-6(5H)-yl methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 760.3 |
| 223 | | 10 | | (1S,3'R,6R,7S,8'E,11'S,12'R)-6-chloro-7'-(7,8-dihydropyrido[4,3-d]pyrimidin-6(5H)-yl methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 760.2 |

TABLE 1-continued

Examples Prepared by the General Methods

| Example Number | Starting Materials | General Method | Product Structure | Product Name | MS Data (M + 1)+ |
|---|---|---|---|---|---|
| 224 | | 10 | | (1S,3'R,6R,7R,8E,11'S,12'R)-6-chloro-7'-((2,2-dioxido-2-thia-6-azaspiro[3.3]hept-6-yl)methyl)-7'-methoxy-11',12'-dimethyl-3,4-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 772.0 |

TABLE 1-continued

Examples Prepared by the General Methods

| Example Number | Starting Materials | General Method | Product Structure | Product Name | MS Data (M + 1)+ |
|---|---|---|---|---|---|
| 225 | | 10 | | (1S,3'R,6'R,7'S,8'E,11'S,12'R)-7'-(((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-7'-(((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.3 |

TABLE 1-continued

Examples Prepared by the General Methods

| Example Number | Starting Materials | General Method | Product Structure | Product Name | MS Data (M + 1)+ |
|---|---|---|---|---|---|
| 226 |  | 10 | 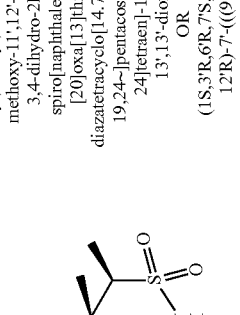 | (1S,3R,6R,7S,8E,11S,12R)-7'-((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one OR (1S,3R,6R,7S,8E,11S,12R)-7'-((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.3 |

TABLE 1-continued

Examples Prepared by the General Methods

| Example Number | Starting Materials | General Method | Product Structure | Product Name | MS Data (M + 1)+ |
|---|---|---|---|---|---|
| 227 | | 10 | | (1S,3′R,6R,7R,8E,11′S,12′R)-6-chloro-7′-methoxy-11′,12′-dimethyl-7-(((9aR)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide AND (1S,3′R,6R,7R,8E,11′S,12′R)-6-chloro-7′-methoxy-11′,12′-dimethyl-7-(((9aR)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 844.3 |

TABLE 1-continued

Examples Prepared by the General Methods

| Example Number | Starting Materials | General Method | Product Structure | Product Name | MS Data (M + 1)+ |
|---|---|---|---|---|---|
| 228 | 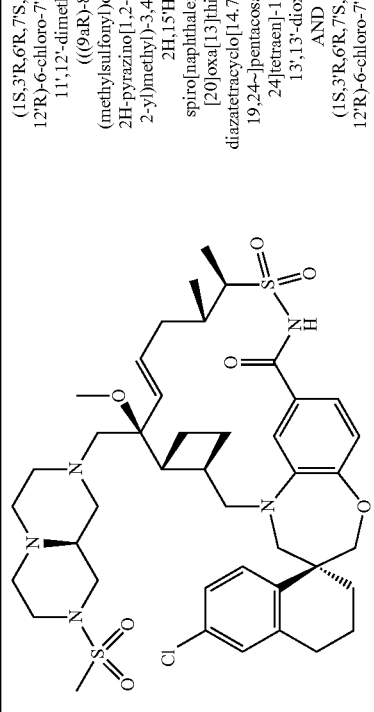  | 10 |  AND 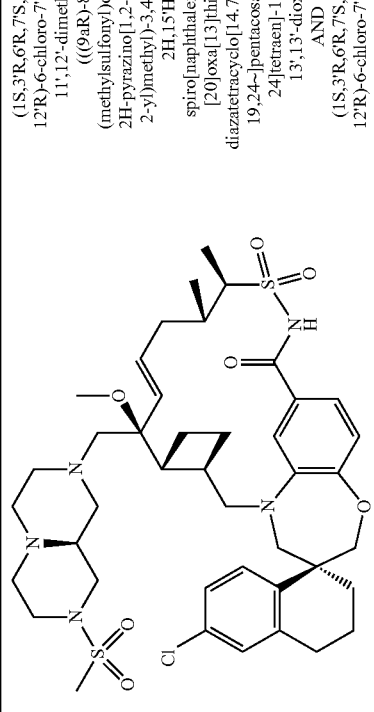 | (1S,3′R,6′R,7S,8E,11′S,12′R)-6-chloro-7′-methoxy-11′,12′-dimethyl-7-(((9aR)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide AND (1S,3′R,6′R,7S,8E,11′S,12′R)-6-chloro-7′-methoxy-11′,12′-dimethyl-7-(((9aS)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 844.0 |

TABLE 1-continued

Examples Prepared by the General Methods

| Example Number | Starting Materials | General Method | Product Structure | Product Name | MS Data (M + 1)+ |
|---|---|---|---|---|---|
| 229 | | 10 | | (1S,3'R,6'R,7'R,8'E,11'S,12'R)-7'-(((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-7'-(((9aR)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.2 |

TABLE 1-continued

Examples Prepared by the General Methods

| Example Number | Starting Materials | General Method | Product Structure | Product Name | MS Data (M + 1)+ |
|---|---|---|---|---|---|
| 230 | (structure) | 10 | (structure) | (1S,3'R,6R,7R,8'E,11'S,12'R)-7-(((9aS)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,8'E,11'S,12'R)-7-(((9aR)-8-acetyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.2 |

TABLE 1-continued

Examples Prepared by the General Methods

| Example Number | Starting Materials | General Method | Product Structure | Product Name | MS Data (M + 1)+ |
|---|---|---|---|---|---|
| 231 | 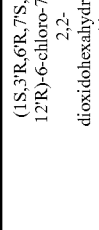 | 10 | 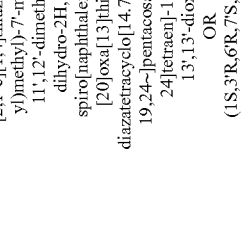 OR  | (1S,3'R,6R,7S,8E,11S,12'R)-6-chloro-7'-(((9aS)-2,2-dioxidohexahydropyrazino[2,1-c][1,4]thiazin-8(1H)-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7S,8E,11S,12'R)-6-chloro-7'-(((9aR)-2,2-dioxidohexahydropyrazino[2,1-c][1,4]thiazin-8(1H)-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 815.1 |

TABLE 1-continued

Examples Prepared by the General Methods

| Example Number | Starting Materials | General Method | Product Structure | Product Name | MS Data (M + 1)+ |
|---|---|---|---|---|---|
| 232 | 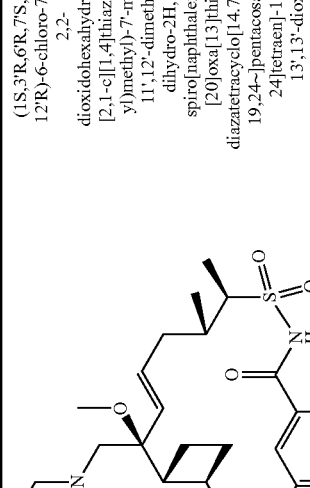 | 10 | 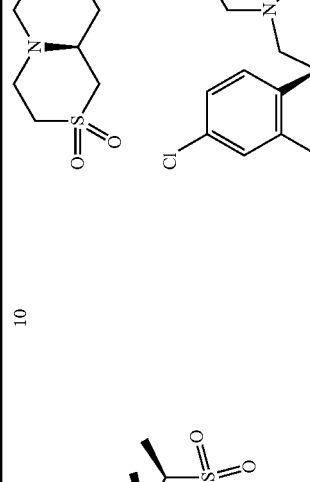 | (1S,3R,6R,7S,8E,11S,12R)-6-chloro-7'-(((9aS)-2,2-dioxidohexahydropyrazino[2,1-c][1,4]thiazin-8(1H)-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3R,6R,7S,8E,11S,12R)-6-chloro-7'-(((9aR)-2,2-dioxidohexahydropyrazino[2,1-c][1,4]thiazin-8(1H)-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 815.1 |

TABLE 1-continued

Examples Prepared by the General Methods

| Example Number | Starting Materials | General Method | Product Structure | Product Name | MS Data (M + 1)+ |
|---|---|---|---|---|---|
| 233 | 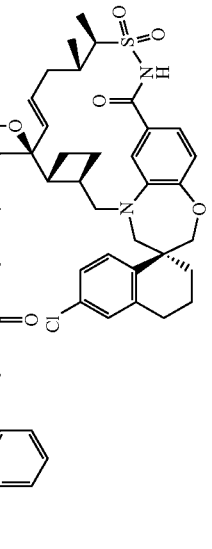 | 10 | 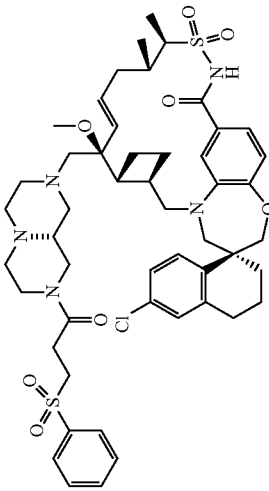 AND 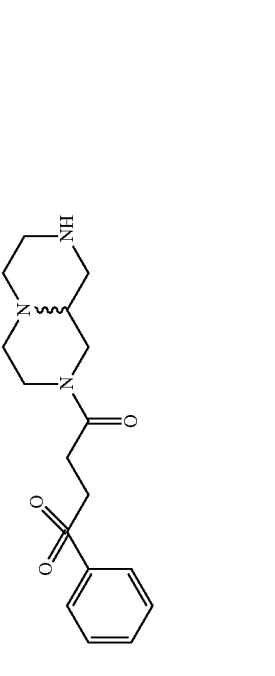 | (1S,3'R,6'R,7S,8E,11S,12'R)-6-chloro-7-methoxy-11',12'-dimethyl-7-(((9aR)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7S,8E,11S,12'R)-6-chloro-7-methoxy-11',12'-dimethyl-7-(((9aS)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 963.7 |

TABLE 1-continued

Examples Prepared by the General Methods

| Example Number | Starting Materials | General Method | Product Structure | Product Name | MS Data (M + 1)+ |
|---|---|---|---|---|---|
| 234 | | Example 276 | | (1S,3'R,6'R,7'S,8'E,11'S,12'R)-7'-(((9aR)-8-acryloyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-7'-(((9aS)-8-acryloyloctahydro-2H-pyrazino[1,2-a]pyrazin-2-yl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 820.3 |

TABLE 1-continued

Examples Prepared by the General Methods

| Example Number | Starting Materials | General Method | Product Structure | Product Name | MS Data (M + 1)+ |
|---|---|---|---|---|---|
| 235 | 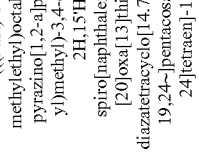 | 10 | 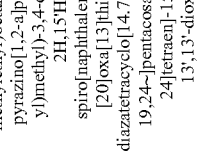 AND 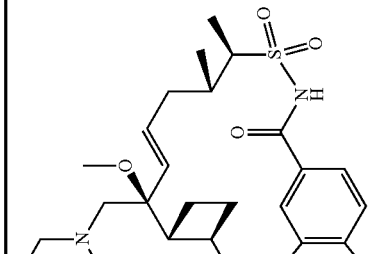 | (1S,3'R,6'R,7'S,8'E,11'S,12'R)-6-chloro-7'-methoxy-11',12'-dimethyl-7-(((9aR)-8-(1-methylethyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-methoxy-11',12'-dimethyl-7-(((9aS)-8-(1-methylethyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 828.0 |

TABLE 1-continued

Examples Prepared by the General Methods

| Example Number | Starting Materials | General Method | Product Structure | Product Name | MS Data (M + 1)+ |
|---|---|---|---|---|---|
| 236 |  (J&W PharmLab) | 10 |  AND | (1S,3'R,6R,7R,8E,11'S,12'R)-6-chloro-7'-hydroxy-11'12'-dimethyl-7'-(9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7R,8E,11'S,12'R)-6-chloro-7'-hydroxy-11'12'-dimethyl-7'-(9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 751.4 |

TABLE 1-continued

Examples Prepared by the General Methods

| Example Number | Starting Materials | General Method | Product Structure | Product Name | MS Data (M + 1)+ |
|---|---|---|---|---|---|
| 237 | | 10 | | (1S,3'R,6R,7R,8E,11'S,12'R)-6-chloro-7'-methoxy-11',12'-dimethyl-7-((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,8E,11'S,12'R)-6-chloro-7'-methoxy-11',12'-dimethyl-7-((9aR)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 844.2 |

TABLE 1-continued

Examples Prepared by the General Methods

| Example Number | Starting Materials | General Method | Product Structure | Product Name | MS Data (M + 1)+ |
|---|---|---|---|---|---|
| 238 | | 10 | | (1S,3'R,6'R,7'R,8'E,11'S,12'R)-6-chloro-7'-methoxy-11'12'-dimethyl-7'-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-methoxy-11'12'-dimethyl-7'-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 844.2 |

TABLE 1-continued

Examples Prepared by the General Methods

| Example Number | Starting Materials | General Method | Product Structure | Product Name | MS Data (M + 1)+ |
|---|---|---|---|---|---|
| 239 | | 10 | | (1S,3'R,6'R,7S,8E,11'S,12'R)-6-chloro-7'-methoxy-11',12'-dimethyl-7'-((4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.7 |

TABLE 1-continued

Examples Prepared by the General Methods

| Example Number | Starting Materials | General Method | Product Structure | Product Name | MS Data (M + 1)+ |
|---|---|---|---|---|---|
| 240 | 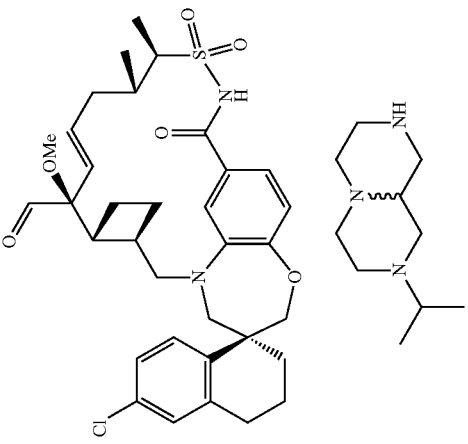 | 10 | 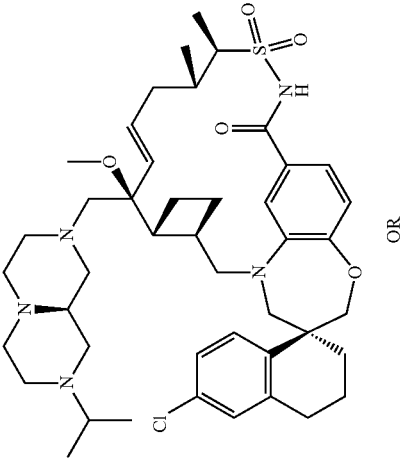 OR 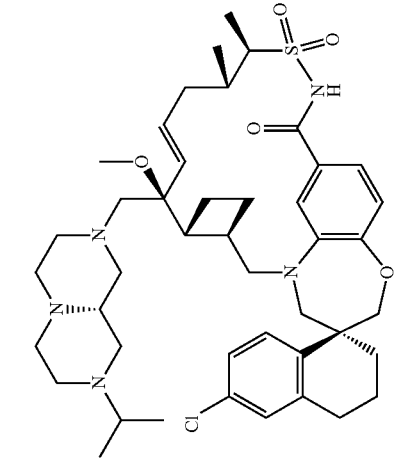 | (1S,3'R,6'R,7'S,8'E,11'S,12'R)-6-chloro-7'-methoxy-11',12'-dimethyl-7'-(((9aS)-8-(1-methylethyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-(((9aR)-8-(1-methylethyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.0 |

TABLE 1-continued

Examples Prepared by the General Methods

| Example Number | Starting Materials | General Method | Product Structure | Product Name | MS Data (M + 1)+ |
|---|---|---|---|---|---|
| 241 | (structure) | 10 | (structure) OR (structure) | (1S,3'R,6'R,7'S,8'E,11'S,12'R)-6-chloro-7'-methoxy-11',12'-dimethyl-7-(((9aS)-8-(1-methylethyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7-(((9aR)-8-(1-methylethyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.0 |

TABLE 1-continued

Examples Prepared by the General Methods

| Example Number | Starting Materials | General Method | Product Structure | Product Name | MS Data (M + 1)+ |
|---|---|---|---|---|---|
| 242 | 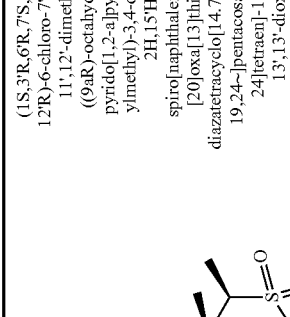 (J&W PharmLab) | 10 | 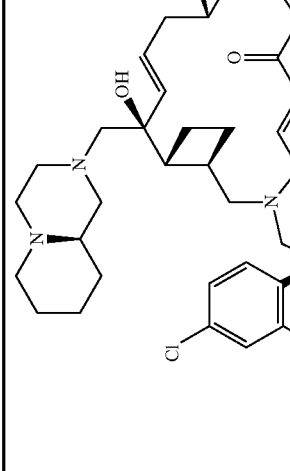 OR 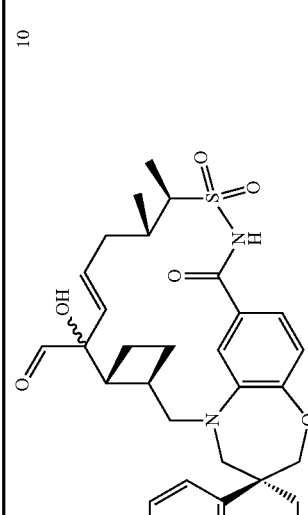 | (1S,3R,6R,7S,8E,11S,12R)-6-chloro-7-hydroxy-11′,12′-dimethyl-7-((9aR)-octahydro-2H-pyrido[1,2-a]pyrazin-2-ylmethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide OR (1S,3R,6R,7R,8E,11S,12R)-6-chloro-7-hydroxy-11′,12′-dimethyl-7-((9aR)-octahydro-2H-pyrido[1,2-a]pyrazin-2-ylmethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 751.4 |

TABLE 1-continued

Examples Prepared by the General Methods

| Example Number | Starting Materials | General Method | Product Structure | Product Name | MS Data (M + 1)+ |
|---|---|---|---|---|---|
| 243 | 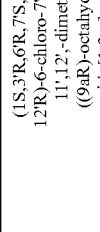 (J&W PharmLab) | 10 | 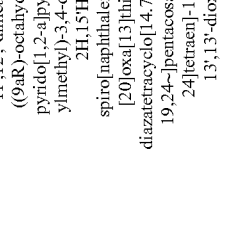 OR  | (1S,3R,6R,7S,8E,11S,12R)-6-chloro-7-hydroxy-11',12',-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3R,6R,7R,8E,11S,12R)-6-chloro-7-hydroxy-11',12',-dimethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 751.4 |

TABLE 1-continued

Examples Prepared by the General Methods

| Example Number | Starting Materials | General Method | Product Structure | Product Name | MS Data (M + 1)+ |
|---|---|---|---|---|---|
| 244 | | 10 | | (1S,3'R,6R,7S,8E,11S,12'R)-6-chloro-7'-methoxy-11',12'-dimethyl-7-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7S,8E,11S,12'R)-6-chloro-7'-methoxy-11',12'-dimethyl-7-(((9aR)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 844.3 |

TABLE 1-continued

Examples Prepared by the General Methods

| Example Number | Starting Materials | General Method | Product Structure | Product Name | MS Data (M + 1)+ |
|---|---|---|---|---|---|
| 245 | | 10 | 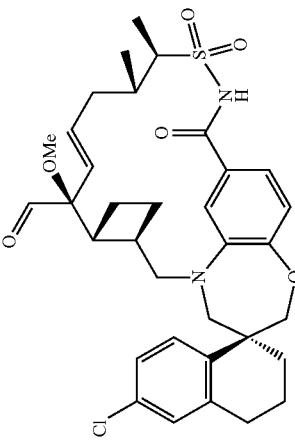 | (1S,3'R,6R,7S,8E,11S,12'R)-6-chloro-7'-methoxy-11',12'-dimethyl-7-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7S,8E,11S,12'R)-6-chloro-7'-methoxy-11',12'-dimethyl-7-(((9aR)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 844.3 |

TABLE 1-continued

Examples Prepared by the General Methods

| Example Number | Starting Materials | General Method | Product Structure | Product Name | MS Data (M + 1)+ |
|---|---|---|---|---|---|
| 246 | | 10 | | (1S,3'R,6'R,7'S,8'E,11'S,12'R)-6-chloro-7'-methoxy-7'-((4-(methoxyacetyl)-1-piperazinyl)methyl)-11'12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.2 |
| 247 | | 10 | | (1S,3'R,6'R,7'S,8'E,11'S,12'R)-6-chloro-7'-((4-ethyl-1-piperazinyl)methyl)-7'-methoxy-11'12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 739.3 |

TABLE 1-continued

Examples Prepared by the General Methods

| Example Number | Starting Materials | General Method | Product Structure | Product Name | MS Data (M + 1)+ |
|---|---|---|---|---|---|
| 248 | (Enamine) | 10 | | (1S,3'R,6'R,7S,8'E,11'S,12'R)-6-chloro-7'-methoxy-11',12'-dimethyl-7'-((4-(2,2,2-trifluoroethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 793.2 |
| 249 | | 10 | | (1S,3'R,6'R,7S,8'E,11'S,12'R)-7'-((acetyl-1-piperazinyl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.3 |

TABLE 1-continued

Examples Prepared by the General Methods

| Example Number | Starting Materials | General Method | Product Structure | Product Name | MS Data (M + 1)+ |
|---|---|---|---|---|---|
| 250 | (structure shown) (Aurum) | 10 | (structure shown) | (1S,3'R,6'R,7S,7'S,8'E,11'S,12'R)-6'-chloro-7'-methoxy-11',12'-dimethyl-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 251 | (Alfa Aesar) | 10 | | (1S,3'R,6'R,7S,7'S,8'E,11'S,12'R)-6-chloro-7'-methoxy-11',12'-dimethyl-7'-((4-phenyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 787.2 |

TABLE 1-continued
Examples Prepared by the General Methods
| Example Number | Starting Materials | General Method | Product Structure | Product Name | MS Data (M + 1)+ |
|---|---|---|---|---|---|
| 252 | 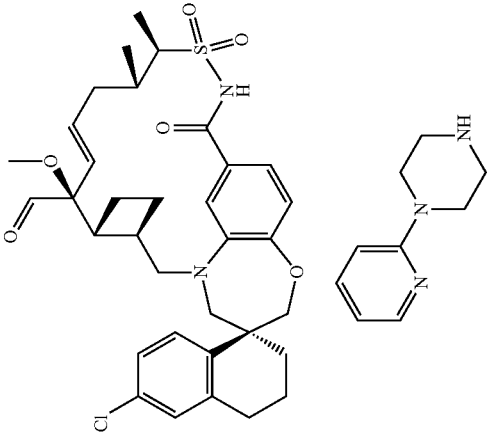 | 10 | 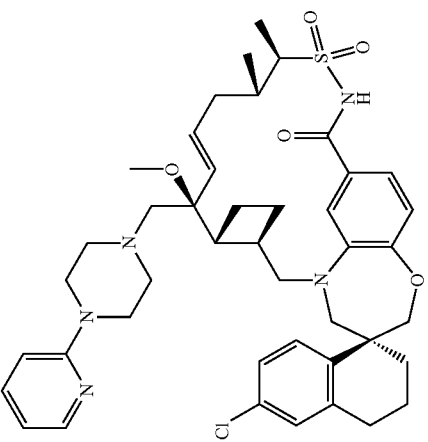 | (1S,3'R,6'R,7S,8E,11'S,12'R)-6-chloro-7'-methoxy-11',12-dimethyl-7'·((4-(2-pyridinyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 788.8 |

TABLE 1-continued

Examples Prepared by the General Methods

| Example Number | Starting Materials | General Method | Product Structure | Product Name | MS Data (M + 1)+ |
|---|---|---|---|---|---|
| 253 | (Butt Park Ltd.) | 10 | | (1S,3'R,6'R,7S,7'S,8'E,11'S,12'R)-6-chloro-7'-methoxy-11',12'-dimethyl-7'-((4-(3-pyridinyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 788.8 |

TABLE 1-continued

Examples Prepared by the General Methods

| Example Number | Starting Materials | General Method | Product Structure | Product Name | MS Data (M + 1)+ |
|---|---|---|---|---|---|
| 254 | (Lancaster Synthesis Ltd.) | 10 | | (1S,3′R,6′R,7S,8′E,11′S,12′R)-6-chloro-7′-methoxy-11′,12′-dimethyl-7′-((4-(4-pyridinyl)-1-piperazinyl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 788.8 |

TABLE 1-continued
Examples Prepared by the General Methods
| Example Number | Starting Materials | General Method | Product Structure | Product Name | MS Data (M + 1)+ |
|---|---|---|---|---|---|
| 255 | 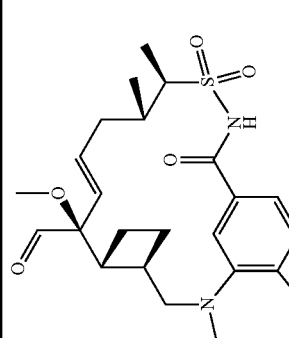 (Enamine) | 10 | 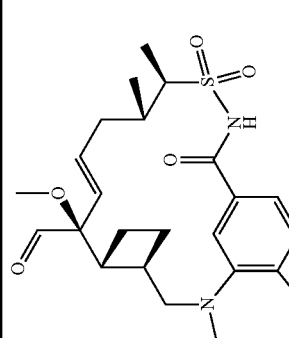 | (1S,3'R,6R,7S,8E,11'S,12'R)-6-chloro-7'-methoxy-11',12'-dimethyl-7'-((4-(1,3-thiazol-2-yl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 794.8 |

TABLE 1-continued

Examples Prepared by the General Methods

| Example Number | Starting Materials | General Method | Product Structure | Product Name | MS Data (M + 1)+ |
|---|---|---|---|---|---|
| 256 | | 10 | | (1S,3'R,6'R,7'S,8'E,11'S,12'R)-6-chloro-7'-methoxy-11',12'-dimethyl-7'-((4-(2-pyrimidinyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 789.9 |
| 257 | | 10 | | (1S,3'R,6'R,7'S,8'E,11'S,12'R)-6-chloro-7'-methoxy-11',12'-dimethyl-7'-((4-(2-pyrazinyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 789.0 |

TABLE 1-continued

Examples Prepared by the General Methods

| Example Number | Starting Materials | General Method | Product Structure | Product Name | MS Data (M + 1)+ |
|---|---|---|---|---|---|
| 258 | (ChemBridge Corporation) | 10 | | (1S,3′R,6′R,7′S,8′E,11′S,12′R)-6-chloro-7′-methoxy-11′,12′-dimethyl-7′-((3-(4-morpholinyl)-1-azetidinyl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 767.8 |

TABLE 1-continued

Examples Prepared by the General Methods

| Example Number | Starting Materials | General Method | Product Structure | Product Name | MS Data (M + 1)+ |
|---|---|---|---|---|---|
| 259 | (Oakwood) | 10 | | 4-((((1S,3'R,6'R,7S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-N,N-dimethyl-1-piperazinecarboxamide | 782.9 |

TABLE 1-continued

Examples Prepared by the General Methods

| Example Number | Starting Materials | General Method | Product Structure | Product Name | MS Data (M + 1)+ |
|---|---|---|---|---|---|
| 260 | (structure) (Ryan Scientific) | 10 | (structure) | (1S,3'R,6'R,7'S,8'E,11'S,12'R)-6'-chloro-7'-methoxy-7'-((3-((2-methoxyethyl)(methyl)amino)-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 769.8 |
| 261 | (structure) (Oakwood) | 10 | (structure) | ethyl (4-(((1S,3'R,6'R,7'S,8'E,11'S,12'R)-6'-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinyl)acetate | 797.0 |

TABLE 1-continued
Examples Prepared by the General Methods
| Example Number | Starting Materials | General Method | Product Structure | Product Name | MS Data (M + 1)+ |
|---|---|---|---|---|---|
| 262 | 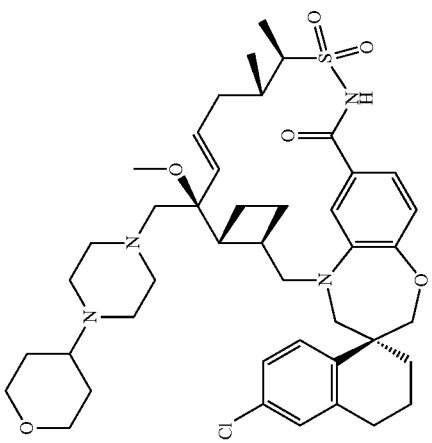 (AstaTecH) | 10 | | (1S,3'R,6R,7'S,8'E,11'S,12'R)-6-chloro-7'-methoxy-11',12'-dimethyl-7'-((4-(tetrahydro-2H-pyran-4-yl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 796.0 |

TABLE 1-continued

Examples Prepared by the General Methods

| Example Number | Starting Materials | General Method | Product Structure | Product Name | MS Data (M + 1)+ |
|---|---|---|---|---|---|
| 263 | (structure shown) (Oakwood) | 10 | (structure shown) | (1S,3'R,6R,7S,8E,11S,12'R)-6-chloro-7-methoxy-11',12'-dimethyl-7-((4-(4-morpholinyl)-1-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 796.0 |

TABLE 1-continued

Examples Prepared by the General Methods

| Example Number | Starting Materials | General Method | Product Structure | Product Name | MS Data (M + 1)+ |
|---|---|---|---|---|---|
| 264 | (J&W PharmLab) | 10 | | (1S,3R,6R,7S,8E,11S,12'R)-6-chloro-7'-methoxy-11',12'-dimethyl-7'-(3-oxa-9-azaspiro[5.5]undec-9-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 780.8 |

TABLE 1-continued

Examples Prepared by the General Methods

| Example Number | Starting Materials | General Method | Product Structure | Product Name | MS Data (M + 1)+ |
|---|---|---|---|---|---|
| 265 | | 10 | | (1S,3R,6R,7S,8E,11S,12R)-6-chloro-7'-methoxy-11',12'-dimethyl-7'-(2-oxa-8-azaspiro[4.5]dec-8-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 766.2 |
| 266 | (J&W PharmLab) | 10 | | methyl 4-((((1S,3R,6R,7S,8E,11S,12R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinecarboxylate | 769.2 |

TABLE 1-continued

Examples Prepared by the General Methods

| Example Number | Starting Materials | General Method | Product Structure | Product Name | MS Data (M + 1)+ |
|---|---|---|---|---|---|
| 267 | | 10 | | (1S,3'R,6'R,7S,8'E,11'S,12'R)-6-chloro-7'-methoxy-11',12'-dimethyl-7'-(2-oxa-7-azaspiro[3.5]non-7-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 752.8 |
| 268 | | 10 | | (1S,3'R,6'R,7S,8'E,11'S,12'R)-6-chloro-7'-methoxy-11',12'-dimethyl-7'-((4-(3-methyl-3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.8 |

TABLE 1-continued

Examples Prepared by the General Methods

| Example Number | Starting Materials | General Method | Product Structure | Product Name | MS Data (M + 1)+ |
|---|---|---|---|---|---|
| 269 | | 10 | | methyl (4-((((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinyl)acetate | 783.8 |

TABLE 1-continued

Examples Prepared by the General Methods

| Example Number | Starting Materials | General Method | Product Structure | Product Name | MS Data (M + 1)+ |
|---|---|---|---|---|---|
| 271 | 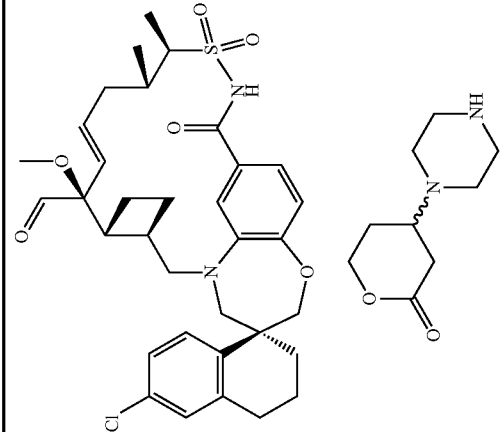 | 10 | 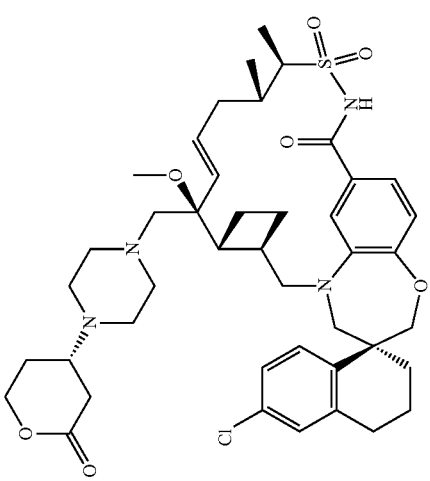 | (1S,3'R,6'R,7'S,8'E,11'S,12'R)-6-chloro-7'-methoxy-11',12'-dimethyl-7'-((4R)-2-oxotetrahydro-2H-pyran-4-yl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-methoxy-11',12'-dimethyl-7'-((4S)-2-oxotetrahydro-2H-pyran-4-yl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 810.0 |

TABLE 1-continued

Examples Prepared by the General Methods

| Example Number | Starting Materials | General Method | Product Structure | Product Name | MS Data (M + 1)+ |
|---|---|---|---|---|---|
| 272 | (ChemShuttle) | 10 | | 3-(4-((((1S,3'R,6'R,7'S,8'E,11'S,12'R)-6-chloro-7'-methoxy-11', 12'-dimethyl-13',13'-dioxido-15'-oxo-3,4-dihydro-2H-spiro[naphthalene-1,22'-[20]oxa[13]thia[1,14]diazatetracyclo[14.7.2.0~3,6.0~19,24]pentacosa[8,16,18,24]tetraen]-7'-yl)methyl)-1-piperazinyl)-3-oxetanecarbonitrile | 792.8 |

TABLE 1-continued

Examples Prepared by the General Methods

| Example Number | Starting Materials | General Method | Product Structure | Product Name | MS Data (M + 1)+ |
|---|---|---|---|---|---|
| 273 |  | 10 |  AND 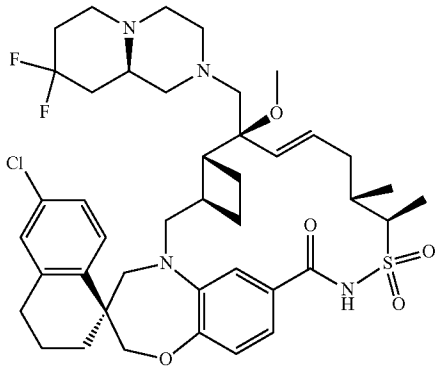 | (1S,3'R,6'R,7'S,8'E,11'S, 12'R)-6-chloro-7'-(((9aR)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S, 12'R)-6-chloro-7'-(((9aS)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 801.9 |

TABLE 1-continued

Examples Prepared by the General Methods

| Example Number | Starting Materials | General Method | Product Structure | Product Name | MS Data (M + 1)+ |
|---|---|---|---|---|---|
| 274 | 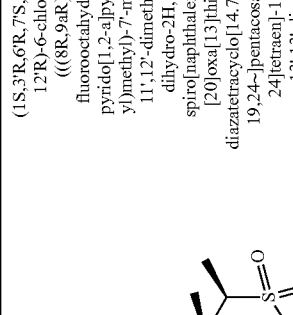 | 10 | 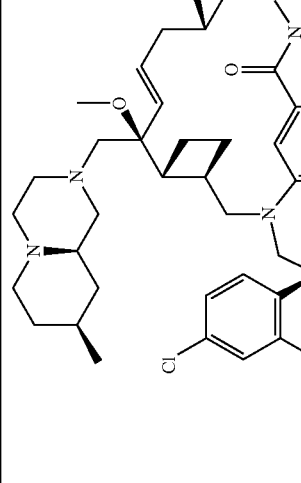 AND 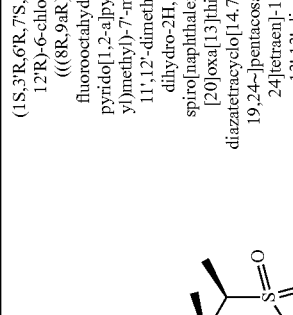 | (1S,3'R,6R,7S,8E,11S,12'R)-6-chloro-7-(((8R,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7S,8E,11S,12'R)-6-chloro-7-(((8R,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.9 |

TABLE 1-continued

Examples Prepared by the General Methods

| Example Number | Starting Materials | General Method | Product Structure | Product Name | MS Data (M + 1)+ |
|---|---|---|---|---|---|
| | | | 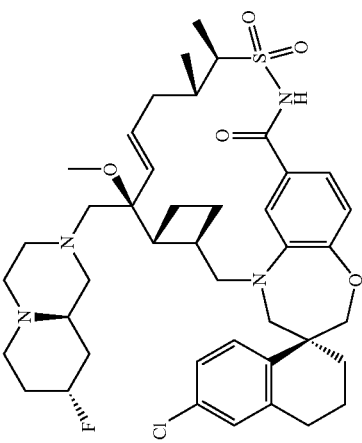 AND 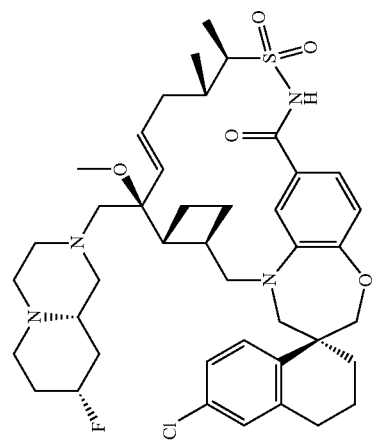 | AND (1S,3'R,6R,7S,8E,11S,12'R)-6-chloro-7-(((8S,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7S,8E,11S,12'R)-6-chloro-7-(((8S,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 275 | (Manchester Organics Ltd.) | 10 | AND | (1S,3'R,6'R,7'S,8'E,11'S,12'R)-6-chloro-7'-methoxy-11',12'-dimethyl-7'-(((3R)-tetrahydro-3-furanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-methoxy-11',12'-dimethyl-7'-(((3S)-tetrahydro-3-furanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.8 |

TABLE 1-continued

Examples Prepared by the General Methods

| Example Number | Starting Materials | General Method | Product Structure | Product Name | MS Data (M + 1)+ |
|---|---|---|---|---|---|
| 277 | | See example 276 | | (1S,3'R,6'R,7'S,8'E,11'S,12'R)-7'-(((9AR)-8-ACRYLOYLOCTAHYDRO-2H-PYRAZINO[1,2-A]PYRAZIN-2-YL)METHYL)-6-CHLORO-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE OR (1S,3'R,6'R,7'S,8'E,11'S,12'R)-7'-(((9AR)-8-ACRYLOYLOCTAHYDRO-2H-PYRAZINO[1,2-A]PYRAZIN-2-YL)METHYL)-6-CHLORO-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~]PENTACOSA[8,16,18,24]TETRAEN]-15'-ONE 13',13'-DIOXIDE | 821.0 |

TABLE 1-continued

Examples Prepared by the General Methods

| Example Number | Starting Materials | General Method | Product Structure | Product Name | MS Data (M + 1)+ |
|---|---|---|---|---|---|
| 278 | | Aqueous hydrolysis of lactone | | (3R)-3-(4-(1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinyl)-5-hyddroxypentanoic acid AND (3S)-3-(4-(1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-1-piperazinyl)-5-hyddroxypentanoic acid | 828.0 |

TABLE 1-continued

Examples Prepared by the General Methods

| Example Number | Starting Materials | General Method | Product Structure | Product Name | MS Data (M + 1)+ |
|---|---|---|---|---|---|
| 279 | 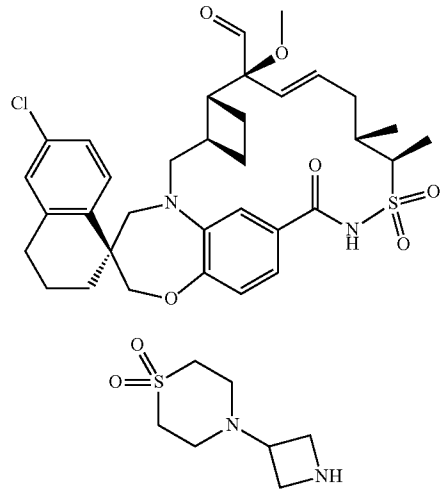<br>(Activate Scientific GmbH) | 10 | 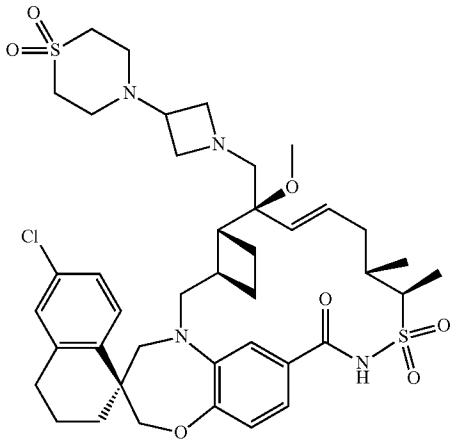 [SMILES: CO[C@@]1(CN2CC(N3CCS(=O)(=O)CC3)C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S, 12'R)-6-chloro-7'-((3-(1,1-dioxido-4-thiomorpholinyl)-1-azetidinyl)methyl)-7'-methoxy-11',12'-dimethyl-3,4-dihydro-2H,15'H-spiro[naphthalene-1,22'-[20]oxa[13]thia[1,14] diazatetracyclo[14.7.2.0~3,6~.0~ 19,24~]pentacosa[8,16,18, 24]tetraen]-15'-one 13',13'-dioxide | 815.1 |

TABLE 1-continued

Examples Prepared by the General Methods

| Example Number | Starting Materials | General Method | Product Structure | Product Name | MS Data (M + 1)+ |
|---|---|---|---|---|---|
| 280 | (ChemShuttle) | 10 | | (1S,3'R,6'R,7'S,8'E,11'S,12'R)-7'-((4-(1-acetyl-3-azetidinyl)-1-piperazinyl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 808.2 |
| 281 | (AstaTech) | 10 | | (1S,3'R,6'R,7'S,8'E,11'S,12'R)-6-chloro-7'-((4-cyclobutyl-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.3 |

TABLE 1-continued
Examples Prepared by the General Methods
| Example Number | Starting Materials | General Method | Product Structure | Product Name | MS Data (M + 1)+ |
|---|---|---|---|---|---|
| 282 | 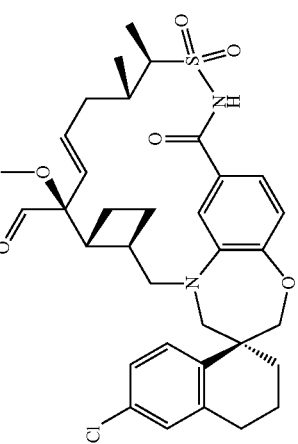 (ChemShuttle) | 10 | 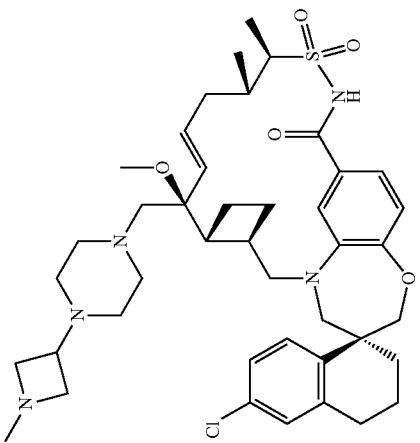 | (1S,3R,6R,7S,8E,11S,12'R)-6-chloro-7'-methoxy-11',12'-dimethyl-7'-((4-(1-methyl-3-azetidinyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 780.2 |

TABLE 1-continued

Examples Prepared by the General Methods

| Example Number | Starting Materials | General Method | Product Structure | Product Name | MS Data (M + 1)+ |
|---|---|---|---|---|---|
| 283 | 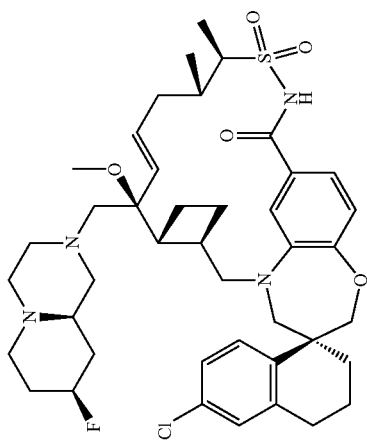 | 10 | 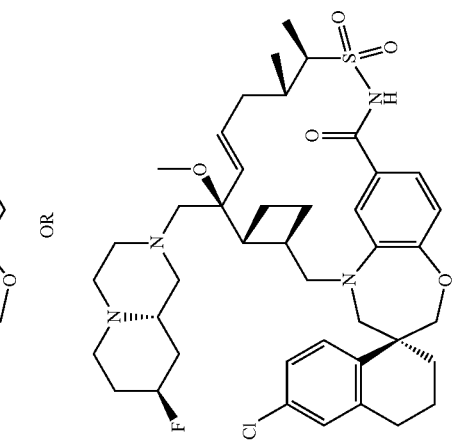 OR 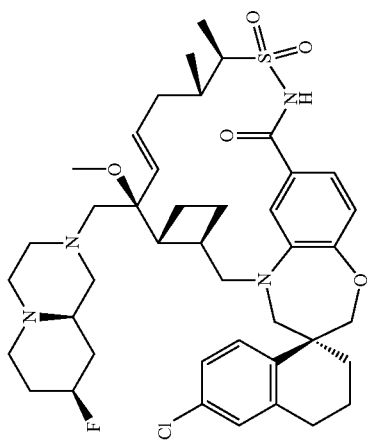 OR | (1S,3'R,6R,7S,8E,11'S,12'R)-6-chloro-7'-(((8R,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7S,8E,11'S,12'R)-6-chloro-7'-(((8R,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.9 |

TABLE 1-continued

Examples Prepared by the General Methods

| Example Number | Starting Materials | General Method | Product Structure | Product Name | MS Data (M + 1)+ |
|---|---|---|---|---|---|
| | | | 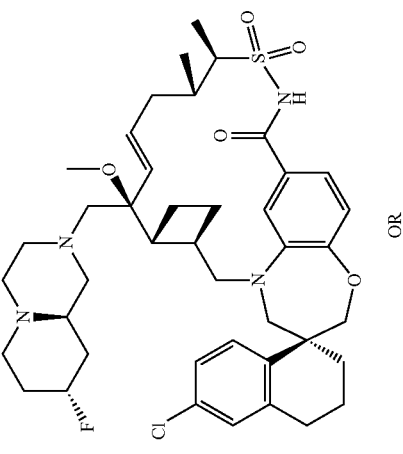 OR 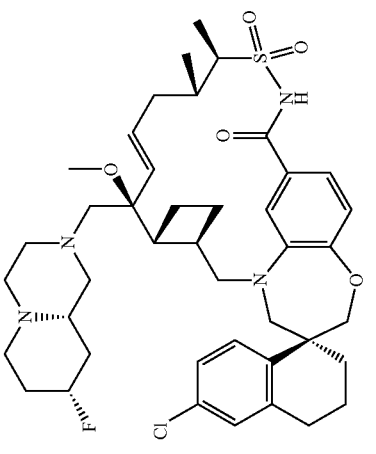 | (1S,3'R,6'R,7'S,8'E,11'S,12'R)-6-chloro-7'-(((8S,9aR)-8-fluorooctahydro-2H-pyrido[1,2-a]pyrazin-2-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-(((8R,9aS)-8-fluorooctahydro-2H-pyrido[1,2-a]pyrazin-2-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 284 | | 10 | | (1S,3'R,6'R,7'S,8'E,11'S,12'R)-6-chloro-7'-(((8R,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-(((8R,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.9 |

TABLE 1-continued

Examples Prepared by the General Methods

| Example Number | Starting Materials | General Method | Product Structure | Product Name | MS Data (M + 1)+ |
|---|---|---|---|---|---|
| | | | 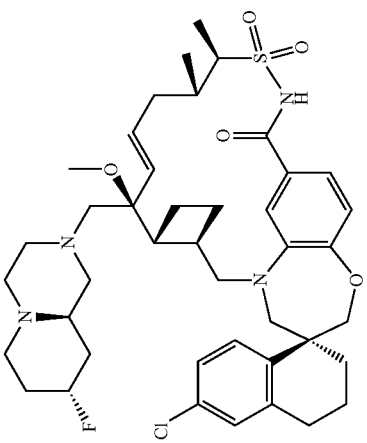 | OR (1S,3'R,6'R,7'S,8'E,11'S,12'R)-6-chloro-7'-(((8S,9aR)-8-fluorooctahydro-2H-pyrido[1,2-a]pyrazin-2-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Or (1S,3'R,6'R,7'S,8'E,11'S,12'R)-6-chloro-7'-(((8S,9aS)-8-fluorooctahydro-2H-pyrido[1,2-a]pyrazin-2-yl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 285 | <br><br>(Manchester Organics Ltd.) | 10 | 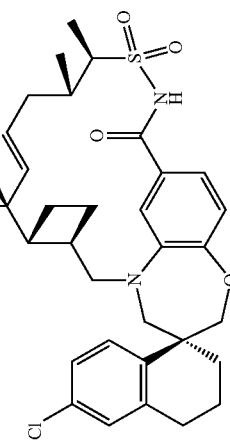 OR 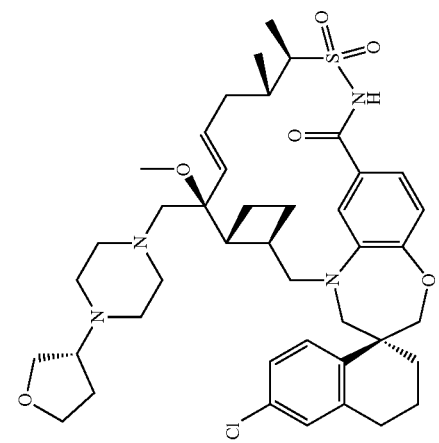 | (1S,3R,6R,7S,8E,11S,12'R)-6-chloro-7'-methoxy-11',12'-dimethyl-7'-((4-((3S)-tetrahydro-3-furanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3R,6R,7S,8E,11S,12'R)-6-chloro-7'-methoxy-11',12'-dimethyl-7'-((4-((3R)-tetrahydro-3-furanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.3 |

TABLE 1-continued

Examples Prepared by the General Methods

| Example Number | Starting Materials | General Method | Product Structure | Product Name | MS Data (M + 1)+ |
|---|---|---|---|---|---|
| 286 |  (Manchester Organics Ltd.) | 10 | 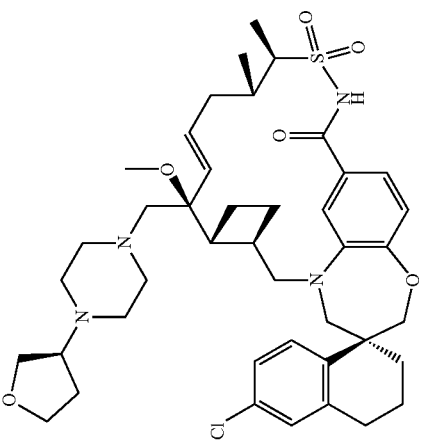 OR 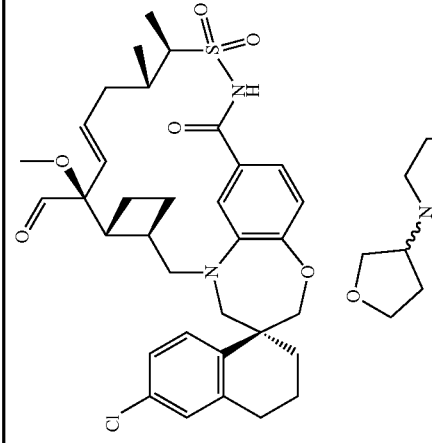 | (1S,3'R,6'R,7'S,8'E,11'S,12'R)-6-chloro-7'-methoxy-11',12'-dimethyl-7'-((4-((3S)-tetrahydro-3-furanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7'-((4-((3R)-tetrahydro-3-furanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.3 |

TABLE 1-continued
Examples Prepared by the General Methods
| Example Number | Starting Materials | General Method | Product Structure | Product Name | MS Data (M + 1)+ |
|---|---|---|---|---|---|
| 287 | 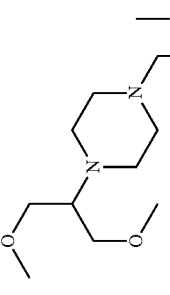 (FCH) | 10 | 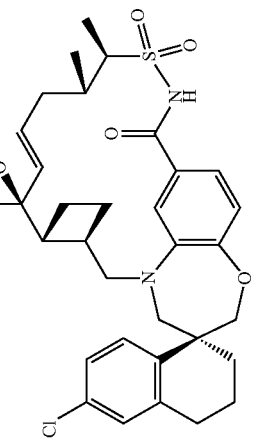 | (1S,3'R,6R,7S,8'E,11'S, 12'R)-6-chloro-7'-methoxy-7'-((4-(2-methoxy-1-(methoxymethyl)ethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 814.0 |

TABLE 1-continued

Examples Prepared by the General Methods

| Example Number | Starting Materials | General Method | Product Structure | Product Name | MS Data (M + 1)+ |
|---|---|---|---|---|---|
| 288 | 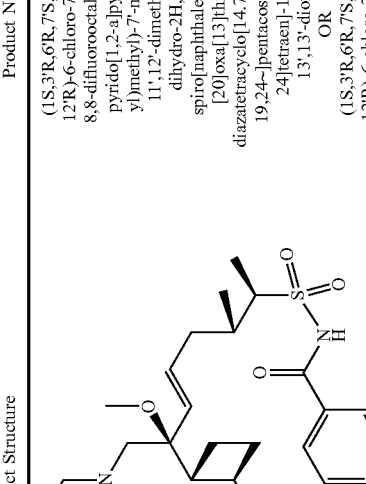 | 10 | 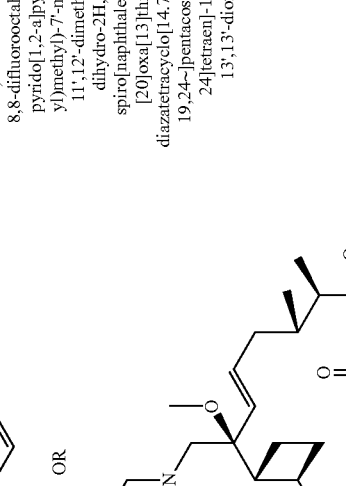 OR 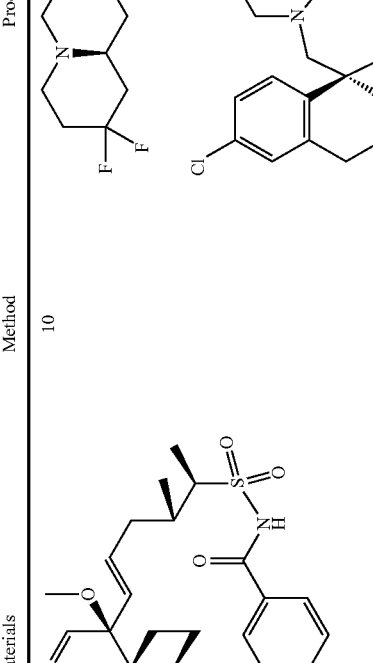 | (1S,3R,6R,7S,8E,11S,12R)-6-chloro-7'-(((9aR)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3R,6R,7S,8E,11S,12R)-6-chloro-7'-(((9aS)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 801.9 |

TABLE 1-continued

Examples Prepared by the General Methods

| Example Number | Starting Materials | General Method | Product Structure | Product Name | MS Data (M + 1)+ |
|---|---|---|---|---|---|
| 289 | | 10 | | (1S,3'R,6'R,7'S,8'E,11'S,12'R)-6-chloro-7'-(((9aR)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-(((9aS)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 801.9 |

TABLE 1-continued

Examples Prepared by the General Methods

| Example Number | Starting Materials | General Method | Product Structure | Product Name | MS Data (M + 1)+ |
|---|---|---|---|---|---|
| 290 | (J&W PharmLab) | 10 | | (1S,3'R,6R,7S,8'E,11'S,12'R)-6-chloro-7'-methoxy-11',12'-dimethyl-7'-((3-methyl-2-oxo-1-oxa-3,8-diazaspiro[4.5]dec-8-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.9 |

TABLE 1-continued
Examples Prepared by the General Methods
| Example Number | Starting Materials | General Method | Product Structure | Product Name | MS Data (M + 1)+ |
|---|---|---|---|---|---|
| 291 | 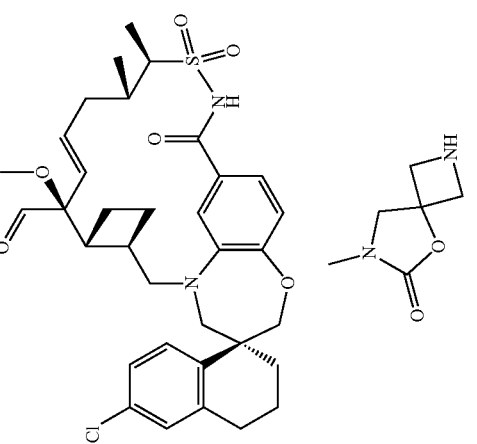 (FCH) | 10 | 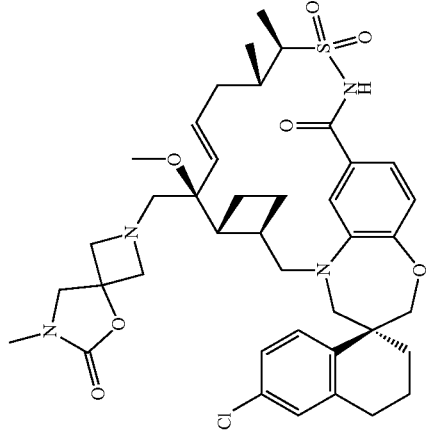 | (1S,3'R,6R,7S,8E,11S,12'R)-6-chloro-7'-methoxy-11',12'-dimethyl-7'-((7-methyl-6-oxo-5-oxa-2,7-diazaspiro[3.4]oct-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.8 |

TABLE 1-continued

Examples Prepared by the General Methods

| Example Number | Starting Materials | General Method | Product Structure | Product Name | MS Data (M + 1)+ |
|---|---|---|---|---|---|
| 292 | 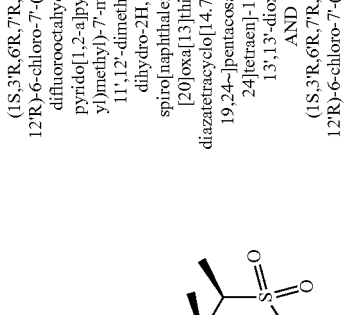 | 10 | 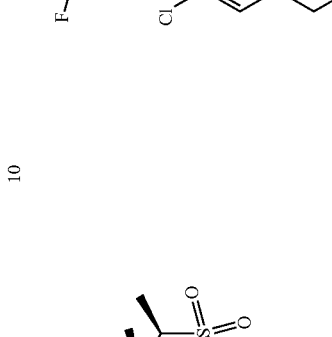 AND 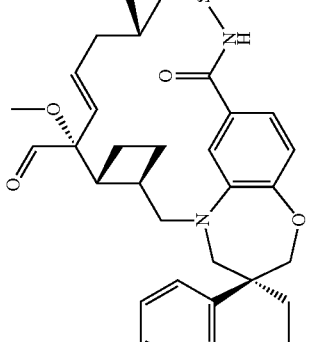 | (1S,3'R,6'R,7'R,8'E,11'S,12'R)-6-chloro-7'-(((9aR)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(((9aS)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 801.9 |
| | 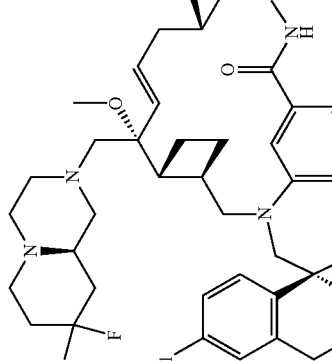 | | | | |

TABLE 1-continued

Examples Prepared by the General Methods

| Example Number | Starting Materials | General Method | Product Structure | Product Name | MS Data (M + 1)+ |
|---|---|---|---|---|---|
| 293 | | 10 | | (1S,3'R,6R,7R,8E,11'S,12'R)-6-chloro-7-(((8R,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7R,8E,11'S,12'R)-6-chloro-7-(((8R,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.9 |

TABLE 1-continued

Examples Prepared by the General Methods

| Example Number | Starting Materials | General Method | Product Structure | Product Name | MS Data (M + 1)+ |
|---|---|---|---|---|---|
| | | | 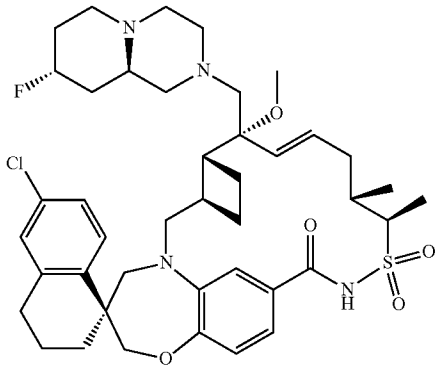 AND 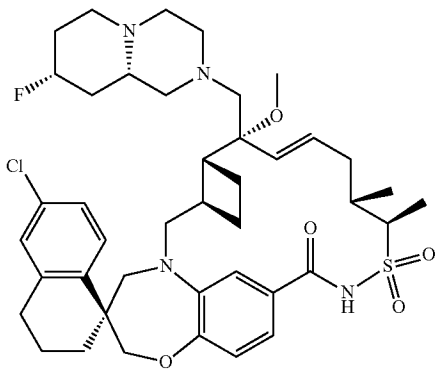 | AND (1S,3'R,6R,7R,8E,11S,12R)-6-chloro-7-(((8S,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6R,7R,8E,11S,12R)-6-chloro-7-(((8S,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 294 | 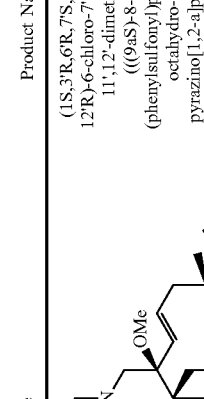 | 10 | 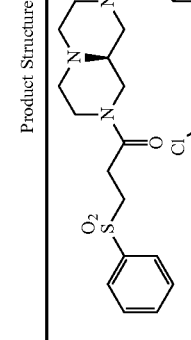 | (1S,3'R,6'R,7'S,8'E,11'S,12'R)-6-chloro-7'-methoxy-11',12'-dimethyl-7-(((9aS)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-methoxy-11',12'-dimethyl-7-(((9aR)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 962.2 |

TABLE 1-continued

Examples Prepared by the General Methods

| Example Number | Starting Materials | General Method | Product Structure | Product Name | MS Data (M + 1)+ |
|---|---|---|---|---|---|
| 295 | 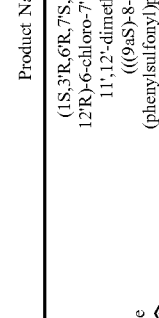 | 10 | 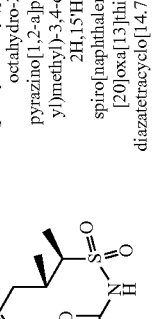 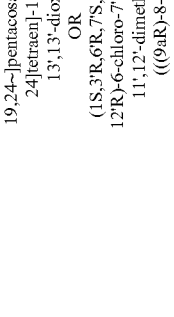 | (1S,3'R,6'R,7S,8E,11'S,12'R)-6-chloro-7-methoxy-11',12'-dimethyl-7-(((9aS)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7S,8E,11'S,12'R)-6-chloro-7-methoxy-11',12'-dimethyl-7-(((9aR)-8-(3-(phenylsulfonyl)propanoyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 962.2 |

TABLE 1-continued

Examples Prepared by the General Methods

| Example Number | Starting Materials | General Method | Product Structure | Product Name | MS Data (M + 1)+ |
|---|---|---|---|---|---|
| 296 | | 10 (in situ hydrolysis of boronate ester) | | (2-acetyl-4-(4-(1S,3'R,6'R,7S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl]-1-piperazinyl)phenyl)boronic acid | 873.2 |

TABLE 1-continued

Examples Prepared by the General Methods

| Example Number | Starting Materials | General Method | Product Structure | Product Name | MS Data (M + 1)+ |
|---|---|---|---|---|---|
| 297 | | 10 | | (1S,3'R,6R,7S,8E,11S,12'R)-6-chloro-7-methoxy-7'-((4-(2-methoxy-1,1-dimethylethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued

Examples Prepared by the General Methods

| Example Number | Starting Materials | General Method | Product Structure | Product Name | MS Data (M + 1)+ |
|---|---|---|---|---|---|
| 298 | | 10 | | (1S,3R,6R,7S,8E,11S,12R)-6-chloro-7'-(((9aR)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3R,6R,7S,8E,11S,12R)-6-chloro-7'-(((9aS)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 801.9 |

TABLE 1-continued

Examples Prepared by the General Methods

| Example Number | Starting Materials | General Method | Product Structure | Product Name | MS Data (M + 1)+ |
|---|---|---|---|---|---|
| 299 | | 10 | | (1S,3'R,6'R,7'R,8'E,11'S, 12'R)-6-chloro-7'-(((9aS)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S, 12'R)-6-chloro-7'-(((9aR)-8,8-difluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 801.9 |

TABLE 1-continued

Examples Prepared by the General Methods

| Example Number | Starting Materials | General Method | Product Structure | Product Name | MS Data (M + 1)+ |
|---|---|---|---|---|---|
| 300 | | 10 | | (1S,3'R,6'R,7S,7'S,8'E,11S,12'R)-6-chloro-7'-((4-(2-hydroxyethyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 755.2 |

TABLE 1-continued

Examples Prepared by the General Methods

| Example Number | Starting Materials | General Method | Product Structure | Product Name | MS Data (M + 1)+ |
|---|---|---|---|---|---|
| 301 | | 10 | | (1S,3'R,6R,7S,8E,11S,12'R)-7-((4-butyl-1-piperazinyl)methyl)-6-chloro-7'-methoxy-11',12'-dimethyl-3,4-dihydro-2H,15H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 302 | | 10 | | (1S,3'R,6R,7S,8E,11S,12'R)-6-chloro-7'-methoxy-7'-((4-(3-methoxypropyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.2 |

TABLE 1-continued

Examples Prepared by the General Methods

| Example Number | Starting Materials | General Method | Product Structure | Product Name | MS Data (M + 1)+ |
|---|---|---|---|---|---|
| 303 | | 10 | | (1S,3'R,6'R,7'S,8'E,11'S,12'R)-6-chloro-7'-((4-(2-ethoxyethyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.3 |

TABLE 1-continued
Examples Prepared by the General Methods
| Example Number | Starting Materials | General Method | Product Structure | Product Name | MS Data (M + 1)+ |
|---|---|---|---|---|---|
| 304 | 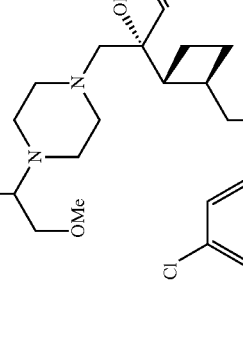 (FCH) | 10 |  | (1S,3'R,6R,7R,8E,11'S,12'R)-6-chloro-7'-methoxy-7'-((4-(2-methoxy-1-(methoxymethyl)ethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 813.2 |

TABLE 1-continued

Examples Prepared by the General Methods

| Example Number | Starting Materials | General Method | Product Structure | Product Name | MS Data (M + 1)+ |
|---|---|---|---|---|---|
| 305 | (AstaTech) | 10 | | (1S,3'R,6'R,7'S,8'E,11'S,12'R)-6-chloro-7'-methoxy-11',12'-dimethyl-7'-((4-(5-pyrimidinyl)-1-piperazinyl)methyl)-3,4-dihydro-2H,15'H-spiro[naphthalene-1,22'-[20]oxa[13]thia[1,14][20]oxa[13]thia[1,14]diazatetracyclo[14.7.2.0~3,6~.0~19,24~]pentacosa[8,16,18,24]tetraen]-15'-one 13',13'-dioxide | 789.9 |
| 306 | (Enamine) | 10 | | (1S,3'R,6'R,7'S,8'E,11'S,12'R)-6-chloro-7'-((4-(2,2-difluoroethyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 775.8 |

TABLE 1-continued

Examples Prepared by the General Methods

| Example Number | Starting Materials | General Method | Product Name | Product Structure | MS Data (M + 1)+ |
|---|---|---|---|---|---|
| 307 | | 10 | (1S,3'R,6'R,7'R,8'E,11'S,12'R)-7'-(4-tert-butyl-1-piperazinyl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | | 767.8 |
| 308 | (Enamine) | 10 | (1S,3'R,6'R,7'S,8'E,11'S,12'R)-7'-((4-(bis(2-methoxyethyl)amino)-1-piperidinyl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | | 842.1 |

TABLE 1-continued

Examples Prepared by the General Methods

| Example Number | Starting Materials | General Method | Product Structure | Product Name | MS Data (M + 1)+ |
|---|---|---|---|---|---|
| 309 | | 10 | | (1S,3'R,6'R,7'S,8'E,11'S, 12'R)-6-chloro-7'-((4-(1,3-dioxolan-2-ylmethyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.9 |

TABLE 1-continued

Examples Prepared by the General Methods

| Example Number | Starting Materials | General Method | Product Structure | Product Name | MS Data (M + 1)+ |
|---|---|---|---|---|---|
| 310 | [structure with piperazine + oxetane (AstaTech)] | 10 (with in situ oxetane hydrolysis) | [structure] | (1S,3R,6R,7S,8E,11S,12R)-6-chloro-7-((4-(3-hydroxy-2-(hydroxymethyl)propyl)-1-piperazinyl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 800.0 |
| 311 | [structure with piperazine + methyl-oxetane (AstaTech)] | 10 | [structure] | (1S,3R,6R,7S,8E,11S,12R)-6-chloro-7-ethoxy-11',12'-dimethyl-7-((4-(3-methyl-3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 796.0 |

TABLE 1-continued

Examples Prepared by the General Methods

| Example Number | Starting Materials | General Method | Product Structure | Product Name | MS Data (M + 1)+ |
|---|---|---|---|---|---|
| 312 | | 10 | | (1S,3'R,6'R,7'S,8'E,11'S,12'R)-7'-((4-bis(2-methoxyethyl)amino)-1-piperidinyl)methyl)-6'-chloro-7'-ethoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 856.2 |
| 313 | (Enamine) | 10 | | (1S,3'R,6'R,7'S,8'E,11'S,12'R)-6'-chloro-7'-methoxy-11',12'-dimethyl-7'-((4-(3-oxetanylmethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.8 |

TABLE 1-continued

Examples Prepared by the General Methods

| Example Number | Starting Materials | General Method | Product Structure | Product Name | MS Data (M + 1)+ |
|---|---|---|---|---|---|
| 314 | | 10 | | (1S,3'R,6R,7R,8E,11'S,12R)-6-chloro-11',12'-dimethyl-methoxy-7'-((1R,4R)-5-(1-methylethyl)-2,5-diazabicyclo[2.2.1] hept-2-yl)methyl)-3,4-dihydro-2H,15'H-spiro[naphthalene-1,22'-[20]oxa[13]thia[1,14] diazatetracyclo[14.7.2.0~3,6~.0~19,24~]pentacosa[8,16,18,24]tetraen]-15'-one 13',13'-dioxide | 765.8 |
| 315 | | 10 | | (1S,3'R,6R,7R,8E,11'S,12R)-6-chloro-11',12'-dimethyl-methoxy-7'-((1S,4S)-5-(1-methylethyl)-2,5-diazabicyclo[2.2.1] hept-2-yl)methyl)-3,4-dihydro-2H,15'H-spiro[naphthalene-1,22'-[20]oxa[13]thia[1,14] diazatetracyclo[14.7.2.0~3,6~.0~19,24~]pentacosa[8,16,18,24]tetraen]-15'-one 13',13'-dioxide | 765.8 |

TABLE 1-continued
Examples Prepared by the General Methods
| Example Number | Starting Materials | General Method | Product Structure | Product Name | MS Data (M + 1)+ |
|---|---|---|---|---|---|
| 316 | 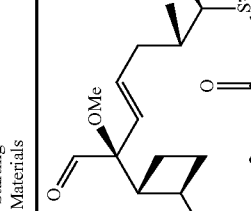 (Enamine) | 10 | 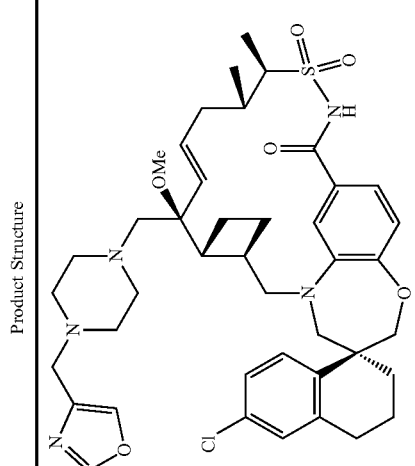 | (1S,3R,6R,7S,8E,11S,12'R)-6-chloro-7'-methoxy-11',12'-dimethyl-7'-((4-((5-methyl-1,2,4-oxadiazol-3-yl)methyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 807.9 |

TABLE 1-continued

Examples Prepared by the General Methods

| Example Number | Starting Materials | General Method | Product Structure | Product Name | MS Data (M + 1)+ |
|---|---|---|---|---|---|
| 317 | (Enamine) | 10 | | (1S,3'R,6'R,7S,8E,11'S,12'R)-6-chloro-7'-methoxy-11',12'-dimethyl-7'-((4-((3-methyl-1,2,4-oxadiazol-5-yl)methyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 807.9 |

TABLE 1-continued
Examples Prepared by the General Methods
| Example Number | Starting Materials | General Method | Product Structure | Product Name | MS Data (M + 1)+ |
|---|---|---|---|---|---|
| 318 | 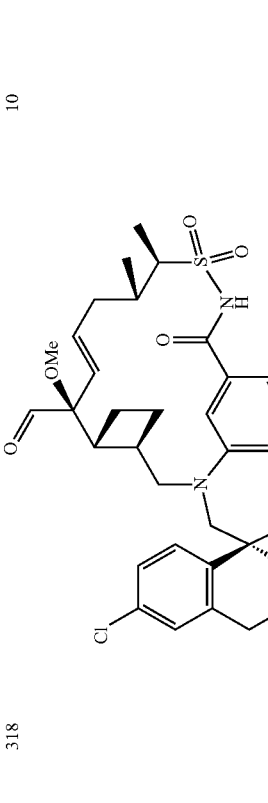 | 10 | 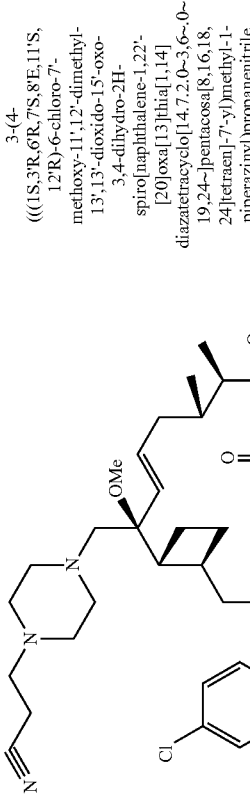 | 3-(4-((((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl-1-piperazinyl)propanenitrile | 764.8 |

TABLE 1-continued

Examples Prepared by the General Methods

| Example Number | Starting Materials | General Method | Product Structure | Product Name | MS Data (M + 1)+ |
|---|---|---|---|---|---|
| 319 | (AstaTech) | 10 | | (1S,3'R,6'R,7'R,8'E,11'S,12'R)-6-chloro-7'-methoxy-11',12'-dimethyl-7-((4-(3-methyl-3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 782.0 |
| 320 | (ChemBridge) | 10 | | (1S,3'R,6'R,7'R,8'E,11'S,12'R)-6-chloro-7'-methoxy-11',12'-dimethyl-7-((6-(1-methylethyl)-2,6-diazaspiro[3.3]hept-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.9 |

TABLE 1-continued

Examples Prepared by the General Methods

| Example Number | Starting Materials | General Method | Product Structure | Product Name | MS Data (M + 1)+ |
|---|---|---|---|---|---|
| 321 | (Enamine) | 10 | | (1S,3'R,6'R,7'S,8'E,11'S,12'R)-6-chloro-7'-methoxy-11',12'-dimethyl-7'-((4-(1,2,4-oxadiazol-3-ylmethyl)-1-piperazinyl)methyl)-3,4-dihydro-2H,15'H-spiro[naphthalene-1,22'-[20]oxa[13]thia[1,14]diazatetracyclo[14.7.2.0~3,6~0~19,24~]pentacosa[8,16,18,24]tetraen]-15'-one 13',13'-dioxide | 793.2 |
| 322 | (Enamine) | 10 | | (1S,3'R,6'R,7'S,8'E,11'S,12'R)-6-chloro-7'-((4-(4,5-dimethyl-1,3-oxazol-2-yl)methyl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~0~19,24~]pentacosa[8,16,18,24]tetraen]-15'-one 13',13'-dioxide | 820.3 |

TABLE 1-continued
Examples Prepared by the General Methods
| Example Number | Starting Materials | General Method | Product Structure | Product Name | MS Data (M + 1)+ |
|---|---|---|---|---|---|
| 323 | <br>(Enamine) | 10 |  | (1S,3'R,6R,7R,7'R,8'E,11'S,12'R)-6-chloro-7'-methoxy-11',12'-dimethyl-7'-((4-(1-methylethyl)-3-oxo-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 324 | | 10 | | (1S,3R,6R,7S,8E,11S,12'R)-6-chloro-7'-methoxy-7-(((3R,5S)-4-(2-methoxyethyl)-3,5-dimethyl-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.3 |

TABLE 1-continued

Examples Prepared by the General Methods

| Example Number | Starting Materials | General Method | Product Structure | Product Name | MS Data (M + 1)+ |
|---|---|---|---|---|---|
| 325 | 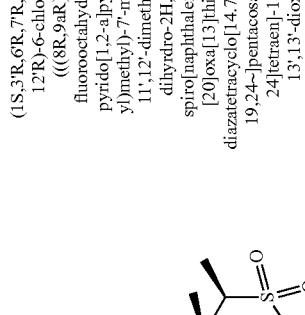 | 10 | 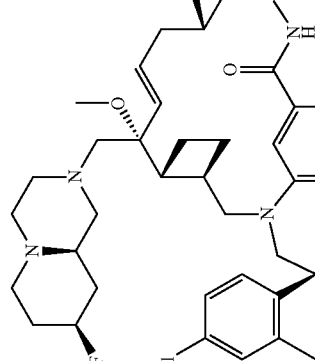 OR 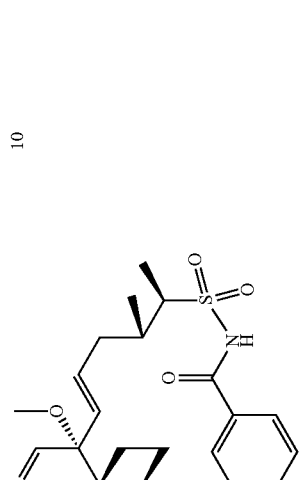 OR | (1S,3'R,6R,7R,7R,8E,11'S,12'R)-6-chloro-7'-(((8R,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,7R,8E,11'S,12'R)-6-chloro-7'-(((8R,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.9 |

TABLE 1-continued

Examples Prepared by the General Methods

| Example Number | Starting Materials | General Method | Product Structure | Product Name | MS Data (M + 1)+ |
|---|---|---|---|---|---|
| | | | 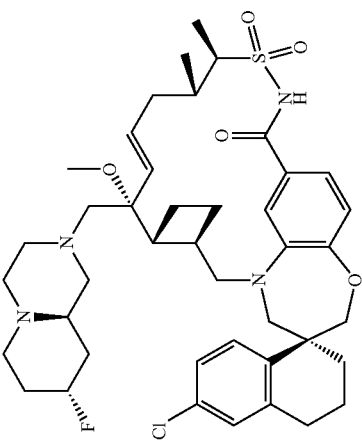 OR 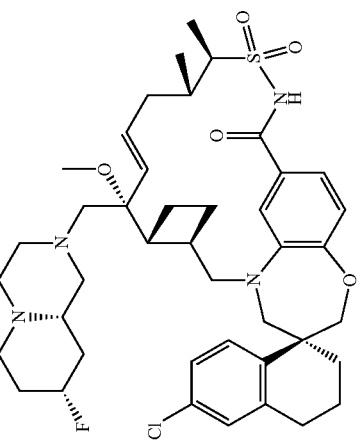 | (1S,3'R,6R,7R,8'E,11'S,12'R)-6-chloro-7-(((8S,9aR)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,8'E,11'S,12'R)-6-chloro-7-(((8S,9aS)-8-fluorooctahydro-2H-pyrido[1,2-a]pyrazin-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 326 | 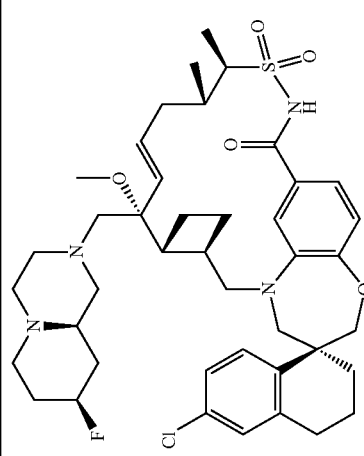 | 10 | 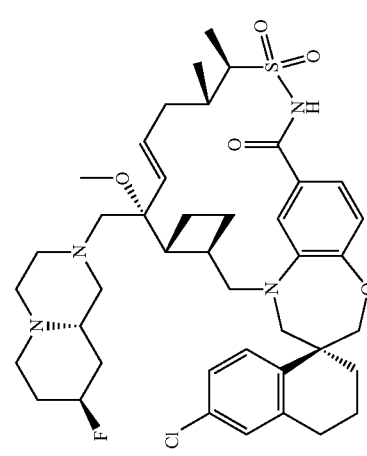 OR 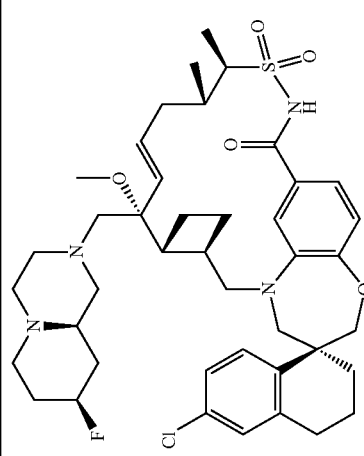 OR | (1S,3′R,6R,7R,8E,11′S,12′R)-6-chloro-7′-(((8R,9aR)-8-fluorooctahydro-2H-pyrido[1,2-a]pyrazin-2-yl)methyl)-7′-methoxy-11′12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide OR (1S,3′R,6R,7R,8E,11′S,12′R)-6-chloro-7′-(((8R,9aS)-8-fluorooctahydro-2H-pyrido[1,2-a]pyrazin-2-yl)methyl)-7′-methoxy-11′12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 783.9 |

TABLE 1-continued

Examples Prepared by the General Methods

| Example Number | Starting Materials | General Method | Product Structure | Product Name | MS Data (M + 1)+ |
|---|---|---|---|---|---|
| | | | 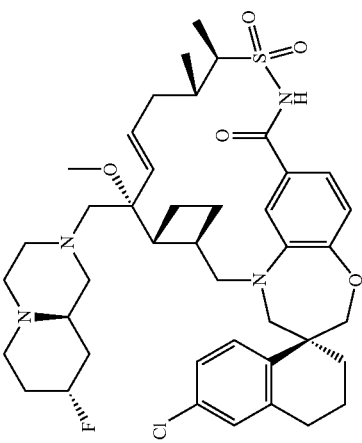 OR 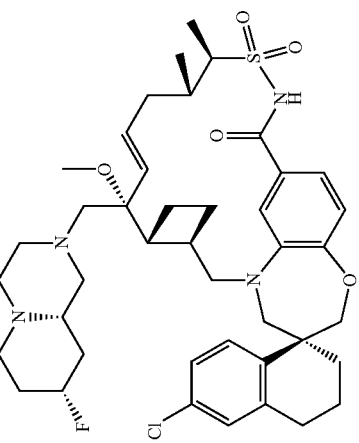 | (1S,3'R,6R,7R,8E,11'S,12'R)-6-chloro-7-(((8S,9aR)-8-fluorooctahydro-2H-pyrido[1,2-a]pyrazin-2-yl)methyl)-7'-methoxy-11'12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6R,7R,8E,11'S,12'R)-6-chloro-7-(((8S,9aS)-8-fluorooctahydro-2H-pyrido[1,2-a]pyrazin-2-yl)methyl)-7'-methoxy-11'12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 327 | (structure shown) (Enamine) | 10 | (structure shown) | (1S,3'R,6R,7R,8E,11'S,12'R)-6-chloro-7'-methoxy-11',12'-dimethyl-7'-((4-(1-methylethyl)-1,4-diazepan-1-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 1-continued

Examples Prepared by the General Methods

| Example Number | Starting Materials | General Method | Product Structure | Product Name | MS Data (M + 1)+ |
|---|---|---|---|---|---|
| 328 | | 10 | | (1S,3'R,6R,7R,8E,11'S, 12'R)-6-chloro-7'-(((3R,5S)-3,5-dimethyl-4-(1-methylethyl)-1-piperazinyl)methyl)-7'-methoxy-11',12'-dimethyl-3,4-dihydro-2H,15'H-spiro[naphthalene-1,22'-[20]oxa[13]thia[1,14] diazatetracyclo[14.7.2.0~3,6~.0~19,24~]pentacosa[8,16,18, 24]tetraen]-15'-one 13',13'-dioxide | 781.3 |
| 329 | | 10 | | (1S,3'R,6R,7R,8E,11'S, 12'R)-6-chloro-7'-(((3R,5S)-3,5-dimethyl-1-piperazinyl)methyl)-7'-methoxy-11',12'-dimethyl-3,4-dihydro-2H,15'H-spiro[naphthalene-1,22'-[20]oxa[13]thia[1,14] diazatetracyclo[14.7.2.0~3,6~.0~19,24~]pentacosa[8,16,18, 24]tetraen]-15'-one 13',13'-dioxide | 739.2 |

TABLE 1-continued

Examples Prepared by the General Methods

| Example Number | Starting Materials | General Method | Product Structure | Product Name | MS Data (M + 1)+ |
|---|---|---|---|---|---|
| 330 | | 10 | | (1S,3'R,6R,7R,8'E,11'S,12'R)-6-chloro-7'-((4-ethyl-3,3-dimethyl-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued

Examples Prepared by the General Methods

| Example Number | Starting Materials | General Method | Product Structure | Product Name | MS Data (M + 1)+ |
|---|---|---|---|---|---|
| 331 | 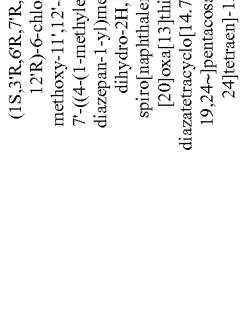 (Enamine) | 10 | 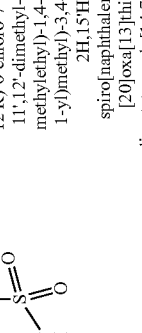 AND  | (1S,3'R,6'R,7'R,8'E,11'S,12'R)-6-chloro-7'-methoxy-11',12'-dimethyl-7'-((4-(1-methylethyl)-1,4-diazepan-1-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-methoxy-11',12'-dimethyl-7'-((4-(1-methylethyl)-1,4-diazepan-1-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued

Examples Prepared by the General Methods

| Example Number | Starting Materials | General Method | Product Structure | Product Name | MS Data (M + 1)+ |
|---|---|---|---|---|---|
| 332 | | 10 | | (1S,3'R,6R,7S,8E,11S,12'R)-6-chloro-7-methoxy-7'-((4-(2-(2-methoxyethoxy)ethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 813.2 |
| 333 | | 10 | | (1S,3'R,6R,7R,8E,11S,12'R)-6-chloro-7-methoxy-7'-((4-(2-methoxy-1,1-dimethylethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued

Examples Prepared by the General Methods

| Example Number | Starting Materials | General Method | Product Structure | Product Name | MS Data (M + 1)+ |
|---|---|---|---|---|---|
| 334 | (ChemShuttle) | 10 | | (1S,3'R,6R,7S,8E,11S,12'R)-6-chloro-7-methoxy-7-((4-(2-methoxyethyl)-3,3-dimethyl-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |
| 335 | (Oakwood) | 10 | | (1S,3'R,6R,7S,8E,11S,12'R)-7-((4-tert-butyl-1-piperazinyl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

| Example Number | Starting Materials | General Method | Product Structure | Product Name | MS Data (M + 1)+ |
|---|---|---|---|---|---|
| 336 | | 10 | | (1S,3′R,6R,7R,8′E,11′S,12′R)-6-chloro-7′-methoxy-11′,12′-dimethyl-7-(((3R,5S)-3,4,5-trimethyl-1-piperazinyl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 753.2 |

TABLE 1-continued

Examples Prepared by the General Methods

| Example Number | Starting Materials | General Method | Product Structure | Product Name | MS Data (M + 1)+ |
|---|---|---|---|---|---|
| 337 | | 10 | | (1S,3'R,6'R,7'R,7S,8'E,11'S,12'R)-6-chloro-7'-methoxy-11',12'-dimethyl-7'-((3S)-3-methyl-4-(1-methylethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |
| 338 | | 10 | | (1S,3'R,6'R,7S,8'E,11'S,12'R)-6-chloro-7'-methoxy-11',12'-dimethyl-7'-((4-(2-pyrimidinylmethyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 803.2 |

TABLE 1-continued

Examples Prepared by the General Methods

| Example Number | Starting Materials | General Method | Product Structure | Product Name | MS Data (M + 1)+ |
|---|---|---|---|---|---|
| 339 | (Ocatava) | 10 | | (1S,3'R,6'R,7'S,8'E,11'S,12'R)-6-chloro-7'-((4-(1,1-dioxido-3-thietanyl)-1-piperazinyl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 815.2 |

TABLE 1-continued

Examples Prepared by the General Methods

| Example Number | Starting Materials | General Method | Product Structure | Product Name | MS Data (M + 1)+ |
|---|---|---|---|---|---|
| 340 | | 10 | | (1S,3R,6R,7S,8E,11S,12R)-6-chloro-7'-((4-(1,4-dioxepan-6-yl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

TABLE 1-continued
Examples Prepared by the General Methods
| Example Number | Starting Materials | General Method | Product Structure | Product Name | MS Data (M + 1)+ |
|---|---|---|---|---|---|
| 341 | 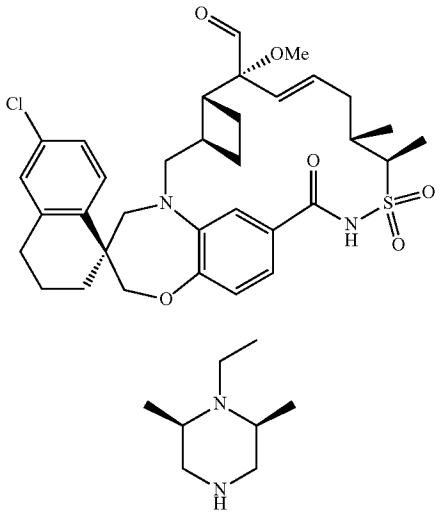 (Enamine) | 10 | 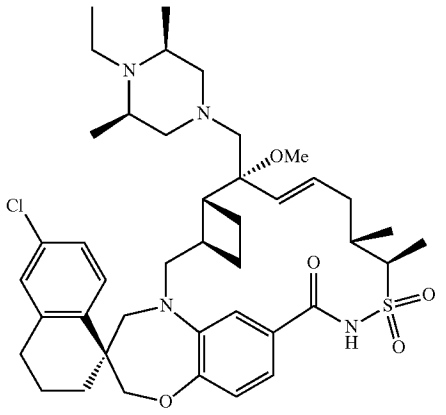 | (1S,3'R,6R,7R,8E,11'S, 12'R)-6-chloro-7'-(((3R,5S)-4-ethyl-3,5-dimethyl-1-piperazinyl)methyl)-7-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.2 |

TABLE 1-continued

Examples Prepared by the General Methods

| Example Number | Starting Materials | General Method | Product Structure | Product Name | MS Data (M + 1)+ |
|---|---|---|---|---|---|
| 342 | | 10 | | (1S,3'R,6R,7R,8E,11'S, 12'R)-6-chloro-7'-((4-(1,4-dioxepan-6-yl)-1-piperazinyl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 811.2 |

TABLE 1-continued

Examples Prepared by the General Methods

| Example Number | Starting Materials | General Method | Product Structure | Product Name | MS Data (M + 1)+ |
|---|---|---|---|---|---|
| 343 | | 10 | | (1S,3'R,6R,7R,7R,8E,11'S, 12'R)-6-chloro-7'-(((3R,5R)-3,5-dimethyl-4-(1-methylethyl)-1-piperazinyl)methyl)-7-methoxy-11',12'-dimethyl-3,4-dihydro-2H, 5'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |

TABLE 1-continued

Examples Prepared by the General Methods

| Example Number | Starting Materials | General Method | Product Structure | Product Name | MS Data (M + 1)+ |
|---|---|---|---|---|---|
| 344 | 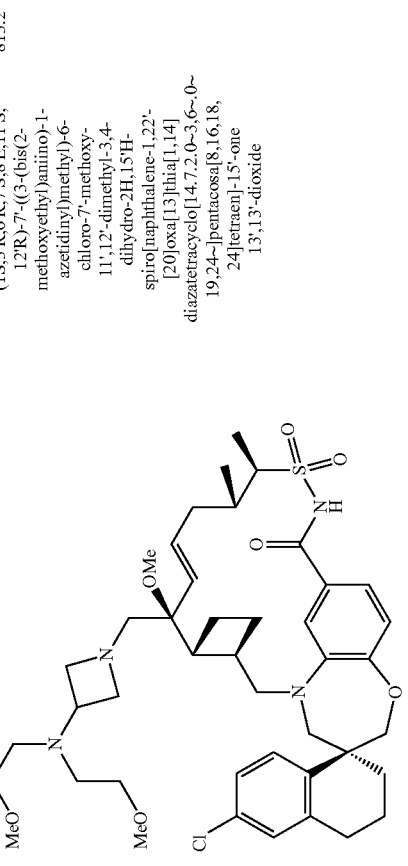 | 10 | 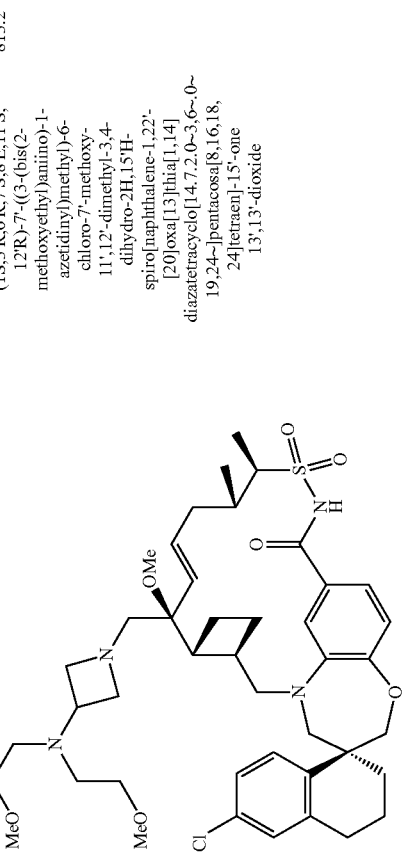 | (1S,3R,6R,7S,8E,11S,12R)-7'-((3-(bis(2-methoxyethyl)amino)-1-azetidinyl)methyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 813.2 |
| 346 | 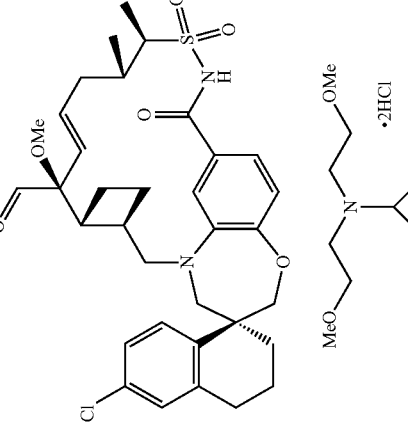<br>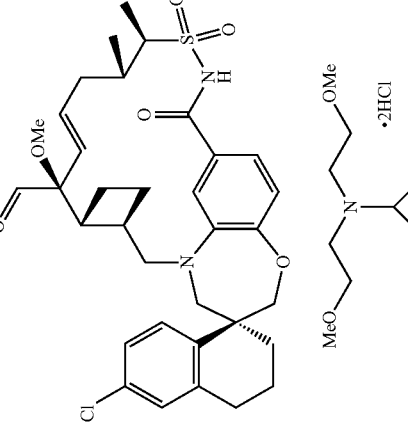 | 5, 9 Example 367, (Step 11) | 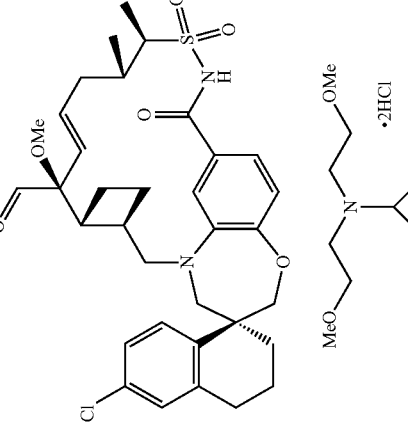 | (1S,3R,6R,7S,8E,11S,12R)-6-chloro-7'-((9aS)-hexahydropyrazino[2,1-c][1,4]oxazin-8(1H)-ylmethyl)-12'-(2-hydroxyethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.2 |

TABLE 1-continued
Examples Prepared by the General Methods
| Example Number | Starting Materials | General Method | Product Structure | Product Name | MS Data (M + 1)+ |
|---|---|---|---|---|---|
| 347 | 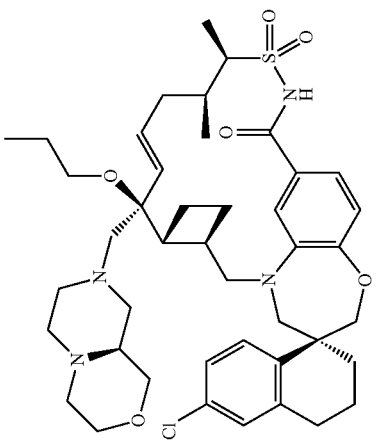 n-Propyl Iodide | 5, 9 | 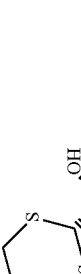 | (1S,3'R,6'R,7'S,8'E,11'S, 12'R)-6-chloro-7'-((9aS)- hexahydropyrazino[2,1- c][1,4]oxazin-8(1H)- ylmethyl)-11',12'- dimethyl-7'-propoxy-3,4- dihydro-2H,15'H- spiro[naphthalene-1,22' [20]oxa[13]thia[1,14] diazatetracyclo[14.7.2.0~3,6~.0~ 19,24~]pentacosa[8,16,18, 24]tetraen]-15'-one 13',13'-dioxide | 795.3 |

TABLE 1-continued

Examples Prepared by the General Methods

| Example Number | Starting Materials | General Method | Product Structure | Product Name | MS Data (M + 1)+ |
|---|---|---|---|---|---|
| 349 | 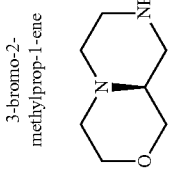<br>3-bromo-2-methylprop-1-ene | 5, Example 348 (Step 2), 9 | 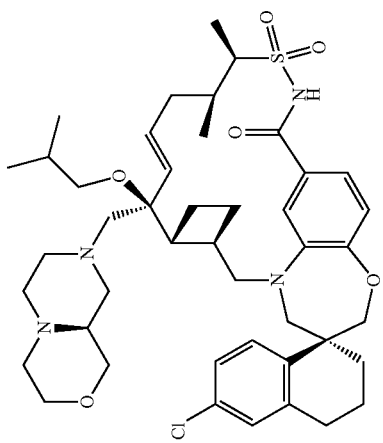 | (1S,3R,6R,7S,8E,11S,12R)-6-chloro-7'-((9aS)-hexahydropyrazino[2,1-c][1,4]oxazin-8(1H)-ylmethyl)-11',12'-dimethyl-7-(2-methylpropoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.2 |

TABLE 1-continued

Examples Prepared by the General Methods

| Example Number | Starting Materials | General Method | Product Structure | Product Name | MS Data (M + 1)+ |
|---|---|---|---|---|---|
| 350 | 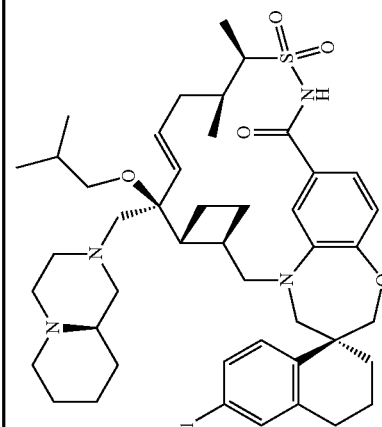<br>3-bromo-2-methylprop-1-ene | 5, Example 348 (Step 2), 8 | 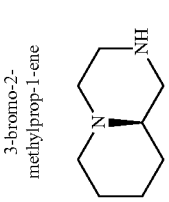 | (1S,3'R,6'R,7'S,8'E,11'S,12'R)-6-chloro-11',12'-dimethyl-7'-(2-methylpropoxy)-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 807.4 |

TABLE 1-continued

Examples Prepared by the General Methods

| Example Number | Starting Materials | General Method | Product Structure | Product Name | MS Data (M + 1)+ |
|---|---|---|---|---|---|
| 351 | allyl bromide | 5, Example 348 (Step 2), 9 | | (1S,3'R,6R,7R,8E,11'S,12'R)-6-chloro-7'-((9aS)-hexahydropyrazino[2,1-c][1,4]oxazin-8(1H)-ylmethyl)-11',12'-dimethyl-7'-propoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.3 |

TABLE 1-continued

Examples Prepared by the General Methods

| Example Number | Starting Materials | General Method | Product Structure | Product Name | MS Data (M + 1)+ |
|---|---|---|---|---|---|
| 352 | allyl bromide | 5, Example 348 (Step 2), 8 | | (1S,3'R,6'R,7'R,8'E,11'S,12'R)-6-chloro-11',12'-dimethyl-7'-((4-(3-oxetanyl)-1-piperazinyl)methyl)-7'-propoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.3 |

TABLE 1-continued

Examples Prepared by the General Methods

| Example Number | Starting Materials | General Method | Product Structure | Product Name | MS Data (M + 1)+ |
|---|---|---|---|---|---|
| 353 | (structure), allyl bromide | 5, Example 348 (Step 2), 8 | (structure) | (1S,3'R,6'R,7'R,8'E,11'S,12'R)-6-chloro-11',12'-dimethyl-7'-((9aR)-octahydro-2H-pyrido[1,2-a]pyrazin-2-ylmethyl)-7'-propoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 793.4 |

TABLE 1-continued

Examples Prepared by the General Methods

| Example Number | Starting Materials | General Method | Product Structure | Product Name | MS Data (M + 1)+ |
|---|---|---|---|---|---|
| 354 | 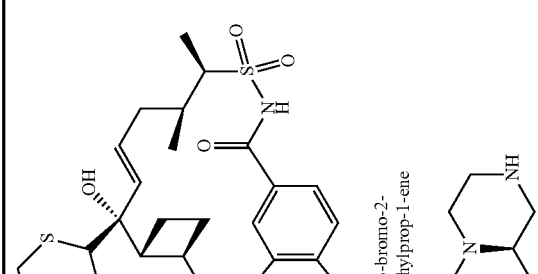 3-bromo-2-methylprop-1-ene | 5, Example 348 (Step 2), 8 | 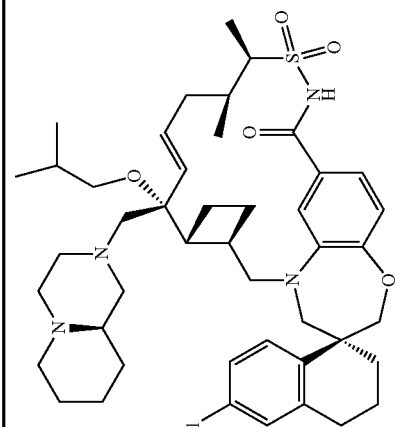 | (1S,3'R,6'R,7'R,8'E,11'S, 12'R)-6-chloro-11',12'-dimethyl-7'-(2-methylpropoxy)-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 807.3 |

TABLE 1-continued

Examples Prepared by the General Methods

| Example Number | Starting Materials | General Method | Product Structure | Product Name | MS Data (M + 1)+ |
|---|---|---|---|---|---|
| 355 | 3-bromo-2-methylprop-1-ene | 5, Example 348 (Step 2), 8 | | (1S,3'R,6'R,7'R,8'E,11'S,12'R)-6-chloro-11',12'-dimethyl-7'-(2-methylpropoxy)-7'-((4-(3-oxetanyl)-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.3 |

TABLE 1-continued

Examples Prepared by the General Methods

| Example Number | Starting Materials | General Method | Product Structure | Product Name | MS Data (M + 1)+ |
|---|---|---|---|---|---|
| 356 | 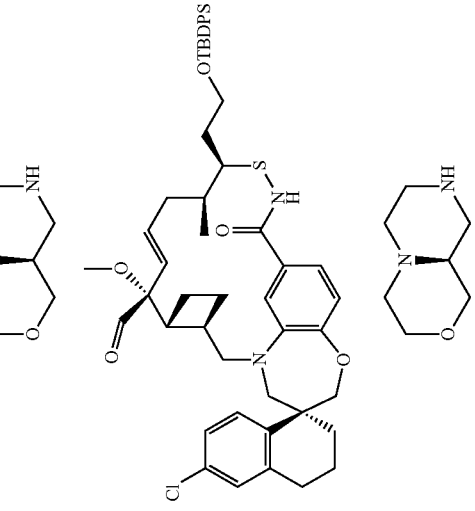 | 5, Example 348 (Step 2, 9) | 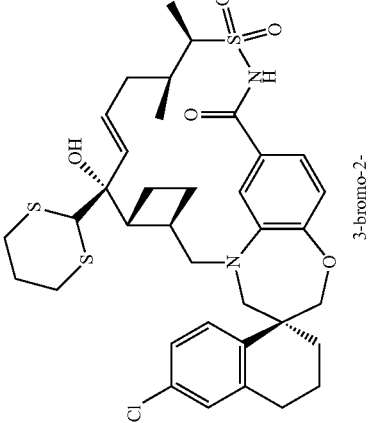 | (1S,3'R,6R,7R,8E,11'S,12'R)-6-chloro-7'-(9aS)-hexahydropyrazino[2,1-c][1,4]oxazin-8(1H)-ylmethyl)-11',12'-dimethyl-7'-(2-methylpropoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 809.4 |
| 357 | 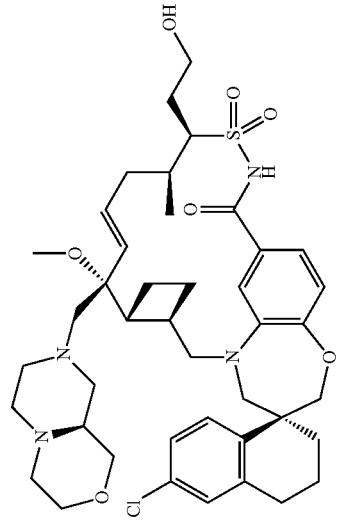 | 9, Example 367 (Step 11) | 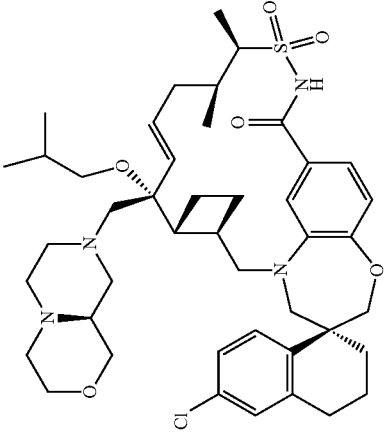 | (1S,3'R,6R,7R,8E,11'S,12'R)-6-chloro-7'-(9aS)-hexahydropyrazino[2,1-c][1,4]oxazin-8(1H)-ylmethyl)-12'-(2-hydroxyethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 797.4 |

TABLE 1-continued

Examples Prepared by the General Methods

| Example Number | Starting Materials | General Method | Product Structure | Product Name | MS Data (M + 1)+ |
|---|---|---|---|---|---|
| 360 | (Example 358) | See example 18 (Step 14) | | (1S,3'R,6'R,7'R,8'E,11'S,12'R)-6-chloro-7'-methoxy-11'-methyl-7'-((9aR)-octahydro-2H-pyrido[1,2-a]pyrazin-2-ylmethyl)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)acetaldehyde | 793.3 |
| 361 | (Example 346) + morpholine | See example 367 (Steps 12, 13) | | (1S,3'R,6'R,7'S,8'E,11'S,12'R)-6-chloro-7'-((9aS)-hexahydropyrazino[2,1-c][1,4]oxazin-8(1H)-ylmethyl)-7'-methoxy-11'-methyl-12'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 866.4 |

TABLE 1-continued

Examples Prepared by the General Methods

| Example Number | Starting Materials | General Method | Product Structure | Product Name | MS Data (M + 1)+ |
|---|---|---|---|---|---|
| 365 | [structure with OMs group]; morpholine | See example 367 (Step 13) | [structure] | (1S,3'R,6R,7R,8'E,11'S,12'R)-6-chloro-7'-methoxy-11'-methyl-12'-(2-(4-morpholinyl)ethyl)-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 864.3 |
| 368 | [structure with OH and dithiane]; allyl bromide; [piperazine structure] | 5, Example 348 (Step 2), 8 | [structure] | (1S,3'R,6R,7R,8'E,11'S,12'R)-6-chloro-11',12'-dimethyl-7'-(((3 R)-3-methyl-4-(2-propanyl)-1-piperazinyl)methyl)-7'-propoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.3 |

TABLE 1-continued

Examples Prepared by the General Methods

| Example Number | Starting Materials | General Method | Product Structure | Product Name | MS Data (M + 1)+ |
|---|---|---|---|---|---|
| 369 | [structure] EI; [structure] (Pharmablock) | 4, 8 | [structure] | (1S,3'R,6R,7S,8E,11'S,12R)-6-chloro-7'-ethoxy-7-((9aS)-hexahydropyrazino[2,1-c][1,4]oxazin-8(1H)-ylmethyl)-12'-(2-methoxyethyl)-11'-methyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 826.2 |
| 370 | [structure] EI; [structure] | 4, 8 | [structure] | (1S,3'R,6R,7S,8E,11'S,12R)-6-chloro-7'-ethoxy-12'-(2-methoxyethyl)-11'-methyl-7-((9aR)-octahydro-2H-pyrido[1,2-a]pyrazin-2-ylmethyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 824.3 |

TABLE 1-continued

Examples Prepared by the General Methods

| Example Number | Starting Materials | General Method | Product Structure | Product Name | MS Data (M + 1)+ |
|---|---|---|---|---|---|
| 371 | | 8 | | (1S,3'R,6'R,7'S,8'E,11'S,12'R)-6'-chloro-7'-methoxy-7'-((4-(2-methoxy-1-(methoxymethyl)ethyl)-1-piperazinyl)methyl)-11',12'-dimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 814.2 |

TABLE 1-continued
Examples Prepared by the General Methods
| Example Number | Starting Materials | General Method | Product Structure | Product Name | MS Data (M + 1)+ |
|---|---|---|---|---|---|
| 372 | 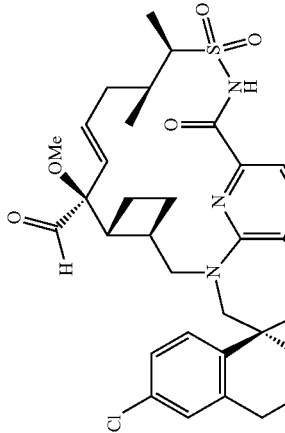 (Aurum) | 8 | 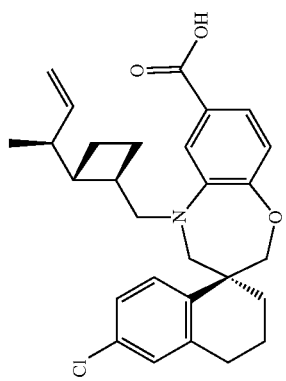 | (1S,3'R,6R,7S,8E,11S,12'R)-6-chloro-7'-methoxy-11',12'-dimethyl-7-((9aR)-octahydro-2H-pyrido[1,2-a]pyrazin-2-ylmethyl)-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 766.3 |

Example 100001

(1S,3'R,6'R,7'S, 8'E,11'S,12'R)-6-chloro-7'-(hydroxymethyl)-7'-methoxy-11',12'-dimethyl-3,4-dihydro-2H,15'H-spiro[naphthalene-1,22'-[2]oxa[13]thia[1,14]diazatetracyclo[14.7.2.0~3,6~.0~19,24~]pentacosa[8,16,18,24]tetraen]-15'-one 13',13'-dioxide

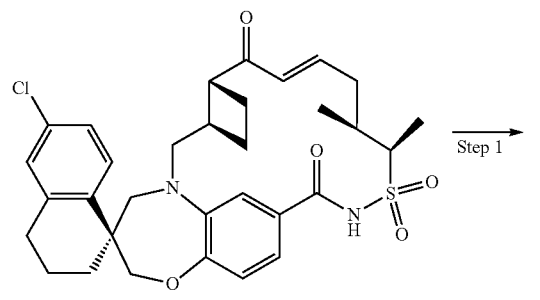

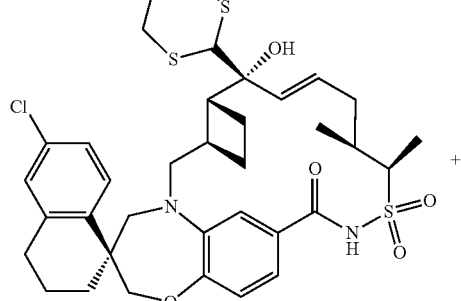

Example 100259

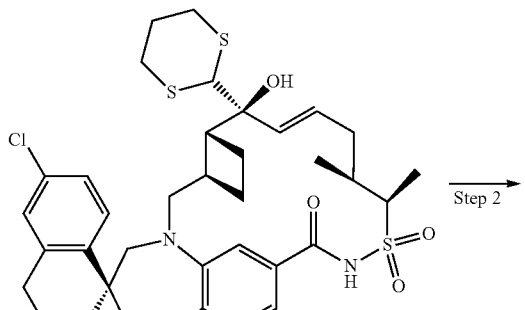

Example 100260

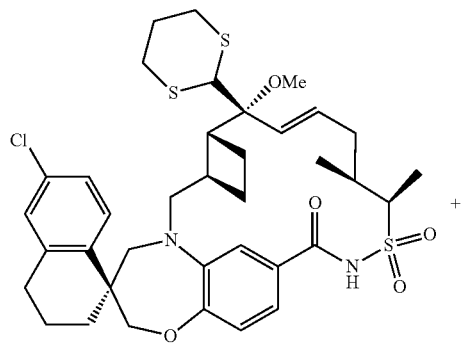

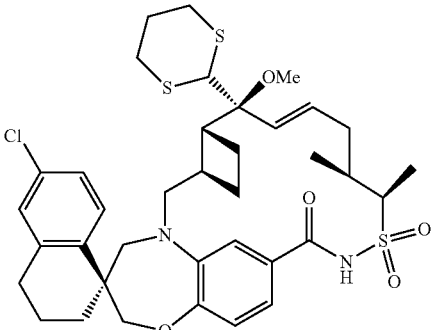

Example 100261

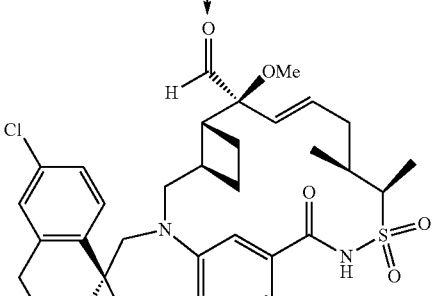

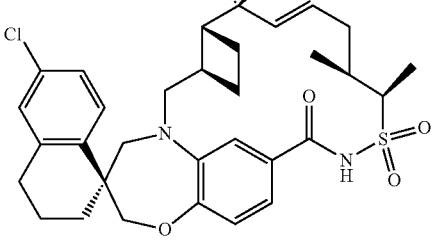

Example 100001

Step 1: (1S,3'R,6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[2]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'S,8'F, 11'S,12'R)-6-chloro-7'-(1,3-dithian-2-yl)-7'-hydroxy-11',12'-dimethyl-3,4-dihydro-2H,15'H-Spiro[naphthalene-1,22'-[2]oxa[13]thia[1,14]diazatetracyclo[14.7.2.0~3,6~.0~19,24~]pentacosa[8,16,18,24]tetraen]-15'-one 13',13'-dioxide To a 250 mL round-bottomed flask was added 1,3-dithiane (4.79 g, 39.8 mmol) and THF (100 mL). The mixture was cooled to −78° C. and n-butyllithium (1.6 M solution in hexane, 22.5 mL, 36.1 mmol) was added over 8 min. The solution was stirred in the −78° C. bath for 30 min. In a separate 100 mL flask was added (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo

[14.7.2.0~3,6~.0~19,24~]pentacosa[8,16,18,24]tetraene]-7',15'-dione 13',13'-dioxide and THF (5 mL). To this was added lanthanum(III) chloride bis lithium chloride complex solution (0.6 M in THF, 60.1 mL, 36.1 mmol) and this was stirred for 5 min at room temperature. The solution was then cooled to −78° C. and added via cannula to the dithiane solution. After 2.5 h at −78° C., the solution was treated with sat NH₄Cl and water. The pH of the solution was adjusted to pH=4 with aqueous 10% citric acid and aqueous NaHCO₃. The solution was extracted with EtOAc and the combined extracts were filtered through Celite. The extracts were washed with water and brine and then dried (Na₂SO₄) and concentrated to afford a mixture of (1S,3'R,6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'S,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a brown oil which was carried on directly to the next step. MS (ESI, +ve ion) m/z 717.5 (M+H)⁺.

Step 2: (1S,3'R,6'R,7'R,8'E,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'S,8'E,11'S,12'R)-6-chloro-7'-(1,3-dithian-2-yl)-7'-methoxy-11',12'-dimethyl-3,4-dihydro-2H,15'H-spiro [naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a resealable vial was added the mixture of (1S,3'R,6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'S,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (6.81 g, 9.49 mmol) and THF (100 mL). The mixture was cooled to 0° C. and potassium bis(trimethylsilyl)amide (1 M in THF, 38.0 mL, 38.0 mmol) was added over 10 min. The solution was stirred at 0° C. for 5 min and then iodomethane (2.36 mL, 38.0 mmol) was added over 3 min. After 2.5 h at 0° C., the solution was poured into saturated NH₄Cl and the pH was adjusted to 4 with 1 M citric acid. The solution was extracted with EtOAc and the combined extracts were washed with brine, dried (Na₂SO₄) and concentrated onto silica. Purification by silica gel chromatography (0% to 35% EtOAc/heptane, with 0.3% AcOH, 330 g Redi-Sep Gold column) afforded (1S,3'R,6'R,7'R,8'E,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1.66 g, 2.27 mmol, 24% yield). MS (ESI, +ve ion) m/z 731.5 (M+H)⁺ and (1S,3'R,6'R,7'S,8'E,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (4.69 g, 6.41 mmol, 68% yield). MS (ESI, +ve ion) m/z 731.5 (M+H)⁺.

Step 3: (1S,3'R,6'R,7'S,8'E,11'S,12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide To a 250 mL round-bottomed flask equipped with a reflux condenser was added (1S,3'R,6'R,7'S,8'E,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1.63 g, 2.23 mmol), acetonitrile (40 mL) and water (10 mL). The mixture was heated to 50° C. and calcium carbonate (1.12 g, 11.1 mmol) and iodomethane (1.38 mL, 22.3 mmol) were added. After 23 h at 50° C., the solution was poured into saturated NH₄Cl and water and then extracted with EtOAc. The combined extracts were washed with brine and then dried (Na₂SO₄) and concentrated onto silica. Purification by silica gel chromatography (0 to 40% EtOAc/heptane (both with 0.3% AcOH), Silicycle HP 120 g column) afforded (1S,3'R,6'R,7'S,8'E,11'S,12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (1.34 g, 2.09 mmol, 94% yield) as a white solid. MS (ESI, +ve ion) m/z 641.3 (M+H)⁺.

Step 4: (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a room temperature solution of (1S,3'R,6'R,7'S,8'E,11'S,12'R)-6-chloro-7'-methoxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide (30 mg, 0.047 mmol) in MeOH (2 mL) and THF (0.5 mL), was added sodium borohydride (17 mg, 0.47 mmol). After 5 min at rt the solution was poured into saturated NaCl and then extracted with EtOAc. The combined extracts were dried (Na₂SO₄) and concentrated. Purification by silica gel chromatography (0% to 60% EtOAc (0.3% AcOH) in heptane (4 g column)) afforded (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (10 mg, 0.016 mmol, 50% yield) as a white solid. ¹H NMR (400 MHz, CHLOROFORM-d) δ 7.95-8.01 (m, 1H), 7.68 (d, J=8.61 Hz, 1H), 7.16-7.20 (m, 1H), 7.10 (dd, J=1.86, 13.99 Hz, 2H), 6.85-6.95 (m, 2H), 5.71-5.80 (m, 1H), 5.67 (d, J=0.98 Hz, 1H), 4.29-4.41 (m, 1H), 4.07 (d, J=4.89 Hz, 3H), 3.87-3.97 (m, 2H), 3.72 (br d, J=14.48 Hz, 1H), 3.26 (d, J=14.28 Hz, 1H), 3.10 (s, 3H), 2.96-3.04 (m, 1H), 2.72-2.80 (m, 2H), 2.56-2.65 (m, 1H), 2.44 (s, 1H), 1.75-2.28 (m, 9H), 1.55-1.71 (m, 1H), 1.50 (d, J=7.04 Hz, 3H), 1.50-1.41 (m, 1H), 1.06 (d, J=6.85 Hz, 3H). One exchangeable proton was not observed. MS (ESI, +ve ion) m/z 643.2 (M+H)⁺.

Example 100002

2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide

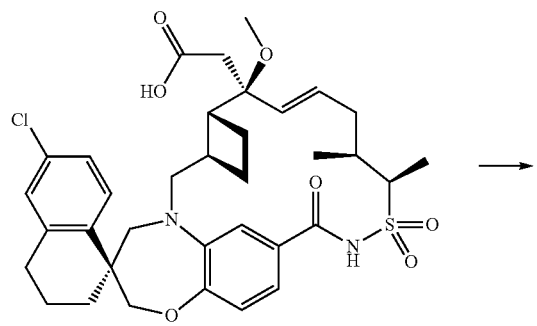

Example 100307

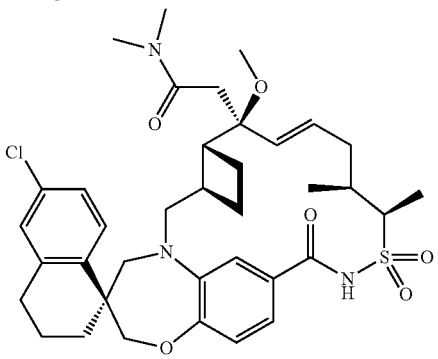

Example 100002

((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (60 mg, 0.089 mmol) was taken up in THF (1.8 mL) and lithium hydroxide (2.0 M in water, 0.18 mL, 0.36 mmol) was added. The mixture was stirred at room temperature for 10 min before being concentrated in vacuo to provide the lithium carboxylate of the starting material as an off-white solid that was used in the amide coupling. HATU (51.0 mg, 0.134 mmol) and dimethylamine (2.0 M in THF, 0.134 mL, 0.268 mmol) were added to a stirred suspension of the lithium carboxylate previously prepared in N,N-dimethylformamide (1.8 mL). The reaction mixture was stirred at room temperature for 10 minutes. The reaction mixture was diluted with water and EtOAc and transferred to a separatory funnel. 1.0 M HCl was added and the phases were mixed. The organic layer was separated and washed sequentially with 1.0 M LiCl and brine then dried over magnesium sulfate and concentrated under reduced pressure. Purification via silica gel flash chromatography using a gradient of 50% to 100% EtOAc+0.3% AcOH in heptane afforded 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18, 24]tetraen]-7'-yl)-N,N-dimethylacetamide (38 mg, 0.054 mmol, 61% yield) as a white solid. $^1$H NMR (300 MHz, CHLOROFORM-d) δ ppm 7.71 (d, J=8.48 Hz, 1H) 7.17 (dd, J=8.77, 2.19 Hz, 1H) 7.07-7.11 (m, 1H) 7.01-7.04 (m, 1H) 6.95-7.00 (m, 1H) 6.88-6.93 (m, 1H) 5.71-5.92 (m, 2H) 4.00-4.11 (m, 3H) 3.84 (br d, J=15.20 Hz, 1H) 3.70 (br d, J=14.03 Hz, 1H) 3.30 (d, J=14.32 Hz, 1H) 3.17 (s, 3H) 3.08-3.15 (m, 2H) 3.06 (s, 3H) 3.01 (s, 1H) 2.94 (s, 3H) 2.65-2.87 (m, 3H) 2.39-2.65 (m, 3H) 2.02-2.21 (m, 4H) 1.51-1.97 (m, 11H) 1.30-1.47 (m, 5H) 1.05 (d, J=6.14 Hz, 3H). MS (ESI, +ve) m/z 666.2 [M-OMe]$^+$.

Example 100003

(1S,3'R,6'R,7'S,8'E,11'S,12'R)-6-chloro-7'-methoxy-11',12'-dimethyl-7'-(2-pyridinyl)-3,4-dihydro-2H,15'H-spiro[naphthalene-1,22' [20]oxa[13]thia[1,14]diazatetracyclo[14.7.2.0~3,6~.0~19,24~]pentacosa[8,16,18,24]tetraen]-15'-one 13',13'-dioxide

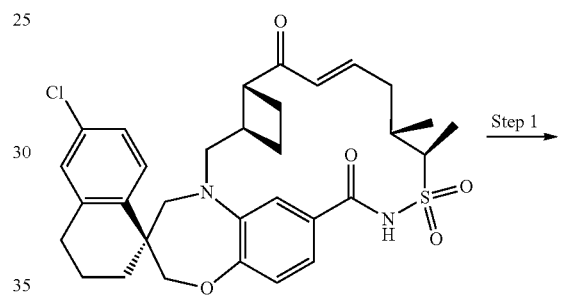

Step 1

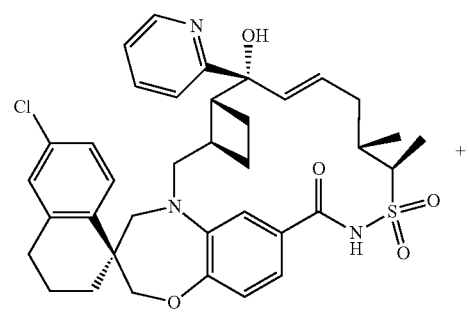

Step 2

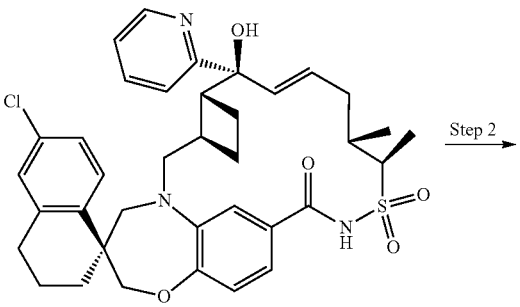

-continued

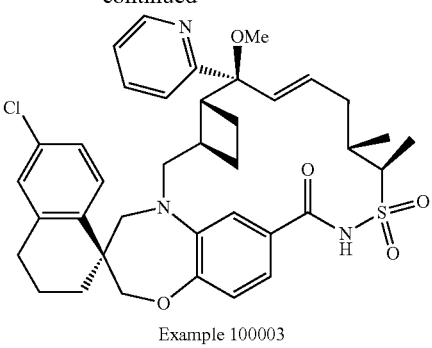

Example 100003

Step 1: (1S,3'R,6'R,7'R,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A solution of 2-bromopyridine (105 μL, 1.1 mmol) in THF (4 mL) was cooled to −78° C. under nitrogen atmosphere. A solution of n-butyllithium in hexanes (2.5 M, 422 μL, 1.1 mmol) was added dropwise and the reaction mixture was stirred for 30 min. A solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (300 mg, 0.5 mmol) in THF (1 mL) was added dropwise and the reaction mixture was allowed to warm to room temperature overnight. An aqueous saturated solution of NH$_4$Cl was added and the reaction mixture was extracted with EtOAc. The organic phase was separated, washed with brine and concentrated under reduced pressure. The yellow solid was purified by column chromatography on silica gel, eluting with a gradient of 0 to 35% EtOAc (containing 0.3% HOAc)/hexane to obtain a mixture of (1S,3'R,6'R,7'R,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a light-yellow solid (129 mg). The mixture was used in the next step without additional purification. MS (ESI, +ve ion) m/z 676.0 (M+H)$^+$.

Step 2: (1S,3'R,6'R,7'S,8'E,11'S,12'R)-6-chloro-7'-methoxy-11',12'-dimethyl-7'-(2-pyridinyl)-3,4-dihydro-2H,15'H-spiro[naphthalene-1,22' [20]oxa[13]thia[1,14]diazatetracyclo[14.7.2.0~3,6~.0~19,24~]pentacosa[8,16,18,24]tetraen]-15'-one 13',13'-dioxide The mixture of (1S,3'R,6'R,7'R,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (129 mg, 0.19 mmol) was dissolved in THF (5 mL) and the solution was cooled with a water bath. Sodium hydride (60% dispersion in mineral oil, 201 mg, 5 mmol) was added in one portion. After 15 min, iodomethane (624 μL, 10 mmol) was added. An additional portion of each NaH and MeI were added after 2 h. An aqueous saturated solution of NH$_4$Cl was added and the reaction mixture was extracted with EtOAc The solvent was removed under reduced pressure. The concentrate was purified by preparative reversed-phase preparative HPLC using a Phenomenex Gemini column, 10 μm, C18, 110 Å, 100×50 mm, 0.1% TFA in CH$_3$CN/H$_2$O, gradient 10% to 100% over 20 min to afford 21 mg of [(1S,3'R,6'R,7'S,8'E,11'S,12'R)-6-chloro-7'-methoxy-1',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide, the second eluting peak, as a white solid. $^1$H NMR (400 MHz, CHLOROFORM-d) δ ppm 1.15 (m, 3H) 1.24-1.34 (m, 2H) 1.48 (m, 3H) 1.61-1.80 (m, 2H) 1.83-1.93 (m, 2H) 1.95-2.07 (m, 3H) 2.19-2.32 (m, 3H) 2.62-2.82 (m, 5H) 3.06 (s, 3H) 3.11-3.21 (m, 2H) 3.70 (m, 1H) 3.96-4.01 (m, 1H) 4.04-4.09 (m, 1H) 4.17 (m, 1H) 5.86-6.02 (m, 2H) 6.92-6.97 (m, 1H) 6.99-7.03 (m, 1H) 7.09 (d, J=8.02 Hz, 2H) 7.18 (dd, J=8.41, 1.96 Hz, 1H) 7.65-7.71 (m, 2H) 8.34-8.40 (m, 2H) 9.02 (d, J=5.09 Hz, 1H). MS (ESI, +ve ion) m/z 690.0 (M+H)$^+$.

Example 100004

(1S,3'R,6'R,7'S,8'E,11'S,12'R)-6-chloro-7'-methoxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

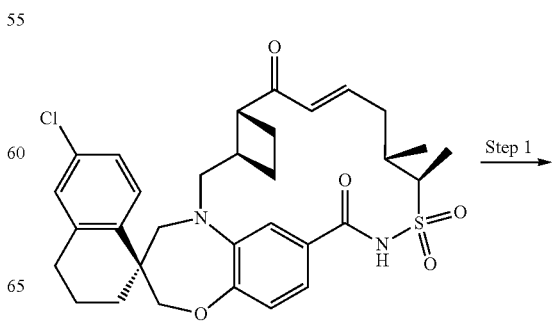

Step 1

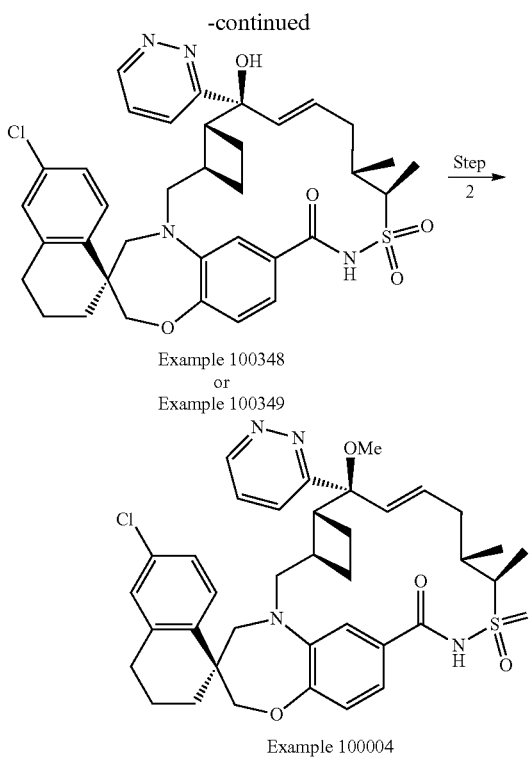

Example 100348
or
Example 100349

Example 100004

Step 1: (1S,3'R,6'R,7'S,8'E,11'S,12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a solution of 2,2,6,6-tetramethylpiperidine (1.06 mL, 6.3 mmol) in THF (28 mL) that was cooled to 0° C. was added a solution of n-butyllithium (2.5 M in THF, 2.4 mL, 6.0 mmol) under nitrogen atmosphere. The reaction was stirred at 0° C. for 25 minutes then cooled to −78° C. A solution of pyridazine (110 µL, 1.5 mmol) in THF (5 mL) was added dropwise, followed by a solution of (1S,3'R,6'R, 8'E,11'S,12'R)-6-chloro-11',12'-dimethyl-3,4-dihydro-2H, 7'H,15'H-spiro[naphthalene-1,22' [20]oxa[13]thia[1,14]diazatetracyclo[14.7.2.0~3,6~.0~19,24~]pentacosa[8,16,18, 24]tetraene]-7',15'-dione 13',13'-dioxide (300 mg, 0.502 mmol) in THF (3 mL). The reaction mixture was allowed to stir at −78° C. for 2 h and quenched by the addition of aqueous saturated ammonium chloride solution. The reaction mixture was extracted with EtOAc. The organic phase was separated, washed with brine and concentrated under reduced pressure to give the crude material. The crude material was purified by silica gel flash chromatography using a gradient of 50% to 100% EtOAc+0.3% AcOH in heptane to provide 106 mg of (1S,3'R,6'R,7'S,8'E,11'S, 12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide, the second eluting peak. MS (ESI, +ve ion) m/z 677.0 (M+H)⁺.

Step 2: (1S,3'R,6'R,7'S,8'E,11'S,12'R)-6-chloro-7'-methoxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19, 24~]pentacosa[8,16,18,24]tetraen]-15'-one 13',13'-dioxide Sodium hydride (60% dispersion in mineral oil, 81 mg, 2.0 mmol) was added in one portion to a solution of (1S,3'R,6'R,7'S,8'E,11'S,12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (137 mg, 0.2 mmol) in tetrahydrofuran (6.7 mL). After 5 min, iodomethane (251 µL, 4.1 mmol) was added and the reaction was stirred for 2 hours. MeOH (3 mL) was added and the reaction mixture was purified by preparative reversed-phase preparative HPLC using a Phenomenex Gemini column, 10 µm, C18, 110 Å, 100×50 mm, 0.1% TFA in CH₃CN/H₂O, gradient 10% to 100% over 20 min. The desired fractions were combined and the solvent was removed under reduced pressure to obtain 92 mg of (1S,3'R,6'R,7'S,8'E,11'S,12'R)-6-chloro-7'-methoxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide as a tan solid. ¹H NMR (400 MHz, CHLOROFORM-d) δ ppm 1.03 (d, J=6.06 Hz, 3H) 1.35 (d, J=6.65 Hz, 3H) 1.72-1.87 (m, 2H) 1.89-2.23 (m, 9H) 2.73-2.84 (m, 3H) 2.94-3.06 (m, 2H) 3.11 (s, 3H) 3.26 (d, J=14.48 Hz, 1H) 3.68 (d, J=7.04 Hz, 1H) 3.75 (d, J=14.48 Hz, 1H) 4.04-4.14 (m, 2H) 4.32 (d, J=15.06 Hz, 1H) 5.43 (br. s., 9H) 5.91 (d, J=16.24 Hz, 1H) 6.85-6.92 (m, 2H) 7.03 (s, 1H) 7.09 (s, 1H) 7.16-7.21 (m, 1H) 7.18 (d, J=8.61 Hz, 1H) 7.70 (d, J=8.41 Hz, 1H) 8.18 (br. s., 2H) 9.48 (br. s., 1H). MS (ESI, +ve ion) m/z 691.0 (M+H)⁺.

Example 100005

2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-methoxyethyl)-N-methylacetamide

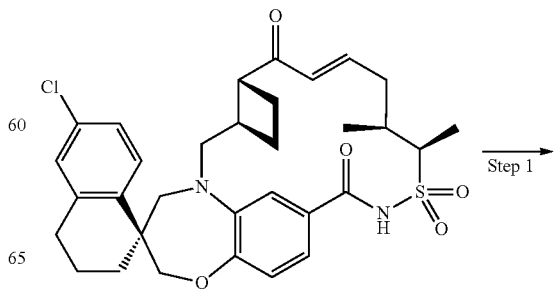

1219
-continued

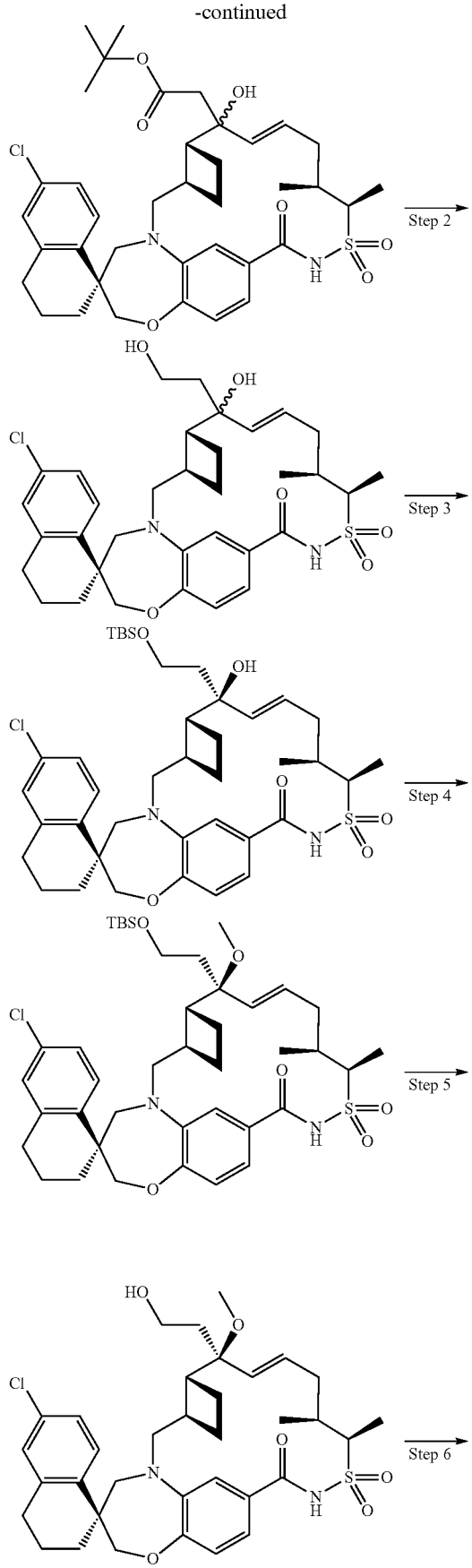

1220
-continued

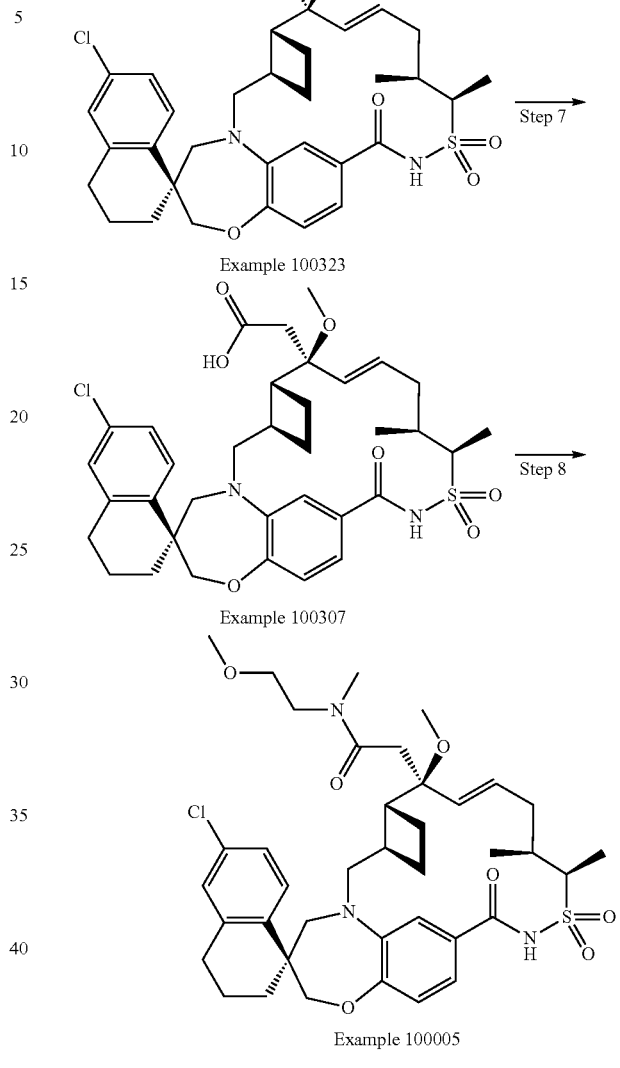

Step 1: 2-methyl-2-propanyl ((1S,3'R,6'R,7'S,8'E, 11'S,12'R)-6-chloro-7'-hydroxy-11',12'-dimethyl-13', 13'-dioxido-15'-oxo-3,4-dihydro-2H-spiro[naphthalene-1,22'-[20]oxa[13]thia[1,14]diazatetracyclo [14.7.2.0~3,6~.0~19,24~]pentacosa[8,16,18,24] tetraen]-7'-yl)acetate and 2-methyl-2-propanyl ((1S, 3'R,6'R,7'R,8'E,11'S,12'R)-6-chloro-7'-hydroxy-11', 12'-dimethyl-13',13'-dioxido-15'-oxo-3,4-dihydro-2H-spiro[naphthalene-1,22'-[20]oxa[13]thia[1,14] diazatetracyclo[14.7.2.0~3,6~.0~19,24~]pentacosa [8,16,18,24]tetraen]-7'-yl)acetate 2-tert-Butoxy-2-oxoethylzinc chloride (0.5 M in diethyl ether, 48.6 mL, 24.28 mmol) was added to a stirred solution of (1S,3'R,6'R,8'E,11'S,12'R)-6-chloro-11',12'-dimethyl-3,4-dihydro-2H,7'H,15'H-spiro[naphthalene-1,22'-[20]oxa[13] thia[1,14]diazatetracyclo[14.7.2.0~3,6~.0~19,24~]pentacosa[8,16,18,24]tetraene]-7',15'-dione 13',13'-dioxide (2.90 g, 4.86 mmol) in tetrahydrofuran (50 mL) under a nitrogen atmosphere. The reaction mixture was stirred at room temperature for 1 h. The reaction mixture was quenched with saturated aqueous NH₄Cl (150 mL) and extracted with EtOAc (100 mL). The organic layer was separated, washed with 9:1 saturated aqueous NH₄Cl:30% aqueous NH₄OH (200 mL), washed with brine (100 mL), dried over MgSO₄, filtered, and concentrated in vacuo to provide a crude mixture of 2-methyl-2-propanyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate and 2-methyl-2-propanyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate that was azeotroped twice with toluene and used directly in the next step. MS (ESI, +ve) m/z 713.3 [M+H]⁺.

Step 2: (1S,3'R,6'R,7'S,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Lithium borohydride (2.0 M solution in tetrahydrofuran, 10.41 mL, 20.82 mmol) was added to a stirred solution of the crude mixture of 2-methyl-2-propanyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate and 2-methyl-2-propanyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate in tetrahydrofuran (25 mL) under a nitrogen atmosphere. The reaction mixture was stirred at room temperature for 16 h. Additional lithium borohydride (2.0 M solution in tetrahydrofuran, 5.21 mL, 10.4 mmol) was added, followed by dropwise addition of methanol (1.69 mL, 41.6 mmol). The reaction mixture was stirred at room temperature for 24 h. Additional methanol (1.687 mL, 41.6 mmol) was added, and the reaction mixture was stirred for another 2.5 h. The reaction mixture was slowly quenched with saturated aqueous NH₄Cl (75 mL) and extracted twice with EtOAc (75 mL). The combined organic layers were separated, washed with brine (60 mL), dried over MgSO₄, filtered, and concentrated in vacuo. Chromatographic purification of the residue (silica gel, 0 to 10% MeOH in DCM) provided a mixture of (1S,3'R,6'R,7'S,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (2.58 g, 4.01 mmol, 96% yield) as a white solid. MS (ESI, +ve) m/z 643.2 [M+H]⁺.

Step 3: (1S,3'R,6'R,7'S,8'E,11'S,12'R)-6-chloro-7'-(2-((dimethyl(2-methyl-2-propanyl)silyl)oxy)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Imidazole (1.274 g, 18.72 mmol) and tert-butyldimethylsilyl chloride (1.41 g, 9.36 mmol) were added to a stirred mixture of (1S,3'R,6'R,7'S,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'R,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (3.01 g, 4.68 mmol) in dichloromethane (50 mL). The reaction mixture was stirred at room temperature for 72 h. Additional tert-butyldimethylsilyl chloride (1.41 g, 9.36 mmol) and imidazole (1.274 g, 18.72 mmol) were added, and the reaction mixture was stirred at room temperature for another 4 h. Additional reagents were added multiple times while stirring at room temperature until the reaction progressed no further upon addition. The reaction mixture was quenched with saturated aqueous NH₄Cl (125 mL) and extracted with DCM (75 mL). The organic layer was separated, dried over MgSO₄, filtered, and concentrated in vacuo. The resulting residue was resubjected to the original reaction conditions and stirred at room temperature for 2 h. The reaction mixture was quenched with saturated aqueous NH₄Cl (125 mL) and extracted with DCM (75 mL). The organic layer was separated, dried over MgSO₄, filtered, and concentrated in vacuo. Chromatographic purification of the residue (silica gel, 0 to 50% EtOAc in heptane) provided (1S,3'R,6'R,7'S,8'E,11'S,12'R)-6-chloro-7'-(2-((dimethyl(2-methyl-2-propanyl)silyl)oxy)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (453 mg, 0.598 mmol, 13% yield), the second diastereomer to elute from the column, as a white solid. ¹H NMR (400 MHz, CHLOROFORM-d) δ ppm 7.99 (1H, s) 7.69 (1H, d, J=8.41 Hz) 7.18 (1H, dd, J=8.51, 2.25 Hz) 7.09 (1H, d, J=2.15 Hz) 6.92-6.96 (3H, m) 5.71-5.78 (1H, m) 5.59 (1H, d, J=16.04 Hz) 4.55 (1H, br. s.) 3.96-4.19 (5H, m) 3.67-3.82 (2H, m) 3.25 (1H, d, J=14.28 Hz) 3.02 (1H, dd, J=15.16, 10.27 Hz) 2.68-2.86 (2H, m) 2.35-2.47 (1H, m) 2.26-2.36 (1H, m) 2.12-2.24 (3H, m) 1.77-2.08 (6H, m) 1.65-1.77 (1H, m) 1.51-1.62 (1H, m) 1.46 (3H, d, J=7.04 Hz) 1.36-1.45 (1H, m) 1.25-1.32 (1H, m) 1.07 (3H, d, J=6.06 Hz) 0.91 (9H, s) 0.10 (6H, d, J=3.33 Hz). MS (ESI, +ve) m/z 757.2 [M+H]⁺.

Step 4: (1S,3'R,6'R,7'S,8'E,11'S,12'R)-6-chloro-7'-(2-((dimethyl(2-methyl-2-propanyl)silyl)oxy)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Sodium hydride (60% dispersion in mineral oil, 119 mg, 2.97 mmol) was added to a stirred solution of (1S,3'R,6'R,7'S,8'E,11'S,12'R)-6-chloro-7'-(2-((dimethyl(2-methyl-2- propanyl)silyl)oxy)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (225 mg, 0.297 mmol) and iodomethane (0.185 mL, 2.97 mmol) in tetrahydrofuran (2 mL). The reaction mixture was stirred at room temperature for 17 h. The reaction mixture was quenched with saturated aqueous NH$_4$Cl (50 mL) and extracted with EtOAc (70 mL). The organic layer was separated, washed with brine (50 mL), dried over MgSO$_4$, filtered, and concentrated in vacuo to provide crude (1S,3'R,6'R,7'S,8'E,11'S,12'R)-6-chloro-7'-(2-((dimethyl(2-methyl-2-propanyl)silyl)oxy)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide that was used directly in the next step. MS (ESI, +ve) m/z 793.3 [M+Na]$^+$.

Step 5: (1S,3'R,6'R,7'S,8'E,11'S,12'R)-6-chloro-7'-(2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Tetrabutylammonium fluoride (1.0 M solution in tetrahydrofuran, 0.356 mL, 0.356 mmol) was added to a stirred solution of (1S,3'R,6'R,7'S,8'E,11'S,12'R)-6-chloro-7'-(2-((dimethyl(2-methyl-2-propanyl)silyl)oxy)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (229 mg, 0.297 mmol) in tetrahydrofuran (1.5 mL). The reaction mixture was stirred at room temperature for 3.5 h. Additional tetrabutylammonium fluoride (1.0 M solution in tetrahydrofuran, 0.356 mL, 0.356 mmol) was added, and the reaction mixture was stirred for another 3 h. The reaction mixture was concentrated. Chromatographic purification of the residue (silica gel, 0 to 100% (EtOAc with 0.3% AcOH) in heptane) provided (1S,3'R,6'R,7'S,8'E,11'S,12'R)-6-chloro-7'-(2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (178 mg, 0.271 mmol, 91% yield) as a white solid. $^1$H NMR (400 MHz, CHLOROFORM-d) δ ppm 8.10 (1H, s) 7.68 (1H, d, J=8.61 Hz) 7.18 (1H, dd, J=8.51, 2.25 Hz) 7.09 (1H, d, J=2.15 Hz) 6.88-6.96 (3H, m) 5.75-5.83 (1H, m) 5.64 (1H, d, J=16.24 Hz) 4.29-4.37 (1H, m) 4.02-4.15 (2H, m) 3.91-3.99 (1H, m) 3.80-3.88 (2H, m) 3.72 (1H, d, J=14.28 Hz) 3.25 (1H, d, J=14.28 Hz) 3.11 (3H, s) 3.02 (1H, dd, J=14.96, 10.66 Hz) 2.69-2.85 (2H, m) 2.59 (1H, q, J=9.06 Hz) 2.34-2.47 (2H, m) 2.12-2.24 (2H, m) 1.76-2.06 (8H, m) 1.58-1.67 (1H, m) 1.50 (3H, d, J=7.04 Hz) 1.38 (1H, t, J=12.91 Hz) 1.06 (3H, d, J=6.85 Hz). MS (ESI, +ve) m/z 657.2 [M+H]$^+$.

Step 6: ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde Dess-Martin periodinane (67.4 mg, 0.159 mmol) was added to a stirred mixture of (1S,3'R,6'R,7'S,8'E,11'S,12'R)-6-chloro-7'-(2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (87 mg, 0.13 mmol) and sodium bicarbonate (111 mg, 1.32 mmol) in dichloromethane (1 mL). The reaction mixture was stirred at room temperature for 45 min. The reaction mixture was quenched with saturated aqueous NaHCO$_3$ (25 mL) and extracted with EtOAc (30 mL). The organic layer was separated, washed with 1 M aqueous Na$_2$S$_2$O$_3$ (20 mL), washed with brine (20 mL), dried over MgSO$_4$, filtered, and concentrated in vacuo to provide crude ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde that was used directly in the next step.

Step 7: ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid A solution of potassium phosphate monobasic (361 mg, 2.66 mmol) and sodium chlorite (240 mg, 2.66 mmol) in water (2 mL) was added to a stirred mixture of ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde (174 mg, 0.266 mmol) and 2-methyl-2-butene (1.407 mL, 13.28 mmol) in tert-butanol (2 mL). The reaction mixture was stirred at room temperature for 45 min. The reaction mixture was diluted with EtOAc (50 mL), washed with 1 M aqueous HCl (40 mL), washed with 1 M Na$_2$S$_2$O$_3$ (40 mL), washed with brine (40 mL), dried over MgSO$_4$, filtered, and concentrated in vacuo. Chromatographic purification of the residue (silica gel, 0 to 100% (EtOAc with 0.3% AcOH) in heptane) provided ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (142 mg, 0.212 mmol, 80% yield) as a white solid. $^1$H NMR (400 MHz, CHLOROFORM-d) δ ppm 8.11 (1H, s) 7.68 (1H, d, J=8.41 Hz) 7.17 (1H, d, J=8.41 Hz) 7.08 (1H, s) 6.87-6.95 (3H, m) 5.80-5.90 (1H, m) 5.72 (1H, d, J=15.85 Hz) 4.36 (1H, q, J=7.17 Hz) 4.07 (2H, s) 3.99 (1H, d, J=15.65 Hz) 3.71 (1H, d, J=14.48 Hz) 3.16-3.27 (5H, m) 3.01 (1H, dd, J=15.55, 10.86 Hz) 2.71-2.84 (3H, m) 2.66 (1H, q, J=9.00 Hz) 2.42 (1H, quin, J=9.15 Hz) 2.12-2.26 (2H, m) 2.01-2.09 (1H, m) 1.83-2.01 (5H, m) 1.79 (1H, d, J=7.24 Hz) 1.57-1.69 (1H, m) 1.51 (3H, d, J=7.04 Hz) 1.35 (1H, t, J=13.11 Hz) 1.06 (3H, d, J=6.65 Hz). MS (ESI, +ve) m/z 671.2 [M+H]$^+$.

Step 8: 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-methoxyethyl)-N-methylacetamide ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (28 mg, 0.042 mmol) was taken up in THF (0.5 mL) and lithium hydroxide (2.0 M in water, 0.083 mL, 0.17 mmol) was added. The mixture was stirred at room temperature for 10 min before being concentrated in vacuo to provide the lithium carboxylate of the starting material as an off-white solid that was used in the amide coupling. HATU (31.7 mg, 0.083 mmol) and N-(2-methoxyethyl)methylamine (0.022 mL, 0.21 mmol) were added to a stirred suspension of the lithium carboxylate previously prepared in N,N-dimethylformamide (0.50 mL). The reaction mixture was stirred at room temperature for 1 h. The reaction mixture was quenched with saturated aqueous NH$_4$Cl (20 mL) and extracted with EtOAc (30 mL). The organic layer was separated, washed with brine (15 mL), dried over MgSO$_4$, filtered, and concentrated in vacuo. Chromatographic purification of the residue (silica gel, 0 to 100% (EtOAc with 0.3% AcOH) in heptane) followed by chromatographic purification (silica gel, 0 to 100% EtOAc in heptane) provided 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-methoxyethyl)-N-methylacetamide (23 mg, 0.031 mmol, 74% yield) as a white solid. $^1$H NMR (400 MHz, CHLOROFORM-d) δ ppm 8.27 (0.4H, s) 8.10 (0.6H, s) 7.69 (1H, d, J=8.61 Hz) 7.17 (1H, dd, J=8.41, 2.15 Hz) 7.08 (1H, d, J=1.96 Hz) 6.90-7.06 (3H, m) 5.84-5.90 (1H, m) 5.72-5.83 (1H, m) 4.28 (0.6H, q, J=7.04 Hz) 4.19 (0.4H, q, J=7.04 Hz) 4.05 (1.2H, s) 4.04 (0.8H, s) 3.95 (0.4H, d, J=10.17 Hz) 3.91 (0.6H, d, J=10.17 Hz) 3.52-3.77 (4H, m) 3.22-3.34 (7H, m) 2.97-3.19 (6H, m) 2.57-2.82 (4H, m) 2.38-2.54 (1H, m) 1.99-2.23 (4H, m) 1.72-1.99 (5H, m) 1.57-1.68 (1H, m) 1.46-1.51 (3H, m) 1.27-1.37 (1H, m) 1.04-1.11 (3H, m). MS (ESI, +ve) m/z 742.2 [M+H]$^+$.

Example 100006

(1S,3'R,6'R,7'S,8'E,11'S,12'R)-7'-(2-(1-azetidinyl)-2-oxoethyl)-6-chloro-7'-methoxy-1',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

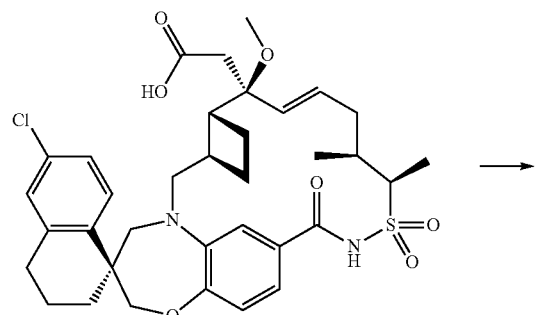

Example 100307

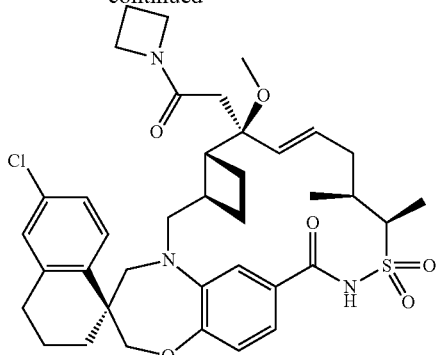

Example 100006

(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (28 mg, 0.042 mmol) was taken up in THF (0.5 mL) and lithium hydroxide (2.0 M in water, 0.083 mL, 0.17 mmol) was added. The mixture was stirred at room temperature for 10 min before being concentrated in vacuo to provide the lithium carboxylate of the starting material as an off-white solid that was used in the amide coupling. HATU (31.7 mg, 0.083 mmol) and azetidine (0.014 mL, 0.209 mmol) were added to a stirred suspension of the lithium carboxylate previously prepared in N,N-dimethylformamide (0.25 mL). The reaction mixture was stirred at room temperature for 1 h. The reaction mixture was quenched with saturated aqueous NH$_4$Cl (10 mL) and extracted with EtOAc (15 mL). The organic layer was separated, washed with brine (10 mL), dried over MgSO$_4$, filtered, and concentrated in vacuo. Chromatographic purification of the residue (silica gel, 0 to 100% (EtOAc with 0.3% AcOH) in heptane) followed by chromatographic purification (silica gel, 0 to 100% EtOAc in heptane) provided (1S,3'R,6'R,7'S,8'E,11'S,12'R)-7'-(2-(1-azetidinyl)-2-oxoethyl)-6-chloro-7'-methoxy-1',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (22 mg, 0.031 mmol, 74% yield) as a white solid. $^1$H NMR (400 MHz, CHLOROFORM-d) δ ppm 8.21 (1H, br s) 7.68 (1H, d, J=8.61 Hz) 7.13-7.20 (1H, m) 7.06-7.09 (1H, m) 6.88-6.97 (3H, m) 5.70-5.86 (2H, m) 4.23-4.39 (3H, m) 3.98-4.11 (5H, m) 3.70 (1H, d, J=14.28 Hz) 3.22-3.32 (2H, m) 3.08-3.18 (4H, m) 2.81-2.88 (1H, m) 2.67-2.79 (2H, m) 2.33-2.46 (2H, m) 2.19-2.31 (2H, m) 1.72-2.19 (9H, m) 1.56-1.69 (1H, m) 1.49 (3H, d, J=6.85 Hz) 1.25-1.36 (1H, m) 1.06 (3H, d, J=6.65 Hz). MS (ESI, +ve) m/z 710.2 [M+H]$^+$.

Example 100007 and Example 100016

(1S,3'R,6'R,7'S,8'E,11'S,12'R)-6-chloro-7',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 100007) and (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 100016)

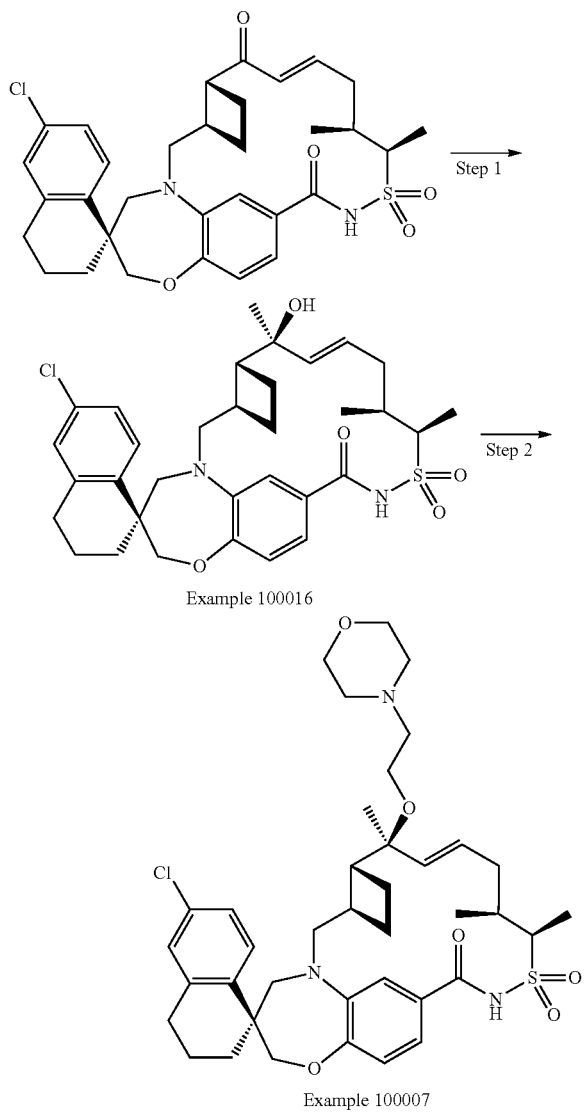

Example 100016

Example 100007

Step 1: (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Lanthanum(III) chloride bis(lithium chloride) complex (0.5 M solution in THF, 0.616 mL, 0.308 mmol) was added to a stirred solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (184 mg, 0.308 mmol) in tetrahydrofuran (3 mL) at 0° C. The mixture was stirred at 0° C. for 45 min before methylmagnesium bromide (3.0 M solution in diethyl ether, 0.462 mL, 1.39 mmol) was added dropwise via syringe. The reaction mixture was allowed to warm to room temperature and stirred for 18 h. The reaction mixture was quenched with saturated aqueous NH$_4$Cl (30 mL) and extracted with EtOAc (45 mL). The organic layer was separated, washed with brine (30 mL), dried over MgSO$_4$, filtered, and concentrated in vacuo. Chromatographic purification of the residue (silica gel, 0 to 75% (EtOAc with 0.3% AcOH) in heptane) provided (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (92 mg, 0.150 mmol, 49% yield), the second diasteromer to elute from the column, as a white solid. $^1$H NMR (400 MHz, DICHLOROMETHANE-d$_2$) δ 7.71 (d, J=8.6 Hz, 1H), 7.18 (dd, J=2.2, 8.5 Hz, 1H), 7.10 (d, J=2.2 Hz, 1H), 7.00-6.89 (m, 3H), 5.90-5.76 (m, 2H), 4.35-4.24 (m, 1H), 4.11-4.04 (m, 2H), 3.84 (br d, J=14.9 Hz, 1H), 3.73 (d, J=14.3 Hz, 1H), 3.28 (d, J=14.3 Hz, 1H), 3.05 (dd, J=10.4, 15.3 Hz, 1H), 2.86-2.70 (m, 2H), 2.46-2.33 (m, 1H), 2.27 (q, J=9.3 Hz, 1H), 2.18-2.10 (m, 1H), 2.07 (br d, J=2.5 Hz, 1H), 2.05-2.01 (m, 2H), 2.02-1.91 (m, 3H), 1.89-1.78 (m, 3H), 1.69-1.60 (m, 1H), 1.52 (s, 3H), 1.47 (d, J=7.2 Hz, 3H), 1.44-1.36 (m, 1H), 1.04 (d, J=6.8 Hz, 3H). MS (ESI, +ve) m/z 613.3 [M+H]$^+$.

Step 2: (1S,3'R,6'R,7'S,8'E,11'S,12'R)-6-chloro-7',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (33 mg, 0.054 mmol), 4-(2-bromoethyl)morpholine hydrobromide (296 mg, 1.08 mmol), and sodium hydride (60% dispersion in mineral oil, 86 mg, 2.2 mmol) were mixed in N,N-dimethylformamide (1.5 mL). The reaction mixture was stirred at room temperature for 20 h. The reaction mixture was quenched with saturated aqueous NH$_4$Cl (20 mL) and extracted two times with EtOAc (30 mL). The combined organic layers were washed with brine (15 mL), dried over MgSO$_4$, filtered, and concentrated in vacuo. Chromatographic purification of the residue (silica gel, 50% to 100% EtOAc in DCM until the starting material eluted and then 0 to 10% (2 M NH$_3$ in MeOH) in DCM) provided (1S,3'R,6'R,7'S,8'E,11'S,12'R)-6-chloro-7',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (25 mg, 0.034 mmol, 64% yield) as an off-white solid. $^1$H NMR (400 MHz, CHLOROFORM-d) δ 7.68 (1H, d, J=8.41 Hz) 7.17 (1H, dd, J=8.41, 2.15 Hz) 7.08 (1H, d, J=2.15 Hz) 6.89-6.96 (3H, m) 5.82 (1H, ddd, J=15.85, 9.59, 2.74 Hz) 5.65 (1H, d, J=15.85 Hz) 4.29 (1H, q, J=7.11 Hz) 4.00-4.11 (2H, m) 3.83 (1H, d, J=14.67 Hz) 3.68-3.77 (5H, m) 3.33-3.46 (2H, m) 3.26 (1H, d, J=14.28 Hz) 3.00 (1H, dd, J=15.16, 10.66 Hz) 2.69-2.84 (2H, m) 2.52-2.61 (6H, m) 2.40 (1H, quin, J=8.95 Hz) 2.28 (1H, q, J=9.13 Hz) 1.74-2.21 (9H, m) 1.52-1.64 (1H, m) 1.48 (3H, d, J=7.04 Hz) 1.33-1.43 (4H, m) 1.04 (3H, d, J=6.85 Hz). MS (ESI, +ve) m/z 726.3 [M+H]$^+$.

Example 100008

2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-(2-methyl-2-propanyl)acetamide

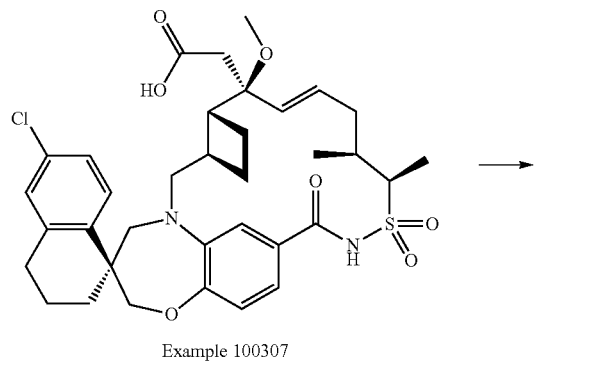

Example 100307

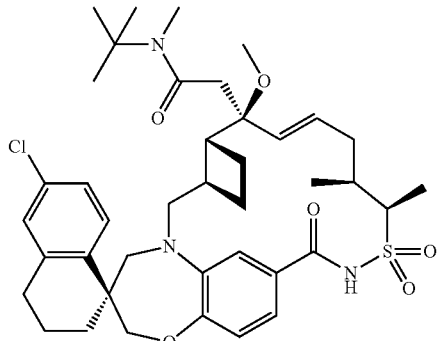

Example 100008

A drop of DMF was added to a stirred solution of oxalyl chloride (10 μL, 0.11 mmol) and ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (37 mg, 0.055 mmol) in dichloromethane (1 mL). The reaction mixture was stirred at room temperature for 20 min before being concentrated in vacuo. The resulting yellow residue was taken up in dichloromethane (1 mL) and N-tert-butylmethylamine (0.066 mL, 0.55 mmol) was added. The reaction mixture was stirred at room temperature for 40 min. The reaction mixture was quenched with saturated aqueous NH$_4$Cl (20 mL) and extracted with EtOAc (30 mL). The organic layer was separated, washed with brine (20 mL), dried over MgSO$_4$, filtered, and concentrated in vacuo. Chromatographic purification of the residue (silica gel, 0 to 50% (EtOAc with 0.3% AcOH) in heptane) provided 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-(2-methyl-2-propanyl)acetamide (18 mg, 0.024 mmol, 44% yield) as an off-white solid. $^1$H NMR (400 MHz, CHLOROFORM-d) δ 8.01 (1H, s) 7.68 (1H, d, J=8.41 Hz) 7.17 (1H, dd, J=8.51, 2.25 Hz) 7.08 (1H, d, J=1.96 Hz) 6.88-6.96 (3H, m) 5.68-5.81 (2H, m) 4.33 (1H, q, J=7.43 Hz) 4.07 (2H, s) 3.85 (1H, d, J=15.06 Hz) 3.71 (1H, d, J=14.28 Hz) 3.22-3.36 (2H, m) 3.11 (3H, s) 3.01-3.09 (5H, m) 2.68-2.84 (2H, m) 2.59 (1H, d, J=15.85 Hz) 2.33-2.44 (1H, m) 2.06-2.23 (2H, m) 1.74-2.06 (7H, m) 1.55-1.66 (1H, m) 1.24-1.52 (13H, m) 1.06 (3H, d, J=6.65 Hz). MS (ESI, +ve) m/z 762.3 [M+Na]$^+$.

Example 100009

2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methylacetamide

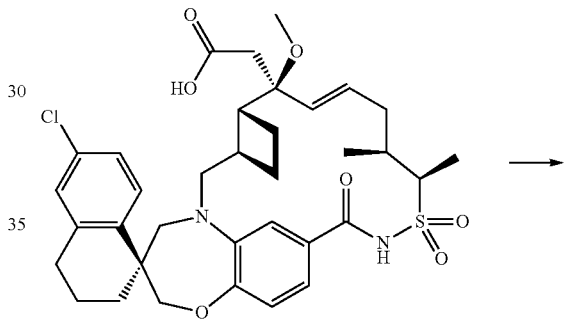

Example 100307

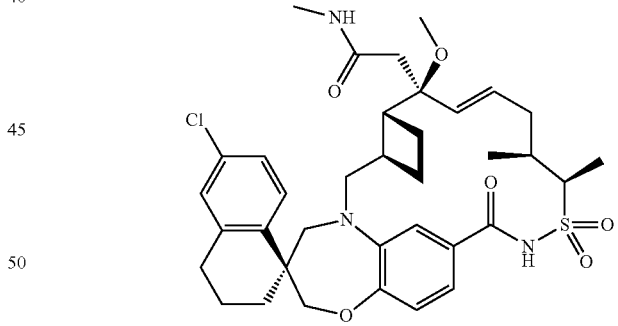

Example 100009

((1S,3'R,6'R,7'S,8'E,11'S,12'R)-6-Chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid (50 mg, 0.074 mmol) was taken up in THF (2 mL) and lithium hydroxide (2.0 M in water, 0.149 mL, 0.358 mmol) was added. The mixture was stirred at room temperature for 10 min before being concentrated in vacuo to provide the lithium carboxylate of the starting material as an off-white solid that was used in the amide coupling. HATU (42.0 mg, 0.112 mmol) and methylamine (2.0 M in THF, 0.112 mL, 0.223 mmol) were added to a stirred suspension of the lithium carboxylate previously prepared in N,N-dimethylformamide (2 mL). The reaction mixture was stirred at room temperature for 30 minutes. The reaction mixture was diluted with water and EtOAc and transferred to a separatory funnel. 1.0 M HCl was added and the phases were mixed. The organic layer was separated and washed sequentially with 1.0 M LiCl and brine then dried over magnesium sulfate and concentrated under reduced pressure. Purification via silica gel flash chromatography using a gradient of 50% to 100% EtOAc with 0.3% AcOH in heptane afforded 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methylacetamide (44 mg, 0.064 mmol, 86% yield) as a white solid. $^1$H NMR (300 MHz, DICHLOROMETHANE-d$_2$) δ 7.69-7.79 (m, 1H) 7.19 (br dd, J=8.84, 1.10 Hz, 1H) 7.12 (s, 1H) 6.88-7.03 (m, 3H) 6.74-6.86 (m, 1H) 5.75-5.89 (m, 1H) 5.62-5.73 (m, 1H) 4.21-4.36 (m, 1H) 4.09 (s, 2H) 3.91-4.04 (m, 1H) 3.72 (br d, J=15.05 Hz, 1H) 3.29 (br d, J=14.03 Hz, 1H) 3.16 (s, 3H) 2.92-3.09 (m, 2H) 2.73-2.90 (m, 6H) 2.51-2.66 (m, 2H) 2.37-2.49 (m, 1H) 1.67-2.25 (m, 11H) 1.48 (br d, J=7.02 Hz, 3H) 1.22-1.43 (m, 6H) 1.06 (br d, J=6.58 Hz, 3H). MS (ESI, +ve) m/z 652.0 [M-OMe]$^+$.

Example 100010

(1S,3'R,6'R,7'S,8'E,11'S,12'R)-6-chloro-7'-methoxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

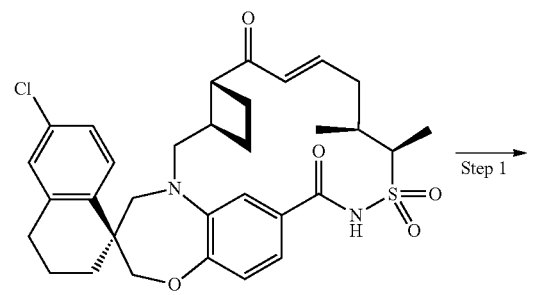

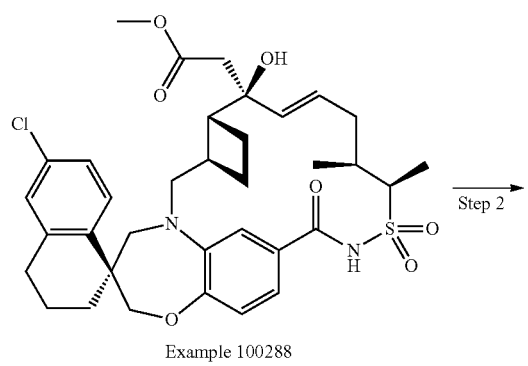

Example 100288

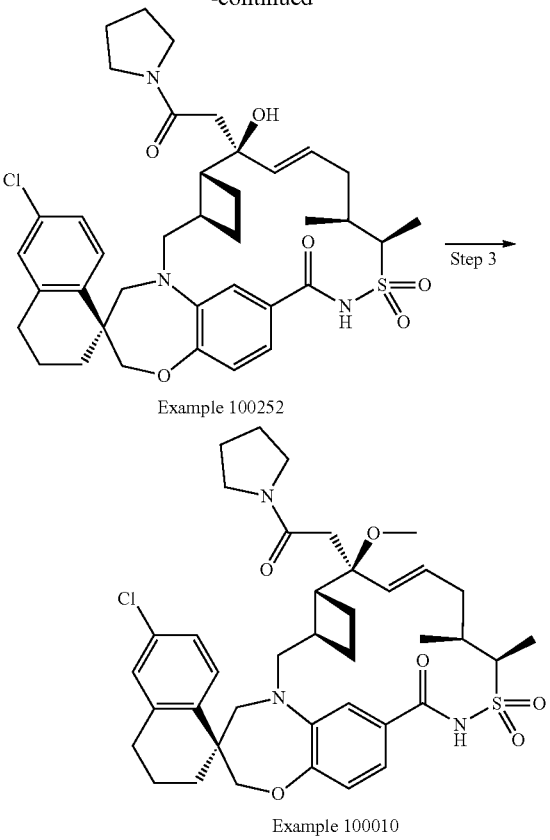

Example 100252

Example 100010

Step 1: methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl) acetate A flame dried round bottom flask was charged with tetrahydrofuran (6.28 mL) and lithium diisopropylamide (2.0 M solution in heptane/tetrahydrofuran/ethylbenzene, 7.54 mL, 15.1 mmol). The solution was cooled to −78° C. then a solution of methyl acetate (1.197 mL, 15.07 mmol) in tetrahydrofuran (6.28 mL) was added dropwise and the reaction was stirred at −78° C. for 45 minutes. The flask was equipped with an addition funnel which was then charged with a solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (1.5 g, 2.5 mmol) in tetrahydrofuran (12.56 mL). The reaction was stirred at −78° C. for 30 minutes. The reaction was quenched with water and warmed to room temperature. The reaction was diluted with water and EtOAc and transferred to a separatory funnel. 1 M HCl was added. The phases were mixed and the organic layer was separated, washed with brine, dried over magnesium sulfate and concentrated under reduced pressure. The crude residue was purified via silica gel flash chromatography using a gradient of 20% to 70% EtOAc with 0.3% AcOH in heptane to afford methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate (0.666 g, 0.992 mmol, 40% yield), the second eluting diastereomer, as a white solid. $^1$H NMR (300 MHz, DICHLOROMETHANE-d$_2$) δ 8.06-8.25 (m, 1H) 7.74 (d, J=8.62 Hz, 1H) 7.20 (br d, J=8.77 Hz, 1H) 7.13 (s, 1H) 6.96 (s, 2H) 6.92 (s, 1H) 5.64-5.81 (m, 2H) 4.06-4.25 (m, 3H) 3.80 (s, 3H) 3.75 (br d, J=14.03 Hz, 1H) 3.70 (s, 1H) 3.31 (d, J=14.18 Hz, 1H) 3.00-3.11 (m, 1H) 2.91-3.00 (m, 1H) 2.69-2.87 (m, 3H) 2.32-2.56 (m, 2H) 1.79-2.21 (m, 9H) 1.59-1.71 (m, 2H) 1.46 (d, J=7.16 Hz, 4H) 1.34-1.39 (m, 4H) 1.06 (d, J=6.58 Hz, 3H). MS (ESI, +ve) m/z 671.2 [M+H]$^+$.

Step 2: (1S,3'R,6'R,7'S,8'E,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a solution of methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate (0.343 g, 0.511 mmol) in THF (10.22 mL) was added lithium hydroxide (2.0 M in water, 0.639 mL, 1.28 mmol). The reaction was stirred at room temperature overnight. The reaction was concentrated under reduced pressure and used without further purification. To a suspension of the lithium carboxylate previously generated in DMF (2.5 mL) was added HATU (0.069 g, 0.18 mmol) followed by pyrrolidine (0.050 mL, 0.60 mmol). The reaction was stirred at room temperature for 30 minutes. The reaction was diluted with water and EtOAc and transferred to a separatory funnel. 1.0 M HCl was added and the phases were mixed. The organic layer was separated then washed sequentially with 1.0 M LiCl and brine then dried over magnesium sulfate and concentrated under reduced pressure. Purification via silica gel flash chromatography using a gradient of 75% to 100% EtOAc with 0.3% AcOH in heptane afforded (1S,3'R,6'R,7'S,8'E,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.0608 g, 0.086 mmol, 71% yield) as a white solid. MS (ESI, +ve) m/z 710.3 [M+H]$^+$.

Step 3: (1S,3'R,6'R,7'S,8'E,11'S,12'R)-6-chloro-7'-methoxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide A solution of (1S,3'R,6'R,7'S,8'E,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.0608 g, 0.086 mmol) in THF (0.856 mL) was cooled to 0° C. before adding sodium hydride (0.017 g, 0.428 mmol). The reaction was stirred for 30 minutes then iodomethane (0.053 mL, 0.856 mmol) was added and the reaction was warmed to room temperature and stirred for 1 hour. A larger portion of iodomethane (0.150 mL) was added and the reaction was allowed to stir at room temperature overnight. An additional portion of MeI (0.15 mL) was added and the reaction was continued at room temperature for 6 h. The reaction was quenched with water and diluted with water and EtOAc. The reaction was transferred to a separatory funnel and 1 M HCl was added. The phases were mixed and the organic layer was separated, washed with brine and dried over magnesium sulfate. The crude material was purified via silica gel flash chromatography using 100% EtOAc with 0.6% AcOH. The reaction was repeated a second time on the same scale and the material from both reactions was combined and further purified by preparative supercritical fluid chromatography SFC using the following conditions: Diol Column (21.2×250 mm, 5 m); 20% MeOH with 20 mM NH$_3$ in CO$_2$ to afford (1S,3'R,6'R,7'S,8'E,11'S,12'R)-6-chloro-7'-methoxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.018 g, 0.025 mmol, 15% yield) as a white solid. $^1$H NMR (300 MHz, DICHLOROMETHANE-d$_2$) δ 7.75 (br d, J=8.18 Hz, 1H) 7.20 (br d, J=8.48 Hz, 1H) 7.12 (br s, 2H) 7.00-7.06 (m, 1H) 6.90-6.98 (m, 1H) 5.75-5.99 (m, 2H) 4.13-4.24 (m, 1H) 4.10 (s, 2H) 3.86-3.96 (m, 1H) 3.74 (br d, J=14.32 Hz, 1H) 3.57-3.68 (m, 2H) 3.41-3.54 (m, 2H) 3.34 (br d, J=14.62 Hz, 1H) 3.07-3.25 (m, 4H) 3.03 (br d, J=15.93 Hz, 1H) 2.69-2.92 (m, 2H) 2.46-2.67 (m, 2H) 2.04-2.26 (m, 4H) 1.74-2.03 (m, 9H) 1.49-1.73 (m, 9H) 1.46 (br d, J=6.72 Hz, 3H) 1.29-1.41 (m, 2H) 1.03-1.14 (m, 3H). MS (ESI, +ve) m/z 692.2 [M-OMe]$^+$.

Example 100011

(1S,3'R,6'R,7'S,8'E, 11'S, 12'R)-6-chloro-7'-(4-((9aS)-hexahydropyrazino[2,1-c][1,4]oxazin-8(1H)-yl)-1-butyn-1-yl)-7'-methoxy-11',12'-dimethyl-3,4-dihydro-2H, 15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

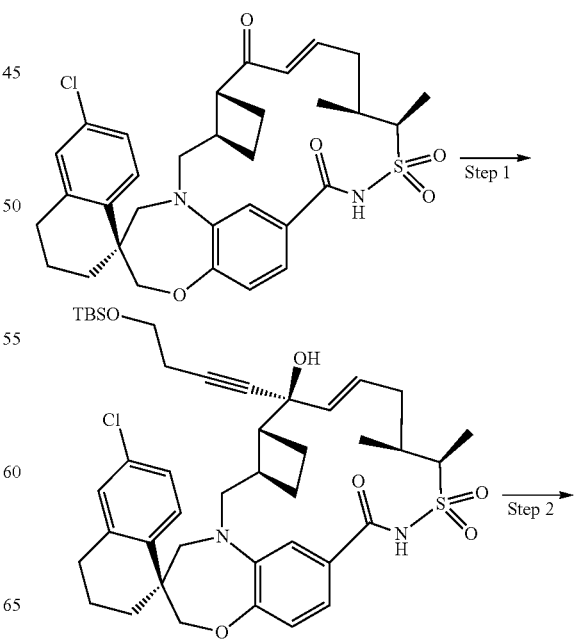

-continued

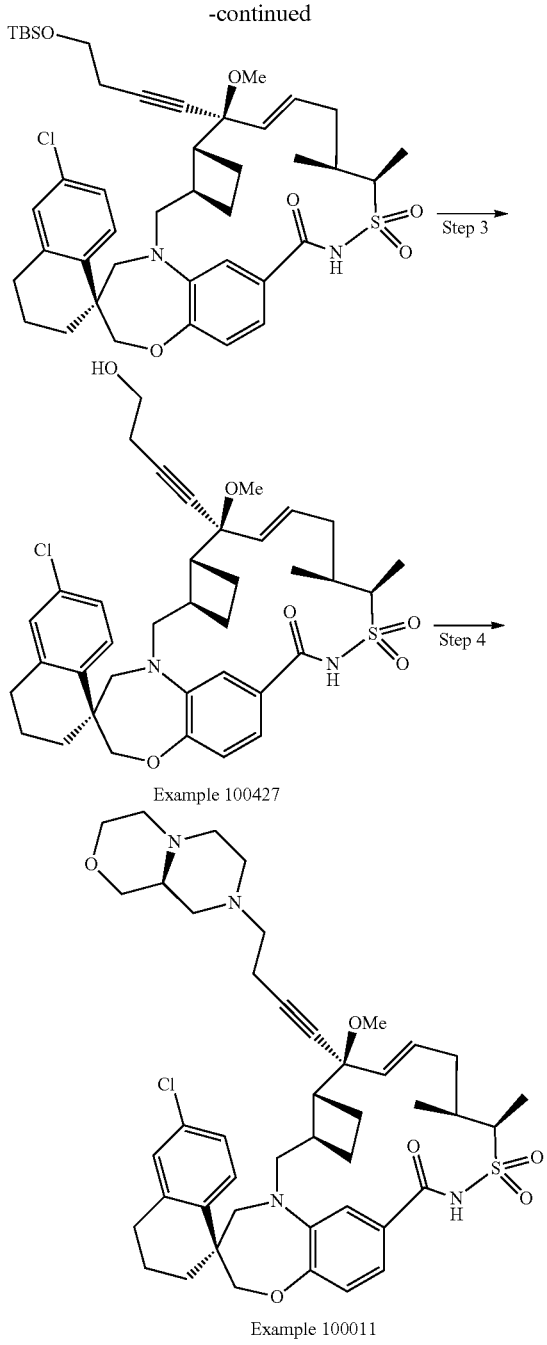

Example 100427

Example 100011

Step 1: (1S,3'R,6',7'S,8'E,11'S,12'R)-6-chloro-7'-(4-((dimethyl(2-methyl-2-propanyl)silyl)oxy)-1-butyn-1-yl)-7'-hydroxy-1',12'-dimethyl-3,4-dihydro-2H,15'H-spiro[naphthalene-1,22'-[20]oxa[13]thia 1,14]diazatetracyclo[14.7.2.0~3,6~.0~19,24~]pentacosa[8,16,18,24]tetraen]-15'-one 13',13'-dioxide To a cooled (−78° C.) solution of 4-(tert-butyldimethylsilyl)-1-butyne (2.50 mL, 12.1 mmol) in tetrahydrofuran (30 mL) was added 2.5 M butyllithium in toluene (4.0 mL, 10 mmol) dropwise via syringe over a period of 15 min. After 1 h, a solution of (1S,3'R,6'R,8'E,11'S,12'R)-6-chloro-11', 12'-dimethyl-3,4-dihydro-2H,7'H, 15'H-spiro[naphthalene-1,22'-[20]oxa[13]thia[1,14]diazatetracyclo[14.7.2.0~3, 6~.0~19,24~]pentacosa[8,16,18,24]tetraene]-7',15'-dione 13',13'-dioxide (1.008 g, 1.688 mmol) in THF (10 mL) was added dropwise and stirred for 1 h. The reaction was quenched with pH 7 buffer (10 mL) and warmed to room temperature. The aqueous layer was extracted with EtOAc (3×). The combined organic layers were washed with brine and dried over Na$_2$SO$_4$. The solution was filtered, evaporated onto silica gel and purified by flash chromatography (Isco, 40 g) eluting with 0.3% AcOH in EtOAc:0.3% AcOH in heptane (0:1 to 1:3) to give (1S,3'R,6'R,7'S,8'E,11'S, 12'R)-6-chloro-7'-(4-((dimethyl(2-methyl-2-propanyl)silyl) oxy)-1-butyn-1-yl)-7'-hydroxy-11',12'-dimethyl-3,4-dihydro-2H,15'H-spiro[naphthalene-1,22'-[20]oxa[13]thia[1, 14]diazatetracyclo[14.7.2.0~3,6~.0~19,24~]pentacosa[8, 16,18,24]tetraen]-15'-one 13',13'-dioxide (468 mg, 36% yield) as a white solid. MS (ESI, +ve ion) m/z 763.4 (M+1)$^+$.

Step 2: (1S,3'R,6'R,7'S,8'E,11'S,12'R)-6-chloro-7'-(4-((dimethyl(2-methyl-2-propanyl)silyl)oxy)-1-butyn-1-yl)-7'-methoxy-11',12'-dimethyl-3,4-dihydro-2H,15'H-spiro[naphthalene-1,22'-[20]oxa[13] thia[1,14]diazatetracyclo[14.7.2.0~3,6~.0~19,24~] pentacosa[8,16,18,24]tetraen]-15'-one 13',13'-dioxide To a cooled (0° C.) solution of (1S,3'R,6'R,7'S,8'E,11'S, 12'R)-6-chloro-7'-(4-((dimethyl(2-methyl-2-propanyl)silyl) oxy)-1-butyn-1-yl)-7'-hydroxy-11',12'-dimethyl-3,4-dihydro-2H,15'H-spiro[naphthalene-1,22'-[20]oxa[13]thia[1, 14]diazatetracyclo[14.7.2.0~3,6~.0~19,24~]pentacosa[8, 16,18,24]tetraen]-15'-one 13',13'-dioxide (0.510 g, 0.653 mmol) in tetrahydrofuran (10 mL) was added 60% sodium hydride in mineral oil (0.211 g, 5.28 mmol) in portions. After 15 min iodomethane (0.160 mL, 2.58 mmol) was added and the reaction was allowed to warm to room temperature overnight. The reaction mixture was quenched with pH 7 buffer and partitioned between EtOAc and water. The aqueous layer was extracted with EtOAc (3×) then the combined organic layers were washed with brine, evaporated onto silica gel and purified by flash chromatography (Isco, 25 g) eluting with 0.3% AcOH in EtOAc: 0.3% AcOH in heptane (0:1 to 1:3) to give (1S,3'R,6'R,7'S,8'E,11'S, 12'R)-6-chloro-7'-(4-((dimethyl(2-methyl-2-propanyl)silyl) oxy)-1-butyn-1-yl)-7'-methoxy-1',12'-dimethyl-3,4-dihydro-2H,15'H-spiro[naphthalene-1,22'-[20]oxa[13]thia[1, 14]diazatetracyclo[14.7.2.0~3,6~.0~19,24~]pentacosa[8, 16,18,24]tetraen]-15'-one 13',13'-dioxide (368 mg, 71% yield) as a white solid. MS (ESI, +ve ion) m/z 795.4 (M+1)$^+$.

Step 3: (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3, 6~.0~19,24~]pentacosa[8,16,18,24]tetraen]-15'-one 13',13'-dioxide To a room temperature solution of (1S,3'R,6'R,7'S,8'E, 11'S,12'R)-6-chloro-7'-(4-((dimethyl(2-methyl-2-propanyl) silyl)oxy)-1-butyn-1-yl)-7'-methoxy-11',12'-dimethyl-3,4-dihydro-2H,15'H-spiro[naphthalene-1,22'-[20]oxa[13]thia [1,14]diazatetracyclo[14.7.2.0~3,6~.0~19,24~]pentacosa[8, 16,18,24]tetraen]-15'-one 13',13'-dioxide (0.365 g, 0.459 mmol) in tetrahydrofuran (5 mL) was added 1 M tetrabutylammonium fluoride in tetrahydrofuran (1.5 mL, 1.5 mmol) via syringe. The reaction was evaporated onto silica gel and purified by flash chromatography (Isco (12 gram HP)) eluting with 0.3% AcOH in EtOAc: 0.3% AcOH in heptane (0:1 to 1:1) to give (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (279 mg, 89% yield) as a white solid. MS (ESI, +ve ion) m/z 681.3 (M+1)+.

Step 4: (1S,3'R,6'R,7'S,8'E,11'S,12'R)-6-chloro-7'-(4-((9aS)-hexahydropyrazino[2,1-c][1,4]oxazin-8(1H)-yl)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a cooled (0° C.) solution of (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.023 g, 0.034 mmol) in dichloromethane (1 mL) was added triethylamine (0.020 mL, 0.14 mmol) followed by methanesulfonyl chloride (0.015 mL, 0.19 mmol) and the reaction was stirred for 20 min. To the reaction was added a slurry of (S)-octahydropyrazino[2,1-c]morpholine dihydrochloride (0.067 g, 0.31 mmol) and triethylamine in dichloromethane (1 mL) and the reaction was stirred at room temperature for 85 h and at 45° C. for 4 h. The reaction was cooled to room temperature, diluted with DCM, evaporated onto silica gel and purified by flash chromatography (Isco, 4 g) eluting with 25% EtOH/EtOAc: heptane (0:1 to 1:0) to give (12.6 mg, 46% yield) light-yellow solid. $^1$H NMR (400 MHz, CD$_2$Cl$_2$) δ 7.72 (d, J=8.41 Hz, 1H), 7.20 (s, 1H), 7.17 (dd, J=8.51, 2.05 Hz, 1H), 7.09 (d, J=2.15 Hz, 1H), 6.85-6.98 (m, 2H), 6.20-6.39 (m, 1H), 5.52 (d, J=15.84 Hz, 1H), 4.32 (d, J=15.65 Hz, 1H), 4.26 (d, J=6.46 Hz, 1H), 4.14 (d, J=12.13 Hz, 1H), 4.00-4.11 (m, 2H), 3.75 (dd, J=11.15, 2.93 Hz, 1H), 3.69 (d, J=14.08 Hz, 1H), 3.51-3.64 (m, 2H), 3.27 (d, J=14.28 Hz, 1H), 3.07-3.19 (m, 4H), 3.01 (dd, J=15.26, 10.37 Hz, 1H), 2.87 (d, J=7.43 Hz, 1H), 2.74-2.83 (m, 3H), 2.50-2.72 (m, 8H), 2.37-2.49 (m, 1H), 2.08-2.27 (m, 7H), 1.77-1.99 (m, 5H), 1.57-1.75 (m, 2H), 1.34-1.51 (m, 4H), 1.03 (d, J=6.85 Hz, 3H). MS (ESI, +ve ion) m/z 805.3 (M+1)+.

Example 100012

(1S,3'R,6'R,7'S,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

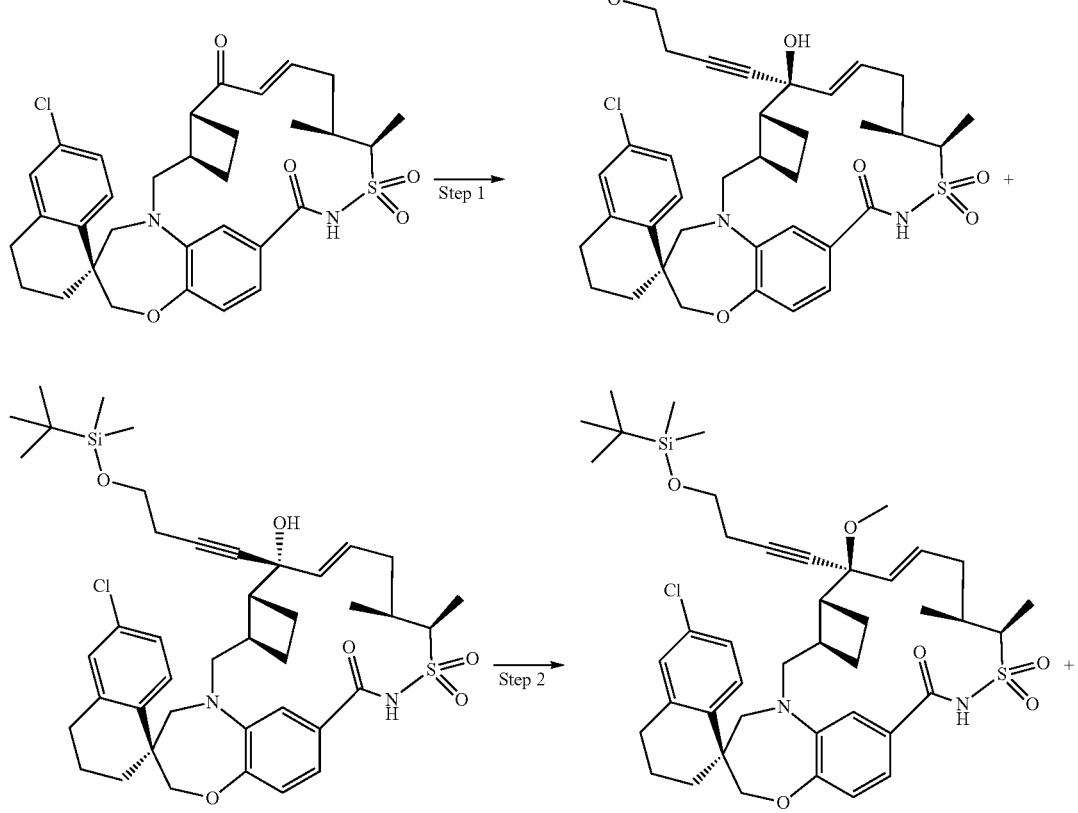

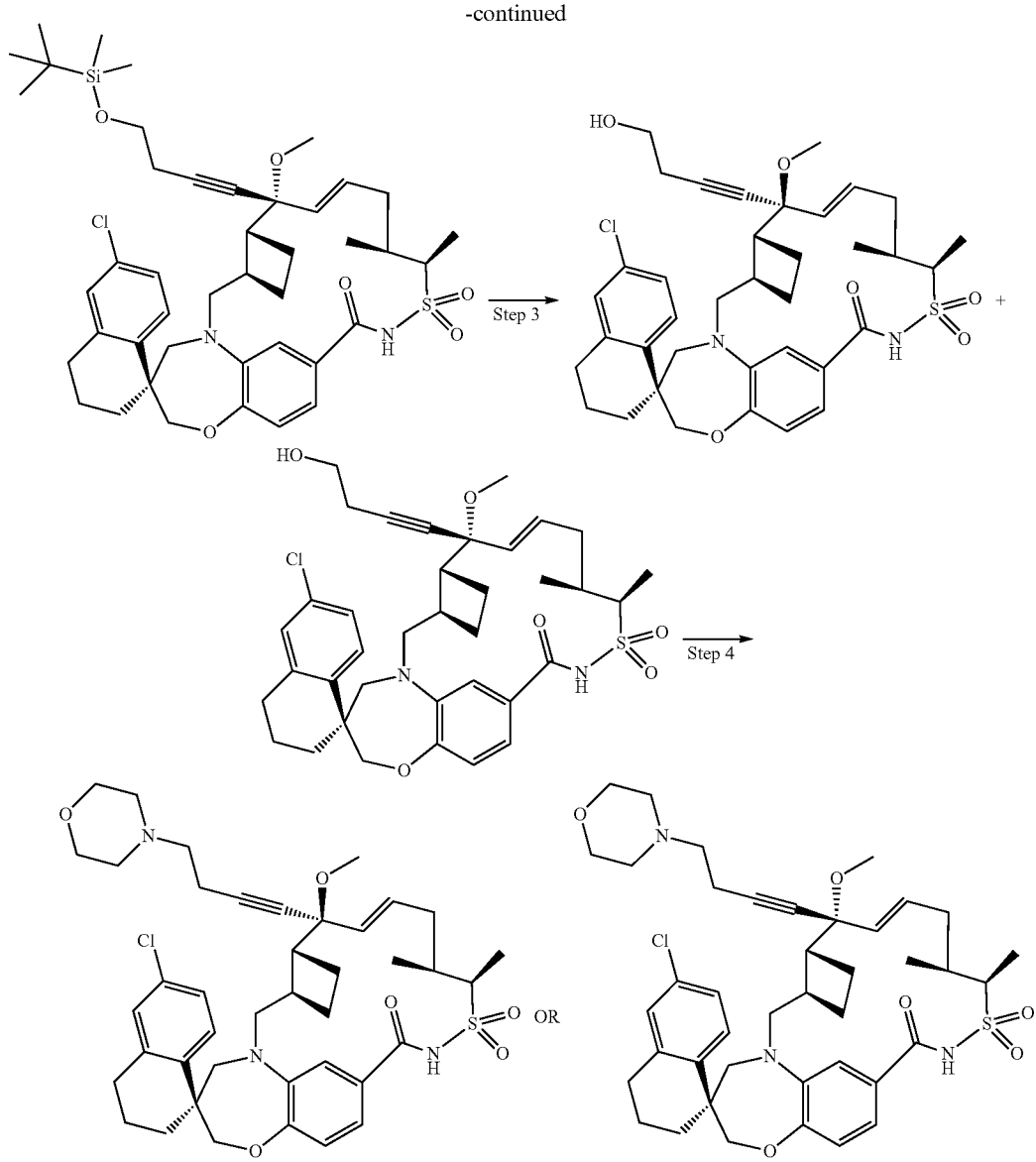

Example 100012

Step 1: (1S,3'R,6'R,7'S,8'E,11'S, 12'R)-6-chloro-7'-(4-((dimethyl(2-methyl-2-propanyl)silyl)oxy)-1-butyn-1-yl)-7'-hydroxy-11,12'-dimethyl-3,4-dihydro-2H, 15'H-spiro[naphthalene-1,22'-[20]oxa[13]thia[1,14]diazatetracyclo[14.7.2.0~3,6~.0~19,24-]pentacosa[8,16,18,24]tetraen]-15'-one 13',13'-dioxide AND (1S,3'R,6'R,7'R,8'E,11S,12R)-6-chloro-7'-(4-((dimethyl(2-methyl-2-propanyl)silyl)oxy)-1-butyn-1-yl)-7'-hydroxy-11,12'-dimethyl-3,4-dihydro-2H, 15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a cooled (−78° C.) solution of 4-(tert-butyldimethylsilyloxy)-1-butyne (0.600 mL, 2.91 mmol) in tetrahydrofuran (9 mL) was added 2.5 M butyllithium solution in toluene (1.00 mL, 2.50 mmol) dropwise over a period of 10 min. After 1 h, a solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7', 15'-dione 13',13'-dioxide (0.249 g, 0.417 mmol) in THF (2 mL) was added dropwise via syringe. After 1 h the reaction mixture was quenched with pH 7 buffer, partitioned between EtOAc and brine and the aqueous layer was extracted with EtOAc (3×). The combined organic layers were evaporated onto silica gel and purified by flash chromatography (Isco, 12 g) eluting with 0.3% AcOH in EtOAc: 0.3% AcOH in heptane (0:1 to 1:3) to give (1S,3'R,6'R,7'S,8'E,11'S,12'R)-6-chloro-7'-(4-((dimethyl(2-methyl-2-propanyl)silyl)oxy)-1-butyn-1-yl)-7'-hydroxy-11',12'-dimethyl-3,4-dihydro-2H, 15'H-spiro[naphthalene-1,22'-[20]oxa[13]thia[1,14]diazatetracyclo[14.7.2.0~3,6~.0~19,24~]tetraen]-15'-one 13',13'-dioxide AND (1S,3'R,6'R,7'R,8'E,11'S,12'R)-6-chloro-7'-(4-((dimethyl(2-methyl-2-propanyl)silyl)oxy)-1-butyn-1-yl)-7'-hydroxy-11',12'-dimethyl-3,4-dihydro-2H,15'H-spiro[naphthalene-1,22'-

[20]oxa[13]thia[1,14]diazatetracyclo[14.7.2.0~3,6~.0~19, 24~]pentacosa[8,16,18,24]tetraen]-15'-one 13',13'-dioxide (254 mg, 78% yield) as a white solid. MS (ESI, +ve ion) m/z 784.5 (M+1)+.

Step 2: (1S,3'R,6'R,7'S,8'E,11'S,12'R)-6-chloro-7'-(4-((dimethyl(2-methyl-2-propanyl)silyl)oxy)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-((dimethyl(2-methyl-2-propanyl)silyl)oxy)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a cooled (0° C.) solution of (1S,3'R,6'R,7'S,8'E,11'S,12'R)-6-chloro-7'-(4-((dimethyl(2-methyl-2-propanyl)silyl)oxy)-1-butyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-((dimethyl(2-methyl-2-propanyl)silyl)oxy)-1-butyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.254 g, 0.325 mmol) in tetrahydrofuran (5 mL) was added 60% NaH in mineral oil (0.105 g, 2.63 mmol) portion wise. After 10 min iodomethane (0.080 mL, 1.3 mmol) was added via syringe and the reaction was allowed to warm to room temperature overnight. The reaction mixture was quenched with pH 7 buffer and partitioned between EtOAc and water. The aqueous layer was extracted with EtOAc (3×) then the combined organic layers were washed with brine, evaporated onto silica gel and purified by flash chromatography (Isco, 25 g) eluting with 0.3% AcOH in EtOAc: 0.3% AcOH in heptane (0:1 to 1:3) to give (1S,3'R,6'R,7'S,8'E,11'S,12'R)-6-chloro-7'-(4-((dimethyl(2-methyl-2-propanyl)silyl)oxy)-1-butyn-1-yl)-7'-methoxy-1',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-((dimethyl(2-methyl-2-propanyl)silyl)oxy)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (173 mg, 67% yield) as a white solid. MS (ESI, +ve ion) m/z 796.3 (M+1)+.

Step 3: (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a room temperature solution of (1S,3'R,6'R,7'S,8'E,11'S,12'R)-6-chloro-7'-(4-((dimethyl(2-methyl-2-propanyl)silyl)oxy)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-((dimethyl(2-methyl-2-propanyl)silyl)oxy)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.173 g, 0.217 mmol) in tetrahydrofuran (3 mL) was added 1 M tetrabutylammonium fluoride solution in THF (0.700 mL, 0.700 mmol). The reaction was partitioned between EtOAc and brine and the organic layer was evaporated onto silica gel and purified by flash chromatography (Isco (12 gram)) eluting with 25% EtOH/EtOAc:heptane (0:1 to 1:0) to give (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (91 mg, 61% yield) as a white solid.

Step 4: (1S,3'R,6'R,7'S,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide To a cooled (0° C.) solution of (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'R,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (0.057 g, 0.084 mmol) in dichloromethane (1.5 mL) was added triethylamine (0.060 mL, 0.43 mmol) followed by methanesulfonyl chloride (0.035 mL, 0.45 mmol) resulting in a yellow mixture. After 15 min morpholine (0.075 mL, 0.86 mmol) was added the reaction was stirred for 1 h. To the reaction was added morpholine (0.035 mL) and the reaction was stirred at room temperature overnight. The reaction mixture was partitioned between CH$_2$Cl2 and brine and the aqueous layer was extracted with CH$_2$Cl2 and brine (2×). The combined organic layers were dried over Na$_2$SO$_4$, filtered and concentrated under reduced pressure to give 110 mg of a yellow tar. The material was purified following a 2-step SFC method: (Step 1: Cyano column, 20% isopropanol/20 mM NH$_3$ 80 g/min Step 2: MSA column, 40% MeOH/20 mM NH$_3$) to give the first eluting isomer, (1S,3'R,6'R,7'S,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo

[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (6 mg, 10% yield) as a white crystalline solid. $^1$H NMR (400 MHz, CD$_2$Cl$_2$) δ 7.72 (d, J=8.41 Hz, 1H), 7.19 (s, 1H), 7.17 (dd, J=8.51, 2.25 Hz, 1H), 7.09 (d, J=2.15 Hz, 1H), 6.80-6.95 (m, 2H), 6.23-6.39 (m, 1H), 5.52 (d, J=15.26 Hz, 1H), 4.39 (d, J=14.87 Hz, 1H), 4.26-4.34 (m, 1H), 4.01-4.14 (m, 2H), 3.69 (d, J=14.08 Hz, 1H), 3.58 (t, J=4.69 Hz, 4H), 3.26 (d, J=14.28 Hz, 1H), 3.12 (s, 3H), 3.00 (dd, J=15.16, 10.47 Hz, 1H), 2.63-2.86 (m, 5H), 2.51-2.63 (m, 2H), 2.51-2.63 (m, 2H), 2.34-2.48 (m, 5H), 2.11-2.24 (m, 2H), 2.04-2.11 (m, 1H), 1.75-2.03 (m, 6H), 1.59-1.72 (m, 1H), 1.46 (d, J=7.24 Hz, 3H), 1.39 (t, J=13.20 Hz, 1H), 1.03 (d, J=6.65 Hz, 3H). MS (ESI, +ve ion) m/z 750.3 (M+1)$^+$.

Example 100013

2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylacetamide N-Butyllithium solution (1.6 M in hexane, 0.83 mL, 1.3 mmol) was added to a solution of diisopropylamine (0.19 mL, 1.3 mmol) in THF (1.0 mL) at 0° C. The solution was stirred at 0° C. for 2 minutes then dimethyl acetamide (0.12 mL, 1.3 mmol) was added. The reaction was then stirred at 0° C. for 7 min. Then a solution of (1S,3'R,6'R,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[16,18,24]triene]-7',15'-dione 13',13'-dioxide (0.040 g, 0.067 mmol) in THF (1.3 mL) was added and maintained at 0° C. for 17 min. The reaction was quenched with saturated ammonium chloride solution and acidified with 1 N HCl to pH 2-3 and extracted with EtOAc. The organic phase was washed with brine and dried over anhydrous sodium sulfate and the filtrate was concentrated under reduced pressure to give the crude product that was purified by preparatory SFC chromatography (CC4 250 mm×21 mm column, Phenomenex; 33 g/minute MeOH (2 M ammonia as a modifier)+27 g/minute CO$_2$ on Thar 200 SFC; outlet pressure=100 bar; temperature=40° C.; wavelength=246 nm; 2.0 mL injection of 30 mg/mL sample solution of 1:1 DCM:MeOH (2.0 mL) to give 2-((1S,3'R,6'R,7'R,11'S,12'R)-6-chloro-7'-hydroxy-11',12'-dimethyl-13',13'-dioxido-15'-oxo-3,4-dihydro-2h-spiro[naphthalene-1,22'-[20]oxa[13]thia[1,14]diazatetracyclo[14.7.2.0~3,6~.0~19,24~]pentacosa[16,18,24]trien]-7'-yl)-n,n-dimethylacetamide (17 mg, 37% yield) as the first eluting diasteromer. $^1$H NMR (400 MHz, DICHLOROMETHANE-d$_2$) δ 7.71 (d, J=8.4 Hz, 1H), 7.16 (dd, J=2.2, 8.5 Hz, 1H), 7.09 (d, J=2.2 Hz, 1H), 7.04-6.98 (m, 2H), 6.97-6.91 (m, 1H), 5.23 (br s, 1H), 4.17-4.06 (m, 3H), 3.68 (d, J=14.3 Hz, 1H), 3.58 (d, J=15.3 Hz, 1H), 3.23 (d, J=14.3 Hz, 1H), 3.17 (s, 3H), 3.02 (dd, J=9.7, 15.4 Hz, 1H), 2.97 (s, 3H), 2.84-2.67 (m, 4H), 2.65-2.54 (m, 1H), 2.46 (quin, J=9.0 Hz, 1H), 2.10-1.97 (m, 2H), 1.96-1.72 (m, 5H), 1.68-1.42 (m, 5H), 1.39 (d, J=7.2 Hz, 3H), 1.37-1.35 (m, 1H), 1.35-1.18 (m, 2H), 0.99 (d, J=6.7 Hz, 3H). MS (ESI, +ve ion) m/z 686.2 (M+1)$^+$.

Example 100014

(1S,3'R,6'R,7'S,8'E,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

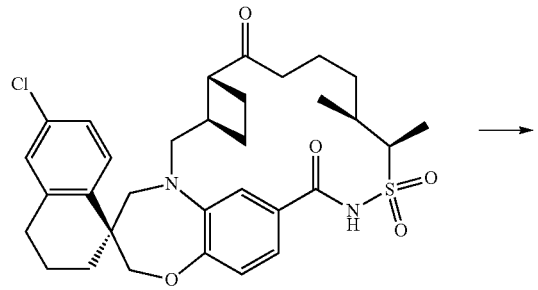

Example 100013

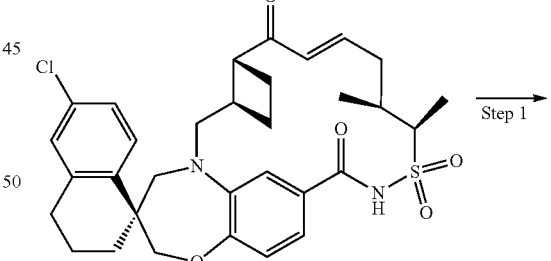

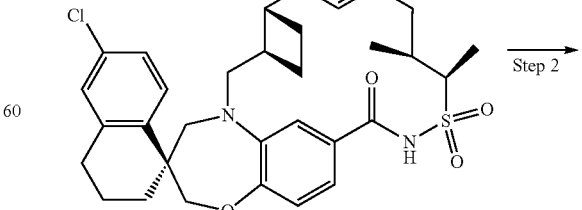

Example 100016

-continued

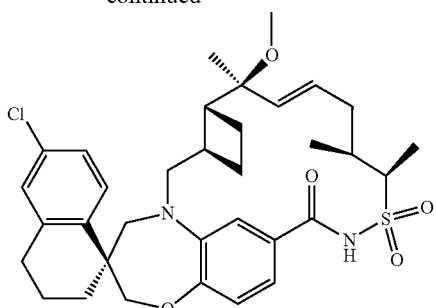

Example 100014

Step 1: (1S,3'R,6'R,7'S,8'E,11'S,12'R)-6-CHLORO-7'-HYDROXY-7',11',12'-TRIMETHYL-3,4-DI-HYDRO-2H,15'H-SPIRO[NAPHTHALENE-1,22'-[20]OXA[13]THIA[1,14]DIAZATETRACYCLO [14.7.2.0~3,6~.0~19,24~]PENT ACOSA[8,16,18, 24]TETRAEN]-15'-ONE 13',13'-DIOXIDE (1S,3'R,6'R,8'E,11'S,12'R)-6-Chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (200 mg, 0.335 mmol) was dissolved in THF (3.00 mL) and cooled to 0° C. Lanthanum (III) chloride bis(lithium chloride) complex solution (0.6 M in THF, 0.63 mL, 0.34 mmol) was added to the solution and the solution was stirred for 45 minutes. The methylmagnesium bromide (3.0 M in diethyl ether solution, 0.50 mL, 1.5 mmol) was added to the solution and allowed to warm to room temperature overnight. Another aliquot of methylmagnesium bromide (3.0 M in diethyl ether solution, 0.502 mL, 1.51 mmol) was added and the reaction was stirred for 30 minutes to completion then quenched with saturated ammonium chloride solution. This solution was then acidified to pH 6.5 and then extracted with EtOAc (2×50 mL). The combined organic layers were then washed with brine (1×20 mL) and dried over sodium sulfate. The residue was then purified by chromatography (silica, 20% to 100% EtOAc (0.3% HOAc):hexanes) to give (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (124 mg, 60% yield) as the second eluting diastereomer. MS (ESI, +ve ion) m/z 613.1 (M+1)$^+$.

Step 2: (1S,3'R,6'R,7'S,8'E,11'S,12'R)-6-CHLORO-7'-METHOXY-7',11',12'-TRIMETHYL-3,4-DI-HYDRO-2H,15'H-SPIRO[NAPHTHALENE-1,22'-[20]OXA[13]THIA[1,14]DIAZATETRACYCLO [14.7.2.0~3,6~.0~19,24~]PENT ACOSA[8,16,18, 24]TETRAEN]-15'-ONE 13',13'-DIOXIDE (1S,3'R,6'R,7'S,8'E,11'S,12'R)-6-Chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (30 mg, 0.049 mmol) was dissolved in tetrahydrofuran (1.0 mL) and cooled to 0° C. Sodium hydride (60% dispersion, 20 mg, 0.49 mmol) was then added and the resulting slurry was stirred for 20 minutes. The methyl iodide (0.031 mL, 0.49 mmol) was then added and the reaction mixture was stirred for 2.5 hours while slowly warming to room temperature. Another aliquot of sodium hydride (60% dispersion, 20 mg, 0.49 mmol) and methyl iodide (0.031 mL, 0.49 mmol) was added and the reaction was stirred for an additional 3.5 h to completion. The reaction was then quenched with dropwise addition of satd. ammonium chloride addition and the mixture was extracted with EtOAc (2×50 mL). The combined organic layers were then washed with brine (1×20 mL) and dried over sodium sulfate. The crude product was purified by chromatography (silica, 0 to 50% EtOAc/hexanes) to give (1S,3'R,6'R,7'S,8'E,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide. (29 mg, 95% yield). $^1$H NMR (400 MHz, DMSO-d$_6$) δ 11.89 (s, 1H), 7.64 (d, J=8.6 Hz, 1H), 7.27 (dd, J=2.1, 8.5 Hz, 1H), 7.17 (d, J=2.0 Hz, 1H), 7.03 (dd, J=1.5, 8.1 Hz, 1H), 6.89 (d, J=8.2 Hz, 1H), 6.79 (s, 1H), 5.72 (dd, J=3.2, 9.3 Hz, 1H), 5.65-5.55 (m, 1H), 4.16-4.08 (m, 1H), 4.07-3.94 (m, 2H), 3.69 (d, J=14.7 Hz, 1H), 3.59 (d, J=14.3 Hz, 1H), 3.24 (d, J=14.3 Hz, 1H), 3.08 (dd, J=9.6, 14.7 Hz, 1H), 2.94 (s, 3H), 2.84-2.62 (m, 2H), 2.36-1.60 (m, 12H), 1.43-1.36 (m, 1H), 1.33 (d, J=7.2 Hz, 3H), 1.30 (s, 3H), 0.96 (d, J=6.7 Hz, 3H). MS (ESI, +ve ion) m/z 627.2 (M+1)$^+$.

Example 100015

(2S,3'R,6'R, 11'S,12'R,22'S)-6''-chloro-11',12'-dimethyl-3'',4''-dihydro-2''H, 15'H-dispiro[1,4-dioxane-2,7'-[20]oxa[13]thia[1,14]diazatetracyclo [14.7.2.0~3,6~.0~19,24~]pentacosa[16,18,24]triene-22',1''-naphthalen]-15'-one 13',13'-dioxide OR (2R,3'R,6'R, 11'S,12'R,22'S)-6''-chloro-11',12'-dimethyl-3'',4''-dihydro-2''H, 15'H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide

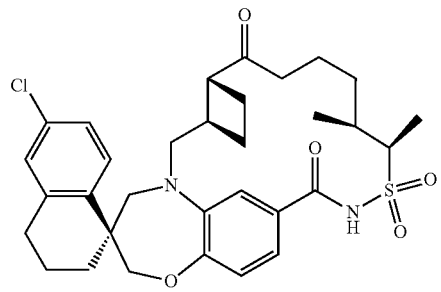 Step 1 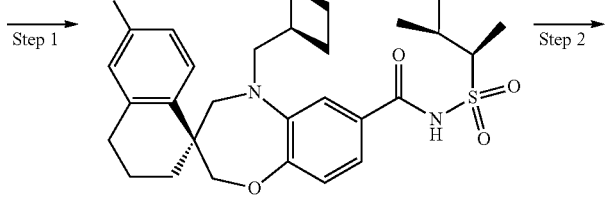 Step 2

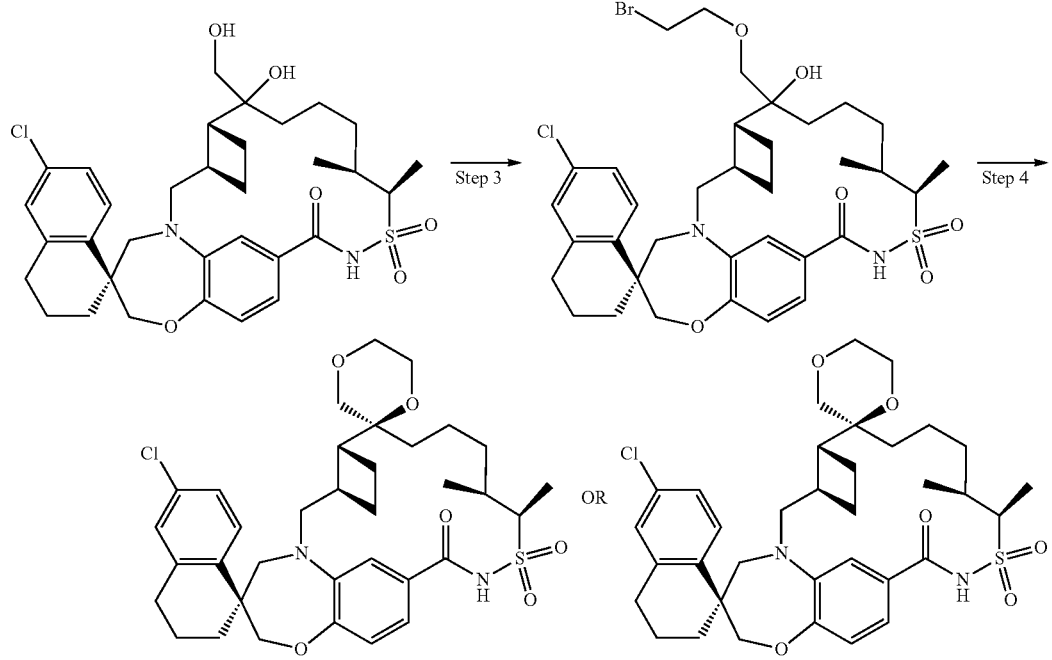

Example 1000015

Step 1: (1S,3'R,6'R,8'E,11'S,12'R)-6-CHLORO-11',12'-DIMETHYL-7'-METHYLIDENE-3,4-DIHYDRO-2H,15'H-SPIRO[NAPHTHALENE-1,22'-[20]OXA[13]THIA[1,14]DIAZATETRACYCLO[14.7.2.~3,6~.0~19,24~]PENTACOSA[8,16,18,24]TETRAEN]-15'-ONE 13',13'-DIOXIDE A solution of methyltriphenylphosphonium bromide (1.80 g, 5.0 mmol) in THF (15 mL) was cooled to 0° C. N-butyllithium solution (2.5 M in hexanes, 1.8 mL, 4.5 mmol) was added dropwise and the solution was stirred at 0° C. for 10 minutes. The solution was added dropwise to a solution of (1S,3'R,6'R,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[16,18,24]triene]-7',15'-dione 13',13'-dioxide (0.30 g, 0.50 mmol) in THF (6.0 mL), cooled in ice bath, until the yellow color persisted. The solution was stirred at 0° C. for 12 min. The reaction mixture was added to stirred ice water (20 mL) and acidified with 1 N HCl to pH 2-4. The organic phase was separated and the aqueous was extracted with EtOAc (50 mL). The organic phase was washed with brine and dried over magnesium sulfate. The filtrate was concentrated to give crude product. The compound was purified by chromatography (silica, 0 to 50% EtOAc (0.3% HOAc: hexanes) to give (1S,3'R,6'R,8'E,11'S,12'R)-6-chloro-11',12'-dimethyl-7'-methylidene-3,4-dihydro-2h, 15'h-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (290 mg, 97% yield). MS (ESI, +ve ion) m/z 595.2 (M+H)+.

Step 2: (1S,3'R,6'R,8'E,11'S,12'R)-6-CHLORO-7'-HYDROXY-7'-(HYDROXYMETHYL)-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA [8,16,18,24]TETRAEN]-15'-ONE 13',13'-DIOXIDE The AD-Mix-alpha mixture (640 mg, 0.43 mmol) was dissolved in a mixture of tert-butanol (10.0 mL) and water (10.0 mL) and cooled to 0° C. (1S,3'R,6'R,8'E,11'S,12'R)-6-Chloro-11',12'-dimethyl-7'-methylidene-3,4-dihydro-2h, 15'h-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (255 mg, 0.428 mmol) was added and the reaction mixture was warmed slowly to room temperature overnight. Another 5.0 mL of t-BuOH was added to homogenize the mixture. The reaction was stirred overnight. Another 320 mg of AD-Mix-alpha mixture was added and the reaction was stirred for an additional three days. The reaction was quenched by adding 575 mg of sodium sulfite at 0° C. and stirring for 45 minutes. The mixture was then extracted with EtOAc (2×25 mL). The combined organic layers were washed with brine (1×20 mL) and dried over sodium sulfate. The crude product was then purified by chromatography (silica, 0 to 100% EtOAc (+0.3% HOAc):heptanes) to give (1S,3'R,6'R,8'E,11'S, 12'R)-6-chloro-7'-hydroxy-7'-(hydroxymethyl)-11',12'-dimethyl-3,4-dihydro-2h, 15'h-spiro[naphthalene-1,22'-[20]oxa[13]thia[1,14]diazatetracyclo[14.7.2.0~3,6~.0~19,24~]]pentacosa[8,16,18,24]tetraen]-15'-one 13',13'-dioxide (31 mg, 12% yield). MS (ESI, +ve ion) m/z 629.2 (M+H)+.

Step 3: (1S,3'R,6'R,11'S,12'R)-7'-((2-BROMOETH-OXY)METHYL)-6-CHLORO-7'-HYDROXY-11', 12'-DIMETHYL-3,4-DIHYDRO-2H,15'H-SPIRO[NAPHTHALENE-1,22'-[20]OXA[13]THIA[1,14]DIAZATETRACYCLO[14.7.2.0~3,6~.0~19,24~] PENT ACOSA[16,18,24]TRIEN]-15'-ONE 13',13'-DIOXIDE (1S,3'R,6'R,8'E,11'S,12'R)-6-Chloro-7'-hydroxy-7'-(hydroxymethyl)-11',12'-dimethyl-3,4-dihydro-2h, 15'h-spiro[naphthalene-1,22'-[20]oxa[13]thia[1,14]diazatetracyclo[14.7.2.0~3,6~.0~19,24~]]pentacosa[8,16,18,24]tetraen]-15'-one 13',13'-dioxide (30.0 mg, 0.048 mmol) was dissolved in THF (1.0 mL) and cooled to 0° C. Sodium hydride (60% dispersion, 19.0 mg, 0.48 mmol) was added and the resulting slurry was stirred for ten minutes, then 2-bromoethyl trifluoromethanesulfonate (Ark Pharm Inc.) (61 mg, 0.24 mmol) was added and the reaction was allowed to slowly warm to room temperature over 45 minutes. The reaction was then quenched with slow addition of water (5 mL) and the mixture was extracted (2×25 mL) with ethyl acetate. The combined organic layers were washed with brine (1×15 mL) and then dried over magnesium sulfate. The residue was then purified by chromatography (silica, 0 to 50% EtOAc (+0.3% HOAc):hexanes) to give (1S,3'R,6'R, 11'S,12'R)-7'-((2-bromoethoxy)methyl)-6-chloro-7'-hydroxy-11',12'-dimethyl-3,4-dihydro-2h, 15'h-spiro[naphthalene-1,22'-[20]oxa[13]thia[1,14]diazatetracyclo[14.7.2.0~3, 6~.0~19,24~]pentacosa[16,18,24]trien]-15'-one 13',13'-dioxide (25 mg, 71% yield). MS (ESI, +ve ion) m/z 739.1 (M+H)⁺.

Step 4: (2S,3'R,6'R,11'S,12'R,22'S)-6''-CHLORO-11',12'-DIMETHYL-3'',4''-DIHYDRO-2''H, 15'H-DISPIRO[1,4-DIOXANE-2,7'-[20]OXA[13]THIA[1,14]DIAZATETRACYCLO[14.7.2.0~3,6~.0~19, 24~]PENT ACOSA[16,18,24]TRIENE-22',1''-NAPHTHALEN]-15'-ONE 13',13'-DIOXIDE OR (2R,3'R,6'R,11'S,12'R,22'S)-6''-CHLORO-11',12'-DIMETHYL-3'',4''-DIHYDRO-2''H, 15'H-DISPIRO[1,4-DIOXANE-2,7'-[20]OXA[13]THIA[1,14]DIAZATETRACYCLO[14.7.2.0~3,6~.0~19,24~] PENT ACOSA[16,18,24]TRIENE-22',1''-NAPHTHALEN]-15'-ONE 13',13'-DIOXIDE (1S,3'R,6'R, 11'S,12'R)-7'-((2-Bromoethoxy)methyl)-6-chloro-7'-hydroxy-11',12'-dimethyl-3,4-dihydro-2h, 15'h-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (25.0 mg, 0.034 mmol) was then dissolved in DMF (0.5 mL) and sodium hydride (60% dispersion, 19 mg, 0.48 mmol) was added. This mixture was then heated to 85° C. for 10 minutes. The reaction mixture was then cooled to room temperature and quenched with dropwise addition of water (5 mL). This mixture was extracted with ethyl acetate (2×20 mL). The combined organic layers were washed with 1 N LiCl solution (1×15 mL) and brine (1×10 mL) and dried over magnesium sulfate. The crude product was the purified by chromatography (silica, 0 to 50% EtOAc (+0.3% HOAc):hexanes) to give (2S,3'R,6'R, 11'S,12'R,22'S)-6''-chloro-11',12'-dimethyl-3'', 4''-dihydro-2''h, 15'h-dispiro[1,4-dioxane-2,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide or (2R,3'R,6'R,11'S,12'R,22'S)-6''-chloro-11',12'-dimethyl-3'',4''-dihydro-2''h,15'h-dispiro[1,4-dioxane-2,7'-[20]oxa[13]thia[1,14]diazatetracyclo[14.7.2.0~3,6~.0~19, 24~]pentacosa[16,18,24]triene-22',1''-naphthalen]-15'-one 13',13'-dioxide (14 mg, 45% yield). ¹H NMR (400 MHz, MeOH) δ 7.73 (d, J=8.4 Hz, 1H), 7.17 (dd, J=2.2, 8.4 Hz, 1H), 7.13-7.08 (m, 2H), 7.02 (d, J=1.6 Hz, 1H), 6.92 (d, J=8.0 Hz, 1H), 4.08 (s, 2H), 4.06-4.01 (m, 1H), 3.76 (d, J=11.9 Hz, 2H), 3.73-3.59 (m, 4H), 3.58-3.49 (m, 1H), 3.46-3.38 (m, 1H), 3.23-3.15 (m, 1H), 3.10 (dd, J=9.1, 15.4 Hz, 1H), 2.86-2.68 (m, 2H), 2.62-2.50 (m, 1H), 2.11-2.03 (m, 1H), 1.96-1.84 (m, 3H), 1.76-1.51 (m, 7H), 1.49-1.40 (m, 1H), 1.36 (d, J=7.0 Hz, 3H), 1.34-1.27 (m, 2H), 1.23-1.19 (m, 2H), 1.01 (d, J=6.8 Hz, 3H). MS (ESI, +ve ion) m/z 657.2 (M+H)⁺.

Example 100017

(1S,3'R,6'R,7'S,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3, 6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

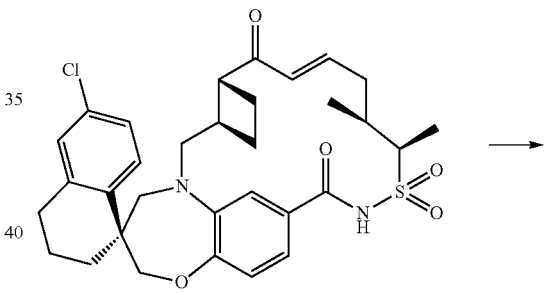

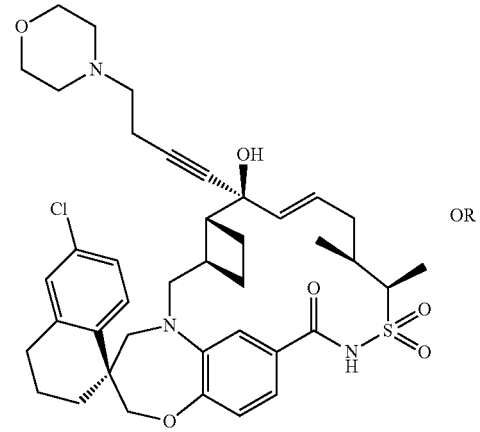

1251

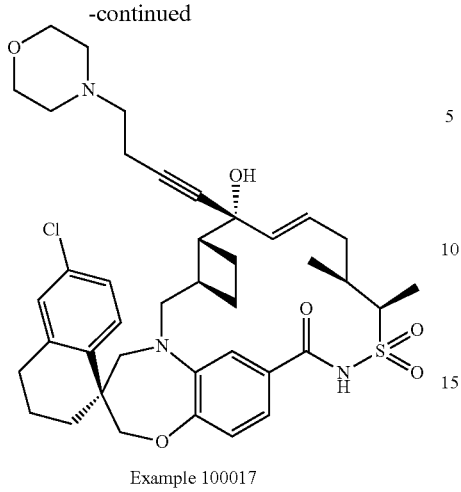

Example 100017

To a cooled (−78° C.) solution of 4-(but-3-yn-1-yl)morpholine (0.163 g, 1.171 mmol) in tetrahydrofuran (3 mL) was added 2.5 M butyllithium solution in toluene (0.400 mL, 1.00 mmol) dropwise via syringe. After 45 min, a solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (0.100 g, 0.167 mmol) in THF (1 mL) was added dropwise. After 1 h, the reaction was quenched with saturated NH$_4$Cl (3 mL) and the mixture was warmed to room temperature. The mixture was extracted with dichloromethane (3×) and the combined organic layers were washed with brine and dried over Na$_2$SO$_4$. The solution was filtered and the filtrate was concentrated under reduced pressure to give an orange oil. The crude material was purified by preparative SFC (Waters Thar 200; Cyano Column (21.1×250 mm, 5 μm) with 18% methanol (20 mM NH$_3$), 82% carbon dioxide; flow rate=95 mL/min, column temperature=40° C., pressure=100 bar, detection at 220 nm) to give the first eluting diastereomer, (1S,3'R,6'R,7'S,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (32 mg, 26%) as a white solid. $^1$H NMR (400 MHz, CD$_2$Cl$_2$) δ 7.72 (d, J=8.41 Hz, 1H), 7.13-7.24 (m, 2H), 7.09 (d, J=1.96 Hz, 1H), 6.83-6.96 (m, 2H), 6.25-6.41 (m, 1H), 5.75 (d, J=15.26 Hz, 1H), 4.38 (d, J=15.06 Hz, 1H), 4.29 (q, J=7.37 Hz, 1H), 3.97-4.13 (m, 2H), 3.69 (d, J=14.08 Hz, 1H), 3.58 (t, J=4.69 Hz, 4H), 3.26 (d, J=14.28 Hz, 1H), 3.00 (dd, J=15.26, 10.37 Hz, 1H), 2.47-2.87 (m, 7H), 2.29-2.46 (m, 5H), 1.80-2.21 (m, 9H), 1.61-1.72 (m, 1H), 1.44 (d, J=7.24 Hz, 3H), 1.33-1.41 (m, 1H), 1.03 (d, J=6.85 Hz, 3H). MS (ESI, +ve ion) m/z 736.2 (M+1)$^+$.

1252

Example 100018

(1S,3'R,6'R,7'S,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

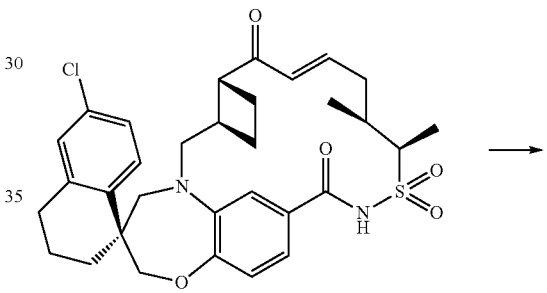

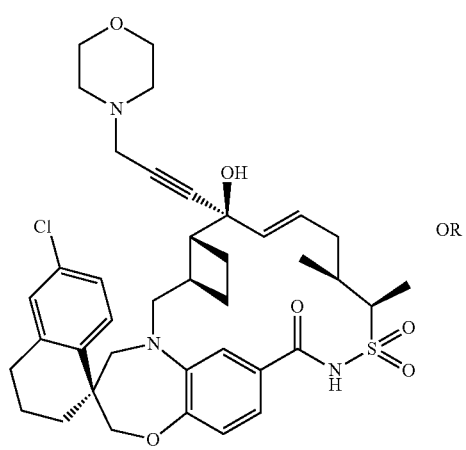

1253

-continued

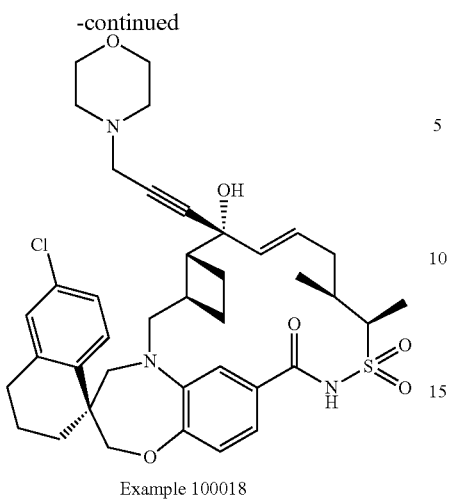

Example 100018

To a cooled (−78° C.) solution of 4-(prop-2-yn-1-yl)morpholine (0.170 mL, 1.35 mmol, Ark Pharm, Inc.) in tetrahydrofuran (3 mL) was added butyllithium solution (2.5 M in toluene, 0.500 mL, 1.25 mmol) dropwise via syringe. After 45 min a solution of (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (0.100 g, 0.167 mmol) in THF (1 mL) was added dropwise. After 1 h, the reaction was quenched with saturated NH₄Cl (3 mL) and the mixture was warmed to room temperature. The mixture was extracted with DCM (3×) and the combined organic layers were washed with brine and dried over Na₂SO₄. The solution was filtered and the filtrate was concentrated under reduced pressure to give a yellow oil. The crude material was purified using preparative SFC (Premier (2×25 cm); 50% methanol/CO₂, 100 bar; 50 mL/min, 254 nm) to give the first eluting isomer, (1S,3'R,6'R,7'S,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (40 mg, 33% yield) as a solid. ¹H NMR (400 MHz, CD₂Cl₂) δ 7.71 (d, J=8.41 Hz, 1H), 7.12-7.23 (m, 2H), 7.09 (d, J=2.15 Hz, 1H), 6.84-6.97 (m, 2H), 6.22-6.40 (m, 1H), 5.78 (d, J=14.87 Hz, 1H), 4.25 (d, J=14.67 Hz, 2H), 4.07 (s, 2H), 3.70 (d, J=14.28 Hz, 1H), 3.59-3.66 (m, 4H), 3.56 (s, 2H), 3.25 (d, J=14.08 Hz, 1H), 3.02 (dd, J=15.16, 10.47 Hz, 1H), 2.67-2.89 (m, 2H), 2.51-2.65 (m, 5H), 2.33-2.49 (m, 1H), 2.02-2.16 (m, 4H), 1.76-2.01 (m, 7H), 1.62-1.73 (m, 1H), 1.43 (d, J=7.04 Hz, 3H), 1.34-1.41 (m, 1H), 1.04 (d, J=6.46 Hz, 3H). MS (ESI, +ve ion) m/z 722.2 (M+1)⁺.

1254

Example 100019

(1S,3'R,6'R,7'S,8'E,11'S,12'R)-6-chloro-7'-hydroxy-11',12'-dimethyl-7'-((2R)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-hydroxy-11',12'-dimethyl-7'-((2S)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-((2S)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-((2R)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

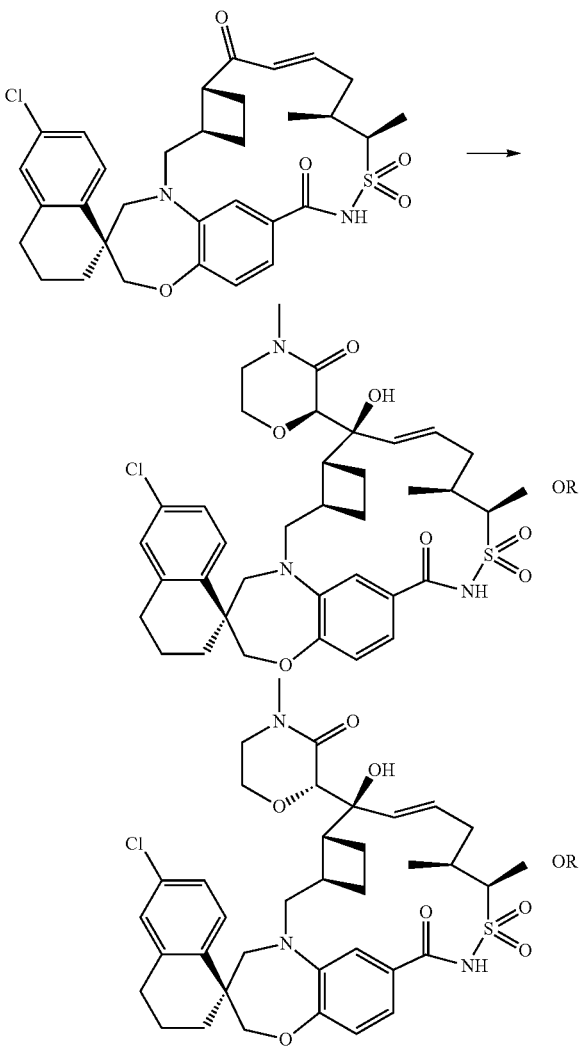

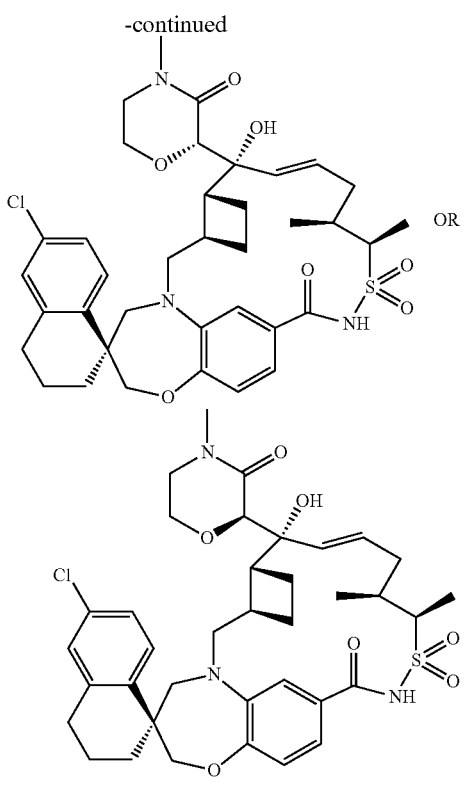

Example 100019

To a solution of diisopropylamine (1.183 mL, 8.44 mmol) in tetrahydrofuran (4.22 mL) at 0° C. was added butyllithium (2.5 M in hexanes, 3.38 mL, 8.44 mmol) for 3 minutes. The solution was then cooled to −78° C. 4-Methylmorpholin-3-one (0.887 mL, 8.44 mmol) was added dropwise and the solution was allowed to stir for 1 hour. (1S,3′R,6′R,8′E,11′S,12′R)-6-Chloro-11′,12′-dimethyl-3,4-dihydro-2H,7′H,15′H-spiro[naphthalene-1,22′-[20]oxa[13]thia[1,14]diazatetracyclo[14.7.2.0~3,6~.0~19,24~]pentacosa[8,16,18,24]tetraene]-7′,15′-dione 13′,13′-dioxide (0.252 g, 0.422 mmol) in a solution of 0.5 mL of THF was added dropwise. Upon completion, saturated ammonium chloride aqueous solution was added. 1 N HCl was added until the pH reached 2-3 and the solution was extracted with EtOAc. The organic extract was washed with saturated NaCl, dried over $Na_2SO_4$, filtered and concentrated in vacuo. The crude product was adsorbed onto a plug of silica gel and chromatographed through a Biotage SNAP Ultra silica gel column (50 g), eluting with a gradient of 10% to 100% EtOAc:EtOH (3:1) in hexane with 0.5% AcOH. The material was further purified by preparative SFC using a Me-sulfone achiral column (21×150 mm, 5 m), 60% methanol with 20 mM $NH_3$, flow rate 60 mL/min, column temperature 40° C., pressure 100 bar, detection at 220 nm. The third isomer to elute was isolated to give (1S,3′R,6′R,7′S,8′E,11′S,12′R)-6-chloro-7′-hydroxy-11′,12′-dimethyl-7′-((2R)-4-methyl-3-oxo-2-morpholinyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide OR (1S,3′R,6′R,7′S,8′E,11′S,12′R)-6-chloro-7′-hydroxy-11′,12′-dimethyl-7′-((2S)-4-methyl-3-oxo-2-morpholinyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide OR (1S,3′R,6′R,7′R,8′E,11′S,12′R)-6-chloro-7′-hydroxy-11′,12′-dimethyl-7′-((2S)-4-methyl-3-oxo-2-morpholinyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide OR (1S,3′R,6′R,7′R,8′E,11′S,12′R)-6-chloro-7′-hydroxy-11′,12′-dimethyl-7′-((2R)-4-methyl-3-oxo-2-morpholinyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one. $^1$H NMR (400 MHz, DMSO-$d_6$) δ 0.92 (d, J=6.06 Hz, 3H) 1.02 (br. s., 2H) 1.36 (t, J=12.72 Hz, 1H) 1.61 (br. s., 3H) 1.87 (br. s., 3H) 1.92-2.13 (m, 3H) 2.25 (d, J=7.63 Hz, 1H) 2.62-2.79 (m, 2H) 2.84 (s, 3H) 2.86-3.06 (m, 3H) 3.29 (br. s., 1H) 3.55 (d, J=13.50 Hz, 1H) 3.71 (br. s., 1H) 3.79-4.01 (m, 4H) 4.10 (d, J=13.30 Hz, 1H) 4.26 (br. s., 1H) 5.33 (br. s., 1H) 5.71 (d, J=15.45 Hz, 1H) 6.17 (br. s., 1H) 6.67-6.84 (m, 1H) 6.98-7.41 (m, 4H) 7.65 (d, J=8.61 Hz, 1H). MS (ESI, +ve ion) m/z 712.2 (M+1)$^+$.

Example 100020

1-((1S,3′R,6′R,7′S,8′E,11′S,12′R)-6-chloro-7′-hydroxy-11′,12′-dimethyl-13′,13′-dioxido-15′-oxo-3,4-dihydro-2H-spiro[naphthalene-1,22′-[20]oxa[13]thia[1,14]diazatetracyclo[14.7.2.0~3,6~.0~19,24~]pentacosa[8,16,18,24]tetraen]-7′-yl)-N,N-dimethylmethanesulfonamide OR 1-((1S,3′R,6′R,7′R,8′E,11′S,12′R)-6-chloro-7′-hydroxy-11′,12′-dimethyl-13′,13′-dioxido-15′-oxo-3,4-dihydro-2H-spiro[naphthalene-1,22′-[20]oxa[13]thia[1,14]diazatetracyclo[14.7.2.0~3,6~.0~19,24~]pentacosa[8,16,18,24]tetraen]-7′-yl)-N,N-dimethylmethanesulfonamide

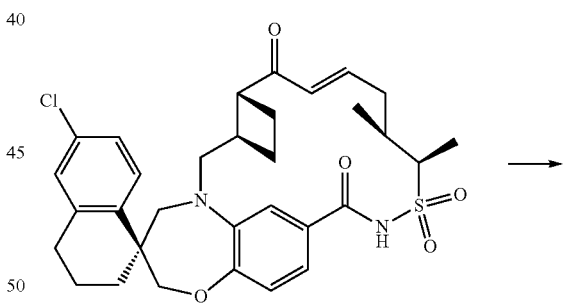

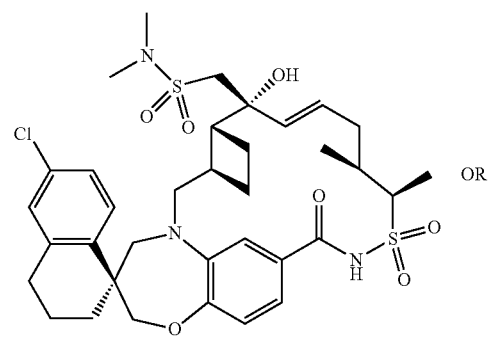

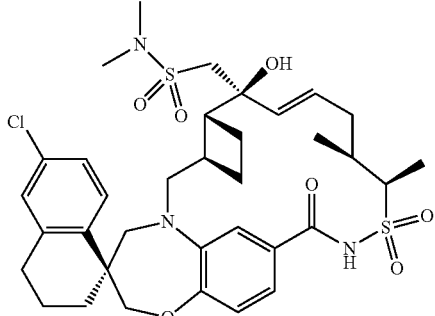

Example 100020

To a solution of N,N-dimethylmethanesulfonamide (206 mg, 1.68 mmol) in 2-methyltetrahydrofuran (4 mL) at 0° C. was added n-butyllithium (1.6 M in hexanes, 0.67 mL, 1.7 mmol), and the reaction was stirred at 0° C. for 5 min. (1S,3'R,6'R,8'E,11'S,12'R)-6-Chloro-11',12'-dimethyl-3,4-dihydro-2H,7'H,15'H-spiro[naphthalene-1,22'-[20]oxa[13]thia[1,14]diazatetracyclo[14.7.2.0~3,6~.0~19,24~]pentacosa[8,16,18,24]tetraene]-7',15'-dione 13',13'-dioxide (100 mg, 0.167 mmol) in 2-methyltetrahydrofuran (1 mL) was added at low temperature and after 15 min quenched with aqueous saturated NH$_4$Cl (50 mL), brine (50 mL) and EtOAc (100 mL). The organic layer was separated, dried (Na$_2$SO$_4$), filtered and concentrated onto silica. Purification by silica gel chromatography (0 to 100% EtOAc (0.3% AcOH) in heptane afforded 1-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide and 1-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide (70 mg, 0.10 mmol, 58% yield) as a mixture of isomers. The mixture was then purified by preparatory SFC chromatography (column: Welko-O1 250 mm×21 mm column, mobile phase: 65:35 (A:B) isocratic, A: liquid CO$_2$, B: methanol (20 mM NH$_3$), flow rate: 70 g/min, column temperature: 40° C., detection: UV at 220 nm), and the first eluting isomer 1-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide OR 1-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide (10 mg, 0.014 mmol, 8% yield) was isolated. $^1$H NMR (400 MHz, CHLOROFORM-d) δ 7.69 (d, J=8.41 Hz, 1H), 7.17 (dd, J=2.25, 8.51 Hz, 1H), 7.09 (d, J=2.15 Hz, 1H), 6.94 (s, 2H), 6.87 (s, 1H), 5.68-5.80 (m, 2H), 4.00-4.22 (m, 4H), 3.67-3.83 (m, 2H), 3.57 (br d, J=14.48 Hz, 1H), 3.20-3.32 (m, 2H), 3.05-3.16 (m, 1H), 2.96 (s, 6H), 2.89-2.93 (m, 1H), 2.69-2.83 (m, 2H), 2.38-2.50 (m, 1H), 2.03-2.17 (m, 3H), 1.85-2.02 (m, 3H), 1.72-1.84 (m, 2H), 1.58-1.70 (m, 2H), 1.46 (d, J=7.24 Hz, 3H), 1.32-1.41 (m, 1H), 1.06 (d, J=6.06 Hz, 3H). One exchangeable proton was not observed. MS (ESI, +ve ion) m/z 720.2 (M+H)$^+$.

Table 2 lists compounds prepared by the General Methods outlined in the present specification.

TABLE 2

Examples Prepared by the General Methods

| Example Number | Structure | Name | MS Dat (M + 1)$^+$ Unless Noted Otherwise |
|---|---|---|---|
| 100001 | 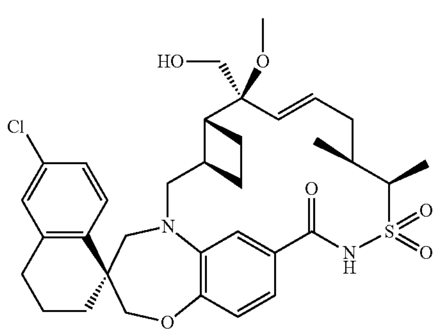 [SMILES: CO[C@@]1(CO)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 643.2 |

TABLE 2-continued

Examples Prepared by the General Methods

| Example Number | Structure | Name | MS Dat (M + 1)+ Unless Noted Otherwise |
|---|---|---|---|
| 100002 | 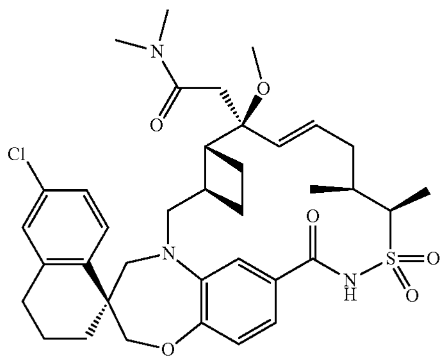 [SMILES: CO[C@@]1(CC(=O)N(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide | 698.2 |
| 100003 | 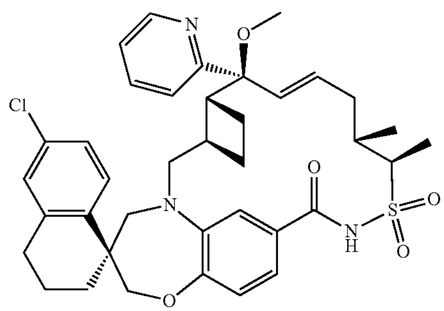 [SMILES: CO[C@@]1(c2ccccn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.2 |
| 100004 | 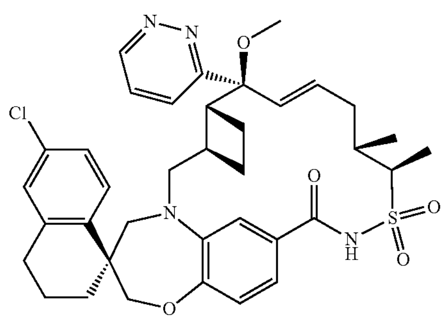 [SMILES: CO[C@@]1(c2cccnn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.2 |
| 100005 | 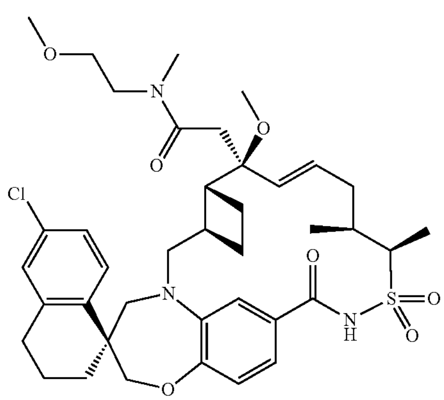 [SMILES: COCCN(C)C(=O)C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-methoxyethyl)-N-methylacetamide | 742.2 |

TABLE 2-continued

Examples Prepared by the General Methods

| Example Number | Structure | Name | MS Dat (M + 1)+ Unless Noted Otherwise |
|---|---|---|---|
| 100006 | 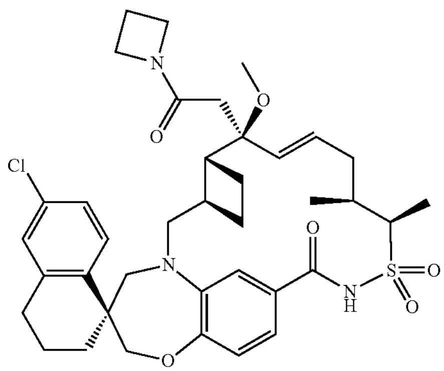 [SMILES: CO[C@@]1(CC(=O)N2CCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-7'-(2-(1-azetidinyl)-2-oxoethyl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.2 |
| 100007 | 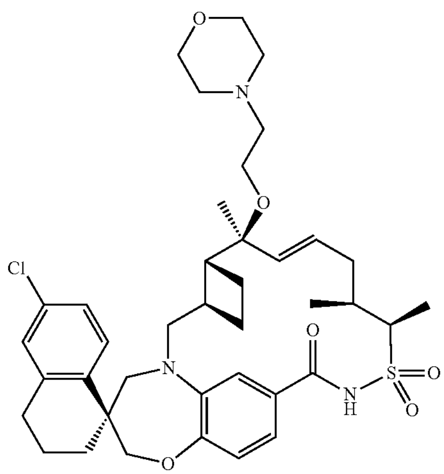 [SMILES: C[C@@H]1[C@@H](C)C/C=C/[C@](C)(OCCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.3 |
| 100008 | 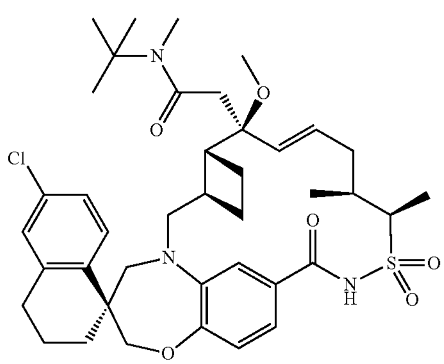 [SMILES: CO[C@@]1(CC(=O)N(C)C(C)(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-(2-methyl-2-propanyl)acetamide | 762.3 |

TABLE 2-continued

Examples Prepared by the General Methods

| Example Number | Structure | Name | MS Dat (M + 1)+ Unless Noted Otherwise |
|---|---|---|---|
| 100009 | 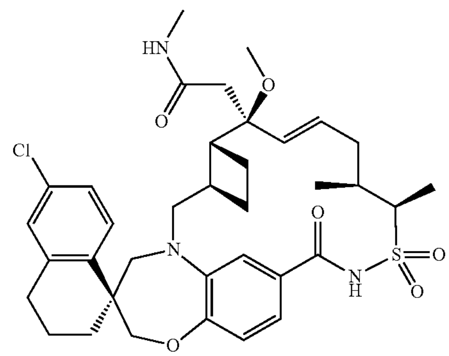 [SMILES: CNC(=O)C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methylacetamide | 684.2 |
| 100010 | 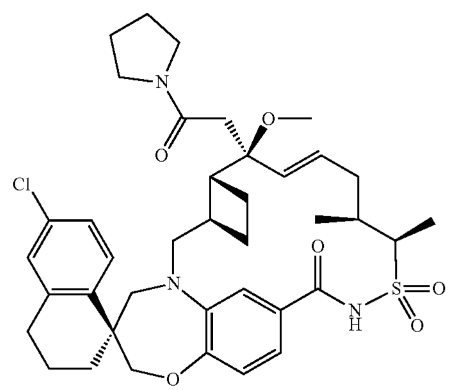 [SMILES: CO[C@@]1(CC(=O)N2CCCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |
| 100011 | 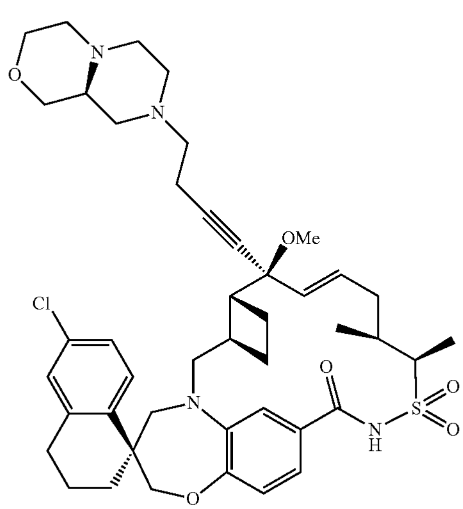 [SMILES: CO[C@@]1(C#CCCN2CCN3CCOC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(4-((9aS)-hexahydropyrazino[2,1-c][1,4]oxazin-8(1H)-yl)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 805.3 |

TABLE 2-continued

Examples Prepared by the General Methods

| Example Number | Structure | Name | MS Dat (M + 1)+ Unless Noted Otherwise |
|---|---|---|---|
| 100012 | 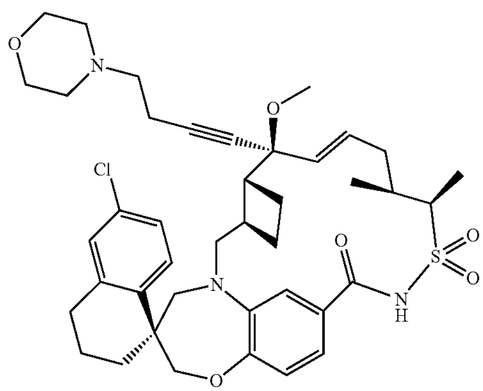 [SMILES: CO[C@@]1(C#CCCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 750.3 |
| | OR | OR | |
| | | (1S,3'R,6'R,7'R,8'E,11'S,12'R)-6-chloro-7'-methoxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100013 | 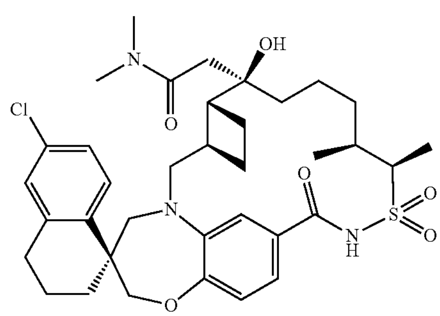 [SMILES: C[C@@H]1[C@@H](C)CCC[C@@](O)(CC(=O)N(C)C)[C@@H]2CC[C@H]2CN2C[C@@]3(CCCc4cc(Cl)ccc43)COc3ccc(cc32)C(=O)NS1(=O)=O] | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylacetamide | 686.2 |
| 100014 | 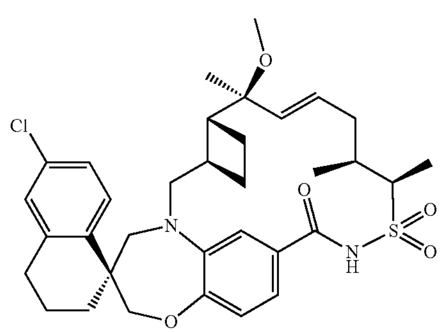 [SMILES: CO[C@@]1(C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 627.2 |

| Example Number | Structure | Name | MS Dat (M + 1)+ Unless Noted Otherwise |
|---|---|---|---|
| 100015 | 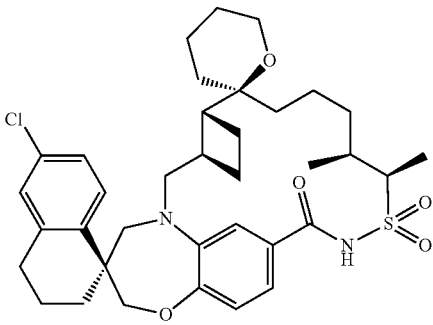 OR 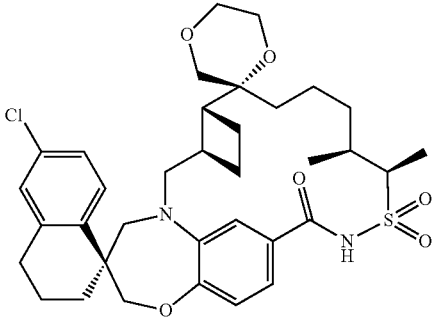 | (2S,3'R,6'R,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide OR (2R,3'R,6'R,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide | 657.2 |
| 100016 | 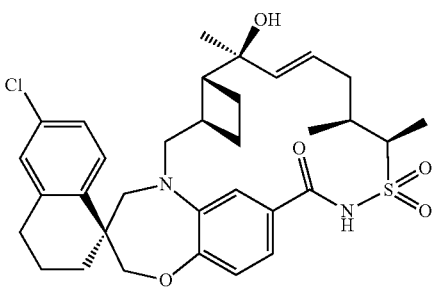 | (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 613.1 |
| 100017 | 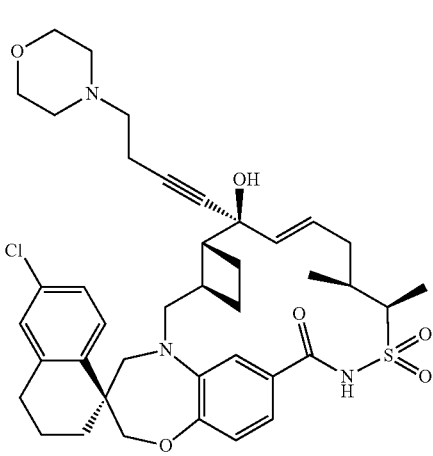 | (1S,3'R,6'R,7'S,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 736.2 |

TABLE 2-continued

Examples Prepared by the General Methods

| Example Number | Structure | Name | MS Dat (M + 1)+ Unless Noted Otherwise |
|---|---|---|---|
| | | (1S,3'R,6'R,7'R,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100018 | 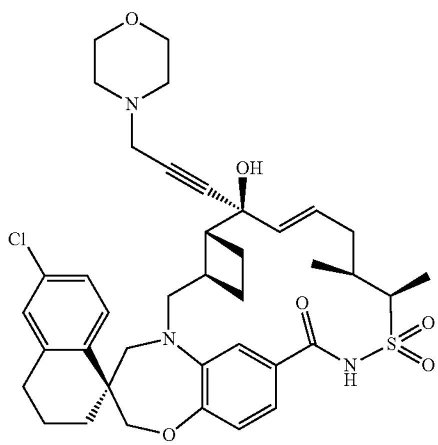 [SMILES: C[C@@H]1[C@@H](C)C/C=C/[C@@](O)(C#CCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 722.2 |
| | | (1S,3'R,6'R,7'R,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100019 | 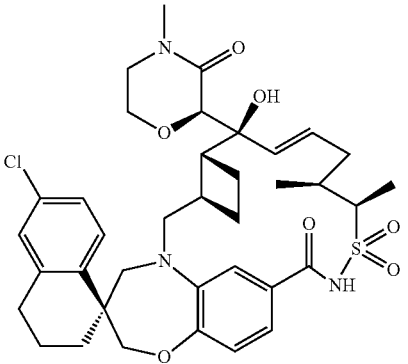 OR 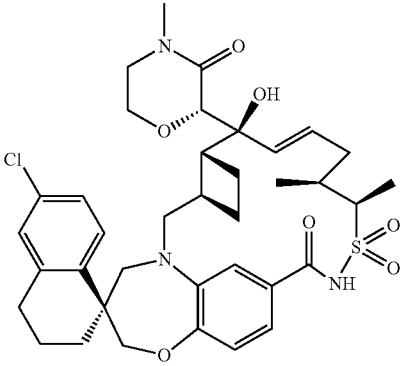 OR 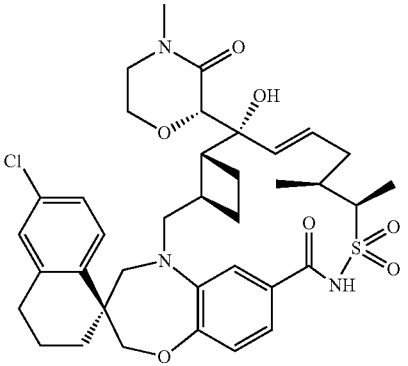 | (1S,3'R,6'R,7'S,8'E,11'S,12'R)-6-chloro-7'-hydroxy-11',12'-dimethyl-7'-((2R)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-hydroxy-11',12'-dimethyl-7'-((2S)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-((2S)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 712.2 |

TABLE 2-continued

Examples Prepared by the General Methods

| Example Number | Structure | Name | MS Dat (M + 1)+ Unless Noted Otherwise |
|---|---|---|---|
| | | (1S,3'R,6'R,7'R,8'E,11'S,12'R)-6-chloro-7'-hydroxy-11',12'-dimethyl-7'-((2R)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100020 | 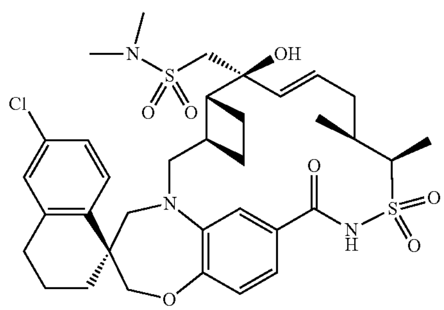 [SMILES: C[C@@H]1[C@@H](C)C/C=C/[C@@](O)(CS(=O)(=O)N(C)C)[C@@H]2CC[C@H]2CN2C[C@@]3(CCCc4cc(Cl)ccc43)COc3ccc(cc32)C(=O)NS1(=O)=O] | 1-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide | 720.2 |
| | | 1-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide | |
| 100021 | 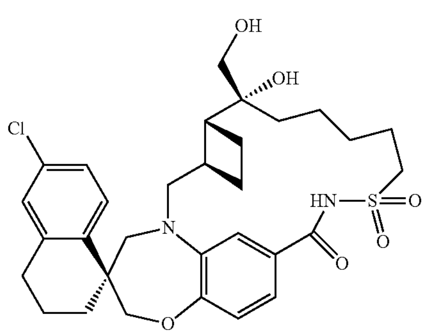 [SMILES: O=C1NS(=O)(=O)CCCCC[C@](O)(CO)[C@@H]2CC[C@H]2CN2C[C@@]3(CCCc4cc(Cl)ccc43)COc3ccc1cc32] | (1S,3'R,6'R,7'R)-6-chloro-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 602.9 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S)-6-chloro-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100022 | 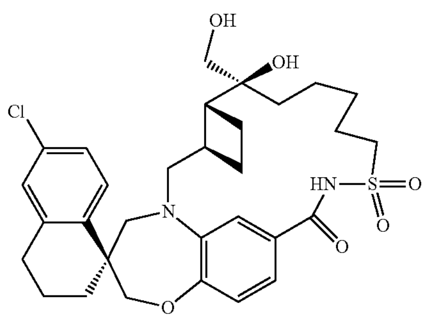 | (1S,3'R,6'R,7'S)-6-chloro-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 603.0 |
| | OR | OR (1S,3'R,6'R,7'R)-6-chloro-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100023 | 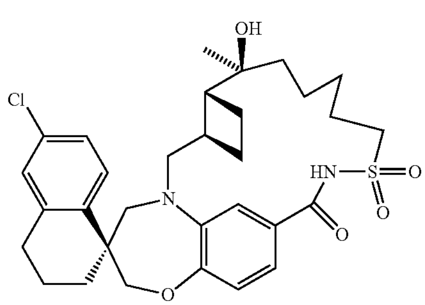 | (1S,3'R,6'R,7'S)-6-chloro-7'-hydroxy-7'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 587.2 |

TABLE 2-continued

Examples Prepared by the General Methods

| Example Number | Structure | Name | MS Dat (M + 1)+ Unless Noted Otherwise |
|---|---|---|---|
| | OR | OR | |
| 100024 | 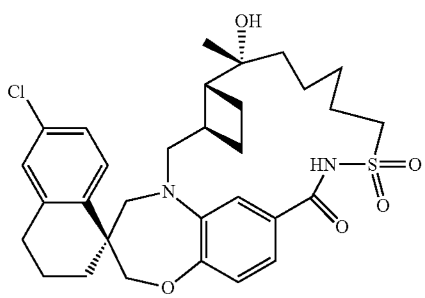 | (1S,3'R,6'R,7'R)-6-chloro-7'-hydroxy-7'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 587.3 |
| | OR | OR | |
| 100025 | 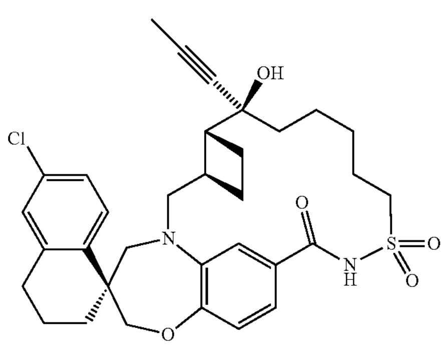 | (1S,3'R,6'R,7'S)-6-chloro-7'-hydroxy-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 611.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R)-6-chloro-7'-hydroxy-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100026 | 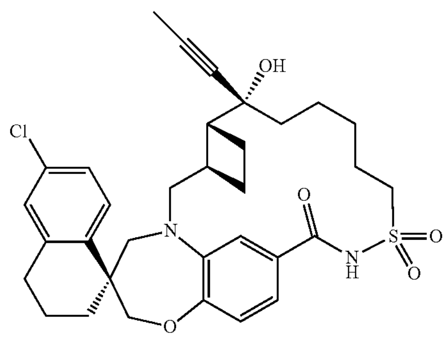 | (1S,3'R,6'R,7'R)-6-chloro-7'-hydroxy-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 611.0 |
| | OR | OR (1S,3'R,6'R,7'S)-6-chloro-7'-hydroxy-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100027 | 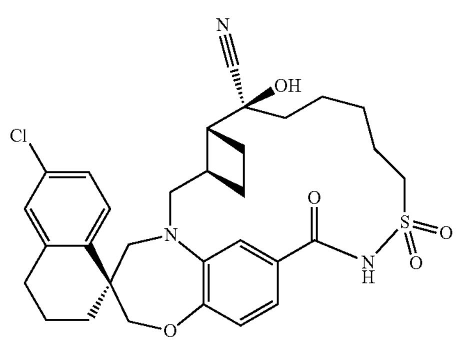 | (1S,3'R,6'R,7'S)-6-chloro-7'-hydroxy-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbonitrile 13',13'-dioxide | 598.0 |

| Example Number | Structure | Name | MS Dat (M + 1)+ Unless Noted Otherwise |
|---|---|---|---|
| | OR | OR (1S,3'R,6'R,7'R)-6-chloro-7'-hydroxy-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbonitrile 13',13'-dioxide | |
| 100028 | 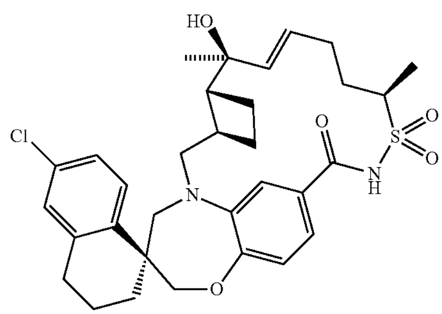 | (1S,3'R,6'R,7'S,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 599.2 |
| | OR | OR (1S,3'R,6'R,7'R,8'E,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR (1S,3'R,6'R,7'S,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100029 | 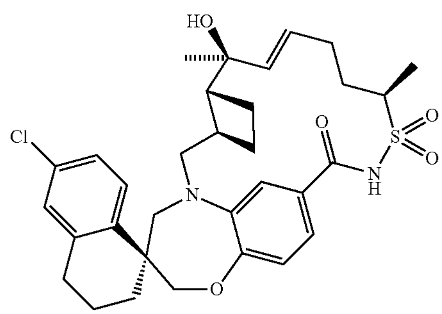 | (1S,3'R,6'R,7'S,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 599.2 |
| | OR | OR (1S,3'R,6'R,7'R,8'E,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR (1S,3'R,6'R,7'S,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR 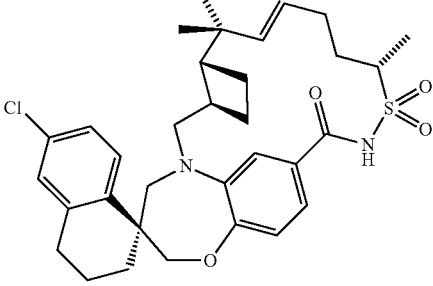 | OR (1S,3'R,6'R,7'R,8'E,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100030 | 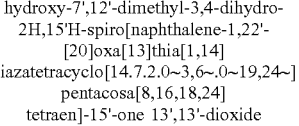 | (1S,3'R,6'R,7'R,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 599.2 |
| | OR 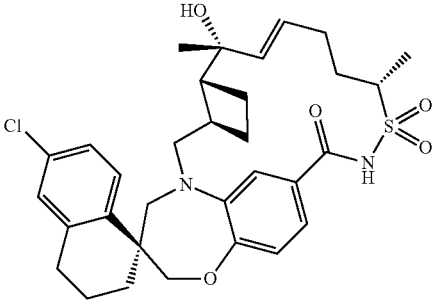 | OR (1S,3'R,6'R,7'S,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100031 | 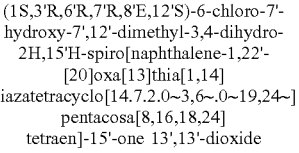 | (1S,3'R,6'R,7'S,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 601.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR (1S,3'R,6'R,7'S,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR (1S,3'R,6'R,7'R,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100032 | 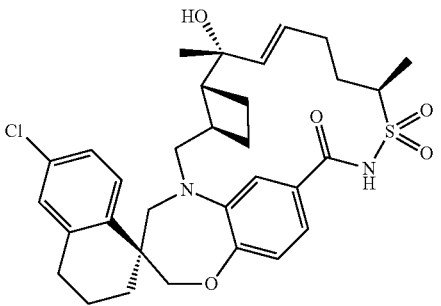 [SMILES: C[C@@H]1CC/C=C/[C@@](C)(O)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'one 13',13'-dioxide | 599.2 |
| | OR | OR | |
| | | (1S,3'R,6'R,7'S,8'E,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'R,8'E,12'S)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'S,8'E,12'R)-6-chloro-7'-hydroxy-7',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100033 | 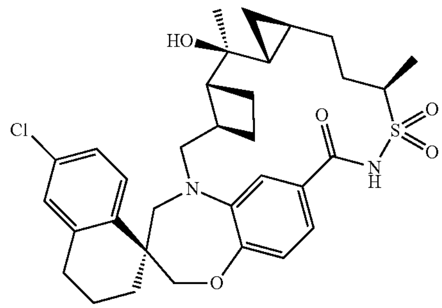 [SMILES: C[C@@H]1CC[C@@H]2C[C@H]2[C@](C)(O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'S,13'R)-6-chloro-7'-hydroxy-7',13'-dimethyl-3,4-dihydro-2H,16'H-spiro[naphthalene-1,23'-[21]oxa[14]thia[1,15]diazapentacyclo[15.7.2.0~3,6~.0~8,10~.0~20,25~]hexacosa[17,19,25]trien]-16'-one 14',14'-dioxide | 613.2 |
| | OR | OR | |
| |  | (1S,3'R,6'R,7'S,8'S,13'R)-6-chloro-7'-hydroxy-7',13'-dimethyl-3,4-dihydro-2H,16'H-spiro[naphthalene-1,23'-[21]oxa[14]thia[1,15]diazapentacyclo[15.7.2.0~3,6~.0~8,10~.0~20,25~]hexacosa[17,19,25]trien]-16'-one 14',14'-dioxide | |
| | OR | OR | |
| |  | (1S,3'R,6'R,7'R,8'R,10'R,13'R)-6-chloro-7'-hydroxy-7',13'-dimethyl-3,4-dihydro-2H,16'H-spiro[naphthalene-1,23'-[21]oxa[14]thia[1,15]diazapentacyclo[15.7.2.0~3,6~.0~8,10~.0~20,25~]hexacosa[17,19,25]trien]-16'-one 14',14'-dioxide | |
| | OR | OR | |
| | 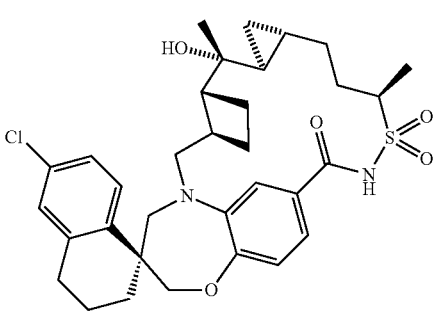 [SMILES: C[C@@H]1CC[C@H]2C[C@@H]2[C@@](C)(O)[C@@H]2CC[C@H]2CN2C[C@@]3(CCCc4cc(Cl)ccc43)COc3ccc(cc32)C(=O)NS1(=O)=O] | (1S,3'R,6'R,7'R,8'R,10'R,13'R)-6-chloro-7'-hydroxy-7',13'-dimethyl-3,4-dihydro-2H,16'H-spiro[naphthalene-1,23'-[21]oxa[14]thia[1,15]diazapentacyclo[15.7.2.0~3,6~.0~8,10~.0~20,25~]hexacosa[17,19,25]trien]-16'-one 14',14'-dioxide | |

TABLE 2-continued

Examples Prepared by the General Methods

| Example Number | Structure | Name | MS Dat (M + 1)+ Unless Noted Otherwise |
|---|---|---|---|
| 100034 | 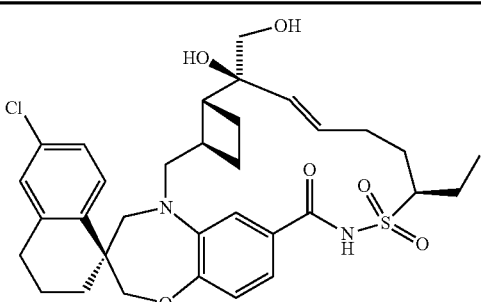<br><br>OR<br><br>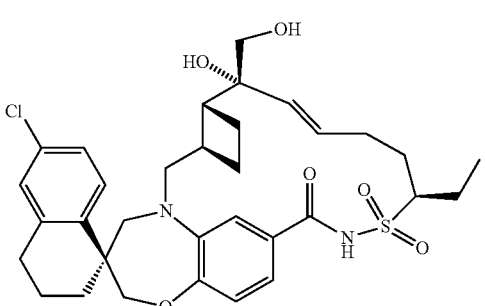 | (1S,3'R,6'R,7'S,8'E,12'R)-6-chloro-12'-ethyl-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,12'R)-6-chloro-12'-ethyl-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 629.0 |
| 100035 | 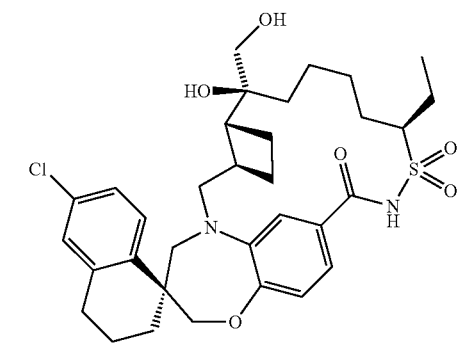 [SMILES: CC[C@@H]1CCCC[C@@](O)(CO)[C@@H]2CC[C@H]2CN2C[C@@]3(CCCc4cc(Cl)ccc43)COc3ccc(cc32)C(=O)NS1(=O)=O]<br><br>OR<br><br>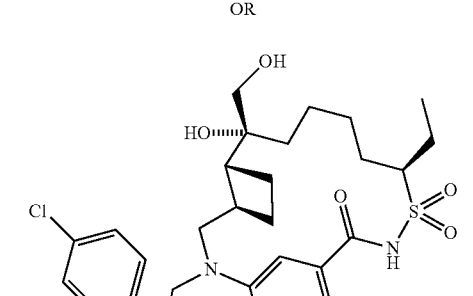 | (1S,3'R,6'R,7'S,12'R)-6-chloro-12'-ethyl-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,12'R)-6-chloro-12'-ethyl-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 631.1 |

TABLE 2-continued

Examples Prepared by the General Methods

| Example Number | Structure | Name | MS Dat (M + 1)+ Unless Noted Otherwise |
|---|---|---|---|
| 100036 | 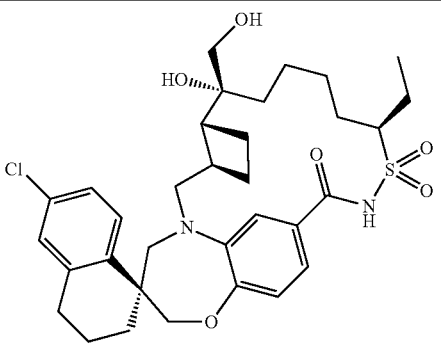<br><br>OR<br><br>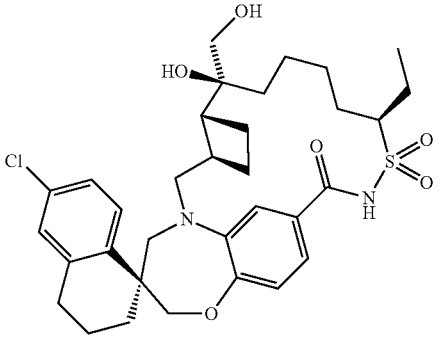 [SMILES: CC[C@@H]1CCCC[C@@](O)(CO)[C@@H]2CC[C@H]2CN2C[C@@]3(CCCc4cc(Cl)ccc43)COc3ccc(cc32)C(=O)NS1(=O)=O] | (1S,3'R,6'R,7'R,12'R)-6-chloro-12'-ethyl-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,12'R)-6-chloro-12'-ethyl-7'-hydroxy-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 631.1 |
| 100037 | 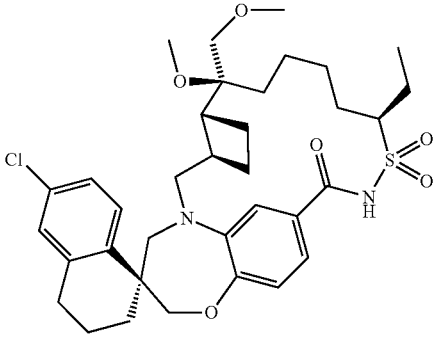 [SMILES: CC[C@@H]1CCCC[C@](COC)(OC)[C@@H]2CC[C@H]2CN2C[C@@]3(CCCc4cc(Cl)ccc43)COc3ccc(cc32)C(=O)NS1(=O)=O]<br><br>OR<br><br>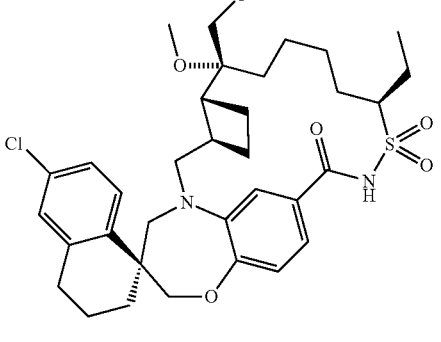 | (1S,3'R,6'R,7'S,12'R)-6-chloro-12'-ethyl-7'-methoxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,12'R)-6-chloro-12'-ethyl-7'-methoxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.1 |

TABLE 2-continued

Examples Prepared by the General Methods

| Example Number | Structure | Name | MS Dat (M + 1)+ Unless Noted Otherwise |
|---|---|---|---|
| 100038 | 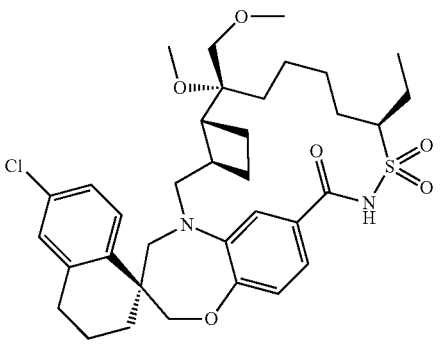 [SMILES: CC[C@@H]1CCCC[C@@](COC)(OC)[C@@H]2CC[C@H]2CN2C[C@@]3(CCCc4cc(Cl)ccc43)COc3ccc(cc32)C(=O)NS1(=O)=O] | (1S,3'R,6'R,7'R,12'R)-6-chloro-12'-ethyl-7'-methoxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,12'R)-6-chloro-12'-ethyl-7'-methoxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.1 |
| 100039 | 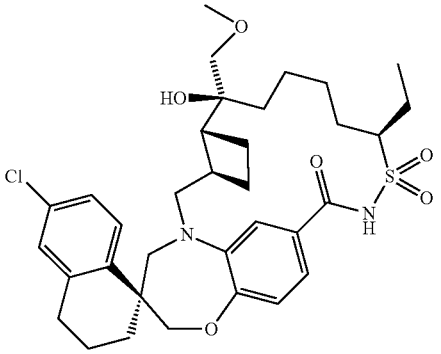 [SMILES: CC[C@@H]1CCCC[C@@](O)(COC)[C@@H]2CC[C@H]2CN2C[C@@]3(CCCc4cc(Cl)ccc43)COc3ccc(cc32)C(=O)NS1(=O)=O] | (1S,3'R,6'R,7'S,12'R)-6-chloro-12'-ethyl-7'-hydroxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,12'R)-6-chloro-12'-ethyl-7'-hydroxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.1 |

TABLE 2-continued

Examples Prepared by the General Methods

| Example Number | Structure | Name | MS Dat (M + 1)+ Unless Noted Otherwise |
|---|---|---|---|
| 100040 | 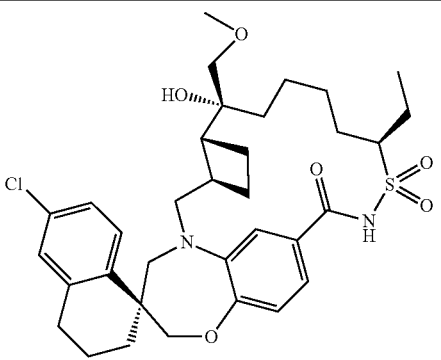<br><br>OR<br><br>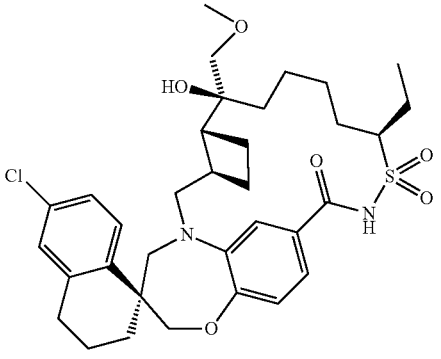 [SMILES: CC[C@@H]1CCCC[C@@](O)(COC)[C@@H]2CC[C@H]2CN2C[C@@]3(CCCc4cc(Cl)ccc43)COc3ccc(cc32)C(=O)NS1(=O)=O] | (1S,3'R,6'R,7'R,12'R)-6-chloro-12'-ethyl-7'-hydroxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,12'R)-6-chloro-12'-ethyl-7'-hydroxy-7'-(methoxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.1 |
| 100041 | 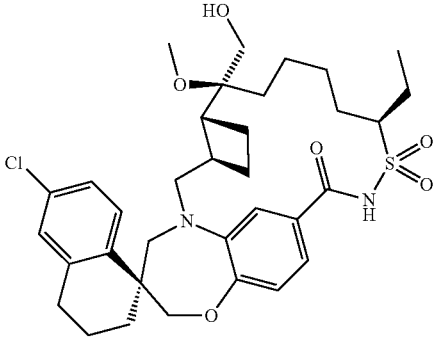 [SMILES: CC[C@@H]1CCCC[C@](CO)(OC)[C@@H]2CC[C@H]2CN2C[C@@]3(CCCc4cc(Cl)ccc43)COc3ccc(cc32)C(=O)NS1(=O)=O]<br><br>OR<br><br>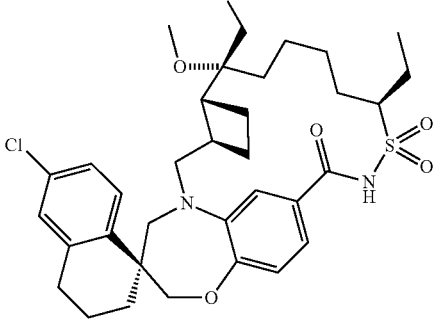 | (1S,3'R,6'R,7'S,12'R)-6-chloro-12'-ethyl-7'-(hydroxymethyl)-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,12'R)-6-chloro-12'-ethyl-7'-(hydroxymethyl)-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.1 |

TABLE 2-continued

Examples Prepared by the General Methods

| Example Number | Structure | Name | MS Dat (M + 1)+ Unless Noted Otherwise |
|---|---|---|---|
| 100042 | 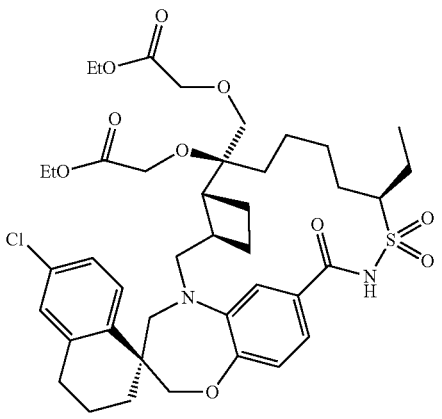 [SMILES: CCOC(=O)COC[C@]1(OCC(=O)OCC)CCCC[C@@H](CC)S(=O)(=O)NC(=O)c2ccc3c(c2)N(C[C@@H]2CC[C@H]21)C[C@@]1(CCCc2cc(Cl)ccc21)CO3]<br><br>OR<br><br>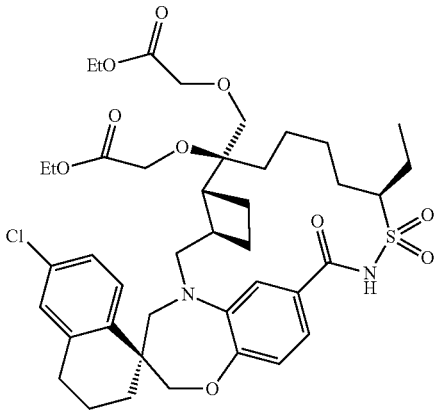 [SMILES: CCOC(=O)COC[C@]1(OCC(=O)OCC)CCCC[C@@H](CC)S(=O)(=O)NC(=O)c2ccc3c(c2)N(C[C@@H]2CC[C@H]21)C[C@@]1(CCCc2cc(Cl)ccc21)CO3] | ethyl (((1S,3'R,6'R,7'S,12'R)-6-chloro-7'-(2-ethoxy-2-oxoethoxy)-12'-ethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methoxy)acetate<br><br>OR<br><br>ethyl (((1S,3'R,6'R,7'R,12'R)-6-chloro-7'-(2-ethoxy-2-oxoethoxy)-12'-ethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methoxy)acetate | 803.1 |
| 100043 | 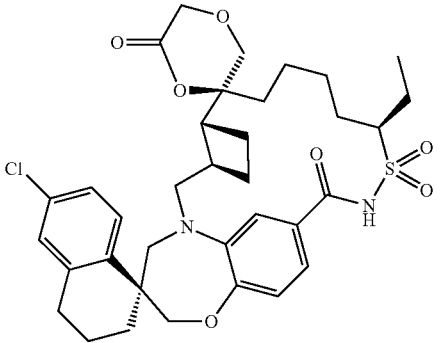 [SMILES: CC[C@@H]1CCCC[C@@]2(COCC(=O)O2)[C@@H]2CC[C@H]2CN2C[C@@]3(CCCc4cc(Cl)ccc43)COc3ccc(cc32)C(=O)NS1(=O)=O] | (2S,3'R,6'R,12'R,22'S)-6''-chloro-12'-ethyl-3'',4''-dihydro-2''H,6H,15'H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalene]-6,15'-dione 13',13'-dioxide | 671.0 |

TABLE 2-continued

Examples Prepared by the General Methods

| Example Number | Structure | Name | MS Dat (M + 1)+ Unless Noted Otherwise |
|---|---|---|---|
| | OR | OR (2R,3'R,6'R,12'R,22'S)-6''-chloro-12'-ethyl-3'',4''-dihydro-2''H,6H,15'H-dispiro[1,4-dioxane-2,7'-[20]oxa[13]thia[1,14]diazatetracyclo[14.7.2.0~3,6~.0~19,24~]pentacosa[16,18,24]triene-22',1'''-naphthalene]-6,15'-dione 13',13'-dioxide | |
| 100044 | 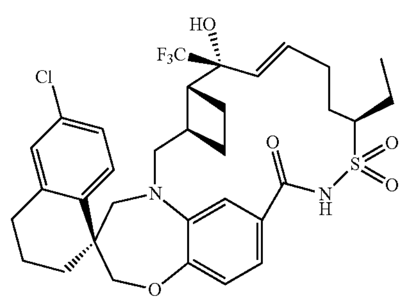 | (1S,3'R,6'R,7'R,8'E,12'R)-6-chloro-12'-ethyl-7'-hydroxy-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.0 |
| | OR | OR (1S,3'R,6'R,7'S,8'E,12'R)-6-chloro-12'-ethyl-7'-hydroxy-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100045 | 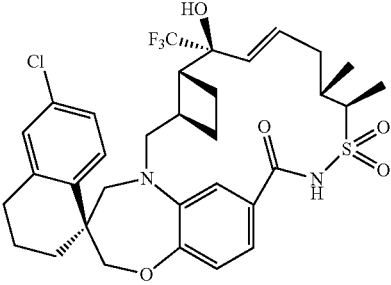 [SMILES: C[C@@H]1[C@@H](C)C/C=C/[C@@](O)(C(F)(F)F)[C@@H]2CC[C@H]2CN2C[C@@]3(CCCc4cc(Cl)ccc43)COc3ccc(cc32)C(=O)NS1(=O)=O]<br>OR<br>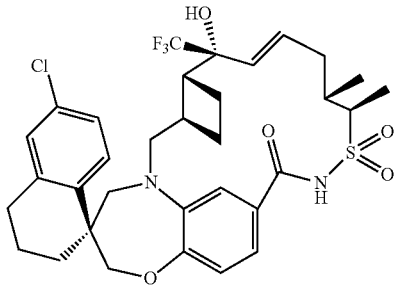 [SMILES: C[C@@H]1[C@@H](C)C/C=C/[C@](O)(C(F)(F)F)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br>OR<br>(1S,3'R,6'R,7'R,8'E,11'S,12'R)-6-chloro-7'-hydroxy-11',12'-dimethyl-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.3 |
| 100046 | 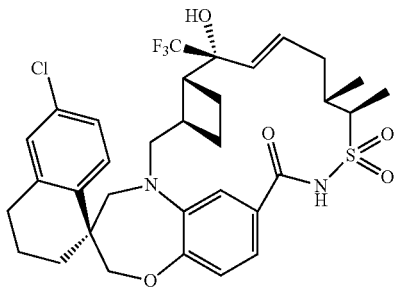 [SMILES: C[C@@H]1[C@@H](C)C/C=C/[C@](O)(C(F)(F)F)[C@@H]2CC[C@H]2CN2C[C@@]3(CCCc4cc(Cl)ccc43)COc3ccc(cc32)C(=O)NS1(=O)=O]<br>OR<br>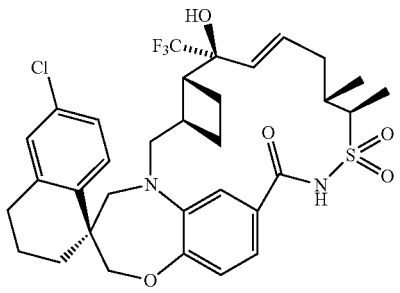 [SMILES: C[C@@H]1[C@@H](C)C/C=C/[C@@](O)(C(F)(F)F)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br>OR<br>(1S,3'R,6'R,7'S,8'E,11'S,12'R)-6-chloro-7'-hydroxy-11',12'-dimethyl-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.3 |

TABLE 2-continued

Examples Prepared by the General Methods

| Example Number | Structure | Name | MS Dat (M + 1)+ Unless Noted Otherwise |
|---|---|---|---|
| 100047 | 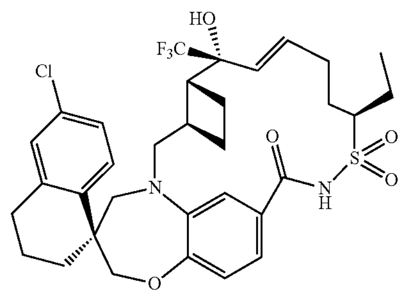 [SMILES: CC[C@@H]1CC/C=C/[C@](O)(C(F)(F)F)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,12'R)-6-chloro-12'-ethyl-7'-hydroxy-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.0 |
| | OR | OR | |
| | | (1S,3'R,6'R,7'S,8'E,12'R)-6-chloro-12'-ethyl-7'-hydroxy-7'-(trifluoromethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13 '-dioxide | |
| 100048 | 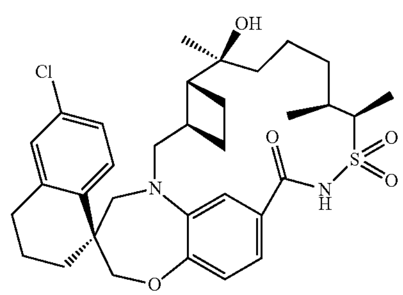 [SMILES: C[C@@H]1[C@@H](C)CCC[C@](C)(O)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 615.2 |
| | OR | OR | |
| | | (1S,3'R,6'R,7'S,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100049 | 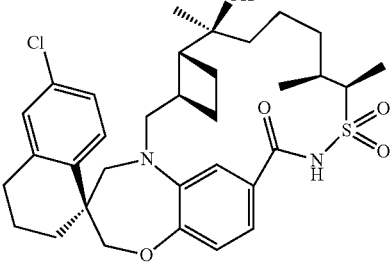<br>OR<br>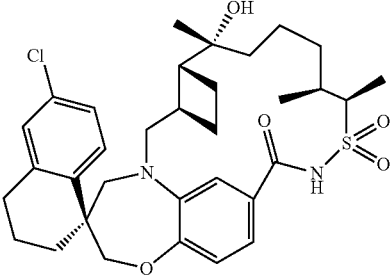 [SMILES: C[C@@H]1[C@@H](C)CCC[C@@](C)(O)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br>OR<br>(1S,3'R,6'R,7'R,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 615.2 |
| 100050 | 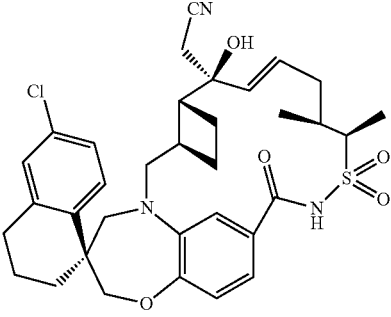 [SMILES: C[C@@H]1[C@@H](C)C/C=C/[C@@](O)(CC#N)[C@@H]2CC[C@H]2CN2C[C@@]3(CCCc4cc(Cl)ccc43)COc3ccc(cc32)C(=O)NS1(=O)=O]<br>OR<br>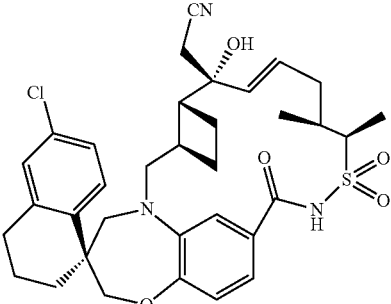 | ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetonitrile<br>OR<br>((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetonitrile | 638.3 |

TABLE 2-continued

Examples Prepared by the General Methods

| Example Number | Structure | Name | MS Dat (M + 1)+ Unless Noted Otherwise |
|---|---|---|---|
| 100051 | 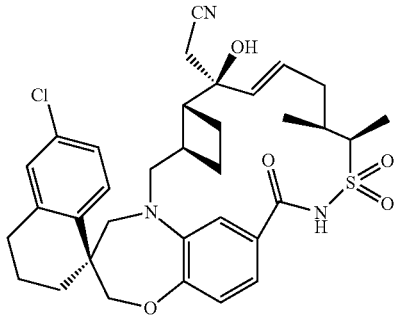 [SMILES: C[C@@H]1[C@@H](C)C/C=C/[C@@](O)(CC#N)[C@@H]2CC[C@H]2CN2C[C@@]3(CCCc4cc(Cl)ccc43)COc3ccc(cc32)C(=O)NS1(=O)=O]<br>OR<br>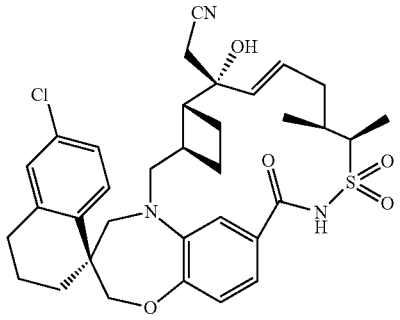 [SMILES: C[C@@H]1[C@@H](C)C/C=C/[C@](O)(CC#N)[C@@H]2CC[C@H]2CN2C[C@@]3(CCCc4cc(Cl)ccc43)COc3ccc(cc32)C(=O)NS1(=O)=O] | ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetonitrile<br>OR<br>((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetonitrile | 638.2 |
| 100052 | 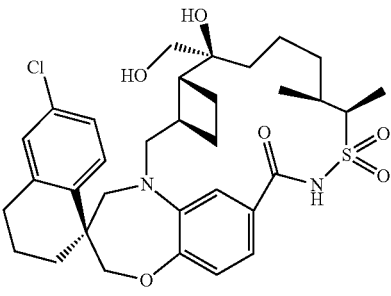<br>OR<br>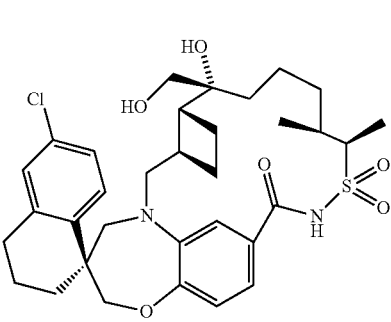 [SMILES: C[C@@H]1[C@@H](C)CCC[C@](O)(CO)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br>OR<br>(1S,3'R,6'R,7'S,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 631.2 |

TABLE 2-continued

Examples Prepared by the General Methods

| Example Number | Structure | Name | MS Dat (M + 1)+ Unless Noted Otherwise |
|---|---|---|---|
| 100053 | 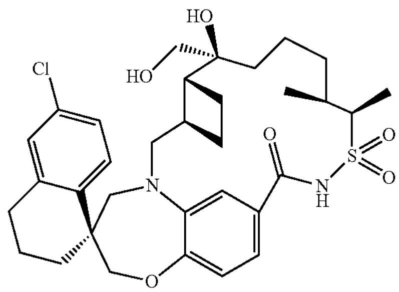 [SMILES: C[C@@H]1[C@@H](C)CCC[C@@](O)(CO)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 631.3 |
| | OR | OR | |
| | | (1S,3'R,6'R,7'R,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100054 | 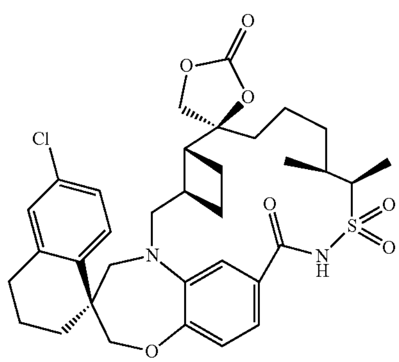 [SMILES: C[C@@H]1[C@@H](C)CCC[C@@]2(COC(=O)O2)[C@@H]2CC[C@H]2CN2C[C@@]3(CCCc4cc(Cl)ccc43)COc3ccc(cc32)C(=O)NS1(=O)=O] | (3'R,4S,6'R,11'S,12'R,22'S)-6''-chloro-11',12'-dimethyl-3'',4''-dihydro-2''H,15'H-dispiro[1,3-dioxolane-4,7'-[20]oxa[13]thia[1,14]diazatetracyclo[14.7.2.0~3,6~.0~19,24~]pentacosa[16,18,24]triene-22',1''-naphthalene]-2,15'-dione 13',13'-dioxide | 657.3 |
| | OR | OR | |
| | | (3'R,4R,6'R,11'S,12'R,22'S)-6''-chloro-11',12'-dimethyl-3'',4''-dihydro-2''H,15'H-dispiro[1,3-dioxolane-4,7'-[20]oxa[13]thia[1,14]diazatetracyclo[14.7.2.0~3,6~.0~19,24~]pentacosa[16,18,24]triene-22',1''-naphthalene]-2,15'-dione 13',13'-dioxide | |

TABLE 2-continued

Examples Prepared by the General Methods

| Example Number | Structure | Name | MS Dat (M + 1)+ Unless Noted Otherwise |
|---|---|---|---|
| 100055 | 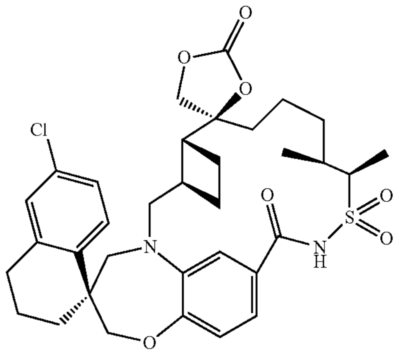 [SMILES: C[C@@H]1[C@@H](C)CCC[C@@]2(COC(=O)O2)[C@@H]2CC[C@H]2CN2C[C@@]3(CCCc4cc(Cl)ccc43)COc3ccc(cc32)C(=O)NS1(=O)=O] | (3'R,4R,6'R,11'S,12'R,22'S)-6''-chloro-11',12'-dimethyl-3'',4''-dihydro-2''H,15'H-dispiro[1,3-dioxolane-4,7'-[20]oxa[13]thia[1,14]diazatetracyclo[14.7.2.0~3,6~.0~19,24~]pentacosa[16,18,24]triene-22',1''-naphthalene]-2,15'-dione 13',13'-dioxide | 657.3 |
|  | OR | OR |  |
|  |  | (3'R,4S,6'R,11'S,12'R,22'S)-6''-chloro-11',12'-dimethyl-3'',4''-dihydro-2''H,15'H-dispiro[1,3-dioxolane-4,7'-[20]oxa[13]thia[1,14]diazatetracyclo[14.7.2.0~3,6~.0~19,24~]pentacosa[16,18,24]triene-22',1''-naphthalene]-2,15'-dione 13',13'-dioxide |  |
| 100056 | 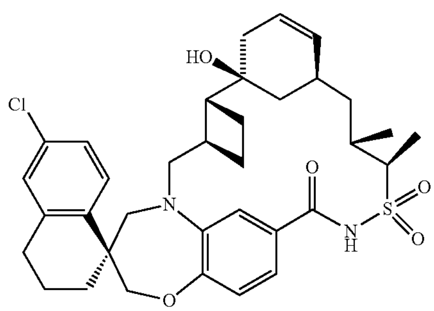 | (1S,3'R,6'R,7'S,11'S,13'S,14'R)-6-chloro-7'-hydroxy-13',14'-dimethyl-3,4-dihydro-2H,17'H-spiro[naphthalene-1,24'-[22]oxa[15]thia[1,16]diazapentacyclo[16.7.2.1~7,11~.0~3,6~.0~21,26~]octacosa[9,18,20,26]tetraen]-17'-one 15',15'-dioxide | 639.1 |
|  | OR | OR |  |
|  |  | (1S,3'R,6'R,7'R,11'S,13'S,14'R)-6-chloro-7'-hydroxy-13',14'-dimethyl-3,4-dihydro-2H,17'H-spiro[naphthalene-1,24'-[22]oxa[15]thia[1,16]diazapentacyclo[16.7.2.1~7,11~.0~3,6~.0~21,26~]octacosa[9,18,20,26]tetraen]-17'-one 15',15'-dioxide |  |

TABLE 2-continued

Examples Prepared by the General Methods

| Example Number | Structure | Name | MS Dat (M + 1)+ Unless Noted Otherwise |
|---|---|---|---|
| 100057 | 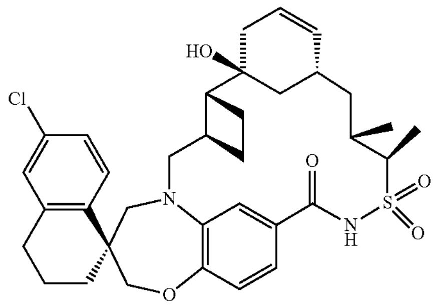 | (1S,3'R,6'R,7'S,11'R,13'S,14'R)-6-chloro-7'-hydroxy-13',14'-dimethyl-3,4-dihydro-2H,17'H-spiro[naphthalene-1,24'-[22]oxa[15]thia[1,16]diazapentacyclo[16.7.2.1~7,11~.0~3,6~.0~21,26~]octacosa[9,18,20,26]tetraen]-17'-one 15',15'-dioxide | 639.1 |
| 100058 | 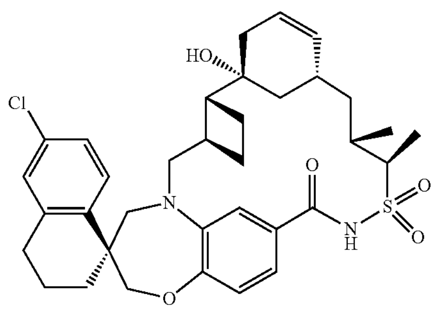 [SMILES: C[C@@H]1[C@@H](C)C[C@H]2C=CC[C@@](O)(C2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,13'S,14'R)-6-chloro-7'-hydroxy-13',14'-dimethyl-3,4-dihydro-2H,17'H-spiro[naphthalene-1,24'-[22]oxa[15]thia[1,16]diazapentacyclo[16.7.2.1~7,11~.0~3,6~.0~21,26~]octacosa[9,18,20,26]tetraen]-17'-one 15',15'-dioxide | 639.0 |
| 100059 | OR | 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methylpropanenitrile OR 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methylpropanenitrile | 666.3 |

TABLE 2-continued

Examples Prepared by the General Methods

| Example Number | Structure | Name | MS Dat (M + 1)+ Unless Noted Otherwise |
|---|---|---|---|
| 100060 | 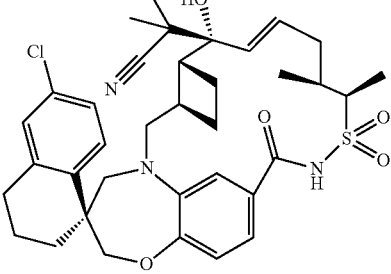<br><br>OR<br><br>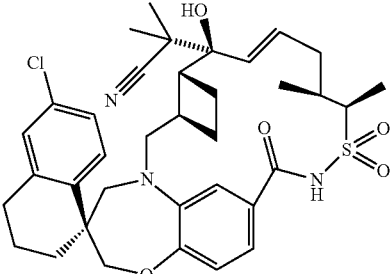 | 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methylpropanenitrile<br><br>OR<br><br>2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methylpropanenitrile | 666.3 |
| 100061 | 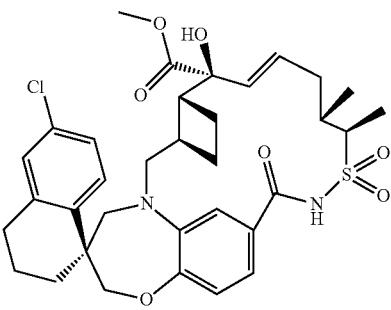 [SMILES: COC(=O)[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]<br><br>OR<br><br>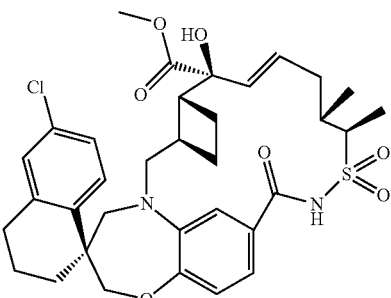 | methyl (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carboxylate 13',13'-dioxide<br><br>OR<br><br>methyl (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carboxylate 13',13'-dioxide | 657.3 |

TABLE 2-continued

Examples Prepared by the General Methods

| Example Number | Structure | Name | MS Dat (M + 1)+ Unless Noted Otherwise |
|---|---|---|---|
| 100062 | 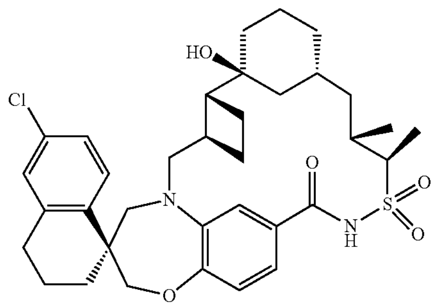 | (1S,3'R,6'R,7'S,11'R,13'S,14'R)-6-chloro-7'-hydroxy-13',14'-dimethyl-3,4-dihydro-2H,17'H-spiro[naphthalene-1,24'-[22]oxa[15]thia[1,16]diazapentacyclo[16.7.2.1~7,11~.0~3,6~.0~21,26~]octacosa[18,20,26]trien]-17'-one 15',15'-dioxide | 641.1 |
| 100063 | 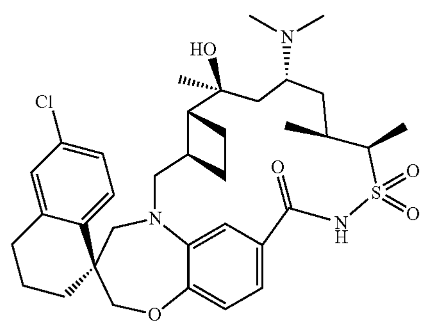 [SMILES: C[C@@H]1[C@@H](C)C[C@@H](N(C)C)C[C@](C)(O)[C@@H]2CC[C@H]2CN2C[C@@]3(CCCc4cc(Cl)ccc43)COc3ccc(cc32)C(=O)NS1(=O)=O] | (1S,3'R,6'R,7'S,9'R,11'S,12'R)-6-chloro-9'-(dimethylamino)-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 657.8 |
| | OR | OR | |
| | | (1S,3'R,6'R,7'S,9'S,11'S,12'R)-6-chloro-9'-(dimethylamino)-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR 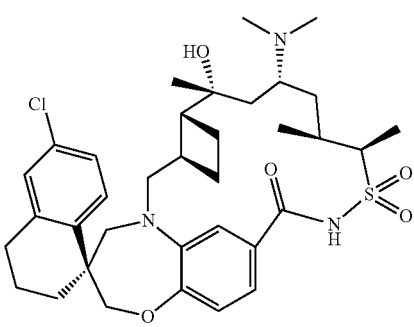 | OR (1S,3'R,6'R,7'R,9'R,11'S,12'R)-6-chloro-9'-(dimethylamino)-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR 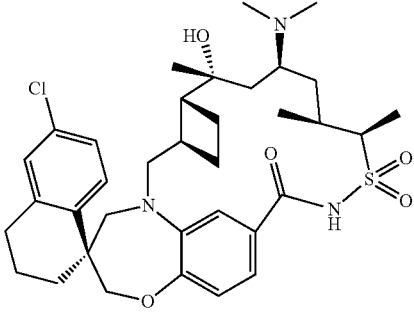 | OR (1S,3'R,6'R,7'R,9'S,11'S,12'R)-6-chloro-9'-(dimethylamino)-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100064 | 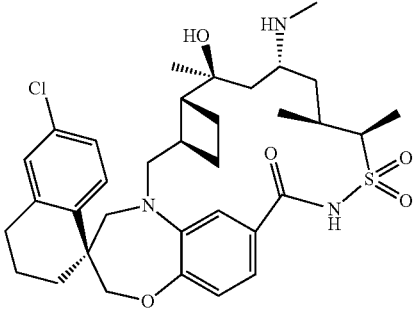 | (1S,3'R,6'R,7'S,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 644.2 |
| | OR 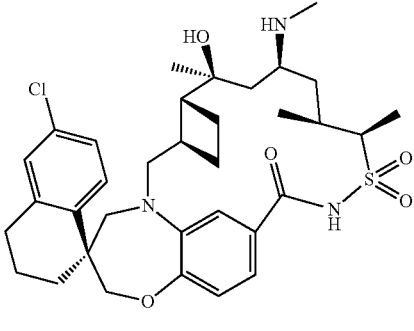 | OR (1S,3'R,6'R,7'S,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR 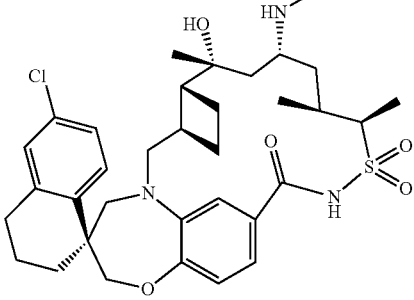 | OR (1S,3'R,6'R,7'R,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR 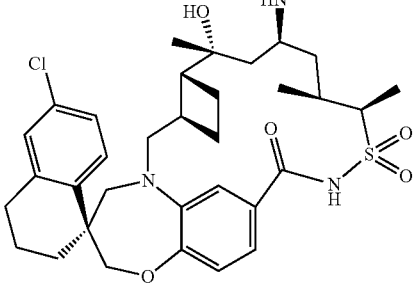 | OR (1S,3'R,6'R,7'R,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100065 | 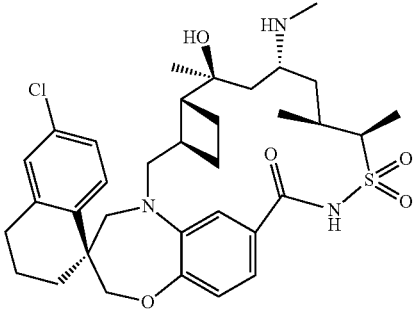 | (1S,3'R,6'R,7'S,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 644.2 |
| | OR 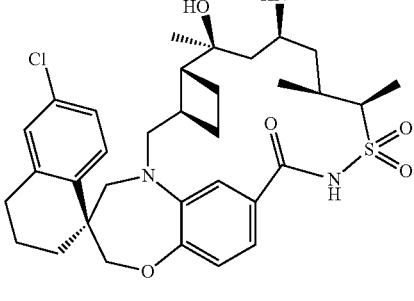 | OR (1S,3'R,6'R,7'S,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR (1S,3'R,6'R,7'R,9'S,11'S,12'R)-6-chloro-7'-hydroxy-7',11',12'-trimethyl-9'-(methylamino)-3,4-dihydro-2H, 15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100066 | 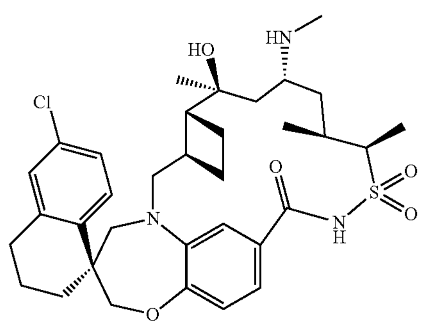 | (1S,3'R,6'R,7'S,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 643.8 |
| | OR | OR (1S,3'R,6'R,7'S,9'S,11'S,12'R)-6-chloro-7'-hydroxy-7,11,12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR 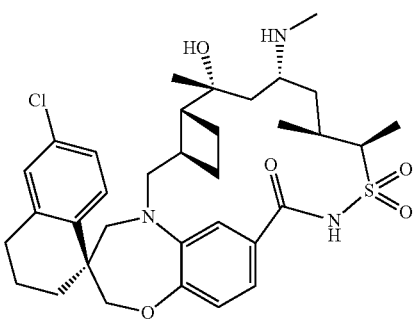 | OR (1S,3'R,6'R,7'R,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR 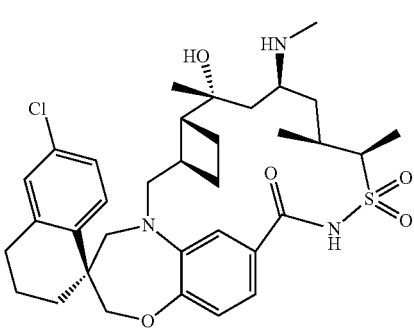 | OR (1S,3'R,6'R,7'R,9'S,11'S,12'R)-6-chloro-7'-hydroxy-7',11',12'-trimethyl-9'-(methylamino)-3,4-dihydro-2H,15'H-spiro[naphthalene-1,22'-[2.0]oxa[13]thia[1,14]diazatetracyclo[14.7.2.0~3,6~.0~19,24~]pentacosa[16,18,24]trien]-15'-one 13',13'-dioxide | |
| 100067 | 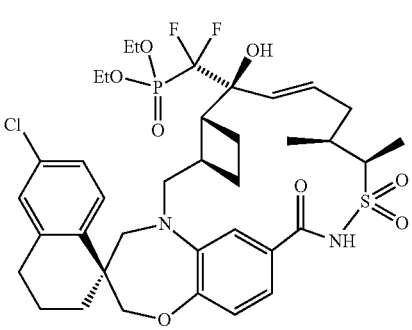 | diethyl (((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)methyl)phosphonate | 785.2 |
| | OR 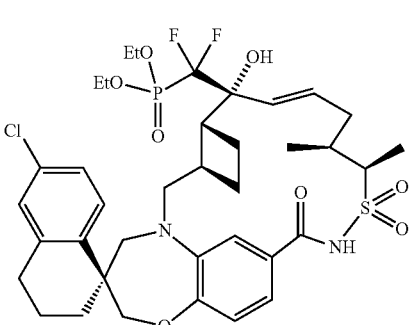 | OR diethyl (((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)methyl)phosphonate | |

TABLE 2-continued

Examples Prepared by the General Methods

| Example Number | Structure | Name | MS Dat (M + 1)+ Unless Noted Otherwise |
|---|---|---|---|
| 100068 | 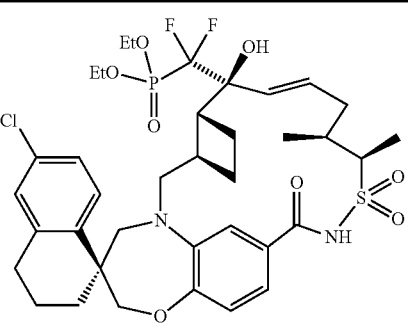 OR 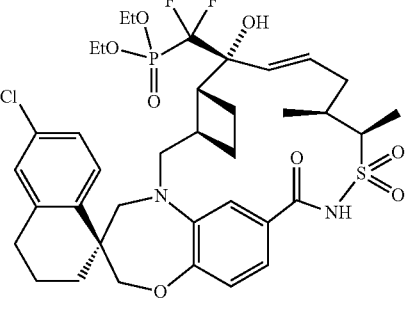 | diethyl (((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)methyl)phosphonate OR diethyl (((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)methyl)phosphonate | 785.2 |
| 100069 | 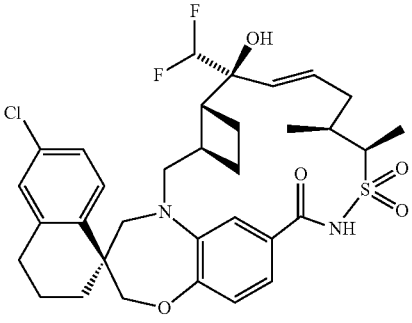 OR 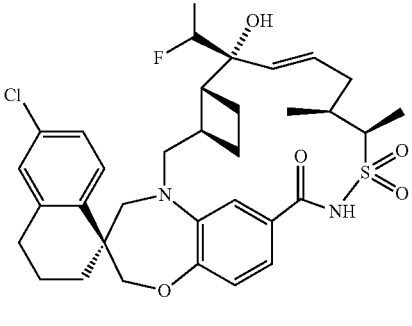 | (1S,3'R,6'R,7'S,8'E,11'S,12'R)-6-chloro-7'-(difluoromethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-(difluoromethyl)-7'-hydroxy-11',12'-dimethyl-3,4-dihydro-2H,15'H-spiro[naphthalene-1,22'-[20]oxa[13]thia[1,14]diazatetracyclo[14.7.2.0~.0~19,24~]pentacosa[16,18,24]tetraen]-15'-one 13',13'-dioxide | 649.3 |

TABLE 2-continued

Examples Prepared by the General Methods

| Example Number | Structure | Name | MS Dat (M + 1)+ Unless Noted Otherwise |
|---|---|---|---|
| 100070 | 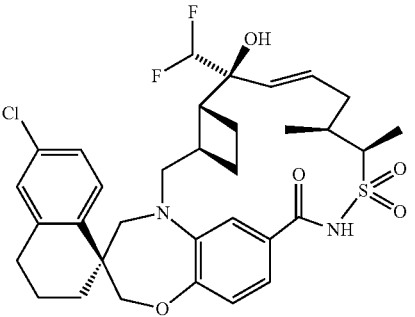 [SMILES: C[C@@H]1[C@@H](C)C/C=C/[C@@](O)(C(F)F)[C@@H]2CC[C@H]2CN2C[C@@]3(CCCc4cc(Cl)ccc43)COc3ccc(cc32)C(=O)NS1(=O)=O]<br>OR<br>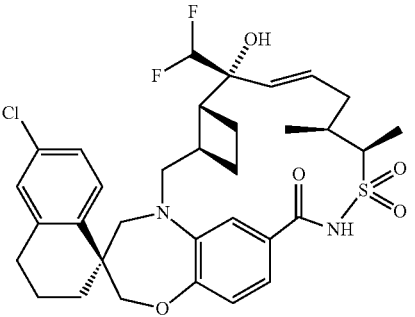 [SMILES: C[C@@H]1[C@@H](C)C/C=C/[C@](O)(C(F)F)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-(difluoromethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-(difluoromethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 649.3 |
| 100071 | 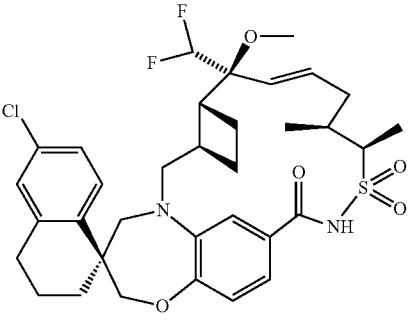 [SMILES: CO[C@@]1(C(F)F)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]<br>OR<br>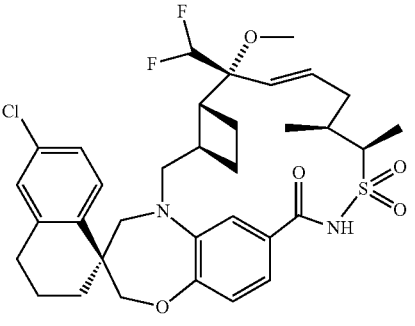 [SMILES: CO[C@]1(C(F)F)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(difluoromethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-(difluoromethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 663.0 |

TABLE 2-continued

Examples Prepared by the General Methods

| Example Number | Structure | Name | MS Dat (M + 1)+ Unless Noted Otherwise |
|---|---|---|---|
| 100072 | 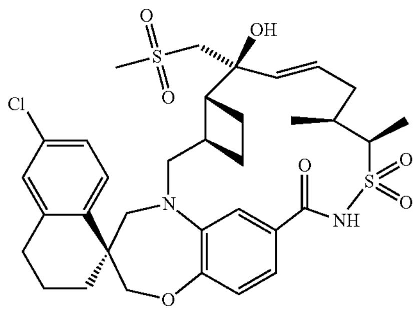 [SMILES: C[C@@H]1[C@@H](C)C/C=C/[C@@](O)(CS(C)(=O)=O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.1 |
| | OR | OR | |
| | | (1S,3'R,6'R,7'R,8'E,11'S,12'R)-6-chloro-7'-hydroxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100073 | 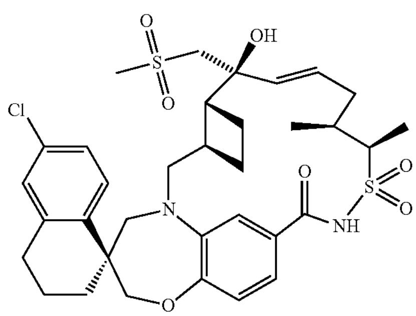 [SMILES: C[C@@H]1[C@@H](C)C/C=C/[C@@](O)(CS(C)(=O)=O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.0 |
| | OR | OR | |
| | | (1S,3'R,6'R,7'R,8'E,11'S,12'R)-6-chloro-7'-hydroxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100074 | | (1S,3'R,6'R,7'S,8'E,11'S,12'R)-6-chloro-7'-hydroxy-11',12'-dimethyl-7'-(((S)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 675.0 |
| | AND | AND | |
| | | (1S,3'R,6'R,7'S,8'E,11'S,12'R)-6-chloro-7'-hydroxy-11',12'-dimethyl-7'-(((R)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'R,8'E,11'S,12'R)-6-chloro-7'-hydroxy-11',12'-dimethyl-7'-(((S)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | AND | AND | |
| | | (1S,3'R,6'R,7'R,8'E,11'S,12'R)-6-chloro-7'-hydroxy-11',12'-dimethyl-7'-(((R)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100075 | 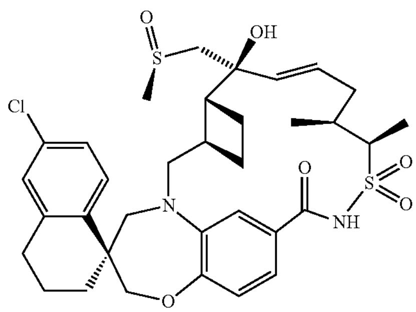 [SMILES: C[C@@H]1[C@@H](C)C/C=C/[C@@](O)(C[S@@](C)=O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(((S)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 675.3 |
| | AND | AND | |
| | | (1S,3'R,6'R,7'S,8'E,11'S,12'R)-6-chloro-7'-hydroxy-11',12'-dimethyl-7'-(((R)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'R,8'E,11'S,12'R)-6-chloro-7'-hydroxy-11',12'-dimethyl-7'-(((S)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | AND | AND | |
| | | (1S,3'R,6'R,7'R,8'E,11'S,12'R)-6-chloro-7'-hydroxy-11',12'-dimethyl-7'-(((R)-methylsulfinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100076 | 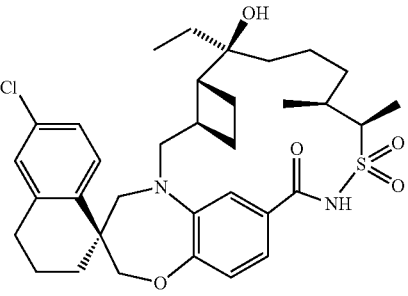 [SMILES: CC[C@]1(O)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3]<br>OR<br>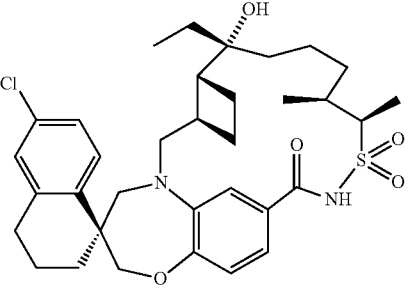 [SMILES: CC[C@@]1(O)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-ethyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,11'S,12'R)-6-chloro-7'-ethyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 629.3 |
| 100077 | 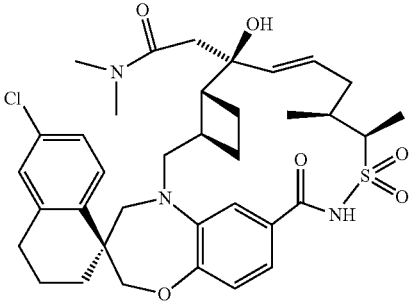 [SMILES: C[C@@H]1[C@@H](C)C/C=C/[C@@](O)(CC(=O)N(C)C)[C@@H]2CC[C@H]2CN2C[C@@]3(CCCc4cc(Cl)ccc43)COc3ccc(cc32)C(=O)NS1(=O)=O]<br>OR<br>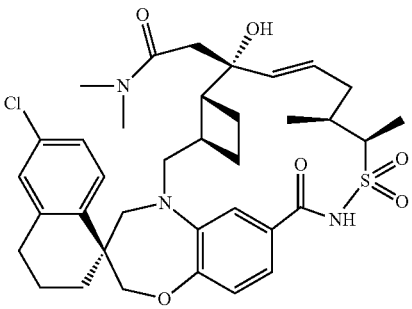 [SMILES: C[C@@H]1[C@@H](C)C/C=C/[C@](O)(CC(=O)N(C)C)[C@@H]2CC[C@H]2CN2C[C@@]3(CCCc4cc(Cl)ccc43)COc3ccc(cc32)C(=O)NS1(=O)=O] | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide<br><br>OR<br><br>2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide | 684.2 |

TABLE 2-continued

Examples Prepared by the General Methods

| Example Number | Structure | Name | MS Dat (M + 1)+ Unless Noted Otherwise |
|---|---|---|---|
| 100078 | 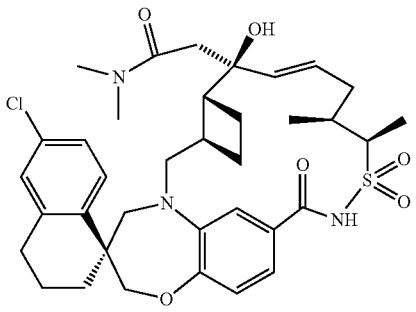 OR 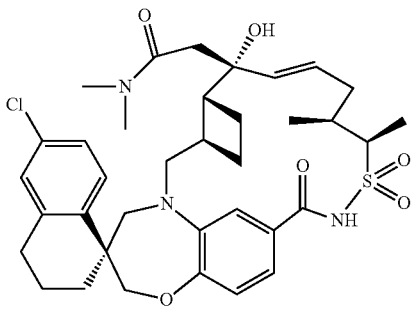 | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide OR 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide | 684.2 |
| 100079 | 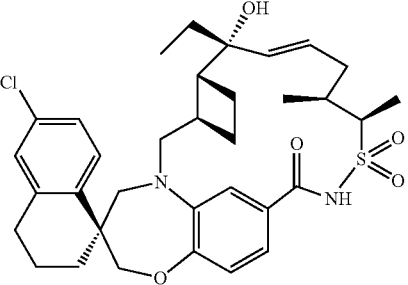 OR 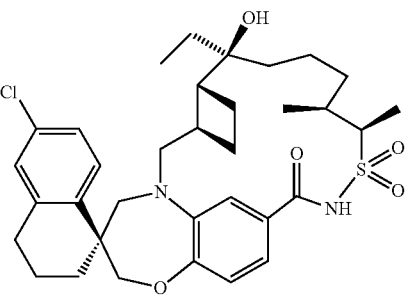 | (1S,3'R,6'R,7'R,11'S,12'R)-6-chloro-7'-ethyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'S,11'S,12'R)-6-chloro-7'-ethyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 629.1 |

TABLE 2-continued

Examples Prepared by the General Methods

| Example Number | Structure | Name | MS Dat (M + 1)+ Unless Noted Otherwise |
|---|---|---|---|
| 100080 | 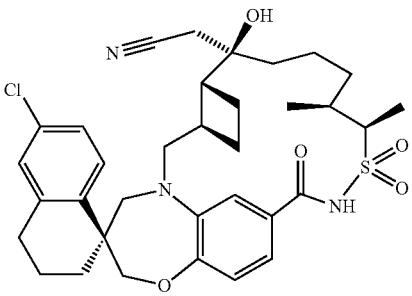 [SMILES: C[C@@H]1[C@@H](C)CCC[C@@](O)(CC#N)[C@@H]2CC[C@H]2CN2C[C@@]3(CCCc4cc(Cl)ccc43)COc3ccc(cc32)C(=O)NS1(=O)=O] | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetonitrile | 640.3 |
|  | OR | OR |  |
|  | 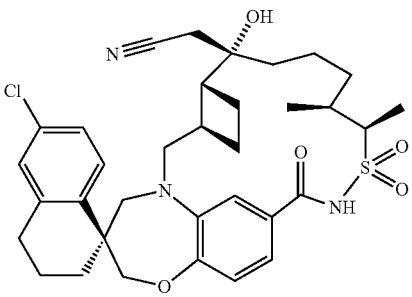 [SMILES: C[C@@H]1[C@@H](C)CCC[C@](O)(CC#N)[C@@H]2CC[C@H]2CN2C[C@@]3(CCCc4cc(Cl)ccc43)COc3ccc(cc32)C(=O)NS1(=O)=O] | ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetonitrile |  |
| 100081 | 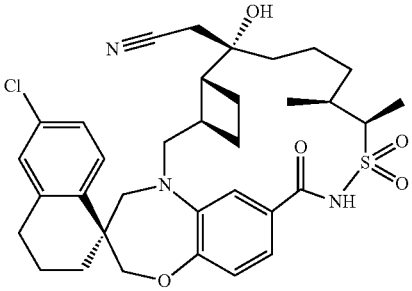 [SMILES: C[C@@H]1[C@@H](C)CCC[C@](O)(CC#N)[C@@H]2CC[C@H]2CN2C[C@@]3(CCCc4cc(Cl)ccc43)COc3ccc(cc32)C(=O)NS1(=O)=O] | ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetonitrile | 640.3 |
|  | OR | OR |  |
|  | 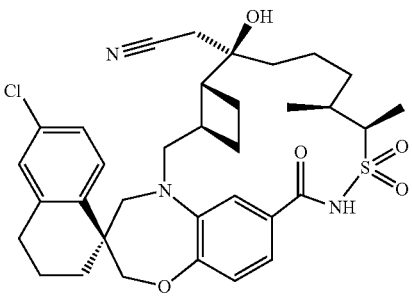 [SMILES: C[C@@H]1[C@@H](C)CCC[C@@](O)(CC#N)[C@@H]2CC[C@H]2CN2C[C@@]3(CCCc4cc(Cl)ccc43)COc3ccc(cc32)C(=O)NS1(=O)=O] | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetonitrile |  |

TABLE 2-continued

Examples Prepared by the General Methods

| Example Number | Structure | Name | MS Dat (M + 1)+ Unless Noted Otherwise |
|---|---|---|---|
| 100082 | 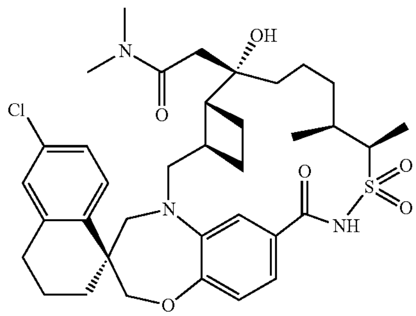 [SMILES: C[C@@H]1[C@@H](C)CCC[C@](O)(CC(=O)N(C)C)[C@@H]2CC[C@H]2CN2C[C@@]3(CCCc4cc(Cl)ccc43)COc3ccc(cc32)C(=O)NS1(=O)=O] | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylacetamide | 686.3 |
| 100083 | 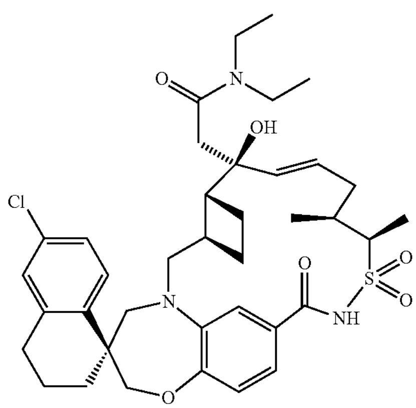 [SMILES: CCN(CC)C(=O)C[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-diethylacetamide<br><br>OR<br><br>2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-diethylacetamide | 712.2 |

TABLE 2-continued

Examples Prepared by the General Methods

| Example Number | Structure | Name | MS Dat (M + 1)+ Unless Noted Otherwise |
|---|---|---|---|
| 100084 | 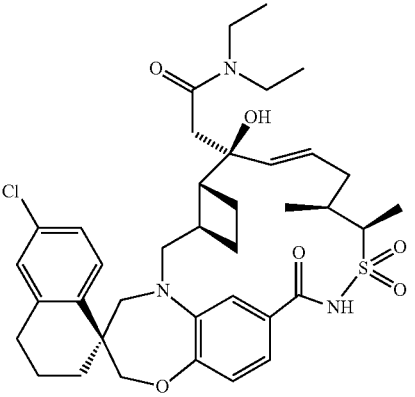 [SMILES: CCN(CC)C(=O)C[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-diethylacetamide | 712.2 |
|  | OR | OR |  |
|  | 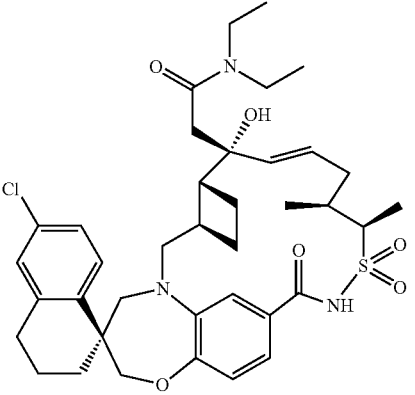 [SMILES: CCN(CC)C(=O)C[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-diethylacetamide |  |
| 100085 | 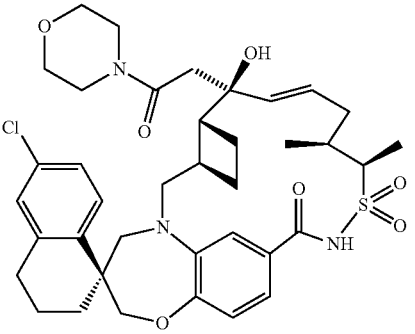 [SMILES: C[C@@H]1[C@@H](C)C/C=C/[C@@](O)(CC(=O)N2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(2-(4-morpholinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.1 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-hydroxy-11',12'-dimethyl-7'-(2-(4-morpholinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100086 | 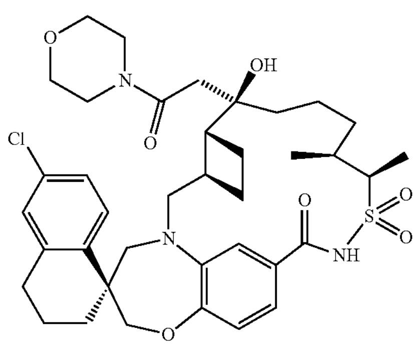 | (1S,3'R,6'R,7'R,11'S,12'R)-6-chloro-7'-hydroxy-11',12'-dimethyl-7'-(2-(4-morpholinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 728.1 |
| | OR | OR (1S,3'R,6'R,7'S,11'S,12'R)-6-chloro-7'-hydroxy-11',12'-dimethyl-7'-(2-(4-morpholinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100087 | 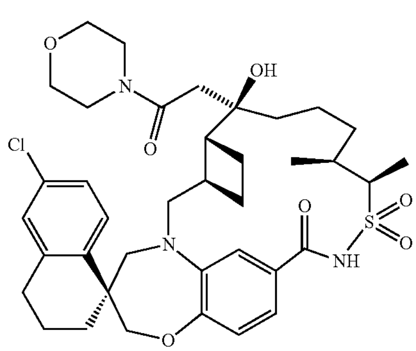 | (1S,3'R,6'R,7'S,11'S,12'R)-6-chloro-7'-hydroxy-11',12'-dimethyl-7'-(2-(4-morpholinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 728.1 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,11'S,12'R)-6-chloro-7'-hydroxy-11',12'-dimethyl-7'-(2-(4-morpholinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100088 | 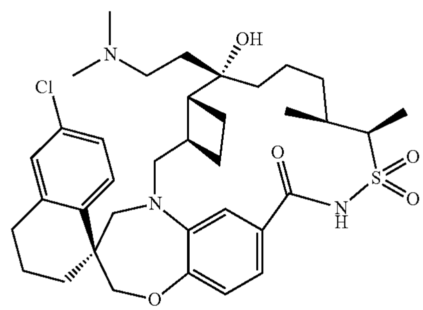 | (1S,3'R,6'R,7'S,11'S,12'R)-6-chloro-7'-(2-(dimethylamino)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 672.3 |
| 100089 | 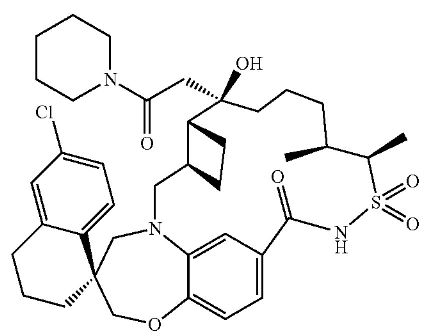 | (1S,3'R,6'R,7'R,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 726.3 |
| | OR | OR | |
| | | (1S,3'R,6'R,7'S,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100090 | 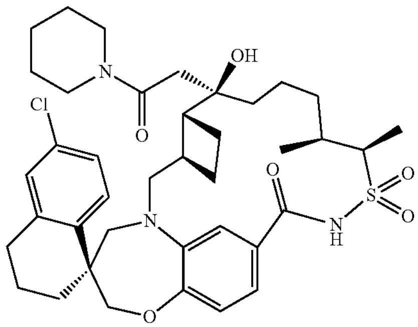 [SMILES: C[C@@H]1[C@@H](C)CCC[C@@](O)(CC(=O)N2CCCCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 726.2 |
| | OR | OR | |
| | | (1S,3'R,6'R,7'S,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100091 | 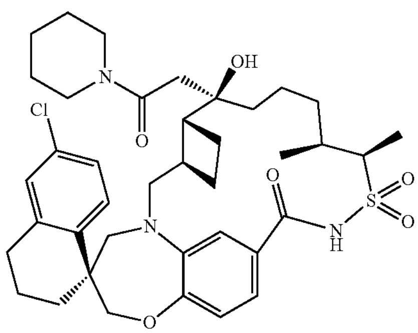 [SMILES: C[C@@H]1[C@@H](C)CCC[C@@](O)(CC(=O)N2CCCCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 712.2 |
| | OR | OR | |
| | | (1S,3'R,6'R,7'S,11'S,12'R)-6-chloro-7'-hydroxy-11',12'-dimethyl-7'-(2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100092 | 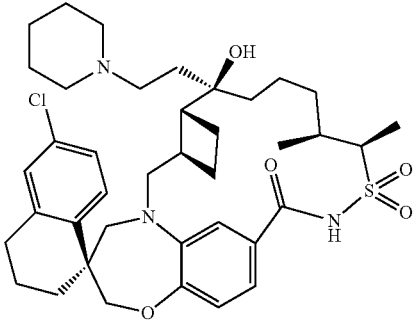<br><br>OR<br><br>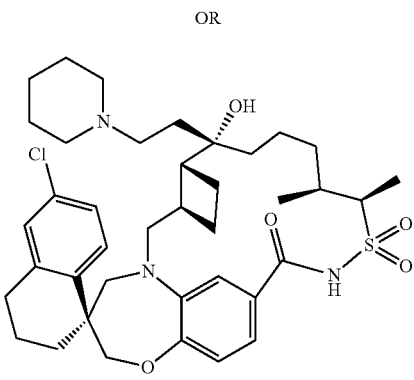 | (1S,3'R,6'R,7'R,11'S,12'R)-6-chloro-7'-hydroxy-11',12'-dimethyl-7'-(2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,11'S,12'R)-6-chloro-7'-hydroxy-11',12'-dimethyl-7'-(2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 712.4 |
| 100093 | 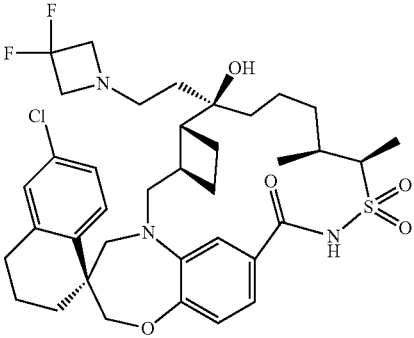 [SMILES: C[C@@H]1[C@@H](C)CCC[C@@](O)(CCN2CC(F)(F)C2)[C@@H]2CC[C@H]2CN2C[C@@]3(CCCc4cc(Cl)ccc43)COc3ccc(cc32)C(=O)NS1(=O)=O]<br><br>OR<br><br>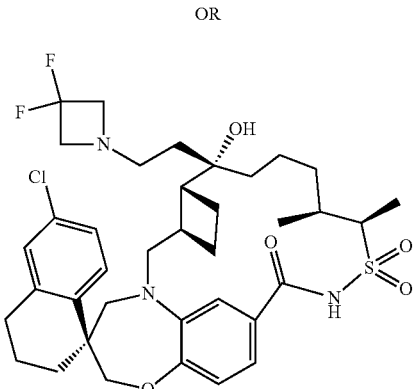 | (1S,3'R,6'R,7'R,11'S,12'R)-6-chloro-7'-(2-(3,3-difluoro-1-azetidinyl)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,11'S,12'R)-6-chloro-7'-(2-(3,3-difluoro-1-azetidinyl)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 720.2 |

TABLE 2-continued

Examples Prepared by the General Methods

| Example Number | Structure | Name | MS Dat (M + 1)+ Unless Noted Otherwise |
|---|---|---|---|
| 100094 | 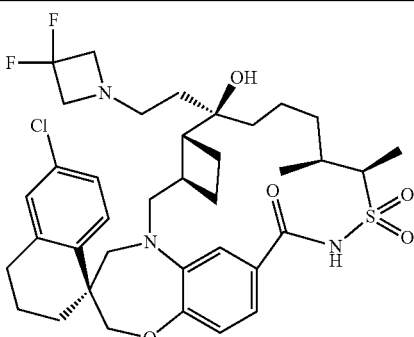<br><br>OR<br><br>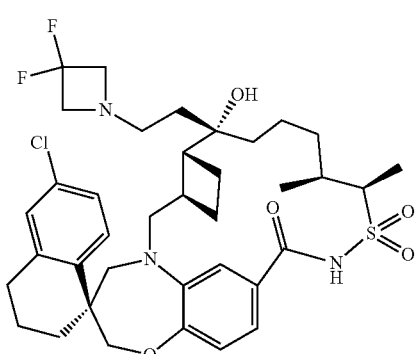 | (1S,3'R,6'R,7'R,11'S,12'R)-6-chloro-7'-(2-(3,3-difluoro-1-azetidinyl)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,11'S,12'R)-6-chloro-7'-(2-(3,3-difluoro-1-azetidinyl)ethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 720.2 |
| 100095 | 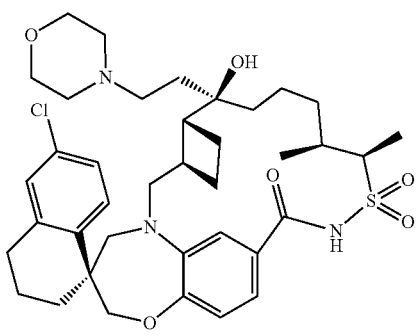 [SMILES: C[C@@H]1[C@@H](C)CCC[C@@](O)(CCN2CCOCC2)[C@@H]2CC[C@H]2CN2C[C@@]3(CCCc4cc(Cl)ccc43)COc3ccc(cc32)C(=O)NS1(=O)=O]<br><br>OR<br><br>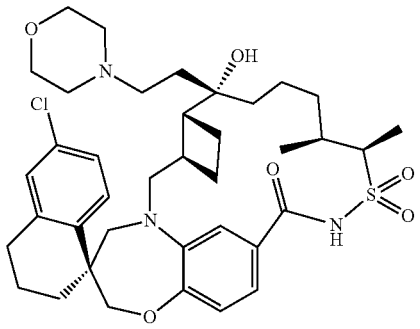 [SMILES: C[C@@H]1[C@@H](C)CCC[C@](O)(CCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,11'S,12'R)-6-chloro-7'-hydroxy-11',12'-dimethyl-7'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 714.3 |

TABLE 2-continued

Examples Prepared by the General Methods

| Example Number | Structure | Name | MS Dat (M + 1)+ Unless Noted Otherwise |
|---|---|---|---|
| 100096 | 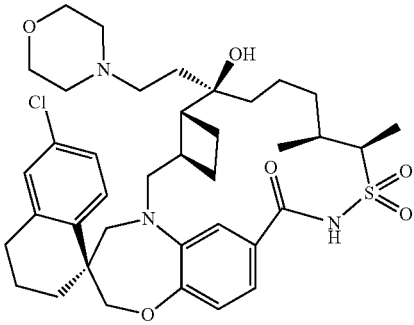 [SMILES: C[C@@H]1[C@@H](C)CCC[C@@](O)(CCN2CCOCC2)[C@@H]2CC[C@H]2CN2C[C@@]3(CCCc4cc(Cl)ccc43)COc3ccc(cc32)C(=O)NS1(=O)=O] <br> OR <br> 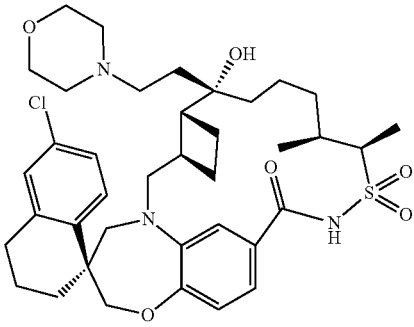 [SMILES: C[C@@H]1[C@@H](C)CCC[C@](O)(CCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide <br> OR <br> (1S,3'R,6'R,7'S,11'S,12'R)-6-chloro-7'-hydroxy-11',12'-dimethyl-7'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 714.3 |
| 100097 | 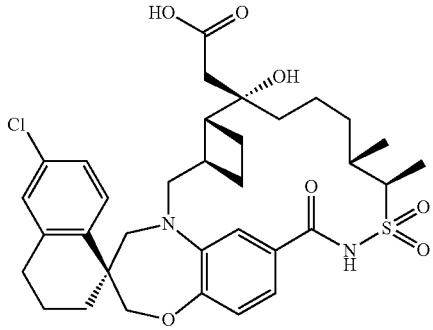 [SMILES: C[C@@H]1[C@@H](C)CCC[C@](O)(CC(=O)O)[C@@H]2CC[C@H]2CN2C[C@@]3(CCCc4cc(Cl)ccc43)COc3ccc(cc32)C(=O)NS1(=O)=O] <br> OR <br> 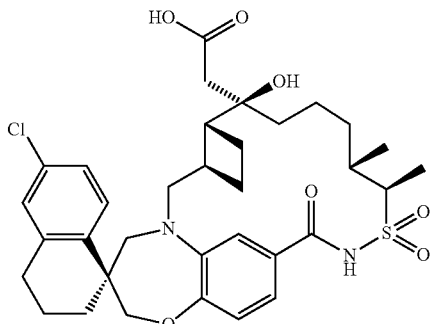 | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetic acid <br> OR <br> ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetic acid | 658.8 |

TABLE 2-continued

Examples Prepared by the General Methods

| Example Number | Structure | Name | MS Dat (M + 1)+ Unless Noted Otherwise |
|---|---|---|---|
| 100098 | 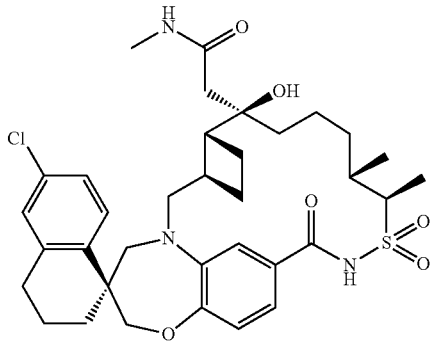 [SMILES: CNC(=O)C[C@]1(O)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] <br> OR <br> 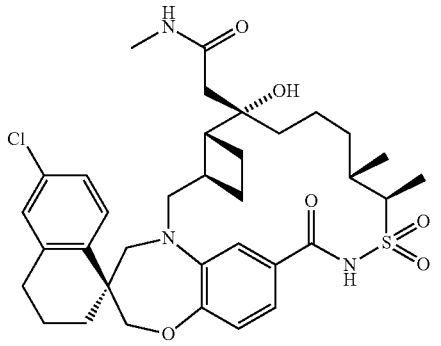 | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methylacetamide <br><br> OR <br><br> 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methylacetamide | 671.9 |
| 100099 | 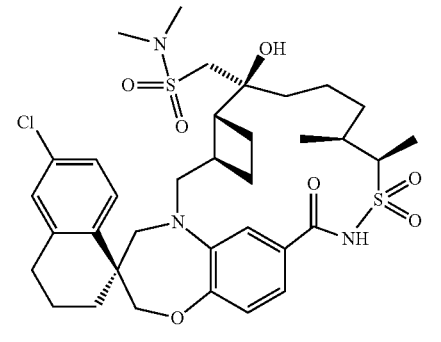 [SMILES: C[C@@H]1[C@@H](C)CCC[C@@](O)(CS(=O)(=O)N(C)C)[C@@H]2CC[C@H]2CN2C[C@@]3(CCCc4cc(Cl)ccc43)COc3ccc(cc32)C(=O)NS1(=O)=O] <br> OR <br> 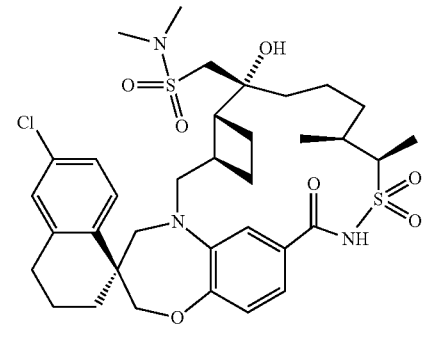 [SMILES: C[C@@H]1[C@@H](C)CCC[C@](O)(CS(=O)(=O)N(C)C)[C@@H]2CC[C@H]2CN2C[C@@]3(CCCc4cc(Cl)ccc43)COc3ccc(cc32)C(=O)NS1(=O)=O] | 1-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylmethanesulfonamide <br><br> OR <br><br> 1-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylmethanesulfonamide | 722.2 |

TABLE 2-continued

Examples Prepared by the General Methods

| Example Number | Structure | Name | MS Dat (M + 1)+ Unless Noted Otherwise |
|---|---|---|---|
| 100100 | 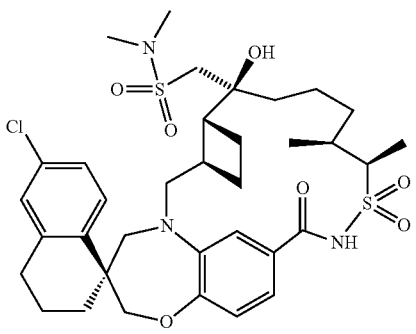 OR 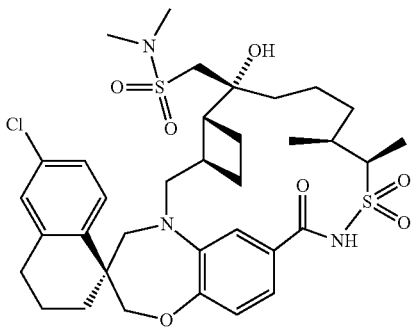 | 1-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylmethanesulfonamide OR 1-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylmethanesulfonamide | 722.3 |
| 100101 | 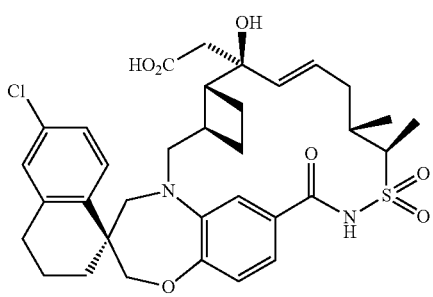 | ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid | 656.8 |
| 100102 | 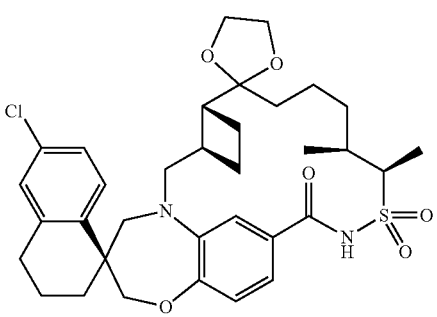 | (3'R,6'R,11'S,12'R,22'S)-6''-chloro-11',12'-dimethyl-3'',4''-dihydro-2''H,15'H-dispiro[1,3-dioxolane-2,7'-[20]oxa[13]thia[1,14]diazatetracyclo[14.7.2.0~3,6~.0~19,24~]pentacosa[16,18,24]triene-22',1'''-naphthalen]-15'-one 13,13-dioxide | 643.3 |

TABLE 2-continued

Examples Prepared by the General Methods

| Example Number | Structure | Name | MS Dat (M + 1)+ Unless Noted Otherwise |
|---|---|---|---|
| 100103 | 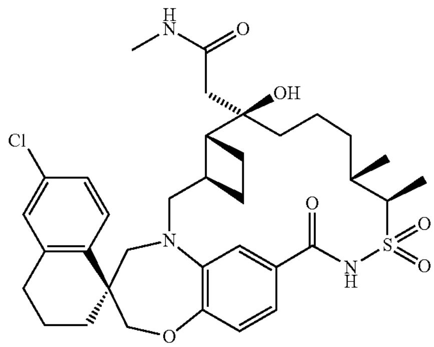 [SMILES: CNC(=O)C[C@]1(O)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methylacetamide | 671.9 |
| | OR | OR | |
| | | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methylacetamide | |
| 100104 | 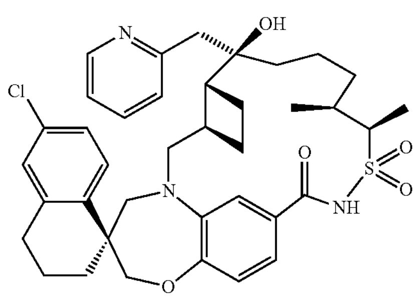 [SMILES: C[C@@H]1[C@@H](C)CCC[C@@](O)(Cc2ccccn2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 692.3 |
| | OR | OR | |
| | | (1S,3'R,6'R,7'S,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100105 | 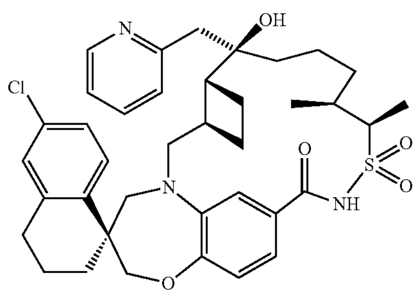 [SMILES: C[C@@H]1[C@@H](C)CCC[C@@](O)(Cc2ccccn2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 692.3 |
| | OR | OR | |
| | | (1S,3'R,6'R,7'S,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100106 | 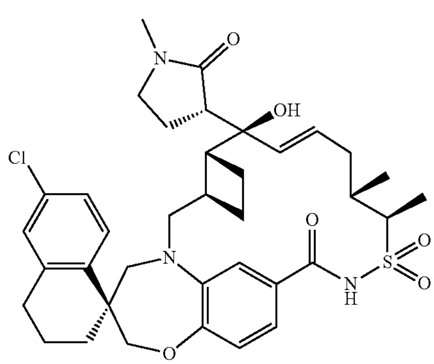 [SMILES: C[C@@H]1[C@@H](C)C/C=C/[C@@](O)([C@@H]2CCN(C)C2=O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.2 |
| | OR | OR | |
| | | (1S,3'R,6'R,7'S,8'E,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR | (1S,3'R,6'R,7'R,8'E,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | (1S,3'R,6'R,7'R,8'E,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100107 | 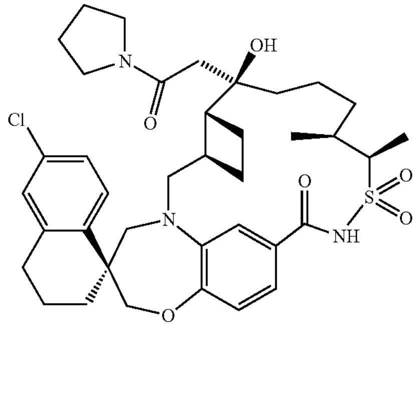 | (1S,3'R,6'R,7'R,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 711.8 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100108 | 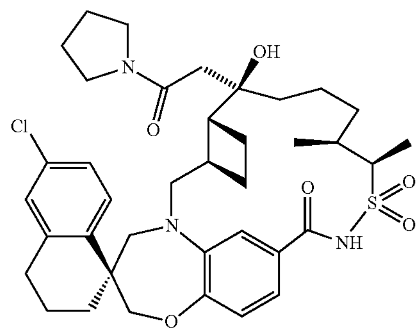 | (1S,3'R,6'R,7'R,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 711.8 |
| | OR | OR (1S,3'R,6'R,7'S,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100109 | 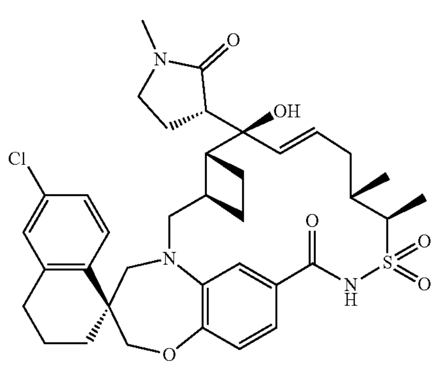 | (1S,3'R,6'R,7'S,8'E,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 695.9 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'R,8'E,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'R,8'E,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100110 | 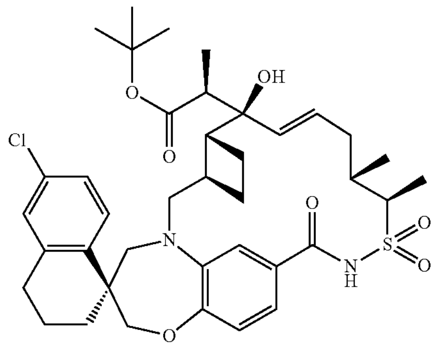 [SMILES: C[C@H](C(=O)OC(C)(C)C)[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-methyl-2-propanyl (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoate | 726.8 |
| | OR | OR | |
| | | 2-methyl-2-propanyl (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoate | |
| | OR | OR | |
| | | 2-methyl-2-propanyl (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoate | |

TABLE 2-continued

Examples Prepared by the General Methods

| Example Number | Structure | Name | MS Dat (M + 1)+ Unless Noted Otherwise |
|---|---|---|---|
| | OR | OR 2-methyl-2-propanyl (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoate | |
| 100111 | 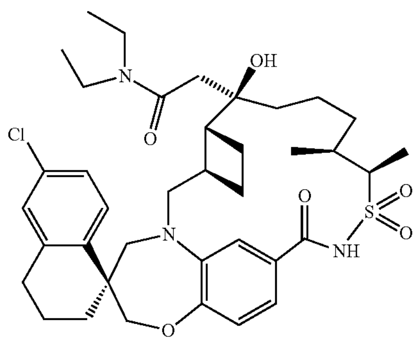 | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-diethylacetamide | 713.9 |
| | OR | OR 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-diethylacetamide | |
| 100112 | 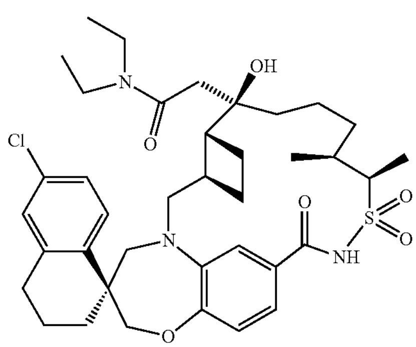 | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-diethylacetamide | 713.9 |

TABLE 2-continued

Examples Prepared by the General Methods

| Example Number | Structure | Name | MS Dat (M + 1)+ Unless Noted Otherwise |
|---|---|---|---|
| | OR | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-diethylacetamide | |
| 100113 | 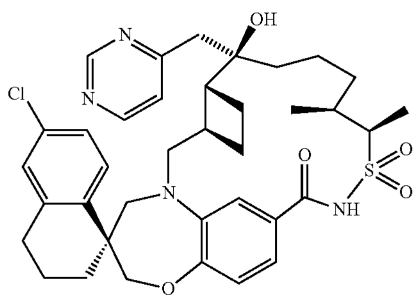 | (1S,3'R,6'R,7'R,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 693.3 |
| | OR | (1S,3'R,6'R,7'S,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100114 | 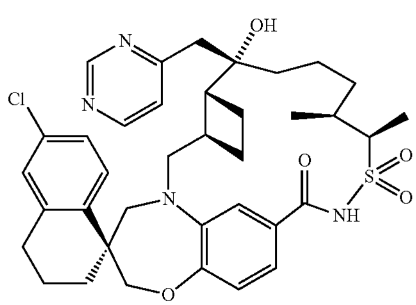 | (1S,3'R,6'R,7'R,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 693.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100115 | 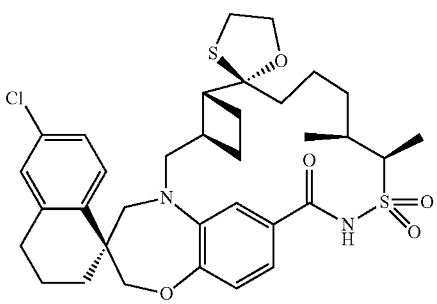 | (1S,3'R,6'R,7'S,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-[1,3]oxathiolan]-15'-one 13',13'-dioxide | 659.3 |
| | OR | OR (1S,3'R,6'R,7'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-[1,3]oxathiolan]-15'-one 13',13'-dioxide | |
| 100116 | 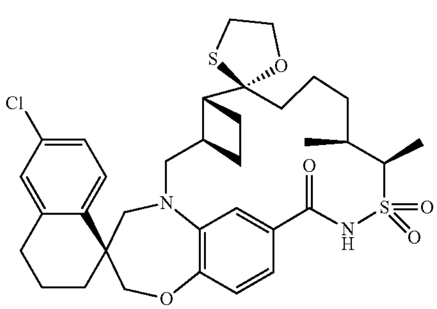 | (1S,3'R,6'R,7'R,11'S,12'R)-6-chloro-11',12'-dimethyl-3,4-dihydro-2H,15'H-[20]oxa[13]thia[1,14]diazatetracyclo[14.7.2.0~3,6~.0~19,24~]pentacosa[16,18,24]triene-7',2''-[1,3]oxathiolan]-15'-one 13',13'-dioxide | 659.3 |

TABLE 2-continued

Examples Prepared by the General Methods

| Example Number | Structure | Name | MS Dat (M + 1)+ Unless Noted Otherwise |
|---|---|---|---|
| | OR | (1S,3'R,6'R,7'S,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-[1,3]oxathiolan]-15'-one 13',13'-dioxide | |
| 100117 | OR | (2R)-2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | 700.4 |
| | OR | (2R)-2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |
| | OR | (2S)-2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |

TABLE 2-continued

Examples Prepared by the General Methods

| Example Number | Structure | Name | MS Dat (M + 1)+ Unless Noted Otherwise |
|---|---|---|---|
| | OR | OR | |
| | | (2S)-2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |
| 100118 | 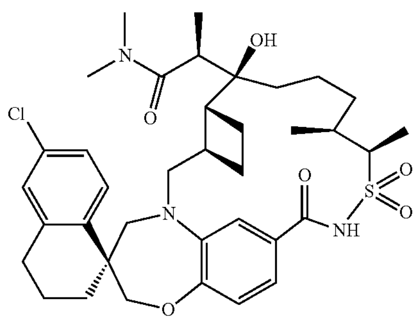 | (2R)-2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | 700.4 |
| | OR | OR | |
| | | (2R)-2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |
| | OR | OR | |
| | | (2S)-2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |

TABLE 2-continued

Examples Prepared by the General Methods

| Example Number | Structure | Name | MS Dat (M + 1)+ Unless Noted Otherwise |
|---|---|---|---|
| | OR | OR (2S)-2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |
| 100119 | 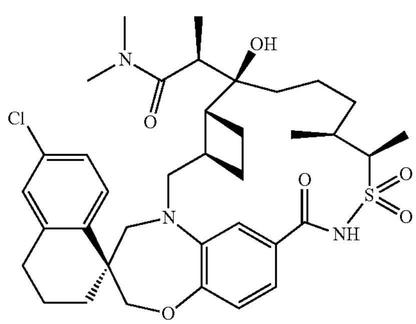 | (2R)-2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | 700.4 |
| | OR | OR (2R)-2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |

TABLE 2-continued

Examples Prepared by the General Methods

| Example Number | Structure | Name | MS Dat (M + 1)+ Unless Noted Otherwise |
|---|---|---|---|
| | | (2S)-2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |
| | | (2S)-2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylpropanamide | |
| 100120 | 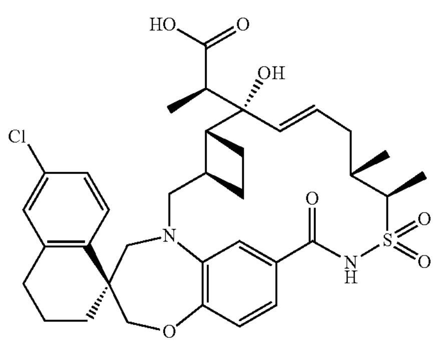 [SMILES: C[C@@H]1[C@@H](C)C/C=C/[C@](O)([C@@H](C)C(=O)O)[C@@H]2CC[C@H]2CN2C[C@@]3(CCCc4cc(Cl)ccc43)COc3ccc(cc32)C(=O)NS1(=O)=O] | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | 670.8 |
| | | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |

TABLE 2-continued

Examples Prepared by the General Methods

| Example Number | Structure | Name | MS Dat (M + 1)+ Unless Noted Otherwise |
|---|---|---|---|
| | OR | OR (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| | OR | OR (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| 100121 | 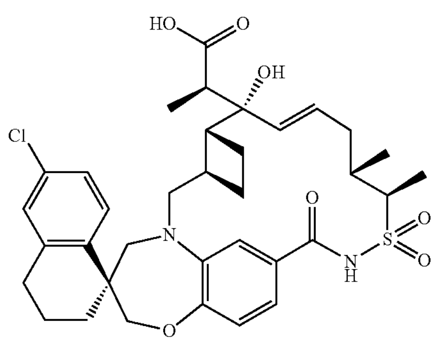 | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | 670.8 |
| | OR | OR (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |

TABLE 2-continued

Examples Prepared by the General Methods

| Example Number | Structure | Name | MS Dat (M + 1)+ Unless Noted Otherwise |
|---|---|---|---|
| | | (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| | | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| 100122 | 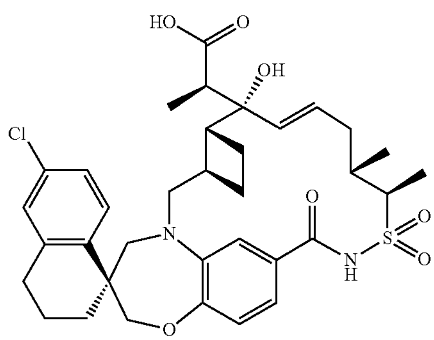 [SMILES: C[C@@H]1[C@@H](C)C/C=C/[C@](O)([C@@H](C)C(=O)O)[C@@H]2CC[C@H]2CN2C[C@@]3(CCCc4cc(Cl)ccc43)COc3ccc(cc32)C(=O)NS1(=O)=O] | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | 670.8 |
| | | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |

TABLE 2-continued

Examples Prepared by the General Methods

| Example Number | Structure | Name | MS Dat (M + 1)+ Unless Noted Otherwise |
|---|---|---|---|
| | OR | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| | OR | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| 100123 | 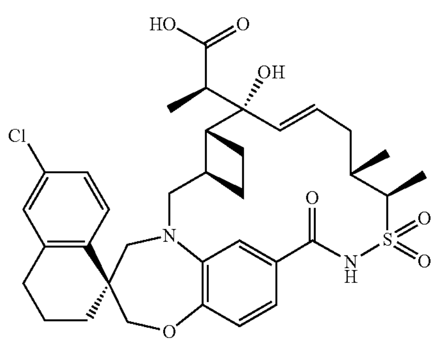 | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | 670.8 |
| | OR | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |

TABLE 2-continued

Examples Prepared by the General Methods

| Example Number | Structure | Name | MS Dat (M + 1)+ Unless Noted Otherwise |
|---|---|---|---|
| | OR<br>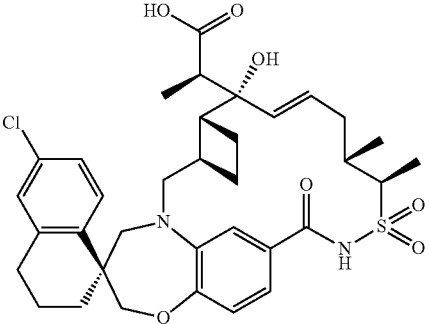 [SMILES: C[C@@H]1[C@@H](C)C/C=C/[C@](O)([C@@H](C)C(=O)O)[C@@H]2CC[C@H]2CN2C[C@@]3(CCCc4cc(Cl)ccc43)COc3ccc(cc32)C(=O)NS1(=O)=O] | OR<br>(2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| | OR<br>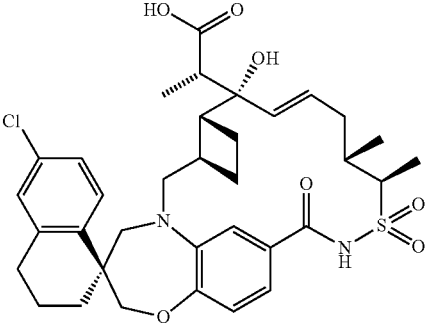 [SMILES: C[C@H](C(=O)O)[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | OR<br>(2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)propanoic acid | |
| 100124 | 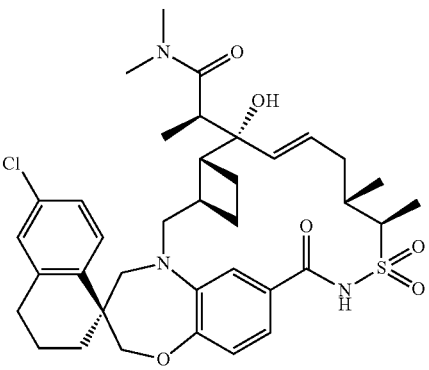 [SMILES: C[C@@H]1[C@@H](C)C/C=C/[C@](O)([C@@H](C)C(=O)N(C)C)[C@@H]2CC[C@H]2CN2C[C@@]3(CCCc4cc(Cl)ccc43)COc3ccc(cc32)C(=O)NS1(=O)=O] | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | 697.7 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (2S)-2-(((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |
| | OR | OR | |
| | | (2R)-2-(((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |
| | OR | OR | |
| | | (2S)-2-(((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |

TABLE 2-continued

Examples Prepared by the General Methods

| Example Number | Structure | Name | MS Dat (M + 1)+ Unless Noted Otherwise |
|---|---|---|---|
| 100125 | 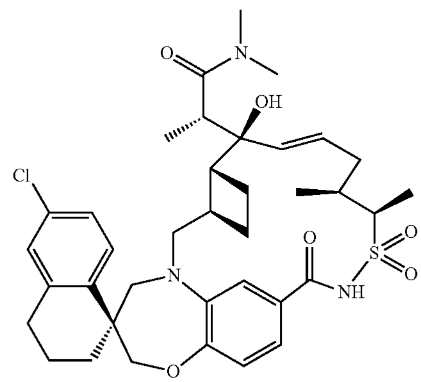 [SMILES: C[C@H](C(=O)N(C)C)[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | 698.2 |
| | OR | OR | |
| | | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |
| | OR | OR | |
| | | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |

TABLE 2-continued

Examples Prepared by the General Methods

| Example Number | Structure | Name | MS Dat (M + 1)+ Unless Noted Otherwise |
|---|---|---|---|
| | OR | OR (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |
| 100126 | 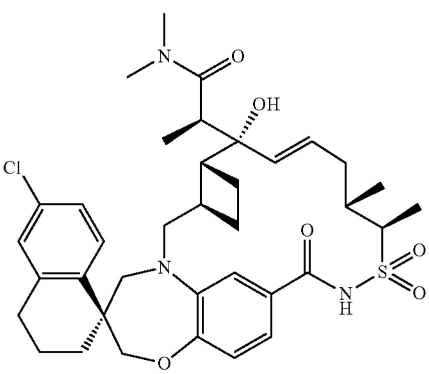 | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | 698.2 |
| | OR | OR (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |

TABLE 2-continued

Examples Prepared by the General Methods

| Example Number | Structure | Name | MS Dat (M + 1)+ Unless Noted Otherwise |
|---|---|---|---|
| | OR | OR | |
| | | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |
| | OR | OR | |
| | | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylpropanamide | |
| 100127 | 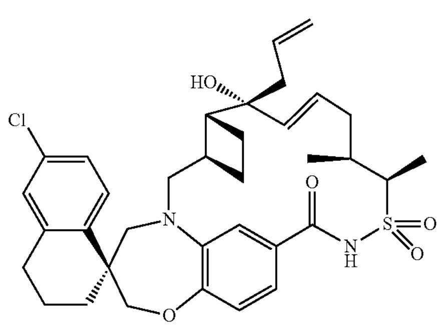 | (1S,3'R,6'R,7'R,8'E,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 639.3 |

TABLE 2-continued

Examples Prepared by the General Methods

| Example Number | Structure | Name | MS Dat (M + 1)+ Unless Noted Otherwise |
|---|---|---|---|
| | AND 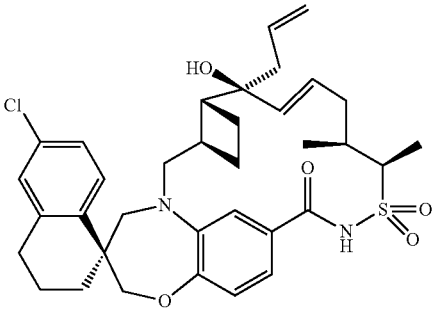 | AND (1S,3'R,6'R,7'S,8'E,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100128 | 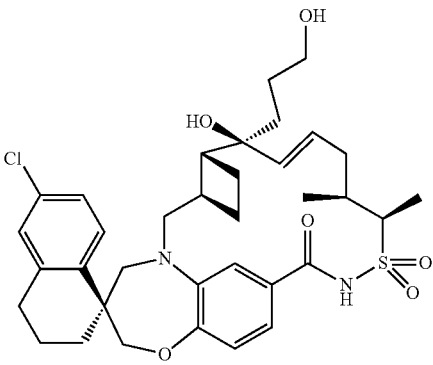 | (1S,3'R,6'R,7'R,8'E,11'S,12'R)-6-chloro-7'-hydroxy-7'-(3-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.4 |
| | AND 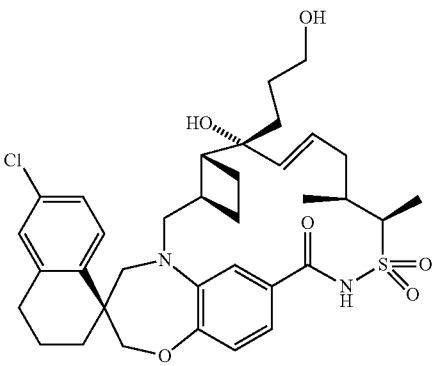 | AND (1S,3'R,6'R,7'S,8'E,11'S,12'R)-6-chloro-7'-hydroxy-7'-(3-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100129 | 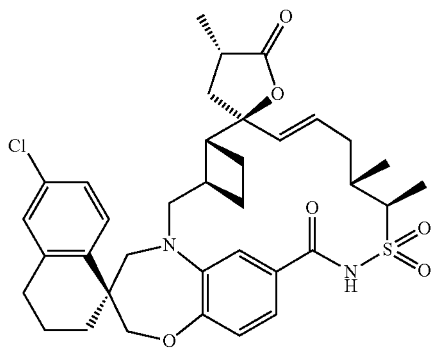 | (2S,3'R,4S,6'R,11'S,12'R,22'S)-6''-chloro-4,11',12'-trimethyl-3,3'',4,4''-tetrahydro-2''H,5H,15'H-dispiro[furan-2,7'-[20]oxa[13]thia[1,14]diazatetracyclo[14.7.2.0~3,6~.0~19,24~]pentacosa[16,18,24]triene-22',1''-naphthalene]-5,15'-dione 13',13'-dioxide | 669.2 |
| | AND | AND | |
| | | (2R,3'R,4S,6'R,11'S,12'R,22'S)-6''-chloro-4,11',12'-trimethyl-3,3'',4,4''-tetrahydro-2''H,5H,15'H-dispiro[furan-2,7'-[20]oxa[13]thia[1,14]diazatetracyclo[14.7.2.0~3,6~.0~19,24~]pentacosa[16,18,24]triene-22',1''-naphthalene]-5,15'-dione 13',13'-dioxide | |
| 100130 | 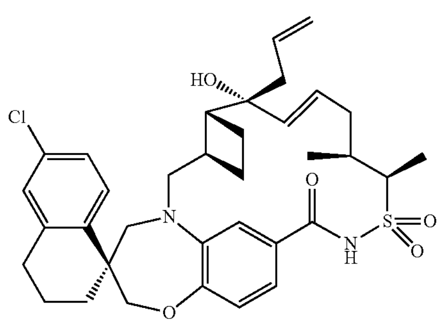 [SMILES: C=CC[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 639.0 |
| | OR | OR | |
| | | (1S,3'R,6'R,7'S,8'E,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100131 | 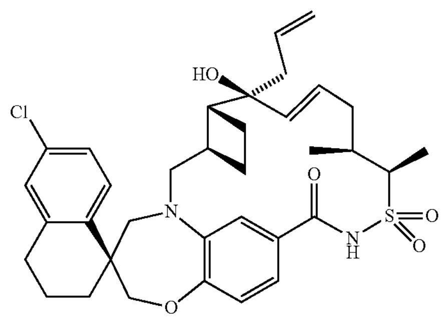 | (1S,3'R,6'R,7'R,8'E,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 639.2 |
| | OR | OR | |
| | | (1S,3'R,6'R,7'S,8'E,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100132 | 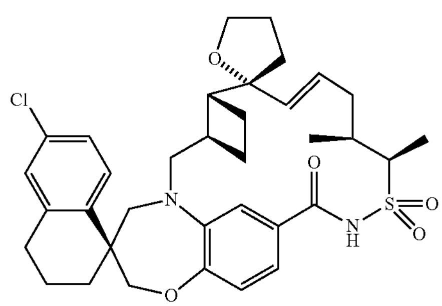 | (2S,3'R,6'R,8'E,11'S,12'R,22'S)-6''-chloro-11',12'-dimethyl-3'',4,4'',5-tetrahydro-2''H,3H,15'H-dispiro[furan-2,7'-[20]oxa[13]thia[1,14]diazatetracyclo[14.7.2.0~3,6~.0~19,24~]pentacosa[8,16,18,24]tetraene-22',1'''-naphthalen]-15'-one 13',13'-dioxide | 639.3 |
| | AND | AND | |
| | | (2R,3'R,6'R,8'E,11'S,12'R,22'S)-6''-chloro-11',12'-dimethyl-3'',4,4'',5-tetrahydro-2''H,3H,15'H-dispiro[furan-2,7'-[20]oxa[13]thia[1,14]diazatetracyclo[14.7.2.0~3,6~.0~19,24~]pentacosa[8,16,18,24]tetraene-22',1'''-naphthalen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100133 | 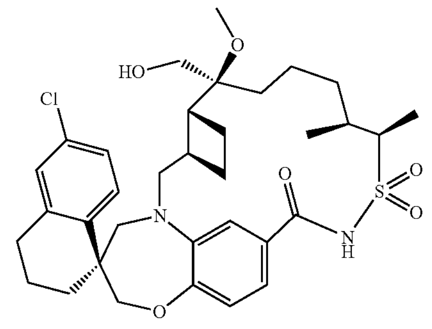 [SMILES: CO[C@@]1(CO)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.2 |
| | OR | OR | |
| | | (1S,3'R,6'R,7'R,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100134 | 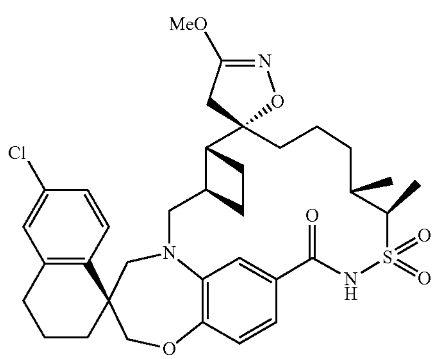 [SMILES: COC1=NO[C@@]2(CCC[C@H](C)[C@@H](C)S(=O)(=O)NC(=O)c3ccc4c(c3)N(C[C@@H]3CC[C@H]32)C[C@@]2(CCCc3cc(Cl)ccc32)CO4)C1] | (1S,3'R,6'R,7'S,11'S,12'R)-6-chloro-3''-methoxy-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | 670.1 |
| | OR | OR | |
| | | (1S,3'R,6'R,7'R,11'S,12'R)-6-chloro-3''-methoxy-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100135 | 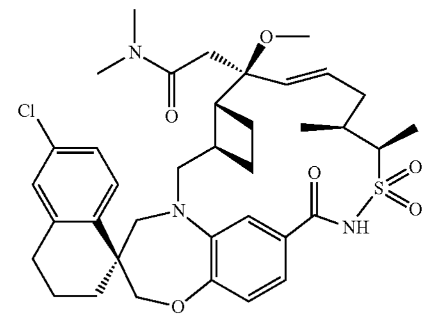 [SMILES: CO[C@@]1(CC(=O)N(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide<br><br>OR<br><br>2-((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide | 720.2 |
| 100136 | 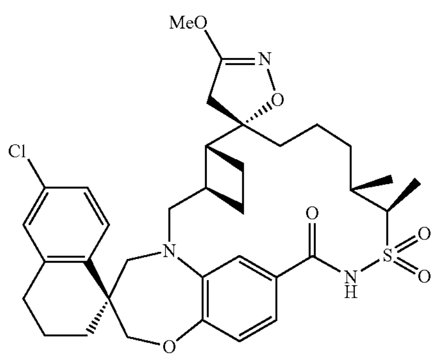 [SMILES: COC1=NO[C@@]2(CCC[C@H](C)[C@@H](C)S(=O)(=O)NC(=O)c3ccc4c(c3)N(C[C@@H]3CC[C@H]32)C[C@@]2(CCCc3cc(Cl)ccc32)CO4)C1] | (1S,3'R,6'R,7'S,11'S,12'R)-6-chloro-3''-(dimethylamino)-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide<br><br>OR<br><br>(1S,3'R,6'R,7'R,11'S,12'R)-6-chloro-3''-(dimethylamino)-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | 683.2 |

TABLE 2-continued

Examples Prepared by the General Methods

| Example Number | Structure | Name | MS Data (M + 1)+ Unless Noted Otherwise |
|---|---|---|---|
| 100137 | 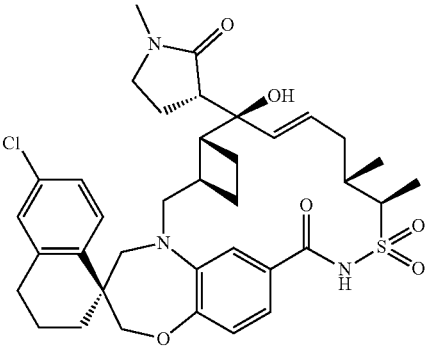 [SMILES: C[C@@H]1[C@@H](C)C/C=C/[C@@](O)([C@@H]2CCN(C)C2=O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.2 |
| | OR | OR | |
| | 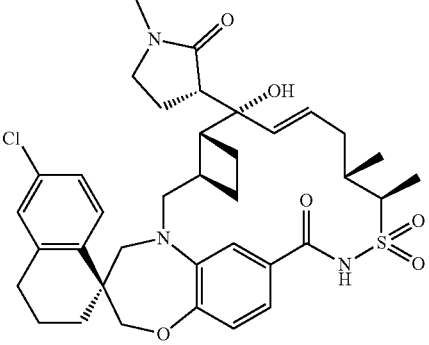 | (1S,3'R,6'R,7'S,8'E,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | 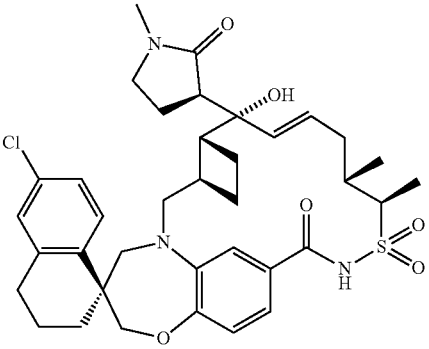 | (1S,3'R,6'R,7'R,8'E,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100138 | 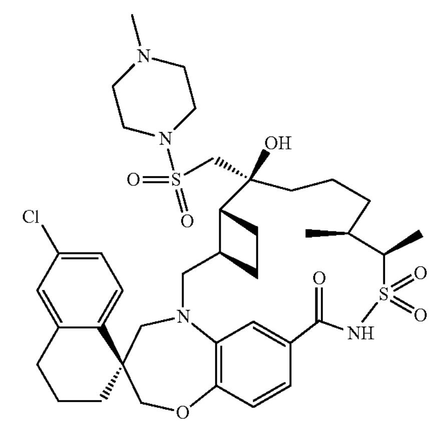 | (1S,3'R,6'R,7'S,11'S,12'R)-6-chloro-7'-hydroxy-11',12'-dimethyl-7'-(((4-methyl-1-piperazinyl)sulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 777.2 |
| | OR | OR | |
| | | (1S,3'R,6'R,7'R,11'S,12'R)-6-chloro-7'-hydroxy-11',12'-dimethyl-7'-(((4-methyl-1-piperazinyl)sulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100139 | 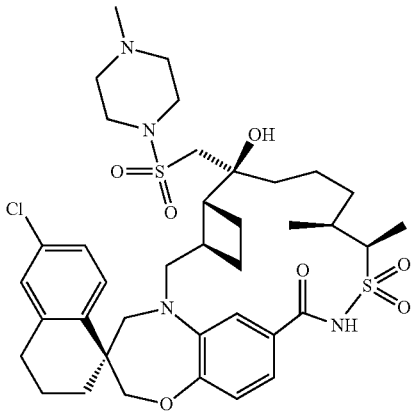 OR 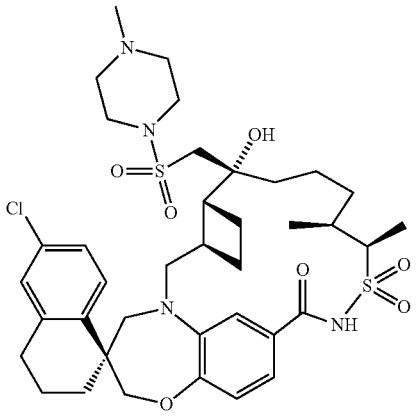 | (1S,3'R,6'R,7'S,11'S,12'R)-6-chloro-7'-hydroxy-11',12'-dimethyl-7'-(((4-methyl-1-piperazinyl)sulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'R,11'S,12'R)-6-chloro-7'-hydroxy-11',12'-dimethyl-7'-(((4-methyl-1-piperazinyl)sulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 777.2 |
| 100140 | 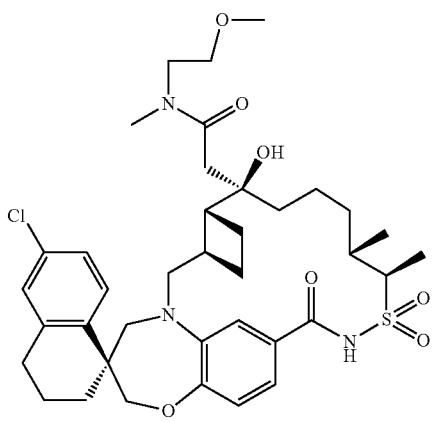 | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylacetamide | 730.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylacetamide | |
| 100141 | 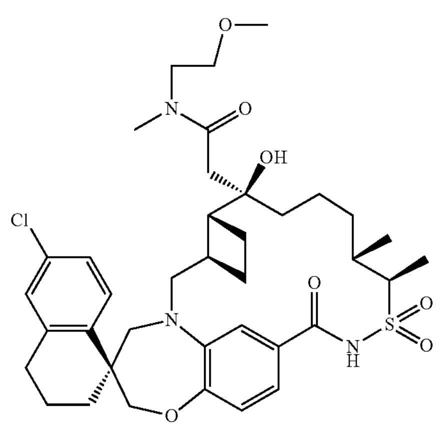 | 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylacetamide | 730.2 |
| | OR | OR | |
| | | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylacetamide | |

TABLE 2-continued

Examples Prepared by the General Methods

| Example Number | Structure | Name | MS Dat (M + 1)+ Unless Noted Otherwise |
|---|---|---|---|
| 100142 | 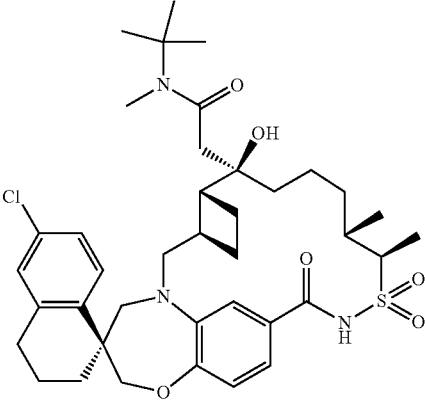 OR 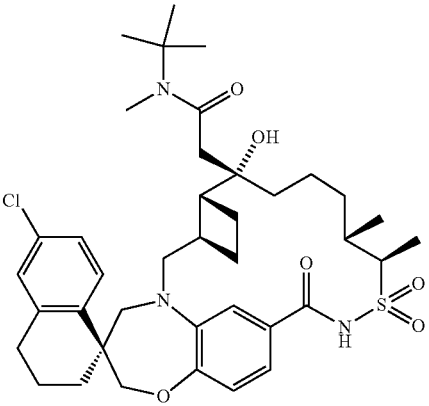 | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)acetamide OR 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)acetamide | 728.3 |
| 100143 | 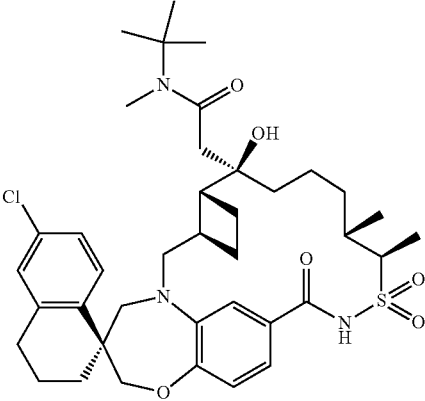 | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)acetamide | 728.2 |

TABLE 2-continued

Examples Prepared by the General Methods

| Example Number | Structure | Name | MS Dat (M + 1)+ Unless Noted Otherwise |
|---|---|---|---|
| | OR 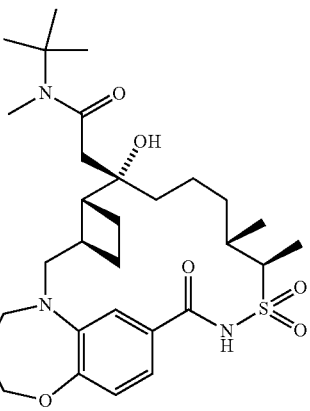 | OR 2-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)acetamide | |
| 100144 | 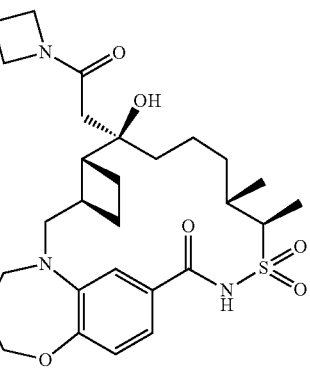 | (1S,3'R,6'R,7'R,11'S,12'R)-7'-(2-(1-azetidinyl)-2-oxoethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.5 |
| | OR 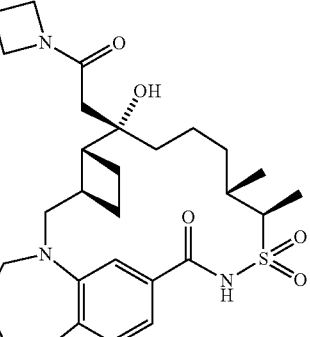 | OR (1S,3'R,6'R,7'S,11'S,12'R)-7'-(2-(1-azetidinyl)-2-oxoethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100145 | 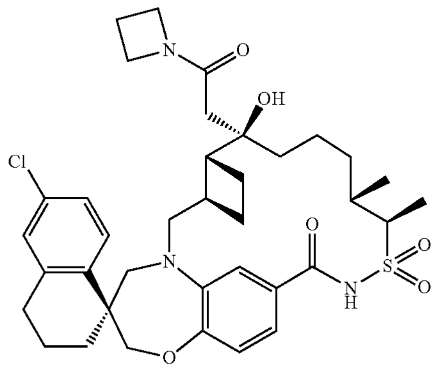 [SMILES: C[C@@H]1[C@@H](C)CCC[C@@](O)(CC(=O)N2CCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-7'-(2-(1-azetidinyl)-2-oxoethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.5 |
| | OR | OR | |
| | | (1S,3'R,6'R,7'S,11'S,12'R)-7'-(2-(1-azetidinyl)-2-oxoethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100146 | 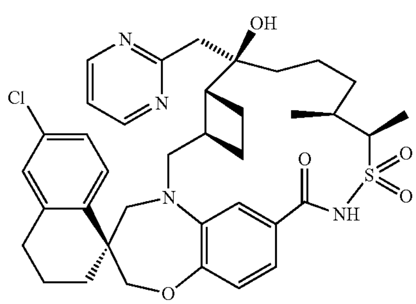 [SMILES: C[C@@H]1[C@@H](C)CCC[C@@](O)(Cc2ncccn2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 693.2 |
| | OR | OR | |
| | | (1S,3'R,6'R,7'S,11'S,12'R)-6-chloro-7'-hydroxy-11',12'-dimethyl-7'-(2-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100147 | 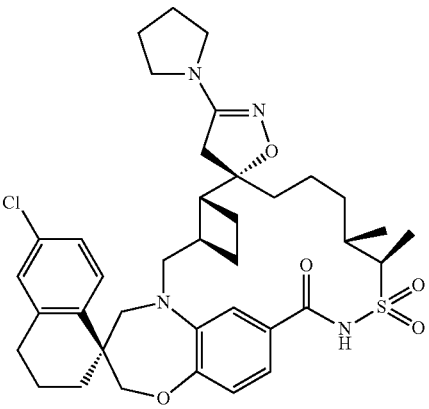 [SMILES: C[C@@H]1[C@@H](C)CCC[C@]2(CC(N3CCCC3)=NO2)[C@@H]2CC[C@H]2CN2C[C@@]3(CCCc4cc(Cl)ccc43)COc3ccc(cc32)C(=O)NS1(=O)=O]<br><br>OR<br><br>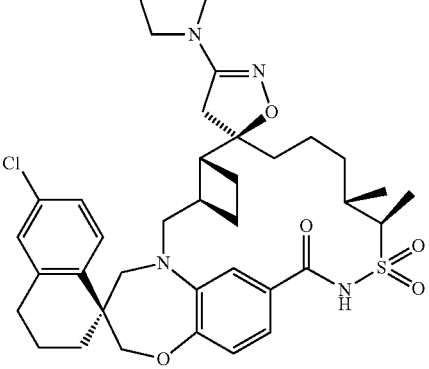 | (1S,3'R,6'R,7'S,11'S,12'R)-6-chloro-11',12'-dimethyl-3"-(1-pyrrolidinyl)-3,4-dihydro-2H,4"H,15'H-dispiro[naphthalene-1,22'-[20]oxa[13]thia[1,14]diazatetracyclo[14.7.2.0~3,6~.0~19,24~]pentacosa[16,18,24]triene-7',5"-[1,2]oxazol]-15'-one 13',13'-dioxide<br><br>OR<br><br>(1S,3'R,6'R,7'R,11'S,12'R)-6-chloro-11',12'-dimethyl-3"-(1-pyrrolidinyl)-3,4-dihydro-2H,4"H,15'H-dispiro[naphthalene-1,22'-[20]oxa[13]thia[1,14]diazatetracyclo[14.7.2.0~3,6~.0~19,24~]pentacosa[16,18,24]triene-7',5"-[1,2]oxazol]-15'-one 13',13'-dioxide | 709.1 |
| 100148 | 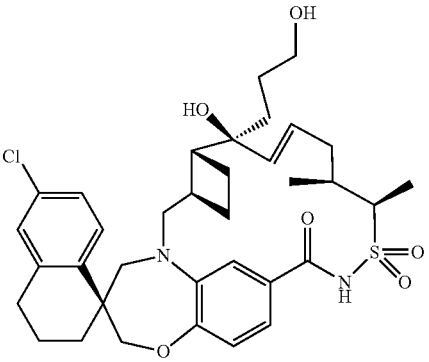 [SMILES: C[C@@H]1[C@@H](C)C/C=C/[C@@](O)(CCCO)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-7'-(3-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-hydroxy-7'-(3-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100149 | 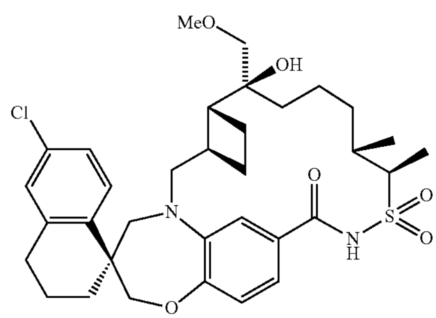 | (1S,3'R,6'R,7'S,11'S,12'R)-6-chloro-7'-hydroxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.2 |
| | OR | OR | |
| | | (1S,3'R,6'R,7'R,11'S,12'R)-6-chloro-7'-hydroxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100150 | 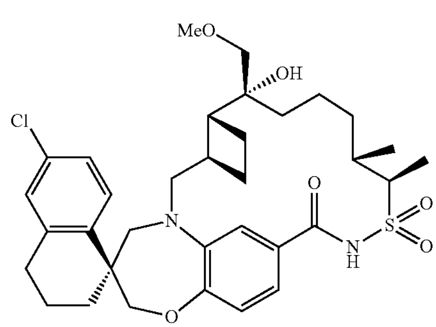 | (1S,3'R,6'R,7'R,11'S,12'R)-6-chloro-7'-hydroxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.2 |

TABLE 2-continued

Examples Prepared by the General Methods

| Example Number | Structure | Name | MS Dat (M + 1)+ Unless Noted Otherwise |
|---|---|---|---|
| | 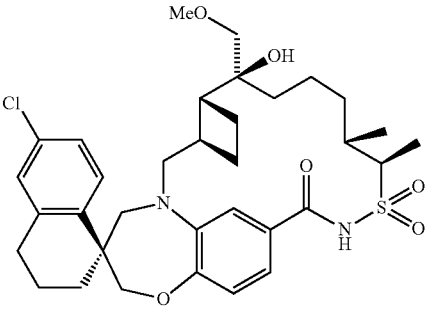 OR | OR (1S,3'R,6'R,7'S,11'S,12'R)-6-chloro-7'-hydroxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100151 | 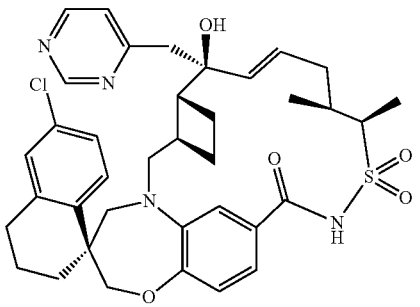 | (1S,3'R,6'R,7'S,8'E,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.2 |
| | 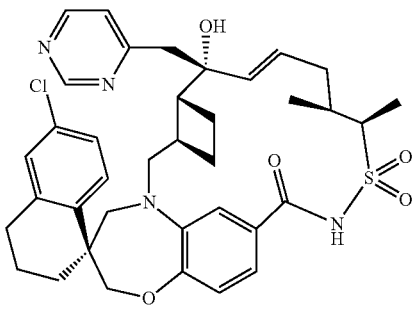 OR | OR (1S,3'R,6'R,7'R,8'E,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100152 | 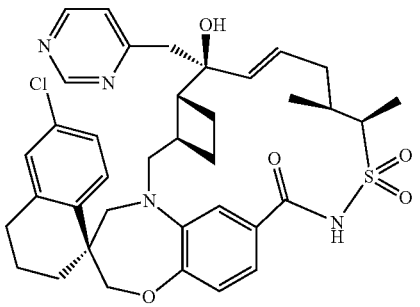 | (1S,3'R,6'R,7'S,8'E,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-hydroxy-11',12'-dimethyl-7'-(4-pyrimidinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100153 | 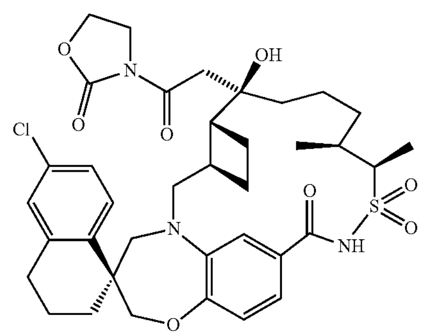 | (1S,3'R,6'R,7'R,11'S,12'R)-6-chloro-7'-hydroxy-11',12'-dimethyl-7'-(2-oxo-2-(2-oxo-1,3-oxazolidin-3-yl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 728.5 |
| | OR | OR (1S,3'R,6'R,7'S,11'S,12'R)-6-chloro-7'-hydroxy-11',12'-dimethyl-7'-(2-oxo-2-(2-oxo-1,3-oxazolidin-3-yl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100154 | 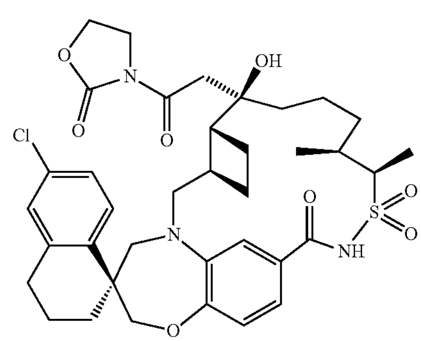 | (1S,3'R,6'R,7'R,11'S,12'R)-6-chloro-7'-hydroxy-11',12'-dimethyl-7'-(2-oxo-2-(2-oxo-1,3-oxazolidin-3-yl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 728.5 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,11'S,12'R)-6-chloro-7'-hydroxy-11',12'-dimethyl-7'-(2-oxo-2-(2-oxo-1,3-oxazolidin-3-yl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100155 | OR | OR (1S,3'R,6'R,7'S,11'S,12'R)-6-chloro-3''-((2-methoxyethyl)(methyl)amino)-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | 727.1 |
| | OR | OR (1S,3'R,6'R,7'R,11'S,12'R)-6-chloro-3''-((2-methoxyethyl)(methyl)amino)-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100156 | 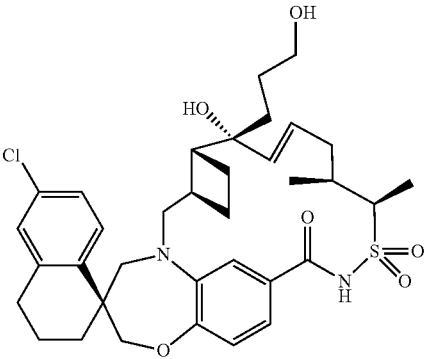 OR 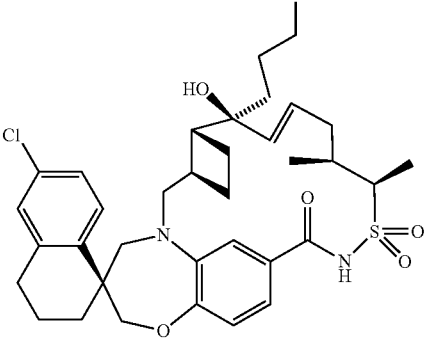 | (1S,3'R,6'R,7'R,8'E,11'S,12'R)-6-chloro-7'-hydroxy-7'-(3-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-hydroxy-7'-(3-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.3 |
| 100157 | 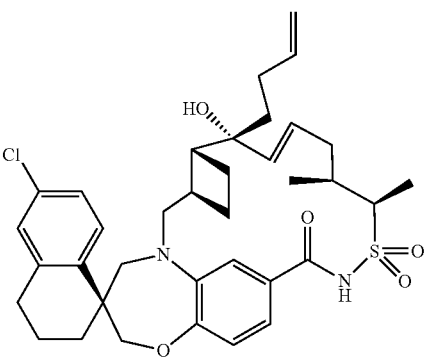 | (1S,3'R,6'R,7'R,8'E,11'S,12'R)-7'-(3-buten-1-yl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 653.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-7'-(3-buten-1-yl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100158 | 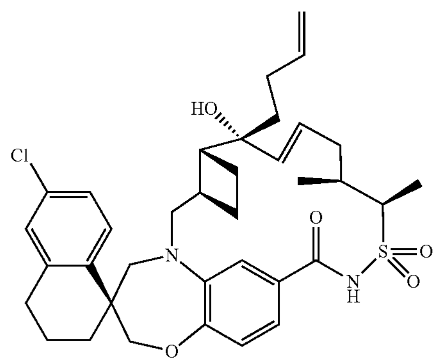 | (1S,3'R,6'R,7'R,8'E,11'S,12'R)-7'-(3-buten-1-yl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 653.0 |
| | OR | OR (1S,3'R,6'R,7'S,8'E,11'S,12'R)-7'-(3-buten-1-yl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100159 | 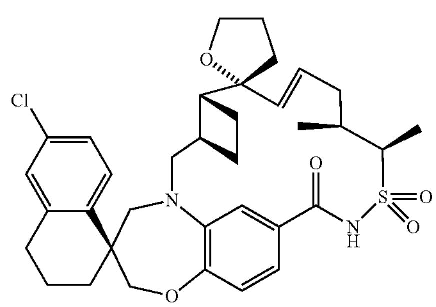 | (2S,3'R,6'R,8'E,11'S,12'R,22'S)-6''-chloro-11',12'-dimethyl-3'',4,4'',5-tetrahydro-2''H,3H,15'H-dispiro[furan-2,7'-[20]oxa[13]thia[1,14]diazatetracyclo[14.7.2.0~3,6~.0~19,24~]pentacosa[8,16,18,24]tetraene-22',1''-naphthalen]-15'-one 13',13'-dioxide | 639.3 |

TABLE 2-continued

Examples Prepared by the General Methods

| Example Number | Structure | Name | MS Dat (M + 1)+ Unless Noted Otherwise |
|---|---|---|---|
| | OR | (2R,3'R,6'R,8'E,11'S,12'R,22'S)-6''-chloro-11',12'-dimethyl-3'',4,4'',5-tetrahydro-2''H,3H,15'H-dispiro[furan-2,7'-[20]oxa[13]thia[1,14]diazatetracyclo[14.7.2.0~3,6~.0~19,24~]pentacosa[8,16,18,24]tetraene-22',1''-naphthalen]-15'-one 13',13'-dioxide | |
| 100160 | 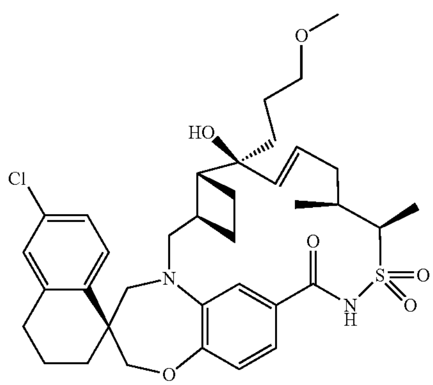 | (1S,3'R,6'R,7'S,8'E,11'S,12'R)-6-chloro-7'-hydroxy-7'-(3-methoxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.4 |
| | OR | (1S,3'R,6'R,7'R,8'E,11'S,12'R)-6-chloro-7'-hydroxy-7'-(3-methoxypropyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100161 | 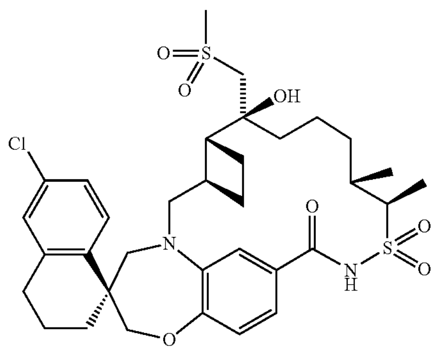 [SMILES: C[C@@H]1[C@@H](C)CCC[C@@](O)(CS(C)(=O)=O)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 693.2 |
|  | AND | AND |  |
|  |  | (1S,3'R,6'R,7'S,11'S,12'R)-6-chloro-7'-hydroxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide |  |
| 100162 | 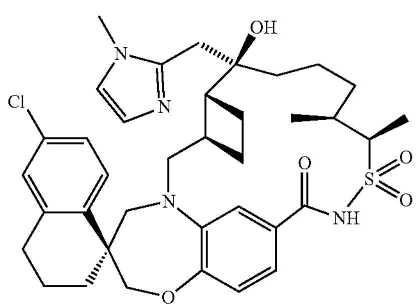 [SMILES: C[C@@H]1[C@@H](C)CCC[C@@](O)(Cc2nccn2C)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-((1-methyl-1H-imidazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 695.5 |
|  | OR | OR |  |
|  |  | (1S,3'R,6'R,7'S,11'S,12'R)-6-chloro-7'-hydroxy-11',12'-dimethyl-7'-((1-methyl-1H-imidazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide |  |

TABLE 2-continued

Examples Prepared by the General Methods

| Example Number | Structure | Name | MS Dat (M + 1)+ Unless Noted Otherwise |
|---|---|---|---|
| 100163 | 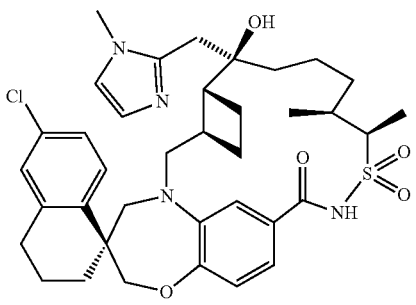 [SMILES: C[C@@H]1[C@@H](C)CCC[C@@](O)(Cc2nccn2C)[C@@H]2CC[C@H]2CN2C[C@@]3(CCCc4cc(Cl)ccc43)COc3ccc(cc32)C(=O)NS1(=O)=O]<br>OR<br>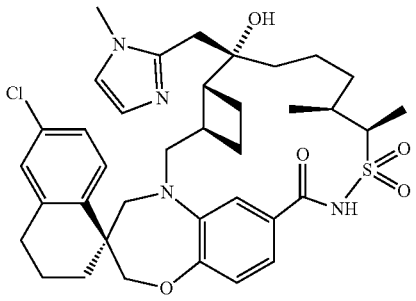 [SMILES: C[C@@H]1[C@@H](C)CCC[C@](O)(Cc2nccn2C)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-((1-methyl-1H-imidazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br>OR<br>(1S,3'R,6'R,7'S,11'S,12'R)-6-chloro-7'-hydroxy-11',12'-dimethyl-7'-((1-methyl-1H-imidazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 695.5 |
| 100164 | 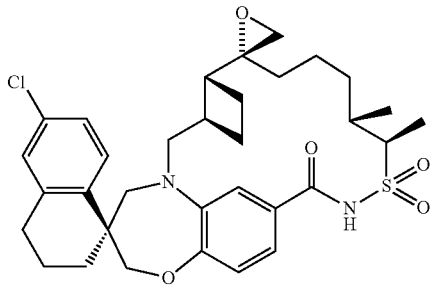<br>AND<br>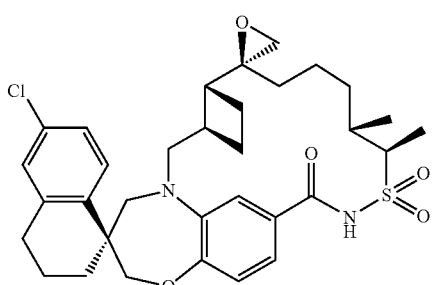 | (1S,3'R,6'R,7'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-oxiran]-15'-one 13',13'-dioxide<br>AND<br>(1S,3'R,6'R,7'S,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-oxiran]-15'-one 13',13'-dioxide | 613.2 |

TABLE 2-continued

Examples Prepared by the General Methods

| Example Number | Structure | Name | MS Dat (M + 1)+ Unless Noted Otherwise |
|---|---|---|---|
| 100165 | 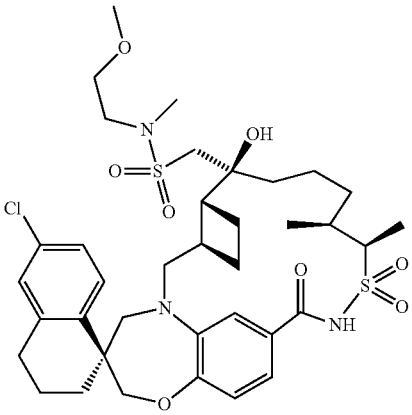 OR 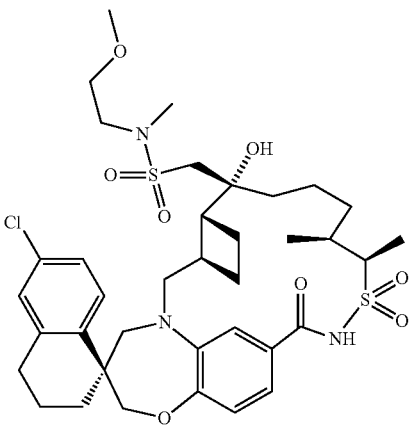 | 1-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-yl)-N-(2-methoxyethyl)-N-methylmethanesulfonamide OR 1-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylmethanesulfonamide | 766.2 |
| 100166 | 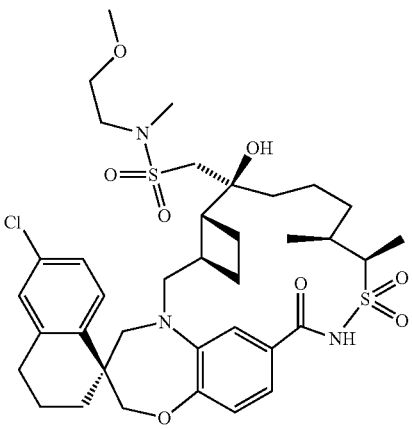 | 1-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylmethanesulfonamide | 766.3 |

TABLE 2-continued

Examples Prepared by the General Methods

| Example Number | Structure | Name | MS Dat (M + 1)+ Unless Noted Otherwise |
|---|---|---|---|
| | OR | OR 1-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-(2-methoxyethyl)-N-methylmethanesulfonamide | |
| 100167 | 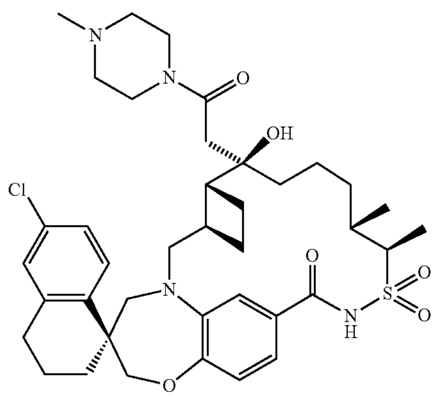 | (1S,3'R,6'R,7'R,11'S,12'R)-6-chloro-7'-hydroxy-11',12'-dimethyl-7'-(2-(4-methyl-1-piperazinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 741.2 |
| | OR | OR (1S,3'R,6'R,7'S,11'S,12'R)-6-chloro-7'-hydroxy-11',12'-dimethyl-7'-(2-(4-methyl-1-piperazinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100168 | 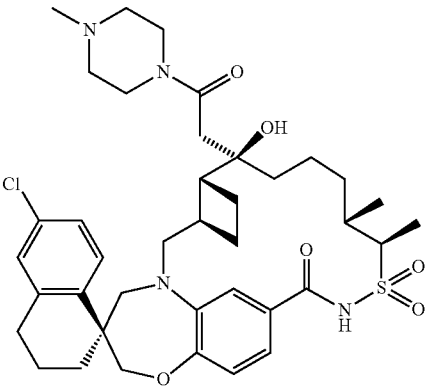 OR 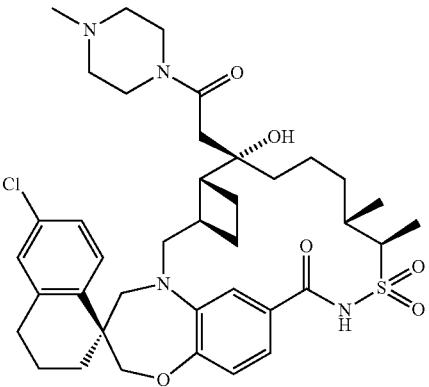 | (1S,3'R,6'R,7'S,11'S,12'R)-6-chloro-7'-hydroxy-11',12'-dimethyl-7'-(2-(4-methyl-1-piperazinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'R,11'S,12'R)-6-chloro-7'-hydroxy-11',12'-dimethyl-7'-(2-(4-methyl-1-piperazinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 741.2 |
| 100169 | 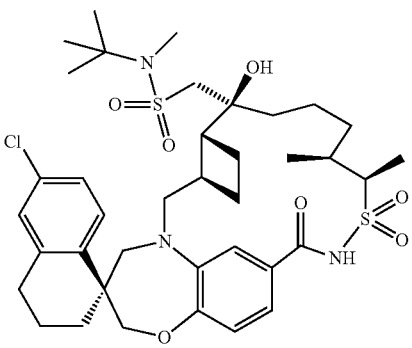 | 1-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)methanesulfonamide | 764.2 |

TABLE 2-continued

Examples Prepared by the General Methods

| Example Number | Structure | Name | MS Dat (M + 1)+ Unless Noted Otherwise |
|---|---|---|---|
| | OR | 1-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)methanesulfonamide | |
| 100170 | 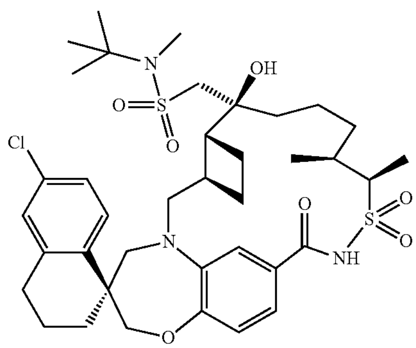 | 1-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)methanesulfonamide | 764.2 |
| | OR | 1-((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-methyl-N-(2-methyl-2-propanyl)methanesulfonamide | |
| 100171 | 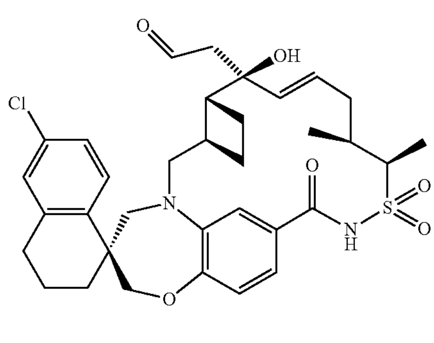 | ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde | 641.5 |

TABLE 2-continued

Examples Prepared by the General Methods

| Example Number | Structure | Name | MS Dat (M + 1)+ Unless Noted Otherwise |
|---|---|---|---|
| | OR | OR | |
| | | ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde | |
| 100172 | 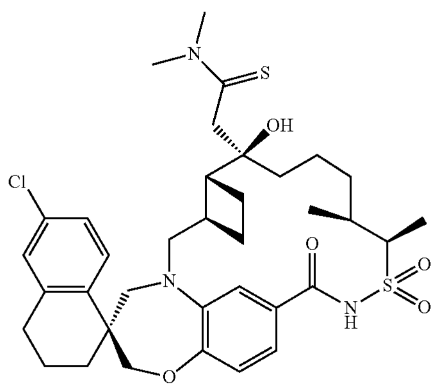 | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylethanethioamide | 702.1 |
| | OR | OR | |
| | | ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylethanethioamide | |

TABLE 2-continued

Examples Prepared by the General Methods

| Example Number | Structure | Name | MS Dat (M + 1)+ Unless Noted Otherwise |
|---|---|---|---|
| 100173 | 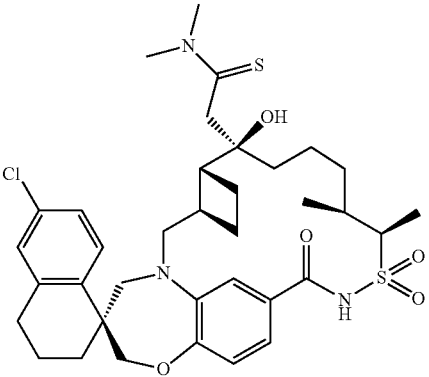 [SMILES: C[C@@H]1[C@@H](C)CCC[C@@](O)(CC(=S)N(C)C)[C@@H]2CC[C@H]2CN2C[C@@]3(CCCc4cc(Cl)ccc43)COc3ccc(cc32)C(=O)NS1(=O)=O] | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylethanethioamide | 702.1 |
| | OR | OR | |
| | 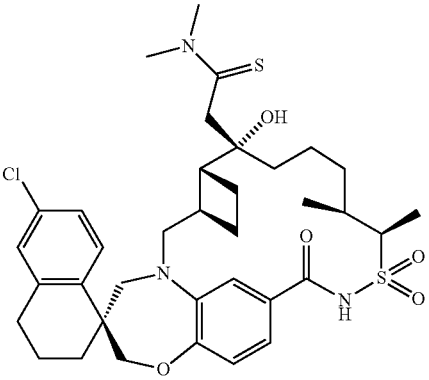 [SMILES: C[C@@H]1[C@@H](C)CCC[C@](O)(CC(=S)N(C)C)[C@@H]2CC[C@H]2CN2C[C@@]3(CCCc4cc(Cl)ccc43)COc3ccc(cc32)C(=O)NS1(=O)=O] | ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylethanethioamide | |
| 100174 | 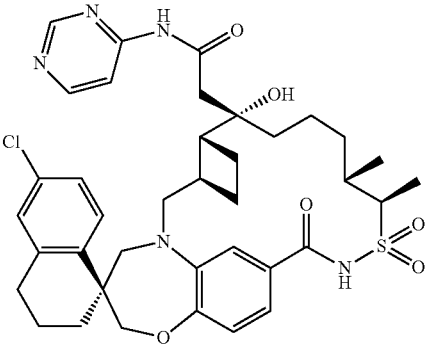 [SMILES: C[C@@H]1[C@@H](C)CCC[C@](O)(CC(=O)Nc2ccncn2)[C@@H]2CC[C@H]2CN2C[C@@]3(CCCc4cc(Cl)ccc43)COc3ccc(cc32)C(=O)NS1(=O)=O] | 2-((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-4-pyrimidinylacetamide | 736.2 |

TABLE 2-continued

Examples Prepared by the General Methods

| Example Number | Structure | Name | MS Dat (M + 1)+ Unless Noted Otherwise |
|---|---|---|---|
| | OR | OR 2-(1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N-4-pyrimidinylacetamide | |
| 100175 | 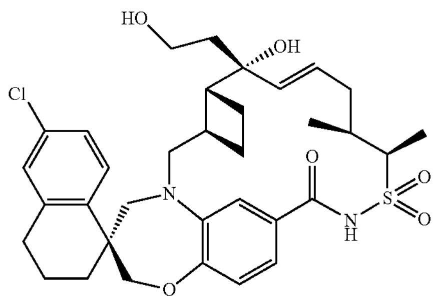 | (1S,3'R,6'R,7'R,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 643.4 |
| | OR | OR (1S,3'R,6'R,7'S,8'E,11'S,12'R)-6-chloro-7'-hydroxy-7'-(2-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100176 | 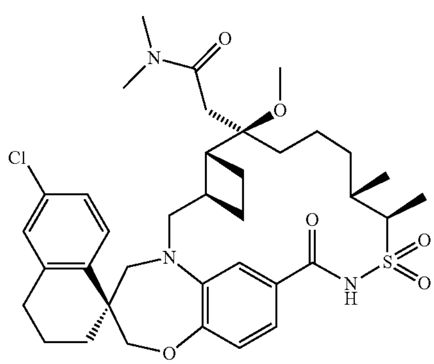 | 2-((1S,3'R,6'R,7'R,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylacetamide | 700.2 |

TABLE 2-continued

Examples Prepared by the General Methods

| Example Number | Structure | Name | MS Dat (M + 1)+ Unless Noted Otherwise |
|---|---|---|---|
| | | 2-((1S,3'R,6'R,7'S,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)-N,N-dimethylacetamide | |
| 100177 | 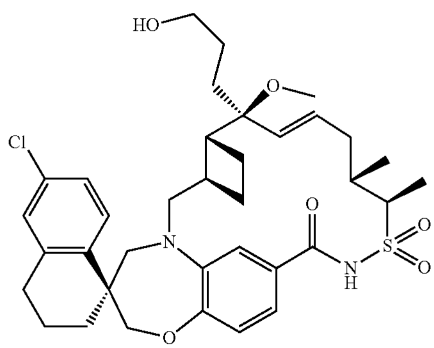 [SMILES: CO[C@@]1(CCCO)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(3-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.2 |
| | | (1S,3'R,6'R,7'R,8'E,11'S,12'R)-6-chloro-7'-(3-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100178 | 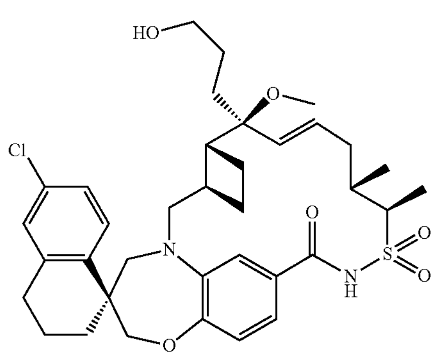 [SMILES: CO[C@@]1(CCCO)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(3-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-(3-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100179 | 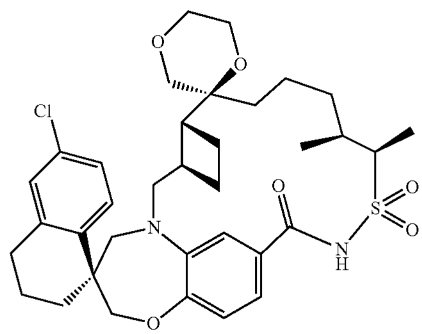 | (2S,3'R,6'R,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[16,18,24]triene-22',1'''-naphthalen]-15'-one 13',13'-dioxide | 657.2 |
| | OR | OR (2R,3'R,6'R,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[16,18,24]triene-22',1'''-naphthalen]-15'-one 13',13'-dioxide | |
| 100180 | 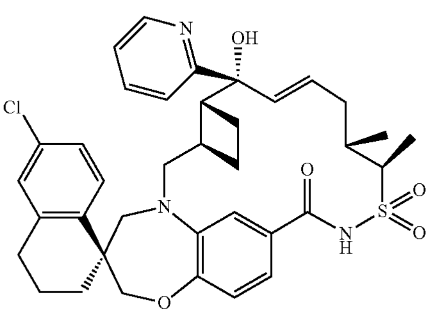 | (1S,3'R,6'R,7'R,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-hydroxy-11,12-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100181 | 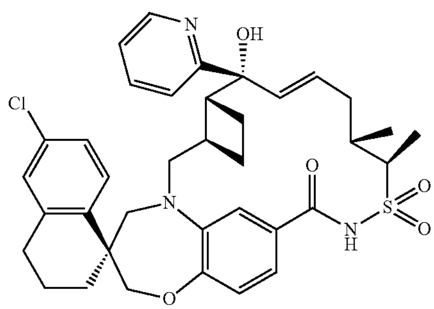 | (1S,3'R,6'R,7'S,8'E,11'S,12'R)-6-chloro-7'-hydroxy-11,12-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |
| | OR | OR (1S,3'R,6'R,7'R,8'E,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100182 | 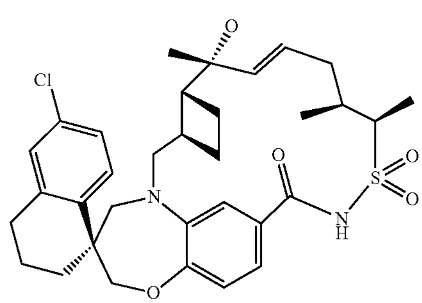 | (1S,3'R,6'R,7'R,8'E,11'S,12'R)-6-chloro-7'-hydroxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 613.1 |

TABLE 2-continued

Examples Prepared by the General Methods

| Example Number | Structure | Name | MS Dat (M + 1)+ Unless Noted Otherwise |
|---|---|---|---|
| 100183 | 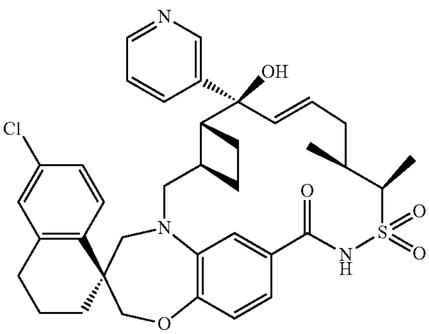 [SMILES: C[C@@H]1[C@@H](C)C/C=C/[C@@](O)(c2cccnc2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.2 |
| | OR | OR | |
| | | (1S,3'R,6'R,7'S,8'E,11'S,12'R)-6-chloro-7'-hydroxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100184 | 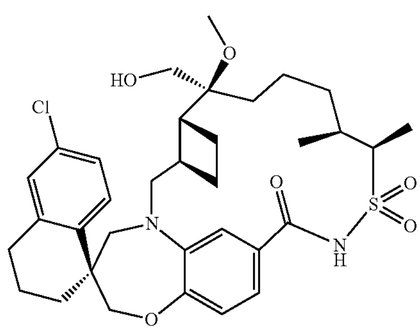 [SMILES: CO[C@@]1(CO)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.2 |
| | OR | OR | |
| | | (1S,3'R,6'R,7'R,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100185 | 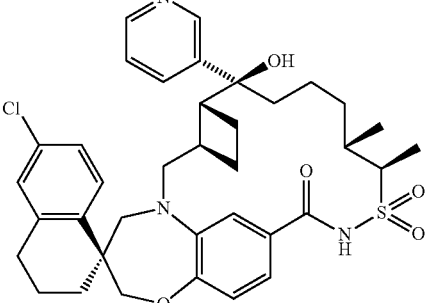 OR 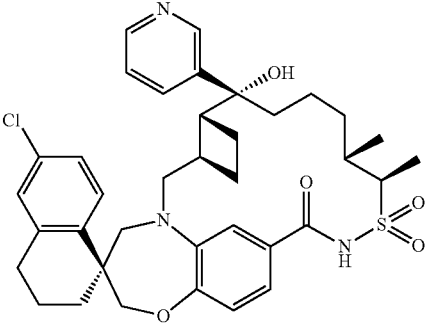 | (1S,3'R,6'R,7'S,11'S,12'R)-6-chloro-7'-hydroxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'R,11'S,12'R)-6-chloro-7'-hydroxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 678.2 |
| 100186 | 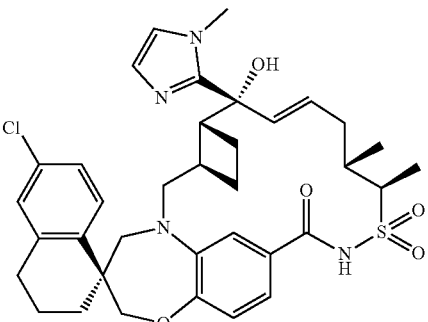 OR 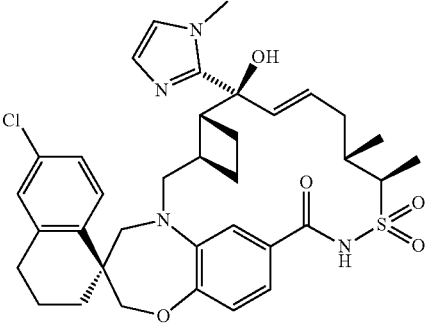 | (1S,3'R,6'R,7'R,8'E,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 679.2 |

TABLE 2-continued

Examples Prepared by the General Methods

| Example Number | Structure | Name | MS Dat (M + 1)+ Unless Noted Otherwise |
|---|---|---|---|
| 100187 | 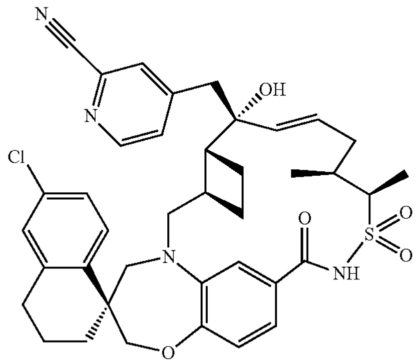 [SMILES: C[C@@H]1[C@@H](C)C/C=C/[C@](O)(Cc2ccnc(C#N)c2)[C@@H]2CC[C@H]2CN2C[C@@]3(CCCc4cc(Cl)ccc43)COc3ccc(cc32)C(=O)NS1(=O)=O] | 4-(((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-2-pyridinecarbonitrile | 715.3 |
| | OR | OR | |
| | | 4-(((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-2-pyridinecarbonitrile | |
| 100188 | 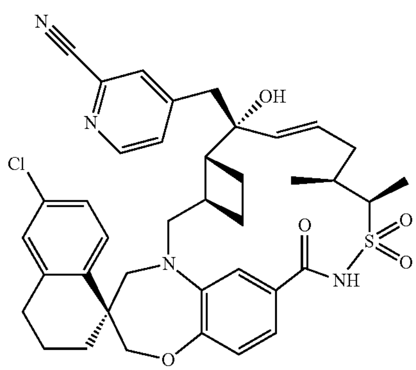 [SMILES: C[C@@H]1[C@@H](C)C/C=C/[C@](O)(Cc2ccnc(C#N)c2)[C@@H]2CC[C@H]2CN2C[C@@]3(CCCc4cc(Cl)ccc43)COc3ccc(cc32)C(=O)NS1(=O)=O] | 4-(((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-2-pyridinecarbonitrile | 715.3 |

| Example Number | Structure | Name | MS Dat (M + 1)+ Unless Noted Otherwise |
|---|---|---|---|
| | OR 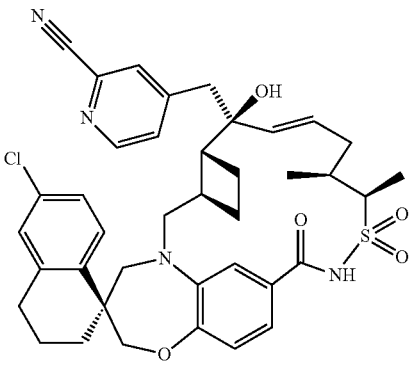 | OR 4-(((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-2-pyridinecarbonitrile | |
| 100189 | 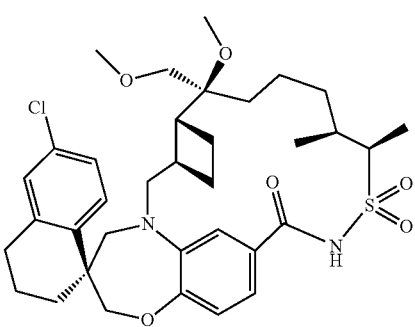 | (1S,3'R,6'R,7'S,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.2 |
| | OR 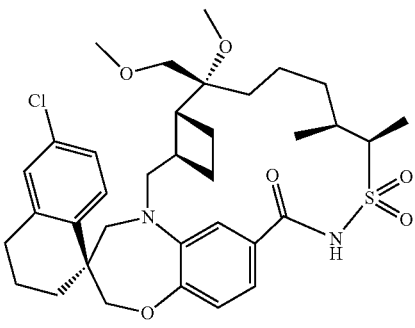 | OR (1S,3'R,6'R,7'R,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100190 | 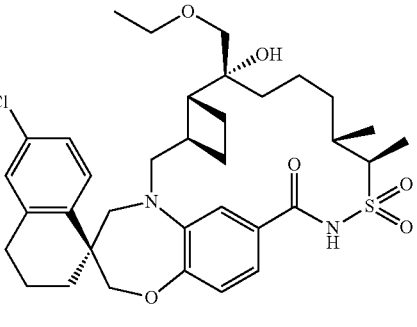 | (1S,3'R,6'R,7'R,11'S,12'R)-6-chloro-7'-(ethoxymethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,11'S,12'R)-6-chloro-7'-(ethoxymethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100191 | 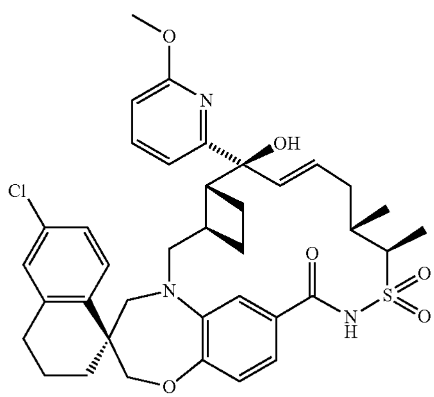 | (1S,3'R,6'R,7'S,8'E,11'S,12'R)-6-chloro-7'-hydroxy-7'-(6-methoxy-2-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 706.2 |
| | OR | OR (1S,3'R,6'R,7'R,8'E,11'S,12'R)-6-chloro-7'-hydroxy-7'-(6-methoxy-2-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100192 | 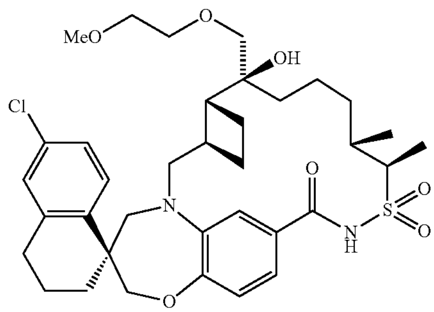 [SMILES: COCCOC[C@]1(O)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 689.2 |
| | OR | OR | |
| | | (1S,3'R,6'R,7'R,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100193 | 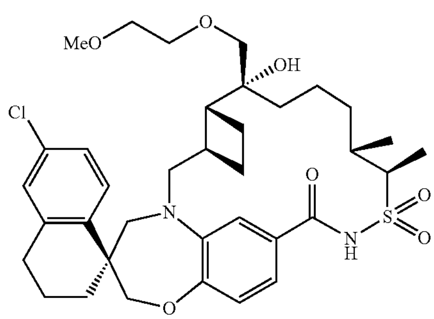 [SMILES: COCCOC[C@@]1(O)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 689.2 |
| | OR | OR | |
| | | (1S,3'R,6'R,7'S,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100194 | 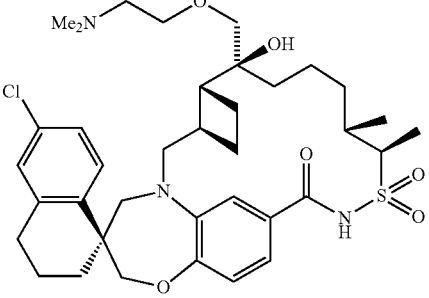 OR 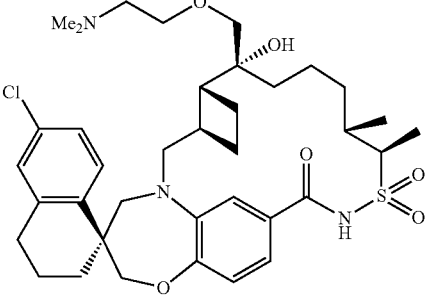 | (1S,3'R,6'R,7'S,11'S,12'R)-6-chloro-7'-((2-(dimethylamino)ethoxy)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'R,11'S,12'R)-6-chloro-7'-((2-(dimethylamino)ethoxy)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 702.2 |
| 100195 | 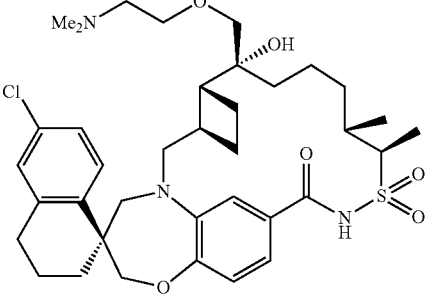 OR 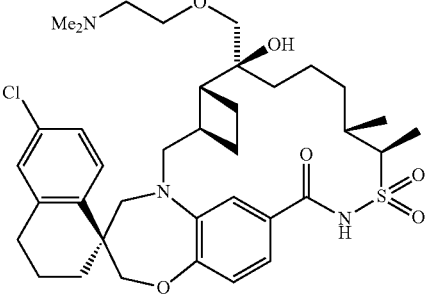 | (1S,3'R,6'R,7'R,11'S,12'R)-6-chloro-7'-((2-(dimethylamino)ethoxy)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'S,11'S,12'R)-6-chloro-7'-((2-(dimethylamino)ethoxy)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 702.2 |

TABLE 2-continued

Examples Prepared by the General Methods

| Example Number | Structure | Name | MS Dat (M + 1)+ Unless Noted Otherwise |
|---|---|---|---|
| 100196 | 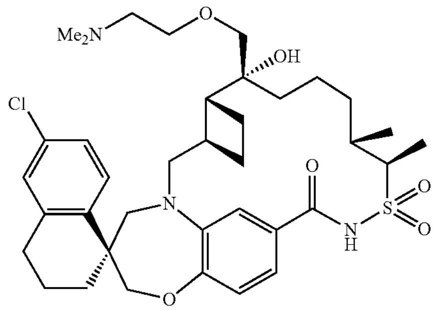 [SMILES: C[C@@H]1[C@@H](C)CCC[C@](O)(COCCN(C)C)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-((2-(dimethylamino)ethoxy)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 702.2 |
| | AND | AND | |
| | | (1S,3'R,6'R,7'S,11'S,12'R)-6-chloro-7'-((2-(dimethylamino)ethoxy)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100197 | 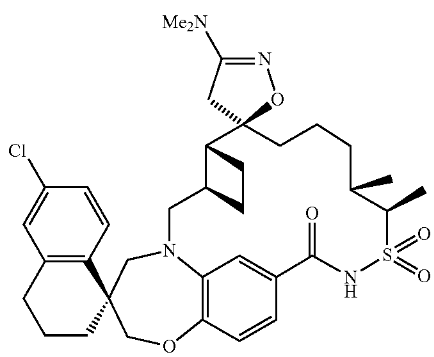 | (1S,3'R,6'R,7'R,11'S,12'R)-6-chloro-3''-(dimethylamino)-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | 683.2 |
| | OR | OR | |
| | | (1S,3'R,6'R,7'S,11'S,12'R)-6-chloro-3''-(dimethylamino)-11',12'-dimethyl-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100198 | 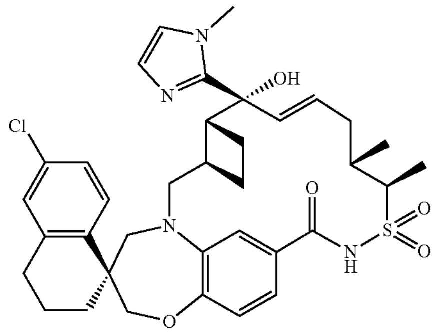 [SMILES: C[C@@H]1[C@@H](C)C/C=C/[C@](O)(c2nccn2C)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 679.2 |
| | OR | OR | |
| | | (1S,3'R,6'R,7'S,8'E,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100199 | 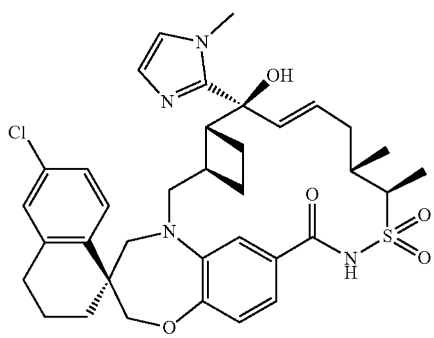 [SMILES: C[C@@H]1[C@@H](C)C/C=C/[C@@](O)(c2nccn2C)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 679.2 |
| | OR | OR | |
| | | (1S,3'R,6'R,7'R,8'E,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100200 | 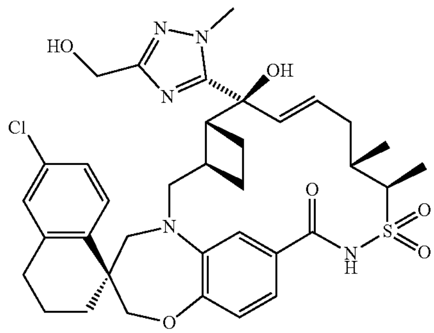 [SMILES: C[C@@H]1[C@@H](C)C/C=C/[C@@](O)(c2nc(CO)nn2C)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-7'-(3-(hydroxymethyl)-1-methyl-1H-1,2,4-triazol-5-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.2 |
| | OR | OR | |
| | | (1S,3'R,6'R,7'R,8'E,11'S,12'R)-6-chloro-7'-hydroxy-7'-(3-(hydroxymethyl)-1-methyl-1H-1,2,4-triazol-5-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100201 | 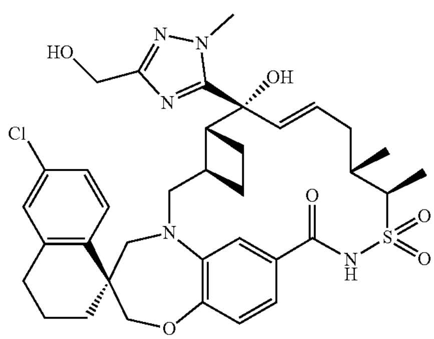 [SMILES: C[C@@H]1[C@@H](C)C/C=C/[C@](O)(c2nc(CO)nn2C)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-7'-(3-(hydroxymethyl)-1-methyl-1H-1,2,4-triazol-5-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.2 |
| | OR | OR | |
| | | (1S,3'R,6'R,7'S,8'E,11'S,12'R)-6-chloro-7'-hydroxy-7'-(3-(hydroxymethyl)-1-methyl-1H-1,2,4-triazol-5-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100202 | 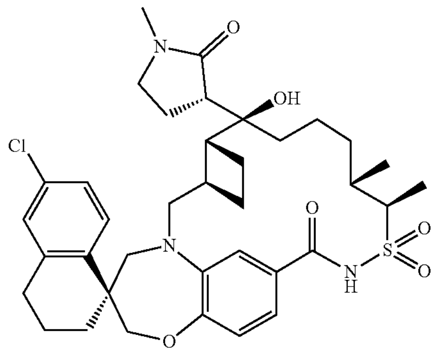 [SMILES: C[C@@H]1[C@@H](C)CCC[C@@](O)([C@@H]2CCN(C)C2=O)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.1 |
| | OR | OR | |
| | | (1S,3'R,6'R,7'R,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR | |
| | | (1S,3'R,6'R,7'S,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100203 | 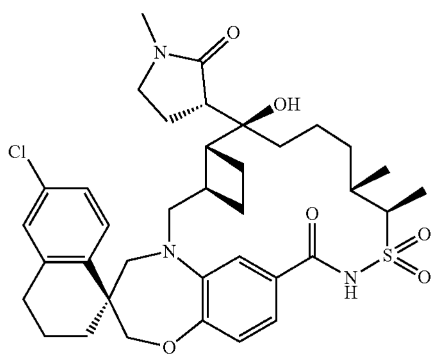 | (1S,3'R,6'R,7'S,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.2 |
| | OR | OR (1S,3'R,6'R,7'R,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR  | OR (1S,3'R,6'R,7'S,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR  | OR (1S,3'R,6'R,7'R,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100204 | 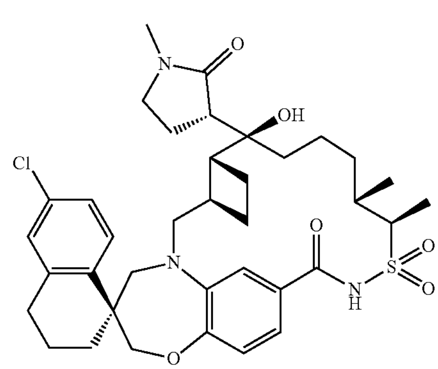 | (1S,3'R,6'R,7'S,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.1 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,11'S,12'R)-6-chloro-7'-hydroxy-11',12'-dimethyl-7'-((3S)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR | |
| | | (1S,3'R,6'R,7'S,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR | |
| | | (1S,3'R,6'R,7'R,11'S,12'R)-6-chloro-7'-hydroxy-11',12'-dimethyl-7'-((3R)-1-methyl-2-oxo-3-pyrrolidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100205 | 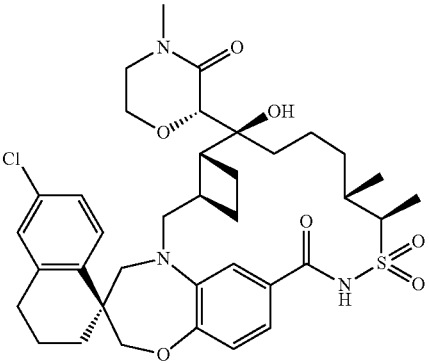 [SMILES: C[C@@H]1[C@@H](C)CCC[C@@](O)([C@@H]2OCCN(C)C2=O)[C@@H]2CC[C@H]2CN2C[C@@]3(CCCc4cc(Cl)ccc43)COc3ccc(cc32)C(=O)NS1(=O)=O]<br>OR<br>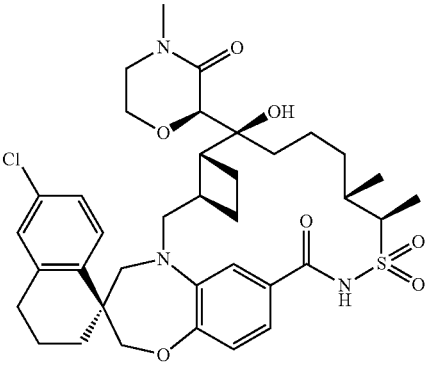 [SMILES: C[C@@H]1[C@@H](C)CCC[C@@](O)([C@H]2OCCN(C)C2=O)[C@@H]2CC[C@H]2CN2C[C@@]3(CCCc4cc(Cl)ccc43)COc3ccc(cc32)C(=O)NS1(=O)=O]<br>OR<br>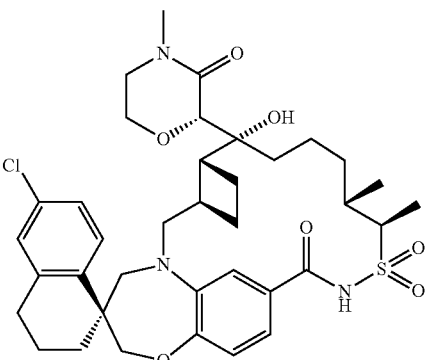 | (1S,3'R,6'R,7'S,11'S,12'R)-6-chloro-7'-hydroxy-11',12'-dimethyl-7'-((2S)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,11'S,12'R)-6-chloro-7'-hydroxy-11',12'-dimethyl-7'-((2R)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,11'S,12'R)-6-chloro-7'-hydroxy-11',12'-dimethyl-7'-((2S)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 714.1 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,11'S,12'R)-6-chloro-7'-hydroxy-11',12'-dimethyl-7'-((2R)-4-methyl-3-oxo-2-morpholinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100206 | 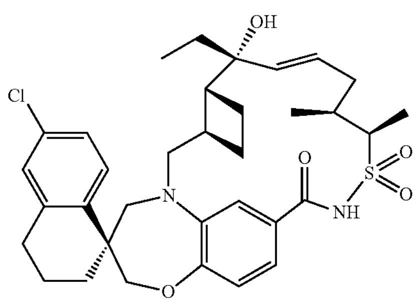 | (1S,3'R,6'R,7'R,8'E,11'S,12'R)-6-chloro-7'-ethyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 627.2 |
| 100207 | 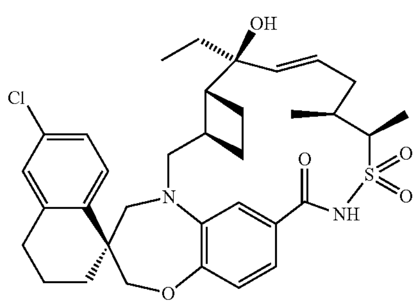 | (1S,3'R,6'R,7'S,8'E,11'S,12'R)-6-chloro-7'-ethyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 627.2 |
| 100208 | 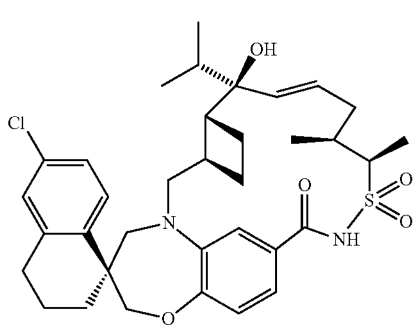 | (1S,3'R,6'R,7'S,8'E,11'S,12'R)-6-chloro-7'-hydroxy-11',12'-dimethyl-7'-(2-propanyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.2 |

TABLE 2-continued

Examples Prepared by the General Methods

| Example Number | Structure | Name | MS Dat (M + 1)+ Unless Noted Otherwise |
|---|---|---|---|
| | OR 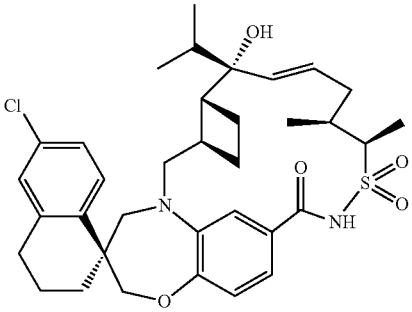 | OR (1S,3'R,6'R,7'R,8'E,11'S,12'R)-6-chloro-7'-hydroxy-11',12'-dimethyl-7'-(2-propanyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100209 | 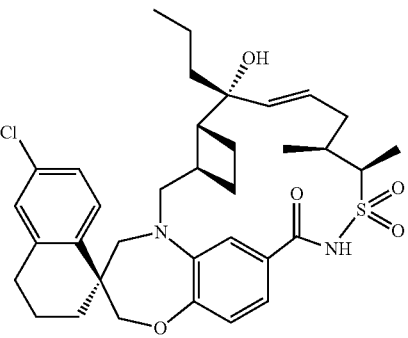 | (1S,3'R,6'R,7'R,8'E,11'S,12'R)-6-chloro-7'-hydroxy-11',12'-dimethyl-7'-propyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.3 |
| | OR 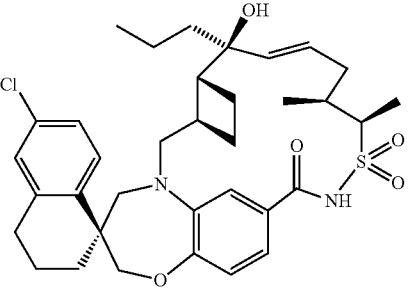 | OR (1S,3'R,6'R,7'S,8'E,11'S,12'R)-6-chloro-7'-hydroxy-11',12'-dimethyl-7'-propyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100210 | 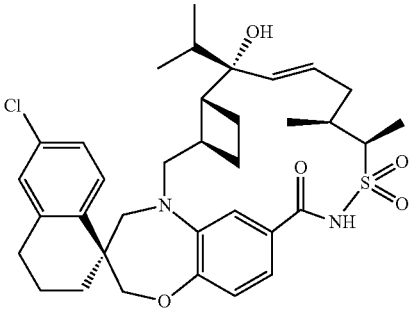 | (1S,3'R,6'R,7'R,8'E,11'S,12'R)-6-chloro-7'-hydroxy-11',12'-dimethyl-7'-(2-propanyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.2 |

TABLE 2-continued

Examples Prepared by the General Methods

| Example Number | Structure | Name | MS Dat (M + 1)+ Unless Noted Otherwise |
|---|---|---|---|
| | OR 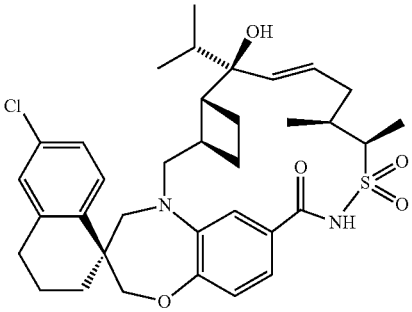 | OR (1S,3'R,6'R,7'S,8'E,11'S,12'R)-6-chloro-7'-hydroxy-11',12'-dimethyl-7'-(2-propanyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100211 | 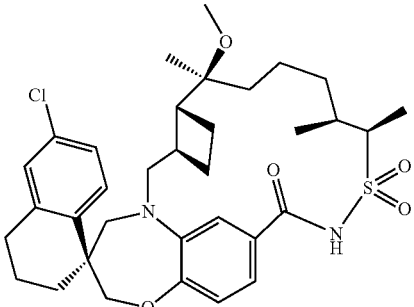 | (1S,3'R,6'R,7'R,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 629.3 |
| | OR 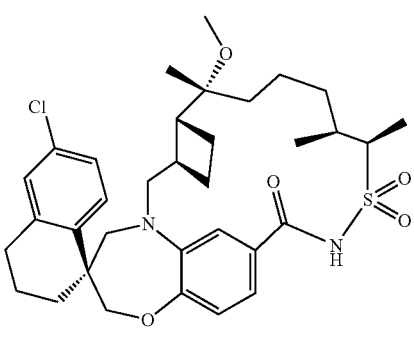 | OR (1S,3'R,6'R,7'S,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100212 | 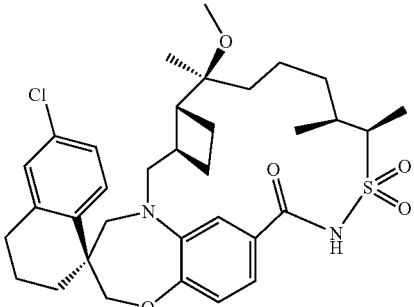 | (1S,3'R,6'R,7'R,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 629.3 |

TABLE 2-continued

Examples Prepared by the General Methods

| Example Number | Structure | Name | MS Dat (M + 1)+ Unless Noted Otherwise |
|---|---|---|---|
| | 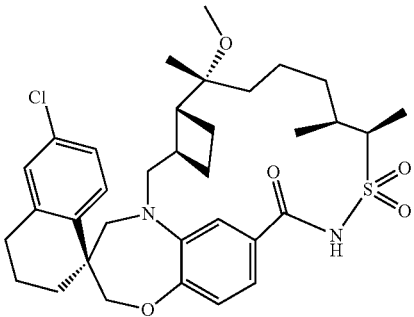 [SMILES: CO[C@]1(C)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-methoxy-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100213 | 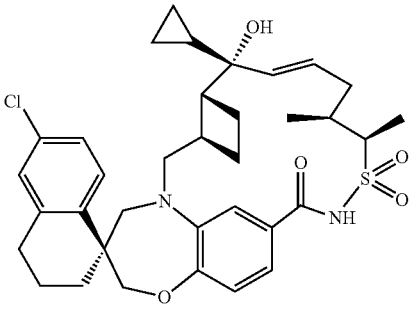 [SMILES: C[C@@H]1[C@@H](C)C/C=C/[C@](O)(C2CC2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-cyclopropyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 639.2 |
| | 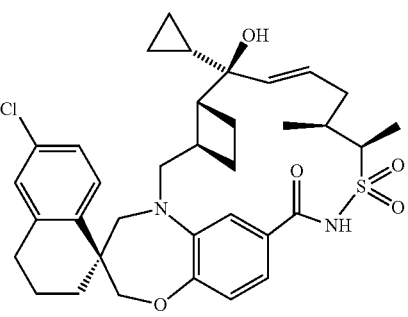 [SMILES: C[C@@H]1[C@@H](C)C/C=C/[C@@](O)(C2CC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-cyclopropyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100214 | 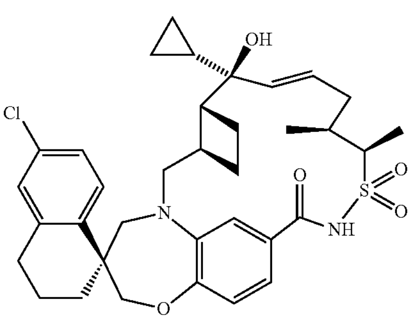 [SMILES: C[C@@H]1[C@@H](C)C/C=C/[C@@](O)(C2CC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-cyclopropyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 639.2 |

TABLE 2-continued

Examples Prepared by the General Methods

| Example Number | Structure | Name | MS Dat (M + 1)+ Unless Noted Otherwise |
|---|---|---|---|
| | OR 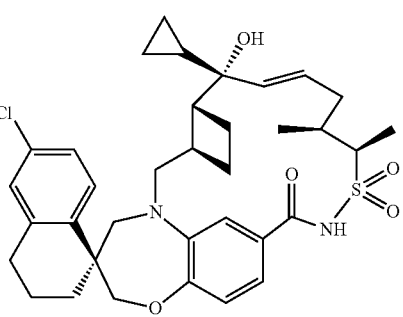 | OR (1S,3'R,6'R,7'R,8'E,11'S,12'R)-6-chloro-7'-cyclopropyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100215 | 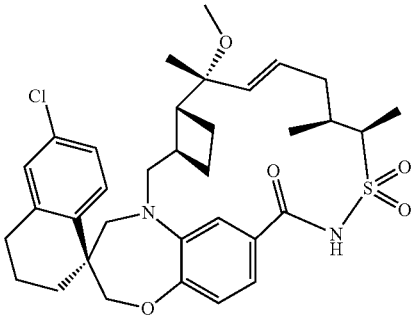 | (1S,3'R,6'R,7'R,8'E,11'S,12'R)-6-chloro-7'-methoxy-7,11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 627.2 |
| 100216 | 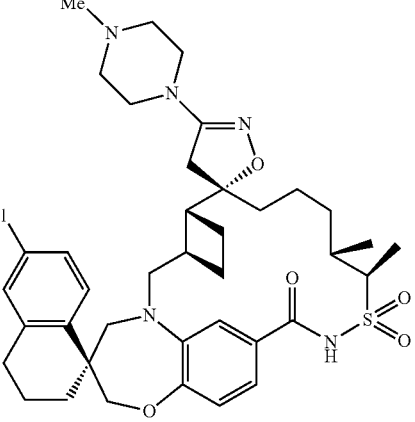 | (1S,3'R,6'R,7'S,11'S,12'R)-6-chloro-11',12'-dimethyl-3"-(4-methyl-1-piperazinyl)-3,4-dihydro-2H,4"H,15'H-dispiro[naphthalene-1,22'-[20]oxa[13]thia[1,14]diazatetracyclo[14.7.2.0~3,6~.0~19,24~]pentacosa[16,18,24]triene-7',5"-[1,2]oxazol]-15'-one 13',13'-dioxide | 738.0 |

TABLE 2-continued

Examples Prepared by the General Methods

| Example Number | Structure | Name | MS Dat (M + 1)+ Unless Noted Otherwise |
|---|---|---|---|
| | OR 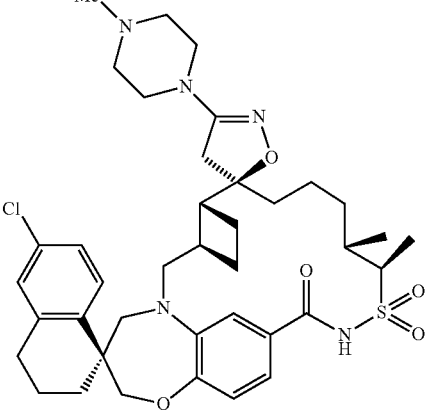 | OR (1S,3'R,6'R,7'R,11'S,12'R)-6-chloro-11',12'-dimethyl-3''-(4-methyl-1-piperazinyl)-3,4-dihydro-2H,4''H,15'H-dispiro[naphthalene-1,22'-[20]oxa[13]thia[1,14]diazatetracyclo[14.7.2.0~3,6~.0~19,24~]pentacosa[16,18,24]triene-7',5''-[1,2]oxazol]-15'-one 13',13'-dioxide | |
| 100217 | 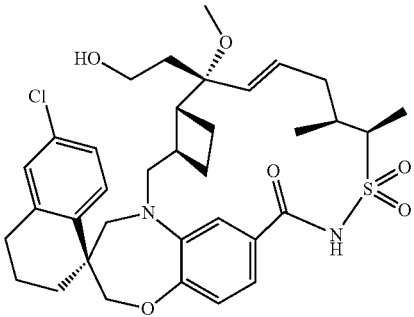 | (1S,3'R,6'R,7'R,8'E,11'S,12'R)-6-chloro-7'-(2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.2 |
| 100218 | 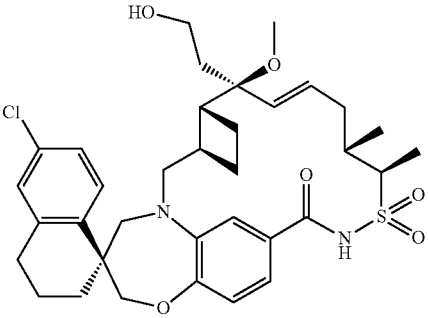 | (1S,3'R,6'R,7'S,8'E,11'S,12'R)-6-chloro-7'-(2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.1 |

TABLE 2-continued

Examples Prepared by the General Methods

| Example Number | Structure | Name | MS Dat (M + 1)+ Unless Noted Otherwise |
|---|---|---|---|
| | OR 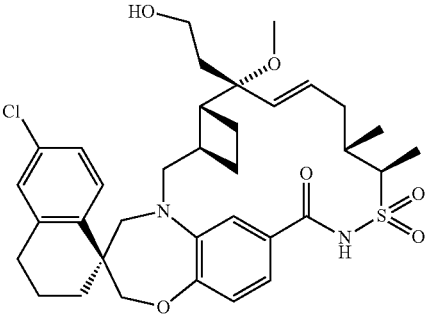 | OR (1S,3'R,6'R,7'R,8'E,11'S,12'R)-6-chloro-7'-(2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100219 | 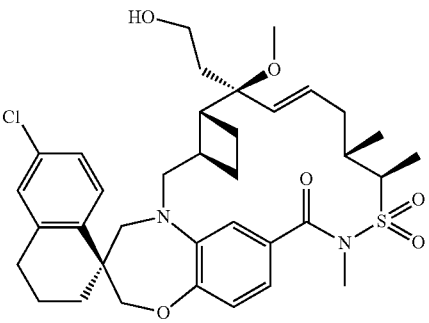 | (1S,3'R,6'R,7'S,8'E,11'S,12'R)-6-chloro-7'-(2-hydroxyethyl)-7'-methoxy-11',12',14'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.1 |
| | OR 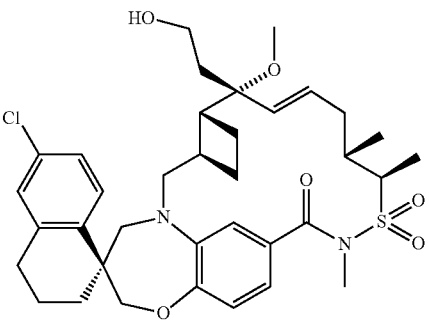 | OR (1S,3'R,6'R,7'R,8'E,11'S,12'R)-6-chloro-7'-(2-hydroxyethyl)-7'-methoxy-11',12',14'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100220 | 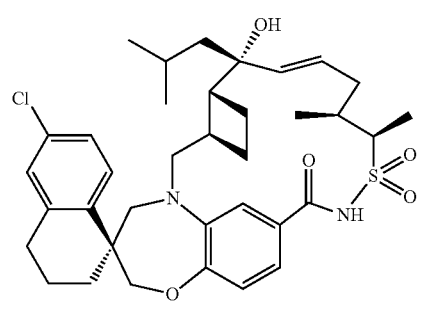 | (1S,3'R,6'R,7'R,8'E,11'S,12'R)-6-chloro-7'-hydroxy-11',12'-dimethyl-7'-(2-methylpropyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 655.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-hydroxy-11',12'-dimethyl-7'-(2-methylpropyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100221 | 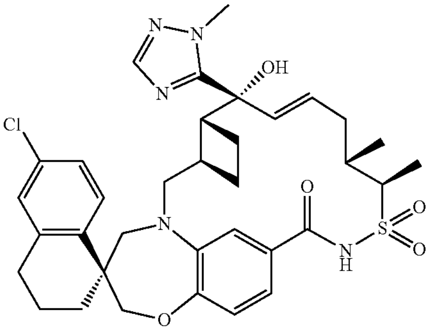 | (1S,3'R,6'R,7'R,8'E,11'S,12'R)-6-chloro-7'-hydroxy-11',12'-dimethyl-7'-(1-methyl-1H-1,2,4-triazol-5-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 680.2 |
| | OR | OR (1S,3'R,6'R,7'S,8'E,11'S,12'R)-6-chloro-7'-hydroxy-11',12'-dimethyl-7'-(1-methyl-1H-1,2,4-triazol-5-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100222 | 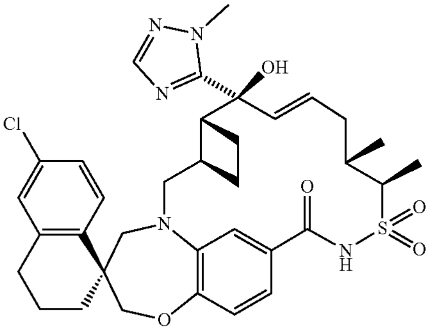 | (1S,3'R,6'S,7'S,8'E,11'S,12'R)-6-chloro-7'-hydroxy-11',12'-dimethyl-7'-(1-methyl-1H-1,2,4-triazol-5-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 680.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-hydroxy-11',12'-dimethyl-7'-(1-methyl-1H-1,2,4-triazol-5-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100223 | 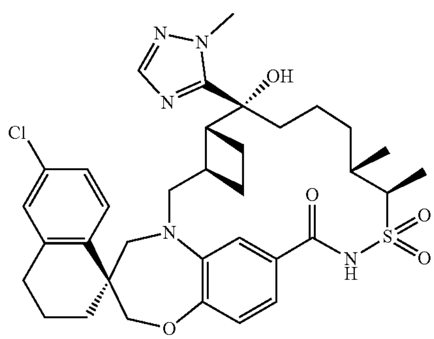 | (1S,3'R,6'R,7'R,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 681.2 |
| 100224 | 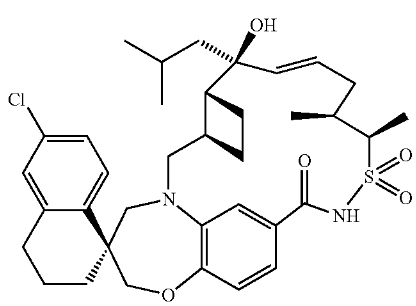 | (1S,3'R,6'R,7'S,8'E,11'S,12'R)-6-chloro-7'-hydroxy-11',12'-dimethyl-7'-(2-methylpropyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 655.2 |
| | OR | OR (1S,3'R,6'R,7'R,8'E,11'S,12'R)-6-chloro-7'-hydroxy-11',12'-dimethyl-7'-(2-methylpropyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100225 | 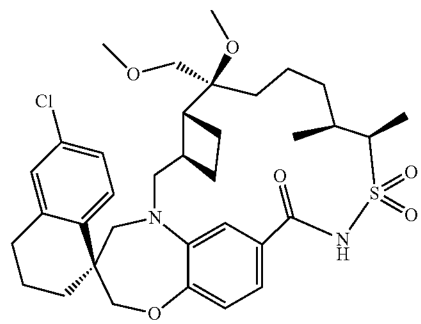 [SMILES: COC[C@]1(OC)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.2 |
| | OR | OR | |
| | | (1S,3'R,6'R,7'R,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100226 | 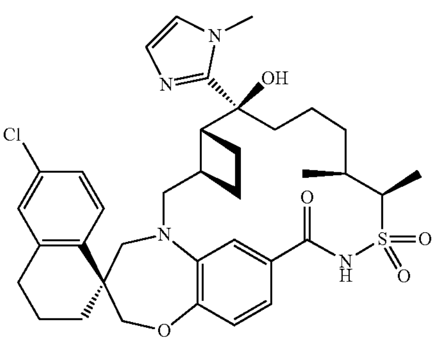 | (1S,3'R,6'R,7'S,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 681.2 |
| | OR | OR | |
| | | (1S,3'R,6'R,7'R,11'S,12'R)-6-chloro-7'-hydroxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100227 | 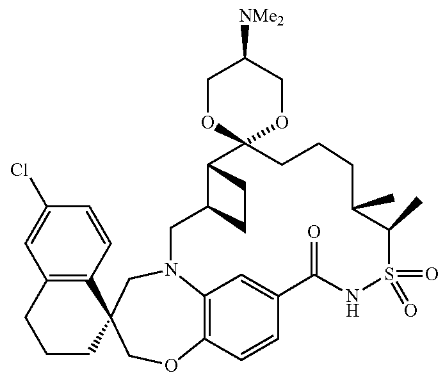 [SMILES: C[C@@H]1[C@@H](C)CCC[C@]2(OC[C@@H](N(C)C)CO2)[C@@H]2CC[C@H]2CN2C[C@@]3(CCCc4cc(Cl)ccc43)COc3ccc(cc32)C(=O)NS1(=O)=O] | (2r,3'R,5R,6'R,11'S,12'R,22'S)-6''-chloro-5-(dimethylamino)-11',12'-dimethyl-3'',4''-dihydro-2''H,15'H-dispiro[1,3-dioxane-2,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide | 700.1 |
| | AND | AND | |
| | | (2s,3'R,5S,6'R,11'S,12'R,22'S)-6''-chloro-5-(dimethylamino)-11',12'-dimethyl-3'',4''-dihydro-2''H,15'H-dispiro[1,3-dioxane-2,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide | |
| 100228 | 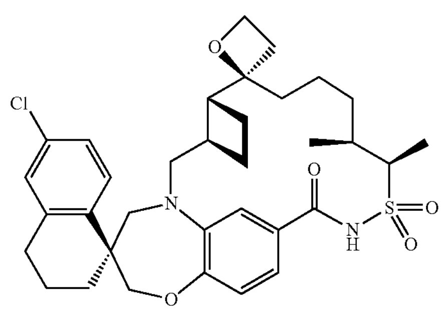 | (1S,3'R,6'R,7'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-oxetan]-15'-one 13',13'-dioxide | 627.2 |
| | OR | OR | |
| | | (1S,3'R,6'R,7'S,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',2''-oxetan]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100229 | 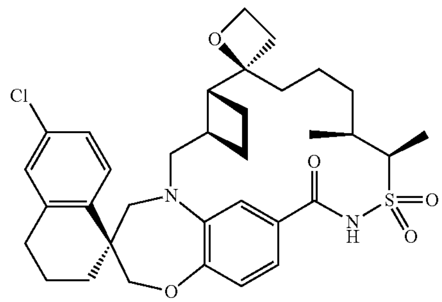 | (1S,3′R,6′R,7′S,11′S,12′R)-6-chloro-11′,12′-dimethyl-3,4-dihydro-2H,15′H-dispiro[naphthalene-1,22′-[20]oxa[13]thia[1,14]diazatetracyclo[14.7.2.0~3,6~.0~19,24~]pentacosa[16,18,24]triene-7′,2″-oxetan]-15′-one 13′,13′-dioxide | 627.2 |
| | OR | OR | |
| | | (1S,3′R,6′R,7′R,11′S,12′R)-6-chloro-11′,12′-dimethyl-3,4-dihydro-2H,15′H-dispiro[naphthalene-1,22′-[20]oxa[13]thia[1,14]diazatetracyclo[14.7.2.0~3,6~.0~19,24~]pentacosa[16,18,24]triene-7′,2″-oxetan]-15′-one 13′,13′-dioxide | |
| 100230 | 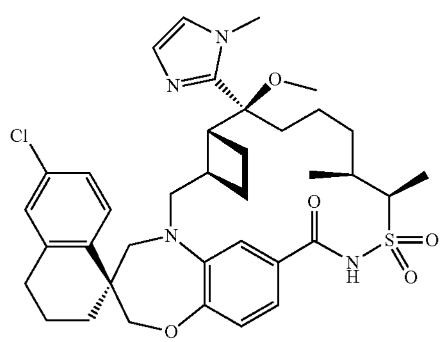 | (1S,3′R,6′R,7′S,11′S,12′R)-6-chloro-7′-methoxy-11′,12′-dimethyl-7′-(1-methyl-1H-imidazol-2-yl)-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide | 695.3 |
| | OR | OR | |
| | | (1S,3′R,6′R,7′R,11′S,12′R)-6-chloro-7′-methoxy-11′,12′-dimethyl-7′-(1-methyl-1H-imidazol-2-yl)-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide | |

TABLE 2-continued

Examples Prepared by the General Methods

| Example Number | Structure | Name | MS Dat (M + 1)+ Unless Noted Otherwise |
|---|---|---|---|
| 100231 | 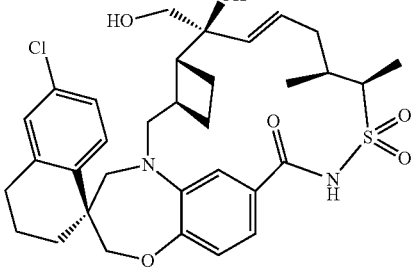<br>OR<br>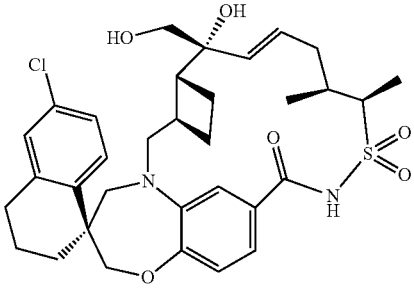 [SMILES: C[C@@H]1[C@@H](C)C/C=C/[C@](O)(CO)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 629.2 |
| 100232 | 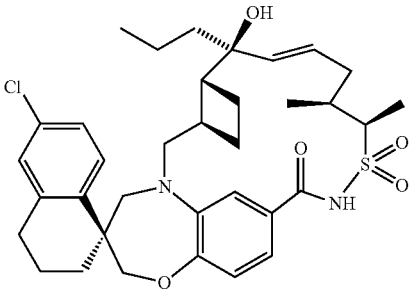 [SMILES: CCC[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]<br>OR<br>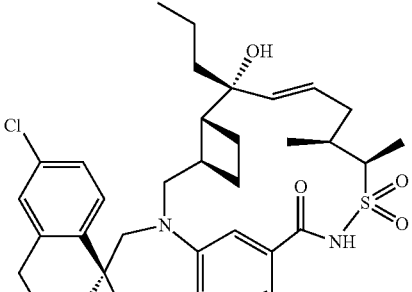 | (1S,3'R,6'R,7'S,8'E,11'S,12'R)-6-chloro-7'-hydroxy-11',12'-dimethyl-7'-propyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-11',12'-dimethyl-7'-propyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.2 |

TABLE 2-continued

Examples Prepared by the General Methods

| Example Number | Structure | Name | MS Dat (M + 1)+ Unless Noted Otherwise |
|---|---|---|---|
| 100233 | 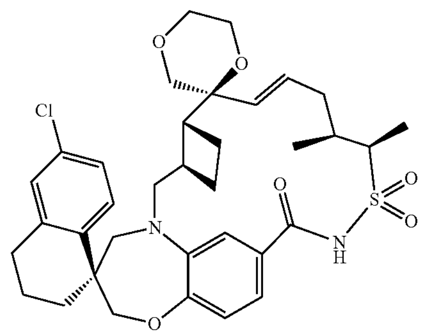 [SMILES: C[C@@H]1[C@@H](C)C/C=C/[C@@]2(COCCO2)[C@@H]2CC[C@H]2CN2C[C@@]3(CCCc4cc(Cl)ccc43)COc3ccc(cc32)C(=O)NS1(=O)=O] | (2S,3'R,6'R,8'E,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[8,16,18,24]tetraene-22',1'''-naphthalen]-15'-one 13',13'-dioxide | 655.2 |
| | OR | OR | |
| | | (2R,3'R,6'R,8'E,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[8,16,18,24]tetraene-22',1'''-naphthalen]-15'-one 13',13'-dioxide | |
| 100234 | 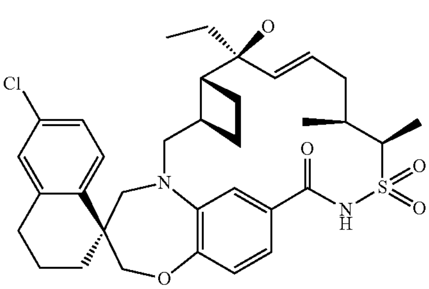 | (1S,3'R,6'R,7'S,8'E,11'S,12'R)-6-chloro-7'-ethyl-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.2 |
| 100235 | 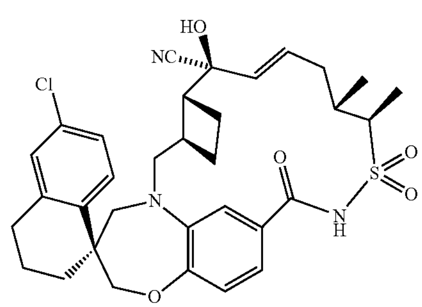 [SMILES: C[C@@H]1[C@@H](C)C/C=C/[C@@](O)(C#N)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbonitrile 13',13'-dioxide | 624.1 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbonitrile 13',13'-dioxide | |
| 100236 | 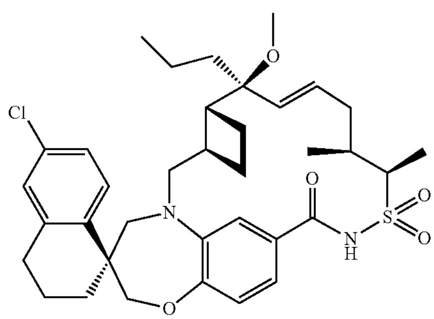 | (1S,3'R,6'R,7'S,8'E,11'S,12'R)-6-chloro-7'-methoxy-11',12'-dimethyl-7-propyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 655.2 |
| | OR | OR | |
| | | (1S,3'R,6'R,7'R,8'E,11S,12'R)-6-chloro-7-methoxy-11',12'-dimethyl-7'-propyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100237 | 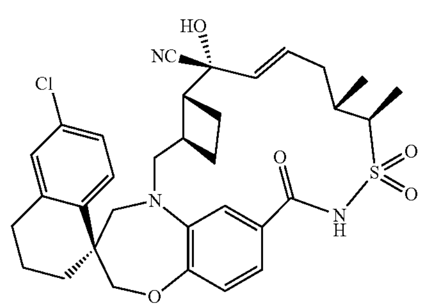 | (1S,3'R,6'R,7'R,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbonitrile 13',13'-dioxide | 624.1 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbonitrile 13',13'-dioxide | |
| 100238 | 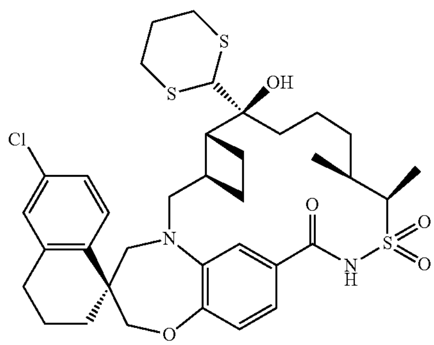 | (1S,3'R,6'R,7'S,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 719.3 |
| | OR | OR (1S,3'R,6'R,7'R,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100239 | 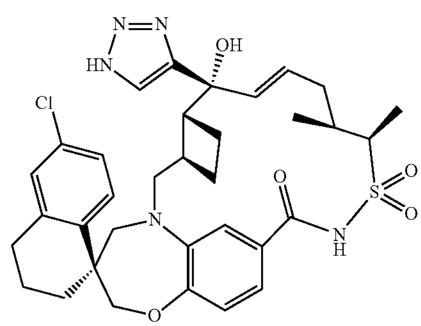 | (1S,3'R,6'R,7'R,8'E,11'S,12'R)-6-chloro-7'-hydroxy-11',12'-dimethyl-7'-(1H-1,2,3-triazol-4-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 666.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-hydroxy-11',12'-dimethyl-7'-(1H-1,2,3-triazol-4-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100240 | 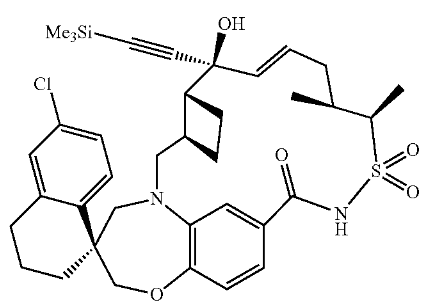 | (1S,3'R,6'R,7'S,8'E,11'S,12'R)-6-chloro-7'-hydroxy-11',12'-dimethyl-7'-((trimethylsilyl)ethynyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.4 |
| | OR | OR (1S,3'R,6'R,7'R,8'E,11'S,12'R)-6-chloro-7'-hydroxy-11',12'-dimethyl-7'-((trimethylsilyl)ethynyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100241 | 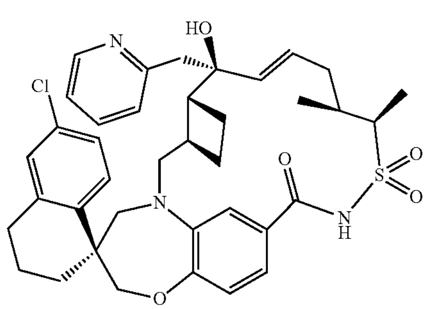 | (1S,3'R,6'R,7'S,8'E,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-hydroxy-11',12'-dimethyl-7'-(2-pyridinylmethyl)-3,4-dihydro-2H,15'H-spiro[naphthale1e-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100242 | 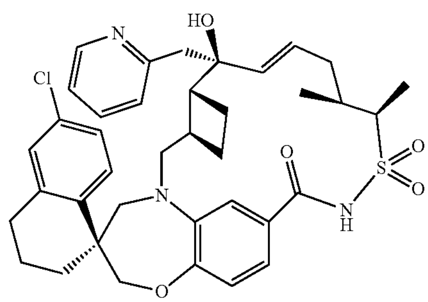 | (1S,3'R,6'R,7'S,8'E,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.3 |
| | OR | OR (1S,3'R,6'R,7'R,8'E,11'S,12'R)-6-chloro-7'-hydroxy-11',12'-dimethyl-7'-(2-pyridinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100243 | 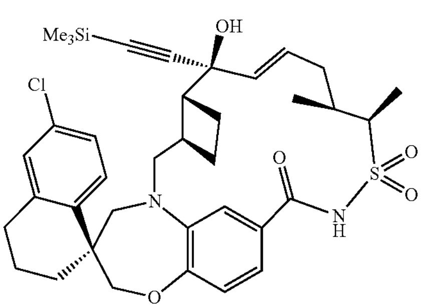 | (1S,3'R,6'R,7'S,8'E,11'S,12'R)-6-chloro-7'-hydroxy-11',12'-dimethyl-7'-((trimethylsilyl)ethynyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.4 |

TABLE 2-continued

Examples Prepared by the General Methods

| Example Number | Structure | Name | MS Dat (M + 1)+ Unless Noted Otherwise |
|---|---|---|---|
| | 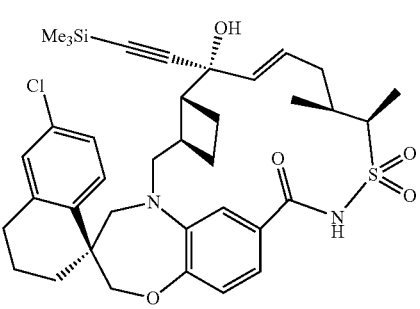 [SMILES: C[C@@H]1[C@@H](C)C/C=C/[C@](O)(C#C[Si](C)(C)C)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-((trimethylsilyl)ethynyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100244 | 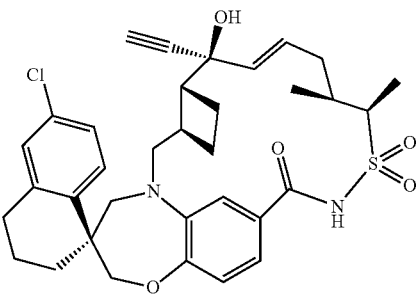 [SMILES: C#C[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-ethynyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 623.5 |
| | 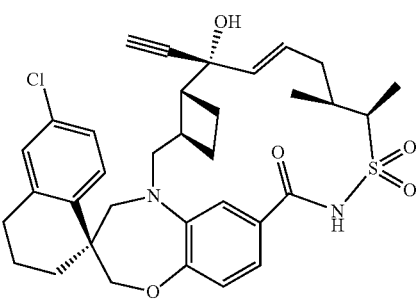 [SMILES: C#C[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-ethynyl-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100245 | 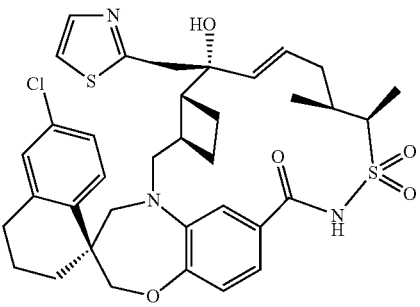 [SMILES: C[C@@H]1[C@@H](C)C/C=C/[C@](O)(Cc2nccs2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.3 |

TABLE 2-continued

Examples Prepared by the General Methods

| Example Number | Structure | Name | MS Dat (M + 1)+ Unless Noted Otherwise |
|---|---|---|---|
| | OR | OR | |
| 100246 | 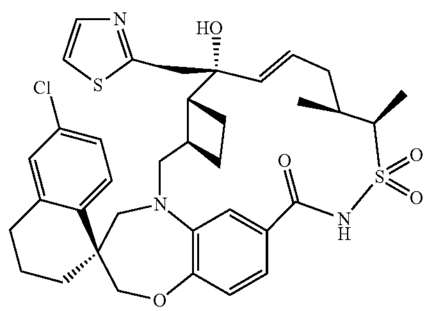 | (1S,3'R,6'R,7'R,8'E,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.2 |
| | OR | OR | |
| 100247 | 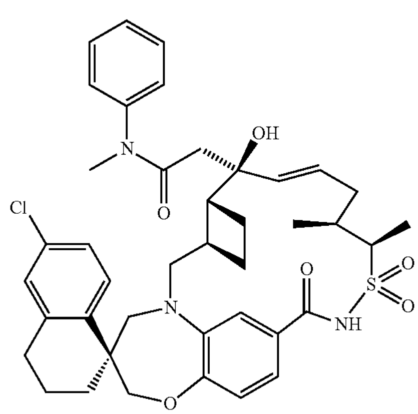 | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-phenylacetamide | 746.3 |

(Additional structures shown with name:
(1S,3'R,6'R,7'S,8'E,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide)

TABLE 2-continued

Examples Prepared by the General Methods

| Example Number | Structure | Name | MS Dat (M + 1)+ Unless Noted Otherwise |
|---|---|---|---|
| | OR 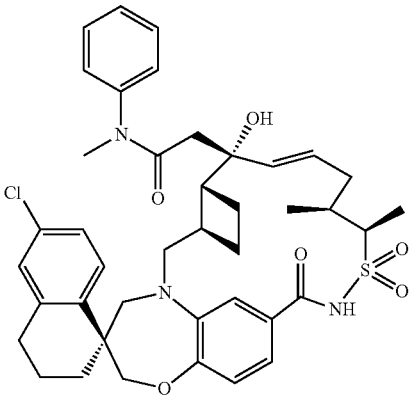 | OR 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-phenylacetamide | |
| 100248 | 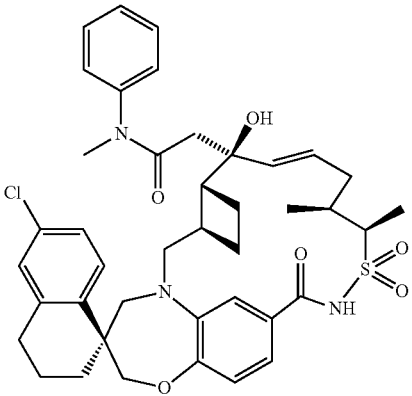 | 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-phenylacetamide | 746.3 |
| | OR 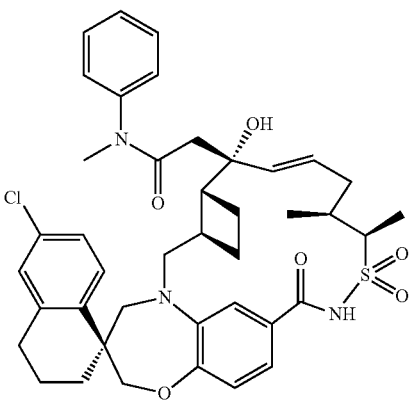 | OR 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-phenylacetamide | |

TABLE 2-continued

Examples Prepared by the General Methods

| Example Number | Structure | Name | MS Dat (M + 1)+ Unless Noted Otherwise |
|---|---|---|---|
| 100249 | 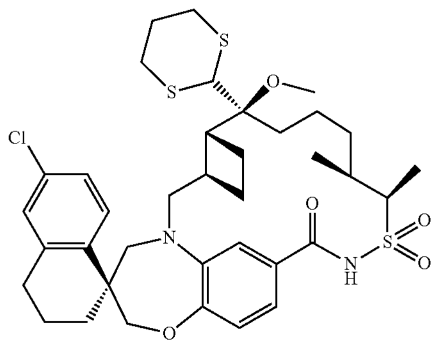 [SMILES: CO[C@@]1(C2SCCCS2)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 733.4 |
| | OR | OR | |
| | | (1S,3'R,6'R,7'R,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100250 | 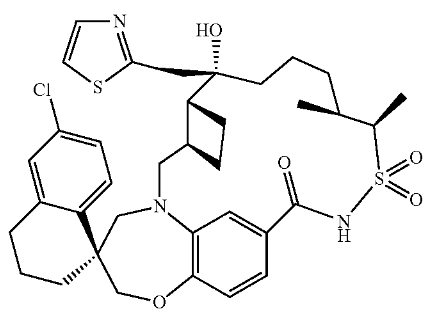 [SMILES: C[C@@H]1[C@@H](C)CCC[C@](O)(Cc2nccs2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.3 |
| | OR | OR | |
| | | (1S,3'R,6'R,7'S,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100251 | 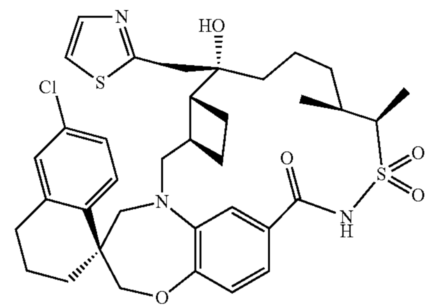 [SMILES: C[C@@H]1[C@@H](C)CCC[C@](O)(Cc2nccs2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.3 |
| | OR | OR | |
| | | (1S,3'R,6'R,7'S,11'S,12'R)-6-chloro-7'-hydroxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100252 | 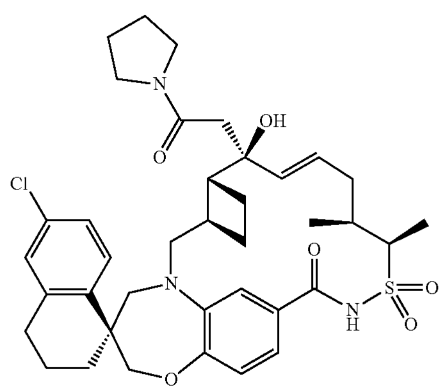 [SMILES: C[C@@H]1[C@@H](C)C/C=C/[C@@](O)(CC(=O)N2CCCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.2 |
| 100253 | 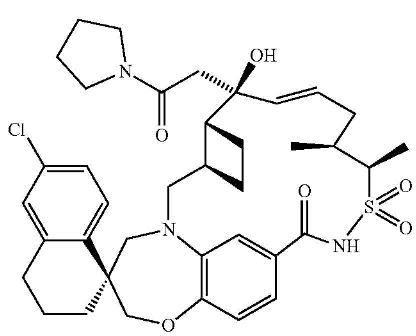 [SMILES: C[C@@H]1[C@@H](C)C/C=C/[C@@](O)(CC(=O)N2CCCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.3 |

TABLE 2-continued

Examples Prepared by the General Methods

| Example Number | Structure | Name | MS Dat (M + 1)+ Unless Noted Otherwise |
|---|---|---|---|
| | OR | (1S,3'R,6'R,7'R,8'E,11'S,12'R)-6-chloro-7'-hydroxy-11',12'-dimethyl-7'-(2-oxo-2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100254 | 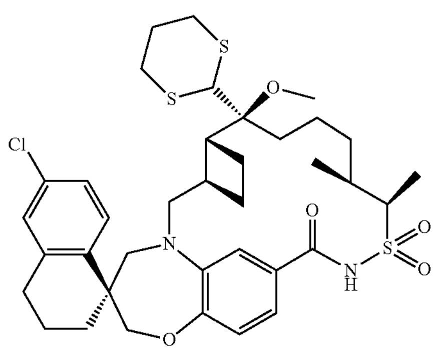 | (1S,3'R,6'R,7'S,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 733.3 |
| | OR | (1S,3'R,6'R,7'R,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100255 | 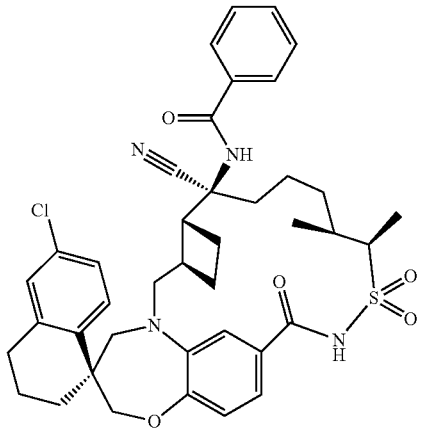 OR 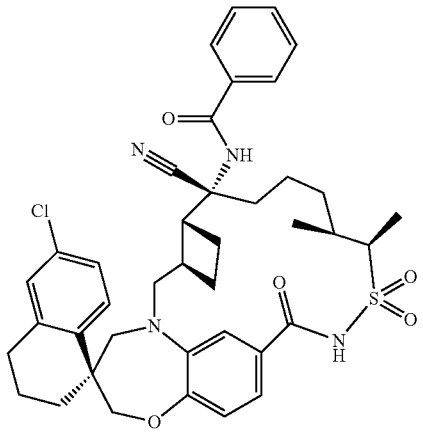 | N-((1S,3'R,6'R,7'S,11'S,12'R)-6-chloro-7'-cyano-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)benzamide OR N-((1S,3'R,6'R,7'R,11'S,12'R)-6-chloro-7'-cyano-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)benzamide | 729.2 |
| 100256 | 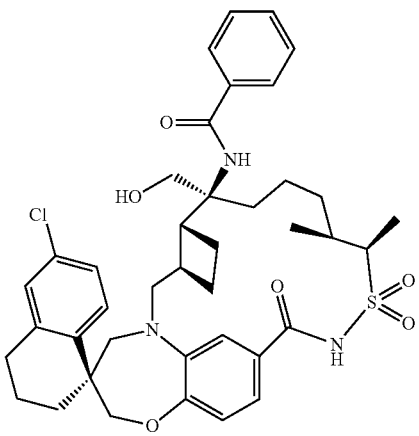 | N-((1S,3'R,6'R,7'S,11'S,12'R)-6-chloro-7'-(hydroxymethyl)-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)benzamide | 734.2 |

TABLE 2-continued

Examples Prepared by the General Methods

| Example Number | Structure | Name | MS Dat (M + 1)+ Unless Noted Otherwise |
|---|---|---|---|
| | OR | N-((1S,3'R,6'R,7'R,11'S,12'R)-6-chloro-7'-(hydroxymethyl)-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)benzamide | |
| 100257 | 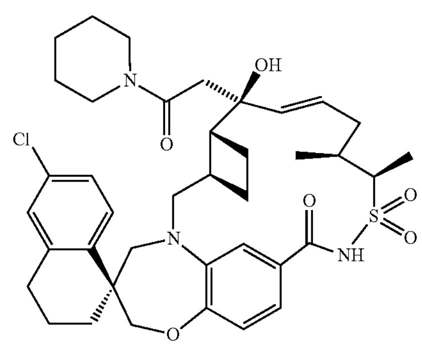 | (1S,3'R,6'R,7'S,8'E,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |
| | OR | (1S,3'R,6'R,7'R,8'E,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100258 | 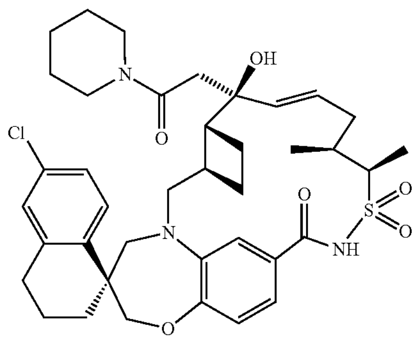 [SMILES: C[C@@H]1[C@@H](C)C/C=C/[C@@](O)(CC(=O)N2CCCCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |
| | OR | OR | |
| | | (1S,3'R,6'R,7'R,8'E,11'S,12'R)-6-chloro-7'-hydroxy-11',12'-dimethyl-7'-(2-oxo-2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100259 | 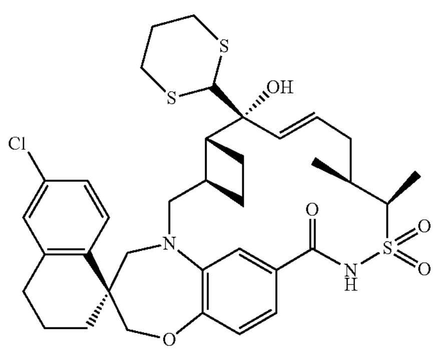 [SMILES: C[C@@H]1[C@@H](C)C/C=C/[C@](O)(C2SCCCS2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 717.0 |
| 100260 | 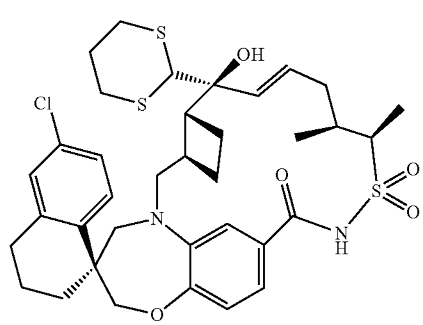 [SMILES: C[C@@H]1[C@@H](C)C/C=C/[C@@](O)(C2SCCCS2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-(1,3-dithian-2-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 717.2 |

TABLE 2-continued

Examples Prepared by the General Methods

| Example Number | Structure | Name | MS Dat (M + 1)+ Unless Noted Otherwise |
|---|---|---|---|
| 100261 | 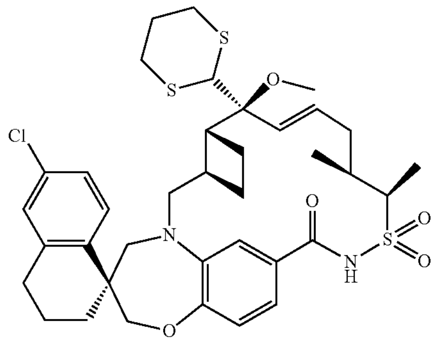 [SMILES: CO[C@@]1(C2SCCCS2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(1,3-dithian-2-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 731.5 |
| 100262 | 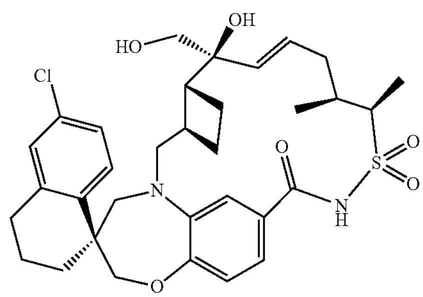 [SMILES: C[C@@H]1[C@@H](C)C/C=C/[C@@](O)(CO)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 629.2 |
| 100263 | 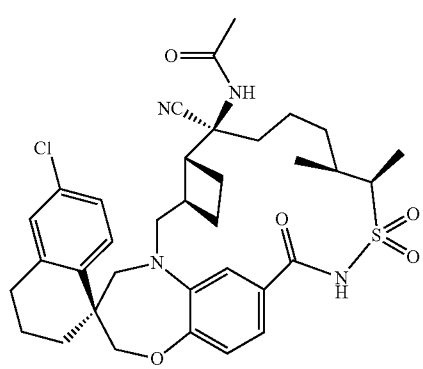 [SMILES: CC(=O)N[C@@]1(C#N)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | N-((1S,3'R,6'R,7'S,11'S,12'R)-6-chloro-7'-cyano-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetamide | 667.2 |

TABLE 2-continued

Examples Prepared by the General Methods

| Example Number | Structure | Name | MS Dat (M + 1)+ Unless Noted Otherwise |
|---|---|---|---|
| | 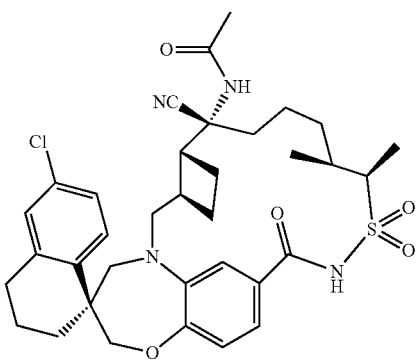 [SMILES: CC(=O)N[C@]1(C#N)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | OR<br><br>N-((1S,3'R,6'R,7'R,11'S,12'R)-6-chloro-7'-cyano-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetamide | |
| 100264 | 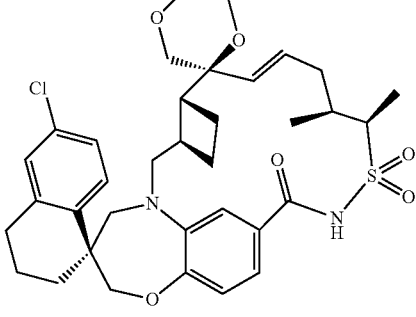 | (2S,3'R,6'R,8'E,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[8,16,18,24]tetraene-22',1''-naphthalen]-15'-one 13',13'-dioxide | 655.2 |
| | 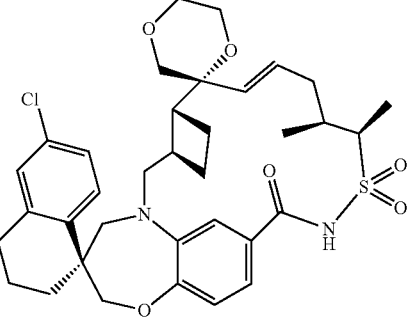 | OR<br><br>(2R,3'R,6'R,8'E,11'S,12'R,22'S)-6''-chloro-11',12'-dimethyl-3'',4''-dihydro-2''H,15'H-dispiro[1,4-dioxane-2,7'-[20]oxa[13]thia[1,14]diazatetracyclo[14.7.2.0~3,6~.0~19,24~]pentacosa[8,16,18,24]tetraene-22',1''-naphthalen]-15'-one 13',13'-dioxide | |
| 100265 | 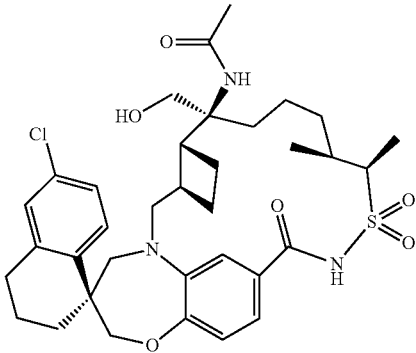 [SMILES: CC(=O)N[C@@]1(CO)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | N-((1S,3'R,6'R,7'S,11'S,12'R)-6-chloro-7'-(hydroxymethyl)-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetamide | 672.2 |

TABLE 2-continued

Examples Prepared by the General Methods

| Example Number | Structure | Name | MS Dat (M + 1)+ Unless Noted Otherwise |
|---|---|---|---|
| | OR 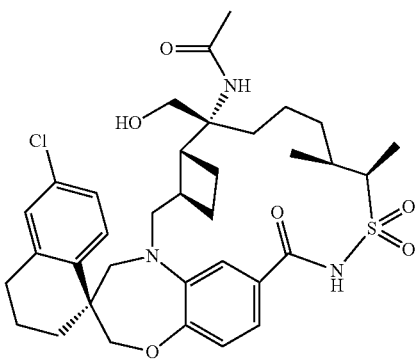 | OR N-((1S,3'R,6'R,7'R,11'S,12'R)-6-chloro-7'-(hydroxymethyl)-11',12'-dimethyl-13',13'-dioxido-15'-oxo-3,4-dihydro-2H-spiro[naphthalene-1,22'-[20]oxa[13]thia[1,14] diazatetracyclo[14.7.2.0~3,6~.0~19,24~] pentacosa[16,18,24] trien]-7'-yl)acetamide | |
| 100266 | 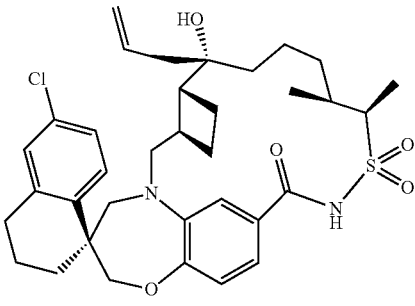 | (1S,3'R,6'R,7'R,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14] diazatetracyclo[14.7.2.0~3,6~.0~19,24~] pentacosa[16,18,24] trien]-15'-one 13',13'-dioxide | 641.2 |
| | OR 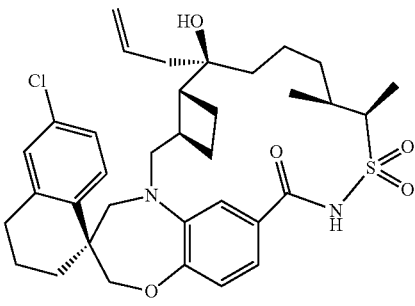 | OR (1S,3'R,6'R,7'S,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14] diazatetracyclo[14.7.2.0~3,6~.0~19,24~] pentacosa[16,18,24] trien]-15'-one 13',13'-dioxide | |
| 100267 | 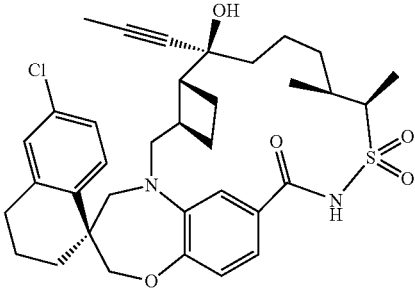 | (1S,3'R,6'R,7'S,11'S,12'R)-6-chloro-7'-hydroxy-11',12'-dimethyl-7'-(1-propyn-1-yl)-3,4-dihydro-2H,15'H-spiro[naphthalene-1,22'-[20]oxa[13]thia[1,14] diazatetracyclo[14.7.2.0~3,6~.0~19,24~] pentacosa[16,18,24] trien]-15'-one 13',13'-dioxide | 639.2 |

TABLE 2-continued

Examples Prepared by the General Methods

| Example Number | Structure | Name | MS Dat (M + 1)+ Unless Noted Otherwise |
|---|---|---|---|
| | OR 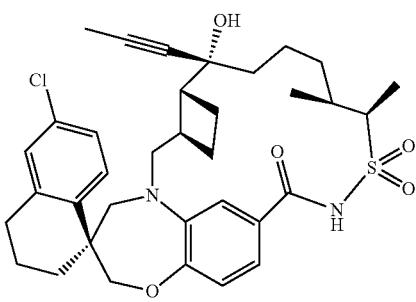 | OR (1S,3'R,6'R,7'R,11'S,12'R)-6-chloro-7'-hydroxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100268 | 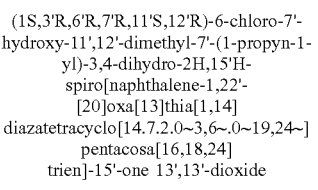 | (1S,3'R,6'R,7'S,11'S,12'R)-6-chloro-7'-hydroxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 639.3 |
| | OR 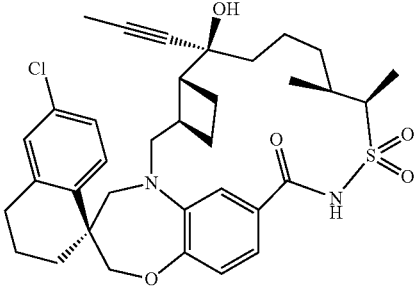 | OR (1S,3'R,6'R,7'R,11'S,12'R)-6-chloro-7'-hydroxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100269 | 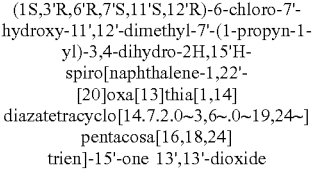 | (1S,3'R,6'R,7'S,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0-19,24~]pentacosa[16,18,24]triene-7',3''-[1,4]oxazinan]-15'-one 13',13'-dioxide | 656.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~.0~19,24~]pentacosa[16,18,24]triene-7',3''-[1,4]oxazinan]-15'-one 13',13'-dioxide | |
| 100270 | 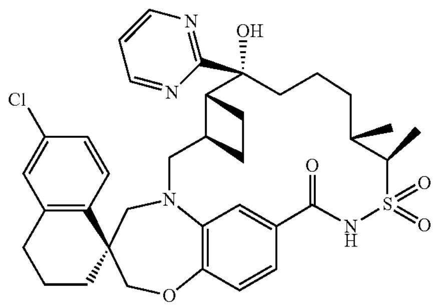 | (1S,3'R,6'R,7'R,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 679.2 |
| | AND | AND (1S,3'R,6'R,7'S,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100271 | 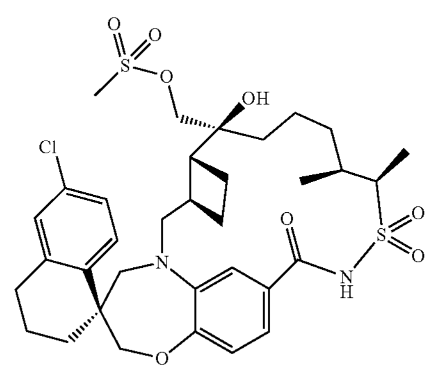 | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methyl methanesulfonate | 709.1 |

TABLE 2-continued

Examples Prepared by the General Methods

| Example Number | Structure | Name | MS Dat (M + 1)+ Unless Noted Otherwise |
|---|---|---|---|
| | OR | OR ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methyl methanesulfonate | |
| 100272 | 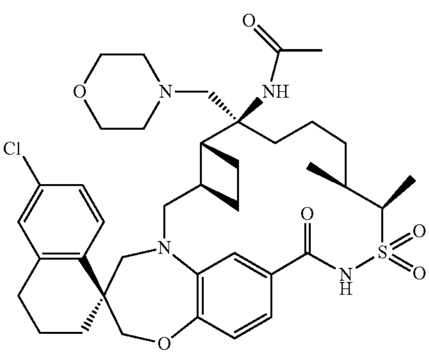 | N-((1S,3'R,6'R,7'S,11'S,12'R)-6-chloro-11',12'-dimethyl-7'-(4-morpholinylmethyl)-13',13'-dioxido-15'-oxo-3,4-dihydro-2H-spiro[naphthalene-1,22'-[20]oxa[13]thia[1,14]diazatetracyclo[7.2.0~3,6~.0~19,24~]pentacosa[16,18,24]trien]-7'-yl)acetamide | 741.2 |
| | OR | OR N-((1S,3'R,6'R,7'R,11'S,12'R)-6-chloro-11',12'-dimethyl-7'-(4-morpholinylmethyl)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)acetamide | |
| 100273 | 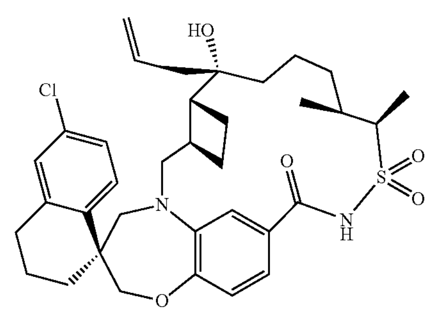 | (1S,3'R,6'R,7'R,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 641.3 |

//

TABLE 2-continued

Examples Prepared by the General Methods

| Example Number | Structure | Name | MS Dat (M + 1)+ Unless Noted Otherwise |
|---|---|---|---|
| | OR 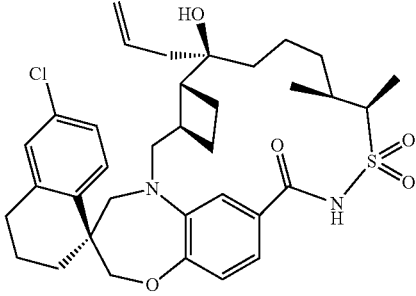 | OR (1S,3'R,6'R,7'S,11'S,12'R)-6-chloro-7'-hydroxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100274 | 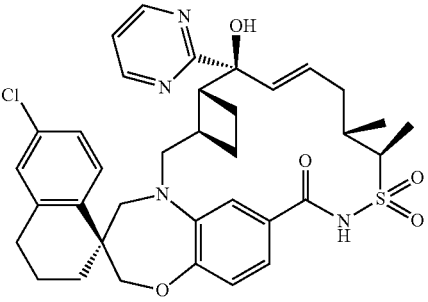 | (1S,3'R,6'R,7'R,8'E,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.3 |
| | OR 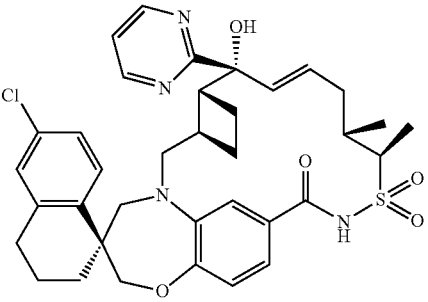 | OR (1S,3'R,6'R,7'S,8'E,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100275 | 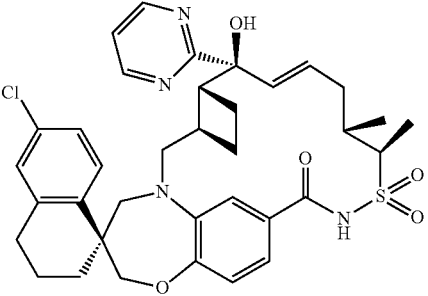 | (1S,3'R,6'R,7'S,8'E,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100276 | 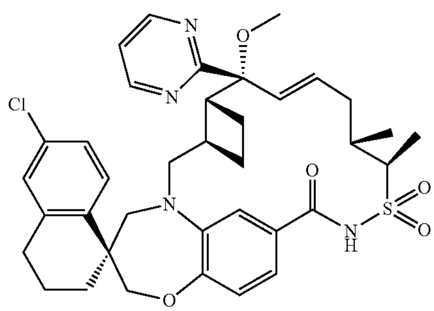 | (1S,3'R,6'R,7'R,11'S,12'R)-6-chloro-7'-methoxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 693.3 |
| | OR | OR (1S,3'R,6'R,7'S,11'S,12'R)-6-chloro-7'-methoxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100277 | 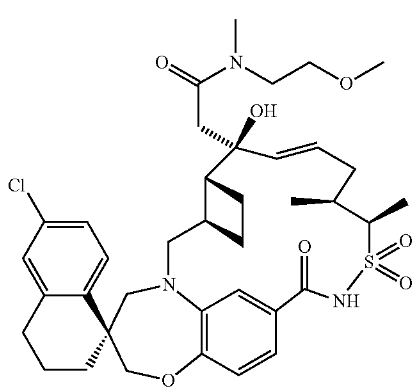 | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-methoxyethyl)-N-methylacetamide | 728.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-methoxyethyl)-N-methylacetamide | |
| 100278 | 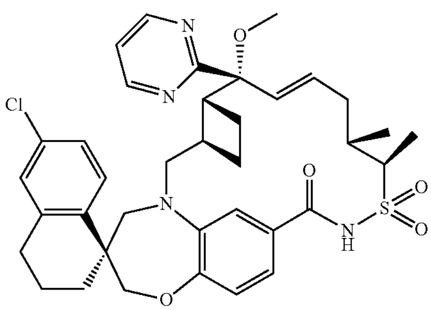 | (1S,3'R,6'R,7'R,8'E,11'S,12'R)-6-chloro-7'-methoxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.2 |
| | OR | OR | |
| | | (1S,3'R,6'R,7'S,8'E,11'S,12'R)-6-chloro-7'-methoxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100279 | 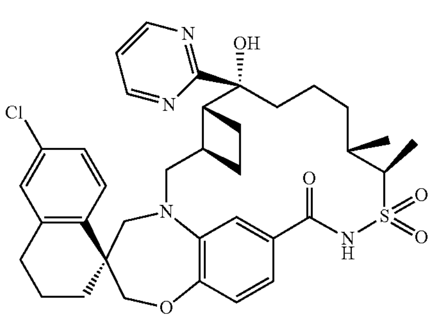 | (1S,3'R,6'R,7'R,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 679.2 |

TABLE 2-continued

Examples Prepared by the General Methods

| Example Number | Structure | Name | MS Dat (M + 1)+ Unless Noted Otherwise |
|---|---|---|---|
| | 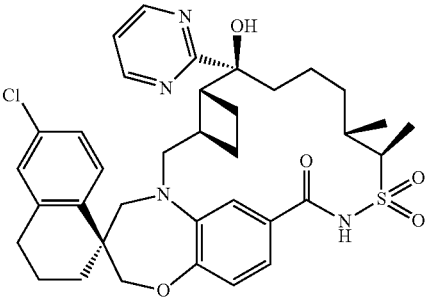 | (1S,3'R,6'R,7'S,11'S,12'R)-6-chloro-7'-hydroxy-11',12'-dimethyl-7'-(2-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100280 | 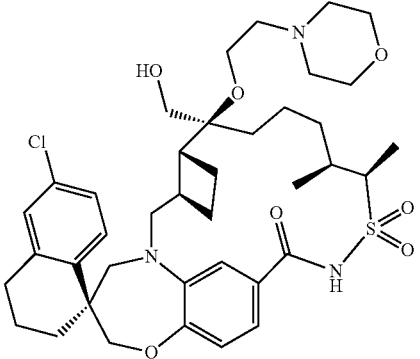 [SMILES: C[C@@H]1[C@@H](C)CCC[C@](CO)(OCCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-(hydroxymethyl)-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 744.3 |
| | 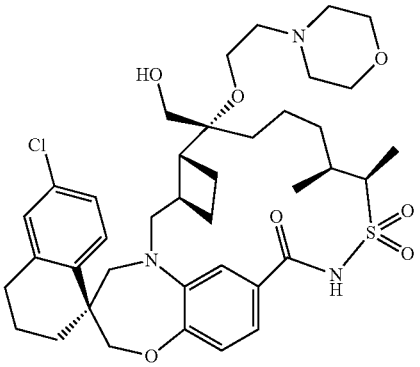 [SMILES: C[C@@H]1[C@@H](C)CCC[C@@](CO)(OCCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-(hydroxymethyl)-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100281 | 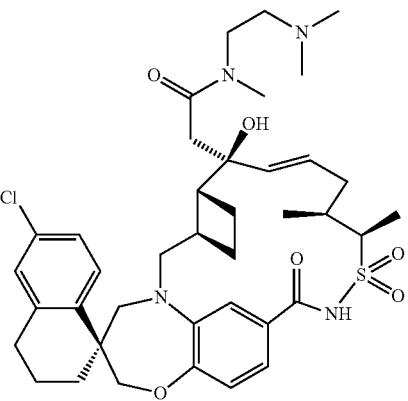 [SMILES: C[C@@H]1[C@@H](C)C/C=C/[C@@](O)(CC(=O)N(C)CCN(C)C)[C@@H]2CC[C@H]2CN2C[C@@]3(CCCc4cc(Cl)ccc43)COc3ccc(cc32)C(=O)NS1(=O)=O]<br><br>OR<br><br>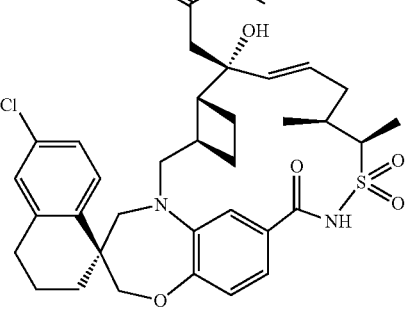 | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-(dimethylamino)ethyl)-N-methylacetamide<br><br>OR<br><br>2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-(dimethylamino)ethyl)-N-methylacetamide | 741.2 |
| 100282 | 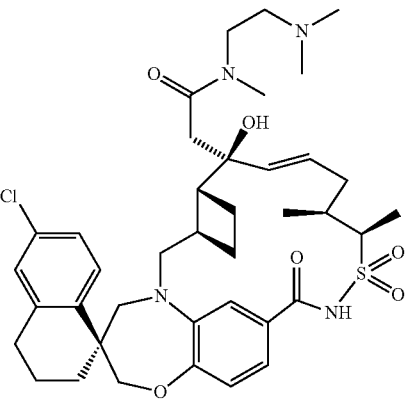 [SMILES: C[C@@H]1[C@@H](C)C/C=C/[C@@](O)(CC(=O)N(C)CCN(C)C)[C@@H]2CC[C@H]2CN2C[C@@]3(CCCc4cc(Cl)ccc43)COc3ccc(cc32)C(=O)NS1(=O)=O] | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-(dimethylamino)ethyl)-N-methylacetamide | 741.3 |

TABLE 2-continued

Examples Prepared by the General Methods

| Example Number | Structure | Name | MS Dat (M + 1)+ Unless Noted Otherwise |
|---|---|---|---|
| | OR | OR 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-(dimethylamino)ethyl)-N-methylacetamide | |
| 100283 | 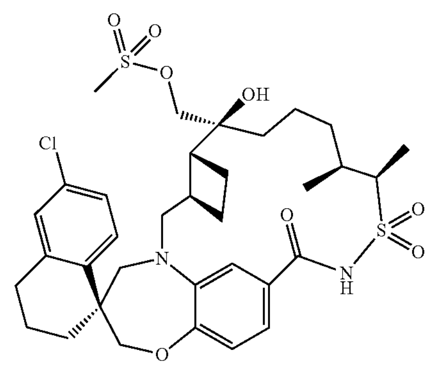 | ((1S,3'R,6'R,7'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methyl methanesulfonate | 709.1 |
| | OR | OR ((1S,3'R,6'R,7'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methyl methanesulfonate | |

TABLE 2-continued

Examples Prepared by the General Methods

| Example Number | Structure | Name | MS Dat (M + 1)+ Unless Noted Otherwise |
|---|---|---|---|
| 100284 | 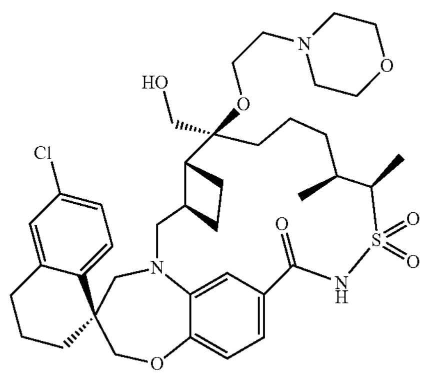 [SMILES: C[C@@H]1[C@@H](C)CCC[C@](CO)(OCCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-(hydroxymethyl)-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,11'S,12'R)-6-chloro-7'-(hydroxymethyl)-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 744.3 |
| 100285 | 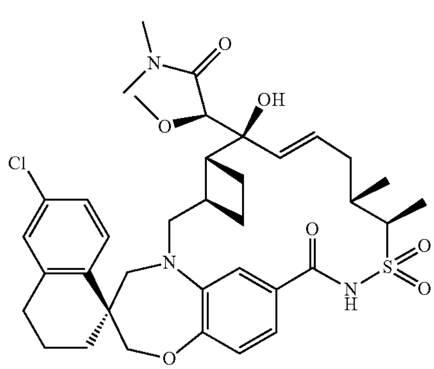 [SMILES: CO[C@@H](C(=O)N(C)C)[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | 714.2 |

TABLE 2-continued

Examples Prepared by the General Methods

| Example Number | Structure | Name | MS Dat (M + 1)+ Unless Noted Otherwise |
|---|---|---|---|
| | OR | OR (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | |
| | OR | OR (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | |
| | OR | OR (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | |

TABLE 2-continued

Examples Prepared by the General Methods

| Example Number | Structure | Name | MS Dat (M + 1)+ Unless Noted Otherwise |
|---|---|---|---|
| 100286 | 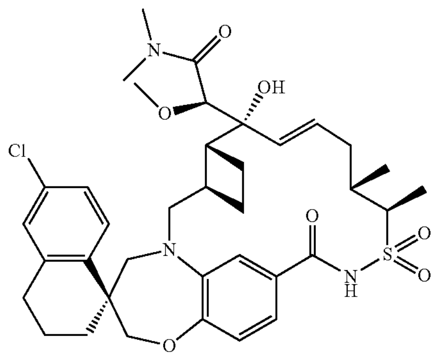 [SMILES: CO[C@@H](C(=O)N(C)C)[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | 714.2 |
| | OR | OR | |
| | | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | |
| | OR | OR | |
| | | (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | |

TABLE 2-continued

Examples Prepared by the General Methods

| Example Number | Structure | Name | MS Dat (M + 1)+ Unless Noted Otherwise |
|---|---|---|---|
| | OR | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-methoxy-N,N-dimethylethanamide | |
| 100287 | 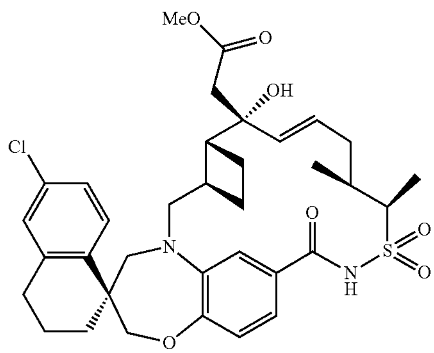 | methyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate | 671.2 |
| 100288 | 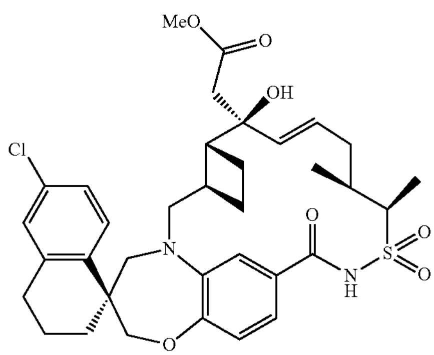 | methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate | 671.2 |
| 100289 | 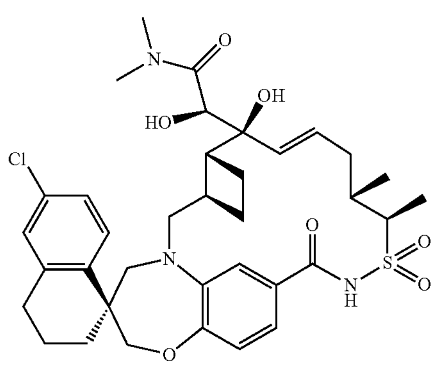 | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | 700.3 |

TABLE 2-continued

Examples Prepared by the General Methods

| Example Number | Structure | Name | MS Dat (M + 1)+ Unless Noted Otherwise |
|---|---|---|---|
| | OR | OR (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | |
| | OR | OR (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylacetamide | |
| | OR | OR (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | |

TABLE 2-continued

Examples Prepared by the General Methods

| Example Number | Structure | Name | MS Dat (M + 1)+ Unless Noted Otherwise |
|---|---|---|---|
| 100290 | 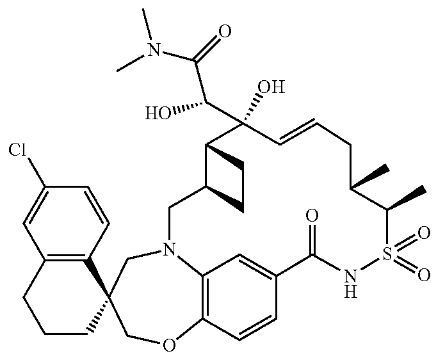 [SMILES: C[C@@H]1[C@@H](C)C/C=C/[C@](O)([C@H](O)C(=O)N(C)C)[C@@H]2CC[C@H]2CN2C[C@@]3(CCCc4cc(Cl)ccc43)COc3ccc(cc32)C(=O)NS1(=O)=O] | (2S)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | 700.3 |
| | OR | OR | |
| | | (2R)-2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | |
| | OR | OR | |
| | | (2S)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | |

TABLE 2-continued

Examples Prepared by the General Methods

| Example Number | Structure | Name | MS Dat (M + 1)+ Unless Noted Otherwise |
|---|---|---|---|
| | | OR | OR |
| | | (2R)-2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2-hydroxy-N,N-dimethylethanamide | |
| 100291 | 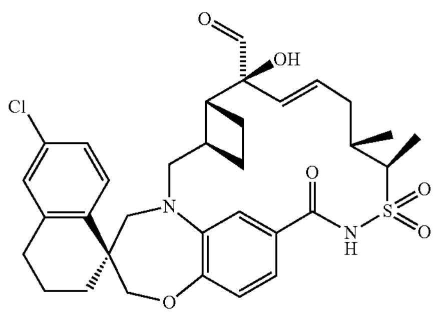 [SMILES: C[C@@H]1[C@@H](C)C/C=C/[C@@](O)(C=O)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-15-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | 627.3 |
| 100292 | 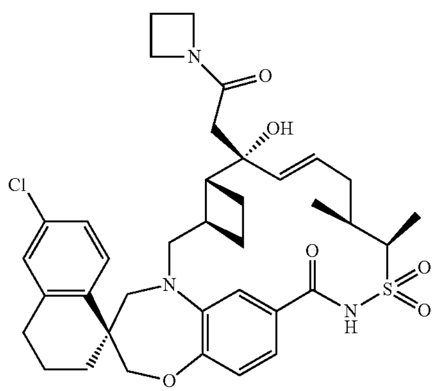 [SMILES: C[C@@H]1[C@@H](C)C/C=C/[C@](O)(CC(=O)N2CCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-7'-(2-(1-azetidinyl)-2-oxoethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.2 |
| 100293 | 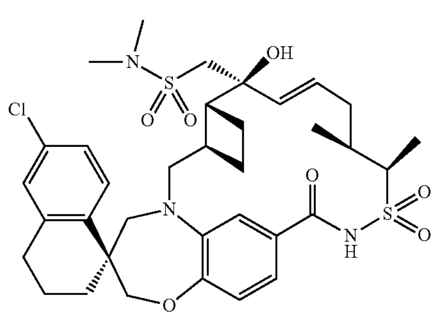 [SMILES: C[C@@H]1[C@@H](C)C/C=C/[C@@](O)(CS(=O)(=O)N(C)C)[C@@H]2CC[C@H]2CN2C[C@@]3(CCCc4cc(Cl)ccc43)COc3ccc(cc32)C(=O)NS1(=O)=O] | 1-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide | 720.2 |

TABLE 2-continued

Examples Prepared by the General Methods

| Example Number | Structure | Name | MS Dat (M + 1)+ Unless Noted Otherwise |
|---|---|---|---|
| | 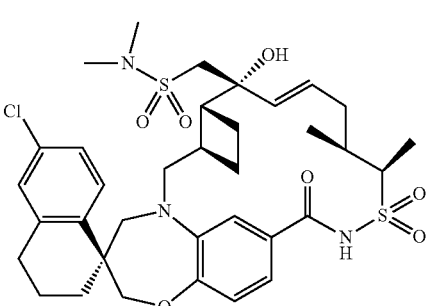 OR | OR 1-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylmethanesulfonamide | |
| 100294 | 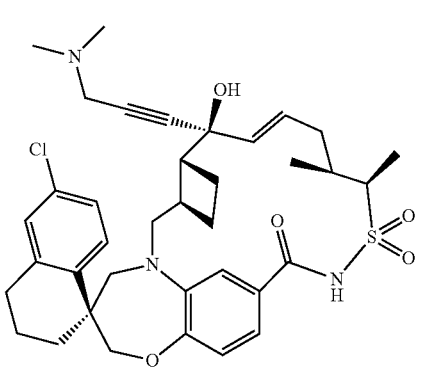 | (1S,3'R,6'R,7'S,8'E,11'S,12'R)-6-chloro-7'-(3-(dimethylamino)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 680.3 |
| | 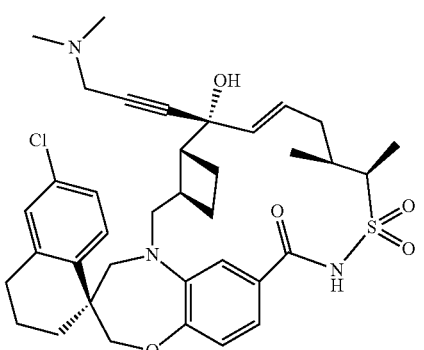 OR | OR (1S,3'R,6'R,7'R,8'E,11'S,12'R)-6-chloro-7'-(3-(dimethylamino)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100295 | 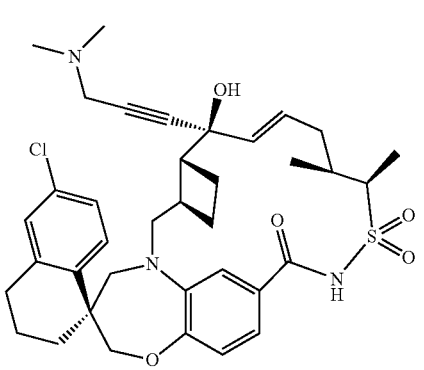 | (1S,3'R,6'R,7'S,8'E,11'S,12'R)-6-chloro-7'-(3-(dimethylamino)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 680.5 |

TABLE 2-continued

Examples Prepared by the General Methods

| Example Number | Structure | Name | MS Dat (M + 1)+ Unless Noted Otherwise |
|---|---|---|---|
| | OR 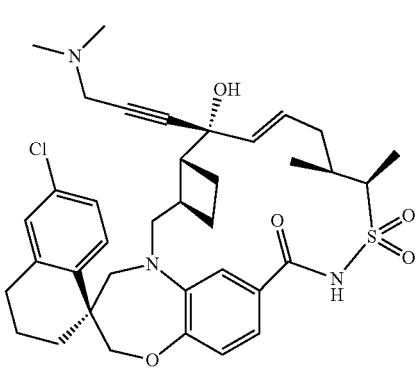 | OR (1S,3'R,6'R,7'R,8'E,11'S,12'R)-6-chloro-7'-(3-(dimethylamino)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100296 | 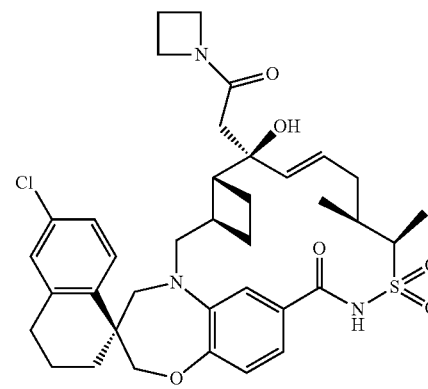 | (1S,3'R,6'R,7S,8'E,11'S,12'R)-7'-(2-(1-azetidinyl)-2-oxoethyl)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.2 |
| 100297 | 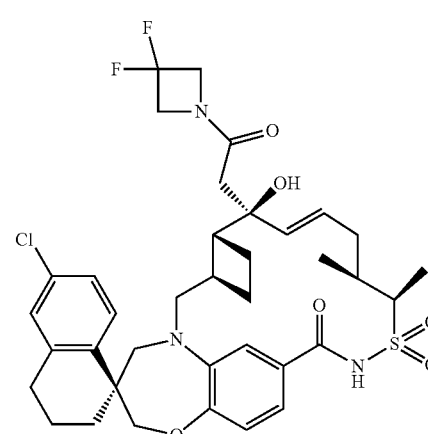 | (1S,3'R,6'R,7'S,8'E,11'S,12'R)-6-chloro-7'-(2-(3,3-difluoro-1-azetidinyl)-2-oxoethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 732.2 |

TABLE 2-continued

Examples Prepared by the General Methods

| Example Number | Structure | Name | MS Dat (M + 1)+ Unless Noted Otherwise |
|---|---|---|---|
| 100298 | 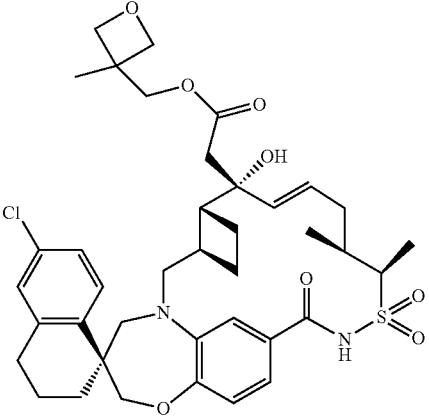 [SMILES: C[C@@H]1[C@@H](C)C/C=C/[C@](O)(CC(=O)OCC2(C)COC2)[C@@H]2CC[C@H]2CN2C[C@@]3(CCCc4cc(Cl)ccc43)COc3ccc(cc32)C(=O)NS1(=O)=O]<br><br>OR<br><br>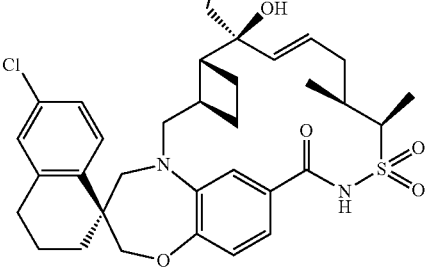 | (3-methyl-3-oxetanyl)methyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate<br><br>OR<br><br>(3-methyl-3-oxetanyl)methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate | 741.2 |
| 100299 | 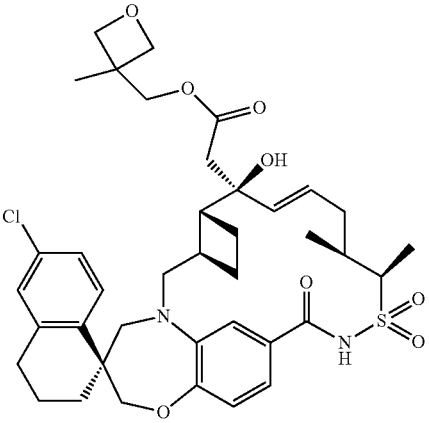 [SMILES: C[C@@H]1[C@@H](C)C/C=C/[C@@](O)(CC(=O)OCC2(C)COC2)[C@@H]2CC[C@H]2CN2C[C@@]3(CCCc4cc(Cl)ccc43)COc3ccc(cc32)C(=O)NS1(=O)=O] | (3-methyl-3-oxetanyl)methyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate | 741.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (3-methyl-3-oxetanyl)methyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetate | |
| 100300 | 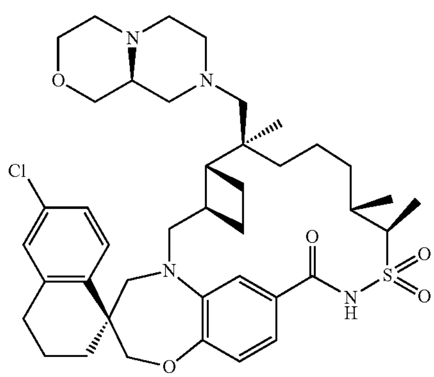 | (1S,3'R,6'R,7'S,11'S,12'R)-6-chloro-7'-((9aS)-hexahydropyrazino[2,1-c][1,4]oxazin-8(1H)-ylmethyl)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 753.3 |
| | OR | OR | |
| | | (1S,3'R,6'R,7'R,11'S,12'R)-6-chloro-7'-((9aS)-hexahydropyrazino[2,1-c][1,4]oxazin-8(1H)-ylmethyl)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100301 | 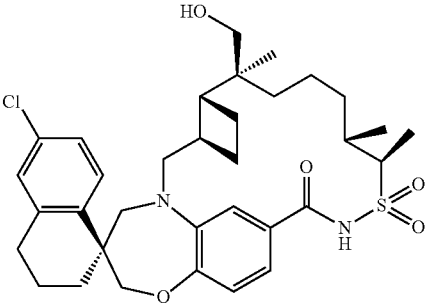 [SMILES: C[C@@H]1[C@@H](C)CCC[C@](C)(CO)[C@@H]2CC[C@H]2CN2C[C@@]3(CCCc4cc(Cl)ccc43)COc3ccc(cc32)C(=O)NS1(=O)=O]<br>OR<br>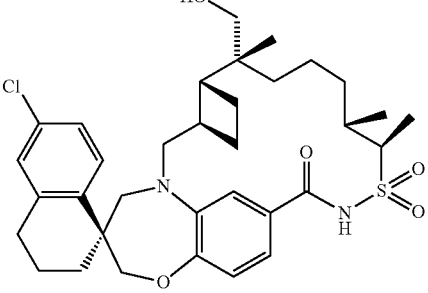 | (1S,3'R,6'R,7'S,11'S,12'R)-6-chloro-7'-(hydroxymethyl)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br>OR<br>(1S,3'R,6'R,7'R,11'S,12'R)-6-chloro-7'-(hydroxymethyl)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 629.4 |
| 100302 | 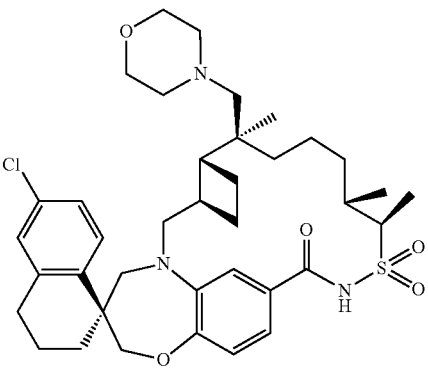 [SMILES: C[C@@H]1[C@@H](C)CCC[C@](C)(CN2CCOCC2)[C@@H]2CC[C@H]2CN2C[C@@]3(CCCc4cc(Cl)ccc43)COc3ccc(cc32)C(=O)NS1(=O)=O]<br>OR<br>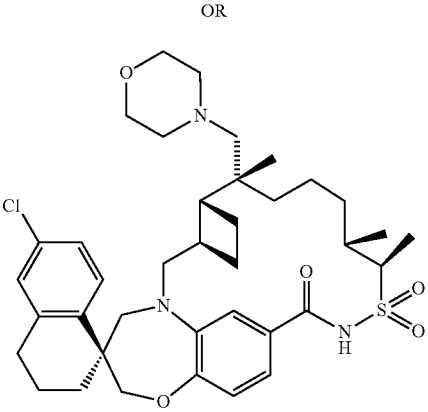 | (1S,3'R,6'R,7'S,11'S,12'R)-6-chloro-7',11',12'-trimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br>OR<br>(1S,3'R,6'R,7'R,11'S,12'R)-6-chloro-7',11',12'-trimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.5 |

TABLE 2-continued

Examples Prepared by the General Methods

| Example Number | Structure | Name | MS Dat (M + 1)+ Unless Noted Otherwise |
|---|---|---|---|
| 100303 | 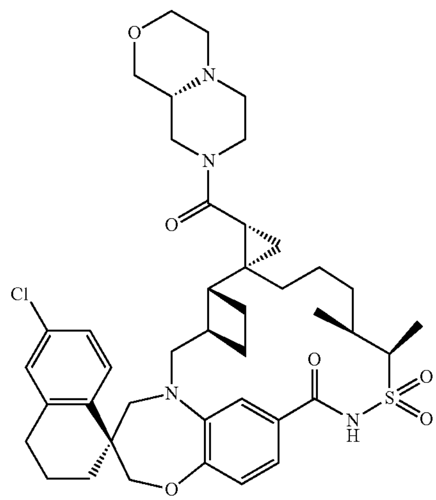 [SMILES: C[C@@H]1[C@@H](C)CCC[C@@]2(C[C@H]2C(=O)N2CCN3CCOC[C@H]3C2)[C@@H]2CC[C@H]2CN2C[C@@]3(CCCc4cc(Cl)ccc43)COc3ccc(cc32)C(=O)NS1(=O)=O] | (1R,2R,3'R,6'R,11'S,12'R,22'S)-6''-chloro-2-((9aR)-hexahydropyrazino[2,1-c][1,4]oxazin-8(1H)-ylcarbonyl)-11',12'-dimethyl-3'',4''-dihydro-2''H,15'H-dispiro[cyclopropane-1,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide | 779.3 |
| | OR | OR | |
| | | (1R,2S,3'R,6'R,11'S,12'R,22'S)-6''-chloro-2-((9aR)-hexahydropyrazino[2,1-c][1,4]oxazin-8(1H)-ylcarbonyl)-11',12'-dimethyl-3'',4''-dihydro-2''H,15'H-dispiro[cyclopropane-1,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100304 | 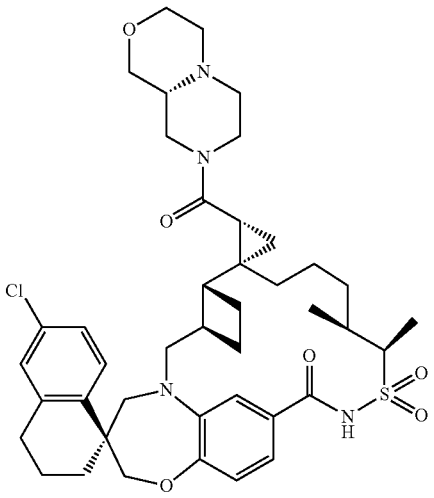 OR 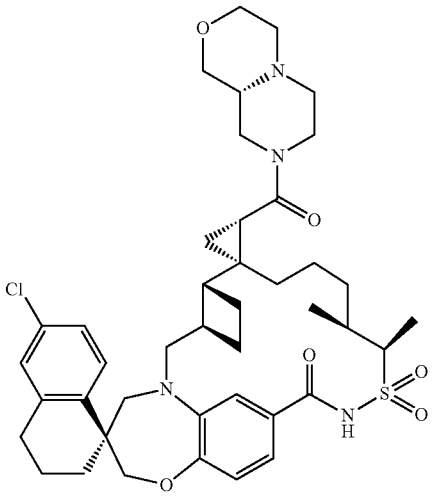 | (1R,2R,3'R,6'R,11'S,12'R,22'S)-6''-chloro-2-((9aR)-hexahydropyrazino[2,1-c][1,4]oxazin-8(1H)-ylcarbonyl)-11',12'-dimethyl-3'',4''-dihydro-2''H,15'H-dispiro[cyclopropane-1,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide<br><br>OR<br><br>(1R,2S,3'R,6'R,11'S,12'R,22'S)-6''-chloro-2-((9aR)-hexahydropyrazino[2,1-c][1,4]oxazin-8(1H)-ylcarbonyl)-11',12'-dimethyl-3'',4''-dihydro-2''H,15'H-dispiro[cyclopropane-1,7'-[20]oxa[13]thia[1,14]diazatetracyclo[14.7.2.0~3,6~.0~19,24~]pentacosa[16,18,24]triene-22',1''-naphthalen]-15'-one 13',13'-dioxide | 779.3 |
| 100305 | 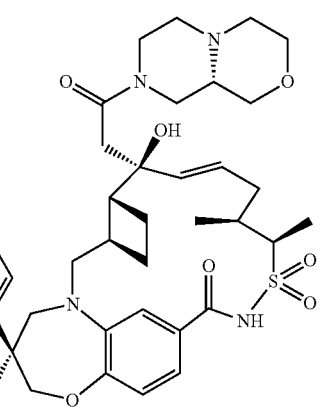 | (1S,3'R,6'R,7'S,8'E,11'S,12'R)-6-chloro-7'-(2-((9aS)-hexahydropyrazino[2,1-c][1,4]oxazin-8(1H)-yl)-2-oxoethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |

TABLE 2-continued

Examples Prepared by the General Methods

| Example Number | Structure | Name | MS Dat (M + 1)+ Unless Noted Otherwise |
|---|---|---|---|
| 100306 | 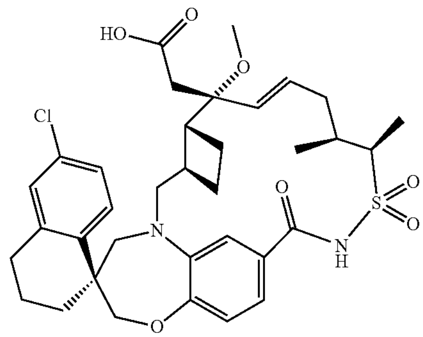 [SMILES: CO[C@]1(CC(=O)O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | ((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid | 671.2 |
| 100307 | 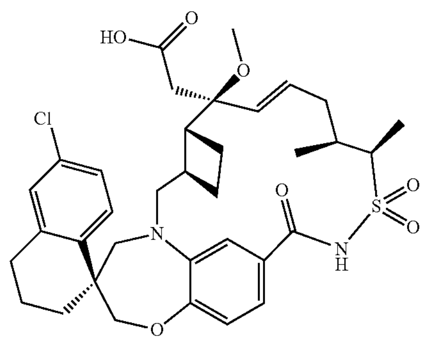 [SMILES: CO[C@@]1(CC(=O)O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetic acid | 671.2 |
| 100308 | | (1S,3'R,6'R,7'S,8'E,11'S,12'R)-6-chloro-7'-(4-(dimethylamino)-1-butyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.5 |
| | OR | OR | |
| | | (1S,3'R,6'R,7'S,8'E,11'S,12'R)-6-chloro-7'-(4-(dimethylamino)-1-butyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Data (M + 1)+ Unless Noted Otherwise |
|---|---|---|---|
| 100309 | 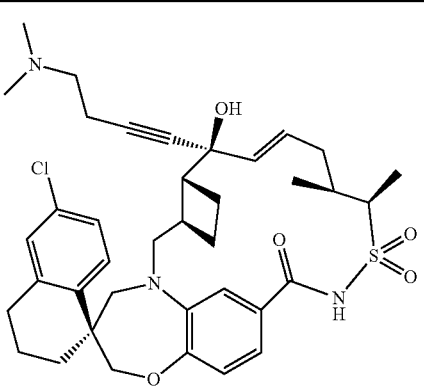 OR 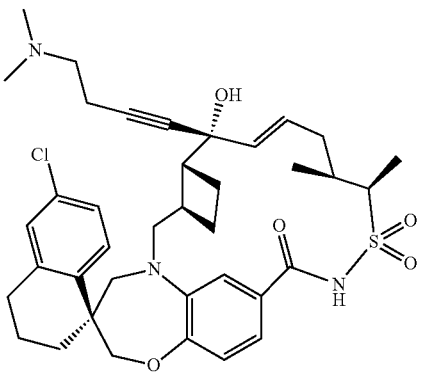 | (1S,3'R,6'R,7'S,8'E,11'S,12'R)-6-chloro-7'-(4-(dimethylamino)-1-butyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-(4-(dimethylamino)-1-butyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.5 |
| 100310 | 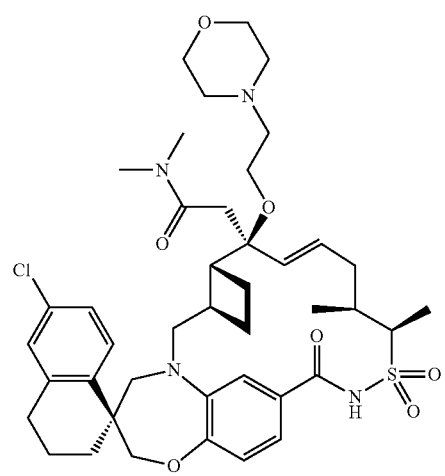 | 2-((1S,3'R,6'R,7'R,8'E,11'S,12'R)-6-chloro-11',12'-dimethyl-7'-(2-(4-morpholinyl)ethoxy)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide | 797.3 |

TABLE 2-continued

Examples Prepared by the General Methods

| Example Number | Structure | Name | MS Dat (M + 1)+ Unless Noted Otherwise |
|---|---|---|---|
| | OR 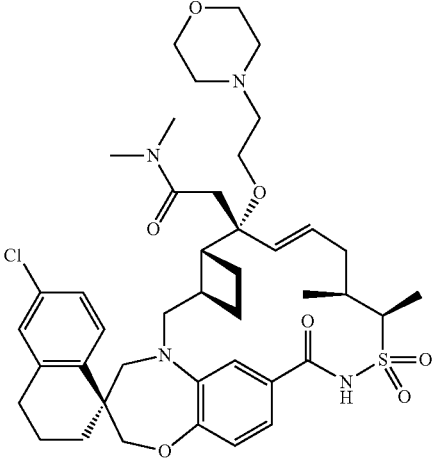 | OR<br>2-((1S,3'R,6'R,7'S,8'E,11'S,12'R)-6-chloro-11',12'-dimethyl-7'-(2-(4-morpholinyl)ethoxy)-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-dimethylacetamide | |
| 100311 | 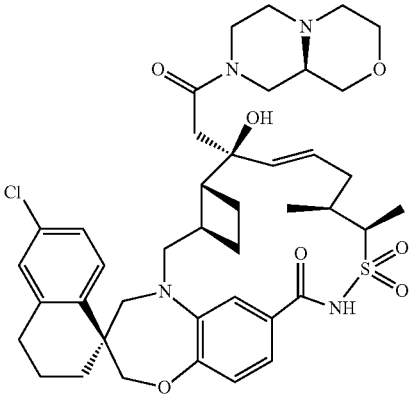 | (1S,3'R,6'R,7'S,8'E,11'S,12'R)-6-chloro-7'-(2-((9aR)-hexahydropyrazino[2,1-c][1,4]oxazin-8(1H)-yl)-2-oxoethyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.2 |
| 100312 | 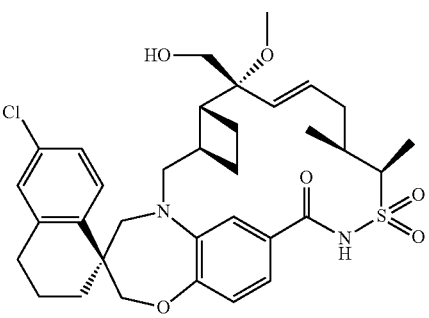 | (1S,3'R,6'R,7'R,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 643.2 |

TABLE 2-continued

Examples Prepared by the General Methods

| Example Number | Structure | Name | MS Dat (M + 1)+ Unless Noted Otherwise |
|---|---|---|---|
| | | (1S,3'R,6'R,7'S,8'E,11'S,12'R)-6-chloro-7'-(hydroxymethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100313 | 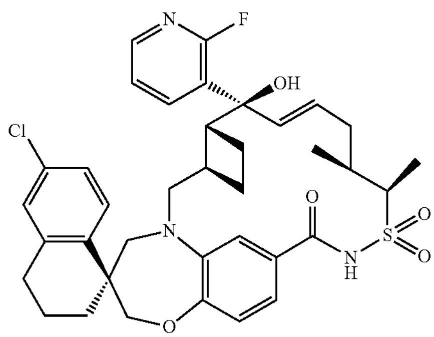 [SMILES: C[C@@H]1[C@@H](C)C/C=C/[C@@](O)(c2cccnc2F)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(2-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.3 |
| | | (1S,3'R,6'R,7'S,8'E,11'S,12'R)-6-chloro-7'-(2-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100314 | 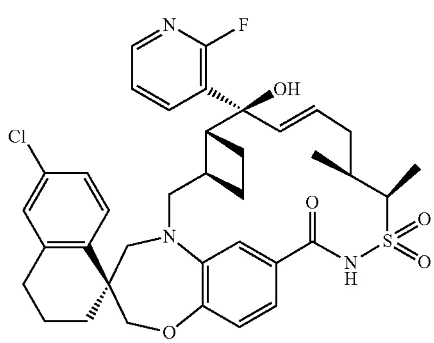 [SMILES: C[C@@H]1[C@@H](C)C/C=C/[C@@](O)(c2cccnc2F)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(2-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-(2-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100315 | 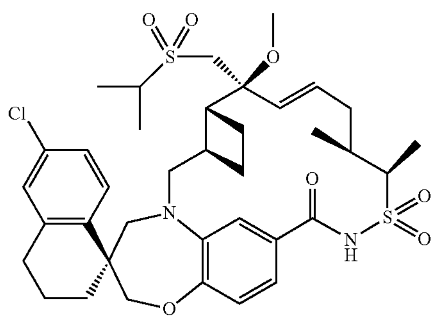 | (1S,3'R,6'R,7'S,8'E,11'S,12'R)-6-chloro-7'-methoxy-11',12'-dimethyl-7'-((2-propanylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 733.3 |
| | OR | OR (1S,3'R,6'R,7'R,8'E,11'S,12'R)-6-chloro-7'-methoxy-11',12'-dimethyl-7'-((2-propanylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100316 | 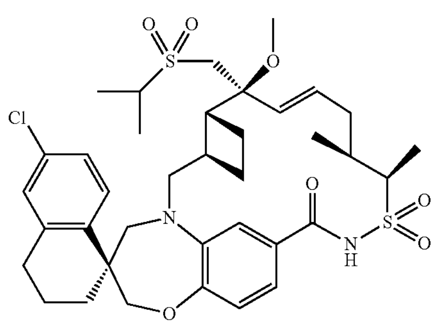 | (1S,3'R,6'R,7'S,8'E,11'S,12'R)-6-chloro-7'-methoxy-11',12'-dimethyl-7'-((2-propanylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 733.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-methoxy-11',12'-dimethyl-7'-((2-propanylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100317 | 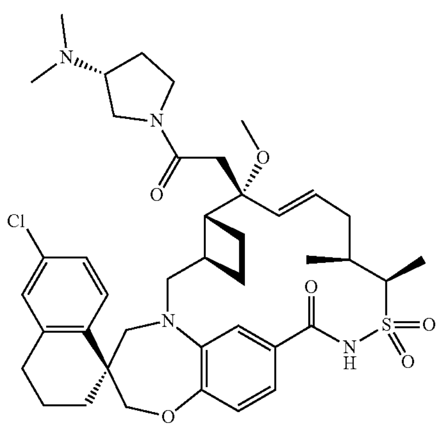 | (1S,3'R,6'R,7'R,8'E,11'S,12'R)-6-chloro-7'-(2-((3R)-3-(dimethylamino)-1-pyrrolidinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |
| | OR | OR | |
| | | (1S,3'R,6'R,7'S,8'E,11'S,12'R)-6-chloro-7'-(2-((3R)-3-(dimethylamino)-1-pyrrolidinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100318 | 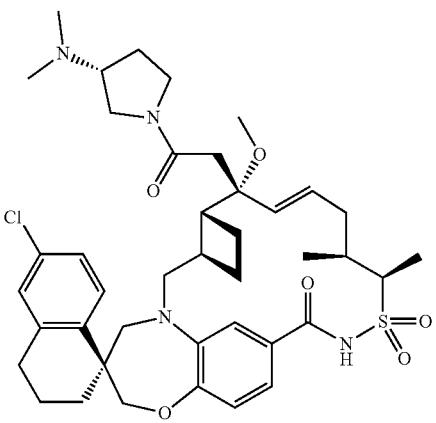<br>OR<br>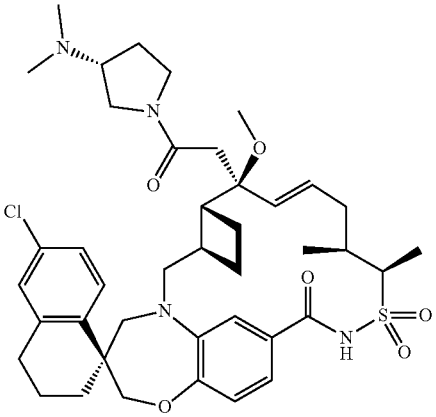 | (1S,3'R,6'R,7'S,8'E,11'S,12'R)-6-chloro-7'-(2-((3R)-3-(dimethylamino)-1-pyrrolidinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-(2-((3R)-3-(dimethylamino)-1-pyrrolidinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |
| 100319 | 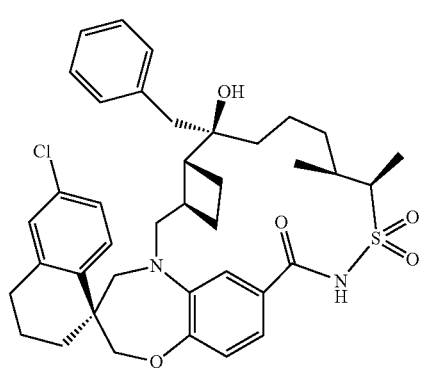 [SMILES: C[C@@H]1[C@@H](C)CCC[C@@](O)(Cc2ccccc2)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-7'-benzyl-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 691.2 |

TABLE 2-continued

Examples Prepared by the General Methods

| Example Number | Structure | Name | MS Dat (M + 1)+ Unless Noted Otherwise |
|---|---|---|---|
| | OR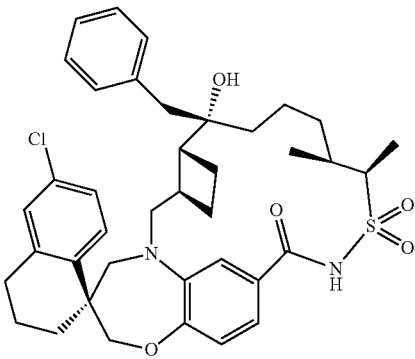 | OR (1S,3'R,6'R,7'R,11'S,12'R)-7'-benzyl-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100320 | 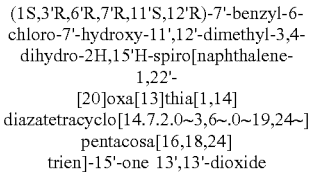 | (1S,3'R,6'R,7'S,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 722.2 |
| | OR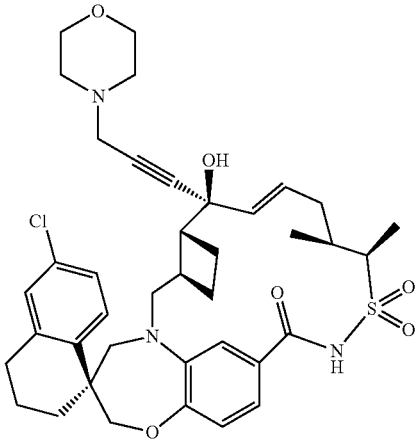 | OR (1S,3'R,6'R,7'R,8'E,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100321 | 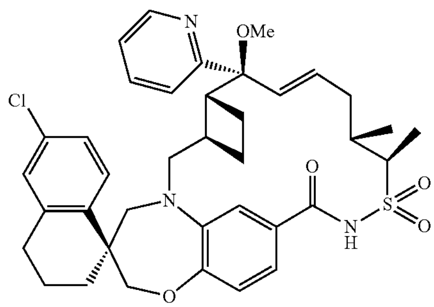 [SMILES: CO[C@@]1(c2ccccn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.0 |
| | OR | OR | |
| | | (1S,3'R,6'R,7'S,8'E,11'S,12'R)-6-chloro-7'-methoxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100322 | 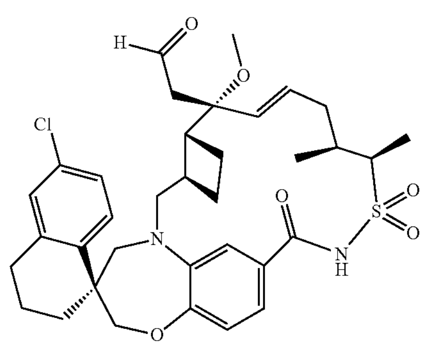 [SMILES: CO[C@]1(CC=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | ((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde | 655.2 |
| 100323 | 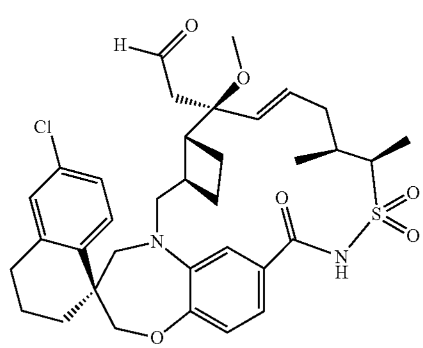 [SMILES: CO[C@@]1(CC=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | ((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetaldehyde | 655.2 |

TABLE 2-continued

Examples Prepared by the General Methods

| Example Number | Structure | Name | MS Dat (M + 1)+ Unless Noted Otherwise |
|---|---|---|---|
| 100324 | 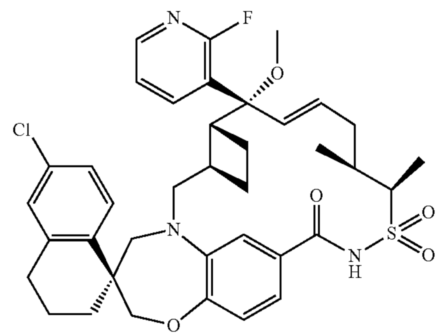 [SMILES: CO[C@]1(c2cccnc2F)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(2-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 707.2 |
| | OR | OR | |
| | | (1S,3'R,6'R,7'S,8'E,11'S,12'R)-6-chloro-7'-(2-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100325 | 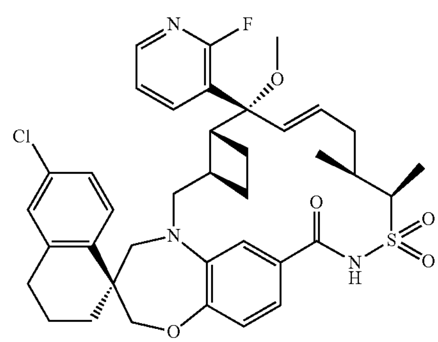 [SMILES: CO[C@]1(c2cccnc2F)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(2-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 707.3 |
| | OR | OR | |
| | | (1S,3'R,6'R,7'S,8'E,11'S,12'R)-6-chloro-7'-(2-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100326 | 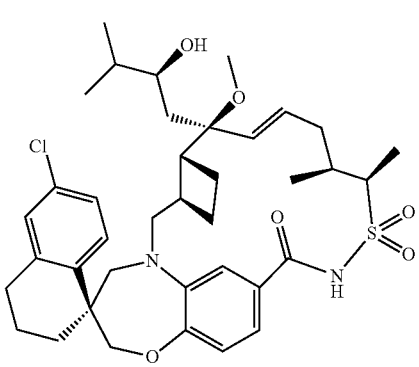 AND 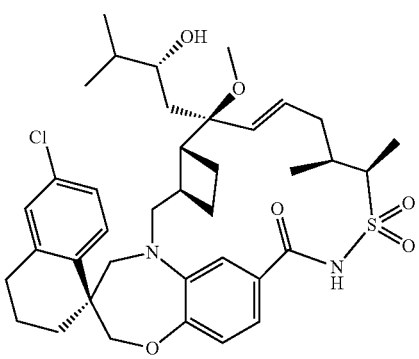 | (1S,3'R,6'R,7'S,8'E,11'S,12'R)-6-chloro-7'-((2R)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide AND (1S,3'R,6'R,7'S,8'E,11'S,12'R)-6-chloro-7'-((2S)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 699.2 |
| 100327 | 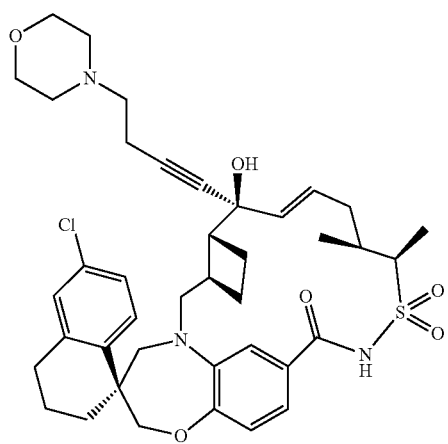 | (1S,3'R,6'R,7'S,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 736.4 |

TABLE 2-continued

Examples Prepared by the General Methods

| Example Number | Structure | Name | MS Dat (M + 1)+ Unless Noted Otherwise |
|---|---|---|---|
| | OR 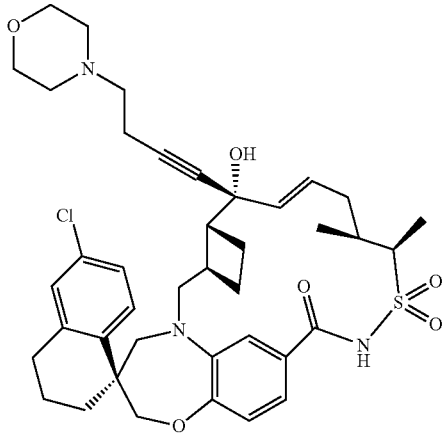 | OR (1S,3'R,6'R,7'R,8'E,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100328 | 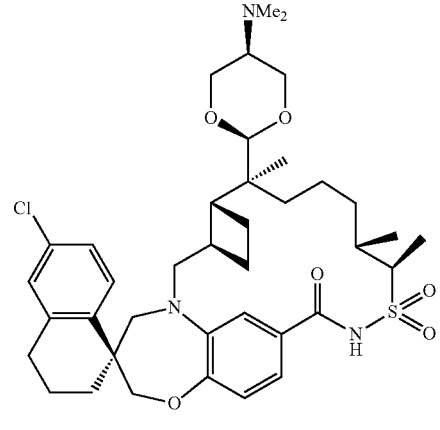 | (1S,3'R,6'R,7'S,11'S,12'R)-6-chloro-7'-(cis-5-(dimethylamino)-1,3-dioxan-2-yl)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 728.3 |
| | OR 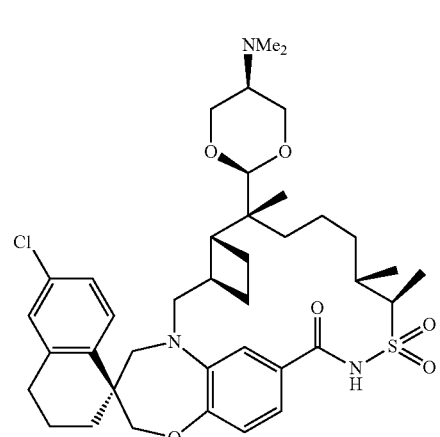 | OR (1S,3'R,6'R,7'R,11'S,12'R)-6-chloro-7'-(cis-5-(dimethylamino)-1,3-dioxan-2-yl)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100329 | 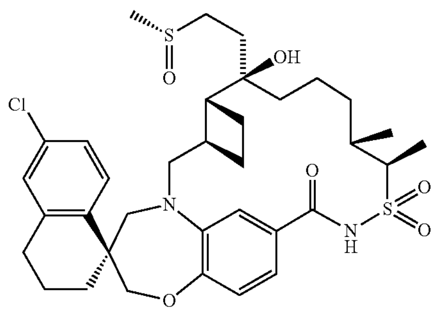 [SMILES: C[C@@H]1[C@@H](C)CCC[C@@](O)(CC[S@@](C)=O)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(2-((R)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 691.3 |
| | AND | AND | |
| | | (1S,3'R,6'R,7'R,11'S,12'R)-6-chloro-7'-hydroxy-11',12'-dimethyl-7'-(2-((S)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR | |
| | | (1S,3'R,6'R,7'S,11'S,12'R)-6-chloro-7'-hydroxy-11',12'-dimethyl-7'-(2-((R)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | AND | AND | |
| | | (1S,3'R,6'R,7'S,11'S,12'R)-6-chloro-7'-hydroxy-11',12'-dimethyl-7'-(2-((S)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100330 | 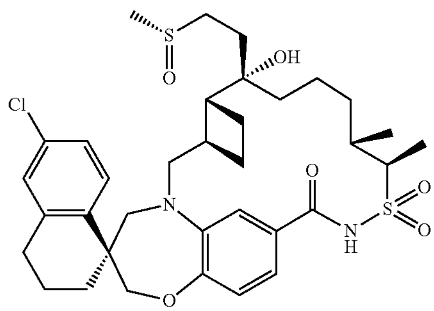 [SMILES: C[C@@H]1[C@@H](C)CCC[C@](O)(CC[S@@](C)=O)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-hydroxy-11',12'-dimethyl-7'-(2-((R)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 691.3 |
| | AND | AND | |
| | | (1S,3'R,6'R,7'S,11'S,12'R)-6-chloro-7'-hydroxy-11',12'-dimethyl-7'-(2-((S)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR | |
| | | (1S,3'R,6'R,7'R,11'S,12'R)-6-chloro-7'-hydroxy-11',12'-dimethyl-7'-(2-((R)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | AND | AND | |
| | | (1S,3'R,6'R,7'R,11'S,12'R)-6-chloro-7'-hydroxy-11',12'-dimethyl-7'-(2-((S)-methylsulfinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100331 | 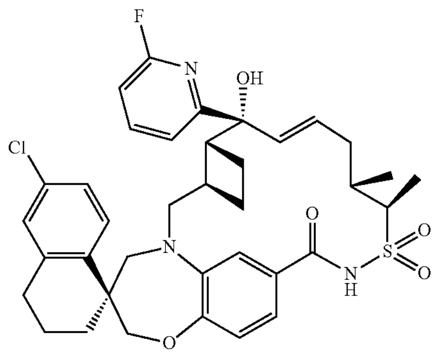 [SMILES: C[C@@H]1[C@@H](C)C/C=C/[C@](O)(c2cccc(F)n2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(6-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| | OR | OR | |
| | | (1S,3'R,6'R,7'S,8'E,11'S,12'R)-6-chloro-7'-(6-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100332 | 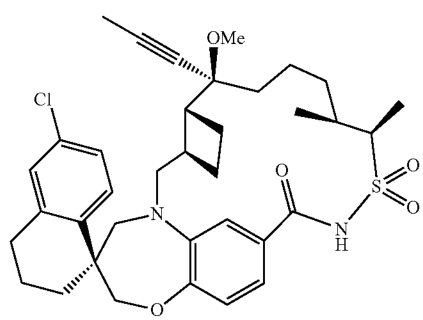 [SMILES: CC#C[C@]1(OC)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-methoxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 653.3 |
| 100333 | 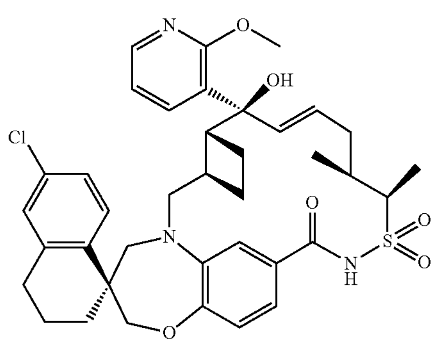 [SMILES: COc1ncccc1[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-7'-(2-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 706.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-hydroxy-7'-(2-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100334 | 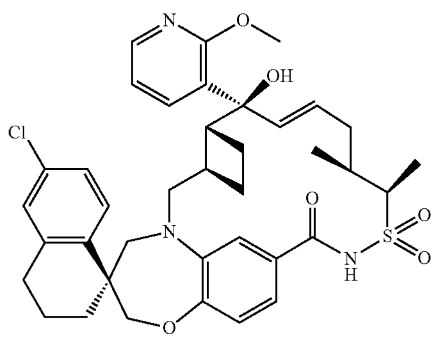 | (1S,3'R,6'R,7'R,8'E,11'S,12'R)-6-chloro-7'-hydroxy-7'-(2-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 706.3 |
| | OR | OR | |
| | | (1S,3'R,6'R,7'S,8'E,11'S,12'R)-6-chloro-7'-hydroxy-7'-(2-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100335 | 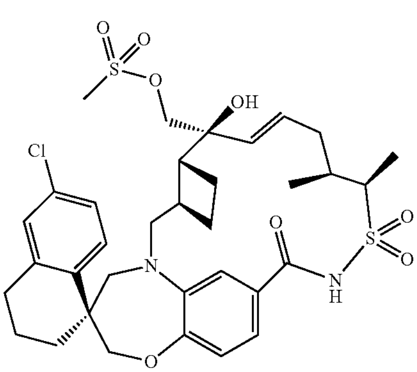 | ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl methanesulfonate | 707.2 |

TABLE 2-continued

Examples Prepared by the General Methods

| Example Number | Structure | Name | MS Dat (M + 1)+ Unless Noted Otherwise |
|---|---|---|---|
| | OR | ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl methanesulfonate | |
| 100336 | 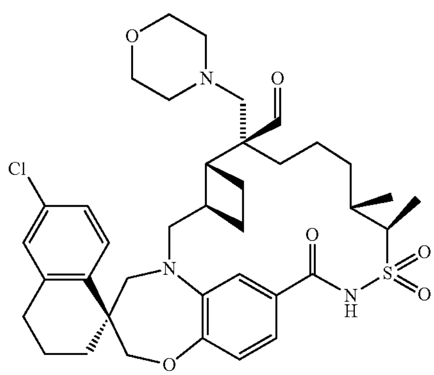 | (1S,3'R,6'R,7'S,11'S,12'R)-6-chloro-11',12'-dimethyl-7'-(4-morpholinylmethyl)-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide | 712.5 |
| | OR | (1S,3'R,6'R,7'R,11'S,12'R)-6-chloro-11',12'-dimethyl-7'-(4-morpholinylmethyl)-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide | |

TABLE 2-continued

Examples Prepared by the General Methods

| Example Number | Structure | Name | MS Dat (M + 1)+ Unless Noted Otherwise |
|---|---|---|---|
| 100337 | 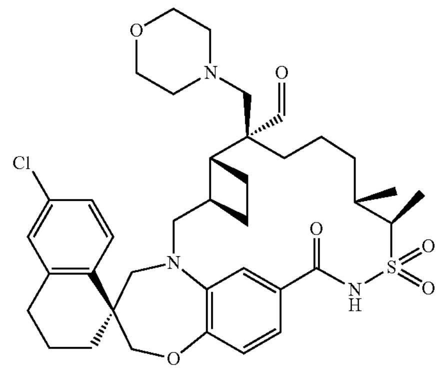 [SMILES: C[C@@H]1[C@@H](C)CCC[C@](C=O)(CN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-11',12'-dimethyl-7'-(4-morpholinylmethyl)-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide | 712.5 |
| | AND | AND | |
| | | (1S,3'R,6'R,7'S,11'S,12'R)-6-chloro-11',12'-dimethyl-7'-(4-morpholinylmethyl)-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide | |
| 100338 | 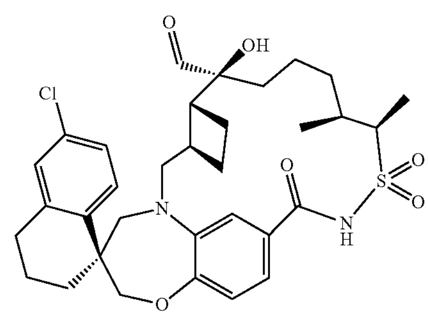 [SMILES: C[C@@H]1[C@@H](C)CCC[C@@](O)(C=O)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide | 629.2 |
| | OR | OR | |
| | | (1S,3'R,6'R,7'R,11'S,12'R)-6-chloro-7'-hydroxy-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]triene]-7'-carbaldehyde 13',13'-dioxide | |

TABLE 2-continued

Examples Prepared by the General Methods

| Example Number | Structure | Name | MS Dat (M + 1)+ Unless Noted Otherwise |
|---|---|---|---|
| 100339 | 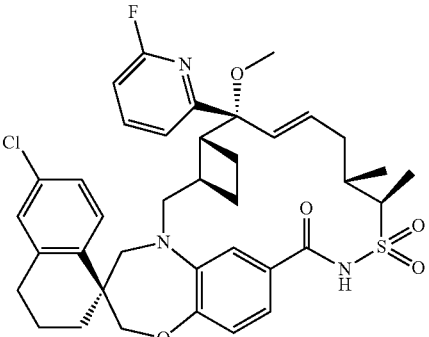<br><br>OR<br><br>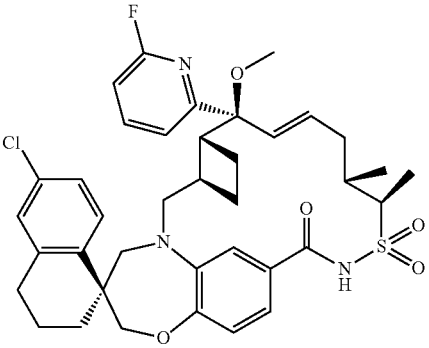 [SMILES: CO[C@@]1(c2cccc(F)n2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(6-fluoro-2-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-(6-fluoro-2-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |
| 100340 | 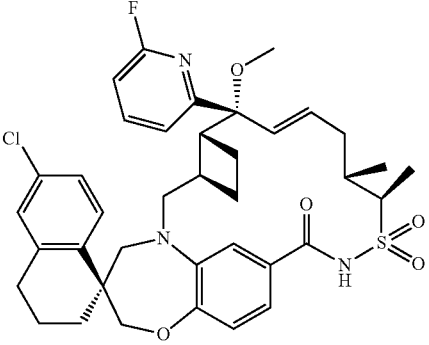 [SMILES: CO[C@]1(c2cccc(F)n2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]<br><br>OR<br><br>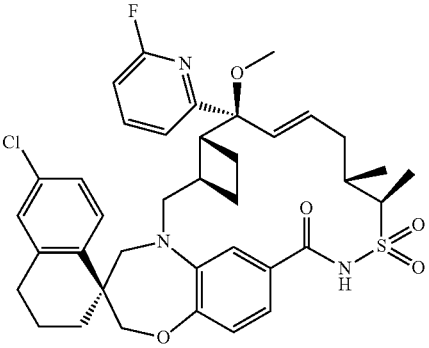 [SMILES: CO[C@@]1(c2cccc(F)n2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(6-fluoro-2-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'S,8'E,11'S,12'R)-6-chloro-7'-(6-fluoro-2-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |

TABLE 2-continued

Examples Prepared by the General Methods

| Example Number | Structure | Name | MS Dat (M + 1)+ Unless Noted Otherwise |
|---|---|---|---|
| 100341 | 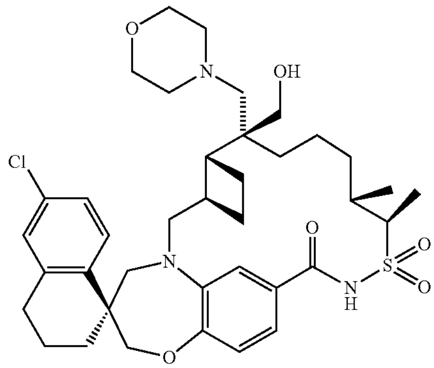 [SMILES: C[C@@H]1[C@@H](C)CCC[C@@](CO)(CN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-(hydroxymethyl)-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 714.3 |
| | OR | OR | |
| | | (1S,3'R,6'R,7'R,11'S,12'R)-6-chloro-7'-(hydroxymethyl)-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100342 | 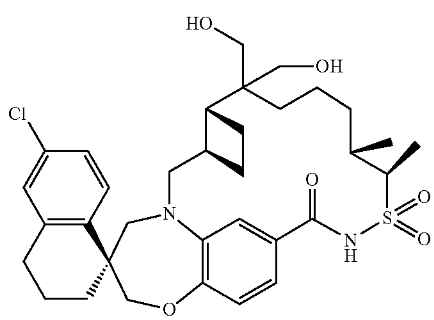 [SMILES: C[C@@H]1[C@@H](C)CCCC(CO)(CO)[C@@H]2CC[C@H]2CN2C[C@@]3(CCCc4cc(Cl)ccc43)COc3ccc(cc32)C(=O)NS1(=O)=O] | (1S,3'R,6'R,11'S,12'R)-6-chloro-7',7'-bis(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 645.2 |
| 100343 | 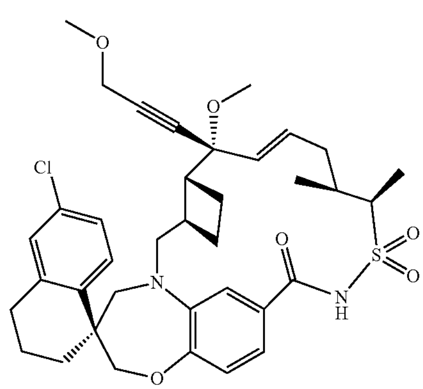 [SMILES: COCC#C[C@@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-7'-(3-methoxy-1-propyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 681.5 |

TABLE 2-continued

Examples Prepared by the General Methods

| Example Number | Structure | Name | MS Dat (M + 1)+ Unless Noted Otherwise |
|---|---|---|---|
| | 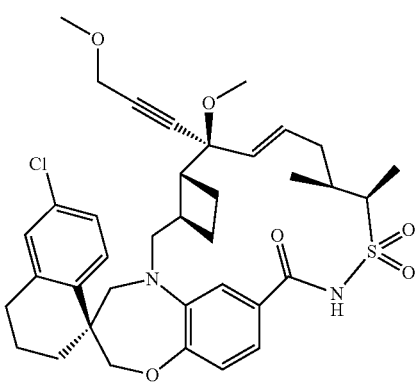 [SMILES: COCC#C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7'-(3-methoxy-1-propyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100344 | 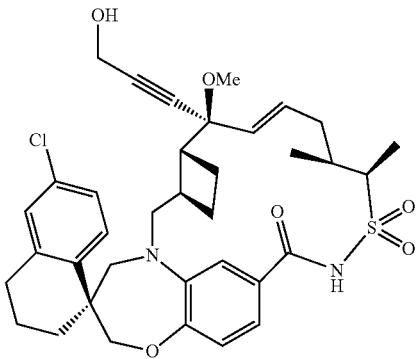 [SMILES: CO[C@@]1(C#CCO)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(3-hydroxy-1-propyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.2 |
| | 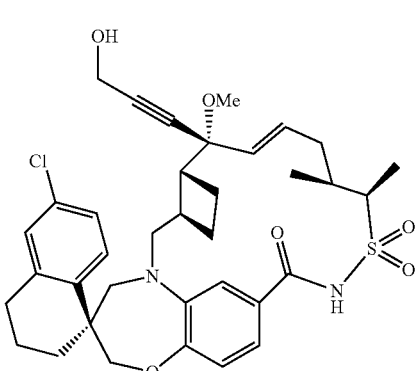 | (1S,3'R,6'R,7'R,8'E,11'S,12'R)-6-chloro-7'-(3-hydroxy-1-propyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100345 | 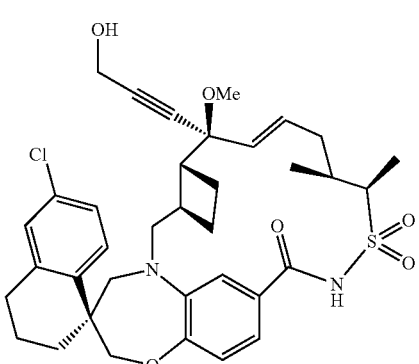<br><br>OR<br><br>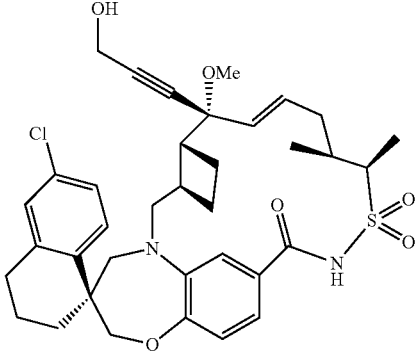 | (1S,3'R,6'R,7'S,8'E,11'S,12'R)-6-chloro-7'-(3-hydroxy-1-propyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-(3-hydroxy-1-propyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.2 |
| 100346 | 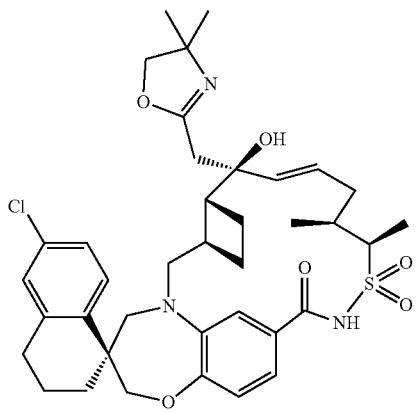 [SMILES: C[C@@H]1[C@@H](C)C/C=C/[C@@](O)(CC2=NC(C)(C)CO2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-((4,4-dimethyl-4,5-dihydro-1,3-oxazol-2-yl)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15-one 13',13'-dioxide|(1S,3'R,6'R,7'S,8'E,11'S,12'R)-6-chloro-7'-((4,4-dimethyl-4,5-dihydro-1,3-oxazol-2-yl)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.0 |

TABLE 2-continued

Examples Prepared by the General Methods

| Example Number | Structure | Name | MS Dat (M + 1)+ Unless Noted Otherwise |
|---|---|---|---|
| | AND | AND | |
| | | (1S,3'R,6'R,7'R,8'E,11'S,12'R)-6-chloro-7'-((4,4-dimethyl-4,5-dihydro-1,3-oxazol-2-yl)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide|(1S,3'R,6'R,7'S,8'E,11'S,12'R)-6-chloro-7'-((4,4-dimethyl-4,5-dihydro-1,3-oxazol-2-yl)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100347 | 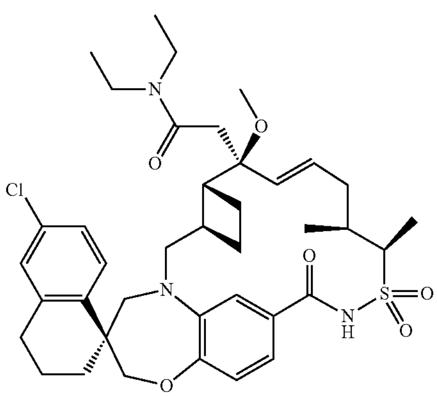 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N,N-diethylacetamide | 748.2 |
| 100348 | 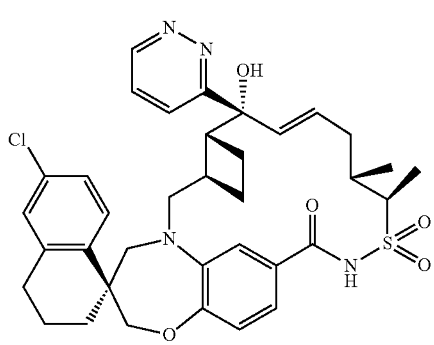 | (1S,3'R,6'R,7'S,8'E,11'S,12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100349 | 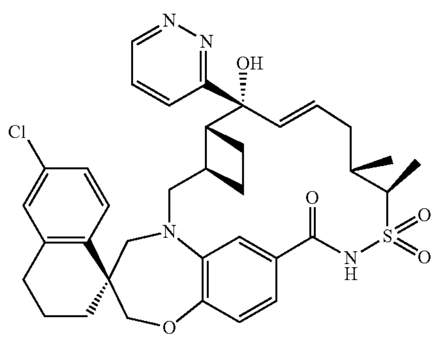 | (1S,3'R,6'R,7'R,8'E,11'S,12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.0 |
| | OR | OR (1S,3'R,6'R,7'S,8'E,11'S,12'R)-6-chloro-7'-hydroxy-11',12'-dimethyl-7'-(3-pyridazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100350 | 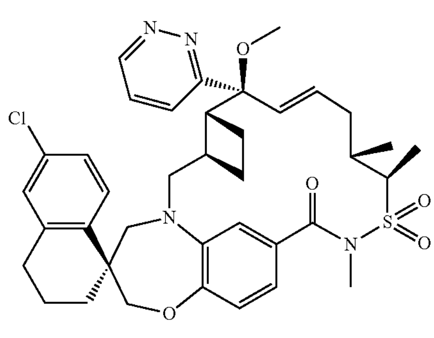 | 3-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-1-methylpyridazin-1-ium | 705.0 |

TABLE 2-continued

Examples Prepared by the General Methods

| Example Number | Structure | Name | MS Dat (M + 1)+ Unless Noted Otherwise |
|---|---|---|---|
| 100351 | 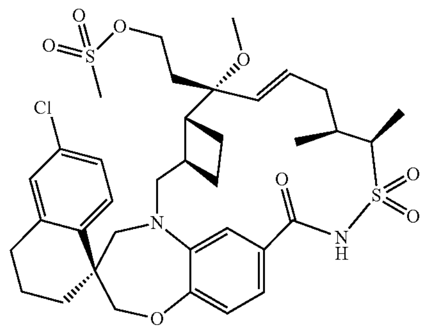 [SMILES: CO[C@]1(CCOS(C)(=O)=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'R,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)ethyl methanesulfonate | 757.1 (M + Na) |
| 100352 | 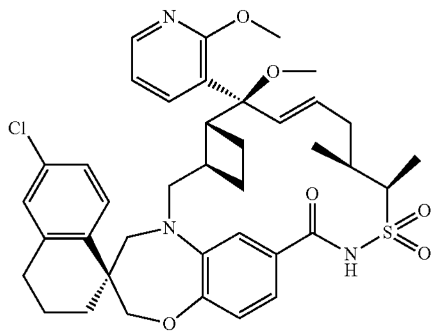 [SMILES: COc1ncccc1[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7'-(2-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-methoxy-7'-(2-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 720.2 |
| 100353 | 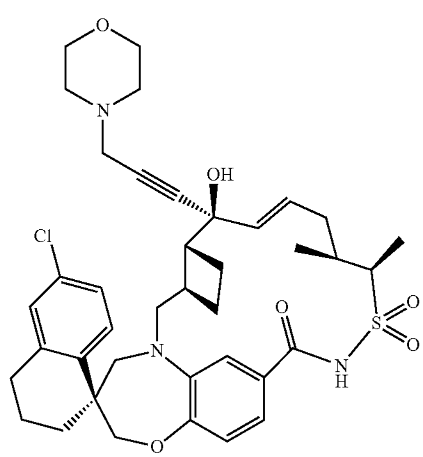 [SMILES: C[C@@H]1[C@@H](C)C/C=C/[C@@](O)(C#CCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 724.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100354 | 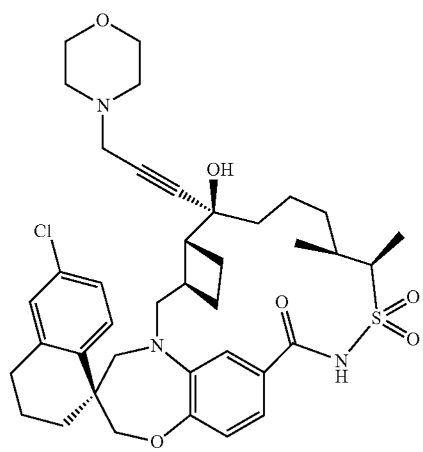 | (1S,3'R,6'R,7'S,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 724.3 |
| | OR | OR (1S,3'R,6'R,7'R,11'S,12'R)-6-chloro-7'-hydroxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100355 | 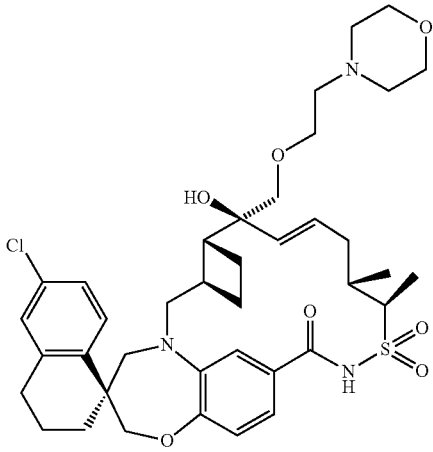 OR 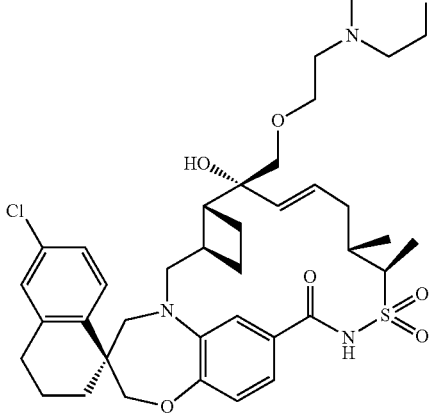 | (1S,3'R,6'R,7'S,8'E,11'S,12'R)-6-chloro-7'-hydroxy-11',12'-dimethyl-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-hydroxy-11',12'-dimethyl-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 742.3 |
| 100356 | 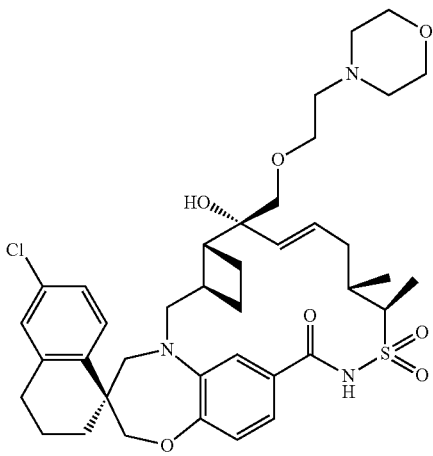 | (1S,3'R,6'R,7'R,8'E,11'S,12'R)-6-chloro-7'-hydroxy-11',12'-dimethyl-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 742.3 |

TABLE 2-continued

Examples Prepared by the General Methods

| Example Number | Structure | Name | MS Dat (M + 1)+ Unless Noted Otherwise |
|---|---|---|---|
| | OR | (1S,3'R,6'S,7'R,8'E,11'S,12'R)-6-chloro-7'-hydroxy-11',12'-dimethyl-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100357 | OR | (1S,3'R,6'R,7'S,8'E,11'S,12'R)-6-chloro-7'-hydroxy-11',12'-dimethyl-7'-(2-pyrazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.0 |
| 100358 | 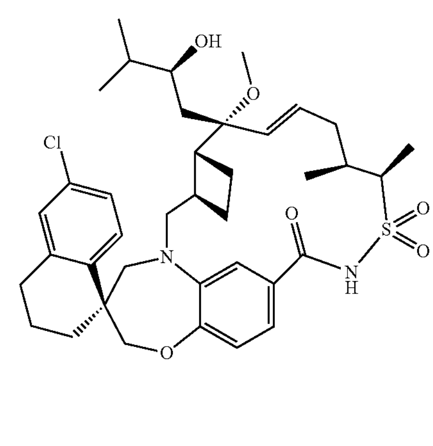 | (1S,3'R,6'R,7'R,8'E,11'S,12'R)-6-chloro-7'-((2S)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 721.5 (M + Na) |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-((2R)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100359 | 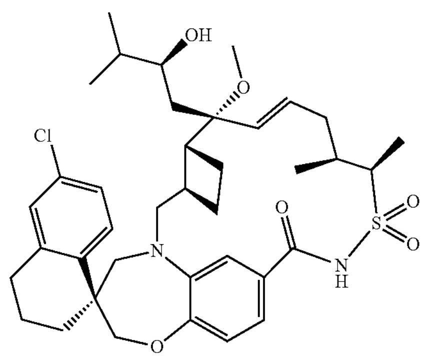 | (1S,3'R,6'R,7'R,8'E,11'S,12'R)-6-chloro-7'-((2S)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 721.5 (M + Na) |
| | OR | OR (1S,3'R,6'R,7'R,8'E,11'S,12'R)-6-chloro-7'-((2R)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100360 | 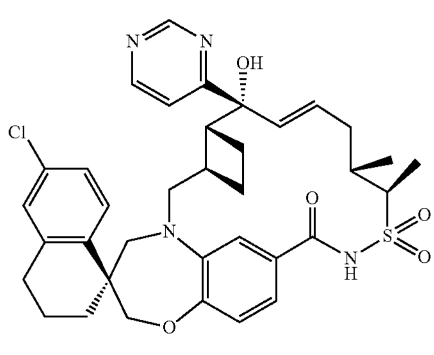 | (1S,3'R,6'R,7'S,8'E,11'S,12'R)-6-chloro-7'-hydroxy-11',12'-dimethyl-7'-(4-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.0 |

TABLE 2-continued

Examples Prepared by the General Methods

| Example Number | Structure | Name | MS Dat (M + 1)+ Unless Noted Otherwise |
|---|---|---|---|
| | | OR (1S,3'R,6'R,7'R,8'E,11'S,12'R)-6-chloro-7'-hydroxy-11',12'-dimethyl-7'-(4-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100361 | 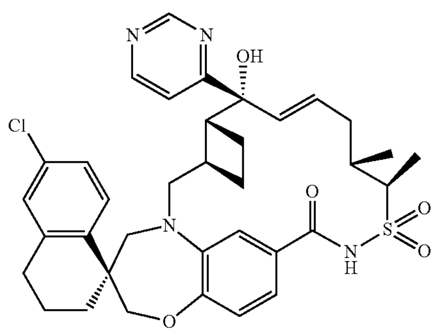 | OR (1S,3'R,6'R,7'R,8'E,11'S,12'R)-6-chloro-7'-hydroxy-11',12'-dimethyl-7'-(4-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.0 |
| | | OR (1S,3'R,6'R,7'S,8'E,11'S,12'R)-6-chloro-7'-hydroxy-11',12'-dimethyl-7'-(4-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100362 | 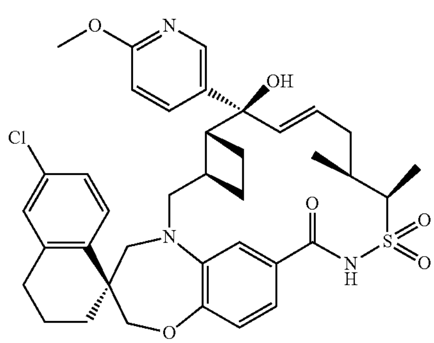 [SMILES: COc1ccc([C@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)cn1] | (1S,3'R,6'R,7'R,8'E,11'S,12'R)-6-chloro-7'-hydroxy-7'-(6-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 706.3 |

TABLE 2-continued

Examples Prepared by the General Methods

| Example Number | Structure | Name | MS Dat (M + 1)+ Unless Noted Otherwise |
|---|---|---|---|
| | 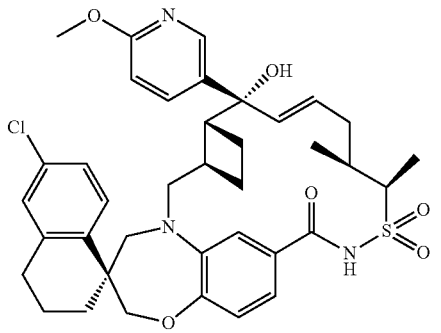 OR | OR (1S,3'R,6'R,7'S,8'E,11'S,12'R)-6-chloro-7'-hydroxy-7'-(6-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100363 | 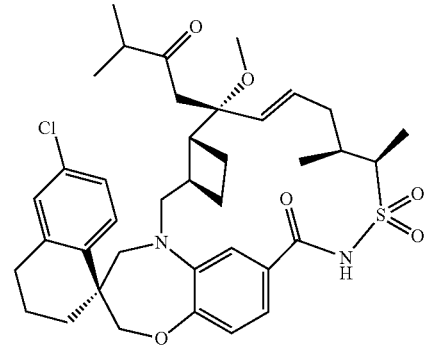 | (1S,3'R,6'R,7'R,8'E,11'S,12'R)-6-chloro-7'-methoxy-11',12'-dimethyl-7'-(3-methyl-2-oxobutyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 697.2 |
| 100364 | 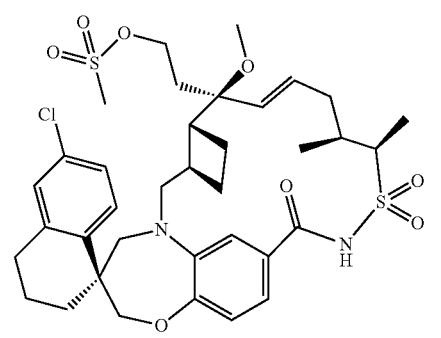 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)ethyl methanesulfonate | 757.2 (M + Na) |
| 100365 | 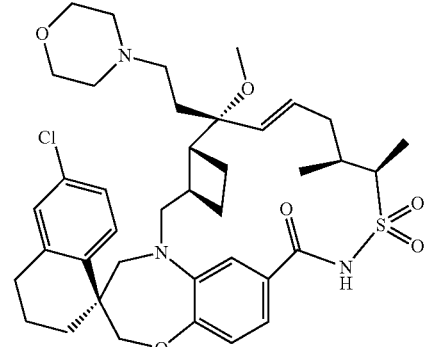 | (1S,3'R,6'R,7'R,8'E,11'S,12'R)-6-chloro-7'-methoxy-11',12'-dimethyl-7'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.3 |

TABLE 2-continued

Examples Prepared by the General Methods

| Example Number | Structure | Name | MS Dat (M + 1)+ Unless Noted Otherwise |
|---|---|---|---|
| 100366 | | (1S,3'R,6'R,7'S,8'E,11'S,12'R)-6-chloro-7'-((2R)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>|(1S,3'R,6'R,7'S,8'E,11'S,12'R)-6-chloro-7'-((2S)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 721.3 (M + Na) |
| 100367 | | (1S,3'R,6'R,7'S,8'E,11'S,12'R)-6-chloro-7'-((2R)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>|(1S,3'R,6'R,7'S,8'E,11'S,12'R)-6-chloro-7'-((2S)-2-hydroxy-3-methylbutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 721.3 (M + Na) |

TABLE 2-continued

Examples Prepared by the General Methods

| Example Number | Structure | Name | MS Dat (M + 1)+ Unless Noted Otherwise |
|---|---|---|---|
| 100368 | 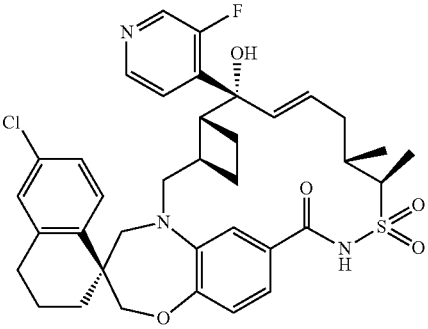 OR 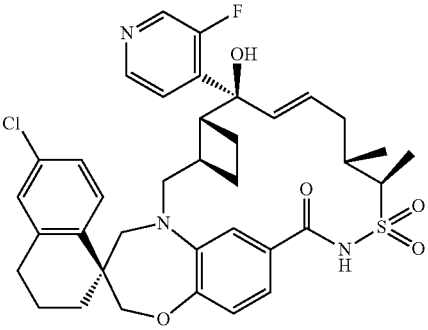 | (1S,3'R,6'R,7'R,8'E,11'S,12'R)-6-chloro-7'-(3-fluoro-4-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-(3-fluoro-4-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| 100369 | 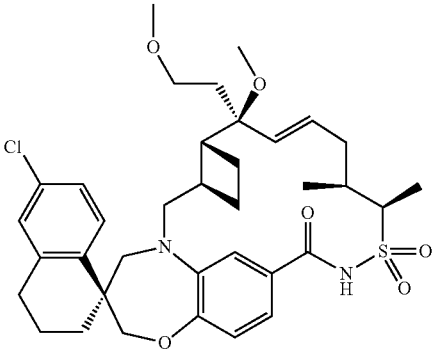 | (1S,3'R,6'R,7'S,8'E,11'S,12'R)-6-chloro-7'-methoxy-7'-(2-methoxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.2 |
| 100370 | 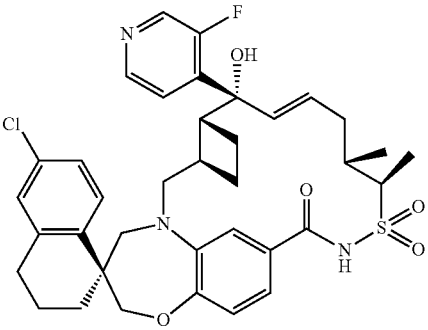 | (1S,3'R,6'R,7'S,8'E,11'S,12'R)-6-chloro-7'-(3-fluoro-4-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-(3-fluoro-4-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100371 | 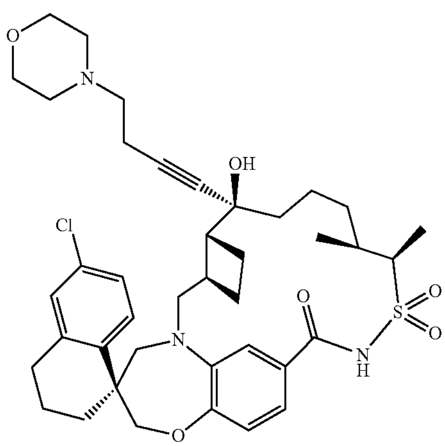 | (1S,3'R,6'R,7'S,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 738.3 |
| | OR | OR (1S,3'R,6'R,7'R,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100372 | 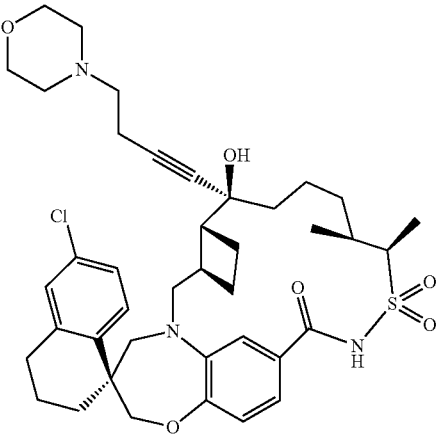 OR 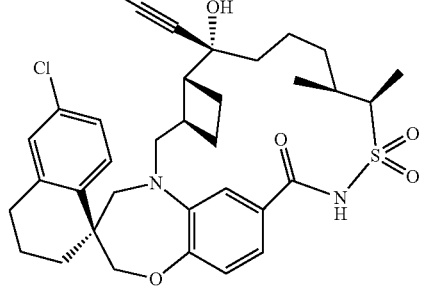 | (1S,3'R,6'R,7'S,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'R,7'R,11'S,12'R)-6-chloro-7'-hydroxy-11',12'-dimethyl-7'-(4-(4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 738.5 |
| 100373 | 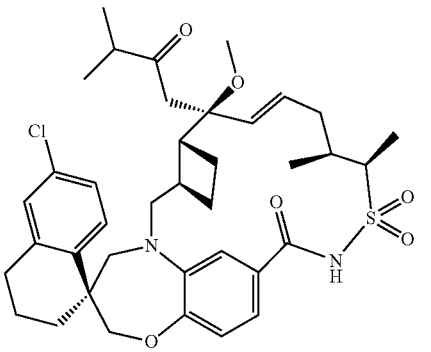 | (1S,3'R,6'R,7'S,8'E,11'S,12'R)-6-chloro-7'-methoxy-11',12'-dimethyl-7'-(3-methyl-2-oxobutyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 719.3 (M + Na) |

TABLE 2-continued

Examples Prepared by the General Methods

| Example Number | Structure | Name | MS Dat (M + 1)+ Unless Noted Otherwise |
|---|---|---|---|
| 100374 | 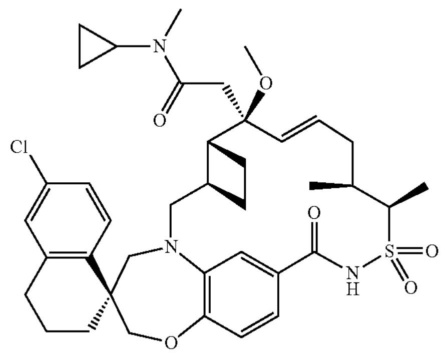 [SMILES: CO[C@@]1(CC(=O)N(C)C2CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-cyclopropyl-N-methylacetamide | 746.3 |
| 100375 | 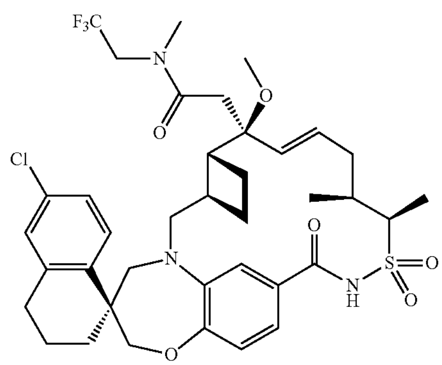 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-(2,2,2-trifluoroethyl)acetamide | 788.3 (M + Na) |
| 100376 | 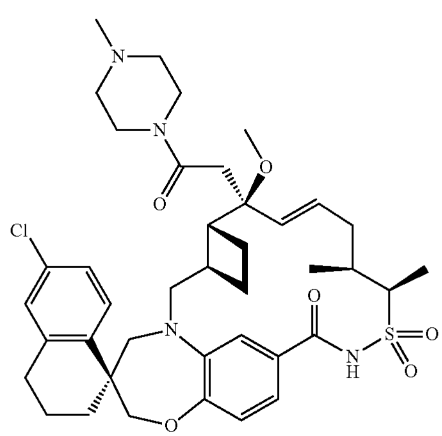 | (1S,3'R,6'R,7'S,8'E,11'S,12'R)-6-chloro-7'-methoxy-11',12'-dimethyl-7'-(2-(4-methyl-1-piperazinyl)-2-oxoethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.3 (M + Na) |

TABLE 2-continued

Examples Prepared by the General Methods

| Example Number | Structure | Name | MS Dat (M + 1)+ Unless Noted Otherwise |
|---|---|---|---|
| 100377 | 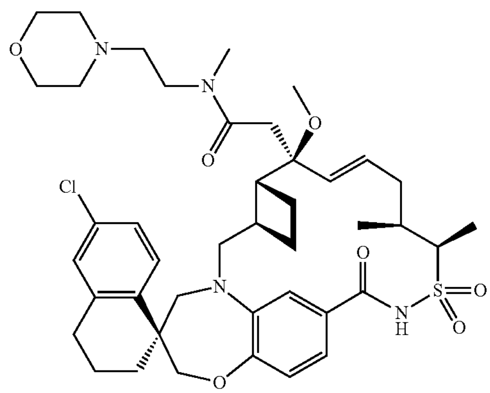 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-methyl-N-(2-(4-morpholinyl)ethyl)acetamide | 797.3 |
| 100378 | 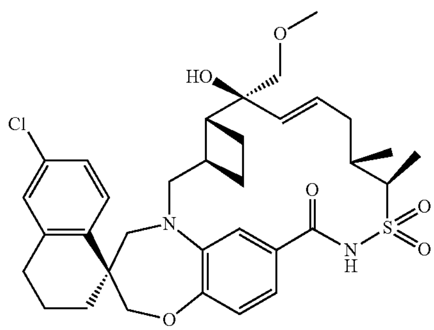 [SMILES: COC[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-hydroxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 643.2 |
| 100379 | | (1S,3'R,6'R,7'S,8'E,11'S,12'R)-6-chloro-7'-methoxy-11',12'-dimethyl-7'-(2-pyrazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 659.0 |
| | OR | OR | |
| | | (1S,3'R,6'R,7'R,8'E,11'S,12'R)-6-chloro-7'-methoxy-11',12'-dimethyl-7'-(2-pyrazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100380 | 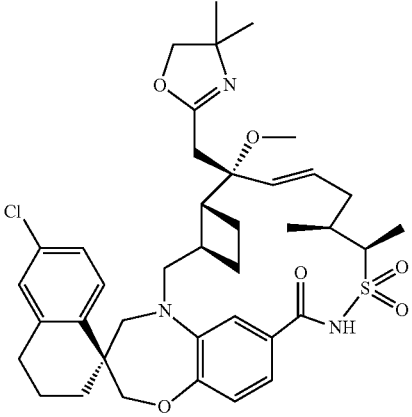 [SMILES: CO[C@]1(CC2=NC(C)(C)CO2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-((4,4-dimethyl-4,5-dihydro-1,3-oxazol-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |
| 100381 | 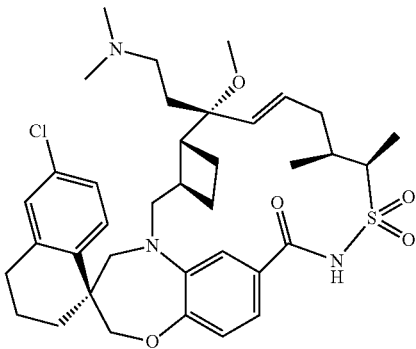 [SMILES: CO[C@]1(CCN(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(2-(dimethylamino)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 684.3 |
| 100382 | 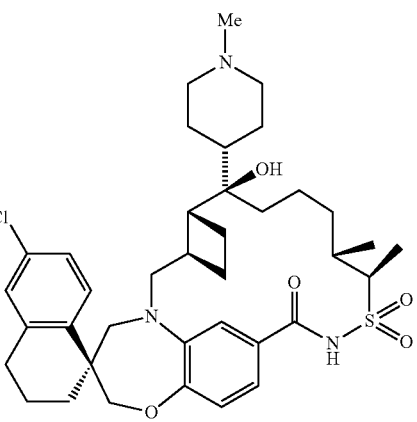 | (1S,3'R,6'R,7'R,11'S,12'R)-6-chloro-7'-hydroxy-11',12'-dimethyl-7'-(1-methyl-4-piperidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.3 |

TABLE 2-continued

Examples Prepared by the General Methods

| Example Number | Structure | Name | MS Dat (M + 1)+ Unless Noted Otherwise |
|---|---|---|---|
| | AND 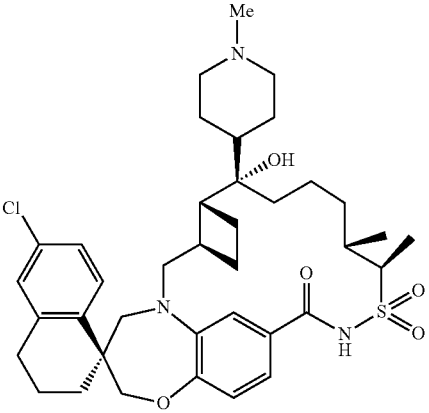 | AND (1S,3'R,6'R,7'S,11'S,12'R)-6-chloro-7'-hydroxy-11',12'-dimethyl-7'-(1-methyl-4-piperidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100383 | 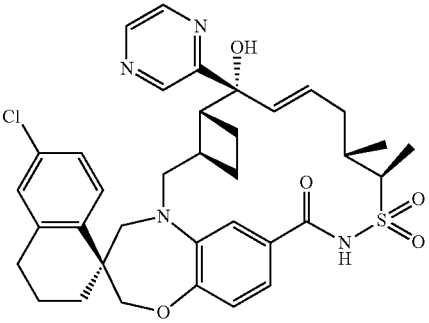 | (1S,3'R,6'R,7'R,8'E,11'S,12'R)-6-chloro-7'-hydroxy-11',12'-dimethyl-7'-(2-pyrazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.0 |
| | OR 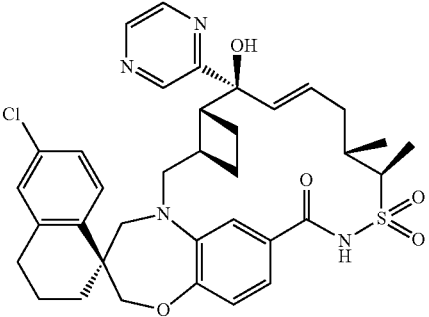 | OR (1S,3'R,6'R,7'S,8'E,11'S,12'R)-6-chloro-7'-hydroxy-11',12'-dimethyl-7'-(2-pyrazinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100384 | 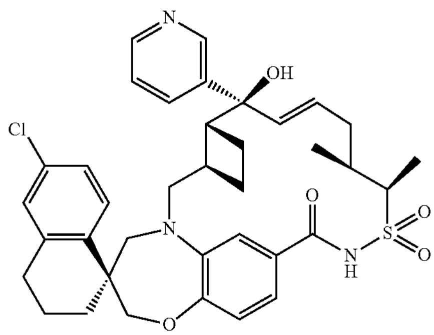 [SMILES: C[C@@H]1[C@@H](C)C/C=C/[C@@](O)(c2cccnc2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.2 |
| | OR | OR | |
| | | (1S,3'R,6'R,7'R,8'E,11'S,12'R)-6-chloro-7'-hydroxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100385 | 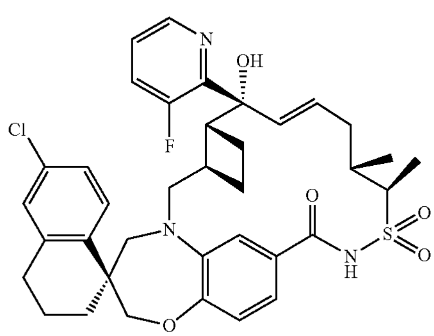 [SMILES: C[C@@H]1[C@@H](C)C/C=C/[C@](O)(c2ncccc2F)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(3-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.3 |

TABLE 2-continued

Examples Prepared by the General Methods

| Example Number | Structure | Name | MS Dat (M + 1)+ Unless Noted Otherwise |
|---|---|---|---|
| | | (1S,3'R,6'R,7'S,8'E,11'S,12'R)-6-chloro-7'-(3-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100386 | 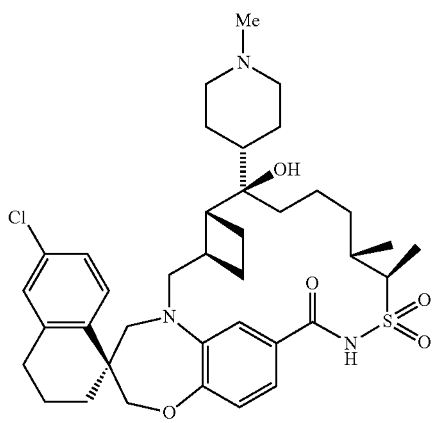 [SMILES: C[C@@H]1[C@@H](C)CCC[C@@](O)(C2CCN(C)CC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(1-methyl-4-piperidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.3 |
| | | (1S,3'R,6'R,7'S,11'S,12'R)-6-chloro-7'-hydroxy-11',12'-dimethyl-7'-(1-methyl-4-piperidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100387 | 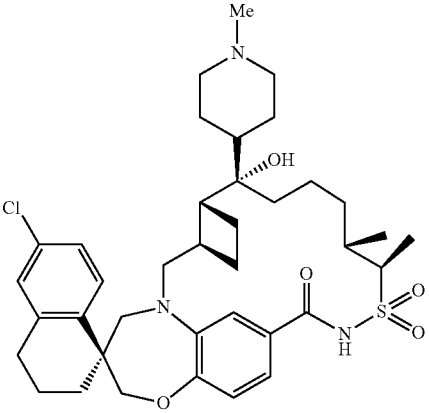 OR 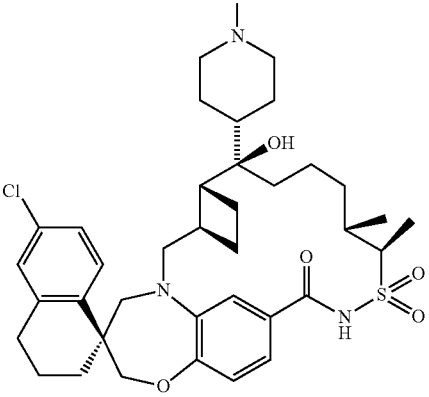 | (1S,3'R,6'R,7'S,11'S,12'R)-6-chloro-7'-hydroxy-11',12'-dimethyl-7'-(1-methyl-4-piperidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'R,11'S,12'R)-6-chloro-7'-hydroxy-11',12'-dimethyl-7'-(1-methyl-4-piperidinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 698.3 |
| 100388 | 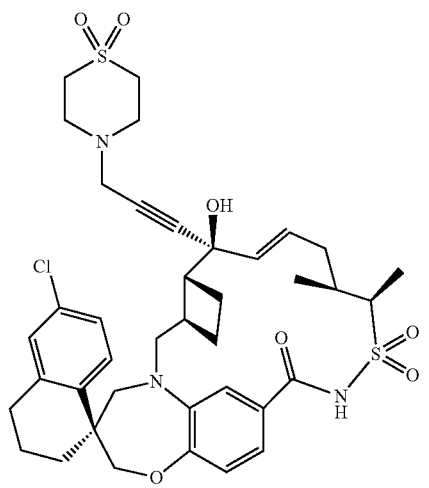 | (1S,3'R,6'R,7'S,8'E,11'S,12'R)-6-chloro-7'-(3-(1,1-dioxido-4-thiomorpholinyl)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 770.4 |

TABLE 2-continued

Examples Prepared by the General Methods

| Example Number | Structure | Name | MS Dat (M + 1)+ Unless Noted Otherwise |
|---|---|---|---|
| | OR 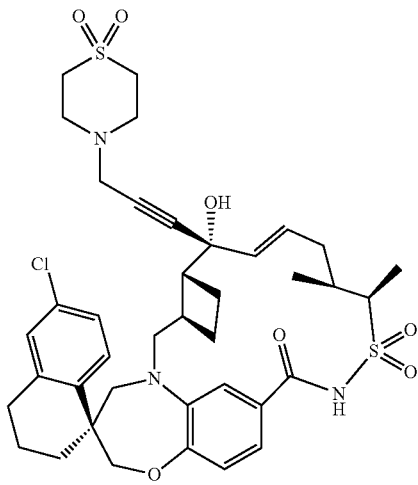 | OR (1S,3'R,6'R,7'R,8'E,11'S,12'R)-6-chloro-7'-(3-(1,1-dioxido-4-thiomorpholinyl)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100389 | 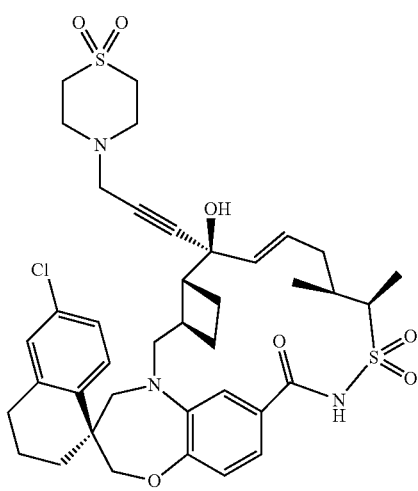 | (1S,3'R,6'R,7'S,8'E,11'S,12'R)-6-chloro-7'-(3-(1,1-dioxido-4-thiomorpholinyl)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 770.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-(3-(1,1-dioxido-4-thiomorpholinyl)-1-propyn-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100390 | 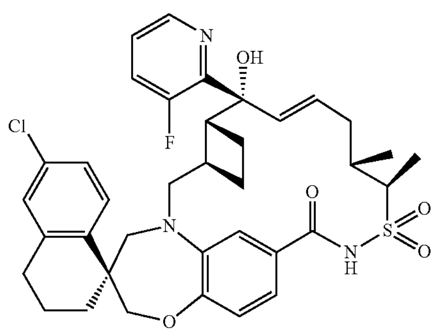 | (1S,3'R,6'R,7'S,8'E,11'S,12'R)-6-chloro-7'-(3-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.3 |
| | OR | OR (1S,3'R,6'R,7'R,8'E,11'S,12'R)-6-chloro-7'-(3-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100391 | 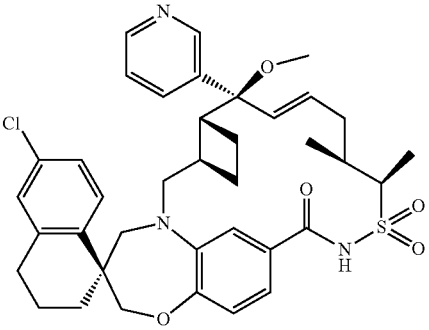 OR 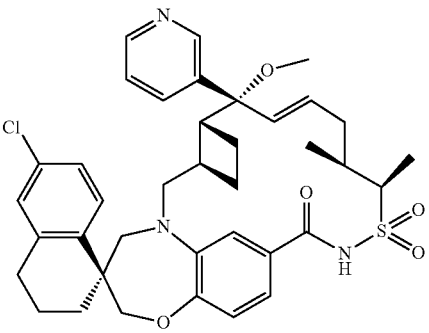 | (1S,3'R,6'R,7'S,8'E,11'S,12'R)-6-chloro-7'-methoxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-methoxy-11',12'-dimethyl-7'-(3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.2 |
| 100392 | 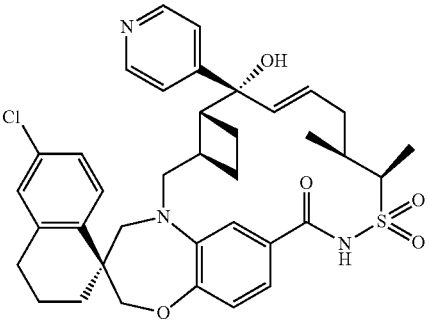 OR 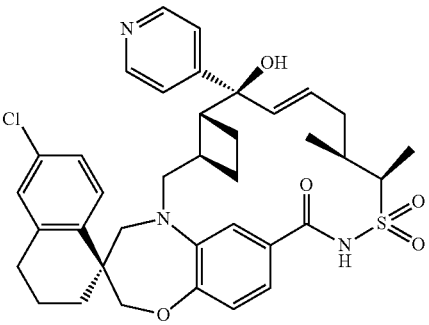 | (1S,3'R,6'R,7'S,8'E,11'S,12'R)-6-chloro-7'-hydroxy-11',12'-dimethyl-7'-(4-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-11',12'-dimethyl-7'-(4-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.2 |

TABLE 2-continued

Examples Prepared by the General Methods

| Example Number | Structure | Name | MS Dat (M + 1)+ Unless Noted Otherwise |
|---|---|---|---|
| 100393 | 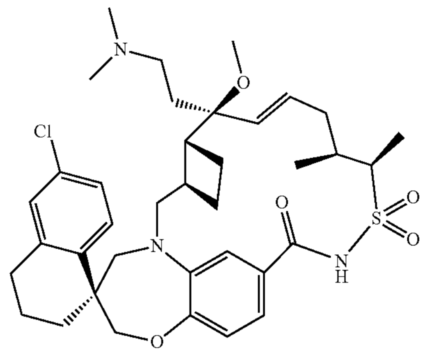 [SMILES: CO[C@@]1(CCN(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-(dimethylamino)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 684.2 |
| 100394 | | (1S,3'R,6'R,7'S,8'E,11'S,12'R)-6-chloro-7'-hydroxy-7'-(3-hydroxy-1-propyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-7'-(3-hydroxy-1-propyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 653.5 |
| 100395 | 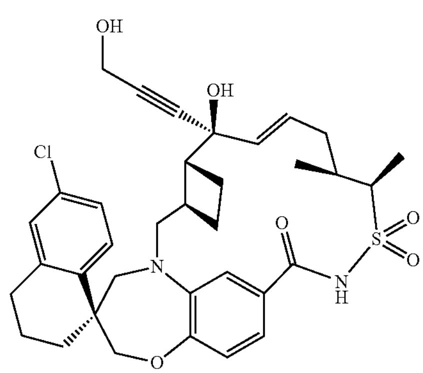 [SMILES: C[C@@H]1[C@@H](C)C/C=C/[C@@](O)(C#CCO)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-7'-(3-hydroxy-1-propyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 653.3 |

TABLE 2-continued

Examples Prepared by the General Methods

| Example Number | Structure | Name | MS Dat (M + 1)+ Unless Noted Otherwise |
|---|---|---|---|
| | | OR (1S,3'R,6'R,7'R,8'E,11'S,12'R)-6-chloro-7'-hydroxy-7'-(3-hydroxy-1-propyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100396 | 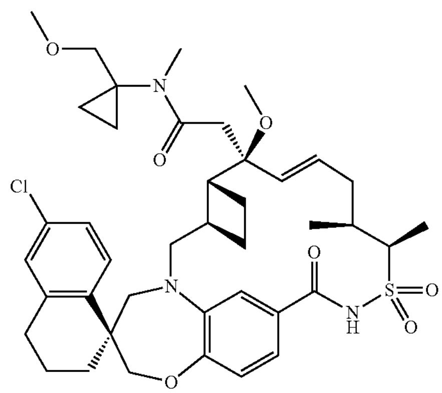 [SMILES: COCC1(N(C)C(=O)C[C@]2(OC)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)CC1] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(1-(methoxymethyl)cyclopropyl)-N-methylacetamide | 790.3 (M + Na) |
| 100397 | 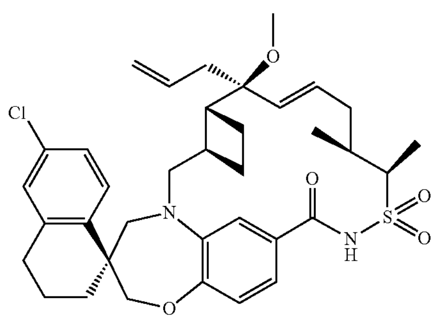 [SMILES: C=CC[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 653.3 |
| | | OR (1S,3'R,6'R,7'R,8'E,11'S,12'R)-6-chloro-7'-methoxy-11',12'-dimethyl-7'-(2-propen-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100398 | 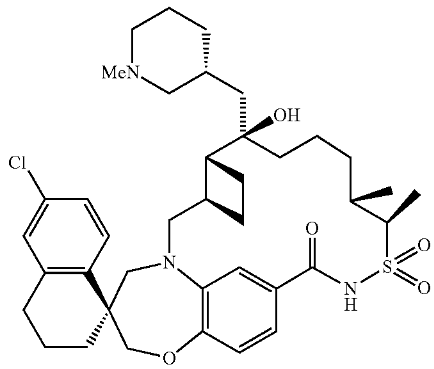 [SMILES: C[C@@H]1[C@@H](C)CCC[C@@](O)(C[C@H]2CCCN(C)C2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-hydroxy-11',12'-dimethyl-7'-(((3R)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 712.4 |
| | AND | AND | |
| | | (1S,3'R,6'R,7'R,11'S,12'R)-6-chloro-7'-hydroxy-11',12'-dimethyl-7'-(((3S)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR | |
| | | (1S,3'R,6'R,7'S,11'S,12'R)-6-chloro-7'-hydroxy-11',12'-dimethyl-7'-(((3R)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | AND 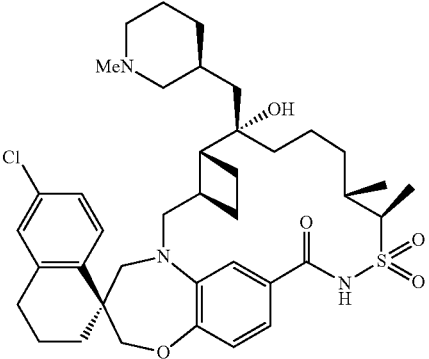 | AND (1S,3'R,6'R,7'S,11'S,12'R)-6-chloro-7'-hydroxy-11',12'-dimethyl-7'-(((3S)-1-methyl-3-piperidinyl)methy)-3,4-dihydro-2H,15'H-spiro[naphthalene-1,22'-[20]oxa[13]thia[1,14]diazatetracyclo[14.7.2.0~3,6~.0~19,24]pentacosa[16,18,24]trien]-15'-one 13',13'-dioxide | |
| 100399 | 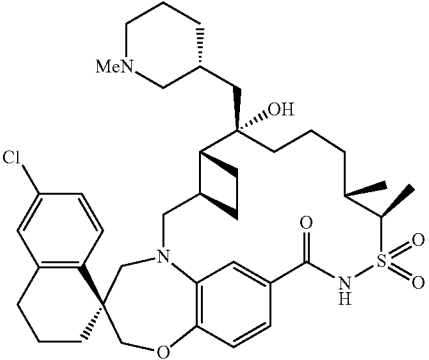 | (1S,3'R,6'R,7'S,11'S,12'R)-6-chloro-7'-hydroxy-11',12'-dimethyl-7'-(((3R)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 712.4 |
| | OR 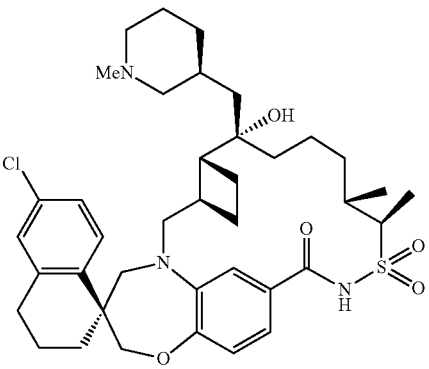 | OR (1S,3'R,6'R,7'S,11'S,12'R)-6-chloro-7'-hydroxy-11',12'-dimethyl-7'-(((3S)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,11'S,12'R)-6-chloro-7'-hydroxy-11',12'-dimethyl-7'-(((3R)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR (1S,3'R,6'R,7'R,11'S,12'R)-6-chloro-7'-hydroxy-11',12'-dimethyl-7'-(((3S)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100400 | 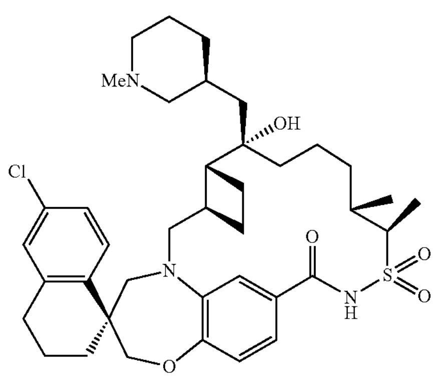 | (1S,3'R,6'R,7'S,11'S,12'R)-6-chloro-7'-hydroxy-11',12'-dimethyl-7'-(((3S)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 712.4 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,11'S,12'R)-6-chloro-7'-hydroxy-11',12'-dimethyl-7'-(((3R)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR (1S,3'R,6'R,7'R,11'S,12'R)-6-chloro-7'-hydroxy-11',12'-dimethyl-7'-(((3R)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | OR | OR (1S,3'R,6'R,7'R,11'S,12'R)-6-chloro-7'-hydroxy-11',12'-dimethyl-7'-(((3S)-1-methyl-3-piperidinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100401 | 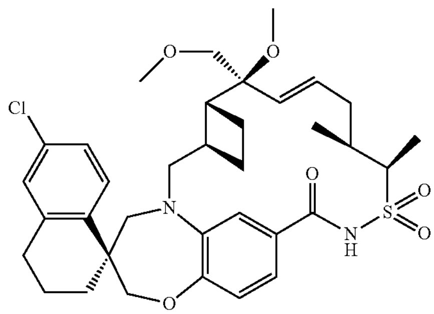 [SMILES: COC[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.2 |
| | OR | OR | |
| | | (1S,3'R,6'R,7'R,8'E,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100402 | 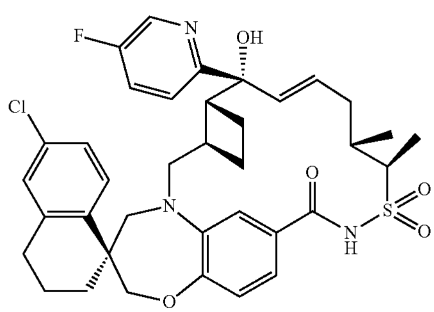 [SMILES: C[C@@H]1[C@@H](C)C/C=C/[C@](O)(c2ccc(F)cn2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-(5-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| | OR | OR | |
| | | (1S,3'R,6'R,7'R,8'E,11'S,12'R)-6-chloro-7'-(5-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100403 | 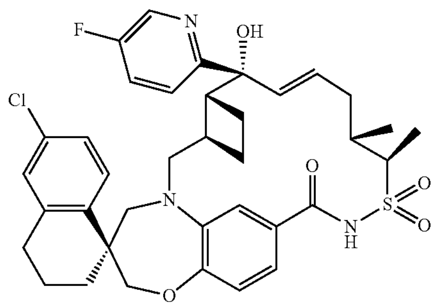 [SMILES: C[C@@H]1[C@@H](C)C/C=C/[C@](O)(c2ccc(F)cn2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(5-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| | OR | OR | |
| | | (1S,3'R,6'R,7'S,8'E,11'S,12'R)-6-chloro-7'-(5-fluoro-2-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100404 | 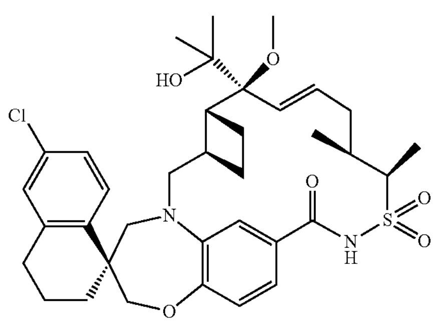 [SMILES: CO[C@@]1(C(C)(C)O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-hydroxy-2-propanyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.3 |
| | OR | OR | |
| | | (1S,3'R,6'R,7'R,8'E,11'S,12'R)-6-chloro-7'-(2-hydroxy-2-propanyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100405 | 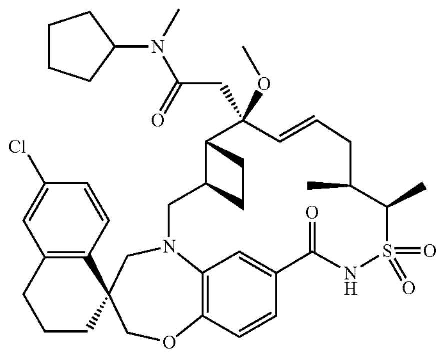 [SMILES: CO[C@@]1(CC(=O)N(C)C2CCCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-cyclopentyl-N-methylacetamide | 774.3 (M + Na) |
| 100406 | 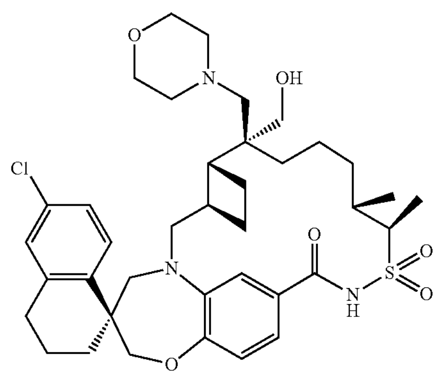 [SMILES: C[C@@H]1[C@@H](C)CCC[C@](CO)(CN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,11'S,12'R)-6-chloro-7'-(hydroxymethyl)-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 714.3 |
| | AND | AND | |
| | | (1S,3'R,6'R,7'S,11'S,12'R)-6-chloro-7'-(hydroxymethyl)-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100407 | 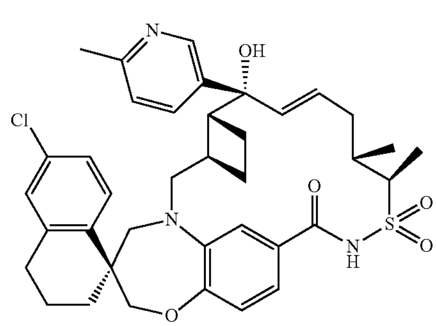 | (1S,3'R,6'R,7'R,8'E,11'S,12'R)-6-chloro-7'-hydroxy-11',12'-dimethyl-7'-(6-methyl-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.0 |

TABLE 2-continued

Examples Prepared by the General Methods

| Example Number | Structure | Name | MS Data (M + 1)+ Unless Noted Otherwise |
|---|---|---|---|
| | OR | OR | |
| | | (1S,3'R,6'R,7'S,8'E,11'S,12'R)-6-chloro-7'-hydroxy-11',12'-dimethyl-7'-(6-methyl-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100408 | 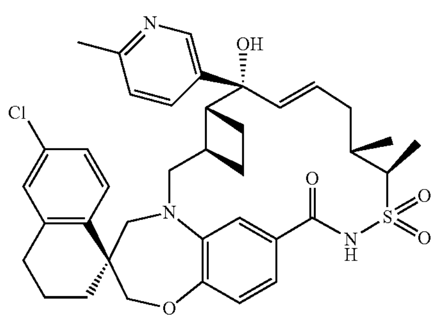 | (1S,3'R,6'R,7'S,8'E,11'S,12'R)-6-chloro-7'-hydroxy-11',12'-dimethyl-7'-(6-methyl-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.0 |
| | OR | OR | |
| | | (1S,3'R,6'R,7'R,8'E,11'S,12'R)-6-chloro-7'-hydroxy-11',12'-dimethyl-7'-(6-methyl-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100409 | 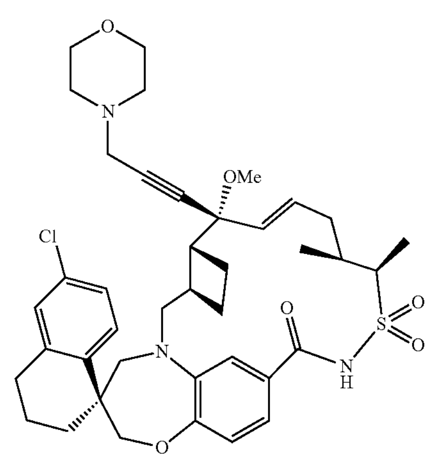 | (1S,3'R,6'R,7'R,8'E,11'S,12'R)-6-chloro-7'-methoxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 736.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-methoxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100410 | 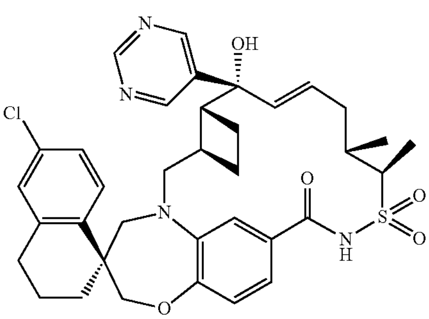 | (1S,3'R,6'R,7'R,8'E,11'S,12'R)-6-chloro-7'-hydroxy-11',12'-dimethyl-7'-(5-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.2 |
| | OR | OR (1S,3'R,6'R,7'S,8'E,11'S,12'R)-6-chloro-7'-hydroxy-11',12'-dimethyl-7'-(5-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100411 | 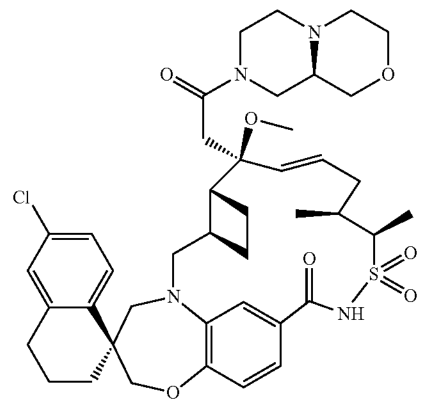 [SMILES: CO[C@@]1(CC(=O)N2CCN3CCOC[C@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-((9aR)-hexahydropyrazino[2,1-c][1,4]oxazin-8(1H)-yl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 795.2 |
| 100412 | 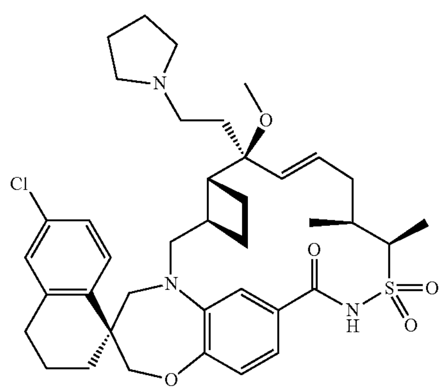 | (1S,3'R,6'R,7'S,8'E,11'S,12'R)-6-chloro-7'-methoxy-11',12'-dimethyl-7'-(2-(1-pyrrolidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.3 |
| 100413 | 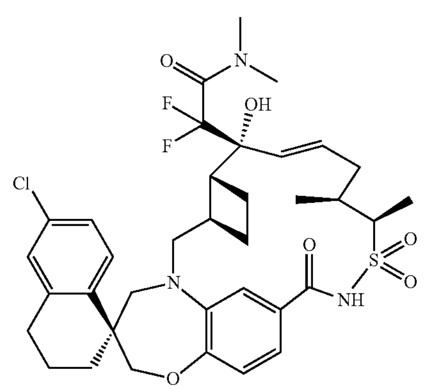 [SMILES: C[C@@H]1[C@@H](C)C/C=C/[C@](O)(C(F)(F)C(=O)N(C)C)[C@@H]2CC[C@H]2CN2C[C@@]3(CCCc4cc(Cl)ccc43)COc3ccc(cc32)C(=O)NS1(=O)=O] | 2-((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2,2-difluoro-N,N-dimethylacetamide | 720.0 |

TABLE 2-continued

Examples Prepared by the General Methods

| Example Number | Structure | Name | MS Dat (M + 1)+ Unless Noted Otherwise |
|---|---|---|---|
| | | 2-((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-2,2-difluoro-N,N-dimethylacetamide | |
| 100414 | 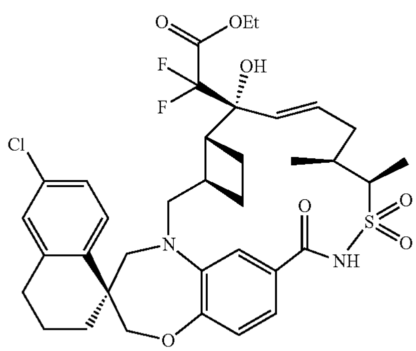 [SMILES: CCOC(=O)C(F)(F)[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | ethyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)acetate | 721.0 |
| | | ethyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)acetate | |

TABLE 2-continued

Examples Prepared by the General Methods

| Example Number | Structure | Name | MS Dat (M + 1)+ Unless Noted Otherwise |
|---|---|---|---|
| 100415 | 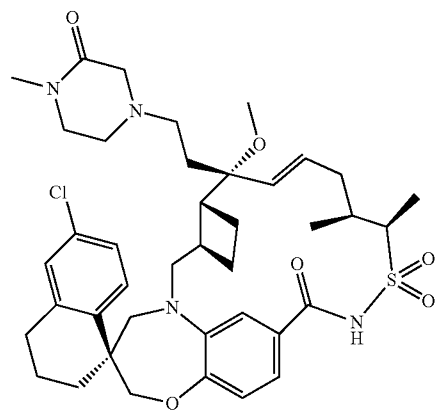 | (1S,3'R,6'R,7'R,8'E,11'S,12'R)-6-chloro-7'-methoxy-11',12'-dimethyl-7'-(2-(4-methyl-3-oxo-1-piperazinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 775.3 (M + Na) |
| 100416 | 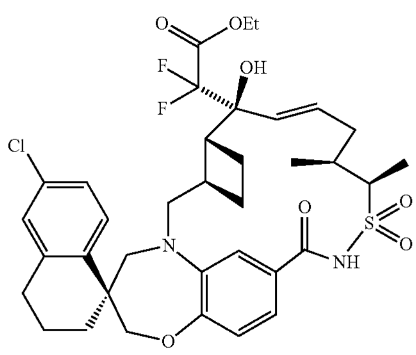 | ethyl ((1S,3'R,6'R,7'S,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)acetate | 721.0 |
| | OR | OR | |
| | | ethyl ((1S,3'R,6'R,7'R,8'E,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)(difluoro)acetate | |

TABLE 2-continued

Examples Prepared by the General Methods

| Example Number | Structure | Name | MS Dat (M + 1)+ Unless Noted Otherwise |
|---|---|---|---|
| 100417 | 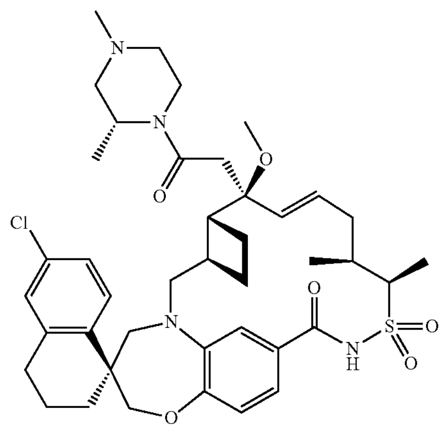 | (1S,3'R,6'R,7'S,8'E,11'S,12'R)-6-chloro-7'-(2-((2R)-2,4-dimethyl-1-piperazinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 789.3 (M + Na) |
| | AND | AND | |
| | | (1S,3'R,6'R,7'S,8'E,11'S,12'R)-6-chloro-7'-(2-((2S)-2,4-dimethyl-1-piperazinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100418 | 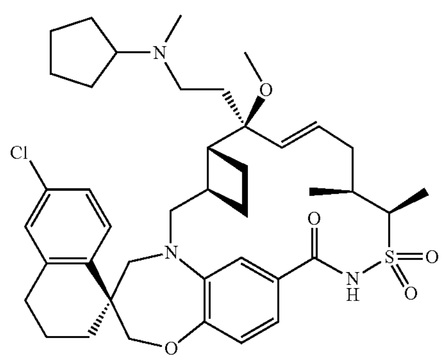 | (1S,3'R,6'R,7'S,8'E,11'S,12'R)-6-chloro-7'-(2-(cyclopentyl(methyl)amino)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 738.3 |

TABLE 2-continued

Examples Prepared by the General Methods

| Example Number | Structure | Name | MS Dat (M + 1)+ Unless Noted Otherwise |
|---|---|---|---|
| 100419 | 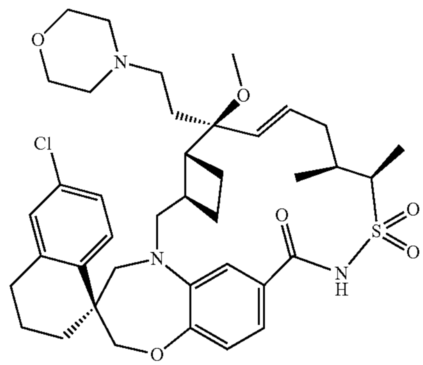 [SMILES: CO[C@@]1(CCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.3 |
| 100420 | | (1S,3'R,6'R,7'R,8'E,11'S,12'R)-6-chloro-7'-(6-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |
| | OR | OR | |
| | | (1S,3'R,6'R,7'S,8'E,11'S,12'R)-6-chloro-7'-(6-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100421 | 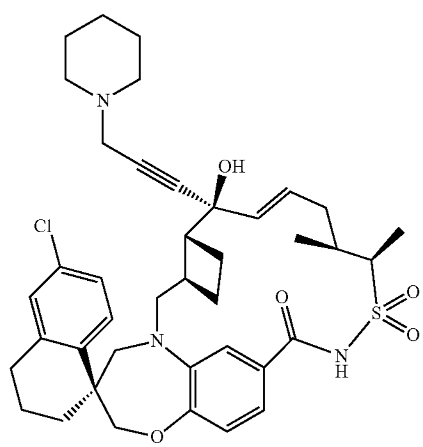 [SMILES: C[C@@H]1[C@@H](C)C/C=C/[C@@](O)(C#CCN2CCCCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(3-(1-piperidinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 720.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-hydroxy-11',12'-dimethyl-7'-(3-(1-piperidinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100422 | 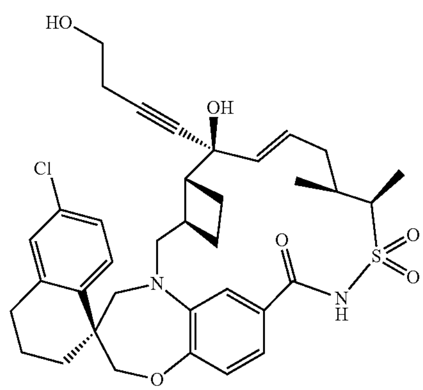 | (1S,3'R,6'R,7'S,8'E,11'S,12'R)-6-chloro-7'-hydroxy-7'-(4-hydroxy-1-butyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.4 |
| | OR | OR | |
| | | (1S,3'R,6'R,7'R,8'E,11'S,12'R)-6-chloro-7'-hydroxy-7'-(4-hydroxy-1-butyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100423 | 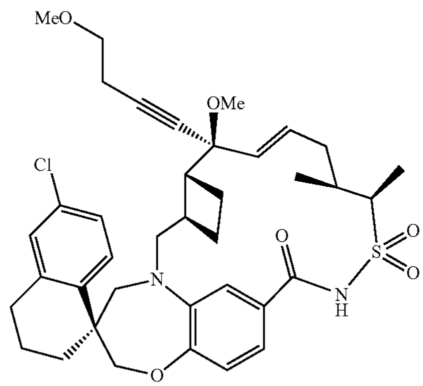 [SMILES: COCCC#C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7'-(4-methoxy-1-butyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 695.3 |
| | OR | OR | |
| | | (1S,3'R,6'R,7'R,8'E,11'S,12'R)-6-chloro-7'-methoxy-7'-(4-methoxy-1-butyn-1-yl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100424 | 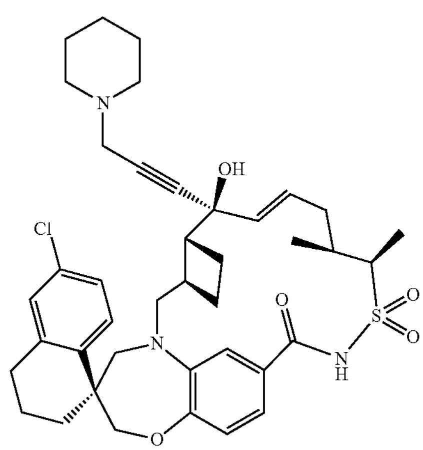 [SMILES: C[C@@H]1[C@@H](C)C/C=C/[C@@](O)(C#CCN2CCCCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(3-(1-piperidinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 720.3 |

TABLE 2-continued

Examples Prepared by the General Methods

| Example Number | Structure | Name | MS Dat (M + 1)+ Unless Noted Otherwise |
|---|---|---|---|
| | OR 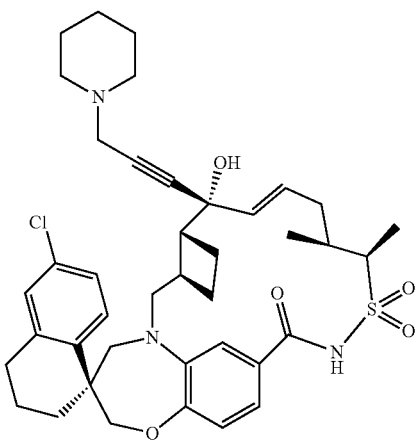 | OR (1S,3'R,6'R,7'R,8'E,11'S,12'R)-6-chloro-7'-hydroxy-11',12'-dimethyl-7'-(3-(1-piperidinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100425 | 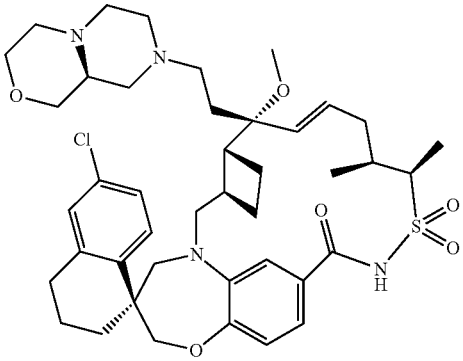 | (1S,3'R,6'R,7'R,8'E,11'S,12'R)-6-chloro-7'-(2-((9aS)-hexahydropyrazino[2,1-c][1,4]oxazin-8(1H)-yl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.4 |
| 100426 | 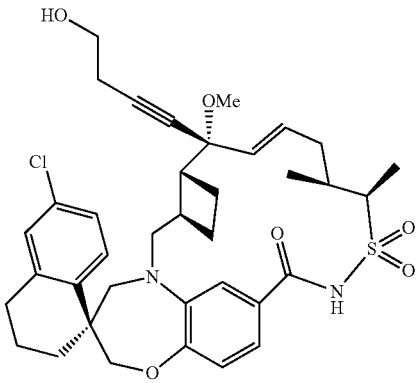 | (1S,3'R,6'R,7'R,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 681.3 |

TABLE 2-continued

Examples Prepared by the General Methods

| Example Number | Structure | Name | MS Dat (M + 1)+ Unless Noted Otherwise |
|---|---|---|---|
| 100427 | 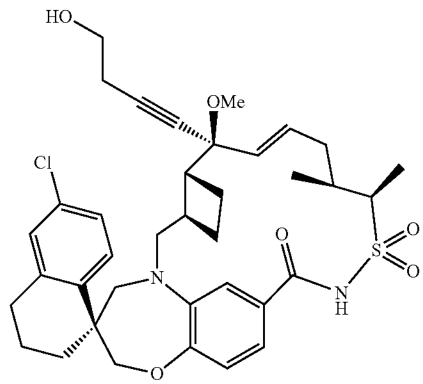 [SMILES: CO[C@@]1(C#CCCO)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(4-hydroxy-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 681.3 |
| 100428 | 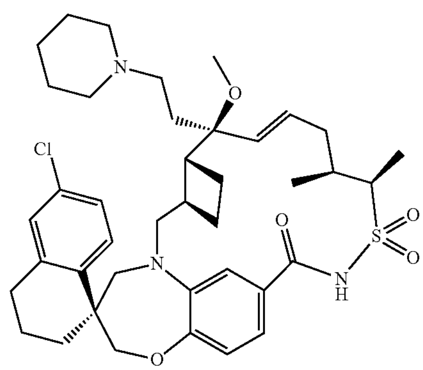 [SMILES: CO[C@@]1(CCN2CCCCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |
| 100429 | 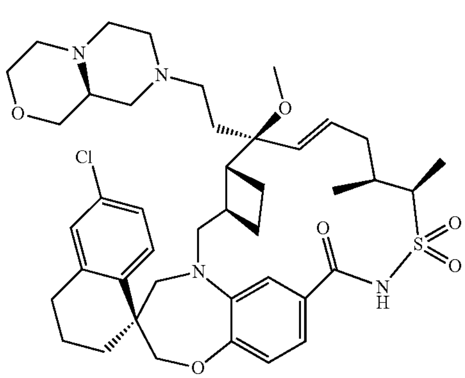 [SMILES: CO[C@@]1(CCN2CCN3CCOC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-((9aS)-hexahydropyrazino[2,1-c][1,4]oxazin-8(1H)-yl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 781.4 |

TABLE 2-continued

Examples Prepared by the General Methods

| Example Number | Structure | Name | MS Dat (M + 1)+ Unless Noted Otherwise |
|---|---|---|---|
| 100430 | 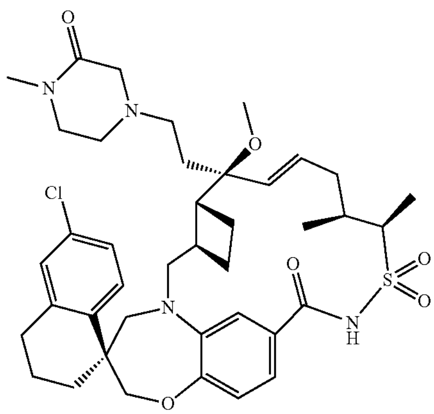 [SMILES: CO[C@@]1(CCN2CCN(C)C(=O)C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-(4-methyl-3-oxo-1-piperazinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.3 |
| 100431 | 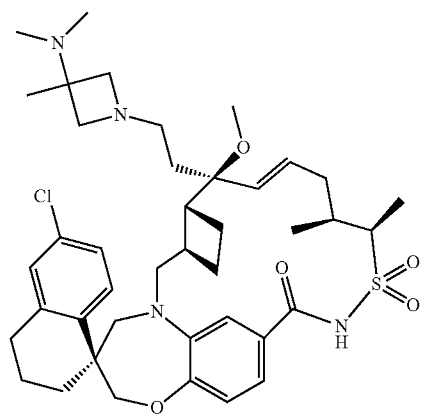 [SMILES: CO[C@@]1(CCN2CC(C)(N(C)C)C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-(3-(dimethylamino)-3-methyl-1-azetidinyl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.3 |
| 100432 | 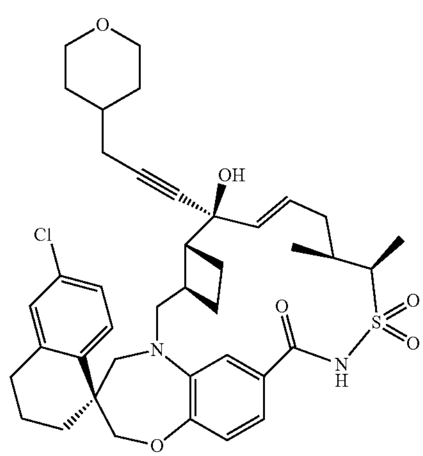 [SMILES: C[C@@H]1[C@@H](C)C/C=C/[C@@](O)(C#CCC2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(3-(tetrahydro-2H-pyran-4-yl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 721.3 |

TABLE 2-continued

Examples Prepared by the General Methods

| Example Number | Structure | Name | MS Dat (M + 1)+ Unless Noted Otherwise |
|---|---|---|---|
| 100433 | 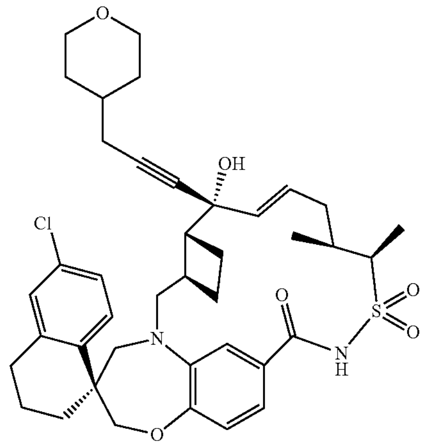 [SMILES: C[C@@H]1[C@@H](C)C/C=C/[C@](O)(C#CCC2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(3-(tetrahydro-2H-pyran-4-yl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 721.3 |
| 100434 | 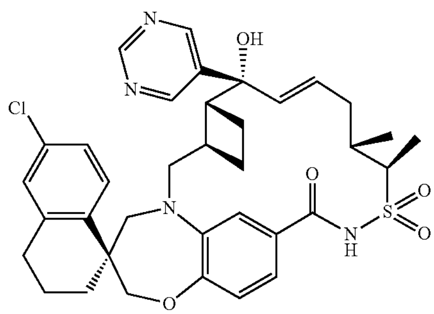 [SMILES: C[C@@H]1[C@@H](C)C/C=C/[C@](O)(c2cncnc2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(5-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-11',12'-dimethyl-7'-(5-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 677.2 |
| 100435 | 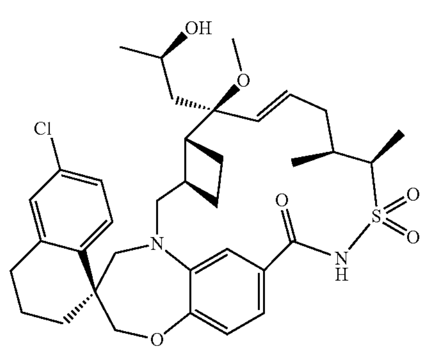 [SMILES: CO[C@@]1(C[C@@H](C)O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((2R)-2-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.2 (M + Na) |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-((2S)-2-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100436 | 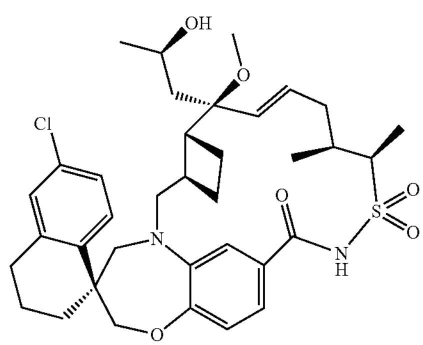 | (1S,3'R,6'R,7'S,8'E,11'S,12'R)-6-chloro-7'-((2R)-2-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.2 (M + Na) |
| | OR | OR | |
| | | (1S,3'R,6'R,7'S,8'E,11'S,12'R)-6-chloro-7'-((2S)-2-hydroxypropyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100437 | 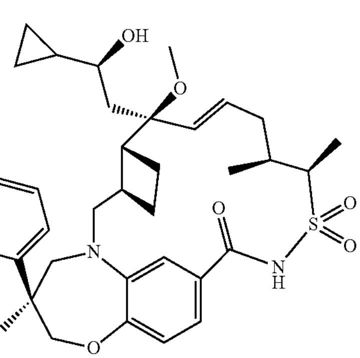 | (1S,3'R,6'R,7'S,8'E,11'S,12'R)-6-chloro-7'-((2R)-2-cyclopropyl-2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 719.3 (M + Na) |

TABLE 2-continued

Examples Prepared by the General Methods

| Example Number | Structure | Name | MS Dat (M + 1)+ Unless Noted Otherwise |
|---|---|---|---|
| | AND | AND | |
| | | (1S,3'R,6'R,7'S,8'E,11'S,12'R)-6-chloro-7'-((2S)-2-cyclopropyl-2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100438 | 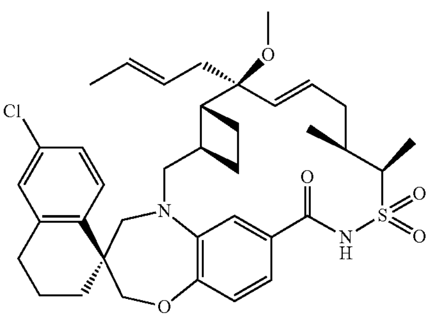 | (1S,3'R,6'R,7'S,8'E,11'S,12'R)-7'-((2E)-2-buten-1-yl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 667.3 |
| | OR | OR | |
| | | (1S,3'R,6'R,7'R,8'E,11'S,12'R)-7'-((2E)-2-buten-1-yl)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100439 | 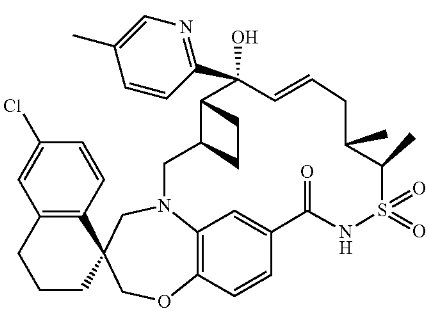 | (1S,3'R,6'R,7'S,8'E,11'S,12'R)-6-chloro-7'-hydroxy-11',12'-dimethyl-7'-(5-methyl-2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 690.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-hydroxy-11',12'-dimethyl-7'-(5-methyl-2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100440 | 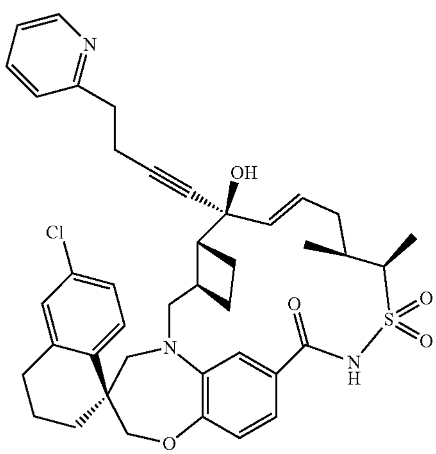 | (1S,3'R,6'R,7'S,8'E,11'S,12'R)-6-chloro-7'-hydroxy-11',12'-dimethyl-7'-(4-(2-pyridinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 728.3 |
| | AND | AND | |
| | | (1S,3'R,6'R,7'R,8'E,11'S,12'R)-6-chloro-7'-hydroxy-11',12'-dimethyl-7'-(4-(2-pyridinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100441 | 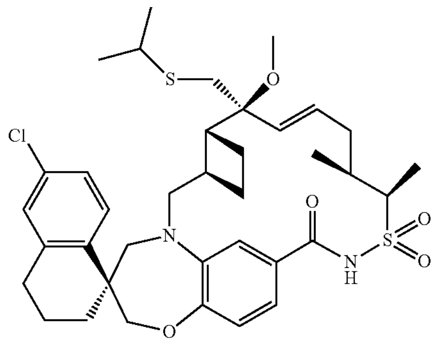 [SMILES: CO[C@@]1(CSC(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((2-propanylsulfanyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 723.2 (M + Na) |
| 100442 | | (1S,3'R,6'R,7'S,8'E,11'S,12'R)-6-chloro-7'-hydroxy-11',12'-dimethyl-7'-((2-propanyloxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.3 |
| | OR | OR | |
| | | (1S,3'R,6'R,7'R,8'E,11'S,12'R)-6-chloro-7'-hydroxy-11',12'-dimethyl-7'-((2-propanyloxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100443 | 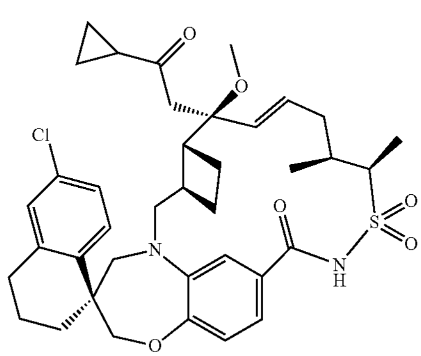 [SMILES: CO[C@@]1(CC(=O)C2CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-cyclopropyl-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 717.2 (M + Na) |

TABLE 2-continued

Examples Prepared by the General Methods

| Example Number | Structure | Name | MS Dat (M + 1)+ Unless Noted Otherwise |
|---|---|---|---|
| 100444 | 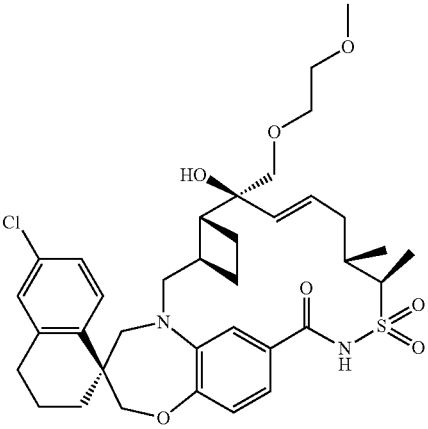 [SMILES: COCCOC[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 687.2 |
| | OR | OR | |
| | 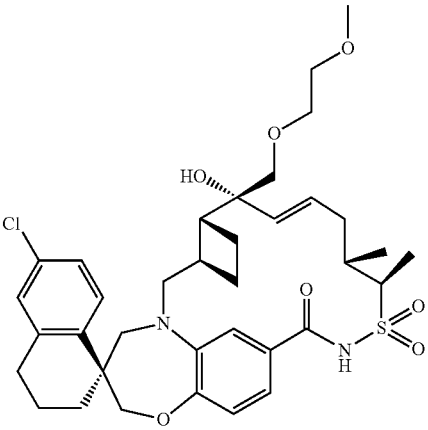 [SMILES: COCCOC[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100445 | 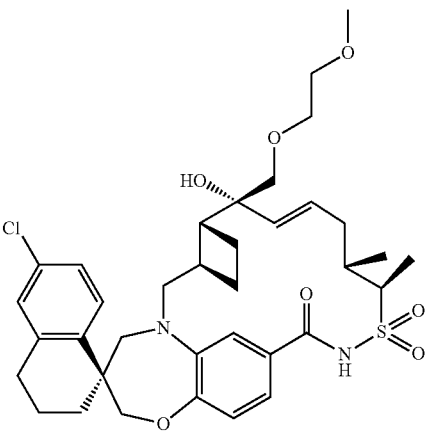 [SMILES: COCCOC[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 687.2 |

TABLE 2-continued

Examples Prepared by the General Methods

| Example Number | Structure | Name | MS Dat (M + 1)+ Unless Noted Otherwise |
|---|---|---|---|
| | 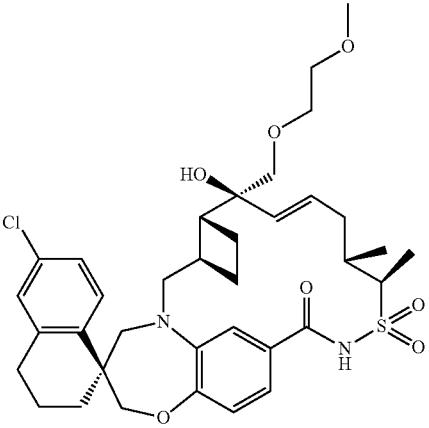 [SMILES: COCCOC[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-hydroxy-7'-((2-methoxyethoxy)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100446 | 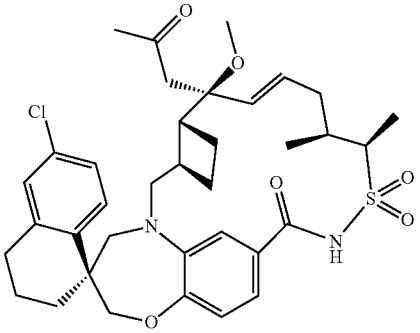 [SMILES: CO[C@@]1(CC(C)=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-oxopropyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.2 (M + Na) |
| 100447 | 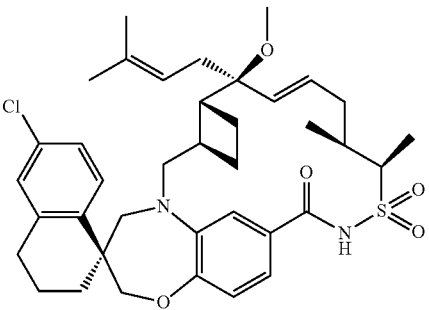 [SMILES: CO[C@@]1(CC=C(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(3-methyl-2-buten-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 681.2 |

TABLE 2-continued

Examples Prepared by the General Methods

| Example Number | Structure | Name | MS Dat (M + 1)+ Unless Noted Otherwise |
|---|---|---|---|
| | | OR<br>(1S,3'R,6'R,7'R,8'E,11'S,12'R)-6-chloro-7'-methoxy-11',12'-dimethyl-7'-(3-methyl-2-buten-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100448 | 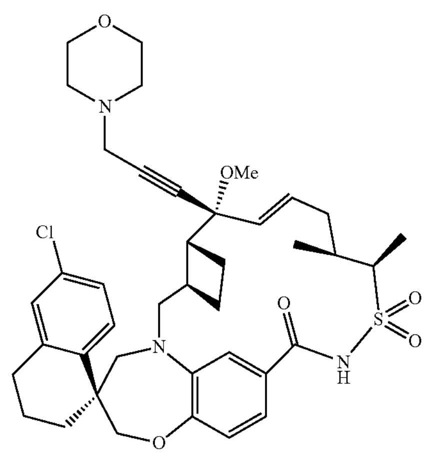 [SMILES: CO[C@]1(C#CCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-11',12'-dimethyl-7'-(3-(4-morpholinyl)-1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 736.3 |
| 100449 | 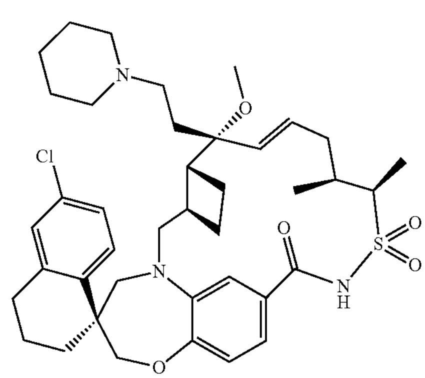 [SMILES: CO[C@]1(CCN2CCCCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-11',12'-dimethyl-7'-(2-(1-piperidinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.4 |

TABLE 2-continued

Examples Prepared by the General Methods

| Example Number | Structure | Name | MS Dat (M + 1)+ Unless Noted Otherwise |
|---|---|---|---|
| 100450 | 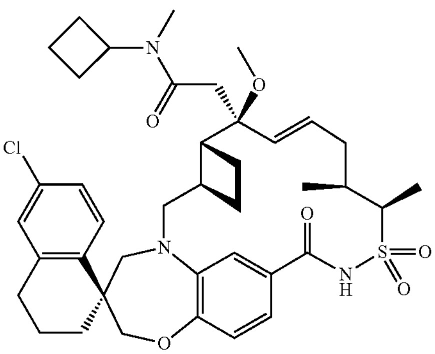 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-cyclobutyl-N-methylacetamide | 738.2 |
| 100451 | 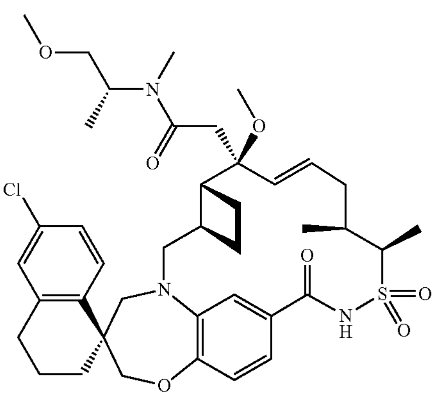 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((2R)-1-methoxy-2-propanyl)-N-methylacetamide | 778.3 (M + Na) |
| | AND | AND | |
| | | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((2S)-1-methoxy-2-propanyl)-N-methylacetamide | |

TABLE 2-continued

Examples Prepared by the General Methods

| Example Number | Structure | Name | MS Dat (M + 1)+ Unless Noted Otherwise |
|---|---|---|---|
| 100452 | 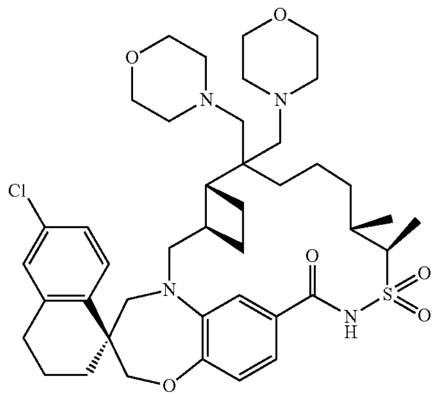 [SMILES: C[C@@H]1[C@@H](C)CCCC(CN2CCOCC2)(CN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,11'S,12'R)-6-chloro-11',12'-dimethyl-7',7'-bis(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 783.5 |
| 100453 | 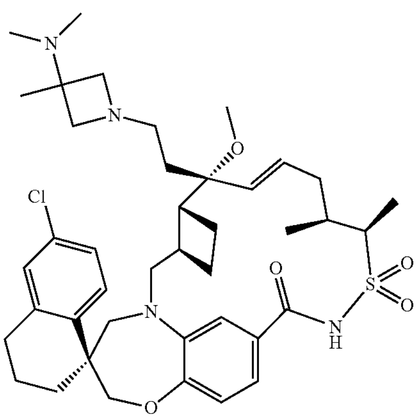 [SMILES: CO[C@]1(CCN2CC(C)(N(C)C)C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(2-(3-(dimethylamino)-3-methyl-1-azetidinyl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 753.3 |
| 100454 | 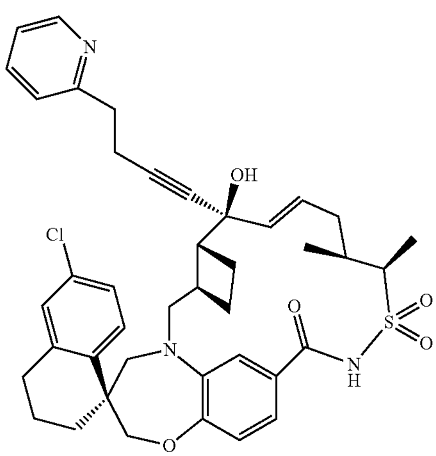 [SMILES: C[C@@H]1[C@@H](C)C/C=C/[C@@](O)(C#CCCc2ccccn2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(4-(2-pyridinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 728.3 |

TABLE 2-continued

Examples Prepared by the General Methods

| Example Number | Structure | Name | MS Dat (M + 1)+ Unless Noted Otherwise |
|---|---|---|---|
| 100455 | 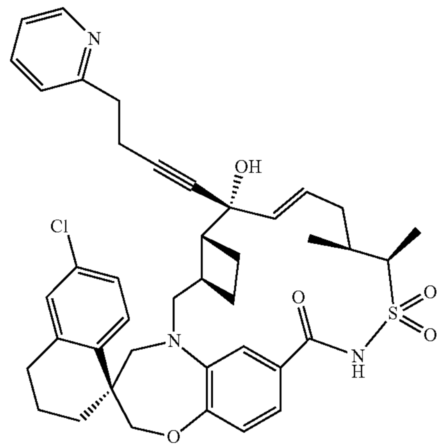 [SMILES: C[C@@H]1[C@@H](C)C/C=C/[C@](O)(C#CCCc2ccccn2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(4-(2-pyridinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.3 (M − H₂O] |
| 100456 | 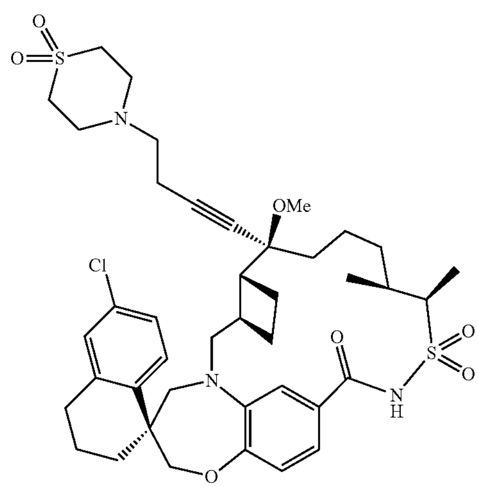 [SMILES: CO[C@@]1(C#CCCN2CCS(=O)(=O)CC2)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(4-(1,1-dioxido-4-thiomorpholinyl)-1-butyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 798.3 |
| 100457 | 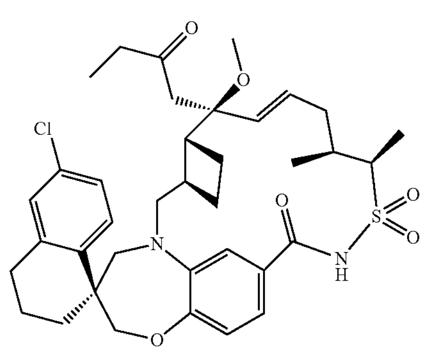 [SMILES: CCC(=O)C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(2-oxobutyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 705.2 (M + Na) |

TABLE 2-continued

Examples Prepared by the General Methods

| Example Number | Structure | Name | MS Dat (M + 1)+ Unless Noted Otherwise |
|---|---|---|---|
| 100458 | 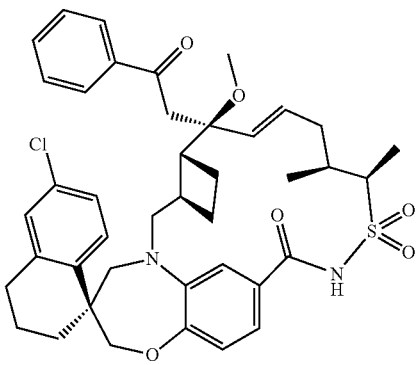 [SMILES: CO[C@@]1(CC(=O)c2ccccc2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3′R,6′R,7′S,8′E,11′S,12′R)-6-chloro-7′-methoxy-11′,12′-dimethyl-7′-(2-oxo-2-phenylethyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 753.2 (M + Na) |
| 100459 | 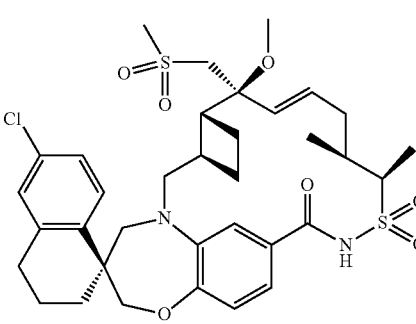 | (1S,3′R,6′R,7′S,8′E,11′S,12′R)-6-chloro-7′-methoxy-11′,12′-dimethyl-7′-((methylsulfonyl)methyl)-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 705.2 |
| 100460 | 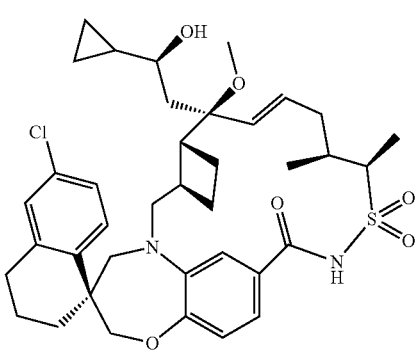 [SMILES: CO[C@@]1(C[C@H](O)C2CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]  OR  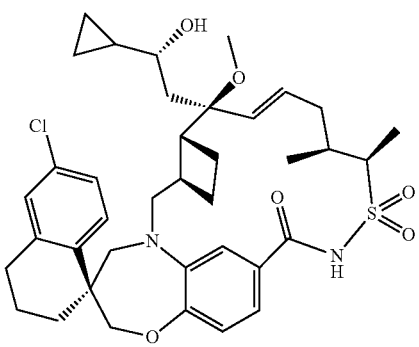 [SMILES: CO[C@@]1(C[C@@H](O)C2CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3′R,6′R,7′S,8′E,11′S,12′R)-6-chloro-7′-((2R)-2-cyclopropyl-2-hydroxyethyl)-7′-methoxy-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide  OR  (1S,3′R,6′R,7′S,8′E,11′S,12′R)-6-chloro-7′-((2S)-2-cyclopropyl-2-hydroxyethyl)-7′-methoxy-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[8,16,18,24]tetraen]-15′-one 13′,13′-dioxide | 697.2 |

TABLE 2-continued

Examples Prepared by the General Methods

| Example Number | Structure | Name | MS Dat (M + 1)+ Unless Noted Otherwise |
|---|---|---|---|
| 100461 | 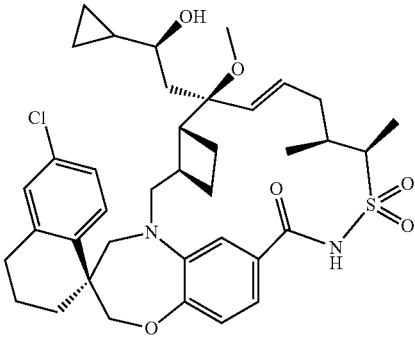 [SMILES: CO[C@@]1(C[C@H](O)C2CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((2R)-2-cyclopropyl-2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 719.3 (M + Na) |
| | OR<br>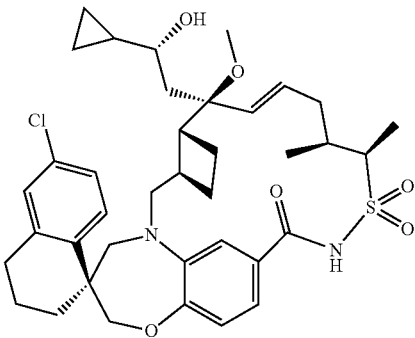 [SMILES: CO[C@@]1(C[C@@H](O)C2CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | OR<br>(1S,3'R,6'R,7'S,8'E,11'S,12'R)-6-chloro-7'-((2S)-2-cyclopropyl-2-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100462 | 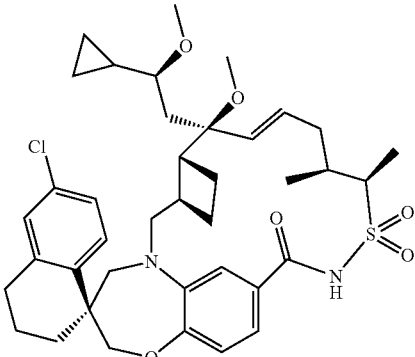 | (1S,3'R,6'R,7'S,8'E,11'S,12'R)-6-chloro-7'-((2S)-2-cyclopropyl-2-methoxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 711.2 |

TABLE 2-continued

Examples Prepared by the General Methods

| Example Number | Structure | Name | MS Dat (M + 1)+ Unless Noted Otherwise |
|---|---|---|---|
| | 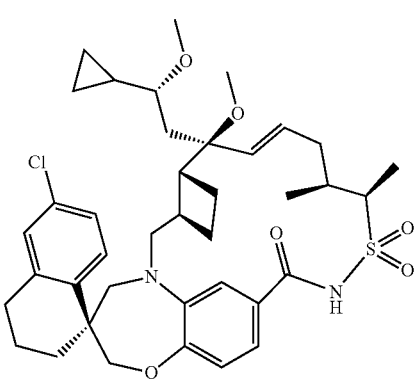 [SMILES: CO[C@H](C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3)C1CC1] | (1S,3'R,6'R,7'S,8'E,11'S,12'R)-6-chloro-7'-((2R)-2-cyclopropyl-2-methoxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100463 | 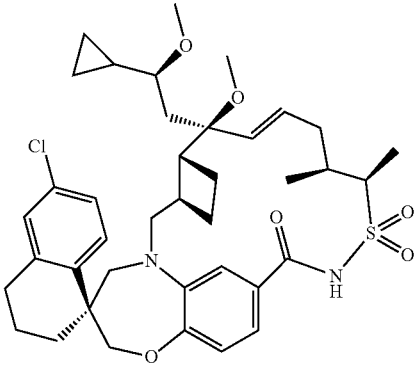 [SMILES: CO[C@@H](C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3)C1CC1] | (1S,3'R,6'R,7'S,8'E,11'S,12'R)-6-chloro-7'-((2S)-2-cyclopropyl-2-methoxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 733.3 (M + Na) |
| | 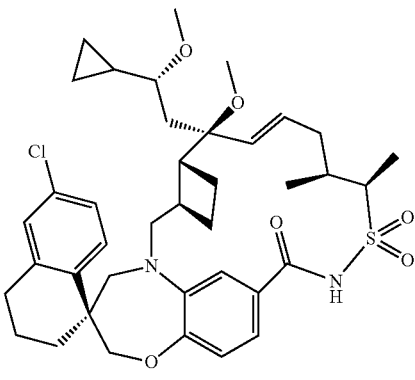 [SMILES: CO[C@H](C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3)C1CC1] | (1S,3'R,6'R,7'S,8'E,11'S,12'R)-6-chloro-7'-((2R)-2-cyclopropyl-2-methoxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100464 | 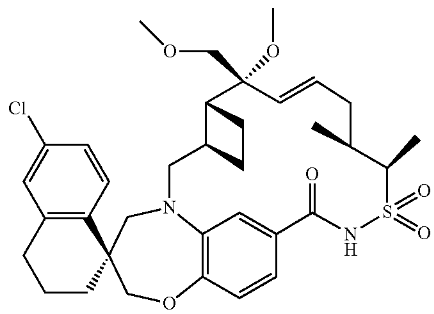 [SMILES: COC[C@@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-7'-(methoxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.2 |
| 100465 | 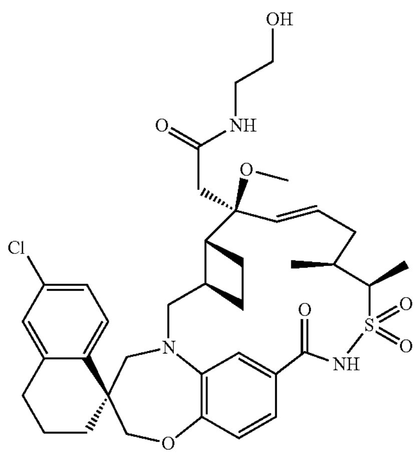 [SMILES: CO[C@@]1(CC(=O)NCCO)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(2-hydroxyethyl)acetamide | 682.0 (M − OMe) |
| 100466 | 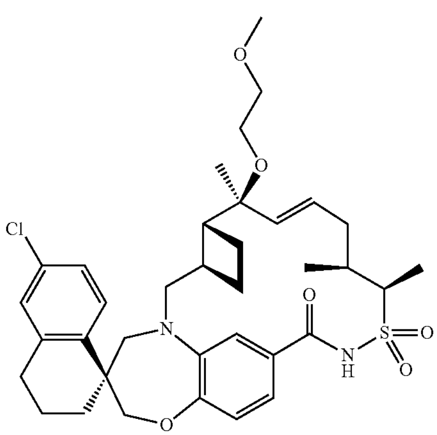 | (1S,3'R,6'R,7'S,8'E,11'S,12'R)-6-chloro-7'-(2-methoxyethoxy)-7',11',12'-trimethyl-3,4-dihydro-2H,15'H-spiro[naphthalene-1,22'-[20]oxa[13]thia[1,14]diazatetracyclo[14.2.0~3,6~.0~19,24~]pentacosa[8,16,18,24]tetraen]-15'-one 13',13'-dioxide | 671.3 |

TABLE 2-continued

Examples Prepared by the General Methods

| Example Number | Structure | Name | MS Dat (M + 1)+ Unless Noted Otherwise |
|---|---|---|---|
| 100467 | 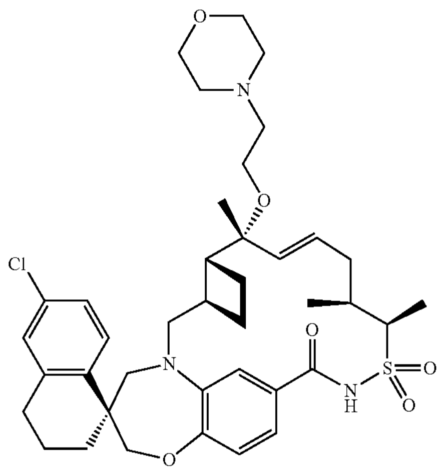 | (1S,3'R,6'R,7'R,8'E,11'S,12'R)-6-chloro-7',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.3 |
| 100468 | 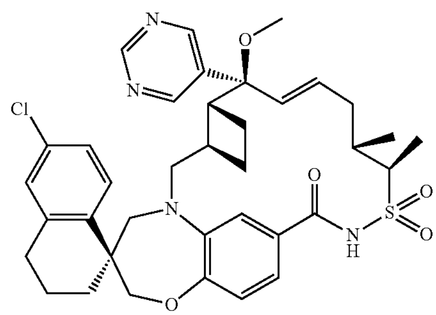 [SMILES: CO[C@@]1(c2cncnc2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(5-pyrimidinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 691.2 |
| 100469 | OR | (1S,3'R,6'R,7'R,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br><br>OR<br><br>(1S,3'R,6'R,7'S,11'S,12'R)-6-chloro-7'-hydroxy-11',12'-dimethyl-7'-(2-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 678.2 |

TABLE 2-continued

Examples Prepared by the General Methods

| Example Number | Structure | Name | MS Dat (M + 1)+ Unless Noted Otherwise |
|---|---|---|---|
| 100470 | 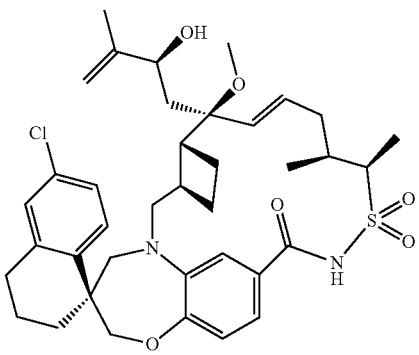 OR 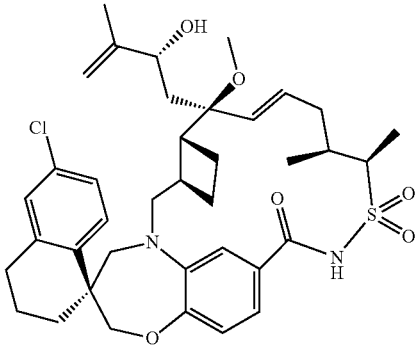 | (1S,3'R,6'R,7'S,8'E,11'S,12'R)-6-chloro-7'-((2S)-2-hydroxy-3-methyl-3-buten-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-((2R)-2-hydroxy-3-methyl-3-buten-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 697.2 |
| 100471 | 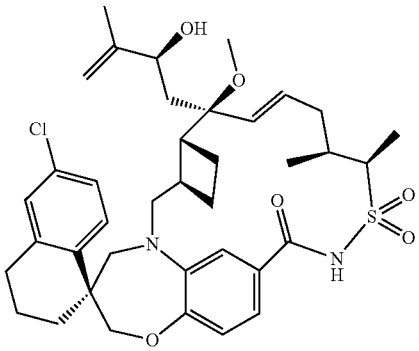 | (1S,3'R,6'R,7'S,8'E,11'S,12'R)-6-chloro-7'-((2S)-2-hydroxy-3-methyl-3-buten-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 697.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-((2R)-2-hydroxy-3-methyl-3-buten-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100472 | 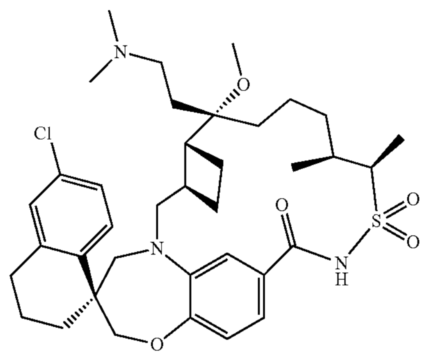 | (1S,3'R,6'R,7'S,11'S,12'R)-6-chloro-7'-(2-(dimethylamino)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 686.3 |
| 100473 | 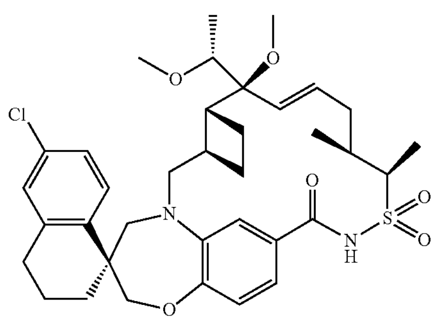 | (1S,3'R,6'R,7'S,8'E,11'S,12'R)-6-chloro-7'-methoxy-7'-((1R)-1-methoxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.3 |
| | OR | OR (1S,3'R,6'R,7'S,8'E,11'S,12'R)-6-chloro-7'-methoxy-7'-((1S)-1-methoxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100474 | 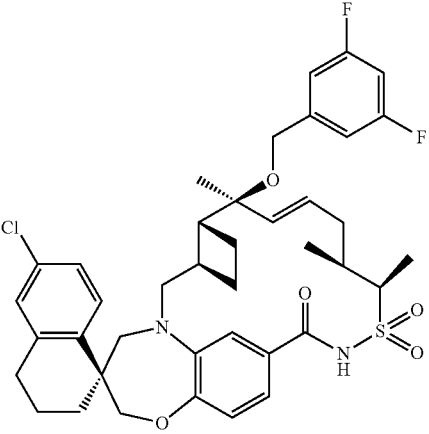 [SMILES: C[C@@H]1[C@@H](C)C/C=C/[C@](C)(OCc2cc(F)cc(F)c2)[C@@H]2CC[C@H]2CN2C[C@@]3(CCCc4cc(Cl)ccc43)COc3ccc(cc32)C(=O)NS1(=O)=O]<br>OR<br>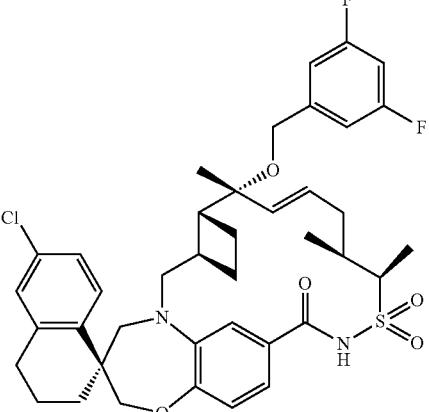 | (1S,3'R,6'R,7'R,8'E,11'S,12'R)-6-chloro-7'-((3,5-difluorobenzyl)oxy)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br>OR<br>(1S,3'R,6'R,7'S,8'E,11'S,12'R)-6-chloro-7'-((3,5-difluorobenzyl)oxy)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 739.2 |
| 100475 | 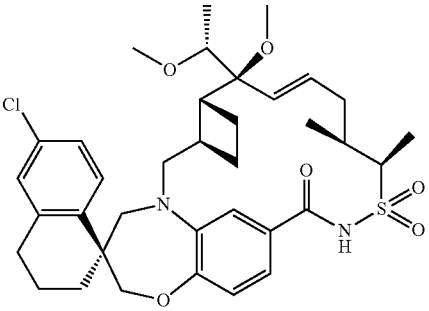 [SMILES: CO[C@H](C)[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7'-((1R)-1-methoxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-methoxy-7'-((1S)-1-methoxyethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100476 | 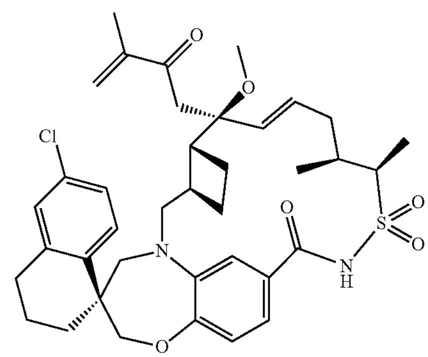 | (1S,3'R,6'R,7'S,8'E,11'S,12'R)-6-chloro-7'-methoxy-11',12'-dimethyl-7'-(3-methyl-2-oxo-3-buten-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 695.3 |
| 100477 | 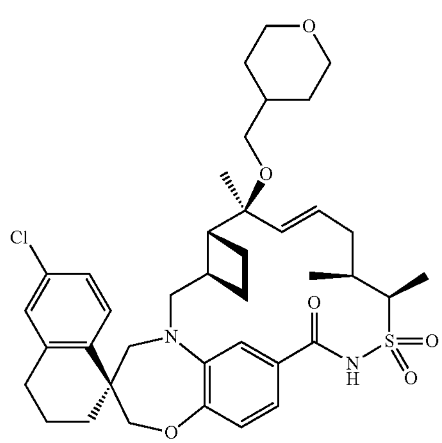 | (1S,3'R,6'R,7'S,8'E,11'S,12'R)-6-chloro-7',11',12'-trimethyl-7'-(tetrahydro-2H-pyran-4-ylmethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 711.3 |

TABLE 2-continued

Examples Prepared by the General Methods

| Example Number | Structure | Name | MS Dat (M + 1)+ Unless Noted Otherwise |
|---|---|---|---|
| 100478 | 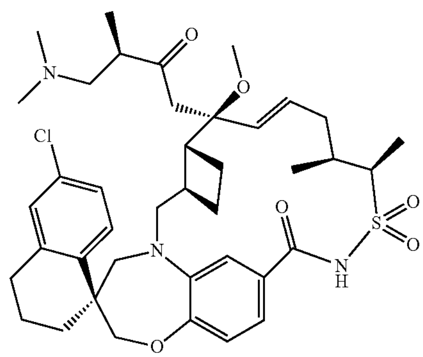 [SMILES: CO[C@@]1(CC(=O)[C@H](C)CN(C)C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((3R)-4-(dimethylamino)-3-methyl-2-oxobutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 740.3 |
|  | OR | OR |  |
|  | | (1S,3'R,6'R,7'S,8'E,11'S,12'R)-6-chloro-7'-((3S)-4-(dimethylamino)-3-methyl-2-oxobutyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide |  |
| 100479 | 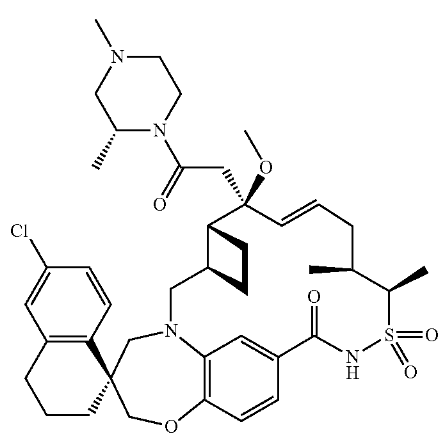 | (1S,3'R,6'R,7'S,8'E,11'S,12'R)-6-chloro-7'-(2-((2R)-2,4-dimethyl-1-piperazinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-(2-((2S)-2,4-dimethyl-1-piperazinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100480 | 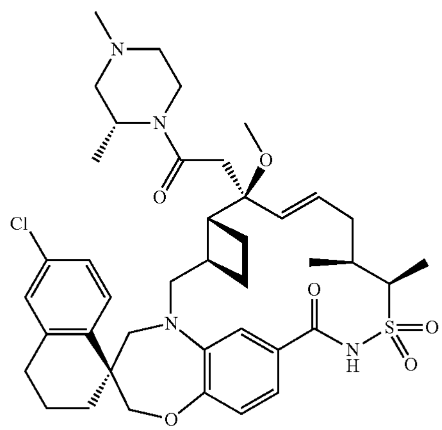 | (1S,3'R,6'R,7'S,8'E,11'S,12'R)-6-chloro-7'-(2-((2S)-2,4-dimethyl-1-piperazinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 767.3 |
| | OR | OR | |
| | | (1S,3'R,6'R,7'S,8'E,11'S,12'R)-6-chloro-7'-(2-((2R)-2,4-dimethyl-1-piperazinyl)-2-oxoethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100481 | 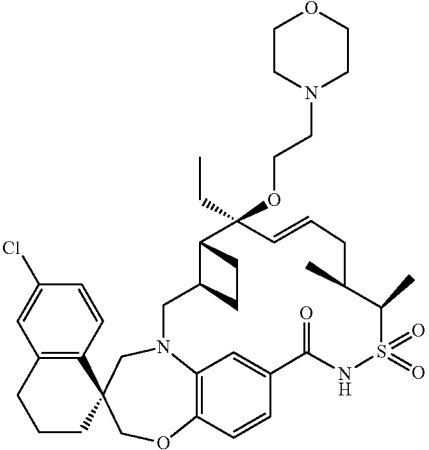 OR 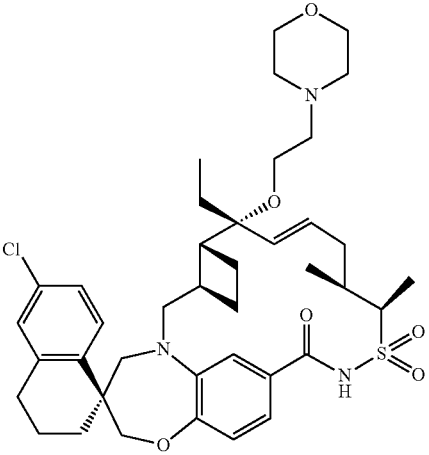 | (1S,3'R,6'R,7'R,8'E,11'S,12'R)-6-chloro-7'-ethyl-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-ethyl-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 740.3 |
| 100482 | 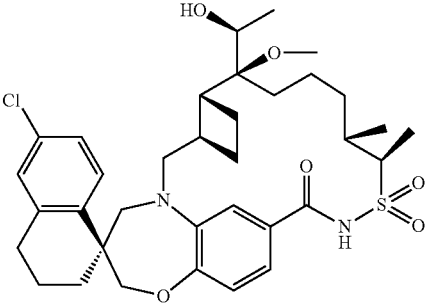 | (1S,3'R,6'R,7'S,11'S,12'R)-6-chloro-7'-((1S)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.2 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,11'S,12'R)-6-chloro-7'-((1R)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 100483 | 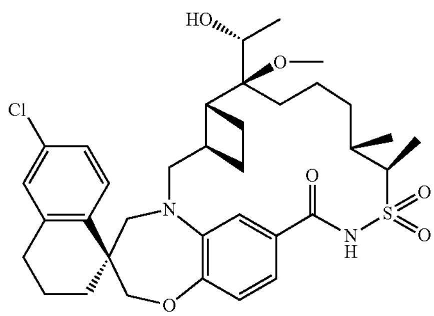 | (1S,3'R,6'R,7'S,11'S,12'R)-6-chloro-7'-((1R)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 659.2 |
| | OR | | |

TABLE 2-continued

Examples Prepared by the General Methods

| Example Number | Structure | Name | MS Dat (M + 1)+ Unless Noted Otherwise |
|---|---|---|---|
| 100484 | 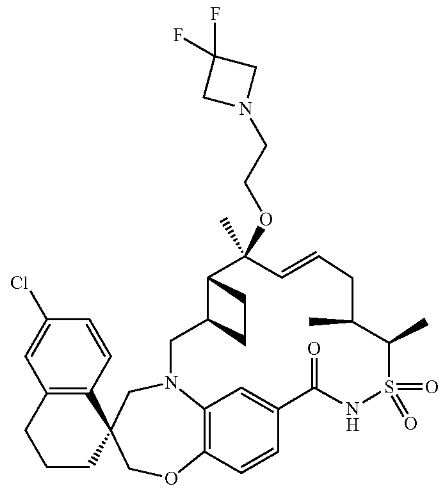 [SMILES: C[C@@H]1[C@@H](C)C/C=C/[C@](C)(OCCN2CC(F)(F)C2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-(2-(3,3-difluoro-1-azetidinyl)ethoxy)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 732.2 |
| 100485 | 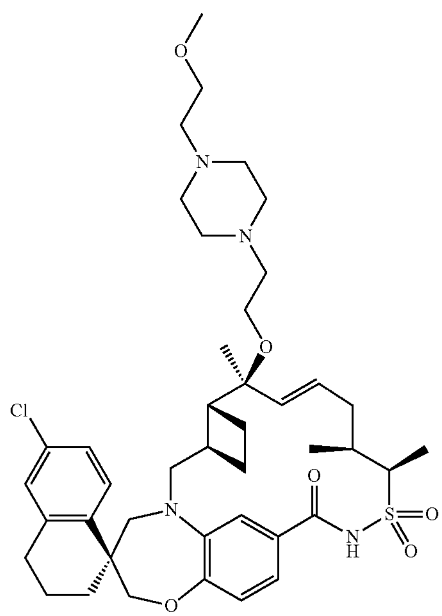 [SMILES: COCCN1CCN(CCO[C@@]2(C)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)CC1] | (1S,3'R,6'R,7'S,8'E,11'S,12'R)-6-chloro-7'-(2-(4-(2-methoxyethyl)-1-piperazinyl)ethoxy)-7',11',12'-trimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 783.3 |
| 100486 | 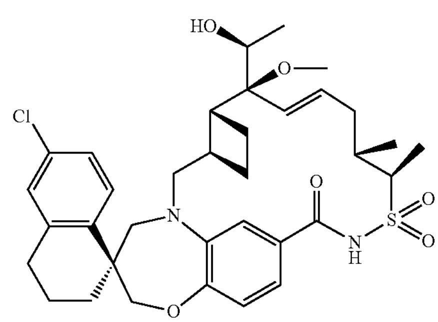 [SMILES: CO[C@@]1([C@H](C)O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((1S)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.3 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'S,8'E,11'S,12'R)-6-chloro-7'-((1R)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100487 | 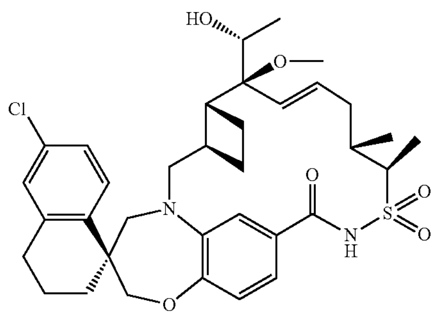 | (1S,3'R,6'R,7'S,8'E,11'S,12'R)-6-chloro-7'-((1R)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.3 |
| | AND | AND (1S,3'R,6'R,7'S,8'E,11'S,12'R)-6-chloro-7'-((1S)-1-hydroxyethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100488 | 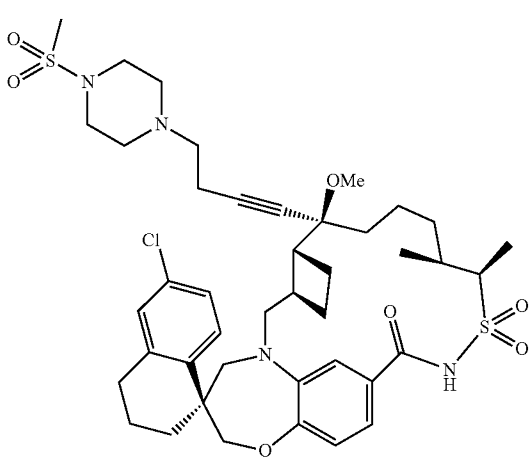 | (1S,3'R,6'R,7'S,8'E,11'S,12'R)-6-chloro-7'-methoxy-11',12'-dimethyl-7'-(4-(4-(methylsulfonyl)-1-piperazinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 827.2 |

TABLE 2-continued

Examples Prepared by the General Methods

| Example Number | Structure | Name | MS Dat (M + 1)+ Unless Noted Otherwise |
|---|---|---|---|
| 100489 | 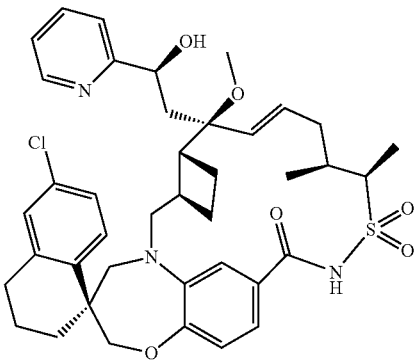 [SMILES: CO[C@@]1(C[C@H](O)c2ccccn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((2S)-2-hydroxy-2-(2-pyridinyl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 734.3 |
| | OR | OR | |
| | 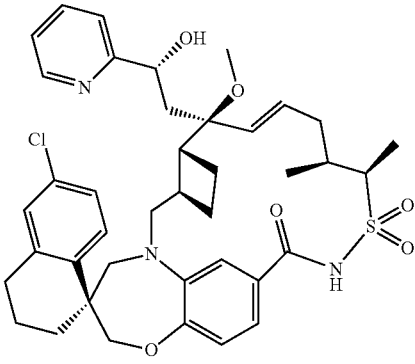 [SMILES: CO[C@@]1(C[C@@H](O)c2ccccn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((2R)-2-hydroxy-2-(2-pyridinyl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100490 | 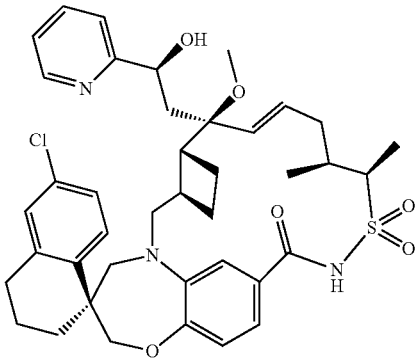 [SMILES: CO[C@@]1(C[C@H](O)c2ccccn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((2S)-2-hydroxy-2-(2-pyridinyl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 734.3 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-((2R)-2-hydroxy-2-(2-pyridinyl)ethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100491 | 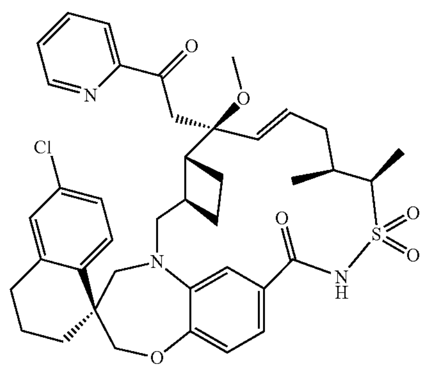 | (1S,3'R,6'R,7'S,8'E,11'S,12'R)-6-chloro-7'-methoxy-11',12'-dimethyl-7'-(2-oxo-2-(2-pyridinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 754.2 (M + Na) |
| 100492 | 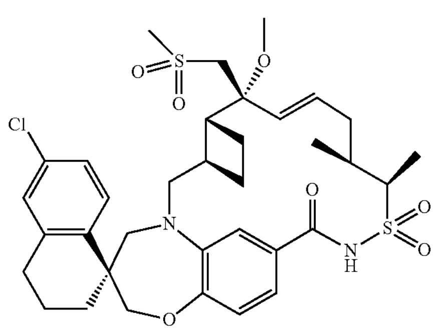 | (1S,3'R,6'R,7'R,8'E,11'S,12'R)-6-chloro-7'-methoxy-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 705.2 |

TABLE 2-continued

Examples Prepared by the General Methods

| Example Number | Structure | Name | MS Dat (M + 1)+ Unless Noted Otherwise |
|---|---|---|---|
| 100493 | 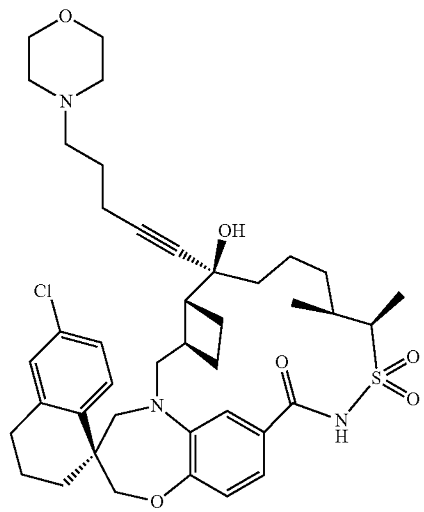 [SMILES: C[C@@H]1[C@@H](C)CCC[C@@](O)(C#CCCCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-hydroxy-11',12'-dimethyl-7'-(5-(4-morpholinyl)-1-pentyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 750.3 |
| 100494 | 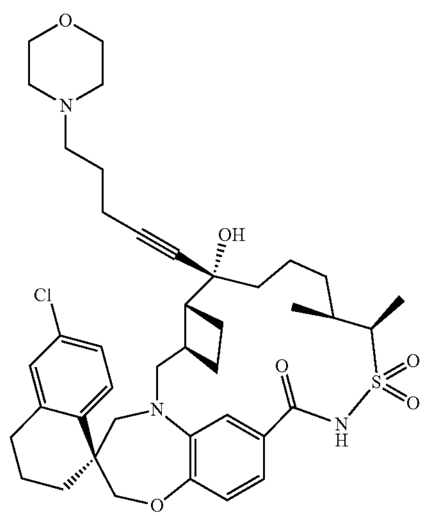 [SMILES: C[C@@H]1[C@@H](C)CCC[C@](O)(C#CCCCN2CCOCC2)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-hydroxy-11',12'-dimethyl-7'-(5-(4-morpholinyl)-1-pentyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 750.3 |
| 100495 | 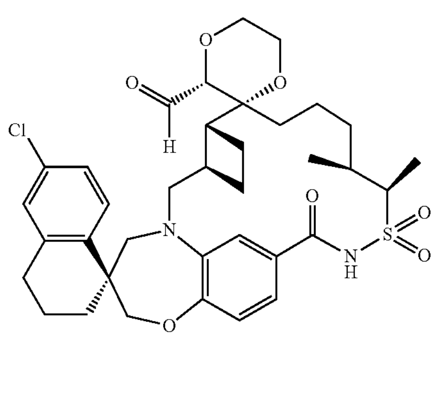 [SMILES: C[C@@H]1[C@@H](C)CCC[C@@]2(OCCO[C@H]2C=O)[C@@H]2CC[C@H]2CN2C[C@@]3(CCCc4cc(Cl)ccc43)COc3ccc(cc32)C(=O)NS1(=O)=O] | (2R,3'R,3'R,6'R,11'S,12'R,22'S)-6''-chloro-11',12'-dimethyl-15'-oxo-3'',4''-dihydro-2''H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalene]-3-carbaldehyde 13',13'-dioxide | 685.3 |

TABLE 2-continued

Examples Prepared by the General Methods

| Example Number | Structure | Name | MS Dat (M + 1)+ Unless Noted Otherwise |
|---|---|---|---|
| | OR | (2R,3S,3'R,6'R,11'S,12'R,22'S)-6''-chloro-11',12'-dimethyl-15'-oxo-3'',4''-dihydro-2''H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalene]-3-carbaldehyde 13',13'-dioxide | |
| | OR | (2S,3'R,3'R,6'R,11'S,12'R,22'S)-6''-chloro-11',12'-dimethyl-15'-oxo-3'',4''-dihydro-2''H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalene]-3-carbaldehyde 13',13'-dioxide | |
| | OR | (2S,3S,3'R,6'R,11'S,12'R,22'S)-6''-chloro-11',12'-dimethyl-15'-oxo-3'',4''-dihydro-2''H-dispiro[1,4-dioxane-2,7'-[20]oxa[13]thia[1,14]diazatetracyclo[14.7.2.0~3,6~.0~19,24~]pentacosa[16,18,24]triene-22',1''-naphthalene]-3-carbaldehyde 13',13'-dioxide | |
| 100496 | 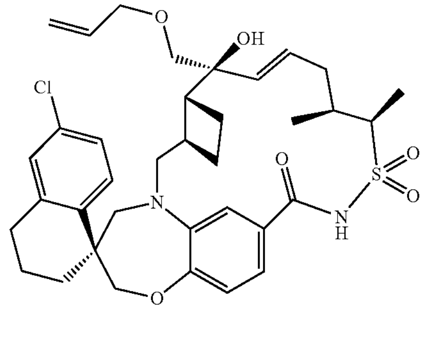 | (1S,3'R,6'R,7'S,8'E,11'S,12'R)-6-chloro-7'-hydroxy-11',12'-dimethyl-7'-((2-propen-1-yloxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 669.2 |

TABLE 2-continued

Examples Prepared by the General Methods

| Example Number | Structure | Name | MS Dat (M + 1)+ Unless Noted Otherwise |
|---|---|---|---|
| | 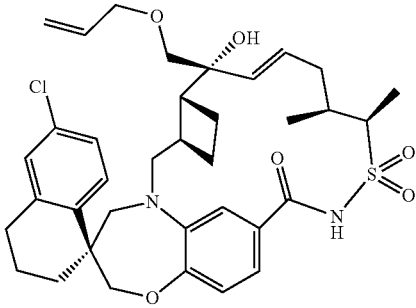 [SMILES: C=CCOC[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-11',12'-dimethyl-7'-((2-propen-1-yloxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100497 | 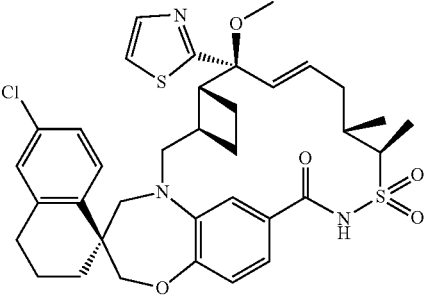 [SMILES: CO[C@@]1(c2nccs2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(1,3-thiazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.0 |
| | 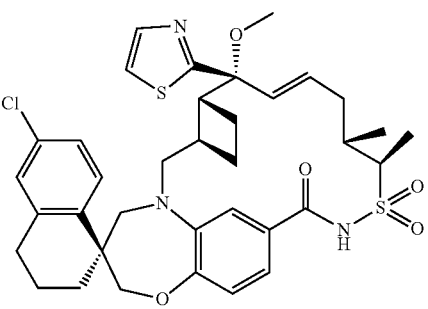 [SMILES: CO[C@]1(c2nccs2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-11',12'-dimethyl-7'-(1,3-thiazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100498 | 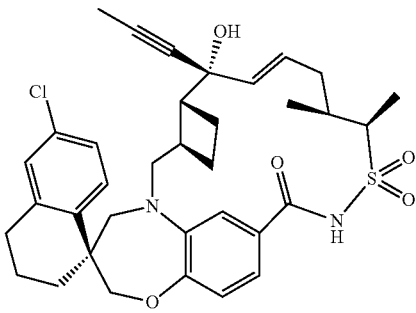 [SMILES: CC#C[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 637.4 |

TABLE 2-continued

Examples Prepared by the General Methods

| Example Number | Structure | Name | MS Dat (M + 1)+ Unless Noted Otherwise |
|---|---|---|---|
| 100499 | 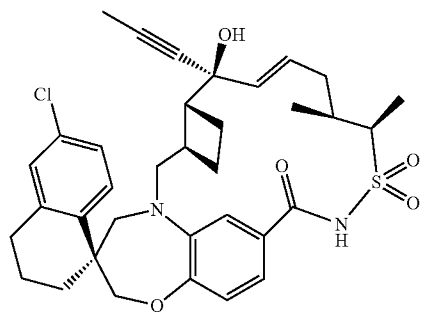 [SMILES: CC#C[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-hydroxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 637.3 |
| 100500 | 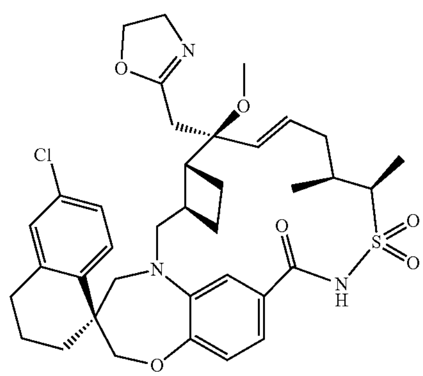 [SMILES: CO[C@@]1(CC2=NCCO2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(4,5-dihydro-1,3-oxazol-2-ylmethyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.2 |
| 100501 | 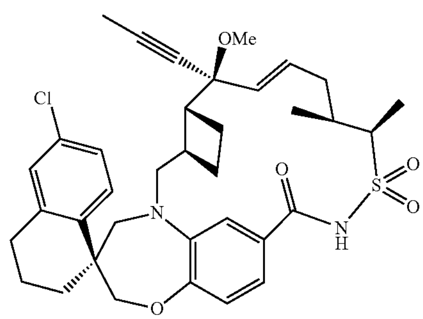 [SMILES: CC#C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(1-propyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 651.2 |
| 100502 | 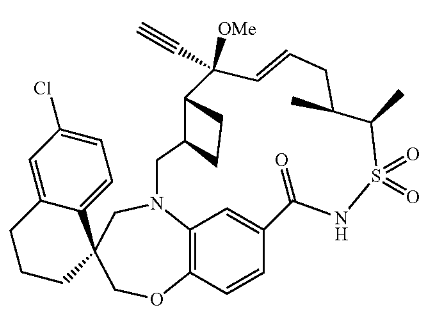 [SMILES: C#C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-ethynyl-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 637.3 |

TABLE 2-continued

Examples Prepared by the General Methods

| Example Number | Structure | Name | MS Dat (M + 1)+ Unless Noted Otherwise |
|---|---|---|---|
| 100503 | 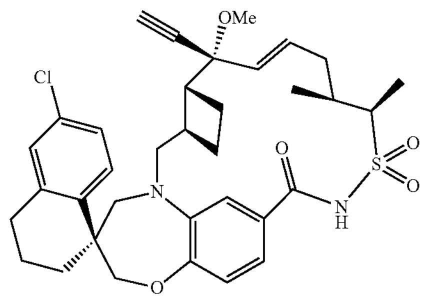 [SMILES: C#C[C@@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-ethynyl-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 637.3 |
| 100504 | 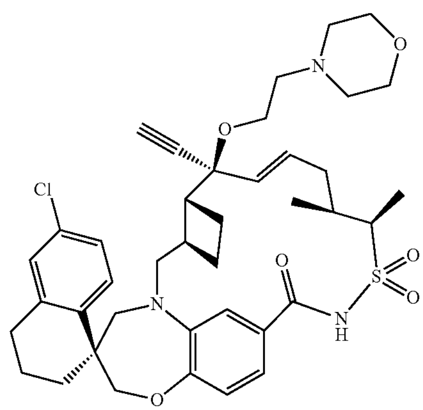 [SMILES: C#C[C@]1(OCCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-ethynyl-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 736.2 |
| 100505 | 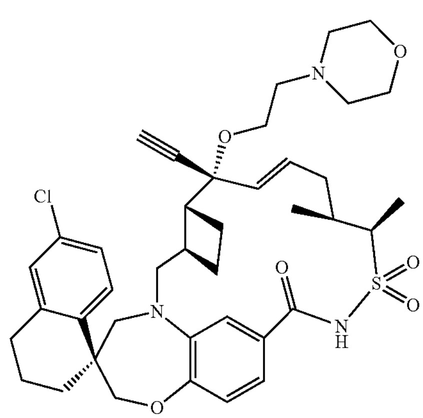 [SMILES: C#C[C@@]1(OCCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-ethynyl-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 736.2 |

TABLE 2-continued

Examples Prepared by the General Methods

| Example Number | Structure | Name | MS Dat (M + 1)+ Unless Noted Otherwise |
|---|---|---|---|
| 100506 | 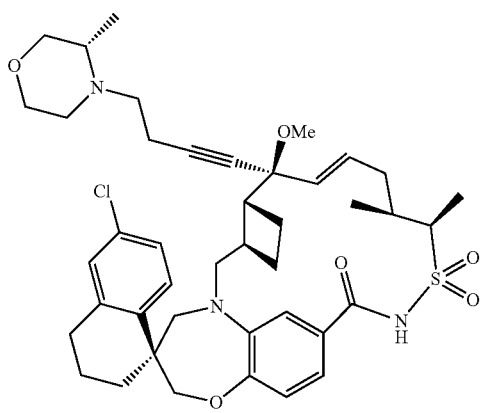 [SMILES: CO[C@@]1(C#CCCN2CCOC[C@@H]2C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(4-((3S)-3-methyl-4-morpholinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 764.2 |
| 100507 | 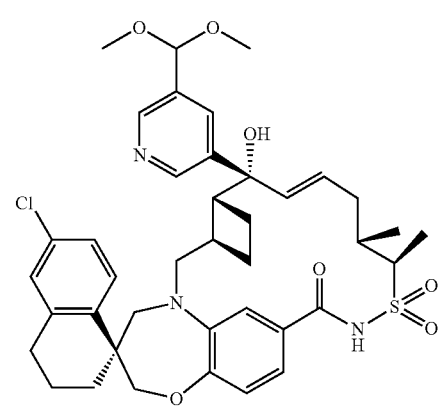 [SMILES: COC(OC)c1cncc([C@@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)c1] | (1S,3'R,6'R,7'R,8'E,11'S,12'R)-6-chloro-7'-(5-(dimethoxymethyl)-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 750.0 |
| | OR<br>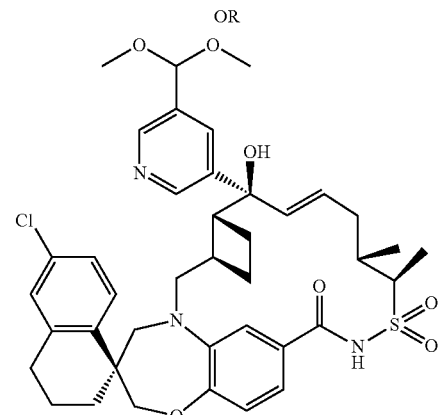 | OR<br>(1S,3'R,6'R,7'S,8'E,11'S,12'R)-6-chloro-7'-(5-(dimethoxymethyl)-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100508 | 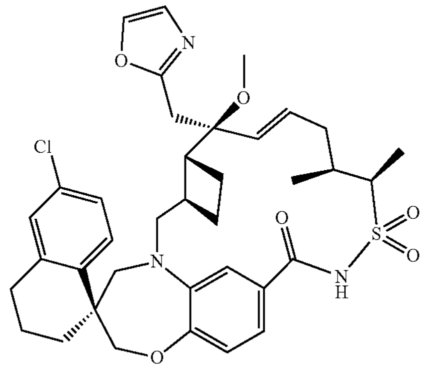 [SMILES: CO[C@@]1(Cc2ncco2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(1,3-oxazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.3 |
| 100509 | 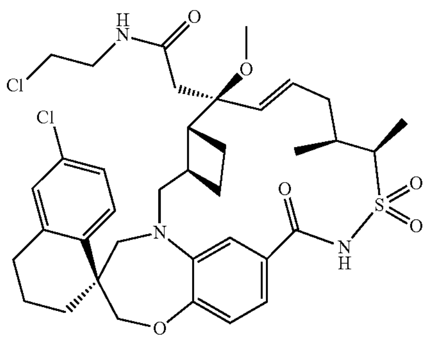 [SMILES: CO[C@@]1(CC(=O)NCCCl)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | N-(2-chloroethyl)-2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetamide | 754.2 (M + Na) |
| 100510 | 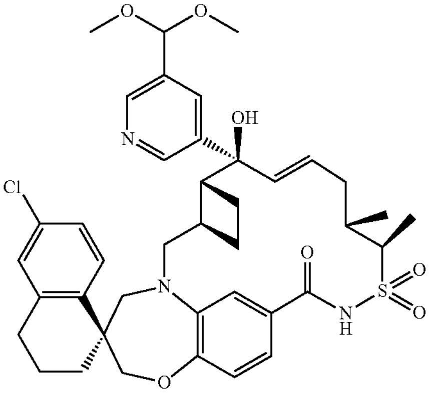 [SMILES: COC(OC)c1cncc([C@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)c1] | (1S,3'R,6'R,7'S,8'E,11'S,12'R)-6-chloro-7'-(5-(dimethoxymethyl)-3-pyridinyl)-7'-hydroxy-11',12'-dimethyl-3,4-dihydro-2H,15'H-spiro[naphthalene-1,22'-[20]oxa[13]thia[1,14]diazatetracyclo[14,7.2.0~3,6~.0~19,24~]pentacosa[8,16,18,24]tetraen]-15'-one 13',13'-dioxide | 750.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-(5-(dimethoxymethyl)-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100511 | 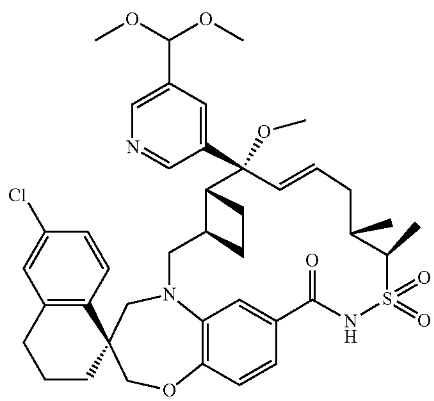 | (1S,3'R,6'R,7'R,8'E,11'S,12'R)-6-chloro-7'-(5-(dimethoxymethyl)-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 764.2 |
| | OR | OR (1S,3'R,6'R,7'S,8'E,11'S,12'R)-6-chloro-7'-(5-(dimethoxymethyl)-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100512 | 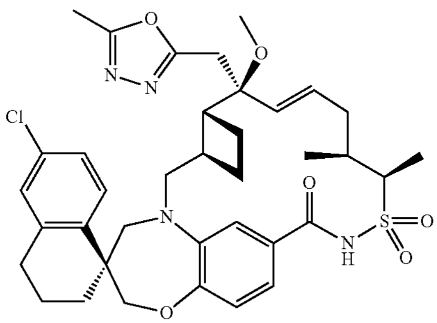 | (1S,3'R,6'R,7'S,8'E,11'S,12'R)-6-chloro-7'-methoxy-11',12'-dimethyl-7'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 709.2 |
| 100513 | 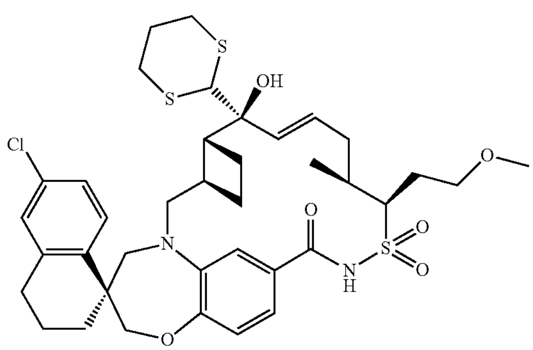 [SMILES: COCC[C@@H]1[C@@H](C)C/C=C/[C@@](O)(C2SCCCS2)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-(1,3-dithian-2-yl)-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 761.0 |
| 100514 | 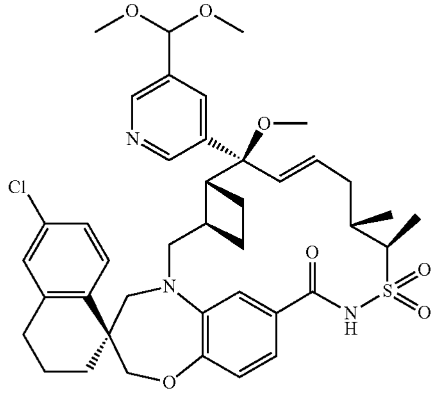 [SMILES: COC(OC)c1cncc([C@]2(OC)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)c1] | (1S,3'R,6'R,7'S,8'E,11'S,12'R)-6-chloro-7'-(5-(dimethoxymethyl)-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 764.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,11'S,12'R)-6-chloro-7'-(5-(dimethoxymethyl)-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100515 | 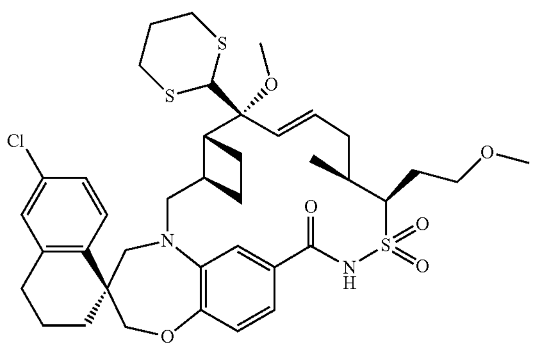 | (1S,3'R,6'R,7'R,8'E,11'S,12'R)-6-chloro-7'-(1,3-dithian-2-yl)-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 775.1 |
| 100516 | 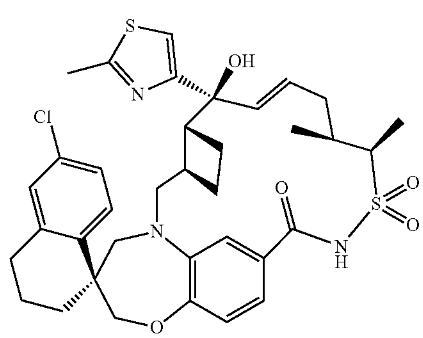 | (1S,3'R,6'R,7'S,8'E,11'S,12'R)-6-chloro-7'-hydroxy-11',12'-dimethyl-7'-(2-methyl-1,3-thiazol-4-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 695.8 |
| 100517 | 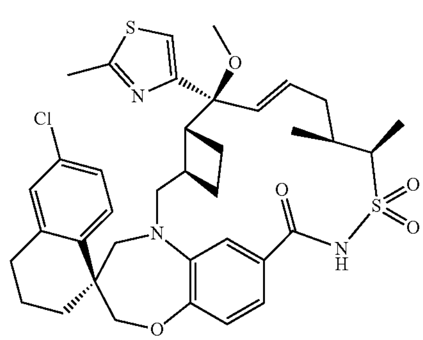 | (1S,3'R,6'R,7'S,8'E,11'S,12'R)-6-chloro-7'-methoxy-11',12'-dimethyl-7'-(2-methyl-1,3-thiazol-4-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.0 |

TABLE 2-continued

Examples Prepared by the General Methods

| Example Number | Structure | Name | MS Dat (M + 1)+ Unless Noted Otherwise |
|---|---|---|---|
| 100518 | 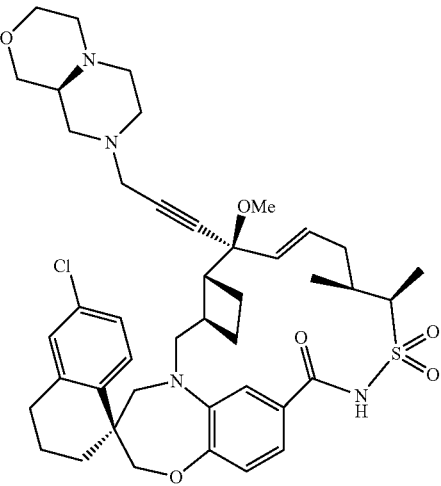 [SMILES: CO[C@@]1(C#CCN2CCN3CCOC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(3-((9aS)-hexahydropyrazino[2,1-c][1,4]oxazin-8(1H)-yl)-1-propyn-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 791.3 |
| 100519 | 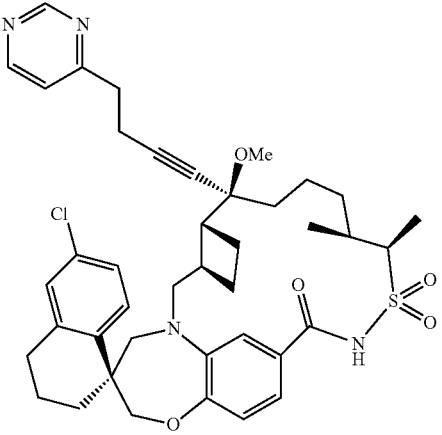 [SMILES: CO[C@@]1(C#CCCc2ccncn2)CCC[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(4-(4-pyrimidinyl)-1-butyn-1-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 743.2 |
| 100520 | 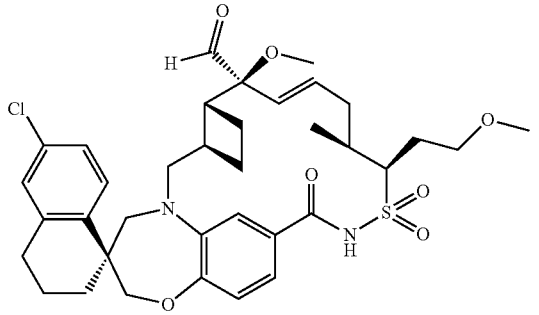 [SMILES: COCC[C@@H]1[C@@H](C)C/C=C/[C@](C=O)(OC)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | 685.1 |

TABLE 2-continued

Examples Prepared by the General Methods

| Example Number | Structure | Name | MS Dat (M + 1)+ Unless Noted Otherwise |
|---|---|---|---|
| 100521 | | (1S,3'R,6'R,7'R,8'E,11'S,12'R)-6-chloro-7'-methoxy-11',12'-dimethyl-7'-(5-(4-morpholinylmethyl)-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide|(1S,3'R,6'R,7'S,8'E,11'S,12'R)-6-chloro-7'-methoxy-11',12'-dimethyl-7'-(5-(4-morpholinylmethyl)-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 789.2 |
| | AND | AND | |
| | | (1S,3'R,6'R,7'S,8'E,11'S,12'R)-6-chloro-7'-methoxy-11',12'-dimethyl-7'-(5-(4-morpholinylmethyl)-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide|(1S,3'R,6'R,7'S,8'E,11'S,12'R)-6-chloro-7'-methoxy-11',12'-dimethyl-7'-(5-(4-morpholinylmethyl)-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100522 | 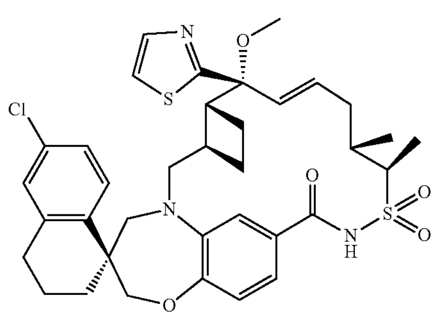 [SMILES: CO[C@]1(c2nccs2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-11',12'-dimethyl-7'-(1,3-thiazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 696.0 |

TABLE 2-continued

Examples Prepared by the General Methods

| Example Number | Structure | Name | MS Dat (M + 1)+ Unless Noted Otherwise |
|---|---|---|---|
| | OR | OR | |
| 100523 | 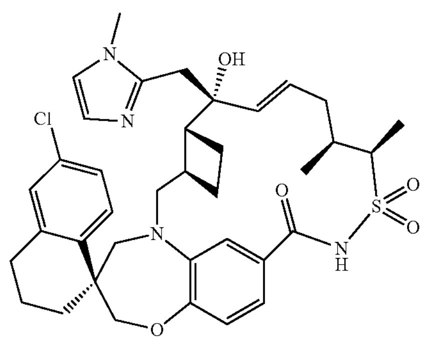 | (1S,3'R,6'R,7'S,8'E,11'S,12'R)-6-chloro-7'-hydroxy-11',12'-dimethyl-7'-((1-methyl-1H-imidazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.0 |
| 100524 | 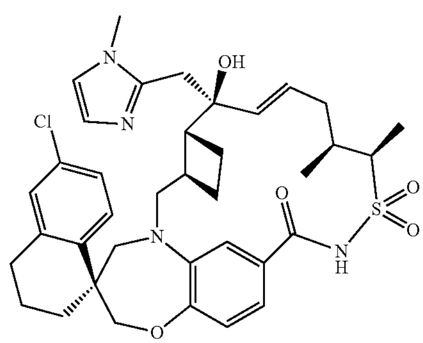 | (1S,3'R,6'R,7'R,8'E,11'S,12'R)-6-chloro-7'-hydroxy-11',12'-dimethyl-7'-((1-methyl-1H-imidazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.0 |
| 100525 | 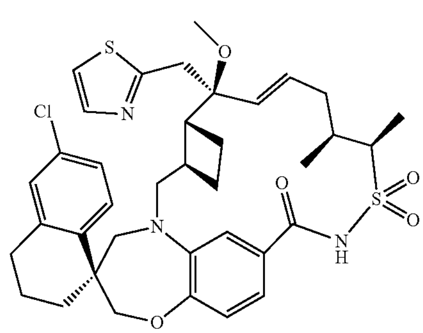 | (1S,3'R,6'R,7'S,8'E,11'S,12'R)-6-chloro-7'-methoxy-11',12'-dimethyl-7'-(1,3-thiazol-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.0 |

Above the 100523 row (unnumbered entry):
(1S,3'R,6'R,7'S,8'E,11'S,12'R)-6-chloro-7'-methoxy-11',12'-dimethyl-7'-(1,3-thiazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide TABLE 2-continued Examples Prepared by the General Methods

| Example Number | Structure | Name | MS Dat (M + 1)+ Unless Noted Otherwise |
|---|---|---|---|
| 100526 | 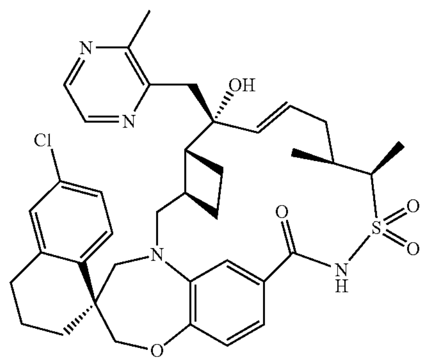 [SMILES: Cc1nccnc1C[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-hydroxy-11',12'-dimethyl-7'-((3-methyl-2-pyrazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 705.0 |
| 100527 | 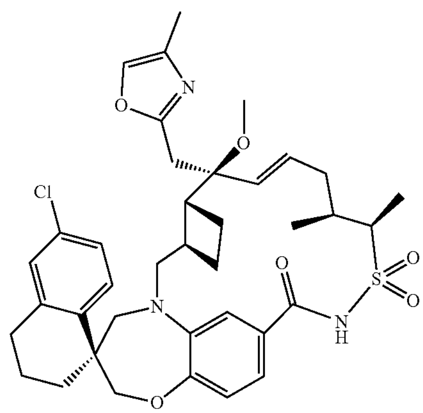 [SMILES: CO[C@@]1(Cc2nc(C)co2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((4-methyl-1,3-oxazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.2 |
| 100528 | 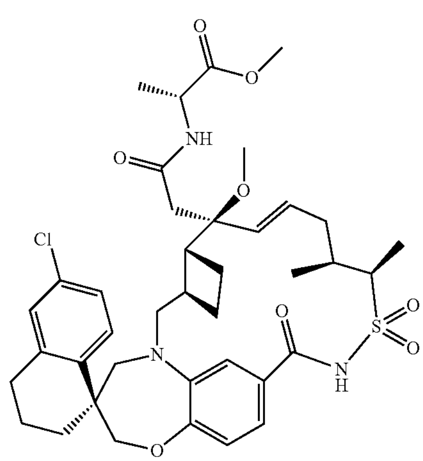 [SMILES: COC(=O)[C@@H](C)NC(=O)C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | methyl N-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)-D-alaninate | 778.3 (M + Na) |

TABLE 2-continued

Examples Prepared by the General Methods

| Example Number | Structure | Name | MS Dat (M + 1)+ Unless Noted Otherwise |
|---|---|---|---|
| 100529 | 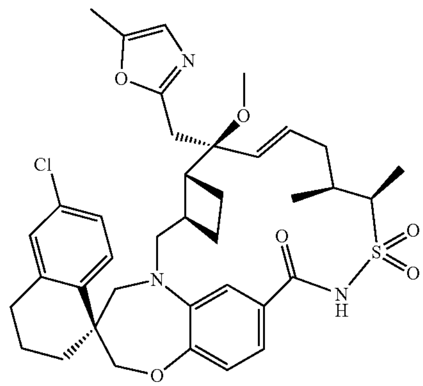 [SMILES: CO[C@@]1(Cc2ncc(C)o2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((5-methyl-1,3-oxazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.2 |
| 100530 | | (1S,3'R,6'R,7'S,8'E,11'S,12'R)-6-chloro-7'-(6-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |
| | OR | OR | |
| | | (1S,3'R,6'R,7'R,8'E,11'S,12'R)-6-chloro-7'-(6-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100531 | 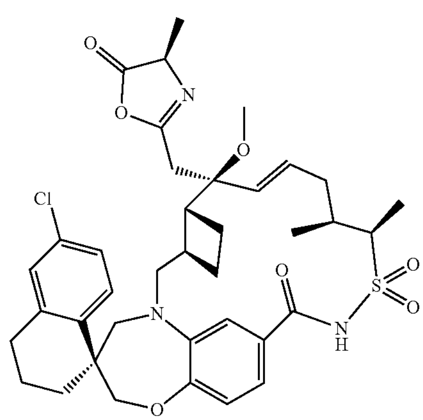 [SMILES: CO[C@@]1(CC2=N[C@H](C)C(=O)O2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-(((4R)-4-methyl-5-oxo-4,5-dihydro-1,3-oxazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |

TABLE 2-continued

Examples Prepared by the General Methods

| Example Number | Structure | Name | MS Dat (M + 1)+ Unless Noted Otherwise |
|---|---|---|---|
| | AND | AND | |
| | | (1S,3'R,6'R,7'S,8'E,11'S,12'R)-6-chloro-7'-methoxy-11',12'-dimethyl-7'-(((4S)-4-methyl-5-oxo-4,5-dihydro-1,3-oxazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100532 | 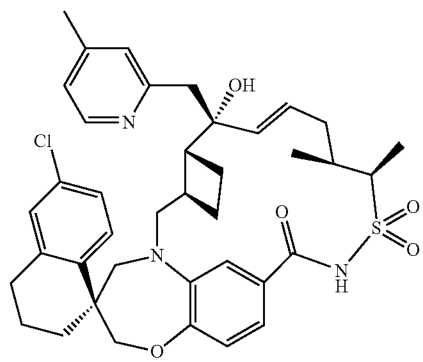 | (1S,3'R,6'R,7'R,8'E,11'S,12'R)-6-chloro-7'-hydroxy-11',12'-dimethyl-7'-((4-methyl-2-pyridinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 704.0 |
| 100533 | 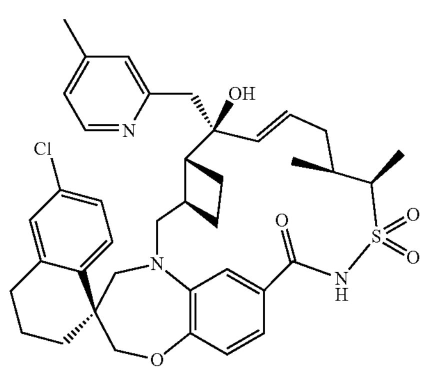 | (1S,3'R,6'R,7'S,8'E,11'S,12'R)-6-chloro-7'-hydroxy-11',12'-dimethyl-7'-((4-methyl-2-pyridinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 704.0 |

TABLE 2-continued

Examples Prepared by the General Methods

| Example Number | Structure | Name | MS Dat (M + 1)+ Unless Noted Otherwise |
|---|---|---|---|
| 100534 | OR<br><br>1p;2p | (1S,3'R,6'R,7'S,8'E,11'S,12'R)-6-chloro-7'-hydroxy-11',12'-dimethyl-7'-(5-phenyl-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'R,8'E,11'S,12'R)-6-chloro-7'-hydroxy-11',12'-dimethyl-7'-(5-phenyl-3-pyridinyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 752.2 |
| 100535 | 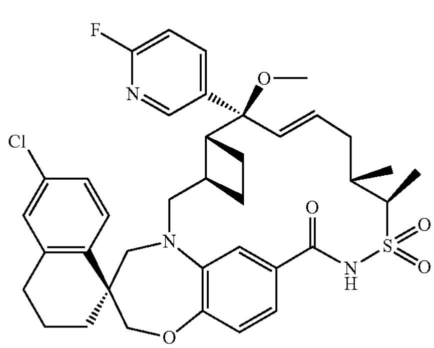 [SMILES: CO[C@@]1(c2ccc(F)nc2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(6-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 676.0 |

TABLE 2-continued

Examples Prepared by the General Methods

| Example Number | Structure | Name | MS Dat (M + 1)+ Unless Noted Otherwise |
|---|---|---|---|
| | OR | OR (1S,3'R,6'R,7'R,8'E,11'S,12'R)-6-chloro-7'-(6-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100536 | 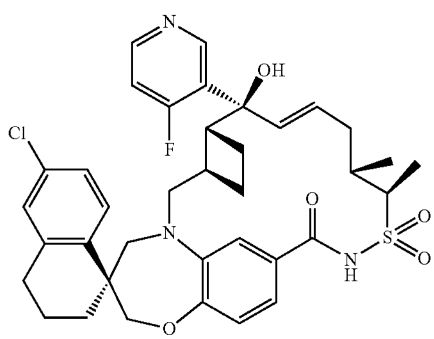 | (1S,3'R,6'R,7'S,8'E,11'S,12'R)-6-chloro-7'-(4-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| | OR | OR (1S,3'R,6'R,7'R,8'E,11'S,12'R)-6-chloro-7'-(4-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100537 | | (1S,3'R,6'R,7'R,8'E,11'S,12'R)-6-chloro-7'-(4-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide|(1S,3'R,6'R,7'S,8'E,11'S,12'R)-6-chloro-7'-(4-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |

TABLE 2-continued

Examples Prepared by the General Methods

| Example Number | Structure | Name | MS Dat (M + 1)+ Unless Noted Otherwise |
|---|---|---|---|
| | AND | AND | |
| | | (1S,3'R,6'R,7'S,8'E,11'S,12'R)-6-chloro-7'-(4-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide|(1S,3'R,6'R,7'S,8'E,11'S,12'R)-6-chloro-7'-(4-fluoro-3-pyridinyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100538 | 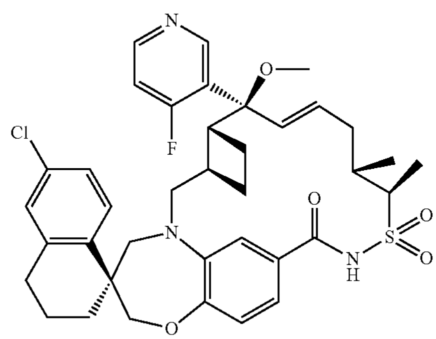 | (1S,3'R,6'R,7'S,8'E,11'S,12'R)-6-chloro-7'-(4-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.0 |
| | OR | OR | |
| | | (1S,3'R,6'R,7'R,8'E,11'S,12'R)-6-chloro-7'-(4-fluoro-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100539 | 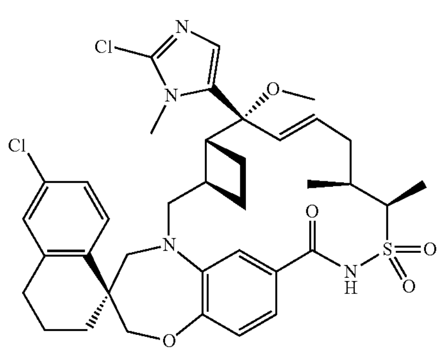 | (1S,3'R,6'R,7'R,8'E,11'S,12'R)-6-chloro-7'-(2-chloro-1-methyl-1H-imidazol-5-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 727.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'S,8'E,11'S,12'R)-6-chloro-7'-(2-chloro-1-methyl-1H-imidazol-5-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100540 | 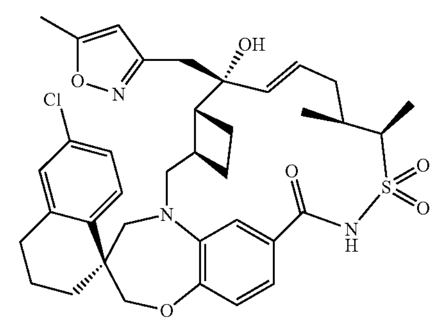 | (1S,3'R,6'R,7'R,8'E,11'S,12'R)-6-chloro-7'-hydroxy-11',12'-dimethyl-7'-((5-methyl-1,2-oxazol-3-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| 100541 | 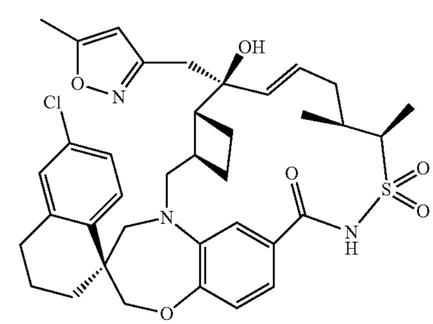 | (1S,3'R,6'R,7'S,8'E,11'S,12'R)-6-chloro-7'-hydroxy-11',12'-dimethyl-7'-((5-methyl-1,2-oxazol-3-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.0 |
| 100542 | 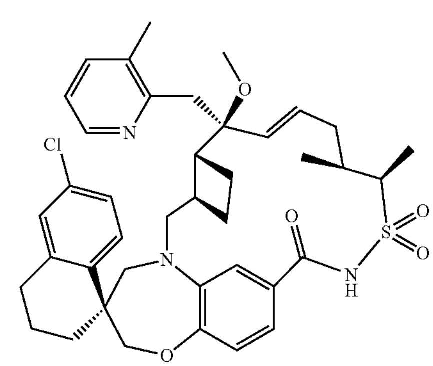 | (1S,3'R,6'R,7'S,8'E,11'S,12'R)-6-chloro-7'-methoxy-11',12'-dimethyl-7'-((3-methyl-2-pyridinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 718.0 |

TABLE 2-continued

Examples Prepared by the General Methods

| Example Number | Structure | Name | MS Dat (M + 1)+ Unless Noted Otherwise |
|---|---|---|---|
| 100543 | 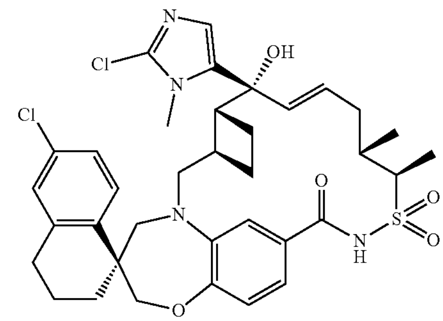 [SMILES: C[C@@H]1[C@@H](C)C/C=C/[C@](O)(c2cnc(Cl)n2C)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(2-chloro-1-methyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 713.2 |
| | OR | OR | |
| | | (1S,3'R,6'R,7'S,8'E,11'S,12'R)-6-chloro-7'-(2-chloro-1-methyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100544 | 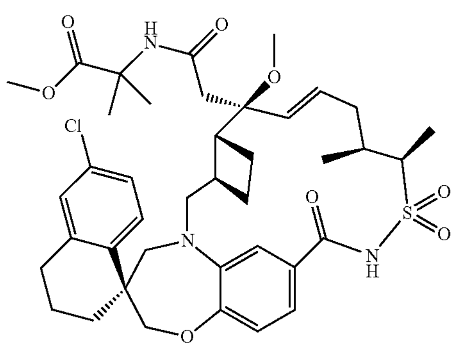 [SMILES: COC(=O)C(C)(C)NC(=O)C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | methyl N-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)-2-methylalaninate | 738.2 (M − OMe) |
| 100545 | 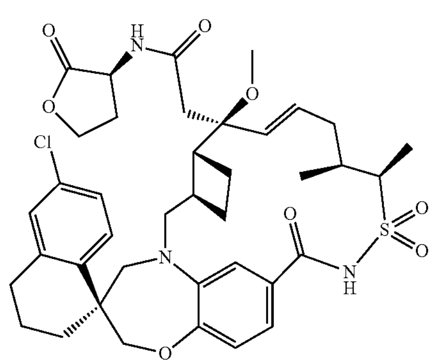 [SMILES: CO[C@@]1(CC(=O)N[C@H]2CCOC2=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((3R)-2-oxotetrahydro-3-furanyl)acetamide | 722.3 (M − OMe) |

TABLE 2-continued

Examples Prepared by the General Methods

| Example Number | Structure | Name | MS Dat (M + 1)+ Unless Noted Otherwise |
|---|---|---|---|
| | AND | AND | |
| | | 2-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((3S)-2-oxotetrahydro-3-furanyl)acetamide | |
| 100546 | 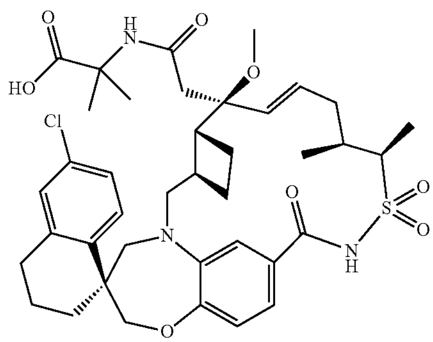 | N-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)-2-methylalanine | 724.2 (M − OMe) |
| 100547 | 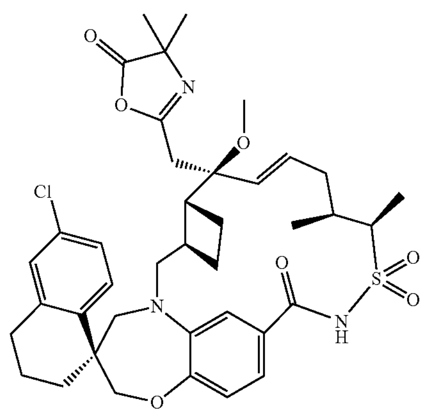 | (1S,3'R,6'R,7'S,8'E,11'S,12'R)-6-chloro-7'-((4,4-dimethyl-5-oxo-4,5-dihydro-1,3-oxazol-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 738.2 |
| 100548 | 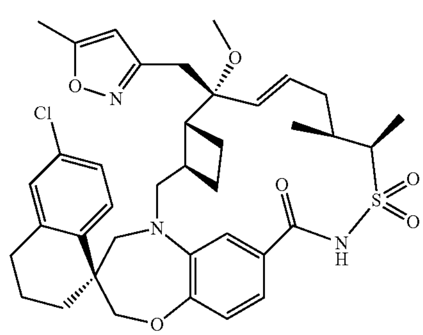 | (1S,3'R,6'R,7'R,8'E,11'S,12'R)-6-chloro-7'-methoxy-11',12'-dimethyl-7'-((5-methyl-1,2-oxazol-3-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.0 |

TABLE 2-continued

Examples Prepared by the General Methods

| Example Number | Structure | Name | MS Dat (M + 1)+ Unless Noted Otherwise |
|---|---|---|---|
| 100549 | 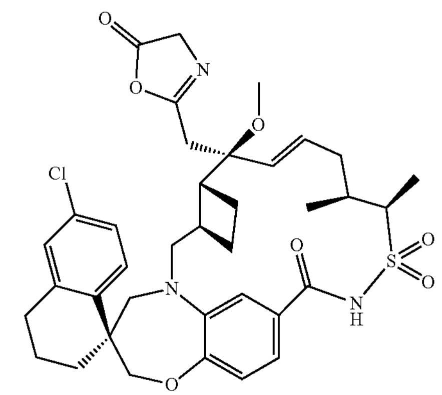 [SMILES: CO[C@@]1(CC2=NCC(=O)O2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((5-oxo-4,5-dihydro-1,3-oxazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 710.3 |
| 100550 | 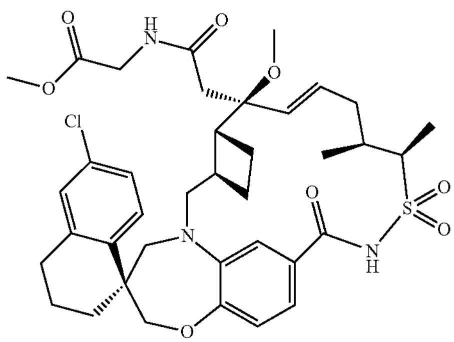 [SMILES: COC(=O)CNC(=O)C[C@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | methyl N-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)glycinate | 710.3 (M − OMe) |
| 100551 | 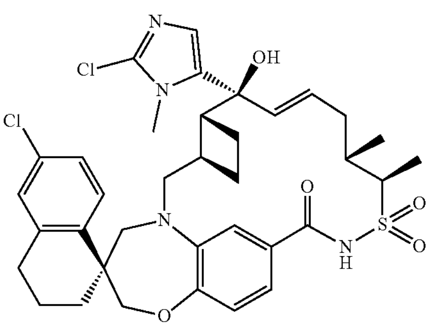 [SMILES: C[C@@H]1[C@@H](C)C/C=C/[C@@](O)(c2cnc(Cl)n2C)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,11'S,12'R)-6-chloro-7'-(2-chloro-1-methyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 713.2 |
| | OR | OR | |
| | | (1S,3'R,6'R,7'R,8'E,11'S,12'R)-6-chloro-7'-(2-chloro-1-methyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100552 | 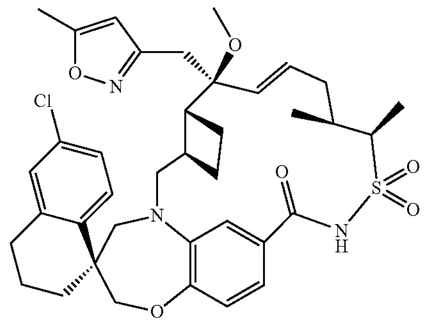 [SMILES: CO[C@@]1(Cc2cc(C)on2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((5-methyl-1,2-oxazol-3-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.0 |
| 100553 | | (1S,3'R,6'R,7'R,8'E,11'S,12'R)-6-chloro-7'-methoxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br><br>OR<br><br>(1S,3'R,6'R,7'S,8'E,11'S,12'R)-6-chloro-7'-methoxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.2 |
| 100554 | 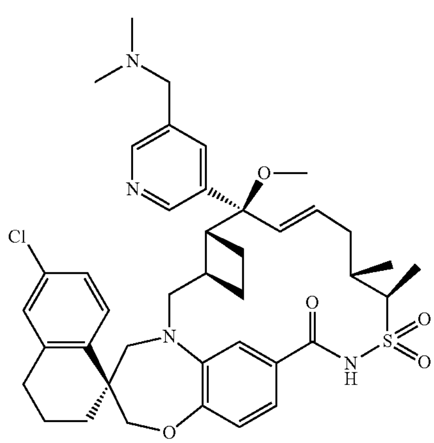 [SMILES: CO[C@@]1(c2cncc(CN(C)C)c2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(5-((dimethylamino)methyl)-3-pyridinyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 747.2 |

TABLE 2-continued

Examples Prepared by the General Methods

| Example Number | Structure | Name | MS Dat (M + 1)+ Unless Noted Otherwise |
|---|---|---|---|
| 100555 | 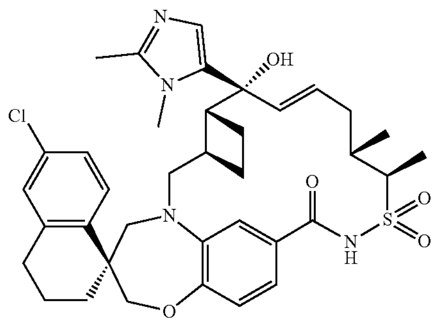 [SMILES: Cc1ncc([C@@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)n1C] | (1S,3'R,6'R,7'R,8'E,11'S,12'R)-6-chloro-7'-(1,2-dimethyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'S,8'E,11'S,12'R)-6-chloro-7'-(1,2-dimethyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.2 |
| 100556 | 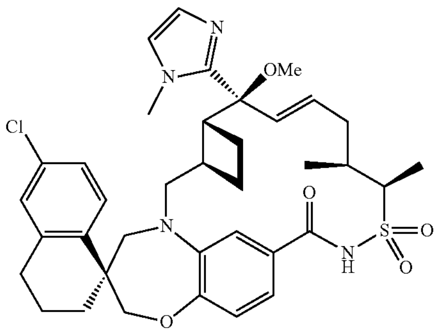 | (1S,3'R,6'R,7'S,8'E,11'S,12'R)-6-chloro-7'-methoxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-methoxy-11',12'-dimethyl-7'-(1-methyl-1H-imidazol-2-yl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.2 |

TABLE 2-continued

Examples Prepared by the General Methods

| Example Number | Structure | Name | MS Dat (M + 1)+ Unless Noted Otherwise |
|---|---|---|---|
| 100557 | 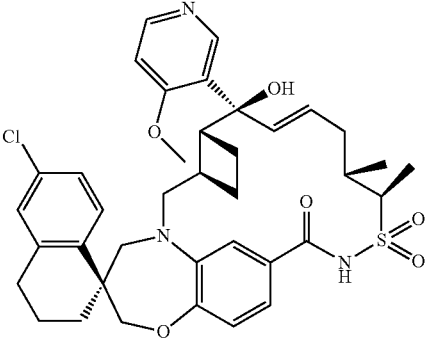 [SMILES: COc1ccncc1[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]<br>OR<br>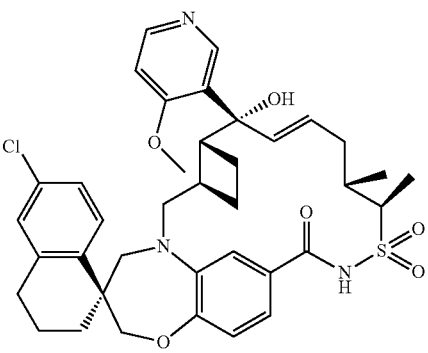 [SMILES: COc1ccncc1[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-hydroxy-7'-(4-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br>OR<br>(1S,3'R,6'R,7'R,8'E,11'S,12'R)-6-chloro-7'-hydroxy-7'-(4-methoxy-3-pyridinyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 706.2 |
| 100558 | 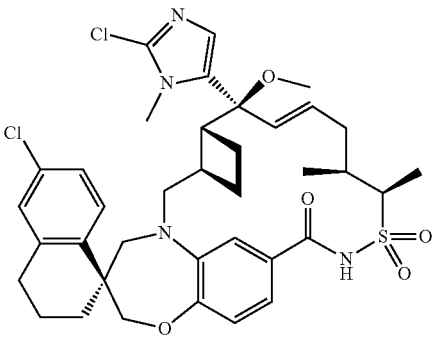<br>OR<br>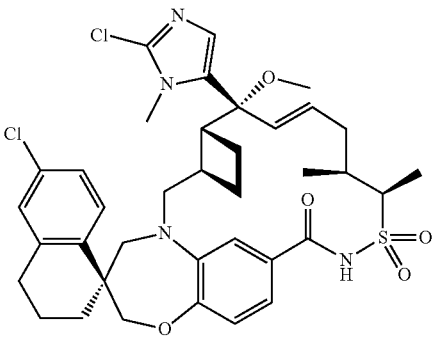 | (1S,3'R,6'R,7'S,8'E,11'S,12'R)-6-chloro-7'-(2-chloro-1-methyl-1H-imidazol-5-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide<br>OR<br>(1S,3'R,6'R,7'R,8'E,11'S,12'R)-6-chloro-7'-(2-chloro-1-methyl-1H-imidazol-5-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 727.1 |

TABLE 2-continued

Examples Prepared by the General Methods

| Example Number | Structure | Name | MS Dat (M + 1)+ Unless Noted Otherwise |
|---|---|---|---|
| 100559 | 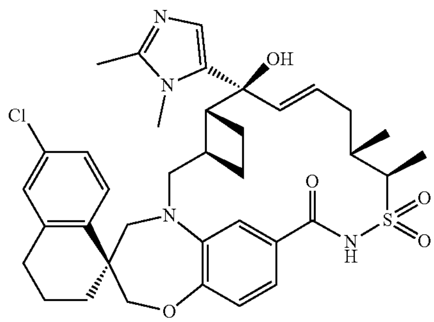 [SMILES: Cc1ncc([C@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)n1C] | (1S,3'R,6'R,7'S,8'E,11'S,12'R)-6-chloro-7'-(1,2-dimethyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 693.2 |
| | OR | OR | |
| | | (1S,3'R,6'R,7'R,8'E,11'S,12'R)-6-chloro-7'-(1,2-dimethyl-1H-imidazol-5-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100560 | 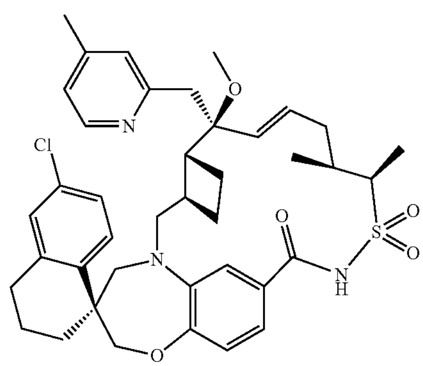 [SMILES: CO[C@@]1(Cc2cc(C)ccn2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((4-methyl-2-pyridinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 718.0 |
| 100561 | 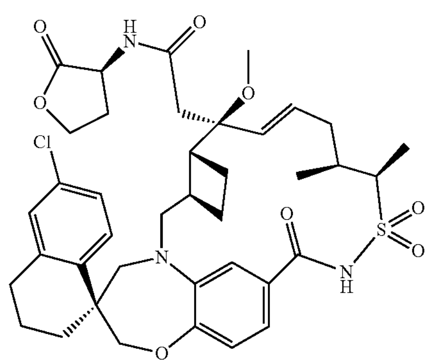 [SMILES: CO[C@@]1(CC(=O)N[C@H]2CCOC2=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((3R)-2-oxotetrahydro-3-furanyl)acetamide | 722.2 (M − OMe) |

TABLE 2-continued

Examples Prepared by the General Methods

| Example Number | Structure | Name | MS Dat (M + 1)+ Unless Noted Otherwise |
|---|---|---|---|
| | OR | OR 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((3S)-2-oxotetrahydro-3-furanyl)acetamide | |
| 100562 | 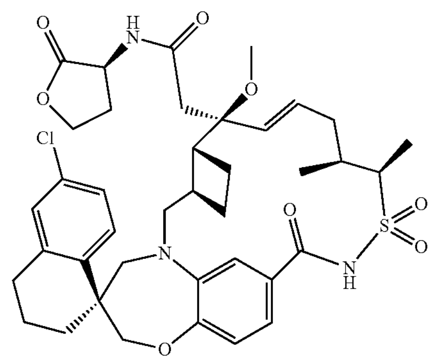 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((3R)-2-oxotetrahydro-3-furanyl)acetamide | 722.2 (M − OMe) |
| | OR | OR 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((3S)-2-oxotetrahydro-3-furanyl)acetamide | |

TABLE 2-continued

Examples Prepared by the General Methods

| Example Number | Structure | Name | MS Dat (M + 1)+ Unless Noted Otherwise |
|---|---|---|---|
| 100563 | 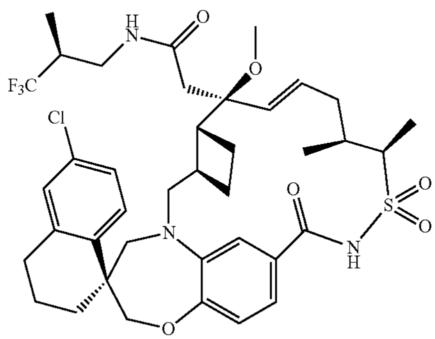 [SMILES: CO[C@@]1(CC(=O)NC[C@H](C)C(F)(F)F)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((2R)-3,3,3-trifluoro-2-hydroxypropyl)acetamide | 750.2 (M − OMe) |
| | AND | AND | |
| | | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-((2S)-3,3,3-trifluoro-2-hydroxypropyl)acetamide | |
| 100564 | 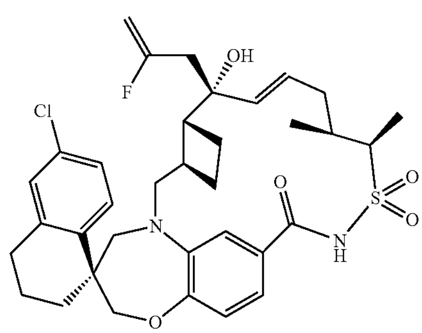 [SMILES: C=C(F)C[C@@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(2-fluoro-2-propen-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.0 |
| 100565 | 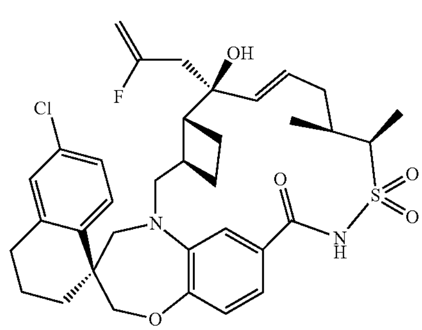 [SMILES: C=C(F)C[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-(2-fluoro-2-propen-1-yl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.0 |

TABLE 2-continued

Examples Prepared by the General Methods

| Example Number | Structure | Name | MS Dat (M + 1)+ Unless Noted Otherwise |
|---|---|---|---|
| 100566 | 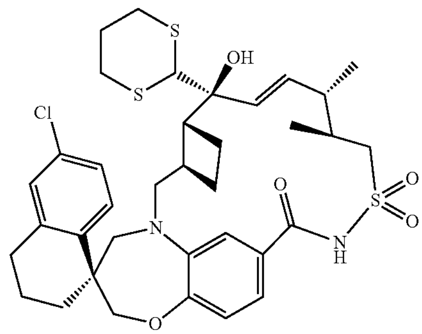 [SMILES: C[C@@H]1CS(=O)(=O)NC(=O)c2ccc3c(c2)N(C[C@@H]2CC[C@H]2[C@](O)(C2SCCCS2)/C=C/[C@@H]1C)C[C@@]1(CCCc2cc(Cl)ccc21)CO3] | (1S,3'R,6'R,7'S,8'E,10'S,11'S)-6-chloro-7'-(1,3-dithian-2-yl)-7'-hydroxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 717.0 |
| 100567 | 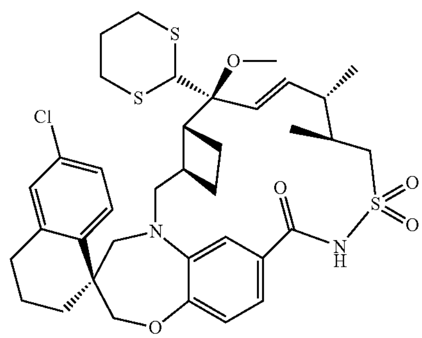 [SMILES: CO[C@@]1(C2SCCCS2)/C=C/[C@H](C)[C@H](C)CS(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,10'S,11'S)-6-chloro-7'-(1,3-dithian-2-yl)-7'-methoxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 731.0 |
| 100568 | 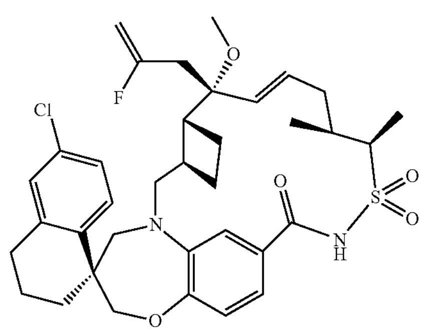 [SMILES: C=C(F)C[C@@]1(OC)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-(2-fluoro-2-propen-1-yl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 671.0 |
| 100569 | 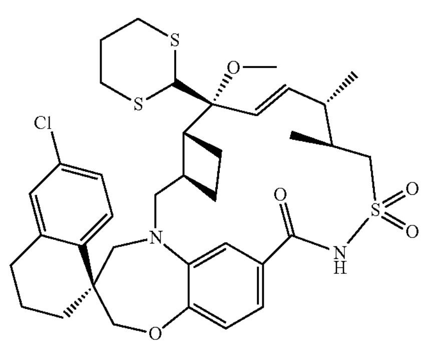 [SMILES: CO[C@]1(C2SCCCS2)/C=C/[C@H](C)[C@H](C)CS(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,10'S,11'S)-6-chloro-7'-(1,3-dithian-2-yl)-7'-methoxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 731.0 |

TABLE 2-continued

Examples Prepared by the General Methods

| Example Number | Structure | Name | MS Dat (M + 1)+ Unless Noted Otherwise |
|---|---|---|---|
| 100570 | 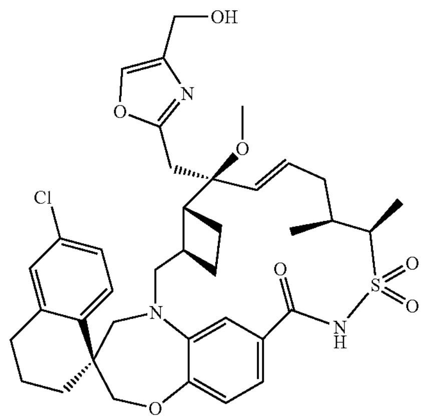 | (1S,3'R,6'R,7'S,8'E,11'S,12'R)-6-chloro-7'-((4-(hydroxymethyl)-1,3-oxazol-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 724.2 |
| 100571 | 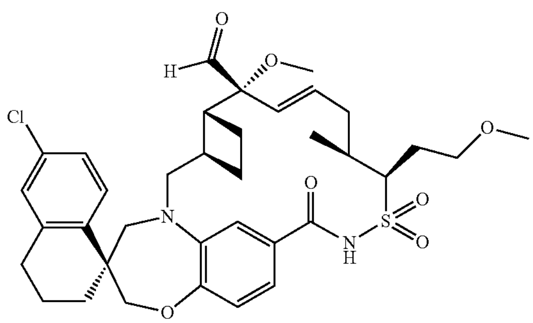 [SMILES: COCC[C@@H]1[C@@H](C)C/C=C/[C@@](C=O)(OC)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-methoxy-12'-(2-methoxyethyl)-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | 685.1 |
| 100572 | 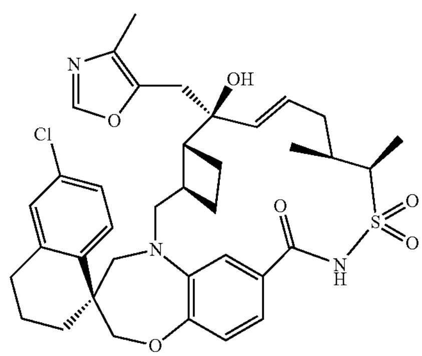 [SMILES: Cc1ncoc1C[C@]1(O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-hydroxy-11',12'-dimethyl-7'-((4-methyl-1,3-oxazol-5-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 694.8 |
| 100573 | 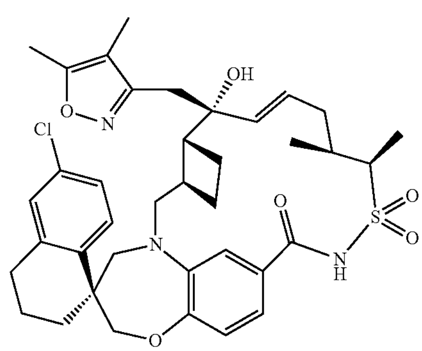 [SMILES: Cc1onc(C[C@@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)c1C] | (1S,3'R,6'R,7'S,8'E,11'S,12'R)-6-chloro-7'-((4,5-dimethyl-1,2-oxazol-3-yl)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.0 |

TABLE 2-continued

Examples Prepared by the General Methods

| Example Number | Structure | Name | MS Dat (M + 1)+ Unless Noted Otherwise |
|---|---|---|---|
| 100574 | 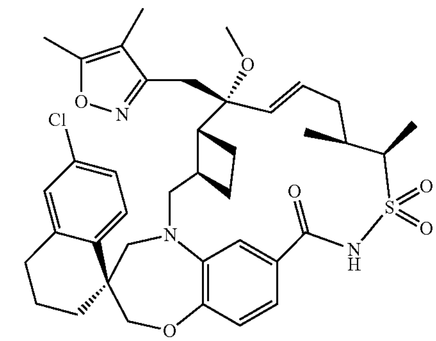 [SMILES: CO[C@]1(Cc2noc(C)c2C)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-((4,5-dimethyl-1,2-oxazol-3-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 722.0 |
| 100575 | 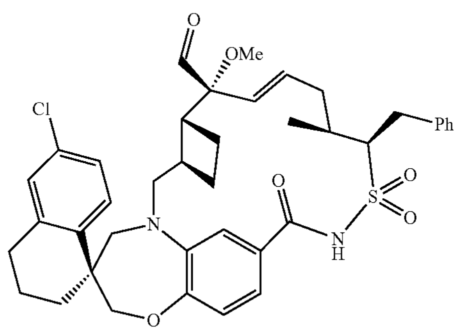 [SMILES: CO[C@]1(C=O)/C=C/C[C@H](C)[C@@H](Cc2ccccc2)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-12'-benzyl-6-chloro-7'-methoxy-11'-methyl-15'-oxo-3,4-dihydro-2H-spiro[naphthalene-1,22'-[20]oxa[13]thia[1,14]diazatetracyclo[14.2.0~3,6~.0~19,24~]pentacosa[8,16,18,24]tetraene]-7'-carbaldehyde 13',13'-dioxide | 717.5 |
| | OR | OR | |
| | | (1S,3'R,6'R,7'S,8'E,11'S,12'R)-12'-benzyl-6-chloro-7'-methoxy-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | |
| | OR | OR | |
| | | (1S,3'R,6'R,7'R,8'E,11'S,12'S)-12'-benzyl-6-chloro-7'-methoxy-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | |

TABLE 2-continued

Examples Prepared by the General Methods

| Example Number | Structure | Name | MS Data (M + 1)+ Unless Noted Otherwise |
|---|---|---|---|
| | OR | OR (1S,3'R,6'R,7'S,8'E,11'S,12S)-12-benzyl-6-chloro-7'-methoxy-11'-methyl-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | |
| 100576 | 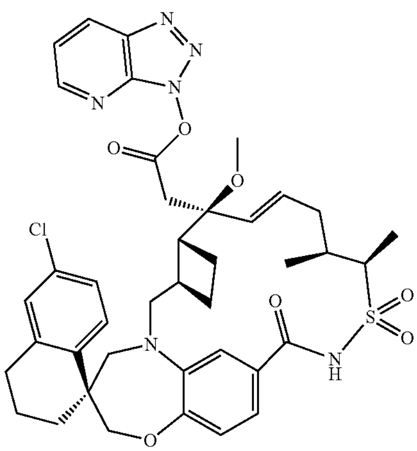 | (1S,3'R,6'R,7'S,8'E,11'S,12'R)-6-chloro-7'-methoxy-11',12'-dimethyl-7'-(2-oxo-2-(3H-[1,2,3]triazolo[4,5-b]pyridin-3-yloxy)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 789.2 |
| 100577 | 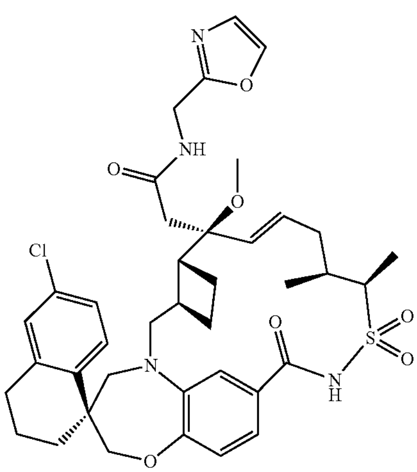 | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)-N-(1,3-oxazol-2-ylmethyl)acetamide | 719.3 (M − OMe) |

TABLE 2-continued

Examples Prepared by the General Methods

| Example Number | Structure | Name | MS Dat (M + 1)+ Unless Noted Otherwise |
|---|---|---|---|
| 100578 | 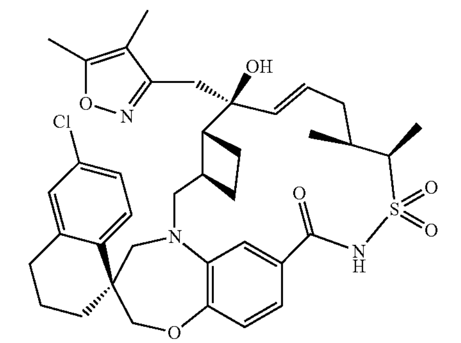 [SMILES: Cc1onc(C[C@]2(O)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)c1C] | (1S,3'R,6'R,7'S,8'E,11'S,12'R)-6-chloro-7'-((4,5-dimethyl-1,2-oxazol-3-yl)methyl)-7'-hydroxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 708.0 |
| 100579 | | (1S,3'R,6'R,7'S,8'E,12'R)-6-chloro-7'-(1,3-dithian-2-yl)-12'-ethyl-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 731.2 |
| | OR | OR | |
| | | (1S,3'R,6'R,7'R,8'E,12'R)-6-chloro-7'-(1,3-dithian-2-yl)-12'-ethyl-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100580 | 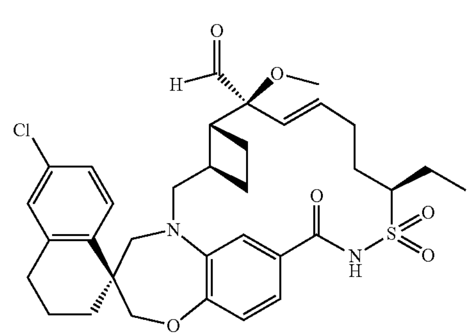 [SMILES: CC[C@@H]1CC/C=C/[C@](C=O)(OC)[C@@H]2CC[C@H]2CN2C[C@@]3(CCCc4cc(Cl)ccc43)COc3ccc(cc32)C(=O)NS1(=O)=O] | (1S,3'R,6'R,7'S,8'E,12'R)-6-chloro-12'-ethyl-7'-methoxy-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | 641.2 |

TABLE 2-continued

Examples Prepared by the General Methods

| Example Number | Structure | Name | MS Dat (M + 1)+ Unless Noted Otherwise |
|---|---|---|---|
| | OR | OR | |
| | | (1S,3'R,6'R,7'R,8'E,12'R)-6-chloro-12'-ethyl-7'-methoxy-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | |
| 100581 | 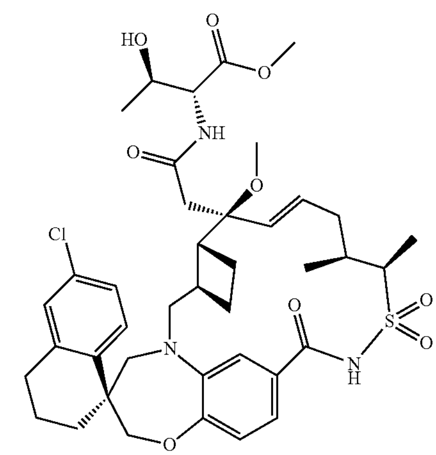 | methyl N-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)-D-allothreoninate | 754.2 (M − OMe) |
| 100582 | 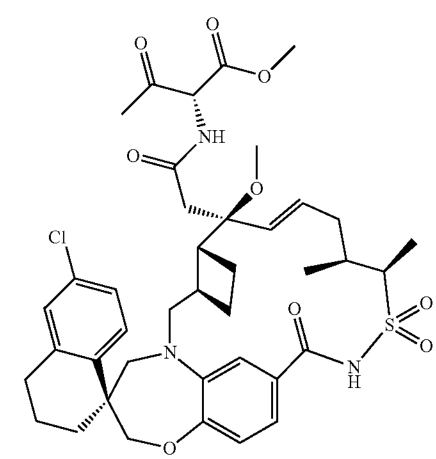 | methyl (2R)-2-(((((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)amino)-3-oxobutanoate | 752.2 (M − OMe) |

TABLE 2-continued

Examples Prepared by the General Methods

| Example Number | Structure | Name | MS Dat (M + 1)+ Unless Noted Otherwise |
|---|---|---|---|
| | AND | AND methyl (2S)-2-((((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetyl)amino)-3-oxobutanoate | |
| 100583 | 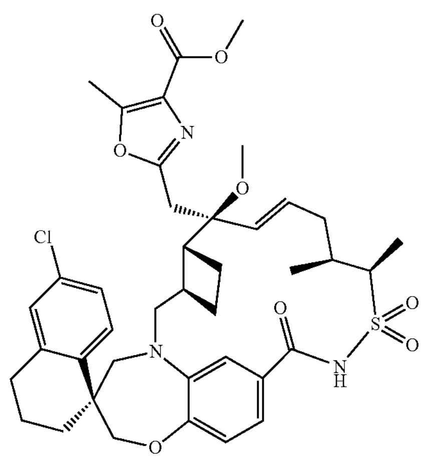 | methyl 2-(((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)methyl)-5-methyl-1,3-oxazole-4-carboxylate | 766.3 |
| 100584 | 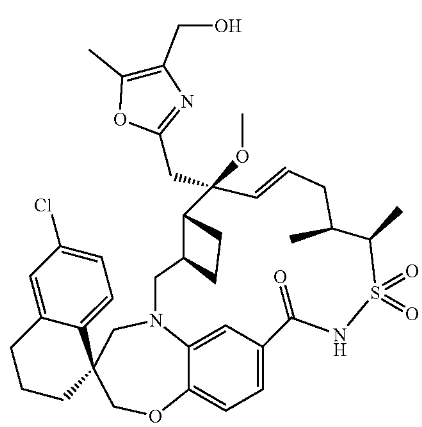 | (1S,3'R,6'R,7'S,8'E,11'S,12'R)-6-chloro-7'-((4-(hydroxymethyl)-5-methyl-1,3-oxazol-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 738.2 |

TABLE 2-continued

Examples Prepared by the General Methods

| Example Number | Structure | Name | MS Dat (M + 1)+ Unless Noted Otherwise |
|---|---|---|---|
| 100585 | 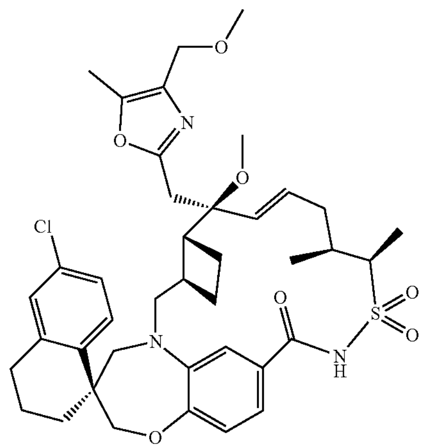 [SMILES: COCc1nc(C[C@]2(OC)/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)oc1C] | (1S,3'R,6'R,7'S,8'E,11'S,12'R)-6-chloro-7'-methoxy-7'-((4-(methoxymethyl)-5-methyl-1,3-oxazol-2-yl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 752.3 |
| 100586 | 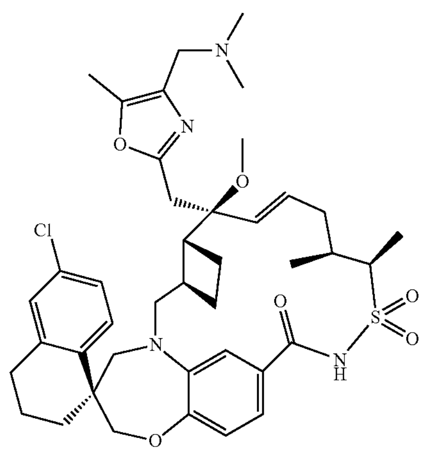 [SMILES: CO[C@@]1(Cc2nc(CN(C)C)c(C)o2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-((4-((dimethylamino)methyl)-5-methyl-1,3-oxazol-2-yl)methyl)-7'-methoxy-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 765.3 |
| 100587 | 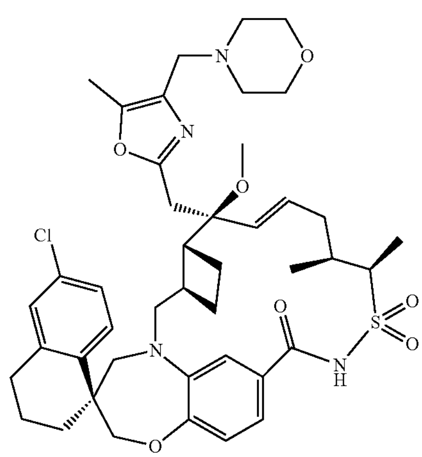 [SMILES: CO[C@@]1(Cc2nc(CN3CCOCC3)c(C)o2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((5-methyl-4-(4-morpholinylmethyl)-1,3-oxazol-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 807.3 |

TABLE 2-continued

Examples Prepared by the General Methods

| Example Number | Structure | Name | MS Dat (M + 1)+ Unless Noted Otherwise |
|---|---|---|---|
| 100588 | 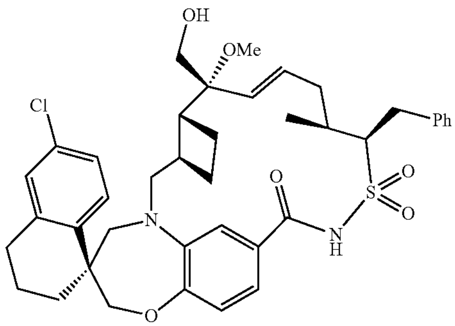 [SMILES: CO[C@]1(CO)/C=C/C[C@H](C)[C@@H](Cc2ccccc2)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-12'-benzyl-6-chloro-7'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 742.2 (M + Na) |
| | OR | OR | |
| | | (1S,3'R,6'R,7'S,8'E,11'S,12'R)-12'-benzyl-6-chloro-7'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'R,8'E,11'S,12'S)-12'-benzyl-6-chloro-7'-(hydroxymethyl)-7'-methoxy-11'-methyl-3,4-dihydro-2H,15'H-spiro[naphthalene-1,22'-20]oxa[13]thia[1,14]diazatetracyclo[14.7.2.0~3,6~.0~19,24~]pentacosa[8,16,18,24]tetraen]-15'-one 13',13'-dioxide | |
| | OR | OR | |
| | | (1S,3'R,6'R,7'S,8'E,11'S,12'S)-12'-benzyl-6-chloro-7'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100589 | 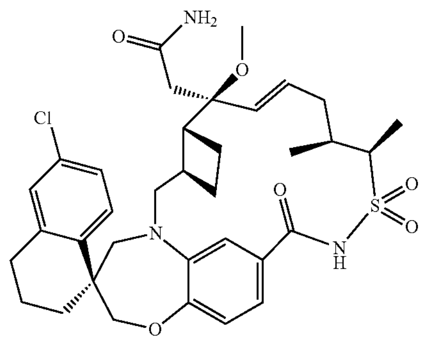 [SMILES: CO[C@@]1(CC(N)=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 2-((1S,3'R,6'R,7'S,8'E,11'S,12'R)-6-chloro-7'-methoxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)acetamide | 638.3 (M − OMe) |
| 100590 | 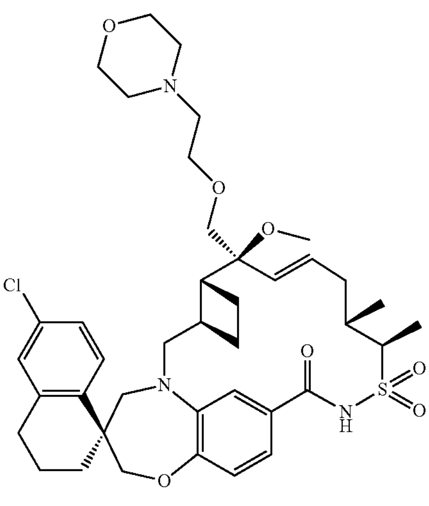 [SMILES: CO[C@@]1(COCCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-11',12'-dimethyl-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 756.2 |
| 100591 | 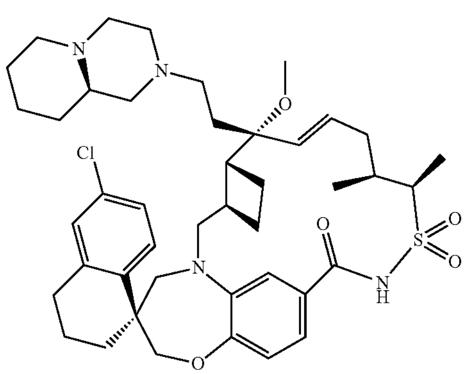 [SMILES: CO[C@]1(CCN2CCN3CCCC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,7'S,8'E,11'S,12'R)-6-chloro-7'-methoxy-11',12'-dimethyl-7'-(2-((9aR)-octahydro-2H-pyrido[1,2-a]pyrazin-2-yl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 779.3 |

TABLE 2-continued

Examples Prepared by the General Methods

| Example Number | Structure | Name | MS Dat (M + 1)+ Unless Noted Otherwise |
|---|---|---|---|
| 100592 | 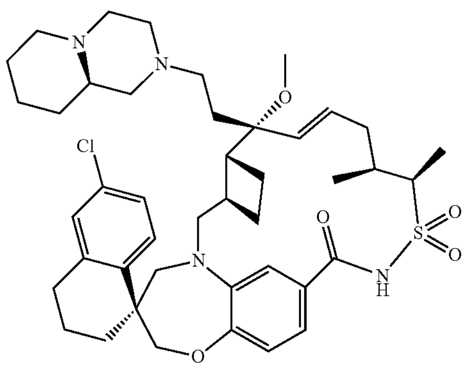 [SMILES: CO[C@]1(CCN2CCN3CCCC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,11'S,12'R)-6-chloro-7'-methoxy-11',12'-dimethyl-7'-(2-((9aR)-octahydro-2H-pyrido[1,2-a]pyrazin-2-yl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 781.2 |
| 100593 | 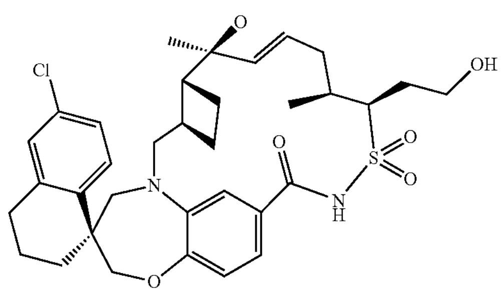 [SMILES: C[C@H]1C/C=C/[C@](C)(O)[C@@H]2CC[C@H]2CN2C[C@@]3(CCCc4cc(Cl)ccc43)COc3ccc(cc32)C(=O)NS(=O)(=O)[C@@H]1CCO] | (1S,3'R,6'R,7'S,8'E,11'S,12'R)-6-chloro-12'-(2-hydroxyethyl)-7'-methoxy-7',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.2 |
| | OR | OR | |
| | | (1S,3'R,6'R,7'R,8'E,11'S,12'R)-6-chloro-12'-(2-hydroxyethyl)-7'-methoxy-7',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100594 | 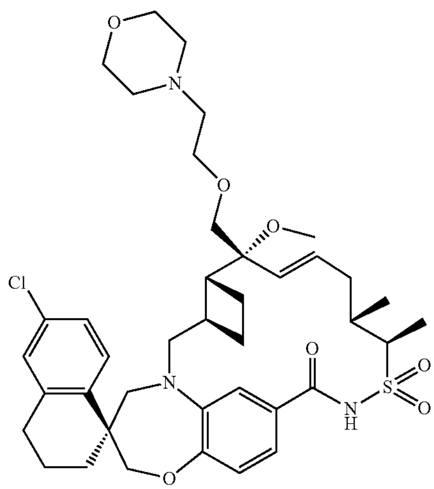 [SMILES: CO[C@]1(COCCN2CCOCC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-7'-methoxy-11',12'-dimethyl-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 756.2 |
| 100595 | 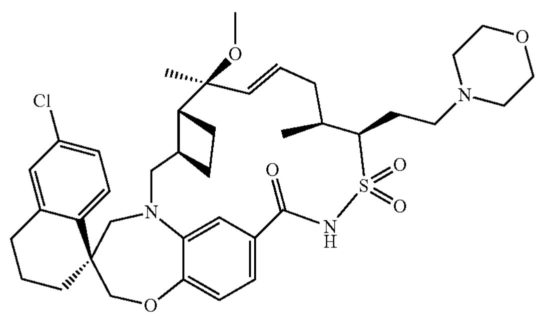 [SMILES: CO[C@@]1(C)/C=C/C[C@H](C)[C@@H](CCN2CCOCC2)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-7'-methoxy-7',11'-dimethyl-12'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.3 |
| | OR | OR | |
| | | (1S,3'R,6'R,7'R,8'E,11'S,12'R)-6-chloro-7'-methoxy-7',11'-dimethyl-12'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100596 | 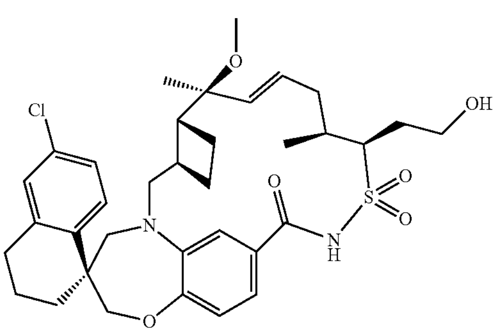 [SMILES: CO[C@@]1(C)/C=C/C[C@H](C)[C@@H](CCO)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'S,8'E,11'S,12'R)-6-chloro-12'-(2-hydroxyethyl)-7'-methoxy-7',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 657.2 |

TABLE 2-continued

Examples Prepared by the General Methods

| Example Number | Structure | Name | MS Dat (M + 1)+ Unless Noted Otherwise |
|---|---|---|---|
| | OR 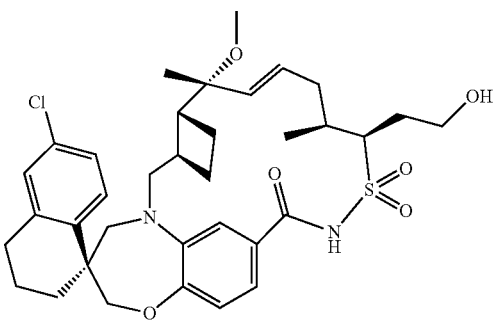 | OR (1S,3'R,6'R,7'R,8'E,11'S,12'R)-6-chloro-12'-(2-hydroxyethyl)-7'-methoxy-7',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |
| 100597 | 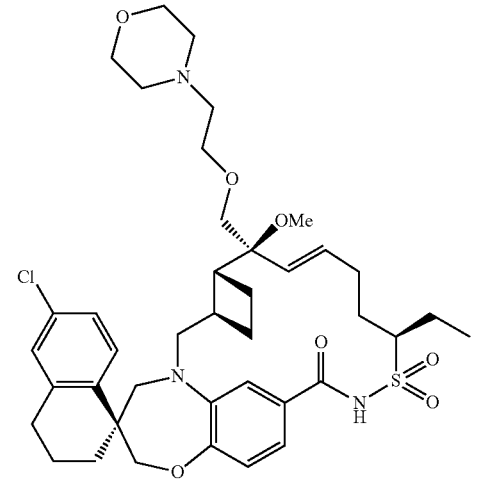 | (1S,3'R,6'R,7'S,8'E,12'R)-6-chloro-12'-ethyl-7'-methoxy-7'-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 756.2 |
| | OR 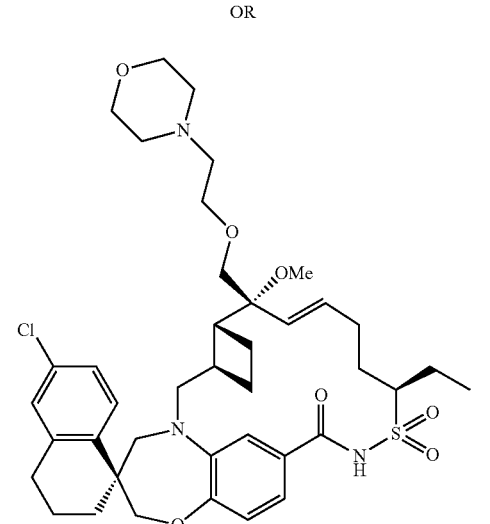 | OR (1S,3'R,6'R,7'R,8'E,12'R)-6-chloro-12'-ethyl-7'-methoxy-7-((2-(4-morpholinyl)ethoxy)methyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Data (M + 1)+ Unless Noted Otherwise |
|---|---|---|---|
| 100598 | 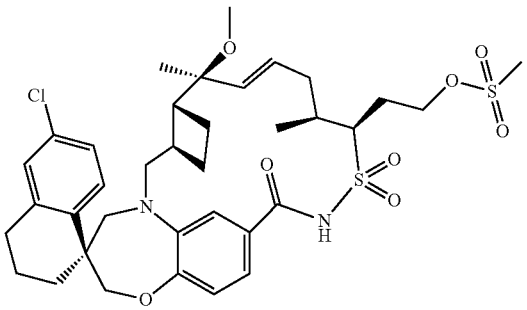 OR 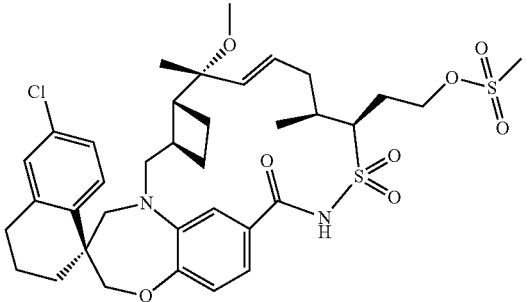 | 2-((1S,3'R,6'R,7'S,8'E,11'S,12'R)-6-chloro-7'-methoxy-7',11'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate OR 2-((1S,3'R,6'R,7'R,8'E,11'S,12'R)-6-chloro-7'-methoxy-7',11'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-12'-yl)ethyl methanesulfonate | 703.3 (M − OMe) |
| 100599 | 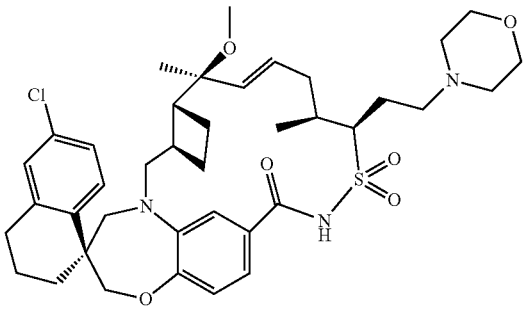 OR 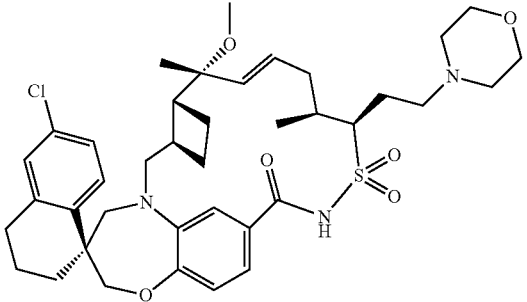 | (1S,3'R,6'R,7'S,8'E,11'S,12'R)-6-chloro-7'-methoxy-7',11'-dimethyl-12'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-methoxy-7',11'-dimethyl-12'-(2-(4-morpholinyl)ethyl)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 726.2 |

TABLE 2-continued

Examples Prepared by the General Methods

| Example Number | Structure | Name | MS Dat (M + 1)+ Unless Noted Otherwise |
|---|---|---|---|
| 100600 | 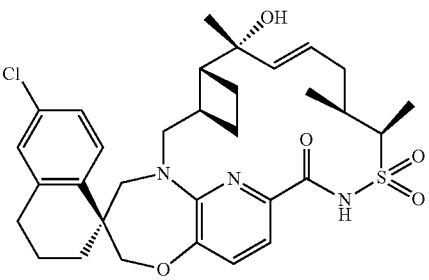 [SMILES: C[C@@H]1[C@@H](C)C/C=C/[C@@](C)(O)[C@@H]2CC[C@H]2CN2C[C@@]3(CCCc4cc(Cl)ccc43)COc3ccc(nc32)C(=O)NS1(=O)=O] | (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 614.0 |
| | OR | OR | |
| | 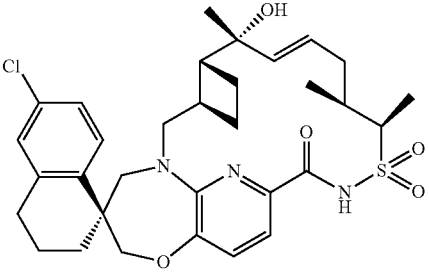 [SMILES: C[C@@H]1[C@@H](C)C/C=C/[C@@](C)(O)[C@@H]2CC[C@H]2CN2C[C@@]3(CCCc4cc(Cl)ccc43)COc3ccc(nc32)C(=O)NS1(=O)=O] | (1S,3'R,6'R,7'R,8'E,11'S,12'R)-6-chloro-7'-hydroxy-7',11',12'-trimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | |
| 100601 | 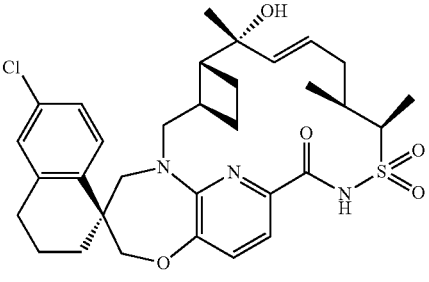 [SMILES: C[C@@H]1[C@@H](C)C/C=C/[C@@](C)(O)[C@@H]2CC[C@H]2CN2C[C@@]3(CCCc4cc(Cl)ccc43)COc3ccc(nc32)C(=O)NS1(=O)=O] | (1S,3'R,6'R,7'R,8'E,11'S,12'R)-6-chloro-7'-hydroxy-7',11',12'-trimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | 614.0 |
| | OR | OR | |
| | 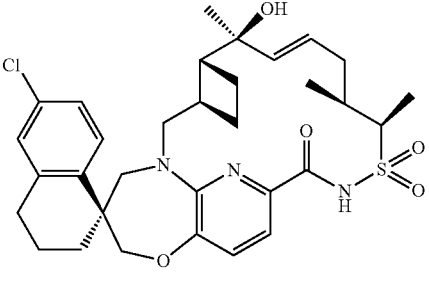 [SMILES: C[C@@H]1[C@@H](C)C/C=C/[C@](C)(O)[C@@H]2CC[C@H]2CN2C[C@@]3(CCCc4cc(Cl)ccc43)COc3ccc(nc32)C(=O)NS1(=O)=O] | (1S,3'R,6'R,7'S,8'E,11'S,12'R)-6-chloro-7'-hydroxy-7',11',12'-trimethyl-3,4-dihydro-2H,15'H-spiro[naphthalene-1,22'-[20]oxa[13]thia[1,14,25]triazatetracyclo[14.7.2.0~3,6~.0~19,24~]pentacosa[8,16,18,24]tetraen]-15'-one 13',13'-dioxide | |

TABLE 2-continued

Examples Prepared by the General Methods

| Example Number | Structure | Name | MS Dat (M + 1)+ Unless Noted Otherwise |
|---|---|---|---|
| 100602 | 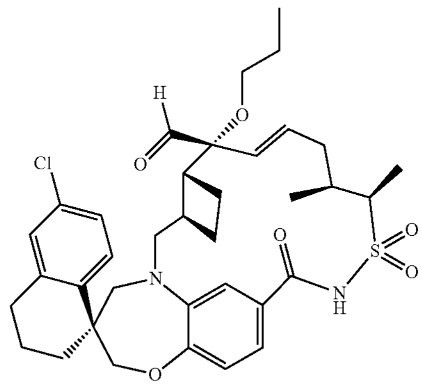 [SMILES: CCCO[C@]1(C=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-11',12'-dimethyl-15'-oxo-7'-propoxy-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | 669.3 |
| 100603 | 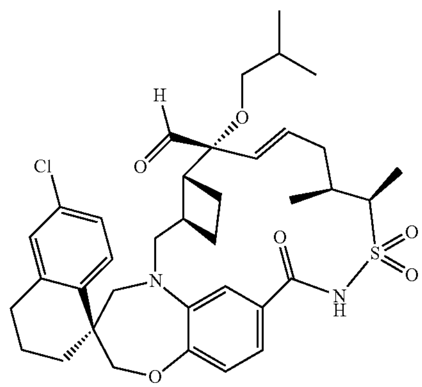 [SMILES: CC(C)CO[C@]1(C=O)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | (1S,3'R,6'R,7'R,8'E,11'S,12'R)-6-chloro-11',12'-dimethyl-7'-(2-methylpropoxy)-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraene]-7'-carbaldehyde 13',13'-dioxide | 683.3 |
| 100604 | 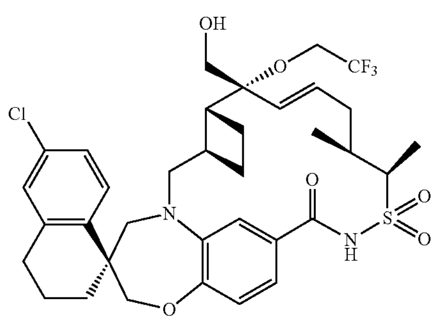 [SMILES: C[C@@H]1[C@@H](C)C/C=C/[C@@](CO)(OCC(F)(F)F)[C@@H]2CC[C@H]2CN2C[C@@]3(CCCc4cc(Cl)ccc43)COc3ccc(cc32)C(=O)NS1(=O)=O] | (1S,3'R,6'R,7'R,8'E,11'S,12'R)-6-chloro-7'-(hydroxymethyl)-11',12'-dimethyl-7'-(2,2,2-trifluoroethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 711.2 |
| | OR | OR | |
| | | (1S,3'R,6'R,7'S,8'E,11'S,12'R)-6-chloro-7'-(hydroxymethyl)-11',12'-dimethyl-7'-(2,2,2-trifluoroethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.2 |

TABLE 2-continued

Examples Prepared by the General Methods

| Example Number | Structure | Name | MS Dat (M + 1)+ Unless Noted Otherwise |
|---|---|---|---|
| 100605 | 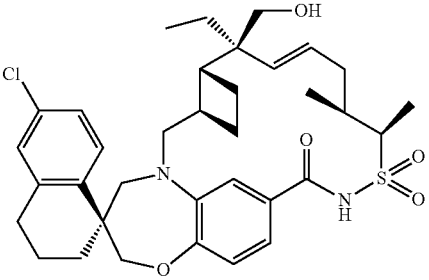 OR 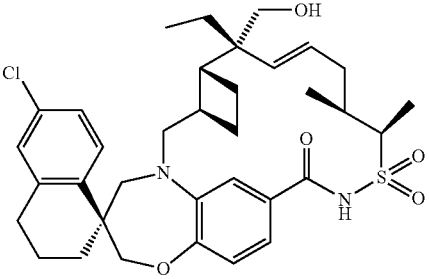 | (1S,3'R,6'R,7'S,8'E,11'S,12'R)-6-chloro-7'-ethyl-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide OR (1S,3'R,6'R,7'R,8'E,11'S,12'R)-6-chloro-7'-ethyl-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide | 641.2 |

General Synthesis of Intermediates

N-Methyl-2-morpholinoethanamine

Step 1: tert-butyl (2-morpholinoethyl)carbamate

A 2-dram vial was charged with di-t-butyldicarbonate (0.459 mL, 2.000 mmol), a magnetic stir bar, and indium (III) chloride (4.42 mg, 0.020 mmol). 4-(2-Aminoethyl) morpholine (0.262 mL, 2 mmol) was then added to the stirring solution. After 1 min, the solution was diluted with EtOAc (2 mL). Water (3 mL) was added and the layers were partitioned. The organic layer was washed with water (2×5 mL), dried over MgSO₄, filtered, and concentrated to afford tert-butyl (2-morpholinoethyl)carbamate as a clear oil. The material was carried forward without further purification.

Step 2: N-methyl-2-morpholinoethanamine

A 125 mL three-neck flask with stir bar was heated with a heat gun under vacuum. Under a positive pressure of nitrogen, a reflux condenser was attached to the middle neck. The flask was charged with tetrahydrofuran (25.00 mL) and lithium aluminium hydride (2 M solution in THF, 0.84 mL, 20 mmol), tert-butyl (2-morpholinoethyl)carbamate (0.46 g, 2 mmol) was added as a solution in THF (8 mL) and the resulting homogenous mixture was heated to reflux for 18 h. The reaction mixture was cooled to 0° C. in an ice-water bath and quenched with sodium sulfate decahydrate. The resulting mixture was filtered through Celite, rinsing with THF. Concentration of the filtrate afforded N-methyl-2-morpholinoethanamine which was used without further purification.

(3S)-1-Cyclobutyl-3-methylhex-5-ene-2-sulfonamide

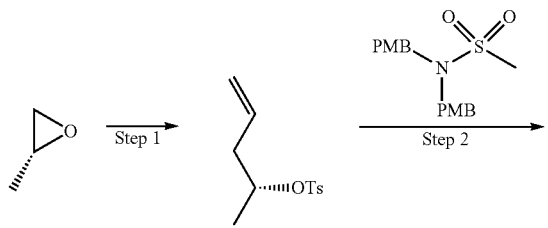

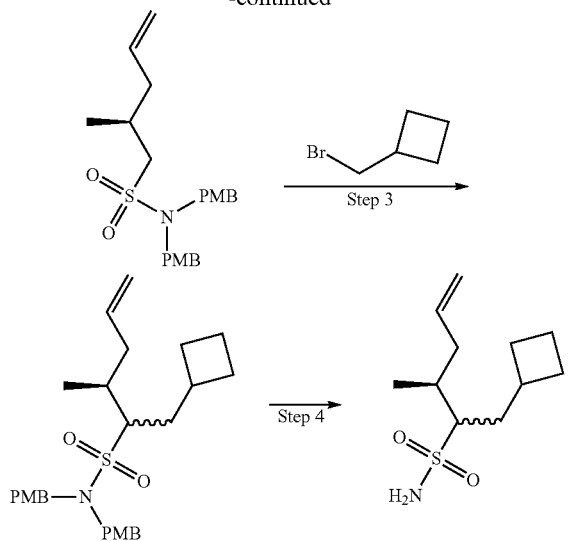

Step 1. (R)-pent-4-en-2-yl 4-methylbenzenesulfonate

To a solution of vinyl magnesium bromide (226 g, 1722 mmol, 1.0 M in THF) was added to CuI (29.5 g, 155 mmol, 0.09 equiv) in THF (200 mL) at −40° C. The reaction mixture was stirred for 30 min followed by a cooled solution of (R)-2-methyloxirane (100 g, 1722 mmol) in THF (500 mL) was added drop wise at the same temperature. The resulting reaction mixture was stirred at −40° C. for 1 h. After the reaction was completed (monitored by TLC), triethylamine (261 g, 2583 mmol) was added at −40° C. After 30 min, cooled solution of p-toluene sulfonyl chloride (427 g, 2238 mmol) in THF (1000 mL) was added slowly to the reaction mixture at same temperature and stirred for 16 h at ambient temperature. After the reaction was completed (monitored by TLC), the reaction mixture was quenched with 1.5 N HCl solution until pH 3.0. The resulting reaction mixture was filtered through celite pad, layers were separated and the aqueous layer was re-extracted with ethyl acetate (2×2000 mL). The combined organic layers were washed with water (800 mL), brine (500 mL), dried over Na$_2$SO$_4$ and concentrated under reduced pressure. The crude product was purified on flash column chromatography (silica gel, 230-400 mesh) using 1% to 2% ethyl acetate in petroleum ether to provide (R)-pent-4-en-2-yl 4-methylbenzenesulfonate (207 g, 50% yield) as a colourless liquid. $^1$H NMR (300 MHz, Chloroform-d) δ 7.83-7.75 (m, 2H), 7.37-7.31 (m, 2H), 5.69-5.52 (m, 1H), 5.09-5.04 (m, 1H), 5.01 (t, J=1.3 Hz, 1H), 4.65 (h, J=6.3 Hz, 1H), 2.45 (s, 3H), 2.37-2.22 (m, 2H), 1.26 (d, J=6.3 Hz, 3H).

Step 2: (S)—N,N-bis(4-methoxybenzyl)-2-methyl-pent-4-ene-1-sulfonamide

To a stirred solution of N,N-bis(4-methoxybenzyl)methanesulfonamide (207 g, 617 mmol) in THF (2000 mL) was added n-BuLi (321 mL, 802 mmol, 2.5 M in hexane) at −78° C. The resulting reaction mixture was stirred for 1 h at same temperature followed by (R)-pent-4-en-2-yl 4-methylbenzenesulfonate (206 g, 858 mmol) in THF (400 mL) was added dropwise at −78° C. The reaction mixture was allowed to warm to ambient temperature and stirred for 16 h. After the reaction was complete (monitored by TLC), the reaction mixture was quenched with saturated ammonium chloride solution, layers were separated and the aqueous layer was extracted with ethyl acetate (2×2000 mL). The combined organic layers were washed with water (1000 mL), brine (600 mL), dried over Na$_2$SO$_4$, filtered and concentrated under reduced pressure. The crude product was purified by flash column chromatography (silica gel, 230-400 mesh) using 2% to 4% ethyl acetate in petroleum ether to provide (S)—N,N-bis(4-methoxybenzyl)-2-methylpent-4-ene-1-sulfonamide (105 g, 42% yield) as a colourless liquid. $^1$H NMR (400 MHz, Chloroform-d) δ 7.25-7.20 (m, 4H), 6.92-6.85 (m, 4H), 5.70 (ddt, J=17.2, 10.2, 7.1 Hz, 1H), 5.12-4.98 (m, 2H), 4.32-4.19 (m, 4H), 3.83 (s, 6H), 2.90-2.80 (m, 1H), 2.66-2.55 (m, 1H), 2.27-2.17 (m, 1H), 2.17-2.02 (m, 2H), 1.11 (d, J=6.7, 3H).

Step 3. (3S)-1-cyclobutyl-N,N-bis(4-methoxybenzyl)-3-methylhex-5-ene-2-sulfonamide To a stirred solution of (S)—N,N-bis(4-methoxybenzyl)-2-methylpent-4-ene-1-sulfonamide (40 g, 99 mmol) in THF (400 mL) was added n-butyl lithium (86.73 mL, 139 mmol, 1.6 M in hexane) at −78° C. The reaction mixture was allowed to stir for 20 min at same temperature. (Bromomethyl)cyclobutane (59.1 g, 396 mmol) was added dropwise at same temperature and stirred for 30 min. The resulting reaction mixture was allowed to warm to ambient temperature and stirred for 16 h. After the reaction was complete (monitored by TLC), the reaction mixture was quenched with saturated ammonium chloride solution, layers were separated and the aqueous layer was extracted with ethyl acetate (2×400 mL). The combined organic layers were washed with water (100 mL), brine (100 mL), dried over Na$_2$SO$_4$, filtered and concentrated under reduced pressure. The crude product was purified by flash column chromatography (silica gel, 230-400 mesh) using 2% to 4% ethyl acetate in petroleum ether as an eluent to provide (3S)-1-cyclobutyl-N,N-bis(4-methoxybenzyl)-3-methylhex-5-ene-2-sulfonamide (33 g, 71% yield) as colourless liquid. $^1$H NMR (300 MHz, Chloroform-d) δ 7.30-7.16 (m, 4H), 6.92-6.80 (m, 4H), 5.13-4.95 (m, 2H), 4.40-4.20 (m, 4H), 3.81 (s, 6H), 2.87-2.63 (m, 2H), 2.16-1.72 (m, 6H), 1.65-1.24 (m, 6H), 1.15-0.81 (m, 3H).

Step 4: (3S)-1-cyclobutyl-3-methylhex-5-ene-2-sulfonamide

To a stirred solution of (3S)-1-cyclobutyl-N,N-bis(4-methoxybenzyl)-3-methylhex-5-ene-2-sulfonamide (33 g, 70.0 mmol), anisole (33 mL) and TFA (33 mL) at 0° C. The resulting reaction mixture was heated to 40° C. for 16 h. After the reaction was complete (monitored by TLC), volatiles were removed under vacuum and the crude was purified by flash column chromatography (silica gel, 230-400 mesh) using 15% to 20% ethyl acetate in petroleum ether as an eluent to yield (3S)-1-cyclobutyl-3-methylhex-5-ene-2-sulfonamide which was further purified by HPLC [Column Sunfire C18 (250 mm×19 mm) 5 μm, 0.1% formic acid in water and acetonitrile, 90 mg/injection, ELSD detector, run time 35 min.] to provide (3S)-1-cyclobutyl-3-methylhex-5-ene-2-sulfonamide (10.3 g, 64% yield) as a colourless liquid. MS (ESI, −ve ion) m/z 230 (M−H)$^-$. $^1$H NMR (400 MHz, DMSO-d$_6$) δ 6.78 (d, J=9.1 Hz, 2H), 5.73 (tdd, J=12.4, 10.1, 6.5 Hz, 1H), 5.05 (tt, J=17.7, 4.5 Hz, 2H), 2.70-2.54 (m, 2H), 2.30 (p, J=7.1 Hz, 1H), 2.00 (dq, J=26.6, 7.3 Hz, 4H), 1.90-1.72 (m, 3H), 1.58 (dtt, J=26.6, 17.4, 8.5 Hz, 3H), 0.94 (ddd, J=14.1, 7.1, 2.1 Hz, 3H).

1-(But-2-yn-1-yl)piperazin-2-one

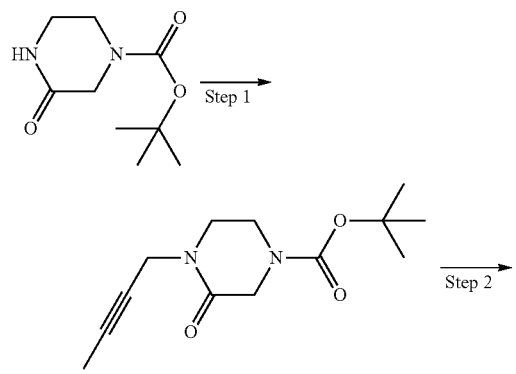

Step 1: tert-butyl 4-(but-2-yn-1-yl)-3-oxopiperazine-1-carboxylate

To a cooled (0° C.) slurry of 60% sodium hydride in mineral oil (0.600 g, 15.00 mmol) in THF (40 mL) was added a solution of 1-Boc-3-oxopiperazine (2.0 g, 9.99 mmol; Combi-Blocks, San Diego, Calif.) in N, N-dimethylformamide (10 mL). After complete addition the reaction was allowed to warm to room temperature for 30 min. The mixture was cooled to 0° C. and treated with 1-bromo-2-butyne (1.2 mL, 13.71 mmol). The reaction was allowed to warm to rt for 30 min. The reaction was quenched with saturated NH$_4$Cl solution, partitioned between EtOAc/brine and the aqueous layer was extracted with EtOAc (3×). The combined organic layers were dried over Na$_2$SO$_4$, filtered and the filtrate was concentrated under reduced pressure to give tert-butyl 4-(but-2-yn-1-yl)-3-oxopiperazine-1-carboxylate as a light-brown liquid.

Step 2: 1-(but-2-yn-1-yl)piperazin-2-one

To a room temperature solution of tert-butyl 4-(but-2-yn-1-yl)-3-oxopiperazine-1-carboxylate (2.52 g, 9.99 mmol) in DCM (40 mL) was added trifluoroacetic acid (10 mL, 135 mmol) via syringe. After 1 h the solvent was removed in vacuo and the residue was dissolved in DCM. The solution was loaded onto an Si-propylsulfonic acid (Silicycle) cartridge eluting with DCM, MeOH then 2 M NH$_3$ in MeOH to give 1-(but-2-yn-1-yl)piperazin-2-one (1.269 g, 83% yield) as a brown oil. $^1$H NMR (400 MHz, CDCl$_3$) δ 4.20 (q, J=2.41 Hz, 2H), 3.52 (s, 2H), 3.42 (t, J=5.48 Hz, 2H), 3.12 (t, J=5.58 Hz, 2H), 1.81 (t, J=2.45 Hz, 3H).

The intermediates shown in the following Table 3 were prepared analogous to the method described above for 1-(but-2-yn-1-yl)piperazin-2-one.

TABLE 3

| Starting Material | Product | Name | MS Data (M + 1)$^+$ |
|---|---|---|---|
| Br~O~O~ | ~O~O~N(piperazinone)NH | 1-(2-(2-methoxyethoxy)ethyl)piperazin-2-one | 203.3 |
| Me$_2$N-CH$_2$CH$_2$-Br · HBr (Matrix Scientific) | Me$_2$N-CH$_2$CH$_2$-N(piperazinone)NH | 1-(2-(dimethylamino)ethyl)piperazin-2-one | 172.1 |

-continued

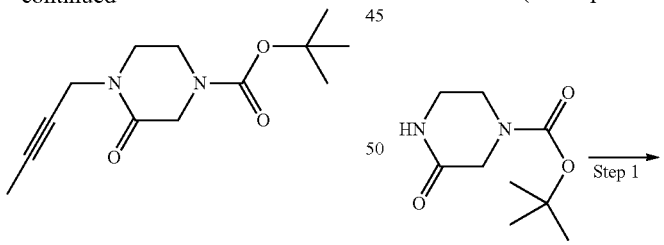

1-(2-Morpholinoethyl)piperazin-2-one

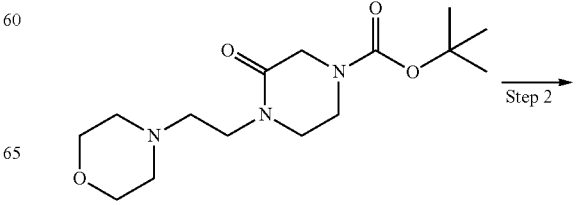

1893

-continued

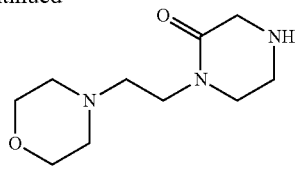

Step 1: tert-butyl 4-(2-morpholinoethyl)-3-oxopiperazine-1-carboxylate

To a room temperature suspension of 1-boc-3-oxopiperazine (2.0 g, 9.99 mmol; Combi-Blocks, San Diego, Calif.), tetrabutylammonium bromide (0.620 g, 1.923 mmol) and potassium hydroxide (1.42 g, 25.3 mmol) in THF (25 mL) was added 4-(2-bromoethyl)morpholine hydrobromide (2.78 g, 10.11 mmol; Combi-Blocks, San Diego, Calif.) as a solid. After stirring at room temperature overnight the mixture was filtered and the filtrate was evaporated onto silica gel and purified by flash chromatography (Isco, (80 gram)) eluting with 2 M $NH_3$ in MeOH:$CH_2Cl_2$ (0:1-1:9) to give tert-butyl 4-(2-morpholinoethyl)-3-oxopiperazine-1-carboxylate (1.923 g, 61% yield) as a solid. MS (ESI, +ve ion) m/z 314.3 (M+1)$^+$.

Step 2: 1-(2-morpholinoethyl)piperazin-2-one

To a room temperature solution of tert-butyl 4-(2-morpholinoethyl)-3-oxopiperazine-1-carboxylate (1.84 g, 5.87 mmol) in DCM (15 mL) was added trifluoroacetic acid (5 mL). After 3 h the solvent was removed under reduced pressure and the residue was dissolved in DCM and loaded onto a plug of Si-propylsulfonic acid (Silicycle) and the plug washed with 1:1 MeOH/DCM to 2 M $NH_3$ in MeOH/DCM. The fractions containing desired product were concentrated under reduced pressure to give 1-(2-morpholinoethyl)piperazin-2-one (1.52 g) as a yellow oil. MS (ESI, +ve ion) m/z 214.1 (M+1)$^+$.

(2S,3S)-3-Methyl-1-phenylhex-5-ene-2-sulfonamide AND (2R,3S)-3-methyl-1-phenylhex-5-ene-2-sulfonamide

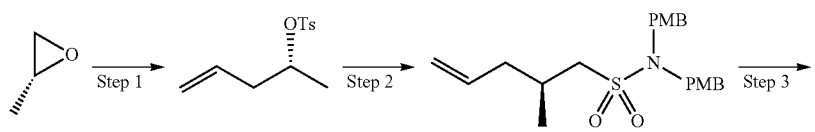

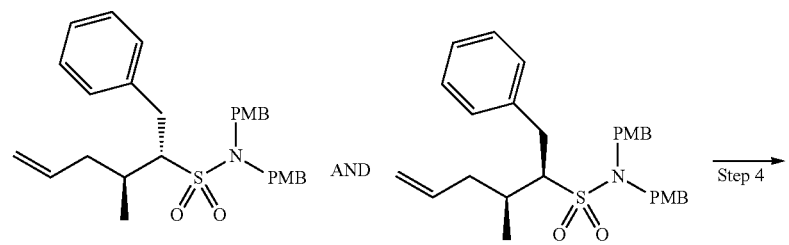

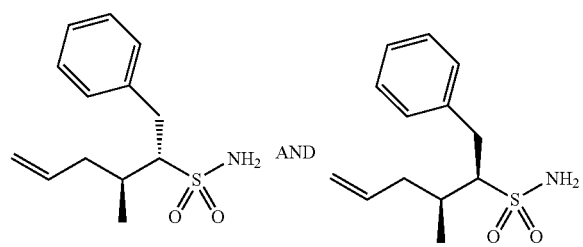

Step 1: (R)-pent-4-en-2-yl 4-methylbenzenesulfonate

To a solution of vinyl magnesium bromide (226 g, 1722 mmol, 1.0 M in THF) was added to CuI (29.5 g, 155 mmol) in THF (200 mL) at −40° C. The reaction mixture was stirred for 30 min followed by a cooled solution of (R)-2-methyloxirane (100 g, 1722 mmol) in THF (500 mL) was added drop wise at the same temperature. The resulting reaction mixture was stirred at −40° C. for 1 h. After the reaction was completed (monitored by TLC), triethylamine (261 g, 2583 mmol) was added at −40° C. After 30 min, cooled solution of p-toluene sulfonyl chloride (427 g, 2238 mmol) in THF (1000 mL) was added slowly to the reaction mixture at same temperature and stirred for 16 h at ambient temperature. After the reaction was completed (monitored by TLC), the reaction mixture was quenched with 1.5 N HCl solution until pH 3.0. The resulting reaction mixture was filtered through celite pad, layers were separated and the aqueous layer was re-extracted with ethyl acetate (2×2000 mL). The combined organic layers were washed with water (800 mL), brine (500 mL), dried over $Na_2SO_4$ and concentrated under reduced pressure. The crude product was purified on flash column chromatography (silica gel, 230-400 mesh) using 1% to 2% ethyl acetate in petroleum ether to provide (R)-pent-4-en-2-yl 4-methylbenzenesulfonate (207 g, 50% yield) as a colourless liquid. $^1$H NMR (300 MHz, Chloroform-d) δ 7.83-7.75 (m, 2H), 7.37-7.31 (m, 2H), 5.69-5.52 (m, 1H), 5.09-5.04 (m, 1H), 5.01 (t, J=1.3 Hz, 1H), 4.65 (h, J=6.3 Hz, 1H), 2.45 (s, 3H), 2.37-2.22 (m, 2H), 1.26 (d, J=6.3 Hz, 3H).

Step 2: (S)—N,N-bis(4-methoxybenzyl)-2-methylpent-4-ene-1-sulfonamide

To a stirred solution of N,N-bis(4-methoxybenzyl)methanesulfonamide (207 g, 617 mmol, 1.0 equiv) in THF (2000 mL) was added n-BuLi (321 mL, 802 mmol, 2.5 M in hexane) at −78° C. The resulting reaction mixture was stirred for 1 h at same temperature followed by (R)-pent-4-en-2-yl 4-methylbenzenesulfonate (206 g, 858 mmol) in THF (400 mL) was added dropwise at −78° C. The reaction mixture was allowed to warm to ambient temperature and stirred for 16 h. After the reaction was complete (monitored by TLC), the reaction mixture was quenched with saturated ammonium chloride solution, layers were separated and the aqueous layer was extracted with ethyl acetate (2×2000 mL). The combined organic layers were washed with water (1000 mL), brine (600 mL), dried over $Na_2SO_4$, filtered and concentrated under reduced pressure. The crude product was purified by flash column chromatography (silica gel, 230-400 mesh) using 2% to 4% ethyl acetate in petroleum ether to provide (S)—N,N-bis(4-methoxybenzyl)-2-methylpent-4-ene-1-sulfonamide (105 g, 42.2% yield) as a colourless liquid. $^1$H NMR (400 MHz, Chloroform-d) δ 7.25-7.20 (m, 4H), 6.92-6.85 (m, 4H), 5.70 (ddt, J=17.2, 10.2, 7.1 Hz, 1H), 5.12-4.98 (m, 2H), 4.32-4.19 (m, 4H), 3.83 (s, 6H), 2.90-2.80 (m, 1H), 2.66-2.55 (m, 1H), 2.27-2.17 (m, 1H), 2.17-2.02 (m, 2H), 1.11 (d, J=6.7, 3H).

Step 3: (2S,3S)—N,N-bis(4-methoxybenzyl)-3-methyl-1-phenylhex-5-ene-2-sulfonamide AND (2R,3 S)—N,N-bis(4-methoxybenzyl)-3-methyl-1-phenylhex-5-ene-2-sulfonamide To a stirred solution of (S)—N,N-bis(4-methoxybenzyl)-2-methylpent-4-ene-1-sulfonamide (65 g, 161 mmol) in THF (650 mL) was added n-butyl lithium (140.9 mL, 226 mmol, 1.6 M in hexane) at −78° C. The reaction mixture was stirred for 20 min at same temperature. (Bromomethyl)benzene (110 g, 644 mmol) was added dropwise at same temperature and stirred for 30 min at −78° C. The resulting reaction mixture was warmed to ambient temperature and stirred for 1 h. After the reaction was complete (monitored by TLC), the reaction mixture was quenched with saturated ammonium chloride solution, layers were separated and the aqueous layer was extracted with ethyl acetate (2×500 mL). The combined organic layers were washed with water (300 mL), brine (100 mL), dried over $Na_2SO_4$, filtered and concentrated under reduced pressure. The crude product was purified by flash column chromatography (silica gel, 230-400 mesh) using 2% to 4% ethyl acetate in petroleum ether as an eluent to provide (2S,3S)—N,N-bis(4-methoxybenzyl)-3-methyl-1-phenylhex-5-ene-2-sulfonamide AND (2R,3S)—N,N-bis(4-methoxybenzyl)-3-methyl-1-phenylhex-5-ene-2-sulfonamide (60.5 g, 76% yield) as a colourless liquid. $^1$H NMR (400 MHz, Chloroform-d) δ 7.28-7.14 (m, 7H), 7.02-6.92 (m, 2H), 6.90-6.84 (m, 4H), 5.60-5.52 (m, 1H), 5.04-4.82 (m, 2H), 4.54-4.32 (m, 2H), 4.10-3.96 (m, 2H), 3.84-3.80 (m, 6H), 3.28-3.12 (m, 2H), 2.98-2.88 (m, 1H), 2.42-2.08 (m, 1H), 2.00-1.76 (m, 2H), 1.18-1.04 (m, 3H).

Step 4: (2S,3S)-3-methyl-1-phenylhex-5-ene-2-sulfonamide AND (2R,3 S)-3-methyl-1-phenylhex-5-ene-2-sulfonamide To a stirred solution of (2S,3S)—N,N-bis(4-methoxybenzyl)-3-methyl-1-phenylhex-5-ene-2-sulfonamide AND (2R,3S)—N,N-bis(4-methoxybenzyl)-3-methyl-1-phenylhex-5-ene-2-sulfonamide (60 g, 122 mmol) in anisole (99 g, 915 mmol) was added TFA (148 g, 1298 mmol) at 0° C. The resulting reaction mixture was heated to 40° C. for 16 h. After the reaction was completed (monitored by TLC), volatiles were removed under reduced pressure and the crude was purified by flash column chromatography (silica gel, 230-400 mesh) using 15% to 20% ethyl acetate in petroleum ether as an eluent to provide (2S,3S)-3-methyl-1-phenylhex-5-ene-2-sulfonamide AND (2R,3S)-3-methyl-1-phenylhex-5-ene-2-sulfonamide (21.5 g, 70% yield) as liquid. MS (ESI, −ve ion) m/z 254.2 (M−1)$^-$. $^1$H NMR (400 MHz, DMSO-d$_6$) δ 7.37-7.15 (m, 5H), 6.94-6.86 (m, 2H), 5.62-5.54 (m, 1H), 4.96-4.70 (m, 2H), 3.32-3.20 (m, 2H), 2.92-2.80 (m, 1H), 2.49-2.28 (m, 1H), 2.10-1.78 (m, 2H), 1.08-0.90 (m, 3H).

(2S,3S)-2,3-Dimethylpent-4-ene-1-sulfonamide

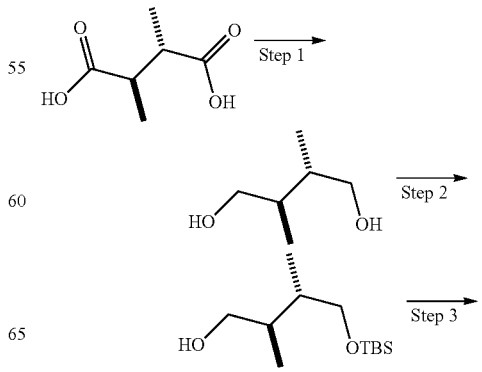

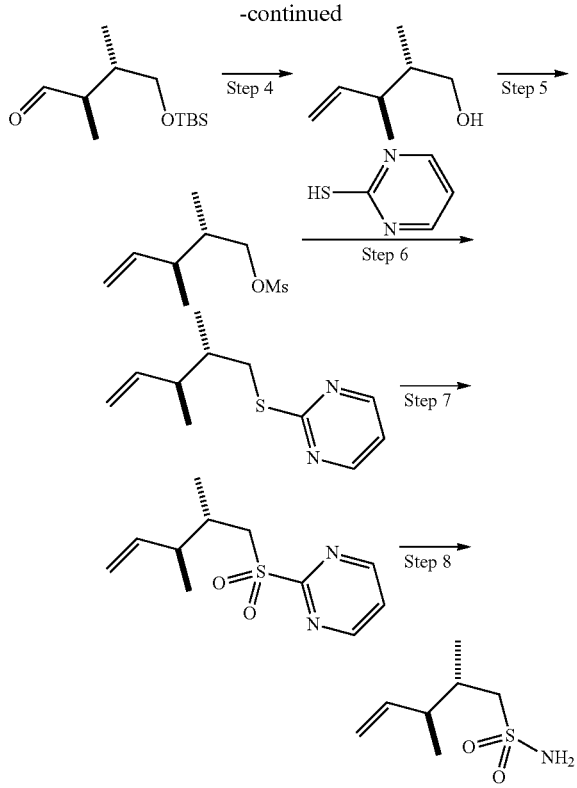

Step 1: meso-2,3-dimethylbutane-1,4-diol

A solution of meso-2,3-dimethylsuccinic acid (50.0 g, 342 mmol) in THF (700 mL) was cooled to 0° C. Lithium aluminum hydride (2.0 M solution in tetrahydrofuran, 428.0 mL, 855.0 mmol) was then cannulated into the addition funnel, and then added into the stirred cooled mixture dropwise over 15 min. After the addition was completed the reaction was allowed to warm to room temperature and stirred for 12 h under a nitrogen atmosphere. The reaction mixture was quenched with MeOH (350 mL) dropwise at 0° C. and then 20% KOH (150 mL) aqueous solution was added slowly. The reaction mixture was stirred at 0° C. for 20 min, EtOAc (1000 mL) was added and the organic phase was dried over MgSO$_4$ filtered and concentrated under reduced pressure to give meso-2,3-dimethylbutane-1,4-diol (40.0 g, 100% yield) which was used as such in next step. MS (ESI, +ve ion) m/z 119.2 (M+H)$^+$.

Step 2: rac-(2R,3S)-4-((tert-butyldimethylsilyl)oxy)-2,3-dimethylbutan-1-ol

To a suspension of sodium hydride (60% dispersion in mineral oil, 20.31 g, 508.0 mmol) in THF (1200 mL) at 0° C. under a N$_2$ atmosphere was added a solution of meso-2,3-dimethylbutane-1,4-diol (40.0 g, 338.0 mmol) in THF (200 mL) dropwise over 20 min. After addition, the reaction was heated at 55° C. for 45 min and cooled to 0° C. The reaction mixture was treated with a solution of tert-butyldimethylsilyl chloride (51.0 g, 338.0 mmol) in THF (200 mL). The reaction was stirred at room temperature for 12 h. The reaction was quenched by adding saturated NH$_4$Cl (500 mL) and diluted with EtOAc (500 mL). The separated aqueous layer was extracted with EtOAc (3×500 mL) and the combined organic extracts was washed with brine, dried over MgSO$_4$, filtered and concentrated under reduced pressure to give rac-(2R,3S)-4-((tert-butyldimethylsilyl)oxy)-2,3-dimethylbutan-1-ol (70.0 g, 301.0 mmol, 89% yield) which was used as such in next step. MS (ESI, +ve ion) m/z 233.0 (M+H)$^+$.

Step 3: rac-(2R,3S)-4-((tert-butyldimethylsilyl)oxy)-2,3-dimethylbutanal

To a solution of rac-(2R,3 S)-4-((tert-butyldimethylsilyl)oxy)-2,3-dimethylbutan-1-ol (70.0 g, 301.0 mmol) and (diacetoxyiodo)benzene (107.0 g, 301.0 mmol) in DCM (250 mL) was added 2,2,6,6-tetramethyl-1-piperidinyloxy (2.35 g, 15.06 mmol) in one portion at room temperature. The reaction mixture was stirred for 12 h at room temperature. The reaction mixture was poured into DCM (500 mL) and washed with saturated aqueous sodium bicarbonate solution (250 mL) and brine (250 mL). The organic layer was dried over MgSO$_4$, and concentrated under reduced pressure. The crude material was purified by column chromatography using silica gel 60-120 mesh, eluting with 0% to 10% EtOAc in hexane to give rac-(2R,3S)-4-((tert-butyldimethylsilyl)oxy)-2,3-dimethylbutanal (45.0 g, 195.0 mmol, 64.7% yield). $^1$H NMR (400 MHz, DMSO-d$_6$) δ 3.51 (dd, J=10.1, 5.2 Hz, 1H), 3.40 (dd, J=10.0, 8.2 Hz, 1H), 2.35-2.22 (m, 2H), 0.94 (d, J=6.8 Hz, 3H), 0.90 (d, J=6.9 Hz, 3H), 0.83 (s, 9H). 0.03 (s, 3H) 0.01 (s, 3H). MS (ESI, +ve) m/z 231.2 (M+H)$^+$.

Step 4: rac-(2S,3S)-2,3-dimethylpent-4-en-1-ol

A solution of methyl triphenylphosphonium bromide (185.0 g, 521.0 mmol) in THF (1500 mL) was treated with n-butyllithium (2.5 M solution in hexane, 174.0 mL, 18.8 mmol) at 0° C. After 10 min, the resulting yellow mixture was allowed to stir at room temperature for 20 min. A solution of rac-(2R,3S)-4-((tert-butyldimethylsilyl)oxy)-2,3-dimethylbutanal (40.0 g, 174.0 mmol) in THF (50 mL) was added to the reaction mixture at −78° C. After 10 min, the reaction mixture was allowed to stirred at 0° C. for 2 h and then quenched with saturated aqueous NH$_4$Cl (500 mL) solution and water (200 mL). Diethylether (500 mL) was added and layers were separated. The aqueous layer was extracted with ether (3×500 mL). The combined organic layer was dried over MgSO$_4$, and concentrated under reduced pressure to get the crude material. The crude compound was dissolved in DCM (300 mL) and treated with 1.0 N HCl in diethylether (250 mL). The reaction mixture was stirred at room temperature for 30 min. The reaction mixture was concentrated under reduced pressure and the crude product was purified by column chromatography using silica gel (60-120 mesh), eluting with 0% to 30% EtOAc in hexane to give rac-(2S,3S)-2,3-dimethylpent-4-en-1-ol (8.0 g, 70.1 mmol, 40.2% yield). $^1$H NMR (300 MHz, DMSO-d$_6$) δ 5.82-5.61 (m, 1H), 5.04-4.87 (m, 2H), 4.37 (t, J=5.2 Hz, 1H), 3.39-3.25 (m, 2H), 3.19 (ddd, J=10.5, 6.7, 5.2 Hz, 1H), 2.33-2.16 (m, 1H), 1.56-1.36 (m, 1H), 0.95 (d, J=6.9 Hz, 3H), 0.76 (d, J=6.9 Hz, 3H). MS (ESI, +ve) m/z 115.1 (M+H)$^+$.

Step 5: rac-(2S,3S)-2,3-dimethylpent-4-en-1-yl methanesulfonate

To a solution of rac-(2S,3S)-2,3-dimethylpent-4-en-1-ol (5.0 g, 43.8 mmol) and triethylamine (13.43 mL, 96.0 mmol) in DCM (200 mL) was added methanesulfonyl chloride (5.12 mL, 65.7 mmol, 1.5 equiv) at 0° C. The reaction mixture was stirred at 0° C. for 1 h. Then the reaction was quenched with saturated NH$_4$Cl (100 mL) solution and extracted with EtOAc (3×200 mL) and the combined organic extracts were washed with brine, dried over MgSO$_4$, filtered and concentrated under reduced pressure to give rac-(2S,3S)-2,3-dimethylpent-4-en-1-yl methanesulfonate which was used without further purification. MS (ESI, +ve) m/z 193.2 (M+H)$^+$.

Step 6: rac-2-(((2S,3S)-2,3-dimethylpent-4-en-1-yl)thio)pyrimidine

A solution of 2-mercapto-pyrimidine (27.5 g, 245.0 mmol) and potassium carbonate (36.3 g, 263.0 mmol) in DMF (1000 mL) was stirred at room temperature for 10 min. A solution of rac-(2S,3S)-2,3-dimethylpent-4-en-1-yl methanesulfonate (337 g, 175.0 mmol) in THF (1000 mL) was added at room temperature. The resulting mixture was heated to 50° C. for 4 h and stirred at room temperature for 12 h. The crude mixture was quenched with cold water (500 mL) and extracted with EtOAc (3×500 mL). The combined organic layer was concentrated under reduced pressure. The crude material was purified by column chromatography (EtOAc/hexanes, 0% to 15%, silica gel) to give rac-2-(((2S,3S)-2,3-dimethylpent-4-en-1-yl)thio)pyrimidine (19.0 g, 91.0 mmol, 52% yield). $^1$H NMR (300 MHz, Chloroform-d) δ 8.50 (d, J=4.7 Hz, 2H), 6.94 (t, J=4.8 Hz, 1H), 5.76 (ddd, J=16.8, 10.6, 8.2 Hz, 1H), 5.19-4.97 (m, 2H), 3.25 (dd, J=13.2, 5.9 Hz, 1H), 2.99 (dd, J=13.1, 7.9 Hz, 1H), 2.50-2.32 (m, 1H), 1.93-1.74 (m, 1H), 1.07 (d, J=6.8 Hz, 3H), 1.00 (d, J=6.9 Hz, 3H). MS (ESI, +ve) m/z 209.0 (M+H)$^+$.

Step 7: rac-2-(((2S,3S)-2,3-dimethylpent-4-en-1-yl)sulfonyl)pyrimidine

To a solution of rac-2-(((2S,3S)-2,3-dimethylpent-4-en-1-yl)thio)pyrimidine (25.0 g, 120.0 mmol) in acetonitrile (500 mL) and water (50 mL) was added sodium tungstate dehydrate (7.92 g, 24.0 mmol) followed by hydrogen peroxide (61.3 mL, 600.0 mmol) at 0° C. The reaction mixture was stirred at room temperature for 16 h. The reaction mixture was quenched with saturated sodium thiosulfate (750 mL). The reaction mixture was extracted with ethylacetate (3×1000 mL) and combined organic layer was dried over sodium-sulphate, filtered and concentrated under reduced pressure to give rac-2-(((2S,3S)-2,3-dimethylpent-4-en-1-yl)sulfonyl)pyrimidine (25.0 g, 104.0 mmol, 86% yield). $^1$H NMR (400 MHz, Chloroform-d) δ 8.98 (d, J=4.8 Hz, 2H), 7.59 (t, J=4.9 Hz, 1H), 5.78-5.59 (m, 1H), 5.14-5.01 (m, 2H), 3.58 (dd, J=14.3, 4.0 Hz, 1H), 3.32 (dd, J=14.3, 8.5 Hz, 1H), 2.48-2.28 (m, 2H), 1.10 (d, J=6.8 Hz, 3H), 1.03 (d, J=6.8 Hz, 3H). MS (ESI, +ve) m/z 241.2 (M+H)$^+$.

Step 8:
rac-(2S,3S)-2,3-dimethylpent-4-ene-1-sulfonamide

To a solution of rac-2-(((2S,3S)-2,3-dimethylpent-4-en-1-yl)sulfonyl)pyrimidine (25.0 g, 104.0 mmol) in methanol (500 mL) was added sodium methoxide (22.48 g, 104.0 mmol). The reaction mixture was stirred at room temperature for 2 h. The reaction mixture was concentrated under reduced pressure. The crude mixture was diluted with water (500 mL) and washed with ethyl acetate (3×250 mL). Sodium acetate (10.24 g, 125 mmol) and hydroxylamine-o-sulfonic acid (14.12 g, 125 mmol) was added to the aqueous layer. The reaction mixture was stirred at room temperature for 12 h. The reaction mixture was extracted with MTBE (3×500 mL) and the combined organic layer was washed with saturated sodium carbonate (2×300 mL), dried over sodium-sulphate, filtered and concentrated under reduced pressure to give rac-(2S,3S)-2,3-dimethylpent-4-ene-1-sulfonamide (14.0 g, 79.0 mmol, 76% yield). $^1$H NMR (400 MHz, Chloroform-d) δ 5.71 (ddd, J=17.8, 10.5, 7.2 Hz, 1H), 5.19-4.92 (m, 4H), 3.19 (dd, J=14.6, 3.7 Hz, 1H), 2.89 (dd, J=14.6, 8.3 Hz, 1H), 2.36 (q, J=6.2 Hz, 1H), 2.19 (th, J=7.5, 4.0, 3.3 Hz, 1H), 1.11 (dd, J=6.6, 2.9 Hz, 3H), 1.03 (dd, J=6.7, 2.9 Hz, 3H). MS (ESI, +ve) m/z 178.2 (M+H)$^+$.

(S)-Hexahyrdopyrazino[2,1-c][1,4]oxazin-4(3H)-one

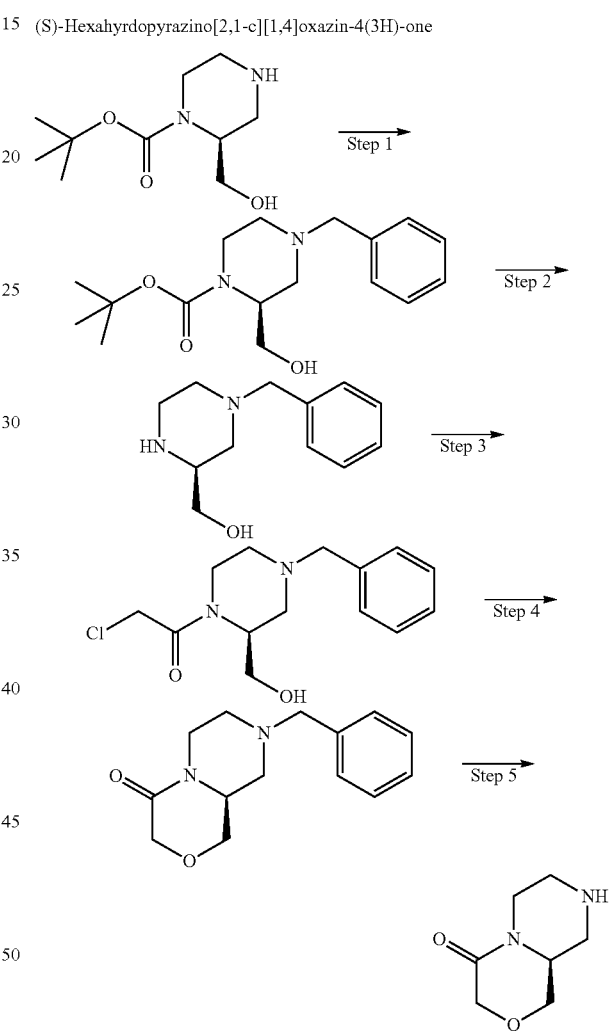

Step 1: (S)-tert-butyl 4-benzyl-2-(hydroxymethyl)piperazine-1-carboxylate

To a solution of (S)-1-boc-2-(hydroxymethyl)piperazine (5.0 g, 23.12 mmol) in 1,2-dichloroethane (100 mL) was added benzaldehyde (7.04 mL, 69.4 mmol). The resulting mixture was then stirred at room temperature for 30 min, and then sodium triacetoxyborohydride (6.85 mL, 46.2 mmol) was added. The resulting mixture was then stirred at room temperature overnight. Then, the mixture was quenched with saturated NaHCO$_3$ (20 mL) and was stirred at room temperature for 10 min. The organic layer was collected and aqueous layer was extracted with EtOAc (1×30 mL). The combined organic extracts were then dried over MgSO₄ and concentrated in vacuo. Chromatographic purification of the residue (silica gel, 0% to 100% EtOAc/heptane) provided (S)-tert-butyl 4-benzyl-2-(hydroxymethyl)piperazine-1-carboxylate (5.86 g, 19.13 mmol, 83% yield) as an oil. MS (ESI, +ve ion) m/z 307.3 (M+H)⁺.

Step 2: (S)-(4-benzylpiperazin-2-yl)methanol

To a solution of (S)-tert-butyl 4-benzyl-2-(hydroxymethyl)piperazine-1-carboxylate (5.86 g, 19.13 mmol) in DCM (30 mL) was added trifluoroacetic acid (11.37 mL, 153 mmol). After addition, the mixture was then stirred at room temperature for 2.5 h. Then, additional trifluoroacetic acid (7 mL) was added and the mixture was stirred at room temperature for an additional 1 h. Then, the mixture was concentrated in vacuo and H₂O (10 mL) was added. The mixture was then adjusted to pH=14 with NaOH (1 N). The mixture was then extracted with EtOAc (3×30 mL). The combined organic extracts were dried over MgSO₄, concentrated, and dried in vacuo at 40° C. overnight provided (S)-(4-benzylpiperazin-2-yl)methanol as an oil that was used without further purification. ¹H NMR (400 MHz, CHLOROFORM-d) δ 7.26-7.38 (5H, m) 3.62-3.81 (2H, m) 3.54 (2H, d, J=4.11 Hz) 3.25-3.35 (2H, m) 3.02-3.14 (1H, m) 2.77-2.90 (2H, m) 2.41 (1H, td, J=11.88, 2.45 Hz) 2.18-2.30 (1H, m). MS (ESI, +ve ion) m/z 207.1 (M+H)⁺.

Step 3: (S)-1-(4-benzyl-2-(hydroxymethyl)piperazin-1-yl)-2-chloroethanone

To a solution of (S)-(4-benzylpiperazin-2-yl)methanol (1.4 g, 6.79 mmol) and triethylamine (2.83 mL, 20.36 mmol) in DCM (5 mL) at 0° C. under N₂ was added chloroacetyl chloride (0.540 mL, 6.79 mmol) dropwise. After addition, the mixture was then stirred at 0° C. for 48 min. Then, MeOH (10 mL) was added and the mixture was concentrated in vacuo. Chromatographic purification of the residue (silica gel, 0% to 100% EtOAc/heptane) provided (S)-1-(4-benzyl-2-(hydroxymethyl)piperazin-1-yl)-2-chloroethanone (530 mg, 1.874 mmol, 27.6% yield) as an oil. MS (ESI, +ve ion) m/z 283.1 (M+H)⁺.

Step 4: (S)-8-benzylhexahydropyrazino[2,1-c][1,4]oxazin-4(3H)-one

To a solution of (S)-1-(4-benzyl-2-(hydroxymethyl)piperazin-1-yl)-2-chloroethanone (530 mg, 1.874 mmol) in THF (40 mL) at 0° C. under N₂ was added potassium tert-butoxide (421 mg, 3.75 mmol). After addition, the mixture was stirred at 0° C. for 2 h. LCMS showed no starting material. Then, MeOH (10 mL) was added and the mixture was concentrated in vacuo. Chromatographic purification of the residue (silica gel, 0% to 100% EtOAc/heptane) provided (S)-8-benzylhexahydropyrazino[2,1-c][1,4]oxazin-4(3H)-one (262 mg, 1.064 mmol, 56.8% yield) as an oil. MS (ESI, +ve ion) m/z 247.1 (M+H)⁺.

Step 4: (S)-hexahydropyrazino[2,1-c][1,4]oxazin-4(3H)-one

A solution of (S)-8-benzylhexahydropyrazino[2,1-c][1,4]oxazin-4(3H)-one (262 mg, 1.064 mmol) and acetic acid (0.123 mL, 2.127 mmol) in methanol (2.5 mL) in a pressure vial was added a solution of palladium (5% on activated carbon, 34 mg, 0.319 mmol) in EtOAc (0.3 mL). Then, the mixture was degassed with hydrogen 5 times, and then was charged with hydrogen at 40 psi. The mixture was then stirred for 3.5 h. LCMS showed some starting material. Then, palladium (5% on activated wood carbon, 34 mg, 0.319 mmol) and acetic acid (0.123 mL, 2.127 mmol) were added. Then, the mixture was degassed 5 times with hydrogen, and then charged with hydrogen at 40 psi. The resulting mixture was stirred at room temperature overnight at 40 psi. Then, the mixture was filtered through celite and the celite was washed with MeOH/EtOAc 1:1 (2×3 mL). The combined filtrates were concentrated and dried in vacuo provided (S)-hexahydropyrazino[2,1-c][1,4]oxazin-4(3H)-one (166 mg, 1.063 mmol, 100% yield) as an oil, which was used without further purification. MS (ESI, +ve ion) m/z 157.1 (M+H)⁺.

(3S,9aS)-3-methylhexahydropyrazino[2,1-c][1,4]oxazin-4(3H)-one AND (3R,9aS)-3-methylhexahydropyrazino[2,1-c][1,4]oxazin-4(3H)-one

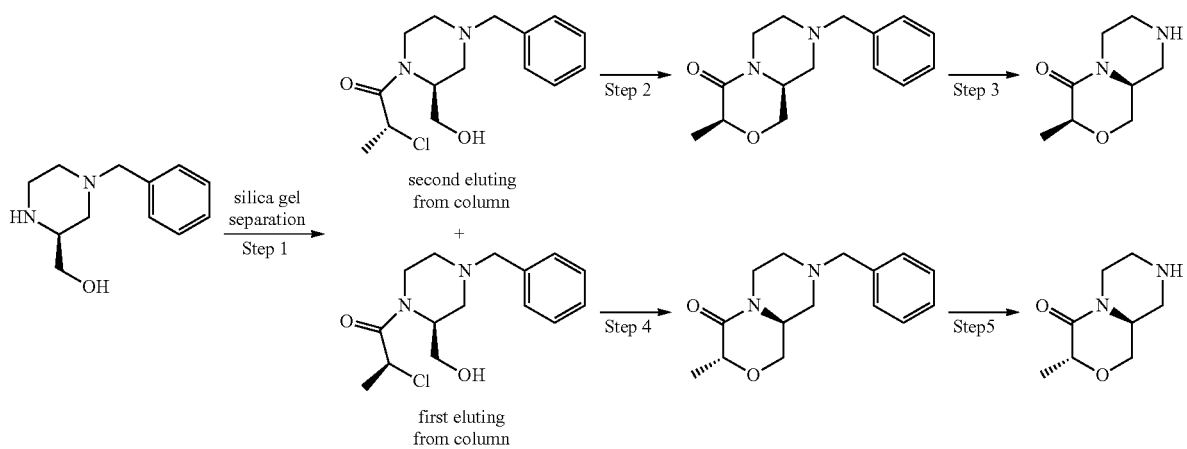

Step 1: (S)-1-((S)-4-benzyl-2-(hydroxymethyl)piperazin-1-yl)-2-chloropropan-1-one AND (R)-1-((S)-4-benzyl-2-(hydroxymethyl)piperazin-1-yl)-2-chloropropan-1-one To a solution of (S)-(4-benzylpiperazin-2-yl)methanol (1.4 g, 6.79 mmol) and triethylamine (2.83 mL, 20.36 mmol) in DCM (10 mL) at 0° C. was added 2-chloropropionyl chloride (0.862 mL, 6.79 mmol). After addition, the mixture was stirred at 0° C. for 2 h. LCMS showed no starting material. Then, MeOH (10 mL) was added and the mixture was concentrated in vacuo. Chromatographic purification of the residue (silica gel, 0% to 100% EtOAc/heptane) provided (S)-1-((S)-4-benzyl-2-(hydroxymethyl)piperazin-1-yl)-2-chloropropan-1-one (176 mg, 0.593 mmol, 8.74% yield) as an oil and the first eluting isomer from the silica gel column. $^1$H NMR (400 MHz, CHLOROFORM-d) δ 7.28-7.40 (5H, m) 4.46-4.73 (2H, m) 4.14 (1H, br s) 3.69-4.03 (3H, m) 3.41-3.63 (2H, m) 3.10 (1H, br s) 2.93 (1H, br s) 2.35 (1H, br s) 2.02-2.23 (1H, m) 1.65-1.69 (3H, m). MS (ESI, +ve ion) m/z 297.0 (M+H)$^+$. In addition, (R)-1-((S)-4-benzyl-2-(hydroxymethyl)piperazin-1-yl)-2-chloropropan-1-one (142 mg, 0.478 mmol, 7.1% yield) was isolated as an oil and the second eluting isomer from the silica gel column. $^1$H NMR (400 MHz, CHLOROFORM-d) δ 7.27-7.40 (5H, m), 4.60-4.72 (1H, m), 4.44-4.59 (1H, m), 3.97 (1H, d, J=4.30 Hz), 3.68-3.93 (3H, m), 3.51 (2H, d, J=18.58 Hz), 3.07 (1H, br s), 2.92 (1H, br s), 2.11-2.45 (2H, m), 1.64-1.73 (3H, m). MS (ESI, +ve ion) m/z 297.0 (M+H)$^+$.

Step 2: (3S,9aS)-8-benzyl-3-methylhexahydropyrazino[2,1-c][1,4]oxazin-4(3H)-one To a solution of (R)-1-((S)-4-benzyl-2-(hydroxymethyl)piperazin-1-yl)-2-chloropropan-1-one (142 mg, 0.478 mmol) in THF (50 mL) under nitrogen at 0° C. was added potassium tert-butoxide (59.1 mg, 0.526 mmol). The resulting mixture was then stirred at 0° C. for 1 h and at room temperature for 10 d. Then, MeOH (10 mL) was added and the mixture was concentrated in vacuo. Chromatographic purification of the residue (silica gel, 0% to 100% EtOAc/heptane) provided (3S,9aS)-8-benzyl-3-methylhexahydropyrazino[2,1-c][1,4]oxazin-4(3H)-one (33 mg, 0.127 mmol, 26.5% yield) as an oil. $^1$H NMR (400 MHz, DICHLOROMETHANE-d$_2$) δ 7.11-7.28 (6H, m), 4.31-4.42 (1H, m), 4.02-4.10 (1H, m), 3.69-3.77 (1H, m), 3.54-3.63 (1H, m), 3.37-3.49 (3H, m), 2.63-2.80 (3H, m), 1.92-2.05 (2H, m), 1.31 (3H, d, J=6.85 Hz). MS (ESI, +ve ion) m/z 261.1 (M+H)$^+$.

Step 3: (3S,9aS)-3-methylhexahydropyrazino[2,1-c][1,4]oxazin-4(3H)-one

To a solution of (3S,9aS)-8-benzyl-3-methylhexahydropyrazino[2,1-c][1,4]oxazin-4(3H)-one (33 mg, 0.127 mmol) in methanol (0.5 mL) was added acetic acid (0.015 mL, 0.254 mmol) and palladium (10 wt % dry basis on activated carbon, wet, degussa type, 6.74 mg, 0.063 mmol). The resulting mixture was then purged with hydrogen, then was charged with hydrogen at 40 psi. The resulting mixture was then stirred at room temperature overnight. Then, the mixture was filtered through celite and the celite was washed with EtOAc (2×3 mL). The combined filtrates were concentrated in vacuo and chromatographic purification of the residue (silica gel, 0% to 50% MeOH/DCM) provided (3S,9aS)-3-methylhexahydropyrazino[2,1-c][1,4]oxazin-4(3H)-one (20 mg, 0.118 mmol, 93% yield) as an oil. $^1$H NMR (400 MHz, DICHLOROMETHANE-d$_2$) δ 4.43-4.58 (1H, m), 4.09-4.19 (1H, m), 3.86 (1H, dd, J=12.52, 4.50 Hz), 3.66-3.75 (1H, m), 3.53 (1H, td, J=7.53, 3.72 Hz), 2.97-3.12 (2H, m), 2.65-2.87 (3H, m), 1.41 (3H, d, J=6.85 Hz). MS (ESI, +ve ion) m/z 171.1 (M+H)$^+$.

Step 4: (3R,9aS)-8-benzyl-3-methylhexahydropyrazino[2,1-c][1,4]oxazin-4(3H)-one To a solution of (S)-1-((S)-4-benzyl-2-(hydroxymethyl)piperazin-1-yl)-2-chloropropan-1-one (176 mg, 0.593 mmol) in THF (50 mL) at 0° C. under nitrogen was added potassium tert-butoxide (100 mg, 0.890 mmol). After addition, the mixture was then stirred at 0° C. for 30 min. LCMS showed no starting material. Then, saturated NaHCO$_3$ (5 mL) was added and the mixture was extracted with EtOAc (2×20 mL). The combined organic extracts were dried over MgSO$_4$, concentrated, and dried in vacuo provided (3R,9aS)-8-benzyl-3-methylhexahydropyrazino[2,1-c][1,4]oxazin-4(3H)-one (154 mg, 0.592 mmol, 100% yield) as an oil, which was used without purification. MS (ESI, +ve ion) m/z 261.0 (M+H)$^+$.

Step 5: (3R,9aS)-3-methylhexahydropyrazino[2,1-c][1,4]oxazin-4(3H)-one

To a solution of (3R,9aS)-8-benzyl-3-methylhexahydropyrazino[2,1-c][1,4]oxazin-4(3H)-one (154 mg, 0.592 mmol) in methanol (2 mL) was added a solution of palladium (10 wt % dry basis on activated carbon, wet, degussa type, 18.89 mg, 0.177 mmol) in EtOAc (0.2 mL). The resulting mixture was then purged with hydrogen five times and charged with hydrogen at 40 psi. The resulting mixture was then stirred for 10 d. Then, the mixture was filtered through celite and the celite was washed with EtOAc (2×5 mL). The combined filtrates were concentrated. Chromatographic purification of the residue (silica gel, 0% to 20% MeOH/DCM) provided (3R,9aS)-3-methylhexahydropyrazino[2,1-c][1,4]oxazin-4(3H)-one (93 mg, 0.546 mmol, 92% yield) as an oil. $^1$H NMR (400 MHz, DICHLOROMETHANE-d$_2$) δ ppm 4.27-4.45 (1H, m), 4.05 (1H, q, J=6.85 Hz), 3.74 (1H, dd, J=12.23, 4.60 Hz), 3.54-3.63 (1H, m), 3.24-3.36 (1H, m), 2.84-2.91 (1H, m), 2.80 (1H, dd, J=11.74, 2.74 Hz), 2.50-2.67 (3H, m), 1.32 (3H, d, J=6.85 Hz). MS (ESI, +ve ion) m/z 171.1 (M+H)$^+$.

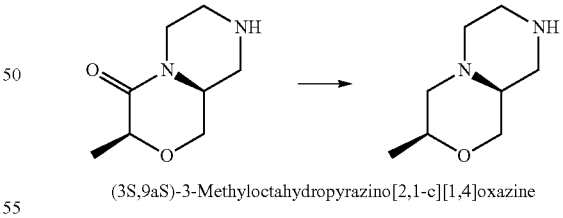

(3S,9aS)-3-Methyloctahydropyrazino[2,1-c][1,4]oxazine

To a solution of (3S,9aS)-3-methylhexahydropyrazino[2,1-c][1,4]oxazin-4(3H)-one (52 mg, 0.306 mmol) in 1,4-dioxane (4 mL) at room temperature under nitrogen was added lithium aluminium hydride (2.0 M in THF, 1.22 mL, 2.44 mmol) dropwise. After addition, the mixture was then stirred at 80° C. for 6 h. Then, the mixture was quenched with 2-propanol (1 mL) at 0° C. followed by saturated Na$_2$SO$_4$ (3 mL). The mixture was then stirred at room temperature for 30 min and then was filtered. The filtered cake was washed with MeOH (2×5 mL). The combined filtrates were concentrated and dried in vacuo. The residue was then dissolved in MeOH (5 mL) and silica gel was added. The mixture was concentrated and dried in vacuo. The solid mixture was then purified by silica gel column chromatography using ISCO instrument (solid loading, 0% to 20% ammonia in MeOH 2 M/DCM) provided (3S,9aS)-3-methyloctahydropyrazino[2,1-c][1,4]oxazine (67 mg, 0.429 mmol, 140% yield) as a solid that contained residual solvent and was used without further purification. $^1$H NMR (400 MHz, CHLOROFORM-d) δ 3.94 (1H, dt, J=6.55, 3.37 Hz), 3.72 (1H, q, J=7.04 Hz), 3.52-3.59 (2H, m), 3.03-3.10 (2H, m), 2.86-2.96 (1H, m), 2.68-2.82 (5H, m), 1.90 (1H, br s), 1.34 (3H, d, J=6.65 Hz). MS (ESI, +ve ion) m/z 157.1 (M+H)$^+$.

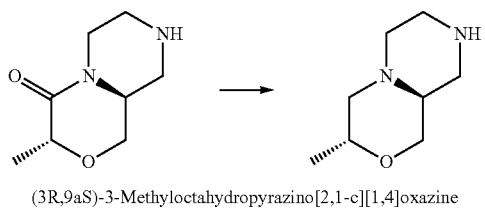

(3R,9aS)-3-Methyloctahydropyrazino[2,1-c][1,4]oxazine

To a solution of (3R,9aS)-3-methylhexahydropyrazino[2,1-c][1,4]oxazin-4(3H)-one (80 mg, 0.470 mmol) in 1,4-dioxane (5 mL) under N$_2$ at room temperature was added lithium aluminium hydride (1.0 M in THF, 1.88 mL, 1.88 mmol) dropwise. After addition, the mixture was stirred at 80° C. for 6 h. Then, the mixture was quenched 2-propanol (1 mL) at 0° C. followed by saturated Na$_2$SO$_4$ (3 mL). The mixture was then stirred at room temperature for 30 min and then was filtered. The filtered cake was washed with MeOH (2×5 mL). The combined filtrates were concentrated and dried in vacuo. The residue was then dissolved in MeOH (5 mL) and silica gel was added. The mixture was concentrated and dried in vacuo. The solid mixture was then purified by silica gel column chromatography using ISCO instrument (solid loading, 0% to 20% ammonia in MeOH 2 M/DCM) provided (3R,9aS)-3-methyloctahydropyrazino[2,1-c][1,4] oxazine (20 mg, 0.128 mmol, 27.2% yield) as an oil. $^1$H NMR (400 MHz, DICHLOROMETHANE-d$_2$) δ 3.92 (1H, ddd, J=6.50, 3.96, 2.25 Hz), 3.42-3.50 (1H, m), 3.30-3.37 (1H, m), 2.79-2.92 (2H, m), 2.53-2.68 (2H, m), 2.37-2.50 (3H, m), 2.06-2.24 (2H, m), 1.90 (1H, br s), 1.33 (3H, d, J=6.65 Hz). MS (ESI, +ve ion) m/z 157.2 (M+H)$^+$.

(R)-Hexahydro-1H-pyrido[1,2-a]pyrazin-4(6H)-one

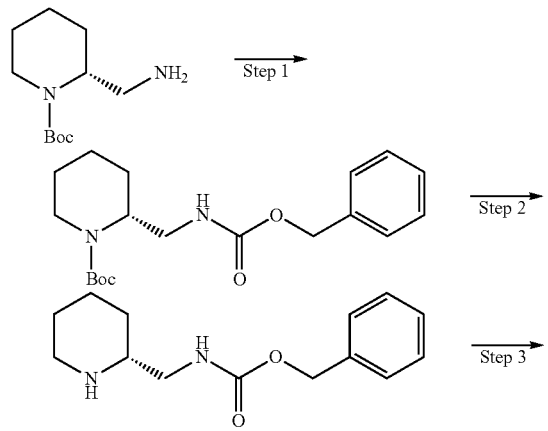

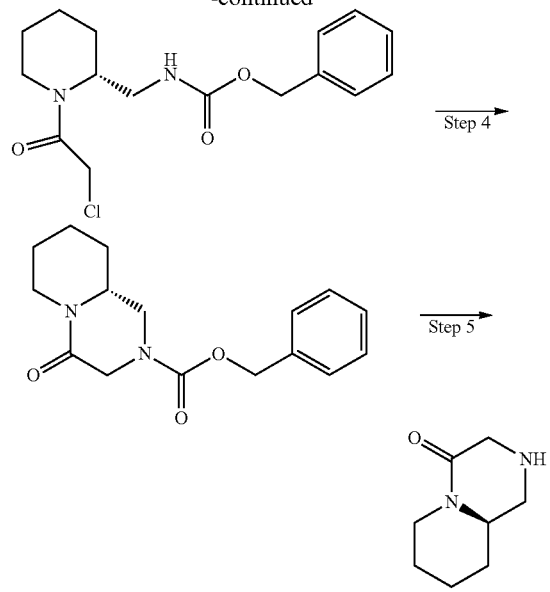

Step 1: (R)-tert-butyl 2-((((benzyloxy)carbonyl) amino)methyl)piperidine-1-carboxylate To a solution of (R)-tert-butyl 2-(aminomethyl)piperidine-1-carboxylate (475 mg, 2.216 mmol) in DCM (5.0 mL) at 0° C. was added iPr$_2$Net (0.424 mL, 2.438 mmol) followed by benzyl chloroformate (0.693 mL, 2.438 mmol). The resulting mixture was then stirred at 0° C. for 2 h and at room temperature for 14 h. Then, saturated NaHCO$_3$ (30 mL) was added to the mixture and the mixture was stirred at room temperature for 3 min. The organic layer was collected and aqueous layer was extracted with EtOAc (1×20 mL). The combined organic extracts were dried over Na$_2$SO$_4$ and concentrated in vacuo. Chromatographic purification of the residue (silica gel, 0% to 100% EtOAc/heptane) provided (R)-tert-butyl 2-((((benzyloxy)carbonyl)amino)methyl)piperidine-1-carboxylate (772 mg, 2.216 mmol, 100% yield) as an oil. MS (ESI, +ve ion) m/z 371.1 (M+Na)$^+$.

Step 2: (R)-benzyl (piperidin-2-ylmethyl)carbamate

A solution of (R)-tert-butyl 2-((((benzyloxy)carbonyl) amino)methyl)piperidine-1-carboxylate (772 mg, 2.216 mmol) in DCM (5 mL) was added trifluoroacetic acid (1.646 mL, 22.16 mmol). The resulting mixture was then stirred at room temperature for 2 h. Then, iPr$_2$Net (3.85 mL, 22.16 mmol) was added dropwise to the mixture at 0° C. and the mixture was stirred at room temperature for 5 min. Then, the mixture was concentrated in vacuo and chromatographic purification of the residue (silica gel, 0% to 100% EtOH: EtOAc (3:1)/heptane) provided (R)-benzyl (piperidin-2-ylmethyl)carbamate (495 mg, 90% yield) as an oil. MS (ESI, +ve ion) m/z 249.2 (M+H)$^+$.

Step 3: (R)-benzyl ((1-(2-chloroacetyl)piperidin-2-yl)methyl)carbamate

To a solution of (R)-benzyl (piperidin-2-ylmethyl)carbamate (150 mg, 0.604 mmol) in 1,2-dichloroethane (1 mL) and DCM (1 mL) at 0° C. under nitrogen was added iPr$_2$Net (0.168 mL, 0.966 mmol) followed by chloroacetyl chloride (0.063 mL, 0.785 mmol). After addition, the mixture was then stirred at 0° C. for 1 h. Then, the mixture was quenched with saturated NaHCO₃ (2.5 mL) and extracted with EtOAc (2×3 mL). The combined organic extracts were then dried over Na₂SO₄ and concentrated in vacuo. Chromatographic purification of the residue (silica gel, 0% to 100% EtOAc/heptane) provided (R)-benzyl ((1-(2-chloroacetyl)piperidin-2-yl)methyl)carbamate (126 mg, 0.388 mmol, 64.2% yield) as a solid. MS (ESI, +ve ion) m/z 325.1 (M+H)⁺.

Step 4: (R)-benzyl 4-oxohexahydro-1H-pyrido[1,2-a]pyrazine-2(6H)-carboxylate

To a solution of (R)-benzyl ((1-(2-chloroacetyl)piperidin-2-yl)methyl)carbamate (126 mg, 0.388 mmol) in tetrahydrofuran (5 mL) was added sodium hydride (60% dispersion in mineral oil, 31 mg, 0.776 mmol) in portions. After addition, the mixture was then stirred at room temperature for 5 h. Then, the mixture was carefully quenched with water (5 mL). The mixture was then extracted with EtOAc (2×10 mL). The combined organic extracts were then dried over Na₂SO₄ and concentrated in vacuo. Chromatographic purification of the residue (silica gel, 0% to 100% EtOAc/heptane) provided (R)-benzyl 4-oxohexahydro-1H-pyrido[1,2-a]pyrazine-2(6H)-carboxylate (112 mg, 0.388 mmol, 100% yield) as an oil. MS (ESI, +ve ion) m/z 289.1 (M+H)⁺.

Step 5: (R)-hexahydro-1H-pyrido[1,2-a]pyrazin-4(6H)-one

To a solution of (R)-benzyl 4-oxohexahydro-1H-pyrido[1,2-a]pyrazine-2(6H)-carboxylate (112 mg, 0.388 mmol) in ethanol (3 mL) was added ammonium formate (122 mg, 1.942 mmol) and 10% palladium on carbon (124 mg, 0.117 mmol). The resulting mixture was then stirred at 70° C. for 1 h. The mixture was filtered through celite and the filter cake was washed with a mixture of EtOAc and MeOH (1:1, 3×2 mL). The combined filtrates were concentrated and chromatographic purification of the residue (silica gel, 0% to 15% 2 M ammonia in MeOH/DCM) provided (R)-hexahydro-1H-pyrido[1,2-a]pyrazin-4(6H)-one (54 mg, 0.350 mmol, 90% yield) as an oil. MS (ESI, +ve ion) m/z 155.1 (M+H)⁺.

1-(Dihydro-1H-pyrazino[1,2-a]pyrazin-2(6H,7H,8H,9H,9aH)-yl)ethanone

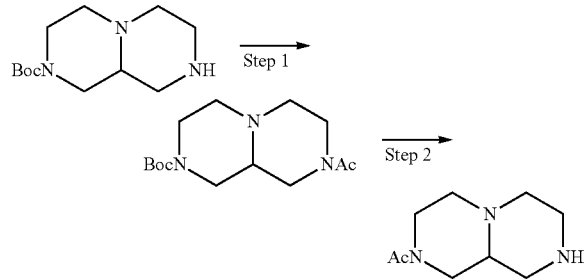

Step 1: tert-butyl 8-acetylhexahydro-1H-pyrazino[1,2-a]pyrazine-2(6H)-carboxylate To stirred solution of tert-butyl hexahydro-1H-pyrazino[1,2-a]pyrazine-2(6H)-carboxylate (0.680 g, 2.82 mmol) in DCM (10 mL) was added at room temperature under argon diisopropylethylamine (1.078 mL, 6.20 mmol) followed by 2,5-dioxopyrrolidin-1-yl acetate (0.885 g, 5.64 mmol) in one portion as a solid. The resulting mixture was stirred at room temperature for 24 h. The crude mixture was directly loaded onto a silica gel precolumn (25 g), previously covered with a layer of sodium bicarbonate, and subjected to flash column chromatography on a 24 g ISCO gold column eluting with 0% to 3% MeOH/DCM to give tert-butyl 8-acetylhexahydro-1H-pyrazino[1,2-a]pyrazine-2(6H)-carboxylate as an oil. This was taken onto the next step without further purification. MS (ESI, +ve ion) m/z 306.4 (M+Na)⁺.

Step 2: 1-(dihydro-1H-pyrazino[1,2-a]pyrazin-2(6H,7H,8H,9H,9aH)-yl)ethanone

To a solution of tert-butyl 8-acetylhexahydro-1H-pyrazino[1,2-a]pyrazine-2(6H)-carboxylate in DCM (10 mL) was added 2,2,2-trifluoroacetic acid (2.0 mL) at room temperature. The resulting mixture was stirred at room temperature overnight and the volatiles were removed to give 1-(hexahydro-1H-pyrazino[1,2-a]pyrazin-2(6H)-yl)ethanone 2,2,2-trifluoroacetate as a solid which was used without further purification.

2-(Methylsulfonyl)octahydro-1H-pyrazino[1,2-a]pyrazine

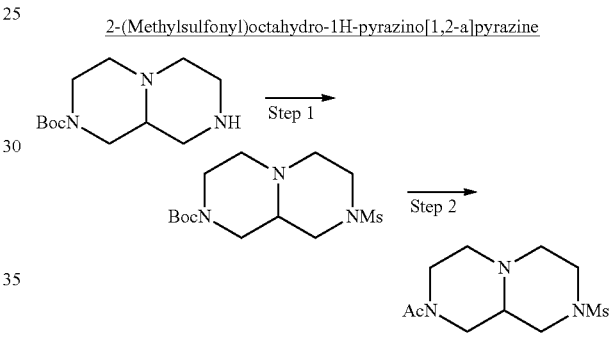

Step 1: tert-butyl 8-(methylsulfonyl)hexahydro-1H-pyrazino[1,2-a]pyrazine-2(6H)-carboxylate To a stirred ice-cooled mixture of tert-butyl hexahydro-1H-pyrazino[1,2-a]pyrazine-2(6H)-carboxylate (1.000 g, 4.14 mmol) and diisopropylethylamine (1.442 mL, 8.29 mmol) in DCM (14 mL) was dropwise added methanesulfonyl chloride (0.385 mL, 4.97 mmol) via a syringe. The resulting mixture was stirred at 0° C. for 10 min and stirred at ambient temperature for 19 h. The volatiles were removed and the residue was loaded onto a silica gel precolumn (25 g) and subjected to combi-flash column chromatography on a 24 g ISCO gold column eluting with 0% to 100% MeOH/DCM to give tert-butyl 8-(methylsulfonyl)hexahydro-1H-pyrazino[1,2-a]pyrazine-2(6H)-carboxylate (1.30 g, 4.07 mmol, 98% yield) as an oil. MS (ESI, +ve ion) m/z 320.1 (M+1)⁺.

Step 2: 2-(methylsulfonyl)octahydro-1H-pyrazino[1,2-a]pyrazine

To a stirred solution of tert-butyl 8-(methylsulfonyl)hexahydro-1H-pyrazino[1,2-a]pyrazine-2(6H)-carboxylate (1.30 g, 4.07 mmol) in DCM (20 mL) was added 2,2,2-trifluoroacetic acid (2.0 mL, 4.14 mmol) via a syringe. The resulting mixture was stirred at room temperature for 2.5 h. Additional TFA (2×2.5 mL) was added over the first 2 h. The volatiles were removed in vacuo and the residue was subjected to high vacuum overnight to give 2.4 g of 2-(methylsulfonyl)octahydro-1H-pyrazino[1,2-a]pyrazine 2,2,2-trifluoroacetate as a solid which was used without further purification. MS (ESI, +ve ion) m/z 220.2 (M+1)⁺.

1-(Dihydro-1H-pyrazino[1,2-a]pyrazin-2(6H,7H,8H,9H,9aH)-yl)-3-(phenylsulfonyl)propan-1-one

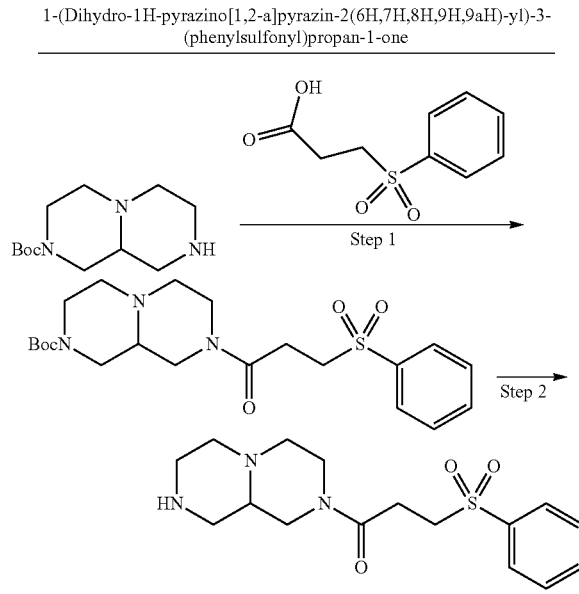

Step 1: tert-butyl 8-(3-(phenylsulfonyl)propanoyl)hexahydro-1H-pyrazino[1,2-a]pyrazine-2(6H)-carboxylate To a stirred mixture of tert-butyl hexahydro-1H-pyrazino[1,2-a]pyrazine-2(6H)-carboxylate (0.46 g, 1.906 mmol) and 3-(phenylsulfonyl)propionic acid (0.490 g, 2.287 mmol) in DCM (6.5 mL) was added at room temperature iPr₂Net (0.829 mL, 4.77 mmol) via a syringe followed by HATU (1.450 g, 3.81 mmol) in one portion as a solid. The resulting mixture was stirred at room temperature for 75 min. The crude mixture was directly loaded onto a silica gel precolumn (25 g) and subjected to combi-flash column chromatography on a 24-g ISCO gold column eluting with 0% to 15% MeOH/DCM to give 1.28 g tert-butyl 8-(3-(phenylsulfonyl)propanoyl)hexahydro-1H-pyrazino[1,2-a]pyrazine-2(6H)-carboxylate as an oil which was taken onto the next step without further purification. MS (ESI, +ve ion) m/z 438.2 (M+1)⁺.

Step 2: 1-(dihydro-1H-pyrazino[1,2-a]pyrazin-2(6H,7H,8H,9H,9aH)-yl)-3-(phenylsulfonyl)propan-1-one A mixture of tert-butyl 8-(3-(phenylsulfonyl)propanoyl)hexahydro-1H-pyrazino[1,2-a]pyrazine-2(6H)-carboxylate (1.28 g, 2.93 mmol) and 2,2,2-trifluoroacetic acid (4.0 mL, 2.93 mmol) in DCM (15 mL) was stirred at room temperature for 50 min. The volatiles were removed and the residue was subjected to high vacuum overnight to give 1.5 g of 1-(dihydro-1H-pyrazino[1,2-a]pyrazin-2(6H,7H,8H,9H,9aH)-yl)-3-(phenylsulfonyl)propan-1-one as an oil that was used without further purification. MS (ESI, +ve ion) m/z 338.1 (M+1)⁺.

2-Isopropyloctahydro-1H-pyrazino[1,2-a]pyrazine

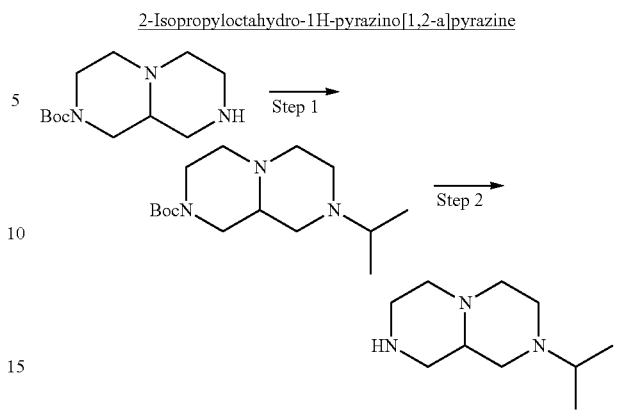

Step 1: tert-butyl 8-isopropylhexahydro-1H-pyrazino[1,2-a]pyrazine-2(6H)-carboxylate A mixture of tert-butyl hexahydro-1H-pyrazino[1,2-a]pyrazine-2(6H)-carboxylate (0.53 g, 2.196 mmol) and acetone (0.806 mL, 10.98 mmol) in DCM (5.0 mL) was stirred at rt for 10 min before sodium triacetoxyhydroborate (2.327 g, 10.98 mmol) was added at room temperature in one portion as a solid. The resulting mixture was stirred at room temperature for 24 h. The reaction was quenched with MeOH (5 mL) and the resulting slurry was directly loaded onto a silica gel precolumn (25 g) and subjected to combi-flash column chromatography on a 12 g ISCO gold column eluting with 0% to 20% MeOH/DCM to give tert-butyl 8-isopropylhexahydro-1H-pyrazino[1,2-a]pyrazine-2(6H)-carboxylate (0.65 g, 2.293 mmol, 104% yield) as an oil. MS (ESI, +ve ion) m/z 284.3 (M+1)⁺.

Step 2: 2-isopropyloctahydro-1H-pyrazino[1,2-a]pyrazine

A mixture of tert-butyl 8-isopropylhexahydro-1H-pyrazino[1,2-a]pyrazine-2(6H)-carboxylate (0.65 g, 2.293 mmol) and 2,2,2-trifluoroacetic acid (4.0 mL, 2.293 mmol) in DCM (15 mL) was stirred at room temperature for 2 h. The volatiles were removed in vacuo and the residue was subjected to high vacuum overnight to give 1.74 g of 2-isopropyloctahydro-1H-pyrazino[1,2-a]pyrazine as an oil that was used without further purification. MS (ESI, +ve ion) m/z 184.2 (M+1)⁺.

(1R,4R)-2-Isopropyl-2,5-diazabicyclo[2.2.1]heptane

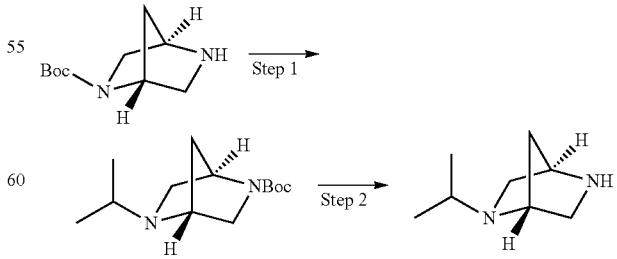

The title compound was synthesized, from (1R,4R)-tert-butyl 2,5-diazabicyclo[2.2.1]heptane-2-carboxylate (AstaTech, Inc.), similarly using the protocol in the synthesis of 2-isopropyloctahydro-1H-pyrazino[1,2-a]pyrazine. MS (ESI, +ve ion) m/z 141.2 (M+1)⁺.

(1S,4S)-2-Isopropyl-2,5-diazabicyclo[2.2.1]heptane

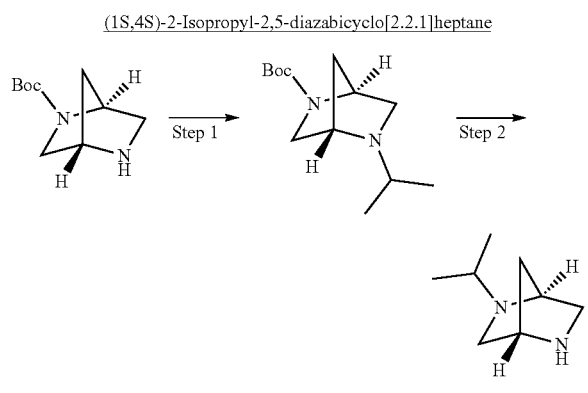

The title compound was synthesized, from (1S,4S)-tert-butyl 2,5-diazabicyclo[2.2.1]heptane-2-carboxylate (AstaTech, Inc.), similarly using the protocol in the synthesis of 2-isopropyloctahydro-1H-pyrazino[1,2-a]pyrazine. MS (ESI, +ve ion) m/z 141.2 (M+1)⁺.

Cis-1-(2-methoxyethyl)-2,6-dimethylpiperazine

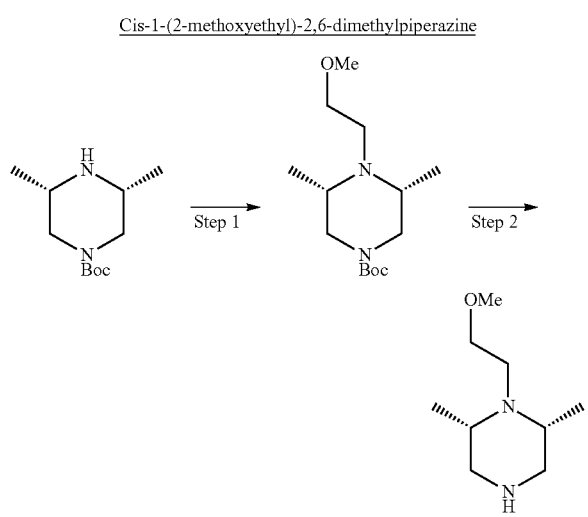

The title compound was synthesized, from cis-tert-butyl 3,5-dimethylpiperazine-1-carboxylate (AK Scientific), similarly using the protocol in the synthesis of 2-isopropyloctahydro-1H-pyrazino[1,2-a]pyrazine. MS (ESI, +ve ion) m/z 173.2 (M+1)⁺.

Cis-1-isopropyl-2,6-dimethylpiperazine and cis-2,6-dimethylpiperazine

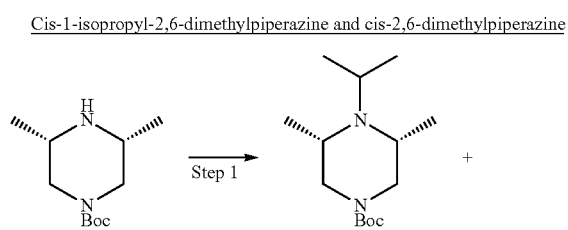

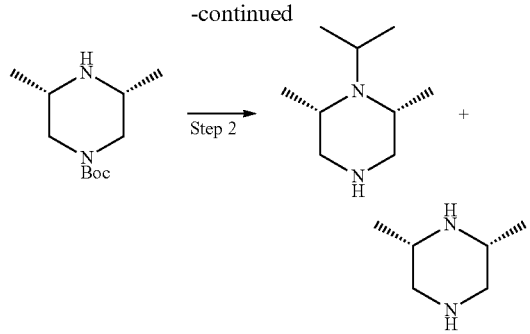

The title compounds were synthesized and used as a mixture, from cis-tert-butyl 3,5-dimethylpiperazine-1-carboxylate (AK Scientific), similarly using the protocol in the synthesis of 2-isopropyloctahydro-1H-pyrazino[1,2-a]pyrazine. MS (ESI, +ve ion) m/z 157.1 and 115.3 (M+1)⁺.

(S)-1-Isopropyl-2-methylpiperazine

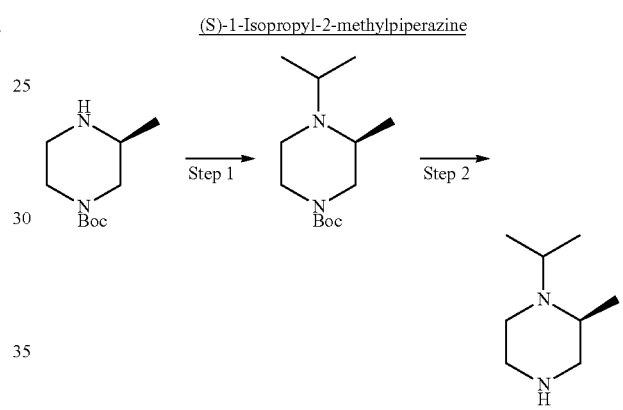

The title compound was synthesized, from (S)-tert-butyl 3-methylpiperazine-1-carboxylate, similarly using the protocol in the synthesis of 2-isopropyloctahydro-1H-pyrazino[1,2-a]pyrazine. MS (ESI, +ve ion) m/z 143.2 (M+1)⁺.

1-(1,4-Dioxepan-6-yl)piperazine

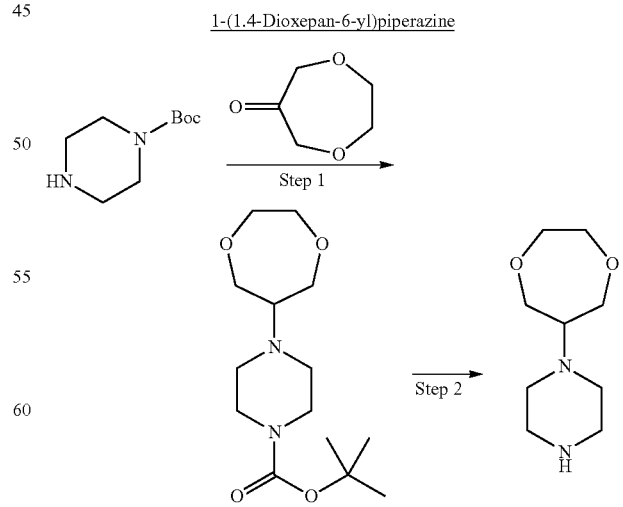

The title compound was synthesized, from 1,4-dioxepan-6-one (Enamine), similarly using the protocol in the synthesis of 2-isopropyloctahydro-1H-pyrazino[1,2-a]pyrazine. MS (ESI, +ve ion) m/z 187.2 (M+1)⁺.

(2S,6S)-1-Isopropyl-2,6-dimethylpiperazine

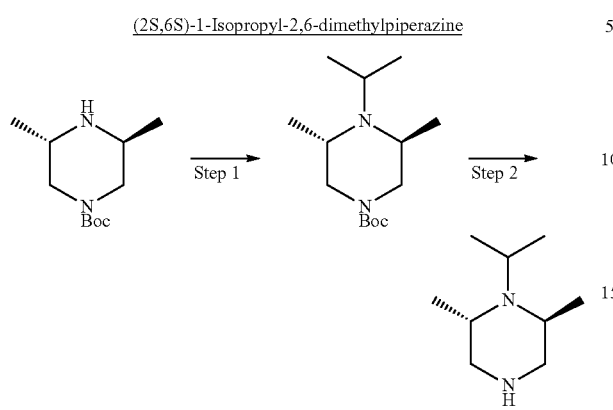

The title compound was synthesized, from (3S,5S)-tert-butyl 3,5-dimethylpiperazine-1-carboxylate (Anichem), similarly using the protocol in the synthesis of 2-isopropyloctahydro-1H-pyrazino[1,2-a]pyrazine. MS (ESI, +ve ion) m/z 157.2 (M+1)⁺.

4-(2-Methoxyethyl)piperazin-2-one

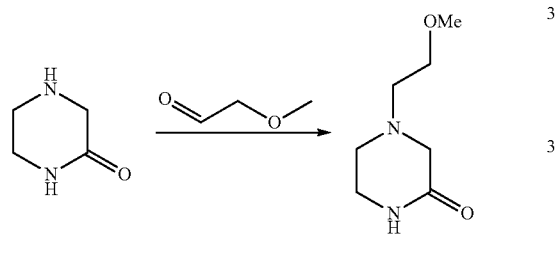

The title compound was synthesized, from piperazin-2-one (AK Scientific), similarly using the protocol in the synthesis (Step 1) of 2-isopropyloctahydro-1H-pyrazino[1,2-a]pyrazine.

1-(Oxetan-3-ylmethyl)piperazine

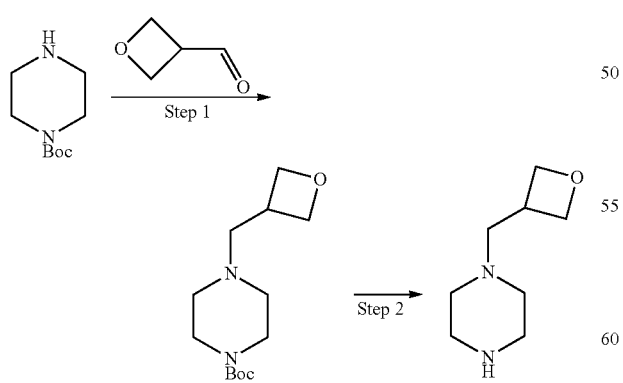

The title compound was synthesized, from tert-butyl piperazine-1-carboxylate, similarly using the protocol in the synthesis of 2-isopropyloctahydro-1H-pyrazino[1,2-a]pyrazine. MS (ESI, +ve ion) m/z 157.1 (M+1)⁺.

4-(Piperazin-1-yl)tetrahydro-2H-pyran-2-one

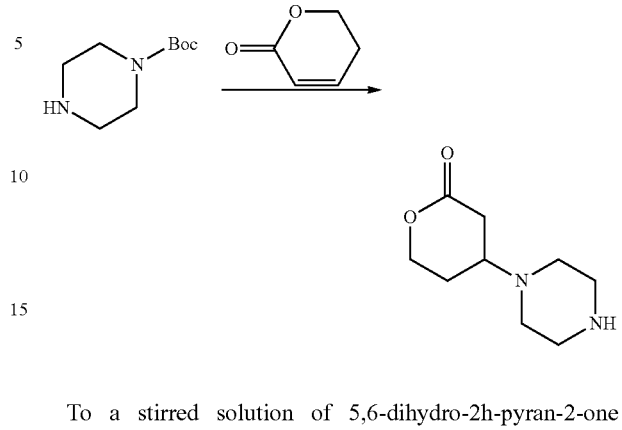

To a stirred solution of 5,6-dihydro-2h-pyran-2-one (0.228 mL, 2.65 mmol) in DCM (1.0 mL) was added under argon a solution of piperazine-1-carboxylic acid tert-butyl ester (469 mg, 2.52 mmol) in DCM (2.0 mL). The resulting mixture was stirred at room temperature for a period of 3 d before trifluoroacetic acid (2.5 mL, 33.7 mmol) was added dropwise via a syringe. The resulting mixture was stirred at room temperature for a period of 2 h. The mixture was concentrated in vacuo and the residue was dried to give impure 4-(piperazin-1-yl)tetrahydro-2H-pyran-2-one. This was used without further purification. MS (ESI, +ve ion) m/z 185.1 (M+1)⁺.

8,8-Difluorooctahydro-1H-pyrido[1,2-a]pyrazine AND 8-flurooctahydro-1H-pyrido[1,2-a]pyrazine

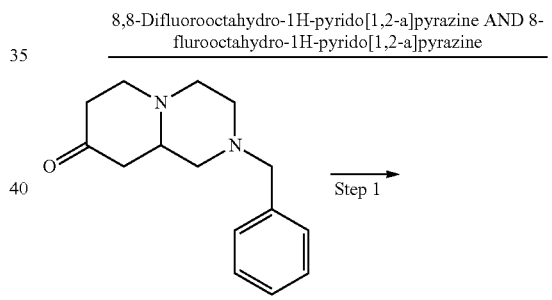

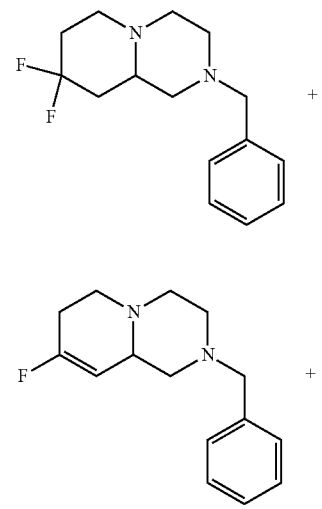

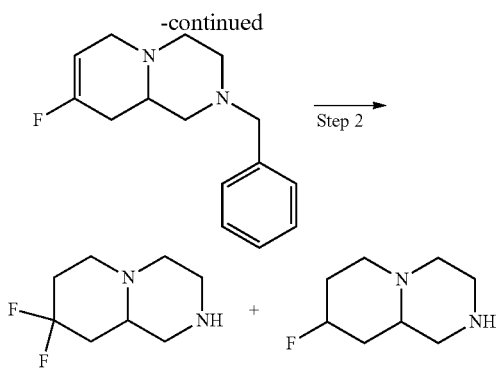

Step 1: 2-benzyl-8,8-difluorooctahydro-1H-pyrido
[1,2-a]pyrazine AND 2-benzyl-8-fluoro-2,3,4,6,7,
9a-hexahydro-1H-pyrido[1,2-a]pyrazine AND
2-benzyl-8-fluoro-2,3,4,6,9,9a-hexahydro-1H-pyrido
[1,2-a]pyrazine To a stirred solution of 2-benzylhexahydro-1H-pyrido[1,
2-a]pyrazin-8(2H)-one (200 mg, 0.819 mmol, AstaTech) in
DCM (5.0 mL) cooled in brine-ice bath was added bis(2-
methoxyethyl)aminosulfur trifluoride solution (50% in THF,
0.989 mL, 2.456 mmol) dropwise via a syringe. The result-
ing mixture was stirred for 2 h at −5° C. and 3 h at ambient
temperature. The crude mixture was directly loaded onto a
silica gel precolumn (25 g) and subjected to flash column
chromatography on a 12 g ISCO gold column eluting with
0% to 10% MeOH/DCM to give 170 mg of a mixture of
2-benzyl-8,8-difluorooctahydro-1H-pyrido[1,2-a]pyrazine,
2-benzyl-8-fluoro-2,3,4,6,7,9a-hexahydro-1H-pyrido[1,2-a]
pyrazine, and 2-benzyl-8-fluoro-2,3,4,6,9,9a-hexahydro-
1H-pyrido[1,2-a]pyrazine. The mixture was directly used in
the next step. MS (ESI, +ve ion) m/z 267.2 and 247.2
(M+1)⁺.

Step 2: 8,8-difluorooctahydro-1H-pyrido[1,2-a]pyra-
zine AND 8-fluorooctahydro-1H-pyrido[1,2-a]pyra-
zine A mixture of 2-benzyl-8,8-difluorooctahydro-1H-pyrido
[1,2-a]pyrazine, 2-benzyl-8-fluoro-2,3,4,6,7,9a-hexahydro-
1H-pyrido[1,2-a]pyrazine and 2-benzyl-8-fluoro-2,3,4,6,9,
9a-hexahydro-1H-pyrido[1,2-a]pyrazine (250 mg, 0.939
mmol) and palladium (5 wt % dry basis on activated carbon,
wet, degussa type, spatula tip) in EtOH (25 mL) and
concentrated hydrochloric acid (5 mL) was hydrogenated
with hydrogen gas at 40-45 psi for a period of 22 h. The
reaction was quenched with water (5 mL) and the mixture
was filtered through a layer of celite covered with sand. The
filtrate was concentrated in vacuo to give 8,8-difluoroocta-
hydro-1H-pyrido[1,2-a]pyrazine AND 8-fluorooctahydro-
1H-pyrido[1,2-a]pyrazine as a colorless film which was used
without further purification. MS (ESI, +ve ion) m/z 177.2
and 159.2 (M+1)⁺.

1-(5-(Piperazin-1-yl)-2-(4,4,5,5-tetramethyl-1,3,2-dioxaborolan-2-
yl)phenyl)ethanone Step 1: tert-butyl 4-(3-acetyl-4-hydroxyphenyl)pip-
erazine-1-carboxylate To a stirred ice-cooled mixture of 5′-bromo-2′-hydroxy-
acetophenone (2.000 g, 9.30 mmol, Oakwood), 1-boc-pip-
erazine (2.77 g, 14.88 mmol), tris(dibenzylideneacetone)
dipalladium(0) (0.426 g, 0.465 mmol), and
2-(dicyclohexylphosphino)-2′-(n,n-dimethylamino)biphenyl
(0.183 g, 0.465 mmol) in THF (20 mL) was added dropwise
lithium bis(trimethylsilyl)amide (1.0 M in THF, 32.6 mL,
32.6 mmol). The resulting mixture was stirred at ambient
temperature for 10 min before it was placed in an oil bath
which was at room temperature. The oil bath was then
heated to 70° C. and the reaction mixture was stirred at this
temperature for 1.5 h. The mixture was cooled in an ice bath
before carefully quenched with ice-cold saturated ammo-
nium chloride aqueous solution. The resulting mixture was
poured into a mixture of 1 N aqueous HCl and saturated
ammonium chloride aqueous solutions and extracted with
10% MeOH/DCM (2×). The combined organics were
washed with saturated ammonium chloride aqueous solu-
tion, dried over anhydrous sodium sulfate, and concentrated
in vacuo. The residue was dissolved in DCM and loaded
onto silica gel precolumn and subjected to flash column
chromatography on a 40 g ISCO gold column eluting with
0% to 4% MeOH/DCM to give 1.84 g tert-butyl 4-(3-acetyl-
4-hydroxyphenyl)piperazine-1-carboxylate that was directly
used in the next step. MS (ESI, +ve ion) m/z 321.2 (M+1)⁺.

Step 2: tert-butyl 4-(3-acetyl-4-(trifluoromethylsul-
fonyloxy)phenyl)piperazine-1-carboxylate To a stirred solution of impure tert-butyl 4-(3-acetyl-4-
hydroxyphenyl)piperazine-1-carboxylate (1.30 g, 4.06 mmol) and triethylamine (2.258 mL, 16.23 mmol) in DCM (15 mL) was added N-phenyl bis-trifluoromethane sulfonimide (2.90 g, 8.12 mmol) in one portion as a solid. The resulting mixture was stirred at ambient temperature for 2.5 d. The crude mixture was directly loaded onto a silica gel precolumn (25 g) and subjected to flash column chromatography on a 40 g ISCO gold column eluting with 10% to 40% EtOAc/Hexanes to give tert-butyl 4-(3-acetyl-4-(((trifluoromethyl)sulfonyl)oxy)phenyl)piperazine-1-carboxylate (1.4 g, 3.09 mmol, 76% yield). MS (ESI, +ve ion) m/z 475.1 (M+1)$^+$.

Step 3: tert-butyl 4-(3-acetyl-4-(4,4,5,5-tetramethyl-1,3,2-dioxaborolan-2-yl)phenyl)piperazine-1-carboxylate A 25-mL single-necked round bottom flash previously charged with tert-butyl 4-(3-acetyl-4-(((trifluoromethyl)sulfonyl)oxy)phenyl)piperazine-1-carboxylate (1.17 g, 2.59 mmol), bis(pinacolato)diboron (1.642 g, 6.46 mmol), (1,1'-bis(diphenylphosphino)ferrocene)dichloropalladium(II) (0.189 g, 0.259 mmol), and potassium acetate (0.888 g, 9.05 mmol) was subjected to 3 cycles of evacuation and backfilling with nitrogen before 1,4-dioxane (12 mL) was added. The resulting mixture under argon was placed in an oil bath and heated to 50° C. and stirred under argon at this temperature for a period of 20 h. The temperature was lowered to 45° C. and the mixture was stirred overnight at this temperature. The crude reaction mixture was run through a silica gel plug. The filtrate was concentrated in vacuo and the residue was dissolved in DCM and loaded onto silica gel precolumn (25 g) and subjected to flash column chromatography on a 24 g ISCO gold column eluting with 0% to 40% EtOAc/hexanes to give tert-butyl 4-(3-acetyl-4-(4,4,5,5-tetramethyl-1,3,2-dioxaborolan-2-yl)phenyl)piperazine-1-carboxylate (380 mg, 0.883 mmol, 34.1% yield) as a solid. MS (ESI, +ve ion) m/z 431.3 (M+1)$^+$.

Step 4: 1-(5-(piperazin-1-yl)-2-(4,4,5,5-tetramethyl-1,3,2-dioxaborolan-2-yl)phenyl)ethanone tert-Butyl 4-(3-acetyl-4-(4,4,5,5-tetramethyl-1,3,2-dioxaborolan-2-yl)phenyl)piperazine-1-carboxylate in DCM was treated with TFA for the removal the Boc group. 1-(5-(piperazin-1-yl)-2-(4,4,5,5-tetramethyl-1,3,2-dioxaborolan-2-yl)phenyl)ethanone was isolated after concentration and used without further purification. MS (ESI, +ve ion) m/z 331.2 (M+1)+.

(2S)—N,N-BIS(4-METHOXYBENZYL)-2-METHYLPENT-4-ENE-1-SULFONAMIDE AND (2R)-N,N-BIS(4-METHOXYBENZYL)-2-METHYL-4-PENTENE-1-SULFONAMIDE

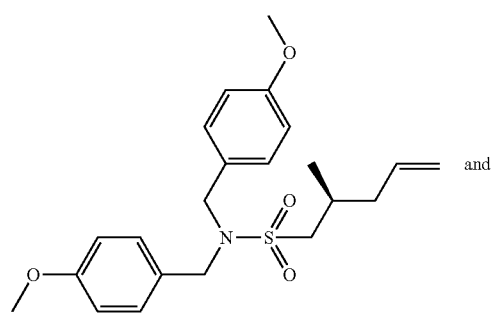
and
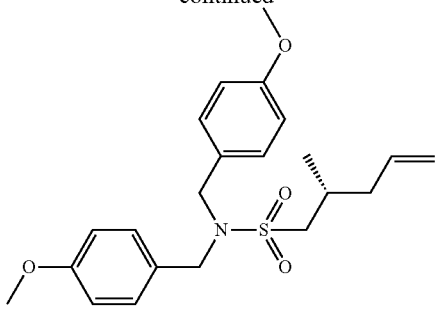

The title compound was prepared from Intermediate EE12 and pent-4-en-2-yl 4-methylbenzenesulfonate following a similar procedure described below.

(2R,3R)-N,N-BIS (4-METHOXYBENZYL)-3-METHYLHEX-5-ENE-2-SULFONAMIDE AND (2S,3R)-N,N-BIS(4-METHOXYBENZYL)-3-METHYLHEX-5-ENE-2-SULFONAMIDE

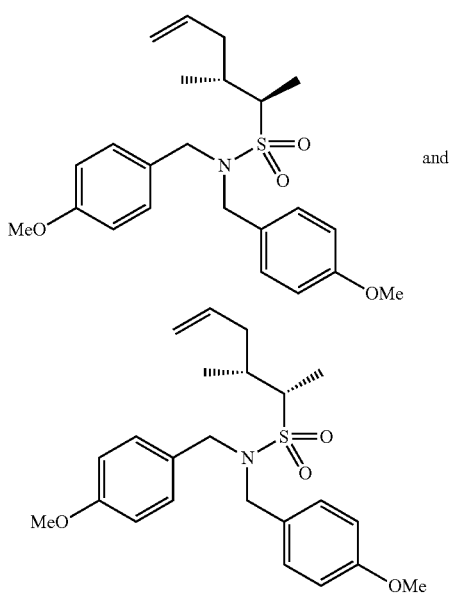

N,N-bis(4-methoxybenzyl)ethanesulfonamide (Intermediate EE13; 1030 mg, 2.95 mmol) was azeotroped in toluene under vacuum for 2 h. Under argon, THF was added and the solution was cooled to −78° C. N-butyllithium solution (2.5 M in hexane, 1.533 mL, 3.83 mmol) was then added and the mixture was stirred at −78° C. for 60 min. (S)-pent-4-en-2-yl 4-methylbenzenesulfonate (prepared according to the procedure by Sigman, M. S. et al., *J. Am. Chem. Soc.*, 2012, 134(28), 11408-11411; 1417 mg, 5.90 mmol) was added as a solution in 3 mL. THF was then added. After 5 min the mixture was allowed to warm to ambient temperature and stirred overnight under argon. The mixture was quenched with satd NH$_4$Cl and extracted with EtOAc, dried over MgSO$_4$, and concentrated. The crude material was injected into a SiO$_2$ gel cartridge and purified by chromatography through a 40 g ISCO column, eluting with 5% to 10% to 20% to 40% EtOAc in hexane, to provide a 2.3:1 mixture of the title compounds (420 mg, 1.00 mmol, 34.1% yield).

Intermediate AA11A (S)-6'-CHLORO-5-(((1R,2R)-2-((S)-1-HYDROXY-ALLYL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLIC ACID

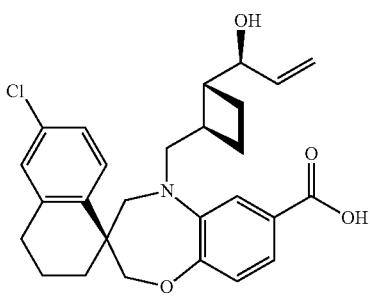

STEP 1: (R)-6-CHLORO-3,4-DIHYDRO-2H-SPIRO[NAPHTHALENE-1,2'-OXIRANE] AND (R)-6-CHLORO-3,4-DIHYDRO-2H-SPIRO[NAPHTHALENE-1,2'-OXIRANE]

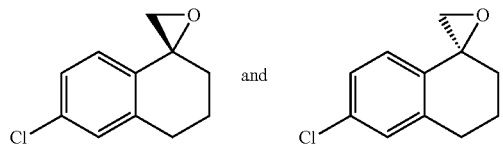 [SMILES: Clc1ccc2c(c1)CCC[C@]21CO1 ; Clc1ccc2c(c1)CCC[C@@]21CO1]

A 2 L 4-necked-RBF was charged with 6-chloro-3,4-dihydro-1(2H)-naphthalenone (123 g, 681 mmol), trimethylsulfonium iodide (143 g, 701 mmol), and DMSO (1100 mL). KOH (76 g, 1362 mmol) (pellets) was added. The suspension was stirred at ambient temperature for 2 days, after which time crude $^1$H NMR showed no remaining starting material. The solution was poured into 800 g of crushed ice, rinsed with MTBE (200 mL), and an additional portion of MTBE (700 mL) was added. The resulting mixture was stirred for 5 min and after partition, the bottom aqueous layer was extracted with MTBE twice (500 mL, 300 mL), and combined with the main MTBE extract. The combined organic stream was washed with brine (2×600 mL) and 330 g of $Al_2O_3$ (neutral) was added. The resulting suspension was stirred for 5 min at 22° C., filtered, and washed with MTBE (400 mL). The filtrate was concentrated to give the product as a red viscous oil (125 g, 94%).

STEP 2: (S)-6-CHLORO-1,2,3,4-TETRAHYDRONAPHTHALENE-1-CARBALDEHYDE AND (R)-6-CHLORO-1,2,3,4-TETRAHYDRONAPHTHALENE-1-CARBALDEHYDE

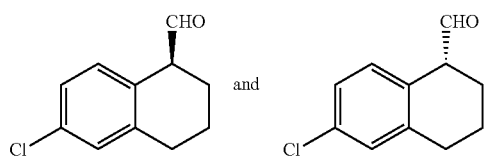 [SMILES: O=C[C@H]1CCCc2cc(Cl)ccc21 ; O=C[C@@H]1CCCc2cc(Cl)ccc21]

A 3 L 3-necked-RBF was charged with racemic 6-chloro-3,4-dihydro-2H-spiro[naphthalene-1,2'-oxirane] (160 g, 822 mmol) and THF (1760 mL). After the batch was cooled to −8° C. with a dry ice/IPA bath, boron trifluoride diethyl etherate (5.07 mL, 41.1 mmol) was added over 3 min. An exotherm raised the batch temp to 10° C. instantly. The batch was stirred at −5 to 0° C. for 5 min, and LC/MS analysis of a sample (quenched into cold $NaHCO_3$ solution) showed complete conversion. The reaction was quenched by the addition of sat. $NaHCO_3$ (300 mL) at −5° C. followed by MTBE (400 mL) and the mixture was transferred to a separatory funnel and rinsed with MTBE (240 mL). After partition, the aqueous layer was discarded along with some white solid (likely boric acid or borax). The organic layer was washed with brine (350 mL) and concentrated under reduced pressure to give a red oil. The crude material was used directly in Step 4.

STEP 3: (6-CHLORO-1,2,3,4-TETRAHYDRONAPHTHALENE-1,1-DIYL)DIMETHANOL

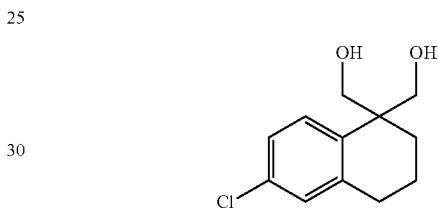

Racemic 6-chloro-1,2,3,4-tetrahydro-1-naphthalenecarbaldehyde was charged onto a 3 L 3-necked-RBF and rinsed with diethylene glycol (1000 mL). Formaldehyde (37% solution in $H_2O$; 652 mL, 8757 mmol) was added and the resulting biphasic emulsion was cooled to 5° C. with a dry ice/IPA bath. KOH (45% aqueous solution, 652 mL, 11.9 mol) was added over ~30 min, maintaining the temperature below 20° C. After complete addition, the batch (20° C.) was slowly heated to 45° C. (Caution: exothermic reaction) and aged for 1 h. HPLC showed complete conversion. Some viscous insoluble tar was formed, which was removed prior to aqueous workup. To the batch was added brine (500 mL) and the mixture was extracted with DCM until the product content in the aqueous phase was less than 5%. The combined DCM extract was concentrated to 750 mL as a red oil, washed with $H_2O$ (500 mL), and the product began to crystallize out. Upon separation, the clear top aqueous layer was discarded and the bottom layer was stirred in ice/$H_2O$ bath for 30 min, filtered, and washed with DCM (~100 mL) and $H_2O$ (100 mL). The product was dried under dry air/vacuum to give a first crop (113 g, 498 mmol, 57% yield). The DCM layer from the resulting mother liquor was separated and concentrated to 200-300 g (KF=0.5%), seeded, and stirred in ice/$H_2O$ bath for 30 min. The product was filtered, washed with DCM (50 mL), and dried in dry air/vacuum to give a second crop (14.3 g, 63.1 mmol, 7% yield) for a combined total yield of 6-chloro-1,2,3,4-tetrahydronaphthalene-1,1-diyl)dimethanol of 127 g (64%).

STEP 4: (S)-(6-CHLORO-1-(HYDROXYM-ETHYL)-1,2,3,4-TETRAHYDRONAPHTHALEN-1-YL)METHYL 4-BROMOBENZOATE

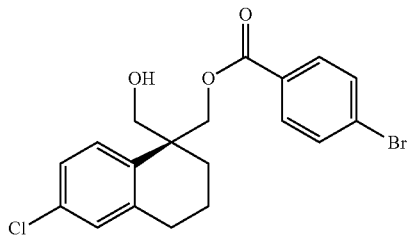 [SMILES: O=C(OC[C@@]1(CO)CCCc2cc(Cl)ccc21)c1ccc(Br)cc1]

To a solution of 2,6-bis((R)-5,5-dibutyl-4-phenyl-4,5-dihydrooxazol-2-yl)pyridine (R,R-Kang Catalyst) (1.57 g, 2.64 mmol) in dry DCM (450 mL), copper(II) chloride (0.355 g, 2.64 mmol) was added and the resulting green colored solution was stirred at rt for 1 h. This solution was added via cannula to a solution of (6-chloro-1,2,3,4-tetrahydronaphthalene-1,1-diyl)dimethanol (30 g, 132.73 mmol) in dry DCM (800 mL). The resulting mixture was cooled to −78° C. and a light green colored precipitation was observed. A solution of 4-bromobenzoyl chloride (34.77 g, 158.79 mmol) in DCM (500 mL) was then slowly added, followed by the dropwise addition of N-ethyl-N-isopropyl-propan-2-amine (20 g, 154 mmol). The resulting reaction mixture was stirred at −78° C. for 3 h, then it was quenched with pH 3 phosphate buffer (1 L) and warmed to ambient temperature with vigorous stirring. The mixture was then diluted with DCM (2 L) and the layers were separated. The organic phase was washed with pH 3 buffer (1 L), sat. NaHCO₃ (1 L), and brine (2 L) then it was dried over Na₂SO₄, filtered, and concentrated. The crude material was purified by column chromatography over SiO₂ gel (100-200 mesh, 80% DCM in hexane) to afford pure (S)-(6-chloro-1-(hydroxymethyl)-1,2,3,4-tetrahydronaphthalen-1-yl)methyl 4-bromobenzoate (45 g, 84%; e.r=91.4:8.6). ChiralCel® OD-H (250 mm×4.6 mm); Mobile Phase: n-Hexane:IPA: 90:10; Run Time: 20 min; flow rate: 1 mL/min; sample preparation: IPA. Retention time (major peak)—9.32 min; Retention time (minor peak)—11.46 min.

STEP 5: (R)-(6-CHLORO-1-FORMYL-1,2,3,4-TETRAHYDRONAPHTHALEN-1-YL)METHYL 4-BROMOBENZOATE

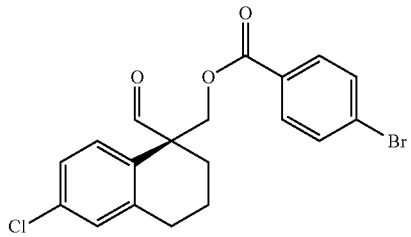 [SMILES: O=C[C@]1(COC(=O)c2ccc(Br)cc2)CCCc2cc(Cl)ccc21]

To a stirred solution of (S)-(6-chloro-1-(hydroxymethyl)-1,2,3,4-tetrahydronaphthalen-1-yl)methyl 4-bromobenzoate (100 g, 244.5 mmol) in DCM (2.5 L), Dess-Martin periodinane (121.4 g, 293.3 mmol) was added at 10° C. The cooling bath was removed after addition and the reaction mixture was stirred for 30 min at ambient temperature. H₂O (9 mL) was then added and the resulting biphasic mixture was stirred at ambient temperature for 30 min. The reaction mixture was cooled to 0° C. and quenched with 2 L of a 1:1 mixture of 10% Na₂S₂O₃/sat. NaHCO₃ solution. The reaction mixture was stirred further at ambient temperature for 10 min, then the layers were separated and the aqueous layer was extracted with EtOAc (2×1.5 L). The combined organic layer was washed with 1 L of 10% Na₂S₂O₃/sat. NaHCO₃ solution and 1 L of brine, then it was dried over Na₂SO₄, filtered, and concentrated. Purification of the residue by column chromatography over SiO₂ gel (100-200 mesh, 5% EtOAc/hexane) provided (R)-(6-chloro-1-formyl-1,2,3,4-tetrahydronaphthalen-1-yl)methyl 4-bromobenzoate (80 g, 81%).

The enantiomeric purity of the title compound could be improved by the following procedure: (R)-(6-chloro-1-formyl-1,2,3,4-tetrahydronaphthalen-1-yl)methyl 4-bromobenzoate (190 g) was added in toluene (950 mL) and heated to 50° C. to complete dissolution. The homogeneous solution was cooled to ambient temperature and seeded with racemic compound. The solution was cooled to −25° C. and aged overnight. The mother liquor was then decanted and concentrated to afford 160 g of enantiomerically enriched (R)-(6-chloro-1-formyl-1,2,3,4-tetrahydronaphthalen-1-yl)methyl 4-bromobenzoate (94% ee as determined by chiral HPLC). Chiral HPLC conditions: Column: ChiralCel® OD-H (250 mm×4.6 mm); Mobile Phase: n-Hexane:IPA: 90:10. Run Time: 20 min. Flow rate: 1 mL/min. Sample preparation: ethanol. Retention time (major peak): 8.488 min (96.97%); Retention time (minor peak): 9.592 min (3.03%).

STEP 6: (R)-(6-CHLORO-1-(DIMETHOXYM-ETHYL)-1,2,3,4-TETRAHYDRONAPHTHALEN-1-YL)METHANOL

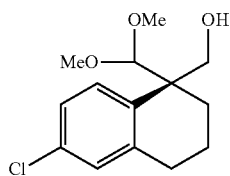 [SMILES: COC(OC)[C@]1(CO)CCCc2cc(Cl)ccc21]

To a solution of (R)-(6-chloro-1-formyl-1,2,3,4-tetrahydronaphthalen-1-yl)methyl 4-bromobenzoate (75 g, 183.8 mmol) in anhydrous MeOH (1 L), p-TsOH (1 g, 9.2 mmol) and trimethyl orthoformate (58.4 mL, 551 mmol) were added and the reaction mixture was refluxed until the starting material was completely consumed (~4 h). The reaction mass was concentrated to 50% volume and diluted with THF (1 L) and 1N NaOH (1 L, 1 mol). The resulting reaction mixture was stirred at 40° C. overnight and then concentrated under reduced pressure. The residue was diluted with EtOAc (1.5 L). The aqueous layer was separated and extracted with EtOAc (2×500 mL) and the combined organic layers were washed with 1N NaOH (1 L) and brine (1 L), dried over Na₂SO₄ and concentrated under reduced pressure. The crude material was purified by column chromatography over 100-200 mesh size SiO₂ gel (10% EtOAc/hexane) to give pure (R)-(6-chloro-1-(dimethoxymethyl)-1,2,3,4-tetrahydronaphthalen-1-yl)methanol as a light brown thick oil (44 g, 89%).

STEP 7: TERT-BUTYL-4-FLUORO-3-NITROBENZOATE

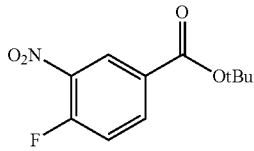 [SMILES: CC(C)(C)OC(=O)c1ccc(F)c([N+](=O)[O-])c1]

To a solution of 4-fluoro-3-nitrobenzoic acid (100 g, 540.2 mmol) in t-butanol (2.5 L), DMAP (13.18 g, 108.04 mmol) and di tert-butyl dicarbonate (248 mL, 1080.4 mmol) were added and the reaction mixture was heated at 40° C. overnight. Upon completion, the reaction mixture was diluted with $H_2O$ and the aqueous phase was extracted with EtOAc (3×1.5 L). The combined organic layer was washed further with $H_2O$ (1×1 L), brine (1×1 L), and dried over $Na_2SO_4$. The solvent was removed under reduced pressure and the crude material thus obtained was purified by column chromatography (100-200 mesh size $SiO_2$ gel, eluting with a gradient of 100% hexane to 5% EtOAc in hexane) affording pure tert-butyl-4-fluoro-3-nitrobenzoate (70 g, 54%) as light yellow solid.

STEP 8: (R)-TERT-BUTYL 4-((6-CHLORO-1-(DIMETHOXYMETHYL)-1,2,3,4-TETRAHYDRONAPHTHALEN-1-YL)METHOXY)-3-NITROBENZOATE

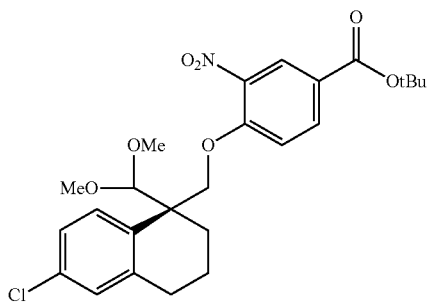 [SMILES: COC(OC)[C@]1(COc2ccc(C(=O)OC(C)(C)C)cc2[N+](=O)[O-])CCCc2cc(Cl)ccc21]

A solution of (R)-(6-chloro-1-(dimethoxymethyl)-1,2,3,4-tetrahydronaphthalen-1-yl)methanol (70 g, 259.2 mmol) in dry THF (3.5 L) was cooled to 0° C. and LiHMDS (1 M in THF; 363 mL, 363 mmol) was added dropwise. After 5 min, a solution of tert-butyl 4-fluoro-3-nitrobenzoate (74.9 g, 311 mmol) in THF (500 mL) was added dropwise via dropping funnel and the resulting mixture was warmed to ambient temperature. Upon completion (~1 h), the mixture was cooled to 0° C., quenched with sat. $NH_4Cl$ solution (1 L) and extracted with EtOAc (3×1 L). The combined organic layers were washed with $NH_4Cl$ (1 L) and brine (1 L), dried over $Na_2SO_4$ and concentrated under reduced pressure. The crude material thus obtained was purified by column chromatography using 100-200 mesh size $SiO_2$ gel (5% EtOAc/hexane) to afford (R)-tert-butyl 4-((6-chloro-1-(dimethoxymethyl)-1,2,3,4-tetrahydronaphthalen-1-yl)methoxy)-3-nitrobenzoate as yellow thick oil (110 g, 87% yield).

STEP 9A: (R)-4-((6-CHLORO-1-FORMYL-1,2,3,4-TETRAHYDRONAPHTHALEN-1-YL)METHOXY)-3-NITROBENZOIC ACID

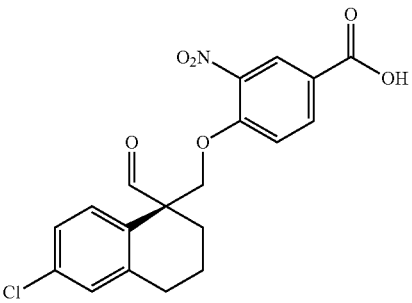 [SMILES: O=C[C@]1(COc2ccc(C(=O)O)cc2[N+](=O)[O-])CCCc2cc(Cl)ccc21]

To a solution of (R)-tert-butyl 4-((6-chloro-1-(dimethoxymethyl)-1,2,3,4-tetrahydronaphthalen-1-yl)methoxy)-3-nitrobenzoate (35 g, 71.25 mmol) in MeCN (1 L), erbium triflate (4.3 g, 7.1 mmol) and $H_2O$ (13 mL) were added. The resulting mixture was heated to 80° C. overnight. The solvent was then removed under reduced pressure and the residue was dissolved in $Et_2O$ (1.5 L) and washed with 1N HCl (500 mL) and brine (500 mL). The organic layer was dried over $Na_2SO_4$, filtered, and concentrated to afford (R)-4-((6-chloro-1-formyl-1,2,3,4-tetrahydronaphthalen-1-yl)methoxy)-3-nitrobenzoic acid (30 g), which was used without further purification.

Alternatively, (R)-4-((6-chloro-1-formyl-1,2,3,4-tetrahydronaphthalen-1-yl)methoxy)-3-nitrobenzoic acid may be prepared from (6-chloro-1,2,3,4-tetrahydronaphthalene-1,1-diyl)dimethanol (Step 4) as follows:

A 250 mL 3-necked-RBF was charged with copper (II) chloride (0.095 g, 0.02 eq), 2,6-bis((R)-5,5-dibutyl-4-phenyl-4,5-dihydrooxazol-2-yl)pyridine (0.42 g, 0.02 eq) and THF (28.5 g, 4V). After inertion with $N_2$, the batch was stirred at 20° C. for 0.5 h. To the homogenous green solution was added (6-chloro-1,2,3,4-tetrahydronaphthalene-1,1-diyl)dimethanol (8.0 g, 1.00 eq) followed by THF (14.2 g, 2V) and 4-methylmorpholine (3.75 g, 1.05 eq). The reaction mixture was cooled to −20° C., and a solution of 1-napthoyl chloride (7.06 g, 1.05 eq) in THF (21.3 g, 3 V) was added to the batch over 0.5 h maintaining the temperature below −15° C. After aging at −20° C. for 20 h, an aliquot of the reaction slurry was sampled and assayed by HPLC. The slurry was directly filtered through a glass-fritted funnel while maintaining the temperature at −20° C. The filter cake was washed with two portions of cold (<−10° C.) THF (2×14.2 g, 2V) rinsed through the reaction vessel. The filter cake (4-methylmorpholine*HCl) was transferred to a labeled container. The mother liquor and washes were concentrated to a minimum volume and distillative solvent swap by charging toluene until the batch volume is 6V and toluene/THF ratio is >98:2 (v/v) as measured by QNMR. To the batch at 20° C. was added heptane (11 g, 2V) and the slurry was heated to 85° C. (dissolution observed). The solution was cooled to 75° C. and charged with seed (0.27 g, 0.02 eq). The slurry was cooled to 20° C. over 3 h and aged for >1 h. The batch was filtered through a glass-fritted filter and the cake was washed with toluene/heptane (3:1 v/v) (11 g, 2V) then toluene/heptane (1:1 v/v) (11 g, 2V). The cake was dried under $N_2$ for 12 h at ambient temperature and the cake was assayed dry by QNMR (<1 wt % toluene and heptane). The product was obtained as an off-white solid (8.75 g, 63% after wt adjustment).

A 60 L jacketed reactor vented with a bleach scrubber was charged with (S)-(6-chloro-1-(hydroxymethyl)-1,2,3,4-tetrahydronaphthalen-1-yl)methyl 1-naphthoate (2.693 Kg, 88.6 wt %, 6.3 mol) followed by DCM (17.9 Kg, 5 vol) and EtNiPr$_2$ (2.84 Kg, 3.5 eq). After N$_2$ inertion, the batch was agitated and cooled to 0° C. To the alcohol slurry mixture in the reactor was added a solution of freshly prepared sulfur trioxide pyridine (2.10 Kg, 2.5 eq of sulfur trioxide pyridine in 7.43 Kg, 3 vol. DMSO) over 30 min while maintaining the batch temperature below 15° C. After addition, HPLC assay showed >99% conversion. The batch was quenched by the addition of H$_2$O (14 L, 5 vol) over ~20 min. maintaining the batch temperature below 15° C. and then toluene (16.8 L, 6 vol) was added. After partition, the organic layer was treated with H$_2$O (14 L, 5 vol) and toluene (16.8 L, 6 vol). The top organic layer was washed with 2 N HCl twice (14 L each, 5 vol) and brine (14 L, 5 vol). The organic layer was drained to a clean container, assayed by HPLC and then transferred back to the clean 60 L reactor through an inline filter. The batch was concentrated to a minimal volume and solvent switched to MeOH until the batch volume was 28 L (10 vol) and MeOH/toluene ratio was 3:1 (v/v) as measured by QNMR. The batch was then transferred to a 30 L jacketed reactor through an inline filter. After adjustment of the batch temperature to 30° C., the batch was seeded with the aldehyde (51 g, 0.02 eq) as a slurry in MeOH (400 mL). After the slurry was aged for 30 min at 30° C., the batch was solvent switched by distillation with MeOH until the batch volume is 11 L (4 vol) and MeOH/toluene ratio is ≥99:1 (v/v). The batch was then cooled to 5° C. and MeOH/H$_2$O mixture (3.70 Kg MeOH+1.34 Kg H$_2$O) was added over 1.5 h to bring the total solvent volume to approximately 5.5 vol and final MeOH/H$_2$O to 90/10 (v/v). The batch was heated to 65° C. over 30 min, and cooled to 20° C. over 2 h and aged for ~2 h. The batch was filtered through an Aurora® filter fitted with ≤25 µm filter cloth. The cake was washed with MeOH/H$_2$O (10:1) (1×2 vol), then MeOH/H$_2$O (2:1) (1×2 vol). The cake was dried under N$_2$ at ambient temperature for ≥4 h until dry to give the product as an off-white solid (1.99 Kg, 72% after wt % adjustment).

A 3-necked 250 mL RBF was charged with (R)-(6-chloro-1-formyl-1,2,3,4-tetrahydronaphthalen-1-yl)methyl 1-naphthoate (10 g, 94.4 wt %, 95.3% LCAP, >99% ee), methanol (100 mL), trimethyl orthoformate (7 mL), and TsOH.H$_2$O (0.24 g). The RBF was inerted with N$_2$, and agitation was initiated. The batch was heated to 60° C. and aged for 2 h. HPLC assay showed ≥98% conversion.

The batch was concentrated under vacuum (~150-190 torr, external temp ~40° C.) to minimal volume using a rotoevaporator. The batch was turned over to THF by charging THF three times (50 mL each time) and distilling under vacuum (~165 torr, external temp ~40° C.). After each of the first two THF charges, the batch was concentrated down to a minimal volume, and after the last THF charge and distillation QNMR analysis of a sample showed the target ratio of >20/1 THF/MeOH (v/v). LiOH.H$_2$O (10.46 g, 10 eq) and H$_2$O (50 mL) were charged to the 3-necked 250 mL RBF. The reaction mixture was heated to 65° C. and aged for 18 h. HPLC assay showed >99% conversion. The batch was cooled to 20° C. and transferred to a 500-mL separatory funnel. MTBE (106 mL) was charged to the separatory funnel and the funnel was shaken well. After settling for 5 min, the bottom aqueous layer was drained. The top organic layer was washed with 20% K$_2$CO$_3$ twice (32 mL and 11 mL). The batch was transferred to a 250 mL RBF. Assay by HPLC showed <2% naphthanoic acid byproduct. The batch was concentrated to a minimal volume at reduced pressure on the rotoevaporator (300 mbar, external temp ~40° C.). The batch was turned over to THF using a rotoevaporator (~250 mbar, external temp ~40° C.) by adding and distilling THF (~50 mL, ~50 mL). After each THF charge, the batch was distilled down to a minimal volume. THF (50 mL) was charged to the 250 mL RBF. KF of a sample showed 0% H$_2$O (≤0.1% acceptable). The batch was polish filtered (60 mL medium-frit funnel) into a clean and dry 250 mL 3-necked-RBF using THF (50 mL) for rinsing and volume adjusting. To the batch was added 4-fluoro-3-nitrobenzoic acid (4.61 g, 1.0 eq), the mixture was cooled to −20° C., and 20% potassium tert-butoxide THF solution (40 mL) was added over 1.5 h, maintaining the batch temperature at −20±10° C. (exothermic). After complete addition, the batch was aged at −20° C. and an aliquot assayed by HPLC after 1.5 h showed 98% conversion. To the batch in the flask was added sat. NH$_4$Cl solution (10 mL), maintaining the temperature at −20±10° C., followed by addition of H$_2$O (20 mL) and MeTHF (34 mL) at −20±20° C. The mixture was warmed to 20° C. and agitated for 13 h. The batch was transferred to a separatory funnel, allowed to settle for ~5 min, and the bottom aqueous layer was removed keeping the rag with the organic stream. The top organic stream was washed with sat. NH$_4$Cl solution (10 mL) and H$_2$O (20 mL) at 20° C. After ~5 min of settling, the aqueous layer was separated. To the total crude organic stream (KF=14%) was added MSA (4 mL) in a 250 mL 3-necked-RBF. The batch was heated to reflux (65° C.) for 25 h and LC assay showed full conversion (≥97%).

The batch was cooled to <20° C. and K$_3$PO$_4$.H$_2$O (4.5 g) and H$_2$O (7 mL) were added. The batch was transferred to a separatory funnel and the bottom aqueous layer was drained to give the aldehyde product crude solution. The combined organic crude stream was concentrated to minimum volume using a rotary evaporator. To the batch in a 500 mL RBF was charged AcOH (~50 mL, ~50 mL) and distilled using a rotary evaporator at reduced pressure (30 mbar, external temp ~40° C.). The THF level was measured by QNMR and none was observed. The mixture was transferred to a 250 mL 3-necked RBF and AcOH was added to adjust the total volume to ~40 mL, when crystallization occurred. To the batch was added H$_2$O (12 mL) over ~1 h. After aging for >1 h, LC assay of supernatant concentration was 9 mg/mL. If concentration is >10 mg/mL then a small portion of H$_2$O (0.2 vol) can be added; after checking by LC, repeat if necessary. The batch was filtered, washed with 20% H$_2$O/AcOH (23 mL) and dried under N$_2$/vacuum for 3.25 h to give the title compound (8.22 g) as an off-white solid (82% yield corrected for purity).

STEP 9B: (R)-TERT BUTYL 4-((6-CHLORO-1-FORMYL-1,2,3,4-TETRAHYDRONAPHTHA-LEN-1-YL)METHOXY)-3-NITROBENZOATE

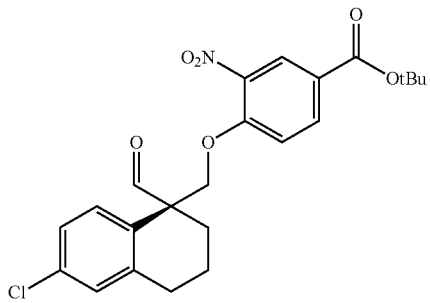 [SMILES: CC(C)(C)OC(=O)c1ccc(OC[C@@]2(C=O)CCCc3cc(Cl)ccc32)c([N+](=O)[O-])c1]

To a solution of (R)-tert-butyl 4-((6-chloro-1-(dimethoxymethyl)-1,2,3,4-tetrahydronaphthalen-1-yl)methoxy)-3-nitrobenzoate (1 g, 2.033 mmol) in anhydrous acetone (41 mL) was added Amberlyst®-15 (1 g, 2.033 mmol; pre-washed with 2×10 mL dry acetone). The mixture was heated to 50° C. for 3.5 h, then filtered and rinsed with DCM. The filtrate was concentrated and dried under high vacuum overnight (it turned a dark red color). LC/MS and NMR analysis suggested ~10% of corresponding carboxylic acid was present as well as 0.5 eq mesityl oxide. The mixture was advanced to Step 11 without further purification.

STEP 10: (S)-6'-CHLORO-3',4,4',5-TETRA-HYDRO-2H,2'H-SPIRO [BENZO [B][1,4]OX-AZEPINE-3,1'-NAPHTHALENE]-7-CARBOX-YLIC ACID

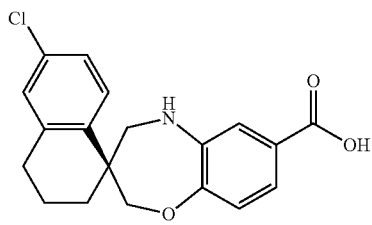 [SMILES: O=C(O)c1ccc2c(c1)NC[C@@]1(CCCc3cc(Cl)ccc31)CO2]

A solution of crude (R)-4-((6-chloro-1-formyl-1,2,3,4-tetrahydronaphthalen-1-yl)methoxy)-3-nitrobenzoic acid (30 g, 77.10 mmol) in AcOH (1 L) was heated to 70° C. and iron powder (28 g, 500 mmol) was added. The resulting mixture was heated for ~4 h at 70° C. AcOH was then removed under reduced pressure and the residue was dissolved in DCE (1 L). Sodium triacetoxy borohydride (46.5 g, 740 mmol) was added portion-wise and the reaction mixture was stirred at ambient temperature for 1 h. The reaction was then quenched with $H_2O$ followed by 10% aqueous citric acid (500 mL). The aqueous phase was extracted with DCM (2×1 L) and the combined organic layer was washed with brine (500 mL), dried over $Na_2SO_4$ and concentrated under reduced pressure. The residue was purified by column chromatography using 100-200 mesh size $SiO_2$ gel (40% EtOAc/hexane) to afford pure (S)-6'-chloro-3',4,4',5-tetrahydro-2H,2'H-spiro[benzo[b][1,4]oxazepine-3,1'-naphthalene]-7-carboxylic acid as white solid (24 g, 99% after two steps).

Alternatively, (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) may be prepared as follows:

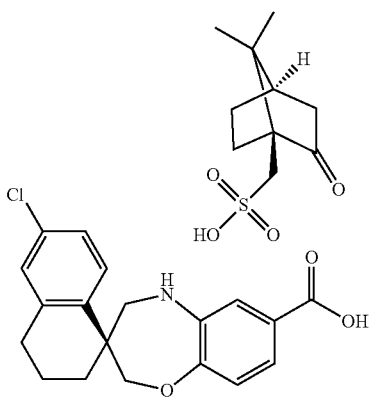

A pressure reactor was charged with (R)-4-((6-chloro-1-formyl-1,2,3,4-tetrahydronaphthalen-1-yl)methoxy)-3-nitrobenzoic acid (20 g, 94 wt %), 5% Pt/S/C wet (2.2 g), THF (400 mL) and titanium isopropoxide (0.5 mL). The reactor was sealed, purged with inert gas (3 cycles, at least once with stirring), and then purged with $H_2$ (1 cycle). The reactor was pressurized with $H_2$ to 70 psig, stirring (950 rpm) was initiated, and the temperature was increased to 90° C. maintaining the $H_2$ pressure in the reactor (70 psig at 22-30° C., 80 psig at 50-60° C. and 90 psig at 88-91° C.). After 16 h, the reactor was cooled to ambient temperature and purged with inert gas (3 cycles). HPLC analysis of the reaction confirmed >98% conversion.

The reaction mixture was filtered through a Celite® pad (2 inch) using additional THF for rinses, and the filtrate was concentrated under reduced pressure at 40° C. To the residue was added IPA (60 mL) and 2-4% aqueous MeOH (10 mL). The mixture was stirred for 10 min and then it was filtered through a Celite® pad (2 inch). MeOH was evaporated under reduced pressure at 40° C. and to the concentrated IPA solution cooled to ambient temperature was added a solution of +CSA (56.0 g) in IPA (200 mL) dropwise over 2 h. After 10% of the CSA solution has been added, the mixture was seeded with crystals of the title compound (10-15 mg) followed by the addition of the remaining CSA solution. After stirring at ambient temperature overnight, the mixture was filtered, and the filter cake was washed with 100 mL of IPA and dried under vacuum/$N_2$ at ambient temperature. The product is isolated as a white solid: (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (85-88% yield, >99.5% ee).

STEP 11A: (S)-METHYL 6'-CHLORO-3',4,4',5-TETRAHYDRO-2H,2'H-SPIRO [BENZO [B][1,4] OXAZEPINE-3,1'-NAPHTHALENE]-7-CARBOXYLATE

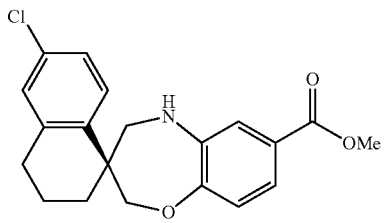 [SMILES: COC(=O)c1ccc2c(c1)NC[C@@]1(CCCc3cc(Cl)ccc31)CO2]

To a solution of (S)-6'-chloro-3',4,4',5-tetrahydro-2H,2'H-spiro[benzo[b][1,4]oxazepine-3,1'-naphthalene]-7-carboxylic acid (130 g, 379 mmol) in methanol (6 L) was added Amberlyst®-15 (130 g, pre-washed with anhydrous methanol) and heated to reflux for 10 h. Amberlyst® was then removed by filtration and rinsed with methanol (3×300 mL). The combined filtrate was concentrated and the residue was purified by column chromatography to give pure (S)-methyl 6'-chloro-3',4,4',5-tetrahydro-2H,2'H-spiro[benzo[b][1,4]oxazepine-3,1'-naphthalene]-7-carboxylate as a white solid (105 g, 77%). Chiral HPLC conditions: Column: Chiral-Cel® OD-H (250 mm×4.6 mm, 5 □m); Mobile Phase: n-Hexane:EtOH: 95:05. Run Time: 25 min. Flow rate: 1 mL/min. Retention time (minor peak): 10.162 min (1.98%); Retention time (major peak): 12.292 min (98.02%).

STEP 11B: (S)-TERTBUTYL 6'-CHLORO-3',4,4',5-TETRAHYDRO-2H,2'H-SPIRO [BENZO[B][1,4] OXAZEPINE-3,1'-NAPHTHALENE]-7-CARBOXYLATE

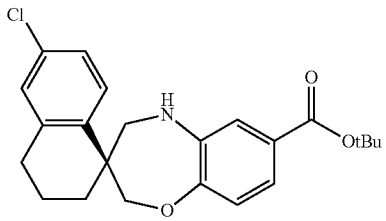 [SMILES: CC(C)(C)OC(=O)c1ccc2c(c1)NC[C@@]1(CCCc3cc(Cl)ccc31)CO2]

To a solution of (R)-tert-butyl 4-((6-chloro-1-formyl-1,2,3,4-tetrahydronaphthalen-1-yl)methoxy)-3-nitrobenzoate (0.9 g, 2.018 mmol) in AcOH (20.22 mL, 353 mmol) at 70° C. was added iron (0.676 g, 12.11 mmol). The mixture was stirred vigorously for 4 h, then concentrated, and the residue was diluted with 20 mL 1,2-DCE. Sodium triacetoxyhydroborate (1.711 g, 8.07 mmol) was added and the mixture was stirred at ambient temperature for 20 min.

Upon quenching by addition of 20 mL H₂O, a thick slurry was formed. 20 mL 10% citric acid solution was added and the mixture became lighter in color. The layers were separated and the aqueous layer was extracted with 2×20 mL DCM. The combined organics were washed with 10 mL 10% citric acid and 10 mL brine, dried over MgSO₄, filtered, and concentrated. The residue was deposited on 3 g SiO₂ gel and purified using 5-10% EtOAc in hexane to give (S)-tert-butyl 6'-chloro-3',4,4',5-tetrahydro-2H,2'H-spiro[benzo[b][1,4]oxazepine-3,1'-naphthalene]-7-carboxylate (557 mg, 1.393 mmol, 69.0% yield). Further elution with 30% EtOAc in Hex provided (S)-6'-chloro-3',4,4',5-tetrahydro-2H,2'H-spiro[benzo[b][1,4]oxazepine-3,1'-naphthalene]-7-carboxylic acid (132 mg, 0.384 mmol, 19.02% yield).

STEP 12: (1R,2S)-1,2-CYCLOBUTANEDIYLDIMETHANOL

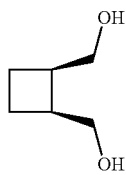

To a rapidly stirred solution of LAH (1.0 M solution in THF, 1000 mL, 1000 mmol) at ambient temperature in a 3000 mL 3-necked RBF under a stream of argon, solid (1R,5S)-3-oxabicyclo[3.2.0]heptane-2,4-dione (40 g, 317 mmol) was gradually added over 2 h, maintaining the internal temperature of the reaction mixture below 50° C. The reaction was stirred overnight at ambient temperature under argon. After 16 h, the reaction mixture was cooled by an ice bath to 10° C., and, under a fast stream of argon, a solution of 36 mL H₂O was added drop wise by addition funnel at a rate that maintained the temperature between 12-15° C., approximately 1 mL/min, with vigorous stirring (500 rpm). The mixture was then vigorously stirred (500 rpm) in the ice-bath for 1 h, then removed from the bath and stirred to rt for 1 h before cooling again with an ice bath to 5-10° C. To the mixture was added 36 mL of a 15% NaOH aqueous solution over a period of 45 min, maintaining the temperature between 10-20° C. To the mixture was added 108 mL H₂O drop wise by addition funnel, maintaining the temperature between 10-20° C., over ~1 h. Upon completed addition of the H₂O, the flask was removed from the ice bath, equilibrated to rt and left to stir vigorously under argon overnight. After stirring for 16 h, the mixture was filtered and the filtrate concentrated under reduced pressure to afford a colorless, slightly opaque oil. The oil was taken up in Et₂O and stirred over anhydrous MgSO₄ and filtered through a pad of Celite®. The filtrate concentrated under reduced pressure to afford 32.8 g of a colorless oil, which was used in the next step without further purification (89% yield).

STEP 13: CIS-CYCLOBUTANE-1,2-DIYLBIS(METHYLENE) DIACETATE

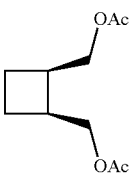 [SMILES: CC(=O)OC[C@H]1CC[C@H]1COC(C)=O]

Ac₂O (2.59 mL; 3.0 eq) was added to the CIS-1,2-cyclobutanediyldimethanol (1.06 g, 9.15 mmol) and the resulting solution was heated to 50° C. After stirring overnight, the mixture was assayed by GC and showed complete conversion. The mixture was then diluted with 15 mL of heptane and concentrated under vacuum to give a clear oil. The oil was dissolved in 15 mL heptane and concentrated back down to an oil (azeotropic removal of Ac₂O) to give the title compound as an oil (1.827 g, 88% yield, 88.3% purity by QNMR using benzyl benzoate as an internal standard).

STEP 14: (((1R,2S)-2-(HYDROXYMETHYL)CYCLOBUTYL)METHYL ACETATE

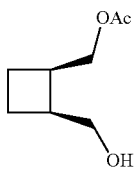 [SMILES: CC(=O)OC[C@@H]1CC[C@@H]1CO]

A 12 L 3-neck-RBF equipped with mechanical stirrer was charged with a 1M sodium citrate solution (prepared by mixing sodium citrate tribasic dihydrate; 682 g, 2320 mmol) and H₂O to reach total volume ~2.3 L) and 3.48 L H₂O (~25° C.). The mixture was cooled using an ice/H₂O bath to ~20.2° C. pH-8.46 (measured with pH probe). Amano Lipase from Pseudomonasfluorescens (41.8 g, 1547 mmol) was then added in one charge (pH ~8.12) and the mixture was vigorously stirred at ambient temperature for ~5 min. (1R,2S)-cyclobutane-1,2-diylbis(methylene) diacetate (348 g, 1547 mmol) was added in one charge and the resulting mixture was stirred vigorously at ambient temperature monitoring internal temperature and pH. After stirring the mixture overnight (~20.9° C. and pH~5.45) an aliquot was collected, extracted with IPAc, diluted with MeCN and analyzed by GC and the reaction was deemed complete (1.21% SM leftover, 0.17% of enantiomer, 1.8% of diol). Celite® (70 g) added to the reaction mixture and the slurry was filtered through a Celite® pad on a medium porosity glass filter (fast filtration, 15-20 min), rinsing with 2.5 L IPA. The biphasic mixture was transferred into a 12 L-extractor and stirred for 1 min. The aqueous layer was separated and extracted with IPAc (1×4 L), and the combined organic extract was concentrated in vacuo obtaining 337.28 g (99.6% ee; ~50-60 mol % of residual IPA by ¹HNMR; QNMR: 37.63 mg+benzyl benzoate (Aldrich catalog#B6630, lot# MKBG9990V, 61.27 mg; Result: ~65 wt %; corrected yield 89%). The crude product was used as such for the next step.

STEP 15: ((1R,2R)-2-FORMYLCYCLOBUTYL)METHYL ACETATE

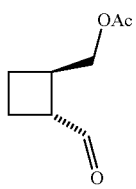 [SMILES: CC(=O)OC[C@@H]1CC[C@H]1C=O]

A 2-L Atlas reactor was charged with ((1R,2S)-2-(hydroxymethyl)cyclobutyl)methyl acetate (126.39 g, 79.6 wt % by QNMR; 636 mmol) and 1 L of DCM and the jacket temperature was set to 20° C. Iodobenzene diacetate (225 g, 700 mmol) was added as a solid (endothermic addition: the temperature decreased to 15° C.). TEMPO (3.97 g, 25.4 mmol) was added as a solid in one portion resulting in a cloudy orange solution, which became clear over the course of 20 min. After stirring at 20° C. overnight, an aliquot was collected, diluted with MeOH, and analyzed by GC. An additional kicker charge of iodobenzene diacetate and TEMPO can be used to push the reaction to completion if necessary. The reaction mixture was then cooled to 1.8° C. (internal temperature, ice/dry ice/H₂O bath) and DIPEA (194 mL, 1113 mol) was added drop-wise via addition funnel over 65 min keeping internal temperature <5° C. The cooling bath was removed and the mixture was allowed to warm to ambient temperature with stirring. After 48 h an aliquot was collected, diluted with methanol, and analyzed by GC showing a 12:1 ratio of trans:cis isomers. The reaction mixture was then cooled to <5° C. (ice/H₂O bath) and H₂O (230 mL) was added over ~10 min (internal temperature reached 14° C.). The organic layer was separated, washed with H₂O (125 mL) and 1M aqueous NaH₂PO₄ (90 mL) and concentrated in vacuo to afford 273.4 g of ((1R,2R)-2-formylcyclobutyl)methyl acetate (QNMR: 68.85 mg+benzyl benzoate (Aldrich catalog# B6630, Lot#MKBG9990V, 72.36 mg). The crude product was used as such for next step.

STEP 16: ((1R,2R)-2-((R)-(1H-BENZO[D][1,2,3]TRIAZOL-1-YL)(HYDROXY)METHYL)CYCLOBUTYL)METHYL ACETATE

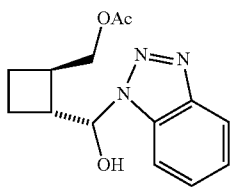 [SMILES: CC(=O)OC[C@@H]1CC[C@H]1C(O)n1nnc2ccccc21]

To a solution of crude ((1R,2R)-2-formylcyclobutyl) methyl acetate (5 g, 10.27 mmol) in 8 mL MTBE was added benzotriazole (1.296 g, 10.00 mmol) as a solid (slightly exothermic). The clear solution became increasingly cloudy and a precipitate formed. The mixture was allowed to equilibrate overnight at ambient temperature then heptane was added (6 mL). After aging for 6 h the mixture was filtered at ambient temperature and washed with 10 mL of 1:1 MTBE/heptane. The white solid was air dried on the frit under vacuum obtaining 2.48 g of ((1R,2R)-2-((R)-(1H-benzo[d][1,2,3]triazol-1-yl)(hydroxy)methyl)cyclobutyl) methyl acetate.

STEP 17: (S)-METHYL 5-(((1S,2R)-2-ACETOXY-CYCLOBUTYL)METHYL)-6'-CHLORO-3',4,4',5-TETRAHYDRO-2H,2'H-SPIRO [BENZO [B][1,4] OXAZEPINE-3,1'-NAPHTHALENE]-7-CARBOXYLATE

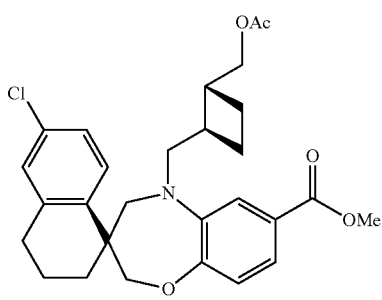

((1R,2R)-2-Formylcyclobutyl)methyl acetate (from Step 16; 4.36 g, 27.9 mmol) was added to a solution of (S)-methyl 6'-chloro-3',4,4',5-tetrahydro-2H,2'H-spiro[benzo[b][1,4]oxazepine-3,1'-naphthalene]-7-carboxylate (5.0 g, 13.97 mmol) (Step 12) in DCM (78 mL) and AcOH (38.8 mL). The solution was stirred at ambient temperature for 10 min, then cooled to 0° C., and sodium cyanoborohydride (1.463 mL, 27.9 mmol) was added slowly over 1 h. The mixture was stirred at 0° C. for 10 min, then poured slowly into cold NaOH solution, and extracted with EtOAc (120 mL). The organic phase was washed with brine, dried over anhydrous Na$_2$SO$_4$, and concentrated. The residue was loaded to a 220 g ISCO gold column and eluted with 0% to 10% EtOAc/hexane to provide the title compound 6.0 g of the title compound as a white solid. m/z (ESI +ve ion) 498.1 (M+H)$^+$.

STEP 18A: (S)-METHYL 6'-CHLORO-5-(((1R,2R)-2-(HYDROXYMETHYL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLATE

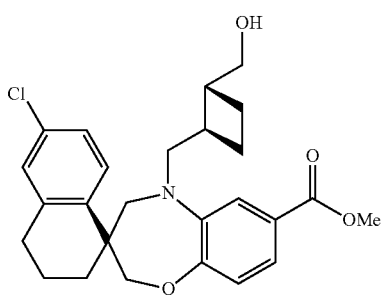

KOH (0.278 mL, 10.14 mmol) was added to a solution of (S)-methyl 5-(((1R,2S)-2-(acetoxymethyl)cyclobutyl)methyl)-6'-chloro-3',4,4',5-tetrahydro-2H,2'H-spiro[benzo[b][1,4]oxazepine-3,1'-naphthalene]-7-carboxylate (from Step 18; 1.530 g, 3.07 mmol) in MeOH (99 mL). The mixture was stirred at ambient temperature for 4 h, then neutralized with 1N HCl to pH=7, and concentrated under reduced pressure. The aqueous residue was extracted with EtOAc (400 mL) and the organic extract was washed with brine, dried over anhydrous Na$_2$SO$_4$, and filtered through a short plug of SiO$_2$ gel to afford the title compound as a white solid. (1.354 g was obtained. m/z (ESI, +ve ion) 456.2 (M+H)$^+$)

Alternatively, (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate may be prepared as follows:

To a slurry of (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (Step 11) (32.22 g, 52.5 mmol) and ((1R,2R)-2-((R)-(1H-benzo[d][1,2,3]triazol-1-yl)(hydroxy)methyl)cyclobutyl)methyl acetate (Step 17) (15.89 g, 57.7 mmol) in DCM (226 mL, 7 mL/g) was added sodium triacetoxyborohydride (13.90 g, 65.6 mmol) in 4 portions over 30 min. Additional ((1R,2R)-2-((R)-(1H-benzo[d][1,2,3]triazol-1-yl)(hydroxy)methyl)cyclobutyl) methyl acetate (2.89 g, 10.50 mmol) and sodium triacetoxyborohydride (2.78 g, 13.12 mmol) were added to drive the reaction to completion (determined by HPLC assay). 80 mL of H$_2$O was then added and the resulting mixture was agitated for 5 min. The layers were separated, the organic phase was washed with 60 mL H$_2$O and 20 mL of brine, and then concentrated to an oil under reduced pressure. The residue was dissolved in 50 mL of MeOH and 40 mL of 5N NaOH were then added at ambient temperature (exothermic). Upon reaction completion (determined by HPLC assay), the reaction mixture was partitioned between 133 mL of MTBE and 35 mL of 1.5 M citric acid. The organic phase was transferred to a RBF and the solvent was exchanged to MeCN via atmospheric distillation. This solution was seeded at 62° C. (a slurry developed), was allowed to reach ambient temperature, and then aged overnight. The slurry was filtered at 20.5° C. through a coarse frit glass sinter funnel and the filter cake was washed using 60 mL of MeCN, then dried in a vacuum oven at 40° C. to constant weight. Final mass: 21.87 g (96.4 wt % by HPLC).

A 100 mL 3-necked-RBF was charged with (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic acid (4.53 g, 1.0 eq), MeOH (45 mL, 10 vol), and then a prepared solution of SOCl$_2$ (11.28 mL, 1.0M in MeCN, 1.1 eq). Under an atmosphere of N$_2$, the batch was heated to 55° C. and stirred for 18 h (or until >99% conversion as determined by HPLC). The reaction mixture was then allowed to cool to 20° C. over 2 h. To the resulting white slurry was added Hunig's base (3.94 mL, 2.2 eq) and after aging for 0.5 h, H$_2$O (9.0 mL, 2 V) was added as antisolvent over 1 h. The white slurry was aged for >2 h and the batch was filtered through a glass-fritted filter and the cake was washed with MeOH/H$_2$O (5:1 v/v) (9.0 mL, 2V) then MeOH/H$_2$O (2:1 v/v) (9.0 mL, 2V). The cake was dried under N$_2$ with vacuum for 12 h at ambient temperature. The product was obtained as a white solid (4.36 g, 92% yield).

STEP 18B: (S)-TERTBUTYL 6'-CHLORO-5-(((1R,2R)-2-(HYDROXYMETHYL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLATE

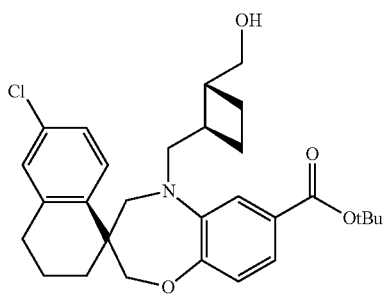

The title compound was synthesized from (S)-tertbutyl 6'-chloro-3',4,4',5-tetrahydro-2H,2'H-spiro[benzo[b][1,4]oxazepine-3,1'-naphthalene]-7-carboxylate (Intermediate AA11A) following the procedures described for Intermediate AA11A, Steps 18-19A).

STEP 19A: (S)-METHYL 6'-CHLORO-5-(((1R,2R)-2-FORMYLCYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLATE

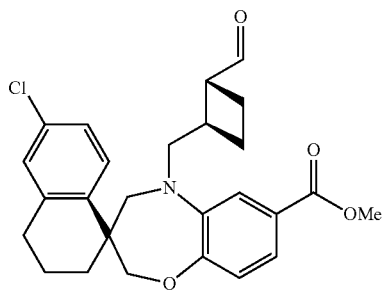

To a cooled (−70° C.) solution of DMSO (7.12 mL, 2.5 eq) and DCM (183 mL, 10 vol) in a 1 L 3-necked-RBF inerted with N$_2$ was added oxalyl chloride (26.1 mL, 1.0M in DCM, 1.3 eq) at a rate to maintain temperature below −70° C. The batch was aged below −70° C. for 30 min and then a prepared solution of (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (from Step 19A; 18.3 g, 1.0 eq) in DCM (183 mL, 10 vol) was added at a rate to maintain reaction temperature <−70° C. The batch was aged for 1.5 h and then Et$_3$N (22.4 mL, 4.0 eq) was added at a rate to maintain batch temperature <−70° C. After aging for 1 h, the batch was allowed to warm to −20° C. and H$_2$O (366 mL, 20 vol) was added. The batch was agitated at 20° C. and the phases separated. The organic layer was washed with 2×1N HCl (183 mL, 10 vol) and brine (183 mL, 10 vol). The organic layer was polish filtered and concentrated in vacuo to afford (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (19.91 g, 94% yield corrected for wt %) as a tan foam.

STEP 19B: (S)-TERTBUTYL 6'-CHLORO-5-(((1R,2R)-2-FORMYLCYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLATE

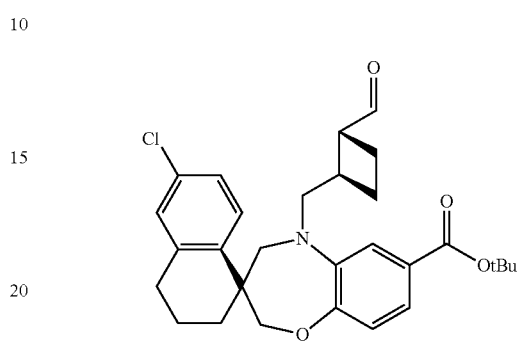

The title compound was synthesized from (S)-tertbutyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (Intermediate AA 11A, Step 19B) following the procedure described for Intermediate AA11A, step 20A.

STEP 20: (S)-METHYL 6'-CHLORO-5-(((1R,2R)-2-((S)-1-HYDROXYALLYL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLATE

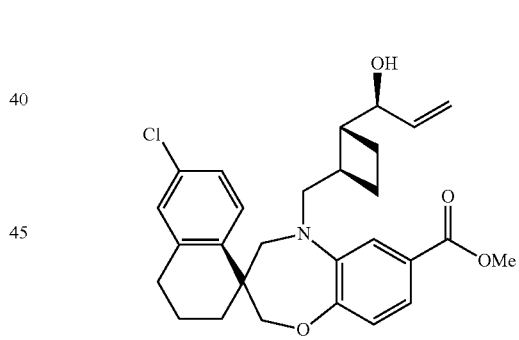

An oven dried 3-necked-RBF equipped with a pressure-equalizing addition funnel, thermocouple, and magnetic stirbar was cooled to ambient temperature under a purge of argon gas. The flask was charged with (1R,2S)-2-morpholino-1-phenylpropan-1-ol (40.2 g, 182 mmol; prepared according to the literature procedure by Brubaker, J. D.; Myers, A. G. *Org. Lett.* 2007, 9, 3523-3525) against a positive pressure of argon. The addition funnel was charged with toluene (450 mL), which was dropped into the reactor. The solution was cooled in an ethyleneglycol-CO$_2$ bath (~−12° C.) and treated with butyllithium solution (2.5 M in hexane, 72.6 mL, 182 mmol), causing a white solid to precipitate that gradually went into solution as it was stirred over 30 min. Divinylzinc solution (605 mL, 182 mmol; prepared according to Brubaker, J. D.; Myers, A. G. *Org. Lett.* 2007, 9, 3523-3525. The concentration of divinylzinc solution was determined by titrating against iodine (Krasovskiy, A.; Knochel, P. Synthesis 2006, 890-891; concentration was generally ~0.25M) was added, and the solution was aged with stirring in the cold bath for 1 h; the internal temperature was −15° C. (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (from Step 20A; 48.5 g, 107 mmol) (azeotroped thrice with toluene) was added as a solution in toluene (200 mL, 150 mL+2×25 mL cannula/vial rinse) via cannula, over ~20 min. The internal temperature rose to −10° C. The mixture was stirred for 90 min while maintaining the internal reaction temperature below −5° C. The addition funnel was charged with 30% w/w aqueous citric acid (450 mL), then the reaction was quenched by adding the solution to the reaction mixture. The reactor was removed from the bath and permitted to stir at ambient temperature. The solution was transferred to a separatory funnel and the flask was rinsed with toluene and 30% aqueous citric acid (50 mL each). The layers were mixed and then separated. The organic layer was washed with $H_2O$ (250 mL), then brine (250 mL), and finally dried with $MgSO_4$. The solution was filtered and concentrated to yield a yellow oil, ~90 g after vacuum overnight, 20:1 dr. This was split into 3 batches and purified by column chromatography 10 to 20% EtOAc/hexane 1.5 kg $SiO_2$, to provide (S)-methyl-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (43.3 g, 84%). The aqueous layer and washings were placed in an ice/$H_2O$ bath and basified to pH >13 by addition of 8N aqueous NaOH. This solution was then extracted with toluene (3×250 mL). The combined organic extracts were washed with $H_2O$ (250 mL) and brine (250 mL), then dried with $MgSO_4$. The solution was filtered and concentrated to recover the ligand in >95% yield.

STEP 21: (S)-6'-CHLORO-5-(((1R,2R)-2-((S)-1-HYDROXYALLYL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLIC ACID

To a solution of (S)-methyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (from Step 21; 4.59 g, 9.52 mmol) in a mixture of THF (18 mL), MeOH (6.00 mL) and $H_2O$ (6.00 mL) was added $LiOH \cdot H_2O$ (0.799 g, 19.05 mmol) and the reaction was stirred at 50° C. for 4 h. The reaction mixture was concentrated to ~15 mL, cooled to 0° C. and acidified with 2N HCl to pH=3. The resulting viscous oil was diluted with 20 mL of $H_2O$ and 50 mL of EtOAc and a clear two-layer mixture was obtained. More EtOAc (ca. 200 mL) was added and the organic layer was separated, washed with brine, dried with $MgSO_4$, filtered and concentrated under reduced pressure. The crude material was loaded onto a column (220 g), and purified with EtOAc in hexane using the following gradient: 0-2.5 min 0% of EtOAc, 2.5-6 min 0-20% EtOAc, 6-35 min 20-60% EtOAc, 35-40 min 70% EtOAc to give (S)-6'-chloro-5-(((1R,2R)-2-((S)-1-hydroxyallyl)cyclobutyl)methyl)-3',4,4',5-tetrahydro-2H,2'H-spiro [benzo[b][1,4] oxazepine-3,1'-naphthalene]-7-carboxylic acid (4.22 g, 9.02 mmol, 95% yield) as a white solid.

Intermediate AA12A (S)-6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLIC ACID

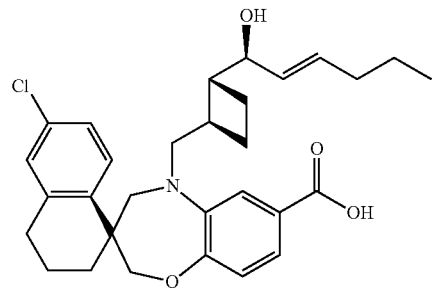

STEP 1A: (S)-METHYL 6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO [BENZO [B][1,4] OXAZEPINE-3,1'-NAPHTHALENE]-7-CARBOXYLATE

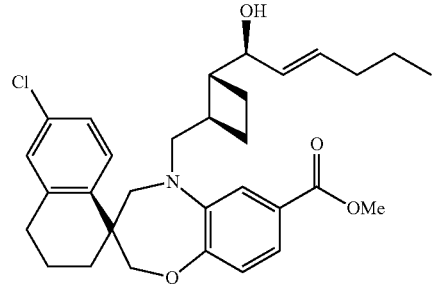

Under argon atmosphere, a dry 3-necked-RBF charged with dry hexane (27 mL) was cooled to 0° C. To this solution was added borane-methyl sulfide complex (3.29 mL, 34.6 mmol) and cyclohexene (7.01 mL, 69.3 mmol) and the mixture was stirred at 0° C. for 2 h. To the resulting white suspension was added 1-pentyne (3.41 mL, 34.6 mmol) and the mixture was stirred at ambient temperature for 0.5 h. The mixture was then cooled to −78° C. and diethylzinc, 1.0 M solution in hexane (32.3 mL, 32.3 mmol) was added. After addition the mixture was warmed to 0° C., stirred for 3 min then recooled to −78° C. This solution was named solution A. A separate flask was charged with a mixture of ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 5.24 g, 11.54 mmol) and (2s)-3-exo-(morpholino)isoborneal (0.486 g, 2.032 mmol) in hexane (50.9 mL) and toluene (16.97 mL). The mixture was stirred at ambient temperature until all solid was dissolved, then cooled to 0° C. Under argon atmosphere 54 mL of solution A was added slowly via syringe during 1.6 h. After stirring for 5 min at 0° C., the mixture was quenched with sat. $NH_4Cl$ solution (70 mL), diluted with $H_2O$ (30 mL) and extracted with EtOAc (3×270 mL), washed with brine, dried over anhydrous Na₂SO₄ and concentrated. The residue was loaded to a 330 g ISCO gold column and eluted with 0% to 5% EtOAc/hexane, to provide the title compound 3.8 g as a white solid. m/z (ESI, +ve ion) 524.1 (M+H)⁺.

STEP 1B: (S)-TERTBUTYL 6'-CHLORO-5-(((1R, 2R)-2-((S,E)-1-HYDROXYHEX-2-EN-1-YL)CYCLOBUTYL)METHYL)-3',4,4',5-TETRAHYDRO-2H,2'H-SPIRO [BENZO[B][1,4]OXAZEPINE-3,1'-NAPHTHALENE]-7-CARBOXYLATE AND (S)-TERTBUTYL 6'-CHLORO-5-(((1R,2R)-2-((R,E)-1-HYDROXYHEX-2-EN-1-YL)CYCLOBUTYL)METHYL)-3',4,4',5-TETRAHYDRO-2H,2'H-SPIRO [BENZO[B][1,4]OXAZEPINE-3,1'-NAPHTHALENE]-7-CARBOXYLATE

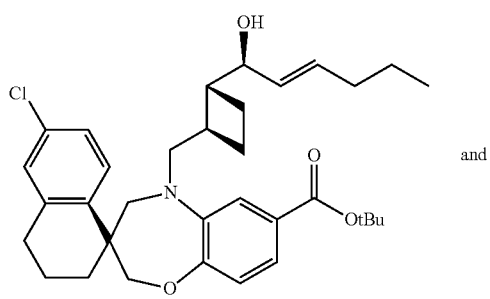

and

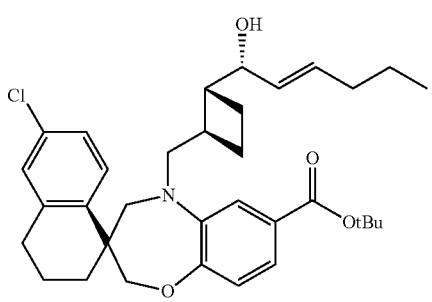

The title compound was synthesized from (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (3.19 g, Intermediate AA11A, Step 20B) following the procedure described for Intermediate AA12A, Step 1A. The crude material was absorbed onto a plug of SiO₂ and purified on a 330 g ISCO gold column eluting with 0 to 15% EtOAc in heptanes over 45 min to provide (S)-tertbutyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (2.36 g). Further elution provided (S)-tert-butyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (0.45 g).

STEP 2: (S)-6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLIC ACID

A mixture of (S)-methyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (from Intermediate AA12A, Step A; 4.6 g, 8.78 mmol) and LiOH.H₂O (3.68 g, 88 mmol) in MeOH (98 mL) and THF (98 mL) (with a few drops of H₂O) was stirred at 50° C. overnight. The solvent was removed and the residue was acidified with 1N HCl to pH 2-3. The mixture was extracted with EtOAc (80 mL×3) and the combined organic layer was washed with brine (10 mL), dried over anhydrous MgSO₄ and concentrated under reduced pressure to give (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (4.25 g, 8.34 mmol, 95% yield).

Alternatively, the title compound may be synthesized as follows:

To a solid mixture of (S)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1B, first eluting isomer, 4.50 g 7.95 mmol) and LiOH.H₂O (1.66 g, 39.7 mmol) was added solvent dioxane/MeOH (1:1) (159 mL). The mixture was heated to 65° C. and stirred overnight. The mixture was then diluted with H₂O and acidified with 1.0 N HCl to pH-4. The organic solvents were evaporated under reduced pressure and to the residue was added H₂O. The aqueous mixture was then extracted with EtOAc three times, and the combined organic extract was concentrated. The residue was purified on a 120 g SiO₂ gel column eluting with a gradient of 0-70% EtOAc in hexane to provide (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (3.80 g, 7.45 mmol, 94% yield).

Intermediate AA13A (S)-6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLIC ACID

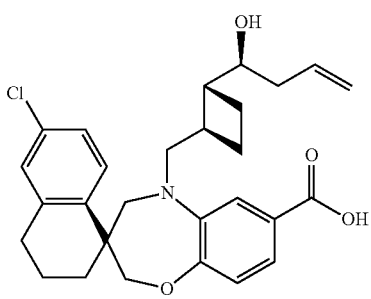

STEP 1A: (S)-METHYL 6'-CHLORO-5-(((1R,2R)-2-((S)-1-HYDROXYBUT-3-EN-1-YL) CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

STEP 1B: (S)-TERTBUTYL 6'-CHLORO-5-(((1R,2R)-2-((S)-1-HYDROXYBUT-3-EN-1-YL) CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

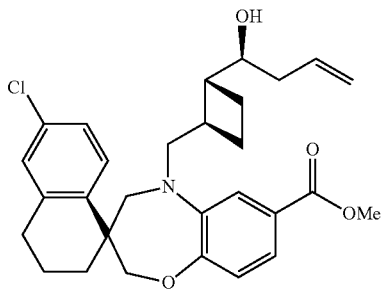

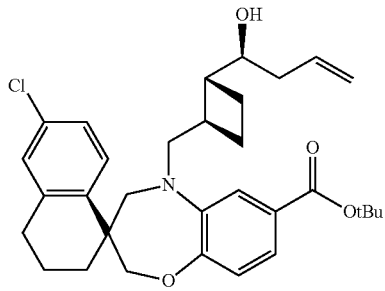

The title compound was synthesized from (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20B; 3.0 g) following the procedure described for Intermediate AA13A, Step 1A. The crude material was purified on a 220 g SiO₂ gel column eluting with 5% EtOAc in hexane over 60 min to provide (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (2.19 g).

An oven-dried 200-mL flask charged with a suspension of (1R,2R)-N-methyl-1-phenyl-1-(((1S,5S,10R)-10-(trimethylsilyl)-9-borabicyclo[3.3.2]decan-9-yl)oxy)propan-2-amine (5.40 g, 14.54 mmol) in Et₂O (73 mL) under argon was cooled to −78° C. and treated with allylmagnesium bromide (13.22 mL, 13.22 mmol) solution, dropwise. The mixture was allowed to warm to ambient temperature and stirred for 1 h. The solution (~0.17 M; solution A) was then recooled to −78° C.

A separate 200 mL flask charged with ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 2.0 g, 4.41 mmol) in Et₂O (22.03 mL) under argon was cooled to −78° C. To this solution was added 40 mL of the above-referenced solution A and the resulting mixture was stirred at −78° C. for 40 min. 4-methylmorpholine 4-oxide (3.10 g, 26.4 mmol) was then added and the mixture was allowed to warm to ambient temperature for 10 min. Methanol (10 mL) was added and the volatile organics were evaporated under reduced pressure at ambient temperature. Additional methanol (100 mL) was added and after stirring at ambient temperature for 1 h the mixture was concentrated. The residue was diluted with EtOAc (450 mL), washed with 1N HCl (15 mL), Na₂CO₃ solution (10 mL), and brine (6 mL), dried over anhydrous Na₂SO₄ and concentrated. The residue was loaded to a 220 g ISCO gold column and eluted with 0% to 5% EtOAc/hexane, to provide 1.88 g of the title compound as a white solid. m/z (ESI, +ve ion) 496.0 (M+H)⁺.

STEP 2: (S)-6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO [BENZO [B][1,4]OXAZEPINE-3,1'-NAPHTHALENE]-7-CARBOXYLIC ACID

A mixture of (S)-methyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (from Intermediate AA13A, Step 1A; 1.88 g, 3.79 mmol) and LiOH solution (1M) (34.1 mL, 34.1 mmol) in MeOH (34 mL) and THF (50 mL) was stirred at 65° C. for 50 min. After cooling to ambient temperature, the mixture was acidified with 1N HCl to pH 2 to 3, extracted with EtOAc (350 mL), dried over anhydrous Na₂SO₄ and concentrated to provide 1.82 g of the title compound as a white solid. m/z (ESI, +ve ion) 482.0 (M+H)⁺.

Alternatively, the title compound may be synthesized as follows:

To a solution of (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA13A, Step 1B; 250 mg, 0.465 mmol) in DCM (3.717 mL) at ambient temperature, TFA (0.929 mL) was added and the reaction mixture was stirred for 4 h. The crude reaction mixture was then concentrated, the residue was taken up in EtOAc, washed once with sat. NaHCO₃, dried over MgSO₄, filtered and concentrated to give a white foam. The crude material was used as such, without further purification.

Intermediate EE11

N,N-BIS(4-METHOXYBENZYL)AMINE

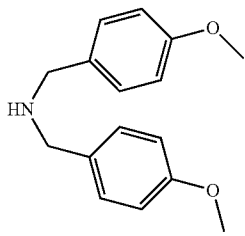 [SMILES: COc1ccc(CNCc2ccc(OC)cc2)cc1]

A solution of 4-methoxybenzaldehyde (Spectrochem; 100 g, 734.5 mmol) and 4-methoxybenzyl amine (G.L.R.; 100 g, 734.5 mmol) in toluene (0.8 L) was refluxed at 130° C. using a Dean-Stark apparatus for 6 h. The reaction was monitored by TLC and upon completion, excess solvent was removed under reduced pressure and the residue was dissolved in methanol (0.8 L). The resulting solution was cooled to 0° C. and sodium borohydride (36.12 g, 954.8 mmol) was added in portions. After complete addition, the reaction mixture was stirred for 3 h at ambient temperature. Methanol was removed, and the residue was diluted with $H_2O$ (1.0 L) and EtOAc (2.0 L). The layers were separated and the aqueous layer was extracted with EtOAc (2×1.0 L). The combined organic layer was washed with $H_2O$, brine, and dried over $Na_2SO_4$. Solvent was removed under reduced pressure and the crude material obtained was purified by column chromatography over $SiO_2$ gel (100-200 mesh size) eluting with a gradient of 100% hexane to 25% EtOAc in hexane affording the title compound (160 g, 84.6%) as a colorless but opaque liquid.

Intermediate EE12

N,N-BIS(4-METHOXYBENZYL)METHANE SULFONAMIDE

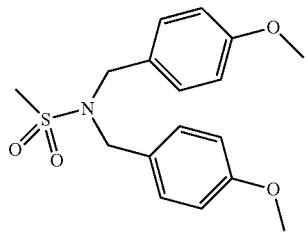

A mixture of methanesulfonamide (Sigma-Aldrich, 5 g, 52.6 mmol), p-methoxybenzyl chloride (14.98 mL, 110 mmol), $K_2CO_3$ anhydrous (36.3 g, 263 mmol) and potassium iodide (0.873 g, 5.26 mmol) in anhydrous 2-butanone (175 mL) was refluxed (75° C.) overnight. The reaction was monitored by TLC and LC/MS and upon completion, the mixture was cooled to ambient temperature, filtered, washed with $Et_2O$ and concentrated. The crude material (17.54 g, 52.3 mmol, 99% yield) was used with no further purification. MS (ESI, positive ion) m/z: 358.1 (M+Na).

Intermediate EE13

N,N-BIS(4-METHOXYBENZYL)ETHANE SULFONAMIDE

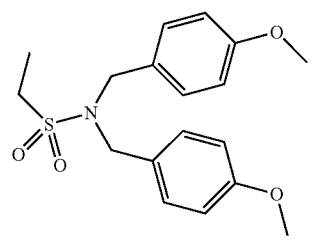 [SMILES: CCS(=O)(=O)N(Cc1ccc(OC)cc1)Cc1ccc(OC)cc1]

To a solution of N,N-bis(4-methoxybenzyl)amine (Intermediate EE11; 200 g, 775.19 mmol) in DCM (2.5 L) was added $Et_3N$ (336.17 mL, 2325.5 mmol), and the reaction mixture was cooled to 0° C. Ethanesulfonyl chloride (95 mL, 1007.75 mmol) was added in drop-wise manner followed by DMAP (19.0 g, 155.03 mmol). The resulting reaction mixture was stirred at ambient temperature for 30 min. The reaction was monitored by TLC and upon completion, the mixture was diluted with $H_2O$ and the layers were separated and the aqueous phase was extracted with DCM (3×1.5 L). The combined organic layer was washed with $H_2O$, brine, and dried over $Na_2SO_4$. The solvent was removed under reduced pressure to afford the crude material which was purified by column chromatography over $SiO_2$ gel (100-200 mesh), eluting with a gradient of 0-12% EtOAc in hexane affording the title compound (145 g, 53.4%) as a white fluffy solid.

Intermediate EE14

N,N-BIS(4-METHOXYBENZYL)PROPANESULFONAMIDE

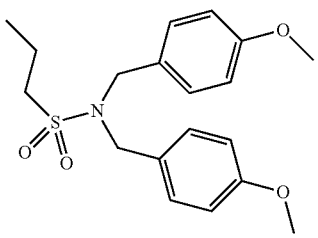 [SMILES: CCCS(=O)(=O)N(Cc1ccc(OC)cc1)Cc1ccc(OC)cc1]

To a solution of N,N-bis(4-methoxybenzyl)amine (Intermediate EE11; 405 g, 1569.7 mmol) in DCM (4.0 L) was added $Et_3N$ (681.0 mL, 4709.3 mmol), and the reaction mixture was cooled to 0° C. Propanesufonyl chloride (231 mL, 2040.6 mmol) was added in a drop-wise manner followed by DMAP (38.3 g, 313.9 mmol). The resulting mixture was stirred at ambient temperature for 30 min. The reaction was monitored by TLC and upon completion, the mixture was diluted with 2.0 L of $H_2O$, the layers were separated and the aqueous phase was extracted with DCM (3×2.0 L). The combined organic layer was washed with $H_2O$, brine, and dried over $Na_2SO_4$. The solvent was removed under reduced pressure to afford the crude material which was purified by column chromatography over $SiO_2$ gel (100-200 mesh), eluting with a gradient of 0-12% EtOAc in hexane affording the title compound (300 g, 52.44%) as white fluffy solid.

Intermediate EE15

BUT-3-ENE-1-SULFONAMIDE

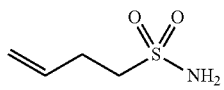

STEP 1: SODIUM BUT-3-ENE-1-SULFONATE

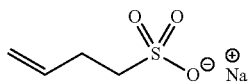

A mixture of 4-bromo-1-butene (LLBChem, 3.01 mL, 29.6 mmol) and sodium sulfite (4.11 g, 32.6 mmol) in H₂O (20 mL) was stirred at 110° C. overnight. The reaction was monitored by TLC and upon completion, H₂O was removed under reduced pressure and the residue was triturated with acetone. The solid obtained was filtered to afford the title compound as a white solid (4.53 g) which was used as such in next step.

STEP 2: BUT-3-ENE-1-SULFONAMIDE

A mixture of sodium but-3-ene-1-sulfonate (4.50 g, 28.5 mmol) and phosphorus oxychloride (70 mL) was stirred at 135° C. for 7 h. Phosphorus oxychloride was then removed under reduced pressure to obtain a dark residue containing a white solid. This residue was diluted with MeCN (20 mL), and then filtered to remove the precipitate. The filtrate was cooled to 0° C. and treated with ammonia solution (30% aqueous) (30 mL) dropwise. After complete addition, the reaction was stirred at 0° C. for 30 min. The mixture was diluted with EtOAc (300 mL), washed with brine, and dried over anhydrous Na₂SO₄. The solvent was removed under reduced pressure and the residue was purified by column chromatography over SiO₂ gel (100-200 mesh; eluting with 1:1 EtOAc/hexane), affording the title compound as a white solid (1.55 g, yield: 40%). MS (ESI, positive ion) m/z: 117.1 (M+1).

Intermediate EE16

N,N-BIS(4-METHOXYBENZYL)BUT-3-ENE-1-SULFONAMIDE

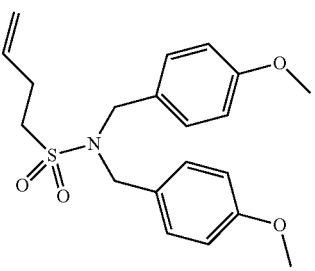 [SMILES: C=CCCS(=O)(=O)N(Cc1ccc(OC)cc1)Cc1ccc(OC)cc1]

A mixture of but-3-ene-1-sulfonamide (Intermediate EE15; 1.5 g, 11.10 mmol), p-methoxybenzyl chloride (3.76 mL, 27.7 mmol), K₂CO₃ anhydrous (7.67 g, 55.5 mmol) and sodium iodide (0.166 g, 1.110 mmol) in anhydrous 2-butanone (55.5 mL) was refluxed (75° C.) overnight. The reaction was monitored by TLC and LC/MS and upon completion, the mixture was cooled to ambient temperature, filtered, and concentrated. The crude material was absorbed onto a plug of SiO₂ gel and purified by chromatography through SiO₂ gel (100-200 mesh), eluting with 0 to 30% EtOAc in hexane, to provide the title compound (4.10 g, 10.92 mmol, 98% yield) as a colorless oil. MS (ESI, positive ion) m/z: 376.2 (M+1).

Intermediate EE17

(R)-PENT-4-ENE-2-SULFONAMIDE

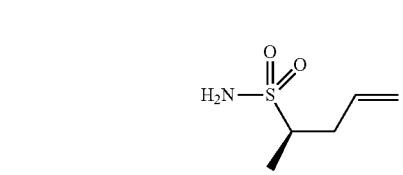

STEP 1: (S)—N,N-BIS(4-METHOXYBENZYL) PENT-4-ENE-2-SULFONAMIDE AND (R)-N,N-BIS(4-METHOXYBENZYL)PENT-4-ENE-2-SULFONAMIDE

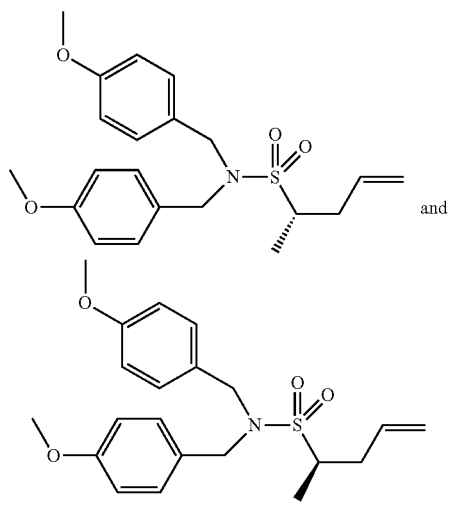

and

N,N-bis(4-methoxybenzyl)but-3-ene-1-sulfonamide (Intermediate EE16; 50.0 g, 133.2 mmol) was azeotroped with toluene and dried under vacuum for 1 h. THF (890 mL) was added and the mixture was cooled to −78° C. Butyl lithium (2.5 M in hexane, 63.9 mL, 159.9 mmol) was then added and the reaction mixture was stirred at −78° C. for 1 h. This anion solution was added slowly to a solution of MeI (16.8 mL, 266.5 mmol) in THF (300 mL) cooled to −78° C. The resulting reaction mixture was stirred for another 15 min at −78° C. On completion of the reaction (monitored by TLC) the mixture was quenched with sat. NH₄Cl solution and extracted with EtOAc. The organic layer was dried over Na₂SO₄ and concentrated under reduced pressure to obtain crude material which was purified by column chromatography over SiO₂ gel eluting with 5-10% EtOAc in hexane to provide the title compound as a racemic mixture (22.0 g) of semisolid nature. Separation of the enantiomers by SFC (Column: Chiralpak® AD-H, 50×250 mm, 5 μm; Mobile Phase A: CO₂; Mobile Phase B: Ethanol; Isocratic: 40% B with CO₂ recycler on; Flow Rate: 200 g/min; Loading: 2.0 mL of sample prepared as above (~100 mg); Detection: UV @ 230 nm; Cycle Time: 5 min; Total Elution Time: 10 min; Instrument: Thar 350 (Lakers)) provided (S)—N,N-bis(4-methoxybenzyl)pent-4-ene-2-sulfonamide as the first eluting isomer (retention time: 2.22 min) and (R)-N,N-bis(4-methoxybenzyl)pent-4-ene-2-sulfonamide as the second eluting isomer (retention time: 2.57 min).

STEP 2: (R)-PENT-4-ENE-2-SULFONAMIDE

To a solution of (R)-N,N-bis(4-methoxybenzyl)pent-4-ene-2-sulfonamide (Intermediate EE17, Step 1, second eluting isomer; 221 mg, 0.567 mmol) in DCM (2.8 mL), was added trifluoroacetic acid (1.7 mL, 22.70 mmol) dropwise (the clear solution very rapidly turned dark). After stirring for 7 h (TLC 30% EtOAc/hexane showed complete loss of starting material) the mixture was diluted with EtOAc, washed with sat. NaHCO₃, back extracted with EtOAc, dried over MgSO₄, and concentrated. The crude material was purified via chromatography (12 g ISCO gold column; 0-40% EtOAc in hexane) to provide (R)-pent-4-ene-2-sulfonamide (70 mg, 0.469 mmol, 83% yield)

Intermediate EE172

(S)-PENT-4-ENE-2-SULFONAMIDE

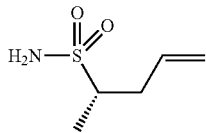

This intermediate was synthesized from (S)—N,N-bis(4-methoxybenzyl)pent-4-ene-2-sulfonamide (Intermediate EE17, Step 1, first eluting isomer) using the procedure described for Intermediate EE17, Step 2.

Intermediate EE18

(R)-HEX-5-ENE-3-SULFONAMIDE

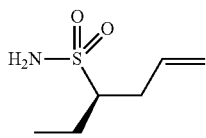

STEP 1: (S)—N,N-BIS(4-METHOXYBENZYL) HEX-5-ENE-3-SULFONAMIDE AND (R)-N,N-BIS(4-METHOXYBENZYL)HEX-5-ENE-3-SULFONAMIDE

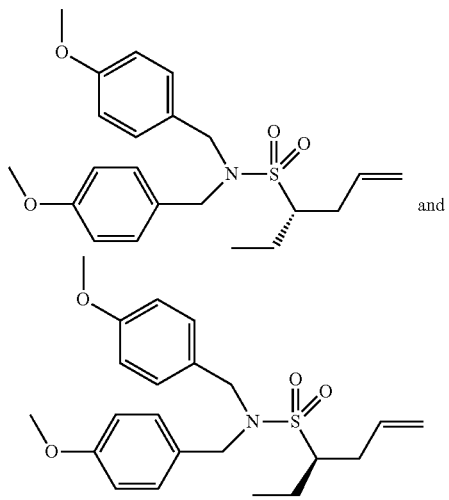

N,N-bis(4-methoxybenzyl)but-3-ene-1-sulfonamide (Intermediate EE16; 40.0 g, 106.6 mmol) was azeotroped in toluene under vacuum for 2 h. THF (700 mL) was added under argon atmosphere and the reaction mixture was cooled to −78° C. Butyl lithium (2.5 M in hexane; 71.6 mL, 127.9 mmol) was added and the reaction mixture was stirred at −78° C. for 1 h. This anion solution was added slowly to a solution of ethyl iodide (36.44 mL, 340.1 mmol) in THF (40 mL) cooled to −78° C. The resulting reaction mixture was then quenched with sat. NH₄Cl solution, allowed to reach ambient temperature and extracted with EtOAc. The organic layer was dried over Na₂SO₄ and concentrated under reduced pressure to obtain crude material which was purified by column chromatography over SiO₂ gel eluting with 5-10% EtOAc in hexane to provide the title compound as a racemic mixture (24 g) of semisolid nature. MS (ESI, positive ion) m/z; 404.03 (M+1). Separation of the enantiomers by SFC (Sample preparation: 14.4 g/200 mL (72 mg/mL) sample solution in MeOH:DCM (3:1); Column: Chiralpak® AD-H, 30×250 mm, 5 μm; Mobile Phase A: CO₂; Mobile Phase B: MeOH (20 mM NH₃); Isocratic: 50% B, Flow Rate: 100 mL/min; Outlet Pressure: 100 bar; Loading: 1.0 mL of sample solution prepared as above (72 mg); Detection: UV @ 227 nm; Cycle Time: 8 min; Total Elution Time: 17 min; Instrument: Thar 350 SFC) provided (S)—N,N-bis(4-methoxybenzyl)hex-5-ene-3-sulfonamide as the first eluting isomer and (R)-N,N-bis(4-methoxybenzyl)hex-5-ene-3-sulfonamide as the second eluting isomer.

STEP 2: (R)-HEX-5-ENE-3-SULFONAMIDE

This intermediate was synthesized from (R)-N,N-bis(4-methoxybenzyl)hex-5-ene-3-sulfonamide (Intermediate EE18, Step 1, second eluting isomer) using the procedure described for Intermediate EE17, Step 2.

Intermediate EE182

(S)-HEX-5-ENE-3-SULFONAMIDE

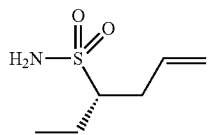

This intermediate was synthesized from (S)—N,N-bis(4-methoxybenzyl)hex-5-ene-3-sulfonamide (Intermediate EE18, Step 1, first eluting isomer) using the procedure described for Intermediate EE17, Step 2.

Intermediate EE19

N,N-BIS (4-METHOXYBENZYL)PENT-4-ENE-1-SULFONAMIDE

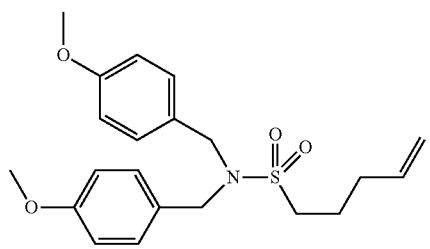 [SMILES: C=CCCCS(=O)(=O)N(Cc1ccc(OC)cc1)Cc1ccc(OC)cc1]

STEP 1: SODIUM PENT-4-ENE-1-SULFONATE

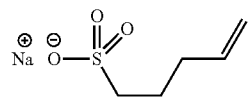

To a 3 L 3-necked-RBF equipped with a mechanical stirrer, a $N_2$ gas inlet, a condenser, and a temperature probe was charged 5-bromo-1-pentene (Sigma Aldrich, 200 g, 1342 mmol), sodium sulfite (Strem Chemicals; 186 g, 1476 mmol), and $H_2O$ (400 mL). The mixture was heated to reflux (set at 100° C. and refluxed at 93-94° C.) 4 h; aliquot NMR showed >95% conversion. The mixture was concentrated and azeotroped with acetone to remove $H_2O$. The crude solid was washed with acetone and filtered to afford sodium pent-4-ene-1-sulfonate (350 g, 2033 mmol).

STEP 2: PENT-4-ENE-1-SULFONAMIDE

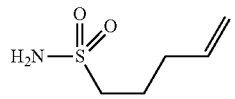

To a 3 L 3-necked-RBF equipped with a mechanical stirrer, a $N_2$ gas inlet, a condenser, and a temperature probe was charged sodium pent-4-ene-1-sulfonate (100 g, 581 mmol) (~150 g of crude material from Step 1) and phosphorus oxychloride (Sigma Aldrich; 532 mL, 5808 mmol). The mixture was heated to 90° C. for 18 h after which the reaction was filtered and the solid was washed with MeCN. The organic solution was concentrated and azeotroped with MeCN to remove $POCl_3$ to afford 85 g pent-4-ene-1-sulfonyl chloride intermediate. This material (solution in 300 mL MeCN) was charged onto a 1 L 3-necked-RBF equipped with a mechanical stirrer, a $N_2$ gas inlet, a condenser, and a temperature probe. The reaction was cooled to 0-5° C. and $NH_4OH$ (Sigma Aldrich; 28% $NH_3$; 404 mL, 2904 mmol) was added slowly over 30 min. The reaction was stirred at 0-5° C. for 1 h, after which EtOAc (300 mL) was added and the mixture was extracted with EtOAc and concentrated to afford pent-4-ene-1-sulfonamide (50 g, 335 mmol, 57.7% yield) as a brown oil.

STEP 3: N,N-BIS(4-METHOXYBENZYL)PENT-4-ENE-1-SULFONAMIDE

The title compound was synthesized from pent-4-ene-1-sulfonamide (4.5 g, 30.2 mmol) following the procedure described for Intermediate EE16. Purification of the crude material provided N,N-bis(4-methoxybenzyl)pent-4-ene-1-sulfonamide (11.4 g, 29.3 mmol, 97% yield) as a colorless oil.

Intermediate EE20

(R)-HEX-5-ENE-2-SULFONAMIDE

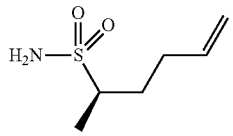

STEP 1: (S)—N,N-BIS(4-METHOXYBENZYL) HEX-5-ENE-2-SULFONAMIDE AND (R)-N,N-BIS(4-METHOXYBENZYL)HEX-5-ENE-2-SULFONAMIDE

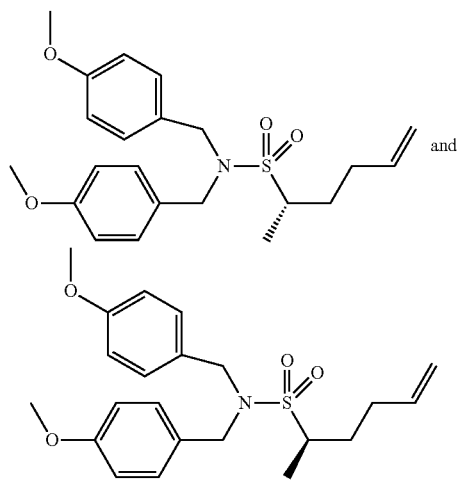

A solution of N,N-bis(4-methoxybenzyl)ethanesulfonamide (Intermediate EE13; 140.0 g, 400.64 mmol) in THF (1.4 L, THF was purged with argon for 15 min before using) was cooled to −78° C. and butyl lithium solution (2.6 M in hexane, 200.0 mL, 520.83 mmol) was added drop-wise. The resulting solution was stirred at −78° C. for 10 min, and 4-bromo-1-butene (73.2 mL, 721.15 mmol) was added over 2 min. After 5 min, the reaction was allowed to reach ambient temperature and stir for 1 h. The reaction was monitored by TLC and upon completion, the mixture was quenched with sat. NH₄Cl solution (400 mL) and the resulting aqueous layer was extracted with EtOAc (2×1.0 L). The combined organic layer was washed with brine and dried over Na₂SO₄. The solvent was removed under reduced pressure to afford the crude material which was purified by column chromatography (SiO₂ gel 100-200 mesh) eluting with a gradient of 0-4% acetone in hexane affording the title compound (racemic mixture, 80.0 g, 49.5%) as a colorless thick oil. MS (ESI, positive ion) m/z: 404.25 (M+1). Separation of the enantiomers by SFC (Sample preparation: 75 g/1.5 L (50 mg/mL) sample solution in MeOH; Column: Chiralpak® IF, 21×250 mm, 5 μm; Mobile Phase A: CO₂; Mobile Phase B: MeOH (0.2% DEA); Isocratic: 40% B; Flow Rate: 80 mL/min; Outlet Pressure: 100 bar; Loading: 3.0 mL of sample solution prepared as above (150 mg); Detection: UV at 225 nm; Cycle Time: 3.9 min; Total Elution Time: 6 min; Instrument: Thar 80 SFC) provided (S)—N,N-bis(4-methoxybenzyl)hex-5-ene-2-sulfonamide as the first eluting isomer and (R)-N,N-bis(4-methoxybenzyl)hex-5-ene-2-sulfonamide as the second eluting isomer.

STEP 2: (R)-HEX-5-ENE-2-SULFONAMIDE

The title compound was synthesized from (R)-N,N-bis(4-methoxybenzyl)hex-5-ene-2-sulfonamide (Intermediate EE20, Step 1, second eluting isomer) using the procedure described for Intermediate EE17, Step 2.

Intermediate EE202

(S)-HEX-5-ENE-2-SULFONAMIDE

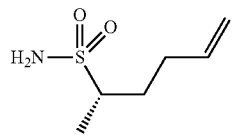

The title compound was synthesized from (S)—N,N-bis(4-methoxybenzyl)hex-5-ene-2-sulfonamide (Intermediate EE20, Step 1, first eluting isomer) using the procedure described for Intermediate EE17, Step 2.

Intermediate EE21

(R)-HEPT-6-ENE-3-SULFONAMIDE

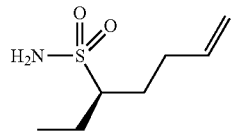

STEP 1: (S)—N,N-BIS(4-METHOXYBENZYL) HEPT-6-ENE-3-SULFONAMIDE AND (R)-N,N-BIS(4-METHOXYBENZYL)HEPT-6-ENE-3-SULFONAMIDE

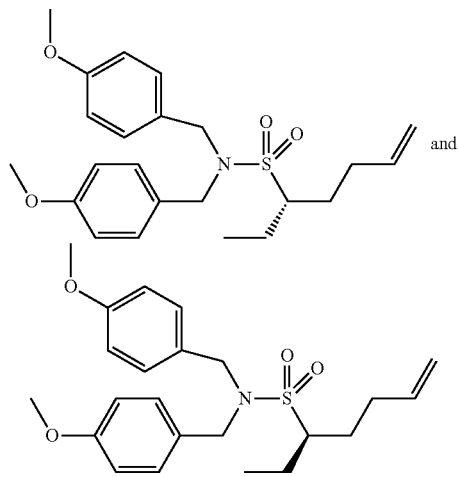

The title compound was synthesized from N,N-bis(4-methoxybenzyl)propanesulfonamide (Intermediate EE14) using the procedure described for Intermediate AA20, Step 1. Separation of the enantiomers by SFC (Sample preparation: 40.55 g/170 mL (238.5 mg/mL) sample solution in MeOH; Column: Chiralpak® AD-H, 50×150 mm, 5 μm; Mobile Phase A: CO₂; Mobile Phase B: MeOH (20 mM NH₃); Isocratic: 50% B; Flow Rate: 190 mL/min; Outlet Pressure: 100 bar; Loading: 1.5 mL of sample solution prepared as above (357.8 mg); Detection: UV at 227 nm; Cycle Time: 17.5 min; Total Elution Time: 21 min; Instrument: Thar 350 SFC) provided (S)—N,N-bis(4-methoxybenzyl)hept-6-ene-3-sulfonamide as the first eluting isomer and (R)-N,N-bis(4-methoxybenzyl)hept-6-ene-3-sulfonamide as the second eluting isomer.

STEP 2: (R)-HEPT-6-ENE-3-SULFONAMIDE

The title compound was synthesized from (R)-N,N-bis(4-methoxybenzyl)hept-6-ene-3-sulfonamide (Intermediate EE21, Step 1, second eluting isomer) using the procedure described for Intermediate EE17, Step 2.

Intermediate EE212

(S)-HEPT-6-ENE-3-SULFONAMIDE

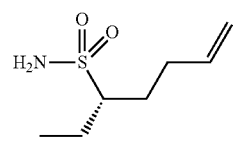

The title compound was synthesized from (S)—N,N-bis (4-methoxybenzyl)hept-6-ene-3-sulfonamide (Intermediate EE21, Step 1, first eluting isomer) using the procedure described for Intermediate EE17, Step 2.

Intermediate EE22

(2R,3S)-3-METHYLHEX-5-ENE-2-SULFONAMIDE

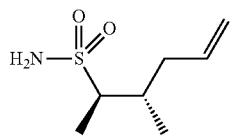

STEP 1: (4S,5S)-4,5-DIMETHYL-1,3,2-DIOXATHIOLANE 2,2-DIOXID

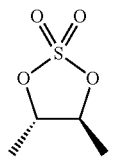

To a 500-mL, 3-necked-RBF (equipped with a H₂O-cooled reflux condenser and an HCl trap) was added (2s,3s)-(+)-2,3-butanediol (Aldrich; 15.00 mL, 166 mmol) and CCl₄ (120 mL). SOCl₂, reagentplus (14.57 mL, 200 mmol) was then added drop wise via a syringe over a period of 20 min and the resulting mixture was heated to 98° C. for 45 min, then allowed to cool to rt. The reaction mixture was then cooled in an ice/H₂O bath, MeCN (120 mL) and H₂O (150 mL) were added followed by ruthenium(III) chloride (0.035 g, 0.166 mmol). Sodium periodate (53.4 g, 250 mmol) was then added slowly portion wise over 30 min. The resulting biphasic brown mixture was stirred vigorously while allowed to reach rt for a period of 1.5 h (internal temperature never increased above rt). TLC (50% EtOAc in heptanes) showed complete conversion. The crude mixture was then poured into ice H₂O and extracted twice with 300 mL of Et₂O. The combined organic layers were washed once with 200 mL of sat. sodium bicarbonate, washed once with 200 mL of brine, dried over Na₂SO₄, and concentrated by rotary evaporation to give (4S,5S)-4,5-dimethyl-1,3,2-dioxathiolane 2,2-dioxide (21.2 g, 139 mmol) as a red oil.

STEP 2: (2S,3S)-3-METHYLHEX-5-EN-2-OL

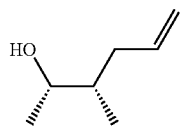

To a 500 mL flask was added (4S,5S)-4,5-dimethyl-1,3,2-dioxathiolane 2,2-dioxide (from Intermediate EE22, Step 1; 21.2 g, 139 mmol) and THF (220 mL) at which time the solution was cooled to −78° C. and was subjected to 3 cycles of evacuation/back-filling with argon. To the solution was added dilithium tetrachlorocuprate(ii), 0.1M solution in THF (69.7 mL, 6.97 mmol). The resulting mixture was stirred at −78° C. for 30 min and then allylmagnesium bromide, 1.0 M solution in Et₂O (397 mL, 397 mmol) was added slowly via cannula over 80 min. The resulting mixture was stirred at 0° C. for 4 h. The mixture was quenched with 200 mL H₂O and allowed to reach rt at which time the volatiles were removed by rotary evaporation. To the aqueous residue was then added 50% H₂SO₄ (150 mL), the mixture was stirred for 5 min, Et₂O was then added (400 mL) and the mixture was stirred vigorously at rt overnight. The layers were separated; the aqueous layer was extracted with 300 mL Et₂O and the combined organic layers were washed with 300 mL of sat. NaHCO₃, dried over Na₂SO₄, filtered and concentrated by rotary evaporation to give (2S,3S)-3-methylhex-5-en-2-ol (6.7 g, 58.7 mmol) as a clear oil.

STEP 3: 2-(((2R,3S)-3-METHYLHEX-5-EN-2-YL)THIO)PYRIMIDINE

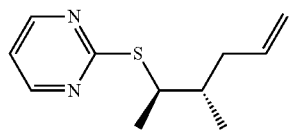

To a 2000 mL dry RBF containing a stirring solution of tributylphosphine (57.7 mL, 231 mmol) in 1000 mL degassed THF (sparged with argon for 30 min plus 5 cycles of pump/add argon) at 0° C. was added diethyl azodicarboxylate (40 wt. % solution in toluene; 103 mL, 262 mmol) drop wise under an atmosphere of argon. A solution of (2S,3S)-3-methylhex-5-en-2-ol (from Intermediate EE22, Step 2; 17.6 g, 154 mmol; dried over Na₂SO₄) was added drop wise as a solution in 50 mL of THF to the solution of phosphine/diethyl azodicarboxylate complex, via syringe-filter (0.45 um). The resulting ROH/diethyl azodicarboxylate/tri-n-butylphosphine mixture was aged at zero degrees for 15 min (solution turned light orange), at which time pyrimidine-2-thiol (49.3 g, 439 mmol) was added gradually to the top of the reaction vessel (as a solid) under positive argon pressure. The reaction was stirred at 0° C. for 1 h then at rt 15 h (reaction not complete at 12 h by LC/MS). The crude reaction was then filtered to remove excess pyrimidine-2-thiol, diluted with 1000 mL of EtOAc, extracted twice with 500 mL of 1 N K₂CO₃, and once with 500 mL of brine. The aqueous layer was back extracted with 300 mL of EtOAc and the combined organic layers were dried over Na₂SO₄. The organic solution was then filtered, the solvent removed by rotary evaporation and the crude filtered to remove the (E)-diethyl diazene-1,2-dicarboxylate generated in the reaction. The filtrate (125 g) was passed through a SiO₂ plug (500 g SiO₂, eluting with 2 L of DCM) to give 75 g of crude product after solvent removal. The crude product was purified again on a Combiflash® (125 g gold SiO₂ column), eluting with 10% EtOAc in heptanes to give 2-(((2R,3S)-3-methylhex-5-en-2-yl)thio)pyrimidine (20.37 g, 98 mmol) as a light yellow oil.

STEP 4: 2-(((2R,3S)-3-METHYLHEX-5-EN-2-YL)SULFONYL)PYRIMIDINE

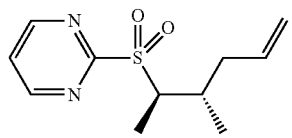

To a 500 mL 3-necked-RBF with a reflux condenser was added phenylphosphonic acid (3.95 g, 24.96 mmol), sodium tungstate oxide dihydrate (8.23 g, 24.96 mmol), tetrabutylammonium sulfate (50 wt. % solution in H₂O, 28.7 mL, 24.96 mmol), a catalytic amount of hydrogen peroxide (30% in H₂O, 12.75 mL, 125 mmol), toluene (200 mL) and 2-(((2R,3S)-3-methylhex-5-en-2-yl)thio)pyrimidine (from Intermediate EE22, Step 3; 52 g, 250 mmol). The reaction was stirred at 45° C. for 5 min at which time hydrogen peroxide 30% in H₂O (58.6 mL, 574 mmol) was added portion wise (10 mL at a time). Five min after the first portion of hydrogen peroxide was added, an exotherm was observed (65° C.), the reaction was taken out of oil bath, the addition was stopped and the flask placed in a H₂O bath until temperature stabilizes. The flask was taken out of the H₂O bath and the portion wise addition of hydrogen peroxide was continued at a rate in which the internal temperature stayed between 45° C. and 55° C. (~40 min). An ice bath was utilized if the temperature went above 60° C. and an oil bath was used if the temperature fell below 45° C. The reaction was then stirred at 45° C. for 1 h. The reaction was diluted with 1400 mL of EtOAc and extracted two times with 500 mL of H₂O and once with 500 mL of brine. The organic layer was dried over Na₂SO₄, filtered, concentrated, and the crude purified on a Combiflash® (330 g gold SiO₂ column per 30 grams of crude), eluting with 0%-50% EtOAc in heptanes to give 2-(((2R,3S)-3-methylhex-5-en-2-yl)sulfonyl)pyrimidine (55.7 g, 232 mmol) as a light yellow oil.

STEP 5: SODIUM (2R,3S)-3-METHYLHEX-5-ENE-2-SULFINATE

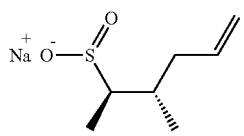

To a solution of 2-(((2R,3S)-3-methylhex-5-en-2-yl)sulfonyl)pyrimidine (from Intermediate EE22, Step 4; 52 g, 216 mmol) in MeOH (400 mL) at rt was added sodium methoxide solution (51.0 mL, 223 mmol) over 70 min. The sodium methoxide was added portion wise, the internal temperature was monitored, and the addition was slowed or the reaction was cooled in a H₂O bath, never letting the internal temperature exceeded 30° C. The mixture was concentrated by rotary evaporation and the waxy solid was triturated with MTBE (add 200 mL MTBE, stir for 1 h using a spatula to break up clumps), filtered (use a stream of N₂ over filter cake), and washed with 100 mL of cold MTBE to obtain sodium (2R,3S)-3-methylhex-5-ene-2-sulfinate (46 g, 250 mmol) as a an off white solid.

STEP 6: (2R,3S)-3-METHYLHEX-5-ENE-2-SULFONAMIDE

To a 1000 mL 3-necked-RBF was added sodium (2R,3S)-3-methylhex-5-ene-2-sulfinate (from Intermediate EE22, Step 5; 46 g, 225 mmol), 500 mL of H₂O and KOAc (44.1 g, 449 mmol) at rt. The flask was place in a 45° C. oil bath and hydroxylamine-O-sulfonic acid (21.09 g, 187 mmol) was added portion wise over 90 min. The internal temperature of the reaction was monitored and the reaction was removed from the oil bath (if needed) to control exotherm (Tmax=55° C.). The reaction was monitored by LC/MS every 10 min and was complete after the addition of 0.83 eq. of hydroxylamine-O-sulfonic acid. The mixture was then cooled to rt and was extracted with 1000 mL of EtOAc. The organic phase was extracted three times with 500 mL of 1 N HCl, two times with 300 mL of sat. sodium bicarbonate, once with 200 mL of brine, dried over Na₂SO₄, filtered, and concentrated by rotary evaporation to provide (2R,3S)-3-methylhex-5-ene-2-sulfonamide (32 g, 181 mmol) as a white solid.

Intermediate 1

(1S,3'R,6'R,7'S,8'E,11'S,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³'⁶.0¹⁹,²⁴]PENTACOSA[8,16,18,24]TETRAEN]-15'-ONE 13',13'-DIOXIDE

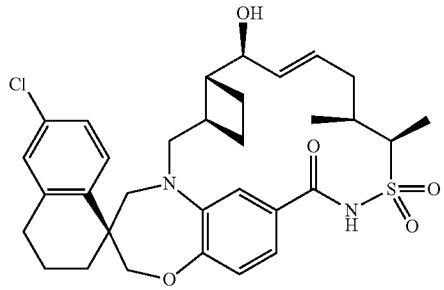 [SMILES: C[C@@H]1[C@@H](C)C/C=C/[C@H](O)[C@@H]2CC[C@H]2CN2C[C@@]3(CCCc4cc(Cl)ccc43)COc3ccc(cc32)C(=O)NS1(=O)=O]

STEP 1: (S)-6'-CHLORO-5-(((1R,2R)-2-((S)-1-HYDROXYALLYL)CYCLOBUTYL)METHYL)-N-(((2R,3 S)-3-METHYLHEX-5-EN-2-YL)SULFONYL)-3',4,4',5-TETRAHYDRO-2H,2'H-SPIRO[BENZO[B][1,4]OXAZEPINE-3,1'-NAPHTHALENE]-7-CARBOXAMIDE

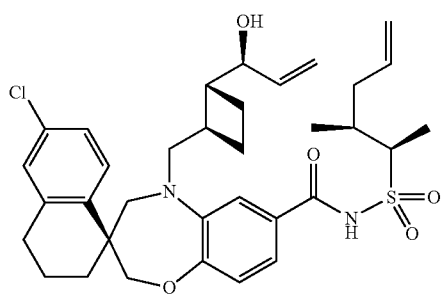 [SMILES: C=CC[C@H](C)[C@@H](C)S(=O)(=O)NC(=O)c1ccc2c(c1)N(C[C@@H]1CC[C@H]1[C@@H](O)C=C)C[C@@]1(CCCc3cc(Cl)ccc31)CO2]

DMAP (3.42 g, 28.0 mmol) was added to a solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A; 7.7 g, 16.45 mmol) and (2R,3S)-3-methylhex-5-ene-2-sulfonamide (Intermediate EE22; 5.83 g, 32.9 mmol) in DCM (411 mL) cooled to 0° C. EDC hydrochloride (6.31 g, 32.9 mmol) was then added slowly portionwise. The mixture was stirred while allowing to reach ambient temperature overnight. The mixture was washed with 1N HCl and brine and the aqueous layer was back-extracted with EtOAc. The combined organics were dried over MgSO₄, filtered and concentrated. The yellow oily residue was loaded onto a 220 ISCO gold column and purified eluting with 0% to 20% EtOAc (containing 0.3% AcOH)/heptanes, to provide (S)-6'-chloro-5-(((1R,2R)-2-((S)-1-hydroxyallyl)cyclobutyl)methyl)-N-(((2R,3 S)-3-methylhex-5-en-2-yl)sulfonyl)-3',4,4',5-tetrahydro-2H,2'H-spiro[benzo[b][1,4]oxazepine-3,1'-naphthalene]-7-carboxamide (7.89 g, 12.58 mmol, 76% yield).

STEP 2: (1S,3'R,6'R,7'S,8'E,11'S,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA [8,16,18,24]TETRAEN]-15'-ONE 13',13'-DIOXIDE

To a 20 L reactor blanketed in argon was charged 14 L of 1,2-DCE. (S)-6'-chloro-5-(((1R,2R)-2-((S)-1-hydroxyallyl)cyclobutyl)methyl)-N-(((2R,3 S)-3-methylhex-5-en-2-yl)sulfonyl)-3',4,4',5-tetrahydro-2H,2'H-spiro[benzo[b][1,4]oxazepine-3,1'-naphthalene]-7-carboxamide (18.75 g, 29.9 mmol) was added as a solution in 400 mL 1,2-DCE followed by a 400 mL rinse. The reactor was sealed and purged with argon. Hoveyda-Grubbs II (1.873 g, 2.99 mmol) was added as a solution in 150 mL of 1,2-DCE followed by a 50 mL rinse. The reactor was heated to 60° C. over 1 h with an argon sweep of the headspace and held at temperature for 9 h. The reaction was quenched by the addition of 2-(2-(vinyloxy)ethoxy)ethanol (1.501 g, 11.36 mmol), cooled to ambient temperature, and concentrated to ~200 mL volume by rotary evaporation. The reaction was transferred to a 1 L RBF and diluted to 500 mL volume with 1,2-DCE. The reaction was treated with 52 g of Silicycle Si-Thiol (SiliCycle Inc., Quebec City, Quebec CANADA Cat# R51030B) with stirring for 9 h at 40° C., filtered and rinsed with 2×65 mL DCM. The solution was passed through a Whatman GF/F filter cup (GE Healthcare Bio-Sciences Pittsburgh, Pa., USA) to afford a transparent yellow solution. The reaction was concentrated to afford a crude product mass of 27.4 g. The residue was slurried in 250 mL IPAc and evaporated to dryness three times. The reaction was suspended in 270 mL IPAc, heated to dissolution, allowed to cool to ambient temperature, and stirred for 18. The solids were filtered and washed with 65 mL IPAc. The solid was air-dried for 30 min then placed under high vacuum for 3 h to afford 12.56 g of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide which is 91.7% by weight. ¹H NMR (500 MHz, CD₂Cl₂) δ 8.06 (s, 1H), 7.71 (d, J=8.56 Hz, 1H), 7.17 (dd, J=8.44, 2.32 Hz, 1H), 7.09 (d, J=2.20 Hz, 1H), 6.91 (s, 3H), 5.81 (ddd, J=14.92, 7.82, 4.16 Hz, 1H), 5.71 (dd, J=15.41, 8.31 Hz, 1H), 4.16-4.26 (m, 2H), 3.83 (d, J=14.43 Hz, 1H), 3.69 (d, J=14.43 Hz, 1H), 3.25 (d, J=14.43 Hz, 1H), 3.04 (dd, J=15.28, 9.66 Hz, 1H), 2.68-2.84 (m, 2H), 2.41 (app qd, J=9.80, 3.70 Hz, 1H), 2.25-2.34 (m, 1H), 1.93-2.00 (m, 5H), 1.74-2.11 (m, 9H), 1.62-1.73 (m, 1H), 1.43 (d, J=7.09 Hz, 3H) 1.35-1.42 (m, 1H) 1.03 (d, J=6.60 Hz, 3H). MS (ESI, +ve ion) m/z 599.2 (M+H)⁺.

Intermediate 2

(1S,3'R,6'R,7'S, 11'S,12'R)-6-CHLORO-7'-HYDROXY-11',12'-DIMETHYL-3,4-DIHYDRO-2H, 15'H-SPIRO[NAPHTHALENE-1,22'-[20]OXA[13]THIA[1,14]DIAZATETRACYCLO[14.7.2.0$^{3,6}$.0$^{19,24}$]PENTACOSA [16,18,24]TRIEN]-15'-ONE 13',13'-DIOXIDE

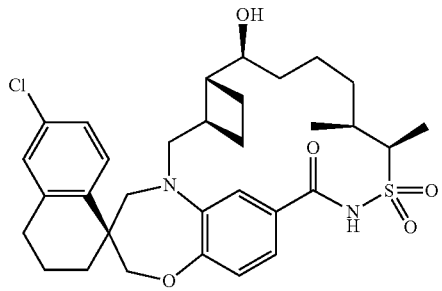 [SMILES: C[C@@H]1[C@@H](C)CCC[C@H](O)[C@@H]2CC[C@H]2CN2C[C@@]3(CCCc4cc(Cl)ccc43)COc3ccc(cc32)C(=O)NS1(=O)=O]

A mixture of (1S,3'R,6'R,7'S,8'E,11'S,12'R)-6-chloro-7'-hydroxy-11',12'-dimethyl-3,4-dihydro-2h, 15'h-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Intermediate 1, 7.5 mg, 0.013 mmol) and platinum (IV) oxide (2.84 mg, 0.013 mmol) in EtOAc (1.536 mL) was stirred under an atmosphere of H₂ (balloon) at ambient temperature for 45 min. The reaction mixture was then filtered through a syringe filter. The crude material was purified by chromatography through a Redi-Sep® pre-packed SiO₂ gel column (4 g), eluting with 15% to 50% EtOAc (containing 0.3% AcOH)/heptanes, to provide the title product. ¹H NMR (400 MHz, CD₂Cl₂) δ 8.24 (br. s., 1H), 7.71 (d, J=8.4 Hz, 1H), 7.17 (dd, J=2.3, 8.4 Hz, 1H), 7.09 (d, J=2.2 Hz, 1H), 7.06 (d, J=1.8 Hz, 1H), 6.99 (dd, J=2.0, 8.0 Hz, 1H), 6.93 (d, J=8.2 Hz, 1H), 4.10 (s, 2H), 4.05 (ddd, J=1.2, 7.2, 14.3 Hz, 1H), 3.82 (d, J=15.3 Hz, 1H), 3.74-3.69 (br. S., 1H), 3.68 (d, J=14.3 Hz, 1H), 3.23 (d, J=14.3 Hz, 1H), 3.06 (dd, J=7.3, 15.4 Hz, 1H), 2.84-2.68 (m, 2H), 2.38 (d, J=3.5 Hz, 2H), 2.08-1.96 (m, 3H), 1.96-1.88 (m, 1H), 1.88-1.75 (m, 2H), 1.74-1.56 (m, 4H), 1.47 (d, J=12.1 Hz, 2H), 1.40 (d, J=7.2 Hz, 3H), 1.32-1.26 (m, 2H), 1.23-1.15 (m, 2H), 1.00 (d, J=6.8 Hz, 3H). MS (ESI, +ve ion) m/z 601.2 (M+H)⁺.

Intermediate 3

(1S,3'R,6'R,8'E,12'S)-6-CHLORO-12'-METHYL-3,4-DIHYDRO-2H,7'H,15'H-SPIRO[NAPHTHALENE-1,22'-[20]OXA[13]THIA[1,14]DIAZATETRACYCLO[14.7.2.0³ʼ⁶.0¹⁹ʼ²⁴]PENTACOSA [8,16,18,24]TETRAENE]-7',15'-DIONE 13',13'-DIOXIDE

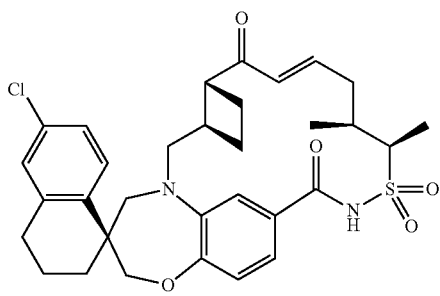 [SMILES: C[C@@H]1[C@@H](C)C/C=C/C(=O)[C@@H]2CC[C@H]2CN2C[C@@]3(CCCc4cc(Cl)ccc43)COc3ccc(cc32)C(=O)NS1(=O)=O]

The allyl alcohol (310 mg, 0.520 mmol, Intermediate 1) was dissolved in DCM (6.0 mL) and cooled to 0° C. Dess-Martin periodinane (270 mg, 0.63 mmol) was then added and the reaction mixture was stirred for 1.5 hours. Another 90 mg of Dess-Martin reagent was added at 0° C. and stirred for an additional 45 minutes. The reaction was quenched with 20 mL of 1M $Na_2S_2O_3$ and allowed to warm to room temperature. The mixture was extracted (3×40 mL) with DCM. The combined organic layers were washed with water (1×30 mL) and then dried over magnesium sulfate. The crude product was purified by medium pressure chromatography (silica, 10 to 100% EtOAc (+0.3% HOAc):Hexanes) to give (1S,3'R,6'R,8'E,12'S)-6-chloro-12'-methyl-3,4-dihydro-2H,7'H,15'H-spiro[naphthalene-1,22'-[20]oxa[13]thia[1,14]diazatetracyclo[14.7.2.0³ʼ⁶.0¹⁹ʼ²⁴]pentacosa[8,16,18,24]tetraene]-7',15'-dione 13',13'-dioxide (230 mg, 0.385 mmol, 74.0% yield). $^1$H NMR (400 MHz, CDCl$_3$) δ 8.32-9.05 (m, 1H), 7.69-7.90 (m, 1H), 7.35-7.48 (m, 1H), 7.17-7.27 (m, 1H), 7.06-7.16 (m, 1H), 6.81-6.99 (m, 2H), 6.59-6.72 (m, 1H), 5.93 (d, J=15.65 Hz, 1H), 4.01-4.24 (m, 3H), 3.74-3.97 (m, 3H), 3.26 (d, J=14.48 Hz, 1H), 2.92-3.16 (m, 2H), 2.69-2.89 (m, 2H), 1.70-2.26 (m, 9H), 1.48-1.56 (m, 3H), 1.35-1.46 (m, 1H), 1.29 (t, J=7.14 Hz, 1H), 1.07-1.19 (m, 3H). m/z (ESI, +ve ion) 596.7 (M+H)⁺.

Intermediate 4

(1S,3'R,6'R, 11'S,12'R)-6-CHLORO-11',12'-DIMETHYL-3,4-DIHYDRO-2H,7'H,15'H-SPIRO[NAPHTHALENE-1,22'-[20]OXA[13]THIA[1,14]DIAZATETRACYCLO[14.7.2.0³ʼ⁶.0¹⁹ʼ²⁴]PENTACOSA [16,18,24]TRIENE]-7',15'-DIONE 13',13'-DIOXIDE

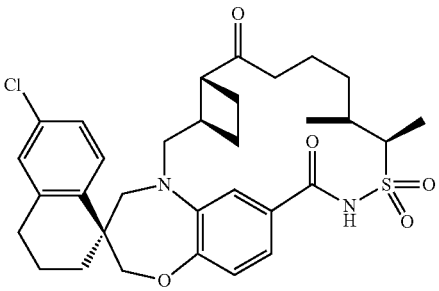 [SMILES: C[C@@H]1[C@@H](C)CCCC(=O)[C@@H]2CC[C@H]2CN2C[C@@]3(CCCc4cc(Cl)ccc43)COc3ccc(cc32)C(=O)NS1(=O)=O]

To a solution of (1S,3'R,6'R,7'S,8'E,11'S,12'R)-6-chloro-7'-hydroxy-11',12'-dimethyl-3,4-dihydro-2h, 15'h-spiro[naphthalene-1,22'-[20]oxa[13]thia[1,14]diazatetracyclo [14.7.2.03,6~.019,24]pentacosa[8,16,18,24]tetraen]-15'-one 13',13'-dioxide (1.20 g, 2.02 mmol, Intermediate 1) in EtOAc (50 mL) was added platinum (IV) oxide (92 g, 0.40 mmol) and the reaction was fitted with a $H_2$ balloon and stirred vigorously for 15 h. The reaction mixture was filtered through Celite and concentrated. The concentrate was dissolved in dichloromethane (20 mL) and then Dess-Martin periodinane (0.95 g, 2.2 mmol) was added in four portions over 5 min at 0° C. After the reaction was stirred at 0° C. for 15 min, the reaction was quenched with 1N sodium thiosulfate solution at 0° C. (10 mL) and stirred vigorously at rt for 30 min. Then the reaction mixture was extracted (EtOAc). The separated organic layer was washed (brine), dried ($Na_2SO_4$), and concentrated under reduced pressure. The residue was purified by silica-gel chromatography (0% to 25% EtOAc/hexane, 0.1% AcOH) to provide (1S,3'R,6'R, 11'S,12'R)-6-chloro-11',12'-dimethyl-3,4-dihydro-2H,7'H, 15'H-spiro[naphthalene-1,22'-[20]oxa[13]thia[1,14]diazatetracyclo [14.7.2.0³ʼ⁶.0¹⁹ʼ²⁴]pentacosa[16,18,24]triene]-7', 15'-dione 13',13'-dioxide as a solid (0.85 g, 70% yield). MS (ESI, +ve ion) m/z 599.2 (M+H)⁺.

Biological Assays

Cell Free Mcl-1:Bim Affinity Assay (Mcl-1 HTRF)

The inhibition of the Mcl-1/Bim interaction was measured using a time-resolved fluorescence resonance energy transfer (TR-FRET) assay. The recombinant human Mcl-1 (C-terminally 6×His tagged Mcl-1 containing residues 171-327) was generated at Amgen Inc (Thousand Oaks, Calif.). A biotinylated peptide derived from human Bim (residues 51-76) was purchased from CPC Scientific (San Jose, Calif.). The TR-FRET assay was conducted in a 384-well white OptiPlate™ (PerkinElmer, Waltham, Mass.) in a total volume of 40 μL. The reaction mixture contained 0.1 nM Mcl-1(171-327), 0.05 nM biotin-Bim(51-76), 0.05 nM LANCE® Eu-W1024 Anti-6×His (PerkinElmer), 0.072 nM Streptavidin-Xlent (Cisbio, Bedford, Mass.), and serially diluted test compounds in the binding buffer of 20 mM Hepes, pH 7.5, 150 mM NaCl, 0.016 mM Brij®35, and 1 mM dithiothreitol. Test compounds were pre-incubated with Mcl-1(171-327) and biotin-Bim (51-76) for 60 min before addition of the detection mixture (LANCE®Eu-W1024 Anti-6×His and Streptavidin-Xlent). The reaction plates were further incubated overnight and then were read on an Envision® multimode reader (PerkinElmer). Fluorescence signals were measured at 620 nm (40-nm bandwidth) and 665 nm (7.5-nm bandwidth) with a 60 s delay after excitation at 320 nm (75-nm bandwidth). The signal ratio at 665/620 nm corresponded to the Mcl-1/Bim interaction and was used in all data analyses. The $IC_{50}$ values of test compounds were determined from duplicate data by analyzing competition curves using a four-parameter sigmoidal model in GraphPad Prism (GraphPad Software, San Diego, Calif.) or in Genedata Screener® (Genedata, Basel, Switzerland).

Cell Viability Assay (OPM-2 10 FBS)

The human multiple myeloma cell line, OPM-2, was cultured in complete growth medium containing RPMI 1640 and 10% fetal bovine serum (FBS). Cells were seeded into 384-well plates at 3000 cells/well density in complete growth medium containing 10% FBS, and incubated for 16 h with serially diluted test compounds in a 37° C. incubator with 5% $CO_2$. Cell viability was tested using CellTiter-Glo2® assay (Promega, Madison, Wis.) according to the manufacturer recommendations. Luminescence was determined using an EnVision® Multilabel plate reader 25 min after the addition of detection reagent. $IC_{50}$ values were then calculated with Xlfit using a logistical 4-parameter fit model in GraphPad Prism (GraphPad Software, San Diego, Calif.) or in Genedata Screener® (Genedata, Basel, Switzerland).

Results for compounds tested in these biological assays are set forth below in Table 4 and Table 5.

TABLE 4

| Example Number | Mcl-1 HTRF $IC_{50}$ (μM) | OPM-2 10% FBS $IC_{50}$ IP (μM) |
|---|---|---|
| 1 | 0.000086 | 0.085 |
| 2 | 0.000109 | 0.076 |
| 3 | 0.000094 | 0.060 |
| 4 | 0.000116 | 0.094 |
| 5 | 0.000098 | 0.040 |
| 6 | 0.000079 | 0.076 |
| 7 | 0.000058 | 0.025 |
| 8 | 0.000053 | 0.025 |
| 9 | 0.000078 | 0.050 |
| 10 | 0.000103 | 0.075 |
| 11 | 0.000098 | 0.051 |
| 12 | 0.000072 | 0.022 |
| 13 | 0.000094 | 0.063 |
| 14 | 0.000080 | 0.059 |
| 15 | 0.000119 | 0.071 |
| 16 | 0.000065 | 0.053 |
| 17 | 0.000073 | 0.034 |
| 18 | 0.000060 | 0.022 |
| 19 | 0.000125 | 0.047 |
| 20 | 0.000082 | 0.022 |
| 21 | 0.000156 | 0.047 |
| 22 | 0.000669 | 2.230 |
| 23 | 0.000071 | 0.024 |
| 24 | 0.000086 | 0.035 |
| 25 | 0.000113 | 0.041 |
| 26 | 0.000079 | 0.032 |
| 27 | 0.000095 | 0.029 |
| 28 | 0.000082 | 0.111 |
| 29 | 0.000249 | 0.186 |
| 30 | 0.000110 | 0.166 |
| 31 | 0.000184 | 0.216 |
| 32 | 0.000128 | 0.147 |
| 33 | 0.008250 | 5.570 |

TABLE 4-continued

| Example Number | Mcl-1 HTRF $IC_{50}$ (μM) | OPM-2 10% FBS $IC_{50}$ IP (μM) |
|---|---|---|
| 34 | 0.000495 | 0.379 |
| 35 | 0.000218 | 0.235 |
| 36 | 0.000554 | 0.518 |
| 37 | 0.000615 | 0.643 |
| 38 | 0.000342 | 0.489 |
| 39 | 0.000377 | 0.389 |
| 40 | 0.000444 | 0.571 |
| 41 | 0.000642 | 0.810 |
| 42 | 0.000170 | 0.149 |
| 43 | 0.001640 | 0.888 |
| 44 | 0.000288 | 1.360 |
| 45 | 0.000245 | 0.891 |
| 46 | 0.000107 | 0.167 |
| 47 | 0.000131 | 0.285 |
| 48 | 0.000140 | 0.407 |
| 49 | 0.000087 | 0.185 |
| 50 | 0.000736 | 1.530 |
| 51 | 0.000072 | 0.099 |
| 52 | 0.000522 | 0.330 |
| 53 | 0.000336 | 0.290 |
| 54 | 0.000173 | 0.129 |
| 55 | 0.000162 | 0.080 |
| 56 | 0.000083 | 0.079 |
| 57 | 0.000258 | 0.090 |
| 58 | 0.000719 | 0.095 |
| 59 | 0.000116 | 0.048 |
| 60 | 0.000287 | 0.129 |
| 61 | 0.000075 | 0.124 |
| 62 | 0.000115 | 0.110 |
| 63 | 0.000173 | 0.582 |
| 64 | 0.000126 | 0.201 |
| 65 | 0.000451 | 1.500 |
| 66 | 0.000246 | 0.318 |
| 67 | 0.000197 | 0.149 |
| 68 | 0.000397 | 1.520 |
| 69 | 0.003830 | 1.480 |
| 70 | 0.001326 | 3.140 |
| 71 | 0.000371 | 1.140 |
| 72 | 0.000800 | 0.185 |
| 73 | 0.000609 | 0.129 |
| 74 | 0.002290 | 3.360 |
| 75 | 0.002047 | 1.610 |
| 76 | 0.003815 | 0.670 |
| 77 | 0.001217 | 0.415 |
| 78 | 0.000573 | 0.175 |
| 79 | 0.001800 | 0.245 |
| 80 | 0.001550 | 0.205 |
| 81 | 0.000140 | 0.112 |
| 82 | 0.000394 | 0.520 |
| 83 | 0.000223 | 0.245 |
| 84 | 0.000106 | 0.061 |
| 85 | 0.000491 | 0.274 |
| 86 | 0.00390 | 7.95 |
| 87 | 0.000127 | 0.141 |
| 88 | 0.000139 | 0.074 |
| 89 | 0.003750 | 8.210 |
| 90 | 0.004660 | 8.980 |
| 91 | 0.000203 | 0.559 |
| 92 | 0.000143 | 0.199 |
| 93 | 0.000530 | 0.924 |
| 94 | 0.000191 | 0.140 |
| 95 | 0.000189 | 0.338 |
| 96 | 0.000114 | 0.111 |
| 97 | 0.000299 | 0.228 |
| 98 | 0.000373 | 0.183 |
| 99 | 0.000243 | 0.310 |
| 100 | 0.000188 | 1.650 |
| 101 | 0.000196 | 0.263 |
| 102 | 0.000182 | 0.416 |
| 103 | 0.000452 | 0.737 |
| 104 | 0.001119 | 0.782 |
| 105 | 0.000423 | 0.655 |
| 106 | 0.000299 | 0.308 |
| 107 | 0.001138 | 0.872 |
| 108 | 0.000198 | 0.116 |
| 109 | 0.001042 | 0.916 |

TABLE 4-continued

| Example Number | Mcl-1 HTRF IC$_{50}$ (μM) | OPM-2 10% FBS IC$_{50}$ IP (μM) |
|---|---|---|
| 110 | 0.000505 | 1.720 |
| 111 | 0.000362 | 0.301 |
| 112 | 0.000617 | 0.654 |
| 113 | 0.001190 | 1.330 |
| 114 | 0.000104 | 0.068 |
| 115 | 0.001370 | 0.686 |
| 116 | 0.000244 | 0.387 |
| 117 | 0.000352 | 0.358 |
| 118 | 0.000215 | 0.558 |
| 119 | 0.000465 | 0.694 |
| 120 | 0.000263 | 0.304 |
| 121 | 0.000084 | 0.120 |
| 122 | 0.000087 | 0.138 |
| 123 | 0.000205 | 0.228 |
| 124 | 0.000646 | 0.598 |
| 125 | 0.006100 | 1.475 |
| 126 | 0.000627 | 0.900 |
| 127 | 0.000395 | 6.120 |
| 128 | 0.000256 | 19.600 |
| 129 | 0.001694 | 2.630 |
| 130 | 0.000920 | 1.580 |
| 131 | 0.000249 | 0.482 |
| 132 | 0.000613 | 0.263 |
| 133 | 0.000189 | 0.136 |
| 134 | 0.004640 | 3.000 |
| 135 | 0.008175 | >33.3 |
| 136 | 0.004700 | 1.020 |
| 137 | 0.004740 | 1.150 |
| 138 | 0.026700 | >33.3 |
| 139 | 0.032017 | >33.3 |
| 140 | 0.000098 | 0.125 |
| 141 | 0.000152 | 0.367 |
| 142 | 0.000157 | 0.174 |
| 143 | 0.000432 | 0.219 |
| 144 | 0.000271 | 0.163 |
| 145 | 0.000124 | 0.113 |
| 146 | 0.000337 | 0.150 |
| 147 | 0.000376 | 0.157 |
| 148 | 0.001200 | 1.610 |
| 149 | 0.000128 | 0.119 |
| 150 | 0.000193 | 0.245 |
| 151 | 0.000843 | 0.462 |
| 152 | 0.000092 | 0.110 |
| 153 | 0.000960 | 10.800 |
| 154 | 0.000197 | 0.554 |
| 155 | 0.000228 | 0.378 |
| 156 | 0.000096 | 0.062 |
| 157 | 0.000126 | 0.121 |
| 158 | 0.000092 | 0.018 |
| 159 | 0.000096 | 0.079 |
| 160 | 0.000221 | 0.148 |
| 161 | 0.000094 | 0.113 |
| 162 | 0.000072 | 0.055 |
| 163 | 0.000179 | 0.130 |
| 164 | 0.000047 | 0.031 |
| 165 | 0.000190 | 0.182 |
| 166 | 0.000107 | 0.050 |
| 167 | 0.000086 | 0.052 |
| 168 | 0.000138 | 0.052 |
| 169 | 0.000140 | 0.074 |
| 170 | 0.000131 | 0.075 |
| 171 | 0.000074 | 0.122 |
| 172 | 0.000137 | 0.055 |
| 173 | 0.000173 | 0.323 |
| 174 | 0.000322 | 0.639 |
| 175 | 0.000069 | 0.064 |
| 176 | 0.000118 | 0.149 |
| 177 | 0.000153 | 0.615 |
| 178 | 0.000177 | 0.071 |
| 179 | 0.000072 | 0.036 |
| 180 | 0.000106 | 0.081 |
| 181 | 0.000324 | 0.074 |
| 182 | 0.000171 | 0.088 |
| 184 | 0.000068 | 0.017 |
| 185 | 0.000170 | 1.060 |
| 186 | 0.000255 | 0.431 |
| 187 | 0.000066 | 0.043 |
| 188 | 0.000084 | 0.038 |
| 189 | 0.000084 | 0.033 |
| 190 | 0.000087 | 0.053 |
| 191 | 0.000096 | 0.042 |
| 192 | 0.000078 | 0.065 |
| 193 | 0.000096 | 0.023 |
| 194 | 0.000148 | 0.054 |
| 195 | 0.000214 | 0.065 |
| 196 | 0.000470 | 0.304 |
| 197 | 0.000364 | 0.129 |
| 198 | 0.000181 | 1.314 |
| 199 | 0.000119 | 0.208 |
| 200 | 0.000315 | 0.583 |
| 201 | 0.000119 | 0.244 |
| 202 | 0.000058 | 0.142 |
| 203 | 0.000113 | 0.112 |
| 204 | 0.000230 | 0.319 |
| 205 | 0.000263 | 0.437 |
| 206 | 0.000223 | 6.300 |
| 207 | 0.000137 | 0.395 |
| 208 | 0.000099 | 0.368 |
| 209 | 0.000552 | 0.437 |
| 210 | 0.000138 | 0.185 |
| 211 | 0.000147 | 0.156 |
| 212 | 0.000122 | 0.307 |
| 213 | 0.000239 | 0.400 |
| 214 | 0.000071 | 0.084 |
| 215 | 0.000149 | 0.107 |
| 216 | 0.000490 | 0.183 |
| 217 | — | 0.192 |
| 218 | 0.000142 | 0.092 |
| 219 | 0.000073 | 0.047 |
| 220 | 0.000052 | 0.042 |
| 221 | 0.000069 | 0.120 |
| 222 | 0.000080 | 0.118 |
| 223 | 0.000251 | 0.258 |
| 224 | 0.000127 | 0.157 |
| 225 | 0.000087 | 0.280 |
| 226 | 0.000057 | 0.049 |
| 227 | 0.000207 | 0.131 |
| 228 | 0.000200 | 0.0931 |
| 229 | 0.000619 | 0.096 |
| 230 | 0.000051 | 0.070 |
| 231 | 0.000061 | 0.098 |
| 232 | 0.000141 | 0.200 |
| 233 | 0.000516 | 0.202 |
| 234 | 0.000163 | 0.071 |
| 235 | 0.000180 | 0.120 |
| 236 | 0.000097 | 0.087 |
| 237 | 0.000130 | 0.064 |
| 238 | 0.000176 | 0.076 |
| 239 | 0.000146 | 0.148 |
| 240 | 0.000128 | 0.141 |
| 241 | 0.000150 | 0.137 |
| 242 | 0.000249 | 0.791 |
| 243 | 0.000078 | 0.106 |
| 244 | 0.001654 | 0.638 |
| 245 | 0.000120 | 0.058 |
| 246 | 0.000099 | 0.138 |
| 247 | 0.000129 | 0.107 |
| 248 | 0.000222 | 0.518 |
| 249 | 0.000063 | 0.114 |
| 250 | 0.000071 | 0.047 |
| 251 | 0.002260 | 3.870 |
| 252 | 0.001375 | 1.800 |
| 253 | 0.000804 | 0.887 |
| 254 | 0.001200 | 0.544 |
| 255 | 0.001740 | 1.480 |
| 256 | 0.000433 | 1.640 |
| 257 | 0.000403 | 0.981 |
| 258 | 0.000069 | 0.095 |
| 259 | 0.000230 | 0.254 |
| 260 | 0.000083 | 0.103 |
| 261 | 0.000153 | 0.146 |
| 262 | 0.000093 | 0.089 |

TABLE 4-continued

| Example Number | Mcl-1 HTRF $IC_{50}$ (μM) | OPM-2 10% FBS $IC_{50}$ IP (μM) |
|---|---|---|
| 263 | 0.000147 | 0.124 |
| 264 | 0.000396 | 0.771 |
| 265 | 0.000423 | 0.578 |
| 266 | 0.000282 | 0.723 |
| 267 | 0.000297 | 0.250 |
| 268 | 0.000065 | 0.072 |
| 269 | 0.000104 | 0.086 |
| 270 | 0.000035 | 4.860 |
| 271 | 0.000031 | 0.359 |
| 272 | 0.000144 | 0.137 |
| 273 | 0.000494 | 0.501 |
| 274 | 0.000285 | 0.232 |
| 275 | 0.000176 | 0.082 |
| 276 | 0.000096 | 0.110 |
| 277 | 0.000058 | 0.057 |
| 278 | 0.000039 | 0.574 |
| 279 | 0.000084 | 0.453 |
| 280 | 0.000052 | 0.073 |
| 281 | 0.000181 | 0.152 |
| 282 | 0.000118 | 0.486 |
| 283 | 0.000354 | 0.839 |
| 284 | 0.000288 | 0.230 |
| 285 | 0.000107 | 0.062 |
| 286 | 0.000155 | 0.050 |
| 287 | 0.000137 | 0.050 |
| 288 | 0.000484 | 0.652 |
| 289 | 0.000214 | 0.131 |
| 290 | 0.000215 | 0.149 |
| 291 | 0.000083 | 0.104 |
| 292 | 0.000356 | 0.399 |
| 293 | 0.000242 | 0.207 |
| 294 | 0.000660 | 0.687 |
| 295 | 0.000321 | 0.104 |
| 296 | 0.000211 | 1.310 |
| 297 | 0.000128 | 0.066 |
| 298 | 0.000279 | 0.262 |
| 299 | 0.000367 | 0.456 |
| 300 | 0.000165 | 0.284 |
| 301 | 0.000196 | 0.141 |
| 302 | 0.000107 | 0.084 |
| 303 | 0.000150 | 0.101 |
| 304 | 0.000226 | 0.239 |
| 305 | 0.000330 | 0.327 |
| 306 | 0.000282 | 0.246 |
| 307 | 0.000087 | 0.041 |
| 308 | 0.000111 | 0.070 |
| 309 | 0.000215 | 0.064 |
| 310 | 0.000117 | 0.517 |
| 311 | 0.000324 | 0.362 |
| 312 | 0.000576 | 0.408 |
| 313 | 0.000225 | 0.131 |
| 314 | 0.000118 | 0.126 |
| 315 | 0.000122 | 0.124 |
| 316 | 0.000166 | 0.047 |
| 317 | 0.000186 | 0.088 |
| 318 | 0.000138 | 0.077 |
| 319 | 0.000081 | 0.087 |
| 320 | 0.000524 | 0.302 |
| 321 | 0.000145 | 0.092 |
| 322 | 0.000145 | 0.087 |
| 323 | 0.000166 | 0.169 |
| 324 | 0.000136 | 0.057 |
| 325 | 0.000180 | 0.192 |
| 326 | 0.000307 | 0.488 |
| 327 | 0.000214 | 0.174 |
| 328 | 0.000087 | 0.048 |
| 329 | 0.000137 | 0.243 |
| 330 | 0.000425 | 0.278 |
| 331 | 0.000184 | 0.230 |
| 332 | 0.000096 | 0.089 |
| 333 | 0.000088 | 0.082 |
| 334 | 0.000186 | 0.159 |
| 335 | 0.000148 | 0.133 |
| 336 | 0.000085 | 0.051 |
| 337 | 0.000090 | 0.059 |
| 338 | 0.000100 | 0.057 |
| 339 | 0.000117 | 0.153 |
| 340 | 0.000128 | 0.060 |
| 341 | 0.000052 | 0.042 |
| 342 | 0.000089 | 0.104 |
| 343 | 0.000093 | 0.094 |
| 344 | 0.000116 | 0.057 |
| 345 | 0.000803 | 1.040 |
| 346 | 0.000062 | 0.066 |
| 347 | 0.000392 | 0.871 |
| 348 | 0.002625 | 5.360 |
| 349 | 0.001610 | 7.790 |
| 350 | 0.012333 | >33.3 |
| 351 | 0.000121 | 0.196 |
| 352 | 0.000111 | 0.162 |
| 353 | 0.000135 | 0.186 |
| 354 | 0.000214 | 0.450 |
| 355 | 0.000172 | 0.272 |
| 356 | 0.000110 | 0.367 |
| 357 | 0.000067 | 0.118 |
| 358 | 0.000066 | 0.144 |
| 359 | 0.002080 | >33.3 |
| 360 | 0.001067 | 2.410 |
| 361 | 0.000101 | 0.028 |
| 362 | 0.000061 | 0.058 |
| 363 | 0.000080 | 0.101 |
| 364 | 0.192500 | >33.3 |
| 365 | 0.000104 | 0.032 |
| 366 | 0.000248 | 0.133 |
| 367 | 0.000201 | 0.273 |
| 368 | 0.000069 | 0.068 |
| 369 | — | 0.071 |
| 370 | — | 0.369 |
| 371 | 0.000101 | 0.043 |
| 372 | 0.000175 | 0.085 |
| 373 | 0.000069 | 0.060 |
| 374 | 0.000095 | 0.041 |
| 375 | 0.000102 | 0.042 |
| 376 | 0.000152 | 0.064 |
| 377 | 0.000130 | 0.055 |
| 378 | 0.001187 | 1.415 |
| 379 | 0.000220 | 0.235 |
| 380 | 0.000712 | 0.338 |
| 381 | 0.000157 | 0.262 |
| 382 | 0.000130 | 0.106 |
| 383 | 0.000194 | 0.182 |
| 384 | 0.000324 | 0.266 |
| 385 | 0.000762 | 0.717 |
| 386 | 0.000273 | 0.211 |
| 387 | 0.000291 | 0.272 |
| 388 | 0.000069 | 0.194 |
| 389 | 0.000218 | 0.278 |
| 390 | 0.000095 | 0.068 |
| 391 | 0.001120 | 1.710 |
| 392 | 0.000443 | 4.610 |
| 393 | 0.000079 | 1.590 |
| 394 | 0.000533 | 0.461 |
| 395 | 0.000302 | 1.960 |
| 396 | 0.000084 | 1.020 |
| 397 | 0.000532 | 1.820 |
| 398 | 0.001007 | 5.585 |
| 399 | 0.000401 | 2.100 |
| 400 | 0.001100 | 2.872 |
| 401 | 0.002380 | 2.170 |
| 402 | 0.001399 | 0.745 |
| 403 | 0.000472 | 0.215 |
| 404 | 0.000565 | 0.319 |
| 405 | 0.000057 | 0.018 |
| 406 | 0.000304 | 0.329 |
| 407 | 0.000751 | 0.567 |
| 408 | 0.000225 | 4.610 |
| 409 | 0.000214 | 0.140 |
| 410 | 0.000327 | 0.247 |
| 411 | 0.000930 | 0.796 |
| 412 | 0.001410 | 0.749 |
| 413 | 0.000257 | 0.145 |
| 414 | 0.000154 | 1.840 |

TABLE 4-continued

| Example Number | Mcl-1 HTRF IC$_{50}$ (µM) | OPM-2 10% FBS IC$_{50}$ IP (µM) |
|---|---|---|
| 415 | 0.000294 | 4.020 |
| 416 | 0.000423 | 6.910 |
| 417 | 0.001750 | 6.320 |
| 418 | 0.000662 | 0.515 |
| 419 | 0.003310 | 2.140 |
| 420 | 0.000176 | 0.080 |
| 421 | 0.001175 | 0.596 |
| 422 | 0.000289 | 0.405 |
| 423 | 0.000269 | 0.626 |
| 424 | — | 2.240 |
| 425 | 0.000281 | 0.086 |
| 426 | 0.001315 | 2.170 |
| 427 | 0.000208 | 0.141 |
| 428 | 0.000154 | 0.316 |
| 429 | 0.000214 | 0.174 |
| 430 | 0.002475 | 1.310 |
| 431 | 0.000555 | 0.206 |
| 432 | 0.000229 | 0.302 |
| 433 | 0.001186 | 1.670 |
| 434 | 0.000585 | 0.913 |
| 435 | 0.000380 | 0.152 |
| 436 | 0.000156 | 3.200 |
| 437 | 0.000201 | 0.080 |
| 438 | 0.000308 | 0.230 |
| 439 | 0.000427 | 0.505 |
| 440 | 0.000140 | 0.038 |
| 441 | 0.000459 | 0.443 |
| 442 | 0.000221 | 0.286 |
| 443 | 0.001255 | 0.555 |
| 444 | 0.000128 | 0.251 |
| 445 | 0.000282 | 0.161 |
| 446 | 0.000776 | 0.446 |
| 447 | 0.000119 | 0.069 |
| 448 | 0.000315 | 0.581 |
| 449 | 0.000449 | 0.290 |
| 450 | 0.000112 | 0.791 |
| 451 | 0.001006 | 1.810 |
| 452 | 0.003375 | 17.200 |
| 453 | 0.000451 | 0.611 |
| 454 | 0.000174 | 0.213 |
| 455 | 0.000104 | 0.110 |
| 456 | 0.001045 | 0.908 |
| 457 | 0.001468 | 2.610 |
| 458 | 0.000848 | 0.439 |
| 459 | 0.000225 | 0.267 |
| 460 | 0.000147 | 0.161 |
| 461 | 0.000111 | 0.218 |
| 462 | 0.000261 | 0.198 |
| 463 | 0.000439 | 0.322 |
| 464 | 0.000387 | 0.426 |
| 465 | 0.000581 | 0.536 |
| 466 | 0.000900 | 0.446 |
| 467 | 0.000223 | 0.173 |
| 468 | 0.001075 | 1.210 |
| 469 | 0.000075 | 0.295 |
| 470 | 0.000156 | 0.122 |
| 471 | 0.000321 | 0.943 |
| 472 | 0.000167 | 0.068 |
| 473 | 0.000112 | 0.025 |
| 474 | 0.000088 | 0.042 |
| 475 | 0.000411 | 0.350 |
| 476 | 0.000223 | 0.173 |
| 477 | 0.000240 | 0.403 |
| 478 | 0.000423 | 0.197 |
| 479 | 0.000315 | 4.980 |
| 480 | 0.000067 | 0.113 |
| 481 | 0.000212 | 1.110 |
| 482 | 0.000180 | 0.590 |
| 483 | 0.000244 | 0.260 |
| 484 | 0.000075 | 0.162 |
| 485 | 0.000292 | 1.210 |
| 486 | 0.000081 | 0.269 |
| 487 | 0.000221 | 1.500 |
| 488 | 0.000076 | 0.183 |
| 489 | 0.000035 | 0.046 |
| 490 | 0.000288 | 1.860 |
| 491 | 0.000096 | 0.453 |
| 492 | 0.000295 | 0.516 |
| 493 | 0.000109 | 0.170 |
| 494 | 0.000276 | 1.480 |
| 495 | 0.000075 | 0.082 |
| 496 | 0.000105 | 0.207 |
| 497 | 0.000469 | 1.210 |
| 498 | 0.000120 | 0.143 |
| 499 | 0.000355 | 0.110 |
| 500 | 0.000147 | 0.078 |
| 501 | 0.000672 | 5.030 |
| 502 | 0.000069 | 0.191 |
| 503 | 0.000331 | 0.200 |
| 504 | 0.000159 | 0.087 |
| 506 | 0.003800 | 7.430 |
| 507 | 0.013700 | >33.3 |
| 508 | 0.000248 | 1.130 |
| 509 | 0.000155 | 0.744 |
| 510 | 0.000258 | 1.520 |
| 511 | 0.000493 | 1.380 |
| 512 | 0.000170 | 0.363 |
| 513 | 0.000235 | 0.383 |
| 514 | 0.000279 | 0.567 |
| 515 | 0.000113 | 0.120 |
| 516 | 0.000254 | 0.209 |
| 517 | 0.000259 | 0.252 |
| 518 | 0.000164 | 0.224 |
| 519 | 0.000157 | 0.116 |
| 520 | 0.000128 | 0.095 |
| 521 | 0.000133 | 0.174 |
| 522 | 0.000142 | 0.110 |
| 523 | 0.000158 | 0.260 |
| 524 | — | 0.135 |
| 525 | 0.000142 | 0.087 |
| 526 | 0.000144 | 0.289 |
| 527 | 0.000804 | 2.190 |
| 528 | 0.000162 | 0.140 |
| 529 | 0.005565 | 2.840 |
| 530 | 0.001200 | 0.530 |
| 531 | 0.000141 | 0.138 |

TABLE 5

| Example Number | Mcl-1 HTRF IC$_{50}$ (µM) | OPM-2 10% FBS IC$_{50}$ IP (µM) |
|---|---|---|
| 100001 | 0.000055 | 0.124 |
| 100002 | 0.000071 | 0.041 |
| 100003 | 0.00042 | 0.238 |
| 100004 | 0.000072 | 0.120 |
| 100005 | 0.000091 | 0.062 |
| 100006 | 0.000081 | 0.131 |
| 100007 | 0.000367 | 0.142 |
| 100008 | 0.000170 | 0.541 |
| 100009 | 0.000128 | 0.216 |
| 100010 | 0.000077 | 0.142 |
| 100011 | 0.000153 | 0.134 |
| 100012 | 0.000275 | 1.131 |
| 100013 | 0.000199 | 0.068 |
| 100014 | 0.000228 | 0.330 |
| 100015 | 0.001040 | 1.003 |
| 100016 | 0.000182 | 0.132 |
| 100017 | 0.000039 | 0.040 |
| 100018 | 0.000061 | 0.049 |
| 100019 | 0.000182 | 0.058 |
| 100020 | 0.000032 | 0.085 |
| 100021 | 0.001053 | — |
| 100022 | 0.000861 | — |
| 100023 | 0.003940 | — |
| 100024 | 0.006155 | — |
| 100025 | 0.002348 | — |
| 100026 | 0.002145 | — |
| 100027 | 0.007340 | — |

TABLE 5-continued

| Example Number | Mcl-1 HTRF IC$_{50}$ (μM) | OPM-2 10% FBS IC$_{50}$ IP (μM) |
|---|---|---|
| 100028 | 0.001257 | — |
| 100029 | 0.008733 | — |
| 100030 | 0.010355 | — |
| 100031 | 0.007450 | — |
| 100032 | 0.000442 | — |
| 100033 | 0.002815 | — |
| 100034 | 0.000877 | — |
| 100035 | 0.000601 | 1.470 |
| 100036 | 0.000889 | 1.980 |
| 100037 | 0.001805 | 1.920 |
| 100038 | 0.001655 | 2.560 |
| 100039 | 0.000563 | 0.744 |
| 100040 | 0.002745 | 4.950 |
| 100041 | 0.003365 | 4.990 |
| 100042 | 0.004860 | 2.220 |
| 100043 | 0.001670 | 7.280 |
| 100044 | 0.031100 | 7.290 |
| 100045 | 0.000308 | 0.342 |
| 100046 | 0.003760 | 0.976 |
| 100047 | 0.005150 | 2.540 |
| 100048 | 0.000187 | 0.551 |
| 100049 | 0.001261 | 2.150 |
| 100050 | 0.001282 | 3.824 |
| 100051 | 0.000217 | 0.502 |
| 100052 | 0.000191 | 0.424 |
| 100053 | 0.000294 | 0.609 |
| 100054 | 0.004110 | 9.060 |
| 100055 | 0.001270 | 4.630 |
| 100056 | 0.000424 | 1.680 |
| 100057 | 0.000568 | 2.600 |
| 100058 | 0.001760 | 3.360 |
| 100059 | 0.011900 | 3.450 |
| 100060 | 0.004010 | 5.980 |
| 100061 | 0.000780 | 0.529 |
| 100062 | 0.004250 | 9.940 |
| 100063 | 0.002320 | 2.260 |
| 100064 | 0.002540 | 3.730 |
| 100065 | 0.004855 | 7.390 |
| 100066 | 0.001430 | 3.820 |
| 100067 | 0.001009 | 0.271 |
| 100068 | 0.004410 | 0.765 |
| 100069 | 0.000457 | 0.250 |
| 100070 | 0.004855 | 1.070 |
| 100071 | 0.001540 | 0.588 |
| 100072 | 0.000451 | 1.720 |
| 100073 | 0.000346 | 1.197 |
| 100074 | 0.000731 | 3.020 |
| 100075 | 0.000671 | 1.817 |
| 100076 | 0.009655 | 2.670 |
| 100077 | 0.000190 | 0.052 |
| 100078 | 0.000409 | 2.720 |
| 100079 | 0.000343 | 0.713 |
| 100080 | 0.000610 | 0.818 |
| 100081 | 0.007330 | 5.930 |
| 100082 | 0.000539 | 0.727 |
| 100083 | 0.000179 | 0.123 |
| 100084 | 0.000745 | 1.488 |
| 100085 | 0.000245 | 0.288 |
| 100086 | 0.000537 | 0.390 |
| 100087 | 0.000864 | 0.187 |
| 100088 | 0.002125 | 1.340 |
| 100089 | 0.000348 | 0.325 |
| 100090 | 0.000795 | 0.798 |
| 100091 | 0.001195 | 1.350 |
| 100092 | 0.004015 | 2.210 |
| 100093 | 0.000291 | 0.554 |
| 100094 | 0.003835 | 4.380 |
| 100095 | 0.000148 | 0.113 |
| 100096 | 0.000624 | 0.517 |
| 100097 | 0.000081 | 5.230 |
| 100098 | 0.000231 | 0.748 |
| 100099 | 0.000659 | 0.349 |
| 100100 | 0.002100 | 1.325 |
| 100101 | 0.000062 | 2.595 |
| 100102 | 0.000990 | 1.430 |
| 100103 | 0.000325 | 0.778 |
| 100104 | 0.000599 | 0.250 |
| 100105 | 0.005930 | 3.660 |
| 100106 | 0.000143 | 0.121 |
| 100107 | 0.000296 | 0.181 |
| 100108 | 0.000436 | 0.358 |
| 100109 | 0.000486 | 2.140 |
| 100110 | 0.001480 | 0.686 |
| 100111 | 0.000352 | 0.687 |
| 100112 | 0.001295 | 1.800 |
| 100113 | 0.000182 | 0.070 |
| 100114 | 0.001052 | 0.491 |
| 100115 | 0.004485 | 2.840 |
| 100116 | 0.003775 | 5.940 |
| 100117 | 0.002405 | 3.170 |
| 100118 | 0.004440 | 3.950 |
| 100119 | 0.001720 | 1.570 |
| 100120 | 0.000067 | 0.635 |
| 100121 | 0.000056 | 2.530 |
| 100122 | 0.000098 | 1.190 |
| 100123 | 0.000092 | 2.660 |
| 100124 | 0.000323 | 0.270 |
| 100125 | 0.000430 | 0.555 |
| 100126 | 0.000183 | 0.041 |
| 100127 | 0.000175 | 0.108 |
| 100128 | 0.000089 | 0.217 |
| 100129 | 0.002400 | 4.870 |
| 100130 | 0.002690 | 2.170 |
| 100131 | 0.000163 | 0.144 |
| 100132 | 0.000543 | 0.675 |
| 100133 | 0.000885 | 0.984 |
| 100134 | 0.000845 | 3.510 |
| 100135 | 0.000173 | 0.161 |
| 100136 | 0.000368 | 0.556 |
| 100137 | 0.000365 | 2.820 |
| 100138 | 0.000549 | 0.342 |
| 100139 | 0.002585 | 0.974 |
| 100140 | 0.000486 | 0.299 |
| 100141 | 0.001058 | 1.370 |
| 100142 | 0.000717 | 0.663 |
| 100143 | 0.001870 | 3.270 |
| 100144 | — | 0.208 |
| 100145 | 0.000357 | 0.945 |
| 100146 | 0.000515 | 0.347 |
| 100147 | 0.000305 | 0.666 |
| 100148 | 0.000113 | 0.239 |
| 100149 | 0.000214 | 0.186 |
| 100150 | 0.001685 | 1.430 |
| 100151 | 0.000120 | 0.071 |
| 100152 | 0.000449 | 0.377 |
| 100153 | 0.000738 | 4.660 |
| 100154 | 0.001720 | 1.070 |
| 100155 | 0.000225 | 0.332 |
| 100156 | 0.000410 | 0.568 |
| 100157 | 0.004810 | 3.210 |
| 100158 | 0.000298 | 0.260 |
| 100159 | 0.000559 | 0.591 |
| 100160 | 0.000169 | 0.078 |
| 100161 | 0.000355 | 0.757 |
| 100162 | 0.003470 | 2.870 |
| 100163 | 0.002790 | 1.000 |
| 100164 | 0.000917 | 0.967 |
| 100165 | 0.000455 | 0.579 |
| 100166 | 0.001765 | 0.945 |
| 100167 | 0.000377 | 0.339 |
| 100168 | 0.000249 | 0.196 |
| 100169 | 0.004825 | 2.270 |
| 100170 | 0.012100 | 7.820 |
| 100171 | 0.000578 | 0.868 |
| 100172 | 0.001295 | 1.570 |
| 100173 | 0.000539 | 0.379 |
| 100174 | 0.002025 | 1.910 |
| 100175 | 0.000149 | 0.452 |
| 100176 | 0.000480 | 0.603 |
| 100177 | 0.000258 | 0.259 |
| 100178 | 0.000432 | 0.237 |
| 100179 | 0.005810 | 0.840 |
| 100180 | 0.004917 | 4.425 |
| 100181 | 0.000537 | 0.226 |

TABLE 5-continued

| Example Number | Mcl-1 HTRF IC$_{50}$ (µM) | OPM-2 10% FBS IC$_{50}$ IP (µM) |
|---|---|---|
| 100182 | 0.000863 | 0.827 |
| 100183 | 0.001340 | 2.245 |
| 100184 | 0.000717 | 0.179 |
| 100185 | 0.008883 | 5.130 |
| 100186 | 0.000377 | 0.312 |
| 100187 | 0.002760 | 3.110 |
| 100188 | 0.000877 | 0.735 |
| 100189 | 0.000820 | 0.701 |
| 100190 | 0.004790 | 2.480 |
| 100191 | 0.001600 | 0.557 |
| 100192 | 0.000192 | 0.149 |
| 100193 | 0.000856 | 1.300 |
| 100194 | 0.000613 | 0.619 |
| 100195 | 0.001075 | 0.625 |
| 100196 | 0.000461 | 0.358 |
| 100197 | 0.000774 | 2.460 |
| 100198 | 0.000307 | 0.399 |
| 100199 | 0.000166 | 0.148 |
| 100200 | 0.000213 | 1.070 |
| 100201 | 0.000086 | 0.307 |
| 100202 | 0.000352 | 0.928 |
| 100203 | 0.000285 | 0.491 |
| 100204 | 0.001655 | 5.270 |
| 100205 | 0.000206 | 0.068 |
| 100206 | 0.001260 | 1.750 |
| 100207 | 0.000141 | 0.215 |
| 100208 | 0.000431 | 0.318 |
| 100209 | 0.002675 | 3.380 |
| 100210 | 0.003475 | 3.360 |
| 100211 | 0.001435 | 4.780 |
| 100212 | 0.000901 | 1.620 |
| 100213 | 0.002845 | 2.020 |
| 100214 | 0.000143 | 0.095 |
| 100215 | 0.000595 | 1.250 |
| 100216 | 0.000311 | 0.374 |
| 100217 | 0.000183 | 0.130 |
| 100218 | 0.000621 | 0.675 |
| 100219 | 0.000401 | 0.974 |
| 100220 | 0.007415 | 6.840 |
| 100221 | 0.000525 | 0.776 |
| 100222 | 0.000182 | 0.222 |
| 100223 | 0.001410 | 2.150 |
| 100224 | 0.000345 | 0.385 |
| 100225 | 0.000639 | 0.882 |
| 100226 | 0.001395 | 0.849 |
| 100227 | 0.000423 | 0.191 |
| 100228 | 0.000558 | 3.300 |
| 100229 | 0.000356 | 1.490 |
| 100230 | 0.000473 | 0.544 |
| 100231 | 0.000312 | 0.350 |
| 100232 | 0.000152 | 0.389 |
| 100233 | 0.001040 | 0.257 |
| 100234 | 0.000237 | 0.449 |
| 100235 | 0.001345 | 0.644 |
| 100236 | 0.001096 | 0.933 |
| 100237 | 0.001740 | 0.996 |
| 100238 | 0.000474 | 0.747 |
| 100239 | 0.000333 | 3.740 |
| 100240 | 0.000385 | 0.266 |
| 100241 | 0.000365 | 0.401 |
| 100242 | 0.002145 | 1.450 |
| 100243 | 0.011500 | 8.670 |
| 100244 | 0.000182 | 0.049 |
| 100245 | 0.001715 | 1.980 |
| 100246 | 0.000326 | 0.114 |
| 100247 | 0.000542 | 0.624 |
| 100248 | 0.011050 | 6.680 |
| 100249 | 0.002995 | 2.270 |
| 100250 | 0.000136 | 0.082 |
| 100251 | 0.003290 | 3.730 |
| 100252 | 0.000112 | 0.077 |
| 100253 | 0.000149 | 0.544 |
| 100254 | 0.004070 | 2.150 |
| 100255 | 0.014450 | 5.020 |
| 100256 | 0.005040 | 1.200 |
| 100257 | 0.000180 | 0.080 |
| 100258 | 0.000553 | 0.519 |
| 100259 | 0.006180 | 1.250 |
| 100260 | 0.000408 | 0.094 |
| 100261 | 0.001220 | 0.533 |
| 100262 | 0.000134 | 0.433 |
| 100263 | 0.001830 | 3.390 |
| 100264 | 0.000384 | 0.600 |
| 100265 | 0.000439 | 0.441 |
| 100266 | 0.000292 | 0.571 |
| 100267 | 0.000166 | 0.274 |
| 100268 | 0.003440 | 3.810 |
| 100269 | 0.000908 | 1.230 |
| 100270 | 0.000776 | 3.72 |
| 100271 | 0.002480 | 6.120 |
| 100272 | 0.000401 | 0.349 |
| 100273 | 0.005655 | 8.660 |
| 100274 | 0.000377 | 0.543 |
| 100275 | 0.000113 | 0.309 |
| 100276 | 0.000326 | 1.528 |
| 100277 | 0.000266 | 0.448 |
| 100278 | 0.000458 | 0.333 |
| 100279 | 0.000777 | 3.25 |
| 100280 | 0.000368 | 0.305 |
| 100281 | 0.000117 | 0.352 |
| 100282 | 0.000268 | 1.280 |
| 100283 | 0.000143 | 0.806 |
| 100284 | 0.000285 | 0.396 |
| 100285 | 0.000241 | 0.642 |
| 100286 | 0.000471 | 1.580 |
| 100287 | 0.000494 | 1.870 |
| 100288 | 0.000103 | 0.089 |
| 100289 | 0.000878 | 3.960 |
| 100290 | 0.000116 | 0.259 |
| 100291 | 0.000137 | 0.281 |
| 100292 | 0.000115 | 0.672 |
| 100293 | 0.000522 | 0.726 |
| 100294 | 0.000118 | 0.116 |
| 100295 | 0.000279 | 0.302 |
| 100297 | 0.000115 | 0.168 |
| 100298 | 0.000140 | 0.199 |
| 100299 | 0.000350 | 0.623 |
| 100300 | 0.000109 | 0.235 |
| 100301 | 0.001315 | 1.930 |
| 100302 | 0.003805 | 4.880 |
| 100303 | 0.003640 | 7.330 |
| 100304 | 0.000311 | 0.464 |
| 100305 | 0.000473 | 1.140 |
| 100306 | 0.000124 | 0.278 |
| 100307 | 0.000049 | 1.030 |
| 100308 | 0.000033 | 1.170 |
| 100309 | 0.000244 | 0.385 |
| 100310 | 0.000152 | 0.120 |
| 100311 | 0.001030 | 1.190 |
| 100312 | 0.000088 | 0.234 |
| 100313 | 0.000129 | 0.143 |
| 100314 | 0.002925 | 2.290 |
| 100315 | 0.000200 | 0.153 |
| 100316 | 0.000276 | 0.375 |
| 100317 | 0.000188 | 0.157 |
| 100318 | 0.000095 | 0.114 |
| 100319 | 0.000126 | 0.506 |
| 100320 | 0.001200 | 2.140 |
| 100321 | 0.000209 | 0.285 |
| 100322 | 0.00223 | 1.54 |
| 100323 | 0.000477 | 1.250 |
| 100324 | 0.000244 | 1.170 |
| 100325 | 0.000182 | 0.482 |
| 100326 | 0.000615 | 0.334 |
| 100327 | 0.000295 | 0.550 |
| 100328 | 0.000261 | 0.180 |
| 100329 | 0.005023 | 1.560 |
| 100330 | 0.000083 | 8.260 |
| 100331 | 0.000192 | 8.260 |
| 100332 | 0.006465 | 4.31 |
| 100333 | 0.002100 | 2.170 |
| 100334 | 0.003273 | 1.470 |
| 100335 | 0.000319 | 0.165 |
| 100336 | 0.001123 | 1.810 |

TABLE 5-continued

| Example Number | Mcl-1 HTRF IC$_{50}$ (μM) | OPM-2 10% FBS IC$_{50}$ IP (μM) |
|---|---|---|
| 100337 | 0.001608 | 2.410 |
| 100338 | 0.000502 | 1.920 |
| 100339 | 0.000186 | 1.380 |
| 100340 | 0.000779 | 0.308 |
| 100341 | 0.0041 | 1.94 |
| 100342 | 0.001685 | 0.782 |
| 100343 | 0.002510 | 0.617 |
| 100344 | 0.000309 | 0.290 |
| 100345 | 0.002420 | 0.218 |
| 100346 | 0.000735 | 0.248 |
| 100347 | 0.000689 | 1.080 |
| 100348 | 0.000135 | 0.125 |
| 100349 | 0.00115 | 0.058 |
| 100350 | 0.000489 | 0.554 |
| 100351 | 0.000115 | 2.02 |
| 100352 | 0.002750 | 0.246 |
| 100353 | 0.000348 | 0.151 |
| 100354 | 0.000109 | 0.147 |
| 100355 | 0.000535 | 0.776 |
| 100356 | 0.000084 | 0.071 |
| 100357 | 0.000224 | 0.399 |
| 100358 | 0.000118 | 0.081 |
| 100359 | 0.001200 | 1.540 |
| 100360 | 0.000848 | 1.230 |
| 100361 | 0.000208 | 0.155 |
| 100362 | 0.000888 | 2.1 |
| 100363 | 0.001383 | 3.810 |
| 100364 | 0.001160 | 1.680 |
| 100365 | 0.000257 | 0.245 |
| 100366 | 0.000198 | 0.168 |
| 100367 | 0.000371 | 0.604 |
| 100368 | 0.000377 | 0.611 |
| 100369 | 0.00283 | 9.92 |
| 100370 | 0.000153 | 0.258 |
| 100371 | 0.00039 | 0.307 |
| 100372 | 0.000165 | 0.833 |
| 100373 | 0.000318 | 0.736 |
| 100374 | 0.000289 | 0.433 |
| 100375 | 0.000070 | 0.176 |
| 100376 | 0.000150 | 0.362 |
| 100377 | 0.000107 | 0.182 |
| 100378 | 0.000037 | 0.111 |
| 100379 | 0.000060 | 0.071 |
| 100380 | 0.000208 | 0.137 |
| 100381 | 0.000328 | 2.910 |
| 100382 | 0.000471 | 0.312 |
| 100383 | 0.000264 | 3.430 |
| 100384 | 0.000821 | 0.729 |
| 100385 | 0.000144 | 0.144 |
| 100386 | 0.004017 | 7.27 |
| 100387 | 0.000175 | 3.760 |
| 100388 | 0.001167 | 2.160 |
| 100389 | 0.000101 | 0.114 |
| 100390 | 0.000186 | 0.649 |
| 100391 | 0.000441 | 0.282 |
| 100392 | 0.000112 | 0.129 |
| 100393 | 0.000164 | 0.211 |
| 100394 | 0.000242 | 0.622 |
| 100395 | 0.000056 | 0.040 |
| 100396 | 0.000272 | 1.470 |
| 100397 | 0.000198 | 0.404 |
| 100398 | 0.000618 | 0.457 |
| 100399 | 0.000280 | 2.810 |
| 100400 | 0.000838 | 1.320 |
| 100401 | 0.001797 | 8.390 |
| 100402 | 0.000098 | 0.133 |
| 100403 | 0.000226 | 0.39 |
| 100404 | 0.002553 | 8.15 |
| 100405 | 0.000545 | 1.120 |
| 100406 | 0.000360 | 0.747 |
| 100407 | 0.000278 | 0.516 |
| 100408 | 0.001353 | 5.62 |
| 100409 | 0.000124 | 0.206 |
| 100410 | 0.000127 | 0.297 |
| 100411 | 0.000584 | 2.1 |
| 100412 | 0.000097 | 0.249 |
| 100413 | 0.000228 | 0.556 |
| 100414 | 0.000626 | 1.270 |
| 100415 | 0.001950 | 2.285 |
| 100416 | 0.000092 | 0.086 |
| 100417 | 0.000345 | 0.379 |
| 100418 | 0.000098 | 0.141 |
| 100419 | 0.000277 | 0.416 |
| 100420 | 0.000112 | 0.161 |
| 100421 | 0.003926 | 4.93 |
| 100422 | 0.000174 | 0.182 |
| 100423 | 0.000056 | 0.099 |
| 100424 | 0.000249 | 0.469 |
| 100425 | 0.000165 | 0.717 |
| 100426 | 0.000197 | 0.110 |
| 100427 | 0.000209 | 0.342 |
| 100428 | 0.000210 | 0.218 |
| 100429 | 0.000176 | 1.420 |
| 100430 | 0.000057 | 0.358 |
| 100431 | 0.000043 | 0.290 |
| 100432 | 0.000228 | 0.711 |
| 100433 | 0.000026 | 0.296 |
| 100434 | 0.000162 | 0.482 |
| 100435 | 0.000055 | 0.305 |
| 100436 | 0.000076 | 0.335 |
| 100437 | 0.000073 | 0.531 |
| 100438 | 0.000169 | 0.547 |
| 100439 | 0.000619 | 2.640 |
| 100440 | 0.000398 | 0.354 |
| 100441 | 0.000133 | 0.154 |
| 100442 | 0.000921 | 3.870 |
| 100443 | 0.000070 | 0.156 |
| 100444 | 0.000098 | 0.646 |
| 100445 | 0.000040 | 0.098 |
| 100446 | 0.000126 | 0.345 |
| 100447 | 0.000050 | 0.184 |
| 100448 | 0.000373 | 1.920 |
| 100449 | 0.000071 | 0.171 |
| 100450 | 0.000336 | 1.910 |
| 100451 | 0.000111 | 0.412 |
| 100452 | 0.000077 | 0.157 |
| 100453 | 0.000927 | 2.930 |
| 100454 | 0.000652 | 0.802 |
| 100455 | 0.000087 | 0.140 |
| 100456 | 0.000565 | 1.230 |
| 100457 | 0.000331 | 0.967 |
| 100458 | 0.000210 | 0.418 |
| 100459 | 0.000685 | 0.732 |
| 100460 | 0.000095 | 0.433 |
| 100461 | 0.000042 | 0.382 |
| 100462 | 0.000304 | 0.652 |
| 100463 | 0.000383 | 1.130 |
| 100464 | — | 1.530 |
| 100465 | 0.000121 | 0.729 |
| 100466 | 0.000043 | 1.440 |
| 100467 | 0.000303 | 0.516 |
| 100468 | 0.000393 | 0.943 |
| 100469 | 0.000085 | 0.325 |
| 100470 | 0.000576 | 9.65 |
| 100471 | 0.000281 | 0.299 |
| 100472 | 0.000651 | 0.357 |
| 100473 | 0.000974 | 0.178 |
| 100474 | 0.000405 | 0.387 |
| 100475 | 0.001365 | 2.710 |
| 100476 | — | 1.340 |
| 100477 | 0.000313 | 0.159 |
| 100478 | 0.003470 | 4.090 |
| 100479 | 0.000758 | 0.332 |
| 100480 | 0.000176 | 0.221 |
| 100481 | 0.000094 | 0.152 |
| 100482 | 0.000183 | 0.105 |
| 100483 | 0.001664 | 1.690 |
| 100484 | 0.003850 | 3.370 |
| 100485 | 0.000192 | 0.272 |
| 100486 | 0.000381 | 0.102 |
| 100487 | 0.000436 | 0.340 |
| 100488 | 0.000389 | 0.346 |
| 100489 | 0.000880 | 0.182 |
| 100490 | 0.000292 | 0.511 |

TABLE 5-continued

| Example Number | Mcl-1 HTRF IC$_{50}$ (µM) | OPM-2 10% FBS IC$_{50}$ IP (µM) |
|---|---|---|
| 100491 | 0.000208 | 0.308 |
| 100492 | 0.000749 | 0.436 |
| 100493 | 0.000322 | 0.512 |
| 100494 | 0.000078 | 0.089 |
| 100495 | 0.000462 | 0.539 |
| 100496 | 0.002665 | 5.060 |
| 100497 | 0.000064 | 0.106 |
| 100498 | 0.000885 | 1.660 |
| 100499 | 0.000509 | 1.120 |
| 100500 | 0.000049 | 0.071 |
| 100501 | 0.000090 | 0.518 |
| 100502 | 0.000290 | 0.393 |
| 100503 | 0.000493 | 0.706 |
| 100504 | 0.000803 | 1.890 |
| 100505 | 0.000165 | 0.137 |
| 100506 | 0.000497 | 1.270 |
| 100507 | 0.000430 | 0.490 |
| 100508 | 0.002734 | 2.500 |
| 100509 | 0.000057 | 0.361 |
| 100510 | 0.000070 | 0.379 |
| 100511 | 0.000070 | 0.430 |
| 100512 | 0.000415 | 1.490 |
| 100513 | 0.000071 | 0.288 |
| 100514 | 0.000088 | 0.231 |
| 100515 | 0.000132 | 0.585 |
| 100516 | 0.003360 | 1.900 |
| 100517 | 0.001059 | 3.460 |
| 100518 | 0.000427 | 0.668 |
| 100519 | 0.000175 | 0.138 |
| 100520 | 0.000549 | 1.690 |
| 100521 | 0.000197 | 0.296 |
| 100522 | 0.000144 | 0.538 |
| 100523 | 0.000812 | 0.622 |
| 100524 | 0.000990 | 0.842 |
| 100525 | 0.003305 | 1.430 |
| 100526 | 0.000387 | 0.826 |
| 100527 | 0.003595 | 3.570 |
| 100528 | 0.000138 | 0.257 |
| 100529 | 0.000287 | 0.245 |
| 100530 | 0.000171 | 0.448 |
| 100531 | 0.000083 | 0.172 |
| 100532 | 0.000053 | 8.637 |
| 100533 | 0.008565 | 3.990 |
| 100534 | 0.000799 | 0.542 |
| 100535 | 0.000570 | 0.964 |
| 100536 | 0.000204 | 0.826 |
| 100537 | 0.000115 | 0.256 |
| 100538 | 0.001470 | 2.400 |
| 100539 | 0.000144 | 0.727 |
| 100540 | 0.000275 | 0.320 |
| 100541 | 0.000760 | 0.826 |
| 100542 | 0.000229 | 0.902 |
| 100543 | 0.000451 | 0.821 |
| 100544 | 0.000171 | 0.306 |
| 100545 | 0.000153 | 0.231 |
| 100546 | 0.000084 | 0.440 |
| 100547 | 0.000031 | 1.860 |
| 100548 | 0.000064 | 8.410 |
| 100549 | 0.002570 | 0.545 |
| 100550 | 0.000059 | 6.859 |
| 100551 | 0.000174 | 0.142 |
| 100552 | 0.000065 | 0.957 |
| 100553 | 0.001040 | 2.790 |
| 100554 | 0.000231 | 0.519 |
| 100555 | 0.000101 | 0.113 |
| 100556 | 0.000113 | 0.734 |
| 100557 | 0.000093 | 0.299 |
| 100558 | 0.000086 | 0.274 |
| 100559 | 0.000113 | 1.030 |
| 100560 | 0.000041 | 2.020 |
| 100561 | 0.000275 | 0.673 |
| 100562 | 0.000057 | 0.532 |
| 100563 | 0.000065 | 0.510 |
| 100564 | 0.000333 | 1.430 |
| 100565 | 0.001540 | 2.060 |
| 100566 | 0.000142 | 0.590 |
| 100567 | 0.000125 | 0.249 |
| 100568 | 0.000431 | 1.540 |
| 100569 | 0.002479 | 2.000 |
| 100570 | 0.003380 | 5.050 |
| 100571 | 0.000076 | 0.922 |
| 100572 | 0.000174 | 1.160 |
| 100573 | 0.002070 | 7.390 |
| 100574 | 0.001420 | 4.320 |
| 100575 | 0.001300 | 2.500 |
| 100576 | 0.001150 | 4.090 |
| 100577 | 0.000045 | 2.020 |
| 100578 | 0.000089 | 0.595 |
| 100579 | 0.000214 | 0.757 |
| 100580 | 0.000877 | 6.580 |
| 100581 | 0.000363 | 1.540 |
| 100582 | 0.000197 | 1.120 |
| 100583 | 0.000124 | 0.411 |
| 100584 | 0.000139 | 0.349 |
| 100585 | 0.000057 | 0.696 |
| 100586 | 0.000074 | 0.453 |
| 100587 | 0.000136 | 0.177 |
| 100588 | 0.000075 | 0.117 |
| 100589 | 0.001835 | 3.330 |
| 100590 | 0.000086 | 0.501 |
| 100591 | 0.000075 | 0.060 |
| 100592 | 0.000275 | 0.139 |
| 100593 | 0.000464 | 0.215 |
| 100594 | 0.000143 | 0.241 |
| 100595 | 0.000157 | 0.133 |
| 100596 | 0.000229 | 0.186 |
| 100597 | 0.000263 | 0.577 |
| 100598 | 0.000077 | 0.188 |
| 100599 | 0.001150 | 1.140 |
| 100600 | 0.000445 | 0.528 |
| 100601 | 0.000114 | 0.239 |
| 100602 | 0.000800 | 2.330 |
| 100603 | 0.000651 | 1.570 |
| 100604 | 0.000723 | 4.110 |
| 100605 | 0.003245 | 7.950 |
| 100606 | 0.000209 | 0.428 |

In-Vivo Data

Tumor Pharmacodynamics (PD)

Figure 2:
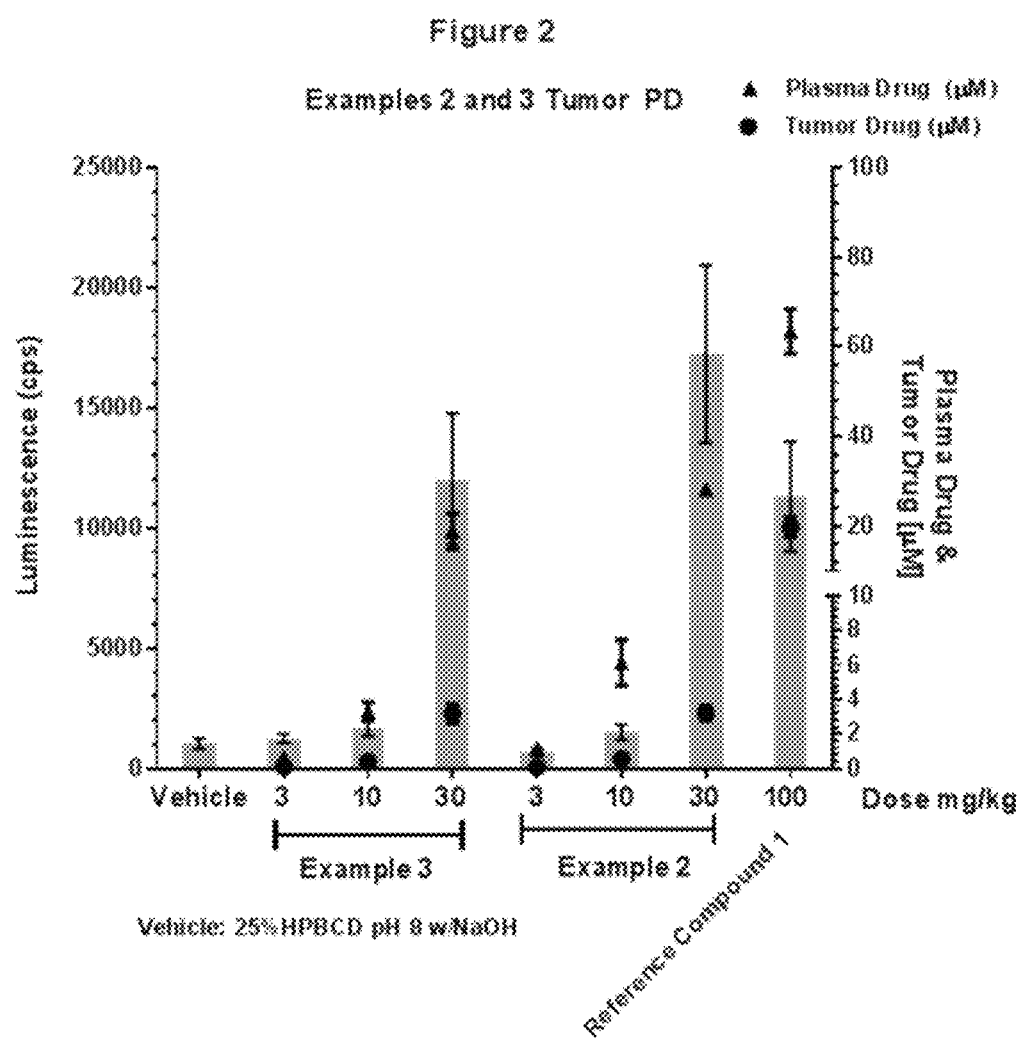
FIG. 2 demonstrates the superior in vivo efficacy of Example 2 and Example 3 relative to Reference Compound 1 in a tumor PD model. Both compounds were dosed orally to female athymic nude mice inoculated with OPM-2 Luc cells.
Figure 3:
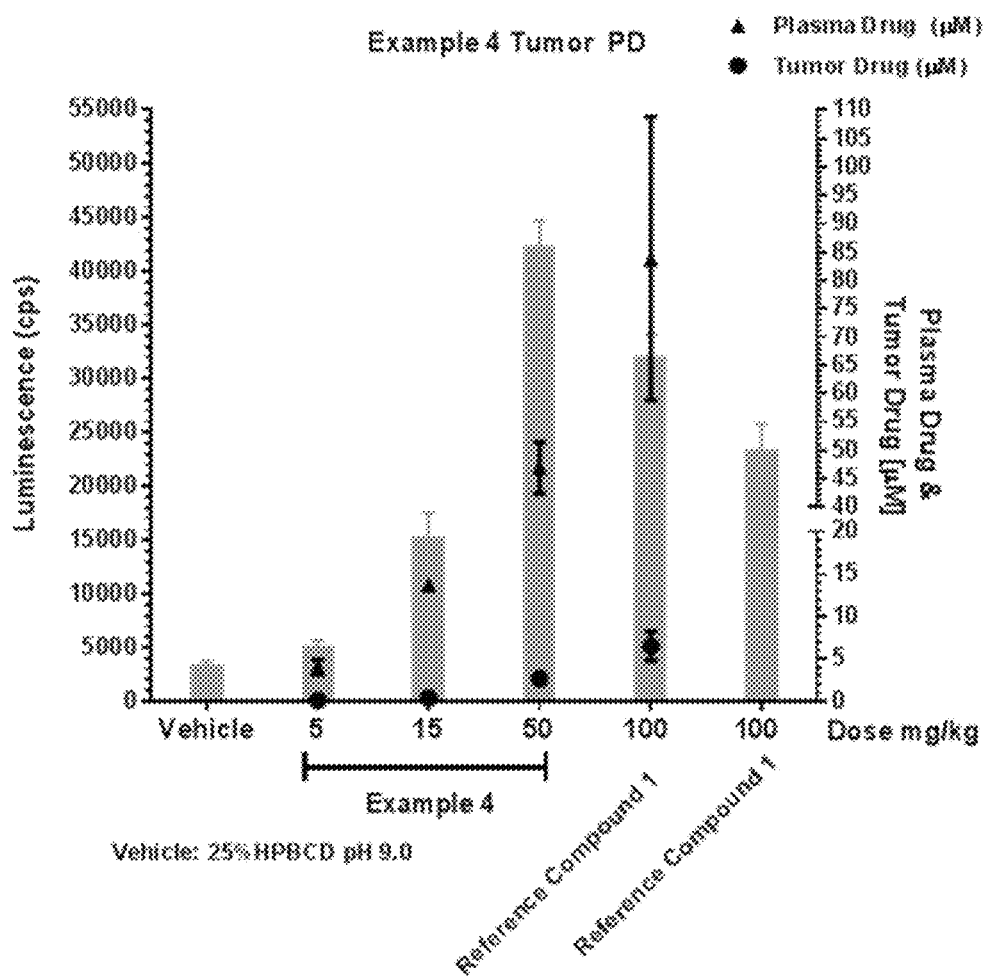
FIG. 3 demonstrates the superior in vivo efficacy of Example 4 relative to Reference Compound 1 in a tumor PD model. Both compounds were dosed orally to female athymic nude mice inoculated with OPM-2 Luc cells.
Figure 4:
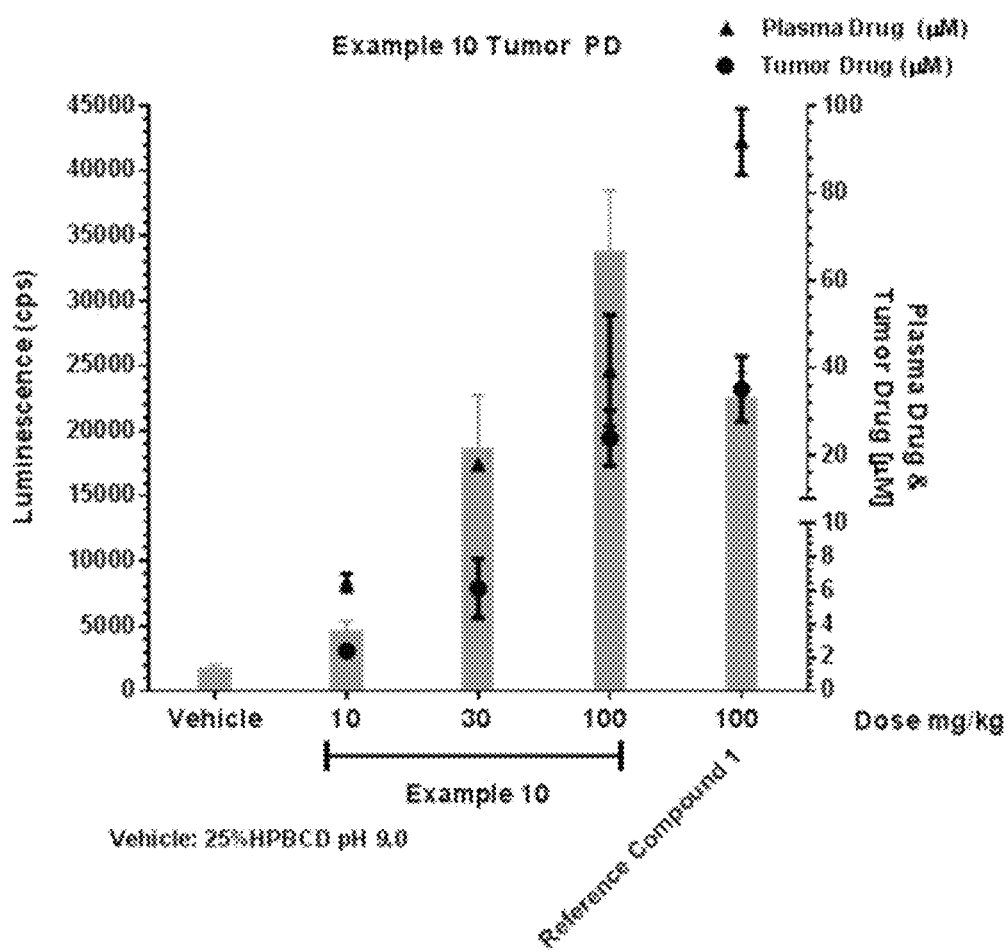
FIG. 4 demonstrates the superior in vivo efficacy of Example 10 relative to Reference Compound 1 in a tumor PD model. Both compounds were dosed orally to female athymic nude mice inoculated with OPM-2 Luc cells.
Figure 5:
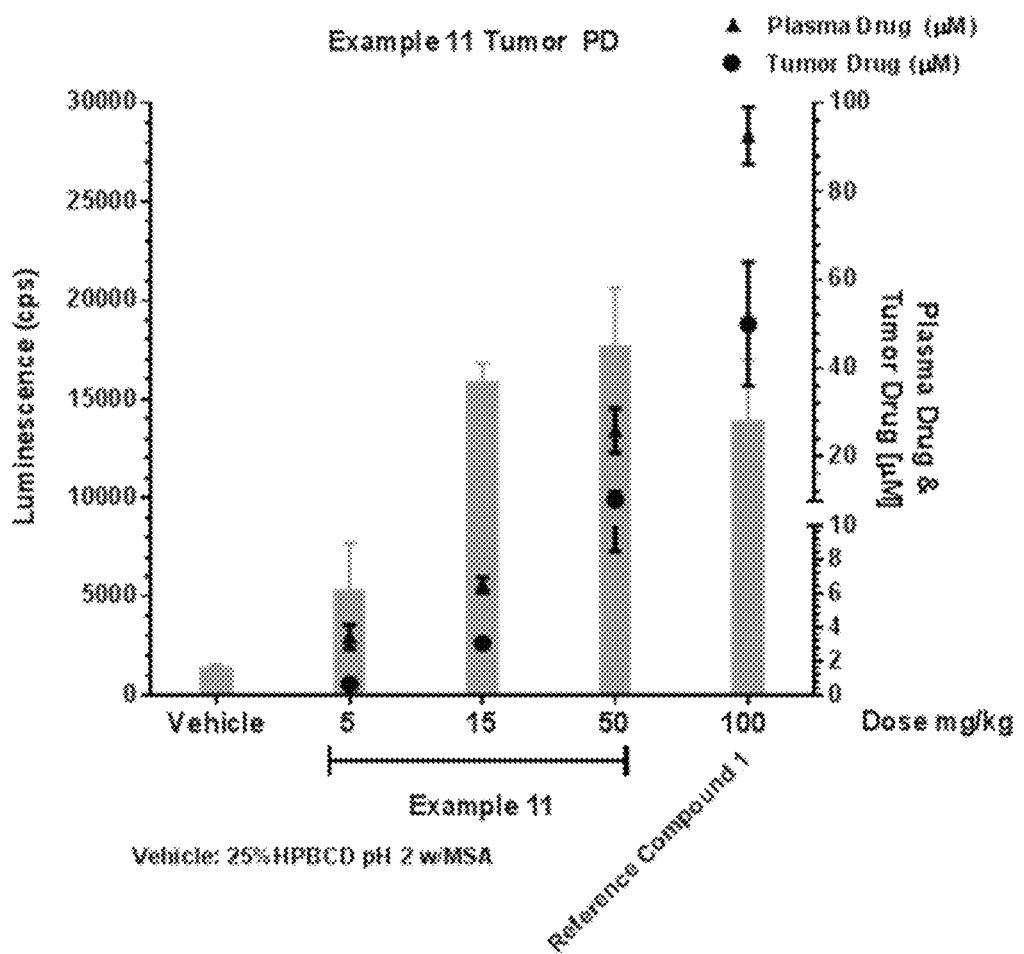
FIG. 5 demonstrates the superior in vivo efficacy of Example 11 relative to Reference Compound 1 in a tumor PD model. Both compounds were dosed orally to female athymic nude mice inoculated with OPM-2 Luc cells.
Figure 6:
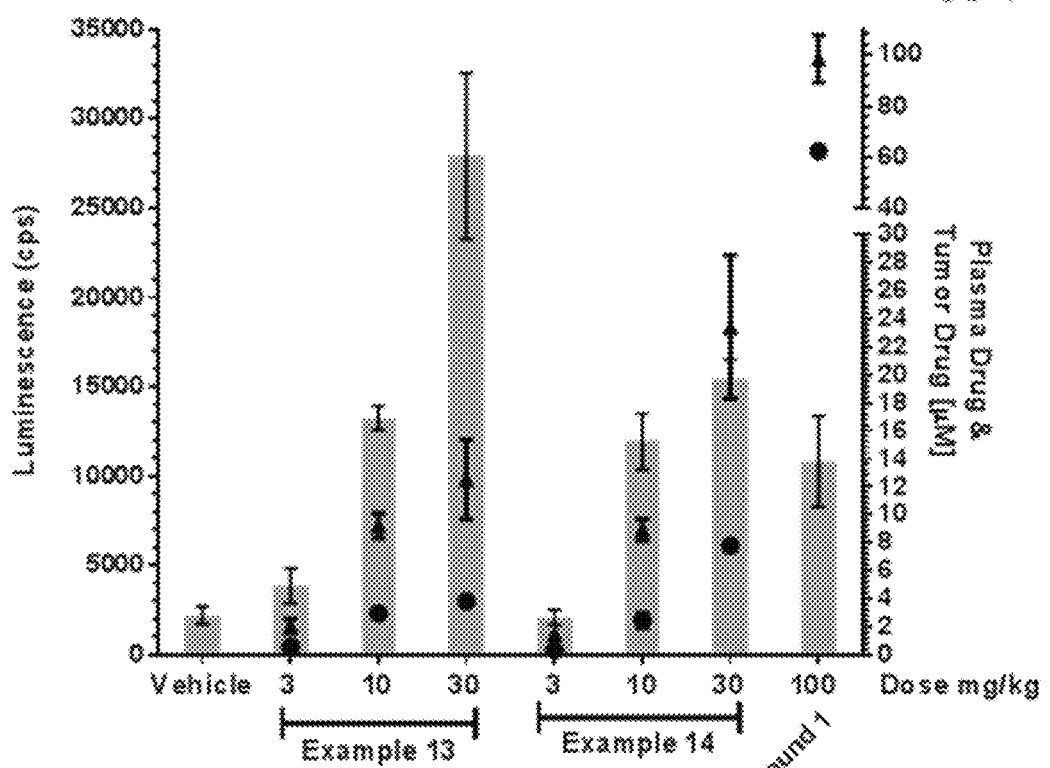
FIG. 6 demonstrates the superior in vivo efficacy of Example 13 and Example 14 relative to Reference Compound 1 in a tumor PD model. Both compounds were dosed orally to female athymic nude mice inoculated with OPM-2 Luc cells.
Figure 7:
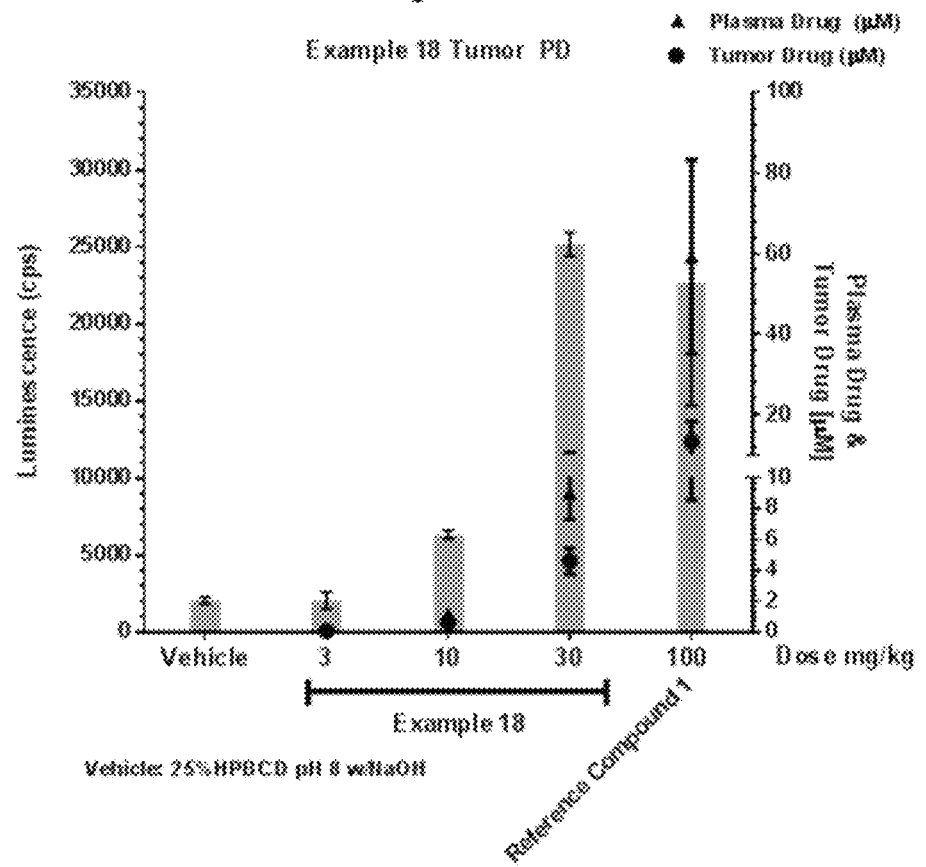
FIG. 7 demonstrates the superior in vivo efficacy of Example 18 relative to Reference Compound 1 in a tumor PD model. Both compounds were dosed orally to female athymic nude mice inoculated with OPM-2 Luc cells.
Figure 8:
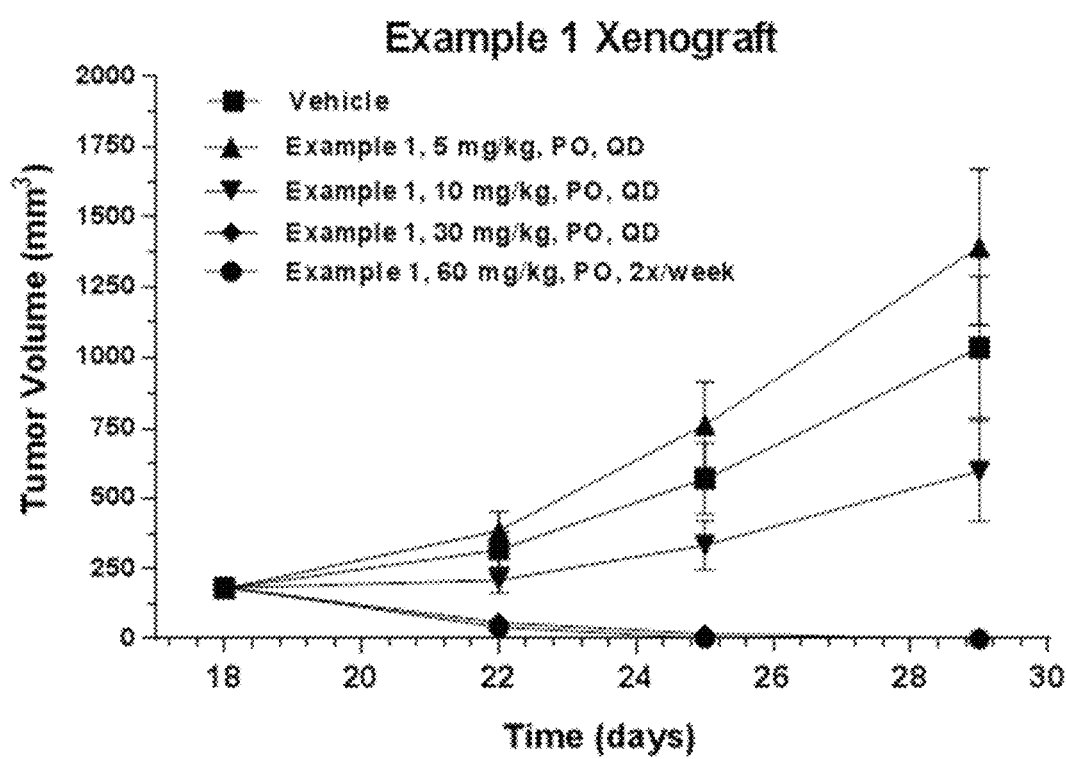
FIG. 8 demonstrates in vivo efficacy of Example 1 in an OPM-2 xenograft efficacy model. Example 1 was dosed orally to female athymic nude mice inoculated with OPM-2 Luc cells.
Figure 9:
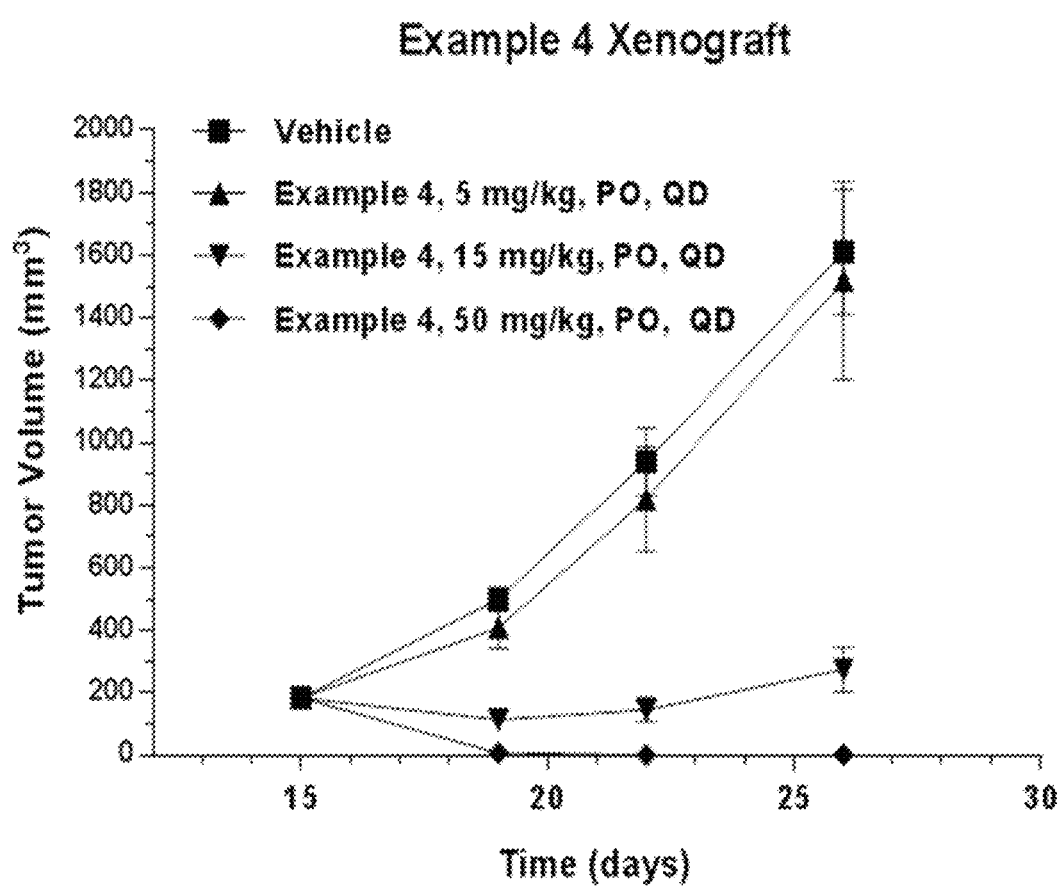
FIG. 9 demonstrates in vivo efficacy of Example 4 in an OPM-2 xenograft efficacy model. Example 1 was dosed orally to female athymic nude mice inoculated with OPM-2 Luc cells.
Figure 10:
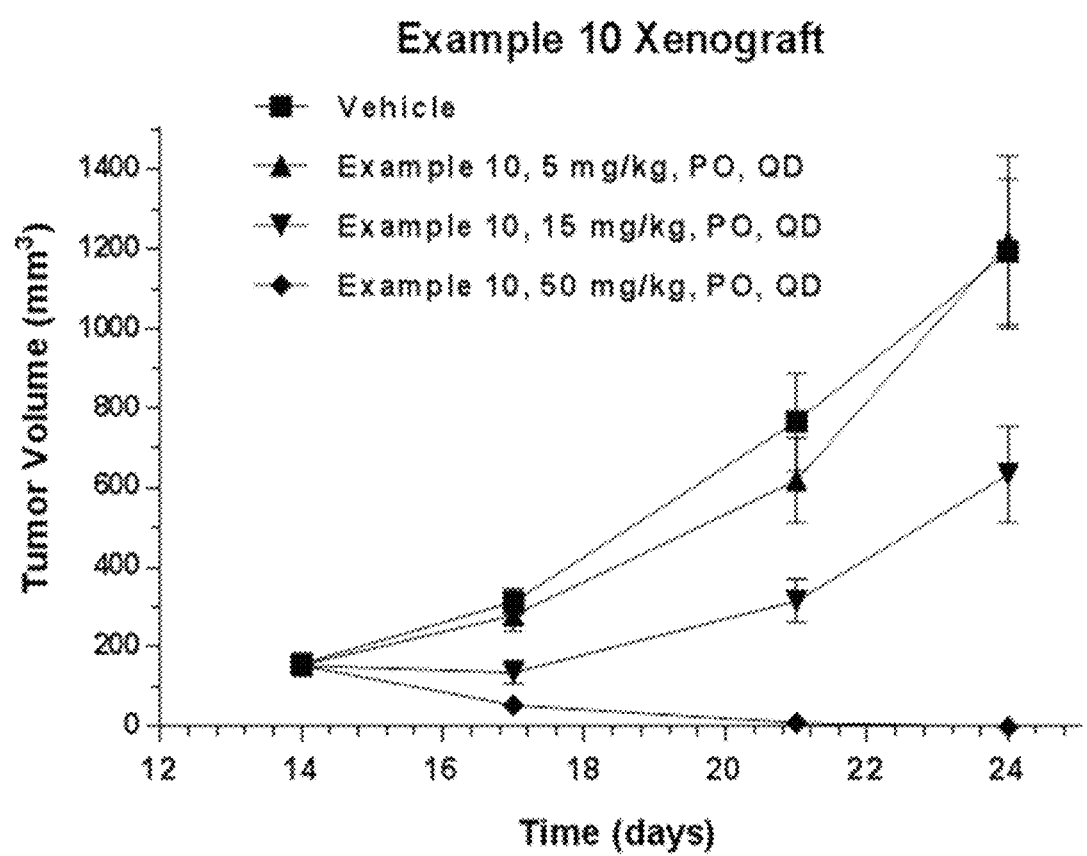
FIG. 10 demonstrates in vivo efficacy of Example 10 in an OPM-2 xenograft efficacy model. Example 1 was dosed orally to female athymic nude mice inoculated with OPM-2 Luc cells.
Figure 11:
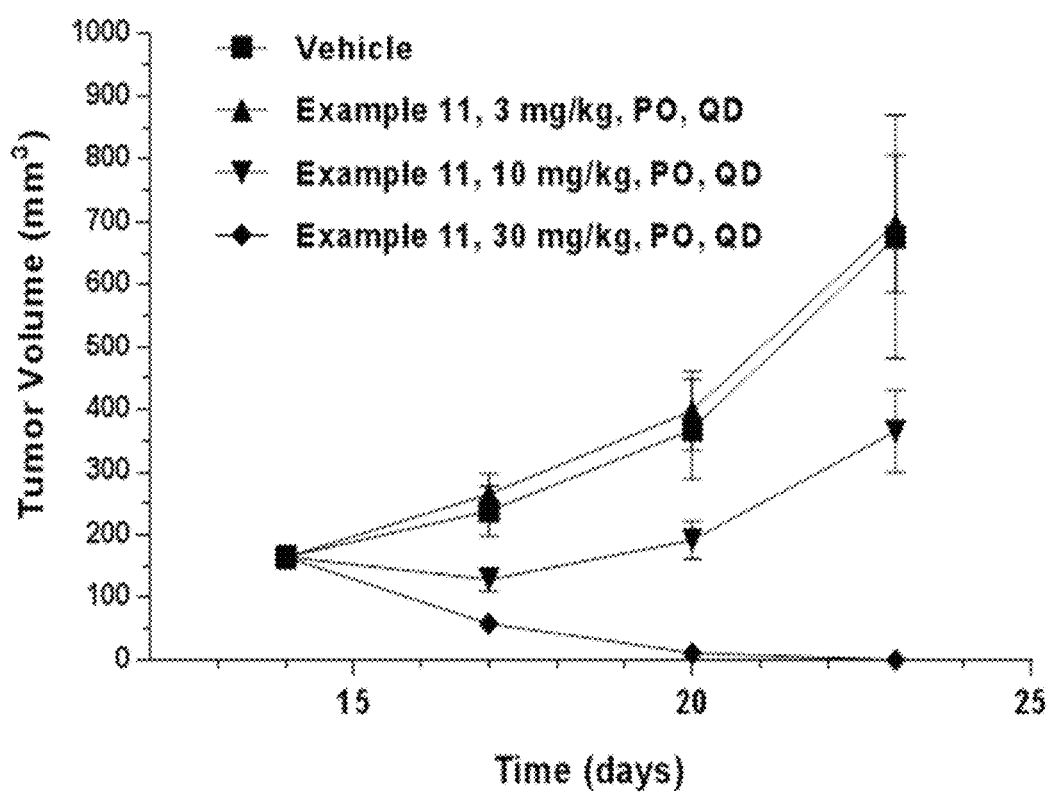
FIG. 11 demonstrates in vivo efficacy of Example 11 in an OPM-2 xenograft efficacy model. Example 1 was dosed orally to female athymic nude mice inoculated with OPM-2 Luc cells.
Figure 12:
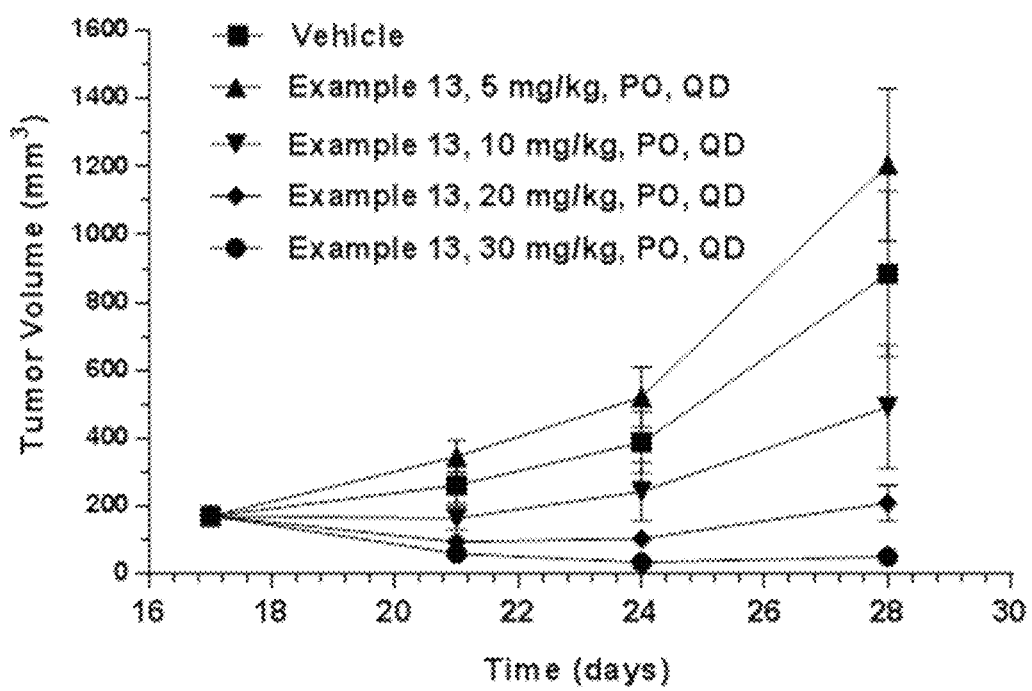
FIG. 12 demonstrates in vivo efficacy of Example 13 in an OPM-2 xenograft efficacy model. Example 1 was dosed orally to female athymic nude mice inoculated with OPM-2 Luc cells.
Figure 13:
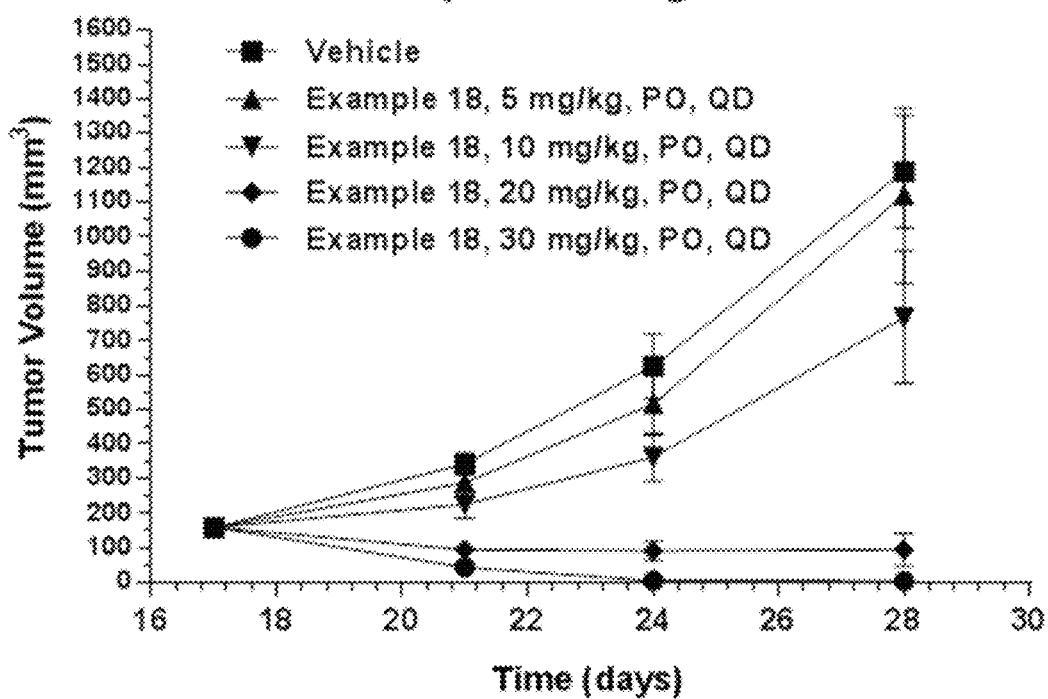
FIG. 13 demonstrates in vivo efficacy of Example 18 in an OPM-2 xenograft efficacy model. Example 1 was dosed orally to female athymic nude mice inoculated with OPM-2 Luc cells.

FIGS. 1-7 illustrate the PD results of the cited Examples. The Reference Compound 1, an internal Amgen MCl-1 inhibitor compound made by one of the general schemes outlined in U.S. Pat. No. 9,562,061, herein incorporated by reference, is (1S,3'R,6'R,7'S,8'E,12'R)-6-chloro-12'-ethyl-7'-methoxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide Reference Compound 1

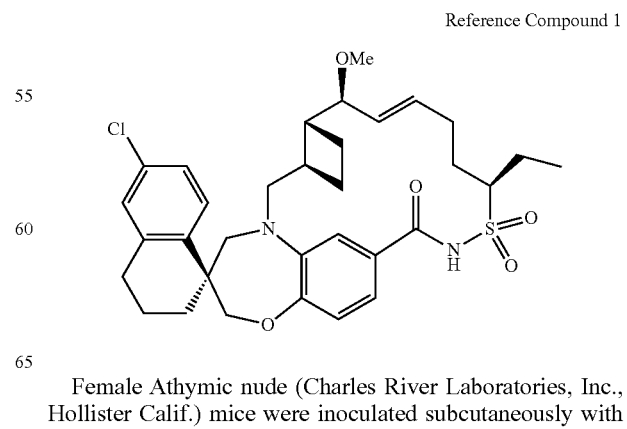

Female Athymic nude (Charles River Laboratories, Inc., Hollister Calif.) mice were inoculated subcutaneously with $5\times10^6$ OPM-2 Luc cells. When tumors reached 300-500 mm³ in size, mice were randomized into treatment groups and harvested 6 hours post single dose of compound at various concentrations. Tumor lysates were analyzed for active Bak using a sandwich ELISA format (Active Bak MSD plate cat #N45ZA-1; Bak detection antibody Abcam Cat# Ab53153 and Sulfo-Tagged by MSD) and read on a MSD reader (S16000). Columns (n=3 per group) represent level of luminescence (cps). Statistical significance was determined by Oneway ANOVA followed by Dunnett's post hoc compared to the vehicle control group. Black diamonds represent drug plasma concentration and circles represent drug concentration in the tumor.

OPM-2 Xenograft

Examples 8-13 illustrate Xenograft data of various compounds of the present invention. Female Athymic nude (Charles River Laboratories, Inc., Hollister Calif.) mice were inoculated subcutaneously with $5\times10^6$ OPM-2 Luc cells. When average tumor volumes reached approximately 155-183 mm³, animals were randomized (n=10/group) and dosed once daily by oral gavage (10-12 days) with test compounds at various concentrations unless notes otherwise. Tumor volume and body weights were recorded twice per week using electronic calipers and an analytical scale. Statistical analysis was performed using Repeated Measures ANOVA (RMANOVA) followed by Dunnett's post-hoc analysis.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended Claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

The invention claimed is:

1. A compound, wherein the compound is selected from:

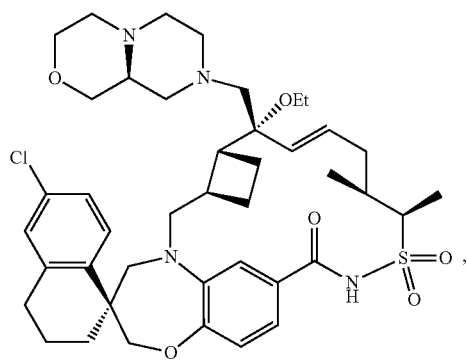

-continued

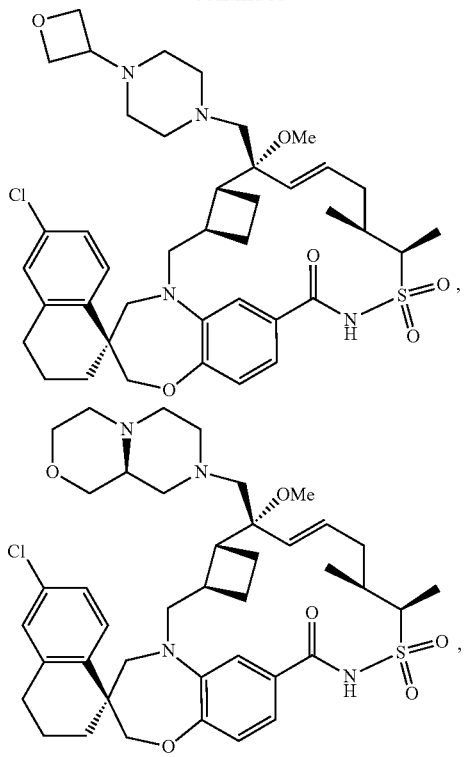

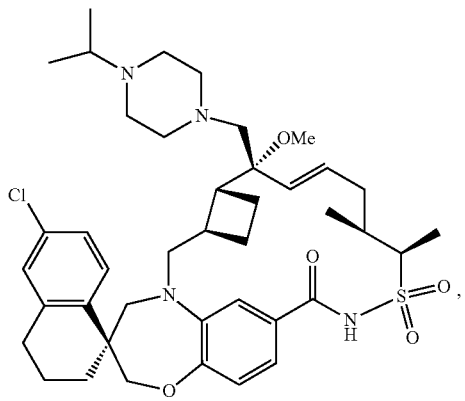

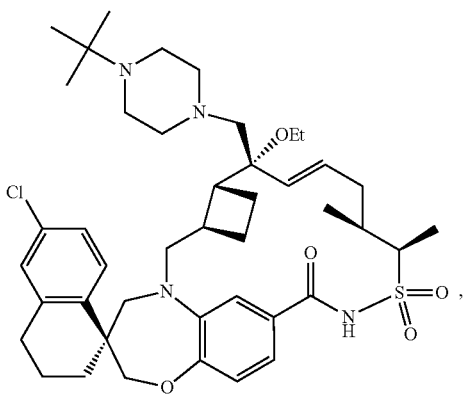

1979
-continued
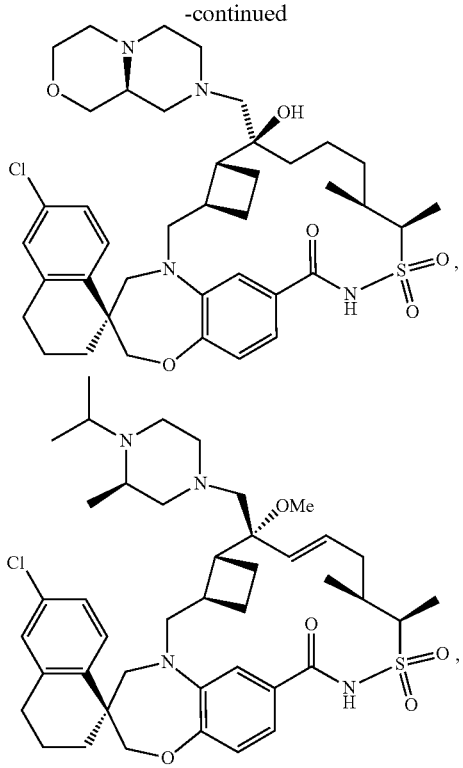
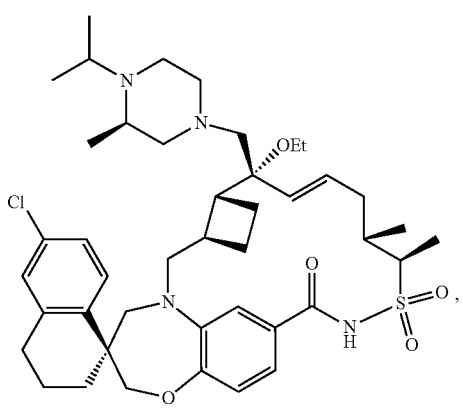
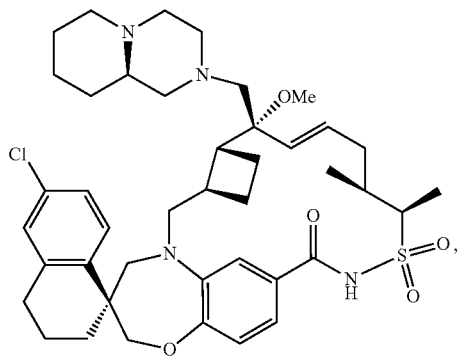
1980
-continued
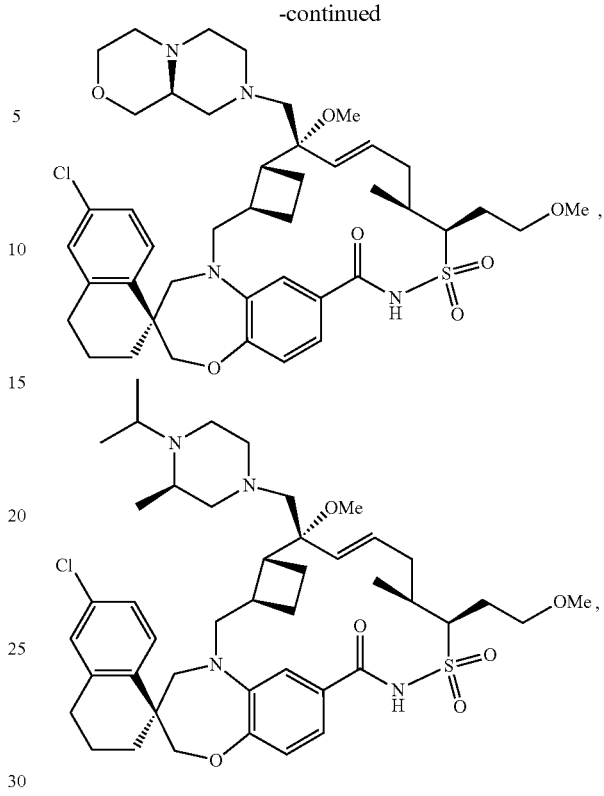
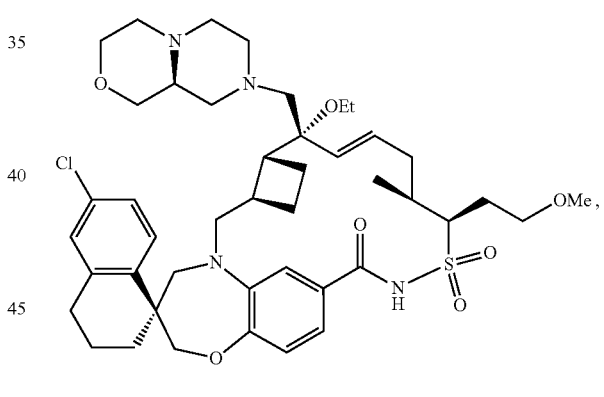
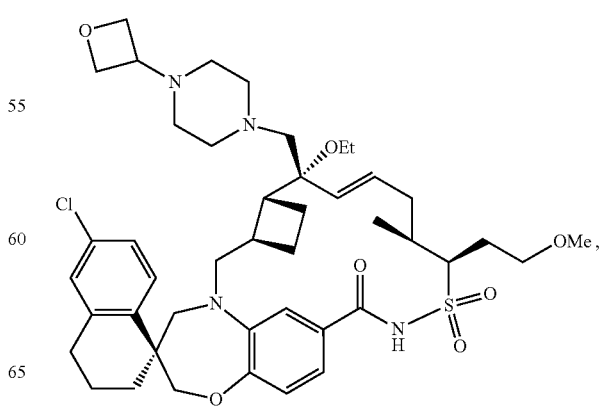

1981
-continued

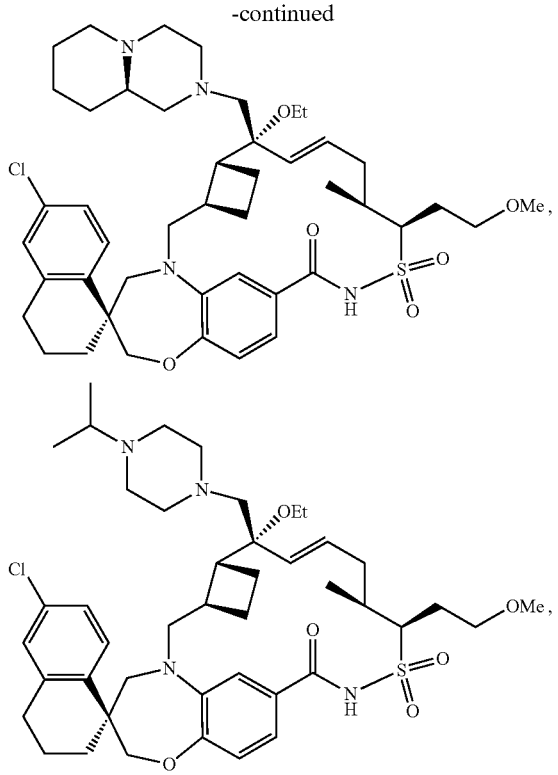

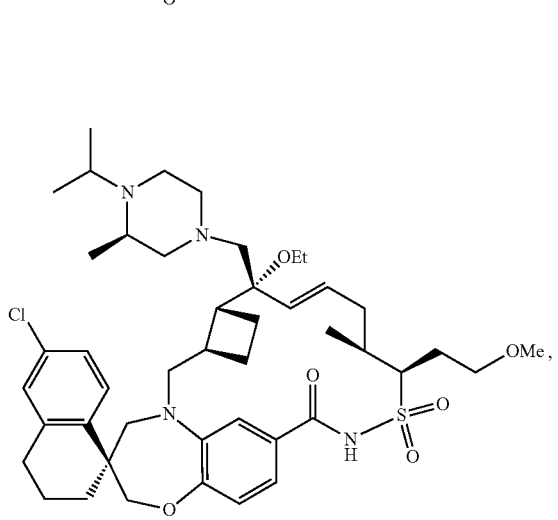

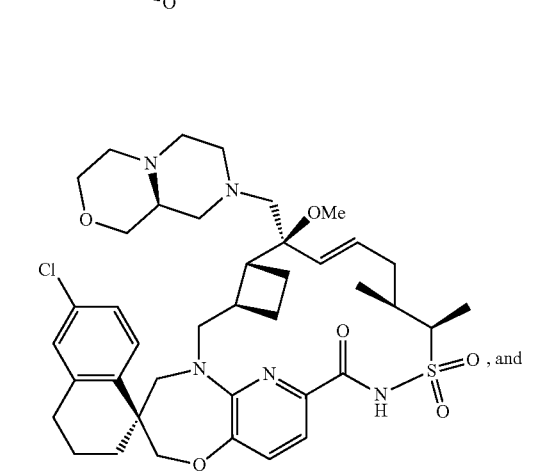

1982
-continued

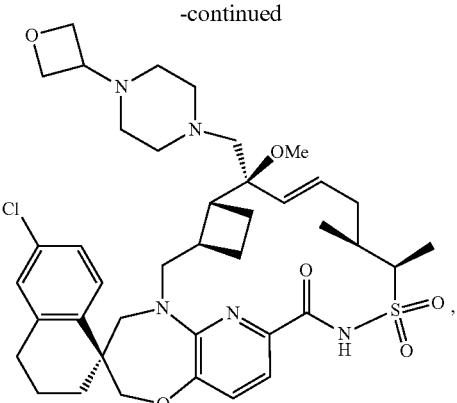

or the stereoisomer thereof, the pharmaceutically acceptable salt thereof, or the pharmaceutically acceptable salt of the stereoisomer thereof.

2. The compound of claim 1 or the pharmaceutically acceptable salt thereof.

3. A pharmaceutical composition comprising the compound of claim 1 or the pharmaceutically acceptable salt thereof, and a pharmaceutically acceptable carrier or diluent.

4. The compound of claim 1, wherein the compound is

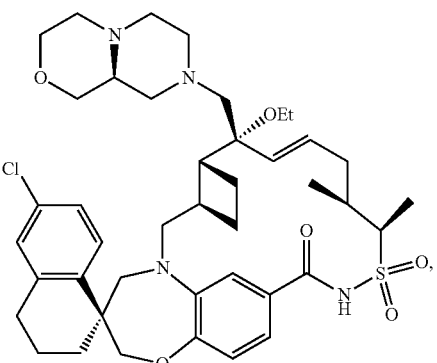

or the pharmaceutically acceptable salt thereof.

5. A pharmaceutical composition comprising the compound of claim 4 or the pharmaceutically acceptable salt thereof, and a pharmaceutically acceptable carrier or diluent.

6. The compound of claim 1, wherein the compound is

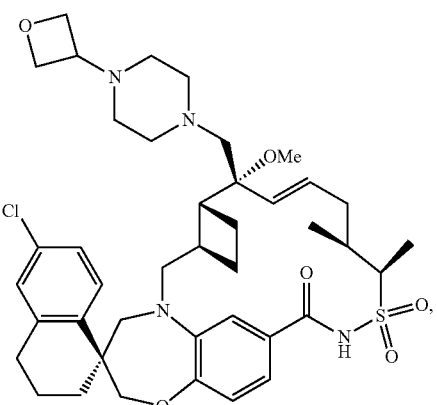

or the pharmaceutically acceptable salt thereof.

7. A pharmaceutical composition comprising the compound of claim 6 or the pharmaceutically acceptable salt thereof, and a pharmaceutically acceptable carrier or diluent.

8. The compound of claim 1, wherein the compound is

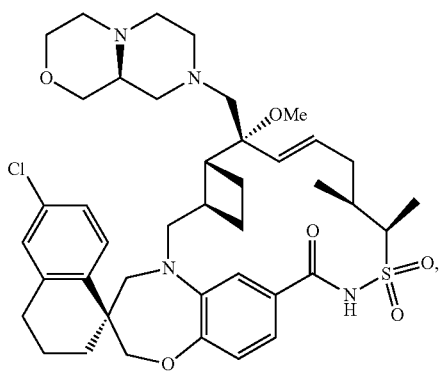 [SMILES: CO[C@]1(CN2CCN3CCOC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

9. A pharmaceutical composition comprising the compound of claim 8 or the pharmaceutically acceptable salt thereof, and a pharmaceutically acceptable carrier or diluent.

10. The compound of claim 1, wherein the compound is

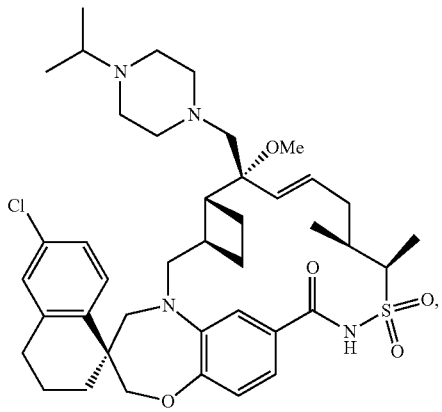 [SMILES: CO[C@]1(CN2CCN(C(C)C)CC2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

11. A pharmaceutical composition comprising the compound of claim 10 or the pharmaceutically acceptable salt thereof, and a pharmaceutically acceptable carrier or diluent.

12. The compound of claim 1, wherein the compound is

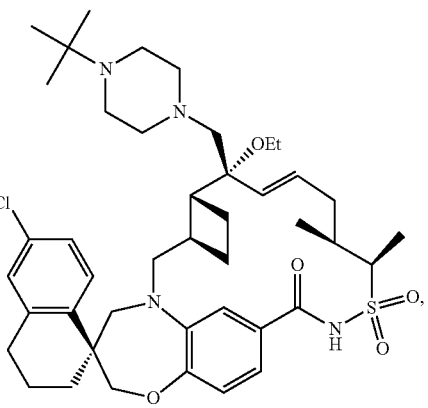

or the pharmaceutically acceptable salt thereof.

13. A pharmaceutical composition comprising the compound of claim 12 or the pharmaceutically acceptable salt thereof, and a pharmaceutically acceptable carrier or diluent.

14. The compound of claim 1, wherein the compound is

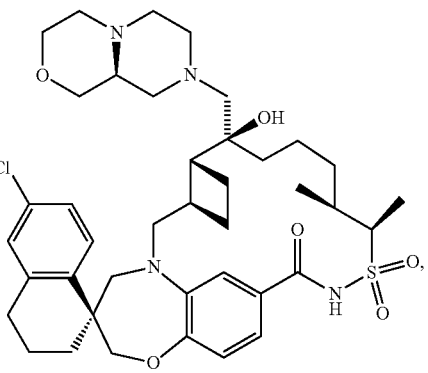

or the pharmaceutically acceptable salt thereof.

15. A pharmaceutical composition comprising the compound of claim 14 or the pharmaceutically acceptable salt thereof, and a pharmaceutically acceptable carrier or diluent.

16. The compound of claim 1, wherein the compound is

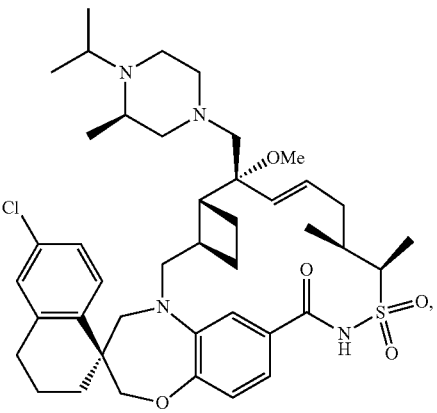 [SMILES: CO[C@]1(CN2CCN(C(C)C)[C@H](C)C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

17. A pharmaceutical composition comprising the compound of claim 16 or the pharmaceutically acceptable salt thereof, and a pharmaceutically acceptable carrier or diluent.

18. The compound of claim 1, wherein the compound is

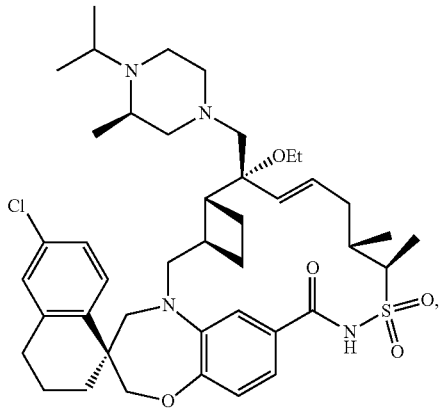 [SMILES: CCO[C@]1(CN2CCN(C(C)C)[C@H](C)C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

19. A pharmaceutical composition comprising the compound of claim 18 or the pharmaceutically acceptable salt thereof, and a pharmaceutically acceptable carrier or diluent.

20. The compound of claim 1, wherein the compound is

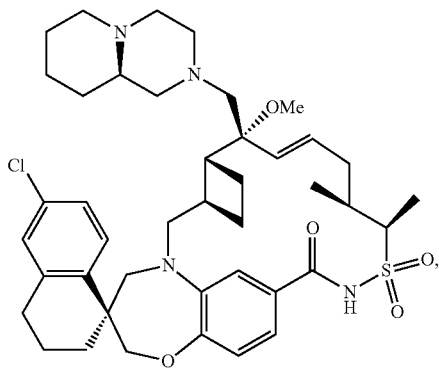 [SMILES: CO[C@]1(CN2CCN3CCCC[C@@H]3C2)/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

21. A pharmaceutical composition comprising the compound of claim 20 or the pharmaceutically acceptable salt thereof, and a pharmaceutically acceptable carrier or diluent.

22. The compound of claim 1, wherein the compound is

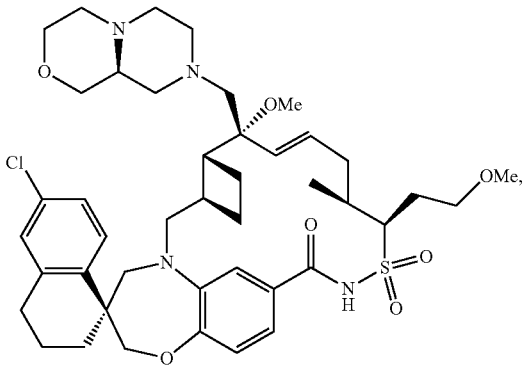 [SMILES: COCC[C@@H]1[C@@H](C)C/C=C/[C@@](CN2CCN3CCOC[C@@H]3C2)(OC)[C@@H]2CC[C@H]2CN2C[C@@]3(CCCc4cc(Cl)ccc43)COc3ccc(cc32)C(=O)NS1(=O)=O]

or the pharmaceutically acceptable salt thereof.

23. A pharmaceutical composition comprising the compound of claim 22 or the pharmaceutically acceptable salt thereof, and a pharmaceutically acceptable carrier or diluent.

24. The compound of claim 1, wherein the compound is

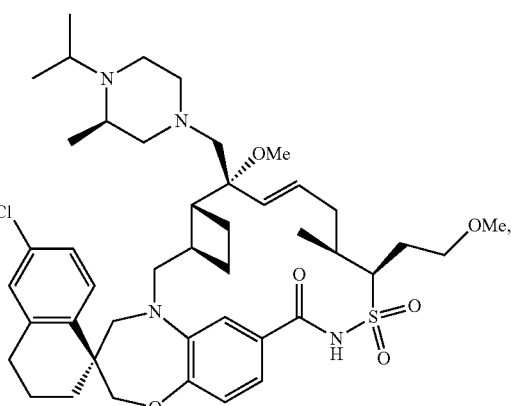

or the pharmaceutically acceptable salt thereof.

25. A pharmaceutical composition comprising the compound of claim 24 or the pharmaceutically acceptable salt thereof, and a pharmaceutically acceptable carrier or diluent.

26. The compound of claim 1, wherein the compound is

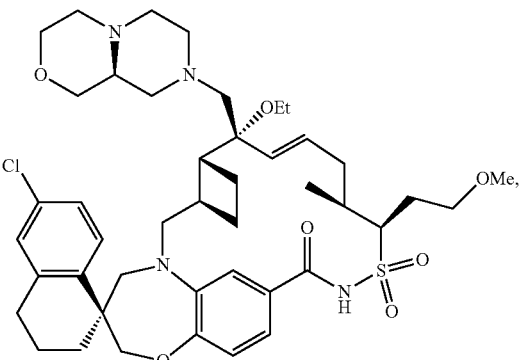

or the pharmaceutically acceptable salt thereof.

27. A pharmaceutical composition comprising the compound of claim 26 or the pharmaceutically acceptable salt thereof, and a pharmaceutically acceptable carrier or diluent.

28. The compound of claim 1, wherein the compound is

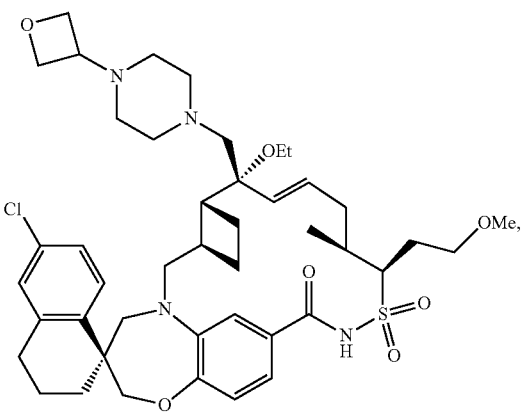 [SMILES: CCO[C@]1(CN2CCN(C3COC3)CC2)/C=C/C[C@H](C)[C@@H](CCOC)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

29. A pharmaceutical composition comprising the compound of claim 28 or the pharmaceutically acceptable salt thereof, and a pharmaceutically acceptable carrier or diluent.

30. The compound of claim 1, wherein the compound is

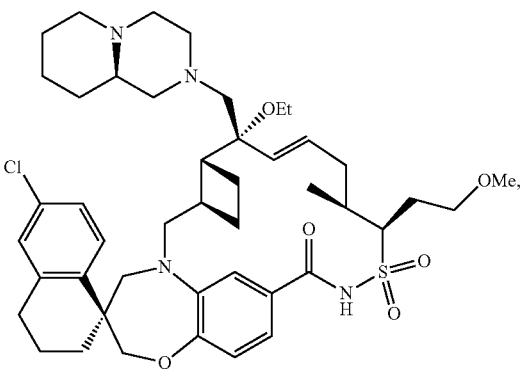 [SMILES: CCO[C@]1(CN2CCN3CCCC[C@@H]3C2)/C=C/C[C@H](C)[C@@H](CCOC)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

31. A pharmaceutical composition comprising the compound of claim 30 or the pharmaceutically acceptable salt thereof, and a pharmaceutically acceptable carrier or diluent.

32. The compound of claim 1, wherein the compound is

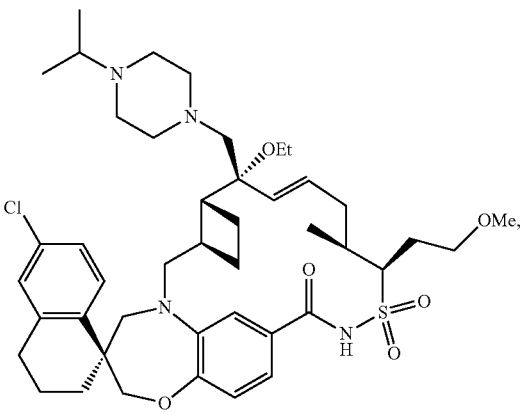 [SMILES: CCO[C@]1(CN2CCN(C(C)C)CC2)/C=C/C[C@H](C)[C@@H](CCOC)S(=O)(=O)NC(=O)c2ccc3c(c2)N(C[C@@H]2CC[C@H]21)C[C@@]1(CCCc2cc(Cl)ccc21)CO3]

or the pharmaceutically acceptable salt thereof.

33. A pharmaceutical composition comprising the compound of claim 32 or the pharmaceutically acceptable salt thereof, and a pharmaceutically acceptable carrier or diluent.

34. The compound of claim 1, wherein the compound is

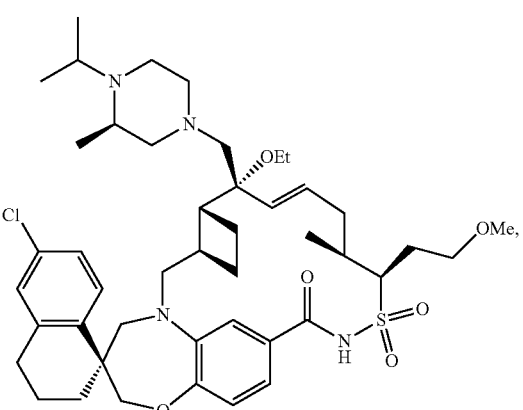

or the pharmaceutically acceptable salt thereof.

35. A pharmaceutical composition comprising the compound of claim 34 or the pharmaceutically acceptable salt thereof, and a pharmaceutically acceptable carrier or diluent.

36. The compound of claim 1, wherein the compound is

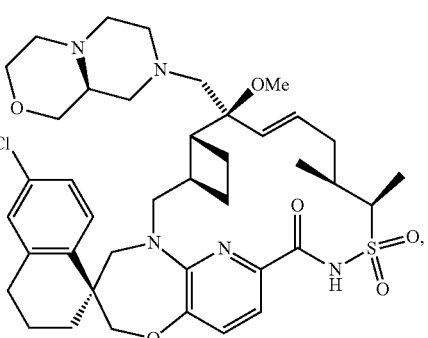

or the pharmaceutically acceptable salt thereof.

37. A pharmaceutical composition comprising the compound of claim 36 or the pharmaceutically acceptable salt thereof, and a pharmaceutically acceptable carrier or diluent.

38. The compound of claim 1, wherein the compound is
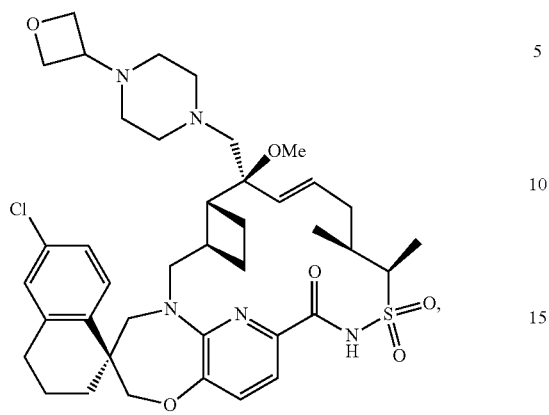
or the pharmaceutically acceptable salt thereof.
39. A pharmaceutical composition comprising the compound of claim 38 or the pharmaceutically acceptable salt thereof, and a pharmaceutically acceptable carrier or diluent.
* * * * *

UNITED STATES PATENT AND TRADEMARK OFFICE
CERTIFICATE OF CORRECTION

PATENT NO. : 10,300,075 B2  
APPLICATION NO. : 15/938001  
DATED : May 28, 2019  
INVENTOR(S) : Brown et al.

Page 1 of 1

It is certified that error appears in the above-identified patent and that said Letters Patent is hereby corrected as shown below:

On the Title Page

Item (60) of the Related U.S. Application Data section, please replace the following phrase:
"Provisional application No. 62/247,230"

With the following phrase:
--Provisional application No. 62/479,230--.

In the Claims

In Claim 1, Column 1981, Lines 60-65 (after the last structure in Column 1981), please replace the following phrase:
", and"

With the following phrase:
--, or--.

Signed and Sealed this  
Sixteenth Day of July, 2019

Andrei Iancu  
*Director of the United States Patent and Trademark Office*